US009096865B2

(12) United States Patent
Vinocur et al.

(10) Patent No.: US 9,096,865 B2
(45) Date of Patent: Aug. 4, 2015

(54) ISOLATED POLYNUCLEOTIDES AND POLYPEPTIDES, AND METHODS OF USING SAME FOR INCREASING NITROGEN USE EFFICIENCY, YIELD, GROWTH RATE, VIGOR, BIOMASS, OIL CONTENT, AND/OR ABIOTIC STRESS TOLERANCE

(75) Inventors: Basia J. Vinocur, Rechovot (IL); Alex Diber, Rishon-LeZion (IL); Hagai Karchi, Moshav Sitriya (IL)

(73) Assignee: Evogene Ltd., Rechovot (IL)

( * ) Notice: Subject to any disclaimer, the term of this patent is extended or adjusted under 35 U.S.C. 154(b) by 700 days.

(21) Appl. No.: 13/377,556

(22) PCT Filed: Jun. 8, 2010

(86) PCT No.: PCT/IB2010/052545
§ 371 (c)(1),
(2), (4) Date: Dec. 11, 2011

(87) PCT Pub. No.: WO2010/143138
PCT Pub. Date: Dec. 16, 2010

(65) Prior Publication Data
US 2012/0096587 A1    Apr. 19, 2012

Related U.S. Application Data

(60) Provisional application No. 61/272,764, filed on Oct. 30, 2009, provisional application No. 61/213,457, filed on Jun. 10, 2009.

(51) Int. Cl.
| | | |
|---|---|---|
| *A01H 1/00* | (2006.01) | |
| *C12N 15/00* | (2006.01) | |
| *C12N 15/82* | (2006.01) | |
| *C07K 14/415* | (2006.01) | |
| *C07H 21/04* | (2006.01) | |

(52) U.S. Cl.
CPC .......... *C12N 15/8247* (2013.01); *C07K 14/415* (2013.01); *C12N 15/8261* (2013.01); *C12N 15/8271* (2013.01); *C12N 15/8273* (2013.01)

(58) Field of Classification Search
None
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,666,828 A | 5/1987 | Gusella | |
| 4,683,202 A | 7/1987 | Mullis | |
| 4,801,531 A | 1/1989 | Frossard | |
| 4,879,219 A | 11/1989 | Wands et al. | |
| 4,943,674 A | 7/1990 | Houck et al. | |
| 4,945,050 A | 7/1990 | Sanford et al. | |
| 5,011,771 A | 4/1991 | Bellet et al. | |
| 5,187,267 A | 2/1993 | Comai et al. | |
| 5,192,659 A | 3/1993 | Simons | |
| 5,268,463 A | 12/1993 | Jefferson | |
| 5,272,057 A | 12/1993 | Smulson et al. | |
| 5,281,521 A | 1/1994 | Trojanowski et al. | |
| 5,296,462 A | 3/1994 | Thomashow | |
| 5,316,931 A | 5/1994 | Donson et al. | |
| 5,356,816 A | 10/1994 | Thomashow | |
| 5,399,680 A | 3/1995 | Zhu et al. | |
| 5,464,765 A | 11/1995 | Coffee et al. | |
| 5,466,785 A | 11/1995 | De Framond | |
| 5,495,070 A | 2/1996 | John | |
| 5,504,200 A | 4/1996 | Hall et al. | |
| 5,521,708 A | 5/1996 | Beretta | |
| 5,569,597 A | 10/1996 | Grimsley et al. | |
| 5,597,718 A | 1/1997 | John et al. | |
| 5,604,121 A | 2/1997 | Hilder et al. | |

(Continued)

FOREIGN PATENT DOCUMENTS

| | | |
|---|---|---|
| AU | 2005229157 | 10/2005 |
| AU | 2005234725 | 12/2005 |

(Continued)

OTHER PUBLICATIONS

Alexandrov et al., N_Geneseq Database, Accession No. AOE77171, US20060150283, see Result 5.*
Advisory Action Before the Filing of an Appeal Brief Dated Dec. 20, 2013 From the US Patent and Trademark Office Re. U.S. Appl. No. 12/834,106.
Applicant-Initiated Interview Summary Dated Dec. 18, 2013 From the US Patent and Trademark Office Re. U.S. Appl. No. 12/834,106.
Communication Pursuant to Article 94(3) EPC Dated Jan. 3, 2013 From the European Patent Office Re. Application No. 09807983.3.
English Summary of Examination Results Dated Dec. 28, 2012 From the National Office of Intellectual Property (NOIP) of Vietnam Re. Application No. 1-2009-02358.

(Continued)

*Primary Examiner* — Phuong Bui

(57) ABSTRACT

Provided are methods of increasing nitrogen use efficiency, yield, biomass, growth rate, vigor, oil content, fiber yield, fiber quality and/or abiotic stress tolerance of a plant by expressing within the plant an exogenous polynucleotide comprising a nucleic acid sequence at least 80% identical to SEQ ID NO:1-467, 785-3047; or an exogenous polynucleotide encoding a polypeptide at least 80% identical to SEQ ID NO:468-784, 3048-4333, 4335-4682. Also provided isolated polynucleotide comprising a nucleic acid sequence selected from the group consisting of SEQ ID NOs:1-467, 785-3047, which can be used to increase nitrogen use efficiency, yield, biomass, growth rate, vigor, oil content, fiber yield, fiber quality and/or abiotic stress tolerance of a plant.

15 Claims, 4 Drawing Sheets

(56) References Cited

U.S. PATENT DOCUMENTS

| | | |
|---|---|---|
| 5,608,142 A | 3/1997 | Barton et al. |
| 5,608,144 A | 3/1997 | Baden et al. |
| 5,608,149 A | 3/1997 | Barry et al. |
| 5,608,152 A | 3/1997 | Kridl et al. |
| 5,620,882 A | 4/1997 | John |
| 5,659,026 A | 8/1997 | Baszczynski et al. |
| 5,693,507 A | 12/1997 | Daniell et al. |
| 5,859,330 A | 1/1999 | Bestwick et al. |
| 5,880,100 A | 3/1999 | Ogiso et al. |
| 5,981,834 A | 11/1999 | John et al. |
| 6,080,914 A | 6/2000 | Conner |
| 6,084,153 A | 7/2000 | Good et al. |
| 6,313,375 B1 | 11/2001 | Jung et al. |
| 6,313,376 B1 | 11/2001 | Jung et al. |
| 6,359,196 B1 | 3/2002 | Lok et al. |
| 6,392,122 B1 | 5/2002 | Clendennen et al. |
| 6,403,862 B1 | 6/2002 | Jiao et al. |
| 6,472,588 B1 | 10/2002 | Haigler et al. |
| 6,670,528 B1 | 12/2003 | Shinozaki et al. |
| 6,720,477 B2 | 4/2004 | Da Costa e Silva et al. |
| 7,214,786 B2 | 5/2007 | Kovalic et al. |
| 7,554,007 B2 | 6/2009 | Ronen et al. |
| 7,812,218 B2 | 10/2010 | Ronen et al. |
| 7,910,800 B2 | 3/2011 | Karchi et al. |
| 8,049,069 B2 | 11/2011 | Wu et al. |
| 8,168,857 B2 | 5/2012 | Ayal et al. |
| 8,426,682 B2 | 4/2013 | Ronen et al. |
| 2002/0046419 A1 | 4/2002 | Choo et al. |
| 2002/0049999 A1 | 4/2002 | Allen et al. |
| 2002/0148007 A1 | 10/2002 | Jiao et al. |
| 2002/0160378 A1 | 10/2002 | Harper et al. |
| 2002/0170088 A1 | 11/2002 | Wilkins |
| 2003/0005485 A1 | 1/2003 | Ohlrogge et al. |
| 2003/0074697 A1 | 4/2003 | Allen et al. |
| 2003/0084485 A1 | 5/2003 | Zhu et al. |
| 2003/0162294 A1 | 8/2003 | Verbruggen |
| 2003/0163839 A1 | 8/2003 | Helentjaris et al. |
| 2003/0233670 A1 | 12/2003 | Edgerton et al. |
| 2004/0006794 A1 | 1/2004 | Wilkins |
| 2004/0019927 A1 | 1/2004 | Sherman et al. |
| 2004/0031072 A1 | 2/2004 | La Rosa et al. |
| 2004/0034888 A1 | 2/2004 | Liu et al. |
| 2004/0123343 A1 | 6/2004 | La Rosa et al. |
| 2004/0172684 A1 | 9/2004 | Kovalic et al. |
| 2004/0181830 A1 | 9/2004 | Kovalic et al. |
| 2005/0108791 A1 | 5/2005 | Edgerton |
| 2006/0048240 A1 | 3/2006 | Alexandrov et al. |
| 2006/0101543 A1 | 5/2006 | Somerville et al. |
| 2006/0107345 A1 | 5/2006 | Alexandrov et al. |
| 2006/0123505 A1 | 6/2006 | Kikuchi et al. |
| 2006/0123516 A1 | 6/2006 | Ronen et al. |
| 2006/0137043 A1 | 6/2006 | Puzio et al. |
| 2006/0143729 A1 | 6/2006 | Alexandrov et al. |
| 2006/0150283 A1 | 7/2006 | Alexandrov et al. |
| 2006/0168684 A1 | 7/2006 | Renz et al. |
| 2006/0174373 A1 | 8/2006 | Gipmans et al. |
| 2006/0179511 A1 | 8/2006 | Chomet et al. |
| 2006/0183137 A1 | 8/2006 | Harper et al. |
| 2006/0195943 A1 | 8/2006 | Feldmann et al. |
| 2006/0206961 A1 | 9/2006 | Cirpus et al. |
| 2006/0260002 A1 | 11/2006 | Ronen et al. |
| 2006/0288451 A1 | 12/2006 | Val et al. |
| 2007/0006345 A1 | 1/2007 | Alexandrov et al. |
| 2007/0006346 A1 | 1/2007 | Alexandrov et al. |
| 2007/0044171 A1 | 2/2007 | Kovalic et al. |
| 2007/0044172 A1 | 2/2007 | Schneeberger et al. |
| 2007/0061916 A1 | 3/2007 | Kovalic et al. |
| 2007/0124833 A1 | 5/2007 | Abad et al. |
| 2007/0169219 A1 | 7/2007 | Nadzan et al. |
| 2007/0214517 A1 | 9/2007 | Alexandrov et al. |
| 2007/0261130 A1 | 11/2007 | Lightner et al. |
| 2008/0072340 A1 | 3/2008 | Troukhan et al. |
| 2008/0076179 A1 | 3/2008 | Hartel et al. |
| 2008/0148432 A1 | 6/2008 | Abad |
| 2008/0196120 A1 | 8/2008 | Wu et al. |
| 2008/0301839 A1 | 12/2008 | Ravanello |
| 2009/0089898 A1 | 4/2009 | Karchi et al. |
| 2009/0093620 A1 | 4/2009 | Kovalic et al. |
| 2009/0094717 A1 | 4/2009 | Troukhan et al. |
| 2009/0126042 A1 | 5/2009 | Ronen et al. |
| 2009/0260109 A1 | 10/2009 | Ronen et al. |
| 2009/0293154 A1 | 11/2009 | Yelin et al. |
| 2010/0037352 A1 | 2/2010 | Alexandrov et al. |
| 2010/0154077 A1 | 6/2010 | Emmanuel et al. |
| 2010/0319088 A1 | 12/2010 | Ronen et al. |
| 2011/0080674 A1 | 4/2011 | Durand |
| 2011/0214206 A1 | 9/2011 | La Rosa et al. |
| 2012/0060234 A1 | 3/2012 | Emmanuel et al. |
| 2012/0084885 A1 | 4/2012 | Alexandrov et al. |
| 2012/0180164 A1 | 7/2012 | Ayal et al. |
| 2012/0222169 A1 | 8/2012 | Ronen et al. |
| 2012/0297504 A1 | 11/2012 | Granevitze et al. |
| 2013/0125258 A1 | 5/2013 | Emmanuel et al. |
| 2013/0167265 A1 | 6/2013 | Panik et al. |
| 2013/0219562 A1 | 8/2013 | Ronen et al. |
| 2013/0239255 A1 | 9/2013 | Ronen et al. |
| 2013/0276169 A1 | 10/2013 | Poraty et al. |
| 2013/0291223 A1 | 10/2013 | Emmanuel et al. |

FOREIGN PATENT DOCUMENTS

| | | |
|---|---|---|
| CN | 1823168 | 8/2006 |
| EP | 0834566 | 4/1998 |
| EP | 0905242 | 3/1999 |
| EP | 1033405 | 9/2000 |
| EP | 1225231 | 7/2002 |
| EP | 1945021 | 7/2008 |
| EP | 2154946 | 2/2010 |
| JP | 2005-052114 | 3/2005 |
| JP | 2005-185101 | 7/2005 |
| RU | 2350653 | 3/2009 |
| WO | WO 93/06710 | 4/1993 |
| WO | WO 93/07278 | 4/1993 |
| WO | WO 94/17194 | 8/1994 |
| WO | WO 95/08914 | 4/1995 |
| WO | WO 96/26639 | 9/1996 |
| WO | WO 96/40924 | 12/1996 |
| WO | WO 01/17333 | 3/2001 |
| WO | WO 01/40250 | 6/2001 |
| WO | WO 02/16655 | 2/2002 |
| WO | WO 02/45485 | 6/2002 |
| WO | WO 02/079403 | 10/2002 |
| WO | WO 02/090557 | 11/2002 |
| WO | WO 03/020025 | 3/2003 |
| WO | WO 03/087313 | 10/2003 |
| WO | WO 03/098186 | 11/2003 |
| WO | WO 2004/035798 | 4/2004 |
| WO | WO 2004/053055 | 6/2004 |
| WO | WO 2004/058963 | 7/2004 |
| WO | WO 2004/081173 | 9/2004 |
| WO | WO 2004/092367 | 10/2004 |
| WO | WO 2004/104162 | 12/2004 |
| WO | WO 2004/111183 | 12/2004 |
| WO | WO 2005/084331 | 9/2005 |
| WO | WO 2005/095614 | 10/2005 |
| WO | WO 2005/108422 | 11/2005 |
| WO | WO 2005/121364 | 12/2005 |
| WO | WO 2006/138012 | 12/2006 |
| WO | WO 2007/020638 | 2/2007 |
| WO | WO 2007/049275 | 5/2007 |
| WO | WO 2007/110314 | 10/2007 |
| WO | WO 2007/113237 | 10/2007 |
| WO | WO 2008/069878 | 6/2008 |
| WO | WO 2008/075364 | 6/2008 |
| WO | WO 2008/122980 | 10/2008 |
| WO | WO 2009/009142 | 1/2009 |
| WO | WO 2009/013750 | 1/2009 |
| WO | WO 2009/083958 | 7/2009 |
| WO | WO 2009/141824 | 11/2009 |
| WO | WO 2009/144311 | 12/2009 |
| WO | WO 2010/020941 | 2/2010 |
| WO | WO 2010/049897 | 5/2010 |
| WO | WO 2010/076756 | 7/2010 |
| WO | WO 2010/100595 | 9/2010 |

(56) References Cited

FOREIGN PATENT DOCUMENTS

| WO | WO 2010/143138 | 12/2010 |
|---|---|---|
| WO | WO 2011/015985 | 2/2011 |
| WO | WO 2011/080674 | 7/2011 |
| WO | WO 2011/135527 | 11/2011 |
| WO | WO 2012/028993 | 3/2012 |
| WO | WO 2012/085862 | 6/2012 |
| WO | WO 2012/150598 | 11/2012 |
| WO | WO 2013/027223 | 2/2013 |
| WO | WO 2013/128448 | 9/2013 |
| WO | WO 2013/179211 | 12/2013 |

OTHER PUBLICATIONS

International Search Report and the Written Opinion Dated Jan. 7, 2013 From the International Searching Authority Re. Application No. PCT/IL2012/050154.
Invitation to Pay Additional Fees Dated Dec. 31, 2012 From the International Searching Authority Re. Application No. PCT/IL2012/050327.
Examination Report Dated Dec. 7, 2012 From the Instituto Mexicano de la Propiedad Industrial Re. Application No. MX/a/2011/003575 and Its Translation Into English.
Patent Examination Report Dated Jan. 4, 2013 From the Australian Government, IP Australia Re. Application No. 2008344935.
Examination Report Dated Jun. 11, 2012 From the Instituto Mexicano de la Propiedad Industrial Re. Application No. MX/a/2011/007294 and Summary in English.
Official Action Dated Jan. 9, 2014 From the US Patent and Trademark Office Re. U.S. Appl. No. 12/992,902.
Bork et al. "Go Hunting in Sequence Databases But Watch Out for the Traps", Trends in Genetics, TIG, 12(10): 425-427, Oct. 1996.
Doerks et al. "Protein Annotation: Detective Work for Function Prediction", Trends in Genetics, TIG, 14(6): 248-250, Jun. 1998.
Smith et al. "The Challenges of Genome Sequence Annotation or 'The Devil Is in the Details'", Nature Biotechnology, 15: 1222-1223, Nov. 1997.
Invitation to Pay Additional Fees Dated Dec. 27, 2011 From the International Searching Authority Re. Application No. PCT/IB2010/052545.
Applicant-Initiated Interview Summary Dated Dec. 20, 2013 From the US Patent and Trademark Office Re. U.S. Appl. No. 13/125,047.
Communication Pursuant to Article 94(3) EPC Dated Dec. 19, 2012 From the European Patent Office Re.: Application No. 04734072.4.
Official Action Dated Dec. 18, 2012 From the US Patent and Trademark Office Re. U.S. Appl. No. 12/834,106.
Benfey et al. "The CaMV 35S Enhancer Contains at Least Two Domains Which Can Confer Different Development and Tissue-Specific Expression Patterns", The EMBO Journal, 8(8): 2195-2202, 1989.
Benfey et al. "The Cauliflower Mosaic Virus 35S Promoter: Combinatorial Regulation of Transcription in Plants", Science, 250(4983): 959-966, Nov. 16, 1990.
Communication Pursuant to Rule 58 EPC or Rule 159 EPC, Invitation to Remedy Deficiencies in the Application Documents Dated Dec. 6, 2013 From the European Patent Office Re. Application No. 11190921.4.
Patent Examination Report Dated Jan. 3, 2014 From the Australian Government, IP Australia Re. Application No. 2008278654.
Communication Pursuant to Rules 70(2) and 70a(2) EPC Dated Mar. 5, 2013 From the European Patent Office Re. Application No. 10785834.2.
Requisition by the Examiner Dated Feb. 12, 2013 From the Canadian Intellectual Property Office Re. Application No. 2,570,195.
Restriction Official Action Dated Mar. 1, 2013 From the US Patent and Trademark Office Re. U.S. Appl. No. 13/254,183.
International Search Report and the Written Opinion Dated Mar. 16, 2012 From the International Searching Authority Re. Application No. PCT/IB2010/052545.
Castelli et al. "*Arabidopsis thaliana* Full-Length cDNA Complete Sequence From Clone GSLTFB52ZA10 of Flowers and Buds of Strain Col-0 of *Arabidopsis thaliana* (Thale Cress)", GeneBank Direct Submission BX829993, Accession No. BX829993, Feb. 6, 2004.
International Preliminary Report on Patentability Dated Mar. 14, 2013 From the International Bureau of WIPO Re. Application No. PCT/IB2011/053697.
Restriction Official Action Dated Apr. 4, 2013 From the US Patent and Trademark Office Re. U.S. Appl. No. 13/125,047.
Notice of Allowance Dated Apr. 8, 2013 From the US Patent and Trademark Office Re. U.S. Appl. No. 12/594,853.
Requisition by the Examiner Dated Mar. 25, 2013 From the Canadian Intellectual Property Office Re. Application No. 2,619,114.
International Preliminary Report on Patentability Dated Apr. 12, 2012 From the Interantional Bureau of WIPO Re. Application No. PCT/IB2010/052545.
International Preliminary Report on Patentability Dated Jul. 4, 2013 From the International Bureau of WIPO Re. Application No. PCT/IB2011/055854.
Examination Report Dated May 23, 2013 From the Instituto Mexicano de la Propiedad Industrial Re. Application No. MX/a/2011/001741 and Its Translation Into English.
Invitation to Pay Additional Fees Dated Jul. 17, 2013 From the International Searching Authority Re. Application No. PCT/IB2013/054374.
Official Action Dated Jul. 26, 2013 From the US Patent and Trademark Office Re. U.S. Appl. No. 13/254,183.
Matsumoto et al. "Os11g0162200 [*Oryza sativa japonica* Group]", Direct GenBank Sequence Submission, GenBank: BAF27672.1, GenBank Accession No. BAF27672, Aug. 11, 2012.
Examination Report Dated Jun. 7, 2013 From the Instituto Mexicano de la Propiedad Industrial Re. Application No. MX/a/2011/003575 and Its Translation Into English.
Examination Report Dated Jun. 20, 2013 From the Instituto Mexicano de la Propiedad Industrial Re. Application No. MX/a/2011/007294 and Its Translation Into English.
Communication Pursuant to Article 94(3) EPC Dated Dec. 8, 2008 From the European Patent Office Re.: Application. No. 04734072.4.
International Preliminary Report on Patentability Dated Dec. 8, 2005 From the International Bureau of WIPO Re.: Application No. PCT/IL2004/000431.
International Preliminary Report on Patentability Dated Jan. 22, 2009 From the International Bureau of WIPO Re.: Application No. PCT/IL2006/001223.
Invitation to Pay Additional Fees Dated Feb. 7, 2008 From the International Searching Authority Re.: Application No. PCT/IL06/001223.
Invitation to Pay Additional Fees Dated Dec. 18, 2008 From the International Searching Authority Re.: Application No. PCT/IL08/01024.
Advisory Action Before the Filing of an Appeal Brief Dated Aug. 5, 2011 From the US Patent and Trademark Office Re. U.S. Appl. No. 12/083,978.
Advisory Action Before the Filing of an Appeal Brief Dated Aug. 29, 2012 From the US Patent and Trademark Office Re. U.S. Appl. No. 12/457,199.
Applicant-Initiated Interview Summary Dated Aug. 6, 2012 From the US Patent and Trademark Office Re. U.S. Appl. No. 12/669,975.
Communication Pursuant to Article 93(3) EPC Dated Jun. 15, 2012 From the European Patent Office Re. Application No. 11154193.4.
Communication Pursuant to Article 94(3) EPC Dated Apr. 3, 2012 From the European Patent Office Re.: Application No. 06766224.7.
Communication Pursuant to Article 94(3) EPC Dated Jul. 4, 2012 From the European Patent Office Re. Application No. 10194223.3.
Communication Pursuant to Article 94(3) EPC Dated Mar. 8, 2011 From the European Patent Office Re.: Application No. 06809784.9.
Communication Pursuant to Article 94(3) EPC Dated Nov. 8, 2010 From the European Patent Office Re.: Application No. 04734072.4.
Communication Pursuant to Article 94(3) EPC Dated Sep. 9, 2009 From the European Patent Office Re.: Application No. 04734072.4.
Communication Pursuant to Article 94(3) EPC Dated May 12, 2010 From the European Patent Office Re.: Application No. 06766224.7.
Communication Pursuant to Article 94(3) EPC Dated Feb. 13, 2009 From the European Patent Office Re.: Application No. 05750089.4.

(56) References Cited

OTHER PUBLICATIONS

Communication Pursuant to Article 94(3) EPC DAted Jul. 13, 2012 From the European Patent Office Re. Application No. 11172514.9.
Communication Pursuant to Article 94(3) EPC Dated Feb. 14, 2012 From the European Patent Office Re.: Application No. 04734072.4.
Communication Pursuant to Article 94(3) EPC Dated Mar. 14, 2011 From the European Patent Office Re. Application No. 07849616.3.
Communication Pursuant to Article 94(3) EPC Dated Nov. 19, 2010 From the European Patent Office Re.: Application No. 06809784.9.
Communication Pursuant to Article 94(3) EPC Dated Jun. 21, 2012 From the European Patent Office Re. Application No. 11154213.0.
Communication Pursuant to Article 94(3) EPC Dated Nov. 27, 2009 From the European Patent Office Re.: Application No. 06809784.9.
Communication Pursuant to Article 94(3) EPC Dated Jun. 29, 2011 From the European Patent Office Re. Application No. 08738191.9.
Communication Pursuant to Rule 55 EPC Dated Mar. 16, 2012 From the European Patent Office Re. Application No. 11190921.4.
Communication Pursuant to Rule 58 EPC or Rule 159 EPC, Invitation to Remedy Deficiencies in the Application Documents Dated Jan. 19, 2012 From the European Patent Office Re. Application No. 11190922.2.
Communication Pursuant to Rule 69 EPC—Reminder Concerning Payment of the Designation Fee (Art. 79(2) EPC) and of the Examination Fee (Art. 94(1) EPC)—and Invitation Pursuant to Rule 70a(1) EPC Dated Jul. 18, 2011 From the European Patent Office Re. Application No. 11154193.4.
Communication Pursuant to Rule 69 EPC—Reminder Concerning Payment of the Designation Fee (Art. 79(2) EPC) and of the Examination Fee (Art. 94(1) EPC)—and Invitation Pursuant to Rule 70a(1) EPC Dated Jul. 25, 2011 From the European Patent Office Re. Application No. 11154213.0.
Communication Pursuant to Rule 70(2) EPC and Reference to Rule 39(1) EPC Dated Sep. 13, 2010 From the European Patent Office Re.: Application No. 09163033.5.
Communication Pursuant to Rules 70(2) and 70a(2) EPC and Reference to Rule 39(1) EPC Dated Dec. 5, 2011 From the European Patent Office Re. Application No. 10194223.3.
Communication Pursuant to Rules 70(2) and 70a(2) EPC and Reference to Rule 39(1) EPC Dated Nov. 7, 2011 From the European Patent Office Re. Application No. 11172514.9.
Communication Pursuant to Rules 70(2) and 70a(2) EPC Dated Jan. 19, 2012 From the European Patent Office Re. Application No. 09807983.3.
Communication Pursuant to Rules 70(2) and 70a(2) EPC Dated Jul. 24, 2012 From the European Patent Office Re. Application No. 10748403.2.
Communication Pursuant to Rules 70(2) and 70a(2) EPC Dated May 24, 2011 From the European Patent Office Re. Application No. 09750276.9.
Communication Relating to the Results of the Partial International Search Dated Jul. 8, 2009 From the International Searching Authority Re.: Application No. PCT/IL2008/001657.
Communication Under Rule 71(3) EPC Dated Jun. 5, 2012 From the European Patent Office Re.: Application No. 06809784.9.
Communiciation Pursuant to Rules 70(2) and 70a(2) EPC Dated Aug. 30, 2010 From the European Patent Office Re. Application No. 08738191.9.
Decision on Granting a Patent for Invention Dated Dec. 7, 2010 From the ROSPATENT, Federal State Institution, Federal Institute for Industrial Property of the Federal Service for Intellectual Property, Patents and Trademarks of the Russian Federation Re. Application No. 2008120395 and Its Translation Into English.
European Search Report and the European Search Opinion Dated Nov. 2, 2011 From the European Patent Office Re. Application No. 10194223.3.
European Search Report and the European Search Opinion Dated Oct. 6, 2011 From the European Patent Office Re. Application No. 11172514.9.
European Search Report and the European Search Opinion Dated Aug. 9, 2010 From the European Patent Office Re.: Application No. 09163033.5.
European Search Report and the European Search Opinion Dated Jun. 14, 2011 From the European Patent Office Re. Application No. 11154193.4.
European Search Report and the European Search Opinion Dated Jun. 21, 2011 From the European Patent Office Re. Application No. 11154213.0.
Examination Report Dated Aug. 1, 2011 From the Government of India, Patent Office Re.: Application No. 158/CHENP/2007.
Examination Report Dated Nov. 3, 2010 From the Government of India, Patent Office Re.: Application No. 158/CHENP/2007.
Examination Report Dated Jun. 6, 2012 From the Federal Service of Intellectual Property, Federal State Budget Institute, Federal Institute of Industrial Property of the Russian Federation Re. Application No. 2011113420 and Its Translation Into English.
Examination Report Dated Jun. 11, 2012 From the Instituto Mexicano de la Propiedad Industrial Re. Application No. MX/a/2011/007294 and Its Translation Into English.
Examination Report Dated Nov. 13, 2007 From the Government of India, Patent Office Re.: Application No. 3482/CHENP/2005.
Examination Report Dated Sep. 14, 2012 From the Australian Government IP Australia Re. Application No. 2007335706.
Examination Report Dated Aug. 16, 2012 From the Instituto Mexicano de la Propiedad Industrial Re. Application No. MX/a/2010/014097 and Its Translation Into English.
Examination Report Dated Feb. 17, 2010 From the Instituto Mexicano de la Propriedad Industrial Re. Application No. PA/a/2005/012565 and Its Summary in English.
Examination Report Dated Apr. 19, 2011 From the Instituto Mexicano de la Propriedad Industrial Re. Application No. MX/a/2008/002262 and Its Summary Into English.
Examination Report Dated Dec. 19, 2011 From the Federal Service of Intellectual Property, Federal State Budget Institute, Federal Institute of Industrial Property of the Russian Federation Re. Application No. 2011113420 and Its Translation Into English.
Examination Report Dated Sep. 22, 2010 From the Instituto Mexicano de la Propriedad Industrial Re. Application No. MX/a/2008/005280 and Its Summary Into English.
Examination Report Dated May 25, 2011 From the Government of India, Patent Office Re.: Application No. 158/CHENP/2007.
Examiner's Report Dated Aug. 1, 2011 From the Australian Government, IP Australia Re. Application No. 2005234725.
Examiner's Report Dated Jan. 10, 2012 From the Australian Government, IP Australia Re. Application No. 2005234725.
Examiner's Report Dated Jan. 13, 2011 From the Australian Government, IP Australia Re.: Application No. 2005252469.
Examiner's Report Dated Jan. 13, 2012 From the Australian Government, IP Australia Re. Application No. 2011239323.
Examiner's Report Dated Mar. 15, 2012 From the Australian Government, IP Australia Re. Application No. 2011239323.
Examiner's Report Dated Dec. 17, 2009 From the Australian Government, IP Australia Re.: Application No. 2005252469.
Examiner's Report Dated Oct. 19, 2011 From the Australian Government, IP Australia Re. Application No. 2006281018.
Examiner's Report Dated Dec. 20, 2010 From the Australian Government, IP Australia Re. Application No. 2005234725.
Examiner's Report Dated Jul. 21, 2011 From the Australian Government, IP Australia Re. Application No. 2005234725.
Examiner's Report Dated Jun. 24, 2011 From the Australian Government, IP Australia Re. Application No. 2006281018.
Examiner's Report Dated Oct. 28, 2011 From the Australian Government, IP Australia Re. Application No. 2006307457.
Examiner's Report Dated Jun. 30, 2011 From the Australian Government, IP Australia Re. Application No. 2006307457.
Examiner's Report Dated Jan. 31, 2012 From the Australian Government, IP Australia Re. Application No. 2006281018.
Examiner's Report Dated Mar. 31, 2011 From the Australian Government, IP Australia Re.: Application No. 2005252469.
International Preliminary Report on Patentability Dated Dec. 1, 2011 From the International Bureau of WIPO Re. Application No. PCT/IL2008/000489.

(56) References Cited

OTHER PUBLICATIONS

International Preliminary Report on Patentability Dated Dec. 2, 2010 From the International Bureau of WIPO Re. Application No. PCT/IL2009/000508.
International Preliminary Report on Patentability Dated Mar. 3, 2011 From the International Bureau of WIPO Re.: Application No. PCT/IB2009/053633.
International Preliminary Report on Patentability Dated Feb. 4, 2010 From the International Bureau of WIPO Re.: Application No. PCT/IL2008/001024.
International Preliminary Report on Patentability Dated Jul. 8, 2010 From the International Bureau of WIPO Re.: Application No. PCT/IL2008/001657.
International Preliminary Report on Patentability Dated Jul. 12, 2012 From the International Bureau of WIPO Re. Application No. PCT/IB2010/056023.
International Preliminary Report on Patentability Dated Jan. 14, 2010 From the International Bureau of WIPO Re.: Application No. PCT/IL2008/000489.
International Preliminary Report on Patentability Dated Sep. 15, 2011 From the International Bureau of WIPO Re. Application No. PCT/IB2010/050871.
International Preliminary Report on Patentability Dated Jan. 21, 2010 From the International Bureau of WIPO Re.: Application No. PCT/IL2007/001590.
International Preliminary Report on Patentability Dated Jan. 22, 2009 From the International Bureau of WIPO Re.: Application No. PCT/IL2006/000947.
International Preliminary Report on Patentability Dated Mar. 29, 2007 From the International Bureau of WIPO Re.: Application No. PCT/IL2005/000627.
International Preliminary Report on Patentability Dated Jan. 30, 2007 From the International Bureau of WIPO Re.: Application No. PCT/IL05/00627.
International Search Report and the Written Opinion Dated Jun. 2, 2010 From the International Searching Authority Re. Application No. PCT/IB09/53633.
International Search Report and the Written Opinion Dated Aug. 6, 2012 From the International Searching Authority Re. Application No. PCT/IB11/53697.
International Search Report and the Written Opinion Dated Dec. 6, 2011 From the International Searching Authority Re. Application No. PCT/IB2011/051843.
International Search Report and the Written Opinion Dated Sep. 6, 2012 From the International Searching Authority Re. Application No. PCT/IB2011/055854.
International Search Report and the Written Opinion Dated Sep. 7, 2010 From the International Searching Authority Re. Application No. PCT/IB10/50871.
International Search Report and the Written Opinion Dated Feb. 17, 2010 From the International Searching Authority Re.: Application No. PCT/IL09/00508.
International Search Report and the Written Opinion Dated Aug. 22, 2011 From the International Searching Authority Re. Application No. PCT/IB2010/056023.
International Search Report and the Written Opinion Dated Nov. 24, 2008 From the International Searching Authority Re.: Application No. PCT/IL08/00489.
International Search Report and the Written Opinion Dated Jul. 29, 2008 From the International Searching Authority Re.: Application No. PCT/IL06/001223.
International Search Report and the Written Opinion Dated Oct. 30, 2009 From the International Searching Authority Re.: Application No. PCT/IL2008/001657.
International Search Report and the Written Opinion Dated Oct. 31, 2011 From the International Searching Authority Re.: Application No. PCT/IL08/00489.
International Search Report Dated Jul. 2, 2009 From the International Searching Authority Re.: Application No. PCT/IL07/01590.
International Search Report Dated Jan. 3, 2007 From the International Searching Authority Re.: Application No. PCT/IL2005/000627.
International Search Report Dated Mar. 4, 2009 From the International Searching Authority Re.: Application No. PCT/IL08/01024.
International Search Report Dated Nov. 4, 2005 From the International Searching Authority Re.: Application No. PCT/IL04/00431.
International Search Report Dated Aug. 27, 2008 From the International Searching Authority Re.: Application No. PCT/IL06/00947.
Invitation to Pay Additional Fees Dated Mar. 2, 2010 From the International Searching Authority Re.: Application No. PCT/IB09/53633.
Invitation to Pay Additional Fees Dated May 8, 2012 From the International Searching Authority Re. Application No. PCT/IB11/53697.
Invitation to Pay Additional Fees Dated Sep. 8, 2006 From the International Searching Authority Re.: Application No. PCT/IL05/00627.
Invitation to Pay Additional Fees Dated Jun. 9, 2011 From the International Searching Authority Re. Application No. PCT/IB2010/056023.
Invitation to Pay Additional Fees Dated Jun. 15, 2012 From the International Searching Authority Re. Application No. PCT/IB2011/055854.
Invitation to Pay Additional Fees Dated Aug. 18, 2011 From the International Searching Authority Re.: Application No. PCT/IL08/00489.
Invitation to Pay Additional Fees Dated Nov. 19, 2009 From the International Searching Authority Re.: Application No. PCT/IL09/00508.
Invitation to Pay Additional Fees Dated Aug. 23, 2005 From the International Search Authority Re. Application No. PCT/IL2004/000431.
Notice of Allowance Dated Dec. 5, 2011 From the US Patent and Trademark Office Re. U.S. Appl. No. 12/448,359.
Notice of Allowance Dated Aug. 11, 2010 From the Instituto Mexican de la Propriedad Industrial Re. Application No. PA/a/2005/012565.
Notice of Allowance Dated Apr. 16, 2010 From the US Patent and Trademark Office Re.: U.S. Appl. No. 11/629,411.
Notice of Allowance Dated Oct. 18, 2010 From the US Patent and Trademark Office Re.: U.S. Appl. No. 11/990,386.
Notice of Grant Dated Jan. 14, 2011 From the Instituto Mexicano de la Propriedad Industrial Re. Application No. MX/a/2008/005280.
Office Action Dated Jan. 2, 2012 From the Israel Patent Office Re. Application No. 206118 and Its Translation Into English.
Office Action Dated Feb. 3, 2011 From the Israel Patent Office Re.: Application No. 172135 and Its Translation Into English.
Office Action Dated Aug. 4, 2010 From the Israel Patent Office Re.: Application No. 172135 and Its Translation Into English.
Office Action Dated Jan. 9, 2009 From the State Intellectual Property Office of the People's Republic of China Re.: Application No. 200480020597.0.
Office Action Dated Nov. 11, 2010 From the Israel Patent Office Re. Application No. 206118 and Its Translation Into English.
Office Action Dated May 13, 2010 From the Israel Patent Office Re. Application No. 180022 and Its Translation Into English.
Office Action Dated Jun. 17, 2010 From the Israel Patent Office Re. Application No. 190918 and Its Translation Into English.
Office Action Dated Oct. 18, 2010 From the Israel Patent Office Re. Application No. 180022 and Its Translation Into English.
Office Action Dated Jun. 19, 2011 From the Israel Patent Office Re. Application No. 199391 and Its Translation Into English.
Office Action Dated Jun. 20, 2011 From the Israel Patent Office Re. Application No. 190918 and Its Translation Into English.
Office Action Dated Jan. 22, 2010 From the State Intellectual Property Office of the People's Republic of China Re.: Application No. 200580027481.4 and Its Translation Into English.
Office Action Dated Sep. 22, 2011 From the Israeli Patent Office Re. Application No. 201242 and Its Translation Into English.
Office Action Dated Jun. 25, 2012 From the State Intellectual Property Office of the People's Republic of China Re.: Application No. 200880109464.9 and Its Translation Into English.
Office Action Dated Apr. 27, 2009 From the Israeli Patent Office Re.: Application No. 172135 and Its Translation Into English.

(56) References Cited

OTHER PUBLICATIONS

Office Action Dated Jan. 31, 2010 From the Israel Patent Office Re.: Application No. 172135 and Its Translation Into English.
Office Letter Dated Jul. 7, 2008 From the Government of India, Patent Office Re.: Application No. 3482/CHENP/2005.
Official Action Dated May 1, 2009 From the US Patent and Trademark Office Re.: U.S. Appl. No. 11/629,411.
Official Action Dated Sep. 2, 2009 From the US Patent and Trademark Office Re.: U.S. Appl. No. 11/629,411.
Official Action Dated Jul. 8, 2011 From the US Patent and Trademark Office Re. U.S. Appl. No. 12/083,978.
Official Action Dated Jun. 8, 2010 From the US Patent and Trademark Office Re.: U.S. Appl. No. 11/629,411.
Official Action Dated Apr. 10, 2012 From the US Patent and Trademark Office Re. U.S. Appl. No. 12/669,975.
Official Action Dated May 10, 2011 From the US Patent and Trademark Office Re. U.S. Appl. No. 12/457,199.
Official Action Dated Jun. 13, 2012 From the US Patent and Trademark Office Re. U.S. Appl. No. 12/594,853.
Official Action Dated May 14, 2012 From the US Patent and Trademark Office Re. U.S. Appl. No. 12/457,199.
Official Action Dated Feb. 15, 2011 From the US Patent and Trademark Office Re. U.S. Appl. No. 12/448,359.
Official Action Dated May 15, 2009 From the US Patent and Trademark Office Re.: U.S. Appl. No. 11/990,386.
Official Action Dated Jul. 17, 2012 From the US Patent and Trademark Office Re. U.S. Appl. No. 12/834,106.
Official Action Dated Aug. 18, 2010 From the US Patent and Trademark Office Re. U.S. Appl. No. 12/083,978.
Official Action Dated Oct. 18, 2007 From the US Patent and Trademark Office Re.: U.S. Appl. No. 11/284,236.
Official Action Dated Jun. 19, 2012 From the US Patent and Trademark Office Re. U.S. Appl. No. 13/450,547.
Official Action Dated Sep. 19, 2011 From the US Patent and Trademark Office Re. U.S. Appl. No. 12/810,855.
Official Action Dated Dec. 21, 2011 From the US Patent and Trademark Office Re. U.S. Appl. No. 12/810,855.
Official Action Dated Aug. 22, 2011 From the US Patent and Trademark Office Re. U.S. Appl. No. 12/457,199.
Official Action Dated Oct. 22, 2009 From the US Patent and Trademark Office Re.: U.S. Appl. No. 11/990,386.
Official Action Dated Nov. 23, 2010 From the US Patent and Trademark Office Re. U.S. Appl. No. 12/083,978.
Official Action Dated Jul. 28, 2008 From the US Patent and Trademark Office Re.: U.S. Appl. No. 11/284,236.
Official Action Dated Apr. 29, 2011 From the US Patent and Trademark Office Re. U.S. Appl. No. 12/448,359.
Partial European Search Report Dated Jul. 12, 2011 From the European Patent Office Re. Application No. 10194223.3.
Partial European Search Report Dated Apr. 19, 2010 From the European Patent Office Re.: Application No. 09163033.5.
Requisition by the Examiner Dated Feb. 2, 2012 From the Canadian Intellectual Property Office Re. Application No. 2,570,195.
Requisition by the Examiner Dated Jun. 15, 2011 From the Canadian Intellectual Property Office Re. Application No. 2,526,440.
Response Dated Jun. 2, 2011 to Office Action of Feb. 3, 2011 From the Israel Patent Office Re.: Application No. 172135.
Response Dated Jul. 3, 2011 to Examination Report of Apr. 19, 2011 From the Instituto Mexicano de la Propriedad Industrial Re. Application No. MX/a/2008/002262 and Its Summary Into English.
Response Dated Oct. 3, 2011 to Examiner's Report of Jun. 24, 2011 From the Australian Government, IP Australia Re. Application No. 2006281018.
Response Dated Jan. 4, 2010 to Official Action of Sep. 2, 2009 From the US Patent and Trademark Office Re.: U.S. Appl. No. 11/629,411.
Response Dated Oct. 4, 2011 to Official Action of Jul. 8, 2011 From the US Patent and Trademark Office Re. U.S. Appl. No. 12/083,978.
Response Dated Dec. 5, 2010 to Office Action of Aug. 4, 2010 From the Israel Patent Office Re.: Application No. 172135.
Response Dated Jul. 6, 2011 to Examiner's Report of Dec. 20, 2010 From the Australian Government, IP Australia Re. Application No. 2005234725.
Response Dated Jun. 6, 2011 to Official Action of May 10, 2011 From the US Patent and Trademark Office Re. U.S. Appl. No. 12/457,199.
Response Dated Jan. 7, 2010 to Communication Pursuant to Article 94(3) EPC of Sep. 9, 2009 From the European Patent Office Re.: Application No. 04734072.4.
Response Dated Mar. 8, 2011 to Examiner's Report of Jan. 13, 2011 From the Australian Government, IP Australia Re.: Application No. 2005252469.
Response Dated Feb. 9, 2011 to Communication Pursuant to Article 94(3) EPC of Nov. 19, 2010 From the European Patent Office Re.: Application No. 06809784.9.
Response Dated Jun. 9, 2011 to Examiner's Report of Dec. 20, 2011 From the Australian Government, IP Australia Re. Application No. 2005234725.
Response Dated Mar. 9, 2011 to Office Action of Nov. 11, 2010 From the Israel Patent Office Re. Application No. 206118.
Response Dated Jan. 10, 2012 to European Search Report and the European Search Opinion of Jun. 14, 2011 From the European Patent Office Re. Application No. 11154193.4.
Response Dated Aug. 11, 2011 to Examination Report of Aug. 1, 2011 From the Government of India, Patent Office Re.: Application No. 158/CHENP/2007.
Response Dated Dec. 12, 2010 to Examiner's Report of Dec. 17, 2009 From the Australian Government, IP Australia Re.: Application No. 2005252469.
Response Dated Oct. 12, 2010 to Communication Pursuant to Article 94(3) EPC of May 12, 2010 From the European Patent Office Re.: Application No. 06766224.7.
Response Dated Sep. 13, 2010 to Office Action Dated May 13, 2010 From the Israel Patent Office Re. Application No. 180022.
Response Dated Dec. 14, 2010 to Examination Report of Sep. 22, 2010 From the Instituto Mexicano de la Propriedad Industrial Re. Application No. MX/a/2008/005280.
Response Dated Feb. 14, 2011 to Supplementary European Search Report and the European Search Opinion of Jul. 29, 2010 From the European Patent Office Re. Application No. 08776651.5.
Response Dated Mar. 14, 2011 to Official Action of Feb. 15, 2011 From the US Patent and Trademark Office Re. U.S. Appl. No. 12/448,359.
Response Dated Oct. 14, 2010 to Office Action of Jun. 17, 2010 From the Israel Patent Office Re. Application No. 190918.
Response Dated Sep. 14, 2010 to Official Action of Aug. 18, 2010 From the US Patent and Trademark Office Re. U.S. Appl. No. 12/083,978.
Response Dated Dec. 15, 2011 to Examiner's Report of Aug. 1, 2011 From the Australian Government, IP Australia Re. Application No. 2005234725.
Response Dated Jun. 15, 2011 to Examiner's Report of Mar. 31, 2011 From the Australian Government, IP Australia Re.: Application No. 2005252469.
Response Dated Jun. 17, 2011 to Examiner's Report of Mar. 31, 2011 From the Australian Government, IP Australia Re.: Application No. 2005252469.
Response Dated May 17, 2010 to Office Action of Jan. 22, 2010 From the State Intellectual Property Office of the People's Republic of China Re.: Application No. 200580027481.4.
Response Dated Oct. 17, 2011 to Requisition by the Examiner of Jun. 15, 2011 From the Canadian Intellectual Property Office Re. Application No. 2,526,440.
Response Dated Oct. 18, 2011 to Official Action of Sep. 19, 2011 From the US Patent and Trademark Office Re. U.S. Appl. No. 12/810,855.
Response Dated Dec. 19, 2011 to Examiner's Report of Oct. 19, 2011 From the Australian Government, IP Australia Re. Application No. 2006281018.
Response Dated Jan. 19, 2011 to Supplementary European Search Report and the European Search Opinion of Jul. 1, 2010 From the European Patent Office Re. Application No. 07849616.3.

(56) References Cited

OTHER PUBLICATIONS

Response Dated Oct. 19, 2011 to Official Action of Apr. 29, 2011 From the US Patent and Trademark Office Re. U.S. Appl. No. 12/448,359.
Response Dated Jul. 20, 2011 to Examination Report of May 25, 2011 From the Government of India, Patent Office Re.: Application No. 158/CHENP/2007.
Response Dated Apr. 21, 2011 to Communication Pursuant to Article 94(3) EPC of Nov. 8, 2010 From the European Patent Office Re.: Application No. 04734072.4.
Response Dated Sep. 21, 2010 to Notice of Allowance of Apr. 16, 2010 From the US Patent and Trademark Office Re.: U.S. Appl. No. 11/629,411.
Response Dated Dec. 22, 2011 to Official Action of Aug. 22, 2011 From the US Patent and Trademark Office Re. U.S. Appl. No. 12/457,199.
Response Dated Feb. 22, 2010 to Official Action of Oct. 22, 2009 From the US Patent and Trademark Office Re.: U.S. Appl. No. 11/990,386.
Response Dated Feb. 23, 2011 to Communication Pursuant to Rule 70(2) EPC and Reference to Rule 39(1) EPC of Sep. 13, 2010 From the European Patent Office Re.: Application No. 09163033.5.
Response Dated Mar. 23, 2011 to Official Action of Nov. 23, 2010 From the US Patent and Trademark Office Re. U.S. Appl. No. 12/083,978.
Response Dated Feb. 24, 2011 to Communciation Pursuant to Rules 70(2) and 70a(2) EPC of Aug. 30, 2010 From the European Patent Office Re. Application No. 08738191.9.
Response Dated Mar. 24, 2011 to Examination Report of Nov. 3, 2010 From the Government of India, Patent Office Re.: Application No. 158/CHENP/2007.
Response Dated Oct. 24, 2010 to Office Action of Sep. 2, 2010 From the ROSPATENT, Federal State Institution, Federal Institute for Industrial Property of the Federal Service for Intellectual Property, Patents and Trademarks of the Russian Federation Re. Application No. 2008120395.
Response Dated Jul. 25, 2011 to Examiner's Report of Jul. 21, 2011 From the Australian Government, IP Australia Re. Application No. 2005234725.
Response Dated Sep. 25, 2011 to Examiner's Report of Jun. 30, 2011 From the Australian Government, IP Australia Re. Application No. 2006307457.
Response Dated Oct. 27, 2011 to Communication Pursuant to Article 94(3) EPC of Jun. 29, 2011 From the European Patent Office Re. Application No. 08738191.9.
Response Dated Oct. 27, 2011 to Office Action of Jul. 1, 2011 From the State Intellectual Property Office of the People's Republic of China Re. Application No. 200880017707.6.
Response Dated Oct. 27, 2011 to Supplementary European Search Report and the European Search Opinion of May 6, 2011 From the European Patent Office Re. Application No. 09750276.9.
Response Dated Jun. 29, 2010 to Examination Report of Feb. 17, 2010 From the Instituto Mexicano de la Propriedad Industrial Re. Application No. PA/a/2005/012565.
Response Dated Jun. 29, 2011 to Communication Pursuant to Article 94(3) EPC of Mar. 8, 2011 From the European Patent Office Re.: Application No. 06809784.9.
Response Dated May 31, 2010 to Office Action of Jan. 31, 2010 From the Israel Patent Office Re.: Application No. 172135.
Response Dated Oct. 31, 2011 to Notification of the First Office Action of Jun. 30, 2011 From the State Intellectual Property Office of the People's Republic of China Re. Application No. 200680047610.0.
Restriction Official Action Dated Feb. 1, 2012 From the US Patent and Trademark Office Re. U.S. Appl. No. 12/669,975.
Restriction Official Action Dated Apr. 11, 2012 From the US Patent and Trademark Office Re. U.S. Appl. No. 12/834,106.
Restriction Official Action Dated Feb. 13, 2012 From the US Patent and Trademark Office Re. U.S. Appl. No. 12/594,853.
Summary of Office Action Dated Sep. 2, 2010 From the ROSPATENT, Federal State Institution, Federal Institute for Industrial Property of the Federal Service for Intellectual Property, Patents and Trademarks of the Russian Federation Re. Application No. 2008120395.
Supplementary European Search Report and the European Search Opinion Dated Feb. 1, 2010 From the European Patent Office Re.: Application No. 06766224.7.
Supplementary European Search Report and the European Search Opinion Dated Jul. 1, 2010 From the European Patent Office Re. Application No. 07849616.3.
Supplementary European Search Report and the European Search Opinion Dated Jan. 2, 2012 From the European Patent Office Re. Application No. 09807983.3.
Supplementary European Search Report and the European Search Opinion Dated Jul. 6, 2012 From the European Patent Office Re. Application No. 10748403.2.
Supplementary European Search Report and the European Search Opinion Dated May 6, 2011 From the European Patent Office Re. Application No. 09750276.9.
Supplementary European Search Report and the European Search Opinion Dated Aug. 11, 2010 From the European Patent Office Re. Application No. 08738191.9.
Supplementary European Search Report and the European Search Opinion Dated Sep. 14, 2009 From the European Patent Office Re.: Application No. 06809784.9.
Supplementary European Search Report and the European Search Opinion Dated Jul. 29, 2010 From the European Patent Office Re. Application No. 08776651.5.
Supplementary European Search Report Dated Apr. 23, 2008 From the European Patent Office Re.: Application No. 05750089.4.
Supplementary European Search Report Dated Oct. 31, 2007 From the European Patent Office Re.: Application No. 04734072.4.
Supplementary Partial European Search Report Dated Aug. 30, 2007 From the European Patent Office Re.: Application No. 04734072.4.
Translation of Decision of Rejection Dated Dec. 9, 2011 From the State Intellectual Property Office of the People's Republic of China Re.: Application No. 200580027481.4.
Translation of Notice of Payment of the Restoration Fee for Unity of Invention Dated Mar. 20, 2009 From the State Intellectual Property Office of the People's Republic of China Re.: Application No. 200580027481.4.
Translation of Notification of the Office Action Dated Dec. 1, 2011 From the State Intellectual Property Office of the People's Republic of China Re. Application No. 200680047610.0.
Translation of Notification of the Office Action Dated Jun. 30, 2011 From the State Intellectual Property Office of the People's Republic of China Re. Application No. 200680047610.0.
Translation of Office Action Dated Jul. 1, 2011 From the State Intellectual Property Office of the People's Republic of China Re. Application No. 200880017707.6.
Translation of Office Action Dated Jan. 4, 2012 From the State Intellectual Property Office of the People's Republic of China Re. Application No. 200880109464.9.
Translation of Office Action Dated Apr. 9, 2012 From the State Intellectual Property Office of the People's Republic of China Re. Application No. 200880017707.6.
Translation of Office Action Dated Jan. 17, 2012 From the State Intellectual Property Office of the People's Republic of China Re. Application No. 201110104274.1.
Translation of Office Action Dated Oct. 19, 2010 From the State Intellectual Property Office of the People's Republic of China Re. Application No. 200680038391.X.
Translation of Office Action Dated Jun. 22, 2011 From the State Intellectual Property Office of the People's Republic of China Re. Application No. 200880127685.9.
Translation of Office Action Dated Dec. 31, 2011 From the State Intellectual Property Office of the People's Republic of China Re. Application No. 200910217137.1.
Translation of the Office Action Dated Jan. 9, 2009 From the State Intellectual Property Office Re.: Application No. 2004800200597.0.
Written Opinion Dated Jul. 2, 2009 From the International Searching Authority Re.: Application No. PCT/IL07/01590.

(56) References Cited

OTHER PUBLICATIONS

Written Opinion Dated Jan. 3, 2007 From the International Searching Authority Re.: Application No. PCT/IL2005/000627.
Written Opinion Dated Mar. 4, 2009 From the International Searching Authority Re.: Application No. PCT/IL08/01024.
Written Opinion Dated Nov. 4, 2005 From the International Searching Authority Re.: Application No. PCT/Il04/00431.
Written Opinion Dated Aug. 27, 2008 From the International Searching Authority Re.: Application No. PCT/IL06/00947.
Adachi et al. "*Oryza sativa japonica* Group cDNA Clone:J023021L06, Full Insert Sequence", Database EMBASE [Online], XP002665608, Retrieved From EBI, Database Accession No. AK099270, Jul. 19, 2003.
Aharon et al. "Overexpression of a Plasma Membrane Aquaporin in Transgenic Tobacco Improves Plant Vigor Under Favorable Growth Conditions But Not Under Drought or Salt Stress", The Plant Cell, 15: 439-447, Feb. 2003.
Alcala et al. "Generation of ESTs From Tomato Fruit Tissue", Database GenBank on STIC, National Center for Biotechnology Information, Accession No. AW932839, 2001.
Apse et al. "Engineering Salt Tolerance in Plants", Current Opinion in Biotechnology, 13: 146-150, 2002.
Apse et al. "Engineering Salt Tolerance in Plants", Current Opinion in Biotechnology, XP003018468, 13(2): 146-150, Apr. 1, 2002.
Bernhardt et al. "The bHLH Genes GLABRA3 (GL3) and Enhancer of GLABRA3 (EGL3) Specify Epidermal Cell Fate in the *Arabidopsis* Root", Development, 130(26): 6431-6439, 2003.
Blast "BLAST Results", 1 P.
Blewitt et al. "BNLGHi10083 Six-Day Cotton Fiber *Gossypium hirsutum* cDNA 5' Similar to (AC004521) Unknown Protein [*Arabidopsis thaliana*], mRNA Sequence", XP002576188, Retrieved Fron EBI Accession No. EMBL:AI728187, Database Accession No. AI728187, Jun. 12, 1999. Sequence.
Blewitt et al. "BNLGHi8081 Six-Day Cotton Fiber *Gossypium hirsutum* cDNA 5' Similar to (AC004521) Unknown Protein [*Arabidopsis thalian*], mRNA Sequence", XP002576189, Retrieved From EBI Accesion No. EMBL:AI730835, Database Accession No. AI730835, Jun. 12, 1999. Sequence.
Blewitt et al. "BNLGHi8396 Six-Day Cotton Fiber *Gossypium hirsutum* cDNA 5' Similar to (AC004521) Unknown Protein [*Arabidopsis thaliana*], mRNA Sequence", XP002576190, Retrieved From EBI Accession No. EMBL:AI27553, Database Accession No. AI27553, Jun. 12, 1999. Sequence.
Blewitt et al. "*Gossypium hirsutum* Strain Acala Maxxa BURP Domain-Containing Protein (BNL1924) mRNA, Complete CDS", GenBank Nucleotide, GenBank Accession No. AY343972, Aug. 16, 2003.
Bowie et al. "Deciphering the Message in Protein Sequences: Tolerance to Amino Acid Substitutions", Science, 247(4948): 1306-1310, Mar. 16, 1990.
Brandle et al. "Perspectives on the Production of Recombinant Proteins in Plants", AgBiotechNet, 3(ABN 070): 1-4, 2001. Abstract.
Cheuk et al. "*Arabidopsis thaliana* At2g46960/F14M4.21 mRNA, Complete CDS", Database EMBL [Online], XP002593835, Retrieved From EBI Accession No. EMBL:AY091688, Database Accession No. AY091688, Apr. 14, 2002.
Daniell et al. "*Solanum bulbocastanum* Chloroplast, Complete Genome", GenBank NCBI, Accession No. NC 007943, Mar. 26, 2010. p. 1, Source, p. 10-11, Nucleotides 46590-47195, Gene 'RPS4'.
Davletova et al. "The Zinc-Finger Protein Zat12 Plays a Central Role in Reactive Oxygen and Abiotic Stress Signaling in *Arabidopsis*", Plant Physiology, 139: 847-856, Oct. 2005.
Feng et al. "Probable Cinnamyl Alcohol Dehydrogenase 6", Darabase UniProt [Online], XP002665609, Retrieved From EBI, Database Accession No. Q7XWU3, Mar. 1, 2004.
Francois et al. "Overexpression of the VvLTP1 Gene Interferes With Somatic Embryo Development in Grapevine", Functional Plant Biology, 35(5): 394-402, 2008.

Fray et al. "Nucleotide Sequence and Expression of a Ripening and Water Stress-Related cDNA From Tomato With Homology to the MIP Class of Membrane Channel Proteins", Plant Molecular Biology, XP009117320, 24(3): 539-543, 1994. Figs.1, 2. & Database UniProt, REcName: Full=Probable Aquaporin PIP-Type pTOM75; AltName: Full=Ripening-Associated Membrane Protein; Short=RAMP, Oct. 1, 1994.
Friedberg "Automated Protein Function Prediction—The Genomic Challenge", Briefings in Bioinformatics, 7(3): 225-242, 2006.
Gardiner et al. "*Zea mays* PCO131392 mRNA Sequence", Database EMBL/GenBank/DDBJ, EBI Database Accession No. AY107021, XP002542347, May 28, 2002. 96,5% Identity in 1118 nt Overlap of AY107021 (1118 nt) With SEQ ID No. 68 (1348 nt) of the Present Application, Abstract.
Gambia et al. "Drought- and Salt-Tolerant Plants Result From Overexpression of the AVP1 H+-Pump", Proc. Natl. Acad. Sci. USA, PNAS, 98(20): 11444-11449, Sep. 25, 2001.
Good et al. "Can Less Yield More? Is Reducing Nutrient Input Into the Environment Compatible With Maintaining Crop Production?", Trends in Plant Science, 9(12): 597-605, Dec. 2004.
Good et al. "Can Less Yield More? Is Reducing Nutrient Input Into the Environment Compatible With Maintaining Crop Production?", Trends in Plant Science, 902): 597-605, Dec. 2004.
Good et al. "Engineering Nitrogen Use Efficiency With Alanine Aminotransferase", Canadian Journal of Botany, 85: 252-262, 2007.
Gowik et al. "cis-Regulatory Elements for Mesophyll-Specific Gene Expression in the C4 Plant *Flaveria trinervia*, the Promoter of the C4 Phosphoenolpyruvate Carboxylase Gene", The Plant Cell, 16: 1077-1090, 2004.
Grover et al. "Understanding Molecular Alphabets of the Plant Abiotic Stress Responses", Current Science, 80(2): 206-216, Jan. 25, 2001.
Guo et al. "Protein Tolerance to Random Amino Acid Change", Proc. Natl. Acad. Sci. USA, PNAS, 101(25): 9205-9210, 2004.
Hachez et al. "Modulating the Expression of Aquaporin Genes in Planta: A Key to Understand Their Physiological Functions?", Biochimica et Biophysica Acta, XP005655605, 1758(8): 1142-1156, Aug. 1, 2006. p. 1151, col. 1, § 2-p. 1153, col. 1, § 1, Table 1.
Hattori et al. "An Acetohydroxy Acid Synthase Mutant Reveals a Single Site Involved in Multiple Herbicide Resistance", Molecular and General Genetics, 246: 419-425, 1995. Abstract!
Hill et al. "Functional Analysis of Conserved Histidines in ADP-Glucose Pyrophosphorylase From *Escherichia coli*", Biochemical and Biophysical Research Communications, 244(2): 573-577, 1998.
Holmstroem et al. "Drought Tolerance in Tobacco", Nature, 379: 683-684, 1996. Abstract.
In et al. "Panax Gingseng mRNA for Cytoplasmic Ribosomal Protein S13, Complete Cds", Database EMBL [Online], Retrieved From EBI Accession No. EMBL, Database Accession No. AB043974, 2000.
Invitrogen "SuperScript® Plasmid System With Gateway® Technology for cDNA Synthesis and Cloning", Invitrogen by Life Technologies, User Manual, Catalog No. 18248-013, Manual Part No. 11108, 44 P., Dec. 22, 2010.
Ishikawa et al. JP 2005-185101: Full Length cDNA of Plant and the Use Thereof, Database EMBL [Online], XP002678022, Retrieved From EBI Accession No. EM_PAT:HV067703, Database Accession No. HV067703, Jul. 15, 2011. Sequence.
Ji et al. "*Gossypium hirsutum* Expansin mRNA, Complete CDs", Database EMBL [Online], XP002474936, Retrieved From EBI Accession No. EMBL:AY189969, Database Accession No. AY189969, May 20, 2003.
Ji et al. "Isolation and Analyses of Genes Preferentially Expressed During Early Cotton Fiber Development by Subtractive PCR and cDNA Array", Nucleic Acids Research, XP002474935, 31(10): 2534-2543, May 15, 2003.
Johansson et al. "The Role of Aquaporins in Cellular and Whole Plant Water Balance," Biochimica et Biophysica Acta 1465: 324-342, 2000.
Kandel et al. "Cloning, Functional Expression, and Characterization of CYP709C1, the First Sub-Terminal Hydroxylase of Long Chain Fatty Acid in Plants", Journal of Biological Chemistry, JBC, 280(43): 35881-35889, Oct. 28, 2005. p. 35887, col. 1, Para 2.

(56) References Cited

OTHER PUBLICATIONS

Kano-Murakami et al. "A Rice Homeotic Gene, OSH1, Causes Unusual Phenotypes in Transgenic Tobacco", FEBS Letters, 334(3): 365-368, Nov. 1993.
Katavic et al. "Utility of the *Arabidopsis* FAE1 and Yeast SLC1-1 Genes for Improvement in Erucic Acid and Oil Content in Rapeseed", Biochemical Society Transactions, 28(6): 935-937, Dec. 2000.
Katavic et al. "Utility of the *Arabidopsis* FAE1 and Yeast SLC1-1 Genes for Improvements in Erucic Acid and Oil Content in Rapeseed", Biochemical Society Transactions, 28: 935-7, 2000. Abstract!
Keskin et al. "A New, Structurally Nonredundant, Diverse Data Set of Protein-Protein Interfaces and Its Implications", Protein Science, 13: 1043-1055, 2004.
Kikuchi et al. "Rice cDNA-Encoded Protein SEQ ID No. 31047", Database Geneseq [Online], XP002678021, Retrieved From EBI Accession No. GSP:AQD37188, Database Accession No. AGD37188, Jun. 12, 2008. Shows 100% Identity to Present SEG ID No. 246 (Protein) and Corresponding Polynucleotide Shows 100 % Identity to SEQ ID No. 7 Over 458 Nucleotides. Abstract.
Kim et al. "*Arabidopsis thaliana* At2g46960/F14M4.21 mRNA, Complete CDS", Database EMBL [Online], XP002593834, Retrieved From EBI Accession No. EMBL:AF367329, Database Accession No. AF367329, Apr. 12, 2001.
Kim et al. "Molecular Cloning of Low-Temperature-Inducible Ribosomal Proteins From Soybean", Journal of Experimental Botany, 55(399): 1153-1155, 2004.
Kirkness et al. "*Lycopersicon esculentum* Clone 133453R, mRNA Sequence", Database EMBL [Online], XP002529190, Retrieved From EBI Accession No. EMBL:BT014251, Database Accession No. BT014251, May 12, 2004.
Kirubakaran et al. "Characterization of a New Antifungal Lipid Transfer Protein From Wheat", Plant Physiology and Biochemistry, 46: 918-927, 2008.
La Rosa et al. "*Oryza sativa* Amino Acid Sequence SEQ ID No. 133688", Database Geneseq [Online], XP002678023, Retrieved From EBI Accession No. GSP:ANM19687, Database Accession No. ANM19687, Dec. 28, 2007. 100% Identity to Present SEQ IFD No. 246, Corresponding Polynucleotide Has 99,6% Identity to Present SEQ ID No. 7 Over 488 Nucleotides. Abstract, Sequence.
La Rosa et al. "*Oryza sativa* Nucleotide Sequence SEQ ID No. 31205", Database Geneseq [Online], XO002678024, Retrieved From EBI Accession No. GSN:ANL17203, Database Accession No. ANL17203, Dec. 28, 2007. Sequence.
Li et al. "*Gossypium hirsutum* Dehydration-Induced Protein RD22-Like Protein (RDL) mRNA, Complete CDS", EBI Accession No. EMBL:AY072821, XP002639385, Database Accession No. AY072821, Dec. 4, 2002. Compound.
Li et al. "Isolation of Genes Preferntially Expressed in Cotton Fibers by cDNA Filter Arrays and RT-PCR", Plant Science, XP002639386, 163(6): 1113-1120, 2002.
Lin et al. "*Arabidopsis thaliana* Chromosome III BAC F7O18 Genomic Sequence, Complete Sequence", GenBank Accession No. AC011437, Oct. 30, 2002.
Liu et al. "Root-Specific Expression of a Western White Pine PR10 Gene Is Mediated by Different Promoter Regions in Transgenic Tobacco", Plant Molecular Biology, 52: 103-120, 2003.
Matsumoto et al. "*Hordeum vulgare* Subsp. *vulgare*, Full-Length cDNA", UniProtKB/TrEMBL, ID: F2DLE8-HORVD, UniProt Accession No. F2DLE8, May 31, 2011.
Maurel "Plant Aquaporins: Novel Functions and Regulation Properties", FEBS Letters, XP022078418, 581(12): 2227-2236, May 25, 2007. p. 2230, col. 2, Last §-p. 2231, col. 1, § 2, Fig.1.
McConnell et al. "Role of PHABULOSA and PHAVOLUTA in Determining Radial Patterning in Shoots", Nature, 411(6338): 709-713, Jun. 7, 2001.
Merriam-Webster "Exogenous Definition", Merrian-Webster On-Line Dictionary, 2010.

NCBI "Protein Sequence (588 Letters)", NCBI BLAST Basic Local Alignment Search Tool, 3 P., Retrieved From the Internet on Nov. 24, 2009.
Ngo et al. "Computational Complexity, Protein Structure Prediction, and the Levinthal Paradox", The Protein Folding Problem and Tertiary Structure Prediction, p. 433, 492-495, 1994.
Nuccio et al. "Metabolic Engineering of Plants for Osmotic Stress Resistance", Current Opinion in Plant Biology, XP002216348, 2(2): 128-134, Apr. 1, 1999.
Orford et al. "Specific Expression of an Expansin Gene During Elongation of Cotton Fibres", Biochimica et Biophysica Acta, XP000866032, 1398(3): 342-346, Jul. 9, 1998. Abstract, p. 343, Fig. 1.
Orzaez et al. "Agroinjection of Tomato Fruits. A Tool for Rapid Functional Analysis of Transgenes Directly in Fruit", Plant Physiology, 140: 3-11, 2006.
Park et al. "Glycine Max Ribosomal Protein S13 (RPS13) mRNA, Complete Cds", Database EMBL [Online], Retreieved From EBI Accession No. EMBL, Database Accession No. AY453393, 2004.
Payne et al. "GL3 Encodes a bHLH Protein That Regulates Trichome Development in *Arabidopsis* Through Interaction With GL1 and TTG1", Genetics, 156: 1349-1362, Nov. 2000.
Payne et al. "Heterologous MYB Genes Distinct From GL1 Enhance Trichome Production When Overexpressed in *Nicotiana tabacum*", Development, 126: 671-682, 1999.
Pilon-Smits et al. "Improved Performance of Transgenic Fructan-Accumulating Tobacco under Drought Stress", Plant Physiology, 107: 125-130, 1995.
Purnelle et al. "*Arabidopsis thaliana* DNA Chromosome 3, BAC Clone F3C22", Database EMBL [Online], XP002640829, Retrieved From EBI Accession No. EMBL:AL353912, Database Accession No. AL 353912, Apr. 27, 2000. Compound.
Quesada et al. "Genetic Architecture of NaCl Tolerance in *Arabidopsis*", Plant Physiology, 130: 951-963, 2002. Abstract!
Saez-Vasquez et al. "Accumulation and Nuclear Targeting of BnC24, a *Brassica napus* Ribosomal Protein Corresponding to a mRNA Accumulating in Response to Cold Treatment", Plant Science, 156(1): 35-46, 2000.
Saijo et al. "Over-Expression of a Single Ca 2+-Dependent Protein Kinase Confers Both Cold and Salt/Drought Tolerance on Rice Plants", The Plant Journal 23(3): 319-327, 2000.
Skriver et al. "Cis-Acting DNA Elements Responsive to Gibberellin and Its Antagonist Abscisic Acid", Proceedings of the National Academy of Sciences USA 88: 7266-7270, 1991.
Smart et al. "MIP Genes Are Down-Regulated Under Drought Stress in *Nicotiana glauca*", Plant and Cell Physiology, XP002455682, 42(7): 686-693, 2001. p. 686, Reference to Database Entry AF290618, p. 692, 1-h col., § 2.
Smart et al. "*Nicotiana glauca* Putative Delta TIP (MIP2) mRNA, Complete Cds", Database EMBL [Online], Retrieved From EBI Accession No. EMBL: AF290618, XP002455682, Database Accession No. AF290618, Jan. 2, 2001.
Sunkar et al. "Small RNAs as Big Players in Plant Abiotic Stress Responses and Nutrient Deprivation", Trends in Plant Science, XP022148764, 12(7): 301-309, Jul. 1, 2007.
Taliercio et al. "GH_TMIRS_129_G10_F Cooton Normalized Library dT Primed *Gossypium hirsutum* cDNA, mRNA Sequence", EMBL-Bank, XP002659970, Retrieved From EBI Accession No. EM_EST:DW508992, Database Accession No. DW508992.
Taliercio et al. "GH_TMIRS_129_G10_R Cotton Normalized Library dT Primed *Gossypium hirsutum* cDNA, mRNA Sequence", EMBL-Bank, XP002659971, Retrieved From EBI Accession No. EM_EST:DW508993, Database Accession No. DW508993.
Tamura et al. "Osmotic Stress Tolerance of Transgenic Tobacco Expressing a Gene Encoding a Membrane-Located Receptor-Like Protein From Tobacco Plants", Plant Physiology, 131(2): 454-462, 2003.
Tanaka et al. "Enhanced Tolerance Against Salt-Stress and Freezing-Stress of *Escherichia coli* Cells Expressing Algal BBC1 Gene", Current Microbiology, 42(3): 173-177, 2001.
Tarczynski et al. "Stress Protection of Transgenic Tobacco by Production of the Osmolytc Mannitol", Science, 259: 508-510, 1993. Abstract!

(56) References Cited

OTHER PUBLICATIONS

Thornton et al. "From Structure to Function: Approaches and Limitations", Nature Structural Biology. Structural Genomic Supplement, Nov. 2000, p. 991-994.
Udall et al. "A Global Assembly of Cotton ESTs", Genome Research, 16(3): 441-450, 2006.
Van der Hoeven et al. "EST301294 Tomato Root During/After Fruit Set, Cornell University *Lycopersicon esculentum* cDNA Clone cLEX1K11 Similar to *Vernicia fordii* Aquaporin, mRNA Sequence", Database EMBL [Online], Retrieved From EBI Accession No. EMBL: AW218814, XP002455680, Database Accession No. AW218814, Dec. 14, 1999. Abstract.
Van der Hoeven et al. "EST301295 Tomato Root During/After Fruit Set, Cornell University *Lycopersicon esculentum* cDNA Clone cLEX1K11 Similar to *Vernicia fordii* Aquaporin, mRNA Sequence", Database EMBL [Online], Retrieved From EBI Accession No. EMBL: AW218815, XP002455681, Database Accession No. AW218815, Dec. 14, 1999. Abstract.
Van der Hoeven et al. "EST312975 Tomato Root During/After Fruit Set, Cornell University *Solanum lycopersicum* cDNA Clone cLEX14O20 5-, mRNA Sequence", GenBank, GenBank Accession No. AW622177.1.
Van der Hoeven et al. "EST428934 Tomato Nutrient Deficient Roots *Lycopersicon esculentum* cDNA Clone cLEW26B2 5' Sequence, mRNA Sequence", Database EMBL, Retrieved From EBI Accession No. EMBL, Database Accession No. BF098413, 2000.
Van Haaren et al. "A Functional Map of the Fruit-Specific Promoter of the Tomato 2A11 Gene", Plant Molecular Biology, 21: 625-640, 1993. Abstract!
Vigeolas et al. "Increasing Seed Oil Content in Oil-Seed Rape (*Brassica napus* L.) by Over-Expression of a Yeast Glycerol-3-Phosphate Dehydrogenase Under the Control of a Seed-Specific Promoter", Plant Biotechnology Journal, 5 Issue: 431-441, 2007. Abstract!
Wallace et al. "Oligonucleotide Probes for the Screening of Recombinant DNA Libraries", Methods in Enzymology, XP002957829, 152: 432-442, Jan. 1, 1987.
Wang et al. "Control of Plant Trichome Development by a Cotton Fiber MYB Gene", The Plant Cell, 16: 2323-2334, Sep. 2004.
Wang et al. "Control of Plant Trichome Development by a Cotton Fiber MYB Gene", The Plant Cell, 16: 2323-2334, Sep. 2004. GenEmbl Database, Accession No. AY641990.
Wang et al. "The Soybean Dof-Type Transcription Factor Genes, GmDof4 and GmDof11, Enhance Lipid Content in the Seeds of Transgenic *Arabidopsis* Plants", The Plant Journal, 52: 716-729, 2007. Abstract!
Wells "Additivity of Mutational Effects in Proteins", Biochemistry, 29 (37): 8509-8517, 1990.
Whisstock et al. "Prediction of Protein Function from Protein Sequence and Structure," Quarterly Reviews of Biophysics 36 (3): 307-340, Aug. 2003.
Wing et al. "An Integrated Analysis of the Genetics, Devlopment, and Evolution of Cotton Fiber", NBCI GenBank Accession No. BE052336, 2000.
Wing et al. "GA_Eb0023E09f *Gossypium arboreum* 7-10 Dpa Fiber Library *Gossypium arboreum* cDNA Clone GA_Eb0023F09f, mRNA Sequence", XP002576191, Retrieved From EBI Accession No. EMBL:BF275177, Database Accession No. BF275177, Nov. 20, 2000. Sequence.
Wing et al. "GA_Eb0026P18f *Gossypium arboreum* 7-10 Dpa Fiber Library *Gossypium arboreum* cDNA Clone GA_Eb0026P18f, mRNA Sequence", Database EMBL [Online], XP002640830, Retrieved From EBI Accession No. EMBL:BF277249, Database Accession No. BF277249, Nov. 20, 2000.
Wu et al. "SubName: Full=Major Intrinsic Protein", Database UniProt [Online], XP002529191, Retrieved From EBI Accession No. UNIPROT:AOFI89, Database Accession No. AOFI89, Nov. 28, 2006.

Xu et al. "Expression of a Late Embryogenesis Abundant Protein Gene, HVA1, From Barley Confers Tolerance to Water Deficit and Salt Stress in Transgenic Rice", Plant Physiology, 110: 249-257, 1996.
Yamada et al. "*Arabidopsis thaliana* Clone RAFL14-87-A16 (R20399) Unknown Protein (At1g60770) mRNA Complete Cds", GenBank Accession No. BT002876, Retrieved From the Internet, Jan. 21, 2010.
Yamada et al. "*Arabidopsis thaliana* Unknown Proein (At3g51610) mRNA, Complete CDS", Database EMBL [Online], XP002640828, Retrieved Fom EBI Accession No. EMBL:AY034915, Database Accession No. AY034915, Jun. 13, 2001. Compound.
Yanagisawa et al. "Diversity and Similarity Among Recognition Sequences of Dof Transcription Factors", The Plant Journal, 17(2): 209-214, 1999.
Yanagisawa et al. "Metabolic Engineering With Dof1 Transcription Factor in Plants: Improved Nitrogen Assimilation and Growth Under Low-Nitrogen Conditions", Proc. Natl. Acad. Sci USA, PNAS, 101(20): 7833-7838, May 18, 2004.
Yanagisawa et al. "Metabolic Engineering With Dof1 Transcription Factor in Plants: Improved Nitrogen Assimilation and Growth Under Low-Nitrogen Conditions", Proc. Natl. Acad. Sci. USA, PNAS, 101(20): 7833-7838, May 18, 2004.
Zabrouskov et al. "Oxidative Metabolism and the Physiological Age of Seed Potatoes Are Affected by Increased Alpha-Linolenate Content", Physiologia Plantarum, 116: 172-185, 2002.
Invitation to Pay Additional Fees Dated Oct. 17, 2012 From the International Searching Authority Re. Application No. PCT/IL2012/050154.
Requisition by the Examiner Dated Aug. 27, 2013 From the Canadian Intellectual Property Office Re. Application No. 2,526,440.
Advisory Action Before the Filing of an Appeal Brief Dated Nov. 19, 2013 From the US Patent and Trademark Office Re. U.S. Appl. No. 12/834,106.
International Search Report and the Written Opinion Dated Nov. 19, 2013 From the International Searching Authority Re. Application No. PCT/IL2013/050725.
Yu et al. "Cell Cycle Checkpoint Protein MAD2 Homolog [*Zea mays*]", Database NCBI [Online], GenBank: AAD30555.1, GenBank Accession No. AAD30555, May 17, 1999.
Communication Under Rule 71(3) EPC Dated Nov. 19, 2012 From the European Patent Office Re. Application No. 08738191.9.
Applicant-Initiated Interview Summary Dated Nov. 20, 2013 From the US Patent and Trademark Office Re. U.S. Appl. No. 13/125,047.
Requisition by the Examiner Dated Oct. 28, 2013 From the Canadian Intellectual Property Office Re. Application No. 2,570,195.
Lazar et al. "Transforming Growth Factor Alpha: Mutation of Aspartic Acid 47 and Leucine 48 Results in Different Biological Activities", Molecular and Cell Biology, 8(3): 1247-1252, Mar. 1988.
Examination Report Dated Oct. 1, 2013 From the Instituto Mexicano de la Propiedad Industrial Re. Application No. MX/a/2010/000975 and Its Translation Into English.
International Preliminary Report on Patentability Dated Nov. 14, 2013 From the International Bureau of WIPO Re. Application No. PCT/IL2012/050154.
Communication Pursuant to Article 94(3) EPC Dated Oct. 23, 2012 From the European Patent Office Re. Application No. 11154213.0.
Examination Report Dated Oct. 15, 2012 From the Instituto Mexicano de la Propiedad Industrial Re. Application No. MX/a/2009/006660 and Its Translation Into English.
Notice of Allowance Dated Nov. 19, 2012 From the US Patent and Trademark Office Re. U.S. Appl. No. 13/450,547.
Patent Examination Report Dated Dec. 12, 2012 From the Australian Government, IP Australia Re. Application No. 2008236316.
Examination Report Dated Dec. 16, 2013 From the Government of India, Patent Office, Intellectual Property Building Re. Application No. 2570/CHENP/2008.
Li et al. "Dehydration-Induced Protein RD22-Like Protein [*Gossypium hirsutum*]", NCBI Database [Online], GenBank: AAL67991.1, GenBank Accession No. AAL67991, Dec. 4, 2002.
Notice of Allowance Dated Jan. 7, 2013 From the US Patent and Trademark Office Re. U.S. Appl. No. 12/457,199.

(56) References Cited

OTHER PUBLICATIONS

Official Action Dated Jan. 18, 2013 From the US Patent and Trademark Office Re. U.S. Appl. No. 12/669,975.
Translation of Notice to Amendment Dated Aug. 31, 2012 From the Thai Patent Office, Department of Intellectual Property Office Re. Application No. 0901000235.
Translation of Office Action Dated Jan. 17, 2013 From the State Intellectual Property Office of the People's Republic of China Re. Application No. 201110104274.1.
Translation of Search Report Dated Jan. 17, 2013 From the State Intellectual Property Office of the People's Republic of China Re. Application No. 201110104274.1.
International Preliminary Report on Patentability Dated Feb. 21, 2013 From the International Bureau of WIPO Re. Application No. PCT/IB2011/051843.
Official Action Dated Feb. 8, 2013 From the US Patent and Trademark Office Re. U.S. Appl. No. 12/594,853.
Supplementary European Search Report and the European Search Opinion Dated Feb. 14, 2013 From the European Patent Office Re. Application No. 10785834.2.
Translation of Office Action Dated Feb. 25, 2013 From the State Intellectual Property Office of the People's Republic of China Re. Application No. 200910217137.1.
Examination Report Dated Mar. 23, 2013 From the Government of India, Patent Office, Intellectual Property Building Re. Application No. 2570/CHENP/2008.
International Search Report and the Written Opinion Dated Apr. 10, 2013 From the International Searching Authority Re. Application No. PCT/IL2012/050327.
Invitation to Pay Additional Fees Dated Apr. 8, 2013 From the International Searching Authority Re. Application No. PCT/IL2013/050172.
Requisition by the Examiner Dated Apr. 11, 2013 From the Canadian Intellectual Property Office Re. Application No. 2,626,592.
Translation of Office Action Dated Mar. 22, 2013 From the State Intellectual Property Office of the People's Republic of China Re. Application No. 200880109464.9.
Soderlund et al. "Sequencing, Mapping, and Analysis of 27,455 Maize Full-Length cDNAs", PLoS Genetics, 5(11): e1000740-1-e1000740-13, Nov. 2009.
Office Action Dated Apr. 1, 2013 From the State Intellectual Property Office of the People's Republic of China Re. Application No. 200880127757.X and Its Translation Into English.
Communication Pursuant to Article 94(3) EPC Dated May 8, 2013 From the European Patent Office Re. Application No. 08776651.5.
International Search Report and the Written Opinion Dated May 12, 2013 From the International Searching Authority Re. Application No. PCT/IL2013/050172.
Official Action Dated May 8, 2013 From the US Patent and Trademark Office Re. U.S. Appl. No. 13/125,047.
Desveaux et al. "Whirly Transcription Factors: Defense Gene Regulation and Beyond", Trends in Plant Science, TiPS, 10(2): 95-102, Feb. 2005.
Young et al. "Hypothetical Protein MTR_7g116270 [*Medicago truncatula*]", Database NCBI [Online], GenBank: AES82688.1, Database Accession No. AES82688, Nov. 21, 2011.
Zhang et al. "Phosphatidic Acid Regulates Microtubule Organization by Interaction With MAP65-1 in Response to Salt Stress in *Arabidopsis*", The Plant Cell, 24: 4555-4576, Nov. 2012.
Official Action Dated May 20, 2013 From the US Patent and Trademark Office Re. U.S. Appl. No. 13/059,231.
Patent Examination Report Dated May 31, 2013 From the Australian Government, IP Australia Re. Application No. 2008278654.
Hirner et al. "*Arabidopsis* LHT1 Is a High-Affinity Transporter for Cellular Amino Acid Uptake in Both Root Epidermis and Leaf Mesophyll", The Plant Cell, 18: 1931-1946, Aug. 2006.
Plant Energy Biology "Protein_Coding: Cationic Amino Acid Transporter 2 (TAIR10)", Plant Energy Biology: SUBA3 Flatfile for AT1G58030.1, Database, 1 P., 2007.

Rolletschek et al. "Ectopic Expression of an Amino Acid Transporter (VfAAP1) in Seeds of Vica narbonensis and Pea Increases Storage Proteins", Plant Physiology, 137: 1236-1249, Apr. 2005.
Su et al. "Molecular and Functional Characterization of a Family of Amino Acid Transporter From *Arabidopsis*", Plant Physiology, 136: 3104-3113, Oct. 2004.
TAIR "Encodes a Member of the Cationic Amino Acid Transporter (CAT) Subfamily of Amino Acid Polyamine Choline Transporters. Localized to the Tonoplast", TAIR, Locus: AT1G58030, TAIR Accession No. Locus:2196245, 4 P., 2013.
TAIR "Protein Kinase Superfamily Protein. Functions in: Protein Serine/Threonine Kinase Activity, Protein Kinase activity, Kinase Activity, ATP Binding ff.", TAIR, Locus: AT5G15080, TAIR Accession No. Locus:2147805, 4 P., 2013.
Examination Report Dated Mar. 13, 2013 From the Instituto Mexican de la Propiedad Industrial Re. Application No. PA/a/2005/009380 and Its Summary in English.
Requisition—Sequence Listing Dated May 8, 2013 From the Canadian Intellectual Property Office Re. Application No. 2,753,616.
Communication Pursuant to Article 94(3) EPC Dated May 29, 2013 From the European Patent Office Re. Application No. 09823171.5.
Official Action Dated Jun. 24, 2013 From the US Patent and Trademark Office Re. U.S. Appl. No. 12/992,902.
Patent Examination Report Dated Jun. 21, 2013 From the Australian Government, IP Australia Re. Application No. 2012241091.
*Arabidopsis* Genome Initiative "Analysis of the Genome Sequence of the Flowering Plant *Arabicopsis thaliana*" Nature, 408: 796-815, Dec. 14, 2000.
Ciddi et al. "Elicitation of *Taxus* sp. Cell Cultures for Production of Taxol", Biotechnology Letters, 17(12): 1343-1346, Dec. 1995.
Kikuchi et al. "*Oryza sativa japonica* Group cDNA Clone:J023131O04, Full Insert Sequence", GenBank Database Accession No. AK072531, Jul. 2, 2013.
Lurin et al. "Genome-Wide Analysis of *Arabidopsis* Pentatricopeptide Repeat Proteins Reveals Their Essential Role in Organelle Biogenesis", The plant Cell, 16: 2089-2103, Aug. 2004.
Terminology "Frequently Asked Questions", Bioinformatics Website, Frequently Asked Questions, 2001.
Theologis et al. "Sequence and Analysis off Chromosome 1 of the Plant *Arabidopsis thaliana*", Nature, 408: 816-820, Dec. 14, 2000.
Patent Examination Report Dated Jun. 27, 2013 From the Australian Government, IP Australia Re. Application No. 2012216482.
Matz et al. "*Gossypium hirsutum* GHDEL65 (ghde165) mRNA, Complete CDS", GenBank Nucleotide, GenBank Accession No. AF336280, Mar. 15, 2001.
International Search Report and the Written Opinion Dated Sep. 1, 2013 From the International Searching Authority Re. Application No. PCT/IB2013/054374.
Bennetzen et al. "*Setaria italica* Strain Yugul SETITScaffold 2 Cont751, Whole Genome Shotgun Sequence", Database NCBI [Online], GenB ank Accession No. AGNK01000751, May 11, 2012.
Briggs et al. "Poly(ADP-Ribosyl)ation in Plants", Trends in Plant Science, 16(7): 372-380, Jul. 31, 2011. p. 378.
NCBI "Predicted: Nudix Hydrolase 16, Mitochondrial-Like [*Setaria italica*]", Database NCBI [Online], NCBI Reference Sequence: XP_004955808, Jun. 26, 2013.
Office Action Dated Oct. 28, 2013 From the State Intellectual Property Office of the People's Republic of China Re. Application No. 201110104274.1 and Its Translation Into English.
Communication Pursuant to Article 94(3) EPC Dated Nov. 7, 2013 From the European Patent Office Re. Application No. 10748403.2.
Communication Pursuant to Rules 70(2) and 70a(2) EPC Dated Nov. 4, 2013 From the European Patent Office Re. Application No. 10840687.7.
Examination Report Dated Aug. 22, 2013 From the Instituto Mexicano de la Propiedad Industrial Re. Application No. MX/a/2011/009044 and Its Translation Into English.
Official Action Dated Oct. 29, 2013 From the US Patent and Trademark Office Re. U.S. Appl. No. 13/059,231.
Seki et al. "Monitoring the Expression Profiles of 7000 *Arabidopsis* Genes Under Drought, Cold and High-Salinity Stresses Using a Full-Length cDNA Microarray", The Plant Journal, 31(3): 279-292, 2002.

(56) References Cited

OTHER PUBLICATIONS

Tobias et al. "Structure of the Cinammyl-Alcohol Dehydrogenase Gene Family in Rice and Promoter Activity of a Member Associated With Lignification", Planta, 220: 678-688, 2005.
Communication Pursuant to Article 94(3) EPC Dated Oct. 23, 2012 From the European Patent Office Re. Application No. 11154193.4.
Requisition by the Examiner Dated Oct. 3, 2012 From the Canadian Intellectual Property Office Re. Application No. 2,526,440.
Translation of Notice of Paying Restoration Fee for Unity of Invention Dated Oct. 29, 2012 From the State Intellectual Property Office of the People's Republic of China Re. Application No. 200880127757.X.
Alcala et al. "EST543159 Tomato Callus *Solanum lycopersicum* cDNA Clone cLEC80A19 5-end, mRNA Sequence", GenBank: BI923254.1, GenBank Accession No. BI923254, Oct. 17, 2001.
Notice of Allowance Dated Nov. 15, 2013 From the US Patent and Trademark Office Re. U.S. Appl. No. 12/669,975.
Communication Pursuant to Article 94(3) EPC Dated Aug. 20, 2013 From the European Patent Office Re. Application No. 11172514.9.
Communication Pursuant to Rules 70(2) and 70a(2) EPC Dated May 7, 2012 From the European Patent Office Re. Application No. 09823171.5.
Examination Report Dated Jun. 25, 2012 From the Instituto Mexicano de la Propiedad Industrial Re. Application No. MX/a/2011/003575 and Its Translation Into English.
International Preliminary Report on Patentability Dated May 12, 2011 From the International Bureau of WIPO Re. Application No. PCT/IB2009/054774.
International Search Report and the Written Opinion Dated Jun. 2, 2010 From the International Searching Authority Re.: Application No. PCT/IB09/54774.
Supplementary European Search Report and the European Search Opinion Dated Apr. 18, 2012 From the European Patent Office Re. Application No. 09823171.5.
Translation of Examination Report Dated Sep. 6, 2010 From the Government of the People's Republic of Bangladesh, Department of Patents, Designs and Trademarks, Ministry of Industries Re. Application No. 275/2009.
Bautista et al. "*Arabidopsis thaliana* At5g06690 mRNA, Complete Cds", Unpublished, The Salk Institute for Biological Studies, La Jolla, CA, USA, GenBank: BT029447, Nov. 15, 2006.
Cheuk et al. "*Arabidopsis thaliana* At2g40550 Gene, Complete CDS", Database EMBL [Online], XP002673499, Retrieved From EBI Accession No. EM_PL: BT022032.1, Database Accession No. BT022032, May 4, 2005.
Rounsley et al. "*Arabidopsis thaliana* Chromosome 2 Clone T2P4 Map CIC10A06, Complete Sequence", Database EMBL [Online], XP002673500, Retrieved From EBI Accession No. EMBL:AC002336, Database Accession No. AC002336, Jul. 18, 1997. Sequence.
Takahashi et al. "The DNA Replication Checkpoint Aids Survival of Plants Deficient in the Novel Replisome Factor ETG1", The EMBO Journal, XP002537888, 27(13): 1840-1851, Jul. 9, 2008 & Supplementary Materials and Methods. Suppl. Fig. S6, p. 1844-1845.
Official Action Dated Sep. 16, 2013 From the US Patent and Trademark Office Re. U.S. Appl. No. 13/125,047.
Translation of Office Action Dated Aug. 28, 2013 From the State Intellectual Property Office of the People's Republic of China Re. Application No. 200880109464.9.
Clontech "Genome Walker™ Universal Kit User Manual", Clontech Laboratories Inc., Cat. No. 638904, PT3042-1 (PR742239), p. 1-30, Apr. 25, 2007.
Zhou et al. "Global Genome Expression Analysis of Rice in Response to Drought and High-Salinity Stresses in Shoot, Flag Leaf, and Panicle", Plant Molecular Biology, 63(5): 591-608, Mar. 2007.
Examination Report Dated Jul. 29, 2013 From the Instituto Mexicano de la Propiedad Industrial Re. Application No. MX/a/2010/012697 and Its Translation Into English.
Official Action Dated Sep. 20, 2013 From the US Patent and Trademark Office Re. U.S. Appl. No. 12/669,975.
Translation of Office Action Dated Sep. 13, 2012 From the State Intellectual Property Office of the People's Republic of China Re. Application No. 200910217137.1.
Communication Pursuant to Article 94(3) EPC Dated Oct. 9, 2013 From the European Patent Office Re. Application No. 08869158.9.
Invitation to Pay Additional Fees Dated Oct. 16, 2013 From the International Searching Authority Re. Application No. PCT/IL2013/050725.
Office Action Dated Sep. 9, 2013 From the State Intellectual Property Office of the People's Republic of China Re. Application No. 200910217137.1 and Its Translation Into English.
Supplementary European Search Report and the European Search Opinion Dated Oct. 15, 2013 From the European Patent Office Re. Application No. 10840687.7.
Liu et al. "Plant Full Length Insert Polypeptide Seqid 64542", Database Geneseq [Online], XP002713973, Retrieved From EBI Accession No. GSP:ADY08727, Database Accession No. ADY08727, Apr. 21, 2005. Polypeptide Has 96.4% Identity to SEQ ID No. 653 and Is Used for the Same Purpose, Abstract, Sequence.
Paterson et al. "*Sorghum bicolor* Chromosome 2, Whole Genome Shotgun Sequence", NCBI Database [Online], Retrieved From EBI Accession No. EMBL:CM000761, Database Accession No. CM000761, Jun. 24, 2009. Sequence.
Paterson et al. "SubName: Full=Putative Uncharacterized Protein Sb02g004350", Database UniProt [Online], XP002713972, Retrieved From EBI Accession No. UNIPROT:C5XB01, Database Accession No. C5XB01, Sep. 1, 2009. Polynucleotide and Polypeptide Molecules Fully Comprising the Present Molecules According to SEQ ID No. 166, 653, Abstract, Sequence.
Restriction Official Action Dated Nov. 13, 2012 From the US Patent and Trademark Office Re. U.S. Appl. No. 12/992,902.
Backhaus et al. "Nucleotide Sequence of a cDNA for a P2 60S Acidic Ribosomal Protein From *Parthenium argentatum*", Plant Physiology, 106: 395, 1994.
Del Pozo et al. "F-Box Proteins and Protein Degradation: An Emerging Theme in Cellular Regulation", Plant Molecular Biology, 44(2): 123-128, Sep. 2000.
Harwood "Plant Fatty Acid Synthesis", The AOCS Lipid Library, 11 P., Apr. 12, 2010.
Communication Pursuant to Article 94(3) EPC Dated Aug. 2, 2013 From the European Patent Office Re. Application No. 10194223.3.
Examination Report Dated Jul. 9, 2013 From the Instituto Mexicano de la Propiedad Industrial Re. Application No. MX/a/2010/007169 and Its Translation Into English.
Examination Report Dated Jun. 26, 2013 From the Instituto Mexicano de la Propiedad Industrial Re. Application No. MX/a/2010/000975 and Its Translation Into English.
Official Action Dated Aug. 12, 2013 From the US Patent and Trademark Office Re. U.S. Appl. No. 12/834,106.
Substantive Examination Report Dated Jul. 31, 2013 From the Intellectual Property Office of the Philippines, Bureau of Patents Re. Application No. 1/2009/501930.

* cited by examiner

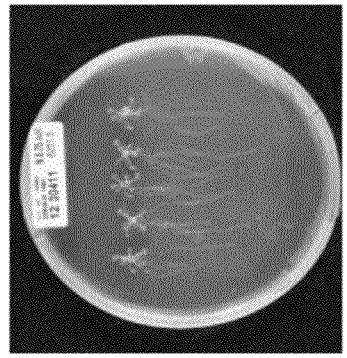
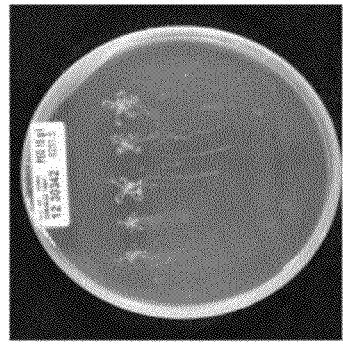
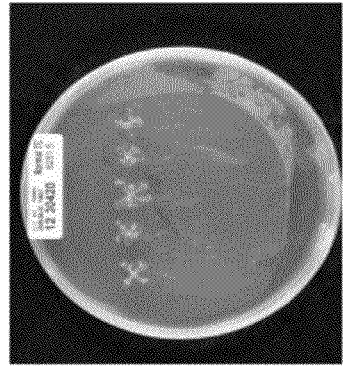
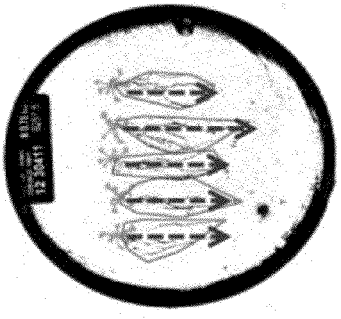
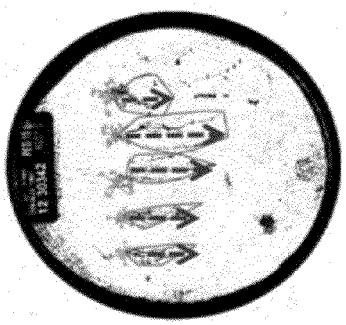
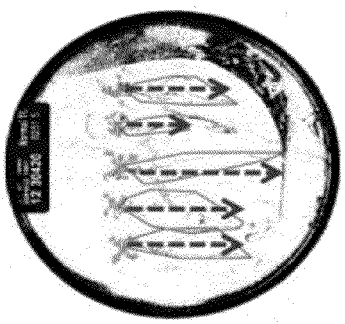
FIG. 3A  FIG. 3C  FIG. 3E
FIG. 3B  FIG. 3D  FIG. 3F
Normal conditions | Osmotic stress (15% PEG) | Nitrogen limiting conditions
FIG. 3

ISOLATED POLYNUCLEOTIDES AND POLYPEPTIDES, AND METHODS OF USING SAME FOR INCREASING NITROGEN USE EFFICIENCY, YIELD, GROWTH RATE, VIGOR, BIOMASS, OIL CONTENT, AND/OR ABIOTIC STRESS TOLERANCE

RELATED APPLICATIONS

This application is a National Phase of PCT Patent Application No. PCT/IB2010/052545 having International filing date of Jun. 8, 2010, which claims the benefit of priority of U.S. Provisional Patent Application Nos. 61/272,764 filed on Oct. 30, 2009, and 61/213,457 filed on Jun. 10, 2009. The contents of the above applications are all incorporated herein by reference.

FIELD AND BACKGROUND OF THE INVENTION

The present invention, in some embodiments thereof, relates to novel polynucleotides and polypeptides which can increase nitrogen use efficiency, fertilizer use efficiency, yield (e.g., seed/grain yield, oil yield), growth rate, vigor, biomass, oil content, fiber yield, fiber quality and/or length, abiotic stress tolerance and/or water use efficiency of a plant.

A common approach to promote plant growth has been, and continues to be, the use of natural as well as synthetic nutrients (fertilizers). Thus, fertilizers are the fuel behind the "green revolution", directly responsible for the exceptional increase in crop yields during the last 40 years, and are considered the number one overhead expense in agriculture. Of the three macronutrients provided as main fertilizers [Nitrogen (N), Phosphate (P) and Potassium (K)], nitrogen is often the rate-limiting element in plant growth and all field crops have a fundamental dependence on inorganic nitrogenous fertilizer. Nitrogen usually needs to be replenished every year, particularly for cereals, which comprise more than half of the cultivated areas worldwide. For example, inorganic nitrogenous fertilizers such as ammonium nitrate, potassium nitrate, or urea, typically accounts for 40% of the costs associated with crops such as corn and wheat.

Nitrogen is an essential macronutrient for the plant, responsible for biosynthesis of amino and nucleic acids, prosthetic groups, plant hormones, plant chemical defenses, etc. In addition, nitrogen is often the rate-limiting element in plant growth and all field crops have a fundamental dependence on inorganic nitrogen. Thus, nitrogen is translocated to the shoot, where it is stored in the leaves and stalk during the rapid step of plant development and up until flowering. In corn for example, plants accumulate the bulk of their organic nitrogen during the period of grain germination, and until flowering. Once fertilization of the plant has occurred, grains begin to form and become the main sink of plant nitrogen. The stored nitrogen can be then redistributed from the leaves and stalk that served as storage compartments until grain formation.

Since fertilizer is rapidly depleted from most soil types, it must be supplied to growing crops two or three times during the growing season. In addition, the low nitrogen use efficiency (NUE) of the main crops (e.g., in the range of only 30-70%) negatively affects the input expenses for the farmer, due to the excess fertilizer applied. Moreover, the over and inefficient use of fertilizers are major factors responsible for environmental problems such as eutrophication of groundwater, lakes, rivers and seas, nitrate pollution in drinking water which can cause methemoglobinemia, phosphate pollution, atmospheric pollution and the like. However, in spite of the negative impact of fertilizers on the environment, and the limits on fertilizer use, which have been legislated in several countries, the use of fertilizers is expected to increase in order support food and fiber production for rapid population growth on limited land resources. For example, it has been estimated that by 2050, more than 150 million tons of nitrogenous fertilizer will be used worldwide annually.

Increased use efficiency of nitrogen by plants should enable crops to be cultivated with lower fertilizer input, or alternatively to be cultivated on soils of poorer quality and would therefore have significant economic impact in both developed and developing agricultural systems.

Genetic improvement of fertilizer use efficiency (FUE) in plants can be generated either via traditional breeding or via genetic engineering.

Attempts to generate plants with increased FUE have been described in U.S. Pat. Appl. No. 20020046419 to Choo, et al.; U.S. Pat. Appl. No. 2005010879 to Edgerton et al.; U.S. Pat. Appl. No. 20060179511 to Chomet et al.; Good, A, et al. 2007 (Engineering nitrogen use efficiency with alanine aminotransferase. Canadian Journal of Botany 85: 252-262); and Good A G et al. 2004 (Trends Plant Sci. 9:597-605).

Yanagisawa et al. (Proc. Natl. Acad. Sci. U.S.A. 2004 101:7833-8) describe D of 1 transgenic plants which exhibit improved growth under low-nitrogen conditions.

U.S. Pat. No. 6,084,153 to Good et al. discloses the use of a stress responsive promoter to control the expression of Alanine Amine Transferase (AlaAT) and transgenic canola plants with improved drought and nitrogen deficiency tolerance when compared to control plants.

The ever-increasing world population and the decreasing availability in arable land for agriculture affect the yield of plants and plant-related products. The global shortage of water supply, desertification, abiotic stress (ABS) conditions (e.g., salinity, drought, flood, suboptimal temperature and toxic chemical pollution), and/or limited nitrogen and fertilizer sources cause substantial damage to agricultural plants such as major alterations in the plant metabolism, cell death, and decreases in plant growth and crop productivity.

Drought is a gradual phenomenon, which involves periods of abnormally dry weather that persists long enough to produce serious hydrologic imbalances such as crop damage, water supply shortage and increased susceptibility to various diseases.

Salinity, high salt levels, affects one in five hectares of irrigated land. None of the top five food crops, i.e., wheat, corn, rice, potatoes, and soybean, can tolerate excessive salt. Detrimental effects of salt on plants result from both water deficit, which leads to osmotic stress (similar to drought stress), and the effect of excess sodium ions on critical biochemical processes. As with freezing and drought, high salt causes water deficit; and the presence of high salt makes it difficult for plant roots to extract water from their environment. Thus, salination of soils that are used for agricultural production is a significant and increasing problem in regions that rely heavily on agriculture, and is worsen by over-utilization, over-fertilization and water shortage, typically caused by climatic change and the demands of increasing population.

Suboptimal temperatures affect plant growth and development through the whole plant life cycle. Thus, low temperatures reduce germination rate and high temperatures result in leaf necrosis. In addition, mature plants that are exposed to excess of heat may experience heat shock, which may arise in various organs, including leaves and particularly fruit, when transpiration is insufficient to overcome heat stress. Heat also damages cellular structures, including organelles and cytoskeleton, and impairs membrane function. Heat shock may produce a decrease in overall protein synthesis, accompanied by expression of heat shock proteins, e.g., chaperones, which are involved in refolding proteins denatured by heat. High-temperature damage to pollen almost always occurs in conjunction with drought stress, and rarely occurs under well-watered conditions. Combined stress can alter plant metabolism in novel ways. Excessive chilling conditions, e.g., low, but above freezing, temperatures affect crops of tropical origins, such as soybean, rice, maize, and cotton. Typical chilling damage includes wilting, necrosis, chlorosis or leakage of ions from cell membranes. Excessive light conditions, which occur under clear atmospheric conditions subsequent to cold late summer/autumn nights, can lead to photoinhibition of photosynthesis (disruption of photosynthesis). In addition, chilling may lead to yield losses and lower product quality through the delayed ripening of maize.

Nutrient deficiencies cause adaptations of the root architecture, particularly notably for example is the root proliferation within nutrient rich patches to increase nutrient uptake. Nutrient deficiencies cause also the activation of plant metabolic pathways which maximize the absorption, assimilation and distribution processes such as by activating architectural changes. Engineering the expression of the triggered genes may cause the plant to exhibit the architectural changes and enhanced metabolism also under other conditions.

In addition, it is widely known that the plants usually respond to water deficiency by creating a deeper root system that allows access to moisture located in deeper soil layers. Triggering this effect will allow the plants to access nutrients and water located in deeper soil horizons particularly those readily dissolved in water like nitrates.

Yield is affected by various factors, such as, the number and size of the plant organs, plant architecture (for example, the number of branches), grains set length, number of filled grains, vigor (e.g. seedling), growth rate, root development, utilization of water, nutrients (e.g., nitrogen) and fertilizers, and stress tolerance.

Crops such as, corn, rice, wheat, canola and soybean account for over half of total human caloric intake, whether through direct consumption of the seeds themselves or through consumption of meat products raised on processed seeds or forage. Seeds are also a source of sugars, proteins and oils and metabolites used in industrial processes. The ability to increase plant yield, whether through increase dry matter accumulation rate, modifying cellulose or lignin composition, increase stalk strength, enlarge meristem size, change of plant branching pattern, erectness of leaves, increase in fertilization efficiency, enhanced seed dry matter accumulation rate, modification of seed development, enhanced seed filling or by increasing the content of oil, starch or protein in the seeds would have many applications in agricultural and non-agricultural uses such as in the biotechnological production of pharmaceuticals, antibodies or vaccines.

Studies have shown that plant adaptations to adverse environmental conditions are complex genetic traits with polygenic nature. Conventional means for crop and horticultural improvements utilize selective breeding techniques to identify plants having desirable characteristics. However, selective breeding is tedious, time consuming and has an unpredictable outcome. Furthermore, limited germplasm resources for yield improvement and incompatibility in crosses between distantly related plant species represent significant problems encountered in conventional breeding. Advances in genetic engineering have allowed mankind to modify the germplasm of plants by expression of genes-of-interest in plants. Such a technology has the capacity to generate crops or plants with improved economic, agronomic or horticultural traits.

WO publication No. 2009/013750 discloses genes, constructs and methods of increasing abiotic stress tolerance, biomass and/or yield in plants generated thereby.

WO publication No. 2008/122980 discloses genes constructs and methods for increasing oil content, growth rate and biomass of plants.

WO publication No. 2008/075364 discloses polynucleotides involved in plant fiber development and methods of using same.

WO publication No. 2007/049275 discloses isolated polypeptides, polynucleotides encoding same, transgenic plants expressing same and methods of using same for increasing fertilizer use efficiency, plant abiotic stress tolerance and biomass.

WO publication No. 2004/104162 discloses methods of increasing abiotic stress tolerance and/or biomass in plants and plants generated thereby.

WO publication No. 2005/121364 discloses polynucleotides and polypeptides involved in plant fiber development and methods of using same for improving fiber quality, yield and/or biomass of a fiber producing plant.

WO publication No. 2007/020638 discloses methods of increasing abiotic stress tolerance and/or biomass in plants and plants generated thereby.

WO publication No. 2009/083958 discloses methods of increasing water use efficiency, fertilizer use efficiency, biotic/abiotic stress tolerance, yield and biomass in plant and plants generated thereby.

WO publication No. 2010/020941 discloses methods of increasing nitrogen use efficiency, abiotic stress tolerance, yield and biomass in plants and plants generated thereby.

WO publication No. 2009/141824 discloses isolated polynucleotides and methods using same for increasing plant utility.

SUMMARY OF THE INVENTION

According to an aspect of some embodiments of the present invention there is provided a method of increasing nitrogen use efficiency, yield, biomass, growth rate, vigor, oil content, fiber yield, fiber quality, and/or abiotic stress tolerance of a plant, comprising expressing within the plant an exogenous polynucleotide comprising a nucleic acid sequence at least 80% identical to SEQ ID NO:1-467, 785-3046 or 3047, thereby increasing the nitrogen use efficiency, yield, biomass, growth rate, vigor, oil content, fiber yield, fiber quality, and/or abiotic stress tolerance of the plant.

According to an aspect of some embodiments of the present invention there is provided a method of increasing nitrogen use efficiency, yield, biomass, growth rate, vigor, oil content, fiber yield, fiber quality, and/or abiotic stress tolerance of a plant, comprising expressing within the plant an exogenous polynucleotide comprising the nucleic acid sequence selected from the group consisting of SEQ ID NOs: 1-467, and 785-3047, thereby increasing the nitrogen use efficiency, yield, biomass, growth rate, vigor, oil content, fiber yield, fiber quality, and/or abiotic stress tolerance of the plant.

According to an aspect of some embodiments of the present invention there is provided a method of increasing nitrogen use efficiency, yield, biomass, growth rate, vigor, oil content, fiber yield, fiber quality, and/or abiotic stress tolerance of a plant, comprising expressing within the plant an exogenous polynucleotide comprising a nucleic acid sequence encoding a polypeptide at least 80% identical to SEQ ID NO:468-784, 3048-4333, 4335-4681 or 4682, thereby increasing the nitrogen use efficiency, yield, biomass, growth rate, vigor, oil content, fiber yield, fiber quality, and/or abiotic stress tolerance of the plant.

According to an aspect of some embodiments of the present invention there is provided a method of increasing nitrogen use efficiency, yield, biomass, growth rate, vigor, oil content, fiber yield, fiber quality, and/or abiotic stress tolerance of a plant, comprising expressing within the plant an exogenous polynucleotide comprising a nucleic acid sequence encoding a polypeptide selected from the group consisting of SEQ ID NOs:468-784, 3048-4333, 4335-4682 and 4334, thereby increasing the nitrogen use efficiency, yield, biomass, growth rate, vigor, oil content, fiber yield, fiber quality, and/or abiotic stress tolerance of the plant.

According to an aspect of some embodiments of the present invention there is provided an isolated polynucleotide comprising a nucleic acid sequence at least 80% identical to SEQ ID NO:1-467, 785-3046 or 3047, wherein the nucleic acid sequence is capable of increasing nitrogen use efficiency, yield, biomass, growth rate, vigor, oil content, fiber yield, fiber quality, and/or abiotic stress tolerance of a plant.

According to an aspect of some embodiments of the present invention there is provided an isolated polynucleotide comprising the nucleic acid sequence selected from the group consisting of SEQ ID NOs:1-467, and 785-3047.

According to an aspect of some embodiments of the present invention there is provided an isolated polynucleotide comprising a nucleic acid sequence encoding a polypeptide which comprises an amino acid sequence at least 80% homologous to the amino acid sequence set forth in SEQ ID NO: 468-784, 3048-4333, 4335-4681 or 4682, wherein the amino acid sequence is capable of increasing nitrogen use efficiency, yield, biomass, growth rate, vigor, oil content, fiber yield, fiber quality, and/or abiotic stress tolerance of the plant.

According to an aspect of some embodiments of the present invention there is provided an isolated polynucleotide comprising a nucleic acid sequence encoding a polypeptide which comprises the amino acid sequence selected from the group consisting of SEQ ID NOs:468-784, 3048-4333, 4335-4682 and 4334.

According to an aspect of some embodiments of the present invention there is provided a nucleic acid construct comprising the isolated polynucleotide of some embodiments of the invention and a promoter for directing transcription of the nucleic acid sequence in a host cell.

According to an aspect of some embodiments of the present invention there is provided an isolated polypeptide comprising an amino acid sequence at least 80% homologous to SEQ ID NO:468-784, 3048-4333, 4335-4681 or 4682, wherein the amino acid sequence is capable of increasing nitrogen use efficiency, yield, biomass, growth rate, vigor, oil content, fiber yield, fiber quality, and/or abiotic stress tolerance of a plant.

According to an aspect of some embodiments of the present invention there is provided an isolated polypeptide comprising the amino acid sequence selected from the group consisting of SEQ ID NOs:468-784, 3048-4333, and 4335-4682.

According to an aspect of some embodiments of the present invention there is provided a plant cell exogenously expressing the polynucleotide of some embodiments of the invention, or the nucleic acid construct of some embodiments of the invention.

According to an aspect of some embodiments of the present invention there is provided a plant cell exogenously expressing the polypeptide of some embodiments of the invention.

According to some embodiments of the invention, the nucleic acid sequence is as set forth in SEQ ID NO:1-467, 785-3046 or 3047.

According to some embodiments of the invention, the polynucleotide consists of the nucleic acid sequence selected from the group consisting of SEQ ID NOs:1-467, and 785-3047.

According to some embodiments of the invention, the nucleic acid sequence encodes an amino acid sequence at least 80% homologous to SEQ ID NO:468-784, 3048-4333, 4335-4681 or 4682.

According to some embodiments of the invention, the nucleic acid sequence encodes the amino acid sequence selected from the group consisting of SEQ ID NOs:468-784, 3048-4333, and 4335-4682.

According to some embodiments of the invention, the plant cell forms part of a plant.

According to some embodiments of the invention, the method further comprising growing the plant expressing the exogenous polynucleotide under the abiotic stress.

According to some embodiments of the invention, the abiotic stress is selected from the group consisting of salinity, drought, water deprivation, flood, etiolation, low temperature, high temperature, heavy metal toxicity, anaerobiosis, nutrient deficiency, nutrient excess, atmospheric pollution and UV irradiation.

According to some embodiments of the invention, the yield comprises seed yield or oil yield.

According to some embodiments of the invention, the promoter is heterologous to the isolated polynucleotide and/or to the host cell.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

GUSintron—the GUS reporter gene (coding sequence and intron). The isolated polynucleotide sequences of the invention were cloned into the vector while replacing the GUSintron reporter gene.

Figure 2:
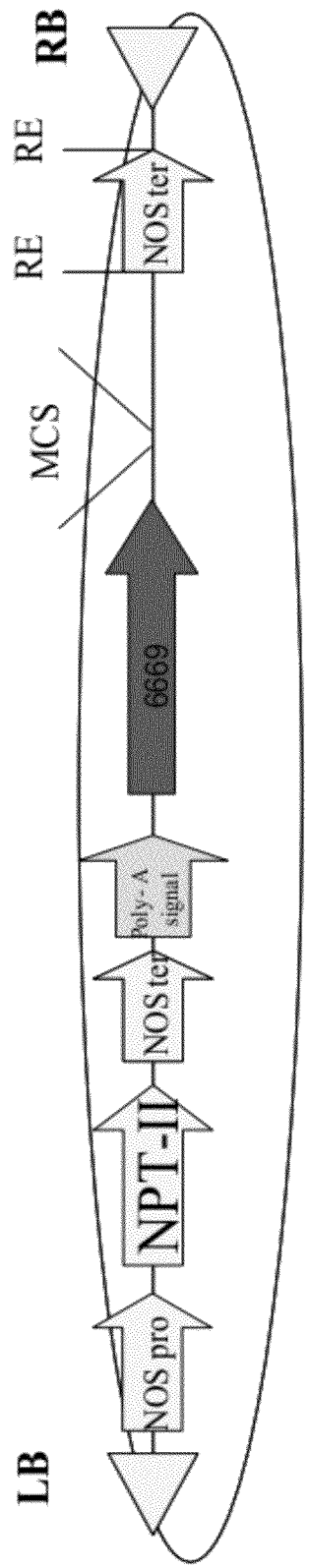

FIG. 2 is a schematic illustration of the modified pGI binary plasmid containing the new At6669 promoter (SEQ ID NO:4687) (pQFN) used for expressing the isolated polynucleotide sequences of the invention. RB—T-DNA right border; LB—T-DNA left border; MCS—Multiple cloning site; RE—any restriction enzyme; NOS pro=nopaline synthase promoter; NPT-II=neomycin phosphotransferase gene; NOS ter=nopaline synthase terminator; Poly-A signal (polyadenylation signal); GUSintron—the GUS reporter gene (coding sequence and intron). The isolated polynucleotide sequences of the invention were cloned into the MCS of the vector.

FIGS. 3A-F are images depicting visualization of root development of transgenic plants exogenously expressing the polynucleotide of some embodiments of the invention when grown in transparent agar plates under normal (FIGS. 3A-B), osmotic stress (15% PEG; FIGS. 3C-D) or nitrogen-limiting (FIGS. 3E-F) conditions. The different transgenes were grown in transparent agar plates for 17 days (7 days nursery and 10 days after transplanting). The plates were photographed every 3-4 days starting at day 1 after transplanting. FIG. 3A—An image of a photograph of plants taken following 10 after transplanting days on agar plates when grown under normal (standard) conditions. FIG. 3B—An image of root analysis of the plants shown in FIG. 3A in which the lengths of the roots measured are represented by arrows. FIG. 3C—An image of a photograph of plants taken following 10 days after transplanting on agar plates, grown under high osmotic (PEG 15%) conditions. FIG. 3D—An image of root analysis of the plants shown in FIG. 3C in which the lengths of the roots measured are represented by arrows. FIG. 3E—An image of a photograph of plants taken following 10 days after transplanting on agar plates, grown under low nitrogen conditions. FIG. 3F—An image of root analysis of the plants shown in FIG. 3E in which the lengths of the roots measured are represented by arrows.

Figure 4:
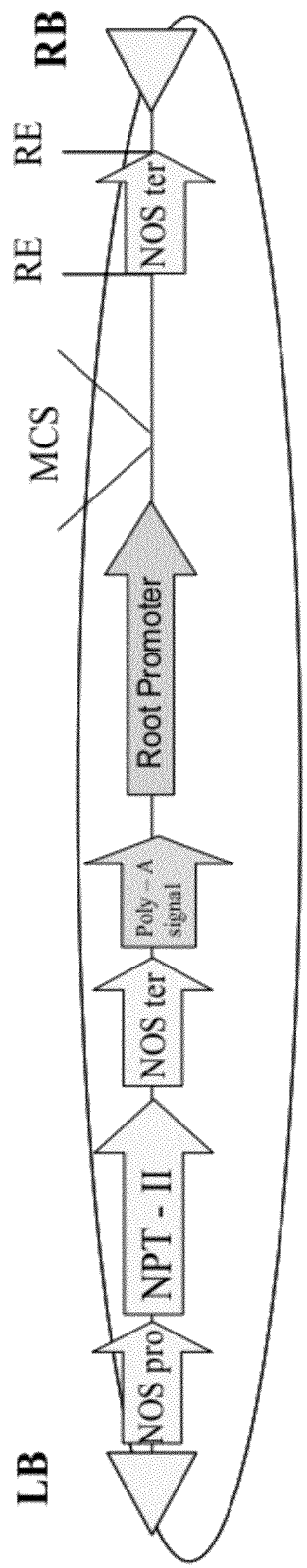

FIG. 4 is a schematic illustration of the modified pGI binary plasmid containing the Root Promoter (pQNa_RP) used for expressing the isolated polynucleotide sequences of the invention. RB—T-DNA right border; LB—T-DNA left border; NOS pro=nopaline synthase promoter; NPT-II=neomycin phosphotransferase gene; NOS ter=nopaline synthase terminator; Poly-A signal (polyadenylation signal); The isolated polynucleotide sequences according to some embodiments of the invention were cloned into the MCS of the vector.

DESCRIPTION OF SPECIFIC EMBODIMENTS OF THE INVENTION

The present invention, in some embodiments thereof, relates to novel polynucleotides and polypeptides, nucleic acid constructs comprising same, host cells expressing same, transgenic plants exogenously expressing same and, more particularly, but not exclusively, to methods of using same for increasing nitrogen use efficiency, fertilizer use efficiency, yield, growth rate, vigor, biomass, oil content, fiber yield, fiber quality, fiber length, abiotic stress tolerance and/or water use efficiency of a plant.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have identified novel polypeptides and polynucleotides which can be used to increase nitrogen use efficiency, fertilizer use efficiency, yield, growth rate, vigor, biomass, oil content, fiber yield, fiber quality, fiber length, abiotic stress tolerance and/or water use efficiency of a plant.

Thus, as shown in the Examples section which follows, the present inventors have utilized bioinformatics tools to identify polynucleotides which enhance nitrogen use efficiency, fertilizer use efficiency, yield (e.g., seed yield, oil yield), growth rate, vigor, biomass, oil content, fiber development (e.g., fiber yield, quality and/or length), abiotic stress tolerance and/or water use efficiency of a plant. Genes which affect the trait-of-interest were identified based on expression profiles of genes of several *Arabidopsis*, Rice, *Sorghum*, Barley, Maize and Tomato ecotypes and tissues (Tables 3-84; Examples 3-16), homology with genes known to affect the trait-of-interest and using digital expression profiles in specific tissues and conditions (Table 1, Example 1).

Homologous polypeptides and polynucleotides having the same function were also identified (Table 2, Example 2). Altogether, these results suggest the use of the novel polynucleotides and polypeptides of the invention for increasing nitrogen use efficiency, fertilizer use efficiency, yield (e.g., seed yield, oil yield), growth rate, vigor, biomass, oil content, fiber yield, fiber quality, fiber length, abiotic stress tolerance and/or water use efficiency of a plant.

Thus, according to an aspect of some embodiments of the invention, there is provided method of increasing fertilizer use efficiency, nitrogen use efficiency, yield, biomass, growth rate, vigor, oil content, fiber yield, fiber quality, fiber length, and/or abiotic stress tolerance of a plant, comprising expressing within the plant an exogenous polynucleotide comprising a nucleic acid sequence at least 80% identical to SEQ ID NO:1-467, 785-3046 or 3047, thereby increasing the fertilizer use efficiency, nitrogen use efficiency, yield, biomass, growth rate, vigor, oil content, fiber yield, fiber length, fiber quality, and/or abiotic stress tolerance of the plant.

As used herein the phrase "fertilizer use efficiency" refers to the metabolic process(es) which lead to an increase in the plant's yield, biomass, vigor, and growth rate per fertilizer unit applied. The metabolic process can be the uptake, spread, absorbent, accumulation, relocation (within the plant) and use of one or more of the minerals and organic moieties absorbed by the plant, such as nitrogen, phosphates and/or potassium.

As used herein the phrase "fertilizer-limiting conditions" refers to growth conditions which include a level (e.g., concentration) of a fertilizer applied which is below the level needed for normal plant metabolism, growth, reproduction and/or viability.

As used herein the phrase "nitrogen use efficiency (NUE)" refers to the metabolic process(es) which lead to an increase in the plant's yield, biomass, vigor, and growth rate per nitrogen unit applied. The metabolic process can be the uptake, spread, absorbent, accumulation, relocation (within the plant) and use of nitrogen absorbed by the plant.

As used herein the phrase "nitrogen-limiting conditions" refers to growth conditions which include a level (e.g., concentration) of nitrogen (e.g., ammonium or nitrate) applied which is below the level needed for normal plant metabolism, growth, reproduction and/or viability.

Improved plant NUE and FUE is translated in the field into either harvesting similar quantities of yield, while implementing less fertilizers, or increased yields gained by implementing the same levels of fertilizers. Thus, improved NUE or FUE has a direct effect on plant yield in the field. Thus, the polynucleotides and polypeptides of some embodiments of the invention positively affect plant yield, seed yield, and plant biomass. In addition, the benefit of improved plant NUE will certainly improve crop quality and biochemical constituents of the seed such as protein yield and oil yield.

As used herein the phrase "plant yield" refers to the amount (e.g., as determined by weight or size) or quantity (numbers) of tissues or organs produced per plant or per growing season. Hence increased yield could affect the economic benefit one can obtain from the plant in a certain growing area and/or growing time.

It should be noted that a plant yield can be affected by various parameters including, but not limited to, plant biomass; plant vigor; growth rate; seed yield; seed or grain quantity; seed or grain quality; oil yield; content of oil, starch and/or protein in harvested organs (e.g., seeds or vegetative parts of the plant); number of flowers (florets) per panicle (expressed as a ratio of number of filled seeds over number of primary panicles); harvest index; number of plants grown per area; number and size of harvested organs per plant and per area; number of plants per growing area (density); number of harvested organs in field; total leaf area; carbon assimilation and carbon partitioning (the distribution/allocation of carbon within the plant); resistance to shade; number of harvestable organs (e.g. seeds), seeds per pod, weight per seed; and modified architecture [such as increase stalk diameter, thickness or improvement of physical properties (e.g. elasticity)].

The term "seed" (also referred to as "grain" or "kernel") as used herein refers to a small embryonic plant enclosed in a covering called the seed coat (usually with some stored food), the product of the ripened ovule of gymnosperm and angiosperm plants which occurs after fertilization and some growth within the mother plant.

As used herein the phrase "seed yield" refers to the number or weight of the seeds per plant, seeds per pod, or per growing area or to the weight of a single seed, or to the oil extracted per seed. Hence seed yield can be affected by seed dimensions (e.g., length, width, perimeter, area and/or volume), number of (filled) seeds and seed filling rate and by seed oil content. Hence increase seed yield per plant could affect the economic benefit one can obtain from the plant in a certain growing area and/or growing time; and increase seed yield per growing area could be achieved by increasing seed yield per plant, and/or by increasing number of plants grown on the same given area.

The phrase "oil content" as used herein refers to the amount of lipids in a given plant organ, either the seeds (seed oil content) or the vegetative portion of the plant (vegetative oil content) and is typically expressed as percentage of dry weight (10% humidity of seeds) or wet weight (for vegetative portion).

It should be noted that oil content is affected by intrinsic oil production of a tissue (e.g., seed, vegetative portion), as well as the mass or size of the oil-producing tissue per plant or per growth period.

In one embodiment, increase in oil content of the plant can be achieved by increasing the size/mass of a plant's tissue(s) which comprise oil per growth period. Thus, increased oil content of a plant can be achieved by increasing the yield, growth rate, biomass and vigor of the plant.

As used herein the phrase "plant biomass" refers to the amount (e.g., measured in grams of air-dry tissue) of a tissue produced from the plant in a growing season, which could also determine or affect the plant yield or the yield per growing area. An increase in plant biomass can be in the whole plant or in parts thereof such as aboveground (harvestable) parts, vegetative biomass, roots and seeds.

As used herein the phrase "growth rate" refers to the increase in plant organ/tissue size per time (can be measured in $cm^2$ per day).

As used herein the phrase "plant vigor" refers to the amount (measured by weight) of tissue produced by the plant in a given time. Hence increased vigor could determine or affect the plant yield or the yield per growing time or growing area. In addition, early vigor (seed and/or seedling) results in improved field stand.

It should be noted that a plant yield can be determined under stress (e.g., abiotic stress, nitrogen-limiting conditions) and/or non-stress (normal) conditions.

As used herein, the phrase "non-stress conditions" refers to the growth conditions (e.g., water, temperature, light-dark cycles, humidity, salt concentration, fertilizer concentration in soil, nutrient supply such as nitrogen, phosphorous and/or potassium), that do not significantly go beyond the everyday climatic and other abiotic conditions that plants may encounter, and which allow optimal growth, metabolism, reproduction and/or viability of a plant at any stage in its life cycle (e.g., in a crop plant from seed to a mature plant and back to seed again). Persons skilled in the art are aware of normal soil conditions and climatic conditions for a given plant in a given geographic location. It should be noted that while the non-stress conditions may include some mild variations from the optimal conditions (which vary from one type/species of a plant to another), such variations do not cause the plant to cease growing without the capacity to resume growth.

The phrase "abiotic stress" as used herein refers to any adverse effect on metabolism, growth, reproduction and/or viability of a plant. Accordingly, abiotic stress can be induced by suboptimal environmental growth conditions such as, for example, salinity, water deprivation, flooding, freezing, low or high temperature, heavy metal toxicity, anaerobiosis, nutrient deficiency, atmospheric pollution or UV irradiation. The implications of abiotic stress are discussed in the Background section.

The phrase "abiotic stress tolerance" as used herein refers to the ability of a plant to endure an abiotic stress without suffering a substantial alteration in metabolism, growth, productivity and/or viability.

As used herein the phrase "water use efficiency (WUE)" refers to the level of organic matter produced per unit of water consumed by the plant, i.e., the dry weight of a plant in relation to the plant's water use, e.g., the biomass produced per unit transpiration.

It should be noted that improved ABST will confer plants with improved vigor also under non-stress conditions, resulting in crops having improved biomass and/or yield e.g., elongated fibers for the cotton industry, higher oil content.

The term "fiber" is usually inclusive of thick-walled conducting cells such as vessels and tracheids and to fibrillar aggregates of many individual fiber cells. Hence, the term "fiber" refers to (a) thick-walled conducting and non-conducting cells of the xylem; (b) fibers of extraxylary origin, including those from phloem, bark, ground tissue, and epidermis; and (c) fibers from stems, leaves, roots, seeds, and flowers or inflorescences (such as those of *Sorghum vulgare* used in the manufacture of brushes and brooms).

Example of fiber producing plants, include, but are not limited to, agricultural crops such as cotton, silk cotton tree (Kapok, *Ceiba pentandra*), desert willow, creosote bush, winterfat, balsa, kenaf, roselle, jute, sisal abaca, flax, corn, sugar cane, hemp, ramie, kapok, coir, bamboo, spanish moss and *Agave* spp. (e.g. sisal).

As used herein the phrase "fiber quality" refers to at least one fiber parameter which is agriculturally desired, or required in the fiber industry (further described hereinbelow). Examples of such parameters, include but are not limited to, fiber length, fiber strength, fiber fitness, fiber weight per unit length, maturity ratio and uniformity (further described hereinbelow.

Cotton fiber (lint) quality is typically measured according to fiber length, strength and fineness. Accordingly, the lint quality is considered higher when the fiber is longer, stronger and finer.

As used herein the phrase "fiber yield" refers to the amount or quantity of fibers produced from the fiber producing plant.

As used herein the term "increasing" refers to at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, increase in nitrogen use efficiency, fertilizer use efficiency, yield, seed yield, growth rate, vigor, biomass, oil content, fiber yield, fiber quality, fiber length, abiotic stress tolerance and/or water use efficiency of a plant of a plant as compared to a native plant [i.e., a plant not modified with the biomolecules (polynucleotide or polypeptides) of the invention, e.g., a non-transformed plant of the same species which is grown under the same growth conditions).

The phrase "expressing within the plant an exogenous polynucleotide" as used herein refers to upregulating the expression level of an exogenous polynucleotide within the plant by introducing the exogenous polynucleotide into a plant cell or plant and expressing by recombinant means, as further described herein below.

As used herein "expressing" refers to expression at the mRNA and optionally polypeptide level.

As used herein, the phrase "exogenous polynucleotide" refers to a heterologous nucleic acid sequence which may not be naturally expressed within the plant or which overexpression thereof in the plant is desired. The exogenous polynucleotide may be introduced into the plant in a stable or transient manner, so as to produce a ribonucleic acid (RNA) molecule and/or a polypeptide molecule. It should be noted that the exogenous polynucleotide may comprise a nucleic acid sequence which is identical or partially homologous to an endogenous nucleic acid sequence of the plant.

The term "endogenous" as used herein refers to any polynucleotide or polypeptide which is present and/or naturally expressed within a plant or a cell thereof.

According to some embodiments of the invention the exogenous polynucleotide comprises a nucleic acid sequence which is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, e.g., 100% identical to the nucleic acid sequence selected from the group consisting of SEQ ID NOs:1-467, and 785-3047.

Identity (e.g., percent homology) can be determined using any homology comparison software, including for example, the BlastN software of the National Center of Biotechnology Information (NCBI) such as by using default parameters.

According to some embodiments of the invention, the homology is a global homology, i.e., an homology over the entire amino acid or nucleic acid sequences of the invention and not over portions thereof.

According to some embodiments of the invention the exogenous polynucleotide is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the polynucleotide selected from the group consisting of SEQ ID NOs:1-467, and 785-3047.

According to some embodiments of the invention the exogenous polynucleotide is set forth by SEQ ID NO:1-467, 785-3046 or 3047.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

The term "isolated" refers to at least partially separated from the natural environment e.g., from a plant cell.

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to some embodiments of the invention, the exogenous polynucleotide of the invention encodes a polypeptide having an amino acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to the amino acid sequence selected from the group consisting of SEQ ID NOs:468-784, 3048-4333, and 4335-4682.

Homology (e.g., percent homology) can be determined using any homology comparison software, including for example, the BlastP or TBLASTN software of the National Center of Biotechnology Information (NCBI) such as by using default parameters, when starting from a polypeptide sequence; or the tBLASTX algorithm (available via the NCBI) such as by using default parameters, which compares the six-frame conceptual translation products of a nucleotide query sequence (both strands) against a protein sequence database.

Homologous sequences include both orthologous and paralogous sequences. The term "paralogous" relates to gene-duplications within the genome of a species leading to paralogous genes. The term "orthologous" relates to homologous genes in different organisms due to ancestral relationship.

One option to identify orthologues in monocot plant species is by performing a reciprocal blast search. This may be done by a first blast involving blasting the sequence-of-interest against any sequence database, such as the publicly available NCBI database which may be found at: Hypertext Transfer Protocol://World Wide Web (dot) ncbi (dot) nlm (dot) nih (dot) gov. If orthologues in rice were sought, the sequence-of-interest would be blasted against, for example, the 28,469 full-length cDNA clones from Oryza sativa Nipponbare available at NCBI. The blast results may be filtered. The full-length sequences of either the filtered results or the non-filtered results are then blasted back (second blast) against the sequences of the organism from which the sequence-of-interest is derived. The results of the first and second blasts are then compared. An orthologue is identified when the sequence resulting in the highest score (best hit) in the first blast identifies in the second blast the query sequence (the original sequence-of-interest) as the best hit. Using the same rational a paralogue (homolog to a gene in the same organism) is found. In case of large sequence families, the ClustalW program may be used [Hypertext Transfer Protocol://World Wide Web (dot) ebi (dot) ac (dot) uk/Tools/clustalw2/index (dot) html], followed by a neighbor-joining tree (Hypertext Transfer Protocol://en (dot) wikipedia (dot) org/wiki/Neighbor-joining) which helps visualizing the clustering.

According to some embodiments of the invention, the exogenous polynucleotide encodes a polypeptide consisting of the amino acid sequence set forth by SEQ ID NO:468-784, 3048-4333, 4335-4682 or 4334.

Nucleic acid sequences encoding the polypeptides of the present invention may be optimized for expression. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N[(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A Table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization Tables such as those provided on-line at the Codon Usage Database through the NIRS (National Institute of Agrobiological Sciences) DNA bank in Japan (Hypertext Transfer Protocol://World Wide Web (dot) kazusa (dot) or (dot) jp/codon/). The Codon Usage Database contains codon usage tables for a number of different species, with each codon usage Table having been statistically determined based on the data present in Genbank.

By using the above Tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

According to some embodiments of the invention, the exogenous polynucleotide is a non-coding RNA.

As used herein the phrase "non-coding RNA" refers to an RNA molecule which does not encode an amino acid sequence (a polypeptide). Examples of such non-coding RNA molecules include, but are not limited to, an antisense RNA, a pre-miRNA (precursor of a microRNA), or a precursor of a Piwi-interacting RNA (piRNA).

Non-limiting examples of non-coding RNA polynucleotides are provided in SEQ ID NOs:214, 215, 216, 466, 467, 967, 968, 969, and 1575.

Thus, the invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

The invention provides an isolated polynucleotide comprising a nucleic acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the polynucleotide selected from the group consisting of SEQ ID NOs:1-467, and 785-3047.

According to some embodiments of the invention the nucleic acid sequence is capable of increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant.

According to some embodiments of the invention the isolated polynucleotide comprising the nucleic acid sequence selected from the group consisting of SEQ ID NOs:1-467, and 785-3047.

According to some embodiments of the invention the isolated polynucleotide is set forth by SEQ ID NO:1-467, 785-3046 or 3047.

The invention provides an isolated polynucleotide comprising a nucleic acid sequence encoding a polypeptide which comprises an amino acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to the amino acid sequence selected from the group consisting of SEQ ID NO:468-784, 3048-4333, and 4335-4682.

According to some embodiments of the invention the amino acid sequence is capable of increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant.

The invention provides an isolated polynucleotide comprising a nucleic acid sequence encoding a polypeptide which comprises the amino acid sequence selected from the group consisting of SEQ ID NOs:468-784, 3048-4333, 4335-4682 and 4334.

The invention provides an isolated polypeptide comprising an amino acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to an amino acid sequence selected from the group consisting of SEQ ID NO: 468-784, 3048-4333, and 4335-4682.

According to some embodiments of the invention, the polypeptide comprising an amino acid sequence selected from the group consisting of SEQ ID NOs:468-784, 3048-4333, 4335-4682 and 4334.

According to some embodiments of the invention, the polypeptide is set forth by SEQ ID NO: 468-784, 3048-4333, 4335-4682 or 4334.

According to some embodiments of the invention, there is provided a nucleic acid construct comprising the isolated polynucleotide of the invention, and a promoter for directing transcription of the nucleic acid sequence of the isolated polynucleotide in a host cell.

The invention also encompasses fragments of the above described polypeptides and polypeptides having mutations, such as deletions, insertions or substitutions of one or more amino acids, either naturally occurring or man induced, either randomly or in a targeted fashion.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalypfus* spp., *Euclea schimperi*, *Eulalia* vi/losa, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, to *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barely, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present invention.

According to some embodiments of the invention, the plant used by the method of the invention is a crop plant such as rice, maize, wheat, barley, peanut, potato, sesame, olive tree, palm oil, banana, soybean, sunflower, canola, sugarcane, alfalfa, millet, leguminosae (bean, pea), flax, lupinus, rapeseed, tobacco, poplar and cotton.

According to some embodiments of the invention, there is provided a plant cell exogenously expressing the polynucleotide of some embodiments of the invention, the nucleic acid construct of some embodiments of the invention and/or the polypeptide of some embodiments of the invention.

According to some embodiments of the invention, expressing the exogenous polynucleotide of the invention within the plant is effected by transforming one or more cells of the plant with the exogenous polynucleotide, followed by generating a mature plant from the transformed cells and cultivating the mature plant under conditions suitable for expressing the exogenous polynucleotide within the mature plant.

According to some embodiments of the invention, the transformation is effected by introducing to the plant cell a nucleic acid construct which includes the exogenous polynucleotide of some embodiments of the invention and at least one promoter for directing transcription of the exogenous polynucleotide in a host cell (a plant cell). Further details of suitable transformation approaches are provided hereinbelow.

As mentioned, the nucleic acid construct according to some embodiments of the invention comprises a promoter sequence and the isolated polynucleotide of the invention.

According to some embodiments of the invention, the isolated polynucleotide is operably linked to the promoter sequence.

A coding nucleic acid sequence is "operably linked" to a regulatory sequence (e.g., promoter) if the regulatory sequence is capable of exerting a regulatory effect on the coding sequence linked thereto.

As used herein, the term "promoter" refers to a region of DNA which lies upstream of the transcriptional initiation site of a gene to which RNA polymerase binds to initiate transcription of RNA. The promoter controls where (e.g., which portion of a plant) and/or when (e.g., at which stage or condition in the lifetime of an organism) the gene is expressed.

According to some embodiments of the invention the promoter is heterologous to the isolated polynucleotide (e.g., derived from another gene or species with respect to the isolated polynucleotide).

According to some embodiments of the invention the promoter is heterologous to the host cell (e.g., derived from another cell type, or species with respect to the host cell).

According to some embodiments of the invention the promoter is heterologous to the isolated polynucleotide and to the host cell.

Any suitable promoter sequence can be used by the nucleic acid construct of the present invention. Preferably the promoter is a constitutive promoter, a tissue-specific, or an abiotic stress-inducible promoter.

Suitable constitutive promoters include, for example, CaMV 35S promoter (SEQ ID NO:4685; Odell et al., Nature 313:810-812, 1985); Arabidopsis At6669 promoter (SEQ ID NO:4684; see PCT Publication No. WO04081173A2); Arabidopsis new At6669 promoter (SEQ ID NO:4687); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al, Plant J Nov; 2(6):837-44, 1992); ubiquitin (Christensen et al, Plant Mol. Biol. 18: 675-689, 1992); Rice cyclophilin (Bucholz et al, Plant Mol. Biol. 25(5):837-43, 1994); Maize H3 histone (Lepetit et al, Mol. Gen. Genet. 231: 276-285, 1992); Actin 2 (An et al, Plant J. 10(1); 107-121, 1996) and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.

Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], seed-preferred promoters [e.g., Napin (originated from Brassica napus which is characterized by a seed specific promoter activity; Stuitje A. R. et. al. Plant Biotechnology Journal 1 (4): 301-309; SEQ ID NO:4686), from seed specific genes (Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson' et al., Plant Mol. Biol. 18: 235-245, 1992), legumin (Ellis, et al. Plant Mol. Biol. 10: 203-214, 1988), Glutelin (rice) (Takaiwa, et al., Mol. Gen. Genet. 208: 15-22, 1986; Takaiwa, et al., FEBS Letts. 221: 43-47, 1987), Zein (Matzke et al Plant Mol Biol, 143). 323-32 1990), napA (Stalberg, et al, Planta 199: 515-519, 1996), Wheat SPA (Albani et al, Plant Cell, 9: 171-184, 1997), sunflower oleosin (Cummins, et al., Plant Mol. Biol. 19: 873-876, 1992)], endosperm specific promoters [e.g., wheat LMW and HMW, glutenin-1 (Mol Gen Genet. 216:81-90, 1989; NAR 17:461-2), wheat a, b and g gliadins (EMB03:1409-15, 1984), Barley ltrl promoter, barley B1, C, D hordein (Theor Appl Gen 98:1253-62, 1999; Plant J 4:343-55, 1993; Mol Gen Genet. 250:750-60, 1996), Barley DOF (Mena et al, The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al, Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (PMB 32:1029-35, 1996)], embryo specific promoters [e.g., rice OSH1 (Sato et al, Proc. Natl. Acad. Sci. USA, 93: 8117-8122), KNOX (Postma-Haarsma et al, Plant Mol. Biol. 39:257-71, 1999), rice oleosin (Wu et at, J. Biochem., 123: 386, 1998)], and flower-specific promoters [e.g., AtPRP4, chalene synthase (chsA) (Van der Meer, et al., Plant Mol. Biol. 15, 95-109, 1990), LAT52 (Twell et al Mol. Gen. Genet. 217:240-245; 1989), apetala-3], and root promoters such as the RootP promoter [SEQ ID NO:4688; Upstream region of the gene ATXTH19 (AT4G30290, Xyloglucan endotransglucosylase/hydrolase 19, described in Vissenberg K, et al. Plant Cell Physiol. 2005 January; 46(1):192-200].

Suitable abiotic stress-inducible promoters include, but not limited to, salt-inducible promoters such as RD29A (Yamaguchi-Shinozalei et al., Mol. Gen. Genet. 236:331-340, 1993); drought-inducible promoters such as maize rab17 gene promoter (Pla et. al., Plant Mol. Biol. 21:259-266, 1993), maize rab28 gene promoter (Busk et. al., Plant J. 11:1285-1295, 1997) and maize Ivr2 gene promoter (Pelleschi et. al., Plant Mol. Biol. 39:373-380, 1999); heat-inducible promoters such as heat tomato hsp80-promoter from tomato (U.S. Pat. No. 5,187,267).

The nucleic acid construct of some embodiments of the invention can further include an appropriate selectable marker and/or an origin of replication. According to some embodiments of the invention, the nucleic acid construct utilized is a shuttle vector, which can propagate both in *E. coli* (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of some embodiments of the invention can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338:274-276). The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S, and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Since processes which increase nitrogen use efficiency, fertilizer use efficiency, oil content, yield, seed yield, fiber yield, fiber quality, fiber length, growth rate, biomass, vigor and/or abiotic stress tolerance of a plant can involve multiple genes acting additively or in synergy (see, for example, in Quesda et al., Plant Physiol. 130:951-063, 2002), the present invention also envisages expressing a plurality of exogenous polynucleotides in a single host plant to thereby achieve superior effect on oil content, yield, growth rate, biomass, vigor and/or abiotic stress tolerance.

Expressing a plurality of exogenous polynucleotides in a single host plant can be effected by co-introducing multiple nucleic acid constructs, each including a different exogenous polynucleotide, into a single plant cell. The transformed cell can than be regenerated into a mature plant using the methods described hereinabove.

Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic messenger RNA including all the different exogenous polynucleotide sequences. To enable co-translation of the different polypeptides encoded by the polycistronic messenger RNA, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all different polypeptides. Alternatively, the construct can include several promoter sequences each linked to a different exogenous polynucleotide sequence.

The plant cell transformed with the construct including a plurality of different exogenous polynucleotides, can be regenerated into a mature plant, using the methods described hereinabove.

Alternatively, expressing a plurality of exogenous polynucleotides in a single host plant can be effected by introducing different nucleic acid constructs, including different exogenous polynucleotides, into a plurality of plants. The regenerated transformed plants can then be cross-bred and resultant progeny selected for superior abiotic stress tolerance, water use efficiency, fertilizer use efficiency, growth, biomass, yield and/or vigor traits, using conventional plant breeding techniques.

According to some embodiments of the invention, the method further comprising growing the plant expressing the exogenous polynucleotide under the abiotic stress.

Non-limiting examples of abiotic stress conditions include, salinity, drought, water deprivation, excess of water (e.g., flood, waterlogging), etiolation, low temperature, high temperature, heavy metal toxicity, anaerobiosis, nutrient deficiency, nutrient excess, atmospheric pollution and UV irradiation.

Thus, the invention encompasses plants exogenously expressing the polynucleotide(s), the nucleic acid constructs and/or polypeptide(s) of the invention. Once expressed within the plant cell or the entire plant, the level of the polypeptide encoded by the exogenous polynucleotide can be determined by methods well known in the art such as, activity assays, Western blots using antibodies capable of specifically binding the polypeptide, Enzyme-Linked Immuno Sorbent Assay (ELISA), radio-immuno-assays (RIA), immunohistochemistry, immunocytochemistry, immunofluorescence and the like.

Methods of determining the level in the plant of the RNA transcribed from the exogenous polynucleotide are well known in the art and include, for example, Northern blot analysis, reverse transcription polymerase chain reaction (RT-PCR) analysis (including quantitative, semi-quantitative or real-time RT-PCR) and RNA-in situ hybridization.

The sequence information and annotations uncovered by the present teachings can be harnessed in favor of classical breeding. Thus, sub-sequence data of those polynucleotides described above, can be used as markers for marker assisted selection (MAS), in which a marker is used for indirect selection of a genetic determinant or determinants of a trait of interest (e.g., biomass, growth rate, oil content, yield, abiotic stress tolerance, water use efficiency, nitrogen use efficiency and/or fertilizer use efficiency). Nucleic acid data of the present teachings (DNA or RNA sequence) may contain or be linked to polymorphic sites or genetic markers on the genome such as restriction fragment length polymorphism (RFLP), microsatellites and single nucleotide polymorphism (SNP), DNA fingerprinting (DFP), amplified fragment length polymorphism (AFLP), expression level polymorphism, polymorphism of the encoded polypeptide and any other polymorphism at the DNA or RNA sequence.

Examples of marker assisted selections include, but are not limited to, selection for a morphological trait (e.g., a gene that affects form, coloration, male sterility or resistance such as the presence or absence of awn, leaf sheath coloration, height, grain color, aroma of rice); selection for a biochemical trait (e.g., a gene that encodes a protein that can be extracted and observed; for example, isozymes and storage proteins); selection for a biological trait (e.g., pathogen races or insect biotypes based on host pathogen or host parasite interaction can be used as a marker since the genetic constitution of an organism can affect its susceptibility to pathogens or parasites).

The polynucleotides and polypeptides described hereinabove can be used in a wide range of economical plants, in a safe and cost effective manner.

Plant lines exogenously expressing the polynucleotide or the polypeptide of the invention are screened to identify those that show the greatest increase of the desired plant trait.

The effect of the transgene (the exogenous polynucleotide encoding the polypeptide) on abiotic stress tolerance can be determined using known methods such as detailed below and in the Examples section which follows.

Abiotic stress tolerance—Transformed (i.e., expressing the transgene) and non-transformed (wild type) plants are exposed to an abiotic stress condition, such as water deprivation, suboptimal temperature (low temperature, high temperature), nutrient deficiency, nutrient excess, a salt stress condition, osmotic stress, heavy metal toxicity, anaerobiosis, atmospheric pollution and UV irradiation.

Salinity tolerance assay—Transgenic plants with tolerance to high salt concentrations are expected to exhibit better germination, seedling vigor or growth in high salt. Salt stress can be effected in many ways such as, for example, by irrigating the plants with a hyperosmotic solution, by cultivating the plants hydroponically in a hyperosmotic growth solution (e.g., Hoagland solution), or by culturing the plants in a hyperosmotic growth medium [e.g., 50% Murashige-Skoog medium (MS medium)]. Since different plants vary considerably in their tolerance to salinity, the salt concentration in the irrigation water, growth solution, or growth medium can be adjusted according to the specific characteristics of the specific plant cultivar or variety, so as to inflict a mild or moderate effect on the physiology and/or morphology of the plants (for guidelines as to appropriate concentration see, Bernstein and Kafkafi, Root Growth Under Salinity Stress In: Plant Roots, The Hidden Half 3rd ed. Waisel Y, Eshel A and Kafkafi U. (editors) Marcel Dekker Inc., New York, 2002, and reference therein).

For example, a salinity tolerance test can be performed by irrigating plants at different developmental stages with increasing concentrations of sodium chloride (for example 50 mM, 100 mM, 200 mM, 400 mM NaCl) applied from the bottom and from above to ensure even dispersal of salt. Following exposure to the stress condition the plants are frequently monitored until substantial physiological and/or morphological effects appear in wild type plants. Thus, the external phenotypic appearance, degree of wilting and overall success to reach maturity and yield progeny are compared between control and transgenic plants.

Quantitative parameters of tolerance measured include, but are not limited to, the average wet and dry weight, growth rate, leaf size, leaf coverage (overall leaf area), the weight of the seeds yielded, the average seed size and the number of seeds produced per plant. Transformed plants not exhibiting substantial physiological and/or morphological effects, or exhibiting higher biomass than wild-type plants, are identified as abiotic stress tolerant plants.

Osmotic tolerance test—Osmotic stress assays (including sodium chloride and mannitol assays) are conducted to determine if an osmotic stress phenotype was sodium chloride-specific or if it was a general osmotic stress related phenotype. Plants which are tolerant to osmotic stress may have more tolerance to drought and/or freezing. For salt and osmotic stress germination experiments, the medium is supplemented for example with 50 mM, 100 mM, 200 mM NaCl or 100 mM, 200 mM NaCl, 400 mM mannitol.

Drought tolerance assay/Osmoticum assay—Tolerance to drought is performed to identify the genes conferring better plant survival after acute water deprivation. To analyze whether the transgenic plants are more tolerant to drought, an osmotic stress produced by the non-ionic osmolyte sorbitol in the medium can be performed. Control and transgenic plants are germinated and grown in plant-agar plates for 4 days, after which they are transferred to plates containing 500 mM sorbitol. The treatment causes growth retardation, then both control and transgenic plants are compared, by measuring plant weight (wet and dry), yield, and by growth rates measured as time to flowering.

Conversely, soil-based drought screens are performed with plants overexpressing the polynucleotides detailed above. Seeds from control *Arabidopsis* plants, or other transgenic plants overexpressing the polypeptide of the invention are germinated and transferred to pots. Drought stress is obtained after irrigation is ceased accompanied by placing the pots on absorbent paper to enhance the soil-drying rate. Transgenic and control plants are compared to each other when the majority of the control plants develop severe wilting. Plants are re-watered after obtaining a significant fraction of the control plants displaying a severe wilting. Plants are ranked comparing to controls for each of two criteria: tolerance to the drought conditions and recovery (survival) following re-watering.

Cold stress tolerance—To analyze cold stress, mature (25 day old) plants are transferred to 4° C. chambers for 1 or 2 weeks, with constitutive light. Later on plants are moved back to greenhouse. Two weeks later damages from chilling period, resulting in growth retardation and other phenotypes, are compared between both control and transgenic plants, by measuring plant weight (wet and dry), and by comparing growth rates measured as time to flowering, plant size, yield, and the like.

Heat stress tolerance—Heat stress tolerance is achieved by exposing the plants to temperatures above 34° C. for a certain period. Plant tolerance is examined after transferring the plants back to 22° C. for recovery and evaluation after 5 days relative to internal controls (non-transgenic plants) or plants not exposed to neither cold or heat stress.

Water use efficiency—can be determined as the biomass produced per unit transpiration. To analyze WUE, leaf relative water content can be measured in control and transgenic plants. Fresh weight (FW) is immediately recorded; then leaves are soaked for 8 hours in distilled water at room temperature in the dark, and the turgid weight (TW) is recorded. Total dry weight (DW) is recorded after drying the leaves at 60° C. to a constant weight. Relative water content (RWC) is calculated according to the following Formula I:

$$RWC=[(FW-DW)/(TW-DW)]\times 100 \qquad \text{Formula I}$$

Fertilizer use efficiency—To analyze whether the transgenic plants are more responsive to fertilizers, plants are grown in agar plates or pots with a limited amount of fertilizer, as described, for example, in Examples 14, 15 and 16, hereinbelow and in Yanagisawa et al (Proc Natl Acad Sci USA. 2004; 101:7833-8). The plants are analyzed for their overall size, time to flowering, yield, protein content of shoot and/or grain. The parameters checked are the overall size of the mature plant, its wet and dry weight, the weight of the seeds yielded, the average seed size and the number of seeds produced per plant. Other parameters that may be tested are: the chlorophyll content of leaves (as nitrogen plant status and the degree of leaf verdure is highly correlated), amino acid and the total protein content of the seeds or other plant parts such as leaves or shoots, oil content, etc. Similarly, instead of providing nitrogen at limiting amounts, phosphate or potassium can be added at increasing concentrations. Again, the same parameters measured are the same as listed above. In this way, nitrogen use efficiency (NUE), phosphate use efficiency (PUE) and potassium use efficiency (KUE) are assessed, checking the ability of the transgenic plants to thrive under nutrient restraining conditions.

Nitrogen use efficiency—To analyze whether the transgenic plants (e.g., *Arabidopsis* plants) are more responsive to nitrogen, plant are grown in 0.75-3 mM (nitrogen deficient conditions) or 6-10 mM (optimal nitrogen concentration). Plants are allowed to grow for additional 25 days or until seed production. The plants are then analyzed for their overall size, time to flowering, yield, protein content of shoot and/or grain/seed production. The parameters checked can be the overall size of the plant, wet and dry weight, the weight of the seeds yielded, the average seed size and the number of seeds produced per plant. Other parameters that may be tested are: the chlorophyll content of leaves (as nitrogen plant status and the degree of leaf greenness is highly correlated), amino acid and the total protein content of the seeds or other plant parts such as leaves or shoots and oil content. Transformed plants not exhibiting substantial physiological and/or morphological effects, or exhibiting higher measured parameters levels than wild-type plants, are identified as nitrogen use efficient plants.

Nitrogen use efficiency assay using plantlets—The assay is done according to Yanagisawa-S. et al. with minor modifications ("Metabolic engineering with Dof1 transcription factor in plants: Improved nitrogen assimilation and growth under low-nitrogen conditions" Proc. Natl. Acad. Sci. USA 101, 7833-7838). Briefly, transgenic plants which are grown for 7-10 days in 0.5×MS [Murashige-Skoog] supplemented with a selection agent are transferred to two nitrogen-limiting conditions: MS media in which the combined nitrogen concentration ($NH_4NO_3$ and $KNO_3$) was 0.75 mM (nitrogen deficient conditions) or 6-15 mM (optimal nitrogen concentration). Plants are allowed to grow for additional 30-40 days and then photographed, individually removed from the Agar (the shoot without the roots) and immediately weighed (fresh weight) for later statistical analysis. Constructs for which only T1 seeds are available are sown on selective media and at least 20 seedlings (each one representing an independent transformation event) are carefully transferred to the nitrogen-limiting media. For constructs for which T2 seeds are available, different transformation events are analyzed. Usually, 20 randomly selected plants from each event are transferred to the nitrogen-limiting media allowed to grow for 3-4 additional weeks and individually weighed at the end of that period. Transgenic plants are compared to control plants grown in parallel under the same conditions. Mock-transgenic plants expressing the uidA reporter gene (GUS) under the same promoter or transgenic plants carrying the same promoter but lacking a reporter gene are used as control.

Nitrogen determination—The procedure for N (nitrogen) concentration determination in the structural parts of the plants involves the potassium persulfate digestion method to convert organic N to $NO_3^-$ (Purcell and King 1996 Argon. J. 88:111-113, the modified $Cd^-$ mediated reduction of $NO_3^-$ to $NO_2^-$ (Vodovotz 1996 Biotechniques 20:390-394) and the measurement of nitrite by the Griess assay (Vodovotz 1996, supra). The absorbance values are measured at 550 nm against a standard curve of $NaNO_2$. The procedure is described in details in Samonte et al. 2006 Agron. J. 98:168-176.

Germination tests—Germination tests compare the percentage of seeds from transgenic plants that could complete the germination process to the percentage of seeds from control plants that are treated in the same manner. Normal conditions are considered for example, incubations at 22° C. under 22-hour light 2-hour dark daily cycles. Evaluation of germination and seedling vigor is conducted between 4 and 14 days after planting. The basal media is 50% MS medium (Murashige and Skoog, 1962 Plant Physiology 15, 473-497).

Germination is checked also at unfavorable conditions such as cold (incubating at temperatures lower than 10° C. instead of 22° C.) or using seed inhibition solutions that contain high concentrations of an osmolyte such as sorbitol (at concentrations of 50 mM, 100 mM, 200 mM, 300 mM, 500 mM, and up to 1000 mM) or applying increasing concentrations of salt (of 50 mM, 100 mM, 200 mM, 300 mM, 500 mM NaCl).

The effect of the transgene on plant's vigor, growth rate, biomass, yield and/or oil content can be determined using known methods.

Plant vigor—The plant vigor can be calculated by the increase in growth parameters such as leaf area, fiber length, rosette diameter, plant fresh weight and the like per time.

Growth rate—The growth rate can be measured using digital analysis of growing plants. For example, images of plants growing in greenhouse on plot basis can be captured every 3 days and the rosette area can be calculated by digital analysis. Rosette area growth is calculated using the difference of rosette area between days of sampling divided by the difference in days between samples.

Evaluation of growth rate can be done by measuring plant biomass produced, rosette area, leaf size or root length per time (can be measured in $cm^2$ per day of leaf area).

Relative growth area can be calculated using Formula II.

Relative growth rate area=Regression coefficient of area along time course.

Seed yield Evaluation of the seed yield per plant can be done by measuring the amount (weight or size) or quantity (i.e., number) of dry seeds produced and harvested from 8-16 plants and divided by the number of plants.

For example, the total seeds from 8-16 plants can be collected, weighted using e.g., an analytical balance and the total weight can be divided by the number of plants. Seed yield per growing area can be calculated in the same manner while taking into account the growing area given to a single plant. Increase seed yield per growing area could be achieved by increasing seed yield per plant, and/or by increasing number of plants capable of growing in a given area.

In addition, seed yield can be determined via the weight of 1000 seeds. The weight of 1000 seeds can be determined as follows: seeds are scattered on a glass tray and a picture is taken. Each sample is weighted and then using the digital analysis, the number of seeds in each sample is calculated.

The 1000 seeds weight can be calculated using formula III:

1000 Seed Weight=number of seed in sample/sample weight×1000            Formula III:

The Harvest Index can be calculated using Formula IV

Harvest Index=Average seed yield per plant/Average dry weight            Formula IV:

Grain protein concentration—Grain protein content (g grain protein $m^{-2}$) is estimated as the product of the mass of grain N (g grain N $m^{-2}$) multiplied by the N/protein conversion ratio of k-5.13 (Mosse 1990, supra). The grain protein concentration is estimated as the ratio of grain protein content per unit mass of the grain (g grain protein $kg^{-1}$ grain).

Fiber length—Fiber length can be measured using fibrograph. The fibrograph system was used to compute length in terms of "Upper Half Mean" length. The upper half mean (UHM) is the average length of longer half of the fiber distribution. The fibrograph measures length in span lengths at a given percentage point (Hypertext Transfer Protocol://World Wide Web (dot) cottoninc (dot) com/ClassificationofCotton/?Pg=4#Length).

According to some embodiments of the invention, increased yield of corn may be manifested as one or more of the following: increase in the number of plants per growing area, increase in the number of ears per plant, increase in the number of rows per ear, number of kernels per ear row, kernel weight, thousand kernel weight (1000-weight), ear length/diameter, increase oil content per kernel and increase starch content per kernel.

As mentioned, the increase of plant yield can be determined by various parameters. For example, increased yield of rice may be manifested by an increase in one or more of the following: number of plants per growing area, number of panicles per plant, number of spikelets per panicle, number of flowers per panicle, increase in the seed filling rate, increase in thousand kernel weight (1000-weight), increase oil content per seed, increase starch content per seed, among others. An increase in yield may also result in modified architecture, or may occur because of modified architecture.

Similarly, increased yield of soybean may be manifested by an increase in one or more of the following: number of plants per growing area, number of pods per plant, number of seeds per pod, increase in the seed filling rate, increase in thousand seed weight (1000-weight), reduce pod shattering, increase oil content per seed, increase protein content per seed, among others. An increase in yield may also result in modified architecture, or may occur because of modified architecture.

Increased yield of canola may be manifested by an increase in one or more of the following: number of plants per growing area, number of pods per plant, number of seeds per pod, increase in the seed filling rate, increase in thousand seed weight (1000-weight), reduce pod shattering, increase oil content per seed, among others. An increase in yield may also result in modified architecture, or may occur because of modified architecture.

Increased yield of cotton may be manifested by an increase in one or more of the following: number of plants per growing area, number of bolls per plant, number of seeds per boll, increase in the seed filling rate, increase in thousand seed weight (1000-weight), increase oil content per seed, improve fiber length, fiber strength, among others. An increase in yield may also result in modified architecture, or may occur because of modified architecture.

Oil content—The oil content of a plant can be determined by extraction of the oil from the seed or the vegetative portion of the plant. Briefly, lipids (oil) can be removed from the plant (e.g., seed) by grinding the plant tissue in the presence of specific solvents (e.g., hexane or petroleum ether) and extracting the oil in a continuous extractor. Indirect oil content analysis can be carried out using various known methods such as Nuclear Magnetic Resonance (NMR) Spectroscopy, which measures the resonance energy absorbed by hydrogen atoms in the liquid state of the sample [See for example, Conway T F. and Earle F R., 1963, Journal of the American Oil Chemists' Society; Springer Berlin/Heidelberg, ISSN: 0003-021X (Print) 1558-9331 (Online)]; the Near Infrared (NI) Spectroscopy, which utilizes the absorption of near infrared energy (1100-2500 nm) by the sample; and a method described in WO/2001/023884, which is based on extracting oil a solvent, evaporating the solvent in a gas stream which forms oil particles, and directing a light into the gas stream and oil particles which forms a detectable reflected light.

Thus, the present invention is of high agricultural value for promoting the yield of commercially desired crops (e.g., biomass of vegetative organ such as poplar wood, or reproductive organ such as number of seeds or seed biomass).

Any of the transgenic plants described hereinabove or parts thereof may be processed to produce a feed, meal, protein or oil preparation, such as for ruminant animals.

The transgenic plants described hereinabove, which exhibit an increased oil content can be used to produce plant oil (by extracting the oil from the plant).

The plant oil (including the seed oil and/or the vegetative portion oil) produced according to the method of the invention may be combined with a variety of other ingredients. The specific ingredients included in a product are determined according to the intended use. Exemplary products include animal feed, raw material for chemical modification, biodegradable plastic, blended food product, edible oil, biofuel, cooking oil, lubricant, biodiesel, snack food, cosmetics, and fermentation process raw material. Exemplary products to be incorporated to the plant oil include animal feeds, human food products such as extruded snack foods, breads, as a food binding agent, aquaculture feeds, fermentable mixtures, food supplements, sport drinks, nutritional food bars, multi-vitamin supplements, diet drinks, and cereal foods.

According to some embodiments of the invention, the oil comprises a seed oil.

According to some embodiments of the invention, the oil comprises a vegetative portion oil.

According to some embodiments of the invention, the plant cell forms a part of a plant.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", an and the include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Experimental and Bioinformatics Methods

RNA extraction—Tissues growing at various growth conditions (as described below) were sampled and RNA was extracted using TRIzol Reagent from Invitrogen [Hypertext Transfer Protocol://World Wide Web (dot) invitrogen (dot) com/content (dot)cfm?pageid=469]. Approximately 30-50 mg of tissue was taken from samples. The weighed tissues were ground using pestle and mortar in liquid nitrogen and resuspended in 500 ml of TRIzol Reagent. To the homogenized lysate, 100 ml of chloroform was added followed by precipitation using isopropanol and two washes with 75% ethanol. The RNA was eluted in 30 ml of RNase-free water. RNA samples were cleaned up using Qiagen's RNeasy minikit clean-up protocol as per the manufacturer's protocol (QIAGEN Inc, CA USA). For convenience, each micro-array expression information tissue type has received an expression Set ID.

Correlation analysis—was performed for selected genes according to some embodiments of the invention, in which the characterized parameters (measured parameters according to the correlation IDs) were used as "x axis" for correlation with the tissue transcriptom which was used as the "Y axis". For each gene and measured parameter a correlation coefficient "R" was calculated (using Pearson correlation) along with a p-value for the significance of the correlation. When the correlation coefficient (R) between the levels of a gene's expression in a certain tissue and a phenotypic performance across ecotypes/variety/hybrid is high in absolute value (between 0.5-1), there is an association between the gene (specifically the expression level of this gene) the phenotypic characteristic (e.g., improved nitrogen use efficiency, abiotic stress tolerance, yield, growth rate and the like).

Example 1

Identifying Genes which Increase Nitrogen Use Efficiency (NUE), Fertilizer Use Efficiency (FUE), Yield, Growth Rate, Vigor, Biomass, Oil Content, Abiotic Stress Tolerance (ABST) and/or Water Use Efficiency (WUE) in Plants The present inventors have identified polynucleotides which upregulation of expression thereof in plants increases nitrogen use efficiency (NUE), fertilizer use efficiency (FUE), yield (e.g., seed yield, oil yield, biomass, grain quantity and/or quality), growth rate, vigor, biomass, oil content, fiber yield, fiber quality, fiber length, abiotic stress tolerance (ABST) and/or water use efficiency (WUE) of a plant.

All nucleotide sequence datasets used here were originated from publicly available databases or from performing sequencing using the Solexa technology (e.g. Barley and Sorghum). Sequence data from 100 different plant species was introduced into a single, comprehensive database. Other information on gene expression, protein annotation, enzymes and pathways were also incorporated. Major databases used include:

Genomes

Arabidopsis genome [TAIR genome version 6 (Hypertext Transfer Protocol://World Wide Web (dot) arabidopsis (dot) org/)]

Rice genome [IRGSP build 4.0 (Hypertext Transfer Protocol://rgp (dot) dna (dot) affrc (dot) go (dot) jp/IRGSP/)].

Poplar [Populus trichocarpa release 1.1 from JGI (assembly release v1.0) (Hypertext Transfer Protocol://World Wide Web (dot) genome (dot) jgi-psf (dot) org/)]

Brachypodium [JGI 4× assembly, Hypertext Transfer Protocol://World Wide Web (dot) brachypodium (dot) org)]

Soybean [DOE-JGI SCP, version GlymaO (Hypertext Transfer Protocol://World Wide Web (dot) phytozome (dot) net/)]

Grape [French-Italian Public Consortium for Grapevine Genome Characterization grapevine genome (Hypertext Transfer Protocol://World Wide Web (dot) genoscope (dot) cns (dot) fr/)]

Castobean [TIGR/J Craig Venter Institute 4× assembly [(Hypertext Transfer Protocol://msc (dot) jcvi (dot) org/ r_communis]

*Sorghum* [DOE-JGI SCP, version Sbi 1 [Hypertext Transfer Protocol://World Wide Web (dot) phytozome (dot) net/)].

Maize [Hypertext Transfer Protocol://maizesequence (dot) org/]

Cucumber [Hypertext Transfer Protocol://cucumber (dot) genomics (dot) org (dot) cn/page/cucumber/index (dot) jsp]

Tomato [Hypertext Transfer Protocol://solgenomics (dot) net/tomato/]

Cassava [Hypertext Transfer Protocol://www (dot) phytozome (dot) net/cassaya (dot) php]

Expressed EST and mRNA Sequences were Extracted from the Following Databases:

GenBank (Hypertext Transfer Protocol://World Wide Web (dot) ncbi (dot) nlm (dot) nih (dot) gov/Genbank/).

RefSeq (Hypertext Transfer Protocol://World Wide Web (dot) ncbi (dot) nlm (dot) nih (dot) gov/RefSeq/).

TAIR (Hypertext Transfer Protocol://World Wide Web (dot) *arabidopsis* (dot) org/).

Protein and Pathway Databases

Uniprot [Hypertext Transfer Protocol://World Wide Web (dot) uniprot (dot) org/].

AraCyc [Hypertext Transfer Protocol://World Wide Web (dot) *arabidopsis* (dot) org/biocyc/index (dot) jsp].

ENZYME [Hypertext Transfer Protocol://expasy (dot) org/enzyme/].

Microarray Datasets were Downloaded from:

GEO (Hypertext Transfer Protocol://World Wide Web.ncbi.nlm.nih.gov/geo/)

TAIR (Hypertext Transfer Protocol://World Wide Web.arabidopsis.org/).

Proprietary micro-array data (See WO2008/122980 and Examples 3-10 below).

QTL and SNPs Information

Gramene [Hypertext Transfer Protocol://World Wide Web (dot) gramene (dot) org/qtl/].

Panzea [Hypertext Transfer Protocol://World Wide Web (dot) panzea (dot) org/index (dot) html].

Soybean QTL: [Hypertext Transfer Protocol://World Wide Web (dot) soybeanbreederstoolbox(dot) com/].

Database Assembly—was performed to build a wide, rich, reliable annotated and easy to analyze database comprised of publicly available genomic mRNA, ESTs DNA sequences, data from various crops as well as gene expression, protein annotation and pathway, QTLs data, and other relevant information.

Database assembly is comprised of a toolbox of gene refining, structuring, annotation and analysis tools enabling to construct a tailored database for each gene discovery project. Gene refining and structuring tools enable to reliably detect splice variants and antisense transcripts, generating understanding of various potential phenotypic outcomes of a single gene. The capabilities of the "LEADS" platform of Compugen LTD for analyzing human genome have been confirmed and accepted by the scientific community [see e.g., "Widespread Antisense Transcription", Yelin, et al. (2003) Nature Biotechnology 21, 379-85; "Splicing of Alu Sequences", Lev-Maor, et al. (2003) Science 300 (5623), 1288-91; "Computational analysis of alternative splicing using EST tissue information", Xie H et al. Genomics 2002], and have been proven most efficient in plant genomics as well.

EST clustering and gene assembly—For gene clustering and assembly of organisms with available genome sequence data (arabidopsis, rice, castorbean, grape, brachypodium, poplar, soybean, sorghum) the genomic LEADS version (GANG) was employed. This tool allows most accurate clustering of ESTs and mRNA sequences on genome, and predicts gene structure as well as alternative splicing events and anti-sense transcription.

For organisms with no available full genome sequence data, "expressed LEADS" clustering software was applied.

Gene annotation—Predicted genes and proteins were annotated as follows:

Sequences blast search [Hypertext Transfer Protocol://blast (dot) ncbi (dot) nlm (dot) nih (dot) gov/Blast (dot) cgi] against all plant UniProt [Hypertext Transfer Protocol://World Wide Web (dot) uniprot (dot) org/] was performed. Open reading frames of each putative transcript were analyzed and longest ORF with higher number of homologues was selected as predicted protein of the transcript. The predicted proteins were analyzed by InterPro [Hypertext Transfer Protocol://World Wide Web (dot) ebi (dot) ac (dot) uk/interpro/].

Blast against proteins from AraCyc and ENZYME databases was used to map the predicted transcripts to AraCyc pathways.

Predicted proteins from different species were compared using blast algorithm [Hypertext Transfer Protocol://World Wide Web (dot) ncbi (dot) nlm (dot) nih (dot) gov/Blast (dot) cgi] to validate the accuracy of the predicted protein sequence, and for efficient detection of orthologs.

Gene expression profiling—Several data sources were exploited for gene expression profiling, namely microarray data and digital expression profile (see below). According to gene expression profile, a correlation analysis was performed to identify genes which are co-regulated under different development stages and environmental conditions and associated with different phenotypes.

Publicly available microarray datasets were downloaded from TAIR and NCBI GEO sites, renormalized, and integrated into the database. Expression profiling is one of the most important resource data for identifying genes important for yield.

A digital expression profile summary was compiled for each cluster according to all keywords included in the sequence records comprising the cluster. Digital expression, also known as electronic Northern Blot, is a tool that displays virtual expression profile based on the EST sequences forming the gene cluster. The tool provides the expression profile of a cluster in terms of plant anatomy (e.g., the tissue/organ in which the gene is expressed), developmental stage (the developmental stages at which a gene can be found) and profile of treatment (provides the physiological conditions under which a gene is expressed such as drought, cold, pathogen infection, etc). Given a random distribution of ESTs in the different clusters, the digital expression provides a probability value that describes the probability of a cluster having a total of N ESTs to contain X ESTs from a certain collection of libraries. For the probability calculations, the following is taken into consideration: a) the number of ESTs in the cluster, b) the number of ESTs of the implicated and related libraries, c) the overall number of ESTs available representing the species. Thereby clusters with low probability values are highly enriched with ESTs from the group of libraries of interest indicating a specialized expression.

Recently, the accuracy of this system was demonstrated by Portnoy et al., 2009 (Analysis Of The Melon Fruit Transcriptome Based On 454 Pyrosequencing) in: Plant & Animal Genomes XVII Conference, San Diego, Calif. Transcriptomic analysis, based on relative EST abundance in data was performed by 454 pyrosequencing of cDNA representing mRNA of the melon fruit. Fourteen double strand cDNA samples obtained from two genotypes, two fruit tissues (flesh and rind) and four developmental stages were sequenced. GS FLX pyrosequencing (Roche/454 Life Sciences) of non-normalized and purified cDNA samples yielded 1,150,657 expressed sequence tags (ESTs) that assembled into 67,477 unigenes (32,357 singletons and 35,120 contigs). Analysis of the data obtained against the Cucurbit Genomics Database [Hypertext Transfer Protocol://World Wide Web (dot) icugi (dot) org/] confirmed the accuracy of the sequencing and assembly. Expression patterns of selected genes fitted well their qRT-PCR data.

Overall, 257 genes were identified to have a major impact on nitrogen use efficiency, fertilizer use efficiency, yield (e.g., seed yield, oil yield, grain quantity and/or quality), growth rate, vigor, biomass, oil content, fiber yield, fiber quality, fiber length, abiotic stress tolerance and/or water use efficiency when expression thereof is increased in plants. The identified genes, their curated polynucleotide and polypeptide sequences, as well as their updated sequences according to GenBank database are summarized in Table 1, hereinbelow.

TABLE 1

Identified polynucleotides for increasing nitrogen use efficiency, fertilizer use efficiency, yield, growth rate, vigor, biomass, oil content, fiber yield, fiber quality, fiber length, abiotic stress tolerance and/or water use efficiency of a plant

| Gene Name | Cluster Name | Organism | Polyn. SEQ ID NO: | Polyp. SEQ ID NO: |
|---|---|---|---|---|
| LNU1 | arabidopsis\|gb165\|AT5G11630 | arabidopsis | 1 | 468 |
| LNU2 | rice\|gb157.2\|BI798989 | rice | 2 | 469 |
| LNU3 | rice\|gb157.2\|AK106493 | rice | 3 | 470 |
| LNU4 | barley\|gb157.3\|BI953357 | barley | 4 | 471 |
| LNU5 | barley\|gb157.3\|BE421774 | barley | 5 | 472 |
| LNU6 | soybean\|gb166\|BI942460 | soybean | 6 | 473 |
| LNU7 | soybean\|gb166\|CD398173 | soybean | 7 | 474 |
| LNU8 | arabidopsis\|gb165\|AT3G18200 | arabidopsis | 8 | 475 |
| LNU9 | rice\|gb157.2\|AU066136 | rice | 9 | 476 |
| LNU10 | rice\|gb157.2\|CB678538 | rice | 10 | 477 |
| LNU11 | rice\|gb157.2\|CB641645 | rice | 11 | 478 |
| LNU12 | rice\|gb157.2\|Y11415 | rice | 12 | 479 |
| LNU13 | rice\|gb157.2\|BI805840 | rice | 13 | 480 |
| LNU14 | arabidopsis\|gb165\|AT2G37860 | arabidopsis | 14 | 481 |
| LNU15 | arabidopsis\|gb165\|AT3G07420 | arabidopsis | 15 | 482 |
| LNU17 | rice\|gb157.2\|BF430745 | rice | 16 | 483 |
| LNU19 | rice\|gb157.2\|CB642397 | rice | 17 | 484 |
| LNU20 | tomato\|gb164\|BG131270 | tomato | 18 | 485 |
| LNU23 | arabidopsis\|gb165\|AT1G23120 | arabidopsis | 19 | 486 |
| LNU24 | arabidopsis\|gb165\|AT1G33110 | arabidopsis | 20 | 487 |
| LNU25 | sorghum\|gb161.xeno\|BE355836 | sorghum | 21 | 488 |
| LNU27 | barley\|gb157.3\|BE196470 | barley | 22 | 489 |
| LNU28 | barley\|gb157.3\|AL500488 | barley | 23 | 490 |
| LNU29 | tomato\|gb164\|AI487919 | tomato | 24 | 491 |
| LNU32 | sorghum\|gb161.xeno\|AW671708 | sorghum | 25 | 492 |
| LNU33 | soybean\|gb166\|CD408405 | soybean | 26 | 493 |
| LNU34 | rice\|gb157.2\|AU030308 | rice | 27 | 494 |
| LNU35 | wheat\|gb164\|BE442655 | wheat | 28 | 495 |
| LNU36 | soybean\|gb168\|BE347766 | soybean | 29 | 496 |
| LNU37 | rice\|gb157.2\|CA767513 | rice | 30 | 497 |
| LNU40 | rice\|gb157.2\|OSU76004 | rice | 31 | 498 |
| LNU43 | soybean\|gb166\|AW349541 | soybean | 32 | 499 |
| LNU44 | soybean\|gb166\|GMU12150 | soybean | 33 | 500 |
| LNU45 | soybean\|gb166\|AW508359 | soybean | 34 | 501 |
| LNU46 | soybean\|gb166\|AW348273 | soybean | 35 | 502 |
| LNU48 | rice\|gb157.3\|BI806333 | rice | 36 | 503 |
| LNU50 | rice\|gb157.3\|AK070604 | rice | 37 | 504 |
| LNU51 | rice\|gb157.3\|AA751405 | rice | 38 | 505 |
| LNU52 | rice\|gb157.3\|AF042333 | rice | 39 | 506 |
| LNU53 | soybean\|gb168\|CA782562 | soybean | 40 | 507 |
| LNU54 | soybean\|gb168\|BF518437 | soybean | 41 | 508 |
| LNU55 | soybean\|gb168\|BQ080255 | soybean | 42 | 509 |
| LNU56 | soybean\|gb168\|BE352719 | soybean | 43 | 510 |
| LNU57 | wheat\|gb164\|BE405851 | wheat | 44 | 511 |
| LNU58 | wheat\|gb164\|BE585823 | wheat | 45 | 512 |
| LNU59 | wheat\|gb164\|BE515786 | wheat | 46 | 513 |
| LNU60 | wheat\|gb164\|BQ901296 | wheat | 47 | 514 |
| LNU61 | wheat\|gb164\|BE498157 | wheat | 48 | 515 |
| LNU63 | wheat\|gb164\|BF429186 | wheat | 49 | 516 |
| LNU64 | wheat\|gb164\|BU100011 | wheat | 50 | 517 |
| LNU65 | rice\|gb157.3\|C28856 | rice | 51 | 518 |
| LNU67 | rice\|gb157.3\|AA749717 | rice | 52 | 519 |
| LNU68 | rice\|gb157.3\|BM421254 | rice | 53 | 520 |
| LNU69 | rice\|gb157.3\|AF458088 | rice | 54 | 521 |
| LNU70 | rice\|gb170\|OS11G48080 | rice | 55 | 522 |
| LNU71 | rice\|gb157.3\|AF210325 | rice | 56 | 523 |
| LNU72 | barley\|gb157.3\|BI954541 | barley | 57 | 524 |
| LNU73 | rice\|gb157.3\|AA754527 | rice | 58 | 525 |
| LNU74 | poplar\|gb170\|AI164893 | poplar | 59 | 526 |

TABLE 1-continued

Identified polynucleotides for increasing nitrogen use efficiency, fertilizer use efficiency, yield, growth rate, vigor, biomass, oil content, fiber yield, fiber quality, fiber length, abiotic stress tolerance and/or water use efficiency of a plant

| Gene Name | Cluster Name | Organism | Polyn. SEQ ID NO: | Polyp. SEQ ID NO: |
|---|---|---|---|---|
| LNU75 | soybean|gb168|AW690409 | soybean | 60 | 527 |
| LNU76 | rice|gb157.3|AA752216 | rice | 61 | 528 |
| LNU79 | cotton|gb164|BF272356 | cotton | 62 | 529 |
| LNU81 | barley|gb157.3|BE421380 | barley | 63 | 530 |
| LNU82 | rice|gb157.3|AU031357 | rice | 64 | 531 |
| LNU83 | soybean|gb168|AW471606 | soybean | 65 | 532 |
| LNU84 | sorghum|gb161.xeno|AI714503 | sorghum | 66 | 533 |
| LNU85 | sorghum|gb161.xeno|AI941787 | sorghum | 67 | 534 |
| LNU86 | maize|gb169.2|AI941972 | maize | 68 | 535 |
| LNU87 | sorghum|gb161.crp|BM325119 | sorghum | 69 | 536 |
| LNU89 | wheat|gb164|BQ236209 | wheat | 70 | 537 |
| LNU94 | tomato|gb164|BF113903 | tomato | 71 | 538 |
| LNU95 | soybean|gb168|BQ741102 | soybean | 72 | 539 |
| LNU96 | rice|gb157.3|AA751884 | rice | 73 | 540 |
| LNU98 | maize|gb164|AI947517 | maize | 74 | 541 |
| LNU100 | cotton|gb164|AI055197 | cotton | 75 | 542 |
| LNU101 | rice|gb157.3|NM001061106 | rice | 76 | 543 |
| LNU104 | soybean|gb168|BQ610458 | soybean | 77 | 544 |
| LNU105 | wheat|gb164|BG606394 | wheat | 78 | 545 |
| LNU106 | wheat|gb164|BF201718 | wheat | 79 | 546 |
| LNU107 | rice|gb157.3|BE040237 | rice | 80 | 547 |
| LNU109 | rice|gb157.3|AU032452 | rice | 81 | 548 |
| LNU110 | rice|gb157.3|CA755769 | rice | 82 | 549 |
| LNU112 | rice|gb157.3|AU057246 | rice | 83 | 550 |
| LNU113 | maize|gb164|AA054793 | maize | 84 | 551 |
| LNU114 | rice|gb157.3|AA752410 | rice | 85 | 552 |
| LNU115 | rice|gb157.3|CB635059 | rice | 86 | 553 |
| LNU116 | rice|gb170|OS10G28240 | rice | 87 | 554 |
| LNU117 | rice|gb157.3|AU081366 | rice | 88 | 555 |
| LNU118 | rice|gb157.3|AU098344 | rice | 89 | 556 |
| LNU119 | rice|gb157.3|AK063703 | rice | 90 | 557 |
| LNU120 | rice|gb170|OS02G37380 | rice | 91 | 558 |
| LNU121 | rice|gb157.3|AU166339 | rice | 92 | 559 |
| LNU122 | rice|gb157.3|BI813219 | rice | 93 | 560 |
| LNU123 | arabidopsis|gb165|AT1G63850 | arabidopsis | 94 | 561 |
| LNU124 | arabidopsis|gb165|AT5G54130T2 | arabidopsis | 95 | 562 |
| LNU126 | arabidopsis|gb165|AT5G58770 | arabidopsis | 96 | 563 |
| LNU127 | arabidopsis|gb165|AT5G61820 | arabidopsis | 97 | 564 |
| LNU128 | arabidopsis|gb165|AT1G21690 | arabidopsis | 98 | 565 |
| LNU129 | arabidopsis|gb165|AT1G53450 | arabidopsis | 99 | 566 |
| LNU130 | arabidopsis|gb165|AT1G76560 | arabidopsis | 100 | 567 |
| LNU131 | arabidopsis|gb165|AT2G41950 | arabidopsis | 101 | 568 |
| LNU132 | arabidopsis|gb165|AT1G68440 | arabidopsis | 102 | 569 |
| LNU133 | arabidopsis|gb165|AT1G72020 | arabidopsis | 103 | 570 |
| LNU134 | arabidopsis|gb165|AT4G12000 | arabidopsis | 104 | 571 |
| LNU135 | arabidopsis|gb165|AT4G38800 | arabidopsis | 105 | 572 |
| LNU136 | arabidopsis|gb165|AT3G26440 | arabidopsis | 106 | 573 |
| LNU138 | barley|gb157.3|AL500952 | barley | 107 | 574 |
| LNU140 | arabidopsis|gb165|AT1G62430 | arabidopsis | 108 | 575 |
| LNU141 | wheat|gb164|BE604062 | wheat | 109 | 576 |
| LNU142 | barley|gb157.3|AJ472814 | barley | 110 | 577 |
| LNU143 | cotton|gb164|BG443936 | cotton | 111 | 578 |
| LNU146 | rice|gb157.3|AA754467 | rice | 112 | 579 |
| LNU147 | cotton|gb164|DT462051 | cotton | 113 | 580 |
| LNU148 | soybean|gb168|CD394513 | soybean | 114 | 581 |
| LNU149 | rice|gb157.3|AK110423 | rice | 115 | 582 |
| LNU150 | cotton|gb164|AW186819 | cotton | 116 | 583 |
| LNU153 | rice|gb157.3|AU166793 | rice | 117 | 584 |
| LNU154 | cotton|gb164|AI054586 | cotton | 118 | 585 |
| LNU155 | cotton|gb164|CO101542 | cotton | 119 | 586 |
| LNU157 | soybean|gb166|CF921687 | soybean | 120 | 587 |
| LNU158 | cotton|gb164|CO082594 | cotton | 121 | 588 |
| LNU161 | soybean|gb168|BE661583 | soybean | 122 | 589 |
| LNU168 | sorghum|gb161.crp|AW927746 | sorghum | 123 | 590 |
| LNU170 | arabidopsis|gb165|AT5G40060 | arabidopsis | 124 | 591 |
| LNU171 | barley|gb157.3|AL501130 | barley | 125 | 592 |
| LNU172 | barley|gb157.3|BI777246 | barley | 126 | 593 |
| LNU173 | barley|gb157.3|BE437951 | barley | 127 | 594 |
| LNU175 | arabidopsis|gb165|AT4G28290 | arabidopsis | 128 | 595 |
| LNU176 | rice|gb157.3|AU062564 | rice | 129 | 596 |
| LNU177 | arabidopsis|gb165|AT1G67740 | arabidopsis | 130 | 597 |
| LNU178 | arabidopsis|gb165|AT1G18300 | arabidopsis | 131 | 598 |

TABLE 1-continued

Identified polynucleotides for increasing nitrogen use efficiency, fertilizer use efficiency, yield, growth rate, vigor, biomass, oil content, fiber yield, fiber quality, fiber length, abiotic stress tolerance and/or water use efficiency of a plant

| Gene Name | Cluster Name | Organism | Polyn. SEQ ID NO: | Polyp. SEQ ID NO: |
|---|---|---|---|---|
| LNU179 | arabidopsis\|gb165\|AT1G53560 | arabidopsis | 132 | 599 |
| LNU180 | arabidopsis\|gb165\|AT1G70230 | arabidopsis | 133 | 600 |
| LNU181 | arabidopsis\|gb165\|AT3G57940 | arabidopsis | 134 | 601 |
| LNU182 | arabidopsis\|gb165\|AT3G08980 | arabidopsis | 135 | 602 |
| LNU183 | arabidopsis\|gb165\|AT1G58340 | arabidopsis | 136 | 603 |
| LNU184 | arabidopsis\|gb165\|AT3G52230 | arabidopsis | 137 | 604 |
| LNU185 | arabidopsis\|gb165\|AT3G63160 | arabidopsis | 138 | 605 |
| LNU186 | arabidopsis\|gb165\|AT2G03350 | arabidopsis | 139 | 606 |
| LNU187 | arabidopsis\|gb165\|AT5G01540 | arabidopsis | 140 | 607 |
| LNU188 | soybean\|gb166\|BU547183 | soybean | 141 | 608 |
| LNU189 | rice\|gb157.3\|BE230329 | rice | 142 | 609 |
| LNU190 | canola\|gb161\|DY007527 | canola | 143 | 610 |
| LNU191 | rice\|gb157.3\|CA753062 | rice | 144 | 611 |
| LNU192 | rice\|gb157.3\|BE040846 | rice | 145 | 612 |
| LNU196 | rice\|gb157.3\|BI809290 | rice | 146 | 613 |
| LNU198 | cotton\|gb164\|CO078561 | cotton | 147 | 614 |
| LNU200 | tomato\|gb164\|BG791292 | tomato | 148 | 615 |
| LNU202 | sorghum\|gb161.xeno\|BE362397 | sorghum | 149 | 616 |
| LNU206 | arabidopsis\|gb165\|AT2G31890 | arabidopsis | 150 | 617 |
| LNU207 | arabidopsis\|gb165\|AT1G70260 | arabidopsis | 151 | 618 |
| LNU210 | arabidopsis\|gb165\|AT3G61060 | arabidopsis | 152 | 619 |
| LNU211 | arabidopsis\|gb165\|AT5G06270 | arabidopsis | 153 | 620 |
| LNU212 | arabidopsis\|gb165\|AT1G28400 | arabidopsis | 154 | 621 |
| LNU213 | arabidopsis\|gb165\|AT5G11690 | arabidopsis | 155 | 622 |
| LNU214 | arabidopsis\|gb165\|AT1G19020 | arabidopsis | 156 | 623 |
| LNU215 | arabidopsis\|gb165\|AT1G08570 | arabidopsis | 157 | 624 |
| LNU216 | rice\|gb157.3\|BI804955 | rice | 158 | 625 |
| LNU217 | rice\|gb157.3\|AT003632 | rice | 159 | 626 |
| LNU218 | arabidopsis\|gb165\|AT5G35460 | arabidopsis | 160 | 627 |
| LNU219 | arabidopsis\|gb165\|AT4G19400 | arabidopsis | 161 | 628 |
| LNU220 | rice\|gb157.3\|AW155256 | rice | 162 | 629 |
| LNU222 | wheat\|gb164\|BE400657 | wheat | 163 | 630 |
| LNU223 | rice\|gb157.3\|BI798260 | rice | 164 | 631 |
| LNU224 | barley\|gb157.3\|BF628111 | barley | 165 | 632 |
| LNU225 | arabidopsis\|gb165\|AT4G27050 | arabidopsis | 166 | 633 |
| LNU228 | barley\|gb157.3\|BF622377 | barley | 167 | 634 |
| LNU229 | tomato\|gb164\|AI484048 | tomato | 168 | 635 |
| LNU230 | rice\|gb157.3\|AU091786 | rice | 169 | 636 |
| LNU232 | rice\|gb157.2\|CA754695 | rice | 170 | 637 |
| LNU234 | arabidopsis\|gb165\|AT1G22140 | arabidopsis | 171 | 638 |
| LNU235 | arabidopsis\|gb165\|AT1G33590 | arabidopsis | 172 | 639 |
| LNU236 | cotton\|gb164\|AI728962 | cotton | 173 | 640 |
| LNU239 | rice\|gb157.2\|BE530901 | rice | 174 | 641 |
| LNU240 | barley\|gb157.3\|AV914239 | barley | 175 | 642 |
| LNU241 | rice\|gb157.2\|CA756471 | rice | 176 | 643 |
| LNU242 | arabidopsis\|gb165\|AT4G01650 | arabidopsis | 177 | 644 |
| LNU243 | barley\|gb157.3\|BQ467891 | barley | 178 | 645 |
| LNU244 | barley\|gb157.3\|AV932151 | barley | 179 | 646 |
| LNU245 | tomato\|gb164\|AI486625 | tomato | 180 | 647 |
| LNU246 | tomato\|gb164\|AI896232 | tomato | 181 | 648 |
| LNU247 | arabidopsis\|gb165\|AT5G15170 | arabidopsis | 182 | 649 |
| LNU249 | arabidopsis\|gb165\|AT5G04980 | arabidopsis | 183 | 650 |
| LNU250 | arabidopsis\|gb165\|AT1G30860 | arabidopsis | 184 | 651 |
| LNU251 | arabidopsis\|gb165\|AT4G04940 | arabidopsis | 185 | 652 |
| LNU253 | soybean\|gb166\|CD407540 | soybean | 186 | 653 |
| LNU254 | arabidopsis\|gb165\|AT1G47670 | arabidopsis | 187 | 654 |
| LNU255 | arabidopsis\|gb165\|AT2G42760 | arabidopsis | 188 | 655 |
| LNU256 | arabidopsis\|gb165\|AT2G43920 | arabidopsis | 189 | 656 |
| LNU257 | arabidopsis\|gb165\|AT3G12090 | arabidopsis | 190 | 657 |
| LNU258 | arabidopsis\|gb165\|AT4G37330 | arabidopsis | 191 | 658 |
| LNU260 | arabidopsis\|gb165\|AT5G07020 | arabidopsis | 192 | 659 |
| LNU261 | arabidopsis\|gb165\|AT5G48470 | arabidopsis | 193 | 660 |
| LNU262 | arabidopsis\|gb165\|AT5G49900 | arabidopsis | 194 | 661 |
| LNU263 | barley\|gb157.3\|AL502706 | barley | 195 | 662 |
| LNU265 | maize\|gb164\|AI396555 | maize | 196 | 663 |
| LNU265 | maize\|gb164\|AI396555 | maize | 196 | 705 |
| LNU266 | maize\|gb164\|AI438792 | maize | 197 | 664 |
| LNU267 | maize\|gb164\|AI973407 | maize | 198 | 665 |
| LNU268 | maize\|gb164\|BE123241 | maize | 199 | 666 |
| LNU271 | rice\|gb157.2\|AU089771 | rice | 200 | 667 |
| LNU274 | rice\|gb157.3\|BI305442 | rice | 201 | 668 |
| LNU275 | rice\|gb170\|OS09G35600 | rice | 202 | 669 |

TABLE 1-continued

Identified polynucleotides for increasing nitrogen use efficiency, fertilizer use efficiency, yield, growth rate, vigor, biomass, oil content, fiber yield, fiber quality, fiber length, abiotic stress tolerance and/or water use efficiency of a plant

| Gene Name | Cluster Name | Organism | Polyn. SEQ ID NO: | Polyp. SEQ ID NO: |
|---|---|---|---|---|
| LNU276 | rice\|gb157.3\|AA753720 | rice | 203 | 670 |
| LNU277 | rice\|gb157.3\|CV723478 | rice | 204 | 671 |
| LNU278 | sorghum\|gb161.xeno\|AW671348 | sorghum | 205 | 672 |
| LNU279 | sorghum\|gb161.xeno\|AW677534 | sorghum | 206 | 673 |
| LNU280 | sorghum\|gb161.crp\|BM660677 | sorghum | 207 | 674 |
| LNU282 | soybean\|gb166\|BI968975 | soybean | 208 | 675 |
| LNU284 | soybean\|gb166\|CA851742 | soybean | 209 | 676 |
| LNU287 | soybean\|gb168\|CD394819 | soybean | 210 | 677 |
| LNU288 | tomato\|gb164\|BG134658 | tomato | 211 | 678 |
| LNU289 | tomato\|gb164\|BG123295 | tomato | 212 | 679 |
| LNU222_H6 | sorghum\|gb161.crp\|AW678240 | sorghum | 213 | 680 |
| LNU125 | arabidopsis\|gb165\|AT4G04925 | arabidopsis | 214 | — |
| LNU201 | rice\|gb157.3\|BI801545 | rice | 215 | — |
| LNU233 | rice\|gb157.3\|AK107825 | rice | 216 | — |
| LNU3 | rice\|gb170\|OS03G51530 | rice | 217 | 470 |
| LNU29 | tomato\|gb164\|AI487919 | tomato | 218 | 681 |
| LNU33 | soybean\|gb168\|AL374064 | soybean | 219 | 493 |
| LNU35 | wheat\|gb164\|BE442655 | wheat | 220 | 682 |
| LNU36 | soybean\|gb168\|BE347766 | soybean | 221 | 496 |
| LNU53 | soybean\|gb168\|CA782562 | soybean | 222 | 683 |
| LNU55 | soybean\|gb168\|BQ080255 | soybean | 223 | 684 |
| LNU57 | wheat\|gb164\|BE405851 | wheat | 224 | 685 |
| LNU60 | wheat\|gb164\|BQ901296 | wheat | 225 | 686 |
| LNU74 | poplar\|gb157.2\|AI164893 | poplar | 226 | 526 |
| LNU83 | soybean\|gb168\|AW471606 | soybean | 227 | 687 |
| LNU89 | wheat\|gb164\|BQ236209 | wheat | 228 | 688 |
| LNU101 | rice\|gb157.3\|NM001061106 | rice | 229 | 689 |
| LNU105 | wheat\|gb164\|BG606394 | wheat | 230 | 690 |
| LNU113 | maize\|gb169.2\|AA054793 | maize | 231 | 691 |
| LNU114 | rice\|gb157.3\|AA752410 | rice | 232 | 692 |
| LNU115 | rice\|gb157.3\|CB635059 | rice | 233 | 693 |
| LNU123 | arabidopsis\|gb165\|AT1G63850 | arabidopsis | 234 | 561 |
| LNU126 | arabidopsis\|gb165\|AT5G58770 | arabidopsis | 235 | 563 |
| LNU143 | cotton\|gb164\|BG443936 | cotton | 236 | 694 |
| LNU147 | cotton\|gb164\|DT462051 | cotton | 237 | 580 |
| LNU148 | soybean\|gb168\|CD394513 | soybean | 238 | 695 |
| LNU158 | cotton\|gb164\|CO082594 | cotton | 239 | 696 |
| LNU170 | arabidopsis\|gb165\|AT5G40060 | arabidopsis | 240 | 697 |
| LNU190 | canola\|gb161\|DY007527 | canola | 241 | 610 |
| LNU192 | rice\|gb157.3\|BE040846 | rice | 242 | 698 |
| LNU198 | cotton\|gb164\|CO078561 | cotton | 243 | 614 |
| LNU200 | tomato\|gb164\|BG791292 | tomato | 244 | 699 |
| LNU202 | sorghum\|gb161.xeno\|BE362397 | sorghum | 245 | 700 |
| LNU229 | tomato\|gb164\|AI484048 | tomato | 246 | 701 |
| LNU236 | cotton\|gb164\|AI728962 | cotton | 247 | 640 |
| LNU240 | barley\|gb157.3\|AV914239 | barley | 248 | 702 |
| LNU241 | rice\|gb170\|OS12G40330 | rice | 249 | 643 |
| LNU242 | arabidopsis\|gb165\|AT4G01650 | arabidopsis | 250 | 703 |
| LNU243 | barley\|gb157.3\|BQ467891 | barley | 251 | 645 |
| LNU244 | barley\|gb157.3\|AV932151 | barley | 252 | 704 |
| LNU249 | arabidopsis\|gb165\|AT5G04980 | arabidopsis | 253 | 650 |
| LNU257 | arabidopsis\|gb165\|AT3G12090 | arabidopsis | 254 | 657 |
| LNU266 | maize\|gb164\|AI438792 | maize | 255 | 706 |
| LNU289 | tomato\|gb164\|BG123295 | tomato | 256 | 679 |
| LNU222_H6 | sorghum\|gb161.crp\|AW678240 | sorghum | 257 | 680 |

Table 1.
"Polyp." = polypeptide;
"Polyn."—Polynucleotide.

Example 2

Identification of Homologous Sequences that Increase Nitrogen use efficiency, fertilizer use efficiency, yield, Growth Rate, Vigor, Biomass, Oil Content, Abiotic Stress Tolerance and/or Water Use Efficiency in Plants The concepts of orthology and paralogy have recently been applied to functional characterizations and classifications on the scale of whole-genome comparisons. Orthologs and paralogs constitute two major types of homologs: The first evolved from a common ancestor by specialization, and the latter is related by duplication events. It is assumed that paralogs arising from ancient duplication events are likely to have diverged in function while true orthologs are more likely to retain identical function over evolutionary time.

To further investigate and identify putative orthologs of the genes affecting nitrogen use efficiency, fertilizer use efficiency, yield (e.g., seed yield, oil yield, biomass, grain quantity and/or quality), growth rate, vigor, biomass, oil content, abiotic stress tolerance and/or water use efficiency, all sequences were aligned using the BLAST (/Basic Local Alignment Search Tool/). Sequences sufficiently similar were tentatively grouped. These putative orthologs were further organized under a Phylogram—a branching diagram (tree) assumed to be a representation of the evolutionary relationships among the biological taxa. Putative ortholog groups were analyzed as to their agreement with the phylogram and in cases of disagreements these ortholog groups were broken accordingly. Expression data was analyzed and the EST libraries were classified using a fixed vocabulary of custom terms such as developmental stages (e.g., genes showing similar expression profile through development with up regulation at specific stage, such as at the seed filling stage) and/or plant organ (e.g., genes showing similar expression profile across their organs with up regulation at specific organs such as seed). The annotations from all the ESTs clustered to a gene were analyzed statistically by comparing their frequency in the cluster versus their abundance in the database, allowing the construction of a numeric and graphic expression profile of that gene, which is termed "digital expression". The rationale of using these two complementary methods with methods of phenotypic association studies of QTLs, SNPs and phenotype expression correlation is based on the assumption that true orthologs are likely to retain identical function over evolutionary time. These methods provide different sets of indications on function similarities between two homologous genes, similarities in the sequence level—identical amino acids in the protein domains and similarity in expression profiles.

The search and identification of homologous genes involves the screening of sequence information available, for example, in public databases, which include but are not limited to the DNA Database of Japan (DDBJ), Genbank, and the European Molecular Biology Laboratory Nucleic Acid Sequence Database (EMBL) or versions thereof or the MIPS database. A number of different search algorithms have been developed, including but not limited to the suite of programs referred to as BLAST programs. There are five implementations of BLAST, three designed for nucleotide sequence queries (BLASTN, BLASTX, and TBLASTX) and two designed for protein sequence queries (BLASTP and TBLASTN) (Coulson, Trends in Biotechnology: 76-80, 1994; Birren et al., Genome Analysis, I: 543, 1997). Such methods involve alignment and comparison of sequences. The BLAST algorithm calculates percent sequence identity and performs a statistical analysis of the similarity between the two sequences. The software for performing BLAST analysis is publicly available through the National Centre for Biotechnology Information. Other such software or algorithms are GAP, BESTFIT, FASTA and TFASTA. GAP uses the algorithm of Needleman and Wunsch (J. Mol. Biol. 48: 443-453, 1970) to find the alignment of two complete sequences that maximizes the number of matches and minimizes the number of gaps.

The homologous genes may belong to the same gene family. The analysis of a gene family may be carried out using sequence similarity analysis. To perform this analysis one may use standard programs for multiple alignments e.g. Clustal W. A neighbor-joining tree of the proteins homologous to the genes of some embodiments of the invention may be used to provide an overview of structural and ancestral relationships. Sequence identity may be calculated using an alignment program as described above. It is expected that other plants will carry a similar functional gene (orthologue) or a family of similar genes and those genes will provide the same preferred phenotype as the genes presented here. Advantageously, these family members may be useful in the methods of some embodiments of the invention. Example of other plants include, but not limited to, barley (*Hordeum vulgare*), Arabidopsis (*Arabidopsis thaliana*), maize (*Zea mays*), cotton (*Gossypium*), Oilseed rape (*Brassica napus*), Rice (*Oryza sativa*), Sugar cane (*Saccharum officinarum*), Sorghum (*Sorghum bicolor*), Soybean (*Glycine max*), Sunflower (*Helianthus annuus*), Tomato (*Lycopersicon esculentum*) and Wheat (*Triticum aestivum*)

The above-mentioned analyses for sequence homology is preferably carried out on a full-length sequence, but may also be based on a comparison of certain regions such as conserved domains. The identification of such domains, would also be well within the realm of the person skilled in the art and would involve, for example, a computer readable format of the nucleic acids of some embodiments of the invention, the use of alignment software programs and the use of publicly available information on protein domains, conserved motifs and boxes. This information is available in the PRODOM (Hypertext Transfer Protocol://World Wide Web (dot) biochem (dot) ucl (dot) ac (dot) uk/bsm/dbbrowser/protocol/prodomqry (dot) html), PIR (Hypertext Transfer Protocol://pir (dot) Georgetown (dot) edu/) or Pfam (Hypertext Transfer Protocol://World Wide Web (dot) sanger (dot) ac (dot) uk/Software/Pfam/) database. Sequence analysis programs designed for motif searching may be used for identification of fragments, regions and conserved domains as mentioned above. Preferred computer programs include, but are not limited to, MEME, SIGNALSCAN, and GENESCAN.

A person skilled in the art may use the homologous sequences provided herein to find similar sequences in other species and other organisms. Homologues of a protein encompass, peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (conservative changes, such as similar hydrophobicity, hydrophilicity, antigenicity, propensity to form or break a-helical structures or 3-sheet structures). Conservative substitution Tables are well known in the art [see for example Creighton (1984) Proteins. W.H. Freeman and Company]. Homologues of a nucleic acid encompass nucleic acids having nucleotide substitutions, deletions and/or insertions relative to the unmodified nucleic acid in question and having similar biological and functional activity as the unmodified nucleic acid from which they are derived.

Polynucleotides and polypeptides with significant homology to the identified genes described in Table 1 (Example 1 above) were identified from the databases using BLAST software using the Blastp and tBlastn algorithms. The query polypeptide sequences were SEQ ID NOs: 468-706 (which are encoded by the polynucleotides SEQ ID NOs:1-257, shown in Table 1 above) and SEQ ID NOs:707-784 (which are encoded by the cloned genes SEQ ID NOs:258-467, shown in Table 59 and the identified homologous sequences are provided in Table 2, below.

TABLE 2

Homologues of the identified genes/polypeptides for increasing nitrogen use
efficiency, fertilizer use efficiency, yield, seed yield, growth rate, vigor, biomass, oil
content, fiber yield, fiber quality, fiber length, abiotic stress tolerance and/or water
use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 785 | LNU1 | canola\|10v1\|CD822833 | 3042 | 468 | 82.8 | globlastp |
| 786 | LNU1 | canola\|gb161\|CD822833 | 3042 | 468 | 82.8 | globlastp |
| 787 | LNU1 | radish\|gb164\|EW724281 | 3043 | 468 | 82.8 | globlastp |
| 788 | LNU1 | canola\|10v1\|CD819354 | 3044 | 468 | 81.9 | globlastp |
| 789 | LNU1 | b_oleracea\|gb161\|EE534144 | 3045 | 468 | 81.7 | globlastp |
| 790 | LNU1 | radish\|gb164\|FD530209 | 3046 | 468 | 81.7 | globlastp |
| 791 | LNU1 | b_rapa\|gb162\|EX016038 | 3047 | 468 | 81.1 | globlastp |
| 792 | LNU1 | b_oleracea\|gb161\|DY026134 | 3048 | 468 | 80.9 | globlastp |
| 793 | LNU1 | canola\|gb161\|CD819354 | 3049 | 468 | 80.9 | globlastp |
| 794 | LNU2 | leymus\|gb166\|EG388463 | 3050 | 469 | 85 | globlastp |
| 795 | LNU2 | wheat\|gb164\|BE427374 | 3051 | 469 | 85 | globlastp |
| 796 | LNU2 | barley\|gb157SOLEXA\|AL507333 | 3052 | 469 | 84.5 | globlastp |
| 797 | LNU2 | maize\|gb170\|AI691484 | 3053 | 469 | 83.6 | globlastp |
| 798 | LNU2 | sugarcane\|10v1\|AA525691 | 3054 | 469 | 83.3 | globlastp |
| 799 | LNU2 | sugarcane\|gb157.3\|AA525691 | 3055 | 469 | 82.9 | globlastp |
| 800 | LNU2 | sorghum\|09v1\|SB10G006850 | 3056 | 469 | 82.5 | globlastp |
| 801 | LNU2 | sorghum\|gb161.crp\|AI881329 | 3056 | 469 | 82.5 | globlastp |
| 802 | LNU2 | switchgrass\|gb167\|FE630265 | 3057 | 469 | 81.9 | globlastp |
| 803 | LNU2 | maize\|gb170\|AI967022 | 3058 | 469 | 81.1 | globlastp |
| 804 | LNU2 | brachypodium\|09v1\|DV476481 | 3059 | 469 | 81 | globlastp |
| 805 | LNU2 | brachypodium\|gb169\|BE427374 | 3059 | 469 | 81 | globlastp |
| 806 | LNU5 | wheat\|gb164\|BE428356 | 3060 | 472 | 98.1 | globlastp |
| 807 | LNU5 | wheat\|gb164\|BQ806386 | 3061 | 472 | 97.7 | globlastp |
| 808 | LNU5 | leymus\|gb166\|EG389542 | 3062 | 472 | 97.2 | globlastp |
| 809 | LNU5 | oat\|10v1\|GR347048 | 3063 | 472 | 90.3 | globlastp |
| 810 | LNU6 | soybean\|gb168\|BE660452 | 3064 | 473 | 90.3 | globlastp |
| 811 | LNU6 | bean\|gb167\|CA901464 | 3065 | 473 | 85.8 | globlastp |
| 812 | LNU6 | cowpea\|gb166\|FF389080 | 3066 | 473 | 83.2 | globlastp |
| 813 | LNU6 | liquorice\|gb171\|FS239924 | 3067 | 473 | 80.9 | globlastp |
| 814 | LNU6 | peanut\|gb167\|AY639025 | 3068 | 473 | 80.6 | globlastp |
| 815 | LNU6 | peanut\|gb171\|AY639025 | 3069 | 473 | 80.6 | globlastp |
| 816 | LNU6 | lotus\|09v1\|LLBF177846 | 3070 | 473 | 80.3 | globlastp |
| 817 | LNU7 | chickpea\|09v2\|GR392103 | 3071 | 474 | 98.4 | globlastp |
| 817 | LNU27 | chickpea\|09v2\|GR392103 | 3071 | 489 | 80 | glotblastn |
| 818 | LNU7 | liquorice\|gb171\|FS238627 | 3072 | 474 | 98.4 | globlastp |
| 818 | LNU27 | liquorice\|gb171\|FS238627 | 3072 | 489 | 80 | glotblastn |
| 819 | LNU7 | liquorice\|gb171\|FS260230 | 3072 | 474 | 98.4 | globlastp |
| 819 | LNU27 | liquorice\|gb171\|FS260230 | 3072 | 489 | 80 | glotblastn |
| 820 | LNU7 | cacao\|gb167\|CU470501 | 3073 | 474 | 98.4 | globlastp |
| 820 | LNU27 | cacao\|gb167\|CU470501 | 3073 | 489 | 80 | glotblastn |
| 821 | LNU7 | cassava\|09v1\|DV445520 | 3072 | 474 | 98.4 | globlastp |
| 821 | LNU27 | cassava\|09v1\|DV445520 | 3072 | 489 | 80 | glotblastn |
| 822 | LNU7 | cassava\|gb164\|DV445520 | 3072 | 474 | 98.4 | globlastp |
| 822 | LNU27 | cassava\|gb164\|DV445520 | 3072 | 489 | 80 | glotblastn |
| 823 | LNU7 | cotton\|gb164\|BE054360 | 3073 | 474 | 98.4 | globlastp |
| 823 | LNU27 | cotton\|gb164\|BE054360 | 3073 | 489 | 80 | glotblastn |
| 824 | LNU7 | cotton\|gb164\|ES793421 | 3073 | 474 | 98.4 | globlastp |
| 824 | LNU27 | cotton\|gb164\|ES793421 | 3073 | 489 | 80 | glotblastn |
| 825 | LNU7 | medicago\|09v1\|AL377934 | 3071 | 474 | 98.4 | globlastp |
| 825 | LNU27 | medicago\|09v1\|AL377934 | 3071 | 489 | 80 | glotblastn |
| 826 | LNU7 | medicago\|gb157.2\|AL377934 | 3071 | 474 | 98.4 | globlastp |
| 826 | LNU27 | medicago\|gb157.2\|AL377934 | 3071 | 489 | 80 | glotblastn |
| 827 | LNU7 | soybean\|gb168\|AI967471 | 3072 | 474 | 98.4 | globlastp |
| 827 | LNU27 | soybean\|gb168\|AI967471 | 3072 | 489 | 80 | glotblastn |
| 828 | LNU7 | soybean\|gb168\|AW348687 | 3072 | 474 | 98.4 | globlastp |
| 828 | LNU27 | soybean\|gb168\|AW348687 | 3072 | 489 | 80 | globlastp |
| 829 | LNU7 | chickpea\|09v2\|FE668992 | 3074 | 474 | 96.72 | glotblastn |
| 829 | LNU27 | chickpea\|09v2\|FE668992 | 3074 | 489 | 80 | glotblastn |
| 830 | LNU7 | pigeonpea\|gb171\|GR471306 | 3075 | 474 | 96.7 | globlastp |
| 830 | LNU27 | pigeonpea\|gb171\|GR471306 | 3075 | 489 | 80 | glotblastn |
| 831 | LNU7 | bean\|gb167\|CA897804 | 3076 | 474 | 96.7 | globlastp |
| 831 | LNU27 | bean\|gb167\|CA897804 | 3076 | 489 | 80 | glotblastn |
| 832 | LNU7 | bean\|gb167\|FD780529 | 3076 | 474 | 96.7 | globlastp |
| 832 | LNU27 | bean\|gb167\|FD780529 | 3076 | 489 | 80 | glotblastn |
| 833 | LNU7 | castorbean\|09v1\|XM002519154 | 3077 | 474 | 96.7 | globlastp |
| 833 | LNU27 | castorbean\|09v1\|XM002519154 | 3077 | 489 | 80.3 | globlastp |
| 834 | LNU7 | castorbean\|gb160\|MDL29889M003271 | 3077 | 474 | 96.7 | globlastp |
| 834 | LNU27 | castorbean\|gb160\|MDL29889M003271 | 3077 | 489 | 80.3 | globlastp |
| 835 | LNU7 | cowpea\|gb166\|FC459169 | 3076 | 474 | 96.7 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Hom. Polyp. SEQ ID NO: | Polyp. to SEQ ID NO: | % global identity | Algor. |
|---|---|---|---|---|---|---|
| 835 | LNU27 | cowpea\|gb166\|FC459169 | 3076 | 489 | 80 | glotblastn |
| 836 | LNU7 | cowpea\|gb166\|FF384333 | 3076 | 474 | 96.7 | globlastp |
| 836 | LNU27 | cowpea\|gb166\|FF384333 | 3076 | 489 | 80 | glotblastn |
| 837 | LNU7 | soybean\|gb168\|CD391265 | 3076 | 474 | 96.7 | globlastp |
| 837 | LNU27 | soybean\|gb168\|CD391265 | 3076 | 489 | 80 | glotblastn |
| 838 | LNU7 | heritiera\|10v1\|SRR005794S0008204 | 3078 | 474 | 95.1 | globlastp |
| 838 | LNU27 | heritiera\|10v1\|SRR005794S0008204 | 3078 | 489 | 80 | glotblastn |
| 839 | LNU7 | cacao\|gb167\|CU492958 | 3079 | 474 | 95.1 | globlastp |
| 840 | LNU7 | cotton\|gb164\|BF274438 | 3080 | 474 | 95.1 | globlastp |
| 840 | LNU27 | cotton\|gb164\|BF274438 | 3080 | 489 | 80 | glotblastn |
| 841 | LNU7 | kiwi\|gb166\|FG419099 | 3081 | 474 | 95.1 | globlastp |
| 842 | LNU7 | papaya\|gb165\|EX229339 | 3082 | 474 | 95.1 | globlastp |
| 842 | LNU27 | papaya\|gb165\|EX229339 | 3082 | 489 | 80 | glotblastn |
| 843 | LNU7 | medicago\|09v1\|LLCO511931 | 3083 | 474 | 93.4 | globlastp |
| 844 | LNU7 | bruguiera\|gb166\|BP940274 | 3084 | 474 | 93.4 | globlastp |
| 844 | LNU27 | bruguiera\|gb166\|BP940274 | 3084 | 489 | 80.3 | globlastp |
| 845 | LNU7 | cassava\|09v1\|CK646795 | 3085 | 474 | 93.4 | globlastp |
| 846 | LNU7 | grape\|gb160\|BQ792422 | 3086 | 474 | 93.4 | globlastp |
| 847 | LNU7 | kiwi\|gb166\|FG400845 | 3087 | 474 | 93.4 | globlastp |
| 848 | LNU7 | kiwi\|gb166\|FG434680 | 3088 | 474 | 93.4 | globlastp |
| 849 | LNU7 | lotus\|09v1\|AI967471 | 3089 | 474 | 93.4 | globlastp |
| 850 | LNU7 | lotus\|gb157.2\|AI967471 | 3089 | 474 | 93.4 | globlastp |
| 851 | LNU7 | medicago\|09v1\|AW171649 | 3090 | 474 | 93.4 | globlastp |
| 852 | LNU7 | medicago\|gb157.2\|AW171649 | 3090 | 474 | 93.4 | globlastp |
| 853 | LNU7 | poplar\|gb170\|AI164188 | 3091 | 474 | 93.4 | globlastp |
| 854 | LNU7 | poplar\|10v1\|BI127039 | 3092 | 474 | 93.4 | globlastp |
| 855 | LNU7 | poplar\|gb170\|BI127039 | 3092 | 474 | 93.4 | globlastp |
| 856 | LNU7 | jatropha\|09v1\|FM887189 | 3093 | 474 | 91.8 | globlastp |
| 857 | LNU7 | rhizophora\|10v1\|SRR005793S0035789 | 3094 | 474 | 91.8 | globlastp |
| 857 | LNU27 | rhizophora\|10v1\|SRR005793S0035789 | 3094 | 489 | 80.3 | globlastp |
| 858 | LNU7 | tea\|10v1\|CV014009 | 3095 | 474 | 91.8 | globlastp |
| 859 | LNU7 | bean\|gb167\|FD789886 | 3096 | 474 | 91.8 | glotblastn |
| 860 | LNU7 | chestnut\|gb170\|SRR006295S0000269 | 3097 | 474 | 91.8 | globlastp |
| 861 | LNU7 | cotton\|gb164\|BF270755 | 3098 | 474 | 91.8 | globlastp |
| 861 | LNU27 | cotton\|gb164\|BF270755 | 3098 | 489 | 80 | glotblastn |
| 862 | LNU7 | peanut\|gb167\|CX128150 | 3099 | 474 | 91.8 | globlastp |
| 863 | LNU7 | peanut\|gb171\|CX128150 | 3099 | 474 | 91.8 | globlastp |
| 864 | LNU7 | peanut\|gb171\|EE126662 | 3099 | 474 | 91.8 | globlastp |
| 865 | LNU7 | poplar\|10v1\|AI164188 | 3100 | 474 | 91.8 | globlastp |
| 866 | LNU7 | spurge\|gb161\|BG354130 | 3101 | 474 | 91.8 | globlastp |
| 866 | LNU27 | spurge\|gb161\|BG354130 | 3101 | 489 | 81 | globlastp |
| 867 | LNU7 | walnuts\|gb166\|CV196459 | 3102 | 474 | 91.8 | globlastp |
| 868 | LNU7 | eucalyptus\|gb166\|CU394883 | 3103 | 474 | 90.3 | globlastp |
| 868 | LNU27 | eucalyptus\|gb166\|CU394883 | 3103 | 489 | 80 | glotblastn |
| 869 | LNU7 | grape\|gb160\|EC927944 | 3104 | 474 | 90.3 | globlastp |
| 870 | LNU7 | cleome_gynandra\|10v1\|SRR015532S0000915 | 3105 | 474 | 90.2 | globlastp |
| 871 | LNU7 | cleome_gynandra\|10v1\|SRR015532S0002395 | 3106 | 474 | 90.2 | globlastp |
| 872 | LNU7 | cleome_spinosa\|10v1\|SRR015531S0004899 | 3107 | 474 | 90.2 | globlastp |
| 873 | LNU7 | cleome_spinosa\|10v1\|SRR015531S0010059 | 3105 | 474 | 90.2 | globlastp |
| 874 | LNU7 | cleome_spinosa\|10v1\|SRR015531S0015400 | 3108 | 474 | 90.2 | globlastp |
| 875 | LNU7 | eggplant\|10v1\|FS005478 | 3109 | 474 | 90.2 | globlastp |
| 875 | LNU27 | eggplant\|10v1\|FS005478 | 3109 | 489 | 80 | globlastp |
| 876 | LNU7 | pepper\|gb171\|GD054049 | 3110 | 474 | 90.2 | globlastp |
| 876 | LNU27 | pepper\|gb171\|GD054049 | 3110 | 489 | 81.7 | globlastp |
| 877 | LNU7 | catharanthus\|gb166\|DT527689 | 3111 | 474 | 90.2 | globlastp |
| 878 | LNU7 | catharanthus\|gb166\|EG556443 | 3111 | 474 | 90.2 | globlastp |
| 879 | LNU7 | oak\|gb170\|SRR006309S0014100 | 3112 | 474 | 90.2 | globlastp |
| 880 | LNU7 | rice\|gb170\|OS01G19840 | 3113 | 474 | 90.2 | globlastp |
| 880 | LNU27 | rice\|gb170\|OS01G19840 | 3113 | 489 | 85 | globlastp |
| 881 | LNU7 | rice\|gb170\|OS05G28750 | 3113 | 474 | 90.2 | globlastp |
| 881 | LNU27 | rice\|gb170\|OS05G28750 | 3113 | 489 | 85 | globlastp |
| 882 | LNU7 | walnuts\|gb166\|EL900862 | 3114 | 474 | 90.2 | globlastp |
| 883 | LNU7 | citrus\|gb166\|BQ623885 | 3115 | 474 | 90.16 | glotblastn |
| 884 | LNU7 | amborella\|gb166\|CK759343 | 3116 | 474 | 88.7 | globlastp |
| 885 | LNU7 | avocado\|10v1\|CK767358 | 3117 | 474 | 88.7 | globlastp |
| 885 | LNU27 | avocado\|10v1\|CK767358 | 3117 | 489 | 80 | glotblastn |
| 886 | LNU7 | avocado\|gb164\|CK767358 | 3117 | 474 | 88.7 | globlastp |
| 886 | LNU27 | avocado\|gb164\|CK767358 | 3117 | 489 | 80 | glotblastn |
| 887 | LNU7 | nuphar\|gb166\|CV004221 | 3118 | 474 | 88.7 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 888 | LNU7 | tomato\|gb164\|BG126482 | 3119 | 474 | 88.52 | glotblastn |
| 888 | LNU27 | tomato\|gb164\|BG126482 | 3119 | 489 | 80 | glotblastn |
| 889 | LNU7 | ipomoea_batatas\|10v1\|BU691209 | 3120 | 474 | 88.5 | globlastp |
| 890 | LNU7 | ipomoea_nil\|10v1\|BJ567189 | 3120 | 474 | 88.5 | globlastp |
| 891 | LNU7 | lotus\|09v1\|CRPLJ010213 | 3121 | 474 | 88.5 | globlastp |
| 892 | LNU7 | tomato\|09v1\|BG126482 | 3122 | 474 | 88.5 | globlastp |
| 892 | LNU27 | tomato\|09v1\|BG126482 | 3122 | 489 | 80 | globlastp |
| 893 | LNU7 | citrus\|gb166\|BQ624128 | 3123 | 474 | 88.5 | globlastp |
| 894 | LNU7 | ipomoea\|gb157.2\|BJ567189 | 3120 | 474 | 88.5 | globlastp |
| 895 | LNU7 | lettuce\|gb157.2\|DW044205 | 3124 | 474 | 88.5 | globlastp |
| 896 | LNU7 | lettuce\|10v1\|DW074561 | 3125 | 474 | 88.5 | globlastp |
| 897 | LNU7 | lettuce\|gb157.2\|DW074561 | 3125 | 474 | 88.5 | globlastp |
| 898 | LNU7 | lettuce\|gb157.2\|DW147214 | 3126 | 474 | 88.5 | globlastp |
| 899 | LNU7 | lovegrass\|gb167\|EH188904 | 3127 | 474 | 88.5 | globlastp |
| 899 | LNU27 | lovegrass\|gb167\|EH188904 | 3127 | 489 | 86.7 | globlastp |
| 900 | LNU7 | melon\|gb165\|AM723109 | 3128 | 474 | 88.5 | globlastp |
| 901 | LNU7 | melon\|gb165\|EB715608 | 3129 | 474 | 88.5 | globlastp |
| 902 | LNU7 | oak\|gb170\|DN950298 | 3130 | 474 | 88.5 | globlastp |
| 903 | LNU7 | potato\|gb157.2\|BQ047073 | 3122 | 474 | 88.5 | globlastp |
| 903 | LNU27 | potato\|gb157.2\|BQ047073 | 3122 | 489 | 80 | globlastp |
| 904 | LNU7 | sunflower\|gb162\|CD849282 | 3131 | 474 | 88.5 | globlastp |
| 905 | LNU7 | thellungiella\|gb167\|BI698609 | 3132 | 474 | 88.5 | globlastp |
| 906 | LNU7 | lettuce\|10v1\|DW044205 | 3124 | 474 | 88.5 | globlastp |
| 907 | LNU7 | arabidopsis_lyrata\|09v1\|JGIAL009087 | 3133 | 474 | 86.9 | globlastp |
| 908 | LNU7 | arabidopsis_lyrata\|09v1\|JGIAL013834 | 3134 | 474 | 86.9 | globlastp |
| 909 | LNU7 | canola\|10v1\|CD816913 | 3135 | 474 | 86.9 | globlastp |
| 910 | LNU7 | canola\|10v1\|CD838406 | 3135 | 474 | 86.9 | globlastp |
| 911 | LNU7 | canola\|10v1\|CN732166 | 3135 | 474 | 86.9 | globlastp |
| 912 | LNU7 | gerbera\|09v1\|AJ754854 | 3136 | 474 | 86.9 | globlastp |
| 913 | LNU7 | ginseng\|10v1\|AB042860 | 3137 | 474 | 86.9 | globlastp |
| 914 | LNU7 | millet\|09v1\|CD724720 | 3138 | 474 | 86.9 | globlastp |
| 914 | LNU27 | millet\|09v1\|CD724720 | 3138 | 489 | 85 | globlastp |
| 915 | LNU7 | salvia\|10v1\|SRR014553S0006508 | 3139 | 474 | 86.9 | globlastp |
| 916 | LNU7 | solanum_phureja\|09v1\|SPHBG126482 | 3140 | 474 | 86.9 | globlastp |
| 917 | LNU7 | sorghum\|gb161.crp\|AI664904 | 3141 | 474 | 86.9 | globlastp |
| 917 | LNU27 | sorghum\|gb161.crp\|AI664904 | 3141 | 489 | 85 | globlastp |
| 918 | LNU7 | arabidopsis\|gb165\|AT3G06680 | 3142 | 474 | 86.9 | globlastp |
| 919 | LNU7 | b_juncea\|gb164\|EVGN00263811010987 | 3135 | 474 | 86.9 | globlastp |
| 920 | LNU7 | b_juncea\|gb164\|EVGN00818312581324 | 3135 | 474 | 86.9 | globlastp |
| 921 | LNU7 | b_juncea\|gb164\|EVGN01551409763163 | 3135 | 474 | 86.9 | globlastp |
| 922 | LNU7 | b_juncea\|gb164\|EVGN01699912462188 | 3135 | 474 | 86.9 | globlastp |
| 923 | LNU7 | b_juncea\|gb164\|EVGN04088908911493 | 3143 | 474 | 86.9 | globlastp |
| 924 | LNU7 | b_oleracea\|gb161\|DY027316 | 3135 | 474 | 86.9 | globlastp |
| 925 | LNU7 | b_rapa\|gb162\|CX267004 | 3135 | 474 | 86.9 | globlastp |
| 926 | LNU7 | b_rapa\|gb162\|CX268468 | 3135 | 474 | 86.9 | globlastp |
| 927 | LNU7 | beet\|gb162\|BI096143 | 3144 | 474 | 86.9 | globlastp |
| 928 | LNU7 | canola\|10v1\|CD811781 | 3135 | 474 | 86.9 | globlastp |
| 929 | LNU7 | canola\|gb161\|CD811781 | 3135 | 474 | 86.9 | globlastp |
| 930 | LNU7 | canola\|10v1\|CD812329 | 3135 | 474 | 86.9 | globlastp |
| 931 | LNU7 | canola\|gb161\|CD812329 | 3135 | 474 | 86.9 | globlastp |
| 932 | LNU7 | canola\|gb161\|CD816913 | 3135 | 474 | 86.9 | globlastp |
| 933 | LNU7 | canola\|gb161\|CN732166 | 3135 | 474 | 86.9 | globlastp |
| 934 | LNU7 | canola\|10v1\|CX278337 | 3135 | 474 | 86.9 | globlastp |
| 935 | LNU7 | canola\|gb161\|CX278337 | 3135 | 474 | 86.9 | globlastp |
| 936 | LNU7 | cenchrus\|gb166\|EB653562 | 3138 | 474 | 86.9 | globlastp |
| 936 | LNU27 | cenchrus\|gb166\|EB653562 | 3138 | 489 | 85 | globlastp |
| 937 | LNU7 | coffea\|10v1\|DV679308 | 3145 | 474 | 86.9 | globlastp |
| 938 | LNU7 | coffea\|gb157.2\|DV679308 | 3145 | 474 | 86.9 | globlastp |
| 939 | LNU7 | dandelion\|gb161\|DY802911 | 3146 | 474 | 86.9 | globlastp |
| 940 | LNU7 | maize\|gb170\|AI941993 | 3147 | 474 | 86.9 | globlastp |
| 940 | LNU27 | maize\|gb170\|AI941993 | 3147 | 489 | 83.3 | globlastp |
| 941 | LNU7 | pepper\|gb157.2\|BM067951 | 3148 | 474 | 86.9 | globlastp |
| 941 | LNU27 | pepper\|gb157.2\|BM067951 | 3148 | 489 | 80 | globlastp |
| 942 | LNU7 | pepper\|gb171\|BM067951 | 3149 | 474 | 86.9 | globlastp |
| 942 | LNU27 | pepper\|gb171\|BM067951 | 3149 | 489 | 80 | globlastp |
| 943 | LNU7 | petunia\|gb166\|EB174600 | 3150 | 474 | 86.9 | globlastp |
| 944 | LNU7 | petunia\|gb171\|EB174600 | 3150 | 474 | 86.9 | globlastp |
| 945 | LNU7 | potato\|gb157.2\|BQ047370 | 3140 | 474 | 86.9 | globlastp |
| 946 | LNU7 | prunus\|gb167\|BI203148 | 3151 | 474 | 86.9 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 947 | LNU7 | radish\|gb164\|EV527807 | 3134 | 474 | 86.9 | globlastp |
| 948 | LNU7 | radish\|gb164\|EV539631 | 3152 | 474 | 86.9 | globlastp |
| 949 | LNU7 | radish\|gb164\|EW732099 | 3135 | 474 | 86.9 | globlastp |
| 950 | LNU7 | radish\|gb164\|EW734121 | 3135 | 474 | 86.9 | globlastp |
| 951 | LNU7 | sorghum\|09v1\|SB09G017140 | 3141 | 474 | 86.9 | globlastp |
| 951 | LNU27 | sorghum\|09v1\|SB09G017140 | 3141 | 489 | 85 | globlastp |
| 952 | LNU7 | sorghum\|09v1\|SB09G017150 | 3153 | 474 | 86.9 | globlastp |
| 952 | LNU27 | sorghum\|09v1\|SB09G017150 | 3153 | 489 | 85 | globlastp |
| 953 | LNU7 | sorghum\|gb161.crp\|AW287208 | 3153 | 474 | 86.9 | globlastp |
| 953 | LNU27 | sorghum\|gb161.crp\|AW287208 | 3153 | 489 | 85 | globlastp |
| 954 | LNU7 | spurge\|gb161\|DV124618 | 3154 | 474 | 86.9 | globlastp |
| 955 | LNU7 | sugarcane\|10v1\|BQ530802 | 3141 | 474 | 86.9 | globlastp |
| 955 | LNU27 | sugarcane\|10v1\|BQ530802 | 3141 | 489 | 85 | globlastp |
| 956 | LNU7 | sugarcane\|gb157.3\|BQ530802 | 3141 | 474 | 86.9 | globlastp |
| 956 | LNU27 | sugarcane\|gb157.3\|BQ530802 | 3141 | 489 | 85 | globlastp |
| 957 | LNU7 | sugarcane\|10v1\|CA118622 | 3141 | 474 | 86.9 | globlastp |
| 957 | LNU27 | sugarcane\|10v1\|CA118622 | 3141 | 489 | 85 | globlastp |
| 958 | LNU7 | sugarcane\|gb157.3\|CA118622 | 3141 | 474 | 86.9 | globlastp |
| 958 | LNU27 | sugarcane\|gb157.3\|CA11862 | 3141 | 489 | 85 | globlastp |
| 959 | LNU7 | switchgrass\|gb167\|DN150845 | 3138 | 474 | 86.9 | globlastp |
| 959 | LNU27 | switchgrass\|gb167\|DN150845 | 3138 | 489 | 85 | globlastp |
| 960 | LNU7 | wheat\|gb164\|CD491023 | 3141 | 474 | 86.9 | globlastp |
| 960 | LNU27 | wheat\|gb164\|CD491023 | 3141 | 489 | 85 | globlastp |
| 961 | LNU7 | potato\|10v1\|BQ047073 | 3140 | 474 | 86.9 | globlastp |
| 962 | LNU7 | banana\|gb167\|DN239847 | 3155 | 474 | 85.5 | globlastp |
| 963 | LNU7 | banana\|gb167\|FL658741 | 3156 | 474 | 85.5 | globlastp |
| 964 | LNU7 | oil_palm\|gb166\|EL683904 | 3157 | 474 | 85.5 | globlastp |
| 965 | LNU7 | canola\|10v1\|BQ704618 | 3158 | 474 | 85.25 | globlastn |
| 966 | LNU7 | dandelion\|gb161\|DY814075 | 3159 | 474 | 85.25 | globlastn |
| 967 | LNU7 | b_nigra\|09v1\|GT069298 | — | 474 | 85.25 | globlastn |
| 968 | LNU7 | petunia\|gb171\|CV300233 | — | 474 | 85.25 | globlastn |
| 969 | LNU7 | thellungiella\|gb167\|BQ087680 | — | 474 | 85.25 | globlastn |
| 970 | LNU7 | basilicum\|10v1\|DY323081 | 3160 | 474 | 85.2 | globlastp |
| 970 | LNU27 | basilicum\|10v1\|DY323081 | 3160 | 489 | 80.3 | globlastp |
| 971 | LNU7 | canola\|10v1\|CD811649 | 3161 | 474 | 85.2 | globlastp |
| 972 | LNU7 | cucumber\|09v1\|CK700790 | 3162 | 474 | 85.2 | globlastp |
| 973 | LNU7 | gerbera\|09v1\|AJ762109 | 3163 | 474 | 85.2 | globlastp |
| 974 | LNU7 | lotus\|09v1\|CRPLJ015426 | 3164 | 474 | 85.2 | globlastp |
| 975 | LNU7 | lotus\|09v1\|CRPLJ021029 | 3164 | 474 | 85.2 | globlastp |
| 976 | LNU7 | lotus\|09v1\|CRPLJ033772 | 3164 | 474 | 85.2 | globlastp |
| 977 | LNU7 | brachypodium\|09v1\|GT762410 | 3165 | 474 | 85.2 | globlastp |
| 977 | LNU27 | brachypodium\|09v1\|GT762410 | 3165 | 489 | 90 | globlastp |
| 978 | LNU7 | brachypodium\|gb169\|BE420561 | 3165 | 474 | 85.2 | globlastp |
| 978 | LNU27 | brachypodium\|gb169\|BE420561 | 3165 | 489 | 90 | globlastp |
| 979 | LNU7 | antirrhinum\|gb166\|AJ559707 | 3166 | 474 | 85.2 | globlastp |
| 980 | LNU7 | apple\|gb157.3\|CN444191 | 3167 | 474 | 85.2 | globlastp |
| 981 | LNU7 | apple\|gb171\|CN444191 | 3167 | 474 | 85.2 | globlastp |
| 982 | LNU7 | apple\|gb157.3\|CN489474 | 3167 | 474 | 85.2 | globlastp |
| 983 | LNU7 | apple\|gb171\|CN489474 | 3167 | 474 | 85.2 | globlastp |
| 984 | LNU7 | arabidopsis\|gb165\|AT3G06700 | 3168 | 474 | 85.2 | globlastp |
| 985 | LNU7 | artemisia\|gb164\|EY054666 | 3169 | 474 | 85.2 | globlastp |
| 986 | LNU7 | b_juncea\|gb164\|EVGN00375713871037P0 | 3170 | 474 | 85.2 | globlastp |
| 987 | LNU7 | b_juncea\|gb164\|EVGN01049614682128 | 3161 | 474 | 85.2 | globlastp |
| 988 | LNU7 | b_rapa\|gb162\|CV432967 | 3161 | 474 | 85.2 | globlastp |
| 989 | LNU7 | basilicum\|gb157.3\|DY323081 | 3160 | 474 | 85.2 | globlastp |
| 989 | LNU27 | basilicum\|gb157.3\|DY323081 | 3160 | 489 | 80.3 | globlastp |
| 990 | LNU7 | beech\|gb170\|SRR006293S0003253 | 3171 | 474 | 85.2 | globlastp |
| 991 | LNU7 | maize\|gb170\|AI600790 | 3172 | 474 | 85.2 | globlastp |
| 991 | LNU27 | maize\|gb170\|AI600790 | 3172 | 489 | 83.3 | globlastp |
| 992 | LNU7 | maize\|gb170\|AI833392 | 3173 | 474 | 85.2 | globlastp |
| 992 | LNU27 | maize\|gb170\|AI833392 | 3173 | 489 | 83.3 | globlastp |
| 993 | LNU7 | poplar\|10v1\|DT492219 | 3174 | 474 | 85.2 | globlastp |
| 994 | LNU7 | poplar\|gb170\|DT492219 | 3174 | 474 | 85.2 | globlastp |
| 995 | LNU7 | radish\|gb164\|EV536346 | 3170 | 474 | 85.2 | globlastp |
| 996 | LNU7 | radish\|gb164\|EV549950 | 3170 | 474 | 85.2 | globlastp |
| 997 | LNU7 | radish\|gb164\|EW714409 | 3170 | 474 | 85.2 | globlastp |
| 998 | LNU7 | radish\|gb164\|EX746273 | 3170 | 474 | 85.2 | globlastp |
| 999 | LNU7 | radish\|gb164\|FD556726 | 3170 | 474 | 85.2 | globlastp |
| 1000 | LNU7 | sunflower\|gb162\|CD846243 | 3175 | 474 | 85.2 | globlastp |

TABLE 2-continued

Homologues of the identified genes/polypeptides for increasing nitrogen use
efficiency, fertilizer use efficiency, yield, seed yield, growth rate, vigor, biomass, oil
content, fiber yield, fiber quality, fiber length, abiotic stress tolerance and/or water
use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 1001 | LNU7 | switchgrass\|gb167\|DN143529 | 3176 | 474 | 85.2 | globlastp |
| 1001 | LNU27 | switchgrass\|gb167\|DN143529 | 3176 | 489 | 83.3 | globlastp |
| 1002 | LNU7 | switchgrass\|gb167\|FL789549 | 3177 | 474 | 85.2 | globlastp |
| 1002 | LNU27 | switchgrass\|gb167\|FL789549 | 3177 | 489 | 83.3 | globlastp |
| 1003 | LNU7 | tamarix\|gb166\|CF198845 | 3178 | 474 | 85.2 | globlastp |
| 1004 | LNU7 | avocado\|10v1\|CK758909 | 3179 | 474 | 83.9 | globlastp |
| 1005 | LNU7 | avocado\|gb164\|CK758909 | 3179 | 474 | 83.9 | globlastp |
| 1006 | LNU7 | banana\|gb167\|FF559899 | 3180 | 474 | 83.9 | globlastp |
| 1007 | LNU7 | banana\|gb167\|FL661163 | 3181 | 474 | 83.9 | globlastp |
| 1008 | LNU7 | lovegrass\|gb167\|EH190358 | 3182 | 474 | 83.61 | glotblastn |
| 1008 | LNU27 | lovegrass\|gb167\|EH190358 | 3182 | 489 | 83.33 | glotblastn |
| 1009 | LNU7 | canola\|10v1\|DW998335 | 3183 | 474 | 83.6 | globlastp |
| 1010 | LNU7 | eggplant\|10v1\|FS009243 | 3184 | 474 | 83.6 | globlastp |
| 1011 | LNU7 | lettuce\|10v1\|DW101911 | 3185 | 474 | 83.6 | globlastp |
| 1012 | LNU7 | orobanche\|10v1\|SRR023189S0004367 | 3186 | 474 | 83.6 | globlastp |
| 1012 | LNU27 | orobanche\|10v1\|SRR023189S0004367 | 3186 | 489 | 80.3 | globlastp |
| 1013 | LNU7 | brachypodium\|09v1\|GT764657 | 3187 | 474 | 83.6 | globlastp |
| 1013 | LNU27 | brachypodium\|09v1\|GT764657 | 3187 | 489 | 88.3 | globlastp |
| 1014 | LNU7 | brachypodium\|gb169\|BE399643 | 3187 | 474 | 83.6 | globlastp |
| 1014 | LNU27 | brachypodium\|gb169\|BE399643 | 3187 | 489 | 88.3 | globlastp |
| 1015 | LNU7 | b_juncea\|gb164\|EVGN00222912251720 | 3188 | 474 | 83.6 | globlastp |
| 1016 | LNU7 | b_juncea\|gb164\|EVGN00516938790398 | 3189 | 474 | 83.6 | globlastp |
| 1017 | LNU7 | canola\|10v1\|CD839275 | 3190 | 474 | 83.6 | globlastp |
| 1018 | LNU7 | canola\|gb161\|CD811649 | 3190 | 474 | 83.6 | globlastp |
| 1019 | LNU7 | canola\|gb161\|H74817 | 3183 | 474 | 83.6 | globlastp |
| 1020 | LNU7 | lettuce\|gb157.2\|DW045025 | 3191 | 474 | 83.6 | globlastp |
| 1021 | LNU7 | lettuce\|10v1\|DW077777 | 3191 | 474 | 83.6 | globlastp |
| 1022 | LNU7 | lettuce\|gb157.2\|DW077777 | 3191 | 474 | 83.6 | globlastp |
| 1023 | LNU7 | lettuce\|gb157.2\|DW077988 | 3191 | 474 | 83.6 | globlastp |
| 1024 | LNU7 | lettuce\|gb157.2\|DW104130 | 3191 | 474 | 83.6 | globlastp |
| 1025 | LNU7 | maize\|gb170\|AI372387 | 3192 | 474 | 83.6 | globlastp |
| 1025 | LNU27 | maize\|gb170\|AI372387 | 3192 | 489 | 81.7 | globlastp |
| 1026 | LNU7 | poppy\|gb166\|FE964149 | 3193 | 474 | 83.6 | globlastp |
| 1027 | LNU7 | triphysaria\|gb164\|EX992128 | 3194 | 474 | 83.6 | globlastp |
| 1027 | LNU27 | triphysaria\|gb164\|EX992128 | 3194 | 489 | 83.3 | globlastp |
| 1028 | LNU7 | lettuce\|10v1\|DW045025 | 3191 | 474 | 83.6 | globlastp |
| 1029 | LNU7 | orobanche\|10v1\|SRR023495S0017698 | 3195 | 474 | 82.3 | globlastp |
| 1030 | LNU7 | tobacco\|gb162\|CV020926 | 3196 | 474 | 82.3 | globlastp |
| 1031 | LNU7 | liriodendron\|gb166\|CK757037 | 3197 | 474 | 82.3 | globlastp |
| 1032 | LNU7 | tobacco\|gb162\|BU673934 | 3195 | 474 | 82.3 | globlastp |
| 1033 | LNU7 | arabidopsis_lyrata\|09v1\|JGIAL017844 | 3198 | 474 | 82 | globlastp |
| 1034 | LNU7 | flax\|09v1\|EU829933 | 3199 | 474 | 82 | globlastp |
| 1035 | LNU7 | monkeyflower\|10v1\|DV206864 | 3200 | 474 | 82 | globlastp |
| 1036 | LNU7 | oat\|10v1\|GO582693 | 3201 | 474 | 82 | globlastp |
| 1036 | LNU27 | oat\|10v1\|GO582693 | 3201 | 489 | 93.3 | globlastp |
| 1037 | LNU7 | oat\|10v1\|GO582779 | 3201 | 474 | 82 | globlastp |
| 1037 | LNU27 | oat\|10v1\|GO582779 | 3201 | 489 | 93.3 | globlastp |
| 1038 | LNU7 | orobanche\|10v1\|SRR023189S0006077 | 3202 | 474 | 82 | globlastp |
| 1038 | LNU27 | orobanche\|10v1\|SRR023189S0006077 | 3202 | 489 | 80.3 | globlastp |
| 1039 | LNU7 | b_juncea\|gb164\|EVGN04206719550893 | 3203 | 474 | 82 | globlastp |
| 1040 | LNU7 | cacao\|gb167\|CU480546 | 3204 | 474 | 82 | globlastp |
| 1041 | LNU7 | dandelion\|gb161\|DY808273 | 3205 | 474 | 82 | globlastp |
| 1042 | LNU7 | dandelion\|gb161\|DY811268 | 3205 | 474 | 82 | globlastp |
| 1043 | LNU7 | dandelion\|gb161\|DY814721 | 3205 | 474 | 82 | globlastp |
| 1044 | LNU7 | lettuce\|gb157.2\|DW101911 | 3206 | 474 | 82 | globlastp |
| 1045 | LNU7 | rose\|10v1\|BQ105463 | 3207 | 474 | 82 | globlastp |
| 1046 | LNU7 | rose\|gb157.2\|BQ105463 | 3207 | 474 | 82 | globlastp |
| 1047 | LNU7 | sunflower\|gb162\|DY905617 | 3205 | 474 | 82 | globlastp |
| 1048 | LNU7 | switchgrass\|gb167\|DN150598 | 3208 | 474 | 82 | globlastp |
| 1048 | LNU27 | switchgrass\|gb167\|DN150598 | 3208 | 489 | 81.7 | globlastp |
| 1049 | LNU7 | cichorium\|gb171\|FL680147 | 3209 | 474 | 81.97 | glotblastn |
| 1050 | LNU7 | cycas\|gb166\|CB093385 | 3210 | 474 | 81.5 | globlastp |
| 1051 | LNU7 | strawberry\|gb164\|CO380923 | 3211 | 474 | 81 | globlastp |
| 1052 | LNU7 | tobacco\|gb162\|CV019192 | 3212 | 474 | 80.6 | globlastp |
| 1053 | LNU7 | ipomoea_batatas\|10v1\|DV037499XX2 | 3213 | 474 | 80.33 | glotblastn |
| 1054 | LNU7 | lotus\|09v1\|BW596153 | 3214 | 474 | 80.33 | glotblastn |
| 1055 | LNU7 | lotus\|gb157.2\|BP059519 | 3215 | 474 | 80.33 | glotblastn |
| 1056 | LNU7 | monkeyflower\|10v1\|CV521685 | 3216 | 474 | 80.3 | globlastp |
| 1057 | LNU7 | solanum_phureja\|09v1\|SPHAF204786 | 3217 | 474 | 80.3 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 1058 | LNU7 | potato\|10v1\|BQ512966 | 3217 | 474 | 80.3 | globlastp |
| 1059 | LNU7 | potato\|gb157.2\|BQ512966 | 3217 | 474 | 80.3 | globlastp |
| 1060 | LNU7 | tobacco\|gb162\|BP530058 | 3218 | 474 | 80.3 | globlastp |
| 1061 | LNU7 | tomato\|09v1\|AF204786 | 3219 | 474 | 80.3 | globlastp |
| 1062 | LNU7 | tomato\|gb164\|AF204786 | 3219 | 474 | 80.3 | globlastp |
| 1063 | LNU7 | cryptomeria\|gb166\|BW992620 | 3220 | 474 | 80 | globlastp |
| 1064 | LNU8 | arabidopsis_lyrata\|09v1\|JGIAL010354 | 3221 | 475 | 93.6 | globlastp |
| 1065 | LNU9 | rice\|gb170\|OS07G37280 | 3222 | 476 | 87.84 | globlastn |
| 1066 | LNU13 | sorghum\|09v1\|SB02G036230 | 3223 | 480 | 81.8 | globlastp |
| 1067 | LNU13 | sorghum\|gb161.crp\|BQ635805 | 3223 | 480 | 81.8 | globlastp |
| 1068 | LNU13 | maize\|gb170\|BI245385 | 3224 | 480 | 80.7 | globlastp |
| 1069 | LNU14 | arabidopsis_lyrata\|09v1\|JGIAL015001 | 3225 | 481 | 96.3 | globlastp |
| 1070 | LNU15 | arabidopsis_lyrata\|09v1\|JGIAL009168 | 3226 | 482 | 94.2 | globlastp |
| 1071 | LNU17 | sorghum\|09v1\|SB03G011640 | 3227 | 483 | 84.6 | globlastp |
| 1072 | LNU17 | sorghum\|gb161.crp\|AI947401 | 3227 | 483 | 84.6 | globlastp |
| 1073 | LNU17 | millet\|09v1\|EVO454PM011107 | 3228 | 483 | 84.1 | globlastp |
| 1074 | LNU17 | sugarcane\|gb157.3\|CA114497 | 3229 | 483 | 84.1 | globlastp |
| 1075 | LNU17 | switchgrass\|gb167\|DN142702 | 3230 | 483 | 82.5 | globlastp |
| 1076 | LNU17 | maize\|gb170\|AI861546 | 3231 | 483 | 81.2 | globlastp |
| 1077 | LNU17 | brachypodium\|09v1\|GT758222 | 3232 | 483 | 80.5 | globlastp |
| 1078 | LNU17 | brachypodium\|gb169\|BQ246612 | 3232 | 483 | 80.5 | globlastp |
| 1079 | LNU19 | maize\|gb170\|DR806345 | 3233 | 484 | 82.6 | globlastp |
| 1080 | LNU19 | sorghum\|gb161.crp\|AW679176 | 3234 | 484 | 80.5 | globlastp |
| 1081 | LNU20 | potato\|gb157.2\|BG888517 | 3235 | 485 | 97.8 | globlastp |
| 1082 | LNU20 | potato\|10v1\|BG888517 | 3236 | 485 | 97.6 | globlastp |
| 1083 | LNU20 | solanum_phureja\|09v1\|SPHBG131270 | 3237 | 485 | 97.4 | globlastp |
| 1084 | LNU20 | pepper\|gb171\|BM062238 | 3238 | 485 | 89.5 | globlastp |
| 1085 | LNU20 | tobacco\|gb162\|EB428440 | 3239 | 485 | 83.74 | globlastn |
| 1086 | LNU23 | arabidopsis_lyrata\|09v1\|JGIAL002476 | 3240 | 486 | 93.2 | globlastp |
| 1087 | LNU23 | radish\|gb164\|EW732145 | 3241 | 486 | 88.5 | globlastp |
| 1088 | LNU24 | arabidopsis_lyrata\|09v1\|JGIAL003443 | 3242 | 487 | 98.2 | globlastp |
| 1089 | LNU24 | radish\|gb164\|EV528988 | 3243 | 487 | 87 | globlastp |
| 1090 | LNU24 | arabidopsis\|gb165\|AT1G33090 | 3244 | 487 | 85.8 | globlastp |
| 1091 | LNU24 | arabidopsis\|gb165\|AT1G33100 | 3245 | 487 | 85.2 | globlastp |
| 1092 | LNU24 | arabidopsis_lyrata\|09v1\|JGIAL003442 | 3246 | 487 | 85 | globlastp |
| 1093 | LNU24 | arabidopsis\|gb165\|AT1G33080 | 3247 | 487 | 83.2 | globlastp |
| 1094 | LNU25 | sugarcane\|10v1\|BQ533886 | 3248 | 488 | 96.1 | globlastp |
| 1095 | LNU25 | sugarcane\|gb157.3\|BQ533886 | 3249 | 488 | 96.1 | globlastp |
| 1096 | LNU25 | maize\|gb170\|AW563076 | 3250 | 488 | 93.6 | globlastp |
| 1097 | LNU25 | switchgrass\|gb167\|FL773555 | 3251 | 488 | 83.3 | globlastp |
| 1098 | LNU27 | wheat\|gb164\|BE399643 | 489 | 489 | 100 | globlastp |
| 1099 | LNU27 | wheat\|gb164\|BE424751 | 489 | 489 | 100 | globlastp |
| 1100 | LNU27 | wheat\|gb164\|BE443944 | 489 | 489 | 100 | globlastp |
| 1101 | LNU27 | rye\|gb164\|BG263912 | 3252 | 489 | 96.7 | globlastp |
| 1102 | LNU27 | fescue\|gb161\|CK803089 | 3253 | 489 | 85 | globlastp |
| 1103 | LNU28 | wheat\|gb164\|BF293133 | 3254 | 490 | 97.1 | globlastp |
| 1104 | LNU28 | pseudoroegneria\|gb167\|FF346547 | 3255 | 490 | 96 | globlastp |
| 1105 | LNU28 | wheat\|gb164\|CA655539 | 3256 | 490 | 95.7 | globlastp |
| 1106 | LNU28 | leymus\|gb166\|EG382149 | 3257 | 490 | 95.5 | globlastp |
| 1107 | LNU28 | brachypodium\|09v1\|GT829440 | 3258 | 490 | 85.2 | globlastp |
| 1108 | LNU28 | brachypodium\|gb169\|BF293133 | 3258 | 490 | 85.2 | globlastp |
| 1109 | LNU29 | solanum_phureja\|09v1\|SPHAI487919 | 3259 | 491 | 91.2 | globlastp |
| 1110 | LNU29 | potato\|gb157.2\|BM405532 | 3260 | 491 | 88.33 | globlastn |
| 1111 | LNU32 | sugarcane\|10v1\|CA070626 | 3261 | 492 | 91.12 | globlastn |
| 1112 | LNU32 | sugarcane\|gb157.3\|CA070626 | 3262 | 492 | 87 | globlastp |
| 1113 | LNU32 | sorghum\|09v1\|SB08G001710 | 3263 | 492 | 85.1 | globlastp |
| 1114 | LNU32 | sorghum\|gb161.crp\|CD463367 | 3263 | 492 | 85.1 | globlastp |
| 1115 | LNU32 | maize\|gb170\|CB604763 | 3264 | 492 | 84.8 | globlastp |
| 1116 | LNU32 | maize\|gb170\|BE552794 | 3265 | 492 | 83.3 | globlastp |
| 1117 | LNU32 | switchgrass\|gb167\|DN144499 | 3266 | 492 | 82.6 | globlastp |
| 1118 | LNU33 | soybean\|gb168\|BQ124735 | 3267 | 493 | 92.95 | globlastn |
| 1119 | LNU33 | lotus\|09v1\|AV776761 | 3268 | 493 | 80.6 | globlastp |
| 1120 | LNU34 | sorghum\|09v1\|SB03G034160 | 3269 | 494 | 87.86 | globlastn |
| 1121 | LNU34 | sorghum\|gb161.crp\|DN212069 | 3270 | 494 | 87.86 | globlastn |
| 1122 | LNU34 | brachypodium\|09v1\|GT773303 | 3271 | 494 | 86.43 | globlastn |
| 1123 | LNU34 | wheat\|gb164\|BG608344 | 3272 | 494 | 85.71 | globlastn |
| 1124 | LNU34 | maize\|gb170\|BE344718 | 3273 | 494 | 85.2 | globlastp |
| 1125 | LNU36 | soybean\|gb168\|BE823007 | 3274 | 496 | 94.3 | globlastp |
| 1126 | LNU36 | soybean\|gb168\|CD398253 | 3275 | 496 | 80.7 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 1127 | LNU43 | soybean|gb168|AI967672 | 3276 | 499 | 94.9 | globlastp |
| 1128 | LNU43 | bean|gb167|CA896732 | 3277 | 499 | 90.4 | globlastp |
| 1129 | LNU43 | liquorice|gb171|FS261351 | 3278 | 499 | 89.9 | globlastp |
| 1130 | LNU43 | cowpea|gb166|FF399439 | 3279 | 499 | 89.3 | globlastp |
| 1131 | LNU43 | peanut|gb171|ES721626 | 3280 | 499 | 88 | globlastp |
| 1132 | LNU43 | peanut|gb167|EE125486 | 3281 | 499 | 87 | globlastp |
| 1133 | LNU43 | peanut|gb171|EE125486 | 3281 | 499 | 87 | globlastp |
| 1134 | LNU43 | lotus|09v1|LLAI967672 | 3282 | 499 | 84.9 | globlastp |
| 1135 | LNU43 | lotus|gb157.2|AI967672 | 3282 | 499 | 84.9 | globlastp |
| 1136 | LNU43 | chickpea|09v2|FE669917 | 3283 | 499 | 84.8 | globlastp |
| 1137 | LNU43 | pea|09v1|GFXPEAATPASEX1 | 3284 | 499 | 81.3 | globlastp |
| 1138 | LNU44 | pigeonpea|gb171|GR464245 | 3285 | 500 | 94.9 | globlastp |
| 1139 | LNU44 | cowpea|gb166|FC459300 | 3286 | 500 | 92.4 | globlastp |
| 1140 | LNU44 | liquorice|gb171|FS238932 | 3287 | 500 | 89.9 | globlastp |
| 1141 | LNU44 | bean|gb167|CB539787 | 3288 | 500 | 87.34 | glotblastn |
| 1142 | LNU44 | bean|gb167|CA899920 | 3289 | 500 | 86.1 | globlastp |
| 1143 | LNU44 | lotus|09v1|LLCN825274 | 3290 | 500 | 86.1 | globlastp |
| 1144 | LNU44 | lotus|gb157.2|CN825274 | 3290 | 500 | 86.1 | globlastp |
| 1145 | LNU44 | soybean|gb168|BQ155489 | 3291 | 500 | 84.7 | globlastp |
| 1146 | LNU44 | bean|gb167|FD799417 | 3292 | 500 | 83.5 | globlastp |
| 1147 | LNU44 | medicago|09v1|AW171675 | 3293 | 500 | 83.5 | globlastp |
| 1148 | LNU44 | medicago|gb157.2|AW171675 | 3293 | 500 | 83.5 | globlastp |
| 1149 | LNU44 | peanut|gb167|CD038813 | 3294 | 500 | 81.2 | globlastp |
| 1150 | LNU44 | peanut|gb171|CD038813 | 3294 | 500 | 81.2 | globlastp |
| 1151 | LNU44 | peanut|gb171|CD038024 | 3295 | 500 | 80 | globlastp |
| 1152 | LNU45 | chickpea|09v2|GR406612 | 501 | 501 | 100 | globlastp |
| 1153 | LNU45 | liquorice|gb171|FS238653 | 501 | 501 | 100 | globlastp |
| 1154 | LNU45 | pea|09v1|AM161941 | 501 | 501 | 100 | globlastp |
| 1155 | LNU45 | pigeonpea|gb171|GR465032 | 501 | 501 | 100 | globlastp |
| 1156 | LNU45 | bean|gb167|CA897298 | 501 | 501 | 100 | globlastp |
| 1157 | LNU45 | chestnut|gb170|SRR006295S0059092 | 501 | 501 | 100 | globlastp |
| 1158 | LNU45 | cowpea|gb166|DR068382 | 501 | 501 | 100 | globlastp |
| 1159 | LNU45 | cowpea|gb166|EG594283 | 501 | 501 | 100 | globlastp |
| 1160 | LNU45 | cowpea|gb166|FC456876 | 501 | 501 | 100 | globlastp |
| 1161 | LNU45 | lotus|09v1|BI419054 | 501 | 501 | 100 | globlastp |
| 1162 | LNU45 | lotus|gb157.2|BI419054 | 501 | 501 | 100 | globlastp |
| 1163 | LNU45 | lotus|09v1|LLCB829590 | 501 | 501 | 100 | globlastp |
| 1164 | LNU45 | lotus|gb157.2|CB829590 | 501 | 501 | 100 | globlastp |
| 1165 | LNU45 | medicago|09v1|BE318806 | 501 | 501 | 100 | globlastp |
| 1166 | LNU45 | medicago|gb157.2|BE318806 | 501 | 501 | 100 | globlastp |
| 1167 | LNU45 | oak|gb170|CR627523 | 501 | 501 | 100 | globlastp |
| 1168 | LNU45 | peanut|gb167|CD037890 | 501 | 501 | 100 | globlastp |
| 1169 | LNU45 | peanut|gb171|CD037890 | 501 | 501 | 100 | globlastp |
| 1170 | LNU45 | peanut|gb171|CD038469 | 501 | 501 | 100 | globlastp |
| 1171 | LNU45 | peanut|gb167|EE126116 | 501 | 501 | 100 | globlastp |
| 1172 | LNU45 | peanut|gb171|EE126116 | 501 | 501 | 100 | globlastp |
| 1173 | LNU45 | peanut|gb167|EE126336 | 501 | 501 | 100 | globlastp |
| 1174 | LNU45 | peanut|gb171|EE126336 | 501 | 501 | 100 | globlastp |
| 1175 | LNU45 | chickpea|09v2|GR392190 | 3296 | 501 | 98.8 | globlastp |
| 1176 | LNU45 | chickpea|09v2|GR392639 | 3297 | 501 | 98.8 | globlastp |
| 1177 | LNU45 | cleome_gynandra|10v1|SRR015532S0009070 | 3296 | 501 | 98.8 | globlastp |
| 1178 | LNU45 | cucumber|09v1|CK086106 | 3298 | 501 | 98.8 | globlastp |
| 1179 | LNU45 | heritiera|10v1|SRR005795S0009553 | 3299 | 501 | 98.8 | globlastp |
| 1180 | LNU45 | heritiera|10v1|SRR005795S0022077 | 3299 | 501 | 98.8 | globlastp |
| 1181 | LNU45 | liquorice|gb171|FS245788 | 3300 | 501 | 98.8 | globlastp |
| 1182 | LNU45 | bean|gb167|CA897297 | 3300 | 501 | 98.8 | globlastp |
| 1183 | LNU45 | beech|gb170|SRR006293S0000924 | 3298 | 501 | 98.8 | globlastp |
| 1184 | LNU45 | cacao|gb167|CU473827 | 3299 | 501 | 98.8 | globlastp |
| 1185 | LNU45 | cassava|gb164|DV442696 | 3298 | 501 | 98.8 | globlastp |
| 1186 | LNU45 | castorbean|09v1|EE256323 | 3298 | 501 | 98.8 | globlastp |
| 1187 | LNU45 | castorbean|gb160|EE256323 | 3298 | 501 | 98.8 | globlastp |
| 1188 | LNU45 | castorbean|09v1|GE636711 | 3298 | 501 | 98.8 | globlastp |
| 1189 | LNU45 | chestnut|gb170|SRR006295S0001785 | 3298 | 501 | 98.8 | globlastp |
| 1190 | LNU45 | cotton|gb164|BE052927 | 3299 | 501 | 98.8 | globlastp |
| 1191 | LNU45 | cotton|gb164|BE053779 | 3299 | 501 | 98.8 | globlastp |
| 1192 | LNU45 | cotton|gb164|BE054840 | 3299 | 501 | 98.8 | globlastp |
| 1193 | LNU45 | cotton|gb164|BF275747 | 3299 | 501 | 98.8 | globlastp |
| 1194 | LNU45 | cotton|gb164|BG444626 | 3299 | 501 | 98.8 | globlastp |
| 1195 | LNU45 | cotton|gb164|CO104281 | 3299 | 501 | 98.8 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 1196 | LNU45 | cowpea\|gb166\|FC460219 | 3300 | 501 | 98.8 | globlastp |
| 1197 | LNU45 | eucalyptus\|gb166\|CB967805 | 3298 | 501 | 98.8 | globlastp |
| 1198 | LNU45 | eucalyptus\|gb166\|CT980235 | 3298 | 501 | 98.8 | globlastp |
| 1199 | LNU45 | medicago\|gb1579.2\|AW329579 | 3296 | 501 | 98.8 | globlastp |
| 1200 | LNU45 | medicago\|09v1\|LLBE239494 | 3296 | 501 | 98.8 | globlastp |
| 1201 | LNU45 | medicago\|gb157.2\|BE239494 | 3296 | 501 | 98.8 | globlastp |
| 1202 | LNU45 | melon\|gb165\|EB714819 | 3298 | 501 | 98.8 | globlastp |
| 1203 | LNU45 | oak\|gb170\|DN950003 | 3298 | 501 | 98.8 | globlastp |
| 1204 | LNU45 | peanut\|gb167\|EH046888 | 3301 | 501 | 98.8 | globlastp |
| 1205 | LNU45 | peanut\|gb171\|EH046888 | 3301 | 501 | 98.8 | globlastp |
| 1206 | LNU45 | rose\|10v1\|BQ104562 | 3302 | 501 | 98.8 | globlastp |
| 1207 | LNU45 | soybean\|gb168\|BM140026 | 3300 | 501 | 98.8 | globlastp |
| 1208 | LNU45 | spurge\|gb161\|BE095304 | 3298 | 501 | 98.8 | globlastp |
| 1209 | LNU45 | cleome_spinosa\|10v1\|GR931938 | 3303 | 501 | 97.7 | globlastp |
| 1210 | LNU45 | cleome_spinosa\|10v1\|SRR015531S0016648 | 3303 | 501 | 97.7 | globlastp |
| 1211 | LNU45 | cleome_spinosa\|10v1\|SRR015531S0024494 | 3303 | 501 | 97.7 | globlastp |
| 1212 | LNU45 | cleome_spinosa\|10v1\|SRR015531S0039098 | 3303 | 501 | 97.7 | globlastp |
| 1213 | LNU45 | cucumber\|09v1\|AM715462 | 3304 | 501 | 97.7 | globlastp |
| 1214 | LNU45 | lettuce\|10v1\|DW075415 | 3305 | 501 | 97.7 | globlastp |
| 1215 | LNU45 | liquorice\|gb171\|FS239649 | 3306 | 501 | 97.7 | globlastp |
| 1216 | LNU45 | monkeyflower\|10v1\|CV519036 | 3307 | 501 | 97.7 | globlastp |
| 1217 | LNU45 | pea\|09v1\|EX570516 | 3308 | 501 | 97.7 | globlastp |
| 1218 | LNU45 | pea\|09v1\|EX571249 | 3309 | 501 | 97.7 | globlastp |
| 1219 | LNU45 | tea\|10v1\|CV013950 | 3310 | 501 | 97.7 | globlastp |
| 1220 | LNU45 | antirrhinum\|gb166\|AJ558887 | 3311 | 501 | 97.7 | globlastp |
| 1221 | LNU45 | beet\|gb162\|BQ592037 | 3312 | 501 | 97.7 | globlastp |
| 1222 | LNU45 | bruguiera\|gb166\|BP941557 | 3313 | 501 | 97.7 | globlastp |
| 1223 | LNU45 | cacao\|gb167\|CF974299 | 3314 | 501 | 97.7 | globlastp |
| 1224 | LNU45 | cacao\|gb167\|CU476326 | 3315 | 501 | 97.7 | globlastp |
| 1225 | LNU45 | cassava\|09v1\|BI325193 | 3316 | 501 | 97.7 | globlastp |
| 1226 | LNU45 | cassava\|gb164\|BI325193 | 3316 | 501 | 97.7 | globlastp |
| 1227 | LNU45 | cassava\|09v1\|CK644610 | 3317 | 501 | 97.7 | globlastp |
| 1228 | LNU45 | cassava\|gb164\|CK644610 | 3317 | 501 | 97.7 | globlastp |
| 1229 | LNU45 | cassava\|09v1\|DV442696 | 3317 | 501 | 97.7 | globlastp |
| 1230 | LNU45 | castorbean\|gb160\|MDL30128M008573 | 3318 | 501 | 97.7 | globlastp |
| 1231 | LNU45 | cycas\|gb166\|CB091386 | 3319 | 501 | 97.7 | globlastp |
| 1232 | LNU45 | cycas\|gb166\|CB092866 | 3319 | 501 | 97.7 | globlastp |
| 1233 | LNU45 | grape\|gb160\|EC932417 | 3320 | 501 | 97.7 | globlastp |
| 1234 | LNU45 | iceplant\|gb164\|BE034168 | 3321 | 501 | 97.7 | globlastp |
| 1235 | LNU45 | lettuce\|gb157.2\|DW075415 | 3305 | 501 | 97.7 | globlastp |
| 1236 | LNU45 | lettuce\|gb157.2\|DW103341 | 3305 | 501 | 97.7 | globlastp |
| 1237 | LNU45 | lettuce\|gb157.2\|DW145378 | 3305 | 501 | 97.7 | globlastp |
| 1238 | LNU45 | prunus\|gb167\|CB821790 | 3322 | 501 | 97.7 | globlastp |
| 1239 | LNU45 | rose\|gb157.2\|BQ104562 | 3323 | 501 | 97.7 | globlastp |
| 1240 | LNU45 | spurge\|gb161\|DV133006 | 3324 | 501 | 97.7 | globlastp |
| 1241 | LNU45 | strawberry\|gb164\|CO379162 | 3325 | 501 | 97.7 | globlastp |
| 1242 | LNU45 | tamarix\|gb166\|CN605485 | 3312 | 501 | 97.7 | globlastp |
| 1243 | LNU45 | walnuts\|gb166\|CV197870 | 3312 | 501 | 97.7 | globlastp |
| 1244 | LNU45 | zamia\|gb166\|DY034316 | 3319 | 501 | 97.7 | globlastp |
| 1245 | LNU45 | canola\|10v1\|CD817525 | 3326 | 501 | 96.51 | globlastn |
| 1246 | LNU45 | blueberry\|10v1\|CF811404 | 3327 | 501 | 96.5 | globlastp |
| 1247 | LNU45 | canola\|10v1\|CD839015 | 3328 | 501 | 96.5 | globlastp |
| 1248 | LNU45 | canola\|10v1\|CN731675 | 3328 | 501 | 96.5 | globlastp |
| 1249 | LNU45 | canola\|10v1\|EE476478 | 3328 | 501 | 96.5 | globlastp |
| 1250 | LNU45 | cleome_gynandra\|10v1\|SRR015532S0012040 | 3329 | 501 | 96.5 | globlastp |
| 1251 | LNU45 | flax\|09v1\|EU829812 | 3330 | 501 | 96.5 | globlastp |
| 1252 | LNU45 | gerbera\|09v1\|AJ761450 | 3331 | 501 | 96.5 | globlastp |
| 1253 | LNU45 | ipomoea_nil\|10v1\|BJ554792 | 3332 | 501 | 96.5 | globlastp |
| 1254 | LNU45 | ipomoea_nil\|10v1\|BJ559906 | 3332 | 501 | 96.5 | globlastp |
| 1255 | LNU45 | ipomoea_nil\|10v1\|CJ742456 | 3332 | 501 | 96.5 | globlastp |
| 1256 | LNU45 | monkeyflower\|10v1\|DV212640 | 3333 | 501 | 96.5 | globlastp |
| 1257 | LNU45 | salvia\|10v1\|CV164158 | 3333 | 501 | 96.5 | globlastp |
| 1258 | LNU45 | salvia\|10v1\|CV165453 | 3333 | 501 | 96.5 | globlastp |
| 1259 | LNU45 | amborella\|gb166\|FD437556 | 3334 | 501 | 96.5 | globlastp |
| 1260 | LNU45 | antirrhinum\|gb166\|AJ560227 | 3335 | 501 | 96.5 | globlastp |
| 1261 | LNU45 | apple\|gb157.3\|CN492050 | 3336 | 501 | 96.5 | globlastp |
| 1262 | LNU45 | apple\|gb171\|CN492050 | 3336 | 501 | 96.5 | globlastp |
| 1263 | LNU45 | apple\|gb157.3\|CN997325 | 3336 | 501 | 96.5 | globlastp |
| 1264 | LNU45 | apple\|gb171\|CN997325 | 3336 | 501 | 96.5 | globlastp |

TABLE 2-continued

Homologues of the identified genes/polypeptides for increasing nitrogen use
efficiency, fertilizer use efficiency, yield, seed yield, growth rate, vigor, biomass, oil
content, fiber yield, fiber quality, fiber length, abiotic stress tolerance and/or water
use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 1265 | LNU45 | b_juncea\|gb164\|EVGN00032311610584 | 3328 | 501 | 96.5 | globlastp |
| 1266 | LNU45 | b_juncea\|gb164\|EVGN00163218130726 | 3328 | 501 | 96.5 | globlastp |
| 1267 | LNU45 | b_juncea\|gb164\|EVGN00242617670457 | 3328 | 501 | 96.5 | globlastp |
| 1268 | LNU45 | b_juncea\|gb164\|EVGN00404524182700 | 3328 | 501 | 96.5 | globlastp |
| 1269 | LNU45 | b_juncea\|gb164\|EVGN00541511341883 | 3328 | 501 | 96.5 | globlastp |
| 1270 | LNU45 | b_juncea\|gb164\|EVGN00673809061646 | 3328 | 501 | 96.5 | globlastp |
| 1271 | LNU45 | b_juncea\|gb164\|EVGN00683412381058 | 3328 | 501 | 96.5 | globlastp |
| 1272 | LNU45 | b_juncea\|gb164\|EVGN01161211992680 | 3328 | 501 | 96.5 | globlastp |
| 1273 | LNU45 | b_juncea\|gb164\|EVGN01304909632819 | 3328 | 501 | 96.5 | globlastp |
| 1274 | LNU45 | b_juncea\|gb164\|EVGN04290618070322 | 3328 | 501 | 96.5 | globlastp |
| 1275 | LNU45 | b_oleracea\|gb161\|AM062107 | 3328 | 501 | 96.5 | globlastp |
| 1276 | LNU45 | b_oleracea\|gb161\|DY027039 | 3328 | 501 | 96.5 | globlastp |
| 1277 | LNU45 | b_oleracea\|gb161\|DY027348 | 3328 | 501 | 96.5 | globlastp |
| 1278 | LNU45 | b_oleracea\|gb161\|DY027603 | 3328 | 501 | 96.5 | globlastp |
| 1279 | LNU45 | b_oleracea\|gb161\|DY029297 | 3328 | 501 | 96.5 | globlastp |
| 1280 | LNU45 | b_rapa\|gb162\|BG544410 | 3328 | 501 | 96.5 | globlastp |
| 1281 | LNU45 | b_rapa\|gb162\|CA992030 | 3328 | 501 | 96.5 | globlastp |
| 1282 | LNU45 | b_rapa\|gb162\|CV432516 | 3328 | 501 | 96.5 | globlastp |
| 1283 | LNU45 | b_rapa\|gb162\|CV433072 | 3328 | 501 | 96.5 | globlastp |
| 1284 | LNU45 | b_rapa\|gb162\|CX266536 | 3328 | 501 | 96.5 | globlastp |
| 1285 | LNU45 | b_rapa\|gb162\|CX268525 | 3328 | 501 | 96.5 | globlastp |
| 1286 | LNU45 | b_rapa\|gb162\|CX270594 | 3328 | 501 | 96.5 | globlastp |
| 1287 | LNU45 | b_rapa\|gb162\|CX273157 | 3328 | 501 | 96.5 | globlastp |
| 1288 | LNU45 | b_rapa\|gb162\|EE530283 | 3328 | 501 | 96.5 | globlastp |
| 1289 | LNU45 | bruguiera\|gb166\|BP948881 | 3337 | 501 | 96.5 | globlastp |
| 1290 | LNU45 | canola\|gb161\|CD812378 | 3328 | 501 | 96.5 | globlastp |
| 1291 | LNU45 | canola\|gb161\|CD812394 | 3328 | 501 | 96.5 | globlastp |
| 1292 | LNU45 | canola\|10v1\|CD812830 | 3328 | 501 | 96.5 | globlastp |
| 1293 | LNU45 | canola\|gb161\|CD812830 | 3328 | 501 | 96.5 | globlastp |
| 1294 | LNU45 | canola\|gb161\|CD812870 | 3328 | 501 | 96.5 | globlastp |
| 1295 | LNU45 | canola\|gb161\|CD817916 | 3328 | 501 | 96.5 | globlastp |
| 1296 | LNU45 | canola\|10v1\|CD818245 | 3328 | 501 | 96.5 | globlastp |
| 1297 | LNU45 | canola\|gb161\|CD818245 | 3328 | 501 | 96.5 | globlastp |
| 1298 | LNU45 | canola\|gb161\|CD818496 | 3328 | 501 | 96.5 | globlastp |
| 1299 | LNU45 | canola\|gb161\|CD821364 | 3328 | 501 | 96.5 | globlastp |
| 1300 | LNU45 | canola\|gb161\|CD834560 | 3328 | 501 | 96.5 | globlastp |
| 1301 | LNU45 | canola\|gb161\|CN731675 | 3328 | 501 | 96.5 | globlastp |
| 1302 | LNU45 | canola\|gb161\|EE476478 | 3328 | 501 | 96.5 | globlastp |
| 1303 | LNU45 | centaurea\|gb166\|EH740133 | 3338 | 501 | 96.5 | globlastp |
| 1304 | LNU45 | centaurea\|gb166\|EH744958 | 3338 | 501 | 96.5 | globlastp |
| 1305 | LNU45 | centaurea\|gb166\|EH785564 | 3331 | 501 | 96.5 | globlastp |
| 1306 | LNU45 | citrus\|gb166\|BQ624315 | 3339 | 501 | 96.5 | globlastp |
| 1307 | LNU45 | citrus\|gb166\|BQ624832 | 3339 | 501 | 96.5 | globlastp |
| 1308 | LNU45 | clover\|gb162\|BB930040 | 3340 | 501 | 96.5 | globlastp |
| 1309 | LNU45 | cryptomeria\|gb166\|BP174475 | 3341 | 501 | 96.5 | globlastp |
| 1310 | LNU45 | cynara\|gb167\|GE585914 | 3331 | 501 | 96.5 | globlastp |
| 1311 | LNU45 | ginger\|gb164\|DY349602 | 3342 | 501 | 96.5 | globlastp |
| 1312 | LNU45 | grape\|gb160\|BE846411 | 3343 | 501 | 96.5 | globlastp |
| 1313 | LNU45 | ipomoea\|gb157.2\|CJ741047 | 3332 | 501 | 96.5 | globlastp |
| 1314 | LNU45 | ipomoea\|gb157.2\|CJ742456 | 3332 | 501 | 96.5 | globlastp |
| 1315 | LNU45 | lettuce\|10v1\|DW044163 | 3331 | 501 | 96.5 | globlastp |
| 1316 | LNU45 | lettuce\|gb157.2\|DW044163 | 3331 | 501 | 96.5 | globlastp |
| 1317 | LNU45 | lettuce\|gb157.2\|DW045774 | 3331 | 501 | 96.5 | globlastp |
| 1318 | LNU45 | lettuce\|gb157.2\|DW103758 | 3331 | 501 | 96.5 | globlastp |
| 1319 | LNU45 | lettuce\|gb157.2\|DW105810 | 3331 | 501 | 96.5 | globlastp |
| 1320 | LNU45 | melon\|gb165\|AM715462 | 3344 | 501 | 96.5 | globlastp |
| 1321 | LNU45 | nuphar\|gb166\|CD474984 | 3345 | 501 | 96.5 | globlastp |
| 1322 | LNU45 | oil_palm\|gb166\|EL684405 | 3346 | 501 | 96.5 | globlastp |
| 1323 | LNU45 | oil_palm\|gb166\|EY413173 | 3342 | 501 | 96.5 | globlastp |
| 1324 | LNU45 | papaya\|gb165\|AM903803 | 3347 | 501 | 96.5 | globlastp |
| 1325 | LNU45 | papaya\|gb165\|EX239749 | 3348 | 501 | 96.5 | globlastp |
| 1326 | LNU45 | pine\|10v1\|AI812758 | 3349 | 501 | 96.5 | globlastp |
| 1327 | LNU45 | pine\|gb157.2\|AI812758 | 3349 | 501 | 96.5 | globlastp |
| 1328 | LNU45 | poplar\|10v1\|AI165443 | 3350 | 501 | 96.5 | globlastp |
| 1329 | LNU45 | poplar\|gb170\|AI165443 | 3350 | 501 | 96.5 | globlastp |
| 1330 | LNU45 | poplar\|10v1\|BI070097 | 3350 | 501 | 96.5 | globlastp |
| 1331 | LNU45 | poplar\|gb170\|BI070097 | 3350 | 501 | 96.5 | globlastp |
| 1332 | LNU45 | poplar\|10v1\|BI119656 | 3350 | 501 | 96.5 | globlastp |
| 1333 | LNU45 | poplar\|gb170\|BI119656 | 3350 | 501 | 96.5 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Hom. Polyp. SEQ ID NO: | Polyp. to SEQ ID NO: | % global identity | Algor. |
|---|---|---|---|---|---|---|
| 1334 | LNU45 | prunus\|gb167\|BU039142 | 3351 | 501 | 96.5 | globlastp |
| 1335 | LNU45 | radish\|gb164\|EV525442 | 3328 | 501 | 96.5 | globlastp |
| 1336 | LNU45 | radish\|gb164\|EV527675 | 3328 | 501 | 96.5 | globlastp |
| 1337 | LNU45 | radish\|gb164\|EV536763 | 3328 | 501 | 96.5 | globlastp |
| 1338 | LNU45 | radish\|gb164\|EV537524 | 3328 | 501 | 96.5 | globlastp |
| 1339 | LNU45 | radish\|gb164\|EW723868 | 3328 | 501 | 96.5 | globlastp |
| 1340 | LNU45 | radish\|gb164\|EW725365 | 3328 | 501 | 96.5 | globlastp |
| 1341 | LNU45 | radish\|gb164\|EW733186 | 3328 | 501 | 96.5 | globlastp |
| 1342 | LNU45 | radish\|gb164\|EW734391 | 3328 | 501 | 96.5 | globlastp |
| 1343 | LNU45 | radish\|gb164\|EX757217 | 3328 | 501 | 96.5 | globlastp |
| 1344 | LNU45 | radish\|gb164\|EX765397 | 3328 | 501 | 96.5 | globlastp |
| 1345 | LNU45 | radish\|gb164\|EX895252 | 3328 | 501 | 96.5 | globlastp |
| 1346 | LNU45 | radish\|gb164\|EY905533 | 3328 | 501 | 96.5 | globlastp |
| 1347 | LNU45 | radish\|gb164\|EY934770 | 3328 | 501 | 96.5 | globlastp |
| 1348 | LNU45 | spruce\|gb162\|CO227497 | 3349 | 501 | 96.5 | globlastp |
| 1349 | LNU45 | strawberry\|gb164\|CO379638 | 3352 | 501 | 96.5 | globlastp |
| 1350 | LNU45 | sunflower\|gb162\|CD849156 | 3331 | 501 | 96.5 | globlastp |
| 1351 | LNU45 | sunflower\|gb162\|CD849309 | 3331 | 501 | 96.5 | globlastp |
| 1352 | LNU45 | triphysaria\|gb164\|EX989107 | 3333 | 501 | 96.5 | globlastp |
| 1353 | LNU45 | triphysaria\|gb164\|EY001721 | 3333 | 501 | 96.5 | globlastp |
| 1354 | LNU45 | zamia\|gb166\|DY036444 | 3353 | 501 | 96.5 | globlastp |
| 1355 | LNU45 | lettuce\|10v1\|DW045774 | 3331 | 501 | 96.5 | globlastp |
| 1356 | LNU45 | lettuce\|10v1\|DW099098 | 3331 | 501 | 96.5 | globlastp |
| 1357 | LNU45 | canola\|10v1\|CD812870 | 3328 | 501 | 96.5 | globlastp |
| 1358 | LNU45 | canola\|10v1\|CD812378 | 3328 | 501 | 96.5 | globlastp |
| 1359 | LNU45 | canola\|10v1\|CD834560 | 3328 | 501 | 96.5 | globlastp |
| 1360 | LNU45 | salvia\|10v1\|SRR014553S0002286 | 3354 | 501 | 95.35 | glotblastn |
| 1361 | LNU45 | b_juncea\|gb164\|EVGN00337914530877 | 3355 | 501 | 95.35 | glotblastn |
| 1362 | LNU45 | canola\|gb161\|EL590902 | 3356 | 501 | 95.35 | glotblastn |
| 1363 | LNU45 | citrus\|gb166\|CF503931 | 3357 | 501 | 95.35 | glotblastn |
| 1364 | LNU45 | safflower\|gb162\|EL403359 | 3358 | 501 | 95.35 | glotblastn |
| 1365 | LNU45 | arabidopsis_lyrata\|09v1\|JGIAL029003 | 3359 | 501 | 95.3 | globlastp |
| 1366 | LNU45 | avocado\|10v1\|FD506790 | 3360 | 501 | 95.3 | globlastp |
| 1367 | LNU45 | cichorium\|gb171\|EH702627 | 3361 | 501 | 95.3 | globlastp |
| 1368 | LNU45 | eggplant\|10v1\|FS000719 | 3362 | 501 | 95.3 | globlastp |
| 1369 | LNU45 | potato\|10v1\|BG589651 | 3363 | 501 | 95.3 | globlastp |
| 1370 | LNU45 | salvia\|10v1\|SRR014553S0005980 | 3364 | 501 | 95.3 | globlastp |
| 1371 | LNU45 | apple\|gb171\|CN490097 | 3365 | 501 | 95.3 | globlastp |
| 1372 | LNU45 | arabidopsis\|gb165\|AT3G61110 | 3366 | 501 | 95.3 | globlastp |
| 1373 | LNU45 | artemisia\|gb164\|EY036326 | 3367 | 501 | 95.3 | globlastp |
| 1374 | LNU45 | artemisia\|gb164\|EY037581 | 3367 | 501 | 95.3 | globlastp |
| 1375 | LNU45 | avocado\|10v1\|CK754126 | 3368 | 501 | 95.3 | globlastp |
| 1376 | LNU45 | avocado\|gb164\|CK754126 | 3368 | 501 | 95.3 | globlastp |
| 1377 | LNU45 | banana\|gb167\|ES435098 | 3369 | 501 | 95.3 | globlastp |
| 1378 | LNU45 | banana\|gb167\|FF560357 | 3370 | 501 | 95.3 | globlastp |
| 1379 | LNU45 | banana\|gb167\|FF562322 | 3371 | 501 | 95.3 | globlastp |
| 1380 | LNU45 | canola\|10v1\|EE455490 | 3372 | 501 | 95.3 | globlastp |
| 1381 | LNU45 | canola\|gb161\|EE455490 | 3372 | 501 | 95.3 | globlastp |
| 1382 | LNU45 | catharanthus\|gb166\|EG561174 | 3373 | 501 | 95.3 | globlastp |
| 1383 | LNU45 | catharanthus\|gb166\|FD415347 | 3373 | 501 | 95.3 | globlastp |
| 1384 | LNU45 | cichorium\|gb166\|DT213797 | 3361 | 501 | 95.3 | globlastp |
| 1385 | LNU45 | cichorium\|gb171\|DT213797 | 3361 | 501 | 95.3 | globlastp |
| 1386 | LNU45 | citrus\|gb166\|CX640799 | 3374 | 501 | 95.3 | globlastp |
| 1387 | LNU45 | cryptomeria\|gb166\|BP174101 | 3375 | 501 | 95.3 | globlastp |
| 1388 | LNU45 | cynara\|gb167\|GE585853 | 3376 | 501 | 95.3 | globlastp |
| 1389 | LNU45 | ginger\|gb164\|DY351710 | 3377 | 501 | 95.3 | globlastp |
| 1390 | LNU45 | ginger\|gb164\|DY358500 | 3377 | 501 | 95.3 | globlastp |
| 1391 | LNU45 | ginger\|gb164\|DY367611 | 3378 | 501 | 95.3 | globlastp |
| 1392 | LNU45 | ipomoea\|gb157.2\|BJ554792 | 3379 | 501 | 95.3 | globlastp |
| 1393 | LNU45 | kiwi\|gb166\|FG410222 | 3380 | 501 | 95.3 | globlastp |
| 1394 | LNU45 | kiwi\|gb166\|FG430714 | 3380 | 501 | 95.3 | globlastp |
| 1395 | LNU45 | kiwi\|gb166\|FG441586 | 3380 | 501 | 95.3 | globlastp |
| 1396 | LNU45 | kiwi\|gb166\|FG461878 | 3380 | 501 | 95.3 | globlastp |
| 1397 | LNU45 | lettuce\|10v1\|DW077971 | 3379 | 501 | 95.3 | globlastp |
| 1398 | LNU45 | lettuce\|gb157.2\|DW077971 | 3379 | 501 | 95.3 | globlastp |
| 1399 | LNU45 | liriodendron\|gb166\|CO999247 | 3377 | 501 | 95.3 | globlastp |
| 1400 | LNU45 | liriodendron\|gb166\|FD495039 | 3377 | 501 | 95.3 | globlastp |
| 1401 | LNU45 | nicotiana_benthamiana\|gb162\|CN744078 | 3367 | 501 | 95.3 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 1402 | LNU45 | oil_palm|gb166|EL681535 | 3381 | 501 | 95.3 | globlastp |
| 1403 | LNU45 | oil_palm|gb166|EL684385 | 3377 | 501 | 95.3 | globlastp |
| 1404 | LNU45 | pepper|gb157.2|CA514595 | 3362 | 501 | 95.3 | globlastp |
| 1405 | LNU45 | pepper|gb171|CA514595 | 3362 | 501 | 95.3 | globlastp |
| 1406 | LNU45 | pine|gb157.2|AA739876 | 3382 | 501 | 95.3 | globlastp |
| 1407 | LNU45 | pine|gb157.2|AI812974 | 3382 | 501 | 95.3 | globlastp |
| 1408 | LNU45 | pine|gb157.2|AL749664 | 3382 | 501 | 95.3 | globlastp |
| 1409 | LNU45 | potato|gb157.2|BE923191 | 3363 | 501 | 95.3 | globlastp |
| 1410 | LNU45 | potato|gb157.2|BF153777 | 3363 | 501 | 95.3 | globlastp |
| 1411 | LNU45 | potato|gb157.2|BG589651 | 3363 | 501 | 95.3 | globlastp |
| 1412 | LNU45 | potato|gb157.2|BM406913 | 3363 | 501 | 95.3 | globlastp |
| 1413 | LNU45 | radish|gb164|EV535745 | 3383 | 501 | 95.3 | globlastp |
| 1414 | LNU45 | rose|10v1|BQ106521 | 3384 | 501 | 95.3 | globlastp |
| 1415 | LNU45 | sesame|gb157.2|BU668222 | 3385 | 501 | 95.3 | globlastp |
| 1416 | LNU45 | spruce|gb162|CO217320 | 3382 | 501 | 95.3 | globlastp |
| 1417 | LNU45 | sunflower|gb162|CD849221 | 3386 | 501 | 95.3 | globlastp |
| 1418 | LNU45 | sunflower|gb162|CD851828 | 3387 | 501 | 95.3 | globlastp |
| 1419 | LNU45 | sunflower|gb162|DY954225 | 3386 | 501 | 95.3 | globlastp |
| 1420 | LNU45 | thellungiella|gb167|BM985525 | 3372 | 501 | 95.3 | globlastp |
| 1421 | LNU45 | tobacco|gb162|CV016291 | 3367 | 501 | 95.3 | globlastp |
| 1422 | LNU45 | tobacco|gb162|CV018253 | 3367 | 501 | 95.3 | globlastp |
| 1423 | LNU45 | tomato|gb164|BG124194 | 3362 | 501 | 95.3 | globlastp |
| 1424 | LNU45 | tomato|gb164|BG126885 | 3362 | 501 | 95.3 | globlastp |
| 1425 | LNU45 | tomato|gb164|BG134762 | 3362 | 501 | 95.3 | globlastp |
| 1426 | LNU45 | pine|10v1|AA739876 | 3382 | 501 | 95.3 | globlastp |
| 1427 | LNU45 | potato|10v1|AJ489106 | 3363 | 501 | 95.3 | globlastp |
| 1428 | LNU45 | potato|10v1|BM406913 | 3363 | 501 | 95.3 | globlastp |
| 1429 | LNU45 | tomato|09v1|BG124194 | 3362 | 501 | 95.3 | globlastp |
| 1430 | LNU45 | arabidopsis_lyrata|09v1|BQ834271 | 3388 | 501 | 94.2 | globlastp |
| 1431 | LNU45 | arabidopsis_lyrata|09v1|JGIAL015965 | 3389 | 501 | 94.2 | globlastp |
| 1432 | LNU45 | ipomoea_batatas|10v1|CB330065 | 3390 | 501 | 94.2 | globlastp |
| 1433 | LNU45 | ipomoea_batatas|10v1|CB330743 | 3391 | 501 | 94.2 | globlastp |
| 1434 | LNU45 | ipomoea_batatas|10v1|CO500840 | 3392 | 501 | 94.2 | globlastp |
| 1435 | LNU45 | monkeyflower|10v1|DV211088 | 3393 | 501 | 94.2 | globlastp |
| 1436 | LNU45 | orobanche|10v1|SRR023189S0002696 | 3394 | 501 | 94.2 | globlastp |
| 1437 | LNU45 | orobanche|10v1|SRR023189S0007530 | 3394 | 501 | 94.2 | globlastp |
| 1438 | LNU45 | solanum_phureja|09v1|SPHBG124194 | 3395 | 501 | 94.2 | globlastp |
| 1439 | LNU45 | apple|gb157.3|CO756008 | 3396 | 501 | 94.2 | globlastp |
| 1440 | LNU45 | arabidopsis|gb165|AT5G47930 | 3397 | 501 | 94.2 | globlastp |
| 1441 | LNU45 | banana|gb167|DN239263 | 3398 | 501 | 94.2 | globlastp |
| 1442 | LNU45 | canola|gb161|EE569888 | 3399 | 501 | 94.2 | globlastp |
| 1443 | LNU45 | catharanthus|gb166|EG560431 | 3400 | 501 | 94.2 | globlastp |
| 1444 | LNU45 | coffea|10v1|DV667447 | 3401 | 501 | 94.2 | globlastp |
| 1445 | LNU45 | coffea|gb157.2|DV667447 | 3401 | 501 | 94.2 | globlastp |
| 1446 | LNU45 | cotton|gb164|BF272631 | 3402 | 501 | 94.2 | globlastp |
| 1447 | LNU45 | dandelion|gb161|DY807943 | 3403 | 501 | 94.2 | globlastp |
| 1448 | LNU45 | ipomoea|gb157.2|CB330743 | 3391 | 501 | 94.2 | globlastp |
| 1449 | LNU45 | nicotiana_benthamiana|gb162|AY310774 | 3404 | 501 | 94.2 | globlastp |
| 1450 | LNU45 | nicotiana_benthamiana|gb162|CN743261 | 3405 | 501 | 94.2 | globlastp |
| 1451 | LNU45 | potato|gb157.2|AJ489106 | 3395 | 501 | 94.2 | globlastp |
| 1452 | LNU45 | potato|gb157.2|BM404024 | 3395 | 501 | 94.2 | globlastp |
| 1453 | LNU45 | radish|gb164|EY920230 | 3406 | 501 | 94.2 | globlastp |
| 1454 | LNU45 | rose|gb157.2|BQ106521 | 3407 | 501 | 94.2 | globlastp |
| 1455 | LNU45 | senecio|gb170|DY662196 | 3408 | 501 | 94.2 | globlastp |
| 1456 | LNU45 | sesame|10v1|BU670278 | 3409 | 501 | 94.2 | globlastp |
| 1457 | LNU45 | tobacco|gb162|CV016119 | 3404 | 501 | 94.2 | globlastp |
| 1458 | LNU45 | triphysaria|gb164|EY020166 | 3410 | 501 | 94.2 | globlastp |
| 1459 | LNU45 | pepper|gb171|BM066089 | 3411 | 501 | 94.19 | glotblastn |
| 1460 | LNU45 | pepper|gb157.2|BM062650 | 3412 | 501 | 94.19 | glotblastn |
| 1461 | LNU45 | avocado|10v1|FD507705 | 3413 | 501 | 93.02 | glotblastn |
| 1462 | LNU45 | barley|gb157SOLEXA|BE411675 | 3414 | 501 | 93.02 | glotblastn |
| 1462 | LNU45 | barley|gb157.3|BE411675 | 3417 | 501 | 93 | globlastp |
| 1463 | LNU45 | physcomitrella|gb157|AW127011 | 3415 | 501 | 93.02 | glotblastn |
| 1464 | LNU45 | eggplant|10v1|FS003716 | 3416 | 501 | 93 | globlastp |
| 1465 | LNU45 | oat|10v1|GO582478 | 3417 | 501 | 93 | globlastp |
| 1466 | LNU45 | orobanche|10v1|SRR023495S0023362 | 3418 | 501 | 93 | globlastp |
| 1467 | LNU45 | physcomitrella|10v1|AW126791 | 3419 | 501 | 93 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 1468 | LNU45 | physcomitrella\|10v1\|AW126917 | 3419 | 501 | 93 | globlastp |
| 1469 | LNU45 | physcomitrella\|10v1\|AW127011 | 3419 | 501 | 93 | globlastp |
| 1470 | LNU45 | apple\|gb157.3\|EB115463 | 3420 | 501 | 93 | globlastp |
| 1471 | LNU45 | b_rapa\|gb162\|EX051142 | 3421 | 501 | 93 | globlastp |
| 1472 | LNU45 | banana\|gb167\|FL658637 | 3422 | 501 | 93 | globlastp |
| 1473 | LNU45 | barley\|gb157SOLEXA\|AL512188 | 3417 | 501 | 93 | globlastp |
| 1474 | LNU45 | barley\|gb157SOLEXA\|BE421731 | 3417 | 501 | 93 | globlastp |
| 1475 | LNU45 | brachypodium\|09v1\|DV471589 | 3417 | 501 | 93 | globlastp |
| 1476 | LNU45 | brachypodium\|gb169\|BE399584 | 3417 | 501 | 93 | globlastp |
| 1477 | LNU45 | brachypodium\|09v1\|DV471799 | 3423 | 501 | 93 | globlastp |
| 1478 | LNU45 | brachypodium\|gb169\|BE416572 | 3423 | 501 | 93 | globlastp |
| 1479 | LNU45 | cenchrus\|gb166\|BM084666 | 3424 | 501 | 93 | globlastp |
| 1480 | LNU45 | dandelion\|gb161\|DY809678 | 3425 | 501 | 93 | globlastp |
| 1481 | LNU45 | dandelion\|gb161\|DY838552 | 3425 | 501 | 93 | globlastp |
| 1482 | LNU45 | ginger\|gb164\|DY361313 | 3426 | 501 | 93 | globlastp |
| 1483 | LNU45 | lettuce\|10v1\|DW044248 | 3427 | 501 | 93 | globlastp |
| 1484 | LNU45 | lettuce\|gb157.2\|DW044248 | 3427 | 501 | 93 | globlastp |
| 1485 | LNU45 | lettuce\|gb157.2\|DW103448 | 3427 | 501 | 93 | globlastp |
| 1486 | LNU45 | lettuce\|gb157.2\|DW126058 | 3427 | 501 | 93 | globlastp |
| 1487 | LNU45 | lettuce\|gb157.2\|DW145140 | 3427 | 501 | 93 | globlastp |
| 1488 | LNU45 | leymus\|gb166\|CN465799 | 3417 | 501 | 93 | globlastp |
| 1489 | LNU45 | maize\|gb170\|LLDQ245642 | 3417 | 501 | 93 | globlastp |
| 1490 | LNU45 | oat\|10v1\|CN817047 | 3417 | 501 | 93 | globlastp |
| 1491 | LNU45 | oat\|gb164\|CN817047 | 3417 | 501 | 93 | globlastp |
| 1492 | LNU45 | petunia\|gb171\|CV299912 | 3428 | 501 | 93 | globlastp |
| 1493 | LNU45 | physcomitrella\|gb157\|AW126791 | 3419 | 501 | 93 | globlastp |
| 1494 | LNU45 | physcomitrella\|gb157\|AW126917 | 3419 | 501 | 93 | globlastp |
| 1495 | LNU45 | pine\|gb157.2\|AW754553 | 3429 | 501 | 93 | globlastp |
| 1496 | LNU45 | poppy\|gb166\|FE965482 | 3430 | 501 | 93 | globlastp |
| 1497 | LNU45 | pseudoroegneria\|gb167\|FF351733 | 3417 | 501 | 93 | globlastp |
| 1498 | LNU45 | radish\|gb164\|FD579539 | 3431 | 501 | 93 | globlastp |
| 1499 | LNU45 | rye\|gb164\|BE494281 | 3417 | 501 | 93 | globlastp |
| 1500 | LNU45 | sugarcane\|gb157.3\|CA287147 | 3417 | 501 | 93 | globlastp |
| 1501 | LNU45 | tobacco\|gb162\|BQ842826 | 3418 | 501 | 93 | globlastp |
| 1502 | LNU45 | wheat\|gb164\|BE399584 | 3417 | 501 | 93 | globlastp |
| 1503 | LNU45 | wheat\|gb164\|BE443667 | 3417 | 501 | 93 | globlastp |
| 1504 | LNU45 | wheat\|gb164\|BF199537 | 3417 | 501 | 93 | globlastp |
| 1505 | LNU45 | wheat\|gb164\|BI751307 | 3417 | 501 | 93 | globlastp |
| 1506 | LNU45 | wheat\|gb164\|CA601804 | 3417 | 501 | 93 | globlastp |
| 1507 | LNU45 | lettuce\|10v1\|DW103448 | 3427 | 501 | 93 | globlastp |
| 1508 | LNU45 | orobanche\|10v1\|SRR023189S0090142 | 3432 | 501 | 92 | globlastp |
| 1509 | LNU45 | millet\|09v1\|EVO454PM260711 | 3433 | 501 | 91.9 | globlastp |
| 1510 | LNU45 | oat\|10v1\|GO586209 | 3434 | 501 | 91.9 | globlastp |
| 1511 | LNU45 | physcomitrella\|10v1\|AW155989 | 3435 | 501 | 91.9 | globlastp |
| 1512 | LNU45 | sorghum\|09v1\|SB01G008260 | 3433 | 501 | 91.9 | globlastp |
| 1513 | LNU45 | sugarcane\|10v1\|CA069593 | 3433 | 501 | 91.9 | globlastp |
| 1514 | LNU45 | arabidopsis\|gb165\|AT2G45710 | 3436 | 501 | 91.9 | globlastp |
| 1515 | LNU45 | fescue\|gb161\|DT686196 | 3437 | 501 | 91.9 | globlastp |
| 1516 | LNU45 | lovegrass\|gb167\|DN481942 | 3438 | 501 | 91.9 | globlastp |
| 1517 | LNU45 | lovegrass\|gb167\|EH188789 | 3439 | 501 | 91.9 | globlastp |
| 1518 | LNU45 | lovegrass\|gb167\|EH192368 | 3440 | 501 | 91.9 | globlastp |
| 1519 | LNU45 | maize\|gb170\|AI622704 | 3433 | 501 | 91.9 | globlastp |
| 1520 | LNU45 | maize\|gb170\|AI973383 | 3433 | 501 | 91.9 | globlastp |
| 1521 | LNU45 | maize\|gb170\|LLBI361219 | 3433 | 501 | 91.9 | globlastp |
| 1522 | LNU45 | maize\|gb170\|T23373 | 3433 | 501 | 91.9 | globlastp |
| 1523 | LNU45 | millet\|09v1\|EB410946 | 3441 | 501 | 91.9 | globlastp |
| 1524 | LNU45 | rice\|gb170\|OS02G27769 | 3442 | 501 | 91.9 | globlastp |
| 1525 | LNU45 | rose\|gb157.2\|EC587400 | 3443 | 501 | 91.9 | globlastp |
| 1526 | LNU45 | sorghum\|09v1\|SB04G018990 | 3433 | 501 | 91.9 | globlastp |
| 1527 | LNU45 | switchgrass\|gb167\|FE610323 | 3433 | 501 | 91.9 | globlastp |
| 1528 | LNU45 | switchgrass\|gb167\|FE616250 | 3433 | 501 | 91.9 | globlastp |
| 1529 | LNU45 | switchgrass\|gb167\|FE631460 | 3433 | 501 | 91.9 | globlastp |
| 1530 | LNU45 | switchgrass\|gb167\|FL725078 | 3433 | 501 | 91.9 | globlastp |
| 1531 | LNU45 | switchgrass\|gb167\|FL741521 | 3433 | 501 | 91.9 | globlastp |
| 1532 | LNU45 | switchgrass\|gb167\|FL849448 | 3433 | 501 | 91.9 | globlastp |
| 1533 | LNU45 | switchgrass\|gb167\|FL940045 | 3433 | 501 | 91.9 | globlastp |
| 1534 | LNU45 | wheat\|gb164\|CA486248 | 3433 | 501 | 91.9 | globlastp |
| 1535 | LNU45 | sugarcane\|10v1\|BQ535468 | 3433 | 501 | 91.9 | globlastp |
| 1536 | LNU45 | sugarcane\|10v1\|BQ535613 | 3433 | 501 | 91.9 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Homolog. Polyp. SEQ ID NO: | Hom. to SEQ ID NO: | % global identity | Algor. |
|---|---|---|---|---|---|---|
| 1537 | LNU45 | orobanche\|10v1\|SRR023189S0004445 | 3444 | 501 | 90.7 | globlastp |
| 1538 | LNU45 | physcomitrella\|10v1\|BJ164117 | 3445 | 501 | 90.7 | globlastp |
| 1539 | LNU45 | amborella\|gb166\|FD430338 | 3446 | 501 | 90.7 | globlastp |
| 1540 | LNU45 | banana\|gb167\|DN239917 | 3447 | 501 | 90.7 | glotblastn |
| 1541 | LNU45 | cacao\|gb167\|CU493520 | 3448 | 501 | 90.7 | globlastp |
| 1542 | LNU45 | cenchrus\|gb166\|EB660456 | 3449 | 501 | 90.7 | globlastp |
| 1543 | LNU45 | dandelion\|gb161\|DY834568 | 3450 | 501 | 90.7 | globlastp |
| 1544 | LNU45 | kiwi\|gb166\|FG418840 | 3451 | 501 | 90.7 | glotblastn |
| 1545 | LNU45 | marchantia\|gb166\|C95731 | 3452 | 501 | 90.7 | globlastp |
| 1546 | LNU45 | rice\|gb170\|OS04G27860 | 3453 | 501 | 90.7 | globlastp |
| 1547 | LNU45 | maize\|gb170\|LLFL411499 | 3454 | 501 | 89.53 | glotblastn |
| 1548 | LNU45 | switchgrass\|gb167\|FE624276 | 3455 | 501 | 89.53 | glotblastn |
| 1549 | LNU45 | rice\|gb170\|OS04G32710 | 3456 | 501 | 89.5 | globlastp |
| 1550 | LNU45 | spikemoss\|gb165\|DN838335 | 3457 | 501 | 89.5 | globlastp |
| 1551 | LNU45 | spikemoss\|gb165\|DN839110 | 3457 | 501 | 89.5 | globlastp |
| 1552 | LNU45 | fern\|gb171\|BP913163 | 3458 | 501 | 88.4 | globlastp |
| 1553 | LNU45 | ginseng\|10v1\|CN845877 | 3459 | 501 | 88.4 | globlastp |
| 1554 | LNU45 | ginseng\|10v1\|GR875257 | 3459 | 501 | 88.4 | globlastp |
| 1555 | LNU45 | rye\|gb164\|BE705802 | 3460 | 501 | 88.4 | globlastp |
| 1556 | LNU45 | canola\|10v1\|CD812394 | 3461 | 501 | 88.3 | globlastp |
| 1557 | LNU45 | fern\|gb171\|DK944513 | 3462 | 501 | 87.2 | globlastp |
| 1558 | LNU45 | b_juncea\|gb164\|EVGN00943108632248 | 3463 | 501 | 87.2 | globlastp |
| 1559 | LNU45 | chlamydomonas\|gb162\|X83694 | 3464 | 501 | 87.2 | globlastp |
| 1560 | LNU45 | volvox\|gb162\|X83694 | 3465 | 501 | 87.2 | globlastp |
| 1561 | LNU45 | citrus\|gb166\|CX663339 | 3466 | 501 | 86 | globlastp |
| 1562 | LNU45 | lovegrass\|gb167\|EH190160 | 3467 | 501 | 86 | globlastp |
| 1563 | LNU45 | mesostigma\|gb166\|DN254596 | 3468 | 501 | 86 | globlastp |
| 1564 | LNU45 | mesostigma\|gb166\|EC728430 | 3468 | 501 | 86 | globlastp |
| 1565 | LNU45 | arabidopsis_lyrata\|09v1\|JGIAL019416 | 3469 | 501 | 84.9 | globlastp |
| 1566 | LNU45 | heritiera\|10v1\|SRR005794S0004655 | 3470 | 501 | 84.9 | globlastp |
| 1567 | LNU45 | arabidopsis\|gb165\|AT3G61111 | 3471 | 501 | 82.6 | globlastp |
| 1568 | LNU45 | rye\|gb164\|BF146222 | 3472 | 501 | 82.6 | globlastp |
| 1569 | LNU45 | wheat\|gb164\|CA606076 | 3473 | 501 | 81.7 | globlastp |
| 1570 | LNU45 | solanum_phureja\|09v1\|SPHCRPSP011443 | 3474 | 501 | 81.4 | glotblastn |
| 1571 | LNU45 | citrus\|gb166\|DY261826 | 3475 | 501 | 81.4 | globlastp |
| 1572 | LNU45 | ostreococcus\|gb162\|XM001421510 | 3476 | 501 | 81.4 | glotblastn |
| 1573 | LNU45 | spruce\|gb162\|ES252989 | 3477 | 501 | 81.4 | globlastp |
| 1574 | LNU45 | switchgrass\|gb167\|GD026676 | 3478 | 501 | 81.4 | glotblastn |
| 1575 | LNU45 | coffea\|10v1\|GR981069 | — | 501 | 81.4 | glotblastn |
| 1576 | LNU46 | soybean\|gb168\|AW428695 | 3479 | 502 | 97.5 | globlastp |
| 1577 | LNU46 | cowpea\|gb166\|FF399962 | 3480 | 502 | 97 | globlastp |
| 1578 | LNU46 | lotus\|09v1\|AW428695 | 3481 | 502 | 96.1 | globlastp |
| 1579 | LNU46 | bean\|gb167\|CA898025 | 3482 | 502 | 96.1 | globlastp |
| 1580 | LNU46 | citrus\|gb166\|CF418615 | 3483 | 502 | 95.7 | globlastp |
| 1581 | LNU46 | cotton\|gb164\|CO109391 | 3484 | 502 | 95.7 | globlastp |
| 1582 | LNU46 | grape\|gb160\|BQ795999 | 3485 | 502 | 95.7 | globlastp |
| 1583 | LNU46 | cucumber\|09v1\|BGI454G0029699 | 3486 | 502 | 95.4 | globlastp |
| 1584 | LNU46 | cowpea\|gb166\|FF400935 | 3487 | 502 | 95.4 | globlastp |
| 1585 | LNU46 | poplar\|10v1\|BI120740 | 3488 | 502 | 95.4 | globlastp |
| 1586 | LNU46 | poplar\|gb170\|BI120740 | 3488 | 502 | 95.4 | globlastp |
| 1587 | LNU46 | cucumber\|09v1\|CV001012 | 3489 | 502 | 95.2 | globlastp |
| 1588 | LNU46 | castorbean\|09v1\|T15123 | 3490 | 502 | 95 | globlastp |
| 1589 | LNU46 | castorbean\|gb160\|T15123 | 3490 | 502 | 95 | globlastp |
| 1590 | LNU46 | kiwi\|gb166\|FG426103 | 3491 | 502 | 95 | globlastp |
| 1591 | LNU46 | cassava\|09v1\|DB921974 | 3492 | 502 | 94.7 | globlastp |
| 1592 | LNU46 | cycas\|gb166\|CB089800 | 3493 | 502 | 94.7 | globlastp |
| 1593 | LNU46 | medicago\|09v1\|AL376549 | 3494 | 502 | 94.7 | globlastp |
| 1594 | LNU46 | medicago\|gb157.2\|AL376549 | 3494 | 502 | 94.7 | globlastp |
| 1595 | LNU46 | spruce\|gb162\|CO226322 | 3495 | 502 | 94.7 | globlastp |
| 1596 | LNU46 | millet\|09v1\|EVO454PM007367 | 3496 | 502 | 94.5 | globlastp |
| 1597 | LNU46 | artemisia\|gb164\|EY071317 | 3497 | 502 | 94.5 | globlastp |
| 1598 | LNU46 | cacao\|gb167\|CU477411 | 3498 | 502 | 94.5 | globlastp |
| 1599 | LNU46 | aquilegia\|10v1\|DR925421 | 3499 | 502 | 94.3 | globlastp |
| 1600 | LNU46 | aquilegia\|gb157.3\|DR925421 | 3499 | 502 | 94.3 | globlastp |
| 1601 | LNU46 | maize\|gb170\|AI932193 | 3500 | 502 | 94.3 | globlastp |
| 1602 | LNU46 | sorghum\|09v1\|SB01G010860 | 3501 | 502 | 94.3 | globlastp |
| 1603 | LNU46 | sorghum\|gb161.crp\|BG051224 | 3501 | 502 | 94.3 | globlastp |
| 1604 | LNU46 | poplar\|10v1\|XM002304585 | 3502 | 502 | 94.1 | globlastp |
| 1605 | LNU46 | cynara\|gb167\|GE577142 | 3503 | 502 | 94.1 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to Polyp. SEQ ID NO: | % global identity | Algor. |
|---|---|---|---|---|---|---|
| 1606 | LNU46 | lettuce\|10v1\|DW046496 | 3504 | 502 | 94.1 | globlastp |
| 1607 | LNU46 | lettuce\|gb157.2\|DW124917 | 3504 | 502 | 94.1 | globlastp |
| 1608 | LNU46 | oil_palm\|gb166\|ES273702 | 3505 | 502 | 94.1 | globlastp |
| 1609 | LNU46 | poplar\|10v1\|BI068703 | 3502 | 502 | 94.1 | globlastp |
| 1610 | LNU46 | poplar\|gb170\|BI068703 | 3502 | 502 | 94.1 | globlastp |
| 1611 | LNU46 | tomato\|09v1\|AI486841 | 3506 | 502 | 94.1 | globlastp |
| 1612 | LNU46 | tomato\|gb164\|AI486841 | 3506 | 502 | 94.1 | globlastp |
| 1613 | LNU46 | solanum_phureja\|09v1\|SPHAI486841 | 3507 | 502 | 93.8 | globlastp |
| 1614 | LNU46 | poplar\|10v1\|BI129155 | 3508 | 502 | 93.8 | globlastp |
| 1615 | LNU46 | poplar\|gb170\|BI129155 | 3508 | 502 | 93.8 | globlastp |
| 1616 | LNU46 | rice\|gb170\|OS03G49580 | 3509 | 502 | 93.8 | globlastp |
| 1617 | LNU46 | switchgrass\|gb167\|FE599427 | 3510 | 502 | 93.8 | globlastp |
| 1618 | LNU46 | switchgrass\|gb167\|FE604633 | 3511 | 502 | 93.8 | globlastp |
| 1619 | LNU46 | centaurea\|gb166\|EL934628 | 3512 | 502 | 93.6 | globlastp |
| 1620 | LNU46 | rice\|gb170\|OS07G39870 | 3513 | 502 | 93.6 | globlastp |
| 1621 | LNU46 | sugarcane\|10v1\|CA089292 | 3514 | 502 | 93.6 | globlastp |
| 1622 | LNU46 | sugarcane\|gb157.3\|CA089292 | 3514 | 502 | 93.6 | globlastp |
| 1623 | LNU46 | monkeyflower\|10v1\|GO963384 | 3515 | 502 | 93.4 | globlastp |
| 1624 | LNU46 | apple\|gb157.3\|CN493322 | 3516 | 502 | 93.4 | globlastp |
| 1625 | LNU46 | apple\|gb171\|CN493322 | 3516 | 502 | 93.4 | globlastp |
| 1626 | LNU46 | maize\|gb170\|BG354242 | 3517 | 502 | 93.4 | globlastp |
| 1627 | LNU46 | sorghum\|09v1\|SB02G037930 | 3518 | 502 | 93.4 | globlastp |
| 1628 | LNU46 | sorghum\|gb161.crp\|AW671733 | 3518 | 502 | 93.4 | globlastp |
| 1629 | LNU46 | strawberry\|gb164\|DY666824 | 3519 | 502 | 93.4 | globlastp |
| 1630 | LNU46 | chestnut\|gb170\|SRR006295S0030165 | 3520 | 502 | 93.1 | globlastp |
| 1631 | LNU46 | cotton\|gb164\|BG439937 | 3521 | 502 | 93.1 | globlastp |
| 1632 | LNU46 | oak\|gb170\|DB998392 | 3522 | 502 | 93.1 | globlastp |
| 1633 | LNU46 | arabidopsis\|gb165\|AT3G2661 | 3523 | 502 | 92.9 | globlastp |
| 1634 | LNU46 | cotton\|gb164\|AI054657 | 3524 | 502 | 92.9 | globlastp |
| 1635 | LNU46 | pine\|10v1\|AI812442 | 3525 | 502 | 92.7 | globlastp |
| 1636 | LNU46 | pine\|gb157.2\|AI812442 | 3525 | 502 | 92.7 | globlastp |
| 1637 | LNU46 | prunus\|gb167\|BU039215 | 3526 | 502 | 92.7 | globlastp |
| 1638 | LNU46 | soybean\|gb168\|AW691393 | 3527 | 502 | 92.7 | globlastp |
| 1639 | LNU46 | pepper\|gb171\|BM063924 | 3528 | 502 | 92.4 | globlastp |
| 1640 | LNU46 | citrus\|gb166\|CB291077 | 3529 | 502 | 92.4 | globlastp |
| 1641 | LNU46 | sunflower\|gb162\|CD845824 | 3530 | 502 | 92.4 | globlastp |
| 1642 | LNU46 | tomato\|09v1\|BG129404 | 3531 | 502 | 92.4 | globlastp |
| 1643 | LNU46 | tomato\|gb164\|BG129404 | 3531 | 502 | 92.4 | globlastp |
| 1644 | LNU46 | arabidopsis_lyrata\|09v1\|JGIAL016770 | 3532 | 502 | 92.2 | globlastp |
| 1645 | LNU46 | apple\|gb157.3\|CN544908 | 3533 | 502 | 92.2 | globlastp |
| 1646 | LNU46 | apple\|gb171\|CN544908 | 3533 | 502 | 92.2 | globlastp |
| 1647 | LNU46 | barley\|gb157SOLEXA\|BE421791 | 3534 | 502 | 92.2 | globlastp |
| 1648 | LNU46 | cowpea\|gb166\|FF399895 | 3535 | 502 | 92.2 | globlastp |
| 1649 | LNU46 | oat\|10v1\|CN820661 | 3536 | 502 | 92 | globlastp |
| 1650 | LNU46 | solanum_phureja\|09v1\|SPHBG129404 | 3537 | 502 | 92 | globlastp |
| 1651 | LNU46 | potato\|10v1\|BF053654 | 3537 | 502 | 92 | globlastp |
| 1652 | LNU46 | potato\|gb157.2\|BF053654 | 3537 | 502 | 92 | globlastp |
| 1653 | LNU46 | soybean\|gb168\|AW428757 | 3538 | 502 | 91.8 | globlastp |
| 1654 | LNU46 | spruce\|gb162\|CO220375 | 3539 | 502 | 91.8 | globlastp |
| 1655 | LNU46 | triphysaria\|gb164\|EX991156 | 3540 | 502 | 91.8 | globlastp |
| 1656 | LNU46 | physcomitrella\|10v1\|BJ175132 | 3541 | 502 | 91.6 | globlastp |
| 1657 | LNU46 | physcomitrella\|gb157\|BJ175017 | 3541 | 502 | 91.6 | globlastp |
| 1658 | LNU46 | canola\|10v1\|CD824781 | 3542 | 502 | 91.5 | globlastp |
| 1659 | LNU46 | oat\|10v1\|BE439128 | 3543 | 502 | 91.5 | globlastp |
| 1660 | LNU46 | brachypodium\|09v1\|DV471205 | 3544 | 502 | 91.5 | globlastp |
| 1661 | LNU46 | brachypodium\|gb169\|BE446313 | 3544 | 502 | 91.5 | globlastp |
| 1662 | LNU46 | papaya\|gb165\|AM904175 | 3545 | 502 | 91.5 | globlastp |
| 1663 | LNU46 | sunflower\|gb162\|DY910709 | 3546 | 502 | 91.5 | globlastp |
| 1664 | LNU46 | barley\|gb157SOLEXA\|BE438955 | 3547 | 502 | 91.3 | globlastp |
| 1665 | LNU46 | canola\|gb161\|DY011567 | 3548 | 502 | 91.3 | globlastp |
| 1666 | LNU46 | fescue\|gb161\|DT700877 | 3549 | 502 | 91.3 | globlastp |
| 1667 | LNU46 | wheat\|gb164\|BU099476 | 3550 | 502 | 91.3 | globlastp |
| 1668 | LNU46 | physcomitrella\|10v1\|BY984317 | 3551 | 502 | 91.2 | globlastp |
| 1669 | LNU46 | physcomitrella\|10v1\|BQ827517 | 3552 | 502 | 90.9 | globlastp |
| 1670 | LNU46 | physcomitrella\|gb157\|BQ827517 | 3553 | 502 | 90.87 | glotblastn |
| 1671 | LNU46 | coffea\|10v1\|DV667361 | 3554 | 502 | 90.8 | globlastp |
| 1672 | LNU46 | potato\|10v1\|BF154263 | 3555 | 502 | 90.8 | globlastp |
| 1673 | LNU46 | potato\|gb157.2\|BF154263 | 3555 | 502 | 90.8 | globlastp |
| 1674 | LNU46 | dandelion\|gb161\|DY809008 | 3556 | 502 | 90.7 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 1675 | LNU46 | canola\|10v1\|EE407094 | 3557 | 502 | 90.6 | globlastp |
| 1676 | LNU46 | pepper\|gb171\|CA523256 | 3558 | 502 | 90.6 | globlastp |
| 1677 | LNU46 | solanum_phureja\|09v1\|SPHAA824687 | 3559 | 502 | 90.6 | globlastp |
| 1678 | LNU46 | solanum_phureja\|09v1\|SPHAJ489160 | 3560 | 502 | 90.6 | globlastp |
| 1679 | LNU46 | canola\|10v1\|CD815302 | 3557 | 502 | 90.6 | globlastp |
| 1680 | LNU46 | canola\|gb161\|CD815302 | 3557 | 502 | 90.6 | globlastp |
| 1681 | LNU46 | medicago\|09v1\|AW691393 | 3561 | 502 | 90.6 | globlastp |
| 1682 | LNU46 | medicago\|gb157.2\|AW691393 | 3561 | 502 | 90.6 | globlastp |
| 1683 | LNU46 | pine\|10v1\|AW010603 | 3562 | 502 | 90.6 | globlastp |
| 1684 | LNU46 | tomato\|09v1\|AA824687 | 3563 | 502 | 90.6 | globlastp |
| 1685 | LNU46 | tomato\|09v1\|AJ489160 | 3564 | 502 | 90.4 | globlastp |
| 1686 | LNU46 | pine\|gb157.2\|AW010603 | 3565 | 502 | 90.4 | globlastp |
| 1687 | LNU46 | tomato\|gb164\|AA824687 | 3566 | 502 | 90.4 | globlastp |
| 1688 | LNU46 | potato\|10v1\|AJ489160 | 3567 | 502 | 90.39 | glotblastn |
| 1689 | LNU46 | arabidopsis_lyrata\|09v1\|JGIAL001354 | 3568 | 502 | 90.2 | globlastp |
| 1690 | LNU46 | monkeyflower\|10v1\|DV209146 | 3569 | 502 | 89.9 | globlastp |
| 1691 | LNU46 | arabidopsis\|gb165\|AT1G12910 | 3570 | 502 | 89.9 | globlastp |
| 1692 | LNU46 | coffea\|gb157.2\|DV667361 | 3571 | 502 | 89.9 | globlastp |
| 1693 | LNU46 | tobacco\|gb162\|CV016199 | 3572 | 502 | 89.5 | globlastp |
| 1694 | LNU46 | radish\|gb164\|EV534949 | 3573 | 502 | 89.47 | glotblastn |
| 1695 | LNU46 | physcomitrella\|10v1\|BJ175017 | 3574 | 502 | 89.4 | globlastp |
| 1696 | LNU46 | spikemoss\|gb165\|FE441264 | 3575 | 502 | 88.1 | globlastp |
| 1697 | LNU46 | arabidopsis_lyrata\|09v1\|JGIAL028997 | 3576 | 502 | 87.9 | globlastp |
| 1698 | LNU46 | arabidopsis\|gb165\|AT5G47880 | 3577 | 502 | 87.9 | globlastp |
| 1699 | LNU46 | spikemoss\|gb165\|FE441265 | 3578 | 502 | 87.6 | globlastp |
| 1700 | LNU46 | radish\|gb164\|EV569528 | 3579 | 502 | 87.5 | globlastp |
| 1701 | LNU46 | canola\|10v1\|CD814349 | 3580 | 502 | 87 | globlastp |
| 1702 | LNU46 | rice\|gb170\|OS01G71270 | 3581 | 502 | 87 | globlastp |
| 1703 | LNU46 | brachypodium\|09v1\|DV469404 | 3582 | 502 | 86.3 | globlastp |
| 1704 | LNU46 | brachypodium\|gb169\|BG606860 | 3582 | 502 | 86.3 | globlastp |
| 1705 | LNU46 | soybean\|gb168\|AL376550 | 3583 | 502 | 86.04 | glotblastn |
| 1706 | LNU46 | medicago\|09v1\|CRPMT036602 | 3584 | 502 | 83.5 | globlastp |
| 1707 | LNU46 | millet\|09v1\|CD724536 | 3585 | 502 | 83.1 | globlastp |
| 1708 | LNU46 | papaya\|gb165\|EX253193 | 3586 | 502 | 81.7 | globlastp |
| 1709 | LNU46 | switchgrass\|gb167\|FE602227 | 3587 | 502 | 80.9 | globlastp |
| 1710 | LNU46 | onion\|gb162\|CF441127 | 3588 | 502 | 80.55 | glotblastn |
| 1711 | LNU46 | sorghum\|09v1\|SB09G018630 | 3589 | 502 | 80.2 | globlastp |
| 1712 | LNU46 | sorghum\|gb161.crp\|BE362758 | 3589 | 502 | 80.2 | globlastp |
| 1713 | LNU48 | switchgrass\|gb167\|FE638525 | 3590 | 503 | 89 | globlastp |
| 1714 | LNU48 | brachypodium\|09v1\|DV472885 | 3591 | 503 | 88.37 | glotblastn |
| 1715 | LNU48 | sorghum\|09v1\|SB02G032700 | 3592 | 503 | 87.2 | globlastp |
| 1716 | LNU48 | sorghum\|gb161.crp\|AW256150 | 3593 | 503 | 86.82 | glotblastn |
| 1717 | LNU48 | maize\|gb170\|AW256150 | 3594 | 503 | 86.6 | globlastp |
| 1718 | LNU51 | sorghum\|09v1\|SB02G028140 | 3595 | 505 | 82.6 | globlastp |
| 1719 | LNU51 | sorghum\|gb161.crp\|AW520040 | 3595 | 505 | 82.6 | globlastp |
| 1720 | LNU51 | maize\|gb170\|AW060000 | 3596 | 505 | 82.2 | globlastp |
| 1721 | LNU51 | sugarcane\|gb157.3\|CA070485 | 3597 | 505 | 81.57 | glotblastn |
| 1722 | LNU51 | brachypodium\|09v1\|GT760634 | 3598 | 505 | 81.5 | globlastp |
| 1723 | LNU51 | barley\|gb157.3\|AL499810 | 3599 | 505 | 81.3 | globlastp |
| 1724 | LNU51 | barley\|gb157SOLEXA\|AL499810 | 3599 | 505 | 81.3 | globlastp |
| 1725 | LNU51 | sugarcane\|10v1\|CA070485 | 3600 | 505 | 81 | globlastp |
| 1726 | LNU52 | sugarcane\|gb157.3\|CA075246 | 3601 | 506 | 92.6 | globlastp |
| 1727 | LNU52 | sorghum\|09v1\|SB01G047930 | 3602 | 506 | 92.4 | globlastp |
| 1728 | LNU52 | sorghum\|gb1618.crp\|AW433438 | 3602 | 506 | 92.4 | globlastp |
| 1729 | LNU52 | brachypodium\|gb169\|BE400443 | 3603 | 506 | 92.01 | glotblastn |
| 1730 | LNU52 | brachypodium\|09v1\|DV470543 | 3604 | 506 | 91.8 | globlastp |
| 1731 | LNU52 | maize\|gb170\|BE123353 | 3605 | 506 | 91.6 | globlastp |
| 1732 | LNU52 | switchgrass\|gb167\|DN141859 | 3606 | 506 | 91 | globlastp |
| 1733 | LNU52 | switchgrass\|gb167\|DN147113 | 3607 | 506 | 90.5 | globlastp |
| 1734 | LNU52 | maize\|gb170\|AW076488 | 3608 | 506 | 89.5 | globlastp |
| 1735 | LNU52 | wheat\|gb164\|BE400443 | 3609 | 506 | 89 | globlastp |
| 1736 | LNU52 | oat\|10v1\|GR316421 | 3610 | 506 | 88 | globlastp |
| 1737 | LNU52 | brachypodium\|gb169\|BE399305 | 3611 | 506 | 87.2 | globlastp |
| 1738 | LNU52 | barley\|gb157SOLEXA\|BF623122 | 3612 | 506 | 87.1 | globlastp |
| 1739 | LNU52 | wheat\|gb164\|BE399305 | 3613 | 506 | 87.1 | globlastp |
| 1740 | LNU52 | barley\|gb157SOLEXA\|AL505656 | 3614 | 506 | 86.5 | globlastp |
| 1741 | LNU52 | brachypodium\|09v1\|GT766862 | 3615 | 506 | 85.5 | globlastp |
| 1742 | LNU56 | bean\|gb167\|CA909969 | 3616 | 510 | 88.8 | globlastp |
| 1743 | LNU56 | cowpea\|gb166\|FC458698 | 3617 | 510 | 88.78 | glotblastn |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to Polyp. SEQ ID NO: | % global identity | Algor. |
|---|---|---|---|---|---|---|
| 1744 | LNU56 | medicago\|09v1\|LLEX523937 | 3618 | 510 | 85.6 | globlastp |
| 1745 | LNU56 | chickpea\|09v2\|GR401628 | 3619 | 510 | 83.6 | globlastp |
| 1746 | LNU56 | peanut\|gb171\|ES762633 | 3620 | 510 | 83 | globlastp |
| 1747 | LNU56 | medicago\|09v1\|AL374335 | 3621 | 510 | 82.1 | globlastp |
| 1748 | LNU56 | medicago\|gb157.2\|AL374335 | 3621 | 510 | 82.1 | globlastp |
| 1749 | LNU56 | prunus\|gb167\|BU043945 | 3622 | 510 | 81 | globlastp |
| 1750 | LNU56 | chestnut\|gb170\|SRR006295S0008375 | 3623 | 510 | 80.5 | globlastp |
| 1751 | LNU56 | poplar\|gb170\|BU876352 | 3624 | 510 | 80.5 | globlastp |
| 1752 | LNU56 | cucumber\|09v1\|AM717347 | 3625 | 510 | 80 | globlastp |
| 1753 | LNU56 | poplar\|10v1\|BU876352 | 3626 | 510 | 80 | globlastp |
| 1754 | LNU57 | wheat\|gb164\|BE431144 | 3627 | 511 | 86.8 | globlastp |
| 1755 | LNU57 | pseudoroegneria\|gb167\|FF351563 | 3628 | 511 | 85.4 | globlastp |
| 1755 | LNU81 | pseudoroegneria\|gb167\|FF351563 | 3628 | 728 | 85.9 | globlastp |
| 1756 | LNU60 | brachypodium\|09v1\|SRR031797S0000144 | 3629 | 514 | 88.2 | globlastp |
| 1756 | LNU84 | brachypodium\|09v1\|SRR031797S0000144 | 3629 | 533 | 80.8 | globlastp |
| 1756 | LNU65 | brachypodium\|09v1\|SRR031797S0000144 | 3629 | 722 | 80.5 | globlastp |
| 1757 | LNU60 | maize\|gb170\|AW562715 | 3630 | 514 | 80.6 | globlastp |
| 1757 | LNU84 | maize\|gb170\|AW562715 | 3630 | 533 | 90.9 | globlastp |
| 1758 | LNU61 | brachypodium\|09v1\|DV488685 | 3631 | 515 | 86.8 | globlastp |
| 1759 | LNU63 | pseudoroegneria\|gb167\|FF366744 | 3632 | 516 | 93.8 | globlastp |
| 1760 | LNU63 | wheat\|gb164\|CD937806 | 3633 | 516 | 90.1 | globlastp |
| 1761 | LNU63 | wheat\|gb164\|BF485055 | 3634 | 516 | 89.3 | globlastp |
| 1762 | LNU63 | barley\|gb157.3\|AL508288 | 3635 | 516 | 82.3 | globlastp |
| 1763 | LNU63 | barley\|gb157SOLEXA\|AL508288 | 3635 | 516 | 82.3 | globlastp |
| 1764 | LNU63 | leymus\|gb166\|EG402462 | 3636 | 516 | 81.8 | globlastp |
| 1765 | LNU64 | wheat\|gb164\|BG907753 | 3637 | 517 | 97.1 | globlastp |
| 1766 | LNU64 | wheat\|gb164\|BQ842100 | 3638 | 517 | 93.1 | globlastp |
| 1766 | LNU98 | wheat\|gb164\|BQ842100 | 3638 | 734 | 80.57 | globtblastn |
| 1767 | LNU64 | brachypodium\|09v1\|GT761032 | 3639 | 517 | 88.25 | globtblastn |
| 1768 | LNU64 | switchgrass\|gb167\|FE631036 | 3640 | 517 | 85.8 | globlastp |
| 1768 | LNU98 | switchgrass\|gb167\|FE631036 | 3640 | 734 | 84.2 | globlastp |
| 1769 | LNU64 | maize\|gb170\|AW438149 | 3641 | 517 | 84.3 | globlastp |
| 1769 | LNU98 | maize\|gb170\|AW438149 | 3641 | 734 | 81.1 | globlastp |
| 1770 | LNU64 | rice\|gb170\|OS06G05700 | 3642 | 517 | 83.9 | globlastp |
| 1770 | LNU98 | rice\|gb170\|OS06G05700 | 3642 | 734 | 81.1 | globlastp |
| 1771 | LNU64 | brachypodium\|gb169\|BE591591 | 3643 | 517 | 80.46 | globtblastn |
| 1772 | LNU67 | brachypodium\|09v1\|GT769610 | 3644 | 519 | 88.4 | globlastp |
| 1773 | LNU67 | barley\|gb157.3\|AL510475 | 3645 | 519 | 86.13 | globtblastn |
| 1774 | LNU67 | barley\|gb157SOLEXA\|AL510475 | 3645 | 519 | 86.13 | globtblastn |
| 1775 | LNU67 | sorghum\|09v1\|SB01G029600 | 3646 | 519 | 85.4 | globlastp |
| 1776 | LNU67 | sugarcane\|10v1\|CA073684 | 3647 | 519 | 85.4 | globlastp |
| 1777 | LNU67 | sugarcane\|gb157.3\|CA073684 | 3648 | 519 | 85.4 | globlastp |
| 1778 | LNU67 | sorghum\|gb161.crp\|AI586547 | 3646 | 519 | 85.4 | globlastp |
| 1779 | LNU67 | maize\|gb170\|AI586547 | 3649 | 519 | 84.2 | globlastp |
| 1780 | LNU67 | brachypodium\|gb169\|BG418808 | 3650 | 519 | 81.3 | globlastp |
| 1781 | LNU67 | switchgrass\|gb167\|FE612667 | 3651 | 519 | 80.3 | globlastp |
| 1782 | LNU69 | brachypodium\|09v1\|DV472747 | 3652 | 521 | 87.1 | globlastp |
| 1783 | LNU69 | oat\|10v1\|GR321530 | 3653 | 521 | 86.36 | globtblastn |
| 1784 | LNU69 | oat\|10v1\|GO589136 | 3654 | 521 | 85.9 | globlastp |
| 1785 | LNU69 | wheat\|gb164\|BE637681 | 3655 | 521 | 85.5 | globlastp |
| 1786 | LNU69 | barley\|gb157SOLEXA\|BI950025 | 3656 | 521 | 84.5 | globlastp |
| 1787 | LNU69 | barley\|gb157.3\|BI950025 | 3657 | 521 | 84.2 | globlastp |
| 1788 | LNU69 | pseudoroegneria\|gb167\|FF340678 | 3658 | 521 | 84.2 | globlastp |
| 1789 | LNU69 | brachypodium\|gb169\|BE637681 | 3659 | 521 | 81.6 | globlastp |
| 1790 | LNU69 | sorghum\|gb161.crp\|BG049299 | 3660 | 521 | 81.2 | globlastp |
| 1791 | LNU69 | maize\|gb170\|AI861497 | 3661 | 521 | 81.2 | globlastp |
| 1792 | LNU69 | sorghum\|09v1\|SB07G026190 | 3660 | 521 | 81.2 | globlastp |
| 1793 | LNU69 | sugarcane\|10v1\|CA090545 | 3662 | 521 | 81.2 | globlastp |
| 1794 | LNU69 | sugarcane\|gb157.3\|CA090545 | 3663 | 521 | 80.8 | globlastp |
| 1795 | LNU71 | rice\|gb170\|OS01G72240 | 3664 | 523 | 83 | globlastp |
| 1796 | LNU71 | oat\|10v1\|GR359520 | 3665 | 523 | 82.39 | globtblastn |
| 1797 | LNU71 | sorghum\|09v1\|SB03G045930 | 3666 | 523 | 82.1 | globlastp |
| 1798 | LNU71 | sorghum\|gb161.crp\|AI396343 | 3666 | 523 | 82.1 | globlastp |
| 1799 | LNU71 | sorghum\|09v1\|SB03G045940 | 3667 | 523 | 81.4 | globlastp |
| 1800 | LNU71 | maize\|gb170\|AI396343 | 3668 | 523 | 81.1 | globlastp |
| 1801 | LNU71 | maize\|gb170\|AI668476 | 3669 | 523 | 80.6 | globlastp |
| 1802 | LNU73 | sorghum\|09v1\|SB01G031850 | 3670 | 525 | 83.6 | globlastp |
| 1803 | LNU73 | sorghum\|gb161.crp\|AI665094 | 3670 | 525 | 83.6 | globlastp |
| 1804 | LNU73 | brachypodium\|09v1\|DV478838 | 3671 | 525 | 81.2 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Homolog. Polyp. SEQ ID NO: | Hom. to Polyp. SEQ ID NO: | % global identity | Algor. |
|---|---|---|---|---|---|---|
| 1805 | LNU73 | brachypodium\|gb169\|BE585945 | 3672 | 525 | 80.9 | globlastp |
| 1806 | LNU73 | oat\|10v1\|GR315201 | 3673 | 525 | 80.8 | globlastp |
| 1807 | LNU73 | leymus\|gb166\|EG395112 | 3674 | 525 | 80.6 | globlastp |
| 1808 | LNU73 | wheat\|gb164\|BE213619 | 3675 | 525 | 80.6 | globlastp |
| 1809 | LNU73 | maize\|gb170\|AI600420 | 3676 | 525 | 80.2 | globlastp |
| 1810 | LNU73 | barley\|gb157SOLEXA\|AL507770 | 3677 | 525 | 80 | globlastp |
| 1811 | LNU74 | poplar\|gb170\|AI164221 | 3678 | 526 | 94.8 | globlastp |
| 1812 | LNU74 | poplar\|10v1\|AI164221 | 3679 | 526 | 94 | globlastp |
| 1813 | LNU74 | cassava\|09v1\|DV441703 | 3680 | 526 | 93.3 | globlastp |
| 1814 | LNU74 | castorbean\|09v1\|EE256800 | 3681 | 526 | 93.3 | globlastp |
| 1815 | LNU74 | cassava\|09v1\|BM260313 | 3682 | 526 | 92.5 | globlastp |
| 1816 | LNU74 | cassava\|gb164\|BM260313 | 3682 | 526 | 92.5 | globlastp |
| 1817 | LNU74 | cassava\|gb164\|DV441703 | 3683 | 526 | 92.5 | globlastp |
| 1818 | LNU74 | castorbean\|gb160\|EE256800 | 3684 | 526 | 92.5 | globlastp |
| 1819 | LNU74 | banana\|gb167\|ES432444 | 3685 | 526 | 91.8 | globlastp |
| 1820 | LNU74 | citrus\|gb166\|BQ624628 | 3686 | 526 | 91.8 | globlastp |
| 1821 | LNU74 | papaya\|gb165\|EX290028 | 3687 | 526 | 91.8 | globlastp |
| 1822 | LNU74 | banana\|gb167\|FL665867 | 3688 | 526 | 91 | globlastp |
| 1823 | LNU74 | papaya\|gb165\|AM903637 | 3689 | 526 | 91 | globlastp |
| 1824 | LNU74 | poplar\|10v1\|BU817024 | 3690 | 526 | 91 | globlastp |
| 1825 | LNU74 | poplar\|gb170\|BU817024 | 3690 | 526 | 91 | globlastp |
| 1826 | LNU74 | kiwi\|gb166\|FG488574 | 3691 | 526 | 90.4 | globlastp |
| 1827 | LNU74 | citrus\|gb166\|BQ624990 | 3692 | 526 | 90.3 | globlastp |
| 1828 | LNU74 | poplar\|10v1\|BU813474 | 3693 | 526 | 90.3 | globlastp |
| 1829 | LNU74 | poplar\|gb170\|BU813474 | 3693 | 526 | 90.3 | globlastp |
| 1830 | LNU74 | bruguiera\|gb166\|BP946426 | 3694 | 526 | 89.6 | globlastp |
| 1831 | LNU74 | sesame\|gb157.2\|BU668642 | 3695 | 526 | 89.6 | globlastp |
| 1832 | LNU74 | sesame\|10v1\|BU667940 | 3696 | 526 | 88.81 | glotblastn |
| 1833 | LNU74 | jatropha\|09v1\|FM893408 | 3697 | 526 | 88.8 | globlastp |
| 1834 | LNU74 | cacao\|gb167\|CU491187 | 3698 | 526 | 88.8 | globlastp |
| 1835 | LNU74 | castorbean\|09v1\|XM002529794 | 3699 | 526 | 88.8 | globlastp |
| 1836 | LNU74 | ginger\|gb164\|DY377849 | 3700 | 526 | 88.8 | globlastp |
| 1837 | LNU74 | grape\|gb160\|BQ797018 | 3701 | 526 | 88.8 | globlastp |
| 1838 | LNU74 | spurge\|gb161\|BE095323 | 3702 | 526 | 88.8 | globlastp |
| 1839 | LNU74 | cleome_gynandra\|10v1\|SRR015532S0006733 | 3703 | 526 | 88.1 | globlastp |
| 1840 | LNU74 | heritiera\|10v1\|SRR005795S0013040 | 3704 | 526 | 88.1 | globlastp |
| 1841 | LNU74 | aquilegia\|10v1\|DR915465 | 3705 | 526 | 88.1 | globlastp |
| 1842 | LNU74 | basilicum\|10v1\|DY341993 | 3706 | 526 | 88.1 | globlastp |
| 1843 | LNU74 | castorbean\|gb160\|MDL28492M000475 | 3707 | 526 | 88.1 | globlastp |
| 1844 | LNU74 | grape\|gb160\|CB004623 | 3708 | 526 | 88.1 | globlastp |
| 1845 | LNU74 | centaurea\|gb166\|EH742056 | 3709 | 526 | 87.9 | globlastp |
| 1846 | LNU74 | apple\|gb171\|CN581387 | 3710 | 526 | 87.3 | globlastp |
| 1847 | LNU74 | solanum_phureja\|09v1\|SPHBG123695 | 3711 | 526 | 87.3 | globlastp |
| 1848 | LNU74 | apple\|gb157.3\|CN444719 | 3712 | 526 | 87.3 | globlastp |
| 1849 | LNU74 | apple\|gb171\|CN444719 | 3712 | 526 | 87.3 | globlastp |
| 1850 | LNU74 | ginger\|gb164\|DY357017 | 3713 | 526 | 87.3 | globlastp |
| 1851 | LNU74 | potato\|gb157.2\|BF153790 | 3711 | 526 | 87.3 | globlastp |
| 1852 | LNU74 | potato\|gb157.2\|BG591609 | 3711 | 526 | 87.3 | globlastp |
| 1853 | LNU74 | spurge\|gb161\|BI993550 | 3714 | 526 | 87.3 | globlastp |
| 1854 | LNU74 | spurge\|gb161\|DV120560 | 3715 | 526 | 87.3 | globlastp |
| 1855 | LNU74 | thellungiella\|gb167\|DN772768 | 3716 | 526 | 87.3 | globlastp |
| 1856 | LNU74 | triphysaria\|gb164\|EX991312 | 3717 | 526 | 87.3 | globlastp |
| 1857 | LNU74 | triphysaria\|gb164\|EX992098 | 3718 | 526 | 87.3 | globlastp |
| 1858 | LNU74 | triphysaria\|gb164\|EX993270 | 3719 | 526 | 87.3 | globlastp |
| 1859 | LNU74 | potato\|10v1\|BF153790 | 3711 | 526 | 87.3 | globlastp |
| 1860 | LNU74 | canola\|10v1\|BQ704346 | 3720 | 526 | 86.6 | globlastp |
| 1861 | LNU74 | canola\|10v1\|CD812655 | 3720 | 526 | 86.6 | globlastp |
| 1862 | LNU74 | canola\|10v1\|CD817750 | 3720 | 526 | 86.6 | globlastp |
| 1863 | LNU74 | canola\|10v1\|CD820979 | 3720 | 526 | 86.6 | globlastp |
| 1864 | LNU74 | canola\|10v1\|CD822847 | 3720 | 526 | 86.6 | globlastp |
| 1865 | LNU74 | canola\|10v1\|CD839803 | 3720 | 526 | 86.6 | globlastp |
| 1866 | LNU74 | canola\|10v1\|CD840413 | 3720 | 526 | 86.6 | globlastp |
| 1867 | LNU74 | cleome_gynandra\|10v1\|SRR015532S0001567 | 3721 | 526 | 86.6 | globlastp |
| 1868 | LNU74 | liquorice\|gb171\|FS239300 | 3722 | 526 | 86.6 | globlastp |
| 1869 | LNU74 | monkeyflower\|10v1\|DV211742 | 3723 | 526 | 86.6 | globlastp |
| 1870 | LNU74 | orobanche\|10v1\|SRR023189S0022715 | 3724 | 526 | 86.6 | globlastp |
| 1871 | LNU74 | rhizophora\|10v1\|SRR005792S0001265 | 3725 | 526 | 86.6 | globlastp |
| 1872 | LNU74 | salvia\|10v1\|CV170183 | 3726 | 526 | 86.6 | globlastp |
| 1873 | LNU74 | b_juncea\|gb164\|EVGN00065811011380 | 3720 | 526 | 86.6 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 1874 | LNU74 | b_juncea\|gb164\|EVGN00096612141341 | 3720 | 526 | 86.6 | globlastp |
| 1875 | LNU74 | b_juncea\|gb164\|EVGN00247926600394 | 3720 | 526 | 86.6 | globlastp |
| 1876 | LNU74 | b_juncea\|gb164\|EVGN00581615062911 | 3720 | 526 | 86.6 | globlastp |
| 1877 | LNU74 | b_juncea\|gb164\|EVGN01024809191906 | 3720 | 526 | 86.6 | globlastp |
| 1878 | LNU74 | b_oleracea\|gb161\|DY025798 | 3720 | 526 | 86.6 | globlastp |
| 1879 | LNU74 | b_oleracea\|gb161\|DY026115 | 3727 | 526 | 86.6 | globlastp |
| 1880 | LNU74 | b_rapa\|gb162\|CA992036 | 3720 | 526 | 86.6 | globlastp |
| 1881 | LNU74 | b_rapa\|gb162\|CX265596 | 3720 | 526 | 86.6 | globlastp |
| 1882 | LNU74 | b_rapa\|gb162\|CX265986 | 3720 | 526 | 86.6 | globlastp |
| 1883 | LNU74 | b_rapa\|gb162\|DY013411 | 3720 | 526 | 86.6 | globlastp |
| 1884 | LNU74 | b_rapa\|gb162\|L35798 | 3720 | 526 | 86.6 | globlastp |
| 1885 | LNU74 | cacao\|gb167\|CU473549 | 3728 | 526 | 86.6 | globlastp |
| 1886 | LNU74 | canola\|gb161\|CD812655 | 3720 | 526 | 86.6 | globlastp |
| 1887 | LNU74 | canola\|gb161\|CD817750 | 3720 | 526 | 86.6 | globlastp |
| 1888 | LNU74 | canola\|gb161\|CD818582 | 3720 | 526 | 86.6 | globlastp |
| 1889 | LNU74 | canola\|gb161\|CD820979 | 3720 | 526 | 86.6 | globlastp |
| 1890 | LNU74 | canola\|gb161\|CD822847 | 3720 | 526 | 86.6 | globlastp |
| 1891 | LNU74 | canola\|gb161\|CD839803 | 3720 | 526 | 86.6 | globlastp |
| 1892 | LNU74 | canola\|gb161\|CN731800 | 3720 | 526 | 86.6 | globlastp |
| 1893 | LNU74 | cotton\|gb164\|AI726252 | 3729 | 526 | 86.6 | globlastp |
| 1894 | LNU74 | cotton\|gb164\|BE054575 | 3730 | 526 | 86.6 | globlastp |
| 1895 | LNU74 | cotton\|gb164\|BF268166 | 3731 | 526 | 86.6 | globlastp |
| 1896 | LNU74 | ginger\|gb164\|DY347722 | 3732 | 526 | 86.6 | globlastp |
| 1897 | LNU74 | kiwi\|gb166\|FG426073 | 3733 | 526 | 86.6 | globlastp |
| 1898 | LNU74 | maize\|gb170\|LLDQ244555 | 3720 | 526 | 86.6 | globlastp |
| 1899 | LNU74 | oil_palm\|gb166\|EL684957 | 3734 | 526 | 86.6 | globlastp |
| 1900 | LNU74 | pepper\|gb171\|CA521239 | 3735 | 526 | 86.6 | globlastp |
| 1901 | LNU74 | radish\|gb164\|EV524672 | 3720 | 526 | 86.6 | globlastp |
| 1902 | LNU74 | radish\|gb164\|EV535208 | 3720 | 526 | 86.6 | globlastp |
| 1903 | LNU74 | radish\|gb164\|EV536989 | 3720 | 526 | 86.6 | globlastp |
| 1904 | LNU74 | radish\|gb164\|EV538098 | 3720 | 526 | 86.6 | globlastp |
| 1905 | LNU74 | radish\|gb164\|EV544188 | 3720 | 526 | 86.6 | globlastp |
| 1906 | LNU74 | radish\|gb164\|EX751329 | 3720 | 526 | 86.6 | globlastp |
| 1907 | LNU74 | radish\|gb164\|EX904913 | 3720 | 526 | 86.6 | globlastp |
| 1908 | LNU74 | radish\|gb164\|T25169 | 3720 | 526 | 86.6 | globlastp |
| 1909 | LNU74 | tamarix\|gb166\|CV791366 | 3736 | 526 | 86.6 | globlastp |
| 1910 | LNU74 | tomato\|09v1\|BG128242 | 3737 | 526 | 86.6 | globlastp |
| 1911 | LNU74 | tomato\|gb164\|BG128242 | 3737 | 526 | 86.6 | globlastp |
| 1912 | LNU74 | triphysaria\|gb164\|BU815081 | 3738 | 526 | 86.6 | globlastp |
| 1913 | LNU74 | sesame\|gb157.2\|BU667940 | 3739 | 526 | 86.57 | glotblastn |
| 1914 | LNU74 | cotton\|gb164\|BE052419 | 3740 | 526 | 86 | globlastp |
| 1915 | LNU74 | cleome_gynandra\|10v1\|SRR015532S0035591 | 3741 | 526 | 85.8 | globlastp |
| 1916 | LNU74 | eggplant\|10v1\|FS014035 | 3742 | 526 | 85.8 | globlastp |
| 1917 | LNU74 | monkeyflower\|10v1\|DV208750 | 3743 | 526 | 85.8 | globlastp |
| 1918 | LNU74 | orobanche\|10v1\|SRR023189S0004356 | 3744 | 526 | 85.8 | globlastp |
| 1919 | LNU74 | potato\|10v1\|BG589981 | 3745 | 526 | 85.8 | globlastp |
| 1920 | LNU74 | rhizophora\|10v1\|SRR005793S0025926 | 3746 | 526 | 85.8 | globlastp |
| 1921 | LNU74 | solanum_phureja\|09v1\|SPHBG128242 | 3745 | 526 | 85.8 | globlastp |
| 1922 | LNU74 | solanum_phureja\|09v1\|SPHBG131313 | 3747 | 526 | 85.8 | globlastp |
| 1923 | LNU74 | antirrhinum\|gb166\|AJ558344 | 3748 | 526 | 85.8 | globlastp |
| 1924 | LNU74 | avocado\|10v1\|CV461343 | 3749 | 526 | 85.8 | globlastp |
| 1925 | LNU74 | banana\|gb167\|DN239293 | 3750 | 526 | 85.8 | globlastp |
| 1926 | LNU74 | basilicum\|gb157.3\|DY341993 | 3751 | 526 | 85.8 | globlastp |
| 1927 | LNU74 | catharanthus\|gb166\|EG554531 | 3752 | 526 | 85.8 | globlastp |
| 1928 | LNU74 | chestnut\|gb170\|SRR006295S0004660 | 3753 | 526 | 85.8 | globlastp |
| 1929 | LNU74 | chestnut\|gb170\|SRR006295S0005476 | 3754 | 526 | 85.8 | globlastp |
| 1930 | LNU74 | kiwi\|gb166\|FG412937 | 3755 | 526 | 85.8 | globlastp |
| 1931 | LNU74 | kiwi\|gb166\|FG418868 | 3756 | 526 | 85.8 | globlastp |
| 1932 | LNU74 | oak\|gb170\|DB996491 | 3754 | 526 | 85.8 | globlastp |
| 1933 | LNU74 | oak\|gb170\|DN950062 | 3753 | 526 | 85.8 | globlastp |
| 1934 | LNU74 | oil_palm\|gb166\|CN600372 | 3757 | 526 | 85.8 | globlastp |
| 1935 | LNU74 | pineapple\|10v1\|DT336533 | 3758 | 526 | 85.8 | globlastp |
| 1936 | LNU74 | potato\|10v1\|BG350007 | 3747 | 526 | 85.8 | globlastp |
| 1937 | LNU74 | potato\|gb157.2\|BG350007 | 3747 | 526 | 85.8 | globlastp |
| 1938 | LNU74 | potato\|gb157.2\|BG589981 | 3745 | 526 | 85.8 | globlastp |
| 1939 | LNU74 | prunus\|gb167\|CB819261 | 3759 | 526 | 85.8 | globlastp |
| 1940 | LNU74 | prunus\|gb167\|CB819309 | 3760 | 526 | 85.8 | globlastp |
| 1941 | LNU74 | radish\|gb164\|EV543656 | 3761 | 526 | 85.8 | globlastp |
| 1942 | LNU74 | strawberry\|gb164\|DY674514 | 3762 | 526 | 85.8 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 1943 | LNU74 | tomato\|09v1\|BG123695 | 3763 | 526 | 85.8 | globlastp |
| 1944 | LNU74 | tomato\|gb164\|BG123695 | 3763 | 526 | 85.8 | globlastp |
| 1945 | LNU74 | tomato\|09v1\|BG131313 | 3764 | 526 | 85.8 | globlastp |
| 1946 | LNU74 | tomato\|gb164\|BG131313 | 3764 | 526 | 85.8 | globlastp |
| 1947 | LNU74 | cleome_spinosa\|10v1\|SRR015531S0000037 | 3765 | 526 | 85.1 | globlastp |
| 1948 | LNU74 | cleome_spinosa\|10v1\|SRR015531S0001284 | 3766 | 526 | 85.1 | globlastp |
| 1949 | LNU74 | cleome_spinosa\|10v1\|SRR015531S0008654 | 3767 | 526 | 85.1 | globlastp |
| 1950 | LNU74 | eggplant\|10v1\|FS000830 | 3768 | 526 | 85.1 | globlastp |
| 1951 | LNU74 | ginseng\|10v1\|CN846360 | 3769 | 526 | 85.1 | globlastp |
| 1952 | LNU74 | ipomoea_batatas\|10v1\|BU691765 | 3770 | 526 | 85.1 | globlastp |
| 1953 | LNU74 | ipomoea_nil\|10v1\|BJ560886 | 3771 | 526 | 85.1 | globlastp |
| 1954 | LNU74 | salvia\|10v1\|CV169031 | 3772 | 526 | 85.1 | globlastp |
| 1955 | LNU74 | apple\|gb157.3\|CN443979 | 3773 | 526 | 85.1 | globlastp |
| 1956 | LNU74 | apple\|gb171\|CN443979 | 3773 | 526 | 85.1 | globlastp |
| 1957 | LNU74 | apple\|gb171\|CN579105 | 3774 | 526 | 85.1 | globlastp |
| 1958 | LNU74 | arabidopsis\|gb165\|AT2G20450 | 3775 | 526 | 85.1 | globlastp |
| 1959 | LNU74 | arabidopsis\|gb165\|AT4G27090 | 3776 | 526 | 85.1 | globlastp |
| 1960 | LNU74 | b_oleracea\|gb161\|DY025895 | 3777 | 526 | 85.1 | globlastp |
| 1961 | LNU74 | cowpea\|gb166\|FF393525 | 3778 | 526 | 85.1 | globlastp |
| 1962 | LNU74 | nuphar\|gb166\|CD475921 | 3779 | 526 | 85.1 | globlastp |
| 1963 | LNU74 | oil_palm\|gb166\|EL689892 | 3780 | 526 | 85.1 | globlastp |
| 1964 | LNU74 | pepper\|gb157.2\|BM062339 | 3781 | 526 | 85.1 | globlastp |
| 1965 | LNU74 | pepper\|gb171\|BM062339 | 3781 | 526 | 85.1 | globlastp |
| 1966 | LNU74 | poppy\|gb166\|FE964687 | 3782 | 526 | 85.1 | globlastp |
| 1967 | LNU74 | tobacco\|gb162\|BQ842878 | 3783 | 526 | 85.1 | globlastp |
| 1968 | LNU74 | tobacco\|gb162\|BQ842898 | 3784 | 526 | 85.1 | globlastp |
| 1969 | LNU74 | tobacco\|gb162\|CV017540 | 3783 | 526 | 85.1 | globlastp |
| 1970 | LNU74 | antirrhinum\|gb166\|AJ786986 | 3785 | 526 | 85.07 | glotblastn |
| 1971 | LNU74 | soybean\|gb168\|AW171724 | 3786 | 526 | 84.33 | glotblastn |
| 1972 | LNU74 | arabidopsis_lyrata\|09v1\|JGIAL025381 | 3787 | 526 | 84.3 | globlastp |
| 1973 | LNU74 | flax\|09v1\|EU830250 | 3788 | 526 | 84.3 | globlastp |
| 1974 | LNU74 | ipomoea_nil\|10v1\|BJ554450 | 3789 | 526 | 84.3 | globlastp |
| 1975 | LNU74 | ipomoea_nil\|10v1\|BJ554544 | 3790 | 526 | 84.3 | globlastp |
| 1976 | LNU74 | avocado\|10v1\|CV460831 | 3791 | 526 | 84.3 | globlastp |
| 1977 | LNU74 | avocado\|gb164\|CV460831 | 3791 | 526 | 84.3 | globlastp |
| 1978 | LNU74 | avocado\|gb164\|CV461343 | 3792 | 526 | 84.3 | globlastp |
| 1979 | LNU74 | bean\|gb167\|CA904056 | 3793 | 526 | 84.3 | globlastp |
| 1980 | LNU74 | canola\|10v1\|EE451770 | 3794 | 526 | 84.3 | globlastp |
| 1981 | LNU74 | cotton\|gb164\|BE052734 | 3795 | 526 | 84.3 | globlastp |
| 1982 | LNU74 | ginger\|gb164\|DY352377 | 3796 | 526 | 84.3 | globlastp |
| 1983 | LNU74 | ipomoea\|gb157.2\|BJ554450 | 3789 | 526 | 84.3 | globlastp |
| 1984 | LNU74 | ipomoea\|gb157.2\|BJ554544 | 3790 | 526 | 84.3 | globlastp |
| 1985 | LNU74 | lettuce\|gb157.2\|DW145600 | 3797 | 526 | 84.3 | globlastp |
| 1986 | LNU74 | liriodendron\|gb166\|CK748217 | 3798 | 526 | 84.3 | globlastp |
| 1987 | LNU74 | maize\|gb170\|LLFL032821 | 3799 | 526 | 84.3 | globlastp |
| 1988 | LNU74 | onion\|gb162\|BQ579932 | 3800 | 526 | 84.3 | globlastp |
| 1989 | LNU74 | pepper\|gb171\|BM061235 | 3801 | 526 | 84.3 | globlastp |
| 1990 | LNU74 | pepper\|gb157.2\|CA521239 | 3802 | 526 | 84.3 | globlastp |
| 1991 | LNU74 | petunia\|gb166\|CV296857 | 3803 | 526 | 84.3 | globlastp |
| 1992 | LNU74 | petunia\|gb171\|CV296857 | 3803 | 526 | 84.3 | globlastp |
| 1993 | LNU74 | poppy\|gb166\|FE965604 | 3804 | 526 | 84.3 | globlastp |
| 1994 | LNU74 | rose\|10v1\|EC588002 | 3805 | 526 | 84.3 | globlastp |
| 1995 | LNU74 | rose\|gb157.2\|EC588002 | 3805 | 526 | 84.3 | globlastp |
| 1996 | LNU74 | strawberry\|gb164\|CO379805 | 3806 | 526 | 84.3 | globlastp |
| 1997 | LNU74 | triphysaria\|gb164\|EX996679 | 3807 | 526 | 84.3 | globlastp |
| 1998 | LNU74 | walnuts\|gb166\|EL900249 | 3808 | 526 | 84.3 | globlastp |
| 1999 | LNU74 | apple\|gb171\|CN444601 | 3809 | 526 | 83.6 | globlastp |
| 2000 | LNU74 | bean\|gb167\|CA897601 | 3810 | 526 | 83.6 | globlastp |
| 2001 | LNU74 | bean\|gb167\|CB543012 | 3811 | 526 | 83.6 | globlastp |
| 2002 | LNU74 | beet\|gb162\|BI095986 | 3812 | 526 | 83.6 | globlastp |
| 2003 | LNU74 | cowpea\|gb166\|FF385283 | 3813 | 526 | 83.6 | globlastp |
| 2004 | LNU74 | ipomoea\|gb157.2\|BU691765 | 3814 | 526 | 83.6 | globlastp |
| 2005 | LNU74 | lettuce\|gb157.2\|DW043837 | 3815 | 526 | 83.6 | globlastp |
| 2006 | LNU74 | lettuce\|gb157.2\|DW048497 | 3816 | 526 | 83.6 | globlastp |
| 2007 | LNU74 | lettuce\|10v1\|DW074549 | 3817 | 526 | 83.6 | globlastp |
| 2008 | LNU74 | lettuce\|gb157.2\|DW074549 | 3817 | 526 | 83.6 | globlastp |
| 2009 | LNU74 | lettuce\|10v1\|DW074794 | 3818 | 526 | 83.6 | globlastp |
| 2010 | LNU74 | lettuce\|gb157.2\|DW074794 | 3818 | 526 | 83.6 | globlastp |
| 2011 | LNU74 | lettuce\|gb157.2\|DW104050 | 3815 | 526 | 83.6 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 2012 | LNU74 | lettuce\|gb157.2\|DW151136 | 3816 | 526 | 83.6 | globlastp |
| 2013 | LNU74 | lotus\|09v1\|CB827421 | 3819 | 526 | 83.6 | globlastp |
| 2014 | LNU74 | lotus\|gb157.2\|CB827421 | 3819 | 526 | 83.6 | globlastp |
| 2015 | LNU74 | pepper\|gb157.2\|BM061235 | 3820 | 526 | 83.6 | globlastp |
| 2016 | LNU74 | soybean\|gb168\|AL373135 | 3821 | 526 | 83.6 | globlastp |
| 2017 | LNU74 | soybean\|gb168\|CA904059 | 3822 | 526 | 83.6 | globlastp |
| 2018 | LNU74 | lettuce\|10v1\|DW043837 | 3815 | 526 | 83.6 | globlastp |
| 2019 | LNU74 | lettuce\|10v1\|DW048497 | 3816 | 526 | 83.6 | globlastp |
| 2020 | LNU74 | blueberry\|10v1\|CF811622 | 3823 | 526 | 83.58 | glotblastn |
| 2021 | LNU74 | arabidopsis_lyrata\|09v1\|JGIAL012515 | 3824 | 526 | 82.8 | globlastp |
| 2022 | LNU74 | cucumber\|09v1\|CK700738 | 3825 | 526 | 82.8 | globlastp |
| 2023 | LNU74 | bean\|gb167\|CA897605 | 3826 | 526 | 82.8 | globlastp |
| 2024 | LNU74 | cichorium\|gb166\|EH700721 | 3827 | 526 | 82.8 | globlastp |
| 2025 | LNU74 | cichorium\|gb171\|EH700721 | 3827 | 526 | 82.8 | globlastp |
| 2026 | LNU74 | clover\|gb162\|BB922889 | 3828 | 526 | 82.8 | globlastp |
| 2027 | LNU74 | coffea\|10v1\|DV665694 | 3829 | 526 | 82.8 | globlastp |
| 2028 | LNU74 | coffea\|gb157.2\|DV665694 | 3829 | 526 | 82.8 | globlastp |
| 2029 | LNU74 | eucalyptus\|gb166\|CT981369 | 3830 | 526 | 82.8 | globlastp |
| 2030 | LNU74 | lettuce\|gb157.2\|DW120158 | 3831 | 526 | 82.8 | globlastp |
| 2031 | LNU74 | lettuce\|gb157.2\|DW148342 | 3831 | 526 | 82.8 | globlastp |
| 2032 | LNU74 | nuphar\|gb166\|CK768054 | 3832 | 526 | 82.8 | globlastp |
| 2033 | LNU74 | prunus\|gb167\|BU040832 | 3833 | 526 | 82.8 | globlastp |
| 2034 | LNU74 | safflower\|gb162\|EL375831 | 3834 | 526 | 82.8 | globlastp |
| 2035 | LNU74 | soybean\|gb168\|AW719570 | 3835 | 526 | 82.8 | globlastp |
| 2036 | LNU74 | triphysaria\|gb164\|EX989915 | 3836 | 526 | 82.8 | globlastp |
| 2037 | LNU74 | lettuce\|10v1\|DW045707 | 3831 | 526 | 82.8 | globlastp |
| 2038 | LNU74 | cucumber\|09v1\|AB008846 | 3837 | 526 | 82.1 | globlastp |
| 2039 | LNU74 | gerbera\|09v1\|AJ758629 | 3838 | 526 | 82.1 | globlastp |
| 2040 | LNU74 | liquorice\|gb171\|FS241908 | 3839 | 526 | 82.1 | globlastp |
| 2041 | LNU74 | rose\|10v1\|EC586454 | 3840 | 526 | 82.1 | globlastp |
| 2042 | LNU74 | lettuce\|gb157.2\|DW045707 | 3841 | 526 | 82.1 | globlastp |
| 2043 | LNU74 | lotus\|09v1\|LLAW163943 | 3842 | 526 | 82.1 | globlastp |
| 2044 | LNU74 | lotus\|gb157.2\|AW163943 | 3842 | 526 | 82.1 | globlastp |
| 2045 | LNU74 | medicago\|09v1\|AJ388670 | 3843 | 526 | 82.1 | globlastp |
| 2046 | LNU74 | medicago\|gb157.2\|AJ388670 | 3843 | 526 | 82.1 | globlastp |
| 2047 | LNU74 | melon\|gb165\|DV635132 | 3837 | 526 | 82.1 | globlastp |
| 2048 | LNU74 | sunflower\|gb162\|CD849558 | 3844 | 526 | 82.1 | globlastp |
| 2049 | LNU74 | sunflower\|gb162\|CD850836 | 3845 | 526 | 82.1 | globlastp |
| 2050 | LNU74 | sunflower\|gb162\|CD853111 | 3846 | 526 | 82.1 | globlastp |
| 2051 | LNU74 | tobacco\|gb162\|EB443461 | 3847 | 526 | 82.1 | globlastp |
| 2052 | LNU74 | petunia\|gb171\|DC240554 | 3848 | 526 | 81.48 | glotblastn |
| 2053 | LNU74 | antirrhinum\|gb166\|AJ789125 | 3849 | 526 | 81.34 | glotblastn |
| 2054 | LNU74 | liriodendron\|gb166\|CK767651 | 3850 | 526 | 81.34 | glotblastn |
| 2055 | LNU74 | cucumber\|09v1\|AM720896 | 3851 | 526 | 81.3 | globlastp |
| 2056 | LNU74 | gerbera\|09v1\|AJ750902 | 3852 | 526 | 81.3 | globlastp |
| 2057 | LNU74 | gerbera\|09v1\|AJ752958 | 3853 | 526 | 81.3 | globlastp |
| 2058 | LNU74 | centaurea\|gb166\|EH740419 | 3854 | 526 | 81.3 | globlastp |
| 2059 | LNU74 | cynara\|gb167\|GE588148 | 3855 | 526 | 81.3 | globlastp |
| 2060 | LNU74 | dandelion\|gb161\|DY837376 | 3856 | 526 | 81.3 | globlastp |
| 2061 | LNU74 | iceplant\|gb164\|BE033656 | 3857 | 526 | 81.3 | globlastp |
| 2062 | LNU74 | melon\|gb165\|AM720896 | 3851 | 526 | 81.3 | globlastp |
| 2063 | LNU74 | melon\|gb165\|EB714459 | 3858 | 526 | 81.3 | globlastp |
| 2064 | LNU74 | peanut\|gb171\|EE125965 | 3859 | 526 | 81.3 | globlastp |
| 2065 | LNU74 | zamia\|gb166\|CB095897 | 3860 | 526 | 81.3 | globlastp |
| 2066 | LNU74 | chickpea\|09v2\|GR398973 | 3861 | 526 | 80.6 | glotblastn |
| 2067 | LNU74 | ginseng\|10v1\|CN846065 | 3862 | 526 | 80.6 | globlastp |
| 2068 | LNU74 | pea\|09v1\|PSU78952 | 3863 | 526 | 80.6 | glotblastn |
| 2069 | LNU74 | artemisia\|gb164\|EY050285 | 3864 | 526 | 80.6 | globlastp |
| 2070 | LNU74 | artemisia\|gb164\|EY052651 | 3865 | 526 | 80.6 | globlastp |
| 2071 | LNU74 | centaurea\|gb166\|EH737655 | 3866 | 526 | 80.6 | globlastp |
| 2072 | LNU74 | medicago\|09v1\|AW686970 | 3867 | 526 | 80.6 | globlastp |
| 2073 | LNU74 | medicago\|gb157.2\|AW686970 | 3867 | 526 | 80.6 | globlastp |
| 2074 | LNU74 | peanut\|gb167\|EE123818 | 3868 | 526 | 80.6 | globlastp |
| 2075 | LNU74 | peanut\|gb171\|EE123818 | 3868 | 526 | 80.6 | globlastp |
| 2076 | LNU74 | peanut\|gb167\|EE125965 | 3869 | 526 | 80.6 | globlastp |
| 2077 | LNU74 | petunia\|gb166\|EB174480 | 3870 | 526 | 80.6 | glotblastn |
| 2078 | LNU74 | spruce\|gb162\|CO234251 | 3871 | 526 | 80.6 | globlastp |
| 2079 | LNU74 | sunflower\|gb162\|CD851355 | 3872 | 526 | 80.6 | globlastp |
| 2080 | LNU74 | tobacco\|gb162\|EB444354 | 3873 | 526 | 80.6 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 2081 | LNU74 | petunia\|gb171\|EB174480 | 3874 | 526 | 80.4 | globlastp |
| 2082 | LNU75 | soybean\|gb168\|BQ453397 | 3875 | 527 | 96.5 | globlastp |
| 2083 | LNU75 | bean\|gb167\|CB540681 | 3876 | 527 | 94.43 | glotblastn |
| 2084 | LNU75 | castorbean\|gb160\|MDL29647M002010 | 3877 | 527 | 83.3 | globlastp |
| 2085 | LNU75 | poplar\|10v1\|CV248257 | 3878 | 527 | 83.2 | globlastp |
| 2086 | LNU75 | poplar\|gb170\|CV248257 | 3878 | 527 | 83.2 | globlastp |
| 2087 | LNU75 | poplar\|10v1\|BU817503 | 3879 | 527 | 82.1 | globlastp |
| 2088 | LNU75 | poplar\|gb170\|BU817503 | 3879 | 527 | 82.1 | globlastp |
| 2089 | LNU75 | cassava\|09v1\|DB930644 | 3880 | 527 | 80.47 | glotblastn |
| 2090 | LNU75 | castorbean\|09v1\|EG661615 | 3881 | 527 | 80.4 | globlastp |
| 2091 | LNU75 | lotus\|09v1\|CRPLJ030481 | 3882 | 527 | 80.2 | globlastp |
| 2092 | LNU76 | brachypodium\|09v1\|DV474282 | 3883 | 528 | 91.8 | globlastp |
| 2093 | LNU76 | oat\|10v1\|SRR020741S0039710 | 3884 | 528 | 91.3 | globlastp |
| 2094 | LNU76 | wheat\|gb164\|BE213625 | 3885 | 528 | 91.3 | globlastp |
| 2095 | LNU76 | barley\|gb157.3\|AJ234439 | 3886 | 528 | 91 | globlastp |
| 2096 | LNU76 | barley\|gb157SOLEXA\|AJ234439 | 3886 | 528 | 91 | globlastp |
| 2097 | LNU76 | sorghum\|09v1\|SB07G028080 | 3887 | 528 | 89.8 | globlastp |
| 2098 | LNU76 | sorghum\|gb161.crp\|AW283835 | 3887 | 528 | 89.8 | globlastp |
| 2099 | LNU76 | switchgrass\|gb167\|DN147961 | 3888 | 528 | 89.1 | globlastp |
| 2100 | LNU76 | maize\|gb170\|BI431326 | 3889 | 528 | 88.3 | globlastp |
| 2101 | LNU76 | ipomoea_nil\|10v1\|BJ557425 | 3890 | 528 | 87.8 | globlastp |
| 2102 | LNU76 | ipomoea\|gb157.2\|BM878831 | 3890 | 528 | 87.8 | globlastp |
| 2103 | LNU76 | tobacco\|gb162\|DV159853 | 3891 | 528 | 87.6 | globlastp |
| 2104 | LNU76 | eggplant\|10v1\|FS024720XX1 | 3892 | 528 | 87.3 | globlastp |
| 2105 | LNU76 | pepper\|gb171\|BM064103 | 3893 | 528 | 87.3 | globlastp |
| 2106 | LNU76 | chestnut\|gb170\|SRR006295S0084519 | 3894 | 528 | 87.3 | globlastp |
| 2107 | LNU76 | solanum_phureja\|09v1\|SPHAA824694 | 3895 | 528 | 87.1 | globlastp |
| 2108 | LNU76 | castorbean\|09v1\|EE254059 | 3896 | 528 | 87.1 | globlastp |
| 2109 | LNU76 | castorbean\|gb160\|EE254059 | 3896 | 528 | 87.1 | globlastp |
| 2110 | LNU76 | maize\|gb170\|SRR014549S0042197 | 3897 | 528 | 87.1 | glotblastn |
| 2111 | LNU76 | tomato\|gb164\|AA824694 | 3898 | 528 | 87.1 | globlastp |
| 2112 | LNU76 | nicotiana_benthamiana\|gb162\|CN741775 | 3899 | 528 | 87.06 | glotblastn |
| 2113 | LNU76 | maize\|gb170\|BE640543 | 3900 | 528 | 86.85 | glotblastn |
| 2114 | LNU76 | cassava\|09v1\|CK641674 | 3901 | 528 | 86.8 | globlastp |
| 2115 | LNU76 | potato\|gb157.2\|BG096473 | 3902 | 528 | 86.8 | globlastp |
| 2116 | LNU76 | cleome_spinosa\|10v1\|SRR015531S0001775 | 3903 | 528 | 86.6 | globlastp |
| 2117 | LNU76 | aquilegia\|10v1\|DR924828 | 3904 | 528 | 86.6 | globlastp |
| 2118 | LNU76 | aquilegia\|gb157.3\|DR924828 | 3904 | 528 | 86.6 | globlastp |
| 2119 | LNU76 | medicago\|09v1\|AW698676 | 3905 | 528 | 86.6 | globlastp |
| 2120 | LNU76 | medicago\|gb157.2\|AW127555 | 3905 | 528 | 86.6 | globlastp |
| 2121 | LNU76 | melon\|gb165\|AF461048 | 3906 | 528 | 86.6 | globlastp |
| 2122 | LNU76 | potato\|gb157.2\|BE919491 | 3907 | 528 | 86.6 | globlastp |
| 2123 | LNU76 | pseudoroegneria\|gb167\|FF361372 | 3908 | 528 | 86.6 | globlastp |
| 2124 | LNU76 | potato\|10v1\|BG096473 | 3909 | 528 | 86.57 | glotblastn |
| 2125 | LNU76 | potato\|10v1\|BE919491 | 3910 | 528 | 86.32 | glotblastn |
| 2126 | LNU76 | cassava\|09v1\|CK641556 | 3911 | 528 | 86.3 | globlastp |
| 2127 | LNU76 | cucumber\|09v1\|AF461048 | 3912 | 528 | 86.3 | globlastp |
| 2128 | LNU76 | leymus\|gb166\|EG397002 | 3913 | 528 | 86.3 | globlastp |
| 2129 | LNU76 | melon\|gb165\|AY066012 | 3914 | 528 | 86.3 | globlastp |
| 2130 | LNU76 | triphysaria\|gb164\|EX982271 | 3915 | 528 | 86.3 | globlastp |
| 2131 | LNU76 | cleome_gynandra\|10v1\|SRR015532S0001935 | 3916 | 528 | 86.1 | globlastp |
| 2132 | LNU76 | cucumber\|09v1\|AY066012 | 3917 | 528 | 85.8 | globlastp |
| 2133 | LNU76 | apple\|gb157.3\|CN488454 | 3918 | 528 | 85.8 | globlastp |
| 2134 | LNU76 | apple\|gb171\|CN488454 | 3918 | 528 | 85.8 | globlastp |
| 2135 | LNU76 | apple\|gb157.3\|CN489537 | 3919 | 528 | 85.8 | globlastp |
| 2136 | LNU76 | apple\|gb171\|CN489537 | 3919 | 528 | 85.8 | globlastp |
| 2137 | LNU76 | b_oleracea\|gb161\|AM394032 | 3920 | 528 | 85.8 | globlastp |
| 2138 | LNU76 | canola\|gb161\|BQ704207 | 3920 | 528 | 85.8 | globlastp |
| 2139 | LNU76 | clover\|gb162\|BB932727 | 3921 | 528 | 85.8 | globlastp |
| 2140 | LNU76 | papaya\|gb165\|EX241410 | 3922 | 528 | 85.8 | globlastp |
| 2141 | LNU76 | peanut\|gb167\|ES752188 | 3923 | 528 | 85.8 | globlastp |
| 2142 | LNU76 | peanut\|gb171\|ES752188 | 3923 | 528 | 85.8 | globlastp |
| 2143 | LNU76 | chickpea\|09v2\|DY475133 | 3924 | 528 | 85.6 | globlastp |
| 2144 | LNU76 | b_juncea\|gb164\|EVGN00028714050635 | 3925 | 528 | 85.6 | globlastp |
| 2145 | LNU76 | b_rapa\|gb162\|CX272671 | 3926 | 528 | 85.6 | globlastp |
| 2146 | LNU76 | canola\|10v1\|CB686087 | 3926 | 528 | 85.6 | globlastp |
| 2147 | LNU76 | canola\|gb161\|CB686087 | 3926 | 528 | 85.6 | globlastp |
| 2148 | LNU76 | cichorium\|gb171\|EH672667 | 3927 | 528 | 85.6 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 2149 | LNU76 | cotton\|gb164\|CO072567 | 3928 | 528 | 85.6 | globlastp |
| 2150 | LNU76 | ginger\|gb164\|DY344931 | 3929 | 528 | 85.6 | globlastp |
| 2151 | LNU76 | lettuce\|gb157.2\|DW047667 | 3930 | 528 | 85.6 | globlastp |
| 2152 | LNU76 | lettuce\|gb157.2\|DW101545 | 3930 | 528 | 85.6 | globlastp |
| 2153 | LNU76 | lettuce\|gb157.2\|DW146107 | 3930 | 528 | 85.6 | globlastp |
| 2154 | LNU76 | walnuts\|gb166\|EL891302 | 3931 | 528 | 85.6 | globlastp |
| 2155 | LNU76 | lettuce\|10v1\|DW047667 | 3930 | 528 | 85.6 | globlastp |
| 2156 | LNU76 | eucalyptus\|gb166\|CD668235 | 3932 | 528 | 85.57 | glotblastn |
| 2157 | LNU76 | lotus\|09v1\|AI967569 | 3933 | 528 | 85.3 | globlastp |
| 2158 | LNU76 | citrus\|gb166\|CF417173 | 3934 | 528 | 85.3 | globlastp |
| 2159 | LNU76 | cotton\|gb164\|CA993018 | 3935 | 528 | 85.3 | globlastp |
| 2160 | LNU76 | sunflower\|gb162\|CD845667 | 3936 | 528 | 85.3 | globlastp |
| 2161 | LNU76 | thellungiella\|gb167\|DN772880 | 3937 | 528 | 85.3 | globlastp |
| 2162 | LNU76 | artemisia\|gb164\|EY032115 | 3938 | 528 | 85.1 | globlastp |
| 2163 | LNU76 | b_rapa\|gb162\|BG544512 | 3939 | 528 | 85.1 | globlastp |
| 2164 | LNU76 | canola\|10v1\|BQ704676 | 3940 | 528 | 85.1 | globlastp |
| 2165 | LNU76 | canola\|gb161\|CX191423 | 3940 | 528 | 85.1 | globlastp |
| 2166 | LNU76 | poplar\|10v1\|BI068844 | 3941 | 528 | 85.1 | globlastp |
| 2167 | LNU76 | poplar\|gb170\|BI068844 | 3942 | 528 | 85.1 | globlastp |
| 2168 | LNU76 | poplar\|10v1\|BI069243 | 3943 | 528 | 85.1 | globlastp |
| 2169 | LNU76 | poplar\|gb170\|BI069243 | 3943 | 528 | 85.1 | globlastp |
| 2170 | LNU76 | radish\|gb164\|EV525299 | 3944 | 528 | 85.1 | globlastp |
| 2171 | LNU76 | banana\|gb167\|DN238082 | 3945 | 528 | 85.07 | glotblastn |
| 2172 | LNU76 | cichorium\|gb166\|EH672667 | 3946 | 528 | 85.07 | glotblastn |
| 2173 | LNU76 | b_oleracea\|gb161\|AM385579 | 3947 | 528 | 84.8 | globlastp |
| 2174 | LNU76 | coffea\|10v1\|DV678645 | 3948 | 528 | 84.8 | globlastp |
| 2175 | LNU76 | coffea\|gb157.2\|DV678645 | 3948 | 528 | 84.8 | globlastp |
| 2176 | LNU76 | cowpea\|gb166\|FC456675 | 3949 | 528 | 84.8 | globlastp |
| 2177 | LNU76 | cleome_gynandra\|10v1\|SRR015532S0005303 | 3950 | 528 | 84.6 | globlastp |
| 2178 | LNU76 | prunus\|gb167\|BU039541 | 3951 | 528 | 84.6 | globlastp |
| 2179 | LNU76 | strawberry\|gb164\|DY667189 | 3952 | 528 | 84.6 | globlastp |
| 2180 | LNU76 | ginger\|gb164\|DY344881 | 3953 | 528 | 84.3 | globlastp |
| 2181 | LNU76 | iceplant\|gb164\|AA842895 | 3954 | 528 | 84.3 | globlastp |
| 2182 | LNU76 | soybean\|gb168\|AI967569 | 3955 | 528 | 84.3 | globlastp |
| 2183 | LNU76 | arabidopsis\|gb165\|AT2G13360 | 3956 | 528 | 84.1 | globlastp |
| 2184 | LNU76 | bean\|gb167\|GFXEU018611X1 | 3957 | 528 | 84.1 | globlastp |
| 2185 | LNU76 | safflower\|gb162\|EL384125 | 3958 | 528 | 84.08 | glotblastn |
| 2186 | LNU76 | arabidopsis_lyrata\|09v1\|JGIAL011701 | 3959 | 528 | 83.8 | globlastp |
| 2187 | LNU76 | soybean\|gb168\|AW719840 | 3960 | 528 | 83.3 | globlastp |
| 2188 | LNU76 | lotus\|09v1\|AW719840 | 3961 | 528 | 82.8 | globlastp |
| 2189 | LNU76 | lotus\|gb157.2\|AW719840 | 3962 | 528 | 82.6 | globlastp |
| 2190 | LNU76 | grape\|gb160\|BM436787 | 3963 | 528 | 82.3 | globlastp |
| 2191 | LNU76 | spruce\|gb162\|CO230132 | 3964 | 528 | 81.1 | globlastp |
| 2192 | LNU76 | centaurea\|gb166\|EL931044 | 3965 | 528 | 81.09 | glotblastn |
| 2193 | LNU76 | pine\|10v1\|CF476545 | 3966 | 528 | 80.4 | globlastp |
| 2194 | LNU76 | pine\|gb157.2\|CF476545 | 3966 | 528 | 80.4 | globlastp |
| 2195 | LNU79 | cacao\|gb167\|CU499480 | 3967 | 529 | 82.8 | globlastp |
| 2196 | LNU83 | soybean\|gb168\|BI974032 | 3968 | 532 | 80.5 | globlastp |
| 2197 | LNU85 | sugarcane\|10v1\|BQ529864 | 3969 | 534 | 98.3 | globlastp |
| 2198 | LNU85 | sugarcane\|gb157.3\|BQ529864 | 3969 | 534 | 98.3 | globlastp |
| 2199 | LNU85 | maize\|gb170\|AI941787 | 3970 | 534 | 94.1 | globlastp |
| 2200 | LNU85 | switchgrass\|gb167\|DN152416 | 3971 | 534 | 91.4 | globlastp |
| 2201 | LNU85 | millet\|09v1\|EVO454PM001540 | 3972 | 534 | 89.9 | globlastp |
| 2202 | LNU85 | rice\|gb170\|OS05G48450 | 3973 | 534 | 88.8 | globlastp |
| 2203 | LNU85 | barley\|gb157.3\|BI954412 | 3974 | 534 | 86.6 | globlastp |
| 2204 | LNU85 | barley\|gb157SOLEXA\|BI954412 | 3974 | 534 | 86.6 | globlastp |
| 2205 | LNU85 | brachypodium\|09v1\|GT758786 | 3975 | 534 | 86.6 | globlastp |
| 2206 | LNU85 | wheat\|gb164\|BE427293 | 3976 | 534 | 84.9 | globlastp |
| 2207 | LNU85 | rice\|gb170\|OS10G40200 | 3977 | 534 | 81.7 | globlastp |
| 2208 | LNU85 | brachypodium\|gb169\|BE402800 | 3978 | 534 | 81.4 | globlastp |
| 2209 | LNU85 | switchgrass\|gb167\|FE658951 | 3979 | 534 | 80.6 | globlastp |
| 2210 | LNU85 | brachypodium\|09v1\|SRR031795S0009845 | 3980 | 534 | 80 | globlastp |
| 2211 | LNU86 | sorghum\|09v1\|SB09G029470 | 3981 | 535 | 85.4 | globlastp |
| 2212 | LNU86 | sorghum\|gb161.crp\|AI941972 | 3981 | 535 | 85.4 | globlastp |
| 2213 | LNU89 | wheat\|gb164\|BG606995 | 3982 | 537 | 98.7 | globlastp |
| 2214 | LNU89 | rice\|gb170\|OS12G16350 | 3983 | 537 | 82.4 | globlastp |
| 2215 | LNU94 | solanum_phureja\|09v1\|SPHAW621975 | 3984 | 538 | 96.4 | globlastp |
| 2216 | LNU94 | solanum_phureja\|09v1\|SPHDV105556 | 3985 | 538 | 94.7 | globlastp |
| 2217 | LNU94 | potato\|10v1\|X98891 | 3986 | 538 | 93.8 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 2218 | LNU94 | potato\|gb157.2\|X98891 | 3986 | 538 | 93.8 | globlastp |
| 2219 | LNU94 | pepper\|gb171\|EF091665 | 3987 | 538 | 90.5 | globlastp |
| 2220 | LNU94 | tobacco\|gb162\|AB042951 | 3988 | 538 | 88.4 | globlastp |
| 2221 | LNU94 | pepper\|gb157.2\|EF091665 | 3989 | 538 | 87.3 | globlastp |
| 2222 | LNU94 | cichorium\|gb171\|DT213190 | 3990 | 538 | 81.44 | glotblastn |
| 2223 | LNU94 | cichorium\|gb166\|DT213190 | 3991 | 538 | 80.49 | glotblastn |
| 2224 | LNU94 | medicago\|09v1\|MTAF000354 | 3992 | 538 | 80.37 | glotblastn |
| 2225 | LNU94 | medicago\|gb157.2\|MTAF000354 | 3992 | 538 | 80.37 | glotblastn |
| 2226 | LNU94 | solanum_phureja\|09v1\|SPHY16125 | 3993 | 538 | 80.34 | glotblastn |
| 2227 | LNU94 | potato\|10v1\|AF156695 | 3993 | 538 | 80.34 | glotblastn |
| 2228 | LNU94 | potato\|gb157.2\|AF156695 | 3993 | 538 | 80.34 | glotblastn |
| 2229 | LNU94 | lettuce\|10v1\|DW051651 | 3994 | 538 | 80.3 | glotblastn |
| 2230 | LNU94 | lettuce\|gb157.2\|DW051651 | 3994 | 538 | 80.3 | glotblastn |
| 2231 | LNU94 | medicago\|09v1\|AW329601 | 3995 | 538 | 80.19 | glotblastn |
| 2232 | LNU94 | medicago\|09v1\|MTAF000355 | 3996 | 538 | 80.15 | glotblastn |
| 2233 | LNU94 | medicago\|gb157.2\|MTAF000355 | 3996 | 538 | 80.15 | glotblastn |
| 2234 | LNU95 | bean\|gb167\|CV543264 | 3997 | 539 | 84.1 | globlastp |
| 2235 | LNU95 | cowpea\|gb166\|FF384522 | 3998 | 539 | 82.2 | globlastp |
| 2236 | LNU100 | cotton\|gb164\|BG440037 | 3999 | 542 | 91.97 | glotblastn |
| 2237 | LNU100 | strawberry\|gb164\|EX657249 | 4000 | 542 | 82.95 | glotblastn |
| 2238 | LNU100 | cassava\|09v1\|DB921063 | 4001 | 542 | 82.9 | globlastp |
| 2239 | LNU100 | poplar\|gb170\|BI069411 | 4002 | 542 | 82.3 | globlastp |
| 2240 | LNU100 | poplar\|gb170\|BI131061 | 4003 | 542 | 82.1 | globlastp |
| 2241 | LNU100 | chestnut\|gb170\|SRR006295S0057433 | 4004 | 542 | 81.97 | glotblastn |
| 2242 | LNU100 | citrus\|gb166\|BQ624837 | 4005 | 542 | 81.89 | glotblastn |
| 2243 | LNU100 | poplar\|10v1\|BI131061 | 4006 | 542 | 81.3 | globlastp |
| 2244 | LNU100 | cowpea\|gb166\|FF394721 | 4007 | 542 | 80.25 | glotblastn |
| 2245 | LNU100 | soybean\|gb168\|AW163881 | 4008 | 542 | 80.25 | glotblastn |
| 2246 | LNU100 | cucumber\|09v1\|CK756513 | 4009 | 542 | 80.2 | globlastp |
| 2247 | LNU100 | bean\|gb167\|CA901142 | 4010 | 542 | 80.2 | globlastp |
| 2248 | LNU100 | medicago\|09v1\|AL369478 | 4011 | 542 | 80.04 | glotblastn |
| 2249 | LNU100 | medicago\|09v1\|AW691643 | 4012 | 542 | 80 | globlastp |
| 2250 | LNU104 | soybean\|gb168\|BG647792 | 4013 | 544 | 95.5 | globlastp |
| 2251 | LNU104 | cowpea\|gb166\|FF382988 | 4014 | 544 | 89.8 | globlastp |
| 2252 | LNU104 | medicago\|09v1\|BG647792 | 4015 | 544 | 82.8 | globlastp |
| 2253 | LNU104 | medicago\|gb157.2\|BG647792 | 4016 | 544 | 82 | glotblastn |
| 2254 | LNU105 | leymus\|gb166\|EG396306 | 4017 | 545 | 95.8 | globlastp |
| 2254 | LNU72 | leymus\|gb166\|EG396306 | 4017 | 725 | 94.2 | globlastp |
| 2255 | LNU105 | pseudoroegneria\|gb167\|FF352468 | 4018 | 545 | 94.2 | globlastp |
| 2255 | LNU72 | pseudoroegneria\|gb167\|FF352468 | 4018 | 725 | 92.7 | globlastp |
| 2256 | LNU105 | oat\|10v1\|CN819266 | 4019 | 545 | 88.8 | globlastp |
| 2256 | LNU72 | oat\|10v1\|CN819266 | 4019 | 725 | 88.4 | globlastp |
| 2257 | LNU106 | wheat\|gb164\|BE426509 | 4020 | 546 | 98.2 | globlastp |
| 2258 | LNU106 | barley\|gb157.3\|AJ234436 | 4021 | 546 | 91.9 | globlastp |
| 2259 | LNU106 | barley\|gb157SOLEXA\|AJ234436 | 4021 | 546 | 91.9 | globlastp |
| 2260 | LNU107 | brachypodium\|09v1\|SRR031795S0019801 | 4022 | 547 | 83.9 | globlastp |
| 2261 | LNU107 | brachypodium\|gb169\|BE637729 | 4022 | 547 | 83.9 | globlastp |
| 2262 | LNU107 | wheat\|gb164\|BE637729 | 4023 | 547 | 82.89 | glotblastn |
| 2263 | LNU109 | sorghum\|09v1\|SB10G000960 | 4024 | 548 | 85.6 | globlastp |
| 2264 | LNU109 | sorghum\|gb161.crp\|AW286123 | 4024 | 548 | 85.6 | globlastp |
| 2265 | LNU109 | brachypodium\|09v1\|GT863831 | 4025 | 548 | 85.2 | globlastp |
| 2266 | LNU109 | brachypodium\|gb169\|BE443129 | 4025 | 548 | 85.2 | globlastp |
| 2267 | LNU109 | pseudoroegneria\|gb167\|FF364297 | 4026 | 548 | 81.3 | globlastp |
| 2268 | LNU115 | sugarcane\|10v1\|CA067152 | 4027 | 553 | 84.3 | globlastp |
| 2269 | LNU115 | sugarcane\|gb157.3\|CA067152 | 4028 | 553 | 84.2 | globlastp |
| 2270 | LNU115 | sorghum\|09v1\|SB07G004420 | 4029 | 553 | 84.1 | globlastp |
| 2271 | LNU115 | maize\|gb170\|AW067055 | 4030 | 553 | 83.9 | globlastp |
| 2272 | LNU115 | brachypodium\|09v1\|TMPLOS03G48850T1 | 4031 | 553 | 80.09 | glotblastn |
| 2273 | LNU115 | rice\|gb170\|OS03G48850 | 4031 | 553 | 80.09 | glotblastn |
| 2274 | LNU116 | sorghum\|09v1\|SB01G021870 | 4032 | 554 | 80.2 | globlastp |
| 2275 | LNU121 | sorghum\|gb161.crp\|CF060003 | 4033 | 559 | 80.7 | globlastp |
| 2276 | LNU121 | brachypodium\|gb169\|BE601610 | 4034 | 559 | 80.39 | glotblastn |
| 2277 | LNU123 | arabidopsis_lyrata\|09v1\|GFXDQ132362X1 | 4035 | 561 | 98.5 | globlastp |
| 2278 | LNU124 | arabidopsis_lyrata\|09v1\|JGIAL029920 | 4036 | 562 | 99.3 | globlastp |
| 2279 | LNU124 | radish\|gb164\|FD967528 | 4037 | 562 | 83.03 | glotblastn |
| 2280 | LNU124 | citrus\|gb166\|CV885509 | 4038 | 562 | 81.08 | glotblastn |
| 2281 | LNU124 | poplar\|10v1\|CX176510 | 4039 | 562 | 80.72 | glotblastn |
| 2282 | LNU124 | poplar\|gb170\|CX176510 | 4039 | 562 | 80.72 | glotblastn |
| 2283 | LNU126 | arabidopsis_lyrata\|09v1\|JGIAL030477 | 4040 | 563 | 94.2 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 2284 | LNU126 | canola\|10v1\|EE444561 | 4041 | 563 | 83.6 | globlastp |
| 2285 | LNU126 | b_rapa\|gb162\|DN964586 | 4042 | 563 | 83.6 | globlastp |
| 2286 | LNU126 | canola\|gb161\|EE444561 | 4043 | 563 | 83.6 | glotblastn |
| 2287 | LNU126 | radish\|gb164\|EX747028 | 4044 | 563 | 81.94 | glotblastn |
| 2288 | LNU126 | b_juncea\|gb164\|EVGN00669227830274P1 | 4045 | 563 | 80.5 | globlastp |
| 2289 | LNU127 | arabidopsis_lyrata\|09v1\|JGIAL030813 | 4046 | 564 | 91.4 | globlastp |
| 2290 | LNU127 | thellungiella\|gb167\|DN772829 | 4047 | 564 | 81.2 | globlastp |
| 2291 | LNU128 | arabidopsis_lyrata\|09v1\|JGIAL002292 | 4048 | 565 | 98.8 | globlastp |
| 2292 | LNU130 | arabidopsis_lyrata\|09v1\|JGIAL007931 | 4049 | 567 | 86.6 | globlastp |
| 2293 | LNU131 | arabidopsis_lyrata\|09v1\|JGIAL015515 | 4050 | 568 | 92.9 | globlastp |
| 2294 | LNU131 | b_oleracea\|gb161\|DY026439 | 4051 | 568 | 82.7 | globlastp |
| 2295 | LNU131 | canola\|gb161\|DY023887 | 4052 | 568 | 82.33 | glotblastn |
| 2296 | LNU131 | canola\|10v1\|ES956350 | 4053 | 568 | 81.95 | glotblastn |
| 2297 | LNU131 | canola\|10v1\|DY023887 | 4054 | 568 | 80.6 | glotblastn |
| 2298 | LNU131 | radish\|gb164\|EW731027 | 4055 | 568 | 80.37 | glotblastn |
| 2299 | LNU131 | radish\|gb164\|EV546624 | 4056 | 568 | 80 | glotblastn |
| 2300 | LNU132 | arabidopsis_lyrata\|09v1\|JGIAL007040 | 4057 | 569 | 94.5 | globlastp |
| 2301 | LNU133 | arabidopsis_lyrata\|09v1\|JGIAL007458 | 4058 | 570 | 95.9 | globlastp |
| 2302 | LNU133 | canola\|10v1\|EE426894 | 4059 | 570 | 87.8 | globlastp |
| 2303 | LNU133 | canola\|gb161\|CX193266 | 4059 | 570 | 87.8 | globlastp |
| 2304 | LNU133 | b_rapa\|gb162\|CV434022 | 4060 | 570 | 86.7 | globlastp |
| 2305 | LNU133 | canola\|gb161\|CD830045 | 4061 | 570 | 86.7 | globlastp |
| 2306 | LNU133 | radish\|gb164\|EV527818 | 4062 | 570 | 86.7 | globlastp |
| 2307 | LNU133 | b_oleracea\|gb161\|AM057011 | 4063 | 570 | 85.7 | globlastp |
| 2308 | LNU133 | b_oleracea\|gb161\|ES948067 | 4064 | 570 | 85.7 | globlastp |
| 2309 | LNU133 | b_rapa\|gb162\|EE516981 | 4065 | 570 | 85.7 | globlastp |
| 2310 | LNU133 | canola\|gb161\|CD822076 | 4066 | 570 | 85.7 | globlastp |
| 2311 | LNU133 | canola\|10v1\|CX193266 | 4063 | 570 | 85.7 | globlastp |
| 2312 | LNU133 | canola\|gb161\|CX193799 | 4063 | 570 | 85.7 | globlastp |
| 2313 | LNU133 | radish\|gb164\|EW725954 | 4067 | 570 | 85.7 | globlastp |
| 2314 | LNU133 | radish\|gb164\|EW729334 | 4068 | 570 | 85.7 | globlastp |
| 2315 | LNU133 | radish\|gb164\|EX770388 | 4068 | 570 | 85.7 | globlastp |
| 2316 | LNU133 | radish\|gb164\|EX774120 | 4068 | 570 | 85.7 | globlastp |
| 2317 | LNU133 | b_juncea\|gb164\|EVGN00336011243437 | 4069 | 570 | 83.7 | globlastp |
| 2318 | LNU133 | b_juncea\|gb164\|EVGN00782708352054 | 4070 | 570 | 83.7 | globlastp |
| 2319 | LNU133 | b_oleracea\|gb161\|AM060067 | 4069 | 570 | 83.7 | globlastp |
| 2320 | LNU133 | b_rapa\|gb162\|CX266396 | 4069 | 570 | 83.7 | globlastp |
| 2321 | LNU133 | canola\|10v1\|BQ704992 | 4069 | 570 | 83.7 | globlastp |
| 2322 | LNU133 | canola\|gb161\|BQ704992 | 4069 | 570 | 83.7 | globlastp |
| 2323 | LNU133 | canola\|10v1\|H07830 | 4069 | 570 | 83.7 | globlastp |
| 2324 | LNU133 | canola\|gb161\|H07830 | 4069 | 570 | 83.7 | globlastp |
| 2325 | LNU133 | radish\|gb164\|EV527349 | 4069 | 570 | 83.7 | globlastp |
| 2326 | LNU133 | radish\|gb164\|EV535700 | 4069 | 570 | 83.7 | globlastp |
| 2327 | LNU133 | radish\|gb164\|EV568761 | 4069 | 570 | 83.7 | globlastp |
| 2328 | LNU133 | radish\|gb164\|EX747596 | 4069 | 570 | 83.7 | globlastp |
| 2329 | LNU133 | radish\|gb164\|FD538859 | 4071 | 570 | 82.7 | globlastp |
| 2330 | LNU133 | thellungiella\|gb167\|DN775946 | 4072 | 570 | 82.7 | globlastp |
| 2331 | LNU133 | b_rapa\|gb162\|EX025487 | 4073 | 570 | 82.47 | glotblastn |
| 2332 | LNU133 | radish\|gb164\|EV545406 | 4074 | 570 | 82.47 | glotblastn |
| 2333 | LNU133 | radish\|gb164\|FD981399 | 4075 | 570 | 81.44 | glotblastn |
| 2334 | LNU134 | arabidopsis_lyrata\|09v1\|JGIAL023230 | 4076 | 571 | 92.8 | globlastp |
| 2335 | LNU136 | arabidopsis_lyrata\|09v1\|JGIAL016753 | 4077 | 573 | 94.8 | globlastp |
| 2336 | LNU136 | canola\|10v1\|EV117254 | 4078 | 573 | 83.71 | glotblastn |
| 2337 | LNU138 | wheat\|gb164\|BE404910 | 4079 | 574 | 98.4 | globlastp |
| 2338 | LNU138 | pseudoroegneria\|gb167\|FF343940 | 4080 | 574 | 97.5 | globlastp |
| 2339 | LNU138 | wheat\|gb164\|BE405302 | 4081 | 574 | 97.2 | globlastp |
| 2340 | LNU138 | oat\|10v1\|GR335867 | 4082 | 574 | 91.5 | globlastp |
| 2341 | LNU138 | brachypodium\|09v1\|DV481179 | 4083 | 574 | 87.4 | globlastp |
| 2342 | LNU138 | brachypodium\|gb169\|BE404910 | 4084 | 574 | 83.91 | glotblastn |
| 2343 | LNU138 | rice\|gb170\|OS05G31750 | 4085 | 574 | 80.6 | globlastp |
| 2344 | LNU140 | canola\|gb161\|ES899922 | 4086 | 575 | 92.4 | globlastp |
| 2345 | LNU141 | barley\|gb157.3\|AV832506 | 4087 | 576 | 80.6 | globlastp |
| 2346 | LNU141 | barley\|gb157SOLEXA\|AV832506 | 4087 | 576 | 80.6 | globlastp |
| 2347 | LNU142 | wheat\|gb164\|BE429302 | 4088 | 577 | 88.1 | globlastp |
| 2348 | LNU143 | cotton\|gb164\|BQ411539 | 4089 | 578 | 83.63 | glotblastn |
| 2349 | LNU147 | heritiera\|10v1\|SRR005795S0005739 | 4090 | 580 | 83.8 | globlastp |
| 2350 | LNU147 | cacao\|gb167\|CU470446 | 4091 | 580 | 83.1 | globlastp |
| 2351 | LNU148 | soybean\|gb168\|CD399473 | 4092 | 581 | 87.7 | globlastp |
| 2352 | LNU148 | cowpea\|gb166\|FG822996 | 4093 | 581 | 81.5 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Hom. Polyp. SEQ ID NO: | Hom. to SEQ ID NO: | % global identity | Algor. |
|---|---|---|---|---|---|---|
| 2353 | LNU150 | antirrhinum\|gb166\|AJ787462 | 4094 | 583 | 84.8 | globlastp |
| 2354 | LNU153 | switchgrass\|gb167\|FE648089 | 4095 | 584 | 91.8 | globlastp |
| 2355 | LNU153 | wheat\|gb164\|CA499728 | 4096 | 584 | 91.5 | globlastp |
| 2356 | LNU153 | sorghum\|09v1\|SB09G000910 | 4097 | 584 | 91.3 | globlastp |
| 2357 | LNU153 | sorghum\|gb161.crp\|AW564938 | 4097 | 584 | 91.3 | globlastp |
| 2358 | LNU153 | maize\|gb170\|AW787777 | 4098 | 584 | 89.5 | globlastp |
| 2359 | LNU153 | oat\|10v1\|GR331123 | 4099 | 584 | 89.08 | globlastn |
| 2360 | LNU153 | switchgrass\|gb167\|FL747998 | 4100 | 584 | 85 | globlastp |
| 2361 | LNU153 | switchgrass\|gb167\|FL711487 | 4101 | 584 | 84.6 | globlastp |
| 2362 | LNU153 | brachypodium\|09v1\|DV482357 | 4102 | 584 | 84.4 | globlastp |
| 2363 | LNU153 | brachypodium\|gb169\|BE420118 | 4102 | 584 | 84.4 | globlastp |
| 2364 | LNU153 | rice\|gb170\|OS01G73970 | 4103 | 584 | 84.3 | globlastp |
| 2365 | LNU153 | barley\|gb157SOLEXA\|BI959596 | 4104 | 584 | 82.9 | globlastp |
| 2366 | LNU153 | sorghum\|09v1\|SB03G047280 | 4105 | 584 | 82.8 | globlastp |
| 2367 | LNU153 | sorghum\|gb161.crp\|BI139689 | 4105 | 584 | 82.8 | globlastp |
| 2368 | LNU153 | barley\|gb157.3\|BI959596 | 4106 | 584 | 82.6 | globlastp |
| 2369 | LNU153 | ginger\|gb164\|DY353392 | 4107 | 584 | 80.6 | globlastp |
| 2370 | LNU157 | soybean\|gb168\|AL365749 | 4108 | 587 | 96.5 | globlastp |
| 2371 | LNU157 | bean\|gb167\|CB540562 | 4109 | 587 | 93 | globlastp |
| 2372 | LNU157 | medicago\|09v1\|AW299124 | 4110 | 587 | 85.7 | globlastp |
| 2373 | LNU161 | soybean\|gb168\|CF808044 | 4111 | 589 | 88.8 | globlastp |
| 2374 | LNU161 | cowpea\|gb166\|FG846783 | 4112 | 589 | 80.8 | globlastp |
| 2375 | LNU168 | maize\|gb170\|AW927746 | 4113 | 590 | 97.2 | globlastp |
| 2376 | LNU168 | sugarcane\|gb157.3\|CA098262 | 4114 | 590 | 97.2 | globlastp |
| 2377 | LNU168 | sugarcane\|10v1\|BU102716 | 4114 | 590 | 97.2 | globlastp |
| 2378 | LNU168 | sugarcane\|gb157.3\|BU102716 | 4115 | 590 | 91.59 | glotblastn |
| 2379 | LNU168 | switchgrass\|gb167\|FL875098 | 4116 | 590 | 83.6 | globlastp |
| 2380 | LNU168 | switchgrass\|gb167\|DN151126 | 4117 | 590 | 82.7 | globlastp |
| 2381 | LNU171 | wheat\|gb164\|CK211341 | 4118 | 592 | 88.1 | globlastp |
| 2382 | LNU171 | wheat\|gb164\|CA712412 | 4119 | 592 | 85.3 | globlastp |
| 2383 | LNU171 | barley\|gb157.3\|BQ740207 | 4120 | 592 | 83.1 | globlastp |
| 2384 | LNU171 | barley\|gb157SOLEXA\|BQ740207 | 4120 | 592 | 83.1 | globlastp |
| 2385 | LNU171 | wheat\|gb164\|BE415592 | 4121 | 592 | 82.39 | glotblastn |
| 2386 | LNU173 | wheat\|gb164\|BE213263 | 4122 | 594 | 90.8 | globlastp |
| 2387 | LNU173 | wheat\|gb164\|BG607192 | 4123 | 594 | 90.2 | globlastp |
| 2388 | LNU173 | oat\|10v1\|Z48431 | 4124 | 594 | 80.3 | globlastp |
| 2389 | LNU175 | arabidopsis_lyrata\|09v1\|JGIAL025246 | 4125 | 595 | 92.5 | globlastp |
| 2390 | LNU175 | canola\|10v1\|CD820948 | 4126 | 595 | 85 | globlastp |
| 2391 | LNU175 | canola\|gb161\|CD820948 | 4126 | 595 | 85 | globlastp |
| 2392 | LNU175 | radish\|gb164\|EW731834 | 4126 | 595 | 85 | globlastp |
| 2393 | LNU176 | rice\|gb170\|OS07G23570 | 4127 | 596 | 85.7 | globlastp |
| 2394 | LNU176 | rice\|gb170\|OS07G44110 | 4128 | 596 | 81.6 | globlastp |
| 2395 | LNU177 | arabidopsis_lyrata\|09v1\|JGIAL006953 | 4129 | 597 | 95.2 | globlastp |
| 2396 | LNU177 | radish\|gb164\|EY932302 | 4130 | 597 | 81.3 | globlastp |
| 2397 | LNU177 | canola\|10v1\|BQ705039 | 4131 | 597 | 80.6 | globlastp |
| 2398 | LNU177 | canola\|10v1\|CN728969 | 4132 | 597 | 80.4 | globlastp |
| 2399 | LNU177 | canola\|gb161\|CN728969 | 4132 | 597 | 80.4 | globlastp |
| 2400 | LNU177 | b_oleracea\|gb161\|DY018716 | 4133 | 597 | 80.1 | globlastp |
| 2401 | LNU177 | b_rapa\|gb162\|EX061625 | 4134 | 597 | 80.1 | globlastp |
| 2402 | LNU177 | canola\|gb161\|BQ705039 | 4135 | 597 | 80.1 | globlastp |
| 2403 | LNU178 | arabidopsis_lyrata\|09v1\|JGIAL001921 | 4136 | 598 | 97.6 | globlastp |
| 2404 | LNU178 | canola\|10v1\|EE542748 | 4137 | 598 | 86.06 | glotblastn |
| 2405 | LNU178 | b_rapa\|gb162\|DN960788 | 4138 | 598 | 84.3 | globlastp |
| 2406 | LNU178 | canola\|gb161\|EL592266 | 4139 | 598 | 84.3 | globlastp |
| 2407 | LNU178 | radish\|gb164\|EV566211 | 4140 | 598 | 84.06 | glotblastn |
| 2408 | LNU178 | canola\|10v1\|EL592266 | 4141 | 598 | 83.8 | globlastp |
| 2409 | LNU178 | b_rapa\|gb162\|DN961047 | 4142 | 598 | 83.3 | globlastp |
| 2410 | LNU178 | radish\|gb164\|EX897481 | 4143 | 598 | 83.1 | globlastp |
| 2411 | LNU180 | arabidopsis_lyrata\|09v1\|JGIAL007244 | 4144 | 600 | 87.8 | globlastp |
| 2412 | LNU181 | arabidopsis_lyrata\|09v1\|JGIAL019086 | 4145 | 601 | 97.3 | globlastp |
| 2413 | LNU181 | arabidopsis\|gb165\|AT1G10490 | 4146 | 601 | 84.1 | globlastp |
| 2414 | LNU181 | arabidopsis_lyrata\|09v1\|JGIAL001043 | 4147 | 601 | 82.6 | globlastp |
| 2415 | LNU182 | arabidopsis_lyrata\|09v1\|JGIAL009295 | 4148 | 602 | 97.4 | globlastp |
| 2416 | LNU182 | canola\|10v1\|CD838490 | 4149 | 602 | 89 | globlastp |
| 2417 | LNU182 | canola\|gb161\|CD838490 | 4149 | 602 | 89 | globlastp |
| 2418 | LNU182 | thellungiella\|gb167\|BY804904 | 4150 | 602 | 87.7 | globlastp |
| 2419 | LNU182 | radish\|gb164\|EX905824 | 4151 | 602 | 87.1 | globlastp |
| 2420 | LNU182 | canola\|10v1\|ES915047 | 4152 | 602 | 87 | globlastp |
| 2421 | LNU182 | canola\|gb161\|ES915047 | 4152 | 602 | 87 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 2422 | LNU183 | arabidopsis_lyrata\|09v1\|JGIAL006103 | 4153 | 603 | 96.2 | globlastp |
| 2423 | LNU184 | arabidopsis_lyrata\|09v1\|JGIAL018440 | 4154 | 604 | 88.4 | globlastp |
| 2424 | LNU185 | arabidopsis_lyrata\|09v1\|JGIAL019672 | 4155 | 605 | 91.3 | globlastp |
| 2425 | LNU185 | thellungiella\|gb167\|BM985521 | 4156 | 605 | 80 | globlastp |
| 2426 | LNU186 | arabidopsis_lyrata\|09v1\|BQ834224 | 4157 | 606 | 98.9 | globlastp |
| 2427 | LNU186 | canola\|10v1\|EE466406 | 4158 | 606 | 96.6 | globlastp |
| 2428 | LNU186 | b_rapa\|gb162\|EX032398 | 4159 | 606 | 96.1 | globlastp |
| 2429 | LNU186 | canola\|gb161\|EE466406 | 4160 | 606 | 96.1 | globlastp |
| 2430 | LNU186 | canola\|10v1\|CN730049 | 4161 | 606 | 95 | globlastp |
| 2431 | LNU186 | canola\|gb161\|CN730049 | 4161 | 606 | 95 | globlastp |
| 2432 | LNU186 | radish\|gb164\|EW725004 | 4162 | 606 | 94.4 | globlastp |
| 2433 | LNU186 | radish\|gb164\|EX746993 | 4162 | 606 | 94.4 | globlastp |
| 2434 | LNU186 | radish\|gb164\|EX755385 | 4162 | 606 | 94.4 | globlastp |
| 2435 | LNU186 | radish\|gb164\|EX763493 | 4163 | 606 | 93.9 | globlastp |
| 2436 | LNU186 | b_rapa\|gb162\|L38047 | 4164 | 606 | 93.3 | globlastp |
| 2437 | LNU186 | radish\|gb164\|EY911865 | 4165 | 606 | 93.3 | globlastp |
| 2438 | LNU186 | cleome_gynandra\|10v1\|SRR015532S0005426 | 4166 | 606 | 88.3 | globlastp |
| 2439 | LNU186 | cleome_spinosa\|10v1\|GR931536 | 4167 | 606 | 88.3 | globlastp |
| 2440 | LNU186 | cotton\|gb164\|BQ403404 | 4168 | 606 | 81 | globlastp |
| 2441 | LNU186 | cacao\|gb167\|CU485964 | 4169 | 606 | 80.4 | globlastp |
| 2442 | LNU186 | cotton\|gb164\|AI728654 | 4170 | 606 | 80.4 | globlastp |
| 2443 | LNU187 | arabidopsis_lyrata\|09v1\|JGIAL019765 | 4171 | 607 | 92.4 | globlastp |
| 2444 | LNU188 | soybean\|gb168\|BE661293 | 4172 | 608 | 90.9 | globlastp |
| 2445 | LNU188 | bean\|gb167\|FE696342 | 4173 | 608 | 80.24 | glotblastn |
| 2446 | LNU190 | b_oleracea\|gb161\|AM388062 | 4174 | 610 | 96.7 | globlastp |
| 2447 | LNU190 | canola\|gb161\|EV105578 | 4175 | 610 | 94.8 | globlastp |
| 2448 | LNU190 | radish\|gb164\|EV544043 | 4176 | 610 | 90.2 | globlastp |
| 2449 | LNU192 | sorghum\|09v1\|SB09G029740 | 4177 | 612 | 92.9 | globlastp |
| 2450 | LNU192 | brachypodium\|gb169\|BE406170 | 4178 | 612 | 90 | globlastp |
| 2451 | LNU192 | brachypodium\|09v1\|GT839119 | 4179 | 612 | 85.9 | globlastp |
| 2452 | LNU192 | sorghum\|gb161.crp\|AW747561 | 4180 | 612 | 82.5 | globlastp |
| 2453 | LNU200 | potato\|10v1\|BQ513965 | 4181 | 615 | 95.9 | globlastp |
| 2454 | LNU200 | potato\|gb157.2\|BQ513965 | 4182 | 615 | 95.3 | globlastp |
| 2455 | LNU200 | solanum_phureja\|09v1\|SPHBG791292 | 4183 | 615 | 93.8 | globlastp |
| 2456 | LNU200 | eggplant\|10v1\|FS057436 | 4184 | 615 | 92.1 | globlastp |
| 2457 | LNU200 | tobacco\|gb162\|DW002634 | 4185 | 615 | 87.7 | globlastp |
| 2458 | LNU206 | arabidopsis_lyrata\|09v1\|JGIAL014285 | 4186 | 617 | 93.3 | globlastp |
| 2459 | LNU207 | arabidopsis_lyrata\|09v1\|JGIAL007246 | 4187 | 618 | 94.9 | globlastp |
| 2460 | LNU207 | canola\|10v1\|H07749 | 4188 | 618 | 84.8 | globlastp |
| 2461 | LNU207 | canola\|gb161\|H07749 | 4188 | 618 | 84.8 | globlastp |
| 2462 | LNU210 | arabidopsis_lyrata\|09v1\|JGIAL019410 | 4189 | 619 | 94.1 | globlastp |
| 2463 | LNU210 | canola\|10v1\|EG019929 | 4190 | 619 | 85.86 | glotblastn |
| 2464 | LNU210 | canola\|gb161\|EG019929 | 4191 | 619 | 85.6 | globlastp |
| 2465 | LNU210 | radish\|gb164\|EW715949 | 4192 | 619 | 81.4 | globlastp |
| 2466 | LNU211 | arabidopsis_lyrata\|09v1\|JGIAL020302 | 4193 | 620 | 97.5 | globlastp |
| 2467 | LNU211 | thellungiella\|gb167\|BY811489 | 4194 | 620 | 96.7 | globlastp |
| 2468 | LNU211 | canola\|10v1\|EE452044 | 4195 | 620 | 90.2 | globlastp |
| 2469 | LNU211 | canola\|10v1\|EE465088 | 4196 | 620 | 90.2 | globlastp |
| 2470 | LNU211 | canola\|gb161\|EE465088 | 4196 | 620 | 90.2 | globlastp |
| 2471 | LNU211 | radish\|gb164\|EX746074 | 4195 | 620 | 90.2 | globlastp |
| 2472 | LNU211 | b_rapa\|gb162\|CV545795 | 4197 | 620 | 89.4 | globlastp |
| 2473 | LNU211 | canola\|10v1\|ES923006 | 4197 | 620 | 89.4 | globlastp |
| 2474 | LNU211 | canola\|gb161\|EE452044 | 4197 | 620 | 89.4 | globlastp |
| 2475 | LNU211 | canola\|10v1\|EE429968 | 4198 | 620 | 88.5 | globlastp |
| 2476 | LNU211 | canola\|gb161\|EE429968 | 4198 | 620 | 88.5 | globlastp |
| 2477 | LNU211 | b_rapa\|gb162\|BG544555 | 4199 | 620 | 86.89 | glotblastn |
| 2478 | LNU211 | b_rapa\|gb162\|CX269583 | 4200 | 620 | 86.89 | glotblastn |
| 2479 | LNU214 | canola\|10v1\|DV643275 | 4201 | 623 | 83 | globlastp |
| 2480 | LNU214 | canola\|gb161\|DV643275 | 4201 | 623 | 83 | globlastp |
| 2481 | LNU214 | b_oleracea\|gb161\|AM057785 | 4202 | 623 | 80.7 | globlastp |
| 2482 | LNU215 | arabidopsis_lyrata\|09v1\|JGIAL000823 | 4203 | 624 | 93.9 | globlastp |
| 2483 | LNU215 | canola\|10v1\|CD837114 | 4204 | 624 | 81.3 | globlastp |
| 2484 | LNU215 | radish\|gb164\|EX902620 | 4205 | 624 | 80.1 | globlastp |
| 2485 | LNU216 | rice\|gb170\|OS12G05440 | 4206 | 625 | 85.6 | globlastp |
| 2486 | LNU216 | maize\|gb170\|LLCF001713 | 4207 | 625 | 81.4 | globlastp |
| 2487 | LNU216 | sorghum\|09v1\|SB05G003100 | 4208 | 625 | 80.27 | glotblastn |
| 2488 | LNU216 | sorghum\|gb161.crp\|BG048909 | 4208 | 625 | 80.27 | glotblastn |
| 2489 | LNU216 | sorghum\|09v1\|SB08G003110 | 4209 | 625 | 80.1 | globlastp |
| 2490 | LNU216 | sorghum\|gb161.crp\|BE918845 | 4209 | 625 | 80.1 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 2491 | LNU216 | maize\|gb170\|CA404041 | 4210 | 625 | 80 | globlastp |
| 2492 | LNU218 | arabidopsis_lyrata\|09v1\|JGIAL027135 | 4211 | 627 | 95.8 | globlastp |
| 2493 | LNU218 | canola\|gb161\|CD836926 | 4212 | 627 | 91.7 | globlastp |
| 2494 | LNU218 | radish\|gb164\|EW725001 | 4213 | 627 | 89.6 | globlastp |
| 2495 | LNU218 | castorbean\|09v1\|XM002514040 | 4214 | 627 | 81.35 | glotblastn |
| 2496 | LNU218 | castorbean\|gb160\|MDL29912M005300 | 4214 | 627 | 81.35 | glotblastn |
| 2497 | LNU218 | grape\|gb160\|BQ792882 | 4215 | 627 | 80.68 | glotblastn |
| 2498 | LNU218 | citrus\|gb166\|CN191381 | 4216 | 627 | 80.58 | glotblastn |
| 2499 | LNU218 | cassava\|09v1\|DB926789 | 4217 | 627 | 80.57 | glotblastn |
| 2500 | LNU218 | poplar\|10v1\|CV236445 | 4218 | 627 | 80.3 | globlastp |
| 2501 | LNU218 | poplar\|gb170\|CV236445 | 4218 | 627 | 80.3 | globlastp |
| 2502 | LNU218 | cucumber\|09v1\|GD175338 | 4219 | 627 | 80.2 | globlastp |
| 2503 | LNU219 | arabidopsis_lyrata\|09v1\|BQ834518 | 4220 | 628 | 99 | globlastp |
| 2504 | LNU219 | aquilegia\|10v1\|DR932989 | 4221 | 628 | 95.9 | globlastp |
| 2505 | LNU219 | canola\|10v1\|CD815027 | 4222 | 628 | 94.6 | globlastp |
| 2506 | LNU219 | canola\|gb161\|CD815027 | 4222 | 628 | 94.6 | globlastp |
| 2507 | LNU219 | radish\|gb164\|EW714771 | 4223 | 628 | 94.4 | globlastp |
| 2508 | LNU219 | b_rapa\|gb162\|EX020921 | 4224 | 628 | 94.1 | globlastp |
| 2509 | LNU219 | canola\|10v1\|CD836405 | 4225 | 628 | 93.9 | globlastp |
| 2510 | LNU219 | canola\|gb161\|CD836405 | 4225 | 628 | 93.9 | globlastp |
| 2511 | LNU219 | radish\|gb164\|EV539520 | 4226 | 628 | 92.6 | globlastp |
| 2512 | LNU219 | cleome_gynandra\|10v1\|SRR015532S0004520 | 4227 | 628 | 88.3 | globlastp |
| 2513 | LNU219 | cleome_spinosa\|10v1\|GR935537 | 4228 | 628 | 85.9 | globlastp |
| 2514 | LNU219 | b_rapa\|gb162\|BG544276 | 4229 | 628 | 84.7 | globlastp |
| 2515 | LNU219 | b_oleracea\|gb161\|AM385469 | 4230 | 628 | 84.4 | globlastp |
| 2516 | LNU219 | canola\|gb161\|CD818834 | 4231 | 628 | 84.4 | globlastp |
| 2517 | LNU219 | canola\|gb161\|T18344 | 4230 | 628 | 84.4 | globlastp |
| 2518 | LNU219 | canola\|10v1\|CD818834 | 4231 | 628 | 84.4 | globlastp |
| 2519 | LNU219 | radish\|gb164\|EV527315 | 4232 | 628 | 83.9 | globlastp |
| 2520 | LNU219 | arabidopsis_lyrata\|09v1\|JGIAL028336 | 4233 | 628 | 83.6 | globlastp |
| 2521 | LNU219 | arabidopsis\|gb165\|AT5G45280 | 4234 | 628 | 82.6 | globlastp |
| 2522 | LNU222 | brachypodium\|09v1\|DV476280 | 4235 | 630 | 91.4 | globlastp |
| 2522 | LNU222_H6 | brachypodium\|09v1\|DV476280 | 4235 | 680 | 91.4 | globlastp |
| 2523 | LNU222 | brachypodium\|gb169\|BE400657 | 4235 | 630 | 91.4 | globlastp |
| 2523 | LNU222_H6 | brachypodium\|gb169\|BE400657 | 4235 | 680 | 91.4 | globlastp |
| 2524 | LNU222 | rice\|gb170\|OS06G47890 | 4236 | 630 | 89.7 | globlastp |
| 2524 | LNU222_H6 | rice\|gb170\|OS06G47890 | 4236 | 680 | 94 | globlastp |
| 2525 | LNU222 | switchgrass\|gb167\|DN143448 | 4237 | 630 | 89.2 | globlastp |
| 2525 | LNU222_H6 | switchgrass\|gb167\|DN143448 | 4237 | 680 | 95.7 | globlastp |
| 2526 | LNU222 | sorghum\|09v1\|SB10G028340 | 680 | 630 | 88 | globlastp |
| 2527 | LNU222 | maize\|gb170\|AI734407 | 4238 | 630 | 87.3 | globlastp |
| 2527 | LNU222_H6 | maize\|gb170\|AI734407 | 4238 | 680 | 90.3 | globlastp |
| 2528 | LNU222 | maize\|gb170\|AI820142 | 4239 | 630 | 83.9 | glotblastn |
| 2528 | LNU222_H6 | maize\|gb170\|AI820142 | 4239 | 680 | 86.53 | glotblastn |
| 2529 | LNU222 | rice\|gb170\|OS02G05700 | 4240 | 630 | 80.16 | glotblastn |
| 2529 | LNU222_H6 | rice\|gb170\|OS02G05700 | 4240 | 680 | 80.2 | globlastp |
| 2530 | LNU222 | brachypodium\|09v1\|GT771721 | 4241 | 630 | 80.1 | glotblastn |
| 2530 | LNU222_H6 | brachypodium\|09v1\|GT771721 | 4241 | 680 | 80.8 | globlastp |
| 2531 | LNU222 | brachypodium\|gb169\|BE406203 | 4241 | 630 | 80.1 | glotblastn |
| 2531 | LNU222_H6 | brachypodium\|gb169\|BE406203 | 4241 | 680 | 80.8 | globlastp |
| 2532 | LNU223 | pseudoroegneria\|gb167\|FF350748 | 4242 | 631 | 87.3 | globlastp |
| 2533 | LNU223 | wheat\|gb164\|BF474058 | 4242 | 631 | 87.3 | globlastp |
| 2534 | LNU223 | maize\|gb170\|AI461537 | 4243 | 631 | 87.2 | globlastp |
| 2535 | LNU223 | oat\|10v1\|CN821280 | 4244 | 631 | 86.9 | globlastp |
| 2536 | LNU223 | sorghum\|09v1\|SB03G026180 | 4245 | 631 | 86.7 | globlastp |
| 2537 | LNU223 | sorghum\|gb161.crp\|Y14675 | 4245 | 631 | 86.7 | globlastp |
| 2538 | LNU223 | brachypodium\|09v1\|DV475278 | 4246 | 631 | 86.6 | globlastp |
| 2539 | LNU223 | brachypodium\|gb169\|BF474058 | 4246 | 631 | 86.6 | globlastp |
| 2540 | LNU223 | switchgrass\|gb167\|FL697289 | 4247 | 631 | 86.6 | globlastp |
| 2541 | LNU223 | barley\|gb157SOLEXA\|AL500275 | 4248 | 631 | 86.2 | globlastp |
| 2542 | LNU223 | leymus\|gb166\|EG378630 | 4249 | 631 | 86 | globlastp |
| 2543 | LNU223 | maize\|gb170\|AI740070 | 4250 | 631 | 85.6 | globlastp |
| 2544 | LNU224 | pseudoroegneria\|gb167\|FF346115 | 4251 | 632 | 97.1 | globlastp |
| 2545 | LNU224 | leymus\|gb166\|EG379498 | 4252 | 632 | 96.4 | globlastp |
| 2546 | LNU224 | wheat\|gb164\|BQ789174 | 4253 | 632 | 96.4 | globlastp |
| 2547 | LNU224 | wheat\|gb164\|BE401267 | 4254 | 632 | 95 | globlastp |
| 2548 | LNU224 | oat\|10v1\|GR322386 | 4255 | 632 | 88.7 | globlastp |
| 2549 | LNU228 | wheat\|gb164\|BE406956 | 4256 | 634 | 89.89 | glotblastn |
| 2550 | LNU229 | potato\|10v1\|BE922224 | 4257 | 635 | 94.6 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Hom. Polyp. SEQ ID NO: | Hom. to SEQ ID NO: | % global identity | Algor. |
|---|---|---|---|---|---|---|
| 2551 | LNU229 | solanum_phureja|09v1|SPHAI484048 | 4258 | 635 | 94.4 | globlastp |
| 2552 | LNU230 | brachypodium|09v1|TMPLOS12G40300T1 | 636 | 636 | 100 | globlastp |
| 2553 | LNU234 | arabidopsis_lyrata|09v1|JGIAL002366 | 4259 | 638 | 94.4 | globlastp |
| 2554 | LNU239 | oat|10v1|GO581462 | 4260 | 641 | 94.8 | globlastp |
| 2555 | LNU239 | oat|10v1|GO587061 | 4261 | 641 | 94.8 | globlastp |
| 2556 | LNU239 | oat|10v1|GO587140 | 4260 | 641 | 94.8 | globlastp |
| 2557 | LNU239 | oat|10v1|GR361871 | 4260 | 641 | 94.8 | globlastp |
| 2558 | LNU239 | sorghum|09v1|SB10G001510 | 4262 | 641 | 94.8 | globlastp |
| 2559 | LNU239 | sorghum|gb161.crp|AW330931 | 4262 | 641 | 94.8 | globlastp |
| 2560 | LNU239 | switchgrass|gb167|FE639067 | 4263 | 641 | 94.8 | globlastp |
| 2561 | LNU239 | millet|09v1|EVO454PM053563 | 4264 | 641 | 93.1 | glotblastn |
| 2562 | LNU239 | oat|10v1|GR361767 | 4265 | 641 | 93.1 | glotblastn |
| 2563 | LNU239 | sugarcane|10v1|BQ533648 | 4266 | 641 | 93.1 | globlastp |
| 2564 | LNU239 | sugarcane|10v1|CA103102 | 4266 | 641 | 93.1 | globlastp |
| 2565 | LNU239 | sugarcane|gb157.3|BQ533648 | 4266 | 641 | 93.1 | globlastp |
| 2566 | LNU239 | oat|10v1|GO581699 | 4267 | 641 | 91.4 | globlastp |
| 2567 | LNU239 | sorghum|09v1|SB10G002810 | 4268 | 641 | 91.4 | globlastp |
| 2568 | LNU239 | maize|gb170|AW330931 | 4269 | 641 | 91.4 | globlastp |
| 2569 | LNU239 | switchgrass|gb167|DN150836 | 4270 | 641 | 89.7 | globlastp |
| 2570 | LNU239 | wheat|gb164|BE413591 | 4271 | 641 | 89.66 | glotblastn |
| 2571 | LNU239 | wheat|gb164|BE443361 | 4272 | 641 | 89.66 | glotblastn |
| 2572 | LNU239 | wheat|gb164|CA613749 | 4273 | 641 | 89.66 | glotblastn |
| 2573 | LNU239 | rye|gb164|BE495091 | 4274 | 641 | 87.93 | glotblastn |
| 2574 | LNU239 | barley|gb157.3|AL501772 | 4275 | 641 | 87.9 | globlastp |
| 2575 | LNU239 | barley|gb157SOLEXA|AL501772 | 4275 | 641 | 87.9 | globlastp |
| 2576 | LNU239 | brachypodium|09v1|DV469471 | 4276 | 641 | 87.9 | globlastp |
| 2577 | LNU239 | brachypodium|gb169|BE413591 | 4276 | 641 | 87.9 | globlastp |
| 2578 | LNU239 | pseudoroegneria|gb167|FF348954 | 4277 | 641 | 87.9 | globlastp |
| 2579 | LNU239 | leymus|gb166|CD808544 | 4278 | 641 | 86.2 | globlastp |
| 2580 | LNU239 | maize|gb170|CD980142 | 4279 | 641 | 84.7 | globlastp |
| 2581 | LNU239 | banana|gb167|FL649074 | 4280 | 641 | 84.48 | glotblastn |
| 2582 | LNU239 | ginger|gb164|DY381315 | 4281 | 641 | 82.76 | glotblastn |
| 2583 | LNU239 | rice|gb170|OS06G03514 | 4282 | 641 | 81 | globlastp |
| 2584 | LNU242 | b_rapa|gb162|EX031422 | 4283 | 644 | 92.45 | glotblastn |
| 2585 | LNU242 | canola|10v1|DY002989 | 4284 | 644 | 88.68 | glotblastn |
| 2586 | LNU242 | radish|gb164|EV566917 | 4285 | 644 | 84.51 | glotblastn |
| 2587 | LNU243 | wheat|gb164|BE414904 | 4286 | 645 | 92.86 | glotblastn |
| 2588 | LNU245 | potato|gb157.2|CK262157 | 4287 | 647 | 93.7 | globlastp |
| 2589 | LNU245 | eggplant|10v1|FS013675 | 4288 | 647 | 89 | globlastp |
| 2590 | LNU245 | potato|gb157.2|BG590426 | 4289 | 647 | 88.3 | globlastp |
| 2591 | LNU245 | solanum_phureja|09v1|SPHAI486625 | 4290 | 647 | 88 | globlastp |
| 2592 | LNU245 | potato|10v1|BG590608 | 4291 | 647 | 81.3 | globlastp |
| 2593 | LNU246 | solanum_phureja|09v1|SPHAI896232 | 4292 | 648 | 97.1 | globlastp |
| 2594 | LNU246 | potato|10v1|BG599206 | 4293 | 648 | 96.8 | globlastp |
| 2595 | LNU246 | potato|gb157.2|BG599206 | 4293 | 648 | 96.8 | globlastp |
| 2596 | LNU247 | arabidopsis_lyrata|09v1|JGIAL021212 | 4294 | 649 | 93.3 | globlastp |
| 2597 | LNU247 | canola|10v1|CN827557 | 4295 | 649 | 87.6 | globlastp |
| 2598 | LNU247 | canola|gb161|CD826643 | 4296 | 649 | 86.83 | glotblastn |
| 2599 | LNU249 | arabidopsis_lyrata|09v1|JGIAL020153 | 4297 | 650 | 96.6 | globlastp |
| 2600 | LNU251 | arabidopsis_lyrata|09v1|JGIAL023392 | 4298 | 652 | 97 | globlastp |
| 2601 | LNU253 | bean|gb167|CB540282 | 4299 | 653 | 92.12 | glotblastn |
| 2602 | LNU253 | cowpea|gb166|FF387997 | 4300 | 653 | 89.16 | glotblastn |
| 2603 | LNU253 | peanut|gb167|EG029988 | 4301 | 653 | 81.37 | glotblastn |
| 2604 | LNU253 | peanut|gb171|EG029988 | 4301 | 653 | 81.37 | glotblastn |
| 2605 | LNU253 | soybean|gb168|BE657859 | 4302 | 653 | 81.3 | globlastp |
| 2606 | LNU254 | arabidopsis_lyrata|09v1|JGIAL004106 | 4303 | 654 | 99.8 | globlastp |
| 2607 | LNU254 | radish|gb164|EV526765 | 4304 | 654 | 97.3 | globlastp |
| 2608 | LNU254 | canola|10v1|CD833572 | 4305 | 654 | 95.8 | globlastp |
| 2609 | LNU254 | radish|gb164|EV526356 | 4306 | 654 | 95.4 | globlastp |
| 2610 | LNU254 | canola|gb161|CD833572 | 4307 | 654 | 93 | globlastp |
| 2611 | LNU254 | cotton|gb164|CO095176 | 4308 | 654 | 90.94 | glotblastn |
| 2612 | LNU254 | cassava|09v1|JGICASSAVA12947VALIDM1 | 4309 | 654 | 90.4 | globlastp |
| 2613 | LNU254 | cucumber|09v1|AM720434 | 4310 | 654 | 90.4 | globlastp |
| 2614 | LNU254 | tomato|09v1|BQ119293 | 4311 | 654 | 90.3 | globlastp |
| 2615 | LNU254 | poplar|10v1|BI131005 | 4312 | 654 | 90.2 | globlastp |
| 2616 | LNU254 | poplar|gb170|BI131005 | 4312 | 654 | 90.2 | globlastp |
| 2617 | LNU254 | solanum_phureja|09v1|SPHBQ119293 | 4313 | 654 | 89.9 | globlastp |
| 2618 | LNU254 | castorbean|09v1|XM002510240 | 4314 | 654 | 89.8 | globlastp |
| 2619 | LNU254 | castorbean|gb160|MDL30170M013940 | 4314 | 654 | 89.8 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 2620 | LNU254 | soybean\|gb168\|AW693383 | 4315 | 654 | 89.8 | globlastp |
| 2621 | LNU254 | chestnut\|gb170\|SRR006295S0002298 | 4316 | 654 | 89.5 | globlastp |
| 2622 | LNU254 | cassava\|09v1\|JGICASSAVA24790VALIDM1 | 4317 | 654 | 89.1 | globlastp |
| 2623 | LNU254 | soybean\|gb168\|BE320506 | 4318 | 654 | 89 | globlastp |
| 2624 | LNU254 | medicago\|09v1\|AL365842 | 4319 | 654 | 88.9 | globlastp |
| 2625 | LNU254 | potato\|10v1\|BQ119293 | 4320 | 654 | 87.5 | globlastp |
| 2626 | LNU254 | potato\|gb157.2\|BQ119293 | 4320 | 654 | 87.5 | globlastp |
| 2627 | LNU254 | aquilegia\|10v1\|DR914712 | 4321 | 654 | 86.4 | globlastp |
| 2628 | LNU254 | monkeyflower\|10v1\|GO954748 | 4322 | 654 | 85.5 | globlastp |
| 2629 | LNU255 | arabidopsis_lyrata\|09v1\|JGIAL015618 | 4323 | 655 | 87.3 | globlastp |
| 2630 | LNU256 | arabidopsis\|gb165\|AT2G43910 | 4324 | 656 | 83.3 | globlastp |
| 2631 | LNU256 | canola\|10v1\|EG020127 | 4325 | 656 | 81.9 | globlastp |
| 2632 | LNU256 | b_rapa\|gb162\|CA992319 | 4326 | 656 | 81.5 | globlastp |
| 2633 | LNU256 | b_rapa\|gb162\|L46502 | 4327 | 656 | 80.6 | globlastp |
| 2634 | LNU256 | b_oleracea\|gb161\|AF387791 | 4328 | 656 | 80.2 | globlastp |
| 2635 | LNU256 | canola\|10v1\|CD812772 | 4329 | 656 | 80.2 | globlastp |
| 2636 | LNU256 | canola\|gb161\|CD812772 | 4329 | 656 | 80.2 | globlastp |
| 2637 | LNU256 | radish\|gb164\|EV524444 | 4330 | 656 | 80.2 | globlastp |
| 2638 | LNU257 | arabidopsis_lyrata\|09v1\|JGIAL009641 | 4331 | 657 | 98.2 | globlastp |
| 2639 | LNU257 | radish\|gb164\|EV543963 | 4332 | 657 | 94.3 | globlastp |
| 2640 | LNU257 | thellungiella\|gb167\|BY830471 | 4333 | 657 | 94 | globlastp |
| 2641 | LNU258 | arabidopsis_lyrata\|09v1\|JGIAL024223 | 4334 | 658 | 90.65 | glotblastn |
| 2642 | LNU260 | thellungiella\|gb167\|DN774718 | 4335 | 659 | 84.9 | globlastp |
| 2643 | LNU260 | b_juncea\|gb164\|EVGN00742808281526 | 4336 | 659 | 82.8 | globlastp |
| 2644 | LNU260 | radish\|gb164\|EV536406 | 4337 | 659 | 80.8 | globlastp |
| 2645 | LNU260 | b_oleracea\|gb161\|DY015251 | 4338 | 659 | 80.51 | glotblastn |
| 2646 | LNU260 | radish\|gb164\|EV566818 | 4339 | 659 | 80.43 | glotblastn |
| 2647 | LNU260 | b_rapa\|gb162\|EX108082 | 4340 | 659 | 80.3 | globlastp |
| 2648 | LNU260 | b_rapa\|gb162\|ES932807 | 4341 | 659 | 80.08 | glotblastn |
| 2649 | LNU260 | canola\|10v1\|CX194829 | 4341 | 659 | 80.08 | glotblastn |
| 2650 | LNU260 | canola\|gb161\|CX194829 | 4341 | 659 | 80.08 | glotblastn |
| 2651 | LNU260 | radish\|gb164\|EV538732 | 4342 | 659 | 80 | globlastp |
| 2652 | LNU261 | arabidopsis_lyrata\|09v1\|JGIAL029133 | 4343 | 660 | 95.2 | globlastp |
| 2653 | LNU261 | radish\|gb164\|EV565501 | 4344 | 660 | 82.9 | globlastp |
| 2654 | LNU262 | arabidopsis_lyrata\|09v1\|JGIAL029381 | 4345 | 661 | 95.2 | globlastp |
| 2655 | LNU263 | wheat\|gb164\|BE403303 | 4346 | 662 | 92.6 | globlastp |
| 2656 | LNU263 | wheat\|gb164\|BE405309 | 4347 | 662 | 92.6 | globlastp |
| 2657 | LNU263 | barley\|gb157SOLEXA\|BE412891 | 4348 | 662 | 91.2 | globlastp |
| 2658 | LNU263 | leymus\|gb166\|EG394979 | 4349 | 662 | 84.5 | glotblastn |
| 2659 | LNU263 | brachypodium\|09v1\|DV474340 | 4350 | 662 | 83.9 | globlastp |
| 2660 | LNU263 | brachypodium\|gb169\|BE445700 | 4350 | 662 | 83.9 | globlastp |
| 2661 | LNU263 | brachypodium\|09v1\|DV473838 | 4351 | 662 | 82.9 | globlastp |
| 2662 | LNU263 | brachypodium\|gb169\|DV473838 | 4351 | 662 | 82.9 | globlastp |
| 2663 | LNU263 | sorghum\|09v1\|SB02G040500 | 4352 | 662 | 80.4 | globlastp |
| 2664 | LNU263 | sorghum\|gb161.crp\|BM382553 | 4352 | 662 | 80.4 | globlastp |
| 2665 | LNU263 | sorghum\|09v1\|SB02G040510 | 4353 | 662 | 80.2 | globlastp |
| 2666 | LNU263 | sorghum\|gb161.crp\|BM661046 | 4353 | 662 | 80.2 | globlastp |
| 2667 | LNU265 | sorghum\|09v1\|SB09G000890 | 4354 | 663 | 92 | globlastp |
| 2668 | LNU265 | sorghum\|gb161.crp\|BE597117 | 4355 | 663 | 86.3 | globlastp |
| 2669 | LNU266 | sorghum\|09v1\|SB03G002900 | 4356 | 664 | 93.6 | globlastp |
| 2670 | LNU266 | sorghum\|gb161.crp\|AI987574 | 4357 | 664 | 87.1 | globlastp |
| 2671 | LNU267 | maize\|gb170\|LLDV514913 | 4358 | 665 | 85.7 | globlastp |
| 2672 | LNU267 | maize\|gb170\|AI637120 | 4359 | 665 | 84 | globlastp |
| 2673 | LNU267 | sugarcane\|10v1\|BQ535909 | 4360 | 665 | 82.6 | globlastp |
| 2674 | LNU267 | sorghum\|09v1\|SB04G022740 | 4361 | 665 | 82.2 | globlastp |
| 2675 | LNU267 | sorghum\|gb161.crp\|AW283751 | 4361 | 665 | 82.2 | globlastp |
| 2676 | LNU267 | switchgrass\|gb167\|FE640888 | 4362 | 665 | 82 | globlastp |
| 2677 | LNU267 | sugarcane\|gb157.3\|BQ535909 | 4363 | 665 | 81.1 | globlastp |
| 2678 | LNU267 | switchgrass\|gb167\|FE621258 | 4364 | 665 | 81.1 | globlastp |
| 2679 | LNU268 | sorghum\|09v1\|SB03G002890 | 4365 | 666 | 94.8 | globlastp |
| 2680 | LNU268 | sorghum\|gb161.crp\|BF656912 | 4365 | 666 | 94.8 | globlastp |
| 2681 | LNU268 | sugarcane\|gb157.3\|CA082317 | 4366 | 666 | 93.8 | globlastp |
| 2682 | LNU268 | maize\|gb170\|LLEE026298 | 4367 | 666 | 92.2 | globlastp |
| 2683 | LNU268 | switchgrass\|gb167\|DN141482 | 4368 | 666 | 91.7 | globlastp |
| 2684 | LNU268 | sugarcane\|10v1\|CA219295 | 4369 | 666 | 86.53 | glotblastn |
| 2685 | LNU268 | barley\|gb157SOLEXA\|BE060428 | 4370 | 666 | 85.5 | globlastp |
| 2686 | LNU268 | brachypodium\|09v1\|GT836297 | 4371 | 666 | 84.5 | globlastp |
| 2687 | LNU271 | brachypodium\|09v1\|GT783626 | 4372 | 667 | 90.2 | globlastp |
| 2688 | LNU271 | brachypodium\|gb169\|BF483222 | 4372 | 667 | 90.2 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 2689 | LNU271 | wheat\|gb164\|BF483222 | 4373 | 667 | 90.2 | globlastp |
| 2690 | LNU271 | wheat\|gb164\|CA700889 | 4373 | 667 | 90.2 | globlastp |
| 2691 | LNU271 | sorghum\|09v1\|SB01G043280 | 4374 | 667 | 89 | globlastp |
| 2692 | LNU271 | sorghum\|gb161.crp\|CD210322 | 4374 | 667 | 89 | globlastp |
| 2693 | LNU271 | oat\|10v1\|GO592793 | 4375 | 667 | 87.9 | globlastp |
| 2694 | LNU271 | switchgrass\|gb167\|DN144438 | 4376 | 667 | 87.3 | globlastp |
| 2695 | LNU271 | maize\|gb170\|CD944785 | 4377 | 667 | 86.1 | globlastp |
| 2696 | LNU271 | maize\|gb170\|H35893 | 4378 | 667 | 85 | globlastp |
| 2697 | LNU271 | millet\|09v1\|EVO454PM060798 | 4379 | 667 | 84.1 | globlastp |
| 2698 | LNU271 | fescue\|gb161\|DT710736 | 4380 | 667 | 83.8 | globlastp |
| 2699 | LNU274 | rice\|gb170\|OS05G01750 | 4381 | 668 | 93 | globlastp |
| 2700 | LNU275 | brachypodium\|09v1\|SRR031797S0128470 | 4382 | 669 | 80.33 | glotblastn |
| 2701 | LNU275 | sorghum\|09v1\|SB02G030360 | 4383 | 669 | 80.3 | globlastp |
| 2702 | LNU275 | maize\|gb170\|DN213402 | 4384 | 669 | 80.1 | globlastp |
| 2703 | LNU278 | switchgrass\|gb167\|FL852997 | 4385 | 672 | 93 | globlastp |
| 2704 | LNU278 | millet\|09v1\|EVO454PM020322 | 4386 | 672 | 90.6 | globlastp |
| 2705 | LNU278 | brachypodium\|09v1\|GT841667 | 4387 | 672 | 88.1 | globlastp |
| 2706 | LNU278 | brachypodium\|gb169\|BG343026 | 4387 | 672 | 88.1 | globlastp |
| 2707 | LNU278 | leymus\|gb166\|EG395159 | 4388 | 672 | 87.9 | globlastp |
| 2708 | LNU278 | oat\|10v1\|GR322586 | 4389 | 672 | 87.4 | globlastp |
| 2709 | LNU278 | maize\|gb170\|DR964461 | 4390 | 672 | 86.4 | globlastp |
| 2710 | LNU278 | maize\|gb170\|DN217333 | 4391 | 672 | 83.1 | globlastp |
| 2711 | LNU278 | rice\|gb170\|OS05G03530 | 4392 | 672 | 83.05 | glotblastn |
| 2712 | LNU278 | sugarcane\|gb157.3\|CA139449 | 4393 | 672 | 81.5 | globlastp |
| 2713 | LNU279 | maize\|gb170\|AW126569 | 4394 | 673 | 92 | globlastp |
| 2714 | LNU279 | maize\|gb170\|DR823071 | 4395 | 673 | 91.7 | globlastp |
| 2715 | LNU279 | maize\|gb170\|CF014369 | 4396 | 673 | 87.1 | globlastp |
| 2716 | LNU279 | maize\|gb170\|CD961214 | 4397 | 673 | 84.8 | globlastp |
| 2717 | LNU279 | sorghum\|09v1\|SB02G037590 | 4398 | 673 | 84.7 | globlastp |
| 2718 | LNU280 | switchgrass\|gb167\|FL809443 | 4399 | 674 | 90.5 | globlastp |
| 2719 | LNU280 | maize\|gb170\|BM498380 | 4400 | 674 | 88.5 | globlastp |
| 2720 | LNU280 | rice\|gb170\|OS11G23790 | 4401 | 674 | 83.8 | globlastp |
| 2721 | LNU280 | brachypodium\|09v1\|DV474046 | 4402 | 674 | 83 | globlastp |
| 2722 | LNU280 | brachypodium\|gb169\|BF482671 | 4403 | 674 | 82.49 | glotblastn |
| 2723 | LNU280 | wheat\|gb164\|BF293467 | 4404 | 674 | 82.28 | glotblastn |
| 2724 | LNU282 | soybean\|gb168\|BQ630236 | 4405 | 675 | 96.9 | globlastp |
| 2725 | LNU282 | medicago\|09v1\|AW686001 | 4406 | 675 | 86.4 | globlastp |
| 2726 | LNU282 | lotus\|09v1\|AI967570 | 4407 | 675 | 81.5 | globlastp |
| 2727 | LNU284 | soybean\|gb168\|CF807230 | 4408 | 676 | 93 | globlastp |
| 2728 | LNU284 | soybean\|gb168\|BQ080894 | 4409 | 676 | 92.8 | globlastp |
| 2729 | LNU284 | soybean\|gb168\|AW351157 | 4410 | 676 | 82.7 | globlastp |
| 2730 | LNU288 | solanum_phureja\|09v1\|SPHBG134658 | 4411 | 678 | 97.7 | globlastp |
| 2731 | LNU288 | potato\|10v1\|BE920963 | 4412 | 678 | 96.7 | globlastp |
| 2732 | LNU288 | potato\|gb157.2\|BE920963 | 4412 | 678 | 96.7 | globlastp |
| 2733 | LNU288 | tobacco\|gb162\|AB014483 | 4413 | 678 | 85.8 | globlastp |
| 2734 | LNU289 | solanum_phureja\|09v1\|SPHBG123295 | 4414 | 679 | 97.2 | globlastp |
| 2735 | LNU289 | potato\|gb157.2\|BG592935 | 4415 | 679 | 96.5 | globlastp |
| 2736 | LNU289 | potato\|10v1\|BG592935 | 4416 | 679 | 95.1 | globlastp |
| 2737 | LNU289 | eggplant\|10v1\|FS024715 | 4417 | 679 | 93.6 | globlastp |
| 2738 | LNU289 | pepper\|gb171\|CK901930 | 4418 | 679 | 81.27 | glotblastn |
| 2739 | LNU222_H6 | sorghum\|09v1\|SB04G003660 | 4419 | 680 | 81.3 | globlastp |
| 2740 | LNU222_H6 | maize\|gb170\|AW928070 | 4420 | 680 | 81 | globlastp |
| 2741 | LNU29 | potato\|10v1\|BM405532 | 3260 | 681 | 89.42 | glotblastn |
| 2742 | LNU35 | rice\|gb170\|OS07G13590 | 4421 | 682 | 89.97 | glotblastn |
| 2743 | LNU35 | sorghum\|09v1\|SB02G007060 | 4422 | 682 | 89.62 | glotblastn |
| 2744 | LNU35 | sorghum\|gb161.crp\|AW067593 | 4422 | 682 | 89.62 | glotblastn |
| 2745 | LNU35 | maize\|gb170\|AI601000 | 4423 | 682 | 89.27 | glotblastn |
| 2746 | LNU35 | barley\|gb157.3\|AV833599 | 4424 | 682 | 89.1 | globlastp |
| 2747 | LNU35 | barley\|gb157SOLEXA\|AV833599 | 4425 | 682 | 89.1 | globlastp |
| 2748 | LNU35 | brachypodium\|gb169\|BE442655 | 4426 | 682 | 86.2 | globlastp |
| 2749 | LNU55 | soybean\|gb168\|SB2GWP093054 | 4427 | 684 | 88.1 | globlastp |
| 2750 | LNU60 | barley\|gb157SOLEXA\|BG368863 | 4428 | 686 | 92.82 | glotblastn |
| 2751 | LNU60 | barley\|gb157.3\|BG368863 | 4428 | 686 | 92.53 | glotblastn |
| 2752 | LNU60 | pseudoroegneria\|gb167\|FF360223 | 4429 | 686 | 81.6 | globlastp |
| 2753 | LNU60 | switchgrass\|gb167\|FL699261 | 4430 | 686 | 80.52 | glotblastn |
| 2754 | LNU83 | cowpea\|gb166\|FF386177 | 4431 | 687 | 89.08 | glotblastn |
| 2755 | LNU83 | peanut\|gb171\|EE124103 | 4432 | 687 | 80.28 | glotblastn |
| 2756 | LNU89 | pseudoroegneria\|gb167\|FF341285 | 4433 | 688 | 95.76 | glotblastn |
| 2757 | LNU89 | maize\|gb170\|AA979933 | 4434 | 688 | 80.08 | glotblastn |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Homolog. Polyp. SEQ ID NO: | Hom. to SEQ ID NO: | % global identity | Algor. |
|---|---|---|---|---|---|---|
| 2758 | LNU115 | rice\|gb170\|OS03G21740 | 4435 | 693 | 83.6 | globlastp |
| 2759 | LNU115 | wheat\|gb164\|BE498586 | 4436 | 693 | 80.1 | glotblastn |
| 2760 | LNU170 | arabidopsis_lyrata\|09v1\|TMPLAT5G40060T1 | 4437 | 697 | 100 | glotblastn |
| 2761 | LNU192 | sugarcane\|gb157.3\|BQ533786 | 4438 | 698 | 93.97 | glotblastn |
| 2762 | LNU192 | switchgrass\|gb167\|FL700814 | 4439 | 698 | 91.11 | glotblastn |
| 2763 | LNU192 | monkeyflower\|10v1\|GR013631 | 4440 | 698 | 86.67 | glotblastn |
| 2764 | LNU192 | poplar\|gb170\|BI138135 | 4441 | 698 | 82.54 | glotblastn |
| 2765 | LNU192 | poplar\|10v1\|BI138135 | 4442 | 698 | 82.22 | glotblastn |
| 2766 | LNU192 | poplar\|10v1\|XM002307099 | 4443 | 698 | 81.88 | glotblastn |
| 2767 | LNU192 | poplar\|gb170\|XM002307099 | 4444 | 698 | 81.88 | glotblastn |
| 2768 | LNU192 | cucumber\|09v1\|CV001584 | 4445 | 698 | 81.59 | glotblastn |
| 2769 | LNU192 | soybean\|gb168\|BQ252456 | 4446 | 698 | 81.27 | glotblastn |
| 2770 | LNU192 | castorbean\|09v1\|XM002532133 | 4447 | 698 | 80.95 | glotblastn |
| 2771 | LNU192 | medicago\|09v1\|AW689616 | 4448 | 698 | 80.95 | glotblastn |
| 2772 | LNU192 | soybean\|gb168\|BM523433 | 4449 | 698 | 80.95 | glotblastn |
| 2773 | LNU229 | potato\|gb157.2\|BE922224 | 4450 | 701 | 93.8 | globlastp |
| 2774 | LNU242 | arabidopsis_lyrata\|09v1\|JGIAL023703 | 4451 | 703 | 88.6 | globlastp |
| 2775 | LNU265 | switchgrass\|gb167\|FE626072 | 4452 | 705 | 86.1 | globlastp |
| 2776 | LNU4 | rye\|gb164\|BE494134 | 4453 | 708 | 95.5 | globlastp |
| 2777 | LNU4 | wheat\|gb164\|BE430340 | 4454 | 708 | 94.2 | globlastp |
| 2778 | LNU4 | wheat\|gb164\|BQ743944 | 4455 | 708 | 93.5 | globlastp |
| 2779 | LNU4 | wheat\|gb164\|CD935835 | 4456 | 708 | 92.9 | globlastp |
| 2780 | LNU4 | brachypodium\|09v1\|DV474688 | 4457 | 708 | 86.4 | globlastp |
| 2781 | LNU4 | brachypodium\|gb169\|BE494134 | 4457 | 708 | 86.4 | globlastp |
| 2782 | LNU4 | oat\|10v1\|GR330356 | 4458 | 708 | 84.4 | globlastp |
| 2783 | LNU4 | barley\|gb157.3\|BI955043 | 4459 | 708 | 84.1 | globlastp |
| 2784 | LNU4 | barley\|gb157SOLEXA\|BI955043 | 4459 | 708 | 84.1 | globlastp |
| 2785 | LNU4 | barley\|gb157SOLEXA\|BE519514 | 4460 | 708 | 81.1 | globlastp |
| 2786 | LNU4 | oat\|10v1\|GR364394 | 4461 | 708 | 80.5 | globlastp |
| 2787 | LNU4 | wheat\|gb164\|CK214316 | 4462 | 708 | 80.4 | globlastp |
| 2788 | LNU28 | oat\|10v1\|GR315782 | 4463 | 712 | 90.9 | globlastp |
| 2789 | LNU28 | sorghum\|09v1\|SB03G008060 | 4464 | 712 | 83.7 | globlastp |
| 2790 | LNU28 | sorghum\|gb161.crp\|AW283962 | 4464 | 712 | 83.7 | globlastp |
| 2791 | LNU28 | sugarcane\|10v1\|CA109293 | 4465 | 712 | 82 | globlastp |
| 2792 | LNU28 | rice\|gb170\|OS01G02870 | 4466 | 712 | 81.7 | globlastp |
| 2793 | LNU28 | sugarcane\|gb157.3\|CA109293 | 4467 | 712 | 81.5 | globlastp |
| 2794 | LNU28 | switchgrass\|gb167\|FE643547 | 4468 | 712 | 80.2 | globlastp |
| 2795 | LNU35 | brachypodium\|09v1\|DV488691 | 4469 | 714 | 85.8 | globlastp |
| 2796 | LNU36 | soybean\|gb168\|BG839931 | 4470 | 715 | 80.4 | globlastp |
| 2797 | LNU54 | soybean\|gb168\|BG839336 | 4471 | 717 | 94.9 | globlastp |
| 2798 | LNU54 | cowpea\|gb166\|FC457406 | 4472 | 717 | 85.5 | globlastp |
| 2799 | LNU54 | bean\|gb167\|CA905321 | 4473 | 717 | 85 | globlastp |
| 2800 | LNU58 | wheat\|gb164\|BE430622 | 4474 | 719 | 88.4 | globlastp |
| 2801 | LNU58 | wheat\|gb164\|CA622084 | 4475 | 719 | 82.8 | globlastp |
| 2802 | LNU58 | wheat\|gb164\|BF484060 | 4476 | 719 | 80.4 | globlastp |
| 2803 | LNU64 | wheat\|gb164\|AJ603788 | 4477 | 721 | 92.2 | globlastp |
| 2803 | LNU98 | wheat\|gb164\|AJ603788 | 4477 | 734 | 80.2 | globlastp |
| 2804 | LNU64 | millet\|09v1\|CD725273 | 4478 | 721 | 83.5 | globlastp |
| 2804 | LNU98 | millet\|09v1\|CD725273 | 4478 | 734 | 82.2 | globlastp |
| 2805 | LNU64 | wheat\|gb164\|BE591591 | 4479 | 721 | 82.6 | globlastp |
| 2805 | LNU98 | wheat\|gb164\|BE591591 | 4479 | 734 | 80.23 | glotblastn |
| 2806 | LNU70 | wheat\|gb164\|BE492123 | 4480 | 724 | 92.41 | glotblastn |
| 2807 | LNU70 | barley\|gb157SOLEXA\|AL506812 | 4481 | 724 | 92.1 | globlastp |
| 2808 | LNU70 | brachypodium\|09v1\|DV469959 | 4482 | 724 | 90.9 | globlastp |
| 2809 | LNU70 | sugarcane\|10v1\|BQ533718 | 4483 | 724 | 90.9 | globlastp |
| 2810 | LNU70 | maize\|gb170\|AA051893 | 4484 | 724 | 90.5 | globlastp |
| 2811 | LNU70 | switchgrass\|gb167\|FE616904 | 4485 | 724 | 90.3 | globlastp |
| 2812 | LNU70 | sorghum\|09v1\|SB02G000720 | 4486 | 724 | 90.2 | globlastp |
| 2813 | LNU70 | maize\|gb170\|LLBM501434 | 4487 | 724 | 89.9 | globlastp |
| 2814 | LNU70 | switchgrass\|gb167\|FE597592 | 4488 | 724 | 89.7 | globlastp |
| 2815 | LNU70 | rice\|gb170\|OS07G01020 | 4489 | 724 | 89.6 | globlastp |
| 2816 | LNU70 | rice\|gb170\|OS10G01080 | 4490 | 724 | 89.2 | globlastp |
| 2817 | LNU70 | oat\|10v1\|GR350932 | 4491 | 724 | 87.7 | glotblastn |
| 2818 | LNU70 | ginger\|gb164\|DY345087 | 4492 | 724 | 87.5 | globlastp |
| 2819 | LNU70 | ginger\|gb164\|DY345406 | 4493 | 724 | 87.5 | globlastp |
| 2820 | LNU70 | leymus\|gb166\|EG378516 | 4494 | 724 | 87.2 | globlastp |
| 2821 | LNU70 | brachypodium\|09v1\|SRR031795S0034512 | 4495 | 724 | 86.9 | globlastp |
| 2822 | LNU70 | barley\|gb157SOLEXA\|BE421769 | 4496 | 724 | 86.7 | globlastp |
| 2823 | LNU70 | antirrhinum\|gb166\|AJ794293 | 4497 | 724 | 86.2 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 2824 | LNU70 | aquilegia\|10v1\|DR915720 | 4498 | 724 | 86.2 | globlastp |
| 2825 | LNU70 | orobanche\|10v1\|SRR023189S0008709 | 4499 | 724 | 86.2 | globlastp |
| 2826 | LNU70 | cleome_gynandra\|10v1\|SRR015532S0033509 | 4500 | 724 | 85.9 | globlastp |
| 2827 | LNU70 | wheat\|gb164\|BE216934 | 4501 | 724 | 85.8 | globlastp |
| 2828 | LNU70 | cotton\|gb164\|AI731099 | 4502 | 724 | 85.6 | globlastp |
| 2829 | LNU70 | cotton\|gb164\|AI727639 | 4503 | 724 | 85.3 | globlastp |
| 2830 | LNU70 | cassava\|09v1\|CK646456 | 4504 | 724 | 84.9 | globlastp |
| 2831 | LNU70 | cleome_gynandra\|10v1\|SRR015532S0002004 | 4505 | 724 | 84.9 | globlastp |
| 2832 | LNU70 | grape\|gb160\|BM436391 | 4506 | 724 | 84.9 | globlastp |
| 2833 | LNU70 | oat\|10v1\|GR314124 | 4507 | 724 | 84.9 | globlastp |
| 2834 | LNU70 | soybean\|gb168\|AL368316 | 4508 | 724 | 84.9 | globlastp |
| 2835 | LNU70 | artemisia\|gb164\|EY100674 | 4509 | 724 | 84.6 | globlastp |
| 2836 | LNU70 | monkeyflower\|10v1\|DV211139 | 4510 | 724 | 84.6 | globlastp |
| 2837 | LNU70 | poplar\|10v1\|BU821620 | 4511 | 724 | 84.6 | globlastp |
| 2838 | LNU70 | soybean\|gb168\|BG583573 | 4512 | 724 | 84.6 | globlastp |
| 2839 | LNU70 | cleome_gynandra\|10v1\|SRR015532S0001986 | 4513 | 724 | 84.4 | globlastp |
| 2840 | LNU70 | apple\|gb171\|CN581367 | 4514 | 724 | 84.3 | globlastp |
| 2841 | LNU70 | aquilegia\|10v1\|DR926939 | 4515 | 724 | 84.3 | globlastp |
| 2842 | LNU70 | bean\|gb167\|AY007525 | 4516 | 724 | 84.3 | globlastp |
| 2843 | LNU70 | cichorium\|gb171\|EH673869 | 4517 | 724 | 84.3 | globlastp |
| 2844 | LNU70 | citrus\|gb166\|CB291221 | 4518 | 724 | 84.3 | globlastp |
| 2845 | LNU70 | lettuce\|10v1\|DW065212 | 4517 | 724 | 84.3 | globlastp |
| 2846 | LNU70 | lettuce\|10v1\|DW074895 | 4517 | 724 | 84.3 | globlastp |
| 2847 | LNU70 | b_rapa\|gb162\|CV650466 | 4519 | 724 | 84 | globlastp |
| 2848 | LNU70 | canola\|10v1\|BQ704215 | 4519 | 724 | 84 | globlastp |
| 2849 | LNU70 | cowpea\|gb166\|FC459209 | 4520 | 724 | 84 | globlastp |
| 2850 | LNU70 | cucumber\|09v1\|BI740201 | 4521 | 724 | 84 | globlastp |
| 2851 | LNU70 | ipomoea_nil\|10v1\|BJ563728 | 4522 | 724 | 84 | globlastp |
| 2852 | LNU70 | pepper\|gb171\|BM059644 | 4523 | 724 | 84 | globlastp |
| 2853 | LNU70 | poplar\|10v1\|BI071183 | 4524 | 724 | 84 | globlastp |
| 2854 | LNU70 | potato\|10v1\|BG350133 | 4525 | 724 | 84 | globlastp |
| 2855 | LNU70 | solanum_phureja\|09v1\|SPHBG127432 | 4525 | 724 | 84 | globlastp |
| 2856 | LNU70 | sunflower\|gb162\|DY910980 | 4526 | 724 | 84 | globlastp |
| 2857 | LNU70 | thellungiella\|gb167\|DN773941 | 4527 | 724 | 84 | globlastp |
| 2858 | LNU70 | b_rapa\|gb162\|CV544377 | 4528 | 724 | 83.7 | globlastp |
| 2859 | LNU70 | canola\|10v1\|CX193292 | 4528 | 724 | 83.7 | globlastp |
| 2860 | LNU70 | canola\|10v1\|EE413831 | 4529 | 724 | 83.7 | globlastp |
| 2861 | LNU70 | canola\|10v1\|EE470024 | 4530 | 724 | 83.7 | globlastp |
| 2862 | LNU70 | chestnut\|gb170\|SRR006295S0008684 | 4531 | 724 | 83.7 | globlastp |
| 2863 | LNU70 | eggplant\|10v1\|FS022577 | 4532 | 724 | 83.7 | globlastp |
| 2864 | LNU70 | nicotiana_benthamiana\|gb162\|CN744951 | 4533 | 724 | 83.7 | globlastp |
| 2865 | LNU70 | tobacco\|gb162\|GFXAY532656X1 | 4533 | 724 | 83.7 | globlastp |
| 2866 | LNU70 | tomato\|09v1\|BG127432 | 4534 | 724 | 83.7 | globlastp |
| 2867 | LNU70 | kiwi\|gb166\|FG409049 | 4535 | 724 | 83.4 | globlastp |
| 2868 | LNU70 | strawberry\|gb164\|CO379446 | 4536 | 724 | 83.4 | globlastp |
| 2869 | LNU70 | arabidopsis_lyrata\|09v1\|BQ834310 | 4537 | 724 | 83.3 | globlastp |
| 2870 | LNU70 | arabidopsis\|gb165\|AT5G01410 | 4537 | 724 | 83.3 | globlastp |
| 2871 | LNU70 | canola\|10v1\|CB686329 | 4538 | 724 | 83.3 | globlastp |
| 2872 | LNU70 | cassava\|09v1\|CK643506 | 4539 | 724 | 83.1 | globlastp |
| 2873 | LNU70 | canola\|10v1\|CB686238 | 4540 | 724 | 83 | globlastp |
| 2874 | LNU70 | clover\|gb162\|BB936964 | 4541 | 724 | 82.7 | globlastp |
| 2875 | LNU70 | lotus\|09v1\|DQ139264 | 4542 | 724 | 82.7 | globlastp |
| 2876 | LNU70 | citrus\|gb166\|CB292808 | 4543 | 724 | 82.4 | globlastp |
| 2877 | LNU70 | lettuce\|10v1\|DW090121 | 4544 | 724 | 82.4 | globlastp |
| 2878 | LNU70 | papaya\|gb165\|EX254443 | 4545 | 724 | 82.4 | globlastp |
| 2879 | LNU70 | strawberry\|gb164\|EX658116 | 4546 | 724 | 82.2 | globlastp |
| 2880 | LNU70 | castorbean\|09v1\|EG661356 | 4547 | 724 | 82.11 | glotblastn |
| 2881 | LNU70 | cotton\|gb164\|DT555568 | 4548 | 724 | 82.1 | globlastp |
| 2882 | LNU70 | cryptomeria\|gb166\|BP175070 | 4549 | 724 | 82.1 | globlastp |
| 2883 | LNU70 | spruce\|gb162\|CO222779 | 4550 | 724 | 82.1 | globlastp |
| 2884 | LNU70 | spruce\|gb162\|CO478481 | 4551 | 724 | 82.1 | globlastp |
| 2885 | LNU70 | cynara\|gb167\|GE587800 | 4552 | 724 | 82.05 | glotblastn |
| 2886 | LNU70 | pine\|10v1\|CO170442 | 4553 | 724 | 81.7 | globlastp |
| 2887 | LNU70 | arabidopsis_lyrata\|09v1\|JGIAL015042 | 4554 | 724 | 81.4 | globlastp |
| 2888 | LNU70 | arabidopsis\|gb165\|AT2G38230 | 4555 | 724 | 81.4 | globlastp |
| 2889 | LNU70 | fern\|gb171\|BP912037 | 4556 | 724 | 81.4 | globlastp |
| 2890 | LNU70 | pine\|10v1\|CF470198 | 4557 | 724 | 81.4 | globlastp |
| 2891 | LNU70 | radish\|gb164\|EY902227 | 4558 | 724 | 81.4 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 2892 | LNU70 | medicago\|09v1\|AW695944 | 4559 | 724 | 81.3 | globlastp |
| 2893 | LNU70 | b_oleracea\|gb161\|AM385028 | 4560 | 724 | 80.9 | globlastp |
| 2894 | LNU70 | cucumber\|09v1\|AM723122 | 4561 | 724 | 80.6 | globlastp |
| 2895 | LNU70 | spikemoss\|gb165\|FE429245 | 4562 | 724 | 80.13 | glotblastn |
| 2896 | LNU70 | spikemoss\|gb165\|FE451328 | 4562 | 724 | 80.13 | glotblastn |
| 2897 | LNU74 | switchgrass\|gb167\|FE639952 | 4563 | 726 | 86.7 | globlastp |
| 2898 | LNU74 | millet\|09v1\|EVO454PM015812 | 4564 | 726 | 86.57 | glotblastn |
| 2899 | LNU74 | switchgrass\|gb167\|FE657764 | 4565 | 726 | 85.9 | globlastp |
| 2900 | LNU74 | rice\|gb170\|OS04G43540 | 4566 | 726 | 85.8 | globlastp |
| 2901 | LNU74 | brachypodium\|09v1\|DV476963 | 4567 | 726 | 85.2 | globlastp |
| 2902 | LNU74 | maize\|gb170\|AI621531 | 4568 | 726 | 85.2 | globlastp |
| 2903 | LNU74 | maize\|gb170\|LLBE128837 | 4568 | 726 | 85.2 | globlastp |
| 2904 | LNU74 | pseudoroegneria\|gb167\|FF342634 | 4569 | 726 | 85.2 | globlastp |
| 2905 | LNU74 | sorghum\|09v1\|SB06G022580 | 4570 | 726 | 85.2 | globlastp |
| 2906 | LNU74 | sorghum\|gb161.crp\|AI901612 | 4570 | 726 | 85.2 | globlastp |
| 2907 | LNU74 | sugarcane\|10v1\|CA073228 | 4568 | 726 | 85.2 | globlastp |
| 2908 | LNU74 | sugarcane\|gb157.3\|CA073228 | 4568 | 726 | 85.2 | globlastp |
| 2909 | LNU74 | oat\|10v1\|CA819453 | 4571 | 726 | 85.1 | globlastp |
| 2910 | LNU74 | brachypodium\|09v1\|DV479778 | 4572 | 726 | 85.1 | globlastp |
| 2911 | LNU74 | brachypodium\|gb169\|BE403473 | 4572 | 726 | 85.1 | globlastp |
| 2912 | LNU74 | rice\|gb170\|OS02G40880 | 4573 | 726 | 85.1 | globlastp |
| 2913 | LNU74 | sugarcane\|gb157.3\|CA084445 | 4574 | 726 | 85.1 | globlastp |
| 2914 | LNU74 | sugarcane\|10v1\|CA084445 | 4574 | 726 | 85.1 | globlastp |
| 2915 | LNU74 | wheat\|gb164\|BE429979 | 4575 | 726 | 84.4 | globlastp |
| 2916 | LNU74 | barley\|gb157.3\|BE421867 | 4576 | 726 | 84.3 | globlastp |
| 2917 | LNU74 | barley\|gb157SOLEXA\|BE421867 | 4576 | 726 | 84.3 | globlastp |
| 2918 | LNU74 | maize\|gb170\|LLDQ244985 | 4577 | 726 | 84.3 | globlastp |
| 2919 | LNU74 | sugarcane\|gb157.3\|CA119465 | 4578 | 726 | 84.3 | globlastp |
| 2920 | LNU74 | switchgrass\|gb167\|FE612757 | 4579 | 726 | 84.3 | globlastp |
| 2921 | LNU74 | switchgrass\|gb167\|FE644412 | 4579 | 726 | 84.3 | globlastp |
| 2922 | LNU74 | wheat\|gb164\|BE403473 | 4577 | 726 | 84.3 | globlastp |
| 2923 | LNU74 | wheat\|gb164\|TAU91834 | 4577 | 726 | 84.3 | globlastp |
| 2924 | LNU74 | oat\|10v1\|GO585574 | 4580 | 726 | 83.7 | globlastp |
| 2925 | LNU74 | fescue\|gb161\|DT690215 | 4581 | 726 | 83.7 | globlastp |
| 2926 | LNU74 | maize\|gb170\|LLDQ245227 | 4582 | 726 | 83.7 | globlastp |
| 2927 | LNU74 | wheat\|gb164\|BE400933 | 4582 | 726 | 83.7 | globlastp |
| 2928 | LNU74 | wheat\|gb164\|BE406339 | 4582 | 726 | 83.7 | globlastp |
| 2929 | LNU74 | eggplant\|10v1\|FS000049 | 4583 | 726 | 83.6 | globlastp |
| 2930 | LNU74 | millet\|09v1\|EVO454PM021136 | 4584 | 726 | 83.6 | globlastp |
| 2931 | LNU74 | sugarcane\|10v1\|CA073639 | 4585 | 726 | 83.6 | globlastp |
| 2932 | LNU74 | lovegrass\|gb167\|EH186458 | 4586 | 726 | 83.6 | globlastp |
| 2933 | LNU74 | maize\|gb170\|LLCF630355 | 4587 | 726 | 83.6 | globlastp |
| 2934 | LNU74 | maize\|gb170\|W21624 | 4587 | 726 | 83.6 | globlastp |
| 2935 | LNU74 | sorghum\|09v1\|SB02G031930 | 4588 | 726 | 83.6 | globlastp |
| 2936 | LNU74 | sorghum\|gb161.crp\|AW011692 | 4588 | 726 | 83.6 | globlastp |
| 2937 | LNU74 | sugarcane\|gb157.3\|CA073639 | 4589 | 726 | 83.6 | globlastp |
| 2938 | LNU74 | barley\|gb157SOLEXA\|AL500999 | 4590 | 726 | 83 | globlastp |
| 2939 | LNU74 | rye\|gb164\|BE587782 | 4591 | 726 | 82.84 | glotblastn |
| 2940 | LNU74 | eucalyptus\|gb166\|CT985211 | 4592 | 726 | 82.8 | globlastp |
| 2941 | LNU74 | maize\|gb170\|AI942046 | 4593 | 726 | 82.8 | globlastp |
| 2942 | LNU74 | maize\|gb170\|LLCF004305 | 4594 | 726 | 82.1 | globlastp |
| 2943 | LNU74 | brachypodium\|gb169\|BE400933 | 4595 | 726 | 81.4 | globlastp |
| 2944 | LNU74 | cotton\|gb164\|BM360100 | 4596 | 726 | 81.34 | glotblastn |
| 2945 | LNU87 | millet\|09v1\|EVO454PM017414 | 4597 | 731 | 91.5 | globlastp |
| 2946 | LNU87 | brachypodium\|09v1\|SRR031797S0046443 | 4598 | 731 | 84.46 | glotblastn |
| 2947 | LNU87 | brachypodium\|gb169\|BF145866 | 4599 | 731 | 82.4 | globlastp |
| 2948 | LNU87 | rice\|gb170\|OS02G12900 | 4600 | 731 | 81.82 | glotblastn |
| 2949 | LNU89 | wheat\|gb164\|BE429720 | 4601 | 732 | 98.2 | globlastp |
| 2950 | LNU89 | barley\|gb157SOLEXA\|BE421794 | 4602 | 732 | 94.8 | globlastp |
| 2951 | LNU89 | oat\|10v1\|CN818133 | 4603 | 732 | 92.7 | globlastp |
| 2952 | LNU89 | brachypodium\|09v1\|DV473902 | 4604 | 732 | 91.1 | globlastp |
| 2953 | LNU89 | leymus\|gb166\|EG390106 | 4605 | 732 | 86.6 | globlastp |
| 2954 | LNU89 | switchgrass\|gb167\|FE650349 | 4606 | 732 | 80.9 | globlastp |
| 2955 | LNU89 | sorghum\|09v1\|SB01G028410 | 4607 | 732 | 80.1 | globlastp |
| 2956 | LNU89 | sorghum\|gb161.crp\|AA979933 | 4607 | 732 | 80.1 | globlastp |
| 2957 | LNU98 | sugarcane\|10v1\|CA151185 | 4608 | 734 | 92.84 | glotblastn |
| 2958 | LNU98 | sugarcane\|gb157.3\|CA151185 | 4609 | 734 | 91.69 | glotblastn |
| 2959 | LNU128 | radish\|gb164\|EV568872 | 4610 | 742 | 93.8 | globlastp |
| 2960 | LNU128 | canola\|10v1\|DY011559 | 4611 | 742 | 93.5 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 2961 | LNU128 | canola\|gb161\|BQ704843 | 4612 | 742 | 93.2 | globlastp |
| 2962 | LNU128 | citrus\|gb166\|CX069720 | 4613 | 742 | 84.37 | glotblastn |
| 2963 | LNU128 | cotton\|gb164\|AJ513046 | 4614 | 742 | 84 | globlastp |
| 2964 | LNU128 | cacao\|gb167\|CU482048 | 4615 | 742 | 83.7 | globlastp |
| 2965 | LNU128 | grape\|gb160\|CB911162 | 4616 | 742 | 83.7 | globlastp |
| 2966 | LNU128 | potato\|10v1\|BG598087 | 4617 | 742 | 83.19 | glotblastn |
| 2967 | LNU128 | potato\|gb157.2\|BG598087 | 4618 | 742 | 83.19 | glotblastn |
| 2968 | LNU128 | solanum_phureja\|09v1\|SPHBG133047 | 4619 | 742 | 82.7 | globlastp |
| 2969 | LNU128 | tomato\|09v1\|BG133047 | 4620 | 742 | 82.7 | globlastp |
| 2970 | LNU128 | tomato\|gb164\|BG133047 | 4620 | 742 | 82.7 | globlastp |
| 2971 | LNU128 | eggplant\|10v1\|FS026981 | 4621 | 742 | 82.4 | globlastp |
| 2972 | LNU128 | cucumber\|09v1\|CSCRP021916 | 4622 | 742 | 82.3 | globlastp |
| 2973 | LNU128 | cassava\|09v1\|DV441652 | 4623 | 742 | 81.9 | globlastp |
| 2974 | LNU128 | kiwi\|gb166\|FG489702 | 4624 | 742 | 81.6 | globlastp |
| 2975 | LNU128 | rice\|gb170\|OS12G07720 | 4625 | 742 | 81.5 | globlastp |
| 2976 | LNU128 | castorbean\|09v1\|GE635249 | 4626 | 742 | 81 | globlastp |
| 2977 | LNU128 | castorbean\|gb160\|MDL29648M002000 | 4626 | 742 | 81 | globlastp |
| 2978 | LNU128 | sugarcane\|10v1\|CA074195 | 4627 | 742 | 80.9 | globlastp |
| 2979 | LNU128 | sugarcane\|gb157.3\|CA074195 | 4627 | 742 | 80.9 | globlastp |
| 2980 | LNU128 | switchgrass\|gb167\|FE607245 | 4628 | 742 | 80.9 | globlastp |
| 2981 | LNU128 | poplar\|gb170\|AI164310 | 4629 | 742 | 80.88 | glotblastn |
| 2982 | LNU128 | peanut\|gb171\|GO332421 | 4630 | 742 | 80.83 | glotblastn |
| 2983 | LNU128 | sorghum\|09v1\|SB08G004780 | 4631 | 742 | 80.6 | globlastp |
| 2984 | LNU128 | sorghum\|gb161.crp\|BM324980 | 4631 | 742 | 80.6 | globlastp |
| 2985 | LNU128 | sorghum\|09v1\|SB01G045530 | 4632 | 742 | 80.6 | globlastp |
| 2986 | LNU128 | sorghum\|gb161.crp\|CB334193 | 4632 | 742 | 80.6 | globlastp |
| 2987 | LNU128 | soybean\|gb168\|BF520452 | 4633 | 742 | 80.5 | globlastp |
| 2988 | LNU128 | apple\|gb157.3\|CN495076 | 4634 | 742 | 80.3 | globlastp |
| 2989 | LNU128 | apple\|gb171\|CN495076 | 4634 | 742 | 80.3 | globlastp |
| 2990 | LNU128 | aquilegia\|10v1\|DR941443 | 4635 | 742 | 80.24 | glotblastn |
| 2991 | LNU128 | monkeyflower\|10v1\|GR109554 | 4636 | 742 | 80.24 | glotblastn |
| 2992 | LNU128 | sunflower\|gb162\|DY947958 | 4637 | 742 | 80.24 | glotblastn |
| 2993 | LNU128 | poplar\|10v1\|AI164310 | 4638 | 742 | 80.2 | globlastp |
| 2994 | LNU129 | arabidopsis_lyrata\|09v1\|JGIAL004858 | 4639 | 743 | 89.6 | globlastp |
| 2995 | LNU129 | canola\|10v1\|CD827308 | 4640 | 743 | 81.2 | globlastp |
| 2996 | LNU129 | canola\|gb161\|CD827308 | 4640 | 743 | 81.2 | globlastp |
| 2997 | LNU135 | arabidopsis_lyrata\|09v1\|JGIAL023957 | 4641 | 747 | 96.6 | globlastp |
| 2998 | LNU135 | thellungiella\|gb167\|BM985897 | 4642 | 747 | 92.5 | globlastp |
| 2999 | LNU135 | b_oleracea\|gb161\|EH416218 | 4643 | 747 | 88.4 | globlastp |
| 3000 | LNU135 | canola\|10v1\|CD821934 | 4643 | 747 | 88.4 | globlastp |
| 3001 | LNU135 | b_rapa\|gb162\|CA991582 | 4644 | 747 | 88 | globlastp |
| 3002 | LNU135 | canola\|10v1\|CD820689 | 4645 | 747 | 88 | globlastp |
| 3003 | LNU135 | canola\|gb161\|CD820689 | 4645 | 747 | 88 | globlastp |
| 3004 | LNU135 | canola\|10v1\|CX189037 | 4646 | 747 | 87.3 | globlastp |
| 3005 | LNU135 | radish\|gb164\|EW735630 | 4647 | 747 | 86.9 | globlastp |
| 3006 | LNU135 | radish\|gb164\|EV567321 | 4648 | 747 | 86.5 | globlastp |
| 3007 | LNU135 | canola\|gb161\|CD821934 | 4649 | 747 | 84.6 | globlastp |
| 3008 | LNU135 | cleome_gynandra\|10v1\|SRR015532S0008526 | 4650 | 747 | 82.4 | globlastp |
| 3009 | LNU140 | arabidopsis_lyrata\|09v1\|JGIAL005684 | 4651 | 748 | 90 | globlastp |
| 3010 | LNU140 | cassava\|09v1\|DV446155 | 4652 | 748 | 81.8 | globlastp |
| 3011 | LNU140 | citrus\|gb166\|CB250310 | 4653 | 748 | 80.29 | glotblastn |
| 3012 | LNU150 | cotton\|gb164\|BE052334 | 4654 | 752 | 96.9 | globlastp |
| 3013 | LNU150 | cacao\|gb167\|CU477864 | 4655 | 752 | 88.9 | globlastp |
| 3014 | LNU150 | heritiera\|10v1\|SRR005795S0012955 | 4656 | 752 | 86.9 | globlastp |
| 3015 | LNU150 | tea\|10v1\|CV013763 | 4657 | 752 | 83.5 | globlastp |
| 3016 | LNU150 | poplar\|10v1\|AI162436 | 4658 | 752 | 81.4 | globlastp |
| 3017 | LNU171 | barley\|gb157SOLEXA\|BE412872 | 4659 | 757 | 96.6 | globlastp |
| 3018 | LNU171 | barley\|gb157.3\|BE412872 | 4660 | 757 | 95.9 | globlastp |
| 3019 | LNU171 | barley\|gb157.3\|BI777448 | 4661 | 757 | 91.8 | globlastp |
| 3020 | LNU171 | barley\|gb157SOLEXA\|BI777448 | 4661 | 757 | 91.8 | globlastp |
| 3021 | LNU171 | wheat\|gb164\|AL822126 | 4662 | 757 | 87.07 | glotblastn |
| 3022 | LNU171 | wheat\|gb164\|BE415359 | 4663 | 757 | 85.7 | globlastp |
| 3023 | LNU171 | wheat\|gb164\|BG607128 | 4664 | 757 | 83.9 | globlastp |
| 3024 | LNU171 | wheat\|gb164\|CA727731 | 4665 | 757 | 81 | globlastp |
| 3025 | LNU172 | wheat\|gb164\|CV774671 | 4666 | 758 | 84.5 | globlastp |
| 3026 | LNU172 | wheat\|gb164\|BQ807177 | 4667 | 758 | 81.8 | globlastp |
| 3027 | LNU172 | wheat\|gb164\|CA621288 | 4668 | 758 | 80.5 | globlastp |
| 3028 | LNU179 | arabidopsis_lyrata\|09v1\|JGIAL004871 | 4669 | 760 | 92.8 | globlastp |
| 3029 | LNU212 | arabidopsis_lyrata\|09v1\|JGIAL002964 | 4670 | 764 | 94.3 | globlastp |

TABLE 2-continued

Homologues of the identified genes/polypeptides for increasing nitrogen use efficiency, fertilizer use efficiency, yield, seed yield, growth rate, vigor, biomass, oil content, fiber yield, fiber quality, fiber length, abiotic stress tolerance and/or water use efficiency of a plant

| Polyn. SEQ ID NO: | Hom. to Gene Name | Cluster Name | Polyp. SEQ ID NO: | Hom. to SEQ ID NO: | % global identity | Algor. |
|---|---|---|---|---|---|---|
| 3030 | LNU212 | radish\|gb164\|EV544090 | 4671 | 764 | 80.9 | globlastp |
| 3031 | LNU212 | canola\|gb161\|H74617 | 4672 | 764 | 80.8 | globlastp |
| 3032 | LNU235 | arabidopsis_lyrata\|09v1\|JGIAL003487 | 4673 | 770 | 93.92 | glotblastn |
| 3033 | LNU235 | radish\|gb164\|EV524630 | 4674 | 770 | 87.7 | globlastp |
| 3034 | LNU235 | thellungiella\|gb167\|BM985688 | 4675 | 770 | 87.42 | glotblastn |
| 3035 | LNU235 | b_rapa\|gb162\|L46407 | 4676 | 770 | 85.6 | globlastp |
| 3036 | LNU250 | arabidopsis_lyrata\|09v1\|JGIAL003223 | 4677 | 775 | 87 | globlastp |
| 3037 | LNU253 | lotus\|gb157.2\|BU494491 | 4678 | 777 | 84.39 | glotblastn |
| 3038 | LNU253 | lotus\|09v1\|LLBU494491 | 4679 | 777 | 83.4 | globlastp |
| 3039 | LNU253 | chickpea\|09v2\|DY475475 | 4680 | 777 | 80.39 | glotblastn |
| 3040 | LNU256 | arabidopsis_lyrata\|09v1\|JGIAL015756 | 4681 | 779 | 83.3 | globlastp |
| 3041 | LNU260 | arabidopsis_lyrata\|09v1\|JGIAL020384 | 4682 | 781 | 95.7 | globlastp |

Table 2: Provided are the homologous polypeptides and polynucleotides of the genes identified in Table 1 and of their cloned genes, which can increase nitrogen use efficiency, fertilizer use efficiency, yield, seed yield, growth rate, vigor, biomass, oil content, fiber yield, fiber quality, fiber length, abiotic stress tolerance and/or water use efficiency of a plant. Homology was calculated as % of identity over the aligned sequences. The query sequences were polypeptide sequences SEQ ID NOs: 468-706, and 707-784 and the subject sequences are polypeptide sequences or polynucleotide sequences which were dynamically translated in all six reading frames identified in the database based on greater than 80% identity to the query polypeptide sequences.
"Polyp." = polypeptide;
"Polyn."—Polynucleotide.
Algor. = Algorithm.
"globlastp"—global homology using blastp;
"glotblastn"—global homology using tblastn.
"Hom."—homologous.

The output of the functional genomics approach described herein is a set of genes highly predicted to improve nitrogen use efficiency, fertilizer use efficiency, yield, seed yield, growth rate, vigor, biomass, oil content, fiber yield, fiber length, fiber quality, abiotic stress tolerance and/or water use efficiency of a plant by increasing their expression.

Although each gene is predicted to have its own impact, modifying the mode of expression of more than one gene or gene product (RNA, polypeptide) is expected to provide an additive or synergistic effect on the desired trait (e.g., nitrogen use efficiency, fertilizer use efficiency, yield, growth rate, vigor, biomass, oil content, abiotic stress tolerance and/or water use efficiency of a plant). Altering the expression of each gene described here alone or of a set of genes together increases the overall yield and/or other agronomic important traits, hence expects to increase agricultural productivity.

Example 3

Production of Arabidopsis Transcriptom and High Throughput Correlation Analysis Using 44K Arabidopsis Oligonucleotide Micro-Array In order to produce a high throughput correlation analysis comparing between plant phenotype and gene expression level, the present inventors utilized a Arabidopsis oligonucleotide micro-array, produced by Agilent Technologies [Hypertext Transfer Protocol://World Wide Web (dot) chem (dot) agilent (dot) com/Scripts/PDS (dot) asp?1 Page=50879]. The array oligonucleotide represents about 44,000 Arabidopsis genes and transcripts. To define correlations between the levels of RNA expression with NUE, yield components or vigor related parameters various plant characteristics of 14 different Arabidopsis ecotypes were analyzed. Among them, ten ecotypes encompassing the observed variance were selected for RNA expression analysis. The correlation between the RNA levels and the characterized parameters was analyzed using Pearson correlation test [Hypertext Transfer Protocol://World Wide Web (dot) davidmlane (dot) com/hyperstat/A34739 (dot) html].

Experimental Procedures

Analyzed Arabidopsis tissues—Two tissues of plants [leaves and stems] growing at two different nitrogen fertilization levels (1.5 mM Nitrogen or 6 mM Nitrogen) were sampled and RNA was extracted as described above. Each micro-array expression information tissue type has received a Set ID as summarized Table 3 below.

TABLE 3

Arabidopsis transcriptom experimental sets

| Expression Set | Set ID |
|---|---|
| Leaves at 1.5 mM Nitrogen fertilization | A |
| Leaves at 6 mM Nitrogen fertilization | B |
| Stems at 1.5 mM Nitrogen fertilization | C |
| Stem at 6 mM Nitrogen fertilization | D |

Table 3.

Arabidopsis yield components and vigor related parameters under different nitrogen fertilization levels assessment—10 Arabidopsis accessions in 2 repetitive plots each containing 8 plants per plot were grown at greenhouse. The growing protocol used was as follows: surface sterilized seeds were sown in Eppendorf tubes containing 0.5× Murashige-Skoog basal salt medium and grown at 23° C. under 12-hour light and 12-hour dark daily cycles for 10 days. Then, seedlings of similar size were carefully transferred to pots filled with a mix of perlite and peat in a 1:1 ratio. Constant nitrogen limiting conditions were achieved by irrigating the plants with a solution containing 1.5 mM inorganic nitrogen in the form of $KNO_3$, supplemented with 2 mM $CaCl_2$, 1.25 mM $KH_2PO_4$, 1.50 mM $MgSO_4$, 5 mM KCl, 0.01 mM $H_3BO_3$ and microelements, while normal irrigation conditions was achieved by applying a solution of 6 mM inorganic nitrogen also in the form of $KNO_3$, supplemented with 2 mM $CaCl_2$, 1.25 mM $KH_2PO_4$, 1.50 mM $MgSO_4$, 0.01 mM $H_3BO_3$ and microelements. To follow plant growth, trays were photographed the day nitrogen limiting conditions were initiated and subsequently every 3 days for about 15 additional days. Rosette plant area was then determined from the digital pictures. Image) software was used for quantifying the plant size from the digital pictures [Hypertext Transfer Protocol://rsb (dot) info (dot) nih (dot) gov/ij/] utilizing proprietary scripts designed to analyze the size of rosette area from individual plants as a function of time. The image analysis system included a personal desktop computer (Intel P4 3.0 GHz processor) and a public domain program—ImageJ 1.37 (Java based image processing program, which was developed at the U.S. National Institutes of Health and freely available on the internet [Hypertext Transfer Protocol://rsbweb (dot) nih (dot) gov/]. Next, analyzed data was saved to text files and processed using the JMP statistical analysis software (SAS institute). Data parameters collected are summarized in Table 4, hereinbelow.

TABLE 4

Arabidopsis correlated parameters (vectors)

| Correlated parameter with | Correlation Id |
|---|---|
| N 1.5 mM; Rosette Area at day 8 [$cm^2$] | 1 |
| N 1.5 mM; Rosette Area at day 10 [$cm^2$] | 2 |
| N 1.5 mM; Plot Coverage at day 8 [%] | 3 |
| N 1.5 mM; Plot Coverage at day 10 [%] | 4 |
| N 1.5 mM; Leaf Number at day 10 | 5 |
| N 1.5 mM; Leaf Blade Area at day 10 [$cm^2$] | 6 |
| N 1.5 mM; RGR of Rosette Area at day 3 [$cm^2$/day] | 7 |
| N 1.5 mM; t50 Flowering [day] | 8 |
| N 1.5 mM; Dry Weight [gr/plant] | 9 |
| N 1.5 mM; Seed Yield [gr/plant] | 10 |
| N 1.5 mM; Harvest Index | 11 |
| N 1.5 mM; 1000 Seeds weight [gr] | 12 |
| N 1.5 mM; seed yield/rosette area at day 10 [gr/$cm^2$] | 13 |
| N 1.5 mM; seed yield/leaf blade [gr/$cm^2$] | 14 |
| N 1.5 mM; % Seed yield reduction compared to N 6 mM | 15 |
| N 1.5 mM; % Biomass reduction compared to N 6 mM | 16 |
| N 1.5 mM; N level/DW [SPAD unit/gr] | 17 |
| N 1.5 mM; DW/N level [gr/SPAD unit] | 18 |
| N 1.5 mM; seed yield/N level [gr/SPAD unit] | 19 |
| N 6 mM; Rosette Area at day 8 [$cm^2$] | 20 |
| N 6 mM; Rosette Area at day 10 [$cm^2$] | 21 |
| N 6 mM; Plot Coverage at day 8 [%] | 22 |
| N 6 mM; Plot Coverage at day 10 [%] | 23 |
| N 6 mM; Leaf Number at day 10 | 24 |
| N 6 mM; Leaf Blade Area at day 10 | 25 |
| N 6 mM; RGR of Rosette Area at day 3 [$cm^2$/gr] | 26 |
| N 6 mM; t50 Flowering [day] | 27 |
| N 6 mM; Dry Weight [gr/plant] | 28 |
| N 6 mM; Seed Yield [gr/plant] | 29 |
| N 6 mM; Harvest Index | 30 |
| N 6 mM; 1000 Seeds weight [gr] | 31 |
| N 6 mM; seed yield/rosette area day at day 10 [gr/$cm^2$] | 32 |
| N 6 mM; seed yield/leaf blade [gr/$cm^2$] | 33 |
| N 6 mM; N level/FW | 34 |
| N 6 mM; DW/N level [gr/SPAD unit] | 35 |
| N 6 mM; N level/DW (SPAD unit/gr plant) | 36 |
| N 6 mM; Seed yield/N unit [gr/SPAD unit] | 37 |

Table 4. "N" = Nitrogen at the noted concentrations; "gr." = grams; "SPAD" = chlorophyll levels; "t50" = time where 50% of plants flowered; "gr/SPAD unit" = plant biomass expressed in grams per unit of nitrogen in plant measured by SPAD. "DW" = plant dry weight; "N level/DW" = plant Nitrogen level measured in SPAD unit per plant biomass [gr]; "DW/N level" = plant biomass per plant [gr]/SPAD unit;

Assessment of NUE, yield components and vigor-related parameters—Ten Arabidopsis ecotypes were grown in trays, each containing 8 plants per plot, in a greenhouse with controlled temperature conditions for about 12 weeks. Plants were irrigated with different nitrogen concentration as described above depending on the treatment applied. During this time, data was collected documented and analyzed. Most of chosen parameters were analyzed by digital imaging.

Digital imaging—Greenhouse assay

An image acquisition system, which consists of a digital reflex camera (Canon EOS 400D) attached with a 55 mm focal length lens (Canon EF-S series) placed in a custom made Aluminum mount, was used for capturing images of plants planted in containers within an environmental controlled greenhouse. The image capturing process is repeated every 2-3 days starting at day 9-12 till day 16-19 (respectively) from transplanting.

An image processing system was used, which consists of a personal desktop computer (Intel P4 3.0 GHz processor) and a public domain program—ImageJ 1.37, Java based image processing software, which was developed at the U.S. National Institutes of Health and is freely available on the internet at Hypertext Transfer Protocol://rsbweb (dot) nih (dot) gov/. Images were captured in resolution of 10 Mega Pixels (3888×2592 pixels) and stored in a low compression JPEG (Joint Photographic Experts Group standard) format. Next, image processing output data was saved to text files and analyzed using the JMP statistical analysis software (SAS institute).

Leaf analysis—Using the digital analysis leaves data was calculated, including leaf number, leaf blade area, Rosette diameter and area.

Relative growth area rate: The relative growth rate of the rosette and the leaves was calculated according to Formula II as described above.

Seed yield and 1000 seeds weight—At the end of the experiment all seeds from all plots were collected and weighed in order to measure seed yield per plant in terms of total seed weight per plant (gr). For the calculation of 1000 seed weight, an average weight of 0.02 grams was measured from each sample, the seeds were scattered on a glass tray and a picture was taken. Using the digital analysis, the number of seeds in each sample was calculated.

Dry weight and seed yield—At the end of the experiment, plant were harvested and left to dry at 30° C. in a drying chamber. The biomass was separated from the seeds, weighed and divided by the number of plants. Dry weight=total weight of the vegetative portion above ground (excluding roots) after drying at 30° C. in a drying chamber.

Harvest Index—The harvest index was calculated using Formula IV as described above.

$T_{50}$ days to flowering—Each of the repeats was monitored for flowering date. Days of flowering was calculated from sowing date till 50% of the plots flowered.

Plant nitrogen level—The chlorophyll content of leaves is a good indicator of the nitrogen plant status since the degree of leaf greenness is highly correlated to this parameter. Chlorophyll content was determined using a Minolta SPAD 502 chlorophyll meter and measurement was performed at time of flowering. SPAD meter readings were done on young fully developed leaf. Three measurements per leaf were taken per plot. Based on this measurement, parameters such as the ratio between seed yield per nitrogen unit [seed yield/N level=seed yield per plant [gr]/SPAD unit], plant DW per nitrogen unit [DW/N level=plant biomass per plant [g]/SPAD unit], and nitrogen level per gram of biomass [N level/DW=SPAD unit/plant biomass per plant (gr)] were calculated.

Percent of seed yield reduction—measures the amount of seeds obtained in plants when grown under nitrogen-limiting conditions compared to seed yield produced at normal nitrogen levels expressed in %.

Experimental Results 10 different *Arabidopsis* accessions (ecotypes) were grown and characterized for 37 parameters as described above. The average for each of the measured parameters was calculated using the JMP software and values are summarized in Table 5 below. Subsequent correlation analysis between the various transcriptom sets (Table 3) and the measured parameters was conducted (Tables 6 and 7 below). Following are the results integrated to the database.

TABLE 5

Measured parameters in *Arabidopsis* accessions

| Treatment | Ecotype | | | | | | | | | |
|---|---|---|---|---|---|---|---|---|---|---|
| | Line-1 | Line-2 | Line-3 | Line-4 | Line-5 | Line-6 | Line-7 | Line-8 | Line-9 | Line-10 |
| N 1.5 mM; Rosette Area at day 8 | 0.760 | 0.709 | 1.061 | 1.157 | 0.996 | 1.000 | 0.910 | 0.942 | 1.118 | 0.638 |
| N 1.5 mM; Rosette Area at day 10 | 1.430 | 1.325 | 1.766 | 1.971 | 1.754 | 1.832 | 1.818 | 1.636 | 1.996 | 1.150 |
| N 1.5 mM; Plot Coverage % at day 8 | 3.221 | 3.003 | 4.497 | 4.902 | 4.220 | 4.238 | 3.858 | 3.990 | 4.738 | 2.705 |
| N 1.5 mM; Plot Coverage % at day 10 | 6.058 | 5.614 | 7.484 | 8.351 | 7.432 | 7.764 | 7.702 | 6.933 | 8.458 | 4.871 |
| N 1.5 mM; Leaf Number at day 10 | 6.875 | 7.313 | 7.313 | 7.875 | 7.938 | 7.750 | 7.625 | 7.188 | 8.625 | 5.929 |
| N 1.5 mM; Leaf Blade Area at day 10 | 0.335 | 0.266 | 0.374 | 0.387 | 0.373 | 0.370 | 0.386 | 0.350 | 0.379 | 0.307 |
| N 1.5 mM; RGR of Rosette Area at day 3 | 0.631 | 0.793 | 0.502 | 0.491 | 0.605 | 0.720 | 0.825 | 0.646 | 0.668 | 0.636 |
| N 1.5 mM; t50 Flowering [day] | 15.967 | 20.968 | 14.836 | 24.708 | 23.566 | 23.698 | 18.059 | 19.488 | 23.568 | 21.888 |
| N 1.5 mM; Dry Weight [gr/plant] | 0.164 | 0.124 | 0.082 | 0.113 | 0.184 | 0.124 | 0.134 | 0.106 | 0.148 | 0.171 |
| N 1.5 mM; Seed Yield [gr/plant] | 0.032 | 0.025 | 0.023 | 0.010 | 0.006 | 0.009 | 0.032 | 0.019 | 0.012 | 0.014 |
| N 1.5 mM; Harvest Index | 0.192 | 0.203 | 0.295 | 0.085 | 0.031 | 0.071 | 0.241 | 0.179 | 0.081 | 0.079 |
| N 1.5 mM; 1000 Seeds weight[gr] | 0.016 | 0.016 | 0.018 | 0.014 | 0.018 | 0.022 | 0.015 | 0.014 | 0.022 | 0.019 |
| N 1.5 mM; seed yield/rosette area day at day 10 | 0.022 | 0.019 | 0.014 | 0.005 | 0.003 | 0.005 | 0.018 | 0.013 | 0.007 | 0.012 |
| N 1.5 mM; seed yield/leaf blade | 0.095 | 0.095 | 0.063 | 0.026 | 0.015 | 0.024 | 0.084 | 0.059 | 0.034 | 0.044 |
| N 1.5 mM; % Seed yield reduction compared to 6 mM | 72.559 | 84.701 | 78.784 | 87.996 | 91.820 | 92.622 | 76.710 | 81.938 | 91.301 | 85.757 |

TABLE 5-continued

Measured parameters in *Arabidopsis* accessions

| Treatment | Ecotype | | | | | | | | | |
|---|---|---|---|---|---|---|---|---|---|---|
| | Line-1 | Line-2 | Line-3 | Line-4 | Line-5 | Line-6 | Line-7 | Line-8 | Line-9 | Line-10 |
| N 1.5 mM; % Biomass reduction compared to 6 mM | 60.746 | 76.706 | 78.560 | 78.140 | 62.972 | 78.641 | 73.192 | 83.068 | 77.190 | 70.120 |
| N 1.5 mM; Spad/FW | 45.590 | | | 42.108 | 28.151 | | 53.111 | | | 67.000 |
| N 1.5 mM; SPAD/DW | 167.300 | | | 241.061 | 157.823 | | 194.977 | | | 169.343 |
| N 1.5 mM; DW/SPAD | 0.006 | | | 0.004 | 0.006 | | 0.005 | | | 0.006 |
| N 1.5 mM; seed yield/spad | 0.001 | | | 0.000 | 0.000 | | 0.001 | | | 0.000 |
| N 6 mM; Rosette Area at day 8 | 0.759 | 0.857 | 1.477 | 1.278 | 1.224 | 1.095 | 1.236 | 1.094 | 1.410 | 0.891 |
| N 6 mM; Rosette Area at day 10 | 1.406 | 1.570 | 2.673 | 2.418 | 2.207 | 2.142 | 2.474 | 1.965 | 2.721 | 1.642 |
| N 6 mM; Plot Coverage % at day 8 | 3.216 | 3.631 | 6.259 | 5.413 | 5.187 | 4.641 | 5.236 | 4.634 | 5.974 | 3.774 |
| N 6 mM; Plot Coverage % at day 10 | 5.957 | 6.654 | 11.324 | 10.244 | 9.352 | 9.076 | 10.485 | 8.327 | 11.528 | 6.958 |
| N 6 mM; Leaf Number at day 10 | 6.250 | 7.313 | 8.063 | 8.750 | 8.063 | 8.750 | 8.375 | 7.125 | 9.438 | 6.313 |
| N 6 mM; Leaf Blade Area at day 10 | 0.342 | 0.315 | 0.523 | 0.449 | 0.430 | 0.430 | 0.497 | 0.428 | 0.509 | 0.405 |
| N 6 mM; RGR of Rosette Area at day 3 | 0.689 | 1.024 | 0.614 | 0.601 | 0.477 | 0.651 | 0.676 | 0.584 | 0.613 | 0.515 |
| N 6 mM; t50 Flowering [day] | 16.371 | 20.500 | 14.635 | 24.000 | 23.378 | 23.595 | 15.033 | 19.750 | 22.887 | 18.804 |
| N 6 mM; Dry Weight [gr/plant] | 0.419 | 0.531 | 0.382 | 0.518 | 0.496 | 0.579 | 0.501 | 0.628 | 0.649 | 0.573 |
| N 6 mM; Seed Yield [gr/plant] | 0.116 | 0.165 | 0.108 | 0.082 | 0.068 | 0.119 | 0.139 | 0.107 | 0.138 | 0.095 |
| N 6 mM; Harvest Index | 0.280 | 0.309 | 0.284 | 0.158 | 0.136 | 0.206 | 0.276 | 0.171 | 0.212 | 0.166 |
| N 6 mM; 1000 Seeds weight[gr] | 0.015 | 0.017 | 0.018 | 0.012 | 0.016 | 0.016 | 0.015 | 0.014 | 0.017 | 0.016 |
| N 6 mM; seed yield/ rosette area day at day 10 | 0.082 | 0.106 | 0.041 | 0.034 | 0.031 | 0.056 | 0.057 | 0.055 | 0.051 | 0.058 |
| N 6 mM; seed yield/leaf blade | 0.339 | 0.526 | 0.207 | 0.183 | 0.158 | 0.277 | 0.281 | 0.252 | 0.271 | 0.235 |
| N 6 mM; Spad/FW | 22.489 | | | 28.268 | 17.641 | | 33.323 | | | 39.003 |
| N 6 mM; DW/SPAD (biomass/N unit) | 0.019 | | | 0.018 | 0.028 | | 0.015 | | | 0.015 |
| N 6 mM; spad/DW (gN/g plant) | 53.705 | | | 54.625 | 35.548 | | 66.479 | | | 68.054 |

TABLE 5-continued

Measured parameters in *Arabidopsis* accessions

| Treatment | Ecotype | | | | | | | | | |
|---|---|---|---|---|---|---|---|---|---|---|
| | Line-1 | Line-2 | Line-3 | Line-4 | Line-5 | Line-6 | Line-7 | Line-8 | Line-9 | Line-10 |
| N 6 mM; Seed yield/N unit | 0.004 | | | 0.003 | 0.002 | | 0.005 | | | 0.003 |

Table 5.
Provided are the measured parameters under various treatments in various ecotypes (*Arabidopsis* accessions).

TABLE 6

Correlation between the expression level of selected LNU genes of some embodiments of the invention in various tissues and the phenotypic performance under normal or low nitrogen fertilization conditions across *Arabidopsis* accessions

| Gene Name | R | P value | Exp. set | Correl. Set ID | Gene Name | R | P value | Exp. set | Correl. Set ID |
|---|---|---|---|---|---|---|---|---|---|
| LNU1 | 0.78 | 7.86E−03 | A | 6 | LNU182 | 0.73 | 1.70E−02 | A | 8 |
| LNU1 | 0.76 | 1.80E−02 | C | 5 | LNU182 | 0.75 | 1.20E−02 | A | 8 |
| LNU1 | 0.75 | 1.33E−02 | A | 2 | LNU182 | 0.75 | 2.09E−02 | C | 8 |
| LNU1 | 0.80 | 4.98E−03 | A | 1 | LNU182 | 0.76 | 1.04E−02 | C | 8 |
| LNU1 | 0.74 | 1.35E−02 | A | 1 | LNU182 | 0.84 | 2.12E−03 | B | 24 |
| LNU1 | 0.72 | 2.87E−02 | C | 1 | LNU182 | 0.81 | 4.08E−03 | B | 24 |
| LNU1 | 0.83 | 3.20E−03 | B | 25 | LNU182 | 0.91 | 6.63E−04 | D | 24 |
| LNU1 | 0.83 | 2.96E−03 | B | 21 | LNU182 | 0.78 | 8.39E−03 | D | 24 |
| LNU1 | 0.86 | 1.27E−03 | B | 20 | LNU182 | 0.75 | 1.17E−02 | B | 27 |
| LNU1 | 0.97 | 4.77E−03 | B | 35 | LNU182 | 0.73 | 1.66E−02 | B | 27 |
| LNU1 | 0.91 | 3.24E−02 | B | 35 | LNU182 | 0.79 | 6.67E−03 | D | 27 |
| LNU123 | 0.90 | 3.72E−02 | A | 18 | LNU183 | 0.80 | 5.90E−03 | C | 10 |
| LNU123 | 0.89 | 4.05E−02 | B | 35 | LNU183 | 0.80 | 5.89E−03 | C | 14 |
| LNU124 | 0.87 | 9.30E−04 | A | 11 | LNU183 | 0.79 | 6.13E−03 | C | 13 |
| LNU124 | 0.81 | 7.91E−03 | C | 11 | LNU183 | 0.71 | 2.06E−02 | B | 31 |
| LNU124 | 0.91 | 2.70E−04 | C | 11 | LNU183 | 0.80 | 5.94E−03 | D | 30 |
| LNU124 | 0.72 | 1.95E−02 | A | 10 | LNU183 | 0.72 | 2.94E−02 | D | 32 |
| LNU124 | 0.91 | 2.78E−04 | A | 10 | LNU184 | 0.87 | 1.08E−03 | C | 11 |
| LNU124 | 0.83 | 6.08E−03 | C | 10 | LNU184 | 0.89 | 4.09E−02 | C | 19 |
| LNU124 | 0.89 | 6.50E−04 | C | 10 | LNU184 | 0.88 | 4.83E−02 | B | 37 |
| LNU124 | 0.96 | 9.63E−03 | A | 19 | LNU184 | 0.93 | 1.98E−02 | B | 37 |
| LNU124 | 0.98 | 2.55E−03 | C | 19 | LNU184 | 0.93 | 2.08E−02 | D | 37 |
| LNU124 | 0.84 | 2.31E−03 | A | 14 | LNU184 | 0.89 | 4.04E−02 | B | 36 |
| LNU124 | 0.75 | 1.96E−02 | C | 14 | LNU185 | 0.99 | 1.83E−03 | C | 18 |
| LNU124 | 0.89 | 5.45E−04 | C | 14 | LNU186 | 0.72 | 1.88E−02 | C | 15 |
| LNU124 | 0.86 | 1.25E−03 | A | 13 | LNU186 | 0.84 | 2.46E−03 | C | 8 |
| LNU124 | 0.79 | 1.20E−02 | C | 13 | LNU186 | 0.73 | 1.71E−02 | D | 27 |
| LNU124 | 0.85 | 2.04E−03 | C | 13 | LNU187 | 0.82 | 6.47E−03 | D | 26 |
| LNU124 | 0.81 | 4.19E−03 | B | 30 | LNU187 | 0.74 | 2.18E−02 | D | 33 |
| LNU124 | 0.89 | 6.61E−04 | D | 30 | LNU187 | 0.88 | 4.65E−02 | B | 37 |
| LNU124 | 0.92 | 2.79E−02 | B | 37 | LNU206 | 0.72 | 1.82E−02 | C | 16 |
| LNU124 | 0.94 | 1.63E−02 | D | 37 | LNU206 | 0.71 | 2.02E−02 | C | 16 |
| LNU125 | 0.76 | 1.06E−02 | A | 11 | LNU206 | 0.71 | 2.05E−02 | A | 2 |
| LNU125 | 0.72 | 1.80E−02 | A | 11 | LNU206 | 0.84 | 2.24E−03 | A | 1 |
| LNU125 | 0.81 | 4.61E−03 | A | 10 | LNU206 | 0.82 | 3.92E−03 | A | 1 |
| LNU125 | 0.83 | 3.17E−03 | A | 10 | LNU206 | 0.75 | 1.24E−02 | B | 20 |
| LNU125 | 0.84 | 4.66E−03 | C | 10 | LNU206 | 0.72 | 1.90E−02 | B | 20 |
| LNU125 | 0.95 | 1.30E−02 | A | 19 | LNU207 | 0.79 | 6.36E−03 | A | 11 |
| LNU125 | 0.88 | 4.88E−02 | C | 19 | LNU210 | 0.73 | 2.64E−02 | C | 11 |
| LNU125 | 0.82 | 3.78E−03 | A | 14 | LNU210 | 0.74 | 1.36E−02 | A | 10 |
| LNU125 | 0.78 | 7.43E−03 | A | 14 | LNU210 | 0.70 | 2.33E−02 | A | 10 |
| LNU125 | 0.83 | 5.88E−03 | C | 14 | LNU210 | 0.74 | 1.38E−02 | A | 14 |
| LNU125 | 0.72 | 1.84E−02 | A | 13 | LNU210 | 0.73 | 1.67E−02 | A | 14 |
| LNU125 | 0.72 | 1.96E−02 | A | 13 | LNU210 | 0.72 | 1.87E−02 | A | 14 |
| LNU125 | 0.82 | 6.30E−03 | C | 13 | LNU210 | 0.78 | 8.31E−03 | A | 13 |
| LNU125 | 0.82 | 3.37E−03 | B | 30 | LNU210 | 0.74 | 1.45E−02 | A | 13 |
| LNU125 | 0.92 | 1.78E−04 | B | 30 | LNU210 | 0.73 | 1.62E−02 | A | 13 |
| LNU125 | 0.71 | 2.11E−02 | D | 30 | LNU210 | 0.74 | 1.49E−02 | B | 30 |
| LNU125 | 0.79 | 5.99E−03 | B | 26 | LNU210 | 0.71 | 2.18E−02 | B | 30 |
| LNU125 | 0.78 | 7.61E−03 | B | 29 | LNU211 | 0.82 | 3.68E−03 | C | 15 |
| LNU125 | 0.78 | 8.34E−03 | B | 29 | LNU211 | 0.77 | 9.05E−03 | C | 15 |
| LNU125 | 0.91 | 3.07E−02 | B | 37 | LNU211 | 0.89 | 5.65E−04 | C | 8 |
| LNU125 | 0.91 | 3.16E−02 | B | 37 | LNU211 | 0.84 | 2.25E−03 | C | 8 |
| LNU126 | 0.77 | 9.60E−03 | A | 11 | LNU211 | 0.80 | 4.99E−03 | D | 27 |
| LNU126 | 0.76 | 1.13E−02 | C | 11 | LNU211 | 0.77 | 8.96E−03 | D | 27 |

TABLE 6-continued

Correlation between the expression level of selected LNU genes of some embodiments of the invention in various tissues and the phenotypic performance under normal or low nitrogen fertilization conditions across *Arabidopsis* accessions

| Gene Name | R | P value | Exp. set | Correl. Set ID | Gene Name | R | P value | Exp. set | Correl. Set ID |
|---|---|---|---|---|---|---|---|---|---|
| LNU126 | 0.87 | 1.01E−03 | A | 10 | LNU213 | 0.75 | 1.26E−02 | C | 9 |
| LNU126 | 0.74 | 2.28E−02 | C | 10 | LNU213 | 0.76 | 1.07E−02 | A | 8 |
| LNU126 | 0.93 | 1.08E−04 | C | 10 | LNU213 | 0.75 | 1.17E−02 | B | 27 |
| LNU126 | 0.92 | 2.83E−02 | C | 19 | LNU215 | 0.80 | 5.41E−03 | A | 11 |
| LNU126 | 0.83 | 3.21E−03 | A | 14 | LNU215 | 0.77 | 9.84E−03 | A | 11 |
| LNU126 | 0.72 | 3.00E−02 | C | 14 | LNU215 | 0.85 | 1.72E−03 | C | 11 |
| LNU126 | 0.94 | 4.77E−05 | C | 14 | LNU215 | 0.75 | 1.16E−02 | C | 11 |
| LNU126 | 0.87 | 1.05E−03 | A | 13 | LNU215 | 0.76 | 1.09E−02 | A | 7 |
| LNU126 | 0.78 | 1.31E−02 | C | 13 | LNU215 | 0.74 | 1.49E−02 | A | 7 |
| LNU126 | 0.95 | 3.71E−05 | C | 13 | LNU215 | 0.90 | 3.85E−04 | A | 10 |
| LNU126 | 0.94 | 1.81E−02 | A | 17 | LNU215 | 0.89 | 6.05E−04 | A | 10 |
| LNU126 | 0.74 | 1.35E−02 | B | 30 | LNU215 | 0.77 | 8.62E−03 | C | 10 |
| LNU126 | 0.88 | 9.14E−04 | D | 30 | LNU215 | 0.91 | 3.00E−02 | A | 19 |
| LNU126 | 0.72 | 1.94E−02 | D | 32 | LNU215 | 0.91 | 3.33E−02 | A | 19 |
| LNU126 | 0.91 | 3.13E−02 | B | 36 | LNU215 | 0.95 | 1.52E−02 | C | 19 |
| LNU127 | 0.73 | 1.55E−02 | A | 12 | LNU215 | 0.90 | 4.04E−04 | A | 14 |
| LNU127 | 0.81 | 4.57E−03 | A | 11 | LNU215 | 0.87 | 9.88E−04 | A | 14 |
| LNU127 | 0.87 | 2.17E−03 | C | 11 | LNU215 | 0.86 | 1.39E−03 | A | 13 |
| LNU127 | 0.81 | 8.03E−03 | C | 11 | LNU215 | 0.84 | 2.45E−03 | A | 13 |
| LNU127 | 0.74 | 1.49E−02 | C | 11 | LNU215 | 0.90 | 4.13E−04 | B | 30 |
| LNU127 | 0.85 | 3.93E−03 | C | 10 | LNU215 | 0.82 | 3.99E−03 | B | 30 |
| LNU127 | 0.75 | 1.95E−02 | C | 10 | LNU215 | 0.71 | 2.18E−02 | B | 26 |
| LNU127 | 0.79 | 6.97E−03 | C | 10 | LNU218 | 0.82 | 7.15E−03 | C | 11 |
| LNU127 | 0.90 | 3.54E−02 | A | 19 | LNU218 | 0.74 | 2.21E−02 | C | 11 |
| LNU127 | 0.92 | 2.63E−02 | C | 19 | LNU218 | 0.70 | 2.31E−02 | C | 11 |
| LNU127 | 0.79 | 1.13E−02 | C | 14 | LNU218 | 0.73 | 1.75E−02 | A | 14 |
| LNU127 | 0.77 | 9.09E−03 | C | 14 | LNU218 | 0.74 | 1.42E−02 | A | 14 |
| LNU127 | 0.80 | 9.01E−03 | C | 13 | LNU218 | 0.72 | 2.72E−02 | C | 14 |
| LNU127 | 0.78 | 7.52E−03 | C | 13 | LNU218 | 0.74 | 1.41E−02 | C | 14 |
| LNU127 | 0.73 | 1.73E−02 | C | 13 | LNU218 | 0.75 | 1.19E−02 | A | 13 |
| LNU127 | 0.89 | 4.17E−02 | A | 17 | LNU218 | 0.76 | 1.05E−02 | A | 13 |
| LNU127 | 0.76 | 1.08E−02 | B | 30 | LNU218 | 0.72 | 3.01E−02 | C | 13 |
| LNU127 | 0.83 | 5.36E−03 | D | 30 | LNU218 | 0.78 | 7.56E−03 | C | 13 |
| LNU127 | 0.81 | 7.93E−03 | D | 30 | LNU219 | 0.79 | 6.18E−03 | C | 16 |
| LNU127 | 0.90 | 3.61E−02 | B | 37 | LNU219 | 0.74 | 1.41E−02 | C | 16 |
| LNU127 | 0.89 | 4.37E−02 | B | 36 | LNU219 | 0.78 | 7.39E−03 | A | 2 |
| LNU127 | 0.92 | 2.87E−02 | B | 34 | LNU219 | 0.76 | 1.13E−02 | A | 2 |
| LNU128 | 0.77 | 9.80E−03 | A | 11 | LNU219 | 0.81 | 4.95E−03 | A | 1 |
| LNU128 | 0.76 | 1.13E−02 | A | 11 | LNU219 | 0.79 | 6.02E−03 | A | 1 |
| LNU128 | 0.81 | 4.54E−03 | C | 11 | LNU219 | 0.97 | 4.90E−03 | A | 17 |
| LNU128 | 0.72 | 1.85E−02 | A | 10 | LNU219 | 0.96 | 8.96E−03 | A | 17 |
| LNU128 | 0.97 | 7.59E−03 | A | 19 | LNU219 | 0.74 | 2.26E−02 | D | 25 |
| LNU128 | 0.95 | 1.40E−02 | A | 19 | LNU219 | 0.74 | 2.40E−02 | D | 25 |
| LNU128 | 0.96 | 1.12E−02 | C | 19 | LNU219 | 0.74 | 1.35E−02 | B | 24 |
| LNU128 | 0.79 | 6.18E−03 | B | 30 | LNU219 | 0.71 | 2.14E−02 | B | 24 |
| LNU128 | 0.73 | 1.73E−02 | B | 30 | LNU219 | 0.78 | 1.40E−02 | D | 24 |
| LNU128 | 0.80 | 9.72E−03 | D | 30 | LNU219 | 0.77 | 1.45E−02 | D | 24 |
| LNU128 | 0.79 | 1.22E−02 | D | 29 | LNU219 | 0.74 | 1.53E−02 | D | 24 |
| LNU128 | 0.91 | 3.39E−02 | B | 37 | LNU219 | 0.73 | 1.76E−02 | D | 24 |
| LNU128 | 0.96 | 1.03E−02 | B | 37 | LNU219 | 0.78 | 7.47E−03 | B | 21 |
| LNU129 | 0.74 | 1.46E−02 | A | 16 | LNU219 | 0.72 | 1.97E−02 | B | 21 |
| LNU129 | 0.70 | 2.35E−02 | A | 16 | LNU219 | 0.78 | 1.36E−02 | D | 21 |
| LNU129 | 0.82 | 6.97E−03 | C | 11 | LNU219 | 0.77 | 1.46E−02 | D | 21 |
| LNU129 | 0.81 | 4.89E−03 | C | 11 | LNU219 | 0.72 | 1.83E−02 | B | 20 |
| LNU129 | 0.79 | 5.99E−03 | C | 11 | LNU219 | 0.70 | 2.31E−02 | B | 20 |
| LNU129 | 0.79 | 1.12E−02 | C | 10 | LNU219 | 0.75 | 1.30E−02 | B | 20 |
| LNU129 | 0.73 | 2.65E−02 | C | 14 | LNU225 | 0.76 | 1.15E−02 | A | 12 |
| LNU129 | 0.73 | 2.56E−02 | C | 13 | LNU225 | 0.71 | 2.08E−02 | A | 5 |
| LNU129 | 0.95 | 1.29E−02 | A | 17 | LNU225 | 0.71 | 2.22E−02 | A | 5 |
| LNU129 | 0.94 | 1.61E−02 | A | 17 | LNU225 | 0.79 | 6.89E−03 | A | 2 |
| LNU129 | 0.92 | 2.87E−02 | A | 17 | LNU225 | 0.82 | 4.02E−03 | A | 2 |
| LNU129 | 0.73 | 2.48E−02 | D | 30 | LNU225 | 0.80 | 5.59E−03 | A | 2 |
| LNU130 | 0.87 | 1.05E−03 | A | 11 | LNU225 | 0.78 | 8.33E−03 | A | 2 |
| LNU130 | 0.92 | 1.88E−04 | A | 10 | LNU225 | 0.80 | 1.03E−02 | C | 2 |
| LNU130 | 0.96 | 1.13E−02 | A | 19 | LNU225 | 0.77 | 1.50E−02 | C | 2 |
| LNU130 | 0.89 | 4.83E−04 | A | 14 | LNU225 | 0.76 | 1.06E−02 | C | 2 |
| LNU130 | 0.89 | 5.74E−04 | A | 13 | LNU225 | 0.74 | 1.49E−02 | C | 2 |
| LNU130 | 0.85 | 1.96E−03 | B | 30 | LNU225 | 0.73 | 1.76E−02 | C | 2 |
| LNU130 | 0.78 | 8.11E−03 | D | 26 | LNU225 | 0.75 | 1.22E−02 | A | 1 |
| LNU130 | 0.73 | 1.70E−02 | D | 33 | LNU225 | 0.75 | 1.30E−02 | A | 1 |
| LNU130 | 0.97 | 6.99E−03 | B | 37 | LNU225 | 0.74 | 2.23E−02 | C | 1 |
| LNU131 | 0.77 | 8.68E−03 | A | 6 | LNU225 | 0.73 | 1.66E−02 | C | 1 |

TABLE 6-continued

Correlation between the expression level of selected LNU genes of some embodiments of the invention in various tissues and the phenotypic performance under normal or low nitrogen fertilization conditions across *Arabidopsis* accessions

| Gene Name | R | P value | Exp. set | Correl. Set ID | Gene Name | R | P value | Exp. set | Correl. Set ID |
|---|---|---|---|---|---|---|---|---|---|
| LNU131 | 0.75 | 1.26E−02 | A | 6 | LNU225 | 0.99 | 7.77E−04 | A | 17 |
| LNU131 | 0.81 | 4.74E−03 | A | 2 | LNU225 | 0.95 | 1.23E−02 | A | 17 |
| LNU131 | 0.80 | 5.22E−03 | A | 2 | LNU225 | 0.98 | 2.52E−03 | A | 17 |
| LNU131 | 0.86 | 1.29E−03 | A | 1 | LNU225 | 0.98 | 2.54E−03 | A | 17 |
| LNU131 | 0.82 | 3.59E−03 | A | 1 | LNU225 | 0.99 | 5.55E−04 | C | 17 |
| LNU131 | 0.92 | 2.64E−02 | A | 17 | LNU225 | 0.99 | 1.27E−03 | C | 17 |
| LNU131 | 0.88 | 4.64E−02 | A | 17 | LNU225 | 0.89 | 4.56E−02 | C | 17 |
| LNU131 | 0.81 | 4.18E−03 | B | 25 | LNU225 | 0.82 | 3.45E−03 | B | 24 |
| LNU131 | 0.74 | 1.40E−02 | B | 25 | LNU225 | 0.80 | 5.23E−03 | B | 24 |
| LNU131 | 0.82 | 3.65E−03 | B | 24 | LNU225 | 0.82 | 3.67E−03 | B | 24 |
| LNU131 | 0.70 | 2.33E−02 | B | 24 | LNU225 | 0.75 | 1.23E−02 | B | 24 |
| LNU131 | 0.84 | 2.46E−03 | B | 21 | LNU225 | 0.75 | 1.26E−02 | B | 24 |
| LNU131 | 0.75 | 1.16E−02 | B | 21 | LNU225 | 0.78 | 1.24E−02 | D | 24 |
| LNU131 | 0.79 | 6.07E−03 | B | 20 | LNU225 | 0.83 | 3.21E−03 | D | 24 |
| LNU131 | 0.74 | 1.36E−02 | B | 20 | LNU225 | 0.81 | 4.76E−03 | D | 24 |
| LNU131 | 0.95 | 1.41E−02 | B | 35 | LNU225 | 0.77 | 8.51E−03 | D | 24 |
| LNU131 | 0.91 | 3.29E−02 | B | 35 | LNU234 | 0.92 | 1.64E−04 | A | 11 |
| LNU132 | 0.94 | 3.82E−05 | A | 11 | LNU234 | 0.76 | 1.03E−02 | A | 11 |
| LNU132 | 0.72 | 2.85E−02 | C | 11 | LNU234 | 0.83 | 2.68E−03 | C | 11 |
| LNU132 | 0.78 | 8.12E−03 | C | 11 | LNU234 | 0.83 | 3.05E−03 | C | 11 |
| LNU132 | 0.72 | 1.81E−02 | A | 10 | LNU234 | 0.80 | 5.47E−03 | A | 10 |
| LNU132 | 0.84 | 2.47E−03 | A | 10 | LNU234 | 0.85 | 3.92E−03 | C | 10 |
| LNU132 | 0.79 | 6.66E−03 | C | 10 | LNU234 | 0.97 | 5.68E−03 | A | 19 |
| LNU132 | 0.94 | 1.85E−02 | A | 19 | LNU234 | 0.97 | 6.49E−03 | C | 19 |
| LNU132 | 0.76 | 1.00E−02 | A | 14 | LNU234 | 0.96 | 1.08E−02 | C | 19 |
| LNU132 | 0.72 | 1.84E−02 | C | 14 | LNU234 | 0.81 | 8.21E−03 | C | 14 |
| LNU132 | 0.74 | 1.49E−02 | A | 13 | LNU234 | 0.81 | 8.76E−03 | C | 13 |
| LNU132 | 0.74 | 1.44E−02 | C | 13 | LNU234 | 0.94 | 1.95E−02 | A | 17 |
| LNU132 | 0.72 | 1.89E−02 | B | 30 | LNU234 | 0.89 | 4.23E−02 | A | 17 |
| LNU132 | 0.89 | 4.59E−02 | B | 37 | LNU234 | 0.90 | 3.87E−02 | C | 17 |
| LNU132 | 0.97 | 7.13E−03 | B | 37 | LNU234 | 0.90 | 8.60E−04 | D | 30 |
| LNU133 | 0.76 | 1.12E−02 | A | 7 | LNU234 | 0.79 | 1.05E−02 | D | 30 |
| LNU133 | 0.71 | 2.03E−02 | A | 7 | LNU234 | 0.87 | 1.12E−03 | D | 30 |
| LNU133 | 0.81 | 7.58E−03 | C | 7 | LNU234 | 0.82 | 4.00E−02 | D | 30 |
| LNU133 | 0.81 | 4.47E−03 | C | 7 | LNU234 | 0.83 | 5.75E−03 | D | 29 |
| LNU133 | 0.82 | 3.45E−03 | B | 29 | LNU234 | 0.76 | 1.69E−02 | D | 29 |
| LNU133 | 0.77 | 9.67E−03 | B | 29 | LNU234 | 0.75 | 2.09E−02 | D | 29 |
| LNU133 | 0.85 | 3.64E−03 | D | 29 | LNU234 | 0.74 | 2.30E−02 | D | 32 |
| LNU133 | 0.79 | 7.02E−03 | D | 29 | LNU234 | 0.72 | 2.75E−02 | D | 33 |
| LNU133 | 0.89 | 4.18E−02 | D | 37 | LNU234 | 0.97 | 6.94E−03 | B | 37 |
| LNU134 | 0.70 | 2.42E−02 | A | 12 | LNU234 | 0.95 | 1.25E−02 | D | 37 |
| LNU134 | 0.74 | 1.39E−02 | A | 7 | LNU234 | 0.89 | 4.04E−02 | D | 37 |
| LNU134 | 0.73 | 1.69E−02 | A | 7 | LNU234 | 0.91 | 3.01E−02 | D | 36 |
| LNU134 | 0.75 | 2.08E−02 | C | 7 | LNU235 | 0.74 | 1.44E−02 | A | 11 |
| LNU134 | 0.72 | 1.85E−02 | C | 2 | LNU235 | 0.73 | 1.66E−02 | A | 11 |
| LNU134 | 0.98 | 2.66E−03 | A | 17 | LNU235 | 0.76 | 1.06E−02 | C | 11 |
| LNU134 | 0.73 | 2.51E−02 | D | 30 | LNU235 | 0.73 | 1.70E−02 | A | 10 |
| LNU134 | 0.80 | 5.04E−03 | B | 24 | LNU235 | 0.73 | 1.75E−02 | A | 14 |
| LNU134 | 0.83 | 3.21E−03 | B | 24 | LNU235 | 0.73 | 2.43E−02 | C | 14 |
| LNU134 | 0.76 | 1.85E−02 | D | 24 | LNU235 | 0.78 | 8.39E−03 | A | 13 |
| LNU134 | 0.83 | 2.67E−03 | D | 24 | LNU235 | 0.79 | 1.20E−02 | D | 30 |
| LNU134 | 0.77 | 9.31E−03 | B | 26 | LNU235 | 0.86 | 2.99E−03 | D | 26 |
| LNU134 | 0.79 | 6.09E−03 | B | 26 | LNU235 | 0.83 | 5.85E−03 | D | 32 |
| LNU134 | 0.86 | 3.03E−03 | D | 26 | LNU235 | 0.84 | 4.39E−03 | D | 33 |
| LNU134 | 0.80 | 5.60E−03 | D | 26 | LNU24 | 0.71 | 2.18E−02 | A | 11 |
| LNU134 | 0.82 | 3.60E−03 | B | 29 | LNU24 | 0.85 | 1.97E−03 | A | 11 |
| LNU134 | 0.79 | 6.62E−03 | B | 29 | LNU24 | 0.78 | 7.95E−03 | C | 11 |
| LNU134 | 0.87 | 2.40E−03 | D | 29 | LNU24 | 0.71 | 2.01E−02 | A | 10 |
| LNU134 | 0.72 | 1.96E−02 | D | 29 | LNU24 | 0.73 | 1.60E−02 | A | 10 |
| LNU134 | 0.71 | 2.04E−02 | B | 32 | LNU24 | 0.79 | 1.15E−02 | C | 10 |
| LNU134 | 0.86 | 1.49E−03 | B | 32 | LNU24 | 0.93 | 2.40E−02 | A | 19 |
| LNU134 | 0.85 | 3.42E−03 | D | 32 | LNU24 | 0.77 | 9.72E−03 | A | 8 |
| LNU134 | 0.86 | 1.25E−03 | D | 32 | LNU24 | 0.73 | 1.73E−02 | B | 27 |
| LNU134 | 0.82 | 3.64E−03 | B | 33 | LNU242 | 0.82 | 3.31E−03 | A | 7 |
| LNU134 | 0.89 | 5.09E−04 | B | 33 | LNU242 | 0.71 | 2.09E−02 | A | 7 |
| LNU134 | 0.91 | 7.35E−04 | D | 33 | LNU242 | 0.88 | 1.66E−03 | C | 7 |
| LNU134 | 0.89 | 5.29E−04 | D | 33 | LNU242 | 0.71 | 2.27E−02 | C | 7 |
| LNU135 | 0.85 | 1.71E−03 | A | 11 | LNU242 | 0.70 | 3.46E−02 | C | 10 |
| LNU135 | 0.72 | 1.90E−02 | A | 10 | LNU242 | 0.91 | 3.06E−02 | C | 17 |
| LNU135 | 0.93 | 2.21E−02 | C | 17 | LNU242 | 0.85 | 1.63E−03 | B | 29 |
| LNU136 | 0.79 | 6.32E−03 | A | 11 | LNU242 | 0.81 | 4.09E−03 | B | 29 |
| LNU136 | 0.96 | 7.92E−03 | A | 17 | LNU242 | 0.83 | 6.09E−03 | D | 29 |

TABLE 6-continued

Correlation between the expression level of selected LNU genes of some embodiments of the invention in various tissues and the phenotypic performance under normal or low nitrogen fertilization conditions across *Arabidopsis* accessions

| Gene Name | R | P value | Exp. set | Correl. Set ID | Gene Name | R | P value | Exp. set | Correl. Set ID |
|---|---|---|---|---|---|---|---|---|---|
| LNU136 | 0.95 | 1.21E−02 | A | 17 | LNU242 | 0.87 | 9.49E−04 | D | 29 |
| LNU136 | 0.90 | 3.77E−02 | C | 17 | LNU247 | 0.78 | 8.28E−03 | A | 12 |
| LNU136 | 0.78 | 1.41E−02 | D | 30 | LNU247 | 0.85 | 1.84E−03 | A | 12 |
| LNU136 | 0.88 | 8.99E−04 | B | 26 | LNU247 | 0.75 | 1.94E−02 | C | 12 |
| LNU136 | 0.80 | 5.26E−03 | B | 33 | LNU247 | 0.80 | 4.99E−03 | C | 12 |
| LNU136 | 0.93 | 2.21E−02 | D | 37 | LNU249 | 0.70 | 2.28E−02 | A | 11 |
| LNU14 | 0.92 | 2.50E−02 | C | 17 | LNU249 | 0.85 | 3.90E−03 | C | 7 |
| LNU14 | 0.72 | 1.89E−02 | B | 25 | LNU249 | 0.87 | 1.07E−03 | A | 10 |
| LNU14 | 0.91 | 3.18E−02 | D | 36 | LNU249 | 0.95 | 1.35E−02 | A | 19 |
| LNU140 | 0.93 | 2.06E−02 | C | 18 | LNU249 | 0.95 | 1.78E−05 | A | 14 |
| LNU140 | 0.81 | 7.85E−03 | C | 7 | LNU249 | 0.92 | 1.31E−04 | A | 13 |
| LNU140 | 0.97 | 7.30E−03 | A | 19 | LNU249 | 0.83 | 2.68E−03 | B | 30 |
| LNU140 | 0.77 | 9.73E−03 | A | 8 | LNU249 | 0.82 | 6.70E−03 | D | 30 |
| LNU140 | 0.85 | 1.72E−03 | B | 26 | LNU249 | 0.75 | 1.88E−02 | D | 30 |
| LNU140 | 0.74 | 1.42E−02 | B | 29 | LNU249 | 0.71 | 2.07E−02 | B | 26 |
| LNU140 | 0.78 | 1.24E−02 | D | 29 | LNU249 | 0.81 | 4.45E−03 | B | 26 |
| LNU140 | 0.81 | 4.46E−03 | B | 32 | LNU249 | 0.80 | 9.94E−03 | D | 26 |
| LNU140 | 0.75 | 2.12E−02 | D | 32 | LNU249 | 0.80 | 5.30E−03 | B | 29 |
| LNU140 | 0.89 | 5.19E−04 | B | 33 | LNU249 | 0.74 | 1.42E−02 | B | 29 |
| LNU140 | 0.76 | 1.65E−02 | D | 33 | LNU249 | 0.82 | 7.33E−03 | D | 29 |
| LNU140 | 0.96 | 1.09E−02 | B | 37 | LNU249 | 0.81 | 8.47E−03 | D | 29 |
| LNU140 | 0.75 | 1.26E−02 | B | 27 | LNU249 | 0.80 | 5.30E−03 | B | 32 |
| LNU15 | 0.70 | 2.30E−02 | A | 9 | LNU249 | 0.85 | 1.90E−03 | B | 32 |
| LNU170 | 0.74 | 1.40E−02 | A | 12 | LNU249 | 0.74 | 2.31E−02 | D | 32 |
| LNU170 | 0.76 | 1.66E−02 | C | 12 | LNU249 | 0.82 | 3.37E−03 | B | 33 |
| LNU170 | 0.73 | 1.71E−02 | A | 16 | LNU249 | 0.83 | 3.29E−03 | B | 33 |
| LNU170 | 0.73 | 1.59E−02 | C | 16 | LNU249 | 0.79 | 1.18E−02 | D | 33 |
| LNU170 | 0.82 | 4.00E−03 | A | 2 | LNU249 | 0.90 | 3.49E−02 | B | 37 |
| LNU170 | 0.79 | 6.10E−03 | A | 2 | LNU250 | 0.78 | 7.39E−03 | A | 11 |
| LNU170 | 0.80 | 9.44E−03 | C | 2 | LNU250 | 0.71 | 2.17E−02 | A | 7 |
| LNU170 | 0.79 | 6.07E−03 | C | 2 | LNU250 | 0.79 | 6.58E−03 | A | 10 |
| LNU170 | 0.88 | 8.83E−04 | A | 1 | LNU250 | 0.95 | 3.35E−05 | A | 10 |
| LNU170 | 0.88 | 6.87E−04 | A | 1 | LNU250 | 0.91 | 3.18E−02 | A | 19 |
| LNU170 | 0.84 | 4.72E−03 | C | 1 | LNU250 | 0.97 | 6.08E−03 | A | 19 |
| LNU170 | 0.87 | 9.86E−04 | C | 1 | LNU250 | 0.83 | 2.77E−03 | A | 14 |
| LNU170 | 0.81 | 8.77E−03 | D | 25 | LNU250 | 0.93 | 7.59E−05 | A | 14 |
| LNU170 | 0.74 | 1.45E−02 | D | 25 | LNU250 | 0.83 | 2.76E−03 | A | 13 |
| LNU170 | 0.81 | 4.61E−03 | B | 24 | LNU250 | 0.92 | 1.63E−04 | A | 13 |
| LNU170 | 0.78 | 8.26E−03 | B | 24 | LNU250 | 0.70 | 3.50E−02 | C | 13 |
| LNU170 | 0.73 | 1.72E−02 | B | 24 | LNU250 | 0.80 | 5.53E−03 | B | 30 |
| LNU170 | 0.80 | 9.62E−03 | D | 24 | LNU250 | 0.78 | 7.75E−03 | B | 29 |
| LNU170 | 0.78 | 7.72E−03 | D | 24 | LNU250 | 0.71 | 2.09E−02 | B | 29 |
| LNU170 | 0.80 | 5.86E−03 | B | 21 | LNU250 | 0.82 | 3.82E−03 | B | 32 |
| LNU170 | 0.81 | 4.63E−03 | B | 21 | LNU250 | 0.75 | 1.17E−02 | B | 33 |
| LNU170 | 0.90 | 9.72E−04 | D | 21 | LNU250 | 0.91 | 3.17E−02 | B | 37 |
| LNU170 | 0.86 | 1.38E−03 | D | 21 | LNU250 | 0.95 | 1.24E−02 | B | 37 |
| LNU170 | 0.80 | 5.15E−03 | B | 20 | LNU251 | 0.75 | 1.32E−02 | A | 6 |
| LNU170 | 0.84 | 2.62E−03 | B | 20 | LNU251 | 0.79 | 6.02E−03 | A | 2 |
| LNU170 | 0.90 | 1.04E−03 | D | 20 | LNU251 | 0.72 | 1.96E−02 | A | 1 |
| LNU170 | 0.89 | 6.02E−04 | D | 20 | LNU251 | 0.73 | 1.68E−02 | B | 24 |
| LNU175 | 0.80 | 5.82E−03 | A | 11 | LNU251 | 0.92 | 2.57E−02 | B | 35 |
| LNU175 | 0.90 | 3.34E−04 | C | 11 | LNU254 | 0.84 | 2.37E−03 | C | 15 |
| LNU175 | 0.98 | 3.47E−03 | C | 19 | LNU254 | 0.88 | 8.39E−04 | C | 8 |
| LNU175 | 0.93 | 2.38E−02 | D | 37 | LNU254 | 0.82 | 4.01E−03 | D | 27 |
| LNU175 | 0.88 | 4.60E−02 | B | 36 | LNU255 | 0.78 | 8.00E−03 | A | 10 |
| LNU175 | 0.91 | 2.97E−02 | B | 34 | LNU255 | 0.89 | 4.54E−02 | A | 19 |
| LNU177 | 0.75 | 1.21E−02 | A | 11 | LNU255 | 0.91 | 3.16E−02 | A | 17 |
| LNU177 | 0.73 | 1.66E−02 | C | 11 | LNU255 | 0.96 | 8.73E−03 | B | 37 |
| LNU177 | 0.73 | 1.68E−02 | C | 10 | LNU255 | 0.99 | 5.16E−04 | B | 36 |
| LNU177 | 0.79 | 6.51E−03 | B | 31 | LNU255 | 0.92 | 2.49E−02 | B | 34 |
| LNU177 | 0.86 | 1.60E−03 | D | 30 | LNU255 | 0.91 | 3.34E−02 | B | 34 |
| LNU177 | 0.77 | 9.90E−03 | D | 32 | LNU256 | 0.76 | 1.78E−02 | C | 11 |
| LNU179 | 0.80 | 5.62E−03 | A | 11 | LNU256 | 0.78 | 7.59E−03 | A | 5 |
| LNU179 | 0.87 | 9.87E−04 | A | 11 | LNU256 | 0.78 | 1.32E−02 | D | 31 |
| LNU179 | 0.90 | 4.59E−04 | C | 11 | LNU256 | 0.71 | 2.19E−02 | D | 30 |
| LNU179 | 0.76 | 1.15E−02 | A | 10 | LNU256 | 0.71 | 2.05E−02 | B | 24 |
| LNU179 | 0.92 | 1.92E−04 | A | 10 | LNU257 | 0.85 | 1.75E−03 | C | 11 |
| LNU179 | 0.72 | 1.95E−02 | C | 10 | LNU257 | 0.74 | 1.43E−02 | A | 7 |
| LNU179 | 0.96 | 1.11E−02 | A | 19 | LNU257 | 0.73 | 1.70E−02 | A | 7 |
| LNU179 | 0.91 | 3.44E−02 | C | 19 | LNU257 | 0.82 | 4.07E−03 | C | 10 |
| LNU179 | 0.84 | 2.27E−03 | A | 14 | LNU257 | 0.90 | 3.65E−02 | C | 19 |
| LNU179 | 0.83 | 2.82E−03 | A | 13 | LNU257 | 0.82 | 3.37E−03 | C | 14 |

TABLE 6-continued

Correlation between the expression level of selected LNU genes of some embodiments
of the invention in various tissues and the phenotypic performance under normal or
low nitrogen fertilization conditions across *Arabidopsis* accessions

| Gene Name | R | P value | Exp. set | Correl. Set ID | Gene Name | R | P value | Exp. set | Correl. Set ID |
|---|---|---|---|---|---|---|---|---|---|
| LNU179 | 0.97 | 6.67E−03 | B | 37 | LNU257 | 0.83 | 2.91E−03 | C | 13 |
| LNU180 | 0.79 | 6.02E−03 | A | 7 | LNU257 | 0.81 | 4.78E−03 | D | 30 |
| LNU180 | 0.76 | 1.04E−02 | A | 7 | LNU258 | 0.75 | 1.31E−02 | A | 11 |
| LNU180 | 0.72 | 1.92E−02 | A | 10 | LNU258 | 0.79 | 6.36E−03 | C | 11 |
| LNU180 | 0.77 | 1.46E−02 | C | 10 | LNU258 | 0.76 | 1.01E−02 | A | 10 |
| LNU180 | 0.91 | 3.24E−02 | A | 19 | LNU258 | 0.80 | 5.41E−03 | C | 10 |
| LNU180 | 0.93 | 1.99E−02 | A | 19 | LNU258 | 0.92 | 2.45E−02 | C | 19 |
| LNU180 | 0.92 | 2.57E−02 | A | 19 | LNU258 | 0.79 | 6.92E−03 | A | 14 |
| LNU180 | 0.70 | 2.41E−02 | A | 14 | LNU258 | 0.87 | 1.11E−03 | C | 14 |
| LNU180 | 0.74 | 2.29E−02 | C | 13 | LNU258 | 0.83 | 2.76E−03 | A | 13 |
| LNU180 | 0.92 | 2.74E−02 | A | 17 | LNU258 | 0.86 | 1.56E−03 | C | 13 |
| LNU180 | 0.86 | 1.55E−03 | B | 29 | LNU258 | 0.76 | 1.09E−02 | D | 30 |
| LNU180 | 0.81 | 4.45E−03 | B | 29 | LNU260 | 0.86 | 1.39E−03 | C | 11 |
| LNU180 | 0.99 | 2.08E−03 | B | 37 | LNU260 | 0.91 | 2.73E−04 | C | 10 |
| LNU180 | 0.88 | 4.67E−02 | B | 37 | LNU260 | 0.93 | 2.34E−02 | C | 19 |
| LNU180 | 0.98 | 4.69E−03 | B | 36 | LNU260 | 0.88 | 7.70E−04 | C | 14 |
| LNU180 | 0.89 | 4.53E−02 | B | 34 | LNU260 | 0.84 | 2.42E−03 | C | 13 |
| LNU181 | 0.72 | 1.80E−02 | A | 2 | LNU260 | 0.78 | 8.14E−03 | D | 30 |
| LNU181 | 0.80 | 5.37E−03 | A | 1 | LNU260 | 0.97 | 7.52E−03 | D | 37 |
| LNU181 | 0.74 | 1.46E−02 | A | 15 | LNU261 | 0.75 | 1.20E−02 | A | 12 |
| LNU181 | 0.82 | 4.04E−03 | B | 24 | LNU261 | 0.75 | 1.32E−02 | A | 12 |
| LNU181 | 0.75 | 1.29E−02 | B | 21 | LNU261 | 0.83 | 2.88E−03 | A | 6 |
| LNU181 | 0.76 | 1.05E−02 | B | 20 | LNU261 | 0.78 | 7.38E−03 | A | 1 |
| LNU181 | 0.91 | 3.17E−02 | B | 35 | LNU261 | 0.73 | 2.66E−02 | D | 31 |
| LNU182 | 0.71 | 3.32E−02 | C | 11 | LNU261 | 0.71 | 3.36E−02 | D | 31 |
| LNU182 | 0.71 | 2.09E−02 | A | 6 | LNU261 | 0.71 | 2.24E−02 | B | 25 |
| LNU182 | 0.79 | 6.26E−03 | A | 5 | LNU261 | 0.71 | 2.04E−02 | B | 24 |
| LNU182 | 0.71 | 2.28E−02 | A | 5 | LNU261 | 0.80 | 5.03E−03 | B | 21 |
| LNU182 | 0.97 | 8.06E−06 | C | 5 | LNU261 | 0.84 | 2.50E−03 | B | 20 |
| LNU182 | 0.78 | 7.68E−03 | C | 5 | LNU261 | 0.94 | 1.78E−02 | B | 35 |
| LNU182 | 0.78 | 7.95E−03 | A | 2 | LNU262 | 0.83 | 3.15E−03 | A | 12 |
| LNU182 | 0.79 | 6.72E−03 | A | 2 | LNU262 | 0.78 | 1.34E−02 | C | 2 |
| LNU182 | 0.80 | 1.04E−02 | C | 2 | LNU262 | 0.79 | 6.53E−03 | A | 15 |
| LNU182 | 0.72 | 1.96E−02 | C | 2 | LNU262 | 0.80 | 5.50E−03 | A | 15 |
| LNU182 | 0.76 | 1.14E−02 | A | 1 | LNU262 | 0.73 | 1.62E−02 | C | 15 |
| LNU182 | 0.77 | 8.53E−03 | A | 1 | LNU262 | 0.72 | 1.97E−02 | A | 8 |
| LNU182 | 0.75 | 2.05E−02 | C | 1 | LNU262 | 0.88 | 8.15E−04 | A | 8 |
| LNU182 | 0.71 | 2.03E−02 | C | 1 | LNU262 | 0.85 | 1.74E−03 | C | 8 |
| LNU182 | 0.77 | 8.65E−03 | A | 15 | LNU262 | 0.81 | 7.58E−03 | D | 24 |
| LNU182 | 0.75 | 1.33E−02 | A | 15 | LNU262 | 0.70 | 2.37E−02 | B | 27 |
| LNU182 | 0.82 | 6.29E−03 | C | 15 | LNU262 | 0.85 | 2.02E−03 | B | 27 |
| LNU182 | 0.82 | 3.37E−03 | C | 15 | LNU8 | 0.75 | 2.09E−02 | C | 5 |

Table 6.
"Correl. Set ID"—correlation set ID according to the correlated parameters Table above.

TABLE 7

Correlation between the expression level of selected LNU orthologs genes of some
embodiments of the invention in various tissues and the phenotypic performance
under normal or low nitrogen fertilization conditions across *Arabidopsis* accessions

| Gene Name | R | P value | Exp. Set | Correl. Set ID | Gene Name | R | P value | Exp. Set | Correl. Set ID |
|---|---|---|---|---|---|---|---|---|---|
| LNU219_H1 | 0.88 | 6.94E−04 | B | 12 | LNU45_H11 | 0.91 | 3.06E−02 | A | 17 |
| LNU76_H3 | 0.77 | 9.83E−03 | B | 12 | LNU46_H3 | 0.89 | 4.47E−02 | A | 17 |
| LNU219_H1 | 0.71 | 2.17E−02 | B | 15 | LNU46_H3 | 0.91 | 3.04E−02 | B | 36 |
| LNU256_H0 | 0.96 | 1.14E−02 | B | 17 | LNU219_H1 | 0.76 | 1.66E−02 | D | 27 |
| LNU219_H1 | 0.79 | 7.10E−03 | C | 15 | LNU219_H1 | 0.78 | 7.31E−03 | C | 27 |
| LNU76_H3 | 0.74 | 1.45E−02 | B | 31 | LNU7_H5 | 0.96 | 9.76E−03 | B | 35 |
| LNU76_H3 | 0.70 | 2.40E−02 | B | 28 | LNU219_H1 | 0.76 | 1.77E−02 | D | 5 |
| LNU46_H5 | 0.73 | 1.67E−02 | B | 28 | LNU7_H5 | 0.70 | 3.41E−02 | D | 5 |
| LNU7_H5 | 0.70 | 2.32E−02 | A | 25 | LNU7_H4 | 0.79 | 1.08E−02 | D | 5 |
| LNU7_H4 | 0.83 | 2.75E−03 | A | 25 | LNU219_H1 | 0.70 | 3.47E−02 | D | 5 |
| LNU7_H4 | 0.80 | 5.94E−03 | C | 25 | LNU219_H1 | 0.71 | 3.13E−02 | D | 1 |
| LNU7_H4 | 0.71 | 2.13E−02 | A | 24 | LNU7_H5 | 0.70 | 3.42E−02 | D | 1 |
| LNU45_H9 | 0.78 | 7.80E−03 | C | 24 | LNU7_H5 | 0.70 | 3.56E−02 | D | 1 |
| LNU24_H2 | 0.90 | 4.44E−04 | B | 26 | LNU219_H1 | 0.79 | 1.17E−02 | D | 8 |

TABLE 7-continued

Correlation between the expression level of selected LNU orthologs genes of some embodiments of the invention in various tissues and the phenotypic performance under normal or low nitrogen fertilization conditions across Arabidopsis accessions

| Gene Name | R | P value | Exp. Set | Correl. Set ID | Gene Name | R | P value | Exp. Set | Correl. Set ID |
|---|---|---|---|---|---|---|---|---|---|
| LNU45_H11 | 0.90 | 4.44E−04 | B | 26 | LNU7_H5 | 0.95 | 1.43E−02 | B | 35 |
| LNU7_H4 | 0.73 | 1.61E−02 | C | 21 | LNU45_H10 | 0.74 | 1.53E−02 | C | 12 |
| LNU7_H4 | 0.75 | 1.18E−02 | C | 20 | LNU76_H3 | 0.73 | 1.56E−02 | C | 9 |
| LNU24_H2 | 0.76 | 1.07E−02 | B | 32 | LNU74_H8 | 0.96 | 8.06E−03 | C | 18 |
| LNU45_H11 | 0.76 | 1.07E−02 | B | 32 | LNU74_H8 | 0.90 | 3.70E−02 | C | 18 |
| LNU24_H2 | 0.86 | 1.39E−03 | B | 33 | LNU76_H3 | 0.90 | 3.91E−02 | C | 18 |
| LNU45_H11 | 0.86 | 1.39E−03 | B | 33 | LNU45_H10 | 0.90 | 3.58E−02 | C | 18 |
| LNU219_H1 | 0.87 | 1.13E−03 | A | 12 | LNU45_H12 | 0.98 | 4.31E−03 | C | 18 |
| LNU7_H4 | 0.82 | 3.80E−03 | A | 6 | LNU256_H0 | 0.71 | 2.03E−02 | C | 11 |
| LNU7_H4 | 0.78 | 7.67E−03 | A | 6 | LNU76_H3 | 0.70 | 2.40E−02 | C | 11 |
| LNU45_H10 | 0.89 | 5.71E−04 | A | 6 | LNU46_H3 | 0.82 | 3.49E−03 | C | 6 |
| LNU45_H9 | 0.73 | 1.76E−02 | A | 5 | LNU45_H9 | 0.71 | 2.22E−02 | C | 5 |
| LNU7_H4 | 0.74 | 1.45E−02 | A | 2 | LNU45_H9 | 0.82 | 3.70E−03 | C | 2 |
| LNU45_H10 | 0.86 | 1.29E−03 | A | 2 | LNU7_H4 | 0.96 | 1.02E−02 | B | 35 |
| LNU45_H9 | 0.80 | 5.07E−03 | A | 2 | LNU219_H1 | 0.89 | 5.64E−04 | C | 8 |
| LNU7_H4 | 0.70 | 2.32E−02 | A | 1 | LNU74_H8 | 0.90 | 3.55E−02 | B | 35 |
| LNU45_H10 | 0.89 | 5.60E−04 | A | 1 | LNU45_H10 | 0.93 | 2.43E−02 | B | 35 |
| LNU45_H9 | 0.74 | 1.49E−02 | A | 1 | LNU45_H10 | 0.91 | 3.00E−02 | B | 35 |
| LNU7_H4 | 0.98 | 2.32E−03 | A | 17 | LNU46_H3 | 0.94 | 1.79E−02 | B | 35 |
|  |  |  |  |  | LNU181_H0 | 0.95 | 1.14E−02 | A | 35 |

Table 7.
"Correl. Set ID"—correlation set ID according to the correlated parameters Table above.

Example 4

Production of Rice Transcriptom Using 44K Rice Oligonucleotide Micro-Array

In order to produce differential expression analysis of rice plants subjected to nitrogen limiting conditions compared to normal (non-limiting) nitrogen conditions, the present inventors have utilized a Rice oligonucleotide micro-array, produced by Agilent Technologies [Hypertext Transfer Protocol://World Wide Web (dot) chem. (dot) agilent (dot) com/Scripts/PDS (dot) asp?1 Page=50879]. The array oligonucleotide represents about 44,000 rice genes and transcripts.

Experimental Procedures

Rice plants grown under different nitrogen fertilization levels assessment—Five rice accessions were grown in 3 repetitive plots, each containing 10 plants, at a net house under semi-hydroponics conditions. Briefly, the growing protocol was as follows: Rice seeds were sown in trays filled with a mix of vermiculite and peat in a 1:1 ratio. Constant nitrogen limiting conditions were achieved by irrigating the plants with a solution containing 0.8 mM inorganic nitrogen in the form of $KNO_3$, supplemented with 1 mM $KH_2PO_4$, 1 mM $MgSO_4$, 3.6 mM $K_2SO_4$ and microelements, while normal nitrogen levels were achieved by applying a solution of 8 mM inorganic nitrogen also in the form of $KNO_3$ with 1 mM $KH_2PO_4$, 1 mM $MgSO_4$, and microelements.

Analyzed rice tissues—All 5 selected rice varieties were pooled in 1 batch per each treatment. Two tissues [leaves and roots] growing at two different nitrogen fertilization levels, 0.8 mM Nitrogen (nitrogen limiting conditions) or 8 mM Nitrogen (normal nitrogen conditions), were sampled and RNA was extracted as described above. For convenience, each micro-array expression information tissue type has received a Set ID as summarized in Table 8 below.

TABLE 8

Rice transcriptom experimental sets

| Expression Set | Set ID |
|---|---|
| Leaves at 0.8 mM Nitrogen fertilization | A |
| Leaves at 8 mM Nitrogen fertilization | B |
| Roots at 0.8 mM Nitrogen fertilization | C |
| Roots at 8 mM Nitrogen fertilization | D |

Table 8.

Experimental Results

Gene up-regulation under reduced nitrogen fertilization levels indicates the involvement of the genes in NUE improvement. LNU116, LNU117, LNU118, LNU119, LNU120, LNU216, LNU217 and LNU276 were upregulated in Set ID C compared to their expression level in Set ID D. In addition, LNU116, LNU121, LNU176, LNU216, LNU217, LNU276 were upregulated in Set ID A compared to their expression level in Set ID B.

Example 5

Production of Arabidopsis Transcriptom and High Throughput Correlation Analysis of Yield, Biomass and/or Vigor Related Parameters Using 44K Arabidopsis Full Genome Oligonucleotide Micro-Array To produce a high throughput correlation analysis comparing between plant phenotype and gene expression level, the present inventors utilized an Arabidopsis thaliana oligonucleotide micro-array, produced by Agilent Technologies [Hypertext Transfer Protocol://World Wide Web (dot) chem. (dot) agilent (dot) com/Scripts/PDS (dot) asp?1 Page=50879]. The array oligonucleotide represents about 40,000 A. thaliana genes and transcripts designed based on data from the TIGR ATH1 v.5 database and Arabidopsis MPSS (University of Delaware) databases. To define correlations between the levels of RNA expression and yield, biomass components or vigor related parameters, various plant characteristics of 15 different *Arabidopsis* ecotypes were analyzed. Among them, nine ecotypes encompassing the observed variance were selected for RNA expression analysis. The correlation between the RNA levels and the characterized parameters was analyzed using Pearson correlation test [Hypertext Transfer Protocol://World Wide Web (dot) davidmlane (dot) com/hyperstat/A34739 (dot) html].

Experimental Procedures

Analyzed *Arabidopsis* tissues—Five tissues at different developmental stages including root, leaf, flower at anthesis, seed at 5 days after flowering (DAF) and seed at 12 DAF, representing different plant characteristics, were sampled and RNA was extracted as described above. Each micro-array expression information tissue type has received a Set ID as summarized in Table 9 below.

TABLE 9

Tissues used for *Arabidopsis* transcriptom expression sets

| Expression Set | Set ID |
|---|---|
| Root | A |
| Leaf | B |
| Flower | C |
| Seed 5 DAF | D |
| Seed 12 DAF | E |

Table 9: Provided are the identification (ID) letters of each of the *Arabidopsis* expression sets (A-E). DAF = days after flowering.

Yield components and vigor related parameters assessment—Eight out of the nine *Arabidopsis* ecotypes were used in each of 5 repetitive blocks (named A, B, C, D and E), each containing 20 plants per plot. The plants were grown in a greenhouse at controlled conditions in 22° C., and the N:P:K fertilizer (20:20:20; weight ratios) [nitrogen (N), phosphorus (P) and potassium (K)] was added. During this time data was collected, documented and analyzed. Additional data was collected through the seedling stage of plants grown in a tissue culture in vertical grown transparent agar plates. Most of chosen parameters were analyzed by digital imaging.

Digital imaging in Tissue culture—A laboratory image acquisition system was used for capturing images of plantlets sawn in square agar plates. The image acquisition system consists of a digital reflex camera (Canon EOS 300D) attached to a 55 mm focal length lens (Canon EF-S series), mounted on a reproduction device (Kaiser RS), which included 4 light units (4×150 Watts light bulb) and located in a darkroom.

Digital imaging in Greenhouse—The image capturing process was repeated every 3-4 days starting at day 7 till day 30. The same camera attached to a 24 mm focal length lens (Canon EF series), placed in a custom made iron mount, was used for capturing images of larger plants sawn in white tubs in an environmental controlled greenhouse. The white tubs were square shape with measurements of 36×26.2 cm and 7.5 cm deep. During the capture process, the tubs were placed beneath the iron mount, while avoiding direct sun light and casting of shadows. This process was repeated every 3-4 days for up to 30 days.

An image analysis system was used, which consists of a personal desktop computer (Intel P43.0 GHz processor) and a public domain program—ImageJ 1.37, Java based image processing program, which was developed at the U.S. National Institutes of Health and is freely available on the internet at Hypertext Transfer Protocol://rsbweb (dot) nih (dot) gov/. Images were captured in resolution of 6 Mega Pixels (3072× 2048 pixels) and stored in a low compression JPEG (Joint Photographic Experts Group standard) format. Next, analyzed data was saved to text files and processed using the JMP statistical analysis software (SAS institute).

Leaf analysis—Using the digital analysis leaves data was calculated, including leaf number, area, perimeter, length and width. On day 30, 3-4 representative plants were chosen from each plot of blocks A, B and C. The plants were dissected, each leaf was separated and was introduced between two glass trays, a photo of each plant was taken and the various parameters (such as leaf total area, laminar length etc.) were calculated from the images. The blade circularity was calculated as laminar width divided by laminar length.

Root analysis—During 17 days, the different ecotypes were grown in transparent agar plates. The plates were photographed every 3 days starting at day 7 in the photography room and the roots development was documented (see examples in FIGS. 3A-F). The growth rate of roots was calculated according to Formula V.

Relative growth rate of root coverage=Regression coefficient of root coverage along time course.　　Formula V:

Vegetative growth rate analysis—was calculated according to Formula VI. The analysis was ended with the appearance of overlapping plants.

Relative vegetative growth rate area=Regression coefficient of vegetative area along time course.　　Formula VI For comparison between ecotypes the calculated rate was normalized using plant developmental stage as represented by the number of true leaves. In cases where plants with 8 leaves had been sampled twice (for example at day 10 and day 13), only the largest sample was chosen and added to the Anova comparison.

Seeds in siliques analysis—On day 70, 15-17 siliques were collected from each plot in blocks D and E. The chosen siliques were light brown color but still intact. The siliques were opened in the photography room and the seeds were scatter on a glass tray, a high resolution digital picture was taken for each plot. Using the images the number of seeds per silique was determined.

Seeds average weight—At the end of the experiment all seeds from plots of blocks A-C were collected. An average weight of 0.02 grams was measured from each sample, the seeds were scattered on a glass tray and a picture was taken. Using the digital analysis, the number of seeds in each sample was calculated.

Oil percentage in seeds—At the end of the experiment all seeds from plots of blocks A-C were collected. Columbia seeds from 3 plots were mixed grounded and then mounted onto the extraction chamber. 210 ml of n-Hexane (Cat No. 080951 Biolab Ltd.) were used as the solvent. The extraction was performed for 30 hours at medium heat 50° C. Once the extraction has ended the n-Hexane was evaporated using the evaporator at 35° C. and vacuum conditions. The process was repeated twice. The information gained from the Soxhlet extractor (Soxhlet, F. Die gewichtsanalytische Bestimmung des Milchfettes, Polytechnisches J. (Dingler's) 1879, 232, 461) was used to create a calibration curve for the Low Resonance NMR. The content of oil of all seed samples was determined using the Low Resonance NMR (MARAN Ultra—Oxford Instrument) and its MultiQuant software package.

Silique length analysis—On day 50 from sowing, 30 siliques from different plants in each plot were sampled in block A. The chosen siliques were green-yellow in color and were collected from the bottom parts of a grown plant's stem. A digital photograph was taken to determine silique's length.

Dry weight and seed yield—On day 80 from sowing, the plants from blocks A-C were harvested and left to dry at 30° C. in a drying chamber. The biomass and seed weight of each plot was separated, measured and divided by the number of plants. Dry weight=total weight of the vegetative portion above ground (excluding roots) after drying at 30° C. in a drying chamber; Seed yield per plant=total seed weight per plant (gr).

Oil yield—The oil yield was calculated using Formula VII.

Seed Oil yield=Seed yield per plant (gr)*Oil % in seed.   Formula VII:

Harvest Index (seed)—The harvest index was calculated using Formula IV (described above).

Experimental Results

Nine different *Arabidopsis* ecotypes were grown and characterized for 18 parameters (named as vectors).

TABLE 10

*Arabidopsis* correlated parameters (vectors)

| Correlated parameter with | Correlation ID |
|---|---|
| Root length day 13 (cm) | 1 |
| Root length day 7 (cm) | 2 |
| Relative root growth (cm/day) day 13 | 3 |
| Fresh weight per plant (gr) at bolting stage | 4 |
| Dry matter per plant (gr) | 5 |
| Vegetative growth rate (cm$^2$/day) till 8 true leaves | 6 |
| Blade circularity | 7 |
| Lamina width (cm) | 8 |
| Lamina length (cm) | 9 |
| Total leaf area per plant (cm) | 10 |
| 1000 Seed weight (gr) | 11 |
| Oil % per seed | 12 |
| Seeds per silique | 13 |
| Silique length (cm) | 14 |
| Seed yield per plant (gr) | 15 |
| Oil yield per plant (mg) | 16 |
| Harvest Index | 17 |
| Leaf width/length | 18 |

Table 10. Provided are the *Arabidopsis* correlated parameters (correlation ID Nos. 1-18). Abbreviations: Cm = centimeter(s); gr = gram(s); mg = milligram(s).

The characterized values are summarized in Tables 11 and 12 below.

TABLE 11

Measured parameters in *Arabidopsis* ecotypes

| Ecotype | 15 | 16 | 12 | 11 | 5 | 17 | 10 | 13 | 14 |
|---|---|---|---|---|---|---|---|---|---|
| An-1 | 0.34 | 118.63 | 34.42 | 0.0203 | 0.64 | 0.53 | 46.86 | 45.44 | 1.06 |
| Col-0 | 0.44 | 138.73 | 31.19 | 0.0230 | 1.27 | 0.35 | 109.89 | 53.47 | 1.26 |
| Ct-1 | 0.59 | 224.06 | 38.05 | 0.0252 | 1.05 | 0.56 | 58.36 | 58.47 | 1.31 |
| Cvi (N8580) | 0.42 | 116.26 | 27.76 | 0.0344 | 1.28 | 0.33 | 56.80 | 35.27 | 1.47 |
| Gr-6 | 0.61 | 218.27 | 35.49 | 0.0202 | 1.69 | 0.37 | 114.66 | 48.56 | 1.24 |
| Kondara | 0.43 | 142.11 | 32.91 | 0.0263 | 1.34 | 0.32 | 110.82 | 37.00 | 1.09 |
| Ler-1 | 0.36 | 114.15 | 31.56 | 0.0205 | 0.81 | 0.45 | 88.49 | 39.38 | 1.18 |
| Mt-0 | 0.62 | 190.06 | 30.79 | 0.0226 | 1.21 | 0.51 | 121.79 | 40.53 | 1.18 |
| Shakdara | 0.55 | 187.62 | 34.02 | 0.0235 | 1.35 | 0.41 | 93.04 | 25.53 | 1.00 |

Table 11.
Provided are the values of each of the parameters measured in *Arabidopsis* ecotypes:
15 = Seed yield per plant (gram);
16 = oil yield per plant (mg);
12 = oil % per seed;
11 = 1000 seed weight (gr);
5 = dry matter per plant (gr);
17 = harvest index;
10 = total leaf area per plant (cm);
13 = seeds per silique;
14 = Silique length (cm).

TABLE 12

Additional measured parameters in *Arabidopsis* ecotypes

| Ecotype | 6 | 3 | 2 | 1 | 4 | 9 | 8 | 18 | 7 |
|---|---|---|---|---|---|---|---|---|---|
| An-1 | 0.313 | 0.631 | 0.937 | 4.419 | 1.510 | 2.767 | 1.385 | 0.353 | 0.509 |
| Col-0 | 0.378 | 0.664 | 1.759 | 8.530 | 3.607 | 3.544 | 1.697 | 0.288 | 0.481 |
| Ct-1 | 0.484 | 1.176 | 0.701 | 5.621 | 1.935 | 3.274 | 1.460 | 0.316 | 0.450 |
| Cvi (N8580) | 0.474 | 1.089 | 0.728 | 4.834 | 2.082 | 3.785 | 1.374 | 0.258 | 0.370 |
| Gr-6 | 0.425 | 0.907 | 0.991 | 5.957 | 3.556 | 3.690 | 1.828 | 0.356 | 0.501 |
| Kondara | 0.645 | 0.774 | 1.163 | 6.372 | 4.338 | 4.597 | 1.650 | 0.273 | 0.376 |
| Ler-1 | 0.430 | 0.606 | 1.284 | 5.649 | 3.467 | 3.877 | 1.510 | 0.305 | 0.394 |

TABLE 12-continued

Additional measured parameters in *Arabidopsis* ecotypes

| | Ecotype | | | | | | | | |
|---|---|---|---|---|---|---|---|---|---|
| | 6 | 3 | 2 | 1 | 4 | 9 | 8 | 18 | 7 |
| Mt-0 | 0.384 | 0.701 | 1.414 | 7.060 | 3.479 | 3.717 | 1.817 | 0.335 | 0.491 |
| Shakdara | 0.471 | 0.782 | 1.251 | 7.041 | 3.710 | 4.149 | 1.668 | 0.307 | 0.409 |

Table 12.
Provided are the values of each of the parameters measured in *Arabidopsis* ecotypes:
6 = Vegetative growth rate (cm²/day) until 8 true leaves;
3 = relative root growth (cm/day) (day 13);
2 = Root length day 7 (cm);
1 = Root length day 13 (cm);
4 = fresh weight per plant (gr) at bolting stage;
9. = Lamima length (cm);
8 = Lamina width (cm);
18 = Leaf width/length;
7 = Blade circularity.

Tables 13 and 14 provide the correlation analyses.

TABLE 13

Correlation between the expression level of selected LNU genes of some embodiments of the invention in various tissues and the phenotypic performance under normal or low nitrogen fertilization conditions across *Arabidopsis* accessions

| Gene Name | R | P value | Exp. set | Corr. Set ID |
|---|---|---|---|---|
| LNU1 | 0.74 | 3.45E−02 | C | 5 |
| LNU1 | 0.83 | 2.02E−02 | D | 5 |
| LNU1 | 0.81 | 2.58E−02 | D | 8 |
| LNU1 | 0.77 | 4.08E−02 | D | 8 |
| LNU1 | 0.97 | 4.59E−05 | B | 3 |
| LNU1 | 0.88 | 4.21E−03 | B | 3 |
| LNU1 | 0.73 | 3.79E−02 | E | 3 |
| LNU1 | 0.92 | 1.10E−03 | A | 14 |
| LNU1 | 0.72 | 4.38E−02 | E | 14 |
| LNU123 | 0.87 | 4.82E−03 | E | 11 |
| LNU123 | 0.82 | 1.22E−02 | C | 6 |
| LNU124 | 0.73 | 3.90E−02 | E | 1 |
| LNU124 | 0.71 | 4.96E−02 | E | 1 |
| LNU125 | 0.79 | 2.07E−02 | A | 7 |
| LNU125 | 0.72 | 4.19E−02 | C | 13 |
| LNU125 | 0.85 | 7.49E−03 | A | 13 |
| LNU126 | 0.80 | 3.09E−02 | D | 3 |
| LNU127 | 0.82 | 2.36E−02 | D | 13 |
| LNU127 | 0.81 | 1.53E−02 | E | 6 |
| LNU129 | 0.74 | 3.42E−02 | C | 5 |
| LNU129 | 0.85 | 1.49E−02 | D | 17 |
| LNU129 | 0.79 | 2.04E−02 | C | 18 |
| LNU129 | 0.73 | 3.85E−02 | B | 12 |
| LNU129 | 0.77 | 2.60E−02 | B | 16 |
| LNU129 | 0.86 | 5.89E−03 | B | 3 |
| LNU129 | 0.82 | 1.25E−02 | B | 15 |
| LNU129 | 0.78 | 2.34E−02 | A | 14 |
| LNU132 | 0.82 | 1.26E−02 | E | 16 |
| LNU132 | 0.94 | 6.45E−04 | E | 15 |
| LNU133 | 0.80 | 3.06E−02 | D | 1 |
| LNU133 | 0.91 | 4.56E−03 | D | 1 |
| LNU134 | 0.78 | 2.26E−02 | B | 11 |
| LNU134 | 0.75 | 3.13E−02 | B | 14 |
| LNU135 | 0.76 | 4.61E−02 | D | 1 |
| LNU135 | 0.84 | 8.88E−03 | B | 6 |
| LNU135 | 0.74 | 3.45E−02 | E | 6 |
| LNU136 | 0.82 | 1.18E−02 | E | 5 |
| LNU136 | 0.79 | 1.85E−02 | C | 4 |
| LNU136 | 0.76 | 2.70E−02 | C | 8 |
| LNU136 | 0.71 | 4.69E−02 | A | 14 |
| LNU136 | 0.82 | 1.18E−02 | C | 10 |
| LNU14 | 0.72 | 4.41E−02 | A | 1 |
| LNU14 | 0.86 | 6.57E−03 | E | 11 |
| LNU14 | 0.75 | 3.20E−02 | B | 15 |
| LNU14 | 0.75 | 3.11E−02 | E | 14 |

TABLE 13-continued

Correlation between the expression level of selected LNU genes of some embodiments of the invention in various tissues and the phenotypic performance under normal or low nitrogen fertilization conditions across *Arabidopsis* accessions

| Gene Name | R | P value | Exp. set | Corr. Set ID |
|---|---|---|---|---|
| LNU140 | 0.71 | 4.67E−02 | C | 15 |
| LNU15 | 0.75 | 3.37E−02 | B | 12 |
| LNU15 | 0.95 | 2.59E−04 | B | 16 |
| LNU15 | 0.91 | 1.48E−03 | B | 15 |
| LNU170 | 0.85 | 7.15E−03 | C | 12 |
| LNU170 | 0.76 | 3.00E−02 | A | 12 |
| LNU170 | 0.75 | 3.30E−02 | C | 16 |
| LNU170 | 0.92 | 1.24E−03 | A | 16 |
| LNU170 | 0.79 | 1.86E−02 | E | 16 |
| LNU170 | 0.76 | 2.96E−02 | E | 3 |
| LNU170 | 0.87 | 4.80E−03 | A | 15 |
| LNU170 | 0.73 | 3.82E−02 | E | 15 |
| LNU175 | 0.81 | 1.49E−02 | A | 17 |
| LNU175 | 0.76 | 4.68E−02 | D | 18 |
| LNU177 | 0.90 | 5.47E−03 | D | 5 |
| LNU177 | 0.96 | 4.41E−04 | D | 8 |
| LNU177 | 0.71 | 4.99E−02 | B | 1 |
| LNU177 | 0.90 | 5.34E−03 | D | 10 |
| LNU178 | 0.82 | 1.26E−02 | C | 1 |
| LNU178 | 0.71 | 4.72E−02 | E | 13 |
| LNU179 | 0.83 | 1.14E−02 | E | 3 |
| LNU179 | 0.73 | 4.13E−02 | B | 11 |
| LNU179 | 0.78 | 2.32E−02 | E | 14 |
| LNU179 | 0.84 | 9.15E−03 | E | 6 |
| LNU181 | 0.75 | 3.03E−02 | B | 7 |
| LNU181 | 0.77 | 2.41E−02 | A | 14 |
| LNU183 | 0.80 | 1.68E−02 | E | 8 |
| LNU183 | 0.77 | 2.68E−02 | E | 10 |
| LNU184 | 0.73 | 3.79E−02 | A | 1 |
| LNU185 | 0.83 | 2.23E−02 | D | 16 |
| LNU185 | 0.77 | 4.27E−02 | D | 3 |
| LNU185 | 0.92 | 1.20E−03 | E | 11 |
| LNU185 | 0.75 | 3.22E−02 | B | 15 |
| LNU185 | 0.82 | 2.27E−02 | D | 15 |
| LNU186 | 0.79 | 1.88E−02 | C | 5 |
| LNU186 | 0.81 | 1.57E−02 | A | 5 |
| LNU186 | 0.80 | 1.59E−02 | E | 5 |
| LNU186 | 0.73 | 4.09E−02 | C | 4 |
| LNU186 | 0.80 | 1.77E−02 | A | 4 |
| LNU186 | 0.74 | 3.39E−02 | C | 9 |
| LNU186 | 0.75 | 3.24E−02 | A | 9 |
| LNU186 | 0.73 | 3.92E−02 | C | 8 |
| LNU186 | 0.82 | 1.17E−02 | A | 8 |
| LNU186 | 0.83 | 1.14E−02 | E | 3 |
| LNU186 | 0.71 | 4.90E−02 | C | 15 |
| LNU186 | 0.79 | 2.05E−02 | A | 10 |
| LNU186 | 0.72 | 4.50E−02 | C | 6 |

TABLE 13-continued

Correlation between the expression level of selected LNU genes of some embodiments of the invention in various tissues and the phenotypic performance under normal or low nitrogen fertilization conditions across *Arabidopsis* accessions

| Gene Name | R | P value | Exp. set | Corr. Set ID |
|---|---|---|---|---|
| LNU187 | 0.81 | 1.38E−02 | A | 9 |
| LNU187 | 0.77 | 2.40E−02 | E | 11 |
| LNU206 | 0.76 | 2.89E−02 | B | 3 |
| LNU207 | 0.83 | 1.08E−02 | E | 17 |
| LNU210 | 0.74 | 3.52E−02 | C | 16 |
| LNU210 | 0.89 | 2.97E−03 | B | 3 |
| LNU210 | 0.74 | 3.61E−02 | B | 11 |
| LNU211 | 0.92 | 1.22E−03 | B | 5 |
| LNU211 | 0.73 | 4.00E−02 | B | 8 |
| LNU212 | 0.85 | 7.78E−03 | A | 7 |
| LNU212 | 0.75 | 3.23E−02 | B | 5 |
| LNU212 | 0.72 | 4.52E−02 | C | 8 |
| LNU212 | 0.93 | 9.64E−04 | B | 8 |
| LNU212 | 0.77 | 2.59E−02 | C | 1 |
| LNU212 | 0.77 | 2.54E−02 | E | 11 |
| LNU212 | 0.77 | 2.63E−02 | B | 10 |
| LNU213 | 0.72 | 4.28E−02 | B | 7 |
| LNU213 | 0.86 | 6.08E−03 | E | 9 |
| LNU213 | 0.75 | 3.39E−02 | C | 3 |
| LNU213 | 0.88 | 3.77E−03 | A | 1 |
| LNU213 | 0.81 | 1.40E−02 | A | 1 |
| LNU213 | 0.85 | 1.66E−02 | D | 14 |
| LNU213 | 0.83 | 1.14E−02 | E | 6 |
| LNU214 | 0.73 | 4.08E−02 | C | 17 |
| LNU215 | 0.86 | 6.04E−03 | C | 3 |
| LNU215 | 0.77 | 2.68E−02 | B | 14 |
| LNU215 | 0.78 | 2.15E−02 | A | 6 |
| LNU218 | 0.81 | 1.53E−02 | A | 12 |
| LNU218 | 0.73 | 3.81E−02 | E | 6 |
| LNU219 | 0.71 | 4.78E−02 | B | 12 |
| LNU219 | 0.78 | 2.20E−02 | B | 16 |
| LNU219 | 0.71 | 4.98E−02 | B | 3 |
| LNU225 | 0.75 | 3.36E−02 | B | 7 |
| LNU225 | 0.81 | 1.58E−02 | C | 18 |
| LNU225 | 0.90 | 2.55E−03 | B | 18 |
| LNU225 | 0.83 | 1.03E−02 | A | 18 |
| LNU225 | 0.75 | 3.27E−02 | E | 18 |
| LNU23 | 0.90 | 2.05E−03 | C | 11 |
| LNU23 | 0.91 | 1.72E−03 | B | 11 |
| LNU234 | 0.71 | 4.90E−02 | E | 9 |
| LNU234 | 0.75 | 3.19E−02 | E | 6 |
| LNU24 | 0.73 | 4.05E−02 | A | 3 |
| LNU247 | 0.81 | 1.51E−02 | C | 13 |
| LNU249 | 0.74 | 3.73E−02 | B | 17 |
| LNU249 | 0.77 | 4.42E−02 | D | 17 |
| LNU249 | 0.75 | 3.35E−02 | E | 6 |
| LNU250 | 0.74 | 3.45E−02 | C | 7 |
| LNU250 | 0.74 | 3.67E−02 | E | 18 |
| LNU250 | 0.71 | 4.84E−02 | E | 12 |
| LNU250 | 0.78 | 2.20E−02 | A | 11 |
| LNU251 | 0.79 | 3.56E−02 | D | 7 |
| LNU251 | 0.85 | 8.12E−03 | B | 13 |
| LNU251 | 0.73 | 3.88E−02 | A | 13 |
| LNU251 | 0.78 | 2.12E−02 | A | 14 |
| LNU254 | 0.83 | 9.96E−03 | B | 5 |
| LNU254 | 0.78 | 2.20E−02 | B | 8 |
| LNU255 | 0.89 | 2.76E−03 | A | 1 |
| LNU256 | 0.79 | 1.85E−02 | E | 3 |
| LNU256 | 0.89 | 2.98E−03 | E | 11 |
| LNU256 | 0.73 | 4.18E−02 | B | 13 |
| LNU256 | 0.78 | 2.10E−02 | E | 14 |
| LNU258 | 0.75 | 3.08E−02 | C | 12 |
| LNU258 | 0.81 | 1.50E−02 | E | 16 |
| LNU258 | 0.83 | 9.93E−03 | E | 15 |
| LNU258 | 0.81 | 1.48E−02 | A | 13 |
| LNU260 | 0.85 | 1.52E−02 | D | 5 |
| LNU260 | 0.79 | 3.43E−02 | D | 8 |
| LNU260 | 0.74 | 3.40E−02 | C | 1 |
| LNU260 | 0.73 | 3.78E−02 | C | 1 |
| LNU260 | 0.83 | 1.10E−02 | E | 1 |
| LNU261 | 0.73 | 3.90E−02 | C | 9 |
| LNU261 | 0.76 | 2.98E−02 | B | 16 |
| LNU261 | 0.85 | 6.86E−03 | A | 1 |
| LNU261 | 0.82 | 2.29E−02 | D | 11 |
| LNU261 | 0.94 | 1.95E−03 | D | 6 |
| LNU262 | 0.77 | 4.15E−02 | D | 7 |
| LNU262 | 0.71 | 4.97E−02 | B | 5 |
| LNU262 | 0.71 | 4.67E−02 | E | 8 |
| LNU262 | 0.87 | 5.11E−03 | E | 16 |
| LNU262 | 0.94 | 4.36E−04 | E | 15 |
| LNU8 | 0.74 | 3.71E−02 | B | 3 |
| LNU8 | 0.84 | 8.67E−03 | A | 3 |
| LNU8 | 0.72 | 4.37E−02 | E | 1 |
| LNU8 | 0.72 | 4.38E−02 | A | 11 |

Table 13. "Correl. Set ID"—correlation set ID according to the correlated parameters Table above.

TABLE 14

Correlation between the expression level of selected LNU orthologs genes of some embodiments of the invention in various tissues and the phenotypic performance under normal or low nitrogen fertilization conditions across *Arabidopsis* accessions

| Gene Name | R | P value | Exp. Set | Correl. Set ID |
|---|---|---|---|---|
| LNU24_H1 | 0.75 | 3.13E−02 | C | 7 |
| LNU46_H3 | 0.75 | 3.24E−02 | C | 9 |
| LNU181_H0 | 0.71 | 4.84E−02 | C | 3 |
| LNU46_H5 | 0.87 | 4.72E−03 | C | 3 |
| LNU76_H3 | 0.76 | 2.75E−02 | C | 2 |
| LNU181_H0 | 0.75 | 3.05E−02 | B | 7 |
| LNU256_H0 | 0.84 | 9.66E−03 | B | 5 |
| LNU46_H4 | 0.73 | 3.78E−02 | B | 8 |
| LNU45_H9 | 0.73 | 4.02E−02 | B | 16 |
| LNU46_H4 | 0.76 | 2.91E−02 | B | 1 |
| LNU24_H0 | 0.74 | 3.72E−02 | B | 11 |
| LNU45_H9 | 0.77 | 2.55E−02 | B | 15 |
| LNU181_H0 | 0.85 | 6.93E−03 | B | 13 |
| LNU24_H0 | 0.73 | 3.87E−02 | B | 14 |
| LNU76_H3 | 0.89 | 3.16E−03 | B | 14 |
| LNU46_H3 | 0.73 | 3.97E−02 | B | 6 |
| LNU256_H0 | 0.77 | 2.56E−02 | A | 5 |
| LNU24_H1 | 0.71 | 4.63E−02 | A | 9 |
| LNU256_H0 | 0.88 | 3.57E−03 | A | 9 |
| LNU46_H4 | 0.85 | 8.11E−03 | A | 3 |
| LNU24_H1 | 0.74 | 3.45E−02 | A | 11 |
| LNU7_H4 | 0.71 | 4.64E−02 | A | 11 |
| LNU181_H0 | 0.75 | 3.26E−02 | A | 14 |
| LNU7_H5 | 0.80 | 1.74E−02 | A | 14 |
| LNU45_H12 | 0.76 | 2.91E−02 | A | 14 |
| LNU24_H1 | 0.80 | 1.77E−02 | A | 6 |
| LNU256_H0 | 0.76 | 2.90E−02 | A | 6 |
| LNU46_H3 | 0.72 | 4.43E−02 | E | 5 |
| LNU219_H1 | 0.77 | 2.49E−02 | E | 8 |
| LNU219_H1 | 0.80 | 1.69E−02 | E | 1 |
| LNU219_H1 | 0.81 | 1.39E−02 | E | 2 |
| LNU24_H0 | 0.86 | 5.99E−03 | E | 11 |
| LNU74_H8 | 0.88 | 3.96E−03 | E | 11 |
| LNU46_H4 | 0.76 | 2.94E−02 | E | 15 |
| LNU181_H0 | 0.84 | 9.43E−03 | E | 14 |
| LNU24_H0 | 0.83 | 1.09E−02 | E | 14 |
| LNU74_H8 | 0.77 | 2.54E−02 | E | 14 |
| LNU74_H9 | 0.76 | 2.93E−02 | E | 14 |
| LNU46_H3 | 0.71 | 4.67E−02 | E | 14 |
| LNU219_H1 | 0.81 | 1.43E−02 | E | 10 |
| LNU76_H3 | 0.88 | 9.64E−03 | D | 5 |
| LNU45_H10 | 0.89 | 6.71E−03 | D | 5 |
| LNU76_H3 | 0.87 | 1.09E−02 | D | 8 |
| LNU45_H10 | 0.95 | 9.46E−04 | D | 8 |

TABLE 14-continued

Correlation between the expression level of selected
LNU orthologs genes of some embodiments of the invention
in various tissues and the phenotypic performance under
normal or low nitrogen fertilization conditions across
*Arabidopsis* accessions

| Gene Name | R | P value | Exp. Set | Correl. Set ID |
|---|---|---|---|---|
| LNU46_H3 | 0.77 | 4.26E−02 | D | 8 |
| LNU45_H9 | 0.88 | 9.11E−03 | D | 2 |
| LNU74_H9 | 0.85 | 1.63E−02 | D | 11 |
| LNU45_H10 | 0.83 | 2.05E−02 | D | 10 |
| LNU45_H12 | 0.76 | 4.62E−02 | D | 6 |

Table 14. "Correl. Set ID"—correlation set ID according to the correlated parameters Table above.

Example 6

Production of Barley Transcriptom and High Throughput Correlation Analysis Using 44K Barley Oligonucleotide Micro-Array In order to produce a high throughput correlation analysis comparing between plant phenotype and gene expression level, the present inventors utilized a Barley oligonucleotide micro-array, produced by Agilent Technologies [Hypertext Transfer Protocol://World Wide Web (dot) chem. (dot) agilent (dot) com/Scripts/PDS (dot) asp?1 Page=50879]. The array oligonucleotide represents about 47,500 Barley genes and transcripts. In order to define correlations between the levels of RNA expression and yield or vigor related parameters, various plant characteristics of 25 different Barley accessions were analyzed. Among them, 13 accessions encompassing the observed variance were selected for RNA expression analysis. The correlation between the RNA levels and the characterized parameters was analyzed using Pearson correlation test [Hypertext Transfer Protocol://World Wide Web (dot) davidmlane (dot) com/hyperstat/A34739 (dot) html].

Experimental Procedures

Analyzed Barley tissues—Five tissues at different developmental stages [meristem, flower, booting spike, stem, flag leaf], representing different plant characteristics, were sampled and RNA was extracted as described above. Each micro-array expression information tissue type has received a Set ID as summarized in Table 15 below.

TABLE 15

Barley transcriptom expression sets

| Expression Set | Set ID |
|---|---|
| Meristem | A |
| Flower | B |
| Booting spike | C |
| Stem | D |
| Flag leaf | E |

Table 15

Barley yield components and vigor related parameters assessment—25 Barley accessions in 4 repetitive blocks (named A, B, C, and D), each containing 4 plants per plot were grown at net house. Plants were phenotyped on a daily basis following the standard descriptor of barley (Table 16, below). Harvest was conducted while 50% of the spikes were dry to avoid spontaneous release of the seeds. Plants were separated to the vegetative part and spikes, of them, 5 spikes were threshed (grains were separated from the glumes) for additional grain analysis such as size measurement, grain count per spike and grain yield per spike. All material was oven dried and the seeds were threshed manually from the spikes prior to measurement of the seed characteristics (weight and size) using scanning and image analysis. The image analysis system included a personal desktop computer (Intel P4 3.0 GHz processor) and a public domain program—ImageJ 1.37 (Java based image processing program, which was developed at the U.S. National Institutes of Health and freely available on the internet [Hypertext Transfer Protocol://rsbweb (dot) nih (dot) gov/]. Next, analyzed data was saved to text files and processed using the JMP statistical analysis software (SAS institute).

TABLE 16

Barley standard descriptors

| Trait | Parameter | Range | Description |
|---|---|---|---|
| Growth habit | Scoring | 1-9 | Prostrate (1) or Erect (9) |
| Hairiness of basal leaves | Scoring | P (Presence)/ A (Absence) | Absence (1) or Presence (2) |
| Stem pigmentation | Scoring | 1-5 | Green (1), Basal only or Half or more (5) |
| Days to Flowering | Days | | Days from sowing to emergence of awns |
| Plant height | Centimeter (cm) | | Height from ground level to top of the longest spike excluding awns |
| Spikes per plant | Number | | Terminal Counting |
| Spike length | Centimeter (cm) | | Terminal Counting 5 spikes per plant |
| Grains per spike | Number | | Terminal Counting 5 spikes per plant |
| Vegetative dry weight | Gram | | Oven-dried for 48 hours at 70° C. |
| Spikes dry weight | Gram | | Oven-dried for 48 hours at 30° C. |

Table 16.

Grains per spike—At the end of the experiment (50% of the spikes were dry) all spikes from plots within blocks A-D are collected. The total number of grains from 5 spikes that were manually threshed was counted. The average grain per spike is calculated by dividing the total grain number by the number of spikes.

Grain average size (cm)—At the end of the experiment (50% of the spikes were dry) all spikes from plots within blocks A-D are collected. The total grains from 5 spikes that were manually threshed were scanned and images were analyzed using the digital imaging system. Grain scanning was done using Brother scanner (model DCP-135), at the 200 dpi resolution and analyzed with Image J software. The average grain size was calculated by dividing the total grain size by the total grain number.

Grain average weight (mgr)—At the end of the experiment (50% of the spikes were dry) all spikes from plots within blocks A-D are collected. The total grains from 5 spikes that were manually threshed were counted and weight. The average weight was calculated by dividing the total weight by the total grain number.

Grain yield per spike (gr)—At the end of the experiment (50% of the spikes were dry) all spikes from plots within blocks A-D are collected. The total grains from 5 spikes that were manually threshed were weight. The grain yield was calculated by dividing the total weight by the spike number.

Spike length analysis—At the end of the experiment (50% of the spikes were dry) all spikes from plots within blocks A-D are collected. The five chosen spikes per plant were measured using measuring tape excluding the awns.

Spike number analysis—At the end of the experiment (50% of the spikes were dry) all spikes from plots within blocks A-D are collected. The spikes per plant were counted.

Growth habit scoring—At the growth stage 10 (booting), each of the plants was scored for its growth habit nature. The scale that was used was 1 for prostate nature till 9 for erect.

Hairiness of basal leaves—At the growth stage 5 (leaf sheath strongly erect; end of tillering), each of the plants was scored for its hairiness nature of the leaf before the last. The scale that was used was 1 for prostate nature till 9 for erect.

Plant height—At the harvest stage (50% of spikes were dry) each of the plants was measured for its height using measuring tape. Height was measured from ground level to top of the longest spike excluding awns.

Days to flowering—Each of the plants was monitored for flowering date. Days of flowering was calculated from sowing date till flowering date.

Stem pigmentation—At the growth stage 10 (booting), each of the plants was scored for its stem color. The scale that was used was 1 for green till 5 for full purple.

Vegetative dry weight and spike yield—At the end of the experiment (50% of the spikes were dry) all spikes and vegetative material from plots within blocks A-D are collected. The biomass and spikes weight of each plot was separated, measured and divided by the number of plants.

Dry weight=total weight of the vegetative portion above ground (excluding roots) after drying at 70° C. in oven for 48 hours;

Spike yield per plant=total spike weight per plant (gr) after drying at 30° C. in oven for 48 hours.

Harvest Index (for barley)—The harvest index is calculated using Formula VIII.

Harvest Index=Average spike dry weight per plant/ (Average vegetative dry weight per plant+Average spike dry weight per plant)    Formula VIII:

TABLE 17

Barley correlated parameters (vectors)

| Correlated parameter with (units) | Correlation Id |
|---|---|
| Grains per spike (numbers) | 1 |
| Grains size (mm²) | 2 |
| Grain weight (miligrams) | 3 |
| Grain Yield per spike (gr/spike) | 4 |
| Spike length (cm) | 5 |
| Spikes per plant (numbers) | 6 |
| Growth habit (scores 1-9) | 7 |
| Hairiness of basal leaves (scoring 1-2) | 8 |
| Plant height (cm) | 9 |
| Days to flowering (days) | 10 |
| Stem pigmentation (scoring 1-5) | 11 |
| Vegetative dry weight (gram) | 12 |
| Harvest Index (ratio) | 13 |

Table 17.

Experimental Results 13 different Barley accessions were grown and characterized for 13 parameters as described above. The average for each of the measured parameter was calculated using the JMP software and values are summarized in Tables 18 and 19 below. Subsequent correlation analysis between the various transcriptom sets (Table 15) and the average parameters, was conducted (Tables 20 and 21). Follow, results were integrated to the database.

TABLE 18

Measured parameters of correlation Ids in Barley accessions

| Accession | 6 | 10 | 3 | 5 | 2 | 1 | 7 |
|---|---|---|---|---|---|---|---|
| Amatzya | 48.85 | 62.40 | 35.05 | 12.04 | 0.27 | 20.23 | 2.60 |
| Ashqelon | 48.27 | 64.08 | 28.06 | 10.93 | 0.23 | 17.98 | 2.00 |
| Canada park | 37.42 | 65.15 | 28.76 | 11.83 | 0.24 | 17.27 | 1.92 |
| Havarim stream | 61.92 | 58.92 | 17.87 | 9.90 | 0.17 | 17.73 | 3.17 |
| Jordan est | 33.27 | 63.00 | 41.22 | 11.68 | 0.29 | 14.47 | 4.33 |
| Klil | 41.69 | 70.54 | 29.73 | 11.53 | 0.28 | 16.78 | 2.69 |
| Maale Efraim | ND | 52.80 | 25.22 | 8.86 | 0.22 | 13.47 | 3.60 |
| Mt Arbel | 40.63 | 60.88 | 34.99 | 11.22 | 0.28 | 14.07 | 3.50 |
| Mt Harif | 62.00 | 58.10 | 20.58 | 11.11 | 0.19 | 21.54 | 3.00 |
| Neomi | 49.33 | 53.00 | 27.50 | 8.58 | 0.22 | 12.10 | 3.67 |
| Neot Kdumim | 50.60 | 60.40 | 37.13 | 10.18 | 0.27 | 14.36 | 2.47 |
| Oren canyon | 43.09 | 64.58 | 29.56 | 10.51 | 0.27 | 15.28 | 3.50 |
| Yeruham | 51.40 | 56.00 | 19.58 | 9.80 | 0.18 | 17.07 | 3.00 |

Table 18. Provided are the values of each of the parameters measured in Barley accessions according to the following correlation identifications (Correlation Ids): 6 = Spikes per plant; 10 = Days to flowering; 3 = Grain weight; 5 = Spike length; 2 = Grains Size; 1 = Grains per spike; 7 = Growth habit.

TABLE 19

Barley accessions, additional measured parameters

| Accession | 8 | 9 | 4 | 11 | 12 | 13 |
|---|---|---|---|---|---|---|
| Amatzya | 1.53 | 134.27 | 3.56 | 1.13 | 78.87 | 0.45 |
| Ashqelon | 1.33 | 130.50 | 2.54 | 2.50 | 66.14 | 0.42 |
| Canada park | 1.69 | 138.77 | 2.58 | 1.69 | 68.49 | 0.40 |
| Havarim stream | 1.08 | 114.58 | 1.57 | 1.75 | 53.39 | 0.44 |
| Jordan est | 1.42 | 127.75 | 3.03 | 2.33 | 68.30 | 0.43 |
| Klil | 1.69 | 129.38 | 2.52 | 2.31 | 74.17 | 0.40 |
| Maale Efraim | 1.30 | 103.89 | 1.55 | 1.70 | 35.35 | 0.52 |
| Mt Arbel | 1.19 | 121.63 | 2.62 | 2.19 | 58.33 | 0.48 |
| Mt Harif | 1.00 | 126.80 | 2.30 | 2.30 | 62.23 | 0.44 |
| Neomi | 1.17 | 99.83 | 1.68 | 1.83 | 38.32 | 0.49 |
| Neot Kdumim | 1.60 | 121.40 | 2.68 | 3.07 | 68.31 | 0.45 |
| Oren canyon | 1.08 | 118.42 | 2.35 | 1.58 | 56.15 | ND |
| Yeruham | 1.17 | 117.17 | 1.67 | 2.17 | 42.68 | ND |

Table 19. Provided are the values of each of the parameters measured in Barley accessions according to the following correlation identifications (Correlation Ids): 8 = Hairiness of basal leaves; 9 = Plant height; 4 = Grain yield per spike; 11 = Stem pigmentation; 12 = Vegetative dry weight; 13 = Harvest Index.

TABLE 20

Correlation between the expression level of selected LNU genes of some embodiments of the invention in various tissues and the phenotypic performance under normal fertilization conditions across barley accessions

| Gene Name | R | P value | Exp. Set ID | Corr. Set ID |
|---|---|---|---|---|
| LNU72 | 0.77 | 6.01E-03 | A | 2 |
| LNU72 | 0.75 | 7.97E-03 | A | 3 |
| LNU72 | 0.75 | 2.03E-02 | A | 3 |
| LNU72 | 0.74 | 2.13E-02 | A | 2 |
| LNU240 | 0.73 | 1.15E-02 | C | 6 |
| LNU240 | 0.70 | 3.44E-02 | C | 6 |
| LNU244 | 0.72 | 4.57E-02 | C | 7 |
| LNU27 | 0.81 | 7.70E-03 | A | 1 |
| LNU27 | 0.78 | 1.24E-02 | A | 9 |
| LNU27 | 0.76 | 1.72E-02 | A | 12 |
| LNU27 | 0.72 | 1.17E-02 | A | 12 |
| LNU28 | 0.80 | 1.02E-02 | C | 2 |
| LNU28 | 0.79 | 1.14E-02 | C | 3 |
| LNU28 | 0.78 | 4.43E-03 | C | 2 |
| LNU28 | 0.78 | 4.67E-03 | C | 3 |
| LNU172 | 0.81 | 1.56E-02 | C | 7 |
| LNU228 | 0.86 | 3.07E-03 | A | 3 |

TABLE 20-continued

Correlation between the expression level of selected LNU genes of some embodiments of the invention in various tissues and the phenotypic performance under normal fertilization conditions across barley accessions

| Gene Name | R | P value | Exp. Set ID | Corr. Set ID |
|---|---|---|---|---|
| LNU228 | 0.86 | 7.60E−04 | A | 3 |
| LNU228 | 0.81 | 7.47E−03 | A | 2 |
| LNU228 | 0.79 | 1.99E−02 | C | 6 |
| LNU228 | 0.79 | 3.90E−03 | C | 6 |
| LNU228 | 0.75 | 7.78E−03 | A | 2 |
| LNU224 | 0.85 | 1.53E−02 | C | 6 |

Table 20. "Correl. Set ID"—correlation set ID according to the correlated parameters Table above.

TABLE 21

Correlation between the expression level of selected LNU orthologs genes of some embodiments of the invention in various tissues and the phenotypic performance under normal fertilization conditions across barley accessions

| Gene Name | R | P value | Exp. Set | Correl. Set ID |
|---|---|---|---|---|
| LNU52_H0 | 0.91 | 5.92E−04 | C | 3 |
| LNU52_H0 | 0.91 | 9.60E−05 | C | 3 |
| LNU89_H0 | 0.76 | 2.80E−02 | C | 3 |
| LNU89_H0 | 0.76 | 2.80E−02 | C | 3 |
| LNU85_H0 | 0.74 | 2.27E−02 | C | 3 |
| LNU85_H0 | 0.74 | 2.27E−02 | C | 3 |
| LNU2_H0 | 0.75 | 1.94E−02 | C | 1 |
| LNU2_H0 | 0.75 | 1.94E−02 | C | 1 |
| LNU2_H0 | 0.73 | 2.65E−02 | C | 1 |
| LNU2_H0 | 0.72 | 1.30E−02 | C | 1 |
| LNU2_H0 | 0.73 | 2.65E−02 | C | 1 |
| LNU2_H0 | 0.72 | 1.30E−02 | C | 1 |
| LNU268_H0 | 0.79 | 4.16E−03 | C | 1 |
| LNU268_H0 | 0.78 | 1.27E−02 | C | 1 |
| LNU52_H0 | 0.93 | 2.81E−04 | C | 2 |
| LNU52_H0 | 0.92 | 5.39E−05 | C | 2 |
| LNU85_H0 | 0.73 | 2.63E−02 | B | 2 |
| LNU85_H0 | 0.73 | 2.63E−02 | B | 2 |
| LNU89_H0 | 0.81 | 1.44E−02 | B | 2 |
| LNU89_H0 | 0.81 | 1.44E−02 | B | 2 |
| LNU85_H0 | 0.74 | 2.21E−02 | B | 2 |
| LNU85_H0 | 0.71 | 1.51E−02 | B | 2 |
| LNU85_H0 | 0.74 | 2.21E−02 | B | 2 |
| LNU85_H0 | 0.71 | 1.51E−02 | B | 2 |
| LNU74_H31 | 0.72 | 3.00E−02 | B | 7 |
| LNU74_H31 | 0.72 | 3.00E−02 | B | 7 |
| LNU85_H0 | 0.83 | 5.97E−03 | B | 8 |
| LNU85_H0 | 0.81 | 2.45E−03 | B | 8 |
| LNU85_H0 | 0.83 | 5.97E−03 | A | 8 |
| LNU85_H0 | 0.81 | 2.45E−03 | A | 8 |
| LNU52_H1 | 0.71 | 4.86E−02 | A | 8 |
| LNU52_H1 | 0.70 | 2.31E−02 | A | 8 |
| LNU52_H1 | 0.71 | 4.86E−02 | A | 8 |
| LNU52_H1 | 0.70 | 2.31E−02 | A | 8 |
| LNU89_H0 | 0.73 | 3.99E−02 | A | 8 |
| LNU89_H0 | 0.73 | 3.99E−02 | A | 8 |
| LNU76_H11 | 0.71 | 3.36E−02 | A | 8 |
| LNU76_H11 | 0.71 | 3.36E−02 | A | 8 |
| LNU2_H0 | 0.81 | 8.66E−03 | A | 9 |
| LNU2_H0 | 0.72 | 1.31E−02 | A | 9 |
| LNU2_H0 | 0.81 | 8.66E−03 | A | 9 |
| LNU2_H0 | 0.72 | 1.31E−02 | A | 9 |
| LNU2_H0 | 0.88 | 1.59E−03 | A | 5 |
| LNU2_H0 | 0.75 | 7.76E−03 | A | 5 |
| LNU2_H0 | 0.88 | 1.59E−03 | A | 5 |
| LNU2_H0 | 0.75 | 7.76E−03 | A | 5 |
| LNU69_H0 | 0.79 | 2.01E−02 | A | 6 |
| LNU69_H0 | 0.79 | 2.01E−02 | A | 6 |
| LNU45_H52 | 0.76 | 4.62E−02 | A | 6 |
| LNU45_H52 | 0.76 | 4.62E−02 | A | 6 |
| LNU51_H0 | 0.86 | 6.78E−03 | A | 6 |

TABLE 21-continued

Correlation between the expression level of selected LNU orthologs genes of some embodiments of the invention in various tissues and the phenotypic performance under normal fertilization conditions across barley accessions

| Gene Name | R | P value | Exp. Set | Correl. Set ID |
|---|---|---|---|---|
| LNU51_H0 | 0.71 | 1.41E−02 | A | 6 |
| LNU51_H0 | 0.86 | 6.78E−03 | A | 6 |
| LNU51_H0 | 0.71 | 1.41E−02 | A | 6 |
| LNU60_H0 | 0.72 | 1.31E−02 | A | 6 |
| LNU60_H0 | 0.72 | 1.31E−02 | A | 6 |
| LNU67_H0 | 0.88 | 3.84E−03 | A | 6 |
| LNU67_H0 | 0.72 | 1.17E−02 | A | 6 |
| LNU67_H0 | 0.88 | 3.84E−03 | A | 6 |
| LNU67_H0 | 0.72 | 1.17E−02 | A | 6 |
| LNU46_H7 | 0.89 | 3.10E−03 | A | 6 |
| LNU46_H7 | 0.83 | 1.45E−03 | A | 6 |
| LNU46_H7 | 0.89 | 3.10E−03 | A | 6 |
| LNU46_H7 | 0.83 | 1.45E−03 | A | 6 |
| LNU35_H0 | 0.87 | 4.90E−03 | A | 6 |
| LNU35_H0 | 0.85 | 8.62E−04 | A | 6 |
| LNU35_H0 | 0.87 | 4.90E−03 | A | 6 |
| LNU35_H0 | 0.85 | 8.62E−04 | A | 6 |

Table 21. "Correl. Set ID"—correlation set ID according to the correlated parameters Table above.

Example 7

Production of *Sorghum* Transcriptom and High Throughput Correlation Analysis with Yield, NUE, and ABST Related Parameters Measured in Fields Using 44K *Sorguhm* Oligonucleotide Micro-Arrays In order to produce a high throughput correlation analysis between plant phenotype and gene expression level, the present inventors utilized a sorghum oligonucleotide microarray, produced by Agilent Technologies [Hypertext Transfer Protocol://World Wide Web (dot) chem. (dot) agilent (dot) com/Scripts/PDS (dot) asp?1 Page=50879]. The array oligonucleotide represents about 44,000 sorghum genes and transcripts. In order to define correlations between the levels of RNA expression with ABST, yield and NUE components or vigor related parameters, various plant characteristics of 17 different sorghum hybrids were analyzed. Among them, 10 hybrids encompassing the observed variance were selected for RNA expression analysis. The correlation between the RNA levels and the characterized parameters was analyzed using Pearson correlation test [Hypertext Transfer Protocol://World Wide Web (dot) davidmlane (dot) com/hyperstat/A34739 (dot) html].

Correlation of *Sorghum* Varieties Across Ecotypes Grown Under Low Nitrogen, Regular Growth and Severe Drought Conditions Experimental Procedures 17 *Sorghum* varieties were grown in 3 repetitive plots, in field. Briefly, the growing protocol was as follows:

1. Regular growth conditions: sorghum plants were grown in the field using commercial fertilization and irrigation protocols.

2. Low Nitrogen fertilization conditions: sorghum plants were fertilized with 50% less amount of nitrogen in the field than the amount of nitrogen applied in the regular growth treatment. All the fertilizer was applied before flowering.

3. Drought stress: sorghum seeds were sown in soil and grown under normal condition until around 35 days from sowing, around V8. At this point, irrigation was stopped, and severe drought stress was developed. In order to define correlations between the levels of RNA expression with NUE, drought, and yield components or vigor related parameters, the 17 different sorghum varieties were analyzed. Among them, 10 varieties encompassing the observed variance were selected for RNA expression analysis. The correlation between the RNA levels and the characterized parameters was analyzed using Pearson correlation test [Hypertext Transfer Protocol://World Wide Web (dot) davidmlane (dot) com/hyperstat/A34739 (dot) html].

Analyzed Sorghum tissues—All 10 selected Sorghum hybrids were sample per each treatment. Plant tissues [Flag leaf, Flower meristem and Flower] growing under low nitrogen, severe drought stress and plants grown under Normal conditions were sampled and RNA was extracted as described above. Each micro-array expression information tissue type has received a Set ID as summarized in Table 22 below.

TABLE 22

Sorghum transcriptom expression sets in field experiments

| Expression Set | Set ID |
| --- | --- |
| Sorghum field/Normal/flower meristem | A |
| Sorghum field/Normal/flower | B |
| Sorghum field/Normal/leaf | C |
| Sorghum field/Low N/flower meristem | D |
| Sorghum field/Low N/flower | E |
| Sorghum field/Low N/leaf | F |
| Sorghum field/Drought/flower meristem | G |
| Sorghum field/Drought/flower | H |
| Sorghum field/Drought/leaf | I |

Table 22: Provided are the sorghum transcriptom expression sets.

The following parameters were collected using digital imaging system:

Average Grain Area ($cm^2$)—At the end of the growing period the grains were separated from the Plant 'Head'. A sample of ~200 grains were weight, photographed and images were processed using the below described image processing system. The grain area was measured from those images and was divided by the number of grains.

Average Grain Length (cm)—At the end of the growing period the grains were separated from the Plant 'Head'. A sample of ~200 grains were weight, photographed and images were processed using the below described image processing system. The sum of grain lengths (longest axis) was measured from those images and was divided by the number of grains.

Head Average Area ($cm^2$) At the end of the growing period 5 'Heads' were, photographed and images were processed using the below described image processing system. The 'Head' area was measured from those images and was divided by the number of 'Heads'.

Head Average Length (cm) At the end of the growing period 5 'Heads' were, photographed and images were processed using the below described image processing system. The 'Head' length (longest axis) was measured from those images and was divided by the number of 'Heads'.

The image processing system was used, which consists of a personal desktop computer (Intel P4 3.0 GHz processor) and a public domain program—ImageJ 1.37, Java based image processing software, which was developed at the U.S. National Institutes of Health and is freely available on the internet at Hypertext Transfer Protocol://rsbweb (dot) nih (dot) gov/. Images were captured in resolution of 10 Mega Pixels (3888×2592 pixels) and stored in a low compression JPEG (Joint Photographic Experts Group standard) format.

Next, image processing output data for seed area and seed length was saved to text files and analyzed using the JMP statistical analysis software (SAS institute).

Additional parameters were collected either by sampling 5 plants per plot or by measuring the parameter across all the plants within the plot.

Total Seed Weight per Head (gr.)—At the end of the experiment (plant 'Heads') heads from plots within blocks A-C were collected. 5 heads were separately threshed and grains were weighted, all additional heads were threshed together and weighted as well. The average grain weight per head was calculated by dividing the total grain weight by number of total heads per plot (based on plot). In case of 5 heads, the total grains weight of 5 heads was divided by 5.

FW Head per Plant gr—At the end of the experiment (when heads were harvested) total and 5 selected heads per plots within blocks A-C were collected separately. The heads (total and 5) were weighted (gr.) separately and the average fresh weight per plant was calculated for total (FW Head/Plant gr based on plot) and for 5 (FW Head/Plant gr based on 5 plants).

Plant height—Plants were characterized for height during growing period at 5 time points. In each measure, plants were measured for their height using a measuring tape. Height was measured from ground level to top of the longest leaf.

Plant leaf number—Plants were characterized for leaf number during growing period at 5 time points. In each measure, plants were measured for their leaf number by counting all the leaves of 3 selected plants per plot.

Relative Growth Rate was calculated using Formulas IX and X.

Relative growth rate of plant height=Regression coefficient of plant height along time course.      Formula IX Relative growth rate of plant leaf number=Regression coefficient of plant leaf number along time course.      Formula X SPAD—Chlorophyll content was determined using a Minolta SPAD 502 chlorophyll meter and measurement was performed 64 days post sowing. SPAD meter readings were done on young fully developed leaf. Three measurements per leaf were taken per plot.

Vegetative dry weight and Heads—At the end of the experiment (when Inflorescence were dry) all Inflorescence and vegetative material from plots within blocks A-C were collected. The biomass and Heads weight of each plot was separated, measured and divided by the number of Heads.

Dry weight=total weight of the vegetative portion above ground (excluding roots) after drying at 70° C. in oven for 48 hours;

Harvest Index (HI) (Sorghum)—The harvest index was calculated using Formula XI.

Harvest Index=Average grain dry weight per Head/(Average vegetative dry weight per Head+Average Head dry weight)      Formula XI:

FW Heads/(FW Heads+FW Plants)—The total fresh weight of heads and their respective plant biomass were measured at the harvest day. The heads weight was divided by the sum of weights of heads and plants.

Experimental Results 17 different sorghum hybrids were grown and characterized for different parameters: The average for each of the measured parameter was calculated using the JMP software (Tables 23-29) and a subsequent correlation analysis was performed (Tables 30-31). Results were then integrated to the database.

TABLE 23

Sorghum correlated parameters (vectors)

| Correlation set | Correlation ID |
|---|---|
| Leaf SPAD 64 Days Post Sowing-normal [SPAD unit] | 1 |
| RGR of Leaf Num-normal | 2 |
| Total Seed Weight/Head gr based on plot-normal [gr] | 3 |
| Head Average Area cm2-normal [cm2] | 4 |
| Head Average Length cm-normal [cm] | 5 |
| Average Seed Area cm2-normal [cm2] | 6 |
| Average Seed Length cm-normal [cm] | 7 |
| FW Head/Plant gr based on plot-normal [gr] | 8 |
| FW per Plant gr based on plot-normal [gr] | 9 |
| Final Plant Height cm-normal [cm] | 10 |
| HI-normal | 11 |
| FW Heads/(FW Heads + FW Plants) all plot-normal [gr] | 12 |
| RGR of Plant Height-normal | 13 |
| FW-Inflorescence per Plant Normal [gr] | 14 |
| DW per Plant Normal [gr] | 15 |
| DW-5 Inflorescence Normal [gr] | 16 |
| Seed Yield Normal [gr] | 17 |
| Leaf No 2 Normal [number] | 18 |
| Plant Height 2 Normal [cm] | 19 |
| SPAD 2 Normal [SPAD unit] | 20 |
| Leaf No 3 Normal [number] | 21 |
| Plant Height 3 Normal [cm] | 22 |
| Leaf No 4 Normal [number] | 23 |
| Plant Height 4 Normal [cm] | 24 |
| Leaf No 5 Normal [number] | 25 |
| Leaf No 6 Normal [number] | 26 |
| Plant Height 6 Normal [cm] | 27 |
| Plant Height 5 Low-N [cm] | 28 |
| FW-Inflorescence per Plant Low-N | 29 |
| DW per Plant Low-N | 30 |
| Seed per Plant Low-N | 31 |
| Seed yield Low-N [gr] | 32 |
| Leaf No 2 Low-N [number] | 33 |
| Plant Height 2 Low-N [cm] | 34 |
| SPAD 2 Low-N | 35 |
| Leaf No 3 Low-N [number] | 36 |
| Plant Height 3 Low-N [cm] | 37 |
| Leaf No 5 Low-N [number] | 38 |
| RGR of Leaf Num-NUE | 39 |
| Total Seed Yield per Head gr based on plot-NUE | 40 |
| Head Average Area cm2-NUE [cm2] | 41 |
| Head Average Perimeter cm-NUE [cm] | 42 |
| Head Average Length cm-NUE [cm] | 43 |
| Head Average Width cm-NUE [cm] | 44 |
| Average Seed Area cm2-NUE [cm2] | 45 |
| Average Seed Length cm-NUE [cm] | 46 |
| FW Head per Plant gr based on plot-NUE [gr] | 47 |
| FW per Plant gr based on plot-NUE [gr] | 48 |
| Leaf SPAD 64 Days Post Sowing-NUE [SPAD unit] | 49 |
| HI-NUE | 50 |
| FW Heads/(FW Heads + FW Plants) all plot-NUE [gr] | 51 |
| FW-Inflorescence per Plant Drought [gr] | 52 |
| Dw per Plant Drought [gr] | 53 |
| Seed per Plant Drought [gr] | 54 |
| DW-5 Inflorescence Drought [gr] | 55 |
| Seed Yield Drought [gr] | 56 |
| Seed Yield (5 heads) gr Drought | 57 |
| Leaf No 2 Drought [number] | 58 |
| Plant Height 2 Drought [cm] | 59 |
| SPAD 2 Drought [SPAD unit] | 60 |
| Leaf No 3 Drought [number] | 61 |
| Plant Height 3 Drought [cm] | 62 |
| Leaf No 4 Drought [number] | 63 |
| Plant Height 4 Drought [cm] | 64 |
| Leaf No 5 Drought [number] | 65 |
| Plant Height 5 Drought [cm] | 66 |
| Leaf No 6 Drought [number] | 67 |
| Plant Height 6 Drought [cm] | 68 |
| Average Seed Area cm2-Drought [cm2] | 69 |
| Average Seed Length cm-Drought [cm] | 70 |
| Total Seed Yield per Head gr based on plot-Drought [gr] | 71 |
| Head Average Area cm2-Drought [cm2] | 72 |
| Head Average Perimeter cm-Drought [cm] | 73 |
| Head Average Length cm-Drought [cm] | 74 |
| Head Average Width cm-Drought [cm] | 75 |
| HI-Drought | 76 |
| RGR of Leaf_Num-Drought | 77 |

Table 23. Provided are the Sorghum correlated parameters (vectors). "gr." = grams; "SPAD" = chlorophyll levels; "FW" = Plant Fresh weight; "DW" = Plant Dry weight; "normal" = standard growth conditions.

TABLE 24

Measured parameters in Sorghum accessions under normal conditions

| Seed ID | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 20 | 43 | 0.10 | 31 | 120 | 26 | 0.11 | 0.39 | 175 | 163 | 95 | 201 | 0.51 | 1.89 | 0.18 |
| 21 |  |  | 26 | 168 | 27 | 0.11 | 0.40 | 223 | 213 | 79 | 127 | 0.51 | 1.62 | 0.68 |
| 22 | 43 | 0.21 | 19 | 85 | 21 | 0.13 | 0.45 | 56 | 335 | 198 | 52 | 0.12 | 3.42 | 0.06 |
| 24 | 45 | 0.19 | 38 | 157 | 27 | 0.13 | 0.45 | 112 | 313 | 234 | 122 | 0.26 | 2.42 | 0.11 |
| 25 | 46 | 0.19 |  |  |  |  |  |  |  | 189 | 55 | 0.12 | 3.12 | 0.07 |
| 26 | 42 | 0.16 |  |  |  |  |  |  |  | 195 | 94 | 0.18 | 3.32 | 0.09 |
| 27 | 45 | 0.20 | 48 | 169 | 31 | 0.11 | 0.40 | 126 | 151 | 117 | 327 | 0.46 | 2.18 | 0.13 |
| 28 | 45 | 0.17 | 31 | 109 | 23 | 0.11 | 0.41 | 108 | 138 | 93 | 231 | 0.43 | 2.19 | 0.11 |
| 29 | 43 | 0.18 | 40 | 135 | 26 | 0.10 | 0.38 | 124 | 168 | 113 | 241 | 0.43 | 2.57 | 0.12 |
| 30 | 46 |  | 38 | 169 | 29 | 0.12 | 0.42 | 103 | 129 | 98 | 304 | 0.44 | 2.05 | 0.10 |
| 31 | 45 |  | 32 | 156 | 28 | 0.12 | 0.43 | 82 | 98 | 98 | 336 | 0.46 | 2.07 | 0.08 |
| 32 | 45 | 0.18 | 33 | 112 | 23 | 0.11 | 0.40 | 78 | 99 | 100 | 350 | 0.45 | 2.55 | 0.08 |
| 33 | 47 | 0.12 | 33 | 155 | 28 | 0.12 | 0.41 | 91 | 112 | 106 | 293 | 0.45 | 2.33 | 0.09 |
| 34 | 44 | 0.21 | 52 | 172 | 30 | 0.11 | 0.40 | 150 | 157 | 151 | 411 | 0.51 | 3.04 | 0.15 |
| 35 | 45 | 0.19 | 36 | 169 | 31 | 0.11 | 0.40 | 109 | 131 | 117 | 285 | 0.46 | 2.33 | 0.11 |
| 36 | 45 | 0.15 | 38 | 163 | 27 | 0.11 | 0.40 | 108 | 136 | 124 | 283 | 0.44 | 2.52 | 0.11 |
| 37 | 43 | 0.24 | 42 | 170 | 29 | 0.11 | 0.39 | 131 | 209 | 126 | 204 | 0.39 | 2.81 | 0.13 |

Table 24: Provided are the values of each of the parameters (as described above) measured in Sorghum accessions (Seed ID) under normal conditions. Growth conditions are specified in the experimental procedure section.

TABLE 25

Additional measured parameters in *Sorghum* accessions under normal growth conditions

| Seed ID | 15 | 16 | 17 | 18 | 19 | 20 | 21 | 22 | 23 | 24 | 25 | 26 | 27 |
|---|---|---|---|---|---|---|---|---|---|---|---|---|---|
| 20 | 0.16 | 0.04 | 1.15 | 5.31 | 10.6 | 43 | 5.44 | 24.5 | 6.73 | 37.3 | 6.75 | 6.73 | 37.3 |
| 21 | 0.25 | 0.06 | 0.48 | 6.08 | 8 | 40.7 | 6.38 | 19.9 | 8.44 | 47.8 | 8.38 | 8.44 | 47.8 |
| 22 | 0.34 | 0.03 | 1.22 | 6 | 16 | 43.3 | 6.56 | 31.1 | 7.25 | 40.1 | 9.81 | 7.25 | 40.1 |
| 24 | 0.31 | 0.03 | 2.61 | 5.44 | 11.9 | 44.7 | 5.75 | 24.5 | 7.88 | 45.9 | 8.81 | 7.88 | 45.9 |
| 25 | 0.46 | 0.07 | 0.99 | 5.38 | 14.2 | 45.8 | 5.12 | 27.2 | 8.12 | 41.4 | 8.69 | 8.12 | 41.4 |
| 26 | 0.36 | 0.05 | 2.67 | 6.31 | 15.3 | 41.6 | 6.31 | 27.2 | 9.12 | 44.9 | 9.5 | 9.12 | 44.9 |
| 27 | 0.15 | 0.05 | 3.59 | 6.12 | 15.7 | 45.2 | 6.19 | 31.2 | 7.5 | 42.1 | 9.19 | 7.5 | 42.1 |
| 28 | 0.14 | 0.03 | 2.12 | 6.06 | 15.9 | 45.1 | 6.06 | 30.2 | 8.25 | 41 | 6.69 | 8.25 | 41 |
| 29 | 0.17 | 0.05 | 2.50 | 6.12 | 14.6 | 43 | 5.62 | 26.2 | 7 | 42.5 | 9 | 7 | 42.1 |
| 30 | 0.13 | 0.04 | 2.78 | 6.44 | 18.4 | 45.6 | 5.94 | 31.9 | 6.75 | 41.9 | 6.75 | 6.75 | 41.9 |
| 31 | 0.10 | 0.02 | 3.16 | 7 | 18.1 | 44.8 | 6 | 32.2 | 8.06 | 43.4 | 6.38 | 8.06 | 43.4 |
| 32 | 0.10 | 0.04 | 3.41 | 6.31 | 17.2 | 45.3 | 6.38 | 29.8 | 6.94 | 39.8 | 7.81 | 6.94 | 39.8 |
| 33 | 0.11 | 0.05 | 2.94 | 6.25 | 14.9 | 46.5 | 6.31 | 28.1 | 7.94 | 40.6 | 7.88 | 7.94 | 40.6 |
| 34 | 0.16 | 0.05 | 2.80 | 6.25 | 13.5 | 44 | 5.94 | 27 | 8.06 | 44.4 | 9.94 | 8.06 | 44.4 |
| 35 | 0.13 | 0.04 | 2.90 | 5.62 | 14.6 | 45.1 | 5.94 | 29.2 | 7.56 | 43.2 | 8.69 | 7.56 | 43.2 |
| 36 | 0.14 | 0.04 | 3.40 | 6.38 | 16.4 | 45.1 | 5.75 | 27.8 | 7.94 | 41 | 8.56 | 7.94 | 41 |
| 37 | 0.21 | 0.06 | 3.16 | 5.88 | 17.3 | 43.1 | 6.56 | 31.6 | 10.3 | | | | |

Table 25: Provided are the values of each of the parameters (as described above) measured in *Sorghum* accessions (Seed ID) under normal conditions. Growth conditions are specified in the experimental procedure section.

TABLE 26

Measured parameters in *Sorghum* accessions under Low nitrogen conditions

| Seed Id | 28 | 29 | 30 | 31 | 32 | 33 | 34 | 35 | 36 | 37 | 38 | 39 | 40 |
|---|---|---|---|---|---|---|---|---|---|---|---|---|---|
| 20 | 52.2 | 0.155 | 0.208 | 0.0221 | 0.563 | 5.47 | 12 | 40.6 | 6 | 27.8 | 7.67 | | 25.9 |
| 21 | 40.6 | 0.122 | 0.138 | 0.0168 | 0.347 | 5.58 | 9.58 | 40.9 | 6.33 | 22.7 | 8.5 | 0.185 | 30.6 |
| 22 | 67.4 | 0.131 | 0.255 | 0.00919 | 0.68 | 5.58 | 13.9 | 45 | 5.83 | 27.8 | 8.83 | 0.186 | 19.4 |
| 24 | 66.2 | 0.241 | 0.402 | 0.104 | 0.94 | 5.25 | 10.6 | 42.3 | 5.25 | 24.1 | 8.83 | 0.219 | 35.6 |
| 25 | 68.1 | 0.069 | 0.234 | 0.00324 | 0.055 | 5 | 14.5 | 45.2 | 5.17 | 30.2 | 8.75 | 0.23 | 25.2 |
| 26 | 77.7 | 0.186 | 0.392 | 0.022 | 1.63 | 5.67 | 15.7 | 40.6 | 6.83 | 31.5 | 10.2 | 0.197 | 22.2 |
| 27 | 54.3 | 0.0621 | 0.0893 | 0.00997 | 0.755 | 5.5 | 13.8 | 44.8 | 6.67 | 32.3 | 8.83 | 0.181 | 50 |
| 28 | 71.8 | 0.039 | 0.0506 | 0.0186 | 0.863 | 5.58 | 15 | 45.1 | 6.25 | 29.9 | 7.33 | 0.213 | 27.5 |
| 29 | 81.6 | 0.0589 | 0.087 | 0.0293 | 1.45 | 6 | 17.5 | 40.6 | 6.25 | 33.2 | 8.58 | | 51.1 |
| 30 | 57.6 | 0.0764 | 0.12 | 0.0105 | 1.06 | 6.17 | 19.4 | 45.4 | 6.25 | 34.6 | 6.42 | | 36.8 |
| 31 | 61.5 | 0.0335 | 0.0372 | 0.0148 | 1.23 | 6.42 | 19.5 | 42.6 | 6.58 | 36.1 | 6.67 | | 29.4 |
| 32 | 74.1 | 0.0422 | 0.0482 | 0.0129 | 1.13 | 5.92 | 18.9 | 44.2 | 7.08 | 32.8 | 8.25 | | 26.7 |
| 33 | 60.7 | 0.0415 | 0.0442 | 0.0182 | 0.48 | 6.25 | 16.2 | 44.6 | 6.83 | 29.7 | 8.17 | 0.115 | 29.4 |
| 34 | 67.6 | 0.132 | 0.232 | 0.0116 | 0.653 | 5.42 | 14.2 | 42.4 | 6 | 27.2 | 10.9 | 0.224 | 51.1 |
| 35 | 59.3 | 0.0608 | 0.116 | 0.0186 | 0.95 | 5.83 | 14.3 | 43.2 | 5.83 | 29.8 | 8.42 | 0.168 | 37 |
| 36 | 61.6 | 0.0443 | 0.123 | 0.0164 | 0.736 | 6.25 | 15.8 | 40.3 | 6.92 | 34 | 8.42 | | 39.9 |
| 37 | 69.3 | 0.185 | 0.343 | 5.83 | 5.25 | 40.8 | 5.58 | 31.8 | 9.67 | | | | 41.8 |

Table 26: Provided are the values of each of the parameters (as described above) measured in *Sorghum* accessions (Seed ID) under low nitrogen conditions. Growth conditions are specified in the experimental procedure section.

TABLE 27

Additional measured parameters in *Sorghum* accessions under low nitrogen growth conditions

| Seed Id | 41 | 42 | 43 | 44 | 45 | 46 | 47 | 48 | 49 | 50 | 51 |
|---|---|---|---|---|---|---|---|---|---|---|---|
| 20 | 96.2 | 56.3 | 23.2 | 5.26 | 0.105 | 0.383 | 215 | 205 | 38.3 | 133 | 0.505 |
| 21 | 215 | 79.2 | 25.6 | 10.4 | 0.111 | 0.402 | 205 | 200 | 39 | 153 | 0.506 |
| 22 | 98.6 | 53.2 | 20.9 | 5.93 | 0.136 | 0.445 | 73.5 | 341 | 42.3 | 56.7 | 0.166 |
| 24 | 183 | 76.2 | 28.4 | 8.25 | 0.121 | 0.417 | 123 | 241 | 40.9 | 195 | 0.391 |
| 25 | 120 | 67.3 | 24.3 | 6.19 | 0.141 | 0.474 | 153 | 538 | 43.1 | 46.9 | 0.21 |
| 26 | 110 | 59.5 | 22.6 | 6.12 | 0.134 | 0.475 | 93.2 | 359 | 39.9 | 63.9 | 0.192 |
| 27 | 172 | 79.3 | 32.1 | 6.8 | 0.119 | 0.411 | 134 | 149 | 42.7 | 342 | 0.476 |
| 28 | 84.8 | 51.5 | 20.4 | 5.25 | 0.117 | 0.405 | 77.4 | 129 | 43.3 | 215 | 0.375 |
| 29 | 156 | 69.9 | 26.7 | 7.52 | 0.116 | 0.409 | 130 | 179 | 39 | 286 | 0.42 |
| 30 | 137 | 66.2 | 26.3 | 6.59 | 0.129 | 0.428 | 99.8 | 124 | 42.7 | 295 | 0.441 |
| 31 | 138 | 67.4 | 25.4 | 6.85 | 0.131 | 0.446 | 76.9 | 101 | 40.1 | 288 | 0.429 |
| 32 | 96.5 | 57.9 | 23.1 | 5.32 | 0.12 | 0.42 | 84.2 | 132 | 44 | 202 | 0.387 |
| 33 | 158 | 70.6 | 27.9 | 7.25 | 0.116 | 0.407 | 92.2 | 118 | 45.4 | 247 | 0.438 |
| 34 | 164 | 73.8 | 28.9 | 7.19 | 0.115 | 0.411 | 139 | 177 | 44.8 | 289 | 0.439 |
| 35 | 138 | 66.9 | 27.6 | 6.27 | 0.107 | 0.4 | 113 | 144 | 42.6 | 254 | 0.442 |

TABLE 27-continued

Additional measured parameters in Sorghum accessions under low nitrogen growth conditions

| Seed Id | 41 | 42 | 43 | 44 | 45 | 46 | 47 | 48 | 49 | 50 | 51 |
|---|---|---|---|---|---|---|---|---|---|---|---|
| 36 | 135 | 65.4 | 25.5 | 6.57 | 0.121 | 0.414 | 95.5 | 127 | 43.8 | 316 | 0.43 |
| 37 | 166 | 76 | 30.3 | 6.82 | 0.109 | 0.395 | 129 | 180 | 46.7 | 232 | 0.417 |

Table 27: Provided are the values of each of the parameters (as described above) measured in Sorghum accessions (Seed ID) under low nitrogen conditions. Growth conditions are specified in the experimental procedure section.

TABLE 28

Measured parameters in Sorghum accessions under drought conditions

| Seed Id | 52 | 53 | 54 | 55 | 56 | 57 | 58 | 59 | 60 | 61 | 62 | 63 |
|---|---|---|---|---|---|---|---|---|---|---|---|---|
| 20 | 0.215 | 0.205 | 0.0259 | 2.36 | 0.653 | 0.251 | 5.33 | 10.8 | 38.3 | 4.5 | 22.2 | 7.75 |
| 21 | 0.205 | 0.2 | 0.0306 | 2.44 | 0.823 | 0.255 | 5.5 | 8 | 39 | 5.75 | 18.5 | 7.92 |
| 22 | 0.0735 | 0.341 | 0.0194 | 3.67 | 1.58 | 0.181 | 5.83 | 16 | 42.3 | 5.75 | 30.3 | 8.67 |
| 24 | 0.123 | 0.241 | 0.0356 | 2.44 | 1.65 | 0.365 | 5.25 | 10.7 | 40.9 | 5.25 | 22.6 | 8.25 |
| 25 | 0.153 | 0.538 | 0.0252 | 2.7 | 0.959 | 0.189 | 5.25 | 13.8 | 43.1 | 5.5 | 27.9 | 8.17 |
| 26 | 0.0932 | 0.359 | 0.0222 | 3.03 | 1.32 | 0.182 | 6.25 | 16.3 | 39.9 | 6 | 32.7 | 9.38 |
| 27 | 0.134 | 0.149 | 0.05 | 2.42 | 3.47 | 0.358 | 6.5 | 15.2 | 42.7 | 6.17 | 32.2 | 9.12 |
| 28 | 0.0774 | 0.129 | 0.0275 | 2.19 | 2.76 | 0.175 | 5.75 | 13.5 | 43.3 | 5.83 | 28.9 | 8.58 |
| 29 | 0.13 | 0.179 | 0.0511 | 2.57 | 4.03 | 0.384 | 6.5 | 16.4 | 39 | 5.17 | 26.8 | 9.5 |
| 30 | 0.0998 | 0.124 | 0.0368 | 2.26 | 3.03 | 0.265 | 6.25 | 17.6 | 42.7 | 5.92 | 34.2 | 7.83 |
| 31 | 0.0769 | 0.101 | 0.0294 | 2.19 | 3.13 | 0.215 | 6.75 | 15.8 | 40.1 | 6.08 | 30.5 | 7.25 |
| 32 | 0.0842 | 0.132 | 0.0267 | 2.16 | 3.13 | 0.182 | 6.25 | 17 | 44 | 5.92 | 30.6 | 9 |
| 33 | 0.0922 | 0.118 | 0.0294 | 2.42 | 2.39 | 0.343 | 6.42 | 13.9 | 45.4 | 6.08 | 27.2 | 7.5 |
| 34 | 0.139 | 0.177 | 0.0511 | 2.71 | 3.34 | 0.479 | 6.33 | 14.8 | 44.8 | 6.08 | 27.6 | 10 |
| 35 | 0.113 | 0.144 | 0.037 | 2.29 | 2.7 | 0.246 | 5.5 | 12.5 | 42.6 | 5.42 | 28 | 8.38 |
| 36 | 0.0955 | 0.127 | 0.0399 | 2.08 | 4.19 | 0.219 | 6.33 | 17.6 | 43.8 | 5.33 | 29.3 | 8.67 |
| 37 | 0.129 | 0.18 | 0.0418 | 2.52 | 2.98 | 0.26 | 5.58 | 15.9 | 46.7 | 5.5 | 30.4 | 10 |

Table 28: Provided are the values of each of the parameters (as described above) measured in Sorghum accessions (Seed ID) under drought conditions. Growth conditions are specified in the experimental procedure section.

TABLE 29

Additional measured parameters in Sorghum accessions under drought growth conditions

| Seed Id | 64 | 65 | 66 | 67 | 68 | 69 | 70 | 71 | 72 | 73 | 74 | 75 | 76 | 77 |
|---|---|---|---|---|---|---|---|---|---|---|---|---|---|---|
| 20 | 38 | 7.08 | 50.2 | 7.75 | 38 | | | 22.1 | 83.1 | 52.8 | 21.6 | 4.83 | 132 | 0.10 |
| 21 | 30.8 | 8.58 | 45.2 | 7.92 | 30.8 | 0.10 | 0.385 | 16.8 | 108 | 64.5 | 21.9 | 6.31 | 128 | 0.18 |
| 22 | 111 | 9.08 | 92.1 | 8.67 | 60.8 | | | 9.19 | 88.7 | 56.6 | 21.6 | 5.16 | 257 | 0.16 |
| 24 | 42.8 | 9 | 67.2 | 8.25 | 42.8 | 0.12 | 0.411 | 104 | 136 | 64.4 | 22 | 7.78 | 257 | 0.22 |
| 25 | 49.6 | 9.58 | 73.9 | 8.17 | 49.6 | | | | | | | | | 0.17 |
| 26 | 49.8 | 9.75 | 100 | 9.38 | 49.8 | 0.11 | 0.41 | 3.24 | 90.8 | 53.2 | 21 | 5.28 | 8.76 | 0.21 |
| 27 | 46.9 | 9.08 | 58.7 | 9.12 | 46.9 | | | 22 | 124 | 71.7 | 28.6 | 5.49 | 248 | 0.15 |
| 28 | 41.9 | 7.75 | 70.8 | 8.58 | 41.9 | 0.10 | 0.373 | 9.97 | 86.1 | 55.6 | 21.3 | 5.04 | 197 | 0.08 |
| 29 | 46.1 | 8.5 | 67.7 | 8.25 | 46.1 | 0.09 | 0.364 | 18.6 | 85.2 | 53 | 20.8 | 5.07 | 213 | 0.14 |
| 30 | 50.2 | 7.08 | 68.5 | 7.83 | 50.2 | | | 29.3 | 113 | 69.8 | 24.7 | 5.77 | 325 | |
| 31 | 43.6 | 6.75 | 65.7 | 13.1 | 43.6 | | | 10.5 | 101 | 65.1 | 24.3 | 5.37 | 282 | 0.11 |
| 32 | 50.8 | 8.25 | 79.2 | 9 | 50.9 | | | 14.8 | 80.4 | 55.3 | 21.9 | 4.66 | 300 | 0.12 |
| 33 | 42.4 | 7.92 | 57.7 | 7.5 | 42.4 | | | 12.9 | 127 | 69.1 | 25 | 6.35 | 292 | 0.11 |
| 34 | 45.5 | 9.83 | 78.6 | 10 | 45.5 | | | 18.2 | 86.4 | 53.3 | 19.5 | 5.58 | 90.2 | 0.27 |
| 35 | 50.4 | 8.5 | 60.8 | 8.38 | 50.4 | | | 11.6 | 92.3 | 56.3 | 20.4 | 5.76 | 105 | 0.13 |
| 36 | 48.8 | 9.17 | 71.2 | 8.67 | 53.8 | | | 18.6 | 77.9 | 49.1 | 16.8 | 5.86 | 148 | 0.12 |
| 37 | 49.8 | 10.6 | 73.9 | 9.5 | 51.4 | 0.12 | 0.406 | 16.4 | 76.9 | 51.9 | 18.9 | 5.1 | 84.6 | |

Table 29: Provided are the values of each of the parameters (as described above) measured in Sorghum accessions (Seed ID) under drought conditions. Growth conditions are specified in the experimental procedure section.

TABLE 30

Correlation between the expression level of selected LNU genes of some embodiments of the invention in various tissues and the phenotypic performance under low nitrogen, normal or drought stress conditions across *Sorghum* accessions

| Gene Name | R | P value | Exp. Set ID | Corr. set | Gene Name | R | P value | Exp. Set ID | Corr. set |
|---|---|---|---|---|---|---|---|---|---|
| LNU280 | 0.75 | 1.91E−02 | B | 6 | LNU278 | 0.75 | 1.19E−02 | G | 67 |
| LNU85 | 0.71 | 3.17E−02 | B | 6 | LNU202 | 0.73 | 2.45E−02 | B | 26 |
| LNU279 | 0.70 | 3.53E−02 | A | 6 | LNU202 | 0.71 | 3.09E−02 | B | 26 |
| LNU32 | 0.85 | 3.53E−03 | A | 6 | LNU84 | 0.79 | 6.65E−03 | I | 58 |
| LNU280 | 0.70 | 3.52E−02 | B | 7 | LNU84 | 0.76 | 1.11E−02 | F | 33 |
| LNU279 | 0.76 | 1.73E−02 | A | 7 | LNU87 | 0.71 | 2.11E−02 | F | 33 |
| LNU32 | 0.86 | 2.96E−03 | A | 7 | LNU25 | 0.74 | 1.38E−02 | D | 33 |
| LNU278 | 0.73 | 1.63E−02 | H | 53 | LNU87 | 0.72 | 1.97E−02 | B | 1 |
| LNU87 | 0.71 | 2.11E−02 | C | 15 | LNU87 | 0.71 | 2.17E−02 | B | 1 |
| LNU280 | 0.89 | 1.22E−03 | B | 9 | LNU202 | 0.71 | 3.11E−02 | B | 24 |
| LNU279 | 0.76 | 1.74E−02 | C | 8 | LNU202 | 0.71 | 3.11E−02 | B | 27 |
| LNU280 | 0.73 | 1.59E−02 | D | 47 | LNU84 | 0.89 | 3.10E−03 | G | 77 |
| LNU87 | 0.83 | 2.92E−03 | D | 47 | LNU84 | 0.80 | 1.82E−02 | G | 77 |
| LNU84 | 0.70 | 2.31E−02 | D | 29 | LNU280 | 0.87 | 4.92E−03 | G | 77 |
| LNU279 | 0.74 | 1.53E−02 | G | 72 | LNU279 | 0.82 | 4.60E−02 | E | 39 |
| LNU84 | 0.80 | 5.67E−03 | I | 74 | LNU84 | 0.72 | 1.82E−02 | I | 56 |
| LNU279 | 0.73 | 1.73E−02 | G | 74 | LNU202 | 0.71 | 2.07E−02 | H | 54 |
| LNU279 | 0.70 | 2.29E−02 | F | 74 | LNU278 | 0.95 | 7.45E−05 | F | 31 |
| LNU84 | 0.72 | 1.86E−02 | I | 73 | LNU280 | 0.76 | 1.86E−02 | D | 31 |
| LNU84 | 0.70 | 2.36E−02 | I | 75 | LNU279 | 0.71 | 2.23E−02 | B | 17 |
| LNU280 | 0.77 | 9.16E−03 | H | 75 | LNU280 | 0.77 | 9.13E−03 | A | 17 |
| LNU278 | 0.78 | 8.14E−03 | B | 11 | LNU87 | 0.72 | 1.97E−02 | B | 20 |
| LNU278 | 0.76 | 1.04E−02 | B | 11 | LNU25 | 0.75 | 1.26E−02 | I | 57 |
| LNU84 | 0.95 | 2.28E−05 | I | 61 | LNU279 | 0.75 | 1.94E−02 | B | 3 |
| LNU278 | 0.71 | 2.26E−02 | E | 36 | LNU202 | 0.76 | 1.82E−02 | B | 3 |
| LNU280 | 0.71 | 2.11E−02 | G | 63 | LNU280 | 0.88 | 1.84E−03 | A | 3 |
| LNU202 | 0.73 | 2.45E−02 | B | 23 | LNU279 | 0.86 | 1.29E−03 | F | 40 |
| LNU280 | 0.76 | 1.15E−02 | G | 65 | LNU84 | 0.75 | 1.27E−02 | D | 40 |
| LNU202 | 0.87 | 1.02E−03 | I | 67 | LNU280 | 0.76 | 1.78E−02 | C | 3 |
| LNU278 | 0.89 | 5.06E−04 | I | 67 | LNU202 | 0.76 | 1.14E−02 | H | 57 |
| | | | | | LNU280 | 0.78 | 8.43E−03 | C | 17 |

Table 30. "Correl. Set ID"—correlation set ID according to the correlated parameters Table above.

TABLE 31

Correlation between the expression level of selected LNU homologous genes of some embodiments of the invention in various tissues and the phenotypic performance under low nitrogen, normal or drought stress conditions across *Sorghum* accessions

| Gene Name | R | P value | Exp. Set | Correl. Set ID | Gene Name | R | P value | Exp. Set | Correl. Set ID |
|---|---|---|---|---|---|---|---|---|---|
| LNU267_H2 | 0.82 | 7.37E−03 | C | 6 | LNU265_H0 | 0.81 | 4.77E−03 | G | 63 |
| LNU267_H2 | 0.82 | 7.37E−03 | C | 6 | LNU265_H0 | 0.72 | 1.84E−02 | G | 63 |
| LNU74_H173 | 0.85 | 3.59E−03 | C | 6 | LNU265_H0 | 0.81 | 4.77E−03 | G | 63 |
| LNU74_H173 | 0.83 | 5.54E−03 | C | 6 | LNU265_H0 | 0.72 | 1.84E−02 | G | 63 |
| LNU74_H173 | 0.85 | 3.59E−03 | C | 6 | LNU153_H6 | 0.80 | 5.43E−03 | G | 63 |
| LNU74_H173 | 0.83 | 5.54E−03 | C | 6 | LNU153_H6 | 0.80 | 5.43E−03 | G | 63 |
| LNU46_H58 | 0.86 | 2.71E−03 | C | 6 | LNU271_H4 | 0.90 | 8.49E−04 | C | 23 |
| LNU46_H58 | 0.73 | 2.66E−02 | C | 6 | LNU271_H4 | 0.90 | 9.96E−04 | C | 23 |
| LNU46_H58 | 0.72 | 2.74E−02 | C | 6 | LNU271_H4 | 0.90 | 8.49E−04 | C | 23 |
| LNU46_H58 | 0.86 | 2.71E−03 | C | 6 | LNU271_H4 | 0.90 | 9.96E−04 | C | 23 |
| LNU46_H58 | 0.73 | 2.66E−02 | C | 6 | LNU45_H259 | 0.71 | 3.28E−02 | C | 23 |
| LNU46_H58 | 0.72 | 2.74E−02 | C | 6 | LNU71_H3 | 0.81 | 4.39E−03 | I | 65 |
| LNU2_H4 | 0.77 | 1.61E−02 | B | 6 | LNU71_H3 | 0.81 | 4.39E−03 | I | 65 |
| LNU2_H4??? | 0.77 | 1.61E−02 | B | 6 | LNU28_H4 | 0.77 | 9.28E−03 | H | 65 |
| LNU2_H4 | 0.77 | 1.61E−02 | B | 6 | LNU28_H4 | 0.76 | 1.12E−02 | H | 65 |
| LNU73_H2 | 0.78 | 1.37E−02 | B | 6 | LNU28_H4 | 0.77 | 9.28E−03 | H | 65 |
| LNU73_H2 | 0.74 | 2.30E−02 | B | 6 | LNU28_H4 | 0.76 | 1.12E−02 | H | 65 |
| LNU73_H2 | 0.78 | 1.37E−02 | B | 6 | LNU71_H3 | 0.72 | 1.99E−02 | G | 65 |
| LNU73_H2 | 0.74 | 2.30E−02 | B | 6 | LNU71_H3 | 0.72 | 1.99E−02 | G | 65 |
| LNU76_H55 | 0.90 | 8.36E−04 | B | 6 | LNU192_H3 | 0.75 | 1.16E−02 | G | 65 |
| LNU76_H55 | 0.79 | 1.10E−02 | B | 6 | LNU192_H3 | 0.75 | 1.16E−02 | G | 65 |
| LNU76_H55 | 0.90 | 8.36E−04 | B | 6 | LNU153_H6 | 0.73 | 1.59E−02 | G | 65 |
| LNU76_H55 | 0.79 | 1.10E−02 | B | 6 | LNU153_H6 | 0.73 | 1.59E−02 | G | 65 |
| LNU35_H4 | 0.72 | 2.88E−02 | B | 6 | LNU109_H2 | 0.82 | 3.46E−03 | F | 38 |
| LNU35_H4 | 0.72 | 2.88E−02 | B | 6 | LNU109_H2 | 0.73 | 1.67E−02 | F | 38 |
| LNU223_H6 | 0.74 | 2.25E−02 | B | 6 | LNU109_H2 | 0.82 | 3.46E−03 | F | 38 |
| LNU223_H6 | 0.74 | 2.25E−02 | B | 6 | LNU109_H2 | 0.73 | 1.67E−02 | F | 38 |

TABLE 31-continued

Correlation between the expression level of selected LNU homologous genes of some embodiments of the invention in various tissues and the phenotypic performance under low nitrogen, normal or drought stress conditions across *Sorghum* accessions

| Gene Name | R | P value | Exp. Set | Correl. Set ID | Gene Name | R | P value | Exp. Set | Correl. Set ID |
|---|---|---|---|---|---|---|---|---|---|
| LNU267_H2 | 0.75 | 2.05E−02 | A | 6 | LNU153_H6 | 0.73 | 1.75E−02 | F | 38 |
| LNU267_H2 | 0.72 | 3.00E−02 | A | 6 | LNU153_H6 | 0.73 | 1.75E−02 | F | 38 |
| LNU267_H2 | 0.75 | 2.05E−02 | A | 6 | LNU28_H4 | 0.90 | 4.11E−04 | E | 38 |
| LNU267_H2 | 0.72 | 3.00E−02 | A | 6 | LNU28_H4 | 0.89 | 5.37E−04 | E | 38 |
| LNU263_H4 | 0.75 | 2.03E−02 | A | 6 | LNU28_H4 | 0.90 | 4.11E−04 | E | 38 |
| LNU263_H4 | 0.75 | 2.07E−02 | A | 6 | LNU28_H4 | 0.89 | 5.37E−04 | E | 38 |
| LNU263_H5 | 0.75 | 1.93E−02 | A | 6 | LNU153_H5 | 0.79 | 6.64E−03 | B | 25 |
| LNU263_H5 | 0.74 | 2.14E−02 | A | 6 | LNU153_H5 | 0.79 | 6.64E−03 | B | 25 |
| LNU263_H4 | 0.75 | 2.03E−02 | A | 6 | LNU45_H258 | 0.77 | 9.31E−03 | A | 25 |
| LNU263_H4 | 0.75 | 2.07E−02 | A | 6 | LNU45_H258 | 0.77 | 9.31E−03 | A | 25 |
| LNU263_H5 | 0.75 | 1.93E−02 | A | 6 | LNU263_H4 | 0.73 | 1.64E−02 | I | 67 |
| LNU263_H5 | 0.74 | 2.14E−02 | A | 6 | LNU263_H4 | 0.71 | 2.20E−02 | I | 67 |
| LNU32_H2 | 0.76 | 1.78E−02 | A | 6 | LNU263_H4 | 0.73 | 1.64E−02 | I | 67 |
| LNU32_H2 | 0.76 | 1.78E−02 | A | 6 | LNU263_H4 | 0.71 | 2.20E−02 | I | 67 |
| LNU109_H2 | 0.88 | 1.67E−03 | A | 6 | LNU19_H1 | 0.75 | 1.26E−02 | H | 67 |
| LNU109_H2 | 0.88 | 1.78E−03 | A | 6 | LNU263_H5 | 0.71 | 2.22E−02 | H | 67 |
| LNU109_H2 | 0.88 | 1.67E−03 | A | 6 | LNU263_H5 | 0.71 | 2.22E−02 | H | 67 |
| LNU109_H2 | 0.88 | 1.78E−03 | A | 6 | LNU271_H4 | 0.83 | 2.65E−03 | H | 67 |
| LNU45_H259 | 0.75 | 1.93E−02 | A | 6 | LNU271_H4 | 0.72 | 1.82E−02 | H | 67 |
| LNU73_H2 | 0.74 | 1.46E−02 | F | 45 | LNU271_H4 | 0.83 | 2.65E−03 | H | 67 |
| LNU73_H2 | 0.74 | 1.46E−02 | F | 45 | LNU271_H4 | 0.72 | 1.82E−02 | H | 67 |
| LNU267_H2 | 0.87 | 2.55E−03 | C | 7 | LNU223_H6 | 0.78 | 7.24E−03 | H | 67 |
| LNU267_H2 | 0.71 | 3.24E−02 | C | 7 | LNU223_H6 | 0.78 | 7.24E−03 | H | 67 |
| LNU267_H2 | 0.87 | 2.55E−03 | C | 7 | LNU271_H4 | 0.90 | 8.49E−04 | C | 26 |
| LNU267_H2 | 0.71 | 3.24E−02 | C | 7 | LNU271_H4 | 0.90 | 9.96E−04 | C | 26 |
| LNU74_H173 | 0.81 | 8.49E−03 | C | 7 | LNU271_H4 | 0.90 | 8.49E−04 | C | 26 |
| LNU74_H173 | 0.77 | 1.44E−02 | C | 7 | LNU271_H4 | 0.90 | 9.96E−04 | C | 26 |
| LNU74_H173 | 0.81 | 8.49E−03 | C | 7 | LNU45_H259 | 0.71 | 3.28E−02 | C | 26 |
| LNU74_H173 | 0.77 | 1.44E−02 | C | 7 | LNU266_H0 | 0.91 | 2.13E−04 | I | 58 |
| LNU46_H58 | 0.85 | 3.94E−03 | C | 7 | LNU266_H0 | 0.87 | 1.17E−03 | I | 58 |
| LNU46_H58 | 0.85 | 3.94E−03 | C | 7 | LNU266_H0 | 0.91 | 2.13E−04 | I | 58 |
| LNU19_H1 | 0.74 | 2.38E−02 | B | 7 | LNU266_H0 | 0.87 | 1.17E−03 | I | 58 |
| LNU73_H2 | 0.74 | 2.27E−02 | B | 7 | LNU271_H4 | 0.86 | 1.38E−03 | I | 58 |
| LNU73_H2 | 0.74 | 2.27E−02 | B | 7 | LNU271_H4 | 0.76 | 1.14E−02 | I | 58 |
| LNU76_H55 | 0.90 | 8.98E−04 | B | 7 | LNU271_H4 | 0.86 | 1.38E−03 | I | 58 |
| LNU76_H55 | 0.76 | 1.78E−02 | B | 7 | LNU271_H4 | 0.76 | 1.14E−02 | I | 58 |
| LNU76_H55 | 0.90 | 8.98E−04 | B | 7 | LNU266_H0 | 0.81 | 4.11E−03 | H | 58 |
| LNU76_H55 | 0.76 | 1.78E−02 | B | 7 | LNU266_H0 | 0.75 | 1.16E−02 | H | 58 |
| LNU223_H6 | 0.76 | 1.80E−02 | B | 7 | LNU266_H0 | 0.81 | 4.11E−03 | H | 58 |
| LNU223_H6 | 0.76 | 1.80E−02 | B | 7 | LNU266_H0 | 0.75 | 1.16E−02 | H | 58 |
| LNU267_H2 | 0.81 | 7.62E−03 | A | 7 | LNU268_H2 | 0.81 | 4.08E−03 | H | 58 |
| LNU267_H2 | 0.79 | 1.15E−02 | A | 7 | LNU268_H2 | 0.80 | 4.97E−03 | H | 58 |
| LNU267_H2 | 0.81 | 7.62E−03 | A | 7 | LNU268_H2 | 0.81 | 4.08E−03 | H | 58 |
| LNU267_H2 | 0.79 | 1.15E−02 | A | 7 | LNU268_H2 | 0.80 | 4.97E−03 | H | 58 |
| LNU263_H4 | 0.76 | 1.81E−02 | A | 7 | LNU121_H1 | 0.74 | 1.37E−02 | E | 33 |
| LNU263_H4 | 0.75 | 1.98E−02 | A | 7 | LNU121_H1 | 0.71 | 2.17E−02 | E | 33 |
| LNU263_H4 | 0.76 | 1.81E−02 | A | 7 | LNU268_H2 | 0.92 | 1.97E−04 | E | 33 |
| LNU263_H4 | 0.75 | 1.98E−02 | A | 7 | LNU268_H2 | 0.90 | 3.81E−04 | E | 33 |
| LNU32_H2 | 0.73 | 2.63E−02 | A | 7 | LNU268_H2 | 0.92 | 1.97E−04 | E | 33 |
| LNU32_H2 | 0.73 | 2.63E−02 | A | 7 | LNU268_H2 | 0.90 | 3.81E−04 | E | 33 |
| LNU109_H2 | 0.88 | 1.95E−03 | A | 7 | LNU48_H1 | 0.85 | 1.63E−03 | E | 33 |
| LNU109_H2 | 0.86 | 2.61E−03 | A | 7 | LNU48_H1 | 0.85 | 1.63E−03 | E | 33 |
| LNU109_H2 | 0.88 | 1.95E−03 | A | 7 | LNU34_H1 | 0.78 | 8.40E−03 | E | 33 |
| LNU109_H2 | 0.86 | 2.61E−03 | A | 7 | LNU34_H1 | 0.78 | 8.40E−03 | E | 33 |
| LNU45_H259 | 0.75 | 2.09E−02 | A | 7 | LNU28_H4 | 0.71 | 2.27E−02 | D | 33 |
| LNU45_H259 | 0.78 | 8.02E−03 | I | 53 | LNU28_H4 | 0.71 | 2.27E−02 | D | 33 |
| LNU45_H259 | 0.78 | 8.02E−03 | I | 53 | LNU45_H259 | 0.86 | 1.53E−03 | D | 33 |
| LNU69_H4 | 0.70 | 2.34E−02 | H | 53 | LNU45_H259 | 0.85 | 1.76E−03 | D | 33 |
| LNU69_H4 | 0.72 | 1.97E−02 | G | 53 | LNU267_H2 | 0.73 | 1.73E−02 | A | 18 |
| LNU2_H4 | 0.71 | 2.09E−02 | B | 15 | LNU267_H2 | 0.71 | 2.20E−02 | A | 18 |
| LNU2_H??? | 0.71 | 2.09E−02 | B | 15 | LNU267_H2 | 0.73 | 1.73E−02 | A | 18 |
| LNU2_H4 | 0.71 | 2.09E−02 | B | 15 | LNU267_H2 | 0.71 | 2.20E−02 | A | 18 |
| LNU267_H2 | 0.77 | 9.13E−03 | B | 15 | LNU73_H2 | 0.73 | 1.55E−02 | A | 18 |
| LNU267_H2 | 0.77 | 9.13E−03 | B | 15 | LNU73_H2 | 0.71 | 2.03E−02 | A | 18 |
| LNU153_H5 | 0.83 | 3.20E−03 | B | 15 | LNU73_H2 | 0.73 | 1.55E−02 | A | 18 |
| LNU153_H5 | 0.83 | 3.20E−03 | B | 15 | LNU73_H2 | 0.71 | 2.03E−02 | A | 18 |
| LNU45_H259 | 0.75 | 1.20E−02 | I | 53 | LNU76_H55 | 0.76 | 1.06E−02 | A | 18 |
| LNU45_H259 | 0.75 | 1.20E−02 | I | 53 | LNU76_H55 | 0.75 | 1.17E−02 | A | 18 |
| LNU28_H4 | 0.76 | 1.02E−02 | G | 53 | LNU76_H55 | 0.76 | 1.06E−02 | A | 18 |
| LNU28_H4 | 0.76 | 1.02E−02 | G | 53 | LNU76_H55 | 0.75 | 1.17E−02 | A | 18 |
| LNU153_H5 | 0.78 | 7.18E−03 | G | 53 | LNU52_H6 | 0.84 | 2.20E−03 | B | 1 |
| LNU153_H5 | 0.78 | 7.18E−03 | G | 53 | LNU52_H6 | 0.74 | 1.36E−02 | B | 1 |

TABLE 31-continued

Correlation between the expression level of selected LNU homologous genes of some embodiments of the invention in various tissues and the phenotypic performance under low nitrogen, normal or drought stress conditions across *Sorghum* accessions

| Gene Name | R | P value | Exp. Set | Correl. Set ID | Gene Name | R | P value | Exp. Set | Correl. Set ID |
|---|---|---|---|---|---|---|---|---|---|
| LNU239_H10 | 0.72 | 1.81E-02 | E | 30 | LNU52_H6 | 0.84 | 2.20E-03 | B | 1 |
| LNU239_H10 | 0.72 | 1.81E-02 | E | 30 | LNU52_H6 | 0.74 | 1.36E-02 | B | 1 |
| LNU121_H1 | 0.73 | 1.72E-02 | D | 30 | LNU46_H60 | 0.72 | 1.85E-02 | B | 1 |
| LNU121_H1 | 0.71 | 2.19E-02 | D | 30 | LNU46_H60 | 0.72 | 1.85E-02 | B | 1 |
| LNU45_H259 | 0.77 | 9.46E-03 | C | 15 | LNU35_H4 | 0.80 | 5.52E-03 | H | 59 |
| LNU45_H259 | 0.74 | 1.43E-02 | C | 15 | LNU35_H4 | 0.77 | 8.61E-03 | H | 59 |
| LNU76_H55 | 0.80 | 5.70E-03 | H | 30 | LNU35_H4 | 0.80 | 5.52E-03 | H | 59 |
| LNU76_H55 | 0.80 | 5.70E-03 | H | 30 | LNU35_H4 | 0.77 | 8.61E-03 | H | 59 |
| LNU28_H4 | 0.80 | 4.98E-03 | G | 30 | LNU73_H2 | 0.78 | 8.29E-03 | F | 34 |
| LNU28_H4 | 0.72 | 1.96E-02 | G | 30 | LNU73_H2 | 0.78 | 8.29E-03 | F | 34 |
| LNU28_H4 | 0.80 | 4.98E-03 | G | 30 | LNU73_H2 | 0.76 | 1.00E-02 | A | 19 |
| LNU28_H4 | 0.72 | 1.96E-02 | G | 30 | LNU73_H2 | 0.72 | 1.95E-02 | I | 62 |
| LNU153_H5 | 0.76 | 1.15E-02 | G | 30 | LNU271_H4 | 0.73 | 1.58E-02 | I | 62 |
| LNU153_H5 | 0.76 | 1.15E-02 | G | 30 | LNU271_H4 | 0.73 | 1.58E-02 | I | 62 |
| LNU52_H6 | 0.71 | 2.05E-02 | F | 30 | LNU35_H4 | 0.75 | 1.25E-02 | H | 62 |
| LNU52_H6 | 0.71 | 2.27E-02 | F | 30 | LNU35_H4 | 0.74 | 1.39E-02 | H | 62 |
| LNU52_H6 | 0.71 | 2.05E-02 | F | 30 | LNU35_H4 | 0.75 | 1.25E-02 | H | 62 |
| LNU52_H6 | 0.71 | 2.27E-02 | F | 30 | LNU35_H4 | 0.74 | 1.39E-02 | H | 62 |
| LNU7_H125 | 0.71 | 2.09E-02 | F | 30 | LNU153_H5 | 0.77 | 9.81E-03 | H | 62 |
| LNU7_H125 | 0.71 | 2.09E-02 | F | 30 | LNU153_H5 | 0.77 | 9.81E-03 | H | 62 |
| LNU7_H124 | 0.71 | 2.09E-02 | F | 30 | LNU239_H10 | 0.75 | 1.29E-02 | A | 22 |
| LNU7_H125 | 0.71 | 2.09E-02 | F | 30 | LNU239_H10 | 0.75 | 1.29E-02 | A | 22 |
| LNU7_H124 | 0.71 | 2.09E-02 | F | 30 | LNU76_H55 | 0.76 | 1.10E-02 | H | 64 |
| LNU7_H125 | 0.71 | 2.09E-02 | F | 30 | LNU76_H55 | 0.76 | 1.10E-02 | H | 64 |
| LNU45_H260 | 0.79 | 6.14E-03 | F | 30 | LNU48_H1 | 0.76 | 1.04E-02 | G | 64 |
| LNU239_H10 | 0.74 | 1.47E-02 | F | 30 | LNU48_H1 | 0.76 | 1.04E-02 | G | 64 |
| LNU239_H10 | 0.74 | 1.47E-02 | F | 30 | LNU28_H4 | 0.89 | 6.25E-04 | G | 64 |
| LNU89_H5 | 0.72 | 1.99E-02 | E | 30 | LNU28_H4 | 0.79 | 7.02E-03 | G | 64 |
| LNU89_H5 | 0.72 | 1.99E-02 | E | 30 | LNU28_H4 | 0.89 | 6.25E-04 | G | 64 |
| LNU266_H0 | 0.79 | 6.53E-03 | D | 30 | LNU28_H4 | 0.79 | 7.02E-03 | G | 64 |
| LNU266_H0 | 0.75 | 1.33E-02 | D | 30 | LNU153_H5 | 0.83 | 2.98E-03 | G | 64 |
| LNU266_H0 | 0.79 | 6.53E-03 | D | 30 | LNU153_H5 | 0.83 | 2.98E-03 | G | 64 |
| LNU266_H0 | 0.75 | 1.33E-02 | D | 30 | LNU271_H4 | 0.82 | 7.37E-03 | C | 24 |
| LNU46_H58 | 0.74 | 1.40E-02 | D | 30 | LNU271_H4 | 0.80 | 9.35E-03 | C | 24 |
| LNU46_H58 | 0.74 | 1.40E-02 | D | 30 | LNU271_H4 | 0.82 | 7.37E-03 | C | 24 |
| LNU2_H4 | 0.72 | 1.77E-02 | B | 15 | LNU271_H4 | 0.80 | 9.35E-03 | C | 24 |
| LNU2_H??? | 0.72 | 1.77E-02 | B | 15 | LNU28_H4 | 0.71 | 3.17E-02 | B | 24 |
| LNU2_H4 | 0.72 | 1.77E-02 | B | 15 | LNU28_H4 | 0.70 | 3.44E-02 | B | 24 |
| LNU73_H2 | 0.71 | 2.04E-02 | B | 15 | LNU28_H4 | 0.71 | 3.17E-02 | B | 24 |
| LNU73_H2 | 0.71 | 2.04E-02 | B | 15 | LNU28_H4 | 0.70 | 3.44E-02 | B | 24 |
| LNU71_H3 | 0.89 | 4.70E-04 | I | 55 | LNU268_H2 | 0.77 | 8.80E-03 | A | 24 |
| LNU71_H3 | 0.75 | 1.32E-02 | I | 55 | LNU268_H2 | 0.77 | 8.80E-03 | A | 24 |
| LNU71_H3 | 0.89 | 4.70E-04 | I | 55 | LNU109_H2 | 0.81 | 4.76E-03 | E | 28 |
| LNU71_H3 | 0.75 | 1.32E-02 | I | 55 | LNU109_H2 | 0.81 | 4.76E-03 | E | 28 |
| LNU192_H3 | 0.78 | 8.36E-03 | I | 55 | LNU45_H259 | 0.76 | 1.10E-02 | E | 28 |
| LNU192_H3 | 0.77 | 9.80E-03 | I | 55 | LNU45_H259 | 0.73 | 1.62E-02 | E | 28 |
| LNU192_H3 | 0.78 | 8.36E-03 | I | 55 | LNU45_H260 | 0.74 | 1.45E-02 | E | 28 |
| LNU192_H3 | 0.77 | 9.80E-03 | I | 55 | LNU45_H260 | 0.72 | 1.98E-02 | E | 28 |
| LNU74_H172 | 0.71 | 2.23E-02 | G | 55 | LNU45_H259 | 0.76 | 1.10E-02 | E | 28 |
| LNU74_H172 | 0.71 | 2.23E-02 | G | 55 | LNU45_H259 | 0.73 | 1.62E-02 | E | 28 |
| LNU192_H3 | 0.76 | 1.03E-02 | G | 55 | LNU48_H1 | 0.75 | 1.16E-02 | H | 68 |
| LNU192_H3 | 0.76 | 1.03E-02 | G | 55 | LNU48_H1 | 0.75 | 1.16E-02 | H | 68 |
| LNU128_H12 | 0.73 | 1.77E-02 | A | 16 | LNU35_H4 | 0.76 | 1.10E-02 | H | 68 |
| LNU128_H12 | 0.73 | 1.77E-02 | A | 16 | LNU35_H4 | 0.76 | 1.10E-02 | H | 68 |
| LNU268_H2 | 0.76 | 1.02E-02 | A | 16 | LNU271_H4 | 0.82 | 7.37E-03 | C | 27 |
| LNU268_H2 | 0.70 | 2.37E-02 | A | 16 | LNU271_H4 | 0.80 | 9.35E-03 | C | 27 |
| LNU268_H2 | 0.76 | 1.02E-02 | A | 16 | LNU271_H4 | 0.82 | 7.37E-03 | C | 27 |
| LNU268_H2 | 0.70 | 2.37E-02 | A | 16 | LNU271_H4 | 0.80 | 9.35E-03 | C | 27 |
| LNU35_H4 | 0.73 | 1.76E-02 | A | 16 | LNU28_H4 | 0.71 | 3.17E-02 | B | 27 |
| LNU35_H4 | 0.73 | 1.76E-02 | A | 16 | LNU28_H4 | 0.70 | 3.44E-02 | B | 27 |
| LNU153_H6 | 0.70 | 2.36E-02 | A | 16 | LNU28_H4 | 0.71 | 3.17E-02 | B | 27 |
| LNU153_H6 | 0.70 | 2.36E-02 | A | 16 | LNU28_H4 | 0.70 | 3.44E-02 | B | 27 |
| LNU73_H2 | 0.71 | 2.14E-02 | B | 10 | LNU268_H2 | 0.77 | 8.80E-03 | A | 27 |
| LNU73_H2 | 0.71 | 2.14E-02 | B | 10 | LNU268_H2 | 0.77 | 8.80E-03 | A | 27 |
| LNU153_H5 | 0.81 | 4.91E-03 | B | 10 | LNU28_H4 | 0.90 | 2.14E-03 | H | 77 |
| LNU153_H5 | 0.81 | 4.91E-03 | B | 10 | LNU28_H4 | 0.90 | 2.19E-03 | H | 77 |
| LNU223_H6 | 0.78 | 7.44E-03 | G | 52 | LNU28_H4 | 0.90 | 2.14E-03 | H | 77 |
| LNU223_H6 | 0.78 | 7.44E-03 | G | 52 | LNU28_H4 | 0.90 | 2.19E-03 | H | 77 |
| LNU52_H6 | 0.73 | 1.60E-02 | B | 14 | LNU153_H6 | 0.74 | 3.50E-02 | H | 77 |
| LNU52_H6 | 0.73 | 1.60E-02 | B | 14 | LNU153_H6 | 0.74 | 3.50E-02 | H | 77 |
| LNU46_H60 | 0.75 | 1.93E-02 | C | 9 | LNU121_H1 | 0.72 | 4.30E-02 | G | 77 |
| LNU46_H60 | 0.75 | 1.93E-02 | C | 9 | LNU121_H1 | 0.72 | 4.30E-02 | G | 77 |

TABLE 31-continued

Correlation between the expression level of selected LNU homologous genes of some embodiments of the invention in various tissues and the phenotypic performance under low nitrogen, normal or drought stress conditions across *Sorghum* accessions

| Gene Name | R | P value | Exp. Set | Correl. Set ID | Gene Name | R | P value | Exp. Set | Correl. Set ID |
|---|---|---|---|---|---|---|---|---|---|
| LNU267_H2 | 0.89 | 1.45E-03 | B | 9 | LNU13_H1 | 0.86 | 5.88E-03 | G | 77 |
| LNU267_H2 | 0.76 | 1.75E-02 | B | 9 | LNU13_H1 | 0.85 | 7.91E-03 | G | 77 |
| LNU267_H2 | 0.89 | 1.45E-03 | B | 9 | LNU13_H1 | 0.86 | 5.88E-03 | G | 77 |
| LNU267_H2 | 0.76 | 1.75E-02 | B | 9 | LNU13_H1 | 0.85 | 7.91E-03 | G | 77 |
| LNU73_H2 | 0.78 | 1.40E-02 | B | 9 | LNU268_H2 | 0.88 | 3.80E-03 | G | 77 |
| LNU73_H2 | 0.70 | 3.39E-02 | B | 9 | LNU268_H2 | 0.81 | 1.59E-02 | G | 77 |
| LNU73_H2 | 0.78 | 1.40E-02 | B | 9 | LNU268_H2 | 0.88 | 3.80E-03 | G | 77 |
| LNU73_H2 | 0.70 | 3.39E-02 | B | 9 | LNU268_H2 | 0.81 | 1.59E-02 | G | 77 |
| LNU153_H5 | 0.73 | 2.46E-02 | B | 9 | LNU7_H125 | 0.87 | 5.38E-03 | G | 77 |
| LNU153_H5 | 0.73 | 2.46E-02 | B | 9 | LNU7_H125 | 0.87 | 5.38E-03 | G | 77 |
| LNU109_H2 | 0.73 | 2.64E-02 | A | 9 | LNU7_H124 | 0.87 | 5.38E-03 | G | 77 |
| LNU109_H2 | 0.72 | 2.89E-02 | A | 9 | LNU71_H3 | 0.89 | 2.92E-03 | G | 77 |
| LNU109_H2 | 0.73 | 2.64E-02 | A | 9 | LNU71_H3 | 0.88 | 3.50E-03 | G | 77 |
| LNU109_H2 | 0.72 | 2.89E-02 | A | 9 | LNU71_H3 | 0.89 | 2.92E-03 | G | 77 |
| LNU35_H4 | 0.74 | 1.46E-02 | F | 48 | LNU71_H3 | 0.88 | 3.50E-03 | G | 77 |
| LNU35_H4 | 0.74 | 1.46E-02 | F | 48 | LNU74_H172 | 0.87 | 5.17E-03 | G | 77 |
| LNU74_H172 | 0.73 | 2.61E-02 | B | 14 | LNU74_H172 | 0.75 | 3.05E-02 | G | 77 |
| LNU74_H172 | 0.73 | 2.61E-02 | B | 14 | LNU74_H172 | 0.87 | 5.17E-03 | G | 77 |
| LNU45_H258 | 0.72 | 2.92E-02 | B | 14 | LNU74_H172 | 0.75 | 3.05E-02 | G | 77 |
| LNU45_H258 | 0.72 | 2.92E-02 | B | 14 | LNU192_H3 | 0.90 | 2.49E-03 | G | 77 |
| LNU153_H6 | 0.72 | 2.81E-02 | A | 14 | LNU192_H3 | 0.86 | 6.31E-03 | G | 77 |
| LNU153_H6 | 0.72 | 2.81E-02 | A | 14 | LNU192_H3 | 0.90 | 2.49E-03 | G | 77 |
| LNU266_H0 | 0.70 | 2.31E-02 | F | 48 | LNU192_H3 | 0.86 | 6.31E-03 | G | 77 |
| LNU266_H0 | 0.70 | 2.31E-02 | F | 48 | LNU7_H125 | 0.87 | 5.38E-03 | G | 77 |
| LNU46_H58 | 0.70 | 2.41E-02 | D | 48 | LNU7_H124 | 0.87 | 5.38E-03 | G | 77 |
| LNU46_H58 | 0.70 | 2.41E-02 | D | 48 | LNU7_H125 | 0.87 | 5.38E-03 | G | 77 |
| LNU216_H3 | 0.71 | 3.12E-02 | C | 8 | LNU265_H0 | 0.74 | 3.66E-02 | G | 77 |
| LNU216_H3 | 0.71 | 3.12E-02 | C | 8 | LNU265_H0 | 0.74 | 3.66E-02 | G | 77 |
| LNU263_H4 | 0.72 | 3.01E-02 | C | 8 | LNU45_H259 | 0.85 | 7.87E-03 | G | 77 |
| LNU263_H5 | 0.79 | 1.06E-02 | C | 8 | LNU45_H259 | 0.81 | 1.42E-02 | G | 77 |
| LNU263_H5 | 0.78 | 1.32E-02 | C | 8 | LNU45_H260 | 0.73 | 3.79E-02 | G | 77 |
| LNU263_H4 | 0.72 | 3.01E-02 | C | 8 | LNU45_H258 | 0.89 | 2.90E-03 | G | 77 |
| LNU263_H5 | 0.79 | 1.06E-02 | C | 8 | LNU45_H258 | 0.85 | 8.01E-03 | G | 77 |
| LNU263_H5 | 0.78 | 1.32E-02 | C | 8 | LNU45_H259 | 0.85 | 7.87E-03 | G | 77 |
| LNU216_H4 | 0.80 | 9.11E-03 | B | 8 | LNU45_H259 | 0.81 | 1.42E-02 | G | 77 |
| LNU216_H3 | 0.81 | 8.55E-03 | B | 8 | LNU45_H258 | 0.89 | 2.90E-03 | G | 77 |
| LNU216_H3 | 0.77 | 1.44E-02 | B | 8 | LNU45_H258 | 0.85 | 8.01E-03 | G | 77 |
| LNU216_H4 | 0.80 | 9.11E-03 | B | 8 | LNU35_H4 | 0.74 | 3.67E-02 | G | 77 |
| LNU216_H3 | 0.81 | 8.55E-03 | B | 8 | LNU35_H4 | 0.74 | 3.67E-02 | G | 77 |
| LNU216_H3 | 0.77 | 1.44E-02 | B | 8 | LNU153_H6 | 0.89 | 2.89E-03 | G | 77 |
| LNU74_H172 | 0.81 | 7.93E-03 | B | 8 | LNU153_H6 | 0.89 | 2.89E-03 | G | 77 |
| LNU74_H172 | 0.81 | 7.93E-03 | B | 8 | LNU74_H173 | 0.75 | 3.19E-02 | A | 2 |
| LNU45_H259 | 0.79 | 1.20E-02 | B | 8 | LNU74_H173 | 0.75 | 3.19E-02 | A | 2 |
| LNU45_H259 | 0.79 | 1.20E-02 | B | 8 | LNU46_H60 | 0.82 | 4.40E-02 | E | 39 |
| LNU153_H6 | 0.80 | 1.00E-02 | B | 8 | LNU46_H58 | 0.82 | 4.70E-02 | E | 39 |
| LNU153_H6 | 0.80 | 1.00E-02 | B | 8 | LNU46_H60 | 0.82 | 4.40E-02 | E | 39 |
| LNU128_H13 | 0.71 | 3.37E-02 | A | 8 | LNU46_H58 | 0.82 | 4.70E-02 | E | 39 |
| LNU128_H12 | 0.80 | 1.04E-02 | A | 8 | LNU7_H125 | 0.85 | 3.33E-02 | D | 39 |
| LNU128_H13 | 0.71 | 3.37E-02 | A | 8 | LNU7_H125 | 0.85 | 3.33E-02 | D | 39 |
| LNU128_H12 | 0.80 | 1.04E-02 | A | 8 | LNU7_H124 | 0.85 | 3.33E-02 | D | 39 |
| LNU51_H2 | 0.71 | 3.07E-02 | A | 8 | LNU7_H125 | 0.85 | 3.33E-02 | D | 39 |
| LNU51_H2 | 0.71 | 3.07E-02 | A | 8 | LNU7_H124 | 0.85 | 3.33E-02 | D | 39 |
| LNU67_H4 | 0.80 | 1.03E-02 | A | 8 | LNU7_H125 | 0.85 | 3.33E-02 | D | 39 |
| LNU265_H0 | 0.82 | 7.21E-03 | A | 8 | LNU271_H4 | 0.82 | 4.76E-02 | D | 39 |
| LNU265_H0 | 0.82 | 7.21E-03 | A | 8 | LNU271_H4 | 0.82 | 4.76E-02 | D | 39 |
| LNU128_H13 | 0.78 | 7.57E-03 | E | 47 | LNU153_H5 | 0.74 | 1.40E-02 | B | 13 |
| LNU128_H12 | 0.78 | 7.39E-03 | E | 47 | LNU153_H5 | 0.74 | 1.40E-02 | B | 13 |
| LNU128_H12 | 0.71 | 2.13E-02 | E | 47 | LNU266_H0 | 0.71 | 2.15E-02 | G | 56 |
| LNU128_H13 | 0.78 | 7.57E-03 | E | 47 | LNU266_H0 | 0.70 | 2.28E-02 | G | 56 |
| LNU128_H12 | 0.78 | 7.39E-03 | E | 47 | LNU266_H0 | 0.71 | 2.15E-02 | G | 56 |
| LNU128_H12 | 0.71 | 2.13E-02 | E | 47 | LNU266_H0 | 0.70 | 2.28E-02 | G | 56 |
| LNU52_H6 | 0.71 | 2.20E-02 | E | 47 | LNU223_H6 | 0.84 | 2.57E-03 | G | 56 |
| LNU52_H6 | 0.71 | 2.20E-02 | E | 47 | LNU223_H6 | 0.70 | 2.34E-02 | G | 56 |
| LNU263_H4 | 0.70 | 2.40E-02 | E | 47 | LNU223_H6 | 0.84 | 2.57E-03 | G | 56 |
| LNU263_H4 | 0.70 | 2.40E-02 | E | 47 | LNU223_H6 | 0.70 | 2.34E-02 | G | 56 |
| LNU52_H6 | 0.79 | 7.10E-03 | B | 12 | LNU73_H2 | 0.73 | 2.55E-02 | F | 32 |
| LNU52_H6 | 0.79 | 7.10E-03 | B | 12 | LNU73_H2 | 0.73 | 2.55E-02 | F | 32 |
| LNU74_H172 | 0.76 | 1.08E-02 | B | 12 | LNU45_H259 | 0.88 | 1.98E-03 | F | 32 |
| LNU74_H172 | 0.74 | 1.40E-02 | B | 12 | LNU45_H259 | 0.88 | 1.98E-03 | F | 32 |
| LNU74_H172 | 0.76 | 1.08E-02 | B | 12 | LNU17_H2 | 0.77 | 1.44E-02 | E | 32 |
| LNU74_H172 | 0.74 | 1.40E-02 | B | 12 | LNU17_H2 | 0.70 | 3.40E-02 | E | 32 |
| LNU35_H4 | 0.81 | 4.84E-03 | E | 29 | LNU17_H2 | 0.77 | 1.44E-02 | E | 32 |

TABLE 31-continued

Correlation between the expression level of selected LNU homologous genes of some embodiments of the invention in various tissues and the phenotypic performance under low nitrogen, normal or drought stress conditions across *Sorghum* accessions

| Gene Name | R | P value | Exp. Set | Correl. Set ID | Gene Name | R | P value | Exp. Set | Correl. Set ID |
|---|---|---|---|---|---|---|---|---|---|
| LNU35_H4 | 0.81 | 4.84E−03 | E | 29 | LNU17_H2 | 0.70 | 3.40E−02 | E | 32 |
| LNU266_H0 | 0.72 | 1.84E−02 | D | 29 | LNU109_H2 | 0.76 | 1.68E−02 | E | 32 |
| LNU266_H0 | 0.70 | 2.29E−02 | D | 29 | LNU109_H2 | 0.76 | 1.68E−02 | E | 32 |
| LNU266_H0 | 0.72 | 1.84E−02 | D | 29 | LNU266_H0 | 0.77 | 9.34E−03 | C | 17 |
| LNU266_H0 | 0.70 | 2.29E−02 | D | 29 | LNU266_H0 | 0.73 | 1.70E−02 | C | 17 |
| LNU216_H3 | 0.71 | 2.23E−02 | G | 52 | LNU266_H0 | 0.77 | 9.34E−03 | C | 17 |
| LNU216_H3 | 0.71 | 2.23E−02 | G | 52 | LNU266_H0 | 0.73 | 1.70E−02 | C | 17 |
| LNU223_H6 | 0.85 | 1.66E−03 | G | 52 | LNU216_H4 | 0.76 | 1.15E−02 | G | 54 |
| LNU223_H6 | 0.71 | 2.11E−02 | G | 52 | LNU216_H3 | 0.80 | 5.03E−03 | G | 54 |
| LNU223_H6 | 0.85 | 1.66E−03 | G | 52 | LNU216_H3 | 0.79 | 6.11E−03 | G | 54 |
| LNU223_H6 | 0.71 | 2.11E−02 | G | 52 | LNU216_H4 | 0.76 | 1.15E−02 | G | 54 |
| LNU35_H4 | 0.76 | 1.01E−02 | E | 29 | LNU216_H3 | 0.80 | 5.03E−03 | G | 54 |
| LNU35_H4 | 0.76 | 1.01E−02 | E | 29 | LNU216_H3 | 0.79 | 6.11E−03 | G | 54 |
| LNU266_H0 | 0.78 | 8.03E−03 | D | 29 | LNU74_H172 | 0.85 | 1.77E−03 | G | 54 |
| LNU266_H0 | 0.76 | 1.10E−02 | D | 29 | LNU74_H172 | 0.85 | 1.77E−03 | G | 54 |
| LNU266_H0 | 0.78 | 8.03E−03 | D | 29 | LNU45_H259 | 0.78 | 7.31E−03 | G | 54 |
| LNU266_H0 | 0.76 | 1.10E−02 | D | 29 | LNU45_H260 | 0.71 | 2.04E−02 | G | 54 |
| LNU153_H6 | 0.73 | 1.69E−02 | A | 29 | LNU45_H259 | 0.78 | 7.31E−03 | G | 54 |
| LNU153_H6 | 0.73 | 1.69E−02 | A | 29 | LNU223_H6 | 0.87 | 9.56E−04 | G | 54 |
| LNU35_H4 | 0.83 | 2.65E−03 | G | 52 | LNU223_H6 | 0.84 | 2.41E−03 | G | 54 |
| LNU35_H4 | 0.83 | 2.65E−03 | G | 52 | LNU223_H6 | 0.87 | 9.56E−04 | G | 54 |
| LNU265_H0 | 0.72 | 1.79E−02 | D | 29 | LNU223_H6 | 0.84 | 2.41E−03 | G | 54 |
| LNU265_H0 | 0.72 | 1.79E−02 | D | 29 | LNU128_H12 | 0.76 | 1.66E−02 | F | 31 |
| LNU263_H4 | 0.73 | 1.67E−02 | C | 12 | LNU128_H12 | 0.74 | 2.35E−02 | F | 31 |
| LNU263_H5 | 0.80 | 5.07E−03 | C | 12 | LNU128_H12 | 0.76 | 1.66E−02 | F | 31 |
| LNU263_H5 | 0.79 | 6.53E−03 | C | 12 | LNU128_H12 | 0.74 | 2.35E−02 | F | 31 |
| LNU263_H4 | 0.73 | 1.67E−02 | C | 12 | LNU69_H4 | 0.86 | 2.75E−03 | F | 31 |
| LNU263_H5 | 0.80 | 5.07E−03 | C | 12 | LNU69_H4 | 0.74 | 2.16E−02 | D | 31 |
| LNU263_H5 | 0.79 | 6.53E−03 | C | 12 | LNU153_H6 | 0.71 | 2.27E−02 | C | 17 |
| LNU216_H4 | 0.81 | 4.94E−03 | B | 12 | LNU153_H6 | 0.71 | 2.27E−02 | C | 17 |
| LNU216_H3 | 0.78 | 7.53E−03 | B | 12 | LNU28_H4 | 0.77 | 9.79E−03 | B | 17 |
| LNU216_H3 | 0.74 | 1.39E−02 | B | 12 | LNU28_H4 | 0.75 | 1.27E−02 | B | 17 |
| LNU216_H4 | 0.81 | 4.94E−03 | B | 12 | LNU28_H4 | 0.77 | 9.79E−03 | B | 17 |
| LNU216_H3 | 0.78 | 7.53E−03 | B | 12 | LNU28_H4 | 0.75 | 1.27E−02 | B | 17 |
| LNU216_H3 | 0.74 | 1.39E−02 | B | 12 | LNU153_H6 | 0.84 | 2.34E−03 | B | 17 |
| LNU74_H172 | 0.82 | 4.02E−03 | B | 12 | LNU153_H6 | 0.84 | 2.34E−03 | B | 17 |
| LNU74_H172 | 0.82 | 4.02E−03 | B | 12 | LNU128_H12 | 0.72 | 2.00E−02 | A | 17 |
| LNU45_H259 | 0.80 | 5.93E−03 | B | 12 | LNU128_H12 | 0.72 | 2.00E−02 | A | 17 |
| LNU45_H259 | 0.80 | 5.93E−03 | B | 12 | LNU13_H1 | 0.80 | 4.97E−03 | A | 17 |
| LNU153_H6 | 0.72 | 1.99E−02 | B | 12 | LNU13_H1 | 0.78 | 7.23E−03 | A | 17 |
| LNU153_H6 | 0.72 | 1.99E−02 | B | 12 | LNU13_H1 | 0.80 | 4.97E−03 | A | 17 |
| LNU128_H12 | 0.76 | 1.11E−02 | A | 12 | LNU13_H1 | 0.78 | 7.23E−03 | A | 17 |
| LNU128_H12 | 0.76 | 1.11E−02 | A | 12 | LNU268_H2 | 0.87 | 1.22E−03 | A | 17 |
| LNU51_H2 | 0.71 | 2.07E−02 | A | 12 | LNU268_H2 | 0.82 | 3.58E−03 | A | 17 |
| LNU51_H2 | 0.71 | 2.07E−02 | A | 12 | LNU268_H2 | 0.87 | 1.22E−03 | A | 17 |
| LNU67_H4 | 0.80 | 5.06E−03 | A | 12 | LNU268_H2 | 0.82 | 3.58E−03 | A | 17 |
| LNU265_H0 | 0.81 | 4.14E−03 | A | 12 | LNU52_H6 | 0.72 | 1.91E−02 | A | 17 |
| LNU265_H0 | 0.81 | 4.14E−03 | A | 12 | LNU52_H6 | 0.72 | 1.91E−02 | A | 17 |
| LNU121_H1 | 0.87 | 1.04E−03 | H | 72 | LNU153_H6 | 0.89 | 5.61E−04 | A | 17 |
| LNU121_H1 | 0.77 | 9.39E−03 | H | 72 | LNU153_H6 | 0.89 | 5.61E−04 | A | 17 |
| LNU121_H1 | 0.87 | 1.04E−03 | H | 72 | LNU13_H1 | 0.79 | 6.40E−03 | I | 60 |
| LNU121_H1 | 0.77 | 9.39E−03 | H | 72 | LNU13_H1 | 0.79 | 6.40E−03 | I | 60 |
| LNU2_H4 | 0.78 | 8.24E−03 | H | 72 | LNU71_H3 | 0.84 | 2.54E−03 | I | 60 |
| LNU2_H??? | 0.78 | 8.24E−03 | H | 72 | LNU71_H3 | 0.83 | 2.96E−03 | I | 60 |
| LNU2_H4 | 0.78 | 8.24E−03 | H | 72 | LNU71_H3 | 0.84 | 2.54E−03 | I | 60 |
| LNU51_H2 | 0.85 | 1.96E−03 | H | 72 | LNU71_H3 | 0.83 | 2.96E−03 | I | 60 |
| LNU51_H2 | 0.85 | 1.96E−03 | H | 72 | LNU74_H172 | 0.74 | 1.44E−02 | I | 60 |
| LNU32_H2 | 0.89 | 5.20E−04 | H | 72 | LNU74_H172 | 0.74 | 1.44E−02 | I | 60 |
| LNU32_H2 | 0.89 | 5.20E−04 | H | 72 | LNU192_H3 | 0.87 | 1.08E−03 | I | 60 |
| LNU266_H0 | 0.73 | 2.68E−02 | A | 4 | LNU192_H3 | 0.72 | 1.77E−02 | I | 60 |
| LNU266_H0 | 0.73 | 2.68E−02 | A | 4 | LNU192_H3 | 0.87 | 1.08E−03 | I | 60 |
| LNU268_H2 | 0.75 | 1.98E−02 | A | 4 | LNU192_H3 | 0.72 | 1.77E−02 | I | 60 |
| LNU268_H2 | 0.72 | 2.84E−02 | A | 4 | LNU46_H60 | 0.73 | 1.71E−02 | I | 60 |
| LNU268_H2 | 0.75 | 1.98E−02 | A | 4 | LNU46_H60 | 0.73 | 1.71E−02 | I | 60 |
| LNU268_H2 | 0.72 | 2.84E−02 | A | 4 | LNU73_H2 | 0.77 | 8.83E−03 | E | 35 |
| LNU153_H6 | 0.77 | 1.48E−02 | A | 4 | LNU35_H4 | 0.76 | 1.00E−02 | E | 35 |
| LNU153_H6 | 0.77 | 1.48E−02 | A | 4 | LNU35_H4 | 0.76 | 1.00E−02 | E | 35 |
| LNU46_H58 | 0.72 | 1.93E−02 | D | 41 | LNU52_H6 | 0.84 | 2.20E−03 | B | 20 |
| LNU46_H58 | 0.72 | 1.93E−02 | D | 41 | LNU52_H6 | 0.74 | 1.36E−02 | B | 20 |
| LNU268_H2 | 0.71 | 2.18E−02 | I | 74 | LNU52_H6 | 0.84 | 2.20E−03 | B | 20 |
| LNU268_H2 | 0.71 | 2.18E−02 | I | 74 | LNU52_H6 | 0.74 | 1.36E−02 | B | 20 |
| LNU121_H1 | 0.83 | 2.88E−03 | H | 74 | LNU46_H60 | 0.72 | 1.85E−02 | B | 20 |

TABLE 31-continued

Correlation between the expression level of selected LNU homologous genes of some embodiments of the invention in various tissues and the phenotypic performance under low nitrogen, normal or drought stress conditions across *Sorghum* accessions

| Gene Name | R | P value | Exp. Set | Correl. Set ID | Gene Name | R | P value | Exp. Set | Correl. Set ID |
|---|---|---|---|---|---|---|---|---|---|
| LNU121_H1 | 0.78 | 8.38E−03 | H | 74 | LNU46_H60 | 0.72 | 1.85E−02 | B | 20 |
| LNU121_H1 | 0.83 | 2.88E−03 | H | 74 | LNU109_H2 | 0.74 | 1.51E−02 | I | 71 |
| LNU121_H1 | 0.78 | 8.38E−03 | H | 74 | LNU109_H2 | 0.74 | 1.51E−02 | I | 71 |
| LNU51_H2 | 0.77 | 9.69E−03 | H | 74 | LNU216_H4 | 0.74 | 1.53E−02 | G | 71 |
| LNU51_H2 | 0.77 | 9.69E−03 | H | 74 | LNU216_H3 | 0.75 | 1.27E−02 | G | 71 |
| LNU192_H3 | 0.77 | 8.74E−03 | H | 74 | LNU216_H3 | 0.74 | 1.41E−02 | G | 71 |
| LNU192_H3 | 0.70 | 2.33E−02 | H | 74 | LNU216_H4 | 0.74 | 1.53E−02 | G | 71 |
| LNU192_H3 | 0.77 | 8.74E−03 | H | 74 | LNU216_H3 | 0.75 | 1.27E−02 | G | 71 |
| LNU192_H3 | 0.70 | 2.33E−02 | H | 74 | LNU216_H3 | 0.74 | 1.41E−02 | G | 71 |
| LNU32_H2 | 0.76 | 1.06E−02 | H | 74 | LNU45_H259 | 0.75 | 2.10E−02 | C | 3 |
| LNU32_H2 | 0.76 | 1.06E−02 | H | 74 | LNU153_H6 | 0.72 | 2.81E−02 | C | 3 |
| LNU89_H5 | 0.71 | 2.03E−02 | H | 74 | LNU153_H6 | 0.72 | 2.81E−02 | C | 3 |
| LNU89_H5 | 0.71 | 2.03E−02 | H | 74 | LNU28_H4 | 0.77 | 1.62E−02 | B | 3 |
| LNU86_H0 | 0.72 | 2.01E−02 | H | 74 | LNU28_H4 | 0.76 | 1.80E−02 | B | 3 |
| LNU86_H0 | 0.72 | 2.01E−02 | H | 74 | LNU28_H4 | 0.77 | 1.62E−02 | B | 3 |
| LNU46_H58 | 0.75 | 1.23E−02 | G | 74 | LNU28_H4 | 0.76 | 1.80E−02 | B | 3 |
| LNU46_H58 | 0.75 | 1.23E−02 | G | 74 | LNU153_H6 | 0.83 | 5.32E−03 | B | 3 |
| LNU153_H5 | 0.71 | 3.05E−02 | B | 5 | LNU153_H6 | 0.83 | 5.32E−03 | B | 3 |
| LNU153_H5 | 0.71 | 3.05E−02 | B | 5 | LNU128_H12 | 0.72 | 2.75E−02 | A | 3 |
| LNU268_H2 | 0.71 | 3.17E−02 | A | 5 | LNU128_H12 | 0.72 | 2.75E−02 | A | 3 |
| LNU268_H2 | 0.71 | 3.29E−02 | A | 5 | LNU13_H1 | 0.80 | 9.65E−03 | A | 3 |
| LNU268_H2 | 0.71 | 3.17E−02 | A | 5 | LNU13_H1 | 0.78 | 1.27E−02 | A | 3 |
| LNU268_H2 | 0.71 | 3.29E−02 | A | 5 | LNU13_H1 | 0.80 | 9.65E−03 | A | 3 |
| LNU153_H6 | 0.80 | 1.01E−02 | A | 5 | LNU13_H1 | 0.78 | 1.27E−02 | A | 3 |
| LNU153_H6 | 0.80 | 1.01E−02 | A | 5 | LNU266_H0 | 0.76 | 1.85E−02 | A | 3 |
| LNU263_H4 | 0.75 | 1.20E−02 | F | 43 | LNU266_H0 | 0.71 | 3.35E−02 | A | 3 |
| LNU263_H4 | 0.75 | 1.32E−02 | F | 43 | LNU266_H0 | 0.76 | 1.85E−02 | A | 3 |
| LNU263_H4 | 0.75 | 1.20E−02 | F | 43 | LNU266_H0 | 0.71 | 3.35E−02 | A | 3 |
| LNU263_H4 | 0.75 | 1.32E−02 | F | 43 | LNU268_H2 | 0.85 | 3.93E−03 | A | 3 |
| LNU46_H58 | 0.72 | 1.86E−02 | D | 43 | LNU268_H2 | 0.79 | 1.06E−02 | A | 3 |
| LNU46_H58 | 0.72 | 1.86E−02 | D | 43 | LNU268_H2 | 0.85 | 3.93E−03 | A | 3 |
| LNU121_H1 | 0.88 | 8.89E−04 | H | 73 | LNU268_H2 | 0.79 | 1.06E−02 | A | 3 |
| LNU121_H1 | 0.78 | 8.16E−03 | H | 73 | LNU52_H6 | 0.75 | 1.94E−02 | A | 3 |
| LNU121_H1 | 0.88 | 8.89E−04 | H | 73 | LNU52_H6 | 0.75 | 1.94E−02 | A | 3 |
| LNU121_H1 | 0.78 | 8.16E−03 | H | 73 | LNU67_H4 | 0.76 | 1.73E−02 | A | 3 |
| LNU2_H4 | 0.72 | 1.80E−02 | H | 73 | LNU192_H3 | 0.73 | 2.47E−02 | A | 3 |
| LNU2_H??? | 0.72 | 1.80E−02 | H | 73 | LNU192_H3 | 0.73 | 2.47E−02 | A | 3 |
| LNU2_H4 | 0.72 | 1.80E−02 | H | 73 | LNU265_H0 | 0.70 | 3.43E−02 | A | 3 |
| LNU51_H2 | 0.84 | 2.50E−03 | H | 73 | LNU265_H0 | 0.70 | 3.43E−02 | A | 3 |
| LNU51_H2 | 0.84 | 2.50E−03 | H | 73 | LNU46_H60 | 0.73 | 2.57E−02 | A | 3 |
| LNU32_H2 | 0.85 | 1.87E−03 | H | 73 | LNU46_H60 | 0.73 | 2.57E−02 | A | 3 |
| LNU32_H2 | 0.85 | 1.87E−03 | H | 73 | LNU153_H6 | 0.96 | 5.15E−05 | A | 3 |
| LNU265_H0 | 0.70 | 2.29E−02 | H | 73 | LNU153_H6 | 0.96 | 5.15E−05 | A | 3 |
| LNU265_H0 | 0.70 | 2.41E−02 | H | 73 | LNU216_H4 | 0.82 | 3.31E−03 | F | 40 |
| LNU265_H0 | 0.70 | 2.29E−02 | H | 73 | LNU216_H3 | 0.86 | 1.42E−03 | F | 40 |
| LNU265_H0 | 0.70 | 2.41E−02 | H | 73 | LNU216_H3 | 0.86 | 1.43E−03 | F | 40 |
| LNU263_H4 | 0.72 | 1.77E−02 | F | 42 | LNU216_H4 | 0.82 | 3.31E−03 | F | 40 |
| LNU263_H4 | 0.71 | 2.06E−02 | F | 42 | LNU216_H3 | 0.86 | 1.42E−03 | F | 40 |
| LNU263_H4 | 0.72 | 1.77E−02 | F | 42 | LNU216_H3 | 0.86 | 1.43E−03 | F | 40 |
| LNU263_H4 | 0.71 | 2.06E−02 | F | 42 | LNU263_H4 | 0.80 | 5.34E−03 | F | 40 |
| LNU46_H58 | 0.75 | 1.27E−02 | D | 42 | LNU263_H4 | 0.80 | 5.88E−03 | F | 40 |
| LNU46_H58 | 0.75 | 1.27E−02 | D | 42 | LNU263_H5 | 0.71 | 2.04E−02 | F | 40 |
| LNU216_H4 | 0.77 | 9.16E−03 | I | 75 | LNU263_H4 | 0.80 | 5.34E−03 | F | 40 |
| LNU216_H4 | 0.77 | 9.16E−03 | I | 75 | LNU263_H4 | 0.80 | 5.88E−03 | F | 40 |
| LNU46_H60 | 0.70 | 2.29E−02 | I | 75 | LNU263_H5 | 0.71 | 2.04E−02 | F | 40 |
| LNU46_H60 | 0.70 | 2.29E−02 | I | 75 | LNU271_H4 | 0.73 | 1.71E−02 | F | 40 |
| LNU2_H4 | 0.75 | 1.24E−02 | H | 75 | LNU271_H4 | 0.73 | 1.71E−02 | F | 40 |
| LNU2_H??? | 0.75 | 1.24E−02 | H | 75 | LNU266_H0 | 0.70 | 2.34E−02 | E | 40 |
| LNU2_H4 | 0.75 | 1.24E−02 | H | 75 | LNU266_H0 | 0.70 | 2.34E−02 | E | 40 |
| LNU32_H2 | 0.73 | 1.67E−02 | H | 75 | LNU74_H173 | 0.73 | 1.63E−02 | D | 40 |
| LNU32_H2 | 0.73 | 1.67E−02 | H | 75 | LNU74_H173 | 0.73 | 1.63E−02 | D | 40 |
| LNU73_H2 | 0.73 | 1.56E−02 | G | 75 | LNU45_H258 | 0.79 | 6.14E−03 | D | 40 |
| LNU32_H2 | 0.75 | 1.25E−02 | G | 75 | LNU45_H258 | 0.79 | 6.14E−03 | D | 40 |
| LNU32_H2 | 0.75 | 1.25E−02 | G | 75 | LNU46_H58 | 0.80 | 5.34E−03 | D | 40 |
| LNU45_H259 | 0.83 | 2.77E−03 | G | 75 | LNU46_H58 | 0.80 | 5.34E−03 | D | 40 |
| LNU45_H259 | 0.78 | 8.22E−03 | G | 75 | LNU266_H0 | 0.79 | 1.14E−02 | C | 3 |
| LNU266_H0 | 0.74 | 1.45E−02 | F | 44 | LNU266_H0 | 0.77 | 1.42E−02 | C | 3 |
| LNU266_H0 | 0.74 | 1.45E−02 | F | 44 | LNU266_H0 | 0.79 | 1.14E−02 | C | 3 |
| LNU73_H2 | 0.70 | 2.37E−02 | G | 76 | LNU266_H0 | 0.77 | 1.42E−02 | C | 3 |
| LNU74_H173 | 0.80 | 5.37E−03 | B | 11 | LNU74_H173 | 0.79 | 1.16E−02 | B | 3 |
| LNU74_H173 | 0.80 | 5.37E−03 | B | 11 | LNU74_H173 | 0.79 | 1.16E−02 | B | 3 |
| LNU266_H0 | 0.72 | 1.93E−02 | A | 11 | LNU192_H3 | 0.76 | 1.74E−02 | B | 3 |

TABLE 31-continued

Correlation between the expression level of selected LNU homologous genes of some embodiments of the invention in various tissues and the phenotypic performance under low nitrogen, normal or drought stress conditions across Sorghum accessions

| Gene Name | R | P value | Exp. Set | Correl. Set ID | Gene Name | R | P value | Exp. Set | Correl. Set ID |
|---|---|---|---|---|---|---|---|---|---|
| LNU266_H0 | 0.72 | 1.93E-02 | A | 11 | LNU192_H3 | 0.76 | 1.74E-02 | B | 3 |
| LNU153_H6 | 0.71 | 2.21E-02 | A | 11 | LNU266_H0 | 0.74 | 2.24E-02 | A | 3 |
| LNU153_H6 | 0.71 | 2.21E-02 | A | 11 | LNU266_H0 | 0.74 | 2.24E-02 | A | 3 |
| LNU266_H0 | 0.81 | 4.88E-03 | F | 50 | LNU268_H2 | 0.77 | 1.61E-02 | A | 3 |
| LNU266_H0 | 0.77 | 9.63E-03 | F | 50 | LNU268_H2 | 0.76 | 1.65E-02 | A | 3 |
| LNU266_H0 | 0.81 | 4.88E-03 | F | 50 | LNU268_H2 | 0.77 | 1.61E-02 | A | 3 |
| LNU266_H0 | 0.77 | 9.63E-03 | F | 50 | LNU268_H2 | 0.76 | 1.65E-02 | A | 3 |
| LNU266_H0 | 0.72 | 2.00E-02 | E | 50 | LNU153_H6 | 0.90 | 9.44E-04 | A | 3 |
| LNU266_H0 | 0.72 | 2.00E-02 | E | 50 | LNU153_H6 | 0.90 | 9.44E-04 | A | 3 |
| LNU266_H0 | 0.80 | 5.96E-03 | D | 50 | LNU216_H3 | 0.70 | 2.30E-02 | F | 32 |
| LNU266_H0 | 0.79 | 7.09E-03 | D | 50 | LNU216_H3 | 0.70 | 2.34E-02 | F | 32 |
| LNU266_H0 | 0.80 | 5.96E-03 | D | 50 | LNU216_H3 | 0.70 | 2.30E-02 | F | 32 |
| LNU266_H0 | 0.79 | 7.09E-03 | D | 50 | LNU216_H3 | 0.70 | 2.34E-02 | F | 32 |
| LNU46_H58 | 0.81 | 4.21E-03 | D | 50 | LNU266_H0 | 0.72 | 1.83E-02 | F | 32 |
| LNU46_H58 | 0.81 | 4.21E-03 | D | 50 | LNU266_H0 | 0.72 | 1.83E-02 | F | 32 |
| LNU266_H0 | 0.72 | 1.96E-02 | I | 61 | LNU51_H2 | 0.74 | 1.40E-02 | I | 57 |
| LNU266_H0 | 0.72 | 1.96E-02 | I | 61 | LNU51_H2 | 0.74 | 1.40E-02 | I | 57 |
| LNU271_H4 | 0.87 | 9.39E-04 | I | 61 | LNU74_H172 | 0.74 | 1.54E-02 | G | 57 |
| LNU271_H4 | 0.85 | 1.86E-03 | I | 61 | LNU74_H172 | 0.70 | 2.39E-02 | G | 57 |
| LNU271_H4 | 0.87 | 9.39E-04 | I | 61 | LNU74_H172 | 0.74 | 1.54E-02 | G | 57 |
| LNU271_H4 | 0.85 | 1.86E-03 | I | 61 | LNU74_H172 | 0.70 | 2.39E-02 | G | 57 |
| LNU45_H259 | 0.80 | 4.99E-03 | F | 36 | LNU45_H259 | 0.76 | 1.14E-02 | G | 57 |
| LNU45_H259 | 0.80 | 4.99E-03 | F | 36 | LNU45_H259 | 0.74 | 1.46E-02 | G | 57 |
| LNU121_H1 | 0.77 | 9.58E-03 | E | 36 | LNU45_H258 | 0.72 | 1.97E-02 | G | 57 |
| LNU121_H1 | 0.77 | 9.26E-03 | E | 36 | LNU45_H258 | 0.71 | 2.04E-02 | G | 57 |
| LNU121_H1 | 0.77 | 9.58E-03 | E | 36 | LNU45_H259 | 0.76 | 1.14E-02 | G | 57 |
| LNU67_H4 | 0.73 | 1.57E-02 | E | 36 | LNU45_H259 | 0.74 | 1.46E-02 | G | 57 |
| LNU86_H0 | 0.74 | 1.37E-02 | E | 36 | LNU45_H258 | 0.72 | 1.97E-02 | G | 57 |
| LNU86_H0 | 0.74 | 1.37E-02 | E | 36 | LNU45_H258 | 0.71 | 2.04E-02 | G | 57 |
| LNU71_H3 | 0.71 | 2.15E-02 | I | 63 | LNU266_H0 | 0.81 | 4.59E-03 | C | 3 |
| LNU71_H3 | 0.71 | 2.15E-02 | I | 63 | LNU266_H0 | 0.79 | 6.43E-03 | C | 3 |
| LNU28_H4 | 0.81 | 4.19E-03 | H | 63 | LNU266_H0 | 0.81 | 4.59E-03 | C | 3 |
| LNU28_H4 | 0.81 | 4.23E-03 | H | 63 | LNU266_H0 | 0.79 | 6.43E-03 | C | 3 |
| LNU28_H4 | 0.81 | 4.19E-03 | H | 63 | LNU74_H173 | 0.70 | 2.36E-02 | B | 3 |
| LNU28_H4 | 0.81 | 4.23E-03 | H | 63 | LNU74_H173 | 0.70 | 2.36E-02 | B | 3 |
| LNU71_H3 | 0.81 | 4.65E-03 | G | 63 | LNU192_H3 | 0.72 | 1.98E-02 | B | 3 |
| LNU71_H3 | 0.77 | 9.48E-03 | G | 63 | LNU192_H3 | 0.72 | 1.98E-02 | B | 3 |
| LNU71_H3 | 0.81 | 4.65E-03 | G | 63 | LNU268_H2 | 0.79 | 6.71E-03 | A | 3 |
| LNU71_H3 | 0.77 | 9.48E-03 | G | 63 | LNU268_H2 | 0.79 | 6.95E-03 | A | 3 |
| LNU192_H3 | 0.77 | 9.48E-03 | G | 63 | LNU268_H2 | 0.79 | 6.71E-03 | A | 3 |
| LNU192_H3 | 0.72 | 1.81E-02 | G | 63 | LNU268_H2 | 0.79 | 6.95E-03 | A | 3 |
| LNU192_H3 | 0.77 | 9.48E-03 | G | 63 | LNU153_H6 | 0.85 | 1.63E-03 | A | 3 |
| LNU192_H3 | 0.72 | 1.81E-02 | G | 63 | LNU153_H6 | 0.85 | 1.63E-03 | A | 3 |

Table 31. "Correl. Set ID"—correlation set ID according to the correlated parameters Table above.

Example 8

Production of Sorghum Transcriptom and High Throughput Correlation Analysis with Yield, NUE, and ABST Related Parameters Measured 1N Semi-Hydroponics Conditions Using 44K Sorguhm Oligonucleotide Micro-Arrays Sorghum vigor related parameters under low nitrogen, 100 mM NaCl, low temperature (10±2° C.) and normal growth conditions—Ten Sorghum hybrids were grown in 3 repetitive plots, each containing 17 plants, at a net house under semi-hydroponics conditions. Briefly, the growing protocol was as follows: Sorghum seeds were sown in trays filled with a mix of vermiculite and peat in a 1:1 ratio. Following germination, the trays were transferred to the high salinity solution (100 mM NaCl in addition to the Full Hoagland solution), low temperature (10±2° C. in the presence of Full Hoagland solution), low nitrogen solution (the amount of total nitrogen was reduced in 90% from the full Hoagland solution (i.e., to a final concentration of 10% from full Hoagland solution, final amount of 1.2 mM N) or at Normal growth solution (Full Hoagland containing 16 mM N solution, at 28±2° C.). Plants were grown at 28±2° C.

Full Hoagland solution consists of: $KNO_3$-0.808 grams/liter, $MgSO_4$—0.12 grams/liter, $KH_2PO_4$—0.172 grams/liter and 0.01% (volume/volume) of 'Super coratin' micro elements (Iron-EDDHA [ethylenediamine-N,N'-bis(2-hydroxyphenylacetic acid)]-40.5 grams/liter; Mn—20.2 grams/liter; Zn 10.1 grams/liter; Co 1.5 grams/liter; and Mo 1.1 grams/liter), solution's pH should be 6.5-6.8].

Analyzed Sorghum tissues—All 10 selected Sorghum hybrids were sampled per each treatment. Three tissues [leaves, meristems and roots] growing at 100 mM NaCl, low temperature (10±2° C.), low Nitrogen (1.2 mM N) or under Normal conditions were sampled and RNA was extracted as described above. Each micro-array expression information tissue type has received a Set ID as summarized in Table 32 below.

TABLE 32

Sorghum transcriptom expression sets under semi hydroponics conditions

| Expression set | Set Id |
|---|---|
| Sorghum roots under Low Nitrogen | A |
| Sorghum leaves under Low Nitrogen | B |
| Sorghum meristems under Low Nitrogen | C |
| Sorghum roots under Normal Growth | D |
| Sorghum leaves under Normal Growth | E |
| Sorghum meristems under Normal Growth | F |
| Sorghum roots under 100 mM NaCl | G |
| Sorghum leaves under 100 mM NaCl | H |
| Sorghum meristems under 100 mM NaCl | I |
| Sorghum roots under cold | J |
| Sorghum leaves under cold | K |
| Sorghum meristems under cold | L |

Table 32: Provided are the Sorghum transcriptom expression sets.
Cold conditions = 10 ± 2° C.;
NaCl = 100 mM NaCl;
low nitrogen = 1.2 mM Nitrogen;
Normal conditions = 16 mM Nitrogen.

Experimental Results 10 different Sorghum hybrids were grown and characterized for the following parameters: "Leaf number Normal"=leaf number per plant under normal conditions (average of five plants); "Plant Height Normal"=plant height under normal conditions (average of five plants); "Root DW"—root dry weight per plant (average of five plants); The average for each of the measured parameter was calculated using the JMP software and values are summarized in Table 34, 35, 36 and 37 below. Subsequent correlation analysis was performed (Tables 38 and 39). Results were then integrated to the database.

TABLE 33

Sorghum correlated parameters (vectors)

| Correlation Set | Correlation ID |
|---|---|
| Plant Height TP1 - Low Nitrogen | 1 |
| Plant Height TP2- Low Nitrogen | 2 |
| Plant Height TP3 - Low Nitrogen | 3 |
| Leaf TP1 - Low Nitrogen | 4 |
| Leaf TP2 - Low Nitrogen | 5 |
| Leaf TP3 - Low Nitrogen | 6 |
| DW Shoot/Plant - Low Nitrogen | 7 |
| DW Root/Plant - Low Nitrogen | 8 |
| SPAD - Low Nitrogen | 9 |
| Plant Height TP1 - 100 mM NaCl | 10 |
| Plant Height TP2 - 100 mM NaCl | 11 |
| Plant Height TP3 - 100 mM NaCl | 12 |
| Leaf TP1 - 100 mM NaCl | 13 |
| Leaf TP2 - 100 mM NaCl | 14 |
| Leaf TP3 - 100 mM NaCl | 15 |
| DW Shoot/Plant - 100 mM NaCl | 16 |
| DW Root/Plant - 100 mM NaCl | 17 |
| SPAD - 100 mM NaCl | 18 |
| Plant Height TP1-Cold | 19 |
| Plant Height TP2- Cold | 20 |
| Leaf TP1 - Cold | 21 |
| Leaf TP2 - Cold | 22 |
| Leaf TP3 - Cold | 23 |
| DW Shoot/Plant - Cold | 24 |
| DW Root/Plant - Cold | 25 |
| SPAD - Cold | 26 |
| Plant Height TP1-Normal | 27 |
| Plant Height TP2-Normal | 28 |
| Leaf TP1 -Normal | 29 |
| Leaf TP2 -Normal | 30 |
| Leaf TP3 -Normal | 31 |
| DW Shoot/Plant - Normal | 32 |
| DW Root/Plant - Normal | 33 |
| SPAD - Normal | 34 |

Table 33: Provided are the Sorghum correlated parameters.
Cold conditions = 10 ± 2° C.;
NaCl = 100 mM NaCl;
low nitrogen = 1.2 mM Nitrogen;
Normal conditions = 16 mM Nitrogen * TP-1-2-3 refers to time points 1, 2 and 3.

TABLE 34

Sorghum accessions, measured parameters under low nitrogen growth conditions

| Seed ID | 1 | 2 | 3 | 4 | 5 | 6 | 7 | 8 | 9 |
|---|---|---|---|---|---|---|---|---|---|
| 20 | 6.73 | 13.3 | 22.2 | 3 | 4 | 3.9 | 0.0823 | 0.0444 | 26.9 |
| 22 | 9.77 | 20.6 | 31.1 | 3.13 | 4.58 | 4.27 | 0.187 | 0.108 | 28 |
| 26 | 12.7 | 23.7 | 34.7 | 3.87 | 4.97 | 4.7 | 0.328 | 0.202 | 29.6 |
| 27 | 8.67 | 18 | 30 | 3.53 | 4.73 | 4.23 | 0.163 | 0.104 | 31.5 |
| 28 | 9.77 | 19.3 | 30.8 | 3.2 | 4.6 | 4.3 | 0.163 | 0.0777 | 29.6 |
| 29 | 9.23 | 19.2 | 29.9 | 3.13 | 4.7 | 4.57 | 0.156 | 0.0858 | 26.8 |
| 30 | 10.3 | 21.9 | 30.9 | 3.13 | 4.97 | 4.63 | 0.259 | 0.13 | 28.5 |
| 31 | 10.1 | 22.1 | 32.4 | 3.3 | 4.87 | 4.67 | 0.199 | 0.0944 | 28.2 |
| 34 | 7.93 | 18.2 | 29.4 | 3.07 | 4.67 | 3.97 | 0.13 | 0.0863 | 30.5 |
| 37 | 8.23 | 21 | 30.7 | 3.07 | 4.57 | 4.1 | 0.184 | 0.0924 | 27.6 |

Table 34: Provided are the values of each of the parameters (as described above) measured in Sorghum accessions (Seed ID) under low nitrogen conditions. Growth conditions are specified in the experimental procedure section.

TABLE 35

Sorghum accessions, measured parameters under 100 mM NaCl growth conditions

| Seed ID | 10 | 11 | 12 | 13 | 14 | 15 | 16 | 17 | 18 |
|---|---|---|---|---|---|---|---|---|---|
| 20 | 7.9 | 14.2 | 21.8 | 3 | 4 | 4 | 0.0943 | 0.05 | 32.7 |
| 22 | 9.5 | 16.3 | 23.2 | 3.13 | 4.37 | 4.13 | 0.186 | 0.104 | 35.1 |
| 26 | 10.9 | 20.4 | 30.4 | 3.4 | 4.87 | 4.57 | 0.202 | 0.124 | 28 |
| 27 | 7.93 | 13.3 | 22.8 | 3.07 | 4.6 | 4.43 | 0.137 | 0.0688 | 30.9 |

TABLE 35-continued

*Sorghum* accessions, measured parameters under 100 mM NaCl growth conditions

| Seed ID | 10 | 11 | 12 | 13 | 14 | 15 | 16 | 17 | 18 |
|---|---|---|---|---|---|---|---|---|---|
| 28 | 9.7 | 15.9 | 23.7 | 3.33 | 4.5 | 4.07 | 0.13 | 0.0757 | 34.5 |
| 29 | 8.53 | 16.5 | 23.3 | 3.07 | 4.53 | 4.33 | 0.133 | 0.0752 | 30 |
| 30 | 8.9 | 15.5 | 22.5 | 3.07 | 4.5 | 4.13 | 0.154 | 0.135 | 32.1 |
| 31 | 10.4 | 18.9 | 26.8 | 3.27 | 4.77 | 4.5 | 0.189 | 0.0955 | 31.9 |
| 34 | 7 | 13.7 | 20.3 | 3 | 4.32 | 3.78 | 0.0993 | 0.165 | 32.5 |
| 37 | 7.83 | 15.8 | 23.6 | 3.07 | 4.2 | 4.2 | 0.124 | 0.139 | 34.3 |

Table 35: Provided are the values of each of the parameters (as described above) measured in *Sorghum* accessions (Seed ID) under 100 mM NaCl growth conditions. Growth conditions are specified in the experimental procedure section.

TABLE 36

*Sorghum* accessions, measured parameters under cold growth conditions

| Seed ID | 19 | 20 | 21 | 22 | 23 | 24 | 25 | 26 |
|---|---|---|---|---|---|---|---|---|
| 20 | 6.5 | 11.2 | 3 | 3.9 | 4.73 | 0.0781 | 0.0681 | 28.6 |
| 22 | 8.77 | 15.9 | 3 | 4.13 | 5.33 | 0.154 | 0.108 | 30.3 |
| 26 | 10.4 | 18.4 | 3.5 | 4.63 | 5.43 | 0.189 | 0.163 | 27 |
| 27 | 6.8 | 12.2 | 3.17 | 4.17 | 5.5 | 0.112 | 0.0935 | 32.3 |
| 28 | 9.03 | 16 | 3.4 | 4.27 | 5.33 | 0.13 | 0.0835 | 28.3 |
| 29 | 9 | 14.6 | 3.2 | 4.23 | 5.07 | 0.165 | 0.114 | 29.9 |
| 30 | 7.97 | 14.6 | 3.13 | 4.2 | 4.5 | 0.152 | 0.137 | 32.5 |
| 31 | 9.17 | 17.3 | 3.07 | 4.3 | 5.4 | 0.15 | 0.127 | 28.6 |
| 34 | 6.5 | 13.4 | 3.07 | 4.17 | 5.37 | 0.112 | 0.108 | 31.7 |
| 37 | 7.23 | 13.9 | 3 | 4 | 5.18 | 0.141 | 0.139 | 29.6 |

Table 36: Provided are the values of each of the parameters (as described above) measured in *Sorghum* accessions (Seed ID) under cold growth conditions. Growth conditions are specified in the experimental procedure section.

TABLE 37

*Sorghum* accessions, measured parameters under regular growth conditions

| Seed ID | 27 | 28 | 29 | 30 | 31 | 32 | 33 | 34 |
|---|---|---|---|---|---|---|---|---|
| 20 | 7.47 | 15 | 3 | 4.17 | 5.33 | 0.101 | 0.0525 | 26.7 |
| 22 | 9.3 | 18.2 | 3.07 | 4.5 | 5.87 | 0.236 | 0.134 | 29.3 |
| 26 | 12.9 | 22.1 | 3.8 | 4.8 | 6.2 | 0.313 | 0.172 | 29.9 |
| 27 | 8.57 | 17.6 | 3.2 | 4.6 | 5.8 | 0.158 | 0.103 | 29.1 |
| 28 | 8.93 | 18.1 | 3.23 | 4.53 | 5.8 | 0.194 | 0.107 | 25 |
| 29 | 8.53 | 18.5 | 3.23 | 4.97 | 5.73 | 0.188 | 0.12 | 24.6 |
| 30 | 10.7 | 22.8 | 3.13 | 4.6 | 5.73 | 0.241 | 0.139 | 30.8 |
| 31 | 10.3 | 22 | 3.43 | 4.93 | 6 | 0.244 | 0.124 | 25.5 |
| 34 | 7.87 | 20 | 3 | 4.5 | 5.6 | 0.185 | 0.0994 | 32.9 |
| 37 | 8.77 | 21.8 | 3 | 4.57 | 6.07 | 0.242 | 0.115 | 33.5 |

Table 37: Provided are the values of each of the parameters (as described above) measured in *Sorghum* accessions (Seed ID) under regular growth conditions. Growth conditions are specified in the experimental procedure section.

TABLE 38

Correlation between the expression level of selected LNU genes of some embodiments of the invention in various tissues and the phenotypic performance under low nitrogen, normal, cold or salinity stress conditions across *Sorghum* accessions

| Gene Name | R | P value | Exp. set | Correl. Set ID | Gene Name | R | P value | Exp. set | Correl. Set ID |
|---|---|---|---|---|---|---|---|---|---|
| LNU202 | 0.71 | 3.35E−02 | I | 17 | LNU84 | 0.76 | 4.81E−02 | A | 5 |
| LNU202 | 0.74 | 1.47E−02 | J | 25 | LNU168 | 0.70 | 3.43E−02 | I | 15 |
| LNU 84 | 0.76 | 4.73E−02 | A | 8 | LNU84 | 0.77 | 4.19E−02 | A | 6 |
| LNU280 | 0.86 | 2.80E−03 | C | 8 | LNU84 | 0.76 | 4.92E−02 | A | 6 |
| LNU84 | 0.88 | 8.76E−03 | A | 7 | LNU168 | 0.95 | 1.13E−03 | A | 6 |
| LNU84 | 0.77 | 4.16E−02 | A | 7 | LNU168 | 0.94 | 1.82E−03 | A | 6 |
| LNU280 | 0.81 | 7.50E−03 | C | 7 | LNU278 | 0.91 | 4.12E−03 | A | 6 |
| LNU84 | 0.75 | 2.05E−02 | L | 24 | LNU84 | 0.73 | 2.50E−02 | L | 20 |
| LNU84 | 0.71 | 3.31E−02 | L | 24 | LNU84 | 0.85 | 1.62E−02 | A | 5 |
| LNU202 | 0.77 | 1.43E−02 | L | 22 | LNU84 | 0.81 | 2.61E−02 | A | 3 |
| LNU202 | 0.77 | 1.56E−02 | L | 22 | | | | | |

Table 38. "Correl. Set ID"—correlation set ID according to the correlated parameters Table above.

TABLE 39

Correlation between the expression level of selected LNU homologous genes of some embodiments of the invention in various tissues and the phenotypic performance under low nitrogen, normal, cold or salinity stress conditions across *Sorghum* accessions

| Gene Name | R | P value | Exp. set | Correl. Set ID | Gene Name | R | P value | Exp. Set | Correl. Set ID |
|---|---|---|---|---|---|---|---|---|---|
| LNU74_H173 | 0.96 | 8.89E−03 | G | 17 | LNU271_H4 | 0.87 | 2.23E−03 | L | 22 |
| LNU74_H173 | 0.89 | 4.39E−02 | G | 17 | LNU265_H0 | 0.88 | 1.56E−03 | L | 22 |
| LNU74_H173 | 0.96 | 8.89E−03 | G | 17 | LNU265_H0 | 0.88 | 1.56E−03 | L | 22 |
| LNU74_H173 | 0.89 | 4.39E−02 | G | 17 | LNU67_H4 | 0.76 | 4.57E−02 | A | 5 |
| LNU52_H6 | 0.73 | 2.48E−02 | I | 17 | LNU74_H173 | 0.82 | 2.44E−02 | A | 5 |
| LNU52_H6 | 0.72 | 2.75E−02 | I | 17 | LNU74_H173 | 0.82 | 2.44E−02 | A | 5 |
| LNU52_H6 | 0.73 | 2.48E−02 | I | 17 | LNU13_H1 | 0.72 | 2.98E−02 | C | 5 |

TABLE 39-continued

Correlation between the expression level of selected LNU homologous genes of some embodiments of the invention in various tissues and the phenotypic performance under low nitrogen, normal, cold or salinity stress conditions across *Sorghum* accessions

| Gene Name | R | P value | Exp. set | Correl. Set ID | Gene Name | R | P value | Exp. Set | Correl. Set ID |
|---|---|---|---|---|---|---|---|---|---|
| LNU52_H6 | 0.72 | 2.75E-02 | I | 17 | LNU13_H1 | 0.72 | 2.98E-02 | C | 5 |
| LNU192_H3 | 0.82 | 6.46E-03 | I | 17 | LNU45_H260 | 0.71 | 3.05E-02 | C | 5 |
| LNU192_H3 | 0.74 | 2.18E-02 | I | 17 | LNU35_H4 | 0.72 | 3.03E-02 | C | 5 |
| LNU192_H3 | 0.82 | 6.46E-03 | I | 17 | LNU35_H4 | 0.72 | 3.03E-02 | C | 5 |
| LNU192_H3 | 0.74 | 2.18E-02 | I | 17 | LNU19_H1 | 0.83 | 5.33E-03 | I | 15 |
| LNU46_H60 | 0.76 | 1.85E-02 | I | 17 | LNU263_H5 | 0.74 | 2.16E-02 | I | 15 |
| LNU46_H60 | 0.76 | 1.85E-02 | I | 17 | LNU263_H5 | 0.74 | 2.18E-02 | I | 15 |
| LNU35_H4 | 0.81 | 7.57E-03 | I | 17 | LNU263_H5 | 0.74 | 2.16E-02 | I | 15 |
| LNU35_H4 | 0.81 | 7.57E-03 | I | 17 | LNU263_H5 | 0.74 | 2.18E-02 | I | 15 |
| LNU2_H4 | 0.72 | 1.93E-02 | J | 25 | LNU45_H260 | 0.74 | 2.36E-02 | C | 6 |
| LNU2_H??? | 0.72 | 1.93E-02 | J | 25 | LNU263_H5 | 0.70 | 3.53E-02 | F | 31 |
| LNU2_H4 | 0.72 | 1.93E-02 | J | 25 | LNU263_H5 | 0.70 | 3.53E-02 | F | 31 |
| LNU48_H1 | 0.71 | 2.11E-02 | J | 25 | LNU45_H260 | 0.99 | 6.05E-04 | G | 10 |
| LNU48_H1 | 0.71 | 2.11E-02 | J | 25 | LNU45_H260 | 0.98 | 3.25E-03 | G | 10 |
| LNU52_H6 | 0.80 | 1.01E-02 | L | 25 | LNU263_H5 | 0.75 | 2.10E-02 | I | 10 |
| LNU52_H6 | 0.77 | 1.61E-02 | L | 25 | LNU263_H5 | 0.74 | 2.18E-02 | I | 10 |
| LNU52_H6 | 0.80 | 1.01E-02 | L | 25 | LNU263_H5 | 0.75 | 2.10E-02 | I | 10 |
| LNU52_H6 | 0.77 | 1.61E-02 | L | 25 | LNU263_H5 | 0.74 | 2.18E-02 | I | 10 |
| LNU48_H1 | 0.80 | 2.98E-02 | A | 8 | LNU271_H4 | 0.93 | 2.36E-04 | L | 19 |
| LNU48_H1 | 0.80 | 2.98E-02 | A | 8 | LNU271_H4 | 0.84 | 4.40E-03 | L | 19 |
| LNU74_H173 | 0.82 | 2.44E-02 | A | 8 | LNU271_H4 | 0.93 | 2.36E-04 | L | 19 |
| LNU74_H173 | 0.82 | 2.46E-02 | A | 8 | LNU271_H4 | 0.84 | 4.40E-03 | L | 19 |
| LNU74_H173 | 0.82 | 2.44E-02 | A | 8 | LNU268_H2 | 0.82 | 2.40E-02 | A | 1 |
| LNU74_H173 | 0.82 | 2.46E-02 | A | 8 | LNU268_H2 | 0.77 | 4.31E-02 | A | 1 |
| LNU89_H5 | 0.86 | 1.24E-02 | A | 8 | LNU268_H2 | 0.82 | 2.40E-02 | A | 1 |
| LNU89_H5 | 0.79 | 3.64E-02 | A | 8 | LNU268_H2 | 0.77 | 4.31E-02 | A | 1 |
| LNU89_H5 | 0.86 | 1.24E-02 | A | 8 | LNU48_H1 | 0.85 | 1.47E-02 | A | 1 |
| LNU89_H5 | 0.79 | 3.64E-02 | A | 8 | LNU48_H1 | 0.85 | 1.47E-02 | A | 1 |
| LNU121_H1 | 0.82 | 6.85E-03 | C | 8 | LNU121_H1 | 0.74 | 2.38E-02 | C | 1 |
| LNU121_H1 | 0.71 | 3.24E-02 | C | 8 | LNU121_H1 | 0.74 | 2.38E-02 | C | 1 |
| LNU121_H1 | 0.82 | 6.85E-03 | C | 8 | LNU13_H1 | 0.70 | 3.39E-02 | C | 1 |
| LNU121_H1 | 0.71 | 3.24E-02 | C | 8 | LNU13_H1 | 0.70 | 3.42E-02 | C | 1 |
| LNU13_H1 | 0.75 | 2.09E-02 | C | 8 | LNU13_H1 | 0.70 | 3.39E-02 | C | 1 |
| LNU13_H1 | 0.72 | 2.77E-02 | C | 8 | LNU13_H1 | 0.70 | 3.42E-02 | C | 1 |
| LNU13_H1 | 0.75 | 2.09E-02 | C | 8 | LNU45_H260 | 0.84 | 4.75E-03 | C | 1 |
| LNU13_H1 | 0.72 | 2.77E-02 | C | 8 | LNU45_H260 | 0.80 | 9.40E-03 | C | 1 |
| LNU67_H4 | 0.80 | 1.02E-02 | C | 8 | LNU109_H2 | 0.78 | 1.40E-02 | F | 27 |
| LNU67_H4 | 0.74 | 2.39E-02 | C | 8 | LNU109_H2 | 0.76 | 1.83E-02 | F | 27 |
| LNU71_H3 | 0.81 | 7.59E-03 | C | 8 | LNU109_H2 | 0.78 | 1.40E-02 | F | 27 |
| LNU71_H3 | 0.81 | 7.59E-03 | C | 8 | LNU109_H2 | 0.76 | 1.83E-02 | F | 27 |
| LNU45_H260 | 0.91 | 5.68E-04 | C | 8 | LNU271_H4 | 0.93 | 2.36E-04 | L | 20 |
| LNU45_H260 | 0.89 | 1.29E-03 | C | 8 | LNU271_H4 | 0.86 | 3.12E-03 | L | 20 |
| LNU268_H2 | 0.83 | 2.04E-02 | A | 7 | LNU271_H4 | 0.93 | 2.36E-04 | L | 20 |
| LNU268_H2 | 0.77 | 4.14E-02 | A | 7 | LNU271_H4 | 0.86 | 3.12E-03 | L | 20 |
| LNU268_H2 | 0.83 | 2.04E-02 | A | 7 | LNU35_H4 | 0.73 | 2.49E-02 | L | 20 |
| LNU268_H2 | 0.77 | 4.14E-02 | A | 7 | LNU35_H4 | 0.73 | 2.49E-02 | L | 20 |
| LNU48_H1 | 0.88 | 9.77E-03 | A | 7 | LNU268_H2 | 0.82 | 2.41E-02 | A | 2 |
| LNU48_H1 | 0.88 | 9.77E-03 | A | 7 | LNU268_H2 | 0.77 | 4.45E-02 | A | 2 |
| LNU89_H5 | 0.78 | 4.02E-02 | A | 7 | LNU268_H2 | 0.82 | 2.41E-02 | A | 2 |
| LNU89_H5 | 0.78 | 4.02E-02 | A | 7 | LNU268_H2 | 0.77 | 4.45E-02 | A | 2 |
| LNU46_H58 | 0.77 | 4.32E-02 | A | 7 | LNU48_H1 | 0.89 | 6.82E-03 | A | 2 |
| LNU46_H58 | 0.77 | 4.32E-02 | A | 7 | LNU48_H1 | 0.89 | 6.82E-03 | A | 2 |
| LNU121_H1 | 0.86 | 2.97E-03 | C | 7 | LNU13_H1 | 0.86 | 2.89E-03 | C | 2 |
| LNU121_H1 | 0.76 | 1.81E-02 | C | 7 | LNU13_H1 | 0.85 | 3.66E-03 | C | 2 |
| LNU121_H1 | 0.86 | 2.97E-03 | C | 7 | LNU13_H1 | 0.86 | 2.89E-03 | C | 2 |
| LNU121_H1 | 0.76 | 1.81E-02 | C | 7 | LNU13_H1 | 0.85 | 3.66E-03 | C | 2 |
| LNU13_H1 | 0.78 | 1.34E-02 | C | 7 | LNU45_H260 | 0.86 | 3.18E-03 | C | 2 |
| LNU13_H1 | 0.78 | 1.39E-02 | C | 7 | LNU45_H260 | 0.80 | 1.01E-02 | C | 2 |
| LNU13_H1 | 0.78 | 1.34E-02 | C | 7 | LNU46_H58 | 0.76 | 1.81E-02 | C | 2 |
| LNU13_H1 | 0.78 | 1.39E-02 | C | 7 | LNU46_H58 | 0.74 | 2.25E-02 | C | 2 |
| LNU67_H4 | 0.80 | 1.00E-02 | C | 7 | LNU46_H58 | 0.76 | 1.81E-02 | C | 2 |
| LNU67_H4 | 0.74 | 2.34E-02 | C | 7 | LNU46_H58 | 0.74 | 2.25E-02 | C | 2 |
| LNU45_H260 | 0.91 | 7.40E-04 | C | 7 | LNU35_H4 | 0.88 | 1.98E-03 | C | 2 |
| LNU45_H260 | 0.90 | 7.93E-04 | C | 7 | LNU35_H4 | 0.88 | 1.98E-03 | C | 2 |
| LNU35_H4 | 0.71 | 3.26E-02 | C | 7 | LNU13_H1 | 0.86 | 3.30E-03 | F | 28 |
| LNU35_H4 | 0.71 | 3.26E-02 | C | 7 | LNU13_H1 | 0.84 | 4.94E-03 | F | 28 |
| LNU45_H260 | 0.88 | 4.81E-03 | G | 16 | LNU13_H1 | 0.86 | 3.30E-03 | F | 28 |
| LNU67_H4 | 0.79 | 1.14E-02 | I | 16 | LNU13_H1 | 0.84 | 4.94E-03 | F | 28 |
| LNU67_H4 | 0.78 | 1.41E-02 | I | 16 | LNU45_H260 | 0.99 | 2.20E-03 | G | 11 |
| LNU263_H5 | 0.71 | 3.36E-02 | I | 16 | LNU45_H260 | 0.95 | 1.24E-02 | G | 11 |
| LNU263_H5 | 0.70 | 3.45E-02 | I | 16 | LNU263_H5 | 0.90 | 9.67E-04 | I | 11 |
| LNU263_H5 | 0.71 | 3.36E-02 | I | 16 | LNU263_H5 | 0.90 | 1.10E-03 | I | 11 |

TABLE 39-continued

Correlation between the expression level of selected LNU homologous genes of some embodiments of the invention in various tissues and the phenotypic performance under low nitrogen, normal, cold or salinity stress conditions across *Sorghum* accessions

| Gene Name | R | P value | Exp. set | Correl. Set ID | Gene Name | R | P value | Exp. Set | Correl. Set ID |
|---|---|---|---|---|---|---|---|---|---|
| LNU263_H5 | 0.70 | 3.45E-02 | I | 16 | LNU263_H5 | 0.90 | 9.67E-04 | I | 11 |
| LNU271_H4 | 0.93 | 3.24E-04 | L | 24 | LNU263_H5 | 0.90 | 1.10E-03 | I | 11 |
| LNU271_H4 | 0.90 | 1.07E-03 | L | 24 | LNU45_H260 | 0.89 | 4.59E-02 | G | 11 |
| LNU271_H4 | 0.93 | 3.24E-04 | L | 24 | LNU263_H5 | 0.94 | 1.36E-04 | I | 11 |
| LNU271_H4 | 0.90 | 1.07E-03 | L | 24 | LNU263_H5 | 0.94 | 1.51E-04 | I | 11 |
| LNU35_H4 | 0.75 | 1.92E-02 | L | 24 | LNU263_H5 | 0.94 | 1.36E-04 | I | 11 |
| LNU35_H4 | 0.75 | 1.92E-02 | L | 24 | LNU263_H5 | 0.94 | 1.51E-04 | I | 11 |
| LNU45_H260 | 0.93 | 2.14E-02 | G | 13 | LNU268_H2 | 0.84 | 1.77E-02 | A | 3 |
| LNU263_H5 | 0.74 | 2.36E-02 | I | 13 | LNU268_H2 | 0.78 | 3.66E-02 | A | 3 |
| LNU263_H5 | 0.74 | 2.38E-02 | I | 13 | LNU268_H2 | 0.84 | 1.77E-02 | A | 3 |
| LNU263_H5 | 0.74 | 2.36E-02 | I | 13 | LNU268_H2 | 0.78 | 3.66E-02 | A | 3 |
| LNU263_H5 | 0.74 | 2.38E-02 | I | 13 | LNU48_H1 | 0.84 | 1.74E-02 | A | 3 |
| LNU267_H2 | 0.71 | 3.39E-02 | L | 21 | LNU48_H1 | 0.84 | 1.74E-02 | A | 3 |
| LNU267_H2 | 0.71 | 3.39E-02 | L | 21 | LNU13_H1 | 0.85 | 3.76E-03 | C | 3 |
| LNU265_H0 | 0.71 | 3.13E-02 | L | 21 | LNU13_H1 | 0.84 | 4.64E-03 | C | 3 |
| LNU265_H0 | 0.71 | 3.13E-02 | L | 21 | LNU13_H1 | 0.85 | 3.76E-03 | C | 3 |
| LNU73_H2 | 0.93 | 2.25E-03 | A | 4 | LNU13_H1 | 0.84 | 4.64E-03 | C | 3 |
| LNU223_H6 | 0.95 | 1.29E-03 | A | 4 | LNU45_H260 | 0.76 | 1.68E-02 | C | 3 |
| LNU223_H6 | 0.92 | 3.52E-03 | A | 4 | LNU45_H260 | 0.70 | 3.44E-02 | C | 3 |
| LNU223_H6 | 0.95 | 1.29E-03 | A | 4 | LNU46_H58 | 0.80 | 9.90E-03 | C | 3 |
| LNU223_H6 | 0.92 | 3.52E-03 | A | 4 | LNU46_H58 | 0.78 | 1.28E-02 | C | 3 |
| LNU7_H125 | 0.79 | 1.17E-02 | C | 4 | LNU46_H58 | 0.80 | 9.90E-03 | C | 3 |
| LNU7_H125 | 0.79 | 1.17E-02 | C | 4 | LNU46_H58 | 0.78 | 1.28E-02 | C | 3 |
| LNU7_H124 | 0.79 | 1.17E-02 | C | 4 | LNU35_H4 | 0.88 | 1.56E-03 | C | 3 |
| LNU71_H3 | 0.73 | 2.62E-02 | C | 4 | LNU35_H4 | 0.88 | 1.56E-03 | C | 3 |
| LNU71_H3 | 0.73 | 2.62E-02 | C | 4 | LNU19_H1 | 0.83 | 5.26E-03 | L | 26 |
| LNU7_H125 | 0.79 | 1.17E-02 | C | 4 | LNU223_H6 | 0.82 | 7.43E-03 | L | 26 |
| LNU7_H124 | 0.79 | 1.17E-02 | C | 4 | LNU223_H6 | 0.82 | 7.43E-03 | L | 26 |
| LNU7_H125 | 0.79 | 1.17E-02 | C | 4 | LNU266_H0 | 0.82 | 2.29E-02 | A | 9 |
| LNU109_H2 | 0.78 | 1.29E-02 | F | 29 | LNU266_H0 | 0.77 | 4.09E-02 | A | 9 |
| LNU109_H2 | 0.77 | 1.50E-02 | F | 29 | LNU266_H0 | 0.82 | 2.29E-02 | A | 9 |
| LNU109_H2 | 0.78 | 1.29E-02 | F | 29 | LNU266_H0 | 0.77 | 4.09E-02 | A | 9 |
| LNU109_H2 | 0.77 | 1.50E-02 | F | 29 | LNU74_H173 | 0.84 | 1.86E-02 | A | 9 |
| LNU263_H5 | 0.90 | 3.77E-02 | G | 14 | LNU74_H173 | 0.83 | 1.95E-02 | A | 9 |
| LNU263_H5 | 0.90 | 3.97E-02 | G | 14 | LNU74_H173 | 0.84 | 1.86E-02 | A | 9 |
| LNU263_H5 | 0.90 | 3.77E-02 | G | 14 | LNU74_H173 | 0.83 | 1.95E-02 | A | 9 |
| LNU263_H5 | 0.90 | 3.97E-02 | G | 14 | LNU45_H260 | 0.79 | 3.54E-02 | A | 9 |
| LNU263_H5 | 0.74 | 2.18E-02 | I | 14 | LNU45_H258 | 0.77 | 4.27E-02 | A | 9 |
| LNU263_H5 | 0.74 | 2.18E-02 | I | 14 | LNU45_H258 | 0.77 | 4.27E-02 | A | 9 |
| LNU263_H5 | 0.74 | 2.18E-02 | I | 14 | LNU46_H60 | 0.79 | 3.44E-02 | A | 9 |
| LNU263_H5 | 0.74 | 2.18E-02 | I | 14 | LNU46_H60 | 0.79 | 3.44E-02 | A | 9 |
| LNU266_H0 | 0.72 | 2.97E-02 | L | 22 | LNU266_H0 | 0.95 | 7.83E-05 | C | 9 |
| LNU266_H0 | 0.72 | 2.97E-02 | L | 22 | LNU266_H0 | 0.91 | 6.80E-04 | C | 9 |
| LNU271_H4 | 0.88 | 1.94E-03 | L | 22 | LNU266_H0 | 0.95 | 7.83E-05 | C | 9 |
| LNU271_H4 | 0.87 | 2.23E-03 | L | 22 | LNU266_H0 | 0.91 | 6.80E-04 | C | 9 |
| LNU271_H4 | 0.88 | 1.94E-03 | L | 22 | LNU265_H0 | 0.82 | 6.68E-03 | D | 34 |
|  |  |  |  |  | LNU265_H0 | 0.82 | 6.68E-03 | D | 34 |

Table 39. "Correl. Set ID"—correlation set ID according to the correlated parameters Table above.

Example 9

Production of Maize Transcriptom and High Throughput Correlation Analysis with Yield and NUE Related Parameters Using 44K Maize Oligonucleotide Micro-Arrays In order to produce a high throughput correlation analysis between plant phenotype and gene expression level, the present inventors utilized a maize oligonucleotide micro-array, produced by Agilent Technologies [Hypertext Transfer Protocol://World Wide Web (dot) chem. (dot) agilent (dot) com/Scripts/PDS (dot) asp?1 Page=50879]. The array oligonucleotide represents about 44,000 maize genes and transcripts. In order to define correlations between the levels of RNA expression with yield and NUE components or vigor related parameters, various plant characteristics of 12 different maize hybrids were analyzed. Among them, 10 hybrids encompassing the observed variance were selected for RNA expression analysis. The correlation between the RNA levels and the characterized parameters was analyzed using Pearson correlation test [Hypertext Transfer Protocol://World Wide Web (dot) davidmlane (dot) com/hyperstat/A34739 (dot) html].

Correlation of Maize Hybrids Across Ecotypes Grown Under Regular Growth conditions Experimental Procedures 12 Maize hybrids were grown in 3 repetitive plots, in field. Maize seeds were planted and plants were grown in the field using commercial fertilization and irrigation protocols. In order to define correlations between the levels of RNA expression with NUE and yield components or vigor related parameters, the 12 different maize hybrids were analyzed. Among them, 10 hybrids encompassing the observed variance were selected for RNA expression analysis. The correlation between the RNA levels and the characterized parameters was analyzed using Pearson correlation test [Hypertext Transfer Protocol://World Wide Web (dot) davidmlane (dot) com/hyperstat/A34739 (dot) html].

Analyzed *Sorghum* tissues—All 10 selected maize hybrids were sample per each treatment. Plant tissues [Flag leaf, Flower meristem, Grain, Cobs, Internodes] growing under Normal conditions were sampled and RNA was extracted as described above. Each micro-array expression information tissue type has received a Set ID as summarized in Table 40 below.

TABLE 40

Maize transcriptom expression sets

| Expression Set | Set ID |
|---|---|
| Maize field/Normal/flower meristem | A |
| Maize field/Normal/Ear | B |
| Maize field/Normal/Grain Distal | C |
| Maize field/Normal/Grain Basal | D |
| Maize field/Normal/Internode | E |
| Maize field/Normal/Leaf | F |

Table 40: Provided are the maize transcriptom expression sets.
Leaf = the leaf below the main ear;
Flower meristem = Apical meristem following male flower initiation;
Ear = the female flower at the anthesis day.
Grain Distal = maize developing grains from the cob extreme area,
Grain Basal = maize developing grains from the cob basal area;
Internodes = internodes located above and below the main ear in the plant.

The following parameters were collected using digital imaging system:

Grain Area ($cm^2$)—At the end of the growing period the grains were separated from the ear. A sample of ~200 grains were weight, photographed and images were processed using the below described image processing system. The grain area was measured from those images and was divided by the number of grains.

Grain Length and Grain width (cm)—At the end of the growing period the grains were separated from the ear. A sample of ~200 grains were weight, photographed and images were processed using the below described image processing system. The sum of grain lengths/or width (longest axis) was measured from those images and was divided by the number of grains.

Ear Area ($cm^2$)—At the end of the growing period 5 ears were, photographed and images were processed using the below described image processing system. The Ear area was measured from those images and was divided by the number of Ears.

Ear Length and Ear Width (cm) At the end of the growing period 5 ears were, photographed and images were processed using the below described image processing system. The Ear length and width (longest axis) was measured from those images and was divided by the number of ears.

The image processing system was used, which consists of a personal desktop computer (Intel P4 3.0 GHz processor) and a public domain program—ImageJ 1.37, Java based image processing software, which was developed at the U.S. National Institutes of Health and is freely available on the internet at Hypertext Transfer Protocol://rsbweb (dot) nih (dot) gov/. Images were captured in resolution of 10 Mega Pixels (3888×2592 pixels) and stored in a low compression JPEG (Joint Photographic Experts Group standard) format. Next, image processing output data for seed area and seed length was saved to text files and analyzed using the JMP statistical analysis software (SAS institute).

Additional parameters were collected either by sampling 6 plants per plot or by measuring the parameter across all the plants within the plot.

Normalized Grain Weight per plant (gr.)—At the end of the experiment all ears from plots within blocks A-C were collected. 6 ears were separately threshed and grains were weighted, all additional ears were threshed together and weighted as well. The average grain weight per ear was calculated by dividing the total grain weight by number of total ears per plot (based on plot). In case of 6 ears, the total grains weight of 6 ears was divided by 6.

Ear FW (gr.)—At the end of the experiment (when ears were harvested) total and 6 selected ears per plots within blocks A-C were collected separately. The plants with (total and 6) were weighted (gr.) separately and the average ear per plant was calculated for total (Ear FW per plot) and for 6 (Ear FW per plant).

Plant height and Ear height—Plants were characterized for height at harvesting. In each measure, 6 plants were measured for their height using a measuring tape. Height was measured from ground level to top of the plant below the tassel. Ear height was measured from the ground level to the place were the main ear is located Leaf number per plant—Plants were characterized for leaf number during growing period at 5 time points. In each measure, plants were measured for their leaf number by counting all the leaves of 3 selected plants per plot.

Relative Growth Rate was calculated using Formulas IX and X (described above).

SPAD—Chlorophyll content was determined using a Minolta SPAD 502 chlorophyll meter and measurement was performed 64 days post sowing. SPAD meter readings were done on young fully developed leaf. Three measurements per leaf were taken per plot. Data were taken after 46 and 54 days after sowing (DPS)

Dry weight per plant—At the end of the experiment (when Inflorescence were dry) all vegetative material from plots within blocks A-C were collected.

Dry weight=total weight of the vegetative portion above ground (excluding roots) after drying at 70° C. in oven for 48 hours;

Harvest Index (HI) (Maize)—The harvest index was calculated using Formula XII.

Harvest Index=Average grain dry weight per Ear/(Average vegetative dry weight per Ear+Average Ear dry weight)  Formula XII:

Percent Filled Ear [%]—it was calculated as the percentage of the Ear area with grains out of the total ear.

Cob diameter [cm]—The diameter of the cob without grains was measured using a ruler.

Kernel Row Number per Ear—The number of rows in each ear was counted.

Experimental Results 12 different maize hybrids were grown and characterized for different parameters: The average for each of the measured parameter was calculated using the JMP software (Tables 42-43) and a subsequent correlation analysis was performed (Tables 44 and 45). Results were then integrated to the database.

TABLE 41

Maize correlated parameters (vectors)

| Correlations | Correlation ID |
|---|---|
| SPAD 54DPS [SPAD units] | 1 |
| SPAD 46DPS [SPAD units] | 2 |
| Growth Rate Leaf Num | 3 |
| Plant Height per Plot [cm] | 4 |
| Ear Height [cm] | 5 |
| Leaf Number per Plant [number] | 6 |
| Ear Length [cm] | 7 |
| Percent Filled Ear [%] | 8 |
| Cob Diameter [mm] | 9 |
| Kernel Row Number per Ear [number] | 10 |
| DW per Plant [gr] | 11 |
| Ear FW per Plant gr] | 12 |
| Normalized Grain Weight per plant [gr] | 13 |
| Ears FW per plot [gr] | 14 |
| Normalized Grain Weight per plot [gr] | 15 |
| Ear Area [cm2] | 16 |
| Ear Width [cm] | 17 |
| Grain Area [cm2] | 18 |
| Grain Length [cm] | 19 |
| Grain Width [cm] | 20 |

Table 41. SPAD 46DPS and SPAD 54DPS: Chlorophyl level after 46 and 54 days after sowing (DPS).

TABLE 42

Measured parameters in Maize accessions under normal conditions

| Seed ID | 1 | 2 | 3 | 4 | 5 | 6 | 7 | 8 | 9 | 10 | 11 |
|---|---|---|---|---|---|---|---|---|---|---|---|
| Line 1 | 54.8 | 55.3 | 0.306 | 287 | 135 | 11.9 | 20.9 | 80.4 | 28.7 | 16.2 | 656 |
| Line 2 | 54.3 | 51.7 | 0.283 | 278 | 135 | 12 | 19.7 | 80.6 | 29 | 16.2 | 658 |
| Line 3 | 57.2 | 56.4 | 0.221 | 270 | 116 | 8.4 | 19.1 | 94.3 | 23.8 | 15 | 472 |
| Line 4 | 56 | 53.5 | 0.281 | 275 | 132 | 11.7 | 20.5 | 82.1 | 28.1 | 16.2 | 641 |
| Line 5 | 59.7 | 55.2 | 0.269 | 238 | 114 | 11.8 | 21.3 | 92.7 | 25.7 | 15.9 | 581 |
| Line 6 | 59.1 | 59.4 | 0.244 | 225 | 94.3 | 12.3 | 18.2 | 82.8 | 25.8 | 15.2 | 569 |
| Line 7 | 58 | 58.5 | 0.244 | 264 | 121 | 12.4 | 19 | 73.2 | 26.4 | 16 | 511 |
| Line 8 | 60.4 | 55.9 | 0.266 | 252 | 108 | 12.2 | 18.6 | 81.1 | 25.2 | 14.8 | 544 |
| Line 9 | 54.8 | 53 | | | | | | | | | |
| Line 10 | 53.3 | 50 | | | | | | | | | |
| Line 11 | 61.1 | 59.7 | 0.301 | 278 | 112 | 12.6 | 21.7 | 91.6 | 26.7 | 15.4 | 522 |
| Line 12 | 51.4 | 53.9 | 0.194 | 164 | 60.4 | 9.28 | 16.7 | 81.1 | 14.3 | 574 | 141 |

Table 42. Provided are the values of each of the parameters (as described above) measured in maize accessions (Seed ID) under regular growth conditions. Growth conditions are specified in the experimental procedure section.

TABLE 43

Additional measured parameters in Maize accessions under regular growth conditions

| Seed ID | 12 | 13 | 14 | 15 | 16 | 17 | 18 | 19 | 20 |
|---|---|---|---|---|---|---|---|---|---|
| Line 1 | 272 | 157 | 280 | 140 | 91.6 | 5.73 | 0.806 | 1.23 | 0.824 |
| Line 2 | 246 | 141 | 278 | 154 | 85.1 | 5.58 | 0.753 | 1.17 | 0.81 |
| Line 3 | 190 | 129 | 190 | 121 | 77.9 | 5.1 | 0.674 | 1.07 | 0.794 |
| Line 4 | 262 | 154 | 288 | 152 | 90.5 | 5.67 | 0.755 | 1.18 | 0.803 |
| Line 5 | 264 | 177 | 248 | 159 | 96 | 5.53 | 0.766 | 1.2 | 0.803 |
| Line 6 | 178 | 120 | 176 | 117 | 72.4 | 5.23 | 0.713 | 1.12 | 0.803 |
| Line 7 | 189 | 120 | 192 | 123 | 74 | 5.22 | 0.714 | 1.14 | 0.791 |
| Line 8 | 197 | 134 | 205 | 131 | 76.5 | 5.33 | 0.753 | 1.13 | 0.837 |
| Line 9 | | | | | | | | | |
| Line 10 | | | | | | | | | |
| Line 11 | 261 | 173 | 264 | 171 | 95.4 | 5.58 | 0.762 | 1.18 | 0.812 |
| Line 12 | 54.3 | 143 | 40.8 | 55.2 | 4.12 | 0.796 | 0.921 | 0.675 | |

Table 43. Provided are the values of each of the parameters (as described above) measured in maize accessions (Seed ID) under regular growth conditions. Growth conditions are specified in the experimental procedure section.

TABLE 44

Correlation between the expression level of selected LNU genes of some embodiments of the invention in various tissues and the phenotypic performance under normal across maize accessions

| Gene Name | R | P value | Exp. set | Correl. Set ID | Gene Name | R | P value | Exp. set | Correl. Set ID |
|---|---|---|---|---|---|---|---|---|---|
| LNU267 | 0.81 | 2.77E−02 | F | 8 | LNU265 | 0.78 | 3.99E−02 | B | 17 |
| LNU113 | 0.76 | 2.86E−02 | C | 9 | LNU265 | 0.76 | 4.86E−02 | B | 5 |
| LNU113 | 0.76 | 2.88E−02 | C | 9 | LNU265 | 0.76 | 4.98E−02 | B | 18 |
| LNU265 | 0.89 | 7.21E−03 | B | 8 | LNU265 | 0.72 | 4.32E−02 | C | 15 |

TABLE 44-continued

Correlation between the expression level of selected LNU genes of some embodiments of the invention in various tissues and the phenotypic performance under normal across maize accessions

| Gene Name | R | P value | Exp. set | Correl. Set ID | Gene Name | R | P value | Exp. set | Correl. Set ID |
|---|---|---|---|---|---|---|---|---|---|
| LNU265 | 0.80 | 3.16E−02 | B | 20 | LNU98 | 0.78 | 3.84E−02 | E | 11 |
| LNU265 | 0.78 | 7.51E−03 | F | 2 | | | | | |

Table 44. "Correl. Set ID"—correlation set ID according to the correlated parameters Table above.

TABLE 45

Correlation between the expression level of selected LNU homologous genes of some embodiments of the invention in various tissues and the phenotypic performance under normal across maize accessions

| Gene Name | R | P value | Exp. Set | Correl. Set ID | Gene Name | R | P value | Exp. Set | Correl. Set ID |
|---|---|---|---|---|---|---|---|---|---|
| LNU74_H112 | 0.84 | 1.67E−02 | B | 11 | LNU34_H0 | 0.82 | 2.26E−02 | F | 3 |
| LNU46_H34 | 0.79 | 3.59E−02 | B | 11 | LNU34_H0 | 0.79 | 3.36E−02 | F | 3 |
| LNU51_H1 | 0.76 | 4.84E−02 | B | 3 | LNU34_H0 | 0.79 | 3.29E−02 | E | 12 |
| LNU52_H5 | 0.86 | 1.37E−02 | B | 18 | LNU34_H0 | 0.79 | 3.57E−02 | F | 3 |
| LNU45_H173 | 0.79 | 3.53E−02 | B | 16 | LNU115_H0 | 0.81 | 2.74E−02 | B | 6 |
| LNU64_H1 | 0.85 | 1.53E−02 | B | 18 | LNU35_H2 | 0.76 | 4.85E−02 | E | 12 |
| LNU64_H1 | 0.85 | 1.54E−02 | B | 18 | LNU74_H111 | 0.71 | 2.23E−02 | F | 12 |
| LNU74_H118 | 0.95 | 3.98E−03 | B | 16 | LNU13_H0 | 0.87 | 1.13E−02 | F | 12 |
| LNU278_H2 | 0.84 | 1.89E−02 | B | 11 | LNU45_H173 | 0.71 | 4.78E−02 | E | 19 |
| LNU216_H0 | 0.96 | 2.60E−03 | B | 11 | LNU51_H1 | 0.88 | 8.90E−03 | B | 6 |
| LNU74_H110 | 0.84 | 1.83E−02 | B | 18 | LNU74_H109 | 0.81 | 2.65E−02 | B | 6 |
| LNU74_H118 | 0.94 | 5.44E−03 | B | 16 | LNU45_H173 | 0.78 | 3.79E−02 | B | 6 |
| LNU34_H0 | 0.76 | 4.59E−02 | B | 18 | LNU279_H2 | 0.92 | 1.08E−03 | C | 9 |
| LNU45_H173 | 0.81 | 4.97E−02 | B | 16 | LNU7_H89 | 0.85 | 3.26E−02 | B | 6 |
| LNU45_H173 | 0.77 | 4.28E−02 | B | 18 | LNU52_H5 | 0.87 | 9.94E−03 | B | 8 |
| LNU35_H2 | 0.90 | 5.70E−03 | B | 18 | LNU74_H110 | 0.95 | 9.33E−04 | B | 8 |
| LNU271_H3 | 0.81 | 1.46E−02 | C | 16 | LNU7_H89 | 0.84 | 3.45E−02 | B | 6 |
| LNU51_H1 | 0.89 | 1.71E−02 | B | 11 | LNU7_H89 | 0.85 | 3.26E−02 | B | 6 |
| LNU271_H3 | 0.76 | 2.73E−02 | C | 16 | LNU7_H89 | 0.84 | 3.45E−02 | B | 6 |
| LNU64_H1 | 0.85 | 1.53E−02 | B | 18 | LNU115_H0 | 0.78 | 1.33E−02 | E | 6 |
| LNU278_H2 | 0.90 | 1.50E−02 | B | 11 | LNU74_H110 | 0.91 | 4.94E−03 | B | 8 |
| LNU64_H1 | 0.85 | 1.54E−02 | B | 18 | LNU279_H1 | 0.74 | 3.49E−02 | C | 9 |
| LNU13_H0 | 0.77 | 2.47E−02 | C | 11 | LNU34_H0 | 0.85 | 7.43E−03 | C | 9 |
| LNU64_H1 | 0.77 | 4.40E−02 | B | 3 | LNU34_H0 | 0.83 | 1.01E−02 | C | 9 |
| LNU64_H1 | 0.76 | 4.82E−02 | B | 3 | LNU52_H4 | 0.78 | 1.26E−02 | E | 6 |
| LNU13_H0 | 0.74 | 3.48E−02 | C | 11 | LNU7_H89 | 0.78 | 1.40E−02 | E | 6 |
| LNU13_H0 | 0.74 | 3.53E−02 | C | 11 | LNU7_H89 | 0.71 | 3.34E−02 | E | 6 |
| LNU52_H5 | 0.76 | 2.93E−02 | C | 11 | LNU34_H0 | 0.81 | 1.54E−02 | C | 9 |
| LNU52_H5 | 0.73 | 4.07E−02 | C | 11 | LNU7_H89 | 0.70 | 3.54E−02 | E | 6 |
| LNU216_H1 | 0.88 | 8.39E−03 | E | 16 | LNU7_H88 | 0.83 | 6.01E−03 | E | 6 |
| LNU52_H5 | 0.86 | 1.39E−02 | E | 16 | LNU74_H111 | 0.76 | 4.89E−02 | F | 19 |
| LNU52_H4 | 0.71 | 4.92E−02 | C | 11 | LNU74_H110 | 0.83 | 2.00E−02 | B | 8 |
| LNU71_H0 | 0.78 | 2.30E−02 | C | 11 | LNU7_H88 | 0.79 | 1.06E−02 | E | 6 |
| LNU279_H2 | 0.77 | 4.29E−02 | E | 16 | LNU7_H88 | 0.78 | 1.28E−02 | E | 6 |
| LNU34_H0 | 0.95 | 8.43E−04 | E | 16 | LNU74_H110 | 0.81 | 2.85E−02 | B | 8 |
| LNU74_H118 | 0.84 | 3.81E−02 | B | 18 | LNU74_H110 | 0.77 | 4.51E−02 | B | 8 |
| LNU74_H111 | 0.71 | 4.86E−02 | E | 16 | LNU52_H5 | 0.92 | 3.01E−03 | B | 20 |
| LNU71_H0 | 0.75 | 3.07E−02 | C | 11 | LNU64_H1 | 0.87 | 1.03E−02 | B | 20 |
| LNU271_H3 | 0.74 | 3.77E−02 | C | 18 | LNU7_H87 | 0.71 | 3.37E−02 | E | 6 |
| LNU271_H2 | 0.71 | 4.67E−02 | C | 11 | LNU64_H1 | 0.87 | 1.18E−02 | B | 20 |
| LNU13_H0 | 0.78 | 3.87E−02 | F | 16 | LNU74_H118 | 0.78 | 1.39E−02 | E | 6 |
| LNU74_H111 | 0.77 | 4.23E−02 | F | 16 | LNU74_H110 | 0.91 | 4.62E−03 | B | 20 |
| LNU7_H87 | 0.84 | 1.84E−02 | B | 14 | LNU74_H112 | 0.91 | 4.94E−03 | B | 8 |
| LNU271_H3 | 0.88 | 3.84E−03 | C | 11 | LNU74_H118 | 0.74 | 2.14E−02 | E | 6 |
| LNU34_H0 | 0.73 | 3.96E−02 | C | 18 | LNU74_H118 | 0.77 | 4.51E−02 | B | 8 |
| LNU115_H0 | 0.77 | 1.54E−02 | E | 18 | LNU74_H118 | 0.74 | 2.22E−02 | E | 6 |
| LNU74_H118 | 0.74 | 2.38E−02 | E | 18 | LNU74_H116 | 0.78 | 1.39E−02 | E | 6 |
| LNU7_H87 | 0.76 | 4.59E−02 | B | 14 | LNU74_H110 | 0.78 | 1.39E−02 | E | 6 |
| LNU271_H3 | 0.78 | 2.29E−02 | C | 11 | LNU74_H110 | 0.73 | 2.44E−02 | E | 6 |
| LNU74_H118 | 0.72 | 2.83E−02 | E | 18 | LNU74_H116 | 0.78 | 1.39E−02 | E | 6 |
| LNU74_H109 | 0.82 | 2.31E−02 | B | 3 | LNU74_H109 | 0.76 | 1.86E−02 | E | 6 |
| LNU279_H2 | 0.86 | 6.55E−03 | C | 11 | LNU74_H109 | 0.73 | 2.54E−02 | E | 6 |
| LNU7_H87 | 0.76 | 4.79E−02 | B | 14 | LNU74_H113 | 0.78 | 1.39E−02 | E | 6 |
| LNU34_H0 | 0.82 | 1.35E−02 | C | 11 | LNU74_H112 | 0.78 | 1.39E−02 | E | 6 |
| LNU85_H2 | 0.71 | 3.12E−02 | E | 18 | LNU74_H112 | 0.73 | 2.44E−02 | E | 6 |
| LNU7_H87 | 0.84 | 1.84E−02 | B | 14 | LNU74_H110 | 0.77 | 4.18E−02 | B | 20 |
| LNU34_H0 | 0.81 | 1.51E−02 | C | 11 | LNU74_H110 | 0.77 | 4.27E−02 | B | 20 |
| LNU34_H0 | 0.78 | 2.29E−02 | C | 11 | LNU74_H110 | 0.77 | 4.39E−02 | B | 20 |

TABLE 45-continued

Correlation between the expression level of selected LNU homologous genes of some embodiments of the invention in various tissues and the phenotypic performance under normal across maize accessions

| Gene Name | R | P value | Exp. Set | Correl. Set ID | Gene Name | R | P value | Exp. Set | Correl. Set ID |
| --- | --- | --- | --- | --- | --- | --- | --- | --- | --- |
| LNU271_H3 | 0.84 | 4.49E−03 | E | 11 | LNU7_H89 | 0.78 | 1.40E−02 | E | 6 |
| LNU271_H3 | 0.77 | 1.58E−02 | E | 11 | LNU74_H112 | 0.77 | 4.39E−02 | B | 20 |
| LNU7_H87 | 0.76 | 4.59E−02 | B | 14 | LNU7_H89 | 0.71 | 3.34E−02 | E | 6 |
| LNU7_H87 | 0.76 | 4.79E−02 | B | 14 | LNU7_H89 | 0.70 | 3.54E−02 | E | 6 |
| LNU69_H2 | 0.76 | 4.75E−02 | E | 11 | LNU7_H88 | 0.83 | 6.01E−03 | E | 6 |
| LNU74_H111 | 0.82 | 2.44E−02 | E | 11 | LNU7_H88 | 0.79 | 1.06E−02 | E | 6 |
| LNU45_H173 | 0.87 | 1.10E−02 | B | 14 | LNU7_H88 | 0.78 | 1.28E−02 | E | 6 |
| LNU279_H1 | 0.88 | 2.09E−02 | B | 10 | LNU7_H87 | 0.71 | 3.37E−02 | E | 6 |
| LNU45_H173 | 0.85 | 1.45E−02 | B | 14 | LNU45_H169 | 0.80 | 1.01E−02 | E | 6 |
| LNU45_H173 | 0.84 | 1.78E−02 | B | 14 | LNU45_H169 | 0.78 | 1.32E−02 | E | 6 |
| LNU76_H37 | 0.76 | 4.93E−02 | E | 18 | LNU45_H168 | 0.82 | 6.36E−03 | E | 6 |
| LNU34_H0 | 0.84 | 3.62E−02 | B | 9 | LNU51_H1 | 0.80 | 3.24E−02 | E | 6 |
| LNU74_H111 | 0.76 | 4.94E−02 | E | 11 | LNU34_H0 | 0.92 | 2.97E−03 | B | 8 |
| LNU76_H38 | 0.76 | 4.93E−02 | E | 18 | LNU279_H2 | 0.83 | 1.99E−02 | E | 6 |
| LNU74_H118 | 0.96 | 2.95E−03 | B | 14 | LNU34_H0 | 0.75 | 3.22E−02 | E | 6 |
| LNU74_H118 | 0.94 | 5.02E−03 | B | 14 | LNU34_H0 | 0.86 | 1.41E−02 | B | 20 |
| LNU46_H35 | 0.83 | 1.99E−02 | E | 11 | LNU34_H0 | 0.81 | 2.64E−02 | B | 20 |
| LNU45_H173 | 0.89 | 1.70E−02 | B | 14 | LNU34_H0 | 0.76 | 4.86E−02 | B | 20 |
| LNU45_H173 | 0.89 | 1.77E−02 | B | 14 | LNU35_H2 | 0.93 | 2.72E−03 | B | 20 |
| LNU279_H2 | 0.84 | 1.76E−02 | E | 18 | LNU64_H1 | 0.87 | 1.03E−02 | B | 20 |
| LNU34_H0 | 0.89 | 6.53E−03 | E | 18 | LNU271_H3 | 0.88 | 3.49E−03 | E | 9 |
| LNU45_H173 | 0.92 | 3.19E−03 | B | 3 | LNU64_H1 | 0.87 | 1.18E−02 | B | 20 |
| LNU48_H0 | 0.75 | 1.31E−02 | F | 11 | LNU271_H3 | 0.80 | 1.78E−02 | E | 9 |
| LNU115_H0 | 0.83 | 2.14E−02 | F | 11 | LNU17_H1 | 0.84 | 3.53E−02 | B | 20 |
| LNU45_H173 | 0.90 | 1.54E−02 | B | 9 | LNU2_H3 | 0.81 | 4.88E−02 | B | 20 |
| LNU45_H173 | 0.83 | 3.90E−02 | B | 14 | LNU48_H0 | 0.93 | 7.37E−03 | B | 20 |
| LNU35_H2 | 0.88 | 2.05E−02 | B | 14 | LNU25_H0 | 0.87 | 2.57E−02 | B | 20 |
| LNU271_H3 | 0.88 | 3.73E−03 | C | 14 | LNU223_H3 | 0.74 | 3.56E−02 | E | 9 |
| LNU271_H3 | 0.79 | 1.87E−02 | C | 14 | LNU25_H0 | 0.85 | 3.39E−02 | B | 20 |
| LNU35_H2 | 0.79 | 3.62E−02 | E | 18 | LNU279_H0 | 0.87 | 2.42E−02 | B | 20 |
| LNU279_H2 | 0.78 | 2.30E−02 | C | 14 | LNU279_H0 | 0.86 | 2.94E−02 | B | 20 |
| LNU216_H1 | 0.94 | 1.76E−03 | E | 14 | LNU279_H2 | 0.92 | 8.63E−03 | B | 20 |
| LNU52_H5 | 0.76 | 4.97E−02 | E | 14 | LNU34_H0 | 0.89 | 6.68E−03 | B | 8 |
| LNU34_H0 | 0.88 | 8.34E−03 | E | 14 | LNU279_H1 | 0.92 | 8.63E−03 | B | 20 |
| LNU13_H0 | 0.85 | 1.65E−02 | F | 14 | LNU34_H0 | 0.81 | 2.75E−02 | B | 8 |
| LNU45_H173 | 0.78 | 3.87E−02 | B | 3 | LNU239_H6 | 0.75 | 3.13E−02 | C | 20 |
| LNU74_H111 | 0.81 | 2.78E−02 | F | 18 | LNU35_H2 | 0.94 | 1.48E−03 | B | 8 |
| LNU45_H173 | 0.77 | 4.38E−02 | B | 3 | LNU85_H2 | 0.84 | 1.89E−02 | B | 8 |
| LNU84_H0 | 0.76 | 4.64E−02 | F | 14 | LNU239_H6 | 0.75 | 3.17E−02 | C | 20 |
| LNU84_H0 | 0.76 | 4.64E−02 | F | 14 | LNU85_H2 | 0.78 | 1.38E−02 | E | 20 |
| LNU64_H1 | 0.87 | 1.14E−02 | B | 5 | LNU85_H2 | 0.77 | 4.20E−02 | B | 8 |
| LNU64_H1 | 0.81 | 2.84E−02 | B | 5 | LNU85_H2 | 0.76 | 1.72E−02 | E | 20 |
| LNU7_H87 | 0.79 | 3.46E−02 | B | 5 | LNU76_H37 | 0.78 | 3.68E−02 | E | 20 |
| LNU35_H2 | 0.76 | 4.90E−02 | F | 18 | LNU19_H0 | 0.82 | 4.69E−02 | B | 8 |
| LNU52_H5 | 0.79 | 3.62E−02 | B | 19 | LNU279_H2 | 0.77 | 4.33E−02 | E | 20 |
| LNU7_H87 | 0.76 | 4.94E−02 | B | 5 | LNU74_H111 | 0.85 | 3.33E−02 | B | 8 |
| LNU64_H1 | 0.78 | 3.97E−02 | B | 19 | LNU45_H169 | 0.91 | 1.17E−02 | B | 8 |
| LNU7_H87 | 0.79 | 3.46E−02 | B | 5 | LNU239_H5 | 0.90 | 1.43E−02 | B | 8 |
| LNU7_H87 | 0.76 | 4.94E−02 | B | 5 | LNU34_H0 | 0.77 | 4.20E−02 | E | 20 |
| LNU35_H2 | 0.78 | 3.76E−02 | B | 3 | LNU64_H1 | 0.70 | 3.41E−02 | E | 8 |
| LNU34_H0 | 0.80 | 2.99E−02 | B | 5 | LNU35_H2 | 0.78 | 3.92E−02 | E | 20 |
| LNU34_H0 | 0.77 | 4.31E−02 | B | 5 | LNU153_H3 | 0.77 | 4.26E−02 | E | 20 |
| LNU35_H2 | 0.77 | 4.28E−02 | B | 5 | LNU19_H0 | 0.75 | 3.05E−02 | E | 20 |
| LNU64_H1 | 0.87 | 1.14E−02 | B | 5 | LNU216_H0 | 0.80 | 1.78E−02 | E | 20 |
| LNU64_H1 | 0.81 | 2.84E−02 | B | 5 | LNU67_H2 | 0.86 | 6.40E−03 | E | 20 |
| LNU64_H1 | 0.78 | 4.04E−02 | B | 19 | LNU271_H2 | 0.87 | 4.49E−03 | E | 20 |
| LNU35_H2 | 0.85 | 3.04E−02 | B | 5 | LNU279_H2 | 0.89 | 3.36E−03 | E | 20 |
| LNU74_H110 | 0.75 | 4.99E−02 | B | 19 | LNU279_H2 | 0.72 | 4.47E−02 | E | 20 |
| LNU13_H0 | 0.72 | 4.54E−02 | C | 5 | LNU279_H1 | 0.72 | 4.47E−02 | E | 20 |
| LNU45_H173 | 0.82 | 2.26E−02 | B | 19 | LNU223_H4 | 0.72 | 1.91E−02 | F | 20 |
| LNU35_H2 | 0.84 | 1.78E−02 | B | 19 | LNU76_H37 | 0.70 | 2.35E−02 | F | 6 |
| LNU279_H2 | 0.90 | 2.37E−03 | C | 5 | LNU74_H111 | 0.81 | 2.70E−02 | F | 20 |
| LNU46_H34 | 0.81 | 1.46E−02 | C | 5 | LNU35_H2 | 0.79 | 3.57E−02 | F | 20 |
| LNU34_H0 | 0.82 | 2.36E−02 | E | 5 | LNU52_H5 | 0.76 | 4.89E−02 | B | 15 |
| LNU64_H1 | 0.78 | 3.97E−02 | B | 19 | LNU74_H110 | 0.80 | 3.12E−02 | B | 15 |
| LNU35_H2 | 0.93 | 2.24E−03 | E | 5 | LNU222_H2 | 0.74 | 2.37E−02 | E | 8 |
| LNU64_H1 | 0.78 | 4.04E−02 | B | 19 | LNU45_H173 | 0.76 | 4.93E−02 | B | 15 |
| LNU74_H111 | 0.78 | 4.02E−02 | F | 5 | LNU64_H1 | 0.70 | 3.41E−02 | E | 8 |
| LNU64_H1 | 0.77 | 4.40E−02 | B | 3 | LNU35_H2 | 0.76 | 4.79E−02 | B | 15 |
| LNU64_H1 | 0.76 | 4.82E−02 | B | 3 | LNU52_H5 | 0.79 | 3.46E−02 | E | 8 |
| LNU74_H118 | 0.94 | 4.87E−03 | B | 19 | LNU74_H118 | 0.91 | 1.27E−02 | B | 15 |
| LNU35_H2 | 0.78 | 3.87E−02 | F | 5 | LNU74_H118 | 0.90 | 1.51E−02 | B | 15 |
| LNU7_H87 | 0.77 | 4.50E−02 | B | 7 | LNU45_H169 | 0.86 | 2.93E−02 | B | 15 |

TABLE 45-continued

Correlation between the expression level of selected LNU homologous genes of some embodiments of the invention in various tissues and the phenotypic performance under normal across maize accessions

| Gene Name | R | P value | Exp. Set | Correl. Set ID | Gene Name | R | P value | Exp. Set | Correl. Set ID |
|---|---|---|---|---|---|---|---|---|---|
| LNU74_H118 | 0.93 | 6.77E−03 | B | 19 | LNU34_H0 | 0.77 | 4.47E−02 | E | 8 |
| LNU7_H87 | 0.77 | 4.50E−02 | B | 7 | LNU45_H169 | 0.84 | 3.68E−02 | B | 15 |
| LNU45_H173 | 0.88 | 2.14E−02 | B | 19 | LNU45_H168 | 0.88 | 2.11E−02 | B | 15 |
| LNU45_H173 | 0.76 | 4.71E−02 | B | 7 | LNU35_H2 | 0.80 | 2.92E−02 | E | 8 |
| LNU74_H118 | 0.88 | 2.01E−02 | B | 7 | LNU216_H1 | 0.78 | 2.36E−02 | E | 8 |
| LNU74_H118 | 0.88 | 2.09E−02 | B | 7 | LNU216_H0 | 0.73 | 4.00E−02 | C | 15 |
| LNU45_H168 | 0.88 | 2.20E−02 | B | 7 | LNU271_H3 | 0.72 | 4.46E−02 | C | 15 |
| LNU271_H3 | 0.80 | 1.70E−02 | C | 7 | LNU51_H1 | 0.71 | 4.94E−02 | E | 8 |
| LNU271_H3 | 0.76 | 2.93E−02 | C | 7 | LNU52_H5 | 0.75 | 3.18E−02 | E | 8 |
| LNU216_H1 | 0.93 | 2.42E−03 | E | 7 | LNU76_H38 | 0.70 | 2.35E−02 | F | 6 |
| LNU45_H173 | 0.87 | 2.25E−02 | B | 19 | LNU271_H3 | 0.71 | 4.85E−02 | C | 15 |
| LNU52_H5 | 0.87 | 1.07E−02 | E | 7 | LNU216_H1 | 0.79 | 3.42E−02 | E | 15 |
| LNU279_H2 | 0.76 | 4.74E−02 | E | 7 | LNU69_H2 | 0.71 | 5.00E−02 | E | 8 |
| LNU34_H0 | 0.92 | 3.25E−03 | E | 7 | LNU52_H5 | 0.87 | 1.18E−02 | E | 15 |
| LNU45_H173 | 0.83 | 4.10E−02 | B | 19 | LNU45_H170 | 0.72 | 4.38E−02 | E | 8 |
| LNU45_H173 | 0.81 | 1.49E−02 | E | 7 | LNU76_H37 | 0.77 | 4.30E−02 | E | 15 |
| LNU45_H173 | 0.74 | 3.39E−02 | E | 7 | LNU45_H173 | 0.72 | 4.38E−02 | E | 8 |
| LNU45_H173 | 0.73 | 4.07E−02 | E | 7 | LNU76_H38 | 0.77 | 4.30E−02 | E | 15 |
| LNU13_H0 | 0.84 | 1.76E−02 | F | 7 | LNU74_H110 | 0.79 | 3.47E−02 | F | 8 |
| LNU52_H5 | 0.77 | 4.42E−02 | B | 17 | LNU74_H110 | 0.76 | 4.66E−02 | F | 8 |
| LNU64_H1 | 0.85 | 1.52E−02 | B | 17 | LNU279_H2 | 0.81 | 2.68E−02 | E | 15 |
| LNU64_H1 | 0.84 | 1.84E−02 | B | 17 | LNU34_H0 | 0.97 | 2.32E−04 | E | 15 |
| LNU74_H110 | 0.80 | 3.12E−02 | B | 17 | LNU45_H173 | 0.74 | 3.52E−02 | E | 15 |
| LNU74_H118 | 0.87 | 2.34E−02 | B | 3 | LNU74_H111 | 0.81 | 2.82E−02 | F | 15 |
| LNU34_H0 | 0.77 | 4.46E−02 | B | 17 | LNU35_H2 | 0.78 | 3.75E−02 | F | 15 |
| LNU74_H118 | 0.85 | 3.35E−02 | B | 3 | LNU52_H5 | 0.77 | 4.49E−02 | B | 13 |
| LNU35_H2 | 0.91 | 1.16E−02 | B | 19 | LNU64_H1 | 0.78 | 4.03E−02 | B | 13 |
| LNU45_H173 | 0.81 | 2.74E−02 | B | 17 | LNU74_H111 | 0.88 | 8.99E−03 | F | 8 |
| LNU35_H2 | 0.89 | 6.82E−03 | B | 17 | LNU74_H110 | 0.84 | 1.89E−02 | B | 13 |
| LNU64_H1 | 0.85 | 1.52E−02 | B | 17 | LNU74_H111 | 0.78 | 3.68E−02 | F | 8 |
| LNU7_H87 | 0.77 | 2.69E−02 | C | 19 | LNU35_H2 | 0.88 | 9.78E−03 | F | 8 |
| LNU7_H87 | 0.75 | 3.33E−02 | C | 19 | LNU45_H173 | 0.78 | 3.75E−02 | B | 13 |
| LNU64_H1 | 0.84 | 1.84E−02 | B | 17 | LNU45_H173 | 0.79 | 3.34E−02 | B | 10 |
| LNU51_H1 | 0.82 | 4.40E−02 | B | 17 | LNU35_H2 | 0.84 | 1.89E−02 | B | 13 |
| LNU74_H118 | 0.94 | 5.68E−03 | B | 17 | LNU7_H89 | 0.82 | 4.69E−02 | B | 10 |
| LNU7_H87 | 0.77 | 2.69E−02 | C | 19 | LNU64_H1 | 0.78 | 4.03E−02 | B | 13 |
| LNU7_H87 | 0.75 | 3.33E−02 | C | 19 | LNU74_H110 | 0.94 | 5.95E−03 | B | 10 |
| LNU271_H3 | 0.87 | 4.80E−03 | C | 19 | LNU74_H112 | 0.94 | 5.95E−03 | B | 10 |
| LNU271_H3 | 0.82 | 1.30E−02 | C | 19 | LNU74_H118 | 0.89 | 1.81E−02 | B | 13 |
| LNU74_H118 | 0.92 | 8.82E−03 | B | 17 | LNU74_H118 | 0.87 | 2.55E−02 | B | 13 |
| LNU45_H173 | 0.93 | 7.66E−03 | B | 17 | LNU216_H0 | 0.73 | 3.89E−02 | C | 13 |
| LNU45_H173 | 0.92 | 8.24E−03 | B | 17 | LNU71_H0 | 0.75 | 3.33E−02 | C | 13 |
| LNU45_H173 | 0.87 | 2.30E−02 | B | 17 | LNU271_H3 | 0.81 | 1.58E−02 | C | 13 |
| LNU35_H2 | 0.85 | 3.01E−02 | B | 17 | LNU7_H89 | 0.82 | 4.69E−02 | B | 10 |
| LNU13_H0 | 0.71 | 4.87E−02 | C | 17 | LNU271_H3 | 0.86 | 6.62E−03 | C | 10 |
| LNU7_H87 | 0.72 | 4.19E−02 | C | 17 | LNU271_H3 | 0.78 | 2.12E−02 | C | 10 |
| LNU71_H0 | 0.77 | 2.47E−02 | C | 17 | LNU271_H3 | 0.78 | 2.34E−02 | C | 13 |
| LNU71_H0 | 0.75 | 3.28E−02 | C | 17 | LNU279_H2 | 0.77 | 2.46E−02 | C | 10 |
| LNU7_H87 | 0.72 | 4.19E−02 | C | 17 | LNU216_H1 | 0.81 | 2.65E−02 | E | 10 |
| LNU271_H3 | 0.89 | 2.99E−03 | C | 17 | LNU52_H5 | 0.87 | 1.14E−02 | E | 13 |
| LNU271_H3 | 0.77 | 2.46E−02 | C | 17 | LNU279_H2 | 0.86 | 1.37E−02 | E | 13 |
| LNU279_H2 | 0.87 | 4.77E−03 | C | 17 | LNU48_H0 | 0.72 | 2.73E−02 | F | 9 |
| LNU34_H0 | 0.72 | 4.57E−02 | C | 17 | LNU64_H1 | 0.84 | 1.85E−02 | B | 4 |
| LNU115_H0 | 0.71 | 3.22E−02 | E | 17 | LNU7_H89 | 0.73 | 1.58E−02 | F | 2 |
| LNU115_H0 | 0.79 | 1.10E−02 | E | 19 | LNU74_H110 | 0.73 | 1.55E−02 | F | 2 |
| LNU74_H118 | 0.72 | 2.72E−02 | E | 19 | LNU84_H0 | 0.77 | 4.38E−02 | E | 10 |
| LNU52_H5 | 0.77 | 4.15E−02 | E | 17 | LNU74_H111 | 0.74 | 2.28E−02 | F | 9 |
| LNU279_H2 | 0.82 | 2.45E−02 | E | 17 | LNU34_H0 | 0.84 | 1.72E−02 | E | 10 |
| LNU34_H0 | 0.92 | 3.49E−03 | E | 17 | LNU74_H111 | 0.72 | 3.03E−02 | F | 9 |
| LNU74_H118 | 0.71 | 3.14E−02 | E | 19 | LNU64_H1 | 0.77 | 4.22E−02 | B | 4 |
| LNU35_H2 | 0.86 | 1.39E−02 | E | 17 | LNU74_H112 | 0.73 | 1.55E−02 | F | 2 |
| LNU74_H111 | 0.83 | 2.11E−02 | F | 17 | LNU74_H110 | 0.87 | 1.17E−02 | B | 4 |
| LNU35_H2 | 0.77 | 4.11E−02 | F | 17 | LNU74_H110 | 0.76 | 4.57E−02 | B | 4 |
| LNU76_H37 | 0.76 | 4.52E−02 | E | 19 | LNU7_H89 | 0.73 | 1.58E−02 | F | 2 |
| LNU7_H87 | 0.91 | 4.98E−03 | B | 12 | LNU45_H169 | 0.72 | 2.73E−02 | F | 9 |
| LNU7_H87 | 0.86 | 1.38E−02 | B | 12 | LNU280_H1 | 0.78 | 8.26E−03 | F | 2 |
| LNU7_H87 | 0.83 | 1.96E−02 | B | 12 | LNU34_H0 | 0.95 | 9.71E−04 | E | 13 |
| LNU7_H87 | 0.91 | 4.98E−03 | B | 12 | LNU34_H0 | 0.82 | 2.41E−02 | F | 4 |
| LNU7_H87 | 0.86 | 1.38E−02 | B | 12 | LNU115_H0 | 0.84 | 3.61E−02 | F | 9 |
| LNU13_H0 | 0.82 | 1.27E−02 | C | 9 | LNU34_H0 | 0.80 | 3.12E−02 | B | 4 |
| LNU13_H0 | 0.79 | 1.89E−02 | C | 9 | LNU35_H2 | 0.83 | 2.10E−02 | B | 4 |
| LNU13_H0 | 0.79 | 1.91E−02 | C | 9 | LNU85_H2 | 0.77 | 4.39E−02 | B | 4 |
| LNU13_H0 | 0.77 | 2.44E−02 | C | 3 | LNU84_H0 | 0.77 | 4.38E−02 | E | 10 |

TABLE 45-continued

Correlation between the expression level of selected LNU homologous genes of some embodiments of the invention in various tissues and the phenotypic performance under normal across maize accessions

| Gene Name | R | P value | Exp. Set | Correl. Set ID | Gene Name | R | P value | Exp. Set | Correl. Set ID |
|---|---|---|---|---|---|---|---|---|---|
| LNU7_H87 | 0.83 | 1.96E-02 | B | 12 | LNU51_H1 | 0.77 | 4.46E-02 | F | 6 |
| LNU13_H0 | 0.77 | 2.56E-02 | C | 3 | LNU74_H111 | 0.74 | 1.41E-02 | F | 10 |
| LNU13_H0 | 0.76 | 2.80E-02 | C | 3 | LNU74_H111 | 0.72 | 1.93E-02 | F | 10 |
| LNU45_H173 | 0.91 | 4.15E-03 | B | 12 | LNU64_H1 | 0.84 | 1.85E-02 | B | 4 |
| LNU45_H173 | 0.91 | 4.63E-03 | B | 12 | LNU84_H0 | 0.79 | 3.42E-02 | F | 10 |
| LNU45_H173 | 0.88 | 9.87E-03 | B | 12 | LNU64_H1 | 0.77 | 4.22E-02 | B | 4 |
| LNU74_H118 | 0.91 | 1.15E-02 | B | 12 | LNU35_H2 | 0.94 | 5.10E-03 | B | 4 |
| LNU74_H118 | 0.89 | 1.69E-02 | B | 12 | LNU7_H89 | 0.81 | 4.97E-02 | F | 9 |
| LNU45_H173 | 0.92 | 9.33E-03 | B | 12 | LNU279_H2 | 0.78 | 2.37E-02 | C | 4 |
| LNU45_H173 | 0.91 | 1.10E-02 | B | 12 | LNU84_H0 | 0.79 | 3.42E-02 | F | 10 |
| LNU52_H5 | 0.83 | 1.06E-02 | C | 9 | LNU19_H0 | 0.91 | 1.21E-02 | B | 8 |
| LNU52_H5 | 0.83 | 1.10E-02 | C | 9 | LNU46_H34 | 0.82 | 1.23E-02 | C | 4 |
| LNU52_H5 | 0.77 | 2.55E-02 | C | 3 | LNU85_H2 | 0.72 | 3.04E-02 | E | 4 |
| LNU45_H173 | 0.87 | 2.48E-02 | B | 12 | LNU45_H169 | 0.90 | 1.43E-02 | B | 8 |
| LNU52_H4 | 0.78 | 2.19E-02 | C | 3 | LNU52_H5 | 0.83 | 2.02E-02 | E | 4 |
| LNU74_H111 | 0.72 | 4.46E-02 | C | 3 | LNU32_H0 | 0.83 | 1.97E-02 | E | 4 |
| LNU52_H4 | 0.75 | 3.11E-02 | C | 9 | LNU45_H169 | 0.89 | 1.83E-02 | B | 8 |
| LNU271_H2 | 0.72 | 4.57E-02 | C | 3 | LNU67_H2 | 0.78 | 3.74E-02 | F | 6 |
| LNU76_H38 | 0.76 | 4.52E-02 | E | 19 | LNU35_H2 | 0.78 | 3.76E-02 | E | 13 |
| LNU279_H2 | 0.83 | 2.06E-02 | E | 19 | LNU64_H1 | 0.73 | 1.70E-02 | F | 13 |
| LNU35_H2 | 0.90 | 1.55E-02 | B | 12 | LNU32_H0 | 0.83 | 2.16E-02 | E | 4 |
| LNU271_H3 | 0.79 | 1.99E-02 | C | 3 | LNU45_H169 | 0.88 | 2.01E-02 | B | 8 |
| LNU13_H0 | 0.72 | 4.60E-02 | C | 12 | LNU74_H111 | 0.78 | 3.76E-02 | F | 1 |
| LNU279_H2 | 0.85 | 7.52E-03 | C | 3 | LNU45_H168 | 0.82 | 4.55E-02 | B | 8 |
| LNU34_H0 | 0.81 | 1.44E-02 | C | 3 | LNU280_H1 | 0.75 | 3.04E-02 | C | 8 |
| LNU71_H0 | 0.77 | 2.60E-02 | C | 12 | LNU64_H1 | 0.73 | 1.70E-02 | F | 13 |
| LNU34_H0 | 0.75 | 3.24E-02 | C | 3 | LNU7_H89 | 0.81 | 4.97E-02 | F | 9 |
| LNU34_H0 | 0.71 | 4.66E-02 | C | 3 | LNU52_H5 | 0.76 | 4.59E-02 | E | 8 |
| LNU74_H111 | 0.72 | 4.32E-02 | C | 9 | LNU34_H0 | 0.82 | 2.30E-02 | F | 6 |
| LNU115_H0 | 0.82 | 7.10E-03 | E | 3 | LNU34_H0 | 0.77 | 4.48E-02 | E | 4 |
| LNU34_H0 | 0.94 | 1.70E-03 | E | 19 | LNU34_H0 | 0.77 | 4.23E-02 | F | 6 |
| LNU115_H0 | 0.78 | 2.16E-02 | E | 19 | LNU34_H0 | 0.76 | 4.74E-02 | F | 6 |
| LNU71_H0 | 0.75 | 3.37E-02 | C | 12 | LNU35_H2 | 0.92 | 3.67E-03 | E | 4 |
| LNU271_H2 | 0.77 | 2.49E-02 | C | 9 | LNU74_H110 | 0.83 | 2.20E-02 | F | 4 |
| LNU74_H118 | 0.72 | 2.92E-02 | E | 3 | LNU76_H37 | 0.76 | 2.84E-02 | E | 8 |
| LNU74_H118 | 0.70 | 3.55E-02 | E | 3 | LNU74_H110 | 0.76 | 4.91E-02 | F | 4 |
| LNU271_H3 | 0.85 | 7.04E-03 | C | 12 | LNU45_H173 | 1.00 | 2.63E-05 | F | 9 |
| LNU279_H2 | 0.95 | 1.30E-03 | E | 3 | LNU45_H173 | 0.99 | 9.74E-05 | F | 9 |
| LNU34_H0 | 0.80 | 3.18E-02 | E | 3 | LNU45_H173 | 0.97 | 1.64E-03 | F | 9 |
| LNU74_H110 | 0.85 | 7.58E-03 | E | 19 | LNU74_H111 | 0.93 | 2.57E-03 | F | 4 |
| LNU271_H3 | 0.72 | 4.44E-02 | C | 12 | LNU76_H38 | 0.76 | 2.84E-02 | E | 8 |
| LNU13_H0 | 0.80 | 3.08E-02 | F | 3 | LNU74_H111 | 0.87 | 1.14E-02 | F | 4 |
| LNU271_H3 | 0.82 | 1.26E-02 | C | 9 | LNU74_H111 | 0.87 | 1.12E-02 | F | 13 |
| LNU74_H112 | 0.85 | 7.58E-03 | E | 19 | LNU35_H2 | 0.94 | 1.58E-03 | F | 4 |
| LNU279_H2 | 0.92 | 1.15E-03 | C | 12 | LNU2_H3 | 0.81 | 2.74E-02 | F | 8 |
| LNU74_H111 | 0.81 | 2.57E-02 | F | 3 | LNU271_H3 | 0.82 | 2.53E-02 | F | 8 |
| LNU216_H1 | 0.89 | 7.80E-03 | E | 12 | LNU35_H2 | 0.83 | 2.02E-02 | F | 13 |

Table 45. "Correl. Set ID"—correlation set ID according to the correlated parameters Table above.

Example 10

Production of Tomato Transcription and High Throughput Correlation Analysis Using 44K Tomato Oligonucleotide Micro-Array In order to produce a high throughput correlation analysis between NUE related phenotypes and gene expression, the present inventors utilized a Tomato oligonucleotide microarray, produced by Agilent Technologies [Hypertext Transfer Protocol://World Wide Web (dot) chem. (dot) agilent (dot) com/Scripts/PDS (dot) asp?1 Page=50879]. The array oligonucleotide represents about 44,000 Tomato genes and transcripts. In order to define correlations between the levels of RNA expression with NUE, ABST, yield components or vigor related parameters various plant characteristics of 18 different Tomato varieties were analyzed. Among them, 10 varieties encompassing the observed variance were selected for RNA expression analysis. The correlation between the RNA levels and the characterized parameters was analyzed using Pearson correlation test [Hypertext Transfer Protocol://World Wide Web (dot) davidmlane (dot) com/hyperstat/A34739 (dot) html].

Correlation of Tomato Varieties Across Ecotypes Grown Under Low Nitrogen, Drought and Regular Growth Conditions Experimental Procedures:

Tomato varieties were grown in 3 repetitive blocks, each containing 6 plants per plot were grown at net house. Briefly, the growing protocol was as follows:

1. Regular growth conditions: Tomato varieties were grown under normal conditions (4-6 Liters/m$^2$ of water per day and fertilized with NPK as recommended in protocols for commercial tomato production).

2. Low Nitrogen fertilization conditions: Tomato varieties were grown under normal conditions (4-6 Liters/m$^2$ per day and fertilized with NPK as recommended in protocols for commercial tomato production) until flower stage. At this time, Nitrogen fertilization was stopped.

3. Drought stress: Tomato variety was grown under normal conditions (4-6 Liters/m² per day) until flower stage. At this time, irrigation was reduced to 50% compared to normal conditions. Plants were phenotyped on a daily basis following the standard descriptor of tomato (Table 47). Harvest was conducted while 50% of the fruits were red (mature). Plants were separated to the vegetative part and fruits, of them, 2 nodes were analyzed for additional inflorescent parameters such as size, number of flowers, and inflorescent weight. Fresh weight of all vegetative material was measured. Fruits were separated to colors (red vs. green) and in accordance with the fruit size (small, medium and large). Next, analyzed data was saved to text files and processed using the JMP statistical analysis software (SAS institute). Data parameters collected are summarized in Table 47, hereinbelow.

Analyzed *Sorghum* tissues—Two tissues at different developmental stages [flower and leaf], representing different plant characteristics, were sampled and RNA was extracted as described above. For convenience, each micro-array expression information tissue type has received a Set ID as summarized in Table 46 below.

TABLE 46

Tomato transcriptom expression sets

| Expression Set | Set ID |
|---|---|
| Leaf grown under Normal Conditions | A |
| Leaf grown under 50% Irrigation | B |
| Flower grown under Normal Conditions | C |
| Flower grown under 50% Irrigation | D |
| Leaf grown under Low Nitrogen | E |
| Flower grown under Low Nitrogen | F |

Table 46. Provided are the identification (ID) letters of each of the tomato expression sets.

The average for each of the measured parameter was calculated using the JMP software and values are summarized in Tables 48, 49 and 50 below. Subsequent correlation analysis was conducted (Tables 51-52) with the correlation coefficient (R) and the p-values. Results were integrated to the database.

TABLE 47

Tomato correlated parameters (vectors)

| Correlation | Correlation ID |
|---|---|
| Fruit Yield/Plant Drought [gr.] | 1 |
| FW/Plant Drought [gr.] | 2 |
| average red fruit weight Drought [gr.] | 3 |
| RWC Drought [%] | 4 |
| Num of flowers (Drought) [number] | 5 |
| Weight flower clusters (Drought) [gr.] | 6 |
| Fruit yield/Plant (Normal) [gr.] | 7 |
| FW/Plant (Normal) [gr.] | 8 |
| average red fruit weight (Normal) [gr.] | 9 |
| SPAD (Normal) [SPAD unit] | 10 |
| RWC (Normal) [%] | 11 |
| SPAD 100% RWC (Normal) | 12 |
| No flowers (Normal) [number] | 13 |
| Weight Flower clusters (Normal) [gr.] | 14 |
| Fruit Yield (NUE) [gr.] | 15 |
| FW/Plant (NUE) [gr.] | 16 |
| average red fruit weight (NUE) [gr.] | 17 |
| SPAD NUE [SPAD unit] | 18 |
| RWC NUE [%] | 19 |
| SPAD 100% RWC (NUE) [SPAD unit] | 20 |

TABLE 47-continued

Tomato correlated parameters (vectors)

| Correlation | Correlation ID |
|---|---|
| No flowers (NUE) [number] | 21 |
| Weight clusters (flowers) (NUE) [gr.] | 22 |

Table 47. Provided are the tomato correlated parameters.

Fruit Yield (grams)—At the end of the experiment [when 50% of the fruit were ripe (red)] all fruits from plots within blocks A-C were collected. The total fruits were counted and weighted. The average fruits weight was calculated by dividing the total fruit weight by the number of fruits.

Plant Fresh Weight (grams)—At the end of the experiment [when 50% of the fruit were ripe (red)] all plants from plots within blocks A-C were collected. Fresh weight was measured (grams).

Inflorescence Weight (grams)—At the end of the experiment [when 50% of the fruits were ripe (red)] two Inflorescence from plots within blocks A-C were collected. The Inflorescence weight (gr.) and number of flowers per inflorescence were counted.

SPAD—Chlorophyll content was determined using a Minolta SPAD 502 chlorophyll meter and measurement was performed at time of flowering. SPAD meter readings were done on young fully developed leaf. Three measurements per leaf were taken per plot.

Water use efficiency (WUE)—can be determined as the biomass produced per unit transpiration. To analyze WUE, leaf relative water content was measured in control and transgenic plants. Fresh weight (FW) was immediately recorded; then leaves were soaked for 8 hours in distilled water at room temperature in the dark, and the turgid weight (TW) was recorded. Total dry weight (DW) was recorded after drying the leaves at 60° C. to a constant weight. Relative water content (RWC) was calculated according to the following Formula I [(FW−DW/TW−DW)×100] as described above.

Plants that maintain high relative water content (RWC) compared to control lines were considered more tolerant to drought than those exhibiting reduced relative water content Experimental Results

TABLE 48

Measured parameters in Tomato accessions under drought conditions

| Seed ID | 1 | 2 | 3 | 4 | 5 | 6 |
|---|---|---|---|---|---|---|
| 612 | 0.467 | 2.62 | 0.00925 | 72.1 | 16.7 | 0.368 |
| 613 | 0.483 | 1.09 | 0.195 | 74.5 | 6.5 | 0.407 |
| 614 | 0.629 | 1.85 | 0.209 | 65.3 | 15.7 | 0.325 |
| 616 | 0.347 | 2.22 | 0.00467 | 72.2 | 20.3 | 0.288 |
| 617 | 2.04 | 2.63 | 0.102 | 66.1 | 11.7 | 0.551 |
| 618 | 0.25 | 2.71 | 0.00193 | 68.3 | 25.3 | 0.311 |
| 620 | 0.045 | 3.41 | 0.0346 | 78.1 | 29.7 | 0.445 |
| 621 | 0.453 | 2.11 | 0.00627 | 18.5 | 17.3 | 0.555 |
| 622 | 0.292 | 1.95 | 0.00527 | 73.2 | 14.7 | 0.304 |
| 623 | 1.02 | 1.76 | 0.00487 | 62.5 | 29.7 | 0.315 |
| 624 | 0.6 | 1.72 | 0.0052 | 67.2 | 15 | 0.308 |
| 625 | 0.494 | 1.92 | 0.012 | 75.8 | 10.3 | 0.311 |
| 626 | 0.272 | 2.21 | 0.00451 | 62.8 | 18.3 | 8.36 |
| 627 | 0.679 | 3.73 | 0.00632 | 70.7 | 12 | 0.288 |
| 628 | 0.14 | 0.754 | 0.303 | 55.8 | 20.3 | 0.342 |
| 629 | 0.529 | 1.76 | 0.138 | 75.2 | 12.7 | 0.441 |
| 630 | 0.554 | 0.626 | 0.0405 | 63.7 | 12.7 | 0.268 |
| 631 | 0.414 | 1.11 | 0.0885 | 62.3 | 11.3 | 0.426 |

Table 48: Provided are the values of each of the parameters (as described above) measured in *Sorghum* accessions (Seed ID) under drought growth conditions. Growth conditions are specified in the experimental procedure section.

TABLE 49

Measured parameters in Tomato accessions under normal conditions

| Seed ID | 7 | 8 | 9 | 10 | 11 | 12 | 13 | 14 |
|---|---|---|---|---|---|---|---|---|
| 612 | 0.826 | 1.53 | 0.0479 | 49.7 | 72.8 | 36.2 | 5.67 | 1.17 |
| 613 | 0.342 | 3.17 | 0.00799 | 37.2 | 76.5 | 28.4 | 19.3 | 0.342 |
| 614 | 0.494 | 3.02 | 0.00823 | 55.8 | 64.3 | 35.9 | 6.33 | 0.693 |
| 616 | 0.121 | 0.844 | 0.286 | 46.4 | 67.1 | 31.1 | 7.67 | 56.3 |
| 617 | 0.487 | 2.24 | 0.00503 | 48.2 | 54.8 | 26.4 | 9.67 | 0.44 |
| 618 | 0.454 | 1.98 | 0.0541 | 43.4 | 77.6 | 33.7 | 8.33 | 11.3 |
| 620 | 0.529 | 0.848 | 0.231 | 42.9 | 58.2 | 25 | 5 | 0.79 |
| 621 | 0.44 | 2.09 | 0.29 | 53.3 | 66.5 | 35.5 | 8.33 | 0.577 |
| 622 | 0.21 | 3.21 | 0.0061 | 58.5 | 64.7 | 37.9 | 10 | 0.73 |
| 623 | 0.31 | 2.75 | 0.0066 | 51.1 | 75.2 | 38.4 | 7 | 0.833 |
| 624 | 0.662 | 1.81 | 0.0577 | 40 | 66.2 | 26.5 | 9 | 0.86 |
| 625 | 0.189 | 3.77 | 0.007 | 47.6 | 63.2 | 30.1 | 8 | 0.5 |
| 626 | 0.852 | 1.89 | 0.0264 | 57.9 | 56.8 | 32.9 | 5.33 | 1.02 |
| 627 | 0.273 | 1.93 | 0.261 | 48.3 | 36 | 17.4 | 8 | 0.7 |
| 628 | 0.347 | 2.14 | 0.0289 | 43.6 | 77.6 | 33.8 | 7.67 | 0.377 |
| 629 | 0.327 | 1.65 | 0.00493 | 54.5 | 100 | 54.5 | 9 | 0.66 |
| 630 | 0.314 | 3.01 | 0.00343 | 41.6 | 63.2 | 26.3 | 10.7 | 0.7 |
| 631 | 0.291 | 2.29 | 0.00887 | 59.1 | 75.1 | 44.4 | 9 | 0.327 |

Table 49: Provided are the values of each of the parameters (as described above) measured in Sorghum accessions (Seed ID) under normal growth conditions. Growth conditions are specified in the experimental procedure section.

TABLE 50

Measured parameters in Tomato accessions under low nitrogen conditions

| Seed Id | 15 | 16 | 17 | 18 | 19 | 20 | 21 | 22 |
|---|---|---|---|---|---|---|---|---|
| 612 | 0.406 | 4.04 | 0.0239 | 38.4 | 74.1 | 28.5 | 19 | 0.533 |
| 613 | 0.66 | 1.21 | 0.191 | 39.4 | 99.1 | 39 | 5.33 | 0.367 |
| 614 | 0.477 | 2.25 | 0.00647 | 47.5 | 69.5 | 33 | 9 | 0.307 |
| 616 | 0.458 | 2.54 | 0.0053 | 37 | 63.2 | 23.4 | 13 | 0.35 |
| 617 | 1.35 | 1.85 | 0.0963 | 44.6 | 77.4 | 34.5 | 10.7 | 0.473 |
| 618 | 0.354 | 3.06 | 0.0044 | 41.7 | 77.9 | 32.5 | 16.7 | 0.249 |
| 620 | 0.00889 | 3.13 | 0.00553 | 34.4 | 80.5 | 27.7 | 6 | 0.293 |
| 621 | 0.509 | 2.54 | 0.00747 | 50 | 67.4 | 33.7 | 16 | 0.467 |
| 622 | 0.436 | 1.84 | 0.0058 | 44.7 | 67.2 | 30 | 15 | 0.4 |
| 623 | 0.468 | 1.52 | 0.0127 | 53.7 | 66.1 | 35.5 | 6 | 0.303 |
| 624 | 1.59 | 1.91 | 0.0212 | 35.7 | 69.6 | 24.8 | 17 | 0.82 |
| 625 | 0.388 | 1.86 | 0.0052 | 58.8 | 69.3 | 40.8 | 13 | 0.4 |
| 626 | 0.323 | 2.47 | 0.00573 | 47.5 | 100 | 47.5 | 8.67 | 0.347 |
| 627 | 0.449 | 2.62 | 0.0475 | 45.2 | 57.7 | 26.1 | 9.33 | 0.428 |
| 628 | 0.143 | 1.08 | 0.357 | 39 | 90.8 | 35.4 | 12.7 | 0.353 |
| 629 | 0.396 | 1.17 | 0.0367 | 45 | 68 | 30.6 | 6.67 | 0.447 |
| 630 | 1.44 | 0.921 | 0.626 | 65.3 | 59.6 | 39 | 9.33 | 0.283 |
| 631 | 0.495 | 1.09 | 1.7 | 72.2 | 37.5 | 0.878 | 0.47 | 0.889 |

Table 50: Provided are the values of each of the parameters (as described above) measured in Sorghum accessions (Seed ID) under low nitrogen growth conditions. Growth conditions are specified in the experimental procedure section.

TABLE 51

Correlation between the expression level of selected LNU genes of some embodiments of the invention in various tissues and the phenotypic performance under low nitrogen, normal or drought stress conditions across Tomato accessions

| Gene Name | R | P value | Exp. set | Correl. Set ID | Gene Name | R | P value | Exp. set | Correl. Set ID |
|---|---|---|---|---|---|---|---|---|---|
| LNU20 | 0.85 | 1.78E−03 | E | 20 | LNU288 | 0.87 | 1.10E−03 | A | 14 |
| LNU245 | 0.95 | 7.41E−05 | F | 17 | LNU288 | 0.83 | 2.98E−03 | A | 9 |
| LNU245 | 0.84 | 2.23E−03 | A | 13 | LNU288 | 0.83 | 3.30E−03 | A | 9 |
| LNU245 | 0.73 | 1.66E−02 | F | 22 | LNU288 | 0.80 | 5.50E−03 | B | 8 |
| LNU246 | 0.71 | 2.25E−02 | B | 5 | LNU288 | 0.77 | 9.78E−03 | A | 14 |
| LNU29 | 1.00 | 5.21E−10 | A | 14 | LNU288 | 0.72 | 1.90E−02 | B | 8 |
| LNU229 | 0.74 | 1.50E−02 | A | 9 | LNU289 | 0.82 | 6.93E−03 | E | 17 |
| LNU229 | 0.72 | 1.80E−02 | A | 14 | LNU289 | 0.75 | 1.22E−02 | B | 6 |
| LNU200 | 0.86 | 1.29E−03 | C | 14 | LNU289 | 0.75 | 1.24E−02 | A | 16 |
|  |  |  |  |  | LNU289 | 0.70 | 3.52E−02 | E | 17 |

Table 51. "Correl. Set ID"—correlation set ID according to the correlated parameters Table above.

TABLE 52

Correlation between the expression level of selected LNU homologous genes of some embodiments of the invention in various tissues and the phenotypic performance under low nitrogen, normal or drought stress conditions across Tomato accessions

| Gene Name | R | P value | Exp. Set | Correl. Set ID | Gene Name | R | P value | Exp. Set | Correl. Set ID |
|---|---|---|---|---|---|---|---|---|---|
| LNU128_H17 | 0.75 | 1.32E−02 | A | 10 | LNU45_H302 | 0.80 | 5.89E−03 | F | 21 |
| LNU128_H17 | 0.73 | 1.76E−02 | A | 10 | LNU45_H302 | 0.76 | 1.08E−02 | F | 21 |
| LNU46_H77 | 0.78 | 7.55E−03 | F | 18 | LNU45_H302 | 0.76 | 1.14E−02 | F | 21 |
| LNU74_H204 | 0.71 | 2.22E−02 | D | 2 | LNU45_H301 | 0.76 | 1.14E−02 | F | 21 |
| LNU45_H302 | 0.71 | 2.28E−02 | D | 2 | LNU45_H300 | 0.82 | 3.93E−03 | D | 4 |
| LNU74_H203 | 0.84 | 2.34E−03 | F | 21 | LNU45_H300 | 0.72 | 1.87E−02 | D | 4 |
| LNU74_H204 | 0.74 | 1.37E−02 | F | 21 | LNU128_H17 | 0.74 | 1.40E−02 | F | 19 |
|  |  |  |  |  | LNU45_H300 | 0.70 | 2.32E−02 | A | 12 |

Table 52. "Correl. Set ID"—correlation set ID according to the correlated parameters Table above.

Correlation of early vigor traits across collection of Tomato ecotypes under Low nitrogen, 300 mM NaCl, and normal growth conditions—Ten tomato hybrids were grown in 3 repetitive plots, each containing 17 plants, at a net house under semi-hydroponics conditions. Briefly, the growing protocol was as follows: Tomato seeds were sown in trays filled with a mix of vermiculite and peat in a 1:1 ratio. Following germination, the trays were transferred to the high salinity solution (300 mM NaCl in addition to the Full Hoagland solution), low nitrogen solution (the amount of total nitrogen was reduced in a 90% from the full Hoagland solution, final amount of 0.8 mM N) or at Normal growth solution (Full Hoagland containing 8 mM N solution, at 28±2° C.). Plants were grown at 28±2° C.

Full Hoagland solution consists of: $KNO_3$—0.808 grams/liter, $MgSO_4$—0.12 grams/liter, $KH_2PO_4$—0.172 grams/liter and 0.01% (volume/volume) of 'Super coratin' micro elements (Iron-EDDHA [ethylenediamine-N,N'-bis(2-hydroxyphenylacetic acid)]-40.5 grams/liter; Mn—20.2 grams/liter; Zn 10.1 grams/liter; Co 1.5 grams/liter; and Mo 1.1 grams/liter), solution's pH should be 6.5-6.8].

Analyzed *Sorghum* tissues—All 10 selected Tomato varieties were sample per each treatment. Three tissues [leaves, meristems and flowers] were sampled and RNA was extracted as described above. For convenience, each micro-array expression information tissue type has received a Set ID as summarized in Table 53 below.

TABLE 53

Tomato transcriptom experimental sets

| Expression Set | Set ID |
| --- | --- |
| Leaves at 300 mM NaCl | A |
| Leaves at Normal conditions | B |
| Leaves at Low Nitrogen conditions | C |
| Roots at 100 mM NaCl | D |
| Roots at Normal conditions | E |
| Roots at Low Nitrogen conditions | F |

Table 53. Provided are the tomato transcriptom experimental sets.

Tomato vigor related parameters—following 5 weeks of growing, plant were harvested and analyzed for Leaf number, plant height, and Plant weight. Next, analyzed data was saved to text files and processed using the JMP statistical analysis software (SAS institute). Data parameters collected are summarize in Table 54, hereinbelow.

TABLE 54

Tomato correlated parameters (vectors)

| Correlation Set | Correlation ID |
| --- | --- |
| Plant height_NUE [cm] | 1 |
| SPAD NUE [SPAD unit] | 2 |
| leaf No NUE [number] | 3 |
| leaf No Normal [number] | 4 |
| Plant height Normal [cm] | 5 |
| SPAD Normal [SPAD unit] | 6 |
| Leaf No NaCl [number] | 7 |
| Plant height NaCl [cm] | 8 |
| Plant biomass_NaCl [gr] | 9 |

Table 54. Provided are the tomato correlated parameters.

Experimental Results 10 different Tomato varieties were grown and characterized for 3 parameters as described above. The average for each of the measured parameter was calculated using the JMP software and values are summarized in Tables 55 below. Subsequent correlation analysis was conducted (Tables 56 and 57). Follow, results were integrated to the database.

TABLE 55

Measured parameters in Tomato accessions under normal, salinity and low nitrogen conditions

| Seed ID | 1 | 2 | 3 | 4 | 5 | 6 | 7 | 8 | 9 |
| --- | --- | --- | --- | --- | --- | --- | --- | --- | --- |
| 1139 | 36.8 | 34.6 | 5.56 | 6.56 | 45.3 | 34.3 | 3.56 | 5.6 | 0.36 |
| 2078 | 39.9 | 24.9 | 6.22 | 6.89 | 47.8 | 25.3 | 3.94 | 6.46 | 0.44 |
| 2958 | 34.4 | 28.6 | 7.22 | 7.33 | 40.8 | 28.1 | 5 | 8.47 | 0.26 |
| 5077 | 47 | 31.6 | 6.78 | 6.22 | 55.3 | 31.4 | 4 | 8.56 | 0.71 |
| 5080 | 46.4 | 29.7 | 5.56 | 6.33 | 56.2 | 30.2 | 3.56 | 8.87 | 0.46 |
| 5084 | 45.4 | 31.8 | 6.56 | 6.44 | 48.7 | 32.4 | 4.39 | 7.56 | 0.54 |
| 5085 | 47.7 | 30.3 | 5.11 | 5.89 | 55.8 | 32.6 | 3.17 | 8.64 | 0.66 |
| 5088 | 39.3 | 30.3 | 5.89 | 5.56 | 37.4 | 28.8 | 3.72 | 5.57 | 0.4 |
| 5089 | 41.8 | 31.3 | 5.56 | 6.11 | 49.6 | 30.9 | 4 | 5.82 | 0.52 |
| 5092 | 41 | 28.8 | 6.33 | 5.67 | 46.3 | 29 | 4.28 | 9.36 | 0.45 |

TABLE 56

Correlation between the expression level of selected LNU genes of some embodiments of the invention in various tissues and the phenotypic performance under low nitrogen, normal or salinity stress conditions across Tomato accessions

| Gene Name | R | P value | Exp. set | Correl. Set ID |
| --- | --- | --- | --- | --- |
| LNU245 | 0.81 | 1.41E-02 | E | 6 |

Table 56. "Correl. Set ID"—correlation set ID according to the correlated parameters Table above.

TABLE 57

Correlation between the expression level of selected LNU homologous genes of some embodiments of the invention in various tissues and the phenotypic performance under low nitrogen, normal or salinity stress conditions across Tomato accessions

| Gene Name | R | P value | Exp. Set | Correl. Set ID | Gene Name | R | P value | Exp. Set | Correl. Set ID |
| --- | --- | --- | --- | --- | --- | --- | --- | --- | --- |
| LNU128_H17 | 0.73 | 4.14E-02 | B | 4 | LNU46_H78 | 0.88 | 4.04E-03 | C | 3 |
| LNU128_H17 | 0.71 | 4.86E-02 | B | 4 | LNU7_H146 | 0.77 | 2.68E-02 | F | 3 |
| LNU128_H17 | 0.72 | 4.35E-02 | E | 4 | LNU74_H204 | 0.71 | 4.70E-02 | F | 3 |
| LNU74_H203 | 0.71 | 4.77E-02 | C | 3 | LNU74_H205 | 0.75 | 1.20E-02 | D | 9 |
| LNU46_H78 | 0.88 | 3.94E-03 | C | 3 | LNU7_H146 | 0.74 | 1.38E-02 | D | 8 |

Table 57. "Correl. Set ID"—correlation set ID according to the correlated parameters Table above.

Example 11

Gene Cloning and Generation of Binary Vectors for Plant Expression

To validate their role in improving yield, selected genes were over-expressed in plants, as follows.

Cloning Strategy

Selected genes from those presented in Examples 1-10 hereinabove were cloned into binary vectors for the generation of transgenic plants. For cloning, the full-length open reading frames (ORFs) were identified. EST clusters and in some cases mRNA sequences were analyzed to identify the entire open reading frame by comparing the results of several translation algorithms to known proteins from other plant species.

In order to clone the full-length cDNAs, reverse transcription (RT) followed by polymerase chain reaction (PCR; RT-PCR) was performed on total RNA extracted from leaves, roots or other plant tissues, growing under normal/limiting or stress conditions. Total RNA extraction, production of cDNA and PCR amplification is performed using standard protocols described elsewhere (Sambrook J., E. F. Fritsch, and T. Maniatis. 1989. Molecular Cloning. A Laboratory Manual, 2nd Ed. Cold Spring Harbor Laboratory Press, New York.) which are well known to those skilled in the art. PCR products are purified using PCR purification kit (Qiagen)

Usually, 2 sets of primers were prepared for the amplification of each gene, via nested PCR (if required). Both sets of primers were used for amplification on cDNA. In case no product was obtained, a nested PCR reaction was performed. Nested PCR was performed by amplification of the gene using external primers and then using the produced PCR product as a template for a second PCR reaction, where the internal set of primers are used. Alternatively, one or two of the internal primers are used for gene amplification, both in the first and the second PCR reactions (meaning only 2-3 primers were designed for a gene). To facilitate further cloning of the cDNAs, an 8-12 bp extension was added to the 5' of each internal primer. The primer extension includes an endonuclease restriction site. The restriction sites were selected using two parameters: (a) the restriction site does not exist in the cDNA sequence; and (b) the restriction sites in the forward and reverse primers were designed such that the digested cDNA was inserted in the sense direction into the binary vector utilized for transformation.

PCR products were digested with the restriction endonucleases (New England BioLabs Inc) according to the sites designed in the primers. Each digested PCR product was inserted into a high copy vector pBlue-script KS plasmid vector [pBlue-script KS plasmid vector, Hypertext Transfer Protocol://World Wide Web (dot) stratagene (dot) com/manuals/212205 (dot) pdf), or into plasmids originated from this vector. In case of the high copy vector originated from pBluescript KS plasmid vector (pGXN or pGXNa), the PCR product was inserted in the high copy plasmid upstream to the NOS terminator (SEQ ID NO:4683) originated from pBI 101.3 binary vector (GenBank Accession No. U12640, nucleotides 4356 to 4693) and downstream to the 35S promoter (SEQ ID NO:4685). The digested products and the linearized plasmid vector are ligated using T4 DNA ligase enzyme (Roche, Switzerland). In some cases PCR products were cloned without digestion into pCR-Blunt II-TOPO vector (Invitrogen).

Sequencing of the inserted genes was performed, using the ABI 377 sequencer (Applied Biosystems). In some cases, after confirming the sequences of the cloned genes, the cloned cDNA accompanied/or not with the NOS terminator was introduced into a modified pGI binary vector containing the At6669 promoter or the RootP promoter via digestion with appropriate restriction endonucleases. In any case the insert was followed by single copy of the NOS terminator (SEQ ID NO:5683).

Several DNA sequences of the selected genes are synthesized by GeneArt [Hypertext Transfer Protocol://World Wide Web (dot) geneart (dot) com/]. Synthetic DNA was designed in silico. Suitable restriction enzymes sites are added to the cloned sequences at the 5' end and at the 3' end to enable later cloning into the desired binary vector.

Figure 1:
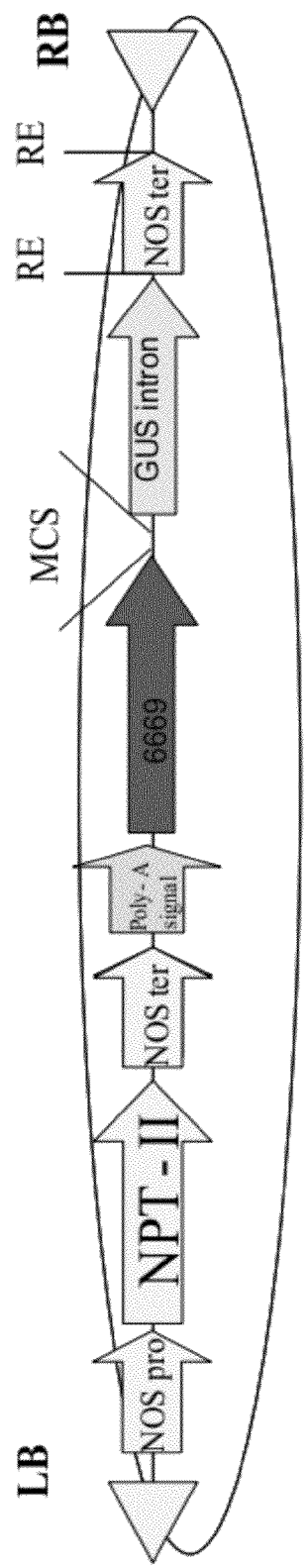
FIG. 1 is a schematic illustration of the modified pGI binary plasmid containing the new At6669 promoter (SEQ ID NO:4687) and the GUSintron (pQYN_6669) used for expressing the isolated polynucleotide sequences of the invention. RB—T-DNA right border; LB—T-DNA left border; MCS—Multiple cloning site; RE—any restriction enzyme; NOS pro=nopaline synthase promoter; NPT-II=neomycin phosphotransferase gene; NOS ter=nopaline synthase terminator; Poly-A signal (polyadenylation signal)

The pPI plasmid vector was constructed by inserting a synthetic poly-(A) signal sequence, originating from pGL3 basic plasmid vector (Promega, GenBank Accession No. U47295; nucleotides 4658-4811) into the HindIII restriction site of the binary vector pBI101.3 (Clontech, GenBank Accession No. U12640). pGI (FIG. 1) was similar to pPI, but the original gene in the backbone was GUS-Intron and not GUS.

The modified pGI vector (pQFN or pQNa_RP) was a modified version of the pGI vector in which the cassette was inverted between the left and right borders so the gene and its corresponding promoter are close to the right border and the NPTII gene was close to the left border.

At6669, the new *Arabidopsis thaliana* promoter sequence (SEQ ID NO:4687) or the Root P promoter sequence (SEQ ID NO:4688) was inserted in the modified pGI binary vector, upstream to the cloned genes, followed by DNA ligation and binary plasmid extraction from positive *E. coli* colonies, as described above. Colonies were analyzed by PCR using the primers covering the insert which were designed to span the introduced promoter and gene. Positive plasmids were identified, isolated and sequenced.

In case genomic DNA was cloned, the genes were amplified by direct PCR on genomic DNA extracted from leaf tissue using the DNAeasy kit (Qiagen Cat. No. 69104).

Table 58 below provides primers used for cloning of selected genes.

TABLE 58

The PCR primers used for cloning the genes of some embodiments of the invention into high copy vectors

| Gene Name | Restriction Enzymes used for cloning | Primers used for amplification |
|---|---|---|
| LNU1 (6669) | BamHI, KpnI | LNU1_EF_BamHI (SEQ IN NO: 4689) AAAGGATCCAAATCTCAGCTTCACCATTCG LNU1_ER2_KpnI (SEQ IN NO: 4690) TTTGGTACCTTTCTTCGAGTCTGGTCTCATTATC |

TABLE 58-continued

The PCR primers used for cloning the genes of some embodiments of the invention into high copy vectors

| Gene Name | Restriction Enzymes used for cloning | Primers used for amplification |
|---|---|---|
| LNU1 (Root_P_F) | BamHI, KpnI | LNU1_EF_BamHI(SEQ IN NO: 4689) AAAGGATCCAAATCTCAGCTTCACCATTCG LNU1_ER2_KpnI(SEQ IN NO: 4690) TTTGGTACCTTTCTTCGAGTCTGGTCTCATTATC |
| LNU10 | | LNU10_NF_XhoI(SEQ IN NO: 4691) AAACTCGAGCATTAAATTCGATCGAGGCTTTC LNU10_EF_XhoI(SEQ IN NO: 4692) AAACTCGAGCAACTCGGTTGCATTAAATTCG LNU10_NR_EcoRV(SEQ IN NO: 4693) AAAGATATCAAATACAGCTTGATGGTCGGTG LNU10_ER_EcoRV(SEQ IN NO: 4694) AAAGATATCTGATATGGACATGTTTGCAAGG |
| LNU100 | BamHI, XhoI | LNU100_EF_BamHI(SEQ IN NO: 4695) AAAGGATCCTAAAGCACTTCACCTTTGCTCC LNU100_ER_XhoI(SEQ IN NO: 4696) AAACTCGAGATACAAATATAACAAGCCAATCATGC |
| LNU101 | BamHI, XhoI | LNU101_NF_BamHI(SEQ IN NO: 4697) AAAGGATCCTATATGTTACACGATGCCGTCC LNU101_NF_BamHI(SEQ IN NO: 4697) AAAGGATCCTATATGTTACACGATGCCGTCC LNU101_NR_XhoI(SEQ IN NO: 4698) AAACTCGAGCGACTCAAATTCATCTTAACAAGC LNU101_NR_XhoI(SEQ IN NO: 4698) AAACTCGAGCGACTCAAATTCATCTTAACAAGC |
| LNU104 | SalI, XbaI | LNU104_ER_XbaI(SEQ IN NO: 4699) AAATCTAGAAAGCAAATTTCGTTTGCAACTC LYD104_EF_BamI(SEQ IN NO: 4700) AAAGGATCCTCCCAATAAACCCTAATTCCTTG LNU104_EF_SalI(SEQ IN NO: 4701) AAAGTCGACTCCATTGGCCGTAGTAGCAG |
| LNU105 | BamHI, XhoI | LNU105_EF_BamHI(SEQ IN NO: 4702) AAAGGATCCCTTCTTCCAGCTCCGGTTC LNU105_ER_XhoI(SEQ IN NO: 4703) AAACTCGAGACTCGTCATCTATGCACTCGAC |
| LNU106 | SalI, XbaI | LNU106_NF_SalI(SEQ IN NO: 4704) AAAGTCGACACGTCTTGGTTTGTCGGTTAAG LNU106_EF_SalI(SEQ IN NO: 4705) AAAGTCGACGTCTCTTCCTCTCCACAAGCAC LNU106_NR_XbaI(SEQ IN NO: 4706) AAATCTAGATACCAGCGATTCATATTGGAGG LNU106_ER_XbaI(SEQ IN NO: 4707) AAATCTAGACGATCTCATAAACGGATTCGAG |
| LNU107 | BamHI, XhoI | LNU107_NF_BamHI(SEQ IN NO: 4708) AAAGGATCCCCATTTCCATATTCCGTCTGTC LNU107_EF_BamHI(SEQ IN NO: 4709) AAAGGATCCCTTCTTCTGCGAATTTCCTCTG LNU107_R_XhoI(SEQ IN NO: 4710) AAACTCGAGCTACAAGCAGATCAACTCAGGGAG LNU107_R_XhoI(SEQ IN NO: 4710) AAACTCGAGCTACAAGCAGATCAACTCAGGGAG |
| LNU109 | XhoI, EcoRV | LNU109_EF_XhoI(SEQ IN NO: 4711) AAACTCGAGAGCTCACACCGATCCAGTAATC LNU109_ER_EcoRV(SEQ IN NO: 4712) AAAGATATCCTTTATGGGAGAGGACATGCAC |
| LNU110 | BamHI, XhoI | LYD110_EF_BamHI(SEQ IN NO: 4713) AAAGGATCCTAACCTCATAGTGTCGACATGG LYD110_ER_KpnI(SEQ IN NO: 4714) AAAGGTACCTTCACCAACTTATACGAACCAC |
| LNU113 | BamHI, XhoI | LNU113_EF_BamHI(SEQ IN NO: 4715) AAAGGATCCGAGCAAGATCAATCCCTCTGC LNU113_ER_XhoI(SEQ IN NO: 4716) AAACTCGAGGAAGAAAGCCATCACAAGCATC |

TABLE 58-continued

The PCR primers used for cloning the genes of some embodiments of the invention into high copy vectors

| Gene Name | Restriction Enzymes used for cloning | Primers used for amplification |
|---|---|---|
| LNU114 | SalI, XbaI | LNU114_EF_SalI(SEQ IN NO: 4717) AAAGTCGACTGGTAGTGAACCGTGAACACAC LNU114_ER_XbaI(SEQ IN NO: 4718) AAATCTAGAACAGGAGCTCAGAAGCTTCAAC |
| LNU115 | SmaI, KpnI | LNU115_EF2_SmaI(SEQ IN NO: 4719) AAACCCGGGGTGTCCCTGTACCAGATCCAC LNU115_ER2_KpnI(SEQ IN NO: 4720) AAAGGTACCCTCCAAAATTATCATTAACACCG |
| LNU116 | BamHI, KpnI | LNU116_NF_BamHI(SEQ IN NO: 4721) AAAGGATCCTTGATCCATTCATCTTTGTTGG LNU116_EF_BamHI(SEQ IN NO: 4722) AAAGGATCCGCTTGTGTTTCTCGAAATTGTG LNU116_R_KpnI(SEQ IN NO: 4723) AAAGGTACCAAGAATGGCCTAAGCTACCGAC LNU116_R_KpnI(SEQ IN NO: 4723) AAAGGTACCAAGAATGGCCTAAGCTACCGAC |
| LNU117 | BamHI, XhoI | LNU117_NF_BamHI(SEQ IN NO: 4724) AAAGGATCCGCATGAGCATGACTCCTCAC LNU117_EF_BamHI(SEQ IN NO: 4725) AAAGGATCCGAGACCAGACGCAGAAGATGTC LNU117_NR_XhoI(SEQ IN NO: 4726) AAACTCGAGACTATTTGCCGTGCATAACGAC LNU117_ER_XhoI(SEQ IN NO: 4727) AAACTCGAGACAAACAACCGCGTAAGAAGAG |
| LNU118 (6669) | BamHI, XhoI | LNU118_NF_BamHI(SEQ IN NO: 4728) AAAGGATCCCTAATTCAGCTAAGGATTTGGAGG LNU118_NR_XhoI(SEQ IN NO: 4729) AAACTCGAGCGCTGACTCGATCGTTGAC |
| LNU118 (Root_P_F) | BamHI, XhoI | LNU118_NF_BamHI(SEQ IN NO: 4728) AAAGGATCCCTAATTCAGCTAAGGATTTGGAGG LNU118_NR_XhoI(SEQ IN NO: 4729) AAACTCGAGCGCTGACTCGATCGTTGAC |
| LNU119 | BamHI, XhoI | LNU119_NF_BamHI(SEQ IN NO: 4730) AAAGGATCCTTGCTACCCACCACGAGAG LNU119_EF_BamHI(SEQ IN NO: 4731) AAAGGATCCATATACGAGCCTTTGCTACCCAC LNU119_NR_XhoI(SEQ IN NO: 4732) AAACTCGAGTGCCAACTGTCTGAGATCTTTC LNU119_ER_XhoI(SEQ IN NO: 4733) AAACTCGAGATTGTGTCTTTGAGCTGCCAAC |
| LNU12 | BamHI, KpnI | LNU12_NF_BamHI(SEQ IN NO: 4734) AAAGGATCCCTAGCGAACTACGTGTGCTCC LNU12_EF_BamHI(SEQ IN NO: 4735) AAAGGATCCGCTCTTCACACGGCTAACG LNU12_NR_KpnI(SEQ IN NO: 4736) AAAGGTACCGTTTCCACGCAAGGAAGAATC LNU12_ER_KpnI(SEQ IN NO: 4737) AAAGGTACCGTTCGATTCGGCTCTGTTTC |
| LNU120 | SalI, XbaI | LNU120_NF_SalI(SEQ IN NO: 4738) AAAGTCGACGTCATCACACATTGGCAGC LNU120_EF_SalI(SEQ IN NO: 4739) AAAGTCGACATCAGTCATCACACATTGGCAG LNU120_NR_XbaI(SEQ IN NO: 4740) AAATCTAGAACATGGTTGATCTTGAGCTGTG LNU120_ER_XbaI(SEQ IN NO: 4741) AAATCTAGACGACATGGTTGATCTTGAGC |
| LNU121 | XhoI, StuI | LNU121_F_XhoI(SEQ IN NO: 4742) AAACTCGAGAAAAACGCGCAATCCCG LNU121_ER_StuI(SEQ IN NO: 4743) TTTAGGCCTGGGTTTGGTCATGTACAGTCAC |
| LNU122 | | LNU122_NF_BamHI(SEQ IN NO: 4744) AAAGGATCCAACGAATAGCCAAGCTCAGTTC |

TABLE 58-continued

The PCR primers used for cloning the genes of some embodiments of the invention into high copy vectors

| Gene Name | Restriction Enzymes used for cloning | Primers used for amplification |
|---|---|---|
| | | LNU122_NR_KpnI(SEQ IN NO: 4745) AAAGGTACCATTTGATTATTTGTGGTGTACAATGC |
| LNU123 | BamHI, XhoI | LNU123_F_BamHI(SEQ IN NO: 4746) AAAGGATCCGATCCGAAAGGATCTCCACC LNU123_F_BamHI(SEQ IN NO: 4746) AAAGGATCCGATCCGAAAGGATCTCCACC LNU123_NR_XhoI(SEQ IN NO: 4747) AAACTCGAGATGCTTCCTCATTGTTTGATCC LNU123_ER_XhoI(SEQ IN NO: 4748) AAACTCGAGATACCAATTCTAACCGTGGTCG |
| LNU124 | BamHI, KpnI | LNU124_NF_BamHI(SEQ IN NO: 4749) AAAGGATCCAATTAATTCGAAAGAGCGGTCAC LNU124_EF_BamHI(SEQ IN NO: 4750) AAAGGATCCATTCACTACATGCACAAGCACG LNU124_NR_KpnI(SEQ IN NO: 4751) AAAGGTACCCTAGATCCAATGGAGAGACAGAGC LNU124_ER_KpnI(SEQ IN NO: 4752) AAAGGTACCAAAGTCTCTGGAGTTGATGAAATTG |
| LNU125 | SalI, SacI | LNU125_F2_Sal(SEQ IN NO: 4753) TTTGTCGACTGACTTTAAAAATTTGAACGTGAA LNU125_R2_Sac(SEQ IN NO: 4754) TTTGAGCTCGTGGAAGGTTACACTGTTGTATTTC |
| LNU126 | BamHI, XhoI | LNU126_F_BamHI(SEQ IN NO: 4755) AATGGATCCCTATCACAAAGCCTAGAGTAAAATCG LNU126_F_BamHI(SEQ IN NO: 4755) AATGGATCCCTATCACAAAGCCTAGAGTAAAATCG LNU126_NR_XhoI(SEQ IN NO: 4756) AAACTCGAGGCAACACAAGGAACTGTACTATCTC LNU126_ER_XhoI(SEQ IN NO: 4757) TTTCTCGAGTCAGCGGTTACTTTGTCGTTAC |
| LNU128 | BamHI, XhoI | LNU128_F_BamHI(SEQ IN NO: 4758) AAAGGATCCAGGCGAAGAAGAGAGAGGAATG LNU128_F_BamHI(SEQ IN NO: 4758) AAAGGATCCAGGCGAAGAAGAGAGAGGAATG LNU128_NR_XhoI(SEQ IN NO: 4759) AAACTCGAGCTATAAGGCACAGGTCCAATTCAAG LNU128_ER_XhoI(SEQ IN NO: 4760) AAACTCGAGTGATTCGATCATGTATTTCACATTG |
| LNU129 | BamHI, XhoI | LNU129_NF_BamHI(SEQ IN NO: 4761) AAAGGATCCGTTTGTCTCGCATGAGGATTTG LNU129_NF_BamHI(SEQ IN NO: 4761) AAAGGATCCGTTTGTCTCGCATGAGGATTTG LNU129_NR_XhoI(SEQ IN NO: 4762) AAACTCGAGTGAAATTTCTCTGTTGGATTGATG LNU129_NR_XhoI(SEQ IN NO: 4762) AAACTCGAGTGAAATTTCTCTGTTGGATTGATG |
| LNU130 | SalI, XbaI | LNU130_F_SalI(SEQ IN NO: 4763) AAAGTCGACCTGAAAGACGAAGAAGAGAAACG LNU130_F_SalI(SEQ IN NO: 4763) AAAGTCGACCTGAAAGACGAAGAAGAGAAACG LNU130_NR_XbaI(SEQ IN NO: 4764) AAATCTAGAATGAACAACGGTTTCAATGGAC LNU130_ER_XbaI(SEQ IN NO: 4765) AAATCTAGAATCGGTGTAAGTGAACACGATG |
| LNU131 | BamHI, XhoI | LNU131_EF_BamHI(SEQ IN NO: 4766) AAAGGATCCCTTCTTCTTCTTCGATTTAGCACAG LNU131_ER_XhoI(SEQ IN NO: 4767) AAACTCGAGCATTGTTGGCTGTATATTTCATCAC |
| LNU132 | SalI, XbaI | LNU132_F_SalI(SEQ IN NO: 4768) AAAGTCGACTCTTTCTGCAGAGATTATGGAGG LNU132_ER_XbaI(SEQ IN NO: 4769) AAATCTAGAAAATCGCAGAGAAGCAAACAGAC |

TABLE 58-continued

The PCR primers used for cloning the genes of some embodiments of the invention into high copy vectors

| Gene Name | Restriction Enzymes used for cloning | Primers used for amplification |
|---|---|---|
| LNU133 | SalI, XbaI | LNU133_EF_SalI(SEQ IN NO: 4770) AAAGTCGACAAATTTCCAGAGAAGTCGTTCATC LNU133_ER_XbaI(SEQ IN NO: 4771) AAATCTAGAATTACAGCATCAAACAGCCAGC |
| LNU134 | BamHI, XhoI | LNU134_NF_BamHI(SEQ IN NO: 4772) AAAGGATCCAGGTTTCTTTCGATTCGTTGAG LNU134_EF_BamHI(SEQ IN NO: 4773) AAAGGATCCGTTATTCTCAATCCTTCCTTCATCC LNU134_NR_XhoI(SEQ IN NO: 4774) AAACTCGAGCTACCTGTACTTTGGGAATAAGCAGAG LNU134_ER_XhoI(SEQ IN NO: 4775) AAACTCGAGGAGTTCTTTCACATCATGGACG |
| LNU135 | BamHI, XhoI | LNU135_EF_BamHI(SEQ IN NO: 4776) AAAGGATCCAGCCGTTTCTTTCCGATTC LNU135_ER_XhoI(SEQ IN NO: 4777) AAACTCGAGACGAGAAATATGATCACTGGAAATC |
| LNU136 | BamHI, KpnI | LNU136_EF_BamHI(SEQ IN NO: 4778) AAAGGATCCTCGGAGACTGAATGATATTGTTTC LNU136_ER_KpnI(SEQ IN NO: 4779) AAAGGTACCTTCAAAGAATGTGTCTTGTGTGTG |
| LNU138 | EcoRV, SalI | LNU138_EF_SalI(SEQ IN NO: 4780) AAAGTCGACATAAAGATCGTCCACAAGGAGG LNU138_ER_EcoRV(SEQ IN NO: 4781) AAAGATATCCAATCAGCATACAAAGGCACAC |
| LNU14 | EcoRV, XhoI | LNU14_EF_XhoI(SEQ IN NO: 4782) AAACTCGAGTTCTTAGGGACCATTCCTCCTC LNU14_R_EcoRV(SEQ IN NO: 4783) AAAGATATCCTATGGTTTCATCAAATAAGACACACA |
| LNU140 | SalI, XbaI | LNU140_NF_SalI(SEQ IN NO: 4784) AAAGTCGACGCTGTTTCTTCCCGATCTTTG LNU140_EF_SalI(SEQ IN NO: 4785) AAAGTCGACGTTAACCTCTCCTCGTTCTCGTC LNU140_NR_XbaI(SEQ IN NO: 4786) AAATCTAGACTATCGAGAGGATTTACAATGGCAG LNU140_ER_XbaI(SEQ IN NO: 4787) AAATCTAGACGAATCATGAGACAAACAAACC |
| LNU141 | BamHI, XhoI | LNU141_NF_BamHI(SEQ IN NO: 4788) AAAGGATCCCGTCTCACTTCATCCCATCC LNU141_EF_BamHI(SEQ IN NO: 4789) AAAGGATCCCTTCCGACCTCACGAAAGC LNU141_NR_XhoI(SEQ IN NO: 4790) AAACTCGAGACGGCTTAAGATTTGTACAGCAC LNU141_ER_XhoI(SEQ IN NO: 4791) AAACTCGAGCACCATCTATGCACGTCAACTG |
| LNU143 | BamHI, XhoI | LNU143_EF_BamHI(SEQ IN NO: 4792) AATGGATCCCAAGCCTACGGTGTTCATGAC LNU143_ER_XhoI(SEQ IN NO: 4793) AAACTCGAGCATCTATAGGGAACACGAATGAGC |
| LNU147 | BamHI, XhoI | LNU147_EF_BamHI(SEQ IN NO: 4794) AAAGGATCCCTCTTCTTGAACATGACAAAGACC LNU147_ER_XhoI(SEQ IN NO: 4795) AAACTCGAGAGGATTCACGCCATACAGTTTAG |
| LNU148 | BamHI, XhoI | LNU148_F_BamHI(SEQ IN NO: 4796) TTTGGATCCGTCTATTGCATTGAGTTGAAATCAC LNU148_F_BamHI(SEQ IN NO: 4796) TTTGGATCCGTCTATTGCATTGAGTTGAAATCAC LNU148_NR_XhoI(SEQ IN NO: 4797) AATCTCGAGTCAATCAAATTGTGTATTCAAATGTATATAC LNU148_ER_XhoI(SEQ IN NO: 4798) TATCTCGAGTCCCAAAATTCAAGCTAACAGTC |

TABLE 58-continued

The PCR primers used for cloning the genes of some
embodiments of the invention into high copy vectors

| Gene Name | Restriction Enzymes used for cloning | Primers used for amplification |
|---|---|---|
| LNU149 | BamHI, XhoI | LNU149_NF_BamHI(SEQ IN NO: 4799) AAAGGATCCATTCAGAATTGGAGAGGGAAGG LNU149_EF_BamHI(SEQ IN NO: 4800) AAAGGATCCCTAGCTCAGGCCATTGAAGAAC LNU149_NR_XhoI(SEQ IN NO: 4801) AAACTCGAGCCGGGTTTACTCAGTATGAAGC LNU149_ER_XhoI(SEQ IN NO: 4802) AAACTCGAGGAGCTTACACGAACGTTTCTCC |
| LNU15 | SalI, XbaI | LNU15_NF_SalI(SEQ IN NO: 4803) AAAGTCGACCTTCTCTCCGCAACACTGAAAC LNU15_EF_SalI(SEQ IN NO: 4804) AAAGTCGACACCAAACTTTGCCTTTCTCTC LNU15_NR_XbaI(SEQ IN NO: 4805) AAATCTAGAGGTTCCTTATTATTTCACACCCAAG LNU15_ER_XbaI(SEQ IN NO: 4806) AAATCTAGAAGAACATCAAATCTAGTCGCAGTG |
| LNU150 | SalI, XbaI | LNU150_EF_SalI(SEQ IN NO: 4807) AAAGTCGACCACCGCTTTGTGGAAACAG LNU150_ER_XbaI(SEQ IN NO: 4808) AAATCTAGAGGCAGTTGCTTCCATTATTGC |
| LNU153 | BamHI, XhoI | LNU153_EF_BamHI(SEQ IN NO: 4809) AAAGGATCCTGTCCACTTTGGTTCCTTCTTC LNU153_ER_XhoI(SEQ IN NO: 4810) AAACTCGAGTGCTCTACAATCATCACCATCC |
| LNU154 | XhoI, EcoRV | LNU154_EF_XhoI(SEQ IN NO: 4811) AAACTCGAGCAAAGAAGAAACTAGTTGTAGGCAGC LNU154_ER_EcoRV(SEQ IN NO: 4812) AAAGATATCTGGTAATGATACAAGCTCAAGCAAC |
| LNU155 | SalI, XbaI | LNU155_EF_SalI(SEQ IN NO: 4813) AAAGTCGACTTCTTTACCCATTATTGCACTCAC LNU155_ER_XbaI(SEQ IN NO: 4814) AAATCTAGACAGTTTCCACAAATTCTCAATTACG |
| LNU157 | SalI, XbaI | LNU157_EF_SalI(SEQ IN NO: 4815) AAAGTCGACCAAAGTTCACACACAGAAGAATCAG LNU157_R_XbaI(SEQ IN NO: 4816) ATTTCTAGATCTTTCAATTACTTCAATTAGCCTCC |
| LNU158 | BamHI, XhoI | LNU158_NF_BamHI(SEQ IN NO: 4817) TTTGGATCCGAAAGTTCCTCACAATCATTTGTC LNU158_EF_BamHI(SEQ IN NO: 4818) TTTGGATCCGCACCCTTTGGTAGATTCTCG LNU158_NR_XhoI(SEQ IN NO: 4819) ATTCTCGAGTCAAAGATTGAAGGTATCATATGCTGTTCA LNU158_ER_XhoI(SEQ IN NO: 4820) TTTCTCGAGTGGTTTGTGGGTAATCTTCTGC |
| LNU161 | SalI, XbaI | LNU161_NF_SalI(SEQ IN NO: 4821) AAAGTCGACACTTTCTCTCTTCGGGTTCTCG LNU161_NF_SalI(SEQ IN NO: 4821) AAAGTCGACACTTTCTCTCTTCGGGTTCTCG LNU161_NR_XbaI(SEQ IN NO: 4822) AAATCTAGAATCGCTTATTTCCGACCACAC LNU161_NR_XbaI(SEQ IN NO: 4822) AAATCTAGAATCGCTTATTTCCGACCACAC |
| LNU168 | XhoI, XbaI | LNU168_EF_XhoI(SEQ IN NO: 4823) AAACTCGAGCTTCCCTTCCATACTTGCTTCC LNU168_ER_SacI(SEQ IN NO: 4824) AAAGAGCTCTGTCACTCAAAGGTAGCTGAGG |
| LNU17 | BamHI, KpnI | LNU17_EF_BamHI(SEQ IN NO: 4825) AAAGGATCCTGCCATAAGCTTCCATCCTATC LNU17_ER_KpnI(SEQ IN NO: 4826) AAAGGTACCTGTGCTTCCTAAGCTTTCAACTC |
| LNU170 | SalI, SacI | LNU170_NF_SalI(SEQ IN NO: 4827) TTAGTCGACATGTAATGGCTACTTCTTCCTCTTCTTG |

TABLE 58-continued

The PCR primers used for cloning the genes of some
embodiments of the invention into high copy vectors

| Gene Name | Restriction Enzymes used for cloning | Primers used for amplification |
|---|---|---|
| | | LNU170_EF_SalI(SEQ IN NO: 4828) TTAGTCGACATGTTCTTCACTGTAATGTAATGGCTAC LNU170_NR_SacI(SEQ IN NO: 4829) ATAGAGCTCCAATGCATGAATTCCTCGTG LNU170_ER_SacI(SEQ IN NO: 4830) TAAGAGCTCCTGATTACGTTAGGTAGGTGTGTATC |
| LNU171 | SalI, XbaI | LNU171_NF_SalI(SEQ IN NO: 4831) AAAGTCGACCTAGCAGAGGCAGAGCCTACAG LNU171_F2_Sal(SEQ IN NO: 4832) AATGTCGACCGATCAACTAGGCAACTAGCA LNU171_NR_XbaI(SEQ IN NO: 4833) AAATCTAGACTACTAAGCATGAACACCTGGTGAG LNU171_R2_Xba(SEQ IN NO: 4834) AAATCTAGAGAGAAATCTGTTCCTGGACACA |
| LNU172 | XhoI, EcoRV | LNU172_EF_XhoI(SEQ IN NO: 4835) AAACTCGAGCGAGCACTTCTCTAGCTCATGC LNU172_ER_EcoRV(SEQ IN NO: 4836) AAAGATATCGAACCCAATCCGAATTAATTGAC |
| LNU173 | SalI, XbaI | LNU173_NF_SalI(SEQ IN NO: 4837) AAAGTCGACACATCGTACGTCCGTTCCAG LNU173_NF_SalI(SEQ IN NO: 4837) AAAGTCGACACATCGTACGTCCGTTCCAG LNU173_NR_XbaI(SEQ IN NO: 4838) AAATCTAGAAACGGAACATTTGAATGACTGC LNU173_NR_XbaI(SEQ IN NO: 4838) AAATCTAGAAACGGAACATTTGAATGACTGC |
| LNU175 | BamHI, XhoI | LNU175_EF_BamHI(SEQ IN NO: 4839) AAAGGATCCTCTCTCATCTGCCTACGGTTG LNU175_ER_XhoI(SEQ IN NO: 4840) AAACTCGAGAATCATGCCTCTTGTCTTGGTG |
| LNU176 | SalI, XbaI | LNU176_NF_SalI(SEQ IN NO: 4841) AAAGTCGACCTCTCTCAAGGTCTCACCAACC LNU176_NR_XbaI(SEQ IN NO: 4842) AAATCTAGATGCATTACACACAGTAACATCATCAG |
| LNU177 | SalI, XbaI | LNU177_NF_SalI(SEQ IN NO: 4843) AAAGTCGACGATCATCATCAGACAATGGCAG LNU177_EF_SalI(SEQ IN NO: 4844) AAAGTCGACAATTTCCATTGGTCCTCCTCTC LNU177_R_XbaI(SEQ IN NO: 4845) AAATCTAGAACATTTGAATCCCAAAGATGATTT LNU177_R_XbaI(SEQ IN NO: 4845) AAATCTAGAACATTTGAATCCCAAAGATGATTT |
| LNU178 | BamHI, XhoI | LNU178_EF_BamHI(SEQ IN NO: 4846) AAAGGATCCTCTCTCTTGTTCTGAATTCGTGG LNU178_ER_XhoI(SEQ IN NO: 4847) AAACTCGAGGACAGAGAGAAGCTATGACCAACTG |
| LNU179 | BamHI, XhoI | LNU179_F_BamHI(SEQ IN NO: 4848) AAAGGATCCGAGATAGAGAGAGAGATAATGGGCA LNU179_ER_XhoI(SEQ IN NO: 4849) AAACTCGAGTGCACACTTAAATCAACAAGCA |
| LNU180 | BamHI, XhoI | LNU180_NF_BamHI(SEQ IN NO: 4850) AAAGGATCCGTTCTATGTTCCTGAAATGGGATT LNU180_EF_BamHI(SEQ IN NO: 4851) AAAGGATCCGAAACAAGCTCCATATCAATAATCAA LNU180_NR_XhoI(SEQ IN NO: 4852) AAACTCGAGGAACGGAAGAAATAACCAACAAA LNU180_ER_XhoI(SEQ IN NO: 4853) AAACTCGAGATGGTTTGAAGAACGGAAGAAA |
| LNU181 | BamHI, KpnI | LNU181_NF_BamHI(SEQ IN NO: 4854) AAAGGATCCGATTTCTTCGTCAGTTGCGTTT LNU181_EF_BamHI(SEQ IN NO: 4855) AAAGGATCCCGGTCCTAAACCCTACTCAACA LNU181_NR_KpnI(SEQ IN NO: 4856) |

TABLE 58-continued

The PCR primers used for cloning the genes of some
embodiments of the invention into high copy vectors

| Gene Name | Restriction Enzymes used for cloning | Primers used for amplification |
|---|---|---|
| | | AAAGGTACCAAATCTCATAGCTTATCATGCTCAAA<br>LNU181_ER_KpnI(SEQ IN NO: 4857)<br>AAAGGTACCTTCAGCCGTATCATCGTCTATTT |
| LNU182 | BamHI, XhoI | LNU182_NF_BamHI(SEQ IN NO: 4858)<br>AAAGGATCCCGTTGTGTTCCAACTCTCATTC<br>LNU182_EF_BamHI(SEQ IN NO: 4859)<br>AAAGGATCCGATTTGCGAGTCGTTGTGTTC<br>LNU182_NR_XhoI(SEQ IN NO: 4860)<br>AAACTCGAGGATCTTGAGGAACATGGAGACG<br>LNU182_ER_XhoI(SEQ IN NO: 4861)<br>AAACTCGAGGTGACTTTGGTTCCGATTTGAG |
| LNU183 | BamHI, XhoI | LNU183_F_BamHI(SEQ IN NO: 4862)<br>AACGGATCCAAGCTCTAGACTTTGTCTCTTTGTCC<br>LNU183_F_BamHI(SEQ IN NO: 4862)<br>AACGGATCCAAGCTCTAGACTTTGTCTCTTTGTCC<br>LNU183_NR_XhoI(SEQ IN NO: 4863)<br>AATCTCGAGTCACACCAATACAACCATAAATAACAC<br>LNU183_ER_XhoI(SEQ IN NO: 4864)<br>AATCTCGAGACTGCTGAAGTCAAAGCTAATTAGAAC |
| LNU184 | BamHI, XhoI | LNU184_NF_BamHI(SEQ IN NO: 4865)<br>AAAGGATCCCCTACCTAATCCACACCGATTC<br>LNU184_EF_BamHI(SEQ IN NO: 4866)<br>AAAGGATCCGAAGTGGAGAGAAGTGACCACC<br>LNU184_NR_XhoI(SEQ IN NO: 4867)<br>AAACTCGAGCAGCATGAGAAGAGATTTCGAG<br>LNU184_ER_XhoI(SEQ IN NO: 4868)<br>AAACTCGAGCAGCAACAACAAGAGATTTGTCC |
| LNU185 | BamHI, XhoI | LNU185_NF_BamHI(SEQ IN NO: 4869)<br>AAAGGATCCACAAACGGTGTGTAAGTGAAGAAG<br>LNU185_EF_BamHI(SEQ IN NO: 4870)<br>AAAGGATCCTCAGTCTGAAGACAAACGGTG<br>LNU185_NR_XhoI(SEQ IN NO: 4871)<br>AAACTCGAGCCGCAGAGGCTTTGTTAAATTC<br>LNU185_ER_XhoI(SEQ IN NO: 4872)<br>AAACTCGAGAAGGACATCATCAAAGCAGTACG |
| LNU186 | BamHI, XhoI | LNU186_EF_BamHI(SEQ IN NO: 4873)<br>AAAGGATCCATTGAGAGTCGCCACAGCTATC<br>LNU186_ER_XhoI(SEQ IN NO: 4874)<br>AAACTCGAGTGGCTTGATAAAGATTTGTGATTTC |
| LNU187 | XhoI, EcoRV | LNU187_NF_XhoI(SEQ IN NO: 4875)<br>AAACTCGAGCTCCTTCTTTACTTCGCTCACC<br>LNU187_EF_XhoI(SEQ IN NO: 4876)<br>AATCTCGAGTTTATCTCCTTCTTTACTTCGCTCAC<br>LNU187_NR_EcoRV(SEQ IN NO: 4877)<br>AATGATATCTTTGAAGCTAAACGATTTGACTAATTC<br>LNU187_ER_EcoRV(SEQ IN NO: 4878)<br>AATGATATCCCGCCACATTCATTTCAG |
| LNU188 | BamHI, XhoI | LNU188_NF_BamHI(SEQ IN NO: 4879)<br>AAAGGATCCAGAGCTTGCTCGGAGAGAGTG<br>LNU188_EF_BamHI(SEQ IN NO: 4880)<br>AAAGGATCCACAGAGAGATGCAGACCTGACC<br>LNU188_NR_XhoI(SEQ IN NO: 4881)<br>AAACTCGAGCCCTGATTCTCCTGTTGAGAAC<br>LNU188_ER_XhoI(SEQ IN NO: 4882)<br>AAACTCGAGTAAAGCTCGATTTCCCTGATTC |
| LNU189 | BamHI, XhoI | LNU189_EF_BamHI(SEQ IN NO: 4883)<br>AAAGGATCCAACAGACTGAATCATCAACGGAC<br>LNU189_ER_XhoI(SEQ IN NO: 4884)<br>AAACTCGAGCACGAGATGATAAGGGTTGGTC |
| LNU19 | XhoI, SacI | LNU19_NF_XhoI(SEQ IN NO: 4885)<br>AAACTCGAGGCAGCTCGTGTGTGATTGAG<br>LNU19_NF_XhoI(SEQ IN NO: 4885)<br>AAACTCGAGGCAGCTCGTGTGTGATTGAG<br>LNU19_NR_SacI(SEQ IN NO: 4886) |

TABLE 58-continued

The PCR primers used for cloning the genes of some
embodiments of the invention into high copy vectors

| Gene Name | Restriction Enzymes used for cloning | Primers used for amplification |
|---|---|---|
| | | AAAGAGCTCTCGTTTCCTACAAATGCAACAG<br>LNU19_NR_SacI(SEQ IN NO: 4886)<br>AAAGAGCTCTCGTTTCCTACAAATGCAACAG |
| LNU196 | BamHI, KpnI | LNU196_NF_BamHI(SEQ IN NO: 4887)<br>AAAGGATCCGATCAATCCTTCTGCGTGTTC<br>LNU196_EF_BamHI(SEQ IN NO: 4888)<br>AAAGGATCCCCATATCACATCTCTGATCAATCC<br>LNU196_NR_KpnI(SEQ IN NO: 4889)<br>AAAGGTACCTACTGTGATCATAAGCTACGTGGAC<br>LNU196_ER_KpnI(SEQ IN NO: 4890)<br>AAAGGTACCGCACAACATGTGGTCAAATTATTC |
| LNU2 | BamHI, KpnI | LNU2_NF_BamHI(SEQ IN NO: 4891)<br>AAAGGATCCCTCCTCTTCCGCTCGAATTTAC<br>LNU2_EF_BamHI(SEQ IN NO: 4892)<br>AAAGGATCCACAACACCACAGCGCTCATAC<br>LNU2_NR_KpnI(SEQ IN NO: 4893)<br>AAAGGTACCAATCCTACCCACAACTGTCTGG<br>LNU2_ER_KpnI(SEQ IN NO: 4894)<br>AAAGGTACCTGAATTCCTCGCAAGAGTTACC |
| LNU20 | SalI, XbaI | LNU20_EF_SalI(SEQ IN NO: 4895)<br>AAAGTCGACGAAGTGTTATTTGGAGGCAAGG<br>LNU20_ER_XbaI(SEQ IN NO: 4896)<br>AAATCTAGAACCATCAAATTTAGCCATGCAC |
| LNU200 | XhoI, SacI | LNU200_NF_XhoI(SEQ IN NO: 4897)<br>AAACTCGAGATTTGGTCATAGTGTCGACATGG<br>LNU200_EF_XhoI(SEQ IN NO: 4898)<br>AAACTCGAGTGTGCTCCAAACTTGAAAGAAAG<br>LNU200_NR_SacI(SEQ IN NO: 4899)<br>AAAGAGCTCGACACGCAAATAGGACACACTG<br>LNU200_ER_SacI(SEQ IN NO: 4900)<br>AAAGAGCTCTTGAGACACGCAAATAGGACAC |
| LNU207 | BamHI, XhoI | LNU207_NF_BamHI(SEQ IN NO: 4901)<br>AAAGGATCCCTTGGAGCTAGGAGACATCGTG<br>LNU207_EF_BamHI(SEQ IN NO: 4902)<br>AAAGGATCCTTATTTCCCTAAATCCTTGGAGC<br>LNU207_NR_XhoI(SEQ IN NO: 4903)<br>AAACTCGAGCTGACCACTTAACACTCTCACTCG<br>LNU207_ER_XhoI(SEQ IN NO: 4904)<br>AAACTCGAGAATCTCCCATACGACACTGACC |
| LNU210 | BamHI, KpnI | LNU210_EF_BamHI(SEQ IN NO: 4905)<br>AAAGGATCCCGATCGATTGGTTTAAATCCTG<br>LNU210_ER_KpnI(SEQ IN NO: 4906)<br>AAAGGTACCTTACAATCACGACCACCTTGTAAC |
| LNU211 | SalI, XbaI | LNU211_NF_SalI(SEQ IN NO: 4907)<br>AAAGTCGACAACCTCCTTCTCAAACCGTAGG<br>LNU211_EF_SalI(SEQ IN NO: 4908)<br>AAAGTCGACAAAGGCCTAAGCTCAAGCAATC<br>LNU211_NR_XbaI(SEQ IN NO: 4909)<br>AAATCTAGAGGAAACCCTAATTTCCTTCTCC<br>LNU211_ER_XbaI(SEQ IN NO: 4910)<br>AAATCTAGAAAAGTTAGTGCTATTCGCGCTC |
| LNU212 | SalI, XbaI | LNU212_F_SalI(SEQ IN NO: 4911)<br>TTTGTCGACCTACTCACATCATGGCTTTCTCC<br>LNU212_ER_XbaI(SEQ IN NO: 4912)<br>ATTTCTAGATTCACCGAATAATATATGCAAACG |
| LNU213 (6669) | BamHI, XhoI | LNU213_EF_BamHI(SEQ IN NO: 4913)<br>AAAGGATCCCAAATTAGGAGGAGCGAGAGC<br>LNU213_ER_XhoI(SEQ IN NO: 4914)<br>AAACTCGAGATGATCAGAAATTCTCAACCACG |
| LNU213 (Root_P_F) | BamHI, XhoI | LNU213_EF_BamHI(SEQ IN NO: 4913)<br>AAAGGATCCCAAATTAGGAGGAGCGAGAGC<br>LNU213_ER_XhoI(SEQ IN NO: 4914)<br>AAACTCGAGATGATCAGAAATTCTCAACCACG |

TABLE 58-continued

The PCR primers used for cloning the genes of some embodiments of the invention into high copy vectors

| Gene Name | Restriction Enzymes used for cloning | Primers used for amplification |
|---|---|---|
| LNU214 | BamHI, XhoI | LNU214_F_BamHI(SEQ IN NO: 4915) AAAGGATCCACTTCAAAGTACAAATTCCATTTCG LNU214_F_BamHI(SEQ IN NO: 4915) AAAGGATCCACTTCAAAGTACAAATTCCATTTCG LNU214_NR_XhoI(SEQ IN NO: 4916) AAACTCGAGCCACAGTAAACAAAGCATTCAAATC LNU214_ER_XhoI(SEQ IN NO: 4917) AAACTCGAGACCCAAACTCGAACAATTTACC |
| LNU215 | BamHI, XhoI | LNU215_EF_BamHI(SEQ IN NO: 4918) AAAGGATCCTTCCTGAGAAAGAAAGCGAAAC LNU215_ER_XhoI(SEQ IN NO: 4919) AAACTCGAGTCCAATCCCATAAGAACTGAGC |
| LNU216 | BamHI, KpnI | LNU216_F_BamHI(SEQ IN NO: 4920) AAAGGATCCACCCAAGCTCACACATCTCC LNU216_F_BamHI(SEQ IN NO: 4920) AAAGGATCCACCCAAGCTCACACATCTCC LNU216_NR_KpnI(SEQ IN NO: 4921) AAAGGTACCATACGAGGAAACCATGACGAAC LNU216_ER_KpnI(SEQ IN NO: 4922) AAAGGTACCCGATTACCCGATTTGTGATTTC |
| LNU217 | BamHI, XhoI | LNU217_NF_BamHI(SEQ IN NO: 4923) AAAGGATCCCGTTCGATCTCTCCCATATAATTC LNU217_EF_BamHI(SEQ IN NO: 4924) AAAGGATCCATCCATCACTCGTTCGATCTC LNU217_NR_XhoI(SEQ IN NO: 4925) AAACTCGAGCTAAATAAAGCATGGCAGACTGTGTC LNU217_ER_XhoI(SEQ IN NO: 4926) AAACTCGAGAGCTCCATCTATTCATTCGTGC |
| LNU218 | SalI, XbaI | LNU218_NF_SalI(SEQ IN NO: 4927) AAAGTCGACAGAAATCTGACCGCAATAATGG LNU218_EF_SalI(SEQ IN NO: 4928) AAAGTCGACTCTACAGAGAAATCTGACCGCA LNU218_NR_XbaI(SEQ IN NO: 4929) AAATCTAGAGATGTATAGCAACAAGAGAAACAAACA LNU218_ER_XbaI(SEQ IN NO: 4930) AAATCTAGAGAATGATGTATAGCAACAAGAGAAACA |
| LNU219 | BamHI, XhoI | LNU219_EF_BamHI(SEQ IN NO: 4931) AAAGGATCCGATGAAGAAGACATCAATGACTGG LNU219_EF_BamHI(SEQ IN NO: 4931) AAAGGATCCGATGAAGAAGACATCAATGACTGG |
| LNU220 | SalI, XbaI | LNU220_NF_SalI(SEQ IN NO: 4932) AAAGTCGACAACCTCGAACTCGAAGCAGAG LNU220_EF_SalI(SEQ IN NO: 4933) AAAGTCGACGAGAGAGACACAAGCCAACCTC LNU220_NR_XbaI(SEQ IN NO: 4934) AAATCTAGAAACAACCACCTCCATCACGTAG LNU220_ER_XbaI(SEQ IN NO: 4935) AAATCTAGACATCCAGCCACTAAATCGTTG |
| LNU223 | XhoI, EcoRV | LNU223_F_XhoI(SEQ IN NO: 4936) AAACTCGAGATTAGAAGCCTTCGGCTTTACG LNU223_F_XhoI(SEQ IN NO: 4936) AAACTCGAGATTAGAAGCCTTCGGCTTTACG LNU223_NR_EcoRV(SEQ IN NO: 4937) AAAGATATCTCTACCTGAGAAATGCTCCCTG LNU223_ER_EcoRV(SEQ IN NO: 4938) AAAGATATCGTGAATATCATGGGTTGACTGG |
| LNU224 | BamHI, KpnI | LNU224_NF_BamHI(SEQ IN NO: 4939) AAAGGATCCATCAACTCGCGACGAATCAG LNU224_EF_BamHI(SEQ IN NO: 4940) AAAGGATCCGAACAGAGAAGAGCATCAACTCG LNU224_NR_KpnI(SEQ IN NO: 4941) AAAGGTACCTATCCCTTGAGTTATTGCCTCG LNU224_ER_KpnI(SEQ IN NO: 4942) AAAGGTACCTCCTGCTACAATGCTATCCACC |

TABLE 58-continued

The PCR primers used for cloning the genes of some
embodiments of the invention into high copy vectors

| Gene Name | Restriction Enzymes used for cloning | Primers used for amplification |
|---|---|---|
| LNU225 | BamHI, KpnI | LNU225_NF_BamHI(SEQ IN NO: 4943) AAAGGATCCTCGGTAAGATTTCTTGGAGCAG LNU225_EF_BamHI(SEQ IN NO: 4944) AAAGGATCCTTCCTCTTCATCATCGACATCC LNU225_NR_KpnI(SEQ IN NO: 4945) AAAGGTACCCTAGCATAACCACGAGAGAGAAAGAG LNU225_ER_KpnI(SEQ IN NO: 4946) AAAGGTACCCTAACAAATGCATAACCACGAGAGAG |
| LNU228 | SalI, XbaI | LNU228_NF_SalI(SEQ IN NO: 4947) AAAGTCGACAACTCTTGCCACACGGGTC LNU228_EF_SalI(SEQ IN NO: 4948) AAAGTCGACAGAAACTCTTGCCACACAGCTC LNU228_NR_XbaI(SEQ IN NO: 4949) AAATCTAGACTATGTGTGTTTCTGCAGGACTTG LNU228_ER_XbaI(SEQ IN NO: 4950) AAATCTAGACTACGTACAAACTCTTATGGCGTGG |
| LNU229 | SalI, SacI | LNU229_F_SalI(SEQ IN NO: 4951) TAAGTCGACAATTTAGCAATGCTCTGTTTCTCTC LNU229_ER_SacI(SEQ IN NO: 4952) ACAGAGCTCAATCATTGATAACACTAAAACTTTCTGC |
| LNU23 | BamHI, KpnI | LNU23_EF_BamHI(SEQ IN NO: 4953) AAAGGATCCAAAGTCAGCGTGAGAGACTGG LNU23_ER_KpnI(SEQ IN NO: 4954) AAAGGTACCCCTTGACACTTCAGATCTATTCTGTG |
| LNU230 | BamHI, KpnI | LNU230_F_BamHI(SEQ IN NO: 4955) TTCGGATCCACCACCCTCACACACGCT LNU230_F_BamHI(SEQ IN NO: 4955) TTCGGATCCACCACCCTCACACACGCT LNU230_NR_KpnI(SEQ IN NO: 4956) AAAGGTACCAAAGTACACCACAGTAGGCGAGA LNU230_ER_KpnI(SEQ IN NO: 4957) AAAGGTACCAAATATGACTGAATTAAGCAGCGAG |
| LNU232 | | LNU232_NF_SalI(SEQ IN NO: 4958) AAAGTCGACACACACTTGGAAGCAAACAACC LNU232_NR_XbaI(SEQ IN NO: 4959) AAATCTAGAGAGACATACACTCCCACTGTCG |
| LNU233 | SalI, XbaI | LNU233_EF_SalI(SEQ IN NO: 4960) AAAGTCGACGCGACCAGATCAGACTCCATC LNU233_ER_XbaI(SEQ IN NO: 4961) TTTTCTAGAGCTTCAAGCGATCCAGACC |
| LNU234 | SalI, BamHI | LNU234_F_SalI(SEQ IN NO: 4962) AAAGTCGACACGTTGAACGATGGGAGC LNU234_ER_BamHI(SEQ IN NO: 4963) AAAGGATCCAGGGATGTAACATTCAACCACC |
| LNU235 | SalI, BamHI | LNU235_F_SalI(SEQ IN NO: 4964) AAAGTCGACCACAATTCACCACCATGAACTC LNU235_ER_BamHI(SEQ IN NO: 4965) AAAGGATCCTGGAGCTAAACTTTATTGGTCACG |
| LNU236 | BamHI, XhoI | LNU236_EF_BamHI(SEQ IN NO: 4966) AAAGGATCCTTAACTGCTTGCCCGTTCAT LNU236_ER_XhoI(SEQ IN NO: 4967) AAACTCGAGGTCTAGAGAGGGAGACGATTGC |
| LNU239 | BamHI, XhoI | LNU239_EF_BamHI(SEQ IN NO: 4968) AAAGGATCCGTTCCTCCTCCTACCTTTGGTC LNU239_ER_XhoI(SEQ IN NO: 4969) AAACTCGAGATGTCCCGTCAACTGAAACAAC |
| LNU24 | BamHI, XhoI | LNU24_NF_BamHI(SEQ IN NO: 4970) AAAGGATCCCCTCTGGTCCTCCATCAGATAC LNU24_EF_BamHI(SEQ IN NO: 4971) AAAGGATCCCTACTTGCTGCTTGGCGTAGAC LNU24_NR_XhoI(SEQ IN NO: 4972) |

TABLE 58-continued

The PCR primers used for cloning the genes of some
embodiments of the invention into high copy vectors

| Gene Name | Restriction Enzymes used for cloning | Primers used for amplification |
|---|---|---|
| | | AAACTCGAGTGTGACGGTGCTAAAGACAATC<br>LNU24_ER_XhoI(SEQ IN NO: 4973)<br>AAACTCGAGTTAGTTGCGAGGACATCAAATC |
| LNU241 | SalI, XbaI | LNU241_NF2_SalI(SEQ IN NO: 4974)<br>TTAGTCGACCTTCGATATCATGGCGTCC<br>LNU241_EF2_SalI(SEQ IN NO: 4975)<br>AATGTCGACTGTCCATATACACTCCTTGCACTC<br>LNU241_NR2_XbaI(SEQ IN NO: 4976)<br>TAATCTAGACGATCTACACAAGAATCAATGGACA<br>LNU241_ER2_XbaI(SEQ IN NO: 4977)<br>TAATCTAGAGCTCCATGGATGTATGAGACC |
| LNU242 | SalI, BamHI | LNU242_F_SalI(SEQ IN NO: 4978)<br>AAAGTCGACGAGAAAAATGTCCATTAGAGCTCAAG<br>LNU242_F_SalI(SEQ IN NO: 4978)<br>AAAGTCGACGAGAAAAATGTCCATTAGAGCTCAAG<br>LNU242_NR_BamHI(SEQ IN NO: 4979)<br>TTTGGATCCCTATATTAACACTACCTCAGCTTGGCT<br>LNU242_ER_BamHI(SEQ IN NO: 4980)<br>TGTGGATCCTGGTATATTCAAAGCCTAAAGATTCAG |
| LNU243 | SalI, XbaI | LNU243_F_SalI(SEQ IN NO: 4981)<br>AAAGTCGACGACGGGTCAATCATGGAGG<br>LNU243_F_SalI(SEQ IN NO: 4981)<br>AAAGTCGACGACGGGTCAATCATGGAGG<br>LNU243_NR_XbaI(SEQ IN NO: 4982)<br>AAATCTAGACTATCAGATCACCCTCAACCTTACC<br>LNU243_ER_XbaI(SEQ IN NO: 4983)<br>AAATCTAGAGGAGTACACACAACACAACACG |
| LNU244 | BamHI, EcoRV | LNU244_NF_BamHI(SEQ IN NO: 4984)<br>TTAGGATCCGGGAAGCGAGCATTATGGAC<br>LNU244_EF_BamHI(SEQ IN NO: 4985)<br>TTTGGATCCCCCTCCTTTCATTATTCTATCCG<br>LNU244_NR_EcoRV(SEQ IN NO: 4986)<br>AAAGATATCTGTTTCATCTGCACTACTTTACCTAGC<br>LNU244_ER_EcoRV(SEQ IN NO: 4987)<br>AAAGATATCGGCAAATAACCAAATGTCTCG |
| LNU245 | XhoI, SacI | LNU245_EF_XhoI(SEQ IN NO: 4988)<br>AAACTCGAGCATCATCTTCTTCTTCTCATTGG<br>LNU245_ER_SacI(SEQ IN NO: 4989)<br>AATGAGCTCCTAGAGATACAACAGACATGTGATCATTG |
| LNU246 | BamHI, XhoI | LNU246_F_BamHI(SEQ IN NO: 4990)<br>AAAGGATCCATAATTTGGAATTGGGTTGCTG<br>LNU246_ER_XhoI(SEQ IN NO: 4991)<br>AAACTCGAGATGGTCTAACCAATATGGGACG |
| LNU247 | | LNU247_EF_BamHI(SEQ IN NO: 4992)<br>AAAGGATCCTCTTGCCCATTATTCTCCATTG<br>LNU247_ER_KpnI(SEQ IN NO: 4993)<br>AAAGGTACCTATCCGTCTGGTTGTTCATCG |
| LNU249 | XhoI, SacI | LNU249_EF_XhoI(SEQ IN NO: 4994)<br>AAACTCGAGGCTCTTGAATTCTCCCTCATACC<br>LNU249_ER_SacI(SEQ IN NO: 4995)<br>AAAGAGCTCGGCAACTTAGCATTTGTGATGC |
| LNU25 | BamHI, XhoI | LNU25_EF_BamHI(SEQ IN NO: 4996)<br>AAAGGATCCATTGACTAGAGCGGGAGGAAAG<br>LNU25_ER_XhoI(SEQ IN NO: 4997)<br>AAACTCGAGCAACAATTGCTAAATTCATGGTG |
| LNU250 | SalI, BamHI | LNU250_NF_SalI(SEQ IN NO: 4998)<br>AAAGTCGACTATCTCCACCGTTTGTTTGTTG<br>LNU250_EF_SalI(SEQ IN NO: 4999)<br>AAAGTCGACTTCATCATCATCGTATCTCCACC<br>LNU250_NR_BamHI(SEQ IN NO: 5000)<br>AAAGGATCCGGGTTTAATGGGTTAGTGAATTCTTC |

TABLE 58-continued

The PCR primers used for cloning the genes of some
embodiments of the invention into high copy vectors

| Gene Name | Restriction Enzymes used for cloning | Primers used for amplification |
|---|---|---|
| | | LNU250_ER_BamHI(SEQ IN NO: 5001)<br>AAAGGATCCAACGCCAAATAACGCAAACTC |
| LNU251 | BamHI, XhoI | LNU251_NF_BamHI(SEQ IN NO: 5002)<br>AAAGGATCCCCGAGGAAACCCTAATTTCTTG<br>LNU251_EF_BamHI(SEQ IN NO: 5003)<br>AAAGGATCCGTTTGCTGTATCTCCTCCATCG<br>LNU251_NR_XhoI(SEQ IN NO: 5004)<br>AAACTCGAGGATAACGTTGACATGTTCCATTTG<br>LNU251_ER_XhoI(SEQ IN NO: 5005)<br>AAACTCGAGAAACCCTATCATCCAATTCAGG |
| LNU253 | BamHI, XhoI | LNU253_EF_BamHI(SEQ IN NO: 5006)<br>AAAGGATCCTATTCCGTGCAAACACAACAAC<br>LNU253_ER_XhoI(SEQ IN NO: 5007)<br>AAACTCGAGAACTGCACTTTCCCTCCTCTTC |
| LNU254 | BamHI, XhoI | LNU254_NF_BamHI(SEQ IN NO: 5008)<br>AAAGGATCCATTTCTTCTCGCACTCTTCACC<br>LNU254_EF_BamHI(SEQ IN NO: 5009)<br>AAAGGATCCCCCTCTAAATAGGGAGTGAGTGAG<br>LNU254_R_XhoI(SEQ IN NO: 5010)<br>AAACTCGAGAACTTCAAACTTCCCAACCAAAC<br>LNU254_R_XhoI(SEQ IN NO: 5010)<br>AAACTCGAGAACTTCAAACTTCCCAACCAAAC |
| LNU255 | SalI, BamHI | LNU255_F_SalI(SEQ IN NO: 5011)<br>AAAGTCGACAACAAACTTTAAACAATGGCTGG<br>LNU255_F_SalI(SEQ IN NO: 5011)<br>AAAGTCGACAACAAACTTTAAACAATGGCTGG<br>LNU255_NR_BamHI(SEQ IN NO: 5012)<br>AAAGGATCCGTTCTGGGTCAATGGTCGTATC<br>LNU255_ER_BamHI(SEQ IN NO: 5013)<br>AAAGGATCCTTATTGGATATGATTGGCCCAC |
| LNU256 | BamHI, XhoI | LNU256_F_BamHI(SEQ IN NO: 5014)<br>AAAGGATCCGCTTGAAGCTTCCCACAACTAC<br>LNU256_F_BamHI(SEQ IN NO: 5014)<br>AAAGGATCCGCTTGAAGCTTCCCACAACTAC<br>LNU256_NR_XhoI(SEQ IN NO: 5015)<br>AAACTCGAGACGGCCTGATAAGCATTCAC<br>LNU256_ER_XhoI(SEQ IN NO: 5016)<br>AAACTCGAGGGAACATGTGACATAACAACAAGG |
| LNU257 | SalI, XbaI | LNU257_EF_SalI(SEQ IN NO: 5017)<br>TTAGTCGACACTACTATGTACAGATTCAGCAACACAG<br>LNU257_ER_XbaI(SEQ IN NO: 5018)<br>AAATCTAGACATATACTCATGCACTCGTAGCA |
| LNU258 | BamHI, KpnI | LNU258_F_BamHI(SEQ IN NO: 5019)<br>AAAGGATCCCCCACAAACAAACAAAATGGA<br>LNU258_ER_KpnI(SEQ IN NO: 5020)<br>AAAGGTACCAGCCCACTAACCCGGTG |
| LNU260 | BamHI, XhoI | LNU260_NF_BamHI(SEQ IN NO: 5021)<br>AAAGGATCCGAACAATCCCAAGATTCTCCTC<br>LNU260_EF_BamHI(SEQ IN NO: 5022)<br>AAAGGATCCGTTACACGCGTAGGCTAGTGG<br>LNU260_NR_XhoI(SEQ IN NO: 5023)<br>AAACTCGAGCACTCAAAGAGAAGTGACAGAGTG<br>LNU260_ER_XhoI(SEQ IN NO: 5024)<br>AAACTCGAGCATTCACTCAAAGAGAAGAGTGACAG |
| LNU261 | BamHI, XhoI | LNU261_F_BamHI(SEQ IN NO: 5025)<br>AATGGATCCTCCGAAACGAGAAAACAAACTATG<br>LNU261_ER_XhoI(SEQ IN NO: 5026)<br>TTTCTCGAGCCGATCAAGATTATTTCAGGACG |
| LNU263 | SalI, XbaI | LNU263_NF_SalI(SEQ IN NO: 5027)<br>AAAGTCGACTCTCAATCTCTCAATCCCGAGT<br>LNU263_EF_SalI(SEQ IN NO: 5028)<br>AAAGTCGACGGACTCAAGCTCACAATCACAA<br>LNU263_R_XbaI(SEQ IN NO: 5029) |

TABLE 58-continued

The PCR primers used for cloning the genes of some embodiments of the invention into high copy vectors

| Gene Name | Restriction Enzymes used for cloning | Primers used for amplification |
|---|---|---|
| | | AATTCTAGATTTCCAAGCTTATCTAGTGCATAACA<br>LNU263_R_XbaI(SEQ IN NO: 5029)<br>AATTCTAGATTTCCAAGCTTATCTAGTGCATAACA |
| LNU266 | BamHI, XhoI | LNU266_NF_BamHI(SEQ IN NO: 5030)<br>AAAGGATCCGAGGAGCTTATCCTGTGCAGC<br>LNU266_EF_BamHI(SEQ IN NO: 5031)<br>AAAGGATCCAACGGAGACCACGTGTGAG<br>LNU266_NR_XhoI(SEQ IN NO: 5032)<br>AAACTCGAGCGCTGCATTGTTTCAAGAATTAC<br>LNU266_ER_XhoI(SEQ IN NO: 5033)<br>AAACTCGAGTAATGAGTTTATAGCCCGCTGC |
| LNU267 | SalI, XbaI | LNU267_NF_SalI(SEQ IN NO: 5034)<br>AAAGTCGACGATTCCAGTCCTCCTCCTGTTC<br>LNU267_EF_SalI(SEQ IN NO: 5035)<br>AAAGTCGACGTCTGGTGTGTGGATGATTCC<br>LNU267_NR_XbaI(SEQ IN NO: 5036)<br>AAATCTAGAATCTTCCATCATCATGCGCTAC<br>LNU267_ER_XbaI(SEQ IN NO: 5037)<br>AAATCTAGATCCGAAATGCTTGTATCATGG |
| LNU268 | XhoI, EcoRV | LNU268_F2_XhoI(SEQ IN NO: 5038)<br>TATCTCGAGCATCCAATTCCACTTCCACAC<br>LNU268_R2_EcoRV(SEQ IN NO: 5039)<br>ATTGATATCCCACATTCAGATCCTCAGTGC |
| LNU27 | SalI, XbaI | LNU27_F_SalI(SEQ IN NO: 5040)<br>AAAGTCGACAGCAGAAGGGATCGGAGATG<br>LNU27_ER_XbaI(SEQ IN NO: 5041)<br>AAATCTAGACATGAAATGAACCTCAGCAGTC |
| LNU271 | BamHI, KpnI | LNU271_EF_BamHI(SEQ IN NO: 5042)<br>AAAGGATCCGCAGAATCGCAGTGCAGAC<br>LNU271_ER_KpnI(SEQ IN NO: 5043)<br>AAAGGTACCCACCAGAAATCACCAATGTGTC |
| LNU274 | SalI, XbaI | LNU274_F_SalI(SEQ IN NO: 5044)<br>AAAGTCGACTGATCGCCGTTGGATCTC<br>LNU274_F_SalI(SEQ IN NO: 5044)<br>AAAGTCGACTGATCGCCGTTGGATCTC<br>LNU274_ER_XbaI(SEQ IN NO: 5045)<br>AAATCTAGAATCTCTGGGTTGAGCGTTACTG<br>LNU274_ER_XbaI(SEQ IN NO: 5045)<br>AAATCTAGAATCTCTGGGTTGAGCGTTACTG |
| LNU276 | BamHI, KpnI | LNU276_EF_BamHI(SEQ IN NO: 5046)<br>AAAGGATCCACACAAGCATCTCCTCTTCTCC<br>LNU276_ER_KpnI(SEQ IN NO: 5047)<br>AAAGGTACCAGAAGTGTGTATTTGTGCCGTG |
| LNU277 | XhoI, EcoRV | LNU277_NF_XhoI(SEQ IN NO: 5048)<br>AAACTCGAGAAGGAATTTGTTTGTTGAAGCTG<br>LNU277_EF_XhoI(SEQ IN NO: 5049)<br>AAACTCGAGTTCGGTTCATCAAATCAGAAGG<br>LNU277_NR_EcoRV(SEQ IN NO: 5050)<br>AAAGATATCATTGCTGGTATCCTGAATCCTG<br>LNU277_ER_EcoRV(SEQ IN NO: 5051)<br>AAAGATATCAATGAAATCGTGTGCCAAATTC |
| LNU278 | | LNU278_NF_SalI(SEQ IN NO: 5052)<br>AAAGTCGACCCAAGAACACAACATCAAGAGC<br>LNU278_EF_SalI(SEQ IN NO: 5053)<br>AAAGTCGACCACCAGACCACTCAGAGAAGTG<br>LNU278_NR_XbaI(SEQ IN NO: 5054)<br>AAATCTAGATGAAACAAATAGAGTACCGCAGG<br>LNU278_ER_XbaI(SEQ IN NO: 5055)<br>AAATCTAGAATTATGCAGACCTGGAAGAAGC |
| LNU279 | SalI, XbaI | LNU279_NF_SalI(SEQ IN NO: 5056)<br>AAAGTCGACGCTTCAACACAACACTTCAGTAAATC<br>LNU279_EF_SalI(SEQ IN NO: 5057)<br>AAAGTCGACTATATGCGTCTGCTTCAACACAAC |

TABLE 58-continued

The PCR primers used for cloning the genes of some embodiments of the invention into high copy vectors

| Gene Name | Restriction Enzymes used for cloning | Primers used for amplification |
|---|---|---|
| | | LNU279_R_XbaI(SEQ IN NO: 5058) AAATCTAGACATCAATCATTGGCTCATTGC LNU279_R_XbaI(SEQ IN NO: 5058) AAATCTAGACATCAATCATTGGCTCATTGC |
| LNU28 | SalI, XbaI | LNU28_EF_SalI(SEQ IN NO: 5059) AAAGTCGACAGCTGAACCACAAGCAGTGAG LNU28_ER_XbaI(SEQ IN NO: 5060) AAATCTAGACACAGTAGGCACCGAAAGTATG |
| LNU280 | BamHI, XhoI | LNU280_F_BamHI(SEQ IN NO: 5061) AAAGGATCCCCATCGCTTCGTTTCCAAG LNU280_F_BamHI(SEQ IN NO: 5061) AAAGGATCCCCATCGCTTCGTTTCCAAG LNU280_NR_XhoI(SEQ IN NO: 5062) AAACTCGAGATCGTTTCTTCCACTCCACTTC LNU280_ER_XhoI(SEQ IN NO: 5063) AAACTCGAGGTTACTTCTGGACTGCACAACG |
| LNU284 | BamHI, XhoI | LNU284_NF_BamHI(SEQ IN NO: 5064) AAAGGATCCGCATAGTCTCTGGTGCAAGAATC LNU284_EF_BamHI(SEQ IN NO: 5065) AAAGGATCCGACAGCATAGTCTCTGGTGCAAG LNU284_NR_XhoI(SEQ IN NO: 5066) AAACTCGAGCAATTCTACAATGGGCCTTGAC LNU284_ER_XhoI(SEQ IN NO: 5067) AAACTCGAGTGATATATGTTAATGCTCACCCAATTC |
| LNU287 | BamHI, XhoI | LNU287_EF_BamHI(SEQ IN NO: 5068) AAAGGATCCATTTATCGGGTCTCTTCCCAAC LNU287_ER_XhoI(SEQ IN NO: 5069) AAACTCGAGTGGATGCCTGTAGCTTGAATTAC |
| LNU288 | BamHI, XhoI | LNU288_EF_BamHI(SEQ IN NO: 5070) AAAGGATCCGCAAAGTTGTAGCCAATGGAAG LNU288_ER_XhoI(SEQ IN NO: 5071) AAACTCGAGGCAAACTTGAGTTGCATTTGAC |
| LNU289 | BamHI, XhoI | LNU289_EF_BamHI(SEQ IN NO: 5072) AAAGGATCCCCCTTCTCTCCATAACGAACC LNU289_ER_XhoI(SEQ IN NO: 5073) AAACTCGAGCTTCTTCTCGGGTTAAAGGGAC |
| LNU29 | BamHI, KpnI | LNU29_F_BamHI(SEQ IN NO: 5074) TTTGGATCCTCATTATCATCAATATGGGTAGAGCTC LNU29_F_BamHI(SEQ IN NO: 5074) TTTGGATCCTCATTATCATCAATATGGGTAGAGCTC LNU29_NR_KpnI(SEQ IN NO: 5075) TTTGGTACCTTAACCTCTTTCGAACTGTTTGTTTG LNU29_ER_KpnI(SEQ IN NO: 5076) ACTGGTACCTTACAACATGTCCAAAAGCTCAGAG |
| LNU3 | SalI, XbaI | LNU3_NF_SalI(SEQ IN NO: 5077) AAAGTCGACAACCACCTGCGATTCTGC LNU3_EF_SalI(SEQ IN NO: 5078) AAAGTCGACGTTCGTCCGCAACAAACC LNU3_NR_XbaI(SEQ IN NO: 5079) AAATCTAGACTAGAGCGGCAATATCATAGCAAAC LNU3_ER_XbaI(SEQ IN NO: 5080) AAATCTAGACTACATCCATGTACAAGCTAACATGC |
| LNU33 | BamHI, XhoI | LNU33_EF_BamHI(SEQ IN NO: 5081) AAAGGATCCTGGCGGCTAAAGTTTGTGAG LNU33_ER_XhoI(SEQ IN NO: 5082) AAACTCGAGTTACACATGGAAGACCTGAACG |
| LNU35 | | LNU35_NF_BamHI(SEQ IN NO: 5083) AAAGGATCCCGGTACAATAGCCGAATTTGAG LNU35_EF_BamHI(SEQ IN NO: 5084) AAAGGATCCAAGCCCAGCCGGTACAATAG LNU35_NR_XhoI(SEQ IN NO: 5085) AAACTCGAGGACTCCAATCAATCTACGGAGC |

TABLE 58-continued

The PCR primers used for cloning the genes of some embodiments of the invention into high copy vectors

| Gene Name | Restriction Enzymes used for cloning | Primers used for amplification |
|---|---|---|
| | | LNU35_ER_XhoI(SEQ IN NO: 5086) AAACTCGAGTGGCACTTTCTAGCAGCCTAAC |
| LNU36 | BamHI, XhoI | LNU36_EF_BamHI(SEQ IN NO: 5087) AAAGGATCCCCCAAACTCCCTTGTGAACTG LNU36_ER_XhoI(SEQ IN NO: 5088) AAACTCGAGTCTAATGTACAACACTGGGCAAAC |
| LNU37 | BamHI, XhoI | LNU37_EF_BamHI(SEQ IN NO: 5089) AAAGGATCCACCAAGTCGCTCAAAGAAACTG LNU37_ER_XhoI(SEQ IN NO: 5090) AAACTCGAGGCACGGTACCTTCTTGTTCTTC |
| LNU4 | BamHI, XhoI | LNU4_NF_BamHI(SEQ IN NO: 5091) AAAGGATCCAGATAGACCCGGAGGAAACAAG LNU4_EF_BamHI(SEQ IN NO: 5092) AAAGGATCCAGGCGCCAACTAATAACCAGAG |
| LNU4 | BamHI, XhoI | LNU4_NR_XhoI(SEQ IN NO: 5093) AAACTCGAGCCCTAGAATAAGAACCACAAATCG LNU4_ER_XhoI(SEQ IN NO: 5094) AAACTCGAGTTCAGAAATTCAAATCACAGTTTCC |
| LNU40 | SalI, XbaI | LNU40_EF_SalI(SEQ IN NO: 5095) AAAGTCGACACCACATATCATCGAGAGTTCG LNU40_ER_XbaI(SEQ IN NO: 5096) AAATCTAGACTTGGTCACTGGCTAGACCATC |
| LNU43 | BamHI, XhoI | LNU43_EF_BamHI(SEQ IN NO: 5097) AAAGGATCCTCTCTCCGACCTAGCGAGAC LNU43_ER_XhoI(SEQ IN NO: 5098) AAACTCGAGTAATTTCAAGGTCTTGCCCAAC |
| LNU44 | SalI, XbaI | LNU44_EF_SalI(SEQ IN NO: 5099) AAAGTCGACCTACCAACTCCGGCTTGTTC LNU44_ER_XbaI(SEQ IN NO: 5100) AAATCTAGACCTTCACACTGATCACTCGTTTC |
| LNU45 | SalI, XbaI | LNU45_F_SalI(SEQ IN NO: 5101) AAAGTCGACCGCTTCTTTCTCACAATGGTTC LNU45_ER_XbaI(SEQ IN NO: 5102) AAATCTAGATGGCTACTATGCCTTGTGGAAG |
| LNU46 | BamHI, SalI | LNU46_EF_SalI(SEQ IN NO: 5103) AAAGTCGACAGGTTGAAGAAGCAACACAAGC LNU46_ER_BamHI(SEQ IN NO: 5104) AAAGGATCCAACACTTCGAATCATGACCTCC |
| LNU48 | BamHI, XhoI | LNU48_EF_BamHI(SEQ IN NO: 5105) AAAGGATCCGATATGGTACAACAACCGAGAGC LNU48_ER_XhoI(SEQ IN NO: 5106) AAACTCGAGGATCATCCCATTTCAAGAGAGC |
| LNU5 (6669) | BamHI, XhoI | LNU5_NF_BamHI(SEQ IN NO: 5107) AAAGGATCCGCTCTCCACTGTCCACGAAC LNU5_EF_BamHI(SEQ IN NO: 5108) AAAGGATCCCAGATTAGTTGGAAGCTTTCTCTTC LNU5_NR_XhoI(SEQ IN NO: 5109) AAACTCGAGTCATCATCTTCCATTGCTCTACC LNU5_ER_XhoI(SEQ IN NO: 5110) AAACTCGAGTTCCTTTCATTATTTGCCAACG |
| LNU5 (Root_P_F) | BamHI, XhoI | LNU5_NF_BamHI(SEQ IN NO: 5107) AAAGGATCCGCTCTCCACTGTCCACGAAC LNU5_EF_BamHI(SEQ IN NO: 5108) AAAGGATCCCAGATTAGTTGGAAGCTTTCTCTTC LNU5_NR_XhoI(SEQ IN NO: 5109) AAACTCGAGTCATCATCTTCCATTGCTCTACC LNU5_ER_XhoI(SEQ IN NO: 5110) AAACTCGAGTTCCTTTCATTATTTGCCAACG |
| LNU50 | SalI, XbaI | LNU50_NF_SalI(SEQ IN NO: 5111) AAAGTCGACAGAACTGATAAGGCCAGTGTCG |

TABLE 58-continued

The PCR primers used for cloning the genes of some embodiments of the invention into high copy vectors

| Gene Name | Restriction Enzymes used for cloning | Primers used for amplification |
|---|---|---|
| | | LNU50_EF_SalI(SEQ IN NO: 5112)<br>AAAGTCGACCGCGGTTAAGTTAGTTGTTGTTG<br>LNU50_NR_XbaI(SEQ IN NO: 5113)<br>AAATCTAGATCCTATGTGTTGTTTAGCTACCAGG<br>LNU50_ER_XbaI(SEQ IN NO: 5114)<br>AAATCTAGATTCGCATTTAAATAACTGTGCTG |
| LNU52 | XhoI, EcoRV | LNU52_NF_XhoI(SEQ IN NO: 5115)<br>AAACTCGAGGGTGGGTGTTGCTTGTACC<br>LNU52_NR_EcoRV(SEQ IN NO: 5116)<br>AAAGATATCCCTCACCAGGTAGGTAGTCTGC |
| LNU53 | BamHI, XhoI | LNU53_NF_BamHI(SEQ IN NO: 5117)<br>AAAGGATCCGAGTGAATTAGAGAAAGGCAAATGG<br>LNU53_EF_BamHI(SEQ IN NO: 5118)<br>AAAGGATCCATCGAGTGAATTAGAGAAAGGCA<br>LNU53_R_XhoI(SEQ IN NO: 5119)<br>AGTCTCGAGTTATGGAAGTTATGAAATACAAGCAGG<br>LNU53_R_XhoI(SEQ IN NO: 5119)<br>AGTCTCGAGTTATGGAAGTTATGAAATACAAGCAGG |
| LNU54 | SalI, XbaI | LNU54_EF_SalI(SEQ IN NO: 5120)<br>AAAGTCGACCAGTTGGCCTTATCCGTATCTC<br>LNU54_R_XbaI(SEQ IN NO: 5121)<br>AAATCTAGAATCCTTGAATCCAAATGAAACG |
| LNU55 | BamHI, XhoI | LNU55_F_BamHI(SEQ IN NO: 5122)<br>AAAGGATCCTGTTAGGGAAGAAGTACTGAAGGTG<br>LNU55_F_BamHI(SEQ IN NO: 5122)<br>AAAGGATCCTGTTAGGGAAGAAGTACTGAAGGTG<br>LNU55_NR_XhoI(SEQ IN NO: 5123)<br>AAACTCGAGGAGGACCAGTTGAATGCCTC<br>LNU55_ER_XhoI(SEQ IN NO: 5124)<br>AAACTCGAGACAGAACTCTAGACTCATGAGGACC |
| LNU56 | SalI, XbaI | LNU56_EF_SalI(SEQ IN NO: 5125)<br>AAAGTCGACACATAACACCTCAAATTCTGTGATTC<br>LNU56_ER_XbaI(SEQ IN NO: 5126)<br>AAATCTAGATGGAGTACACAACAGATGGCTG |
| LNU57 | SalI, XbaI | LNU57_NF_SalI(SEQ IN NO: 5127)<br>AAAGTCGACCTGAGGGACTGTTCCAGCTC<br>LNU57_EF_SalI(SEQ IN NO: 5128)<br>AAAGTCGACACACAAGAAACACCTGAGGGAC<br>LNU57_NR_XbaI(SEQ IN NO: 5129)<br>AAATCTAGACTATTTATTATCACAGCCATCCATCG<br>LNU57_ER_XbaI(SEQ IN NO: 5130)<br>AAATCTAGACTATTGGCAGGCACACTGATATG |
| LNU58 | | LNU58_NF_SalI(SEQ IN NO: 5131)<br>AAAGTCGACCCAAGCTAACGAGCAGTAGCAC<br>LNU58_EF_SalI(SEQ IN NO: 5132)<br>AAAGTCGACGATAGCCAAGCTAACGAGCAGTAG<br>LNU58_NR_XbaI(SEQ IN NO: 5133)<br>AAATCTAGAGTTCTTCTTCGTGGTTTCCAAC<br>LNU58_ER_XbaI(SEQ IN NO: 5134)<br>AAATCTAGAAGACCAGAAACATCTCCGTTTG |
| LNU6 | BamHI, XhoI | LNU6_NF_BamHI(SEQ IN NO: 5135)<br>AAAGGATCCCAACACCGCTCATCTTCTCTTC<br>LNU6_NR_XhoI(SEQ IN NO: 5136)<br>AAACTCGAGCAACCGAAGGTGCTTATCGTC |
| LNU60 | | LNU60_NF_BamHI(SEQ IN NO: 5137)<br>AAAGGATCCACTCTGAACTGAAGCGAAGTCC<br>LNU60_NF_BamHI(SEQ IN NO: 5137)<br>AAAGGATCCACTCTGAACTGAAGCGAAGTCC<br>LNU60_NR_XhoI(SEQ IN NO: 5138)<br>AAACTCGAGTCTTCTCTGTTGCTGGAGAAGC<br>LNU60_NR_XhoI(SEQ IN NO: 5138) |
| LNU61 | | AAACTCGAGTCTTCTCTGTTGCTGGAGAAGC<br>LNU61_NF_BamHI(SEQ IN NO: 5139) |

TABLE 58-continued

The PCR primers used for cloning the genes of some embodiments of the invention into high copy vectors

| Gene Name | Restriction Enzymes used for cloning | Primers used for amplification |
|---|---|---|
| | | AAAGGATCCCCATTATATTGCTCGCGAGTTC<br>LNU61_NR_XhoI(SEQ IN NO: 5140)<br>AAACTCGAGCAGTAGCATCAAAGAAACCATCG |
| LNU63 | SalI, XbaI | LNU63_EF_SalI(SEQ IN NO: 5141)<br>AAAGTCGACGATCTTATCCTCGGCGAAGC<br>LNU63_ER_XbaI(SEQ IN NO: 5142)<br>AAATCTAGAGCAGTAGGGATGTGTCAACAAG |
| LNU64 | BamHI, XhoI | LNU64_NF_BamHI(SEQ IN NO: 5143)<br>AAAGGATCCTACCCTGTCTCTCCTCCAGC<br>LNU64_NR_XhoI(SEQ IN NO: 5144)<br>AAACTCGAGATTTCTGCGTACACCAAGAACC |
| LNU65 | BamHI, XhoI | LNU65_F_BamHI(SEQ IN NO: 5145)<br>AAAGGATCCATTTCCTCCTTCCCTTGCAC<br>LNU65_ER_XhoI(SEQ IN NO: 5146)<br>AAACTCGAGAGGCATTTGAAACTGGTTGATG |
| LNU67 | | LNU67_F_XhoI(SEQ IN NO: 5147)<br>AAACTCGAGTTACTCTCTCCGCCCTCCTAAAC<br>LNU67_F_XhoI(SEQ IN NO: 5147)<br>AAACTCGAGTTACTCTCTCCGCCCTCCTAAAC<br>LNU67_NR_SacI(SEQ IN NO: 5148)<br>AAAGAGCTCCTGTTATTATGTGCTGCCAACG<br>LNU67_ER_SacI(SEQ IN NO: 5149)<br>AAAGAGCTCAGGAGTTCACCTTGGAGATCAG |
| LNU68 | BamHI, KpnI | LNU68_EF_BamHI(SEQ IN NO: 5150)<br>AAAGGATCCTATACAGCCTAGAACAACTGCTTGC<br>LNU68_ER_KpnI(SEQ IN NO: 5151)<br>AAAGGTACCTCATGTCAGTATCTCAGGCGTC |
| LNU69 | BamHI, XhoI | LNU69_EF_BamHI(SEQ IN NO: 5152)<br>AAAGGATCCCAGCAGCAGCTAGGGTTTAGAG<br>LNU69_ER_XhoI(SEQ IN NO: 5153)<br>AAACTCGAGAACAATGAAGATGGTCTCAATGC |
| LNU7 | SalI, XbaI | LNU7_F_SalI(SEQ IN NO: 5154)<br>AAAGTCGACGAACTGCACCTTCACCTTCC<br>LNU7_ER_XbaI(SEQ IN NO: 5155)<br>AAATCTAGAGGTCTTCAGCAGAAACCAGG |
| LNU70 | SalI, XbaI | LNU70_NF_SalI_Jap(SEQ IN NO: 5156)<br>AAAGTCGACATTCCACTCCACCTCGTCC<br>LNU70_EF_SalI_Jap(SEQ IN NO: 5157)<br>AAAGTCGACAATCCACTACTATTCCACTCCACC<br>LNU70_NR_XbaI_Jap(SEQ IN NO: 5158)<br>AAATCTAGACGGCAGTAGAGAAGTGCTATTG<br>LNU70_ER_XbaI_Jap(SEQ IN NO: 5159)<br>AAATCTAGAGCAATTTGGCATGGTAATGAG |
| LNU71 | BamHI, KpnI | LNU71_NF_BamHI(SEQ IN NO: 5160)<br>AAAGGATCCTTCTCTCGTCTCGGCTCAAG<br>LNU71_EF_BamHI(SEQ IN NO: 5161)<br>AAAGGATCCCAAGTCTCGTGCTCTCACTCTC<br>LNU71_NR_KpnI(SEQ IN NO: 5162)<br>AAAGGTACCGCATGTGAATTACGAACCACAG<br>LNU71_ER_KpnI(SEQ IN NO: 5163)<br>AAAGGTACCAACGAAATTGTTGCTGGGATAG |
| LNU72 | BamHI, XhoI | LNU72_NF_BamHI(SEQ IN NO: 5164)<br>AAAGGATCCGTTGGTCACCACCCAAACTC<br>LNU72_NR_XhoI(SEQ IN NO: 5165)<br>AAACTCGAGGCACTGGAGTACTGGACAAGTG |
| LNU73 | XhoI, SacI | LNU73_EF_XhoI(SEQ IN NO: 5166)<br>AAACTCGAGACATATACACACCGGGCCAC<br>LNU73_ER_SacI(SEQ IN NO: 5167)<br>AAAGAGCTCCAAATGTTGCGTCGATCAAG |
| LNU74 | SalI, XbaI | LNU74_NF_SalI(SEQ IN NO: 5168)<br>AAAGTCGACGCATCTTCCTTAGCTCGCTC |

TABLE 58-continued

The PCR primers used for cloning the genes of some
embodiments of the invention into high copy vectors

| Gene Name | Restriction Enzymes used for cloning | Primers used for amplification |
|---|---|---|
| | | LNU74_EF_SalI(SEQ IN NO: 5169)<br>AAAGTCGACATTTCTGCATCTTCCTTAGCTCG<br>LNU74_NR_XbaI(SEQ IN NO: 5170)<br>AAATCTAGACTGGCCAGGTAAGAGTGACTTG<br>LNU74_ER_XbaI(SEQ IN NO: 5171)<br>AAATCTAGATGATCCACTAAGTAGCAGAACAAGG |
| LNU76 | BamHI, KpnI | LNU76_EF_BamHI(SEQ IN NO: 5172)<br>AAAGGATCCAAATCATCAGCACAAGATCGAG<br>LNU76_ER_KpnI(SEQ IN NO: 5173)<br>AAAGGTACCCTACAATAGGATTAATTTGCCGCTG |
| LNU79 | XhoI, EcoRV | LNU79_EF_XhoI(SEQ IN NO: 5174)<br>AAACTCGAGACGAGAATCGCTGAACCTCA<br>LNU79_R_EcoRV(SEQ IN NO: 5175)<br>AAAGATATCAAGGAATCAAACTCCAGTTCTCAA |
| LNU8 | SalI, XbaI | LNU8_F_SalI(SEQ IN NO: 5176)<br>AAAGTCGACGGAAAAGAAGAGCTCAAGAAGAA<br>LNU8_F_SalI(SEQ IN NO: 5176)<br>AAAGTCGACGGAAAAGAAGAGCTCAAGAAGAA<br>LNU8_NR_XbaI(SEQ IN NO: 5177)<br>TTTTCTAGATCATGAGAGACCCACTTGAGGAG<br>LNU8_ER_XbaI(SEQ IN NO: 5178)<br>TATTCTAGATCAATTGTATGAGAGACCCACTTG |
| LNU81 | SalI, XbaI | LNU81_NF_SalI(SEQ IN NO: 5179)<br>AAAGTCGACGGGACTGTTGAAGCTCTGC<br>LNU81_EF_SalI(SEQ IN NO: 5180)<br>AAAGTCGACGAAACACCTGAGGGACTGTTG<br>LNU81_NR_XbaI(SEQ IN NO: 5181)<br>AAATCTAGAACAGCACTGGTGGTTGAAGAAC<br>LNU81_ER_XbaI(SEQ IN NO: 5182)<br>AAATCTAGAAATTACAGCCATCCATCCAATC |
| LNU82 | BamHI, XhoI | LNU82_NF_BamHI(SEQ IN NO: 5183)<br>AAAGGATCCGAACACGCTCTCTTCCAAAGC<br>LNU82_EF_BamHI(SEQ IN NO: 5184)<br>AAAGGATCCGAAGAACAAGACGAACACGCTC<br>LNU82_NR_XhoI(SEQ IN NO: 5185)<br>AAACTCGAGAGGCTACCAATCCACATCAGAC<br>LNU82_ER_XhoI(SEQ IN NO: 5186)<br>AAACTCGAGTATTCCAATCCAATCAACCAGG |
| LNU83 | BamHI, KpnI | LNU83_F_BamHI(SEQ IN NO: 5187)<br>AAAGGATCCGAAGGAGGCAATGGCTCG<br>LNU83_ER_KpnI(SEQ IN NO: 5188)<br>AAAGGTACCAGGAGCTCGACTCAAACATCTG |
| LNU84 | BamHI, KpnI | LNU84_F_BamHI(SEQ IN NO: 5189)<br>TTAGGATCCGAGCCCCATTCCATTCTTC<br>LNU84_F_BamHI(SEQ IN NO: 5189)<br>TTAGGATCCGAGCCCCATTCCATTCTTC<br>LNU84_NR_KpnI(SEQ IN NO: 5190)<br>AAAGGTACCCCAGCCAGGATCAGATCAAG<br>LNU84_ER_KpnI(SEQ IN NO: 5191)<br>TTAGGTACCATTTCCTTGTCAGGTCCAGC |
| LNU85 | SalI, XbaI | LNU85_EF_SalI(SEQ IN NO: 5192)<br>AAAGTCGACATTTGGGACATCGTCTCCTTC<br>LNU85_ER_XbaI(SEQ IN NO: 5193)<br>AAATCTAGAAAACAAACAAGGCAGAGTCCAC |
| LNU86 | BamHI, XhoI | LNU86_NF_BamHI(SEQ IN NO: 5194)<br>AAAGGATCCGGGACAGGACTGTTGGAAGTC<br>LNU86_EF_BamHI(SEQ IN NO: 5195)<br>AAAGGATCCAGCACACGTTCGTCTTCCTC<br>LNU86_NR_XhoI(SEQ IN NO: 5196)<br>AAACTCGAGCAGTGTTGTGGTAATGAGGTCG<br>LNU86_ER_XhoI(SEQ IN NO: 5197)<br>AAACTCGAGACTCAAGTGGCTCTCTCAGGAC |

TABLE 58-continued

The PCR primers used for cloning the genes of some embodiments of the invention into high copy vectors

| Gene Name | Restriction Enzymes used for cloning | Primers used for amplification |
|---|---|---|
| LNU87 | SalI, XbaI | LNU87_EF_SalI(SEQ IN NO: 5198) AAAGTCGACGATTTGAAGCTCCCAGTTCTTG LNU87_ER_XbaI(SEQ IN NO: 5199) AAATCTAGACTACAATGAAATGAAATCCTGGAAGG |
| LNU89 | BamHI, XhoI | LNU89_NF_BamHI(SEQ IN NO: 5200) AAAGGATCCCAACTCGAAAGGCTCCATTG LNU89_EF_BamHI(SEQ IN NO: 5201) AAAGGATCCGGTCTCCTCATCGAGTCCAAC LNU89_NR_XhoI(SEQ IN NO: 5202) AAACTCGAGCCGCAGCCAGGATTATATCAC LNU89_ER_XhoI(SEQ IN NO: 5203) AAACTCGAGCTTCAGCTTTGGAGAGCAACC |
| LNU9 | SalI, XbaI | LNU9_NF_SalI(SEQ IN NO: 5204) AAAGTCGACCGTGAGGTTAACAACAAGAACAAG LNU9_EF_SalI(SEQ IN NO: 5205) AAAGTCGACCAATTGCCAAGTACTCTCTGAGC LNU9_NR_XbaI(SEQ IN NO: 5206) AAATCTAGATCAGCACTGTCCATTCAGGTAG LNU9_ER_XbaI(SEQ IN NO: 5207) AAATCTAGACTCACGCTTGGATTGGATTAC |
| LNU94 | SalI, SacI | LNU94_NF_SalI(SEQ IN NO: 5208) TTTGTCGACTTAGGCATTATGGCTGTGGG LNU94_EF_SalI(SEQ IN NO: 5209) TTTGTCGACTTTGAACCAATTTTAGGCATTATGG LNU94_NR_SacI(SEQ IN NO: 5210) TTCGAGCTCTCATTTAATGATCTCATGCTTCTCC LNU94_ER_SacI(SEQ IN NO: 5211) TTCGAGCTCTGCAACAAACAAGCTTACACAATAC |
| LNU95 | BamHI, XhoI | LNU95_NF_BamHI(SEQ IN NO: 5212) AAAGGATCCAGAAACCTCGACCCATTTCAG LNU95_EF_BamHI(SEQ IN NO: 5213) AAAGGATCCCCTCCAAATTGTAATCTAAACCTGC LNU95_NR_XhoI(SEQ IN NO: 5214) AAACTCGAGCAAACACCACTCATGACTCCAC LNU95_ER_XhoI(SEQ IN NO: 5215) AAACTCGAGTTCTCCCAGCAAACTTTCTCAC |
| LNU96 | SalI, XbaI | LNU96_EF_SalI(SEQ IN NO: 5216) AAAGTCGACCGGTTCGTCTAGTCGTCTTCC LNU96_ER_XbaI(SEQ IN NO: 5217) AAATCTAGAAGCTCAGAGAAAGCAGGTTCAG |
| LNU98 | BamHI, KpnI | LNU98_NF_BamHI(SEQ IN NO: 5218) AAAGGATCCGAAGCGACTCCAAGAAGCAG LNU98_EF_BamHI(SEQ IN NO: 5219) AAAGGATCCCTCGTCTGTGTCTGCCTACTCC LNU98_NR_KpnI(SEQ IN NO: 5220) AAAGGTACCTGACACCATTCAGACCAAAGTG LNU98_ER_KpnI(SEQ IN NO: 5221) AAAGGTACCCCATGTCCTGGAAATATGTCTG |

Table 58. Provided are the PCR primers used for cloning the genes of some embodiments of the invention. Fwd = forward primer; Rev = reverse primer; Nested = nested primer for PCR (internal primer); External = external primer for PCR. NF = nested forward; EF-external forward; NR-nested reverse; ER-external reverse.

TABLE 59

Genes cloned from cDNA libraries or genomic DNA in a High copy number plasmid

| Gene Name | High copy plasmid | Amplified from | | Polynucleotide SEQ ID NO: | Polypeptide SEQ ID NO: |
|---|---|---|---|---|---|
| | | Organism | Origin | | |
| LNU1 | pKS (Pks_J) | ARABIDOPSIS Arabidopsis thaliana Kondara | cDNA | 258 | 707 |

TABLE 59-continued

Genes cloned from cDNA libraries or genomic DNA in a High copy number plasmid

| Gene Name | High copy plasmid | Amplified from Organism | Origin | Polynucleotide SEQ ID NO: | Polypeptide SEQ ID NO: |
|---|---|---|---|---|---|
| LNU10 | Topo B | RICE *Oryza sativa* L. *Indica* Lebbonet | cDNA | 267 | 477 |
| LNU100 | pKS (Pks__J) | COTTON *Gossypium hirsutum* ND | cDNA | 331 | 735 |
| LNU101 | pKS (Pks__J) | RICE *Oryza sativa* L. *Japonica* LEMONT | cDNA | 332 | 736 |
| LNU104 | pGXN (pKG + Nos + 35S) | SOYBEAN *Glycine max* 58-261 | cDNA | 333 | 737 |
| LNU105 | pKS (Pks__J) | WHEAT *Triticum aestivum* L. | cDNA | 334 | 738 |
| LNU106 | pGXN (pKG + Nos + 35S) | WHEAT *Triticum aestivum* L. ND | cDNA | 335 | 739 |
| LNU107 | pKS (Pks__J) | RICE *Oryza sativa* L. *Japonica* Nipponbare | cDNA | 336 | 547 |
| LNU109 | pKS (Pks__J) | RICE *Oryza sativa* L. *Indica* Lebbonet | cDNA | 337 | 548 |
| LNU11 |  |  | GeneArt | 268 | 478 |
| LNU110 | pKS (Pks__J) | RICE *Oryza sativa* L. *Indica* TEBBONET | cDNA | 338 | 549 |
| LNU112 |  |  | GeneArt | 339 | 550 |
| LNU113 | pKS (Pks__J) | MAIZE *Zea mays* L. OH43 | cDNA | 340 | 740 |
| LNU114 | pGXN (pKG + Nos + 35S) | RICE *Oryza sativa* L. *Japonica* ND | cDNA | 341 | 552 |
| LNU115 | pKS (Pks__J) | RICE *Oryza sativa* L. *Japonica* Nipponbare | cDNA | 342 | 553 |
| LNU116 | pKS (Pks__J) | RICE *Oryza sativa* L. *Japonica* LEMONT | cDNA | 343 | 554 |
| LNU117 | pKS (Pks__J) | RICE *Oryza sativa* L. *Japonica* ND | cDNA | 344 | 555 |
| LNU118 | pKS (Pks__J) | RICE *Oryza sativa* L. *Indica* TEBBONET | cDNA | 345 | 556 |
| LNU119 | pKS (Pks__J) | RICE *Oryza sativa* L. *Japonica* Nipponbare | cDNA | 346 | 557 |
| LNU12 | pKS (Pks__J) | RICE *Oryza sativa* L. *Indica* Lebbonet | cDNA | 269 | 709 |
| LNU120 | pGXN (pKG + Nos + 35S) | RICE *Oryza sativa* L. *Japonica* LEMONT | cDNA | 347 | 558 |
| LNU121 | pGXNa | RICE *Oryza sativa* L. *Japonica* Nipponbare | cDNA | 348 | 559 |
| LNU122 | Topo B | RICE *Oryza sativa* L. *Indica* Lebbonet | cDNA | 349 | 560 |
| LNU123 | pKS (Pks__J) | ARABIDOPSIS *Arabidopsis thaliana* Kondara | cDNA | 350 | 741 |
| LNU124 | pKS (Pks__J) | ARABIDOPSIS *Arabidopsis thaliana* Kondara | cDNA | 351 | 562 |
| LNU125 | pGXN (pKG + Nos + 35S) | ARABIDOPSIS *Arabidopsis thaliana* Kondara | Genomic | 466 | — |
| LNU126 | pKS (Pks__J) | ARABIDOPSIS *Arabidopsis thaliana* Kondara | cDNA | 352 | 563 |

TABLE 59-continued

Genes cloned from cDNA libraries or genomic DNA in a High copy number plasmid

| Gene Name | High copy plasmid | Amplified from Organism | Origin | Polynucleotide SEQ ID NO: | Polypeptide SEQ ID NO: |
|---|---|---|---|---|---|
| LNU127 | | | GeneArt | 353 | 564 |
| LNU128 | pKS (Pks_J) | ARABIDOPSIS Arabidopsis thaliana Kondara | cDNA | 354 | 742 |
| LNU129 | pKS (Pks_J) | ARABIDOPSIS Arabidopsis thaliana Kondara | cDNA | 355 | 743 |
| LNU13 | | | GeneArt | 270 | 480 |
| LNU130 | pGXN (pKG + Nos + 35S) | ARABIDOPSIS Arabidopsis thaliana Kondara | cDNA | 356 | 744 |
| LNU131 | pKS (Pks_J) | ARABIDOPSIS Arabidopsis thaliana Kondara | cDNA | 357 | 568 |
| LNU132 | pGXN (pKG + Nos + 35S) | ARABIDOPSIS Arabidopsis thaliana Kondara | cDNA | 358 | 569 |
| LNU133 | pGXN (pKG + Nos + 35S) | ARABIDOPSIS Arabidopsis thaliana Kondara | cDNA | 359 | 745 |
| LNU134 | pKS (Pks_J) | ARABIDOPSIS Arabidopsis thaliana Kondara | cDNA | 360 | 746 |
| LNU135 | pKS (Pks_J) | ARABIDOPSIS Arabidopsis thaliana Kondara | cDNA | 361 | 747 |
| LNU136 | pKS (Pks_J) | ARABIDOPSIS Arabidopsis thaliana Columbia wt | cDNA | 362 | 573 |
| LNU138 | pKS (Pks_J) | BARLEY Hordeum vulgare L. Manit | cDNA | 363 | 574 |
| LNU14 | pKS (Pks_J) | ARABIDOPSIS Arabidopsis thaliana Kondara | cDNA | 271 | 710 |
| LNU140 | pGXN (pKG + Nos + 35S) | ARABIDOPSIS Arabidopsis thaliana Kondara | cDNA | 364 | 748 |
| LNU141 | pKS (Pks_J) | WHEAT Triticum aestivum L. | cDNA | 365 | 749 |
| LNU142 | | | GeneArt | 366 | 577 |
| LNU143 | pKS (Pks_J) | COTTON Gossypium hirsutum ND | cDNA | 367 | 750 |
| LNU147 | pKS (Pks_J) | COTTON Gossypium hirsutum Akala | cDNA | 368 | 580 |
| LNU148 | pKS (Pks_J) | SOYBEAN Glycine max 58-261 | cDNA | 369 | 695 |
| LNU149 | pKS (Pks_J) | RICE Oryza sativa L. Japonica ND | cDNA | 370 | 751 |
| LNU15 | pGXN (pKG + Nos + 35S) | ARABIDOPSIS Arabidopsis thaliana Kondara | cDNA | 272 | 711 |
| LNU150 | pGXN (pKG + Nos + 35S) | COTTON Gossypium hirsutum ND | cDNA | 371 | 752 |
| LNU153 | pKS (Pks_J) | RICE Oryza sativa L. Japonica LEMONT | cDNA | 372 | 753 |
| LNU154 | pKS (Pks_J) | COTTON Gossypium hirsutum ND | cDNA | 373 | 754 |
| LNU155 | pGXN (pKG + Nos + 35S) | COTTON Gossypium hirsutum ND | cDNA | 374 | 755 |
| LNU157 | pGXN (pKG + Nos + 35S) | SOYBEAN Glycine max 58-261 | cDNA | 375 | 587 |

TABLE 59-continued

Genes cloned from cDNA libraries or genomic DNA in a High copy number plasmid

| Gene Name | High copy plasmid | Amplified from Organism | Origin | Polynucleotide SEQ ID NO: | Polypeptide SEQ ID NO: |
|---|---|---|---|---|---|
| LNU158 | pKS (Pks_J) | COTTON *Gossypium hirsutum* Akala | cDNA | 376 | 588 |
| LNU161 | pGXN (pKG + Nos + 35S) | SOYBEAN *Glycine max* 58-261 | cDNA | 377 | 589 |
| LNU168 | pGXNa | SORGHUM *Sorghum bicolor* ND | cDNA | 378 | 590 |
| LNU17 | pKS (Pks_J) | RICE *Oryza sativa* L. Japonica ND | cDNA | 273 | 483 |
| LNU170 | pGXN (pKG + Nos + 35S) | ARABIDOPSIS *Arabidopsis thaliana* Kondara | cDNA | 379 | 756 |
| LNU171 | pGXN (pKG + Nos + 35S) | BARLEY *Hordeum vulgare* L. Manit | cDNA | 380 | 757 |
| LNU172 | pKS (Pks_J) | BARLEY *Hordeum vulgare* L. Manit | cDNA | 381 | 758 |
| LNU173 | pGXN (pKG + Nos + 35S) | BARLEY *Hordeum vulgare* L. ND | cDNA | 382 | 594 |
| LNU175 | pKS (Pks_J) | ARABIDOPSIS *Arabidopsis thaliana* Kondara | cDNA | 383 | 595 |
| LNU176 | pGXN (pKG + Nos + 35S) | RICE *Oryza sativa* L. Japonica ND | cDNA | 384 | 759 |
| LNU177 | pGXN (pKG + Nos + 35S) | ARABIDOPSIS *Arabidopsis thaliana* Kondara | cDNA | 385 | 597 |
| LNU178 | pKS (Pks_J) | ARABIDOPSIS *Arabidopsis thaliana* Kondara | cDNA | 386 | 598 |
| LNU179 | pKS (Pks_J) | ARABIDOPSIS *Arabidopsis thaliana* Kondara | cDNA | 387 | 760 |
| LNU180 | pKS (Pks_J) | ARABIDOPSIS *Arabidopsis thaliana* Kondara | cDNA | 388 | 600 |
| LNU181 | pKS (Pks_J) | ARABIDOPSIS *Arabidopsis thaliana* Kondara | cDNA | 389 | 761 |
| LNU182 | pKS (Pks_J) | ARABIDOPSIS *Arabidopsis thaliana* ND | cDNA | 390 | 602 |
| LNU183 | pKS (Pks_J) | ARABIDOPSIS *Arabidopsis thaliana* Kondara | cDNA | 391 | 603 |
| LNU184 | pKS (Pks_J) | ARABIDOPSIS *Arabidopsis thaliana* ND | cDNA | 392 | 604 |
| LNU185 | pKS (Pks_J) | ARABIDOPSIS *Arabidopsis thaliana* Kondara | cDNA | 393 | 605 |
| LNU186 | pKS (Pks_J) | ARABIDOPSIS *Arabidopsis thaliana* Kondara | cDNA | 394 | 606 |
| LNU187 | pKS (Pks_J) | ARABIDOPSIS *Arabidopsis thaliana* Kondara | cDNA | 395 | 762 |
| LNU188 | pKS (Pks_J) | SOYBEAN *Glycine max* 58-261 | cDNA | 396 | 608 |
| LNU189 | pKS (Pks_J) | RICE *Oryza sativa* L. Japonica ND | cDNA | 397 | 609 |
| LNU19 | pGXNa | RICE *Oryza sativa* L. Japonica Nipponbare | cDNA | 274 | 484 |
| LNU190 | | | GeneArt | 398 | 610 |

TABLE 59-continued

Genes cloned from cDNA libraries or genomic DNA in a High copy number plasmid

| Gene Name | High copy plasmid | Amplified from Organism | Origin | Polynucleotide SEQ ID NO: | Polypeptide SEQ ID NO: |
|---|---|---|---|---|---|
| LNU191 | | | GeneArt | 399 | 611 |
| LNU192 | | | GeneArt | 400 | 612 |
| LNU196 | pKS (Pks_J) | RICE *Oryza sativa* L. *Japonica* Nipponbare | cDNA | 401 | 613 |
| LNU198 | | | GeneArt | 402 | 614 |
| LNU2 | pKS (Pks_J) | RICE *Oryza sativa* L. *Japonica* LEMONT | cDNA | 259 | 469 |
| LNU20 | pGXN (pKG + Nos + 35S) | TOMATO *Lycopersicum esculentum* M82 | cDNA | 275 | 485 |
| LNU200 | pGXNa | TOMATO *Lycopersicum esculentum* M82 | cDNA | 403 | 615 |
| LNU201 | | | GeneArt | 215 | — |
| LNU206 | | | GeneArt | 404 | 617 |
| LNU207 | pKS (Pks_J) | ARABIDOPSIS *Arabidopsis thaliana* Kondara | cDNA | 405 | 618 |
| LNU210 | pKS (Pks_J) | ARABIDOPSIS *Arabidopsis thaliana* Kondara | cDNA | 406 | 763 |
| LNU211 | pGXN (pKG + Nos + 35S) | ARABIDOPSIS *Arabidopsis thaliana* Kondara | cDNA | 407 | 620 |
| LNU212 | pGXN (pKG + Nos + 35S) | ARABIDOPSIS *Arabidopsis thaliana* Kondara | cDNA | 408 | 764 |
| LNU213 | pKS (Pks_J) | ARABIDOPSIS *Arabidopsis thaliana* Columbia wt | cDNA | 409 | 622 |
| LNU214 | pKS (Pks_J) | ARABIDOPSIS *Arabidopsis thaliana* Kondara | cDNA | 410 | 765 |
| LNU215 | pKS (Pks_J) | ARABIDOPSIS *Arabidopsis thaliana* Kondara | cDNA | 411 | 624 |
| LNU216 | pKS (Pks_J) | RICE *Oryza sativa* L. *Japonica* LEMONT | cDNA | 412 | 625 |
| LNU217 | pKS (Pks_J) | RICE *Oryza sativa* L. *Indica* TEBBONET | cDNA | 413 | 626 |
| LNU218 | pGXN (pKG + Nos + 35S) | ARABIDOPSIS *Arabidopsis thaliana* Kondara | cDNA | 414 | 627 |
| LNU219 | pKS (Pks_J) | ARABIDOPSIS *Arabidopsis thaliana* Kondara | cDNA | 415 | 766 |
| LNU220 | pGXN (pKG + Nos + 35S) | RICE *Oryza sativa* L. *Japonica* LEMONT | cDNA | 416 | 767 |
| LNU222_H6 | | | GeneArt | 465 | 680 |
| LNU223 | pKS (Pks_J) | RICE *Oryza sativa* L. *Japonica* Nipponbare | cDNA | 417 | 631 |
| LNU224 | pKS (Pks_J) | BARLEY *Hordeum vulgare* L. ND | cDNA | 418 | 632 |
| LNU225 | pKS (Pks_J) | ARABIDOPSIS *Arabidopsis thaliana* Kondara | cDNA | 419 | 768 |
| LNU228 | pGXN (pKG + Nos + 35S) | BARLEY *Hordeum vulgare* L. Manit | cDNA | 420 | 634 |
| LNU229 | pGXN (pKG + Nos + 35S) | TOMATO *Lycopersicum esculentum* M82 | cDNA | 421 | 635 |
| LNU23 | pKS (Pks_J) | ARABIDOPSIS *Arabidopsis* | cDNA | 276 | 486 |

TABLE 59-continued

Genes cloned from cDNA libraries or genomic DNA in a High copy number plasmid

| Gene Name | High copy plasmid | Amplified from Organism | Origin | Polynucleotide SEQ ID NO: | Polypeptide SEQ ID NO: |
|---|---|---|---|---|---|
| LNU230 | pKS (Pks_J) | RICE *Oryza sativa* L. *Japonica* LEMONT | cDNA | 422 | 636 |
| LNU232 | Topo B | RICE *Oryza sativa* L. *Japonica* LEMONT | cDNA | 423 | 769 |
| LNU233 | pGXN (pKG + Nos + 35S) | RICE *Oryza sativa* L. *Japonica* ND | Genomic | 467 | — |
| LNU234 | pKS (Pks_J) | ARABIDOPSIS *Arabidopsis thaliana* Kondara | cDNA | 424 | 638 |
| LNU235 | pKS (Pks_J) | ARABIDOPSIS *Arabidopsis thaliana* Kondara | cDNA | 425 | 770 |
| LNU236 | pKS (Pks_J) | COTTON *Gossypium hirsutum* Akala | cDNA | 426 | 771 |
| LNU239 | pKS (Pks_J) | RICE *Oryza sativa* L. *Japonica* Nipponbare | cDNA | 427 | 641 |
| LNU24 | pKS (Pks_J) | ARABIDOPSIS *Arabidopsis thaliana* Kondara | cDNA | 277 | 487 |
| LNU241 | pGXN (pKG + Nos + 35S) | RICE *Oryza sativa* L. *Japonica* LEMONT | cDNA | 428 | 643 |
| LNU242 | pKS (Pks_J) | ARABIDOPSIS *Arabidopsis thaliana* Columbia wt | cDNA | 429 | 644 |
| LNU243 | pGXN (pKG + Nos + 35S) | BARLEY *Hordeum vulgare* L. Manit | cDNA | 430 | 645 |
| LNU244 | pKS (Pks_J) | BARLEY *Hordeum vulgare* L. Manit | cDNA | 431 | 772 |
| LNU245 | pGXNa | TOMATO *Lycopersicum esculentum* M82 | cDNA | 432 | 773 |
| LNU246 | pKS (Pks_J) | TOMATO *Lycopersicum esculentum* M82 | cDNA | 433 | 648 |
| LNU247 | Topo B | ARABIDOPSIS *Arabidopsis thaliana* Kondara | cDNA | 434 | 774 |
| LNU249 | pGXN (pKG + Nos + 35S) | ARABIDOPSIS *Arabidopsis thaliana* Columbia wt | cDNA | 435 | 650 |
| LNU25 | pKS (Pks_J) | SORGHUM *Sorghum bicolor* ND | cDNA | 278 | 488 |
| LNU250 | pKS (Pks_J) | ARABIDOPSIS *Arabidopsis thaliana* Kondara | cDNA | 436 | 775 |
| LNU251 | pKS (Pks_J) | ARABIDOPSIS *Arabidopsis thaliana* Kondara | cDNA | 437 | 776 |
| LNU253 | pKS (Pks_J) | SOYBEAN *Glycine max* 58-261 | cDNA | 438 | 777 |
| LNU254 | pKS (Pks_J) | ARABIDOPSIS *Arabidopsis thaliana* Kondara | cDNA | 439 | 654 |
| LNU255 | pKS (Pks_J) | ARABIDOPSIS *Arabidopsis thaliana* Kondara | cDNA | 440 | 778 |
| LNU256 | pKS (Pks_J) | ARABIDOPSIS *Arabidopsis thaliana* Kondara | cDNA | 441 | 779 |

TABLE 59-continued

Genes cloned from cDNA libraries or genomic DNA in a High copy number plasmid

| Gene Name | High copy plasmid | Amplified from Organism | Origin | Polynucleotide SEQ ID NO: | Polypeptide SEQ ID NO: |
|---|---|---|---|---|---|
| LNU257 | pGXN (pKG + Nos + 35S) | ARABIDOPSIS Arabidopsis thaliana Kondara | cDNA | 442 | 657 |
| LNU258 | pKS (Pks_J) | ARABIDOPSIS Arabidopsis thaliana Kondara | cDNA | 443 | 780 |
| LNU260 | pKS (Pks_J) | ARABIDOPSIS Arabidopsis thaliana Kondara | cDNA | 444 | 781 |
| LNU261 | pKS (Pks_J) | ARABIDOPSIS Arabidopsis thaliana Kondara | cDNA | 445 | 782 |
| LNU262 | | | GeneArt | 446 | 661 |
| LNU263 | pGXN (pKG + Nos + 35S) | BARLEY Hordeum vulgare L. Manit | cDNA | 447 | 662 |
| LNU265 | | | GeneArt | 448 | 663 |
| LNU266 | pKS (Pks_J) | MAIZE Zea mays L. OH43 | cDNA | 449 | 783 |
| LNU267 | pGXN (pKG + Nos + 35S) | MAIZE Zea mays L. B73 | cDNA | 450 | 665 |
| LNU268 | pKS (Pks_J) | MAIZE Zea mays L. OH43 | cDNA | 451 | 666 |
| LNU27 | pGXN (pKG + Nos + 35S) | BARLEY Hordeum vulgare L. Manit | cDNA | 279 | 489 |
| LNU271 | pKS (Pks_J) | RICE Oryza sativa L. Indica TEBBONET | cDNA | 452 | 667 |
| LNU274 | pGXN (pKG + Nos + 35S) | RICE Oryza sativa L. Japonica LEMONT | cDNA | 453 | 668 |
| LNU275 | | | GeneArt | 454 | 669 |
| LNU276 | pKS (Pks_J) | RICE Oryza sativa L. Indica TEBBONET | cDNA | 455 | 784 |
| LNU277 | pKS (Pks_J) | RICE Oryza sativa L. Japonica ND | cDNA | 456 | 671 |
| LNU278 | Topo B | SORGHUM Sorghum bicolor ND | cDNA | 457 | 672 |
| LNU279 | pGXN (pKG + Nos + 35S) | SORGHUM Sorghum bicolor ND | cDNA | 458 | 673 |
| LNU28 | pGXN (pKG + Nos + 35S) | BARLEY Hordeum vulgare L. Manit | cDNA | 280 | 712 |
| LNU280 | pKS (Pks_J) | SORGHUM Sorghum bicolor ND | cDNA | 459 | 674 |
| LNU282 | | | GeneArt | 460 | 675 |
| LNU284 | pKS (Pks_J) | SOYBEAN Glycine max 40-219 | cDNA | 461 | 676 |
| LNU287 | pKS (Pks_J) | SOYBEAN Glycine max 40-219 | cDNA | 462 | 677 |
| LNU288 | pKS (Pks_J) | TOMATO Lycopersicum esculentum M82 | cDNA | 463 | 678 |
| LNU289 | pKS (Pks_J) | TOMATO Lycopersicum esculentum M82 | cDNA | 464 | 679 |
| LNU29 | pKS (Pks_J) | RICE Oryza sativa L. Japonica Nipponbare | cDNA | 281 | 491 |
| LNU3 | pGXN (pKG + Nos + 35S) | RICE Oryza sativa L. Japonica LEMONT | cDNA | 260 | 470 |
| LNU32 | | | GeneArt | 282 | 492 |

TABLE 59-continued

Genes cloned from cDNA libraries or genomic DNA in a High copy number plasmid

| Gene Name | High copy plasmid | Amplified from Organism | Origin | Polynucleotide SEQ ID NO: | Polypeptide SEQ ID NO: |
|---|---|---|---|---|---|
| LNU33 | pKS (Pks_J) | SOYBEAN *Glycine max* 58-261 | cDNA | 283 | 713 |
| LNU35 | Topo B | WHEAT *Triticum aestivum* L. ND | cDNA | 284 | 714 |
| LNU36 | pKS (Pks_J) | SOYBEAN *Glycine max* 58-261 | cDNA | 285 | 715 |
| LNU37 | pKS (Pks_J) | RICE *Oryza sativa* L. *Japonica* LEMONT | cDNA | 286 | 497 |
| LNU4 | pKS (Pks_J) | BARLEY *Hordeum vulgare* L. *Manit* | cDNA | 261 | 708 |
| LNU40 | pGXN (pKG + Nos + 35S) | RICE *Oryza sativa* L. *Japonica* PECOS + RICE *Oryza sativa* L. *Japonica* LEMONT | cDNA | 287 | 498 |
| LNU43 | pKS (Pks_J) | SOYBEAN *Glycine max* 58-261 | cDNA | 288 | 499 |
| LNU44 | pGXN (pKG + Nos + 35S) | SOYBEAN *Glycine max* 58-261 | cDNA | 289 | 500 |
| LNU45 | pGXN (pKG + Nos + 35S) | SOYBEAN *Glycine max* 58-261 | cDNA | 290 | 501 |
| LNU46 | pKS (Pks_J) | SOYBEAN *Glycine max* 58-261 | cDNA | 291 | 502 |
| LNU48 | pKS (Pks_J) | RICE *Oryza sativa* L. *Japonica* Nipponbare | cDNA | 292 | 503 |
| LNU5 | pKS (Pks_J) | BARLEY *Hordeum vulgare* L. ND | cDNA | 262 | 472 |
| LNU50 | pGXN (pKG + Nos + 35S) | RICE *Oryza sativa* L. *Japonica* ND | cDNA | 293 | 504 |
| LNU51 | | | GeneArt | 294 | 505 |
| LNU52 | pKS (Pks_J) | RICE *Oryza sativa* L. *Japonica* ND | cDNA | 295 | 506 |
| LNU53 | pKS (Pks_J) | SOYBEAN *Glycine max* 58-261 | cDNA | 296 | 716 |
| LNU54 | pGXN (pKG + Nos + 35S) | SOYBEAN *Glycine max* 58-261 | cDNA | 297 | 717 |
| LNU55 | pKS (Pks_J) | SOYBEAN *Glycine max* 58-261 | cDNA | 298 | 718 |
| LNU56 | pGXN (pKG + Nos + 35S) | SOYBEAN *Glycine max* 40-219 | cDNA | 299 | 510 |
| LNU57 | pGXN (pKG + Nos + 35S) | WHEAT *Triticum aestivum* L. ND | cDNA | 300 | 511 |
| LNU58 | Topo B | WHEAT *Triticum aestivum* L. ND | cDNA | 301 | 719 |
| LNU59 | | | GeneArt | 302 | 513 |
| LNU6 | pKS (Pks_J) | SOYBEAN *Glycine max* 58-261 | cDNA | 263 | 473 |
| LNU60 | Topo B | WHEAT *Triticum aestivum* L. ND | cDNA | 303 | 514 |
| LNU61 | Topo B | WHEAT *Triticum aestivum* L. ND | cDNA | 304 | 720 |
| LNU63 | pGXN (pKG + Nos + 35S) | WHEAT *Triticum aestivum* L. ND | cDNA | 305 | 516 |
| LNU64 | pKS (Pks_J) | WHEAT *Triticum aestivum* L. ND | cDNA | 306 | 721 |

TABLE 59-continued

Genes cloned from cDNA libraries or genomic DNA in a High copy number plasmid

| Gene Name | High copy plasmid | Amplified from Organism | Origin | Polynucleotide SEQ ID NO: | Polypeptide SEQ ID NO: |
|---|---|---|---|---|---|
| LNU65 | pKS (Pks_J) | RICE *Oryza sativa* L. *Japonica* ND | cDNA | 307 | 722 |
| LNU67 | Topo B | RICE *Oryza sativa* L. *Japonica* ND | cDNA | 308 | 723 |
| LNU68 | pKS (Pks_J) | RICE *Oryza sativa* L. *Japonica* LEMONT | cDNA | 309 | 520 |
| LNU69 | pKS (Pks_J) | RICE *Oryza sativa* L. *Japonica* LEMONT | cDNA | 310 | 521 |
| LNU7 | pGXN (pKG + Nos + 35S) | SOYBEAN *Glycine max* 40-219 | cDNA | 264 | 474 |
| LNU70 | pGXN (pKG + Nos + 35S) | RICE *Oryza sativa* L. *Japonica* LEMONT | cDNA | 311 | 724 |
| LNU71 | pKS (Pks_J) | RICE *Oryza sativa* L. *Japonica* Nipponbare | cDNA | 312 | 523 |
| LNU72 | pKS (Pks_J) | BARLEY *Hordeum vulgare* L. *Manit* | cDNA | 313 | 725 |
| LNU73 | pGXNa | RICE *Oryza sativa* L. *Indica* TEBBONET | cDNA | 314 | 525 |
| LNU74 | pGXN (pKG + Nos + 35S) | POPLAR *Populus* ND ND | cDNA | 315 | 726 |
| LNU75 | | | GeneArt | 316 | 527 |
| LNU76 | pKS (Pks_J) | RICE *Oryza sativa* L. *Indica* TEBBONET | cDNA | 317 | 528 |
| LNU79 | pKS (Pks_J) | COTTON *Gossypium hirsutum* ND | cDNA | 318 | 727 |
| LNU8 | pGXN (pKG + Nos + 35S) | *ARABIDOPSIS Arabidopsis thaliana* Columbia wt | cDNA | 265 | 475 |
| LNU81 | pGXN (pKG + Nos + 35S) | BARLEY *Hordeum vulgare* L. *Manit* | cDNA | 319 | 728 |
| LNU82 | pKS (Pks_J) | RICE *Oryza sativa* L. *Japonica* LEMONT | cDNA | 320 | 531 |
| LNU83 | pKS (Pks_J) | SOYBEAN *Glycine max* 58-261 | cDNA | 321 | 532 |
| LNU84 | pKS (Pks_J) | SORGHUM *Sorghum bicolor* ND | cDNA | 322 | 729 |
| LNU85 | pGXN (pKG + Nos + 35S) | SORGHUM *Sorghum bicolor* ND | cDNA | 323 | 534 |
| LNU86 | pKS (Pks_J) | MAIZE *Zea mays* L. OH43 | cDNA | 324 | 730 |
| LNU87 | pGXN (pKG + Nos + 35S) | SORGHUM *Sorghum bicolor* ND | cDNA | 325 | 731 |
| LNU89 | pKS (Pks_J) | WHEAT *Triticum aestivum* L. | cDNA | 326 | 732 |
| LNU9 | pGXN (pKG + Nos + 35S) | RICE *Oryza sativa* L. *Japonica* ND | cDNA | 266 | 476 |
| LNU94 | pGXN (pKG + Nos + 35S) | TOMATO *Lycopersicum esculentum* M82 | cDNA | 327 | 538 |
| LNU95 | pKS (Pks_J) | SOYBEAN *Glycine max* 58-261 | cDNA | 328 | 539 |

TABLE 59-continued

Genes cloned from cDNA libraries or genomic DNA in a High copy number plasmid

| Gene Name | High copy plasmid | Amplified from Organism | Origin | Polynucleotide SEQ ID NO: | Polypeptide SEQ ID NO: |
|---|---|---|---|---|---|
| LNU96 | pGXN (pKG + Nos + 35S) | RICE *Oryza sativa* L. *Japonica* LEMONT | cDNA | 329 | 733 |
| LNU98 | pKS (Pks_J) | MAIZE *Zea mays* L. B73 | cDNA | 330 | 734 |

Table 59.
"Polyn."—Polynucleotide;
"Polyp."—polypeptide.

Example 12

Transforming *Agrobacterium tumefaciens* Cells with Binary Vectors Harboring Putative Genes Each of the binary vectors described in Example 11 above were used to transform *Agrobacterium* cells. Two additional binary constructs, having only the At6669, or the RootP promoter or no additional promoter were used as negative controls.

The binary vectors were introduced to *Agrobacterium tumefaciens* GV301, or LB4404 competent cells (about $10^9$ cells/mL) by electroporation. The electroporation was performed using a MicroPulser electroporator (Biorad), 0.2 cm cuvettes (Biorad) and EC-2 electroporation program (Biorad). The treated cells were cultured in LB liquid medium at 28° C. for 3 hours, then plated over LB agar supplemented with gentamycin (50 mg/L; for *Agrobacterium* strains GV301) or streptomycin (300 mg/L; for *Agrobacterium* strain LB4404) and kanamycin (50 mg/L) at 28° C. for 48 hours. *Agrobacterium* colonies, which were developed on the selective media, were further analyzed by PCR using the primers designed to span the inserted sequence in the pPI plasmid. The resulting PCR products were isolated and sequenced as described in Example 11 above, to verify that the correct polynucleotide sequences of the invention are properly introduced to the *Agrobacterium* cells.

Example 13

Transformation of *Arabidopsis thaliana* Plants with the Polynucleotides of the Invention

*Arabidopsis thaliana* Columbia plants ($T_0$ plants) were transformed using the Floral Dip procedure described by Clough and Bent, 1998 (Floral dip: a simplified method for *Agrobacterium*-mediated transformation of *Arabidopsis thaliana*. Plant J 16:735-43) and by Desfeux et al., 2000 (Female Reproductive Tissues Are the Primary Target of *Agrobacterium*-Mediated Transformation by the *Arabidopsis* Floral-Dip Method. Plant Physiol, July 2000, Vol. 123, pp. 895-904), with minor modifications. Briefly, $T_0$ Plants were sown in 250 ml pots filled with wet peat-based growth mix. The pots are covered with aluminum foil and a plastic dome, kept at 4° C. for 3-4 days, then uncovered and incubated in a growth chamber at 18-24° C. under 16/8 hour light/dark cycles. The $T_0$ plants were ready for transformation six days before anthesis.

Single colonies of *Agrobacterium* carrying the binary constructs, were generated as described in Examples 11 and 12 above. Colonies were cultured in LB medium supplemented with kanamycin (50 mg/L) and gentamycin (50 mg/L). The cultures were incubated at 28° C. for 48 hours under vigorous shaking and then centrifuged at 4000 rpm for 5 minutes. The pellets comprising the *Agrobacterium* cells were re-suspended in a transformation medium containing half-strength (2.15 g/L) Murashige-Skoog (Duchefa); 0.044 µM benzylamino purine (Sigma); 112 µg/L B5 Gambourg vitamins (Sigma); 5% sucrose; and 0.2 ml/L Silwet L-77 (OSI Specialists, CT) in double-distilled water, at pH of 5.7.

Transformation of $T_0$ plants was performed by inverting each plant into an *Agrobacterium* suspension, such that the above ground plant tissue was submerged for 3-5 seconds. Each inoculated $T_0$ plant was immediately placed in a plastic tray, then covered with clear plastic dome to maintain humidity and was kept in the dark at room temperature for 18 hours, to facilitate infection and transformation. Transformed (transgenic) plants were then uncovered and transferred to a greenhouse for recovery and maturation. The transgenic $T_0$ plants were grown in the greenhouse for 3-5 weeks until siliques are brown and dry. Seeds were harvested from plants and kept at room temperature until sowing.

For generating $T_1$ and $T_2$ transgenic plants harboring the genes, seeds collected from transgenic $T_0$ plants were surface-sterilized by soaking in 70% ethanol for 1 minute, followed by soaking in 5% sodium hypochloride and 0.05% triton for 5 minutes. The surface-sterilized seeds were thoroughly washed in sterile distilled water then placed on culture plates containing half-strength Murashige-Skoog (Duchefa); 2% sucrose; 0.8% plant agar; 50 mM kanamycin; and 200 mM carbenicylin (Duchefa). The culture plates were incubated at 4° C. for 48 hours, then transferred to a growth room at 25° C. for an additional week of incubation. Vital $T_1$ *Arabidopsis* plants were transferred to fresh culture plates for another week of incubation. Following incubation the $T_1$ plants were removed from culture plates and planted in growth mix contained in 250 ml pots. The transgenic plants were allowed to grow in a greenhouse to maturity. Seeds harvested from $T_1$ plants were cultured and grown to maturity as $T_2$ plants under the same conditions as used for culturing and growing the $T_1$ plants.

Example 14

Evaluating Transgenic *Arabidopsis* NUE Under Low or Normal Nitrogen Conditions Using In Vitro (Tissue Culture) Assays Assay 1: Plant Growth Under Low and Favorable Nitrogen Concentration Levels Surface sterilized seeds were sown in basal media [50% Murashige-Skoog medium (MS) supplemented with 0.8% plant agar as solidifying agent] in the presence of Kanamycin (used as a selecting agent). After sowing, plates were transferred for 2-3 days for stratification at 4° C. and then grown at 25° C. under 12-hour light 12-hour dark daily cycles for 7 to 10 days. At this time point, seedlings randomly chosen were carefully transferred to plates containing ½ MS media (15 mM N) for the normal nitrogen concentration treatment and 0.75 mM nitrogen for the low nitrogen concentration treatments. For experiments performed in $T_2$ lines, each plate contained 5 seedlings of the same transgenic event, and 3-4 different plates (replicates) for each event. For each polynucleotide of the invention at least four-five independent transformation events were analyzed from each construct. For experiments performed in $T_1$ lines, each plate contained 5 seedlings of 5 independent transgenic events and 3-4 different plates (replicates) were planted. In total, for $T_1$ lines, 20 independent events were evaluated. Plants expressing the polynucleotides of the invention were compared to the average measurement of the control plants (empty vector or GUS reporter gene under the same promoter) used in the same experiment.

Digital imaging—A laboratory image acquisition system, which consists of a digital reflex camera (Canon EOS 300D) attached with a 55 mm focal length lens (Canon EF-S series), mounted on a reproduction device (Kaiser RS), which includes 4 light units (4×150 Watts light bulb) and located in a darkroom, is used for capturing images of plantlets sawn in agar plates.

The image capturing process is repeated every 3-4 days starting at day 1 till day 10 (see for example the images in FIGS. 3A-B). An image analysis system was used, which consists of a personal desktop computer (Intel P4 3.0 GHz processor) and a public domain program—ImageJ 1.39 [Java based image processing program which was developed at the U.S. National Institutes of Health and freely available on the internet at Hypertext Transfer Protocol://rsbweb (dot) nih (dot) gov/]. Images were captured in resolution of 10 Mega Pixels (3888×2592 pixels) and stored in a low compression JPEG (Joint Photographic Experts Group standard) format. Next, analyzed data was saved to text files and processed using the JMP statistical analysis software (SAS institute).

Seedling analysis—Using the digital analysis seedling data was calculated, including leaf area, root coverage and root length.

The relative growth rate for the various seedling parameters was calculated according to the following formulas XIII, V (described above) and XIV.

Relative growth rate of leaf area=Regression coefficient of leaf area along time course.   Formula XIII:

Relative growth rate of root length=Regression coefficient of root length along time course.   Formula XIV:

At the end of the experiment, plantlets were removed from the media and weighed for the determination of plant fresh weight. Plantlets were then dried for 24 hours at 60° C., and weighed again to measure plant dry weight for later statistical analysis. Growth rate was determined by comparing the leaf area coverage, root coverage and root length, between each couple of sequential photographs, and results are used to resolve the effect of the gene introduced on plant vigor under optimal conditions. Similarly, the effect of the gene introduced on biomass accumulation, under optimal conditions, was determined by comparing the plants' fresh and dry weight to that of control plants (containing an empty vector or the GUS reporter gene under the same promoter). From every construct created, 3-5 independent transformation events are examined in replicates.

Statistical analyses—To identify genes conferring significantly improved plant vigor or enlarged root architecture, the results obtained from the transgenic plants were compared to those obtained from control plants. To identify outperforming genes and constructs, results from the independent transformation events tested were analyzed separately. To evaluate the effect of a gene event over a control the data was analyzed by Student's t-test and the p value is calculated. Results were considered significant if p<0.1. The JMP statistics software package was used (Version 5.2.1, SAS Institute Inc., Cary, N.C., USA).

Experimental Results:

The genes presented in Tables 60-63 showed a significant improvement in plant NUE since they produced larger plant biomass (plant fresh and dry weight and leaf area) in T2 generation (Tables 60-61) or T1 generation (Tables 62-63) when grown under limiting nitrogen growth conditions, compared to control plants. The genes were cloned under the regulation of a constitutive promoter (At6669) or root preferred promoter (RootP). The evaluation of each gene was carried out by testing the performance of different number of events. Some of the genes were evaluated in more than one tissue culture assay. The results obtained in these second experiments were significantly positive as well.

TABLE 60

Genes showing improved plant performance at nitrogen deficient conditions (T2 generation)

| Gene Name | Event # | Plant Biomass Fresh Weight [gr.] | | | Gene Name | Event # | Plant Biomass Dry Weight [gr.] | | |
|---|---|---|---|---|---|---|---|---|---|
| | | Ave. | p-value | % incr. | | | Ave. | p-value | % incr. |
| CONT. | — | 0.125 | — | 0.0 | CONT. | — | 0.005 | — | 0.0 |
| LNU100 | 14474.3 | 0.198 | 0.046 | 58.5 | LNU100 | 14474.3 | 0.009 | 0.023 | 74.5 |
| LNU100 | 14473.1 | 0.145 | 0.099 | 15.8 | LNU100 | 14473.1 | 0.006 | 0.196 | 16.7 |
| LNU100 | 14473.3 | 0.132 | 0.728 | 5.7 | LNU104 | 25033.3 | 0.007 | 0.059 | 40.2 |
| LNU104 | 25033.3 | 0.166 | 0.090 | 32.5 | LNU104 | 25034.1 | 0.006 | 0.310 | 17.2 |
| LNU104 | 25034.1 | 0.130 | 0.761 | 3.9 | LNU213 | 24654.4 | 0.010 | 0.079 | 97.5 |
| LNU213 | 24654.4 | 0.228 | 0.068 | 82.1 | LNU213 | 24653.2 | 0.009 | 0.000 | 77.0 |
| LNU213 | 24653.2 | 0.183 | 0.007 | 46.2 | LNU213 | 24651.1 | 0.006 | 0.454 | 10.3 |
| LNU213 | 24651.1 | 0.134 | 0.538 | 7.6 | LNU218 | 24781.7 | 0.008 | 0.221 | 48.0 |
| LNU218 | 24781.7 | 0.169 | 0.355 | 35.0 | LNU218 | 24783.2 | 0.007 | 0.041 | 44.1 |
| LNU218 | 24783.2 | 0.160 | 0.034 | 28.3 | LNU4 | 25134.2 | 0.008 | 0.017 | 59.3 |
| LNU4 | 25134.1 | 0.186 | 0.009 | 49.2 | LNU4 | 25134.1 | 0.008 | 0.013 | 50.0 |
| LNU4 | 25134.2 | 0.181 | 0.051 | 45.1 | LNU48 | 24802.2 | 0.010 | 0.026 | 104.4 |

TABLE 60-continued

Genes showing improved plant performance at nitrogen deficient conditions (T2 generation)

| Gene Name | Event # | Plant Biomass Fresh Weight [gr.] | | | Gene Name | Event # | Plant Biomass Dry Weight [gr.] | | |
|---|---|---|---|---|---|---|---|---|---|
| | | Ave. | p-value | % incr. | | | Ave. | p-value | % incr. |
| LNU48 | 24802.2 | 0.223 | 0.017 | 78.4 | LNU48 | 24804.4 | 0.007 | 0.014 | 42.6 |
| LNU48 | 24803.2 | 0.151 | 0.082 | 20.9 | LNU48 | 24803.2 | 0.007 | 0.036 | 40.2 |
| LNU48 | 24804.4 | 0.146 | 0.090 | 16.5 | LNU8 | 25063.1 | 0.011 | 0.040 | 118.6 |
| LNU8 | 25063.1 | 0.244 | 0.026 | 95.6 | LNU8 | 25063.6 | 0.009 | 0.175 | 76.5 |
| LNU8 | 25063.6 | 0.182 | 0.150 | 45.4 | LNU8 | 25062.2 | 0.005 | 0.689 | 6.9 |
| LNU94 | 24833.3 | 0.167 | 0.027 | 34.0 | LNU94 | 24833.3 | 0.008 | 0.001 | 47.5 |
| LNU94 | 24834.1 | 0.160 | 0.030 | 27.7 | LNU94 | 24834.1 | 0.007 | 0.008 | 46.6 |
| LNU94 | 24834.4 | 0.133 | 0.660 | 6.7 | LNU94 | 24834.4 | 0.006 | 0.359 | 15.7 |
| CONT. | — | 0.110 | — | 0.0 | CONT. | — | 0.005 | — | 0.0 |
| LNU1 | 24681.3 | 0.178 | 0.041 | 60.9 | LNU1 | 24682.2 | 0.008 | 0.015 | 64.4 |
| LNU1 | 24682.2 | 0.155 | 0.069 | 40.8 | LNU1 | 24681.3 | 0.008 | 0.018 | 53.7 |
| LNU1 | 24684.1 | 0.141 | 0.037 | 28.1 | LNU1 | 24681.1 | 0.007 | 0.062 | 29.3 |
| LNU1 | 24681.1 | 0.130 | 0.167 | 17.9 | LNU1 | 24684.1 | 0.007 | 0.036 | 28.3 |
| LNU1 | 24682.1 | 0.120 | 0.640 | 8.5 | LNU1 | 24682.1 | 0.006 | 0.279 | 21.5 |
| LNU133 | 24744.3 | 0.178 | 0.005 | 61.2 | LNU133 | 24741.1 | 0.009 | 0.022 | 79.5 |
| LNU133 | 24741.1 | 0.174 | 0.020 | 57.2 | LNU133 | 24744.3 | 0.009 | 0.001 | 79.0 |
| LNU133 | 24741.2 | 0.117 | 0.614 | 5.5 | LNU133 | 24741.2 | 0.006 | 0.105 | 21.5 |
| LNU133 | 24744.2 | 0.115 | 0.651 | 4.5 | LNU133 | 24744.2 | 0.006 | 0.322 | 11.7 |
| LNU175 | 24732.4 | 0.220 | 0.076 | 99.3 | LNU175 | 24732.4 | 0.012 | 0.054 | 127.3 |
| LNU175 | 24732.1 | 0.191 | 0.001 | 72.7 | LNU175 | 24732.1 | 0.010 | 0.006 | 100.0 |
| LNU175 | 24734.4 | 0.153 | 0.155 | 38.4 | LNU175 | 24734.4 | 0.008 | 0.135 | 52.7 |
| LNU178 | 14611.5 | 0.167 | 0.005 | 50.8 | LNU175 | 24731.2 | 0.005 | 0.566 | 6.3 |
| LNU178 | 14614.5 | 0.141 | 0.050 | 27.5 | LNU178 | 14611.5 | 0.009 | 0.002 | 70.7 |
| LNU178 | 14612.1 | 0.119 | 0.527 | 8.2 | LNU178 | 14614.5 | 0.007 | 0.031 | 38.0 |
| LNU178 | 14611.1 | 0.114 | 0.751 | 3.3 | LNU178 | 14611.1 | 0.006 | 0.448 | 10.7 |
| LNU215 | 24664.3 | 0.174 | 0.046 | 57.8 | LNU215 | 24664.3 | 0.008 | 0.012 | 54.1 |
| LNU215 | 24661.4 | 0.115 | 0.781 | 4.0 | LNU215 | 24661.4 | 0.006 | 0.592 | 9.8 |
| LNU24 | 24971.2 | 0.173 | 0.026 | 56.6 | LNU215 | 24664.2 | 0.006 | 0.567 | 7.3 |
| LNU24 | 24973.1 | 0.164 | 0.014 | 48.2 | LNU24 | 24973.1 | 0.009 | 0.030 | 67.8 |
| LNU24 | 24971.4 | 0.140 | 0.317 | 26.8 | LNU24 | 24971.2 | 0.008 | 0.044 | 63.9 |
| LNU6 | 24992.3 | 0.176 | 0.003 | 59.8 | LNU24 | 24971.4 | 0.008 | 0.193 | 46.3 |
| LNU6 | 24994.1 | 0.137 | 0.085 | 24.0 | LNU24 | 24972.1 | 0.006 | 0.307 | 11.2 |
| LNU6 | 24994.2 | 0.128 | 0.208 | 16.3 | LNU6 | 24992.3 | 0.009 | 0.013 | 67.8 |
| LNU6 | 24993.3 | 0.122 | 0.581 | 10.2 | LNU6 | 24994.2 | 0.007 | 0.040 | 35.1 |
| LNU6 | 24994.5 | 0.118 | 0.554 | 6.8 | LNU6 | 24994.1 | 0.006 | 0.081 | 25.4 |
| LNU82 | 24823.1 | 0.133 | 0.171 | 20.5 | LNU6 | 24993.3 | 0.006 | 0.434 | 12.7 |
| LNU9 | 25001.3 | 0.155 | 0.200 | 40.5 | LNU6 | 24994.5 | 0.006 | 0.322 | 12.7 |
| LNU9 | 25001.1 | 0.138 | 0.268 | 25.4 | LNU82 | 24823.1 | 0.006 | 0.086 | 24.4 |
| LNU9 | 25003.1 | 0.123 | 0.419 | 11.3 | LNU9 | 25001.3 | 0.007 | 0.102 | 33.7 |
| CONT. | — | 0.104 | — | 0.0 | LNU9 | 25001.1 | 0.007 | 0.162 | 33.2 |
| LNU120 | 25463.7 | 0.172 | 0.047 | 66.1 | LNU9 | 25003.1 | 0.006 | 0.360 | 19.0 |
| LNU120 | 25463.3 | 0.151 | 0.018 | 45.3 | CONT. | — | 0.005 | — | 0.0 |
| LNU124 | 14501.7 | 0.179 | 0.001 | 72.5 | LNU120 | 25463.7 | 0.007 | 0.230 | 48.7 |
| LNU124 | 14502.7 | 0.120 | 0.105 | 15.5 | LNU120 | 25463.3 | 0.006 | 0.025 | 21.5 |
| LNU124 | 14501.1 | 0.117 | 0.229 | 12.9 | LNU124 | 14501.7 | 0.007 | 0.018 | 41.5 |
| LNU132 | 14101.9 | 0.131 | 0.316 | 26.1 | LNU132 | 14101.9 | 0.005 | 0.616 | 7.7 |
| LNU132 | 14102.9 | 0.126 | 0.145 | 21.4 | LNU140 | 14112.7 | 0.010 | 0.012 | 110.3 |
| LNU140 | 14112.7 | 0.198 | 0.000 | 90.9 | LNU180 | 24724.3 | 0.012 | 0.000 | 148.2 |
| LNU140 | 14111.6 | 0.120 | 0.473 | 16.0 | LNU180 | 24723.3 | 0.006 | 0.044 | 32.3 |
| LNU140 | 14114.8 | 0.118 | 0.251 | 13.9 | LNU20 | 24932.4 | 0.005 | 0.414 | 10.8 |
| LNU140 | 14112.6 | 0.114 | 0.467 | 9.9 | LNU36 | 25562.3 | 0.009 | 0.130 | 82.6 |
| LNU180 | 24724.3 | 0.272 | 0.000 | 162.1 | LNU71 | 25853.4 | 0.007 | 0.043 | 53.3 |
| LNU180 | 24723.3 | 0.201 | 0.010 | 93.9 | CONT. | — | 0.005 | — | 0.0 |
| LNU180 | 24722.2 | 0.110 | 0.700 | 6.2 | LNU1 | 24681.3 | 0.007 | 0.295 | 45.1 |
| LNU196 | 25534.1 | 0.138 | 0.168 | 32.7 | LNU1 | 24683.2 | 0.005 | 0.703 | 4.9 |
| LNU196 | 25533.1 | 0.119 | 0.207 | 15.0 | LNU110 | 24952.2 | 0.015 | 0.450 | 215.1 |
| LNU20 | 24932.4 | 0.149 | 0.119 | 43.4 | LNU110 | 24952.3 | 0.008 | 0.159 | 60.0 |
| LNU20 | 24933.2 | 0.112 | 0.591 | 7.4 | LNU110 | 24953.3 | 0.006 | 0.466 | 18.6 |
| LNU36 | 25562.3 | 0.193 | 0.138 | 85.9 | LNU110 | 24953.2 | 0.006 | 0.276 | 13.3 |
| LNU36 | 25562.4 | 0.115 | 0.538 | 10.9 | LNU175 | 24732.2 | 0.008 | 0.127 | 66.8 |
| LNU71 | 25853.4 | 0.187 | 0.035 | 79.9 | LNU175 | 24733.4 | 0.005 | 0.748 | 5.9 |
| LNU71 | 25852.4 | 0.117 | 0.413 | 13.2 | LNU19 | 25151.1 | 0.006 | 0.094 | 25.0 |
| CONT. | — | 0.117 | — | 0.0 | LNU19 | 25153.3 | 0.006 | 0.456 | 24.5 |
| LNU1 | 24681.3 | 0.156 | 0.381 | 32.5 | LNU215 | 24664.2 | 0.008 | 0.001 | 70.0 |
| LNU1 | 24683.2 | 0.133 | 0.365 | 13.5 | LNU215 | 24663.3 | 0.005 | 0.272 | 12.8 |
| LNU110 | 24953.3 | 0.164 | 0.014 | 40.1 | LNU215 | 24663.4 | 0.005 | 0.339 | 10.7 |
| LNU110 | 24952.3 | 0.164 | 0.248 | 39.7 | LNU27 | 24873.4 | 0.007 | 0.097 | 46.7 |
| LNU110 | 24953.2 | 0.130 | 0.389 | 11.1 | LNU27 | 24873.1 | 0.007 | 0.161 | 45.7 |
| LNU175 | 24732.2 | 0.182 | 0.105 | 55.4 | LNU27 | 24872.4 | 0.005 | 0.541 | 6.5 |
| LNU175 | 24733.4 | 0.139 | 0.069 | 18.7 | LNU44 | 24924.2 | 0.019 | 0.270 | 304.1 |
| LNU175 | 24734.4 | 0.128 | 0.430 | 9.5 | LNU44 | 24924.3 | 0.009 | 0.055 | 100.2 |
| LNU19 | 25151.1 | 0.186 | 0.081 | 58.6 | LNU44 | 24922.3 | 0.005 | 0.770 | 8.1 |

TABLE 60-continued

Genes showing improved plant performance at nitrogen deficient conditions (T2 generation)

| Gene Name | Event # | Plant Biomass Fresh Weight [gr.] | | | Gene Name | Event # | Plant Biomass Dry Weight [gr.] | | |
|---|---|---|---|---|---|---|---|---|---|
| | | Ave. | p-value | % incr. | | | Ave. | p-value | % incr. |
| LNU19 | 25153.3 | 0.155 | 0.241 | 32.5 | LNU44 | 24923.3 | 0.005 | 0.576 | 5.4 |
| LNU19 | 25151.11 | 0.129 | 0.581 | 10.0 | LNU54 | 24903.5 | 0.012 | 0.004 | 154.8 |
| LNU215 | 24664.2 | 0.196 | 0.020 | 67.1 | LNU54 | 24903.3 | 0.008 | 0.014 | 79.0 |
| LNU215 | 24663.4 | 0.147 | 0.139 | 25.4 | LNU54 | 24901.2 | 0.008 | 0.049 | 75.3 |
| LNU215 | 24663.3 | 0.128 | 0.466 | 8.9 | LNU79 | 24884.4 | 0.011 | 0.028 | 122.5 |
| LNU215 | 24661.4 | 0.127 | 0.595 | 8.4 | LNU79 | 24884.3 | 0.008 | 0.050 | 72.1 |
| LNU27 | 24873.1 | 0.205 | 0.097 | 74.4 | LNU79 | 24881.1 | 0.007 | 0.041 | 47.8 |
| LNU27 | 24873.4 | 0.172 | 0.044 | 46.2 | LNU79 | 24882.2 | 0.005 | 0.321 | 13.3 |
| LNU27 | 24872.4 | 0.130 | 0.200 | 10.6 | CONT. | — | 0.006 | — | 0.0 |
| LNU44 | 24924.3 | 0.239 | 0.019 | 103.9 | LNU109 | 24891.5 | 0.009 | 0.009 | 52.1 |
| LNU44 | 24924.2 | 0.218 | 0.056 | 85.8 | LNU109 | 24892.6 | 0.008 | 0.184 | 38.3 |
| LNU44 | 24922.3 | 0.151 | 0.203 | 28.6 | LNU109 | 24892.6 | 0.008 | 0.164 | 29.3 |
| LNU44 | 24923.3 | 0.123 | 0.759 | 4.5 | LNU109 | 24891.2 | 0.007 | 0.371 | 28.0 |
| LNU54 | 24903.5 | 0.259 | 0.000 | 121.0 | LNU110 | 24952.1 | 0.015 | 0.000 | 162.5 |
| LNU54 | 24901.2 | 0.201 | 0.005 | 70.9 | LNU110 | 24953.2 | 0.010 | 0.036 | 79.1 |
| LNU54 | 24903.3 | 0.166 | 0.071 | 41.4 | LNU110 | 24952.3 | 0.009 | 0.153 | 51.6 |
| LNU79 | 24884.4 | 0.247 | 0.003 | 110.9 | LNU110 | 24954.3 | 0.007 | 0.063 | 27.1 |
| LNU79 | 24884.3 | 0.190 | 0.031 | 61.6 | LNU133 | 24744.3 | 0.011 | 0.020 | 90.7 |
| LNU79 | 24881.1 | 0.169 | 0.074 | 44.2 | LNU133 | 24741.1 | 0.010 | 0.091 | 63.2 |
| LNU79 | 24882.2 | 0.135 | 0.113 | 14.9 | LNU133 | 24741.2 | 0.008 | 0.006 | 37.5 |
| CONT. | — | 0.138 | — | 0.0 | LNU133 | 24744.2 | 0.007 | 0.220 | 21.1 |
| LNU109 | 24892.5 | 0.200 | 0.181 | 44.6 | LNU133 | 24742.2 | 0.006 | 0.581 | 5.7 |
| LNU109 | 24891.5 | 0.179 | 0.056 | 29.3 | LNU19 | 25151.1 | 0.011 | 0.124 | 86.9 |
| LNU109 | 24891.2 | 0.179 | 0.351 | 29.1 | LNU27 | 24873.4 | 0.012 | 0.015 | 107.9 |
| LNU109 | 24892.6 | 0.160 | 0.417 | 15.9 | LNU44 | 24922.3 | 0.014 | 0.009 | 136.3 |
| LNU110 | 24952.1 | 0.333 | 0.006 | 140.4 | LNU44 | 24923.1 | 0.007 | 0.129 | 25.0 |
| LNU110 | 24953.2 | 0.224 | 0.053 | 61.9 | LNU44 | 24924.3 | 0.007 | 0.191 | 21.6 |
| LNU110 | 24952.3 | 0.189 | 0.257 | 36.4 | LNU54 | 24901.2 | 0.009 | 0.041 | 59.4 |
| LNU133 | 24744.3 | 0.213 | 0.014 | 54.0 | LNU54 | 24903.5 | 0.009 | 0.036 | 58.5 |
| LNU133 | 24741.1 | 0.176 | 0.226 | 27.1 | LNU54 | 24902.4 | 0.009 | 0.037 | 52.9 |
| LNU133 | 24741.2 | 0.175 | 0.056 | 26.5 | LNU6 | 24994.5 | 0.009 | 0.047 | 55.1 |
| LNU133 | 24744.2 | 0.150 | 0.549 | 8.5 | LNU6 | 24992.3 | 0.009 | 0.018 | 54.6 |
| LNU19 | 25151.1 | 0.198 | 0.151 | 42.8 | LNU6 | 24994.1 | 0.007 | 0.450 | 22.0 |
| LNU27 | 24873.4 | 0.235 | 0.021 | 70.0 | LNU6 | 24994.2 | 0.007 | 0.201 | 14.3 |
| LNU44 | 24922.3 | 0.259 | 0.004 | 86.9 | LNU79 | 24884.4 | 0.010 | 0.008 | 79.1 |
| LNU44 | 24923.1 | 0.162 | 0.055 | 17.1 | LNU79 | 24882.2 | 0.010 | 0.005 | 64.5 |
| LNU44 | 24924.3 | 0.156 | 0.511 | 12.6 | LNU79 | 24881.1 | 0.008 | 0.049 | 45.2 |
| LNU54 | 24901.2 | 0.215 | 0.060 | 55.2 | LNU79 | 24884.3 | 0.007 | 0.204 | 21.6 |
| LNU54 | 24903.5 | 0.188 | 0.013 | 36.2 | CONT. | — | 0.004 | — | 0.0 |
| LNU54 | 24902.4 | 0.187 | 0.003 | 35.2 | LNU109 | 24892.8 | 0.009 | 0.040 | 152.1 |
| LNU6 | 24992.3 | 0.177 | 0.118 | 27.9 | LNU109 | 24891.2 | 0.009 | 0.005 | 140.4 |
| LNU6 | 24994.5 | 0.174 | 0.084 | 25.8 | LNU109 | 24892.5 | 0.005 | 0.058 | 48.6 |
| LNU6 | 24994.1 | 0.165 | 0.300 | 19.0 | LNU109 | 24891.5 | 0.005 | 0.205 | 35.6 |
| LNU6 | 24994.2 | 0.144 | 0.779 | 4.4 | LNU143 | 25971.5 | 0.006 | 0.039 | 65.1 |
| LNU79 | 24884.4 | 0.218 | 0.020 | 57.8 | LNU143 | 25975.3 | 0.006 | 0.183 | 58.9 |
| LNU79 | 24882.2 | 0.206 | 0.105 | 48.6 | LNU143 | 25972.1 | 0.005 | 0.046 | 47.9 |
| LNU79 | 24881.1 | 0.169 | 0.118 | 21.8 | LNU143 | 25975.2 | 0.005 | 0.118 | 41.1 |
| CONT. | — | 0.113 | — | 0.0 | LNU143 | 25971.2 | 0.004 | 0.699 | 6.8 |
| LNU109 | 24892.8 | 0.192 | 0.149 | 69.7 | LNU154 | 14601.6 | 0.007 | 0.067 | 104.1 |
| LNU109 | 24891.2 | 0.178 | 0.028 | 57.7 | LNU154 | 14604.7 | 0.007 | 0.095 | 102.7 |
| LNU109 | 24892.5 | 0.139 | 0.350 | 23.4 | LNU154 | 14604.6 | 0.007 | 0.101 | 80.8 |
| LNU109 | 24891.5 | 0.121 | 0.763 | 6.9 | LNU154 | 14602.8 | 0.006 | 0.092 | 52.1 |
| LNU143 | 25972.1 | 0.143 | 0.231 | 26.2 | LNU154 | 14604.4 | 0.005 | 0.233 | 36.3 |
| LNU143 | 25975.3 | 0.132 | 0.524 | 16.8 | LNU196 | 25532.2 | 0.010 | 0.019 | 164.4 |
| LNU143 | 25971.5 | 0.124 | 0.536 | 9.9 | LNU196 | 25534.1 | 0.007 | 0.075 | 93.2 |
| LNU154 | 14604.7 | 0.167 | 0.182 | 47.9 | LNU196 | 25531.2 | 0.006 | 0.150 | 54.8 |
| LNU154 | 14604.6 | 0.164 | 0.116 | 45.2 | LNU196 | 25532.1 | 0.005 | 0.350 | 38.4 |
| LNU154 | 14601.6 | 0.154 | 0.353 | 36.3 | LNU207 | 24642.5 | 0.008 | 0.086 | 119.2 |
| LNU196 | 25532.2 | 0.220 | 0.017 | 94.9 | LNU207 | 24642.4 | 0.008 | 0.029 | 115.1 |
| LNU196 | 25534.1 | 0.172 | 0.103 | 52.6 | LNU207 | 24644.18 | 0.007 | 0.040 | 78.8 |
| LNU196 | 25531.2 | 0.140 | 0.382 | 24.3 | LNU207 | 24641.1 | 0.004 | 0.564 | 11.0 |
| LNU196 | 25532.1 | 0.121 | 0.716 | 7.6 | LNU288 | 14562.12 | 0.005 | 0.045 | 49.3 |
| LNU207 | 24642.5 | 0.177 | 0.042 | 56.6 | LNU288 | 14562.7 | 0.005 | 0.181 | 45.2 |
| LNU207 | 24642.4 | 0.166 | 0.022 | 47.3 | LNU288 | 14562.9 | 0.005 | 0.292 | 36.3 |
| LNU207 | 24644.18 | 0.152 | 0.058 | 34.8 | LNU288 | 14562.1 | 0.004 | 0.408 | 21.9 |
| LNU288 | 14562.9 | 0.120 | 0.720 | 5.8 | LNU288 | 14564.9 | 0.004 | 0.427 | 17.1 |
| LNU50 | 26024.2 | 0.153 | 0.131 | 35.4 | LNU50 | 26024.2 | 0.006 | 0.085 | 58.9 |
| LNU52 | 25723.2 | 0.242 | 0.001 | 114.0 | LNU50 | 26025.4 | 0.005 | 0.080 | 39.0 |
| LNU52 | 25721.4 | 0.172 | 0.302 | 52.1 | LNU50 | 26023.2 | 0.005 | 0.207 | 37.0 |
| LNU52 | 25721.3 | 0.125 | 0.624 | 10.3 | LNU50 | 26022.1 | 0.004 | 0.464 | 19.9 |
| CONT. | — | 0.125 | — | 0.0 | LNU50 | 26023.5 | 0.004 | 0.507 | 13.0 |
| LNU143 | 25975.2 | 0.132 | 0.701 | 6.0 | LNU52 | 25723.2 | 0.012 | 0.001 | 230.8 |

TABLE 60-continued

Genes showing improved plant performance at nitrogen deficient conditions (T2 generation)

| Gene Name | Event # | Plant Biomass Fresh Weight [gr.] Ave. | p-value | % incr. | Gene Name | Event # | Plant Biomass Dry Weight [gr.] Ave. | p-value | % incr. |
|---|---|---|---|---|---|---|---|---|---|
| LNU154 | 14602.8 | 0.152 | 0.202 | 21.6 | LNU52 | 25721.4 | 0.009 | 0.172 | 134.2 |
| LNU154 | 14604.4 | 0.140 | 0.688 | 12.4 | LNU52 | 25721.3 | 0.006 | 0.062 | 54.8 |
| LNU154 | 14601.6 | 0.133 | 0.706 | 6.7 | LNU52 | 25721.1 | 0.005 | 0.481 | 32.2 |
| LNU207 | 24642.5 | 0.227 | 0.038 | 81.8 | CONT. | — | 0.006 | — | 0.0 |
| LNU207 | 24641.1 | 0.197 | 0.068 | 58.0 | LNU143 | 25975.3 | 0.006 | 0.736 | 5.7 |
| LNU207 | 24642.4 | 0.155 | 0.239 | 24.6 | LNU154 | 14602.8 | 0.008 | 0.061 | 36.7 |
| LNU211 | 24771.1 | 0.143 | 0.348 | 14.4 | LNU154 | 14601.6 | 0.006 | 0.592 | 10.2 |
| LNU211 | 24774.4 | 0.135 | 0.764 | 7.9 | LNU207 | 24642.5 | 0.011 | 0.028 | 91.5 |
| LNU52 | 25723.2 | 0.202 | 0.194 | 61.8 | LNU207 | 24641.1 | 0.008 | 0.094 | 51.5 |
| LNU52 | 25721.2 | 0.191 | 0.018 | 52.8 | LNU207 | 24642.4 | 0.007 | 0.244 | 28.1 |
| LNU52 | 25723.1 | 0.183 | 0.022 | 46.8 | LNU211 | 24771.1 | 0.009 | 0.007 | 60.5 |
| LNU52 | 25721.1 | 0.170 | 0.140 | 36.2 | LNU211 | 24774.4 | 0.007 | 0.411 | 18.7 |
| LNU69 | 14572.8 | 0.192 | 0.089 | 54.2 | LNU52 | 25721.2 | 0.009 | 0.029 | 59.2 |
| LNU69 | 14571.1 | 0.164 | 0.335 | 31.7 | LNU52 | 25721.1 | 0.009 | 0.065 | 56.0 |
| LNU69 | 14572.9 | 0.131 | 0.794 | 5.2 | LNU52 | 25723.2 | 0.008 | 0.176 | 48.4 |
| CONT. | — | 0.123 | — | 0.0 | LNU52 | 25723.1 | 0.007 | 0.241 | 23.7 |
| LNU150 | 24842.9 | 0.199 | 0.000 | 61.6 | LNU69 | 14571.1 | 0.008 | 0.095 | 48.4 |
| LNU150 | 24841.9 | 0.168 | 0.204 | 36.0 | LNU69 | 14572.8 | 0.006 | 0.278 | 14.7 |
| LNU150 | 24843.5 | 0.152 | 0.280 | 23.5 | LNU69 | 14572.9 | 0.006 | 0.482 | 12.0 |
| LNU179 | 24632.5 | 0.185 | 0.008 | 49.8 | CONT. | — | 0.006 | — | 0.0 |
| LNU179 | 24631.9 | 0.146 | 0.079 | 18.6 | LNU150 | 24842.9 | 0.009 | 0.000 | 60.6 |
| LNU232 | 26003.7 | 0.148 | 0.137 | 20.4 | LNU150 | 24841.9 | 0.007 | 0.462 | 19.7 |
| LNU235 | 26185.3 | 0.182 | 0.161 | 47.4 | LNU179 | 24632.5 | 0.008 | 0.139 | 42.3 |
| LNU235 | 26184.4 | 0.173 | 0.171 | 40.6 | LNU235 | 26184.4 | 0.008 | 0.111 | 43.6 |
| LNU242 | 25473.1 | 0.184 | 0.064 | 48.9 | LNU235 | 26185.3 | 0.007 | 0.425 | 21.4 |
| LNU242 | 25474.1 | 0.158 | 0.012 | 28.1 | LNU242 | 25473.1 | 0.007 | 0.047 | 23.5 |
| LNU242 | 25471.1 | 0.151 | 0.138 | 22.4 | LNU242 | 25474.1 | 0.007 | 0.335 | 11.2 |
| LNU76 | 26423.1 | 0.181 | 0.032 | 46.5 | LNU242 | 25471.1 | 0.006 | 0.525 | 8.2 |
| LNU76 | 26421.2 | 0.163 | 0.150 | 31.9 | LNU76 | 26423.1 | 0.008 | 0.048 | 38.0 |
| LNU76 | 26425.1 | 0.148 | 0.327 | 20.1 | LNU76 | 26421.2 | 0.007 | 0.155 | 23.5 |
| LNU76 | 26421.1 | 0.145 | 0.294 | 18.0 | LNU76 | 26425.1 | 0.007 | 0.569 | 12.9 |
| LNU76 | 26422.2 | 0.136 | 0.415 | 10.4 | LNU76 | 26421.1 | 0.006 | 0.730 | 5.6 |
| LNU95 | 13985.11 | 0.211 | 0.001 | 71.2 | LNU95 | 13985.11 | 0.011 | 0.001 | 84.9 |
| LNU95 | 13985.15 | 0.145 | 0.495 | 17.6 | LNU95 | 13985.12 | 0.007 | 0.535 | 13.3 |
| LNU95 | 13985.12 | 0.144 | 0.439 | 16.7 | LNU95 | 13985.15 | 0.007 | 0.716 | 11.6 |
| CONT. | — | 0.128 | — | 0.0 | CONT. | — | 0.006 | — | 0.0 |
| LNU118 | 14013.8 | 0.187 | 0.095 | 46.0 | LNU118 | 14013.6 | 0.010 | 0.019 | 70.3 |
| LNU118 | 14013.6 | 0.182 | 0.009 | 41.9 | LNU118 | 14012.15 | 0.008 | 0.122 | 41.6 |
| LNU118 | 14012.15 | 0.166 | 0.282 | 29.8 | LNU118 | 14013.8 | 0.008 | 0.070 | 38.2 |
| LNU150 | 24841.9 | 0.163 | 0.240 | 27.0 | LNU118 | 14012.12 | 0.007 | 0.604 | 12.1 |
| LNU150 | 24842.9 | 0.136 | 0.793 | 6.2 | LNU150 | 24841.6 | 0.007 | 0.213 | 19.8 |
| LNU150 | 24841.6 | 0.135 | 0.634 | 5.2 | LNU150 | 24841.9 | 0.007 | 0.506 | 13.4 |
| LNU179 | 24631.7 | 0.161 | 0.036 | 25.9 | LNU179 | 24631.7 | 0.008 | 0.031 | 36.0 |
| LNU179 | 24631.6 | 0.148 | 0.451 | 15.4 | LNU179 | 24631.6 | 0.007 | 0.225 | 19.4 |
| LNU179 | 24631.9 | 0.137 | 0.728 | 7.2 | LNU232 | 26001.5 | 0.008 | 0.191 | 41.6 |
| LNU232 | 26001.5 | 0.161 | 0.388 | 25.6 | LNU232 | 26003.6 | 0.006 | 0.660 | 8.7 |
| LNU235 | 26185.2 | 0.241 | 0.023 | 88.2 | LNU235 | 26184.4 | 0.013 | 0.002 | 115.2 |
| LNU235 | 26184.4 | 0.237 | 0.006 | 85.1 | LNU235 | 26185.2 | 0.012 | 0.020 | 99.8 |
| LNU235 | 26184.2 | 0.211 | 0.044 | 64.6 | LNU235 | 26184.2 | 0.010 | 0.019 | 72.4 |
| LNU235 | 26182.1 | 0.147 | 0.303 | 14.3 | LNU242 | 25474.1 | 0.007 | 0.042 | 26.6 |
| LNU242 | 25474.1 | 0.148 | 0.306 | 15.6 | LNU288 | 14563.9 | 0.011 | 0.003 | 83.1 |
| LNU288 | 14563.9 | 0.232 | 0.000 | 81.1 | LNU288 | 14562.1 | 0.010 | 0.004 | 65.6 |
| LNU288 | 14562.1 | 0.208 | 0.025 | 62.0 | LNU288 | 14564.9 | 0.007 | 0.114 | 23.6 |
| LNU288 | 14564.9 | 0.169 | 0.117 | 31.9 | LNU288 | 14562.7 | 0.007 | 0.420 | 15.9 |
| LNU288 | 14562.7 | 0.166 | 0.237 | 29.2 | LNU76 | 26421.2 | 0.009 | 0.307 | 56.1 |
| LNU76 | 26421.2 | 0.193 | 0.330 | 50.5 | LNU76 | 26423.1 | 0.008 | 0.313 | 41.6 |
| LNU76 | 26423.1 | 0.176 | 0.314 | 37.7 | LNU76 | 26422.2 | 0.007 | 0.489 | 18.1 |
| LNU76 | 26422.2 | 0.151 | 0.434 | 18.1 | LNU95 | 13985.16 | 0.014 | 0.005 | 133.6 |
| LNU95 | 13985.16 | 0.250 | 0.003 | 94.8 | LNU95 | 13985.12 | 0.011 | 0.000 | 92.9 |
| LNU95 | 13985.12 | 0.239 | 0.001 | 86.4 | LNU95 | 13985.15 | 0.011 | 0.020 | 86.1 |
| LNU95 | 13985.15 | 0.223 | 0.008 | 74.1 | LNU95 | 13985.19 | 0.007 | 0.490 | 11.7 |
| LNU95 | 13985.19 | 0.136 | 0.658 | 6.5 | CONT. | — | 0.007 | — | 0.0 |
| CONT. | — | 0.149 | — | 0.0 | LNU101 | 27632.7 | 0.007 | 0.435 | 9.2 |
| LNU101 | 27632.7 | 0.179 | 0.122 | 19.6 | LNU101 | 27632.1 | 0.007 | 0.685 | 5.9 |
| LNU128 | 26515.3 | 0.210 | 0.062 | 40.6 | LNU101 | 27635.1 | 0.007 | 0.516 | 4.4 |
| LNU192 | 28315.2 | 0.200 | 0.012 | 33.7 | LNU128 | 26515.3 | 0.010 | 0.081 | 45.4 |
| LNU206 | 27621.2 | 0.180 | 0.159 | 20.7 | LNU192 | 28315.2 | 0.009 | 0.015 | 33.5 |
| LNU211 | 24771.1 | 0.208 | 0.018 | 39.5 | LNU192 | 28313.3 | 0.008 | 0.598 | 4.4 |
| LNU211 | 24773.2 | 0.162 | 0.576 | 8.8 | LNU206 | 27621.2 | 0.008 | 0.001 | 23.8 |
| LNU282 | 27563.3 | 0.204 | 0.036 | 36.4 | LNU211 | 24771.1 | 0.011 | 0.059 | 66.6 |
| LNU282 | 27562.1 | 0.164 | 0.466 | 9.7 | LNU211 | 24773.2 | 0.008 | 0.451 | 22.3 |
| LNU69 | 14571.1 | 0.208 | 0.022 | 39.5 | LNU211 | 24773.1 | 0.007 | 0.509 | 5.9 |

TABLE 60-continued

Genes showing improved plant performance at nitrogen deficient conditions (T2 generation)

| Gene Name | Event # | Plant Biomass Fresh Weight [gr.] | | | Gene Name | Event # | Plant Biomass Dry Weight [gr.] | | |
|---|---|---|---|---|---|---|---|---|---|
| | | Ave. | p-value | % incr. | | | Ave. | p-value | % incr. |
| LNU75 | 27572.1 | 0.163 | 0.669 | 8.9 | LNU282 | 27563.3 | 0.010 | 0.018 | 54.7 |
| LNU75 | 27572.2 | 0.153 | 0.779 | 2.3 | LNU282 | 27563.1 | 0.008 | 0.141 | 17.1 |
| CONT. | — | 0.121 | — | 0.0 | LNU282 | 27562.1 | 0.007 | 0.571 | 7.7 |
| LNU101 | 27632.5 | 0.151 | 0.151 | 25.2 | LNU69 | 14571.1 | 0.011 | 0.000 | 58.1 |
| LNU118 | 14013.6 | 0.194 | 0.050 | 60.0 | LNU69 | 14572.9 | 0.007 | 0.722 | 6.2 |
| LNU118 | 14013.9 | 0.155 | 0.605 | 28.5 | LNU75 | 27572.2 | 0.008 | 0.191 | 18.5 |
| LNU118 | 14012.15 | 0.153 | 0.053 | 26.6 | LNU75 | 27572.1 | 0.007 | 0.647 | 7.4 |
| LNU118 | 14012.12 | 0.128 | 0.683 | 5.7 | CONT. | — | 0.005 | — | 0.0 |
| LNU206 | 27621.1 | 0.208 | 0.003 | 72.3 | LNU101 | 27632.5 | 0.006 | 0.003 | 36.7 |
| LNU206 | 27622.1 | 0.208 | 0.033 | 72.2 | LNU118 | 14013.6 | 0.007 | 0.027 | 59.8 |
| LNU206 | 27621.2 | 0.207 | 0.062 | 71.3 | LNU118 | 14012.15 | 0.007 | 0.008 | 50.7 |
| LNU206 | 27622.4 | 0.162 | 0.285 | 34.0 | LNU118 | 14013.8 | 0.005 | 0.693 | 9.9 |
| LNU249 | 26153.1 | 0.209 | 0.002 | 73.0 | LNU118 | 14013.9 | 0.005 | 0.674 | 6.2 |
| LNU249 | 26154.2 | 0.168 | 0.104 | 39.1 | LNU206 | 27621.1 | 0.010 | 0.003 | 112.9 |
| LNU282 | 27563.1 | 0.205 | 0.000 | 69.2 | LNU206 | 27622.1 | 0.010 | 0.056 | 110.7 |
| LNU282 | 27565.2 | 0.172 | 0.081 | 42.2 | LNU206 | 27621.2 | 0.010 | 0.073 | 109.1 |
| LNU282 | 27565.1 | 0.136 | 0.457 | 12.7 | LNU206 | 27622.4 | 0.007 | 0.230 | 57.6 |
| LNU288 | 14564.8 | 0.255 | 0.004 | 110.8 | LNU249 | 26153.1 | 0.010 | 0.010 | 114.5 |
| LNU288 | 14563.9 | 0.252 | 0.001 | 108.8 | LNU249 | 26154.2 | 0.008 | 0.229 | 65.7 |
| LNU288 | 14562.9 | 0.180 | 0.001 | 48.7 | LNU249 | 26152.4 | 0.005 | 0.454 | 11.5 |
| LNU288 | 14563.6 | 0.156 | 0.052 | 29.3 | LNU249 | 26152.2 | 0.005 | 0.664 | 6.7 |
| LNU288 | 14562.7 | 0.127 | 0.720 | 5.0 | LNU282 | 27563.1 | 0.008 | 0.006 | 78.0 |
| LNU75 | 27572.3 | 0.278 | 0.010 | 130.0 | LNU282 | 27565.2 | 0.007 | 0.125 | 53.9 |
| LNU75 | 27572.2 | 0.250 | 0.054 | 107.0 | LNU282 | 27565.1 | 0.005 | 0.749 | 5.6 |
| LNU75 | 27571.4 | 0.245 | 0.014 | 102.6 | LNU288 | 14563.9 | 0.011 | 0.005 | 144.5 |
| LNU75 | 27571.2 | 0.227 | 0.000 | 88.0 | LNU288 | 14564.8 | 0.010 | 0.009 | 120.4 |
| CONT. | — | 0.144 | — | 0.0 | LNU288 | 14562.9 | 0.007 | 0.048 | 58.7 |
| LNU11 | 28204.3 | 0.154 | 0.501 | 7.1 | LNU288 | 14563.6 | 0.007 | 0.085 | 52.8 |
| LNU183 | 24863.1 | 0.152 | 0.610 | 5.5 | LNU288 | 14562.7 | 0.006 | 0.116 | 24.9 |
| LNU201 | 28222.2 | 0.161 | 0.452 | 11.8 | LNU75 | 27572.2 | 0.014 | 0.054 | 192.2 |
| LNU268 | 26045.1 | 0.163 | 0.186 | 13.5 | LNU75 | 27572.3 | 0.012 | 0.011 | 153.1 |
| CONT. | — | 0.137 | — | 0.0 | LNU75 | 27571.2 | 0.010 | 0.002 | 117.2 |
| LNU11 | 28205.1 | 0.201 | 0.011 | 46.8 | LNU75 | 27571.4 | 0.010 | 0.003 | 109.7 |
| LNU11 | 28203.2 | 0.180 | 0.062 | 31.3 | CONT. | — | 0.006 | — | 0.0 |
| LNU11 | 28204.1 | 0.150 | 0.569 | 9.5 | LNU11 | 28204.3 | 0.007 | 0.121 | 26.6 |
| LNU11 | 28202.5 | 0.150 | 0.669 | 9.5 | LNU11 | 28205.2 | 0.006 | 0.737 | 7.7 |
| LNU11 | 28205.2 | 0.143 | 0.634 | 4.5 | LNU14 | 27823.2 | 0.006 | 0.686 | 2.1 |
| LNU112 | 28212.1 | 0.178 | 0.123 | 29.8 | LNU183 | 24863.1 | 0.006 | 0.752 | 4.3 |
| LNU112 | 28212.4 | 0.156 | 0.058 | 14.2 | LNU201 | 28222.2 | 0.006 | 0.679 | 9.4 |
| LNU112 | 28212.3 | 0.155 | 0.158 | 12.9 | LNU201 | 28223.1 | 0.006 | 0.773 | 3.0 |
| LNU14 | 27821.4 | 0.179 | 0.108 | 30.8 | LNU268 | 26044.2 | 0.007 | 0.291 | 21.0 |
| LNU14 | 27821.3 | 0.177 | 0.103 | 29.4 | LNU268 | 26045.1 | 0.007 | 0.087 | 18.0 |
| LNU14 | 27824.2 | 0.162 | 0.113 | 18.6 | CONT. | — | 0.006 | — | 0.0 |
| LNU183 | 24864.6 | 0.205 | 0.005 | 49.5 | LNU11 | 28205.1 | 0.008 | 0.211 | 27.7 |
| LNU183 | 24863.1 | 0.203 | 0.097 | 48.0 | LNU11 | 28204.1 | 0.007 | 0.466 | 13.3 |
| LNU183 | 24863.12 | 0.195 | 0.001 | 42.5 | LNU11 | 28203.2 | 0.007 | 0.514 | 9.6 |
| LNU183 | 24865.1 | 0.182 | 0.012 | 33.1 | LNU11 | 28202.5 | 0.007 | 0.747 | 8.8 |
| LNU191 | 28325.4 | 0.182 | 0.127 | 32.8 | LNU112 | 28212.1 | 0.009 | 0.100 | 38.2 |
| LNU191 | 28323.1 | 0.177 | 0.021 | 29.0 | LNU112 | 28212.3 | 0.007 | 0.185 | 16.5 |
| LNU191 | 28324.2 | 0.167 | 0.070 | 21.7 | LNU112 | 28212.4 | 0.007 | 0.598 | 6.0 |
| LNU191 | 28321.3 | 0.157 | 0.137 | 14.5 | LNU14 | 27821.4 | 0.008 | 0.083 | 28.9 |
| LNU201 | 28222.2 | 0.230 | 0.047 | 68.1 | LNU14 | 27821.3 | 0.008 | 0.212 | 22.1 |
| LNU201 | 28221.3 | 0.163 | 0.247 | 19.2 | LNU14 | 27824.2 | 0.007 | 0.268 | 13.3 |
| LNU201 | 28223.3 | 0.162 | 0.280 | 18.1 | LNU183 | 24863.12 | 0.009 | 0.005 | 51.4 |
| LNU268 | 26041.4 | 0.190 | 0.160 | 39.0 | LNU183 | 24864.6 | 0.009 | 0.030 | 49.8 |
| LNU268 | 26043.4 | 0.156 | 0.297 | 13.7 | LNU183 | 24863.1 | 0.009 | 0.013 | 42.6 |
| CONT. | — | 0.126 | — | 0.0 | LNU183 | 24865.1 | 0.009 | 0.029 | 42.6 |
| LNU107 | 14584.9 | 0.221 | 0.167 | 74.4 | LNU191 | 28325.4 | 0.009 | 0.063 | 37.8 |
| LNU107 | 14583.8 | 0.175 | 0.117 | 38.3 | LNU191 | 28323.1 | 0.008 | 0.017 | 30.5 |
| LNU107 | 14585.5 | 0.137 | 0.598 | 8.5 | LNU191 | 28324.2 | 0.007 | 0.554 | 7.2 |
| LNU116 | 14492.5 | 0.201 | 0.237 | 58.9 | LNU191 | 28321.3 | 0.007 | 0.689 | 5.2 |
| LNU116 | 14494.5 | 0.188 | 0.192 | 48.8 | LNU201 | 28222.2 | 0.012 | 0.014 | 86.3 |
| LNU116 | 14492.9 | 0.178 | 0.105 | 40.7 | LNU201 | 28221.3 | 0.009 | 0.158 | 38.6 |
| LNU116 | 14493.6 | 0.160 | 0.439 | 26.3 | LNU201 | 28223.3 | 0.007 | 0.290 | 20.1 |
| LNU121 | 25642.2 | 0.233 | 0.043 | 83.8 | LNU268 | 26041.4 | 0.009 | 0.138 | 44.2 |
| LNU121 | 27713.4 | 0.190 | 0.006 | 50.0 | LNU268 | 26043.4 | 0.007 | 0.746 | 5.2 |
| LNU121 | 27711.1 | 0.188 | 0.010 | 48.7 | CONT. | — | 0.005 | — | 0.0 |
| LNU121 | 27713.1 | 0.164 | 0.155 | 29.3 | LNU107 | 14583.8 | 0.009 | 0.034 | 86.2 |
| LNU126 | 25343.1 | 0.199 | 0.011 | 57.4 | LNU107 | 14584.9 | 0.008 | 0.021 | 73.0 |
| LNU126 | 25345.1 | 0.175 | 0.153 | 38.4 | LNU107 | 14585.5 | 0.006 | 0.282 | 24.3 |
| LNU126 | 25343.3 | 0.172 | 0.095 | 36.3 | LNU116 | 14492.9 | 0.008 | 0.017 | 66.1 |
| LNU158 | 27433.3 | 0.201 | 0.015 | 58.6 | LNU116 | 14492.5 | 0.007 | 0.048 | 54.5 |

TABLE 60-continued

Genes showing improved plant performance at nitrogen deficient conditions (T2 generation)

| Gene Name | Event # | Plant Biomass Fresh Weight [gr.] | | | Gene Name | Event # | Plant Biomass Dry Weight [gr.] | | |
|---|---|---|---|---|---|---|---|---|---|
| | | Ave. | p-value | % incr. | | | Ave. | p-value | % incr. |
| LNU158 | 27433.2 | 0.187 | 0.075 | 47.6 | LNU116 | 14494.5 | 0.007 | 0.101 | 43.9 |
| LNU158 | 27432.5 | 0.156 | 0.399 | 23.5 | LNU116 | 14493.6 | 0.005 | 0.544 | 7.9 |
| LNU177 | 24762.6 | 0.214 | 0.018 | 69.3 | LNU121 | 25642.2 | 0.010 | 0.017 | 106.3 |
| LNU182 | 25384.1 | 0.219 | 0.001 | 73.0 | LNU121 | 27713.4 | 0.009 | 0.001 | 83.1 |
| LNU182 | 25384.2 | 0.170 | 0.154 | 34.3 | LNU121 | 27713.1 | 0.007 | 0.010 | 48.1 |
| LNU182 | 25384.5 | 0.152 | 0.450 | 20.3 | LNU121 | 27711.1 | 0.007 | 0.010 | 47.6 |
| LNU182 | 27521.4 | 0.139 | 0.537 | 10.2 | LNU126 | 25343.1 | 0.009 | 0.022 | 97.4 |
| LNU2 | 25713.1 | 0.186 | 0.107 | 47.2 | LNU126 | 25345.1 | 0.008 | 0.145 | 59.3 |
| LNU2 | 27842.3 | 0.157 | 0.298 | 23.9 | LNU126 | 25343.3 | 0.007 | 0.085 | 39.7 |
| LNU2 | 27842.1 | 0.134 | 0.697 | 6.0 | LNU158 | 27433.3 | 0.010 | 0.015 | 107.4 |
| LNU225 | 25991.5 | 0.212 | 0.003 | 67.5 | LNU158 | 27432.5 | 0.008 | 0.100 | 69.3 |
| LNU225 | 25991.2 | 0.190 | 0.157 | 49.9 | LNU158 | 27433.2 | 0.008 | 0.092 | 59.8 |
| LNU239 | 26284.1 | 0.156 | 0.273 | 23.1 | LNU177 | 24762.6 | 0.008 | 0.001 | 77.8 |
| LNU239 | 26283.2 | 0.138 | 0.528 | 9.0 | LNU177 | 24764.9 | 0.006 | 0.184 | 32.3 |
| LNU83 | 27681.4 | 0.161 | 0.237 | 27.5 | LNU177 | 24765.2 | 0.006 | 0.282 | 21.2 |
| LNU83 | 27684.1 | 0.157 | 0.208 | 24.0 | LNU182 | 25384.1 | 0.010 | 0.000 | 107.4 |
| LNU83 | 27685.1 | 0.138 | 0.522 | 9.1 | LNU182 | 25384.2 | 0.008 | 0.006 | 77.2 |
| CONT. | — | 0.118 | — | 0.0 | LNU182 | 27521.4 | 0.007 | 0.006 | 39.2 |
| LNU107 | 14584.9 | 0.230 | 0.000 | 95.3 | LNU182 | 25384.5 | 0.006 | 0.172 | 30.7 |
| LNU107 | 14585.2 | 0.178 | 0.001 | 50.9 | LNU2 | 25713.1 | 0.008 | 0.060 | 74.1 |
| LNU107 | 14583.8 | 0.161 | 0.043 | 36.1 | LNU2 | 27842.3 | 0.007 | 0.037 | 43.9 |
| LNU107 | 14585.5 | 0.128 | 0.604 | 8.2 | LNU2 | 27842.1 | 0.006 | 0.035 | 27.5 |
| LNU116 | 14492.5 | 0.235 | 0.000 | 98.7 | LNU225 | 25991.5 | 0.011 | 0.000 | 136.0 |
| LNU116 | 14493.6 | 0.211 | 0.001 | 78.9 | LNU225 | 25991.2 | 0.010 | 0.186 | 115.3 |
| LNU116 | 14494.5 | 0.186 | 0.118 | 57.7 | LNU239 | 26284.1 | 0.007 | 0.012 | 40.7 |
| LNU116 | 14492.9 | 0.157 | 0.046 | 33.4 | LNU239 | 26283.2 | 0.005 | 0.576 | 9.5 |
| LNU116 | 14491.5 | 0.146 | 0.044 | 23.7 | LNU239 | 26281.1 | 0.005 | 0.686 | 9.0 |
| LNU121 | 27711.1 | 0.220 | 0.007 | 86.6 | LNU57 | 27854.5 | 0.005 | 0.373 | 13.2 |
| LNU121 | 27713.4 | 0.218 | 0.004 | 84.4 | LNU83 | 27684.1 | 0.007 | 0.162 | 47.1 |
| LNU121 | 25642.2 | 0.215 | 0.002 | 81.9 | LNU83 | 27681.4 | 0.007 | 0.169 | 41.1 |
| LNU121 | 27713.1 | 0.209 | 0.000 | 76.9 | CONT. | — | 0.004 | — | 0.0 |
| LNU121 | 27713.3 | 0.136 | 0.357 | 15.2 | LNU107 | 14584.9 | 0.010 | 0.002 | 148.1 |
| LNU126 | 25343.1 | 0.181 | 0.029 | 53.3 | LNU107 | 14585.2 | 0.007 | 0.021 | 84.0 |
| LNU126 | 25341.1 | 0.153 | 0.415 | 29.7 | LNU107 | 14583.8 | 0.007 | 0.055 | 70.4 |
| LNU126 | 25343.3 | 0.133 | 0.604 | 12.4 | LNU107 | 14585.5 | 0.005 | 0.107 | 24.7 |
| LNU126 | 25345.1 | 0.125 | 0.730 | 6.0 | LNU116 | 14492.5 | 0.010 | 0.000 | 140.7 |
| LNU158 | 27433.3 | 0.260 | 0.000 | 120.3 | LNU116 | 14494.5 | 0.008 | 0.000 | 109.3 |
| LNU158 | 27432.5 | 0.219 | 0.011 | 85.5 | LNU116 | 14493.6 | 0.008 | 0.000 | 104.9 |
| LNU158 | 27433.2 | 0.200 | 0.106 | 69.9 | LNU116 | 14492.9 | 0.007 | 0.131 | 74.7 |
| LNU158 | 27434.1 | 0.140 | 0.454 | 18.3 | LNU116 | 14491.5 | 0.006 | 0.000 | 58.6 |
| LNU177 | 24764.12 | 0.227 | 0.027 | 92.6 | LNU121 | 25642.2 | 0.009 | 0.022 | 122.8 |
| LNU177 | 24763.6 | 0.161 | 0.172 | 36.3 | LNU121 | 27713.1 | 0.008 | 0.022 | 105.6 |
| LNU177 | 24764.9 | 0.154 | 0.225 | 30.4 | LNU121 | 27711.1 | 0.008 | 0.051 | 104.9 |
| LNU182 | 25384.1 | 0.175 | 0.039 | 48.6 | LNU121 | 27713.4 | 0.008 | 0.006 | 95.1 |
| LNU182 | 25384.6 | 0.173 | 0.038 | 47.0 | LNU121 | 27713.3 | 0.006 | 0.228 | 47.5 |
| LNU182 | 25384.5 | 0.135 | 0.513 | 14.4 | LNU126 | 25343.1 | 0.007 | 0.010 | 77.2 |
| LNU2 | 27842.1 | 0.210 | 0.001 | 78.2 | LNU126 | 25343.3 | 0.005 | 0.246 | 27.2 |
| LNU2 | 27842.3 | 0.175 | 0.043 | 48.6 | LNU126 | 25341.1 | 0.005 | 0.314 | 25.3 |
| LNU2 | 25713.1 | 0.132 | 0.702 | 11.5 | LNU126 | 25343.4 | 0.005 | 0.257 | 17.9 |
| LNU2 | 27845.2 | 0.127 | 0.715 | 7.9 | LNU126 | 25345.1 | 0.004 | 0.624 | 4.9 |
| LNU225 | 25991.3 | 0.282 | 0.013 | 138.6 | LNU158 | 27433.3 | 0.011 | 0.001 | 180.9 |
| LNU225 | 25991.2 | 0.223 | 0.003 | 89.0 | LNU158 | 27433.2 | 0.010 | 0.082 | 138.3 |
| LNU225 | 25991.8 | 0.189 | 0.000 | 60.3 | LNU158 | 27432.5 | 0.010 | 0.012 | 137.0 |
| LNU225 | 25991.1 | 0.159 | 0.143 | 34.7 | LNU177 | 24764.12 | 0.010 | 0.012 | 147.5 |
| LNU239 | 26281.1 | 0.152 | 0.239 | 28.9 | LNU177 | 24763.6 | 0.007 | 0.049 | 67.3 |
| LNU239 | 26284.2 | 0.149 | 0.094 | 26.5 | LNU177 | 24762.6 | 0.006 | 0.249 | 17.3 |
| LNU239 | 26284.1 | 0.136 | 0.439 | 14.9 | LNU177 | 24765.2 | 0.005 | 0.333 | 16.0 |
| LNU239 | 26283.2 | 0.130 | 0.353 | 9.8 | LNU182 | 25384.1 | 0.008 | 0.006 | 93.8 |
| LNU57 | 27852.1 | 0.198 | 0.010 | 68.0 | LNU182 | 25384.6 | 0.007 | 0.019 | 74.1 |
| LNU57 | 27851.2 | 0.192 | 0.061 | 62.3 | LNU182 | 25384.5 | 0.005 | 0.160 | 26.5 |
| LNU57 | 27854.5 | 0.143 | 0.077 | 21.2 | LNU182 | 25384.2 | 0.005 | 0.450 | 16.0 |
| LNU57 | 27854.3 | 0.140 | 0.256 | 18.5 | LNU2 | 27842.1 | 0.009 | 0.027 | 131.5 |
| LNU83 | 27685.1 | 0.288 | 0.001 | 143.9 | LNU2 | 27842.3 | 0.007 | 0.104 | 66.7 |
| LNU83 | 27685.2 | 0.201 | 0.003 | 70.6 | LNU2 | 25713.1 | 0.007 | 0.362 | 63.0 |
| LNU83 | 27681.4 | 0.164 | 0.041 | 38.7 | LNU2 | 27845.2 | 0.006 | 0.161 | 52.5 |
| CONT. | — | 0.127 | — | 0.0 | LNU2 | 27845.3 | 0.005 | 0.028 | 30.2 |
| LNU17 | 13991.1 | 0.145 | 0.39 | 14.5 | LNU225 | 25991.2 | 0.011 | 0.007 | 161.1 |
| LNU17 | 13993.9 | 0.135 | 0.71 | 6.1 | LNU225 | 25991.3 | 0.010 | 0.051 | 139.5 |
| | | | | | LNU225 | 25991.8 | 0.007 | 0.001 | 64.2 |
| | | | | | LNU225 | 25991.1 | 0.005 | 0.067 | 31.5 |
| | | | | | LNU239 | 26284.2 | 0.007 | 0.054 | 63.6 |
| | | | | | LNU239 | 26281.1 | 0.006 | 0.190 | 54.9 |

TABLE 60-continued

Genes showing improved plant performance at nitrogen deficient conditions (T2 generation)

| Gene Name | Event # | Ave. | p-value | % incr. | Gene Name | Event # | Ave. | p-value | % incr. |
|---|---|---|---|---|---|---|---|---|---|
| | | | | | LNU239 | 26283.2 | 0.006 | 0.043 | 41.4 |
| | | | | | LNU239 | 26284.1 | 0.005 | 0.414 | 14.8 |
| | | | | | LNU57 | 27852.1 | 0.009 | 0.000 | 133.3 |
| | | | | | LNU57 | 27851.2 | 0.009 | 0.006 | 110.5 |
| | | | | | LNU57 | 27854.5 | 0.006 | 0.046 | 41.4 |
| | | | | | LNU57 | 27854.3 | 0.005 | 0.404 | 19.8 |
| | | | | | LNU83 | 27685.1 | 0.010 | 0.000 | 156.2 |
| | | | | | LNU83 | 27685.2 | 0.009 | 0.000 | 111.7 |
| | | | | | LNU83 | 27681.4 | 0.007 | 0.018 | 80.9 |
| | | | | | LNU83 | 27682.1 | 0.004 | 0.479 | 6.8 |

Table 60.
"CONT."—Control;
"Ave."—Average;
"% Incr." = % increment.

TABLE 61

Genes showing improved plant performance at nitrogen deficient conditions (T2 generation)

Leaf Area [cm2]

| Gene Name | Event # | Average | p-value | % increment |
|---|---|---|---|---|
| CONTROL | — | 0.559 | — | 0.0 |
| LNU100 | 14474.3 | 0.877 | 0.032 | 56.8 |
| LNU100 | 14473.1 | 0.646 | 0.097 | 15.5 |
| LNU104 | 25033.3 | 0.794 | 0.005 | 41.9 |
| LNU104 | 25034.1 | 0.742 | 0.047 | 32.6 |
| LNU104 | 25032.2 | 0.581 | 0.749 | 3.8 |
| LNU213 | 24654.4 | 1.040 | 0.036 | 86.0 |
| LNU213 | 24653.2 | 0.896 | 0.000 | 60.1 |
| LNU213 | 24651.1 | 0.607 | 0.343 | 8.5 |
| LNU218 | 24781.7 | 0.777 | 0.116 | 38.8 |
| LNU218 | 24783.2 | 0.775 | 0.086 | 38.5 |
| LNU4 | 25134.2 | 0.858 | 0.002 | 53.4 |
| LNU4 | 25134.1 | 0.703 | 0.183 | 25.6 |
| LNU48 | 24802.2 | 0.897 | 0.009 | 60.3 |
| LNU48 | 24803.2 | 0.757 | 0.005 | 35.3 |
| LNU48 | 24804.2 | 0.726 | 0.066 | 29.8 |
| LNU8 | 25063.1 | 0.974 | 0.002 | 74.0 |
| LNU8 | 25063.6 | 0.863 | 0.111 | 54.3 |
| LNU8 | 25062.2 | 0.593 | 0.706 | 5.9 |
| LNU94 | 24833.3 | 0.761 | 0.034 | 36.0 |
| LNU94 | 24834.4 | 0.692 | 0.208 | 23.7 |
| LNU94 | 24834.1 | 0.680 | 0.234 | 21.6 |
| CONTROL | — | 0.765 | — | 0.0 |
| LNU1 | 24681.3 | 0.979 | 0.168 | 28.0 |
| LNU1 | 24684.1 | 0.918 | 0.237 | 20.1 |
| LNU1 | 24682.1 | 0.916 | 0.285 | 19.8 |
| LNU1 | 24682.2 | 0.879 | 0.477 | 14.9 |
| LNU1 | 24681.1 | 0.848 | 0.515 | 10.9 |
| LNU1 | 24683.2 | 0.822 | 0.641 | 7.5 |
| LNU133 | 24744.3 | 1.103 | 0.062 | 44.3 |
| LNU133 | 24741.1 | 1.024 | 0.081 | 33.8 |
| LNU133 | 24744.2 | 0.822 | 0.651 | 7.5 |
| LNU175 | 24732.4 | 1.207 | 0.033 | 57.8 |
| LNU175 | 24732.1 | 1.192 | 0.019 | 55.9 |
| LNU175 | 24734.4 | 0.938 | 0.207 | 22.7 |
| LNU178 | 14614.5 | 1.132 | 0.047 | 48.0 |
| LNU178 | 14611.5 | 0.986 | 0.123 | 28.9 |
| LNU178 | 14612.1 | 0.832 | 0.567 | 8.8 |
| LNU178 | 14611.1 | 0.809 | 0.729 | 5.8 |
| LNU215 | 24664.3 | 1.083 | 0.061 | 41.6 |
| LNU215 | 24661.4 | 0.820 | 0.659 | 7.2 |
| LNU24 | 24973.1 | 1.022 | 0.103 | 33.7 |
| LNU24 | 24971.2 | 0.985 | 0.119 | 28.8 |
| LNU24 | 24971.4 | 0.971 | 0.301 | 27.0 |
| LNU6 | 24992.3 | 1.049 | 0.063 | 37.2 |
| LNU6 | 24994.1 | 0.885 | 0.347 | 15.8 |
| LNU6 | 24993.3 | 0.855 | 0.506 | 11.8 |
| LNU6 | 24994.2 | 0.815 | 0.696 | 6.6 |
| LNU82 | 24823.1 | 0.911 | 0.252 | 19.1 |
| LNU9 | 25001.3 | 0.892 | 0.361 | 16.7 |
| LNU9 | 25003.1 | 0.879 | 0.416 | 14.9 |
| LNU9 | 25001.1 | 0.829 | 0.663 | 8.4 |
| CONTROL | — | 0.561 | — | 0.0 |
| LNU120 | 25463.7 | 0.758 | 0.001 | 35.0 |
| LNU120 | 25463.3 | 0.749 | 0.003 | 33.4 |
| LNU124 | 14501.7 | 0.767 | 0.019 | 36.6 |
| LNU124 | 14501.1 | 0.666 | 0.072 | 18.6 |
| LNU124 | 14502.7 | 0.645 | 0.018 | 14.9 |
| LNU132 | 14102.7 | 0.622 | 0.288 | 10.9 |
| LNU132 | 14102.9 | 0.622 | 0.258 | 10.8 |
| LNU140 | 14112.7 | 0.953 | 0.000 | 69.8 |
| LNU140 | 14111.6 | 0.686 | 0.046 | 22.2 |
| LNU140 | 14112.6 | 0.593 | 0.465 | 5.6 |
| LNU140 | 14114.8 | 0.582 | 0.553 | 3.7 |
| LNU180 | 24724.3 | 0.975 | 0.003 | 73.6 |
| LNU180 | 24723.3 | 0.774 | 0.044 | 37.8 |
| LNU196 | 25534.1 | 0.674 | 0.165 | 20.0 |
| LNU196 | 25533.1 | 0.631 | 0.476 | 12.4 |
| LNU20 | 24932.4 | 0.644 | 0.190 | 14.6 |
| LNU20 | 24933.2 | 0.640 | 0.421 | 14.0 |
| LNU36 | 25562.3 | 0.860 | 0.107 | 53.1 |
| LNU36 | 25562.4 | 0.574 | 0.750 | 2.2 |
| LNU71 | 25853.4 | 0.835 | 0.005 | 48.8 |
| CONTROL | — | 0.597 | — | 0.0 |
| LNU1 | 24681.3 | 0.695 | 0.438 | 16.4 |
| LNU110 | 24952.3 | 0.872 | 0.056 | 46.1 |
| LNU110 | 24953.3 | 0.789 | 0.110 | 32.1 |
| LNU110 | 24953.2 | 0.674 | 0.308 | 12.9 |
| LNU175 | 24732.2 | 0.832 | 0.032 | 39.4 |
| LNU175 | 24733.4 | 0.725 | 0.105 | 21.3 |
| LNU19 | 25151.1 | 0.881 | 0.006 | 47.6 |
| LNU19 | 25153.3 | 0.746 | 0.119 | 25.0 |
| LNU215 | 24664.2 | 0.846 | 0.000 | 41.8 |
| LNU215 | 24663.4 | 0.735 | 0.007 | 23.1 |
| LNU215 | 24663.3 | 0.648 | 0.325 | 8.5 |
| LNU27 | 24873.1 | 0.899 | 0.039 | 50.5 |
| LNU27 | 24873.4 | 0.742 | 0.035 | 24.3 |
| LNU27 | 24872.4 | 0.647 | 0.344 | 8.3 |

TABLE 61-continued

Genes showing improved plant performance at nitrogen deficient conditions (T2 generation)

| Gene Name | Event # | Leaf Area [cm2] Average | p-value | % increment |
|---|---|---|---|---|
| LNU44 | 24924.3 | 1.069 | 0.023 | 79.0 |
| LNU44 | 24924.2 | 0.826 | 0.027 | 38.3 |
| LNU44 | 24922.3 | 0.706 | 0.156 | 18.2 |
| LNU54 | 24903.5 | 1.040 | 0.002 | 74.1 |
| LNU54 | 24901.2 | 0.902 | 0.042 | 51.1 |
| LNU54 | 24903.3 | 0.743 | 0.098 | 24.5 |
| LNU79 | 24884.4 | 0.963 | 0.010 | 61.3 |
| LNU79 | 24881.1 | 0.850 | 0.006 | 42.4 |
| LNU79 | 24884.3 | 0.742 | 0.061 | 24.3 |
| LNU79 | 24882.2 | 0.666 | 0.164 | 11.5 |
| CONTROL | — | 0.764 | — | 0.0 |
| LNU109 | 24891.5 | 1.021 | 0.020 | 33.7 |
| LNU109 | 24892.5 | 0.939 | 0.200 | 22.9 |
| LNU109 | 24891.2 | 0.908 | 0.308 | 18.8 |
| LNU109 | 24892.6 | 0.882 | 0.367 | 15.5 |
| LNU110 | 24952.1 | 1.492 | 0.000 | 95.2 |
| LNU110 | 24953.2 | 1.101 | 0.014 | 44.1 |
| LNU110 | 24952.3 | 1.054 | 0.094 | 37.9 |
| LNU133 | 24744.3 | 1.192 | 0.002 | 56.1 |
| LNU133 | 24741.1 | 1.023 | 0.009 | 33.9 |
| LNU133 | 24741.2 | 0.961 | 0.005 | 25.8 |
| LNU133 | 24744.2 | 0.795 | 0.706 | 4.0 |
| LNU19 | 25151.1 | 1.069 | 0.003 | 39.9 |
| LNU27 | 24873.4 | 1.224 | 0.000 | 60.2 |
| LNU44 | 24922.3 | 1.153 | 0.000 | 50.9 |
| LNU44 | 24924.3 | 0.915 | 0.236 | 19.8 |
| LNU44 | 24923.1 | 0.820 | 0.501 | 7.3 |
| LNU54 | 24901.2 | 1.131 | 0.002 | 48.1 |
| LNU54 | 24903.5 | 1.035 | 0.037 | 35.4 |
| LNU54 | 24902.4 | 0.938 | 0.009 | 22.7 |
| LNU6 | 24994.5 | 1.104 | 0.015 | 44.5 |
| LNU6 | 24992.3 | 1.026 | 0.021 | 34.2 |
| LNU79 | 24884.4 | 1.154 | 0.001 | 51.0 |
| LNU79 | 24881.1 | 1.031 | 0.029 | 34.9 |
| LNU79 | 24882.2 | 0.958 | 0.080 | 25.3 |
| LNU79 | 24884.3 | 0.855 | 0.382 | 12.0 |
| CONTROL | — | 0.512 | — | 0.0 |
| LNU109 | 24891.2 | 1.067 | 0.004 | 108.5 |
| LNU109 | 24892.8 | 1.053 | 0.000 | 105.8 |
| LNU109 | 24891.5 | 0.737 | 0.082 | 43.9 |
| LNU109 | 24892.5 | 0.600 | 0.244 | 17.2 |
| LNU143 | 25975.3 | 0.755 | 0.030 | 47.5 |
| LNU143 | 25972.1 | 0.734 | 0.029 | 43.3 |
| LNU143 | 25975.2 | 0.694 | 0.055 | 35.6 |
| LNU143 | 25971.5 | 0.623 | 0.129 | 21.7 |
| LNU143 | 25971.2 | 0.560 | 0.491 | 9.5 |
| LNU154 | 14604.7 | 0.936 | 0.002 | 82.9 |
| LNU154 | 14604.6 | 0.843 | 0.015 | 64.7 |
| LNU154 | 14601.6 | 0.804 | 0.070 | 57.1 |
| LNU154 | 14602.8 | 0.692 | 0.156 | 35.2 |
| LNU154 | 14604.4 | 0.672 | 0.077 | 31.2 |
| LNU196 | 25532.2 | 1.156 | 0.001 | 125.8 |
| LNU196 | 25534.1 | 0.890 | 0.025 | 73.9 |
| LNU196 | 25531.2 | 0.727 | 0.028 | 42.0 |
| LNU196 | 25532.1 | 0.626 | 0.373 | 22.2 |
| LNU207 | 24642.5 | 0.947 | 0.003 | 85.0 |
| LNU207 | 24642.4 | 0.914 | 0.004 | 78.5 |
| LNU207 | 24644.18 | 0.804 | 0.009 | 57.1 |
| LNU207 | 24644.13 | 0.561 | 0.593 | 9.5 |
| LNU207 | 24641.1 | 0.532 | 0.760 | 4.0 |
| LNU288 | 14562.12 | 0.735 | 0.024 | 43.5 |
| LNU288 | 14562.7 | 0.708 | 0.037 | 38.2 |
| LNU288 | 14562.1 | 0.658 | 0.173 | 28.5 |
| LNU288 | 14564.9 | 0.637 | 0.101 | 24.5 |
| LNU288 | 14562.9 | 0.633 | 0.180 | 23.6 |
| LNU50 | 26024.2 | 0.863 | 0.013 | 68.6 |
| LNU50 | 26023.2 | 0.740 | 0.016 | 44.6 |
| LNU50 | 26025.4 | 0.644 | 0.088 | 25.8 |
| LNU50 | 26022.1 | 0.577 | 0.407 | 12.7 |
| LNU50 | 26023.5 | 0.559 | 0.452 | 9.2 |
| LNU52 | 25723.2 | 1.263 | 0.000 | 146.7 |
| LNU52 | 25721.4 | 0.968 | 0.048 | 89.0 |
| LNU52 | 25721.3 | 0.888 | 0.006 | 73.4 |
| LNU52 | 25723.1 | 0.534 | 0.750 | 4.4 |
| CONTROL | — | 0.646 | — | 0.0 |
| LNU143 | 25975.2 | 0.707 | 0.290 | 9.4 |
| LNU154 | 14602.8 | 0.829 | 0.010 | 28.2 |
| LNU154 | 14604.4 | 0.759 | 0.253 | 17.4 |
| LNU154 | 14601.6 | 0.708 | 0.296 | 9.6 |
| LNU207 | 24642.5 | 1.001 | 0.002 | 54.9 |
| LNU207 | 24641.1 | 0.823 | 0.047 | 27.3 |
| LNU207 | 24642.4 | 0.718 | 0.180 | 11.1 |
| LNU211 | 24774.4 | 2.327 | 0.386 | 260.0 |
| LNU52 | 25721.1 | 0.934 | 0.011 | 44.5 |
| LNU52 | 25723.2 | 0.872 | 0.025 | 34.8 |
| LNU52 | 25723.1 | 0.848 | 0.118 | 31.2 |
| LNU52 | 25721.2 | 0.771 | 0.151 | 19.3 |
| LNU69 | 14571.1 | 0.824 | 0.041 | 27.5 |
| LNU69 | 14572.9 | 0.790 | 0.167 | 22.2 |
| LNU69 | 14572.8 | 0.759 | 0.195 | 17.4 |
| CONTROL | — | 0.727 | — | 0.0 |
| LNU150 | 24842.9 | 1.108 | 0.000 | 52.3 |
| LNU150 | 24841.9 | 0.795 | 0.437 | 9.3 |
| LNU179 | 24632.5 | 0.939 | 0.038 | 29.0 |
| LNU179 | 24631.9 | 0.785 | 0.612 | 7.9 |
| LNU232 | 26003.7 | 0.798 | 0.443 | 9.7 |
| LNU235 | 26184.4 | 0.947 | 0.035 | 30.2 |
| LNU235 | 26185.3 | 0.941 | 0.203 | 29.4 |
| LNU242 | 25473.1 | 0.907 | 0.012 | 24.6 |
| LNU242 | 25474.1 | 0.783 | 0.529 | 7.6 |
| LNU242 | 25471.1 | 0.747 | 0.760 | 2.7 |
| LNU76 | 26423.1 | 0.971 | 0.002 | 33.5 |
| LNU76 | 26421.2 | 0.836 | 0.200 | 14.9 |
| LNU76 | 26425.1 | 0.832 | 0.444 | 14.3 |
| LNU95 | 13985.11 | 0.973 | 0.012 | 33.8 |
| LNU95 | 13985.12 | 0.801 | 0.537 | 10.2 |
| CONTROL | — | 0.678 | — | 0.0 |
| LNU118 | 14013.6 | 0.809 | 0.165 | 19.4 |
| LNU118 | 14012.15 | 0.784 | 0.111 | 15.7 |
| LNU150 | 24841.9 | 0.798 | 0.251 | 17.8 |
| LNU150 | 24841.6 | 0.753 | 0.467 | 11.1 |
| LNU150 | 24842.9 | 0.714 | 0.775 | 5.4 |
| LNU179 | 24631.6 | 0.828 | 0.134 | 22.2 |
| LNU179 | 24631.7 | 0.812 | 0.089 | 19.9 |
| LNU179 | 24632.7 | 0.736 | 0.202 | 8.6 |
| LNU179 | 24631.9 | 0.709 | 0.743 | 4.6 |
| LNU232 | 26001.5 | 0.814 | 0.170 | 20.2 |
| LNU232 | 26003.3 | 0.707 | 0.611 | 4.3 |
| LNU235 | 26185.2 | 1.143 | 0.000 | 68.7 |
| LNU235 | 26184.4 | 1.125 | 0.000 | 66.0 |
| LNU235 | 26184.2 | 0.975 | 0.001 | 44.0 |
| LNU242 | 25474.1 | 0.884 | 0.056 | 30.5 |
| LNU288 | 14563.9 | 0.967 | 0.029 | 42.8 |
| LNU288 | 14562.1 | 0.937 | 0.025 | 38.3 |
| LNU288 | 14564.9 | 0.838 | 0.020 | 23.6 |
| LNU288 | 14562.7 | 0.781 | 0.228 | 15.2 |
| LNU76 | 26421.2 | 0.880 | 0.269 | 29.8 |
| LNU76 | 26423.1 | 0.838 | 0.247 | 23.7 |
| LNU76 | 26422.2 | 0.824 | 0.154 | 21.6 |
| LNU95 | 13985.16 | 1.257 | 0.001 | 85.6 |
| LNU95 | 13985.15 | 1.211 | 0.000 | 78.7 |
| LNU95 | 13985.12 | 0.949 | 0.003 | 40.1 |
| LNU95 | 13985.19 | 0.745 | 0.358 | 9.9 |
| CONTROL | — | 0.644 | — | 0.0 |
| LNU101 | 27632.7 | 0.828 | 0.020 | 28.6 |
| LNU101 | 27632.1 | 0.664 | 0.486 | 3.2 |
| LNU128 | 26515.3 | 0.894 | 0.004 | 38.8 |
| LNU192 | 28315.2 | 0.798 | 0.011 | 23.9 |
| LNU192 | 28313.2 | 0.657 | 0.721 | 2.1 |
| LNU206 | 27621.2 | 0.750 | 0.086 | 16.5 |
| LNU211 | 24771.1 | 0.708 | 0.169 | 10.0 |
| LNU282 | 27563.3 | 0.835 | 0.029 | 29.7 |
| LNU282 | 27563.1 | 0.800 | 0.089 | 24.3 |
| LNU282 | 27562.1 | 0.750 | 0.319 | 16.5 |

TABLE 61-continued

Genes showing improved plant performance at nitrogen deficient conditions (T2 generation)

| Gene Name | Event # | Leaf Area [cm2] Average | p-value | % increment |
|---|---|---|---|---|
| LNU69 | 14571.1 | 0.896 | 0.001 | 39.3 |
| LNU69 | 14572.9 | 0.696 | 0.553 | 8.1 |
| LNU75 | 27572.1 | 0.745 | 0.054 | 15.7 |
| LNU75 | 27572.2 | 0.730 | 0.246 | 13.5 |
| CONTROL | — | 0.564 | — | 0.0 |
| LNU206 | 27621.2 | 0.981 | 0.131 | 73.9 |
| LNU206 | 27621.1 | 0.863 | 0.037 | 52.9 |
| LNU206 | 27622.1 | 0.791 | 0.037 | 40.2 |
| LNU206 | 27622.4 | 0.707 | 0.099 | 25.3 |
| LNU249 | 26153.1 | 0.869 | 0.008 | 54.0 |
| LNU249 | 26154.2 | 0.738 | 0.044 | 30.7 |
| LNU249 | 26152.4 | 0.605 | 0.555 | 7.2 |
| LNU282 | 27563.1 | 0.761 | 0.014 | 34.7 |
| LNU282 | 27565.2 | 0.753 | 0.097 | 33.4 |
| LNU288 | 14563.9 | 0.883 | 0.000 | 56.4 |
| LNU288 | 14564.8 | 0.854 | 0.009 | 51.2 |
| LNU288 | 14562.9 | 0.698 | 0.015 | 23.6 |
| LNU288 | 14563.6 | 0.634 | 0.331 | 12.3 |
| LNU75 | 27572.3 | 0.949 | 0.000 | 68.1 |
| LNU75 | 27572.2 | 0.829 | 0.064 | 46.9 |
| LNU75 | 27571.4 | 0.795 | 0.000 | 40.8 |
| LNU75 | 27571.2 | 0.781 | 0.005 | 38.3 |
| CONTROL | — | 0.721 | — | 0.0 |
| LNU11 | 28204.3 | 0.762 | 0.570 | 5.7 |
| LNU112 | 28212.4 | 0.757 | 0.585 | 5.0 |
| LNU14 | 27823.2 | 0.776 | 0.442 | 7.7 |
| LNU183 | 24863.1 | 0.926 | 0.009 | 28.4 |
| LNU183 | 24863.12 | 0.915 | 0.019 | 26.9 |
| LNU183 | 24864.6 | 0.812 | 0.539 | 12.7 |
| LNU183 | 24865.1 | 0.795 | 0.318 | 10.3 |
| LNU201 | 28223.1 | 0.821 | 0.208 | 14.0 |
| LNU201 | 28222.2 | 0.746 | 0.733 | 3.6 |
| LNU268 | 26044.2 | 0.805 | 0.386 | 11.7 |
| LNU268 | 26045.1 | 0.761 | 0.572 | 5.6 |
| CONTROL | — | 0.666 | — | 0.0 |
| LNU11 | 28205.1 | 0.858 | 0.048 | 28.9 |
| LNU11 | 28204.1 | 0.729 | 0.372 | 9.5 |
| LNU11 | 28205.2 | 0.708 | 0.399 | 6.3 |
| LNU112 | 28212.4 | 0.772 | 0.015 | 16.0 |
| LNU112 | 28212.1 | 0.760 | 0.022 | 14.1 |
| LNU112 | 28212.3 | 0.690 | 0.781 | 3.7 |
| LNU14 | 27821.3 | 0.826 | 0.009 | 24.1 |
| LNU14 | 27821.4 | 0.813 | 0.053 | 22.2 |
| LNU14 | 27824.2 | 0.708 | 0.564 | 6.4 |
| LNU183 | 24864.6 | 1.097 | 0.018 | 64.7 |
| LNU183 | 24863.12 | 0.968 | 0.016 | 45.5 |
| LNU183 | 24865.1 | 0.954 | 0.031 | 43.4 |
| LNU183 | 24863.1 | 0.881 | 0.002 | 32.3 |
| LNU191 | 28325.4 | 0.775 | 0.076 | 16.3 |
| LNU191 | 28324.2 | 0.756 | 0.146 | 13.5 |
| LNU191 | 28321.3 | 0.690 | 0.556 | 3.6 |
| LNU201 | 28222.2 | 0.929 | 0.017 | 39.6 |
| LNU201 | 28223.3 | 0.788 | 0.167 | 18.3 |
| LNU268 | 26041.4 | 0.741 | 0.203 | 11.2 |
| LNU268 | 26043.4 | 0.722 | 0.338 | 8.5 |
| CONTROL | — | 0.523 | — | 0.0 |
| LNU107 | 14583.8 | 0.794 | 0.010 | 51.7 |
| LNU107 | 14585.5 | 0.656 | 0.055 | 25.4 |
| LNU107 | 14584.9 | 0.597 | 0.505 | 14.2 |
| LNU116 | 14494.5 | 0.877 | 0.002 | 67.7 |
| LNU116 | 14492.9 | 0.728 | 0.082 | 39.1 |
| LNU116 | 14492.5 | 0.664 | 0.045 | 27.0 |
| LNU116 | 14493.6 | 0.550 | 0.734 | 5.1 |
| LNU121 | 25642.2 | 0.892 | 0.013 | 70.5 |
| LNU121 | 27711.1 | 0.880 | 0.001 | 68.2 |
| LNU121 | 27713.4 | 0.878 | 0.000 | 67.7 |
| LNU121 | 27713.1 | 0.799 | 0.055 | 52.7 |
| LNU126 | 25343.1 | 0.723 | 0.170 | 38.2 |
| LNU126 | 25345.1 | 0.713 | 0.065 | 36.3 |
| LNU126 | 25343.3 | 0.638 | 0.325 | 21.9 |
| LNU158 | 27433.3 | 0.797 | 0.030 | 52.4 |
| LNU158 | 27433.2 | 0.793 | 0.055 | 51.5 |
| LNU158 | 27432.5 | 0.670 | 0.383 | 28.1 |
| LNU177 | 24762.6 | 0.950 | 0.000 | 81.6 |
| LNU177 | 24764.9 | 0.637 | 0.256 | 21.7 |
| LNU177 | 24765.2 | 0.564 | 0.702 | 7.7 |
| LNU182 | 25384.1 | 0.855 | 0.016 | 63.4 |
| LNU182 | 25384.5 | 0.649 | 0.148 | 24.1 |
| LNU182 | 25384.2 | 0.641 | 0.348 | 22.5 |
| LNU182 | 27521.4 | 0.640 | 0.063 | 22.4 |
| LNU2 | 27842.1 | 0.621 | 0.249 | 18.7 |
| LNU2 | 25713.1 | 0.585 | 0.478 | 11.8 |
| LNU2 | 27845.2 | 0.582 | 0.352 | 11.3 |
| LNU2 | 27842.3 | 0.566 | 0.556 | 8.1 |
| LNU225 | 25991.5 | 0.686 | 0.194 | 31.1 |
| LNU225 | 25991.2 | 0.625 | 0.456 | 19.6 |
| LNU239 | 26283.2 | 0.628 | 0.351 | 20.0 |
| LNU239 | 26284.1 | 0.602 | 0.230 | 15.0 |
| LNU57 | 27854.5 | 0.548 | 0.725 | 4.7 |
| LNU83 | 27684.1 | 0.790 | 0.021 | 51.1 |
| CONTROL | — | 0.400 | — | 0.0 |
| LNU107 | 14584.9 | 0.579 | 0.031 | 44.7 |
| LNU107 | 14585.2 | 0.511 | 0.131 | 27.8 |
| LNU107 | 14583.8 | 0.461 | 0.129 | 15.2 |
| LNU107 | 14585.5 | 0.420 | 0.690 | 5.0 |
| LNU116 | 14492.5 | 0.713 | 0.020 | 78.1 |
| LNU116 | 14494.5 | 0.702 | 0.015 | 75.3 |
| LNU116 | 14492.9 | 0.589 | 0.061 | 47.2 |
| LNU116 | 14493.6 | 0.563 | 0.130 | 40.7 |
| LNU116 | 14491.5 | 0.489 | 0.343 | 22.2 |
| LNU121 | 27713.1 | 0.833 | 0.031 | 108.0 |
| LNU121 | 27711.1 | 0.636 | 0.082 | 58.9 |
| LNU121 | 27713.4 | 0.635 | 0.003 | 58.8 |
| LNU121 | 25642.2 | 0.557 | 0.065 | 39.2 |
| LNU126 | 25343.1 | 0.559 | 0.086 | 39.7 |
| LNU126 | 25343.3 | 0.521 | 0.289 | 30.1 |
| LNU126 | 25341.1 | 0.472 | 0.329 | 18.0 |
| LNU158 | 27433.3 | 0.898 | 0.001 | 124.4 |
| LNU158 | 27432.5 | 0.712 | 0.035 | 77.8 |
| LNU158 | 27433.2 | 0.649 | 0.056 | 62.2 |
| LNU158 | 27434.5 | 0.415 | 0.797 | 3.6 |
| LNU177 | 24764.12 | 0.500 | 0.376 | 24.8 |
| LNU177 | 24763.6 | 0.453 | 0.543 | 13.1 |
| LNU177 | 24762.6 | 0.449 | 0.578 | 12.1 |
| LNU182 | 25384.6 | 0.609 | 0.015 | 52.2 |
| LNU182 | 25384.2 | 0.542 | 0.059 | 35.3 |
| LNU2 | 27842.1 | 0.653 | 0.007 | 63.1 |
| LNU2 | 27842.3 | 0.549 | 0.109 | 37.1 |
| LNU2 | 27845.3 | 0.435 | 0.627 | 8.5 |
| LNU225 | 25991.2 | 0.693 | 0.001 | 73.2 |
| LNU225 | 25991.3 | 0.673 | 0.058 | 68.2 |
| LNU225 | 25991.8 | 0.605 | 0.000 | 51.1 |
| LNU225 | 25991.1 | 0.456 | 0.393 | 13.9 |
| LNU239 | 26283.2 | 0.513 | 0.120 | 28.2 |
| LNU239 | 26284.1 | 0.477 | 0.331 | 19.3 |
| LNU239 | 26284.2 | 0.468 | 0.353 | 16.9 |
| LNU239 | 26281.1 | 0.465 | 0.317 | 16.1 |
| LNU57 | 27854.5 | 0.496 | 0.354 | 24.0 |
| LNU57 | 27852.1 | 0.478 | 0.152 | 19.5 |
| LNU57 | 27851.2 | 0.441 | 0.510 | 10.1 |
| LNU57 | 27854.3 | 0.424 | 0.779 | 6.0 |
| LNU83 | 27685.1 | 0.793 | 0.009 | 98.1 |
| LNU83 | 27685.2 | 0.579 | 0.123 | 44.7 |
| LNU83 | 27681.4 | 0.507 | 0.120 | 26.6 |
| CONTROL | 12033.3 | 0.426 | — | 0.0 |
| LNU129 | 27501.2 | 0.681 | <0.05 | 59.9 |
| LNU129 | 27502.4 | 0.579 | <0.05 | 36.0 |
| LNU129 | 27503.4 | 0.475 | <0.6 | 11.4 |
| LNU129 | 27504.2 | 0.779 | <0.05 | 82.9 |
| LNU129 | 27504.3 | 0.657 | <0.05 | 54.0 |
| LNU147 | 27512.1 | 0.550 | <0.05 | 29.1 |
| LNU147 | 27513.2 | 0.554 | <0.05 | 30.1 |
| LNU147 | 27514.1 | 0.552 | <0.05 | 29.7 |
| LNU147 | 27514.2 | 0.730 | <0.05 | 71.4 |

TABLE 61-continued

Genes showing improved plant performance at nitrogen deficient conditions (T2 generation)

| | | Leaf Area [cm2] | | |
|---|---|---|---|---|
| Gene Name | Event # | Average | p-value | % increment |
| LNU153 | 24851.3 | 0.621 | <0.05 | 45.9 |
| LNU153 | 24851.4 | 0.504 | <0.5 | 18.3 |
| LNU189 | 26382.3 | 0.950 | <0.05 | 122.9 |
| LNU189 | 26382.4 | 0.779 | <0.05 | 82.9 |
| LNU189 | 26383.1 | 0.613 | <0.05 | 43.9 |
| LNU189 | 26385.1 | 0.688 | <0.05 | 61.6 |
| LNU189 | 26385.2 | 0.493 | <0.6 | 15.8 |
| LNU219 | 27461.1 | 0.804 | <0.05 | 88.7 |
| LNU219 | 27462.1 | 0.781 | <0.05 | 83.3 |
| LNU219 | 27462.2 | 0.903 | <0.05 | 112.0 |
| LNU219 | 27464.1 | 0.622 | <0.05 | 46.0 |
| LNU219 | 27464.2 | 0.458 | <0.6 | 7.4 |
| LNU256 | 26211.2 | 0.519 | <0.2 | 21.8 |
| LNU256 | 26212.3 | 0.864 | <0.05 | 102.9 |
| LNU256 | 26213.1 | 0.617 | <0.05 | 44.9 |
| LNU256 | 26214.1 | 0.667 | <0.05 | 56.6 |
| LNU257 | 26254.1 | 0.568 | <0.05 | 33.4 |
| LNU257 | 26254.3 | 0.980 | <0.05 | 130.0 |
| LNU257 | 26254.7 | 0.842 | <0.05 | 97.6 |
| LNU257 | 26255.2 | 0.515 | <0.2 | 20.9 |
| LNU257 | 26255.3 | 0.505 | <0.05 | 18.4 |
| LNU261 | 27401.4 | 0.527 | <0.2 | 23.7 |
| LNU261 | 27402.4 | 0.477 | <0.05 | 11.9 |
| LNU261 | 27403.2 | 0.728 | <0.05 | 71.0 |
| LNU261 | 27405.1 | 0.609 | <0.05 | 42.9 |
| LNU261 | 27405.3 | 0.537 | <0.1 | 26.0 |
| LNU33 | 25552.2 | 0.745 | <0.05 | 74.9 |
| LNU33 | 25553.2 | 0.571 | <0.05 | 34.1 |
| LNU33 | 25553.3 | 0.594 | <0.05 | 39.5 |
| LNU35 | 27421.2 | 0.713 | <0.05 | 67.5 |
| LNU35 | 27422.1 | 0.556 | <0.05 | 30.4 |
| LNU35 | 27423.3 | 0.859 | <0.05 | 101.6 |
| LNU35 | 27424.3 | 0.662 | <0.05 | 55.4 |
| LNU35 | 27424.5 | 0.593 | <0.05 | 39.2 |
| LNU50 | 26022.1 | 0.853 | <0.05 | 100.1 |
| LNU50 | 26023.2 | 0.839 | <0.05 | 96.9 |
| LNU50 | 26023.3 | 0.501 | <0.05 | 17.6 |
| LNU50 | 26024.1 | 0.557 | <0.05 | 30.7 |
| LNU50 | 26025.3 | 1.031 | <0.05 | 142.1 |
| LNU70 | 25311.4 | 0.835 | <0.05 | 96.0 |
| LNU70 | 25313.1 | 0.534 | <0.05 | 25.3 |
| LNU70 | 25313.2 | 0.801 | <0.05 | 88.0 |
| LNU70 | 25315.1 | 0.501 | <0.2 | 17.7 |

Table 61.

TABLE 62

Genes showing improved plant performance at nitrogen deficient conditions (T1 generation)

| | Plant Biomass Fresh Weight [gr.] | | | | Plant Biomass Dry Weight [gr.] | | |
|---|---|---|---|---|---|---|---|
| Gene Name | Ave. | p-value | % incr. | Gene Name | Ave. | p-value | % incr. |
| CONTROL | 0.145 | — | 0.0 | CONTROL | 0.008 | — | 0.0 |
| LNU154 | 0.146 | 0.982 | 0.4 | LNU121 | 0.008 | 0.715 | 6.8 |
| CONTROL | 0.099 | — | 0.0 | CONTROL | 0.005 | — | 0.0 |
| LNU127 | 0.106 | 0.594 | 7.3 | LNU127 | 0.006 | 0.595 | 8.1 |
| LNU188 | 0.110 | 0.481 | 11.4 | LNU188 | 0.005 | 0.890 | 2.9 |
| LNU2 | 0.108 | 0.419 | 9.8 | LNU239 | 0.006 | 0.552 | 18.1 |
| LNU239 | 0.110 | 0.642 | 11.2 | LNU255 | 0.007 | 0.245 | 27.1 |
| LNU255 | 0.116 | 0.170 | 17.9 | LNU258 | 0.006 | 0.806 | 6.7 |
| LNU265 | 0.102 | 0.740 | 3.7 | LNU265 | 0.006 | 0.408 | 13.8 |
| LNU275 | 0.137 | 0.080 | 39.1 | LNU275 | 0.007 | 0.079 | 35.7 |
| LNU58 | 0.119 | 0.239 | 20.6 | LNU32 | 0.008 | 0.018 | 45.7 |
| LNU83 | 0.111 | 0.621 | 12.6 | LNU58 | 0.008 | 0.033 | 51.9 |
| CONTROL | 0.126 | — | 0.0 | CONTROL | 0.005 | — | 0.0 |
| LNU115 | 0.133 | 0.698 | 5.2 | LNU176 | 0.006 | 0.136 | 14.0 |
| CONTROL | 0.116 | — | 0.0 | LNU284 | 0.005 | 0.855 | 3.2 |
| LNU225 | 0.127 | 0.548 | 9.9 | CONTROL | 0.006 | — | 0.0 |
| LNU262 | 0.128 | 0.317 | 10.5 | LNU115 | 0.006 | 0.775 | 5.8 |
| LNU59 | 0.117 | 0.921 | 1.6 | CONTROL | 0.005 | — | 0.0 |
| LNU60 | 0.148 | 0.188 | 27.9 | LNU225 | 0.005 | 0.527 | 9.4 |
| | | | | LNU262 | 0.006 | 0.081 | 32.4 |
| | | | | LNU266 | 0.006 | 0.247 | 24.4 |
| | | | | LNU29 | 0.005 | 0.614 | 10.5 |
| | | | | LNU59 | 0.006 | 0.195 | 33.0 |
| | | | | LNU60 | 0.006 | 0.208 | 38.9 |

Table 62.
"Ave."—Average;
"% Incr." = % increment.

TABLE 63

Genes showing improved plant performance at nitrogen deficient conditions (T1 generation)

| | | Leaf Area [cm2] | | |
|---|---|---|---|---|
| Gene Name | Time Point | Average | p-value | % increment |
| CONTROL | Leaf_Area_TP2 | 0.283 | — | 0.0 |
| LNU154 | Leaf_Area_TP2 | 0.290 | 0.703 | 2.4 |
| CONTROL | Leaf_Area_TP3 | 0.571 | — | 0.0 |
| LNU154 | Leaf_Area_TP3 | 0.582 | 0.817 | 1.9 |
| CONTROL | Leaf_Area_TP1 | 0.104 | — | 0.0 |
| LNU127 | Leaf_Area_TP1 | 0.113 | 0.515 | 8.3 |
| LNU275 | Leaf_Area_TP1 | 0.156 | 0.001 | 49.6 |
| CONTROL | Leaf_Area_TP2 | 0.269 | — | 0.0 |
| LNU127 | Leaf_Area_TP2 | 0.287 | 0.447 | 6.6 |
| LNU2 | Leaf_Area_TP2 | 0.302 | 0.123 | 12.4 |
| LNU255 | Leaf_Area_TP2 | 0.272 | 0.896 | 1.2 |
| LNU275 | Leaf_Area_TP2 | 0.404 | 0.000 | 50.1 |
| LNU83 | Leaf_Area_TP2 | 0.291 | 0.500 | 8.1 |
| CONTROL | Leaf_Area_TP3 | 0.639 | — | 0.0 |
| LNU127 | Leaf_Area_TP3 | 0.647 | 0.862 | 1.3 |
| LNU188 | Leaf_Area_TP3 | 0.655 | 0.867 | 2.6 |
| LNU2 | Leaf_Area_TP3 | 0.662 | 0.602 | 3.6 |
| LNU58 | Leaf_Area_TP3 | 0.714 | 0.443 | 11.9 |
| LNU83 | Leaf_Area_TP3 | 0.677 | 0.705 | 6.1 |
| CONTROL | Leaf_Area_TP1 | 0.118 | — | 0.0 |
| LNU123 | Leaf_Area_TP1 | 0.120 | 0.881 | 1.5 |
| LNU134 | Leaf_Area_TP1 | 0.138 | 0.038 | 17.3 |
| LNU198 | Leaf_Area_TP1 | 0.119 | 0.901 | 1.0 |
| CONTROL | Leaf_Area_TP2 | 0.329 | — | 0.0 |
| LNU134 | Leaf_Area_TP2 | 0.346 | 0.587 | 5.1 |
| CONTROL | Leaf_Area_TP1 | 0.097 | — | 0.0 |
| LNU262 | Leaf_Area_TP1 | 0.120 | 0.161 | 23.9 |
| LNU266 | Leaf_Area_TP1 | 0.107 | 0.475 | 10.8 |
| LNU59 | Leaf_Area_TP1 | 0.099 | 0.746 | 2.7 |
| LNU60 | Leaf_Area_TP1 | 0.102 | 0.491 | 5.8 |
| CONTROL | Leaf_Area_TP2 | 0.271 | — | 0.0 |
| LNU262 | Leaf_Area_TP2 | 0.299 | 0.009 | 10.4 |
| LNU60 | Leaf_Area_TP2 | 0.278 | 0.808 | 2.6 |
| CONTROL | Leaf_Area_TP3 | 0.567 | — | 0.0 |
| LNU243 | Leaf_Area_TP3 | 0.573 | 0.910 | 1.0 |
| LNU262 | Leaf_Area_TP3 | 0.618 | 0.253 | 9.0 |
| LNU60 | Leaf_Area_TP3 | 0.600 | 0.649 | 5.7 |

Table 63.

The genes presented in Tables 64-65 showed a significant improvement in plant NUE since they produced a larger root biomass (root length and root coverage) when grown under limiting nitrogen growth conditions, compared to control-plants. Plants producing larger root biomass have better possibilities to absorb larger amount of nitrogen from soil. The genes were cloned under the regulation of a constitutive promoter (At6669) or root preferred promoter (RootP). The evaluation of each gene was performed by testing the performance of different number of events. Some of the genes were evaluated in more than one tissue culture assay. This second experiment confirmed the significant increment in root performance. Event with p-value <0.1 was considered statistically significant

TABLE 64

Genes showing improved root performance at nitrogen deficient conditions (T2 generation)

| | | Roots Length [cm] | | | | | Roots Coverage [cm2] | | |
|---|---|---|---|---|---|---|---|---|---|
| Gene Name | Event # | Ave. | p-value | % incr. | Gene Name | Event # | Ave. | p-value | % incr. |
| CONTROL | — | 5.460 | — | 0.0 | CONT. | — | 6.069 | — | 0.0 |
| LNU100 | 14474.3 | 7.008 | 0.000 | 28.3 | LNU100 | 14474.3 | 9.816 | 0.031 | 61.7 |
| LNU100 | 14471.4 | 6.667 | 0.013 | 22.1 | LNU100 | 14473.1 | 6.948 | 0.313 | 14.5 |
| LNU100 | 14473.1 | 6.461 | 0.026 | 18.3 | LNU100 | 14471.4 | 6.929 | 0.190 | 14.2 |
| LNU100 | 14474.4 | 6.309 | 0.001 | 15.5 | LNU104 | 25033.3 | 7.325 | 0.131 | 20.7 |
| LNU104 | 25034.1 | 6.942 | 0.283 | 27.1 | LNU104 | 25034.1 | 6.679 | 0.275 | 10.0 |
| LNU104 | 25033.3 | 6.252 | 0.044 | 14.5 | LNU213 | 24653.2 | 9.230 | 0.002 | 52.1 |
| LNU104 | 25033.1 | 5.902 | 0.151 | 8.1 | LNU213 | 24654.4 | 8.585 | 0.198 | 41.4 |
| LNU104 | 25032.2 | 5.707 | 0.571 | 4.5 | LNU213 | 24653.1 | 6.920 | 0.321 | 14.0 |
| LNU104 | 25032.1 | 5.563 | 0.688 | 1.9 | LNU213 | 24651.1 | 6.367 | 0.523 | 4.9 |
| LNU213 | 24653.2 | 6.677 | 0.003 | 22.3 | LNU218 | 24783.2 | 8.791 | 0.090 | 44.8 |
| LNU213 | 24653.1 | 6.371 | 0.056 | 16.7 | LNU218 | 24781.7 | 6.766 | 0.632 | 11.5 |
| LNU213 | 24654.4 | 6.357 | 0.060 | 16.4 | LNU4 | 25134.2 | 7.955 | 0.057 | 31.1 |
| LNU213 | 24651.1 | 6.202 | 0.002 | 13.6 | LNU4 | 25134.1 | 6.933 | 0.347 | 14.2 |
| LNU213 | 24652.4 | 6.124 | 0.053 | 12.2 | LNU4 | 25131.1 | 6.521 | 0.371 | 7.4 |
| LNU218 | 24783.2 | 6.533 | 0.071 | 19.6 | LNU48 | 24802.2 | 10.147 | 0.001 | 67.2 |
| LNU218 | 24781.1 | 6.273 | 0.001 | 14.9 | LNU48 | 24804.4 | 8.757 | 0.018 | 44.3 |
| LNU218 | 24781.7 | 5.757 | 0.545 | 5.4 | LNU48 | 24802.1 | 6.538 | 0.497 | 7.7 |
| LNU218 | 24781.2 | 5.575 | 0.526 | 2.1 | LNU48 | 24803.2 | 6.474 | 0.601 | 6.7 |
| LNU4 | 25131.1 | 6.811 | 0.000 | 24.7 | LNU8 | 25063.1 | 11.923 | 0.014 | 96.4 |
| LNU4 | 25134.2 | 6.809 | 0.000 | 24.7 | LNU8 | 25063.6 | 7.772 | 0.469 | 28.0 |
| LNU4 | 25134.1 | 6.092 | 0.453 | 11.6 | LNU8 | 25062.2 | 6.228 | 0.714 | 2.6 |
| LNU4 | 25133.3 | 5.643 | 0.584 | 3.3 | LNU94 | 24833.3 | 7.631 | 0.136 | 25.7 |
| LNU48 | 24804.4 | 6.762 | 0.001 | 23.9 | LNU94 | 24834.4 | 6.753 | 0.519 | 11.3 |
| LNU48 | 24802.2 | 6.606 | 0.003 | 21.0 | CONT. | — | 7.564 | — | 0.0 |
| LNU48 | 24803.2 | 5.911 | 0.242 | 8.3 | LNU1 | 24684.1 | 10.889 | 0.001 | 44.0 |
| LNU48 | 24802.1 | 5.777 | 0.362 | 5.8 | LNU1 | 24682.2 | 10.883 | 0.255 | 43.9 |
| LNU8 | 25063.1 | 7.395 | 0.008 | 35.4 | LNU1 | 24681.1 | 10.585 | 0.067 | 39.9 |
| LNU8 | 25062.2 | 6.064 | 0.213 | 11.1 | LNU1 | 24681.3 | 9.005 | 0.160 | 19.0 |
| LNU8 | 25062.1 | 5.830 | 0.105 | 6.8 | LNU1 | 24682.1 | 8.490 | 0.214 | 12.2 |
| LNU8 | 25063.6 | 5.778 | 0.674 | 5.8 | LNU133 | 24744.3 | 13.831 | 0.022 | 82.8 |
| LNU94 | 24833.3 | 6.716 | 0.002 | 23.0 | LNU133 | 24741.1 | 12.418 | 0.009 | 64.2 |
| LNU94 | 24834.4 | 6.389 | 0.022 | 17.0 | LNU133 | 24741.2 | 9.300 | 0.015 | 22.9 |
| LNU94 | 24833.1 | 5.531 | 0.737 | 1.3 | LNU133 | 24744.2 | 8.947 | 0.166 | 18.3 |
| CONT. | — | 6.635 | — | 0.0 | LNU133 | 24742.2 | 8.706 | 0.318 | 15.1 |
| LNU1 | 24684.1 | 7.260 | 0.000 | 9.4 | LNU175 | 24732.4 | 16.185 | 0.044 | 114.0 |
| LNU1 | 24681.1 | 7.070 | 0.179 | 6.6 | LNU175 | 24732.1 | 15.203 | 0.003 | 101.0 |
| LNU133 | 24744.3 | 7.399 | 0.028 | 11.5 | LNU175 | 24734.4 | 10.409 | 0.050 | 37.6 |
| LNU133 | 24741.2 | 7.040 | 0.003 | 6.1 | LNU175 | 24731.2 | 8.880 | 0.165 | 17.4 |
| LNU133 | 24741.1 | 6.975 | 0.033 | 5.1 | LNU175 | 24733.4 | 8.589 | 0.374 | 13.6 |
| LNU133 | 24742.2 | 6.937 | 0.281 | 4.6 | LNU178 | 14611.5 | 13.504 | 0.018 | 78.5 |
| LNU175 | 24732.1 | 7.839 | 0.003 | 18.2 | LNU178 | 14611.1 | 10.597 | 0.123 | 40.1 |
| LNU175 | 24732.4 | 7.594 | 0.135 | 14.5 | LNU178 | 14614.5 | 10.444 | 0.173 | 38.1 |
| LNU175 | 24734.4 | 7.437 | 0.021 | 12.1 | LNU178 | 14611.4 | 8.568 | 0.168 | 13.3 |
| LNU175 | 24733.4 | 6.965 | 0.158 | 5.0 | LNU178 | 14612.1 | 8.562 | 0.317 | 13.2 |
| LNU178 | 14611.5 | 7.651 | 0.025 | 15.3 | LNU215 | 24664.3 | 12.121 | 0.051 | 60.2 |
| LNU178 | 14614.5 | 7.431 | 0.081 | 12.0 | LNU215 | 24661.4 | 9.556 | 0.117 | 26.3 |
| LNU178 | 14611.1 | 7.198 | 0.027 | 8.5 | LNU215 | 24664.2 | 9.327 | 0.011 | 23.3 |
| LNU178 | 14612.1 | 6.985 | 0.005 | 5.3 | LNU215 | 24663.4 | 8.874 | 0.121 | 17.3 |
| LNU178 | 14611.4 | 6.889 | 0.092 | 3.8 | LNU24 | 24973.1 | 12.870 | 0.010 | 70.1 |
| LNU215 | 24664.3 | 7.586 | 0.001 | 14.3 | LNU24 | 24971.4 | 11.398 | 0.014 | 50.7 |
| LNU215 | 24661.4 | 7.127 | 0.146 | 7.4 | LNU24 | 24971.2 | 10.449 | 0.001 | 38.1 |
| LNU215 | 24664.2 | 7.087 | 0.002 | 6.8 | LNU24 | 24972.2 | 8.338 | 0.479 | 10.2 |
| LNU215 | 24663.4 | 7.006 | 0.167 | 5.6 | LNU24 | 24971.3 | 8.036 | 0.493 | 6.2 |
| LNU24 | 24973.1 | 7.751 | 0.000 | 16.8 | LNU6 | 24992.3 | 12.812 | 0.028 | 69.4 |
| LNU24 | 24971.4 | 7.021 | 0.243 | 5.8 | LNU6 | 24994.2 | 10.067 | 0.055 | 33.1 |
| LNU6 | 24992.3 | 7.266 | 0.108 | 9.5 | LNU6 | 24993.3 | 9.314 | 0.126 | 23.1 |
| LNU6 | 24994.2 | 7.159 | 0.021 | 7.9 | LNU6 | 24994.5 | 9.037 | 0.390 | 19.5 |
| LNU6 | 24994.5 | 7.027 | 0.388 | 5.9 | LNU6 | 24994.1 | 8.410 | 0.406 | 11.2 |
| LNU82 | 24823.1 | 7.050 | 0.186 | 6.3 | LNU82 | 24823.1 | 10.020 | 0.110 | 32.5 |
| LNU82 | 24824.2 | 7.029 | 0.092 | 5.9 | LNU82 | 24824.2 | 9.584 | 0.087 | 26.7 |
| LNU82 | 24824.3 | 6.741 | 0.511 | 1.6 | LNU82 | 24824.3 | 8.475 | 0.310 | 12.0 |
| LNU9 | 25001.1 | 7.345 | 0.072 | 10.7 | LNU82 | 24824.1 | 8.462 | 0.562 | 11.9 |
| LNU9 | 25003.1 | 7.308 | 0.021 | 10.2 | LNU9 | 25001.1 | 10.896 | 0.012 | 44.0 |
| LNU9 | 25001.3 | 7.027 | 0.076 | 5.9 | LNU9 | 25003.1 | 10.296 | 0.099 | 36.1 |
| LNU9 | 25001.2 | 6.762 | 0.730 | 1.9 | LNU9 | 25001.2 | 9.602 | 0.217 | 26.9 |

TABLE 64-continued

Genes showing improved root performance at nitrogen deficient conditions (T2 generation)

| | | Roots Length [cm] | | | | | Roots Coverage [cm2] | | |
|---|---|---|---|---|---|---|---|---|---|
| Gene Name | Event # | Ave. | p-value | % incr. | Gene Name | Event # | Ave. | p-value | % incr. |
| CONT. | — | 6.780 | — | 0.0 | LNU9 | 25001.3 | 9.441 | 0.085 | 24.8 |
| LNU120 | 25463.7 | 7.505 | 0.017 | 10.7 | CONT. | — | 7.438 | — | 0.0 |
| LNU120 | 25463.3 | 7.104 | 0.329 | 4.8 | LNU120 | 25463.7 | 11.666 | 0.000 | 56.8 |
| LNU124 | 14502.1 | 7.180 | 0.348 | 5.9 | LNU120 | 25463.3 | 8.314 | 0.249 | 11.8 |
| LNU132 | 14102.7 | 7.563 | 0.022 | 11.6 | LNU124 | 14502.1 | 9.538 | 0.258 | 28.2 |
| LNU132 | 14102.9 | 7.351 | 0.021 | 8.4 | LNU124 | 14501.7 | 9.283 | 0.341 | 24.8 |
| LNU140 | 14112.6 | 7.272 | 0.087 | 7.3 | LNU124 | 14502.7 | 8.218 | 0.448 | 10.5 |
| LNU140 | 14112.7 | 7.233 | 0.076 | 6.7 | LNU124 | 14501.1 | 7.888 | 0.721 | 6.0 |
| LNU140 | 14114.8 | 7.140 | 0.189 | 5.3 | LNU132 | 14102.7 | 9.324 | 0.165 | 25.4 |
| LNU140 | 14111.6 | 6.988 | 0.530 | 3.1 | LNU132 | 14102.9 | 9.217 | 0.025 | 23.9 |
| LNU180 | 24724.3 | 7.931 | 0.000 | 17.0 | LNU140 | 14112.7 | 12.797 | 0.001 | 72.0 |
| LNU180 | 24723.3 | 6.980 | 0.532 | 3.0 | LNU140 | 14111.6 | 9.362 | 0.025 | 25.9 |
| LNU20 | 24932.4 | 6.886 | 0.733 | 1.6 | LNU140 | 14112.6 | 7.974 | 0.374 | 7.2 |
| LNU36 | 25562.3 | 7.270 | 0.279 | 7.2 | LNU140 | 14114.8 | 7.954 | 0.540 | 6.9 |
| LNU36 | 25562.4 | 7.219 | 0.142 | 6.5 | LNU180 | 24724.3 | 13.032 | 0.003 | 75.2 |
| CONT. | — | 6.252 | — | 0.0 | LNU180 | 24723.3 | 10.374 | 0.006 | 39.5 |
| LNU1 | 24682.1 | 7.163 | 0.035 | 14.6 | LNU180 | 24721.4 | 7.814 | 0.644 | 5.1 |
| LNU1 | 24681.1 | 7.118 | 0.033 | 13.8 | LNU20 | 24932.4 | 9.646 | 0.029 | 29.7 |
| LNU1 | 24684.1 | 6.592 | 0.311 | 5.4 | LNU20 | 24933.2 | 8.359 | 0.594 | 12.4 |
| LNU110 | 24953.2 | 7.215 | 0.025 | 15.4 | LNU36 | 25562.3 | 11.458 | 0.143 | 54.0 |
| LNU110 | 24954.3 | 6.459 | 0.513 | 3.3 | LNU36 | 25562.4 | 8.949 | 0.356 | 20.3 |
| LNU110 | 24952.3 | 6.390 | 0.745 | 2.2 | LNU71 | 25853.4 | 9.497 | 0.169 | 27.7 |
| LNU175 | 24734.4 | 6.980 | 0.074 | 11.6 | CONT. | — | 7.471 | — | 0.0 |
| LNU175 | 24732.2 | 6.789 | 0.217 | 8.6 | LNU1 | 24682.1 | 7.871 | 0.605 | 5.3 |
| LNU175 | 24732.1 | 6.684 | 0.291 | 6.9 | LNU110 | 24952.3 | 9.457 | 0.430 | 26.6 |
| LNU175 | 24733.4 | 6.405 | 0.644 | 2.4 | LNU110 | 24953.2 | 7.893 | 0.671 | 5.6 |
| LNU215 | 24664.2 | 7.333 | 0.014 | 17.3 | LNU175 | 24732.2 | 10.614 | 0.087 | 42.1 |
| LNU215 | 24663.4 | 7.264 | 0.028 | 16.2 | LNU175 | 24732.1 | 8.454 | 0.362 | 13.1 |
| LNU215 | 24661.4 | 7.235 | 0.020 | 15.7 | LNU19 | 25151.1 | 8.732 | 0.331 | 16.9 |
| LNU215 | 24663.3 | 7.010 | 0.122 | 12.1 | LNU215 | 24664.2 | 10.890 | 0.014 | 45.8 |
| LNU215 | 24663.1 | 6.620 | 0.320 | 5.9 | LNU215 | 24663.4 | 9.659 | 0.016 | 29.3 |
| LNU27 | 24873.1 | 7.237 | 0.033 | 15.8 | LNU215 | 24663.3 | 8.611 | 0.239 | 15.2 |
| LNU27 | 24873.4 | 6.541 | 0.520 | 4.6 | LNU215 | 24661.4 | 8.607 | 0.103 | 15.2 |
| LNU27 | 24871.4 | 6.422 | 0.617 | 2.7 | LNU27 | 24873.1 | 11.099 | 0.106 | 48.5 |
| LNU44 | 24923.3 | 7.316 | 0.022 | 17.0 | LNU27 | 24873.4 | 8.805 | 0.231 | 17.8 |
| LNU44 | 24924.2 | 7.272 | 0.018 | 16.3 | LNU44 | 24924.2 | 11.478 | 0.024 | 53.6 |
| LNU44 | 24922.3 | 7.169 | 0.045 | 14.7 | LNU44 | 24924.3 | 10.805 | 0.114 | 44.6 |
| LNU54 | 24901.2 | 7.648 | 0.030 | 22.3 | LNU44 | 24922.3 | 10.586 | 0.205 | 41.7 |
| LNU54 | 24902.4 | 7.438 | 0.010 | 19.0 | LNU44 | 24923.3 | 9.478 | 0.026 | 26.9 |
| LNU54 | 24903.5 | 7.013 | 0.120 | 12.2 | LNU54 | 24903.5 | 12.998 | 0.000 | 74.0 |
| LNU54 | 24903.3 | 6.934 | 0.256 | 10.9 | LNU54 | 24901.2 | 11.545 | 0.124 | 54.5 |
| LNU54 | 24902.7 | 6.461 | 0.603 | 3.3 | LNU54 | 24903.3 | 11.231 | 0.101 | 50.3 |
| LNU79 | 24882.2 | 7.312 | 0.018 | 16.9 | LNU54 | 24902.4 | 9.290 | 0.026 | 24.3 |
| LNU79 | 24881.1 | 7.287 | 0.017 | 16.5 | LNU79 | 24884.4 | 11.593 | 0.001 | 55.2 |
| LNU79 | 24884.4 | 7.052 | 0.043 | 12.8 | LNU79 | 24881.1 | 11.528 | 0.010 | 54.3 |
| LNU79 | 24883.2 | 6.742 | 0.224 | 7.8 | LNU79 | 24884.3 | 9.294 | 0.179 | 24.4 |
| CONT. | — | 6.833 | — | 0.0 | LNU79 | 24882.2 | 8.705 | 0.104 | 16.5 |
| LNU109 | 24892.8 | 7.289 | 0.058 | 6.7 | CONT. | — | 8.911 | — | 0.0 |
| LNU109 | 24891.5 | 7.107 | 0.314 | 4.0 | LNU109 | 24891.5 | 11.274 | 0.022 | 26.5 |
| LNU110 | 24952.1 | 8.060 | 0.001 | 18.0 | LNU109 | 24892.6 | 10.560 | 0.281 | 18.5 |
| LNU110 | 24952.3 | 6.969 | 0.733 | 2.0 | LNU109 | 24891.2 | 9.241 | 0.800 | 3.7 |
| LNU133 | 24744.3 | 7.713 | 0.005 | 12.9 | LNU110 | 24952.1 | 19.086 | 0.000 | 114.2 |
| LNU133 | 24741.1 | 7.500 | 0.051 | 9.8 | LNU110 | 24952.3 | 12.178 | 0.071 | 36.7 |
| LNU133 | 24742.2 | 6.891 | 0.785 | 0.8 | LNU110 | 24953.2 | 10.598 | 0.334 | 18.9 |
| LNU19 | 25151.1 | 7.230 | 0.230 | 5.8 | LNU110 | 24954.3 | 9.930 | 0.306 | 11.4 |
| LNU27 | 24873.4 | 7.547 | 0.015 | 10.5 | LNU133 | 24744.3 | 14.915 | 0.004 | 67.4 |
| LNU27 | 24871.4 | 7.040 | 0.366 | 3.0 | LNU133 | 24741.1 | 12.618 | 0.097 | 41.6 |
| LNU44 | 24922.3 | 7.636 | 0.008 | 11.8 | LNU133 | 24742.2 | 10.314 | 0.139 | 15.7 |
| LNU54 | 24901.2 | 7.770 | 0.003 | 13.7 | LNU133 | 24741.2 | 9.795 | 0.366 | 9.9 |
| LNU54 | 24903.5 | 6.959 | 0.693 | 1.9 | LNU19 | 25151.1 | 12.769 | 0.053 | 43.3 |
| LNU6 | 24992.3 | 7.592 | 0.020 | 11.1 | LNU27 | 24873.4 | 14.340 | 0.000 | 60.9 |
| LNU6 | 24994.5 | 7.248 | 0.156 | 6.1 | LNU44 | 24922.3 | 16.486 | 0.000 | 85.0 |
| LNU79 | 24884.4 | 7.615 | 0.008 | 11.4 | LNU54 | 24901.2 | 14.207 | 0.007 | 59.4 |
| LNU79 | 24881.1 | 7.315 | 0.048 | 7.1 | LNU54 | 24903.5 | 10.705 | 0.215 | 20.1 |
| LNU79 | 24882.2 | 6.938 | 0.704 | 1.5 | LNU6 | 24992.3 | 14.206 | 0.025 | 59.4 |
| CONT. | — | 6.439 | — | 0.0 | LNU6 | 24994.5 | 11.407 | 0.229 | 28.0 |
| LNU109 | 24892.8 | 7.505 | 0.066 | 16.6 | LNU6 | 24994.2 | 9.941 | 0.232 | 11.6 |
| LNU109 | 24891.5 | 6.844 | 0.408 | 6.3 | LNU79 | 24884.4 | 15.230 | 0.000 | 70.9 |
| LNU143 | 25975.3 | 7.404 | 0.086 | 15.0 | LNU79 | 24881.1 | 11.673 | 0.018 | 31.0 |
| LNU143 | 25972.1 | 7.221 | 0.137 | 12.1 | LNU79 | 24882.2 | 10.918 | 0.273 | 22.5 |
| LNU143 | 25971.2 | 6.746 | 0.523 | 4.8 | LNU79 | 24884.3 | 10.381 | 0.258 | 16.5 |
| LNU143 | 25971.5 | 6.725 | 0.555 | 4.4 | LNU79 | 24883.2 | 9.300 | 0.577 | 4.4 |
| LNU154 | 14604.7 | 7.068 | 0.230 | 9.8 | CONT. | — | 6.329 | — | 0.0 |

TABLE 64-continued

Genes showing improved root performance at nitrogen deficient conditions (T2 generation)

| | | Roots Length [cm] | | | | | Roots Coverage [cm2] | | |
|---|---|---|---|---|---|---|---|---|---|
| Gene Name | Event # | Ave. | p-value | % incr. | Gene Name | Event # | Ave. | p-value | % incr. |
| LNU154 | 14604.6 | 6.971 | 0.293 | 8.3 | LNU109 | 24892.8 | 12.163 | 0.002 | 92.2 |
| LNU154 | 14601.6 | 6.857 | 0.438 | 6.5 | LNU109 | 24891.5 | 9.351 | 0.067 | 47.8 |
| LNU196 | 25532.2 | 7.657 | 0.044 | 18.9 | LNU109 | 24891.2 | 9.220 | 0.134 | 45.7 |
| LNU196 | 25534.1 | 7.153 | 0.231 | 11.1 | LNU143 | 25975.3 | 8.893 | 0.016 | 40.5 |
| LNU196 | 25533.1 | 6.825 | 0.414 | 6.0 | LNU143 | 25972.1 | 8.480 | 0.043 | 34.0 |
| LNU196 | 25532.1 | 6.745 | 0.628 | 4.7 | LNU143 | 25975.2 | 7.944 | 0.277 | 25.5 |
| LNU207 | 24642.5 | 7.512 | 0.065 | 16.7 | LNU143 | 25971.5 | 7.539 | 0.396 | 19.1 |
| LNU207 | 24644.18 | 7.441 | 0.076 | 15.6 | LNU154 | 14601.6 | 9.541 | 0.108 | 50.8 |
| LNU207 | 24642.4 | 7.339 | 0.109 | 14.0 | LNU154 | 14604.6 | 9.238 | 0.039 | 46.0 |
| LNU207 | 24644.13 | 6.858 | 0.410 | 6.5 | LNU154 | 14604.7 | 8.969 | 0.032 | 41.7 |
| LNU288 | 14564.9 | 7.527 | 0.062 | 16.9 | LNU154 | 14602.8 | 8.206 | 0.375 | 29.7 |
| LNU288 | 14562.1 | 7.058 | 0.217 | 9.6 | LNU196 | 25532.2 | 14.062 | 0.001 | 122.2 |
| LNU288 | 14562.7 | 6.960 | 0.350 | 8.1 | LNU196 | 25534.1 | 11.123 | 0.166 | 75.8 |
| LNU288 | 14562.9 | 6.822 | 0.401 | 5.9 | LNU196 | 25532.1 | 8.240 | 0.335 | 30.2 |
| LNU50 | 26023.2 | 7.381 | 0.093 | 14.6 | LNU196 | 25531.2 | 6.924 | 0.550 | 9.4 |
| LNU50 | 26023.5 | 7.254 | 0.124 | 12.7 | LNU196 | 25533.1 | 6.629 | 0.666 | 4.7 |
| LNU50 | 26024.2 | 7.129 | 0.249 | 10.7 | LNU207 | 24642.4 | 11.713 | 0.059 | 85.1 |
| LNU50 | 26025.3 | 6.750 | 0.499 | 4.8 | LNU207 | 24642.5 | 10.786 | 0.013 | 70.4 |
| LNU52 | 25723.2 | 7.754 | 0.034 | 20.4 | LNU207 | 24644.18 | 9.470 | 0.036 | 49.6 |
| LNU52 | 25721.4 | 7.203 | 0.191 | 11.9 | LNU207 | 24644.13 | 8.136 | 0.302 | 28.6 |
| LNU52 | 25723.1 | 6.913 | 0.377 | 7.3 | LNU288 | 14562.1 | 8.997 | 0.162 | 42.2 |
| LNU52 | 25721.1 | 6.720 | 0.614 | 4.4 | LNU288 | 14562.7 | 8.395 | 0.113 | 32.6 |
| CONT. | — | 5.633 | — | 0.0 | LNU288 | 14564.9 | 8.299 | 0.036 | 31.1 |
| LNU143 | 25975.2 | 6.753 | 0.015 | 19.9 | LNU288 | 14562.12 | 7.258 | 0.206 | 14.7 |
| LNU143 | 25975.3 | 6.608 | 0.003 | 17.3 | LNU288 | 14562.9 | 7.135 | 0.346 | 12.7 |
| LNU143 | 25971.5 | 6.566 | 0.020 | 16.6 | LNU50 | 26023.2 | 9.476 | 0.034 | 49.7 |
| LNU143 | 25972.1 | 6.543 | 0.041 | 16.1 | LNU50 | 26024.2 | 9.283 | 0.125 | 46.7 |
| LNU143 | 25971.2 | 6.461 | 0.006 | 14.7 | LNU50 | 26025.4 | 8.172 | 0.053 | 29.1 |
| LNU154 | 14602.8 | 6.492 | 0.016 | 15.2 | LNU50 | 26023.5 | 7.519 | 0.204 | 18.8 |
| LNU154 | 14601.6 | 6.149 | 0.108 | 9.2 | LNU50 | 26022.1 | 6.843 | 0.599 | 8.1 |
| LNU207 | 24642.5 | 6.965 | 0.011 | 23.6 | LNU52 | 25723.2 | 14.598 | 0.005 | 130.7 |
| LNU207 | 24641.1 | 6.872 | 0.016 | 22.0 | LNU52 | 25721.4 | 10.374 | 0.100 | 63.9 |
| LNU207 | 24642.4 | 6.413 | 0.011 | 13.8 | LNU52 | 25721.3 | 10.089 | 0.085 | 59.4 |
| LNU211 | 24771.1 | 7.033 | 0.007 | 24.8 | LNU52 | 25723.1 | 7.096 | 0.545 | 12.1 |
| LNU211 | 24771.3 | 6.030 | 0.095 | 7.0 | CONT. | — | 8.555 | — | |
| LNU211 | 24774.4 | 5.978 | 0.569 | 6.1 | LNU143 | 25975.2 | 9.977 | 0.289 | 16.6 |
| LNU52 | 25723.1 | 7.106 | 0.004 | 26.1 | LNU143 | 25975.3 | 9.097 | 0.708 | 6.3 |
| LNU52 | 25721.2 | 6.927 | 0.005 | 23.0 | LNU154 | 14602.8 | 10.155 | 0.142 | 18.7 |
| LNU52 | 25721.1 | 6.506 | 0.021 | 15.5 | LNU207 | 24642.5 | 11.122 | 0.079 | 30.0 |
| LNU52 | 25723.2 | 5.812 | 0.660 | 3.2 | LNU207 | 24641.1 | 10.558 | 0.138 | 23.4 |
| LNU69 | 14571.1 | 7.049 | 0.003 | 25.1 | LNU207 | 24642.4 | 9.609 | 0.289 | 12.3 |
| LNU69 | 14573.3 | 6.658 | 0.008 | 18.2 | LNU211 | 24771.1 | 9.940 | 0.183 | 16.2 |
| LNU69 | 14572.9 | 6.285 | 0.020 | 11.6 | LNU52 | 25721.1 | 12.111 | 0.081 | 41.6 |
| LNU69 | 14572.8 | 6.259 | 0.025 | 11.1 | LNU52 | 25723.1 | 11.473 | 0.179 | 34.1 |
| CONT. | — | 5.748 | — | 0.0 | LNU52 | 25721.2 | 11.153 | 0.205 | 30.4 |
| LNU150 | 24842.9 | 7.210 | 0.000 | 25.4 | LNU52 | 25723.2 | 10.026 | 0.431 | 17.2 |
| LNU150 | 24841.9 | 7.204 | 0.001 | 25.3 | LNU69 | 14571.1 | 11.815 | 0.106 | 38.1 |
| LNU150 | 24843.5 | 6.754 | 0.062 | 17.5 | LNU69 | 14572.9 | 9.516 | 0.423 | 11.2 |
| LNU179 | 24632.5 | 7.693 | 0.000 | 33.8 | LNU69 | 14572.8 | 9.471 | 0.279 | 10.7 |
| LNU179 | 24631.9 | 7.481 | 0.004 | 30.1 | CONT. | — | 7.365 | — | 0.0 |
| LNU179 | 24631.6 | 6.733 | 0.008 | 17.1 | LNU150 | 24842.9 | 13.108 | 0.000 | 78.0 |
| LNU179 | 24631.7 | 6.139 | 0.210 | 6.8 | LNU150 | 24841.9 | 9.862 | 0.067 | 33.9 |
| LNU232 | 26003.3 | 6.837 | 0.002 | 18.9 | LNU150 | 24843.5 | 9.813 | 0.252 | 33.2 |
| LNU232 | 26001.5 | 6.830 | 0.057 | 18.8 | LNU179 | 24632.5 | 12.877 | 0.028 | 74.8 |
| LNU232 | 26003.7 | 6.060 | 0.359 | 5.4 | LNU179 | 24631.9 | 10.523 | 0.117 | 42.9 |
| LNU232 | 26001.7 | 6.004 | 0.436 | 4.5 | LNU179 | 24631.6 | 7.714 | 0.754 | 4.7 |
| LNU235 | 26184.4 | 7.751 | 0.000 | 34.8 | LNU232 | 26003.7 | 9.269 | 0.098 | 25.9 |
| LNU235 | 26185.3 | 7.381 | 0.005 | 28.4 | LNU232 | 26003.3 | 7.728 | 0.720 | 4.9 |
| LNU235 | 26182.1 | 6.699 | 0.017 | 16.5 | LNU235 | 26184.4 | 13.577 | 0.001 | 84.3 |
| LNU235 | 26184.2 | 6.546 | 0.026 | 13.9 | LNU235 | 26185.3 | 11.955 | 0.064 | 62.3 |
| LNU235 | 26185.2 | 6.094 | 0.276 | 6.0 | LNU235 | 26182.1 | 8.994 | 0.179 | 22.1 |
| LNU242 | 25474.1 | 7.362 | 0.001 | 28.1 | LNU235 | 26184.2 | 8.691 | 0.167 | 18.0 |
| LNU242 | 25473.1 | 7.108 | 0.003 | 23.7 | LNU242 | 25473.1 | 12.344 | 0.000 | 67.6 |
| LNU242 | 25473.3 | 6.390 | 0.073 | 11.2 | LNU242 | 25474.1 | 10.746 | 0.086 | 45.9 |
| LNU242 | 25471.1 | 6.244 | 0.148 | 8.6 | LNU76 | 26425.1 | 11.223 | 0.020 | 52.4 |
| LNU242 | 25472.1 | 5.879 | 0.763 | 2.3 | LNU76 | 26421.2 | 10.070 | 0.047 | 36.7 |
| LNU76 | 26425.1 | 7.027 | 0.001 | 22.2 | LNU76 | 26423.1 | 9.805 | 0.046 | 33.1 |
| LNU76 | 26423.1 | 6.864 | 0.017 | 19.4 | LNU76 | 26421.1 | 8.691 | 0.466 | 18.0 |
| LNU76 | 26421.2 | 6.813 | 0.066 | 18.5 | LNU95 | 13985.11 | 12.944 | 0.033 | 75.7 |
| LNU76 | 26421.1 | 6.590 | 0.106 | 14.6 | LNU95 | 13985.15 | 9.432 | 0.058 | 28.1 |
| LNU95 | 13985.11 | 7.431 | 0.000 | 29.3 | LNU95 | 13985.12 | 9.399 | 0.182 | 27.6 |
| LNU95 | 13985.19 | 7.114 | 0.004 | 23.8 | LNU95 | 13985.19 | 9.281 | 0.368 | 26.0 |
| LNU95 | 13985.15 | 6.928 | 0.001 | 20.5 | LNU95 | 13985.16 | 7.914 | 0.569 | 7.5 |

TABLE 64-continued

Genes showing improved root performance at nitrogen deficient conditions (T2 generation)

| | | Roots Length [cm] | | | | | Roots Coverage [cm2] | | |
|---|---|---|---|---|---|---|---|---|---|
| Gene Name | Event # | Ave. | p-value | % incr. | Gene Name | Event # | Ave. | p-value | % incr. |
| LNU95 | 13985.12 | 6.791 | 0.036 | 18.1 | CONT. | — | 9.009 | — | 0.0 |
| LNU95 | 13985.16 | 6.612 | 0.048 | 15.0 | LNU232 | 26001.5 | 11.019 | 0.177 | 22.3 |
| CONT. | — | 6.930 | — | 0.0 | LNU235 | 26184.4 | 14.496 | 0.000 | 60.9 |
| LNU179 | 24631.6 | 7.162 | 0.374 | 3.4 | LNU235 | 26185.2 | 14.127 | 0.017 | 56.8 |
| LNU232 | 26001.5 | 7.624 | 0.145 | 10.0 | LNU235 | 26184.2 | 10.838 | 0.207 | 20.3 |
| LNU232 | 26003.3 | 7.555 | 0.005 | 9.0 | LNU242 | 25474.1 | 10.306 | 0.406 | 14.4 |
| LNU235 | 26184.4 | 8.109 | 0.000 | 17.0 | LNU288 | 14563.9 | 12.963 | 0.135 | 43.9 |
| LNU235 | 26184.2 | 7.760 | 0.006 | 12.0 | LNU288 | 14562.1 | 10.884 | 0.044 | 20.8 |
| LNU235 | 26185.2 | 7.656 | 0.031 | 10.5 | LNU288 | 14564.9 | 10.080 | 0.495 | 11.9 |
| LNU242 | 25474.1 | 7.198 | 0.532 | 3.9 | LNU76 | 26421.2 | 11.857 | 0.344 | 31.6 |
| LNU288 | 14564.9 | 7.294 | 0.201 | 5.3 | LNU76 | 26422.2 | 9.715 | 0.723 | 7.8 |
| LNU288 | 14562.7 | 7.126 | 0.571 | 2.8 | LNU76 | 26423.1 | 9.480 | 0.777 | 5.2 |
| LNU288 | 14563.6 | 7.066 | 0.547 | 2.0 | LNU95 | 13985.16 | 13.851 | 0.037 | 53.7 |
| LNU288 | 14563.9 | 7.050 | 0.623 | 1.7 | LNU95 | 13985.12 | 12.566 | 0.179 | 39.5 |
| LNU76 | 26421.2 | 7.262 | 0.303 | 4.8 | LNU95 | 13985.15 | 12.253 | 0.037 | 36.0 |
| LNU95 | 13985.16 | 7.835 | 0.000 | 13.1 | CONT. | — | 7.303 | — | 0.0 |
| LNU95 | 13985.15 | 7.095 | 0.521 | 2.4 | LNU101 | 27632.7 | 10.044 | 0.030 | 37.5 |
| CONT. | — | 6.277 | — | 0.0 | LNU101 | 27635.1 | 8.226 | 0.494 | 12.6 |
| LNU101 | 27632.7 | 7.595 | 0.000 | 21.0 | LNU101 | 27632.1 | 8.137 | 0.145 | 11.4 |
| LNU101 | 27635.1 | 6.518 | 0.421 | 3.8 | LNU128 | 26515.3 | 12.337 | 0.000 | 68.9 |
| LNU128 | 26515.3 | 7.668 | 0.001 | 22.2 | LNU128 | 26511.5 | 9.896 | 0.028 | 35.5 |
| LNU128 | 26511.5 | 7.477 | 0.000 | 19.1 | LNU128 | 26515.2 | 8.997 | 0.171 | 23.2 |
| LNU128 | 26515.2 | 6.784 | 0.237 | 8.1 | LNU128 | 26511.4 | 7.501 | 0.709 | 2.7 |
| LNU192 | 28315.2 | 7.732 | 0.000 | 23.2 | LNU192 | 28315.2 | 11.544 | 0.001 | 58.1 |
| LNU192 | 28313.2 | 7.474 | 0.001 | 19.1 | LNU192 | 28313.2 | 10.093 | 0.000 | 38.2 |
| LNU192 | 28312.2 | 6.813 | 0.031 | 8.5 | LNU192 | 28313.3 | 8.887 | 0.209 | 21.7 |
| LNU192 | 28313.3 | 6.626 | 0.429 | 5.6 | LNU192 | 28312.2 | 7.667 | 0.532 | 5.0 |
| LNU206 | 27621.2 | 6.916 | 0.023 | 10.2 | LNU206 | 27621.2 | 10.347 | 0.011 | 41.7 |
| LNU206 | 27622.1 | 6.838 | 0.191 | 8.9 | LNU206 | 27621.1 | 8.702 | 0.012 | 19.2 |
| LNU211 | 24771.1 | 7.325 | 0.008 | 16.7 | LNU206 | 27622.1 | 8.138 | 0.108 | 11.4 |
| LNU282 | 27562.1 | 7.580 | 0.017 | 20.8 | LNU211 | 24771.1 | 11.295 | 0.035 | 54.7 |
| LNU282 | 27563.1 | 7.388 | 0.005 | 17.7 | LNU211 | 24773.2 | 9.318 | 0.074 | 27.6 |
| LNU282 | 27563.3 | 7.299 | 0.045 | 16.3 | LNU282 | 27562.1 | 12.185 | 0.026 | 66.8 |
| LNU282 | 27565.2 | 6.768 | 0.224 | 7.8 | LNU282 | 27563.3 | 10.979 | 0.012 | 50.3 |
| LNU69 | 14571.1 | 7.603 | 0.000 | 21.1 | LNU282 | 27563.1 | 10.436 | 0.037 | 42.9 |
| LNU69 | 14573.5 | 6.811 | 0.135 | 8.5 | LNU282 | 27565.2 | 8.007 | 0.266 | 9.6 |
| LNU75 | 27572.1 | 7.450 | 0.000 | 18.7 | LNU69 | 14571.1 | 12.531 | 0.002 | 71.6 |
| LNU75 | 27572.2 | 7.264 | 0.069 | 15.7 | LNU69 | 14573.5 | 9.289 | 0.077 | 27.2 |
| LNU75 | 27571.4 | 6.677 | 0.333 | 6.4 | LNU75 | 27572.2 | 11.342 | 0.094 | 55.3 |
| LNU75 | 27572.3 | 6.590 | 0.407 | 5.0 | LNU75 | 27572.1 | 9.625 | 0.022 | 31.8 |
| CONT. | — | 5.813 | — | 0.0 | LNU75 | 27572.3 | 8.378 | 0.398 | 14.7 |
| LNU101 | 27632.5 | 6.807 | 0.016 | 17.1 | LNU75 | 27571.4 | 7.934 | 0.591 | 8.6 |
| LNU101 | 27632.6 | 6.150 | 0.322 | 5.8 | CONT. | — | 6.735 | — | 0.0 |
| LNU118 | 14012.15 | 5.962 | 0.626 | 2.6 | LNU101 | 27632.5 | 8.284 | 0.190 | 23.0 |
| LNU128 | 26515.3 | 6.716 | 0.035 | 15.5 | LNU118 | 14012.15 | 8.399 | 0.071 | 24.7 |
| LNU128 | 26511.5 | 6.226 | 0.315 | 7.1 | LNU206 | 27621.2 | 12.586 | 0.032 | 86.9 |
| LNU206 | 27621.2 | 7.622 | 0.001 | 31.1 | LNU206 | 27622.4 | 11.079 | 0.012 | 64.5 |
| LNU206 | 27622.4 | 7.043 | 0.014 | 21.2 | LNU206 | 27622.1 | 10.117 | 0.052 | 50.2 |
| LNU206 | 27622.1 | 6.757 | 0.103 | 16.2 | LNU206 | 27621.1 | 9.288 | 0.118 | 37.9 |
| LNU249 | 26152.4 | 6.759 | 0.189 | 16.3 | LNU249 | 26153.1 | 10.203 | 0.102 | 51.5 |
| LNU249 | 26153.1 | 6.492 | 0.102 | 11.7 | LNU249 | 26154.2 | 9.330 | 0.208 | 38.5 |
| LNU249 | 26151.1 | 6.359 | 0.283 | 9.4 | LNU249 | 26152.4 | 8.642 | 0.232 | 28.3 |
| LNU249 | 26154.2 | 6.342 | 0.316 | 9.1 | LNU282 | 27563.1 | 10.545 | 0.026 | 56.6 |
| LNU249 | 26152.2 | 6.191 | 0.197 | 6.5 | LNU282 | 27565.2 | 10.509 | 0.072 | 56.0 |
| LNU282 | 27565.2 | 7.232 | 0.001 | 24.4 | LNU282 | 27562.1 | 7.008 | 0.765 | 4.1 |
| LNU282 | 27563.1 | 6.899 | 0.017 | 18.7 | LNU288 | 14563.9 | 12.005 | 0.018 | 78.3 |
| LNU282 | 27562.1 | 6.530 | 0.069 | 12.3 | LNU288 | 14563.6 | 9.606 | 0.173 | 42.6 |
| LNU282 | 27565.1 | 6.410 | 0.188 | 10.3 | LNU288 | 14564.8 | 9.604 | 0.090 | 42.6 |
| LNU282 | 27563.3 | 6.409 | 0.205 | 10.2 | LNU288 | 14562.9 | 9.080 | 0.007 | 34.8 |
| LNU288 | 14563.6 | 6.954 | 0.003 | 19.6 | LNU288 | 14562.7 | 8.511 | 0.202 | 26.4 |
| LNU288 | 14562.7 | 6.914 | 0.014 | 18.9 | LNU75 | 27572.2 | 13.524 | 0.039 | 100.8 |
| LNU288 | 14563.9 | 6.862 | 0.016 | 18.0 | LNU75 | 27571.2 | 11.853 | 0.022 | 76.0 |
| LNU288 | 14562.9 | 6.355 | 0.078 | 9.3 | LNU75 | 27572.3 | 11.191 | 0.014 | 66.2 |
| LNU288 | 14564.8 | 6.291 | 0.244 | 8.2 | LNU75 | 27571.4 | 9.627 | 0.064 | 42.9 |
| LNU75 | 27572.2 | 7.464 | 0.003 | 28.4 | CONT. | — | 11.156 | — | 0.0 |
| LNU75 | 27571.2 | 7.428 | 0.000 | 27.8 | LNU112 | 28212.4 | 12.419 | 0.271 | 11.3 |
| LNU75 | 27571.4 | 7.346 | 0.000 | 26.4 | LNU183 | 24865.1 | 12.047 | 0.600 | 8.0 |
| LNU75 | 27572.3 | 7.114 | 0.001 | 22.4 | LNU183 | 24863.1 | 11.863 | 0.548 | 6.3 |
| CONT. | — | 6.748 | — | 0.0 | LNU201 | 28222.2 | 12.100 | 0.653 | 8.5 |
| LNU11 | 28205.2 | 7.162 | 0.194 | 6.1 | LNU201 | 28223.1 | 11.563 | 0.780 | 3.6 |
| LNU112 | 28212.4 | 7.424 | 0.065 | 10.0 | LNU268 | 26044.2 | 13.230 | 0.270 | 18.6 |
| LNU14 | 27821.3 | 7.205 | 0.162 | 6.8 | CONT. | — | 8.642 | — | 0.0 |
| LNU14 | 27823.2 | 6.881 | 0.653 | 2.0 | LNU11 | 28205.2 | 11.985 | 0.010 | 38.7 |

TABLE 64-continued

Genes showing improved root performance at nitrogen deficient conditions (T2 generation)

| | | Roots Length [cm] | | | | | Roots Coverage [cm2] | | |
|---|---|---|---|---|---|---|---|---|---|
| Gene Name | Event # | Ave. | p-value | % incr. | Gene Name | Event # | Ave. | p-value | % incr. |
| LNU14 | 27824.2 | 6.880 | 0.664 | 2.0 | LNU11 | 28203.2 | 11.222 | 0.219 | 29.9 |
| LNU14 | 27821.1 | 6.873 | 0.710 | 1.8 | LNU11 | 28205.1 | 11.099 | 0.083 | 28.4 |
| LNU201 | 28223.3 | 7.200 | 0.199 | 6.7 | LNU11 | 28202.5 | 11.048 | 0.171 | 27.8 |
| LNU201 | 28222.2 | 7.189 | 0.180 | 6.5 | LNU11 | 28204.1 | 9.232 | 0.632 | 6.8 |
| LNU201 | 28223.1 | 7.123 | 0.287 | 5.6 | LNU112 | 28212.1 | 11.083 | 0.103 | 28.3 |
| LNU201 | 28222.3 | 7.105 | 0.263 | 5.3 | LNU112 | 28212.4 | 9.361 | 0.431 | 8.3 |
| LNU268 | 26044.2 | 7.215 | 0.173 | 6.9 | LNU14 | 27821.3 | 14.480 | 0.003 | 67.6 |
| LNU268 | 26041.6 | 7.074 | 0.272 | 4.8 | LNU14 | 27821.4 | 11.236 | 0.153 | 30.0 |
| CONT. | — | 6.558 | — | 0.0 | LNU14 | 27824.2 | 9.792 | 0.285 | 13.3 |
| LNU11 | 28205.2 | 7.549 | 0.054 | 15.1 | LNU14 | 27821.1 | 9.067 | 0.556 | 4.9 |
| LNU11 | 28202.5 | 7.066 | 0.043 | 7.7 | LNU183 | 24864.6 | 16.882 | 0.000 | 95.4 |
| LNU11 | 28205.1 | 6.967 | 0.082 | 6.2 | LNU183 | 24865.1 | 13.996 | 0.010 | 62.0 |
| LNU11 | 28203.2 | 6.673 | 0.705 | 1.8 | LNU183 | 24863.12 | 13.932 | 0.002 | 61.2 |
| LNU112 | 28212.1 | 7.029 | 0.091 | 7.2 | LNU183 | 24863.1 | 11.228 | 0.071 | 29.9 |
| LNU112 | 28212.4 | 6.855 | 0.357 | 4.5 | LNU191 | 28325.4 | 11.845 | 0.144 | 37.1 |
| LNU14 | 27821.3 | 7.453 | 0.004 | 13.6 | LNU191 | 28323.1 | 11.545 | 0.092 | 33.6 |
| LNU14 | 27821.4 | 7.112 | 0.086 | 8.4 | LNU191 | 28321.3 | 10.102 | 0.059 | 16.9 |
| LNU14 | 27824.2 | 6.705 | 0.664 | 2.2 | LNU191 | 28324.2 | 9.088 | 0.641 | 5.2 |
| LNU14 | 27821.1 | 6.617 | 0.785 | 0.9 | LNU201 | 28222.2 | 13.603 | 0.012 | 57.4 |
| LNU183 | 24864.6 | 7.736 | 0.001 | 18.0 | LNU201 | 28223.3 | 12.364 | 0.053 | 43.1 |
| LNU183 | 24863.12 | 7.306 | 0.109 | 11.4 | LNU201 | 28221.3 | 9.939 | 0.105 | 15.0 |
| LNU183 | 24863.1 | 6.908 | 0.265 | 5.3 | LNU201 | 28223.1 | 9.431 | 0.624 | 9.1 |
| LNU183 | 24865.1 | 6.901 | 0.514 | 5.2 | LNU268 | 26041.4 | 10.798 | 0.011 | 25.0 |
| LNU201 | 28222.2 | 7.686 | 0.001 | 17.2 | LNU268 | 26041.6 | 10.549 | 0.191 | 22.1 |
| LNU201 | 28223.3 | 7.225 | 0.075 | 10.2 | LNU268 | 26043.4 | 10.366 | 0.163 | 20.0 |
| LNU201 | 28223.1 | 6.881 | 0.350 | 4.9 | CONT. | — | 8.826 | — | 0.0 |
| LNU268 | 26041.6 | 7.361 | 0.030 | 12.3 | LNU107 | 14583.8 | 12.388 | 0.135 | 40.4 |
| LNU268 | 26041.4 | 7.076 | 0.043 | 7.9 | LNU107 | 14585.5 | 10.429 | 0.192 | 18.2 |
| CONT. | — | 6.688 | — | 0.0 | LNU107 | 14584.9 | 9.576 | 0.645 | 8.5 |
| LNU107 | 14585.5 | 6.948 | 0.465 | 3.9 | LNU116 | 14492.9 | 12.023 | 0.153 | 36.2 |
| LNU107 | 14584.9 | 6.902 | 0.582 | 3.2 | LNU116 | 14494.5 | 11.609 | 0.162 | 31.5 |
| LNU107 | 14583.8 | 6.876 | 0.677 | 2.8 | LNU116 | 14492.5 | 10.826 | 0.224 | 22.7 |
| LNU121 | 27711.1 | 7.515 | 0.022 | 12.4 | LNU121 | 27713.4 | 13.101 | 0.024 | 48.4 |
| LNU121 | 27713.4 | 7.131 | 0.040 | 6.6 | LNU121 | 25642.2 | 12.536 | 0.016 | 42.0 |
| LNU121 | 25642.2 | 6.832 | 0.534 | 2.2 | LNU121 | 27711.1 | 12.183 | 0.025 | 38.0 |
| LNU126 | 25345.1 | 7.223 | 0.030 | 8.0 | LNU121 | 27713.1 | 9.357 | 0.718 | 6.0 |
| LNU126 | 25343.1 | 7.063 | 0.039 | 5.6 | LNU126 | 25345.1 | 12.082 | 0.186 | 36.9 |
| LNU126 | 25343.3 | 6.914 | 0.580 | 3.4 | LNU126 | 25343.1 | 11.624 | 0.066 | 31.7 |
| LNU158 | 27433.3 | 7.724 | 0.001 | 15.5 | LNU126 | 25343.3 | 10.159 | 0.512 | 15.1 |
| LNU158 | 27433.2 | 7.263 | 0.050 | 8.6 | LNU158 | 27433.3 | 13.205 | 0.003 | 49.6 |
| LNU158 | 27432.5 | 7.064 | 0.448 | 5.6 | LNU158 | 27432.5 | 13.036 | 0.262 | 47.7 |
| LNU177 | 24764.9 | 7.526 | 0.199 | 12.5 | LNU158 | 27433.2 | 11.539 | 0.083 | 30.7 |
| LNU177 | 24762.6 | 7.459 | 0.001 | 11.5 | LNU177 | 24762.6 | 13.660 | 0.000 | 54.8 |
| LNU177 | 24764.12 | 7.090 | 0.429 | 6.0 | LNU177 | 24764.9 | 10.753 | 0.487 | 21.8 |
| LNU177 | 24765.2 | 6.840 | 0.490 | 2.3 | LNU177 | 24765.2 | 9.467 | 0.570 | 7.3 |
| LNU182 | 25384.1 | 7.669 | 0.032 | 14.7 | LNU182 | 25384.1 | 14.203 | 0.000 | 60.9 |
| LNU182 | 27521.4 | 7.285 | 0.044 | 8.9 | LNU182 | 27521.4 | 12.084 | 0.082 | 36.9 |
| LNU182 | 25384.5 | 6.920 | 0.233 | 3.5 | LNU182 | 25384.2 | 9.950 | 0.536 | 12.7 |
| LNU2 | 27842.1 | 7.230 | 0.111 | 8.1 | LNU182 | 25384.5 | 9.279 | 0.725 | 5.1 |
| LNU2 | 27842.3 | 6.891 | 0.222 | 3.0 | LNU2 | 27842.1 | 10.901 | 0.082 | 23.5 |
| LNU225 | 25991.5 | 7.854 | 0.000 | 17.4 | LNU2 | 27842.3 | 10.146 | 0.166 | 15.0 |
| LNU225 | 25991.3 | 7.318 | 0.004 | 9.4 | LNU225 | 25991.5 | 16.802 | 0.002 | 90.4 |
| LNU225 | 25991.2 | 7.306 | 0.164 | 9.2 | LNU225 | 25991.2 | 13.379 | 0.239 | 51.6 |
| LNU239 | 26284.1 | 7.073 | 0.262 | 5.8 | LNU239 | 26284.1 | 10.137 | 0.231 | 14.9 |
| LNU57 | 27852.1 | 7.119 | 0.122 | 6.5 | LNU57 | 27852.1 | 9.278 | 0.731 | 5.1 |
| LNU83 | 27681.4 | 7.284 | 0.166 | 8.9 | LNU83 | 27681.4 | 10.944 | 0.214 | 24.0 |
| LNU83 | 27682.1 | 6.944 | 0.535 | 3.8 | LNU83 | 27684.1 | 9.726 | 0.592 | 10.2 |
| CONT. | — | 6.610 | — | 0.0 | CONT. | — | 8.649 | — | 0.0 |
| LNU107 | 14584.9 | 7.452 | 0.011 | 12.7 | LNU107 | 14584.9 | 13.777 | 0.006 | 59.3 |
| LNU116 | 14492.5 | 6.844 | 0.603 | 3.5 | LNU107 | 14583.8 | 10.320 | 0.189 | 19.3 |
| LNU121 | 27711.1 | 7.402 | 0.015 | 12.0 | LNU107 | 14585.2 | 9.003 | 0.660 | 4.1 |
| LNU121 | 27713.1 | 7.140 | 0.136 | 8.0 | LNU116 | 14492.5 | 12.926 | 0.175 | 49.5 |
| LNU121 | 27713.4 | 6.865 | 0.366 | 3.9 | LNU116 | 14494.5 | 11.992 | 0.193 | 38.6 |
| LNU121 | 25642.2 | 6.793 | 0.733 | 2.8 | LNU116 | 14493.6 | 9.901 | 0.185 | 14.5 |
| LNU126 | 25343.1 | 7.627 | 0.015 | 15.4 | LNU121 | 25642.2 | 12.625 | 0.067 | 46.0 |
| LNU126 | 25345.1 | 6.880 | 0.247 | 4.1 | LNU121 | 27711.1 | 12.159 | 0.059 | 40.6 |
| LNU126 | 25343.3 | 6.774 | 0.579 | 2.5 | LNU121 | 27713.1 | 11.980 | 0.126 | 38.5 |
| LNU126 | 25343.4 | 6.743 | 0.602 | 2.0 | LNU121 | 27713.4 | 10.723 | 0.212 | 24.0 |
| LNU158 | 27433.3 | 7.700 | 0.001 | 16.5 | LNU126 | 25343.1 | 12.591 | 0.061 | 45.6 |
| LNU158 | 27432.5 | 7.579 | 0.003 | 14.7 | LNU126 | 25343.3 | 9.454 | 0.636 | 9.3 |
| LNU158 | 27433.2 | 7.218 | 0.174 | 9.2 | LNU126 | 25343.4 | 9.346 | 0.489 | 8.1 |
| LNU158 | 27434.5 | 7.076 | 0.202 | 7.1 | LNU158 | 27433.3 | 14.173 | 0.003 | 63.9 |
| LNU177 | 24764.12 | 7.403 | 0.005 | 12.0 | LNU158 | 27432.5 | 12.764 | 0.002 | 47.6 |

TABLE 64-continued

Genes showing improved root performance at nitrogen deficient conditions (T2 generation)

| | | Roots Length [cm] | | | | | Roots Coverage [cm2] | | |
|---|---|---|---|---|---|---|---|---|---|
| Gene Name | Event # | Ave. | p-value | % incr. | Gene Name | Event # | Ave. | p-value | % incr. |
| LNU177 | 24765.2 | 7.050 | 0.223 | 6.7 | LNU158 | 27433.2 | 10.182 | 0.303 | 17.7 |
| LNU177 | 24763.6 | 6.895 | 0.320 | 4.3 | LNU177 | 24764.12 | 12.256 | 0.002 | 41.7 |
| LNU182 | 27521.4 | 7.048 | 0.183 | 6.6 | LNU177 | 24763.6 | 9.330 | 0.473 | 7.9 |
| LNU182 | 25384.5 | 6.953 | 0.377 | 5.2 | LNU177 | 24762.6 | 9.229 | 0.375 | 6.7 |
| LNU182 | 25384.2 | 6.938 | 0.392 | 5.0 | LNU182 | 25384.6 | 9.479 | 0.435 | 9.6 |
| LNU182 | 25384.6 | 6.861 | 0.470 | 3.8 | LNU182 | 25384.1 | 9.407 | 0.565 | 8.8 |
| LNU2 | 27842.1 | 7.658 | 0.002 | 15.9 | LNU182 | 25384.5 | 9.310 | 0.530 | 7.6 |
| LNU2 | 27842.3 | 7.291 | 0.010 | 10.3 | LNU2 | 27842.1 | 12.557 | 0.031 | 45.2 |
| LNU2 | 25713.1 | 6.781 | 0.432 | 2.6 | LNU2 | 27842.3 | 10.135 | 0.121 | 17.2 |
| LNU225 | 25991.3 | 7.597 | 0.009 | 14.9 | LNU2 | 25713.1 | 9.741 | 0.417 | 12.6 |
| LNU225 | 25991.1 | 7.436 | 0.021 | 12.5 | LNU225 | 25991.3 | 14.898 | 0.000 | 72.2 |
| LNU225 | 25991.2 | 7.232 | 0.026 | 9.4 | LNU225 | 25991.2 | 13.446 | 0.031 | 55.5 |
| LNU225 | 25991.8 | 7.229 | 0.041 | 9.4 | LNU225 | 25991.8 | 11.180 | 0.011 | 29.3 |
| LNU225 | 25991.5 | 7.188 | 0.033 | 8.7 | LNU225 | 25991.1 | 10.790 | 0.067 | 24.8 |
| LNU239 | 26284.2 | 7.240 | 0.074 | 9.5 | LNU239 | 26284.2 | 11.555 | 0.003 | 33.6 |
| LNU239 | 26281.1 | 7.010 | 0.093 | 6.1 | LNU239 | 26281.1 | 8.866 | 0.720 | 2.5 |
| LNU239 | 26284.1 | 6.697 | 0.763 | 1.3 | LNU57 | 27852.1 | 13.264 | 0.000 | 53.4 |
| LNU57 | 27852.1 | 7.461 | 0.005 | 12.9 | LNU57 | 27851.2 | 12.792 | 0.028 | 47.9 |
| LNU57 | 27851.2 | 7.231 | 0.067 | 9.4 | LNU57 | 27854.5 | 10.651 | 0.061 | 23.1 |
| LNU57 | 27854.3 | 7.077 | 0.107 | 7.1 | LNU57 | 27854.3 | 9.037 | 0.488 | 4.5 |
| LNU57 | 27854.5 | 7.063 | 0.150 | 6.8 | LNU83 | 27685.1 | 14.008 | 0.002 | 62.0 |
| LNU83 | 27685.2 | 7.614 | 0.010 | 15.2 | LNU83 | 27685.2 | 11.664 | 0.041 | 34.9 |
| LNU83 | 27685.1 | 7.587 | 0.001 | 14.8 | LNU83 | 27681.4 | 11.522 | 0.020 | 33.2 |
| LNU83 | 27681.4 | 7.289 | 0.017 | 10.3 | CONT. | — | 10.064 | — | |
| LNU83 | 27682.1 | 7.010 | 0.337 | 6.0 | LNU17 | 13991.1 | 11.488 | 0.32 | 14.1 |
| CONT. | — | 6.95 | — | 0.0 | CONT. | 12033.3 | 6.301 | | 0.0 |
| LNU17 | 13991.1 | 7.33 | 0.24 | 5.3 | LNU129 | 27501.2 | 10.049 | <0.05 | 59.5 |
| LNU17 | 13991.14 | 7.11 | 0.62 | 2.1 | LNU129 | 27502.4 | 8.465 | <0.05 | 34.3 |
| CONT. | — | 6.181 | — | 0.0 | LNU129 | 27503.4 | 8.035 | <0.05 | 27.5 |
| LNU129 | 27501.2 | 7.291 | <0.1 | 17.9 | LNU129 | 27504.2 | 9.203 | <0.05 | 46.0 |
| LNU129 | 27502.4 | 6.724 | <0.1 | 8.8 | LNU129 | 27504.3 | 10.684 | <0.05 | 69.6 |
| LNU129 | 27503.4 | 6.617 | <0.2 | 7.1 | LNU147 | 27511.4 | 8.137 | <0.05 | 29.1 |
| LNU129 | 27504.3 | 7.254 | <0.1 | 17.4 | LNU147 | 27512.1 | 7.206 | | 14.4 |
| LNU147 | 27511.4 | 6.549 | <0.5 | 5.9 | LNU147 | 27513.2 | 9.441 | <0.05 | 49.8 |
| LNU147 | 27512.1 | 6.521 | <0.5 | 5.5 | LNU147 | 27514.1 | 8.236 | <0.05 | 30.7 |
| LNU147 | 27514.2 | 6.686 | <0.1 | 8.2 | LNU147 | 27514.2 | 9.705 | <0.05 | 54.0 |
| LNU189 | 26382.4 | 7.221 | <0.1 | 16.8 | LNU153 | 24851.3 | 7.510 | | 19.2 |
| LNU189 | 26383.1 | 6.520 | <0.5 | 5.5 | LNU153 | 24851.4 | 7.033 | | 11.6 |
| LNU189 | 26385.1 | 6.833 | <0.1 | 10.5 | LNU189 | 26382.3 | 11.910 | <0.05 | 89.0 |
| LNU219 | 27462.1 | 7.278 | <0.1 | 17.7 | LNU189 | 26382.4 | 12.085 | <0.05 | 91.8 |
| LNU219 | 27462.2 | 6.981 | <0.1 | 12.9 | LNU189 | 26383.1 | 9.119 | <0.05 | 44.7 |
| LNU256 | 26211.2 | 6.754 | <0.1 | 9.3 | LNU189 | 26385.1 | 10.337 | <0.05 | 64.0 |
| LNU256 | 26212.3 | 6.691 | <0.1 | 8.2 | LNU219 | 27461.1 | 9.304 | <0.05 | 47.7 |
| LNU256 | 26214.1 | 7.064 | <0.1 | 14.3 | LNU219 | 27462.1 | 14.273 | <0.05 | 126.5 |
| LNU257 | 26254.1 | 7.230 | <0.1 | 17.0 | LNU219 | 27462.2 | 11.156 | <0.05 | 77.1 |
| LNU257 | 26254.3 | 7.714 | <0.1 | 24.8 | LNU219 | 27464.2 | 7.151 | | 13.5 |
| LNU257 | 26255.2 | 6.760 | <0.1 | 9.4 | LNU256 | 26211.2 | 7.359 | | 16.8 |
| LNU257 | 26255.3 | 6.777 | <0.1 | 9.6 | LNU256 | 26212.3 | 10.694 | <0.05 | 69.7 |
| LNU261 | 27401.4 | 7.082 | <0.1 | 14.6 | LNU256 | 26213.1 | 9.008 | <0.05 | 43.0 |
| LNU261 | 27403.2 | 6.719 | <0.1 | 8.7 | LNU256 | 26214.1 | 11.063 | <0.05 | 75.6 |
| LNU261 | 27405.1 | 6.970 | <0.1 | 12.8 | LNU257 | 26254.1 | 9.639 | <0.05 | 53.0 |
| LNU261 | 27405.3 | 6.748 | <0.1 | 9.2 | LNU257 | 26254.3 | 15.465 | <0.05 | 145.4 |
| LNU33 | 25552.2 | 6.847 | <0.1 | 10.8 | LNU257 | 26254.7 | 9.843 | <0.05 | 56.2 |
| LNU33 | 25553.3 | 6.888 | <0.1 | 11.4 | LNU257 | 26255.2 | 6.589 | <0.8 | 4.6 |
| LNU35 | 27421.2 | 6.636 | <0.2 | 7.4 | LNU257 | 26255.3 | 7.862 | <0.2 | 24.8 |
| LNU35 | 27423.3 | 6.966 | <0.1 | 12.7 | LNU261 | 27401.4 | 8.612 | <0.05 | 36.7 |
| LNU35 | 27424.3 | 6.633 | <0.2 | 7.3 | LNU261 | 27403.2 | 9.379 | <0.05 | 48.8 |
| LNU50 | 26022.1 | 6.629 | <0.2 | 7.2 | LNU261 | 27405.1 | 8.806 | <0.05 | 39.8 |
| LNU50 | 26023.2 | 6.948 | <0.1 | 12.4 | LNU261 | 27405.3 | 8.021 | <0.2 | 27.3 |
| LNU50 | 26023.3 | 6.821 | <0.1 | 10.3 | LNU33 | 25552.2 | 9.471 | <0.05 | 50.3 |
| LNU50 | 26025.3 | 7.624 | <0.1 | 23.3 | LNU33 | 25553.2 | 7.380 | <0.4 | 17.1 |
| LNU70 | 25311.4 | 7.590 | <0.1 | 22.8 | LNU33 | 25553.3 | 7.792 | <0.2 | 23.7 |
| LNU70 | 25313.2 | 6.816 | <0.1 | 10.3 | LNU33 | 25555.1 | 7.261 | <0.4 | 15.2 |
| | | | | | LNU35 | 27421.2 | 8.163 | <0.2 | 29.5 |
| | | | | | LNU35 | 27422.1 | 8.300 | <0.05 | 31.7 |
| | | | | | LNU35 | 27423.3 | 11.263 | <0.05 | 78.7 |
| | | | | | LNU35 | 27424.3 | 8.953 | <0.05 | 42.1 |
| | | | | | LNU35 | 27424.4 | 8.455 | <0.05 | 34.2 |
| | | | | | LNU50 | 26022.1 | 10.653 | <0.05 | 69.1 |
| | | | | | LNU50 | 26023.2 | 12.657 | <0.05 | 100.9 |
| | | | | | LNU50 | 26023.3 | 7.219 | <0.5 | 14.6 |
| | | | | | LNU50 | 26024.1 | 7.889 | <0.2 | 25.2 |
| | | | | | LNU50 | 26025.3 | 15.671 | <0.05 | 148.7 |

TABLE 64-continued

Genes showing improved root performance at nitrogen deficient conditions (T2 generation)

| Gene Name | Event # | Roots Length [cm] Ave. | p-value | % incr. | Gene Name | Event # | Roots Coverage [cm2] Ave. | p-value | % incr. |
|---|---|---|---|---|---|---|---|---|---|
| | | | | | LNU70 | 25311.4 | 14.371 | <0.05 | 128.1 |
| | | | | | LNU70 | 25313.1 | 7.720 | <0.1 | 22.5 |
| | | | | | LNU70 | 25313.2 | 10.792 | <0.05 | 71.3 |

Table 64.
"CONT."—Control;
"Ave."—Average;
"% Incr." = % increment.

TABLE 65

Genes showing improved root performance at nitrogen deficient conditions (T1 generation)

| Gene Name | Time Point | Roots Length [cm] Ave. | p-value | % incr. | Gene Name | Time Point | Roots Coverage [cm2] Ave. | p-value | % incr. |
|---|---|---|---|---|---|---|---|---|---|
| CONT. | Roots Length TP1 | 0.252 | — | 0.0 | CONT. | Roots Coverage TP1 | 0.017 | — | 0.0 |
| LNU107 | Roots Length TP1 | 0.477 | 0.000 | 89.1 | LNU107 | Roots Coverage TP1 | 0.052 | 0.011 | 212.2 |
| LNU118 | Roots Length TP1 | 0.338 | 0.000 | 33.8 | LNU118 | Roots Coverage TP1 | 0.039 | 0.001 | 138.7 |
| LNU121 | Roots Length TP1 | 0.492 | 0.004 | 95.1 | LNU121 | Roots Coverage TP1 | 0.083 | 0.010 | 400.7 |
| LNU141 | Roots Length TP1 | 0.435 | 0.020 | 72.4 | LNU141 | Roots Coverage TP1 | 0.042 | 0.103 | 155.4 |
| LNU150 | Roots Length TP1 | 0.355 | 0.024 | 40.5 | LNU150 | Roots Coverage TP1 | 0.042 | 0.005 | 153.3 |
| LNU154 | Roots Length TP1 | 0.439 | 0.001 | 74.0 | LNU154 | Roots Coverage TP1 | 0.066 | 0.012 | 300.8 |
| LNU210 | Roots Length TP1 | 0.401 | 0.001 | 59.0 | LNU210 | Roots Coverage TP1 | 0.053 | 0.009 | 218.2 |
| LNU68 | Roots Length TP1 | 0.403 | 0.038 | 59.7 | LNU68 | Roots Coverage TP1 | 0.054 | 0.066 | 227.3 |
| CONT. | Roots Length TP2 | 2.097 | — | 0.0 | CONT. | Roots Coverage TP2 | 1.275 | — | 0.0 |
| LNU107 | Roots Length TP2 | 2.164 | 0.741 | 3.2 | LNU121 | Roots Coverage TP2 | 1.928 | 0.021 | 51.2 |
| LNU121 | Roots Length TP2 | 2.638 | 0.033 | 25.8 | LNU150 | Roots Coverage TP2 | 1.350 | 0.667 | 5.8 |
| LNU150 | Roots Length TP2 | 2.296 | 0.318 | 9.5 | LNU154 | Roots Coverage TP2 | 1.296 | 0.891 | 1.6 |
| LNU154 | Roots Length TP2 | 2.493 | 0.015 | 18.9 | LNU210 | Roots Coverage TP2 | 1.289 | 0.935 | 1.1 |
| LNU210 | Roots Length TP2 | 2.280 | 0.244 | 8.7 | LNU68 | Roots Coverage TP2 | 1.350 | 0.607 | 5.9 |
| LNU68 | Roots Length TP2 | 2.524 | 0.010 | 20.4 | CONT. | Roots Coverage TP3 | 3.537 | — | 0.0 |
| CONT. | Roots Length TP3 | 4.072 | — | 0.0 | LNU121 | Roots Coverage TP3 | 5.046 | 0.001 | 42.7 |

TABLE 65-continued

Genes showing improved root performance at nitrogen deficient conditions (T1 generation)

| | | Roots Length [cm] | | | | | Roots Coverage [cm2] | | |
|---|---|---|---|---|---|---|---|---|---|
| Gene Name | Time Point | Ave. | p-value | % incr. | Gene Name | Time Point | Ave. | p-value | % incr. |
| LNU121 | Roots Length TP3 | 4.586 | 0.100 | 12.6 | LNU150 | Roots Coverage TP3 | 3.751 | 0.574 | 6.0 |
| LNU154 | Roots Length TP3 | 4.448 | 0.335 | 9.2 | LNU154 | Roots Coverage TP3 | 3.718 | 0.766 | 5.1 |
| LNU210 | Roots Length TP3 | 4.153 | 0.766 | 2.0 | CONT. | Roots Coverage TP1 | 0.045 | — | 0.0 |
| LNU68 | Roots Length TP3 | 4.387 | 0.324 | 7.7 | LNU127 | Roots Coverage TP1 | 0.119 | 0.184 | 164.9 |
| CONT. | Roots Length TP1 | 0.324 | — | 0.0 | LNU188 | Roots Coverage TP1 | 0.051 | 0.521 | 14.3 |
| LNU127 | Roots Length TP1 | 0.561 | 0.073 | 73.0 | LNU2 | Roots Coverage TP1 | 0.090 | 0.023 | 100.2 |
| LNU188 | Roots Length TP1 | 0.423 | 0.046 | 30.3 | LNU239 | Roots Coverage TP1 | 0.076 | 0.002 | 69.8 |
| LNU2 | Roots Length TP1 | 0.518 | 0.002 | 59.7 | LNU255 | Roots Coverage TP1 | 0.063 | 0.180 | 39.0 |
| LNU239 | Roots Length TP1 | 0.512 | 0.000 | 57.7 | LNU265 | Roots Coverage TP1 | 0.089 | 0.026 | 97.7 |
| LNU255 | Roots Length TP1 | 0.496 | 0.005 | 53.0 | LNU275 | Roots Coverage TP1 | 0.131 | 0.003 | 192.0 |
| LNU265 | Roots Length TP1 | 0.455 | 0.003 | 40.4 | LNU32 | Roots Coverage TP1 | 0.074 | 0.017 | 64.8 |
| LNU275 | Roots Length TP1 | 0.552 | 0.000 | 70.0 | LNU57 | Roots Coverage TP1 | 0.092 | 0.001 | 105.0 |
| LNU32 | Roots Length TP1 | 0.525 | 0.162 | 61.7 | LNU58 | Roots Coverage TP1 | 0.096 | 0.012 | 112.6 |
| LNU57 | Roots Length TP1 | 0.493 | 0.000 | 51.9 | LNU83 | Roots Coverage TP1 | 0.121 | 0.001 | 168.7 |
| LNU58 | Roots Length TP1 | 0.509 | 0.001 | 56.8 | CONT. | Roots Coverage TP2 | 1.456 | — | 0.0 |
| LNU83 | Roots Length TP1 | 0.563 | 0.006 | 73.5 | LNU127 | Roots Coverage TP2 | 1.703 | 0.344 | 16.9 |
| CONT. | Roots Length TP2 | 2.393 | — | 0.0 | LNU188 | Roots Coverage TP2 | 1.489 | 0.877 | 2.3 |
| LNU127 | Roots Length TP2 | 2.701 | 0.092 | 12.9 | LNU2 | Roots Coverage TP2 | 1.535 | 0.657 | 5.4 |
| LNU265 | Roots Length TP2 | 2.427 | 0.804 | 1.4 | LNU239 | Roots Coverage TP2 | 1.488 | 0.894 | 2.2 |
| LNU275 | Roots Length TP2 | 2.955 | 0.012 | 23.5 | LNU265 | Roots Coverage TP2 | 1.738 | 0.138 | 19.4 |
| LNU57 | Roots Length TP2 | 2.718 | 0.057 | 13.6 | LNU275 | Roots Coverage TP2 | 3.354 | 0.000 | 130.4 |
| LNU58 | Roots Length TP2 | 2.980 | 0.007 | 24.6 | LNU57 | Roots Coverage TP2 | 1.990 | 0.088 | 36.6 |
| LNU83 | Roots Length TP2 | 2.943 | 0.041 | 23.0 | LNU58 | Roots Coverage TP2 | 2.071 | 0.130 | 42.2 |
| CONT. | Roots Length TP3 | 4.661 | — | 0.0 | LNU83 | Roots Coverage TP2 | 2.185 | 0.081 | 50.1 |

TABLE 65-continued

Genes showing improved root performance at nitrogen deficient conditions (T1 generation)

| Gene Name | Time Point | Roots Length [cm] Ave. | p-value | % incr. | Gene Name | Time Point | Roots Coverage [cm2] Ave. | p-value | % incr. |
|---|---|---|---|---|---|---|---|---|---|
| LNU127 | Roots Length TP3 | 4.923 | 0.369 | 5.6 | CONT. | Roots Coverage TP3 | 4.725 | — | 0.0 |
| LNU217 | Roots Length TP3 | 4.893 | 0.607 | 5.0 | LNU127 | Roots Coverage TP3 | 5.855 | 0.232 | 23.9 |
| LNU265 | Roots Length TP3 | 4.843 | 0.629 | 3.9 | LNU188 | Roots Coverage TP3 | 5.162 | 0.605 | 9.2 |
| LNU275 | Roots Length TP3 | 5.711 | 0.030 | 22.5 | LNU217 | Roots Coverage TP3 | 4.962 | 0.782 | 5.0 |
| LNU57 | Roots Length TP3 | 5.252 | 0.111 | 12.7 | LNU239 | Roots Coverage TP3 | 5.289 | 0.707 | 11.9 |
| LNU58 | Roots Length TP3 | 6.931 | 0.000 | 48.7 | LNU265 | Roots Coverage TP3 | 6.215 | 0.141 | 31.5 |
| LNU83 | Roots Length TP3 | 5.573 | 0.047 | 19.6 | LNU275 | Roots Coverage TP3 | 11.302 | 0.000 | 139.2 |
| CONT. | Roots Length TP1 | 0.251 | — | 0.0 | LNU32 | Roots Coverage TP3 | 5.220 | 0.272 | 10.5 |
| LNU176 | Roots Length TP1 | 0.377 | 0.004 | 50.3 | LNU57 | Roots Coverage TP3 | 5.808 | 0.095 | 22.9 |
| LNU186 | Roots Length TP1 | 0.387 | 0.000 | 54.2 | LNU58 | Roots Coverage TP3 | 11.015 | 0.002 | 133.1 |
| LNU187 | Roots Length TP1 | 0.469 | 0.000 | 87.1 | LNU83 | Roots Coverage TP3 | 6.154 | 0.195 | 30.2 |
| LNU214 | Roots Length TP1 | 0.455 | 0.005 | 81.4 | CONT. | Roots Coverage TP1 | 0.018 | — | 0.0 |
| LNU223 | Roots Length TP1 | 0.422 | 0.000 | 68.4 | LNU176 | Roots Coverage TP1 | 0.047 | 0.000 | 161.9 |
| LNU233 | Roots Length TP1 | 0.416 | 0.000 | 66.1 | LNU186 | Roots Coverage TP1 | 0.038 | 0.024 | 111.9 |
| LNU245 | Roots Length TP1 | 0.432 | 0.000 | 72.3 | LNU187 | Roots Coverage TP1 | 0.036 | 0.065 | 102.1 |
| LNU247 | Roots Length TP1 | 0.391 | 0.049 | 56.0 | LNU214 | Roots Coverage TP1 | 0.055 | 0.003 | 207.0 |
| LNU251 | Roots Length TP1 | 0.483 | 0.026 | 92.8 | LNU223 | Roots Coverage TP1 | 0.053 | 0.008 | 192.3 |
| LNU284 | Roots Length TP1 | 0.302 | 0.089 | 20.5 | LNU233 | Roots Coverage TP1 | 0.055 | 0.001 | 205.8 |
| LNU289 | Roots Length TP1 | 0.541 | 0.000 | 115.9 | LNU245 | Roots Coverage TP1 | 0.052 | 0.005 | 190.1 |
| LNU70 | Roots Length TP1 | 0.346 | 0.027 | 38.0 | LNU247 | Roots Coverage TP1 | 0.058 | 0.010 | 221.7 |
| LNU85 | Roots Length TP1 | 0.515 | 0.001 | 105.6 | LNU251 | Roots Coverage TP1 | 0.048 | 0.011 | 167.7 |
| LNU86 | Roots Length TP1 | 0.432 | 0.000 | 72.3 | LNU284 | Roots Coverage TP1 | 0.025 | 0.241 | 36.0 |
| CONT. | Roots Length TP2 | 2.217 | — | 0.0 | LNU289 | Roots Coverage TP1 | 0.064 | 0.000 | 253.0 |
| LNU176 | Roots Length TP2 | 2.309 | 0.686 | 4.2 | LNU70 | Roots Coverage TP1 | 0.042 | 0.010 | 132.3 |

TABLE 65-continued

Genes showing improved root performance at nitrogen deficient conditions (T1 generation)

| Gene Name | Time Point | Roots Length [cm] Ave. | p-value | % incr. | Gene Name | Time Point | Roots Coverage [cm2] Ave. | p-value | % incr. |
|---|---|---|---|---|---|---|---|---|---|
| LNU214 | Roots Length TP2 | 2.541 | 0.142 | 14.6 | LNU85 | Roots Coverage TP1 | 0.067 | 0.000 | 273.2 |
| LNU223 | Roots Length TP2 | 2.466 | 0.095 | 11.2 | LNU86 | Roots Coverage TP1 | 0.066 | 0.005 | 266.8 |
| LNU233 | Roots Length TP2 | 2.570 | 0.086 | 15.9 | CONT. | Roots Coverage TP2 | 1.074 | — | 0.0 |
| LNU245 | Roots Length TP2 | 2.500 | 0.087 | 12.7 | LNU176 | Roots Coverage TP2 | 1.326 | 0.300 | 23.4 |
| LNU247 | Roots Length TP2 | 2.725 | 0.109 | 22.9 | LNU214 | Roots Coverage TP2 | 1.406 | 0.080 | 30.9 |
| LNU251 | Roots Length TP2 | 2.349 | 0.343 | 5.9 | LNU223 | Roots Coverage TP2 | 1.293 | 0.141 | 20.4 |
| LNU284 | Roots Length TP2 | 2.335 | 0.488 | 5.3 | LNU233 | Roots Coverage TP2 | 1.428 | 0.093 | 32.9 |
| LNU289 | Roots Length TP2 | 2.995 | 0.000 | 35.1 | LNU245 | Roots Coverage TP2 | 1.265 | 0.125 | 17.8 |
| LNU70 | Roots Length TP2 | 2.416 | 0.313 | 9.0 | LNU247 | Roots Coverage TP2 | 1.536 | 0.005 | 43.0 |
| LNU85 | Roots Length TP2 | 2.854 | 0.059 | 28.7 | LNU284 | Roots Coverage TP2 | 1.377 | 0.377 | 28.2 |
| LNU86 | Roots Length TP2 | 2.359 | 0.242 | 6.4 | LNU289 | Roots Coverage TP2 | 1.643 | 0.001 | 53.0 |
| CONT. | Roots Length TP3 | 3.944 | — | 0.0 | LNU70 | Roots Coverage TP2 | 1.242 | 0.329 | 15.6 |
| LNU176 | Roots Length TP3 | 4.150 | 0.692 | 5.2 | LNU85 | Roots Coverage TP2 | 1.648 | 0.094 | 53.4 |
| LNU214 | Roots Length TP3 | 4.160 | 0.286 | 5.5 | LNU86 | Roots Coverage TP2 | 1.180 | 0.402 | 9.9 |
| LNU223 | Roots Length TP3 | 4.286 | 0.266 | 8.7 | CONT. | Roots Coverage TP3 | 3.404 | — | 0.0 |
| LNU233 | Roots Length TP3 | 4.303 | 0.439 | 9.1 | LNU176 | Roots Coverage TP3 | 3.971 | 0.527 | 16.7 |
| LNU245 | Roots Length TP3 | 4.127 | 0.664 | 4.6 | LNU214 | Roots Coverage TP3 | 4.249 | 0.169 | 24.9 |
| LNU247 | Roots Length TP3 | 4.561 | 0.249 | 15.7 | LNU223 | Roots Coverage TP3 | 3.730 | 0.596 | 9.6 |
| LNU251 | Roots Length TP3 | 3.996 | 0.778 | 1.3 | LNU233 | Roots Coverage TP3 | 4.290 | 0.194 | 26.0 |
| LNU289 | Roots Length TP3 | 4.422 | 0.344 | 12.1 | LNU245 | Roots Coverage TP3 | 3.652 | 0.665 | 7.3 |
| LNU70 | Roots Length TP3 | 4.245 | 0.393 | 7.6 | LNU247 | Roots Coverage TP3 | 5.428 | 0.035 | 59.5 |
| LNU85 | Roots Length TP3 | 4.550 | 0.343 | 15.4 | LNU284 | Roots Coverage TP3 | 4.593 | 0.294 | 34.9 |
| CONT. | Roots Length TP1 | 0.787 | — | 0.0 | LNU289 | Roots Coverage TP3 | 4.654 | 0.209 | 36.7 |
| LNU105 | Roots Length TP1 | 0.875 | 0.213 | 11.2 | LNU70 | Roots Coverage TP3 | 3.701 | 0.708 | 8.7 |

TABLE 65-continued

Genes showing improved root performance at nitrogen deficient conditions (T1 generation)

| | Roots Length [cm] | | | | | Roots Coverage [cm2] | | | |
|---|---|---|---|---|---|---|---|---|---|
| Gene Name | Time Point | Ave. | p-value | % incr. | Gene Name | Time Point | Ave. | p-value | % incr. |
| LNU123 | Roots Length TP1 | 0.837 | 0.514 | 6.3 | LNU85 | Roots Coverage TP3 | 4.066 | 0.532 | 19.5 |
| LNU13 | Roots Length TP1 | 0.795 | 0.911 | 0.9 | CONT. | Roots Coverage TP1 | 0.233 | — | 0.0 |
| LNU134 | Roots Length TP1 | 0.871 | 0.124 | 10.6 | LNU105 | Roots Coverage TP1 | 0.261 | 0.329 | 12.1 |
| LNU190 | Roots Length TP1 | 0.821 | 0.614 | 4.3 | LNU123 | Roots Coverage TP1 | 0.238 | 0.912 | 1.9 |
| LNU198 | Roots Length TP1 | 0.819 | 0.606 | 4.1 | LNU134 | Roots Coverage TP1 | 0.284 | 0.151 | 21.8 |
| LNU200 | Roots Length TP1 | 1.049 | 0.020 | 33.3 | LNU190 | Roots Coverage TP1 | 0.262 | 0.395 | 12.5 |
| CONT. | Roots Length TP2 | 3.113 | — | 0.0 | LNU198 | Roots Coverage TP1 | 0.257 | 0.466 | 10.4 |
| LNU105 | Roots Length TP2 | 3.270 | 0.198 | 5.1 | LNU200 | Roots Coverage TP1 | 0.348 | 0.006 | 49.4 |
| LNU134 | Roots Length TP2 | 3.134 | 0.799 | 0.7 | CONT. | Roots Coverage TP2 | 2.289 | — | 0.0 |
| LNU190 | Roots Length TP2 | 3.121 | 0.943 | 0.3 | LNU198 | Roots Coverage TP2 | 2.307 | 0.891 | 0.8 |
| LNU198 | Roots Length TP2 | 3.190 | 0.558 | 2.5 | LNU200 | Roots Coverage TP2 | 2.426 | 0.708 | 6.0 |
| LNU200 | Roots Length TP2 | 3.511 | 0.295 | 12.8 | CONT. | Roots Coverage TP1 | 0.029 | — | 0.0 |
| CONT. | Roots Length TP1 | 0.308 | — | 0.0 | LNU243 | Roots Coverage TP1 | 0.071 | 0.210 | 146.6 |
| LNU243 | Roots Length TP1 | 0.507 | 0.184 | 64.4 | LNU244 | Roots Coverage TP1 | 0.049 | 0.147 | 70.0 |
| LNU244 | Roots Length TP1 | 0.481 | 0.061 | 55.9 | LNU262 | Roots Coverage TP1 | 0.049 | 0.097 | 71.8 |
| LNU262 | Roots Length TP1 | 0.432 | 0.048 | 40.2 | LNU29 | Roots Coverage TP1 | 0.047 | 0.117 | 62.4 |
| LNU29 | Roots Length TP1 | 0.406 | 0.242 | 31.7 | LNU51 | Roots Coverage TP1 | 0.095 | 0.003 | 228.5 |
| LNU51 | Roots Length TP1 | 0.610 | 0.003 | 98.0 | LNU60 | Roots Coverage TP1 | 0.043 | 0.351 | 48.4 |
| LNU60 | Roots Length TP1 | 0.330 | 0.681 | 6.9 | CONT. | Roots Coverage TP2 | 1.681 | — | 0.0 |
| CONT. | Roots Length TP2 | 2.538 | — | 0.0 | LNU225 | Roots Coverage TP2 | 1.688 | 0.972 | 0.4 |
| LNU243 | Roots Length TP2 | 2.561 | 0.935 | 0.9 | LNU262 | Roots Coverage TP2 | 1.827 | 0.531 | 8.7 |
| LNU262 | Roots Length TP2 | 2.725 | 0.293 | 7.4 | LNU51 | Roots Coverage TP2 | 1.934 | 0.479 | 15.1 |
| LNU29 | Roots Length TP2 | 2.690 | 0.470 | 6.0 | LNU60 | Roots Coverage TP2 | 2.225 | 0.191 | 32.3 |
| LNU51 | Roots Length TP2 | 3.044 | 0.220 | 19.9 | CONT. | Roots Coverage TP3 | 4.355 | — | 0.0 |

TABLE 65-continued

Genes showing improved root performance at nitrogen deficient conditions (T1 generation)

| | Roots Length [cm] | | | | Roots Coverage [cm2] | | | |
|---|---|---|---|---|---|---|---|---|
| Gene Name | Time Point | Ave. | p-value | % incr. | Gene Name | Time Point | Ave. | p-value | % incr. |
| LNU60 | Roots Length TP2 | 2.872 | 0.149 | 13.2 | LNU225 | Roots Coverage TP3 | 5.308 | 0.168 | 21.9 |
| CONT. | Roots_Length_TP3 | 4.714 | — | 0.0 | LNU243 | Roots Coverage TP3 | 4.393 | 0.935 | 0.9 |
| LNU51 | Roots_Length_TP3 | 4.998 | 0.709 | 6.0 | LNU262 | Roots Coverage TP3 | 4.744 | 0.431 | 8.9 |
| LNU60 | Roots_Length_TP3 | 5.050 | 0.471 | 7.1 | LNU266 | Roots Coverage TP3 | 4.867 | 0.449 | 11.8 |
| | | | | | LNU29 | Roots Coverage TP3 | 4.473 | 0.781 | 2.7 |
| | | | | | LNU51 | Roots Coverage TP3 | 4.551 | 0.792 | 4.5 |
| | | | | | LNU60 | Roots Coverage TP3 | 6.276 | 0.084 | 44.1 |

Table 65.
"CONT."—Control;
"Ave."—Average;
"% Incr." = % increment.

The genes listed in Tables 66, 67, 68 and 69 have improved plant growth rate (growth rate of the leaf area, root coverage and root length) when grown under limiting nitrogen growth conditions, compared to control plants. Plants showing fast growth rate show a better plant establishment in soil under nitrogen deficient conditions. Faster growth was observed when growth rate of leaf area and root length and coverage was measured. The genes were cloned under the regulation of a constitutive promoter (At6669) or root preferred promoter (RootP). The evaluation of each gene was performed by testing the performance of different number of events. Some of the genes were evaluated in more than one tissue culture assay and the results obtained where positive as well. Event with p-value <0.1 was considered statistically significant.

TABLE 66

Genes showing improved plant growth rate at nitrogen deficient conditions (T2 generation)

| | | RGR Of Leaf Area | | | | | RGR Of Roots Coverage | | |
|---|---|---|---|---|---|---|---|---|---|
| Gene Name | Event # | Ave. | p-value | % incr. | Gene Name | Event # | Ave. | p-value | % incr. |
| CONT. | — | 0.055 | — | 0.0 | CONT. | — | 0.728 | — | 0.0 |
| LNU100 | 14474.3 | 0.088 | 0.002 | 60.1 | LNU100 | 14474.3 | 1.190 | 0.000 | 63.4 |
| LNU100 | 14473.1 | 0.065 | 0.103 | 18.6 | LNU100 | 14473.1 | 0.840 | 0.202 | 15.4 |
| LNU104 | 25033.3 | 0.077 | 0.004 | 39.3 | LNU100 | 14471.4 | 0.837 | 0.160 | 15.0 |
| LNU104 | 25034.1 | 0.072 | 0.038 | 31.5 | LNU104 | 25033.3 | 0.891 | 0.075 | 22.4 |
| LNU213 | 24654.4 | 0.096 | 0.005 | 73.8 | LNU104 | 25034.1 | 0.762 | 0.650 | 4.7 |
| LNU213 | 24653.2 | 0.086 | 0.000 | 55.7 | LNU213 | 24653.2 | 1.117 | 0.000 | 53.4 |
| LNU213 | 24651.1 | 0.060 | 0.464 | 8.2 | LNU213 | 24654.4 | 1.027 | 0.051 | 41.1 |
| LNU218 | 24783.2 | 0.076 | 0.044 | 37.9 | LNU213 | 24653.1 | 0.837 | 0.214 | 14.9 |
| LNU218 | 24781.7 | 0.075 | 0.070 | 35.8 | LNU213 | 24651.1 | 0.760 | 0.628 | 4.4 |
| LNU4 | 25134.1 | 0.081 | 0.001 | 47.6 | LNU218 | 24783.2 | 1.061 | 0.012 | 45.7 |
| LNU4 | 25134.1 | 0.065 | 0.267 | 17.5 | LNU218 | 24781.7 | 0.814 | 0.498 | 11.9 |
| LNU48 | 24802.2 | 0.089 | 0.001 | 61.2 | LNU4 | 25134.2 | 0.965 | 0.013 | 32.6 |
| LNU48 | 24803.2 | 0.071 | 0.019 | 28.6 | LNU4 | 25134.1 | 0.832 | 0.252 | 14.2 |
| LNU48 | 24804.4 | 0.070 | 0.060 | 27.8 | LNU4 | 25131.1 | 0.762 | 0.625 | 4.7 |
| LNU8 | 25063.1 | 0.091 | 0.000 | 65.8 | LNU48 | 24802.2 | 1.237 | 0.000 | 69.9 |
| LNU8 | 25063.6 | 0.080 | 0.076 | 44.7 | LNU48 | 24804.4 | 1.063 | 0.001 | 46.0 |
| LNU94 | 24833.3 | 0.074 | 0.023 | 34.5 | LNU48 | 24802.1 | 0.776 | 0.586 | 6.6 |
| LNU94 | 24834.1 | 0.063 | 0.392 | 14.3 | LNU48 | 24803.2 | 0.771 | 0.607 | 5.9 |
| LNU94 | 24834.4 | 0.062 | 0.403 | 13.4 | LNU8 | 25063.1 | 1.435 | 0.000 | 97.1 |
| CONT. | — | 0.081 | — | 0.0 | LNU8 | 25063.6 | 0.933 | 0.267 | 28.1 |
| LNU1 | 24681.3 | 0.104 | 0.206 | 28.0 | LNU94 | 24833.3 | 0.922 | 0.042 | 26.6 |
| LNU1 | 24682.1 | 0.097 | 0.321 | 19.8 | LNU94 | 24834.4 | 0.805 | 0.441 | 10.6 |
| LNU1 | 24684.1 | 0.097 | 0.296 | 19.3 | CONT. | — | 0.887 | — | 0.0 |
| LNU1 | 24681.1 | 0.095 | 0.370 | 17.0 | LNU1 | 24682.2 | 1.298 | 0.113 | 46.3 |
| LNU1 | 24682.2 | 0.092 | 0.542 | 12.9 | LNU1 | 24684.1 | 1.291 | 0.000 | 45.5 |

TABLE 66-continued

Genes showing improved plant growth rate at nitrogen deficient conditions (T2 generation)

| Gene Name | Event # | RGR Of Leaf Area Ave. | p-value | % incr. | Gene Name | Event # | RGR Of Roots Coverage Ave. | p-value | % incr. |
|---|---|---|---|---|---|---|---|---|---|
| LNU133 | 24744.3 | 0.114 | 0.079 | 40.6 | LNU1 | 24681.1 | 1.248 | 0.019 | 40.6 |
| LNU133 | 24741.1 | 0.105 | 0.096 | 29.6 | LNU1 | 24681.3 | 1.092 | 0.095 | 23.1 |
| LNU133 | 24744.2 | 0.087 | 0.712 | 6.9 | LNU1 | 24682.1 | 0.989 | 0.258 | 11.5 |
| LNU175 | 24732.4 | 0.129 | 0.022 | 59.1 | LNU133 | 24744.3 | 1.638 | 0.001 | 84.6 |
| LNU175 | 24732.1 | 0.124 | 0.007 | 53.3 | LNU133 | 24741.1 | 1.461 | 0.000 | 64.7 |
| LNU175 | 24734.4 | 0.095 | 0.350 | 17.4 | LNU133 | 24741.2 | 1.071 | 0.021 | 20.7 |
| LNU175 | 24731.2 | 0.087 | 0.712 | 7.0 | LNU133 | 24744.2 | 1.049 | 0.150 | 18.3 |
| LNU178 | 14614.5 | 0.115 | 0.078 | 41.9 | LNU133 | 24742.2 | 1.020 | 0.263 | 14.9 |
| LNU178 | 14611.5 | 0.106 | 0.129 | 30.8 | LNU175 | 24732.4 | 1.929 | 0.002 | 117.4 |
| LNU178 | 14612.1 | 0.089 | 0.587 | 9.5 | LNU175 | 24732.1 | 1.756 | 0.000 | 97.9 |
| LNU178 | 14611.1 | 0.085 | 0.782 | 5.0 | LNU175 | 24734.4 | 1.182 | 0.014 | 33.3 |
| LNU215 | 24664.3 | 0.113 | 0.068 | 39.1 | LNU175 | 24731.2 | 1.070 | 0.115 | 20.6 |
| LNU215 | 24661.4 | 0.087 | 0.711 | 6.9 | LNU175 | 24733.4 | 1.019 | 0.271 | 14.9 |
| LNU24 | 24973.1 | 0.104 | 0.160 | 28.2 | LNU178 | 14611.5 | 1.630 | 0.000 | 83.7 |
| LNU24 | 24971.2 | 0.101 | 0.203 | 24.2 | LNU178 | 14611.1 | 1.245 | 0.035 | 40.3 |
| LNU24 | 24971.4 | 0.100 | 0.374 | 23.4 | LNU178 | 14614.5 | 1.219 | 0.066 | 37.4 |
| LNU6 | 24992.3 | 0.106 | 0.084 | 31.0 | LNU178 | 14612.1 | 1.002 | 0.265 | 13.0 |
| LNU6 | 24994.1 | 0.092 | 0.476 | 13.4 | LNU178 | 14611.4 | 0.985 | 0.237 | 11.0 |
| LNU6 | 24993.3 | 0.089 | 0.601 | 10.2 | LNU215 | 24664.3 | 1.409 | 0.003 | 58.8 |
| LNU6 | 24994.2 | 0.088 | 0.658 | 8.3 | LNU215 | 24661.4 | 1.132 | 0.043 | 27.6 |
| LNU82 | 24823.1 | 0.095 | 0.328 | 17.5 | LNU215 | 24664.2 | 1.100 | 0.015 | 24.0 |
| LNU82 | 24824.1 | 0.086 | 0.758 | 6.3 | LNU215 | 24663.4 | 1.034 | 0.121 | 16.5 |
| LNU9 | 25003.1 | 0.093 | 0.468 | 14.8 | LNU24 | 24973.1 | 1.501 | 0.000 | 69.2 |
| LNU9 | 25001.3 | 0.089 | 0.598 | 10.1 | LNU24 | 24971.4 | 1.350 | 0.001 | 52.2 |
| CONT. | — | 0.058 | — | 0.0 | LNU24 | 24971.2 | 1.271 | 0.001 | 43.3 |
| LNU120 | 25463.7 | 0.081 | 0.001 | 39.9 | LNU24 | 24973.3 | 0.965 | 0.419 | 8.8 |
| LNU120 | 25463.3 | 0.074 | 0.019 | 27.4 | LNU24 | 24972.1 | 0.952 | 0.578 | 7.3 |
| LNU124 | 14501.7 | 0.079 | 0.007 | 36.5 | LNU6 | 24992.3 | 1.524 | 0.001 | 71.8 |
| LNU124 | 14502.7 | 0.068 | 0.125 | 17.3 | LNU6 | 24994.2 | 1.176 | 0.024 | 32.5 |
| LNU124 | 14501.1 | 0.065 | 0.277 | 12.6 | LNU6 | 24994.5 | 1.067 | 0.264 | 20.3 |
| LNU132 | 14102.9 | 0.066 | 0.251 | 14.0 | LNU6 | 24993.3 | 1.045 | 0.147 | 17.8 |
| LNU132 | 14102.7 | 0.064 | 0.379 | 10.6 | LNU6 | 24994.1 | 1.012 | 0.332 | 14.1 |
| LNU140 | 14112.7 | 0.097 | 0.000 | 67.6 | LNU82 | 24823.1 | 1.167 | 0.036 | 31.5 |
| LNU140 | 14111.6 | 0.070 | 0.081 | 21.0 | LNU82 | 24824.2 | 1.126 | 0.036 | 27.0 |
| LNU140 | 14114.8 | 0.063 | 0.435 | 8.5 | LNU82 | 24824.3 | 0.979 | 0.370 | 10.4 |
| LNU140 | 14112.6 | 0.060 | 0.732 | 3.8 | LNU82 | 24824.1 | 0.978 | 0.555 | 10.2 |
| LNU180 | 24724.3 | 0.099 | 0.000 | 71.3 | LNU9 | 25001.1 | 1.294 | 0.001 | 45.8 |
| LNU180 | 24723.3 | 0.080 | 0.009 | 37.5 | LNU9 | 25003.1 | 1.232 | 0.023 | 38.9 |
| LNU196 | 25534.1 | 0.069 | 0.171 | 18.6 | LNU9 | 25001.2 | 1.118 | 0.135 | 26.0 |
| LNU196 | 25533.1 | 0.066 | 0.349 | 14.2 | LNU9 | 25001.3 | 1.117 | 0.041 | 25.9 |
| LNU20 | 24932.4 | 0.068 | 0.174 | 17.3 | CONT. | — | 0.908 | — | 0.0 |
| LNU20 | 24933.2 | 0.065 | 0.390 | 12.7 | LNU120 | 25463.7 | 1.427 | 0.000 | 57.3 |
| LNU36 | 25562.3 | 0.085 | 0.024 | 46.0 | LNU120 | 25463.3 | 1.010 | 0.346 | 11.3 |
| LNU71 | 25853.4 | 0.087 | 0.001 | 50.3 | LNU124 | 14502.1 | 1.162 | 0.095 | 28.1 |
| LNU71 | 25852.4 | 0.060 | 0.773 | 3.2 | LNU124 | 14501.7 | 1.135 | 0.152 | 25.0 |
| CONT. | — | 0.060 | — | 0.0 | LNU124 | 14502.7 | 1.003 | 0.415 | 10.6 |
| LNU1 | 24681.3 | 0.073 | 0.306 | 20.5 | LNU124 | 14501.1 | 0.960 | 0.683 | 5.8 |
| LNU110 | 24952.3 | 0.090 | 0.013 | 48.7 | LNU132 | 14102.7 | 1.130 | 0.095 | 24.5 |
| LNU110 | 24953.3 | 0.079 | 0.110 | 30.2 | LNU132 | 14102.9 | 1.129 | 0.060 | 24.4 |
| LNU110 | 24953.2 | 0.069 | 0.323 | 14.0 | LNU140 | 14112.7 | 1.571 | 0.000 | 73.0 |
| LNU175 | 24732.2 | 0.087 | 0.008 | 44.2 | LNU140 | 14111.6 | 1.145 | 0.048 | 26.2 |
| LNU175 | 24733.4 | 0.070 | 0.218 | 16.4 | LNU140 | 14112.6 | 0.970 | 0.554 | 6.9 |
| LNU19 | 25151.1 | 0.090 | 0.001 | 48.9 | LNU140 | 14114.8 | 0.966 | 0.603 | 6.5 |
| LNU19 | 25153.3 | 0.079 | 0.063 | 31.5 | LNU180 | 24724.3 | 1.590 | 0.000 | 75.2 |
| LNU215 | 24664.2 | 0.091 | 0.000 | 50.8 | LNU180 | 24723.3 | 1.265 | 0.004 | 39.4 |
| LNU215 | 24663.4 | 0.078 | 0.016 | 28.4 | LNU180 | 24721.4 | 0.942 | 0.765 | 3.8 |
| LNU215 | 24663.3 | 0.071 | 0.182 | 17.5 | LNU20 | 24932.4 | 1.177 | 0.028 | 29.7 |
| LNU215 | 24661.4 | 0.065 | 0.558 | 7.1 | LNU20 | 24933.2 | 1.021 | 0.453 | 12.5 |
| LNU27 | 24873.1 | 0.088 | 0.012 | 45.4 | LNU36 | 25562.3 | 1.375 | 0.017 | 51.5 |
| LNU27 | 24873.4 | 0.080 | 0.048 | 32.1 | LNU36 | 25562.4 | 1.090 | 0.208 | 20.1 |
| LNU27 | 24872.4 | 0.067 | 0.357 | 11.3 | LNU71 | 25853.4 | 1.170 | 0.066 | 29.0 |
| LNU44 | 24924.3 | 0.112 | 0.001 | 84.9 | CONT. | — | 0.869 | — | 0.0 |
| LNU44 | 24924.2 | 0.089 | 0.004 | 48.1 | LNU1 | 24682.1 | 0.948 | 0.453 | 9.2 |
| LNU44 | 24922.3 | 0.076 | 0.072 | 25.2 | LNU110 | 24952.3 | 1.151 | 0.199 | 32.5 |
| LNU54 | 24903.5 | 0.102 | 0.000 | 69.7 | LNU110 | 24953.2 | 0.948 | 0.500 | 9.1 |
| LNU54 | 24901.2 | 0.097 | 0.005 | 60.2 | LNU175 | 24732.2 | 1.291 | 0.013 | 48.7 |
| LNU54 | 24903.3 | 0.078 | 0.058 | 29.8 | LNU175 | 24732.1 | 1.018 | 0.248 | 17.2 |
| LNU79 | 24884.4 | 0.102 | 0.000 | 68.5 | LNU175 | 24734.4 | 0.927 | 0.633 | 6.7 |
| LNU79 | 24881.1 | 0.088 | 0.003 | 46.2 | LNU19 | 25151.1 | 1.046 | 0.194 | 20.4 |
| LNU79 | 24884.3 | 0.077 | 0.045 | 27.7 | LNU215 | 24664.2 | 1.315 | 0.001 | 51.4 |
| LNU79 | 24882.2 | 0.068 | 0.280 | 13.4 | LNU215 | 24663.4 | 1.179 | 0.010 | 35.8 |
| CONT. | — | 0.078 | — | 0.0 | LNU215 | 24663.3 | 1.033 | 0.208 | 19.0 |
| LNU109 | 24891.5 | 0.105 | 0.016 | 35.4 | LNU215 | 24661.4 | 1.030 | 0.127 | 18.6 |

TABLE 66-continued

Genes showing improved plant growth rate at nitrogen deficient conditions (T2 generation)

| | RGR Of Leaf Area | | | | | RGR Of Roots Coverage | | |
|---|---|---|---|---|---|---|---|---|
| Gene Name | Event # | Ave. | p-value | % incr. | Gene Name | Event # | Ave. | p-value | % incr. |
| LNU109 | 24892.5 | 0.097 | 0.142 | 24.5 | LNU215 | 24663.1 | 0.907 | 0.688 | 4.5 |
| LNU109 | 24892.6 | 0.095 | 0.219 | 21.5 | LNU27 | 24873.1 | 1.325 | 0.016 | 52.6 |
| LNU109 | 24891.2 | 0.088 | 0.462 | 12.6 | LNU27 | 24873.4 | 1.072 | 0.138 | 23.5 |
| LNU110 | 24952.1 | 0.155 | 0.000 | 99.4 | LNU44 | 24924.2 | 1.395 | 0.002 | 60.7 |
| LNU110 | 24952.3 | 0.111 | 0.031 | 42.2 | LNU44 | 24924.3 | 1.315 | 0.018 | 51.4 |
| LNU110 | 24953.2 | 0.106 | 0.030 | 36.6 | LNU44 | 24922.3 | 1.296 | 0.044 | 49.2 |
| LNU133 | 24744.3 | 0.121 | 0.000 | 55.2 | LNU44 | 24923.3 | 1.123 | 0.025 | 29.3 |
| LNU133 | 24741.1 | 0.103 | 0.017 | 32.5 | LNU54 | 24903.5 | 1.573 | 0.000 | 81.2 |
| LNU133 | 24741.2 | 0.097 | 0.033 | 25.0 | LNU54 | 24901.2 | 1.405 | 0.015 | 61.7 |
| LNU133 | 24744.2 | 0.088 | 0.329 | 13.5 | LNU54 | 24903.3 | 1.367 | 0.008 | 57.3 |
| LNU133 | 24742.2 | 0.083 | 0.581 | 6.3 | LNU54 | 24902.4 | 1.137 | 0.031 | 30.9 |
| LNU19 | 25151.1 | 0.106 | 0.007 | 36.3 | LNU79 | 24881.1 | 1.407 | 0.001 | 62.0 |
| LNU27 | 24873.4 | 0.125 | 0.000 | 60.1 | LNU79 | 24884.4 | 1.407 | 0.000 | 61.9 |
| LNU44 | 24922.3 | 0.113 | 0.000 | 44.6 | LNU79 | 24884.3 | 1.127 | 0.095 | 29.8 |
| LNU44 | 24924.3 | 0.091 | 0.308 | 17.0 | LNU79 | 24882.2 | 1.053 | 0.073 | 21.2 |
| LNU44 | 24923.1 | 0.085 | 0.518 | 8.7 | LNU79 | 24883.2 | 0.899 | 0.782 | 3.5 |
| LNU54 | 24901.2 | 0.119 | 0.000 | 52.2 | CONT. | — | 1.054 | — | 0.0 |
| LNU54 | 24903.5 | 0.104 | 0.031 | 33.2 | LNU109 | 24891.5 | 1.313 | 0.018 | 24.6 |
| LNU54 | 24902.4 | 0.094 | 0.056 | 20.3 | LNU109 | 24892.6 | 1.256 | 0.186 | 19.1 |
| LNU6 | 24994.5 | 0.112 | 0.005 | 43.2 | LNU110 | 24952.1 | 2.265 | 0.000 | 114.9 |
| LNU6 | 24992.3 | 0.107 | 0.012 | 36.7 | LNU110 | 24952.3 | 1.456 | 0.012 | 38.1 |
| LNU79 | 24884.4 | 0.120 | 0.000 | 54.1 | LNU110 | 24953.2 | 1.221 | 0.308 | 15.8 |
| LNU79 | 24881.1 | 0.107 | 0.012 | 36.9 | LNU110 | 24954.3 | 1.163 | 0.333 | 10.4 |
| LNU79 | 24882.2 | 0.098 | 0.056 | 26.4 | LNU133 | 24744.3 | 1.717 | 0.000 | 62.9 |
| LNU79 | 24884.3 | 0.092 | 0.228 | 18.2 | LNU133 | 24741.1 | 1.470 | 0.026 | 39.5 |
| CONT. | — | 0.052 | — | 0.0 | LNU133 | 24742.2 | 1.203 | 0.166 | 14.2 |
| LNU109 | 24892.8 | 0.104 | 0.000 | 101.5 | LNU133 | 24741.2 | 1.123 | 0.527 | 6.5 |
| LNU109 | 24891.2 | 0.104 | 0.002 | 100.4 | LNU19 | 25151.1 | 1.490 | 0.008 | 41.3 |
| LNU109 | 24891.5 | 0.072 | 0.136 | 38.7 | LNU27 | 24873.4 | 1.673 | 0.000 | 58.7 |
| LNU109 | 24892.5 | 0.060 | 0.394 | 15.2 | LNU44 | 24922.3 | 1.944 | 0.000 | 84.4 |
| LNU143 | 25975.3 | 0.081 | 0.021 | 56.0 | LNU54 | 24901.2 | 1.669 | 0.000 | 58.4 |
| LNU143 | 25972.1 | 0.074 | 0.032 | 42.5 | LNU54 | 24903.5 | 1.243 | 0.185 | 18.0 |
| LNU143 | 25975.2 | 0.069 | 0.088 | 34.3 | LNU6 | 24992.3 | 1.678 | 0.001 | 59.2 |
| LNU143 | 25971.5 | 0.066 | 0.085 | 26.9 | LNU6 | 24994.5 | 1.323 | 0.144 | 25.5 |
| LNU143 | 25971.2 | 0.060 | 0.346 | 16.5 | LNU6 | 24994.2 | 1.157 | 0.317 | 9.7 |
| LNU154 | 14604.7 | 0.092 | 0.002 | 78.6 | LNU79 | 24884.4 | 1.756 | 0.000 | 66.6 |
| LNU154 | 14604.6 | 0.086 | 0.006 | 66.7 | LNU79 | 24881.1 | 1.355 | 0.008 | 28.6 |
| LNU154 | 14601.6 | 0.077 | 0.098 | 48.3 | LNU79 | 24882.2 | 1.263 | 0.206 | 19.8 |
| LNU154 | 14602.8 | 0.069 | 0.185 | 34.0 | LNU79 | 24884.3 | 1.223 | 0.225 | 16.1 |
| LNU154 | 14604.4 | 0.069 | 0.082 | 33.4 | LNU79 | 24883.2 | 1.101 | 0.613 | 4.5 |
| LNU196 | 25532.2 | 0.113 | 0.000 | 117.6 | CONT. | — | 0.737 | — | 0.0 |
| LNU196 | 25534.1 | 0.089 | 0.017 | 71.3 | LNU109 | 24892.8 | 1.439 | 0.000 | 95.2 |
| LNU196 | 25531.2 | 0.073 | 0.034 | 40.4 | LNU109 | 24891.2 | 1.093 | 0.066 | 48.3 |
| LNU196 | 25532.1 | 0.065 | 0.357 | 25.8 | LNU109 | 24891.5 | 1.071 | 0.028 | 45.2 |
| LNU207 | 24642.5 | 0.094 | 0.001 | 82.1 | LNU143 | 25975.3 | 1.056 | 0.012 | 43.2 |
| LNU207 | 24642.4 | 0.094 | 0.001 | 81.0 | LNU143 | 25972.1 | 0.980 | 0.035 | 32.9 |
| LNU207 | 24644.18 | 0.080 | 0.006 | 54.8 | LNU143 | 25975.2 | 0.917 | 0.233 | 24.3 |
| LNU207 | 24641.1 | 0.056 | 0.655 | 7.3 | LNU143 | 25971.5 | 0.877 | 0.338 | 19.0 |
| LNU207 | 24644.13 | 0.055 | 0.786 | 5.7 | LNU154 | 14604.6 | 1.099 | 0.009 | 49.0 |
| LNU288 | 14562.12 | 0.075 | 0.048 | 44.1 | LNU154 | 14601.6 | 1.081 | 0.079 | 46.6 |
| LNU288 | 14562.7 | 0.075 | 0.022 | 44.1 | LNU154 | 14604.7 | 1.015 | 0.024 | 37.7 |
| LNU288 | 14562.1 | 0.069 | 0.154 | 32.5 | LNU154 | 14602.8 | 0.982 | 0.253 | 33.2 |
| LNU288 | 14564.9 | 0.066 | 0.089 | 27.6 | LNU196 | 25532.2 | 1.650 | 0.000 | 123.9 |
| LNU288 | 14562.9 | 0.064 | 0.261 | 23.7 | LNU196 | 25534.1 | 1.327 | 0.052 | 80.0 |
| LNU50 | 26024.2 | 0.085 | 0.007 | 64.1 | LNU196 | 25532.1 | 0.971 | 0.248 | 31.7 |
| LNU50 | 26023.2 | 0.073 | 0.028 | 40.6 | LNU196 | 25531.2 | 0.817 | 0.525 | 10.8 |
| LNU50 | 26025.4 | 0.065 | 0.125 | 26.0 | LNU196 | 25533.1 | 0.783 | 0.607 | 6.2 |
| LNU50 | 26022.1 | 0.062 | 0.321 | 19.8 | LNU207 | 24642.4 | 1.393 | 0.010 | 89.0 |
| LNU50 | 26023.5 | 0.056 | 0.558 | 9.1 | LNU207 | 24642.5 | 1.164 | 0.002 | 57.9 |
| LNU52 | 25723.2 | 0.126 | 0.000 | 143.1 | LNU207 | 24644.18 | 1.102 | 0.010 | 49.5 |
| LNU52 | 25721.4 | 0.094 | 0.034 | 81.1 | LNU207 | 24644.13 | 0.920 | 0.279 | 24.8 |
| LNU52 | 25721.3 | 0.086 | 0.008 | 66.2 | LNU288 | 14562.1 | 1.018 | 0.124 | 38.1 |
| CONT. | — | 0.064 | — | 0.0 | LNU288 | 14562.7 | 0.987 | 0.056 | 33.9 |
| LNU143 | 25975.2 | 0.075 | 0.257 | 15.9 | LNU288 | 14564.9 | 0.939 | 0.037 | 27.3 |
| LNU154 | 14602.8 | 0.079 | 0.120 | 22.7 | LNU288 | 14562.12 | 0.823 | 0.473 | 11.7 |
| LNU154 | 14604.4 | 0.070 | 0.618 | 8.3 | LNU288 | 14562.9 | 0.823 | 0.387 | 11.7 |
| LNU207 | 24642.5 | 0.092 | 0.008 | 43.2 | LNU50 | 26023.2 | 1.105 | 0.011 | 49.9 |
| LNU207 | 24641.1 | 0.079 | 0.154 | 22.6 | LNU50 | 26024.2 | 1.085 | 0.063 | 47.2 |
| LNU207 | 24642.4 | 0.069 | 0.560 | 7.5 | LNU50 | 26025.4 | 0.978 | 0.038 | 32.6 |
| LNU211 | 24774.4 | 0.271 | 0.173 | 321.2 | LNU50 | 26023.5 | 0.855 | 0.264 | 16.0 |
| LNU52 | 25721.1 | 0.091 | 0.013 | 42.2 | LNU50 | 26022.1 | 0.810 | 0.542 | 9.9 |
| LNU52 | 25723.2 | 0.085 | 0.074 | 31.7 | LNU52 | 25723.2 | 1.741 | 0.000 | 136.1 |
| LNU52 | 25723.1 | 0.081 | 0.191 | 25.5 | LNU52 | 25721.4 | 1.195 | 0.045 | 62.1 |

TABLE 66-continued

Genes showing improved plant growth rate at nitrogen deficient conditions (T2 generation)

| | | RGR Of Leaf Area | | | | | RGR Of Roots Coverage | | |
|---|---|---|---|---|---|---|---|---|---|
| Gene Name | Event # | Ave. | p-value | % incr. | Gene Name | Event # | Ave. | p-value | % incr. |
| LNU52 | 25721.2 | 0.073 | 0.369 | 13.7 | LNU52 | 25721.3 | 1.193 | 0.024 | 61.8 |
| LNU69 | 14571.1 | 0.081 | 0.108 | 26.1 | LNU52 | 25723.1 | 0.805 | 0.623 | 9.2 |
| LNU69 | 14572.9 | 0.079 | 0.197 | 23.1 | CONT. | — | 1.006 | — | 0.0 |
| LNU69 | 14572.8 | 0.074 | 0.362 | 14.4 | LNU143 | 25975.2 | 1.194 | 0.208 | 18.7 |
| CONT. | — | 0.072 | — | 0.0 | LNU143 | 25975.3 | 1.085 | 0.620 | 7.8 |
| LNU150 | 24842.9 | 0.115 | 0.006 | 60.7 | LNU154 | 14602.8 | 1.225 | 0.116 | 21.7 |
| LNU150 | 24841.9 | 0.082 | 0.477 | 15.1 | LNU207 | 24642.5 | 1.333 | 0.028 | 32.4 |
| LNU179 | 24632.5 | 0.097 | 0.103 | 35.0 | LNU207 | 24641.1 | 1.265 | 0.082 | 25.7 |
| LNU179 | 24631.9 | 0.084 | 0.441 | 16.8 | LNU207 | 24642.4 | 1.159 | 0.228 | 15.2 |
| LNU232 | 26003.7 | 0.083 | 0.456 | 15.9 | LNU211 | 24771.1 | 1.136 | 0.330 | 12.9 |
| LNU235 | 26184.4 | 0.101 | 0.063 | 40.9 | LNU52 | 25721.1 | 1.458 | 0.019 | 44.8 |
| LNU235 | 26185.3 | 0.100 | 0.080 | 40.3 | LNU52 | 25723.1 | 1.362 | 0.084 | 35.4 |
| LNU242 | 25473.1 | 0.096 | 0.109 | 33.9 | LNU52 | 25721.2 | 1.328 | 0.093 | 32.0 |
| LNU242 | 25474.1 | 0.079 | 0.639 | 9.9 | LNU52 | 25723.2 | 1.208 | 0.271 | 20.1 |
| LNU242 | 25471.1 | 0.079 | 0.638 | 9.8 | LNU69 | 14571.1 | 1.398 | 0.027 | 38.9 |
| LNU76 | 26423.1 | 0.097 | 0.093 | 35.9 | LNU69 | 14572.9 | 1.140 | 0.342 | 13.2 |
| LNU76 | 26421.2 | 0.089 | 0.241 | 24.9 | LNU69 | 14572.8 | 1.105 | 0.378 | 9.8 |
| LNU76 | 26425.1 | 0.086 | 0.377 | 19.5 | CONT. | — | 0.860 | — | 0.0 |
| LNU76 | 26421.1 | 0.077 | 0.746 | 7.3 | LNU150 | 24842.9 | 1.560 | 0.001 | 81.4 |
| LNU95 | 13985.11 | 0.101 | 0.055 | 40.8 | LNU150 | 24841.9 | 1.169 | 0.141 | 36.0 |
| LNU95 | 13985.15 | 0.079 | 0.623 | 10.3 | LNU150 | 24843.5 | 1.141 | 0.199 | 32.7 |
| LNU95 | 13985.12 | 0.076 | 0.784 | 5.9 | LNU179 | 24632.5 | 1.501 | 0.005 | 74.5 |
| CONT. | — | 0.067 | — | 0.0 | LNU179 | 24631.9 | 1.269 | 0.062 | 47.5 |
| LNU118 | 14013.6 | 0.078 | 0.267 | 16.4 | LNU179 | 24631.6 | 0.933 | 0.723 | 8.5 |
| LNU118 | 14012.15 | 0.076 | 0.371 | 12.9 | LNU232 | 26003.7 | 1.110 | 0.227 | 29.1 |
| LNU150 | 24841.6 | 0.077 | 0.375 | 13.8 | LNU235 | 26184.4 | 1.576 | 0.001 | 83.3 |
| LNU150 | 24841.9 | 0.075 | 0.470 | 11.0 | LNU235 | 26185.3 | 1.416 | 0.013 | 64.7 |
| LNU150 | 24842.9 | 0.072 | 0.666 | 7.1 | LNU235 | 26182.1 | 1.048 | 0.361 | 21.8 |
| LNU179 | 24631.6 | 0.079 | 0.251 | 17.0 | LNU235 | 26184.2 | 1.019 | 0.431 | 18.5 |
| LNU179 | 24631.7 | 0.078 | 0.279 | 15.7 | LNU242 | 25473.1 | 1.482 | 0.004 | 72.3 |
| LNU179 | 24632.7 | 0.072 | 0.601 | 7.2 | LNU242 | 25474.1 | 1.275 | 0.056 | 48.3 |
| LNU232 | 26001.5 | 0.082 | 0.155 | 21.2 | LNU76 | 26425.1 | 1.342 | 0.026 | 56.1 |
| LNU232 | 26003.3 | 0.070 | 0.741 | 4.7 | LNU76 | 26421.2 | 1.194 | 0.112 | 38.8 |
| LNU235 | 26184.4 | 0.115 | 0.000 | 71.6 | LNU76 | 26423.1 | 1.177 | 0.128 | 36.9 |
| LNU235 | 26185.2 | 0.113 | 0.000 | 68.3 | LNU76 | 26421.1 | 1.021 | 0.471 | 18.7 |
| LNU235 | 26184.2 | 0.094 | 0.007 | 39.9 | LNU95 | 13985.11 | 1.522 | 0.003 | 76.9 |
| LNU235 | 26182.1 | 0.071 | 0.718 | 5.1 | LNU95 | 13985.15 | 1.128 | 0.194 | 31.2 |
| LNU242 | 25474.1 | 0.098 | 0.004 | 45.3 | LNU95 | 13985.19 | 1.100 | 0.280 | 27.9 |
| LNU288 | 14563.9 | 0.096 | 0.006 | 43.3 | LNU95 | 13985.12 | 1.090 | 0.273 | 26.8 |
| LNU288 | 14562.1 | 0.090 | 0.024 | 33.5 | LNU95 | 13985.16 | 0.947 | 0.670 | 10.1 |
| LNU288 | 14562.7 | 0.081 | 0.183 | 20.1 | CONT. | — | 1.017 | — | 0.0 |
| LNU288 | 14564.9 | 0.080 | 0.203 | 18.5 | LNU232 | 26001.5 | 1.259 | 0.085 | 23.7 |
| LNU76 | 26421.2 | 0.090 | 0.068 | 33.6 | LNU235 | 26184.4 | 1.645 | 0.000 | 61.7 |
| LNU76 | 26422.2 | 0.086 | 0.063 | 28.3 | LNU235 | 26185.2 | 1.636 | 0.000 | 60.8 |
| LNU76 | 26423.1 | 0.086 | 0.099 | 27.9 | LNU235 | 26184.2 | 1.205 | 0.181 | 18.4 |
| LNU95 | 13985.16 | 0.126 | 0.000 | 87.0 | LNU242 | 25474.1 | 1.210 | 0.179 | 19.0 |
| LNU95 | 13985.15 | 0.113 | 0.000 | 68.6 | LNU288 | 14563.9 | 1.512 | 0.002 | 48.6 |
| LNU95 | 13985.12 | 0.092 | 0.013 | 36.2 | LNU288 | 14562.1 | 1.225 | 0.102 | 20.4 |
| CONT. | — | 0.066 | — | 0.0 | LNU288 | 14564.9 | 1.119 | 0.472 | 10.0 |
| LNU101 | 27632.7 | 0.080 | 0.040 | 21.0 | LNU288 | 14562.7 | 1.065 | 0.698 | 4.7 |
| LNU128 | 26515.3 | 0.087 | 0.003 | 30.2 | LNU76 | 26421.2 | 1.389 | 0.037 | 36.6 |
| LNU192 | 28315.2 | 0.085 | 0.007 | 27.6 | LNU76 | 26423.1 | 1.131 | 0.435 | 11.1 |
| LNU192 | 28313.2 | 0.070 | 0.605 | 5.1 | LNU76 | 26422.2 | 1.123 | 0.483 | 10.4 |
| LNU206 | 27621.2 | 0.077 | 0.140 | 15.4 | LNU95 | 13985.16 | 1.594 | 0.000 | 56.7 |
| LNU211 | 24771.1 | 0.073 | 0.298 | 10.1 | LNU95 | 13985.12 | 1.420 | 0.014 | 39.6 |
| LNU211 | 24773.2 | 0.071 | 0.480 | 7.1 | LNU95 | 13985.15 | 1.417 | 0.004 | 39.3 |
| LNU282 | 27563.3 | 0.082 | 0.030 | 22.7 | CONT. | — | 0.870 | — | 0.0 |
| LNU282 | 27563.1 | 0.078 | 0.103 | 17.4 | LNU101 | 27632.7 | 1.210 | 0.000 | 39.0 |
| LNU282 | 27562.1 | 0.075 | 0.286 | 12.5 | LNU101 | 27632.1 | 0.985 | 0.153 | 13.2 |
| LNU69 | 14571.1 | 0.089 | 0.001 | 33.3 | LNU101 | 27635.1 | 0.976 | 0.280 | 12.1 |
| LNU75 | 27572.2 | 0.072 | 0.395 | 8.8 | LNU128 | 26515.3 | 1.467 | 0.000 | 68.5 |
| LNU75 | 27572.1 | 0.072 | 0.379 | 8.5 | LNU128 | 26511.5 | 1.191 | 0.000 | 36.8 |
| CONT. | — | 0.056 | — | 0.0 | LNU128 | 26515.2 | 1.071 | 0.024 | 23.0 |
| LNU118 | 14012.15 | 0.059 | 0.772 | 3.7 | LNU128 | 26511.5 | 0.891 | 0.790 | 2.4 |
| LNU206 | 27621.2 | 0.097 | 0.018 | 72.5 | LNU192 | 28315.2 | 1.393 | 0.000 | 60.0 |
| LNU206 | 27621.1 | 0.085 | 0.007 | 50.7 | LNU192 | 28313.2 | 1.211 | 0.000 | 39.2 |
| LNU206 | 27622.1 | 0.077 | 0.021 | 37.3 | LNU192 | 28313.3 | 1.079 | 0.026 | 23.9 |
| LNU206 | 27622.4 | 0.073 | 0.068 | 29.9 | LNU192 | 28312.2 | 0.927 | 0.454 | 6.5 |
| LNU249 | 26153.1 | 0.084 | 0.003 | 48.8 | LNU206 | 27621.2 | 1.252 | 0.000 | 43.9 |
| LNU249 | 26154.2 | 0.071 | 0.081 | 26.7 | LNU206 | 27621.1 | 1.059 | 0.023 | 21.6 |
| LNU249 | 26152.4 | 0.060 | 0.659 | 6.4 | LNU206 | 27622.1 | 0.985 | 0.140 | 13.2 |
| LNU282 | 27563.1 | 0.076 | 0.016 | 34.7 | LNU211 | 24771.1 | 1.374 | 0.000 | 57.8 |
| LNU282 | 27565.2 | 0.075 | 0.051 | 33.1 | LNU211 | 24773.2 | 1.127 | 0.006 | 29.5 |

TABLE 66-continued

Genes showing improved plant growth rate at nitrogen deficient conditions (T2 generation)

| | RGR Of Leaf Area | | | | | RGR Of Roots Coverage | | |
|---|---|---|---|---|---|---|---|---|
| Gene Name | Event # | Ave. | p-value | % incr. | Gene Name | Event # | Ave. | p-value | % incr. |
| LNU288 | 14564.8 | 0.087 | 0.001 | 55.1 | LNU282 | 27562.1 | 1.477 | 0.000 | 69.7 |
| LNU288 | 14563.9 | 0.082 | 0.000 | 46.0 | LNU282 | 27563.3 | 1.333 | 0.000 | 53.2 |
| LNU288 | 14562.9 | 0.070 | 0.066 | 25.0 | LNU282 | 27563.1 | 1.262 | 0.000 | 45.0 |
| LNU288 | 14563.6 | 0.065 | 0.305 | 14.8 | LNU282 | 27565.2 | 0.966 | 0.204 | 11.0 |
| LNU288 | 14562.7 | 0.060 | 0.678 | 5.9 | LNU69 | 14571.1 | 1.528 | 0.000 | 75.6 |
| LNU75 | 27572.3 | 0.094 | 0.000 | 67.3 | LNU69 | 14573.5 | 1.115 | 0.004 | 28.2 |
| LNU75 | 27572.2 | 0.081 | 0.019 | 43.6 | LNU69 | 14572.9 | 0.895 | 0.798 | 2.9 |
| LNU75 | 27571.2 | 0.081 | 0.004 | 43.3 | LNU75 | 27572.2 | 1.373 | 0.000 | 57.8 |
| LNU75 | 27571.4 | 0.079 | 0.005 | 40.0 | LNU75 | 27572.1 | 1.152 | 0.001 | 32.4 |
| CONT. | — | 0.076 | — | 0.0 | LNU75 | 27572.3 | 1.006 | 0.148 | 15.6 |
| LNU112 | 28212.4 | 0.082 | 0.565 | 7.8 | LNU75 | 27571.4 | 0.957 | 0.334 | 9.9 |
| LNU14 | 27823.2 | 0.083 | 0.490 | 9.5 | CONT. | — | 0.804 | — | 0.0 |
| LNU183 | 24863.1 | 0.098 | 0.030 | 29.7 | LNU101 | 27632.5 | 0.982 | 0.112 | 22.2 |
| LNU183 | 24863.12 | 0.091 | 0.130 | 20.4 | LNU118 | 14012.15 | 1.037 | 0.038 | 29.1 |
| LNU183 | 24864.6 | 0.085 | 0.487 | 12.6 | LNU118 | 14012.12 | 0.843 | 0.692 | 4.9 |
| LNU183 | 24865.1 | 0.080 | 0.652 | 6.2 | LNU206 | 27621.2 | 1.502 | 0.000 | 86.9 |
| LNU201 | 28223.1 | 0.084 | 0.410 | 11.6 | LNU206 | 27622.4 | 1.352 | 0.000 | 68.3 |
| LNU201 | 28222.2 | 0.078 | 0.792 | 3.6 | LNU206 | 27622.1 | 1.218 | 0.004 | 51.5 |
| LNU268 | 26044.2 | 0.083 | 0.520 | 9.7 | LNU206 | 27621.1 | 1.124 | 0.018 | 39.9 |
| CONT. | — | 0.066 | — | 0.0 | LNU249 | 26153.1 | 1.209 | 0.007 | 50.5 |
| LNU11 | 28205.1 | 0.089 | 0.021 | 34.1 | LNU249 | 26154.2 | 1.142 | 0.032 | 42.0 |
| LNU11 | 28205.2 | 0.075 | 0.357 | 12.2 | LNU249 | 26152.4 | 1.042 | 0.075 | 29.6 |
| LNU11 | 28204.1 | 0.074 | 0.414 | 11.5 | LNU249 | 26151.1 | 0.841 | 0.753 | 4.7 |
| LNU11 | 28203.2 | 0.072 | 0.539 | 7.7 | LNU282 | 27563.1 | 1.273 | 0.001 | 58.4 |
| LNU112 | 28212.4 | 0.081 | 0.105 | 22.1 | LNU282 | 27565.2 | 1.273 | 0.002 | 58.4 |
| LNU112 | 28212.1 | 0.078 | 0.181 | 17.6 | LNU282 | 27562.1 | 0.836 | 0.765 | 4.0 |
| LNU112 | 28212.3 | 0.076 | 0.356 | 14.5 | LNU288 | 14563.9 | 1.420 | 0.000 | 76.7 |
| LNU14 | 27821.3 | 0.091 | 0.009 | 36.3 | LNU288 | 14563.6 | 1.166 | 0.018 | 45.1 |
| LNU14 | 27821.4 | 0.080 | 0.139 | 21.0 | LNU288 | 14564.8 | 1.158 | 0.007 | 44.1 |
| LNU14 | 27824.2 | 0.073 | 0.440 | 10.6 | LNU288 | 14562.9 | 1.104 | 0.004 | 37.3 |
| LNU183 | 24864.6 | 0.108 | 0.000 | 63.2 | LNU288 | 14562.7 | 1.029 | 0.064 | 28.1 |
| LNU183 | 24863.12 | 0.099 | 0.001 | 49.5 | LNU75 | 27572.2 | 1.648 | 0.000 | 105.0 |
| LNU183 | 24865.1 | 0.095 | 0.009 | 42.5 | LNU75 | 27571.2 | 1.413 | 0.000 | 75.8 |
| LNU183 | 24863.1 | 0.089 | 0.012 | 34.3 | LNU75 | 27572.3 | 1.342 | 0.000 | 67.0 |
| LNU191 | 28325.4 | 0.081 | 0.112 | 21.4 | LNU75 | 27571.4 | 1.151 | 0.007 | 43.2 |
| LNU191 | 28324.2 | 0.078 | 0.228 | 17.5 | CONT. | — | 1.337 | — | 0.0 |
| LNU191 | 28321.3 | 0.073 | 0.438 | 10.2 | LNU112 | 28212.4 | 1.471 | 0.446 | 10.0 |
| LNU191 | 28323.1 | 0.073 | 0.468 | 9.9 | LNU183 | 24865.1 | 1.454 | 0.553 | 8.7 |
| LNU201 | 28222.2 | 0.097 | 0.004 | 46.8 | LNU183 | 24863.1 | 1.423 | 0.621 | 6.5 |
| LNU201 | 28223.3 | 0.083 | 0.110 | 25.1 | LNU201 | 28222.2 | 1.426 | 0.669 | 6.7 |
| LNU201 | 28221.3 | 0.075 | 0.365 | 12.4 | LNU268 | 26044.2 | 1.586 | 0.220 | 18.6 |
| LNU268 | 26043.4 | 0.077 | 0.218 | 16.2 | CONT. | — | 1.041 | — | 0.0 |
| LNU268 | 26041.4 | 0.075 | 0.332 | 13.4 | LNU11 | 28205.2 | 1.468 | 0.006 | 41.0 |
| CONT. | — | 0.051 | — | 0.0 | LNU11 | 28203.2 | 1.369 | 0.063 | 31.5 |
| LNU107 | 14583.8 | 0.076 | 0.007 | 48.4 | LNU11 | 28202.5 | 1.338 | 0.069 | 28.6 |
| LNU107 | 14585.5 | 0.065 | 0.100 | 26.5 | LNU11 | 28205.1 | 1.338 | 0.045 | 28.5 |
| LNU107 | 14584.9 | 0.057 | 0.561 | 11.1 | LNU11 | 28204.1 | 1.126 | 0.564 | 8.1 |
| LNU116 | 14494.5 | 0.085 | 0.001 | 65.8 | LNU11 | 28204.3 | 1.091 | 0.747 | 4.8 |
| LNU116 | 14492.9 | 0.080 | 0.008 | 55.0 | LNU112 | 28212.1 | 1.350 | 0.044 | 29.7 |
| LNU116 | 14492.5 | 0.067 | 0.072 | 29.7 | LNU112 | 28212.4 | 1.142 | 0.464 | 9.7 |
| LNU116 | 14493.6 | 0.057 | 0.537 | 10.1 | LNU14 | 27821.3 | 1.766 | 0.000 | 69.6 |
| LNU121 | 27713.4 | 0.092 | 0.000 | 78.5 | LNU14 | 27821.4 | 1.364 | 0.053 | 31.0 |
| LNU121 | 27711.1 | 0.085 | 0.001 | 65.3 | LNU14 | 27824.2 | 1.190 | 0.288 | 14.3 |
| LNU121 | 25642.2 | 0.084 | 0.002 | 62.9 | LNU14 | 27821.1 | 1.095 | 0.671 | 5.2 |
| LNU121 | 27713.1 | 0.072 | 0.042 | 40.8 | LNU183 | 24864.6 | 2.078 | 0.000 | 99.6 |
| LNU126 | 25345.1 | 0.074 | 0.016 | 43.6 | LNU183 | 24863.12 | 1.703 | 0.000 | 63.6 |
| LNU126 | 25343.1 | 0.068 | 0.132 | 32.1 | LNU183 | 24865.1 | 1.690 | 0.000 | 62.4 |
| LNU126 | 25343.3 | 0.063 | 0.254 | 21.7 | LNU183 | 24863.1 | 1.371 | 0.041 | 31.7 |
| LNU126 | 25343.4 | 0.054 | 0.749 | 5.2 | LNU191 | 28325.4 | 1.453 | 0.029 | 39.5 |
| LNU158 | 27433.3 | 0.077 | 0.009 | 49.2 | LNU191 | 28323.1 | 1.404 | 0.028 | 34.9 |
| LNU158 | 27433.2 | 0.075 | 0.023 | 45.8 | LNU191 | 28321.3 | 1.246 | 0.174 | 19.7 |
| LNU158 | 27432.5 | 0.065 | 0.225 | 25.7 | LNU191 | 28324.2 | 1.114 | 0.606 | 7.0 |
| LNU158 | 27434.1 | 0.054 | 0.759 | 5.3 | LNU201 | 28222.2 | 1.662 | 0.000 | 59.6 |
| LNU177 | 24762.6 | 0.092 | 0.000 | 79.8 | LNU201 | 28223.3 | 1.505 | 0.008 | 44.6 |
| LNU177 | 24764.9 | 0.063 | 0.216 | 22.4 | LNU201 | 28221.3 | 1.212 | 0.212 | 16.4 |
| LNU177 | 24765.2 | 0.060 | 0.389 | 16.0 | LNU201 | 28223.1 | 1.150 | 0.497 | 10.5 |
| LNU182 | 25384.1 | 0.083 | 0.002 | 61.9 | LNU268 | 26041.4 | 1.323 | 0.039 | 27.0 |
| LNU182 | 27521.4 | 0.069 | 0.028 | 34.9 | LNU268 | 26041.6 | 1.273 | 0.137 | 22.3 |
| LNU182 | 25384.5 | 0.065 | 0.128 | 26.1 | LNU268 | 26043.4 | 1.270 | 0.108 | 22.0 |
| LNU182 | 25384.2 | 0.057 | 0.590 | 11.4 | CONT. | — | 1.034 | — | 0.0 |
| LNU2 | 27842.1 | 0.062 | 0.219 | 20.8 | LNU107 | 14583.8 | 1.442 | 0.035 | 39.5 |
| LNU2 | 27845.2 | 0.059 | 0.329 | 15.1 | LNU107 | 14585.5 | 1.213 | 0.242 | 17.3 |
| LNU2 | 27842.3 | 0.057 | 0.510 | 10.6 | LNU107 | 14584.9 | 1.101 | 0.695 | 6.5 |

TABLE 66-continued

Genes showing improved plant growth rate at nitrogen deficient conditions (T2 generation)

| | RGR Of Leaf Area | | | | | RGR Of Roots Coverage | | | |
|---|---|---|---|---|---|---|---|---|---|
| Gene Name | Event # | Ave. | p-value | % incr. | Gene Name | Event # | Ave. | p-value | % incr. |
| LNU225 | 25991.5 | 0.062 | 0.329 | 20.6 | LNU116 | 14492.9 | 1.463 | 0.032 | 41.6 |
| LNU225 | 25991.2 | 0.057 | 0.617 | 11.8 | LNU116 | 14494.5 | 1.394 | 0.053 | 34.8 |
| LNU239 | 26283.2 | 0.057 | 0.544 | 11.4 | LNU116 | 14492.5 | 1.305 | 0.120 | 26.2 |
| LNU57 | 27854.5 | 0.059 | 0.385 | 14.1 | LNU121 | 27713.4 | 1.552 | 0.003 | 50.1 |
| LNU57 | 27852.1 | 0.054 | 0.717 | 5.9 | LNU121 | 25642.2 | 1.486 | 0.007 | 43.8 |
| LNU83 | 27684.1 | 0.076 | 0.011 | 47.3 | LNU121 | 27711.1 | 1.463 | 0.009 | 41.5 |
| LNU83 | 27685.1 | 0.055 | 0.672 | 7.2 | LNU121 | 27713.1 | 1.117 | 0.615 | 8.0 |
| LNU83 | 27685.2 | 0.055 | 0.693 | 6.7 | LNU126 | 25345.1 | 1.417 | 0.058 | 37.1 |
| CONT. | — | 0.039 | — | 0.0 | LNU126 | 25343.1 | 1.367 | 0.043 | 32.3 |
| LNU107 | 14584.9 | 0.060 | 0.086 | 53.1 | LNU126 | 25343.3 | 1.164 | 0.485 | 12.6 |
| LNU107 | 14585.2 | 0.051 | 0.216 | 30.4 | LNU158 | 27432.5 | 1.551 | 0.020 | 50.0 |
| LNU107 | 14583.8 | 0.049 | 0.326 | 23.7 | LNU158 | 27433.3 | 1.537 | 0.002 | 48.7 |
| LNU116 | 14494.5 | 0.071 | 0.002 | 80.2 | LNU158 | 27433.2 | 1.367 | 0.047 | 32.3 |
| LNU116 | 14492.5 | 0.068 | 0.008 | 74.3 | LNU177 | 24762.6 | 1.619 | 0.000 | 56.6 |
| LNU116 | 14492.9 | 0.056 | 0.084 | 43.8 | LNU177 | 24764.9 | 1.270 | 0.280 | 22.8 |
| LNU116 | 14493.6 | 0.056 | 0.136 | 42.3 | LNU177 | 24765.2 | 1.115 | 0.596 | 7.9 |
| LNU116 | 14491.5 | 0.049 | 0.340 | 24.1 | LNU182 | 25384.1 | 1.674 | 0.000 | 61.9 |
| LNU121 | 27713.1 | 0.082 | 0.002 | 108.5 | LNU182 | 27521.4 | 1.443 | 0.020 | 39.6 |
| LNU121 | 27711.1 | 0.061 | 0.060 | 55.3 | LNU182 | 25384.2 | 1.184 | 0.409 | 14.5 |
| LNU121 | 27713.4 | 0.056 | 0.194 | 42.8 | LNU2 | 27842.1 | 1.272 | 0.118 | 23.0 |
| LNU121 | 25642.2 | 0.053 | 0.123 | 36.0 | LNU2 | 27842.3 | 1.202 | 0.253 | 16.3 |
| LNU126 | 25343.3 | 0.055 | 0.137 | 39.2 | LNU225 | 25991.5 | 1.957 | 0.000 | 89.3 |
| LNU126 | 25343.1 | 0.055 | 0.193 | 39.0 | LNU225 | 25991.2 | 1.568 | 0.068 | 51.7 |
| LNU126 | 25341.1 | 0.047 | 0.375 | 19.0 | LNU239 | 26284.1 | 1.173 | 0.351 | 13.4 |
| LNU158 | 27433.3 | 0.090 | 0.000 | 129.9 | LNU57 | 27852.1 | 1.108 | 0.646 | 7.1 |
| LNU158 | 27432.5 | 0.071 | 0.013 | 80.3 | LNU83 | 27681.4 | 1.299 | 0.154 | 25.7 |
| LNU158 | 27433.2 | 0.062 | 0.028 | 56.8 | LNU83 | 27684.1 | 1.142 | 0.536 | 10.5 |
| LNU177 | 24764.12 | 0.052 | 0.297 | 31.3 | CONT. | — | 1.042 | — | 0.0 |
| LNU177 | 24763.6 | 0.045 | 0.587 | 13.9 | LNU107 | 14584.9 | 1.679 | 0.000 | 61.1 |
| LNU177 | 24762.6 | 0.044 | 0.637 | 11.6 | LNU107 | 14583.8 | 1.266 | 0.094 | 21.5 |
| LNU182 | 25384.6 | 0.062 | 0.027 | 58.1 | LNU107 | 14585.2 | 1.110 | 0.538 | 6.5 |
| LNU182 | 25384.2 | 0.055 | 0.062 | 39.4 | LNU116 | 14492.5 | 1.582 | 0.011 | 51.8 |
| LNU2 | 27842.1 | 0.065 | 0.020 | 64.9 | LNU116 | 14494.5 | 1.474 | 0.038 | 41.4 |
| LNU2 | 27842.3 | 0.052 | 0.204 | 33.2 | LNU116 | 14493.6 | 1.214 | 0.133 | 16.5 |
| LNU2 | 27845.2 | 0.043 | 0.792 | 9.5 | LNU121 | 25642.2 | 1.548 | 0.003 | 48.6 |
| LNU225 | 25991.2 | 0.067 | 0.005 | 70.3 | LNU121 | 27711.1 | 1.483 | 0.008 | 42.3 |
| LNU225 | 25991.3 | 0.064 | 0.033 | 62.1 | LNU121 | 27713.1 | 1.469 | 0.024 | 41.0 |
| LNU225 | 25991.8 | 0.062 | 0.006 | 58.4 | LNU121 | 27713.4 | 1.299 | 0.148 | 24.6 |
| LNU225 | 25991.1 | 0.044 | 0.590 | 12.8 | LNU126 | 25343.1 | 1.533 | 0.005 | 47.1 |
| LNU239 | 26283.2 | 0.046 | 0.481 | 17.6 | LNU126 | 25343.4 | 1.138 | 0.399 | 9.2 |
| LNU239 | 26284.2 | 0.045 | 0.606 | 14.6 | LNU126 | 25343.3 | 1.135 | 0.547 | 9.0 |
| LNU239 | 26284.1 | 0.045 | 0.517 | 14.4 | LNU158 | 27433.3 | 1.718 | 0.000 | 64.9 |
| LNU239 | 26281.1 | 0.044 | 0.624 | 12.7 | LNU158 | 27432.5 | 1.552 | 0.001 | 48.9 |
| LNU57 | 27854.5 | 0.054 | 0.171 | 38.4 | LNU158 | 27433.2 | 1.223 | 0.182 | 17.4 |
| LNU57 | 27852.1 | 0.045 | 0.560 | 13.4 | LNU177 | 24764.12 | 1.480 | 0.002 | 42.0 |
| LNU83 | 27685.1 | 0.082 | 0.001 | 108.8 | LNU177 | 24763.6 | 1.139 | 0.446 | 9.3 |
| LNU83 | 27685.2 | 0.055 | 0.217 | 39.2 | LNU177 | 24762.6 | 1.106 | 0.569 | 6.1 |
| LNU83 | 27681.4 | 0.053 | 0.102 | 34.0 | LNU182 | 25384.1 | 1.145 | 0.434 | 9.8 |
| | | | | | LNU182 | 25384.6 | 1.137 | 0.510 | 9.1 |
| | | | | | LNU182 | 25384.5 | 1.120 | 0.583 | 7.5 |
| | | | | | LNU2 | 27842.1 | 1.510 | 0.005 | 44.9 |
| | | | | | LNU2 | 27842.3 | 1.235 | 0.123 | 18.5 |
| | | | | | LNU2 | 25713.1 | 1.173 | 0.395 | 12.5 |
| | | | | | LNU225 | 25991.3 | 1.802 | 0.000 | 72.9 |
| | | | | | LNU225 | 25991.2 | 1.638 | 0.000 | 57.2 |
| | | | | | LNU225 | 25991.8 | 1.355 | 0.035 | 30.0 |
| | | | | | LNU225 | 25991.1 | 1.290 | 0.106 | 23.8 |
| | | | | | LNU239 | 26284.2 | 1.385 | 0.010 | 32.9 |
| | | | | | LNU57 | 27852.1 | 1.618 | 0.000 | 55.3 |
| | | | | | LNU57 | 27851.2 | 1.559 | 0.001 | 49.6 |
| | | | | | LNU57 | 27854.5 | 1.285 | 0.052 | 23.3 |
| | | | | | LNU57 | 27854.3 | 1.105 | 0.534 | 6.1 |
| | | | | | LNU83 | 27685.1 | 1.715 | 0.000 | 64.6 |
| | | | | | LNU83 | 27685.2 | 1.417 | 0.007 | 36.0 |
| | | | | | LNU83 | 27681.4 | 1.399 | 0.006 | 34.2 |

Table 66.
"CONT."—Control;
"Ave."—Average;
"% Incr." = % increment.

TABLE 67

Genes showing improved plant growth rate at nitrogen deficient conditions (T2 generation)

| Gene Name | Event # | RGR Of Roots Length Average | p-value | % increment |
|---|---|---|---|---|
| CONTROL | — | 0.508 | — | 0.0 |
| LNU100 | 14471.4 | 0.596 | 0.019 | 17.4 |
| LNU100 | 14474.3 | 0.592 | 0.005 | 16.6 |
| LNU100 | 14473.1 | 0.577 | 0.062 | 13.6 |
| LNU100 | 14474.4 | 0.545 | 0.162 | 7.3 |
| LNU104 | 25034.1 | 0.610 | 0.280 | 20.2 |
| LNU104 | 25033.3 | 0.554 | 0.201 | 9.1 |
| LNU213 | 24653.2 | 0.581 | 0.019 | 14.5 |
| LNU213 | 24652.4 | 0.535 | 0.389 | 5.3 |
| LNU213 | 24654.4 | 0.531 | 0.578 | 4.6 |
| LNU213 | 24653.1 | 0.522 | 0.713 | 2.8 |
| LNU218 | 24783.2 | 0.579 | 0.142 | 14.1 |
| LNU4 | 25134.2 | 0.594 | 0.003 | 16.9 |
| LNU4 | 25131.1 | 0.531 | 0.379 | 4.5 |
| LNU48 | 24802.2 | 0.600 | 0.009 | 18.1 |
| LNU48 | 24804.4 | 0.578 | 0.015 | 13.9 |
| LNU8 | 25063.1 | 0.640 | 0.004 | 26.0 |
| LNU94 | 24833.3 | 0.561 | 0.109 | 10.5 |
| CONTROL | — | 0.573 | — | 0.0 |
| LNU1 | 24684.1 | 0.638 | 0.209 | 11.2 |
| LNU1 | 24681.3 | 0.625 | 0.192 | 9.1 |
| LNU1 | 24682.2 | 0.617 | 0.679 | 7.6 |
| LNU1 | 24681.1 | 0.597 | 0.605 | 4.1 |
| LNU133 | 24744.3 | 0.624 | 0.454 | 8.9 |
| LNU133 | 24741.1 | 0.589 | 0.728 | 2.7 |
| LNU133 | 24742.2 | 0.587 | 0.795 | 2.4 |
| LNU175 | 24732.4 | 0.666 | 0.280 | 16.2 |
| LNU175 | 24732.1 | 0.613 | 0.486 | 6.9 |
| LNU175 | 24731.2 | 0.596 | 0.623 | 4.0 |
| LNU175 | 24734.4 | 0.592 | 0.710 | 3.3 |
| LNU175 | 24733.4 | 0.586 | 0.713 | 2.3 |
| LNU178 | 14611.5 | 0.692 | 0.028 | 20.7 |
| LNU178 | 14611.4 | 0.624 | 0.288 | 8.9 |
| LNU178 | 14614.5 | 0.616 | 0.404 | 7.4 |
| LNU178 | 14611.1 | 0.610 | 0.435 | 6.4 |
| LNU178 | 14612.1 | 0.587 | 0.696 | 2.5 |
| LNU215 | 24661.4 | 0.639 | 0.125 | 11.5 |
| LNU215 | 24664.3 | 0.634 | 0.227 | 10.6 |
| LNU24 | 24973.1 | 0.626 | 0.223 | 9.2 |
| LNU24 | 24971.4 | 0.608 | 0.532 | 6.1 |
| LNU24 | 24971.3 | 0.602 | 0.471 | 5.0 |
| LNU6 | 24992.3 | 0.639 | 0.244 | 11.4 |
| LNU6 | 24994.2 | 0.594 | 0.617 | 3.6 |
| LNU82 | 24824.3 | 0.596 | 0.551 | 4.0 |
| LNU82 | 24824.1 | 0.596 | 0.664 | 4.0 |
| LNU82 | 24823.1 | 0.596 | 0.623 | 3.9 |
| LNU9 | 25001.1 | 0.648 | 0.159 | 13.1 |
| LNU9 | 25003.1 | 0.647 | 0.066 | 12.9 |
| LNU9 | 25001.2 | 0.624 | 0.297 | 8.9 |
| LNU9 | 25001.3 | 0.592 | 0.636 | 3.3 |
| CONTROL | — | 0.676 | — | 0.0 |
| LNU120 | 25463.7 | 0.756 | 0.081 | 11.7 |
| LNU120 | 25463.3 | 0.689 | 0.770 | 1.9 |
| LNU132 | 14102.9 | 0.708 | 0.416 | 4.7 |
| LNU132 | 14102.7 | 0.690 | 0.752 | 2.1 |
| LNU140 | 14112.7 | 0.723 | 0.288 | 7.0 |
| LNU140 | 14112.6 | 0.690 | 0.737 | 2.0 |
| LNU180 | 24724.3 | 0.760 | 0.046 | 12.4 |
| CONTROL | — | 0.559 | — | 0.0 |
| LNU1 | 24681.1 | 0.707 | 0.009 | 26.5 |
| LNU1 | 24682.1 | 0.698 | 0.025 | 24.8 |
| LNU1 | 24683.2 | 0.628 | 0.204 | 12.4 |
| LNU1 | 24684.1 | 0.578 | 0.720 | 3.3 |
| LNU110 | 24953.2 | 0.682 | 0.044 | 22.0 |
| LNU110 | 24952.3 | 0.593 | 0.566 | 6.0 |
| LNU110 | 24954.3 | 0.589 | 0.576 | 5.4 |
| LNU175 | 24734.4 | 0.670 | 0.058 | 19.9 |
| LNU175 | 24732.2 | 0.645 | 0.220 | 15.4 |
| LNU175 | 24732.1 | 0.607 | 0.424 | 8.5 |
| LNU175 | 24733.1 | 0.602 | 0.491 | 7.7 |
| LNU19 | 25151.1 | 0.607 | 0.536 | 8.6 |
| LNU215 | 24663.4 | 0.729 | 0.007 | 30.4 |
| LNU215 | 24661.4 | 0.699 | 0.013 | 24.9 |
| LNU215 | 24664.2 | 0.683 | 0.040 | 22.2 |
| LNU215 | 24663.3 | 0.668 | 0.126 | 19.5 |
| LNU215 | 24663.1 | 0.632 | 0.187 | 13.1 |
| LNU27 | 24873.1 | 0.662 | 0.093 | 18.4 |
| LNU27 | 24873.4 | 0.631 | 0.234 | 12.9 |
| LNU27 | 24871.4 | 0.575 | 0.763 | 2.9 |
| LNU44 | 24924.2 | 0.724 | 0.009 | 29.4 |
| LNU44 | 24922.3 | 0.717 | 0.013 | 28.3 |
| LNU44 | 24923.3 | 0.668 | 0.073 | 19.5 |
| LNU44 | 24924.3 | 0.610 | 0.456 | 9.1 |
| LNU54 | 24901.2 | 0.786 | 0.002 | 40.5 |
| LNU54 | 24902.4 | 0.733 | 0.003 | 31.2 |
| LNU54 | 24903.3 | 0.653 | 0.227 | 16.8 |
| LNU54 | 24902.7 | 0.645 | 0.151 | 15.3 |
| LNU54 | 24903.5 | 0.634 | 0.241 | 13.4 |
| LNU79 | 24882.2 | 0.682 | 0.026 | 22.0 |
| LNU79 | 24881.1 | 0.679 | 0.057 | 21.4 |
| LNU79 | 24884.4 | 0.675 | 0.041 | 20.7 |
| LNU79 | 24884.3 | 0.626 | 0.303 | 12.1 |
| LNU79 | 24883.2 | 0.604 | 0.426 | 8.0 |
| CONTROL | — | 0.579 | — | 0.0 |
| LNU109 | 24892.8 | 0.635 | 0.116 | 9.7 |
| LNU109 | 24892.6 | 0.608 | 0.476 | 5.0 |
| LNU109 | 24891.2 | 0.593 | 0.755 | 2.4 |
| LNU110 | 24952.1 | 0.729 | 0.049 | 25.9 |
| LNU110 | 24952.3 | 0.624 | 0.341 | 7.9 |
| LNU133 | 24741.1 | 0.641 | 0.157 | 10.7 |
| LNU133 | 24744.3 | 0.628 | 0.417 | 8.5 |
| LNU19 | 25151.1 | 0.660 | 0.070 | 13.9 |
| LNU27 | 24873.4 | 0.675 | 0.052 | 16.6 |
| LNU44 | 24922.3 | 0.654 | 0.110 | 13.0 |
| LNU54 | 24901.2 | 0.711 | 0.036 | 22.7 |
| LNU6 | 24992.3 | 0.662 | 0.126 | 14.3 |
| LNU6 | 24994.5 | 0.617 | 0.380 | 6.6 |
| LNU79 | 24881.1 | 0.642 | 0.082 | 10.9 |
| LNU79 | 24884.4 | 0.622 | 0.408 | 7.5 |
| LNU79 | 24882.2 | 0.598 | 0.637 | 3.3 |
| LNU79 | 24883.2 | 0.590 | 0.762 | 1.9 |
| CONTROL | — | 0.530 | — | 0.0 |
| LNU109 | 24892.8 | 0.658 | 0.032 | 24.3 |
| LNU109 | 24891.2 | 0.573 | 0.550 | 8.1 |
| LNU109 | 24891.5 | 0.552 | 0.715 | 4.2 |
| LNU143 | 25972.1 | 0.665 | 0.035 | 25.5 |
| LNU143 | 25975.3 | 0.619 | 0.137 | 16.8 |
| LNU143 | 25971.2 | 0.593 | 0.274 | 12.0 |
| LNU143 | 25971.5 | 0.588 | 0.323 | 11.0 |
| LNU154 | 14604.6 | 0.619 | 0.131 | 16.9 |
| LNU154 | 14602.8 | 0.591 | 0.440 | 11.6 |
| LNU154 | 14604.7 | 0.588 | 0.371 | 11.0 |
| LNU196 | 25532.2 | 0.675 | 0.013 | 27.4 |
| LNU196 | 25534.1 | 0.645 | 0.113 | 21.9 |
| LNU196 | 25533.1 | 0.596 | 0.226 | 12.6 |
| LNU196 | 25532.1 | 0.554 | 0.782 | 4.5 |
| LNU207 | 24642.4 | 0.656 | 0.046 | 23.8 |
| LNU207 | 24644.18 | 0.593 | 0.272 | 12.0 |
| LNU207 | 24642.5 | 0.557 | 0.654 | 5.2 |
| LNU207 | 24644.13 | 0.546 | 0.800 | 3.1 |
| LNU288 | 14562.7 | 0.624 | 0.142 | 17.8 |
| LNU288 | 14564.9 | 0.602 | 0.177 | 13.6 |
| LNU288 | 14562.1 | 0.586 | 0.349 | 10.6 |
| LNU288 | 14562.9 | 0.568 | 0.454 | 7.2 |
| LNU50 | 26024.2 | 0.615 | 0.205 | 16.1 |
| LNU50 | 26023.2 | 0.603 | 0.254 | 13.9 |
| LNU50 | 26023.5 | 0.586 | 0.290 | 10.6 |
| LNU50 | 26025.4 | 0.580 | 0.453 | 9.6 |
| LNU52 | 25723.2 | 0.681 | 0.034 | 28.6 |
| LNU52 | 25721.4 | 0.604 | 0.276 | 14.1 |
| LNU52 | 25721.3 | 0.566 | 0.561 | 6.9 |
| CONTROL | — | 0.496 | — | 0.0 |
| LNU143 | 25975.2 | 0.614 | 0.010 | 23.7 |
| LNU143 | 25971.2 | 0.600 | 0.007 | 20.9 |
| LNU143 | 25971.5 | 0.577 | 0.071 | 16.3 |
| LNU143 | 25972.1 | 0.571 | 0.096 | 15.1 |

TABLE 67-continued

Genes showing improved plant growth rate at nitrogen deficient conditions (T2 generation)

| Gene Name | Event # | RGR Of Roots Length Average | p-value | % increment |
|---|---|---|---|---|
| LNU143 | 25975.3 | 0.560 | 0.056 | 12.9 |
| LNU154 | 14602.8 | 0.583 | 0.030 | 17.5 |
| LNU154 | 14601.6 | 0.556 | 0.146 | 12.1 |
| LNU207 | 24642.5 | 0.651 | 0.005 | 31.2 |
| LNU207 | 24641.1 | 0.636 | 0.005 | 28.2 |
| LNU207 | 24642.4 | 0.582 | 0.026 | 17.3 |
| LNU211 | 24771.1 | 0.631 | 0.009 | 27.3 |
| LNU211 | 24774.4 | 0.557 | 0.286 | 12.2 |
| LNU211 | 24771.3 | 0.546 | 0.192 | 10.1 |
| LNU52 | 25723.1 | 0.635 | 0.008 | 28.1 |
| LNU52 | 25721.2 | 0.632 | 0.002 | 27.4 |
| LNU52 | 25721.1 | 0.605 | 0.030 | 22.0 |
| LNU52 | 25723.2 | 0.531 | 0.460 | 7.1 |
| LNU69 | 14571.1 | 0.653 | 0.004 | 31.7 |
| LNU69 | 14573.3 | 0.603 | 0.037 | 21.6 |
| LNU69 | 14572.9 | 0.583 | 0.014 | 17.6 |
| LNU69 | 14572.8 | 0.565 | 0.051 | 14.0 |
| LNU69 | 14573.7 | 0.520 | 0.567 | 4.8 |
| CONTROL | — | 0.489 | — | 0.0 |
| LNU150 | 24841.9 | 0.673 | 0.034 | 37.7 |
| LNU150 | 24842.9 | 0.631 | 0.096 | 29.1 |
| LNU150 | 24843.5 | 0.533 | 0.611 | 9.1 |
| LNU179 | 24631.6 | 0.674 | 0.032 | 38.1 |
| LNU179 | 24631.9 | 0.673 | 0.037 | 37.8 |
| LNU179 | 24632.5 | 0.608 | 0.166 | 24.5 |
| LNU179 | 24631.7 | 0.598 | 0.193 | 22.5 |
| LNU179 | 24632.7 | 0.535 | 0.585 | 9.4 |
| LNU232 | 26001.5 | 0.572 | 0.345 | 17.1 |
| LNU232 | 26003.7 | 0.568 | 0.349 | 16.3 |
| LNU232 | 26003.3 | 0.561 | 0.394 | 14.9 |
| LNU232 | 26001.2 | 0.552 | 0.454 | 13.1 |
| LNU232 | 26003.6 | 0.523 | 0.689 | 7.0 |
| LNU235 | 26185.3 | 0.674 | 0.037 | 37.9 |
| LNU235 | 26184.4 | 0.628 | 0.114 | 28.6 |
| LNU235 | 26185.2 | 0.611 | 0.146 | 25.2 |
| LNU235 | 26184.2 | 0.606 | 0.175 | 24.0 |
| LNU235 | 26182.1 | 0.556 | 0.429 | 13.9 |
| LNU242 | 25474.1 | 0.646 | 0.076 | 32.2 |
| LNU242 | 25473.1 | 0.635 | 0.095 | 30.1 |
| LNU242 | 25473.3 | 0.596 | 0.205 | 22.0 |
| LNU242 | 25471.1 | 0.542 | 0.524 | 11.0 |
| LNU76 | 26423.1 | 0.676 | 0.030 | 38.5 |
| LNU76 | 26425.1 | 0.645 | 0.069 | 32.0 |
| LNU76 | 26421.2 | 0.605 | 0.193 | 23.9 |
| LNU76 | 26421.1 | 0.568 | 0.383 | 16.2 |
| LNU95 | 13985.11 | 0.663 | 0.046 | 35.7 |
| LNU95 | 13985.15 | 0.632 | 0.092 | 29.3 |
| LNU95 | 13985.19 | 0.628 | 0.115 | 28.5 |
| LNU95 | 13985.12 | 0.565 | 0.375 | 15.7 |
| LNU95 | 13985.16 | 0.565 | 0.369 | 15.6 |
| CONTROL | — | 0.552 | — | 0.0 |
| LNU118 | 14012.15 | 0.580 | 0.661 | 5.0 |
| LNU150 | 24843.5 | 0.647 | 0.138 | 17.1 |
| LNU150 | 24841.6 | 0.576 | 0.712 | 4.3 |
| LNU150 | 24841.9 | 0.571 | 0.776 | 3.3 |
| LNU179 | 24632.5 | 0.600 | 0.471 | 8.6 |
| LNU179 | 24631.7 | 0.583 | 0.640 | 5.5 |
| LNU179 | 24631.6 | 0.572 | 0.762 | 3.4 |
| LNU232 | 26003.3 | 0.600 | 0.461 | 8.5 |
| LNU232 | 26001.5 | 0.581 | 0.672 | 5.2 |
| LNU235 | 26185.2 | 0.653 | 0.151 | 18.2 |
| LNU235 | 26184.4 | 0.648 | 0.155 | 17.2 |
| LNU235 | 26184.2 | 0.618 | 0.309 | 11.8 |
| LNU242 | 25474.1 | 0.608 | 0.403 | 10.1 |
| LNU288 | 14562.7 | 0.622 | 0.286 | 12.7 |
| LNU288 | 14564.9 | 0.608 | 0.389 | 10.1 |
| LNU288 | 14563.9 | 0.607 | 0.402 | 9.8 |
| LNU288 | 14563.6 | 0.595 | 0.502 | 7.8 |
| LNU288 | 14562.1 | 0.588 | 0.576 | 6.4 |
| LNU76 | 26423.1 | 0.635 | 0.217 | 15.0 |
| LNU76 | 26421.2 | 0.623 | 0.279 | 12.8 |
| LNU76 | 26422.2 | 0.602 | 0.443 | 9.0 |
| LNU95 | 13985.16 | 0.657 | 0.123 | 19.0 |
| LNU95 | 13985.15 | 0.621 | 0.282 | 12.4 |
| LNU95 | 13985.11 | 0.594 | 0.519 | 7.5 |
| CONTROL | — | 0.580 | — | 0.0 |
| LNU101 | 27632.7 | 0.664 | 0.135 | 14.5 |
| LNU128 | 26511.5 | 0.645 | 0.229 | 11.2 |
| LNU128 | 26515.3 | 0.594 | 0.788 | 2.5 |
| LNU192 | 28315.2 | 0.675 | 0.088 | 16.5 |
| LNU192 | 28313.2 | 0.671 | 0.114 | 15.7 |
| LNU192 | 28312.2 | 0.645 | 0.212 | 11.3 |
| LNU192 | 28313.3 | 0.606 | 0.632 | 4.6 |
| LNU206 | 27622.1 | 0.648 | 0.211 | 11.8 |
| LNU211 | 24771.1 | 0.745 | 0.004 | 28.5 |
| LNU282 | 27562.1 | 0.686 | 0.067 | 18.3 |
| LNU282 | 27563.3 | 0.667 | 0.138 | 15.1 |
| LNU282 | 27563.1 | 0.653 | 0.174 | 12.6 |
| LNU282 | 27565.2 | 0.616 | 0.513 | 6.2 |
| LNU69 | 14571.1 | 0.706 | 0.020 | 21.7 |
| LNU69 | 14573.5 | 0.610 | 0.578 | 5.2 |
| LNU75 | 27572.2 | 0.616 | 0.530 | 6.2 |
| LNU75 | 27572.1 | 0.613 | 0.539 | 5.8 |
| CONTROL | — | 0.556 | — | 0.0 |
| LNU101 | 27632.5 | 0.605 | 0.353 | 8.7 |
| LNU101 | 27632.6 | 0.585 | 0.555 | 5.2 |
| LNU118 | 14012.15 | 0.655 | 0.047 | 17.7 |
| LNU118 | 14012.12 | 0.604 | 0.370 | 8.6 |
| LNU128 | 26515.3 | 0.617 | 0.231 | 10.9 |
| LNU128 | 26511.5 | 0.591 | 0.498 | 6.2 |
| LNU206 | 27622.4 | 0.676 | 0.029 | 21.6 |
| LNU206 | 27621.2 | 0.640 | 0.181 | 15.0 |
| LNU206 | 27622.1 | 0.605 | 0.401 | 8.7 |
| LNU249 | 26154.2 | 0.597 | 0.477 | 7.4 |
| LNU249 | 26151.1 | 0.589 | 0.576 | 5.8 |
| LNU249 | 26152.4 | 0.588 | 0.631 | 5.8 |
| LNU249 | 26152.2 | 0.573 | 0.726 | 3.0 |
| LNU282 | 27563.1 | 0.639 | 0.143 | 14.9 |
| LNU282 | 27565.2 | 0.629 | 0.151 | 13.0 |
| LNU282 | 27563.3 | 0.595 | 0.477 | 7.0 |
| LNU282 | 27562.1 | 0.582 | 0.633 | 4.6 |
| LNU288 | 14562.7 | 0.708 | 0.006 | 27.2 |
| LNU288 | 14563.6 | 0.652 | 0.069 | 17.2 |
| LNU288 | 14562.9 | 0.645 | 0.068 | 16.0 |
| LNU288 | 14563.9 | 0.631 | 0.178 | 13.4 |
| LNU288 | 14564.8 | 0.583 | 0.608 | 4.9 |
| LNU75 | 27572.2 | 0.725 | 0.003 | 30.4 |
| LNU75 | 27571.4 | 0.652 | 0.063 | 17.2 |
| LNU75 | 27572.3 | 0.636 | 0.111 | 14.3 |
| LNU75 | 27571.2 | 0.627 | 0.179 | 12.8 |
| CONTROL | — | 0.596 | — | 0.0 |
| LNU14 | 27821.3 | 0.619 | 0.681 | 3.9 |
| LNU183 | 24863.1 | 0.615 | 0.740 | 3.2 |
| LNU201 | 28222.2 | 0.639 | 0.479 | 7.3 |
| LNU201 | 28223.1 | 0.615 | 0.747 | 3.1 |
| LNU201 | 28222.3 | 0.613 | 0.765 | 2.9 |
| LNU268 | 26041.6 | 0.661 | 0.241 | 10.8 |
| LNU268 | 26044.2 | 0.647 | 0.386 | 8.6 |
| LNU268 | 26045.1 | 0.619 | 0.666 | 3.9 |
| CONTROL | — | 0.607 | — | 0.0 |
| LNU11 | 28205.2 | 0.732 | 0.021 | 20.7 |
| LNU11 | 28202.5 | 0.650 | 0.304 | 7.2 |
| LNU11 | 28205.1 | 0.640 | 0.404 | 5.6 |
| LNU112 | 28212.4 | 0.669 | 0.188 | 10.3 |
| LNU112 | 28212.1 | 0.637 | 0.527 | 5.0 |
| LNU14 | 27821.3 | 0.678 | 0.147 | 11.8 |
| LNU14 | 27821.1 | 0.637 | 0.469 | 5.0 |
| LNU14 | 27824.2 | 0.628 | 0.661 | 3.6 |
| LNU14 | 27821.4 | 0.621 | 0.752 | 2.5 |
| LNU183 | 24864.6 | 0.773 | 0.000 | 27.4 |
| LNU183 | 24863.12 | 0.683 | 0.164 | 12.6 |
| LNU183 | 24863.1 | 0.669 | 0.163 | 10.2 |
| LNU191 | 28325.4 | 0.659 | 0.293 | 8.7 |
| LNU191 | 28321.3 | 0.645 | 0.407 | 6.4 |
| LNU191 | 28324.2 | 0.627 | 0.654 | 3.4 |
| LNU191 | 28323.1 | 0.621 | 0.727 | 2.4 |

TABLE 67-continued

Genes showing improved plant growth rate at nitrogen deficient conditions (T2 generation)

| Gene Name | Event # | RGR Of Roots Length Average | p-value | % increment |
|---|---|---|---|---|
| LNU201 | 28222.2 | 0.735 | 0.009 | 21.1 |
| LNU201 | 28223.3 | 0.668 | 0.214 | 10.2 |
| LNU201 | 28223.1 | 0.662 | 0.256 | 9.1 |
| LNU201 | 28221.3 | 0.624 | 0.731 | 2.8 |
| LNU268 | 26041.6 | 0.694 | 0.059 | 14.4 |
| LNU268 | 26041.4 | 0.690 | 0.066 | 13.8 |
| LNU268 | 26043.4 | 0.623 | 0.696 | 2.7 |
| CONTROL | — | 0.580 | — | 0.0 |
| LNU107 | 14584.9 | 0.616 | 0.595 | 6.3 |
| LNU116 | 14492.5 | 0.654 | 0.142 | 12.8 |
| LNU116 | 14492.9 | 0.644 | 0.255 | 11.0 |
| LNU116 | 14494.5 | 0.610 | 0.603 | 5.2 |
| LNU121 | 27711.1 | 0.715 | 0.026 | 23.3 |
| LNU121 | 25642.2 | 0.629 | 0.325 | 8.5 |
| LNU121 | 27713.4 | 0.613 | 0.581 | 5.7 |
| LNU126 | 25345.1 | 0.612 | 0.569 | 5.4 |
| LNU126 | 25343.1 | 0.598 | 0.765 | 3.1 |
| LNU158 | 27433.3 | 0.652 | 0.199 | 12.3 |
| LNU158 | 27433.2 | 0.647 | 0.220 | 11.5 |
| LNU158 | 27432.5 | 0.644 | 0.297 | 11.0 |
| LNU158 | 27434.1 | 0.614 | 0.523 | 5.9 |
| LNU177 | 24764.9 | 0.642 | 0.365 | 10.7 |
| LNU177 | 24762.6 | 0.628 | 0.398 | 8.2 |
| LNU177 | 24764.12 | 0.620 | 0.512 | 6.9 |
| LNU182 | 25384.1 | 0.699 | 0.065 | 20.5 |
| LNU182 | 27521.4 | 0.611 | 0.610 | 5.3 |
| LNU225 | 25991.5 | 0.657 | 0.230 | 13.2 |
| LNU225 | 25991.8 | 0.648 | 0.196 | 11.8 |
| LNU225 | 25991.2 | 0.615 | 0.602 | 6.0 |
| LNU225 | 25991.3 | 0.603 | 0.668 | 4.0 |
| LNU239 | 26284.2 | 0.597 | 0.754 | 3.0 |
| LNU57 | 27854.5 | 0.618 | 0.456 | 6.6 |
| LNU57 | 27852.1 | 0.615 | 0.577 | 6.0 |
| LNU83 | 27682.1 | 0.677 | 0.105 | 16.8 |
| LNU83 | 27681.4 | 0.631 | 0.462 | 8.7 |
| CONTROL | — | 0.620 | — | 0.0 |
| LNU107 | 14584.9 | 0.711 | 0.447 | 14.8 |
| LNU107 | 14585.2 | 0.678 | 0.597 | 9.5 |
| LNU107 | 14583.8 | 0.655 | 0.757 | 5.6 |
| LNU116 | 14492.5 | 0.689 | 0.531 | 11.2 |
| LNU121 | 27711.1 | 0.703 | 0.460 | 13.5 |
| LNU121 | 27713.1 | 0.702 | 0.488 | 13.2 |
| LNU121 | 25642.2 | 0.653 | 0.776 | 5.4 |
| LNU126 | 25343.1 | 0.688 | 0.580 | 11.1 |
| LNU126 | 25343.4 | 0.652 | 0.767 | 5.1 |
| LNU158 | 27433.3 | 0.695 | 0.530 | 12.1 |
| LNU158 | 27432.5 | 0.687 | 0.570 | 10.9 |
| LNU158 | 27434.5 | 0.655 | 0.768 | 5.7 |
| LNU177 | 24763.6 | 0.662 | 0.710 | 6.9 |
| LNU177 | 24765.2 | 0.659 | 0.732 | 6.4 |
| LNU177 | 24764.12 | 0.652 | 0.778 | 5.3 |
| LNU182 | 25384.2 | 0.653 | 0.764 | 5.4 |
| LNU2 | 27842.3 | 0.709 | 0.460 | 14.4 |
| LNU2 | 27842.1 | 0.703 | 0.466 | 13.5 |
| LNU225 | 25991.3 | 0.666 | 0.693 | 7.5 |
| LNU225 | 25991.2 | 0.656 | 0.747 | 5.9 |
| LNU225 | 25991.8 | 0.655 | 0.756 | 5.8 |
| LNU225 | 25991.1 | 0.650 | 0.791 | 5.0 |
| LNU57 | 27854.3 | 0.693 | 0.520 | 11.9 |
| LNU57 | 27852.1 | 0.680 | 0.615 | 9.7 |
| LNU57 | 27854.5 | 0.652 | 0.779 | 5.2 |
| LNU83 | 27685.1 | 0.718 | 0.421 | 15.9 |
| LNU83 | 27685.2 | 0.710 | 0.446 | 14.6 |
| LNU83 | 27681.4 | 0.661 | 0.722 | 6.7 |

Table 67.

TABLE 68

Genes showing improved plant growth rate at nitrogen deficient conditions (T1 generation)

| Gene Name | RGR Of Leaf Area Ave. | p-value | % incr. | Gene Name | RGR Of Roots Coverage Ave. | p-value | % incr. |
|---|---|---|---|---|---|---|---|
| CONT. | 0.057 | — | 0.0 | CONT. | 0.440 | — | 0.0 |
| LNU121 | 0.059 | 0.705 | 3.5 | LNU121 | 0.620 | 0.003 | 41.0 |
| LNU154 | 0.061 | 0.457 | 6.5 | LNU150 | 0.464 | 0.668 | 5.4 |
| CONT. | 0.067 | — | 0.0 | LNU154 | 0.456 | 0.793 | 3.7 |
| LNU188 | 0.070 | 0.724 | 5.4 | CONT. | 0.585 | — | 0.0 |
| LNU2 | 0.070 | 0.703 | 4.4 | LNU127 | 0.717 | 0.182 | 22.6 |
| LNU255 | 0.068 | 0.888 | 1.6 | LNU188 | 0.639 | 0.589 | 9.2 |
| LNU265 | 0.067 | 0.946 | 0.8 | LNU217 | 0.616 | 0.741 | 5.3 |
| LNU58 | 0.078 | 0.290 | 16.5 | LNU239 | 0.652 | 0.570 | 11.4 |
| LNU83 | 0.072 | 0.600 | 7.7 | LNU265 | 0.766 | 0.076 | 30.9 |
| CONT. | 0.059 | — | 0.0 | LNU275 | 1.396 | 0.000 | 138.7 |
| LNU243 | 0.061 | 0.723 | 3.8 | LNU32 | 0.643 | 0.615 | 9.9 |
| LNU262 | 0.062 | 0.532 | 5.9 | LNU57 | 0.714 | 0.134 | 22.1 |
| LNU60 | 0.062 | 0.618 | 5.7 | LNU58 | 1.365 | 0.000 | 133.3 |
|  |  |  |  | LNU83 | 0.754 | 0.094 | 28.9 |
|  |  |  |  | CONT. | 0.423 | — | 0.0 |
|  |  |  |  | LNU176 | 0.490 | 0.470 | 15.9 |
|  |  |  |  | LNU214 | 0.524 | 0.228 | 23.9 |
|  |  |  |  | LNU223 | 0.460 | 0.658 | 8.6 |
|  |  |  |  | LNU233 | 0.529 | 0.217 | 25.1 |
|  |  |  |  | LNU245 | 0.450 | 0.741 | 6.3 |
|  |  |  |  | LNU247 | 0.671 | 0.019 | 58.6 |
|  |  |  |  | LNU284 | 0.571 | 0.166 | 34.9 |
|  |  |  |  | LNU289 | 0.574 | 0.115 | 35.6 |
|  |  |  |  | LNU70 | 0.457 | 0.700 | 8.1 |
|  |  |  |  | LNU85 | 0.500 | 0.436 | 18.1 |
|  |  |  |  | CONT. | 0.541 | — | 0.0 |
|  |  |  |  | LNU225 | 0.661 | 0.108 | 22.2 |
|  |  |  |  | LNU262 | 0.587 | 0.477 | 8.5 |
|  |  |  |  | LNU266 | 0.606 | 0.382 | 12.1 |
|  |  |  |  | LNU29 | 0.553 | 0.840 | 2.3 |
|  |  |  |  | LNU51 | 0.557 | 0.826 | 3.0 |
|  |  |  |  | LNU60 | 0.779 | 0.008 | 44.1 |
|  |  |  |  | CONT. | 0.454 | — | 0.0 |
|  |  |  |  | LNU171 | 0.767 | 0.04 | 70.0 |
|  |  |  |  | LNU222_H6 | 0.4711 | 0.88 | 4.0 |

Table 68.
"CONT."—Control;
"Ave."—Average;
"% Incr." = % increment.

TABLE 69

Genes showing improved plant growth rate at nitrogen deficient conditions (T1 generation)

| Gene Name | Event # | RGR Of Roots Length Average | p-value | % increment |
|---|---|---|---|---|
| CONTROL | — | 0.477 | — | 0.0 |
| LNU121 | 27711 | 0.512 | 0.373 | 7.2 |
| LNU154 | 14601 | 0.501 | 0.551 | 5.0 |
| LNU68 | 14031 | 0.498 | 0.586 | 4.3 |
| CONTROL | — | 0.542 | — | 0.0 |
| LNU127 | 27601 | 0.545 | 0.939 | 0.6 |
| LNU217 | 28231 | 0.576 | 0.469 | 6.3 |
| LNU265 | 30261 | 0.548 | 0.886 | 1.2 |
| LNU275 | 30341 | 0.645 | 0.030 | 19.0 |
| LNU57 | 27851 | 0.595 | 0.226 | 9.8 |
| LNU58 | 27671 | 0.803 | 0.000 | 48.1 |
| LNU83 | 27681 | 0.626 | 0.073 | 15.5 |
| CONTROL | — | 0.462 | — | 0.0 |
| LNU176 | 29501 | 0.472 | 0.815 | 2.2 |
| LNU214 | 29521 | 0.463 | 0.960 | 0.3 |
| LNU223 | 29561 | 0.483 | 0.503 | 4.6 |
| LNU233 | 29461 | 0.486 | 0.538 | 5.2 |
| LNU245 | 29831 | 0.462 | 0.996 | 0.0 |

TABLE 69-continued

Genes showing improved plant growth rate at nitrogen deficient conditions (T1 generation)

| | | RGR Of Roots Length | | |
|---|---|---|---|---|
| Gene Name | Event # | Average | p-value | % increment |
| LNU247 | 29571 | 0.521 | 0.147 | 12.9 |
| LNU289 | 29741 | 0.485 | 0.579 | 5.1 |
| LNU70 | 29591 | 0.487 | 0.460 | 5.6 |
| LNU85 | 29551 | 0.504 | 0.380 | 9.2 |
| CONTROL | — | 0.551 | — | 0.0 |
| LNU60 | 29991 | 0.590 | 0.365 | 7.1 |

Table 69.

The genes listed in Tables 70, 71, 72 and 73 improved plant NUE when grown at standard nitrogen concentration levels. These genes produced larger plant biomass (plant fresh and dry weight and leaf area) when grown under standard nitrogen growth conditions, compared to control plants. Larger plant biomass under this growth conditions indicates the high ability of the plant to better metabolize the nitrogen present in the medium. The genes were cloned under the regulation of a constitutive promoter (At6669) or root preferred promoter (RootP). The evaluation of each gene was performed by testing the performance of different number of events. Some of the genes were evaluated in more than one tissue culture assay and the results obtained where positive as well. Event with p-value <0.1 was considered statistically significant

TABLE 70

Genes showing improved plant performance at standard nitrogen growth conditions (T2 generation)

| | | Plant Biomass Fresh weight [gr.] | | | | | Plant Biomass Dry Weight [gr.] | | |
|---|---|---|---|---|---|---|---|---|---|
| Gene Name | Event # | Ave. | p-value | % incr. | Gene Name | Event # | Ave. | p-value | % incr. |
| CONT. | — | 0.130 | — | 0.0 | CONT. | — | 0.005 | — | 0.0 |
| LNU100 | 14474.3 | 0.199 | 0.219 | 52.9 | LNU100 | 14474.3 | 0.010 | 0.123 | 102.5 |
| LNU100 | 14474.4 | 0.137 | 0.727 | 5.3 | LNU100 | 14474.4 | 0.006 | 0.378 | 23.5 |
| LNU104 | 25034.1 | 0.184 | 0.296 | 41.6 | LNU104 | 25033.3 | 0.007 | 0.224 | 39.5 |
| LNU104 | 25033.3 | 0.170 | 0.199 | 30.9 | LNU213 | 24654.4 | 0.011 | 0.107 | 108.3 |
| LNU213 | 24654.4 | 0.228 | 0.080 | 75.1 | LNU213 | 24653.2 | 0.011 | 0.003 | 104.9 |
| LNU213 | 24653.2 | 0.212 | 0.012 | 62.6 | LNU213 | 24651.1 | 0.007 | 0.073 | 36.1 |
| LNU213 | 24651.1 | 0.160 | 0.114 | 22.6 | LNU218 | 24783.2 | 0.012 | 0.100 | 124.8 |
| LNU218 | 24783.2 | 0.239 | 0.098 | 84.1 | LNU218 | 24781.7 | 0.007 | 0.089 | 28.4 |
| LNU218 | 24781.7 | 0.156 | 0.144 | 19.7 | LNU4 | 25134.1 | 0.007 | 0.070 | 38.6 |
| LNU4 | 25134.1 | 0.165 | 0.065 | 26.5 | LNU48 | 24803.2 | 0.008 | 0.139 | 47.3 |
| LNU48 | 24803.2 | 0.177 | 0.060 | 35.7 | LNU48 | 24802.2 | 0.007 | 0.102 | 32.3 |
| LNU48 | 24802.2 | 0.155 | 0.420 | 19.2 | LNU48 | 24804.4 | 0.006 | 0.382 | 18.2 |
| LNU48 | 24804.4 | 0.138 | 0.716 | 5.7 | LNU8 | 25063.1 | 0.008 | 0.045 | 63.3 |
| LNU8 | 25063.1 | 0.192 | 0.136 | 47.6 | LNU8 | 25062.2 | 0.007 | 0.183 | 44.9 |
| LNU8 | 25062.2 | 0.173 | 0.236 | 32.8 | LNU8 | 25063.6 | 0.006 | 0.207 | 19.2 |
| LNU8 | 25063.6 | 0.140 | 0.548 | 7.6 | LNU94 | 24833.3 | 0.006 | 0.234 | 19.7 |
| CONT. | — | 0.115 | — | 0.0 | LNU94 | 24834.1 | 0.006 | 0.607 | 11.4 |
| LNU1 | 24681.3 | 0.162 | 0.123 | 40.8 | CONT. | — | 0.006 | — | 0.0 |
| LNU1 | 24682.2 | 0.125 | 0.542 | 9.1 | LNU1 | 24681.3 | 0.009 | 0.141 | 44.4 |
| LNU1 | 24684.1 | 0.122 | 0.376 | 6.3 | LNU1 | 24682.2 | 0.007 | 0.548 | 12.0 |
| LNU1 | 24682.1 | 0.121 | 0.387 | 5.3 | LNU133 | 24741.1 | 0.015 | 0.046 | 142.4 |
| LNU133 | 24741.1 | 0.264 | 0.035 | 130.1 | LNU133 | 24744.3 | 0.014 | 0.033 | 120.8 |
| LNU133 | 24744.3 | 0.238 | 0.054 | 107.4 | LNU175 | 24732.1 | 0.011 | 0.086 | 68.4 |
| LNU175 | 24734.4 | 0.179 | 0.058 | 55.6 | LNU175 | 24734.4 | 0.010 | 0.067 | 52.4 |
| LNU175 | 24732.1 | 0.173 | 0.101 | 50.8 | LNU175 | 24732.4 | 0.008 | 0.264 | 33.2 |
| LNU175 | 24732.4 | 0.155 | 0.181 | 35.2 | LNU175 | 24731.2 | 0.007 | 0.367 | 16.0 |
| LNU175 | 24731.2 | 0.145 | 0.100 | 26.7 | LNU178 | 14614.5 | 0.009 | 0.121 | 39.2 |
| LNU178 | 14614.5 | 0.153 | 0.109 | 32.8 | LNU178 | 14611.5 | 0.009 | 0.060 | 37.2 |
| LNU178 | 14611.5 | 0.148 | 0.091 | 28.6 | LNU178 | 14611.1 | 0.007 | 0.505 | 10.0 |
| LNU178 | 14611.1 | 0.134 | 0.313 | 16.7 | LNU215 | 24664.3 | 0.013 | 0.002 | 104.8 |
| LNU215 | 24664.3 | 0.231 | 0.004 | 100.8 | LNU215 | 24661.4 | 0.007 | 0.498 | 13.6 |
| LNU215 | 24661.4 | 0.136 | 0.260 | 18.1 | LNU24 | 24973.1 | 0.010 | 0.156 | 67.2 |
| LNU24 | 24971.4 | 0.178 | 0.025 | 55.3 | LNU24 | 24971.4 | 0.009 | 0.034 | 40.8 |
| LNU24 | 24973.1 | 0.172 | 0.126 | 50.1 | LNU24 | 24971.2 | 0.007 | 0.253 | 19.2 |
| LNU24 | 24971.2 | 0.135 | 0.129 | 17.7 | LNU6 | 24992.3 | 0.016 | 0.075 | 150.4 |
| LNU6 | 24992.3 | 0.308 | 0.086 | 168.0 | LNU82 | 24823.1 | 0.010 | 0.231 | 63.2 |
| LNU6 | 24993.3 | 0.135 | 0.561 | 17.3 | LNU9 | 25001.3 | 0.011 | 0.004 | 81.6 |
| LNU6 | 24994.1 | 0.123 | 0.466 | 7.1 | LNU9 | 25001.1 | 0.007 | 0.657 | 5.6 |
| LNU6 | 24994.5 | 0.118 | 0.679 | 3.0 | CONT. | — | 0.004 | — | 0.0 |
| LNU82 | 24823.1 | 0.198 | 0.212 | 72.8 | LNU120 | 2546.37 | 0.007 | 0.030 | 71.6 |
| LNU9 | 25001.3 | 0.201 | 0.011 | 75.4 | LNU120 | 25463.3 | 0.005 | 0.152 | 29.7 |
| LNU9 | 25001.1 | 0.128 | 0.321 | 11.2 | LNU120 | 25463.6 | 0.005 | 0.070 | 22.6 |
| CONT. | — | 0.090 | — | 0.0 | LNU124 | 14501.7 | 0.006 | 0.008 | 65.2 |
| LNU120 | 25463.7 | 0.144 | 0.021 | 60.4 | LNU124 | 14501.1 | 0.005 | 0.070 | 35.5 |
| LNU120 | 25463.3 | 0.126 | 0.003 | 40.2 | LNU124 | 14502.7 | 0.004 | 0.578 | 5.8 |
| LNU120 | 25463.6 | 0.120 | 0.279 | 33.0 | LNU132 | 14102.7 | 0.005 | 0.136 | 34.2 |
| LNU120 | 25464.1 | 0.095 | 0.707 | 5.6 | LNU132 | 14101.9 | 0.004 | 0.507 | 12.9 |
| LNU124 | 14501.7 | 0.151 | 0.006 | 68.2 | LNU132 | 14102.9 | 0.004 | 0.330 | 9.0 |
| LNU124 | 14501.1 | 0.132 | 0.065 | 47.0 | LNU132 | 14102.6 | 0.004 | 0.650 | 5.2 |
| LNU124 | 14502.1 | 0.117 | 0.342 | 30.1 | LNU140 | 14112.7 | 0.007 | 0.192 | 72.3 |

TABLE 70-continued

Genes showing improved plant performance at standard nitrogen growth conditions (T2 generation)

| | | Plant Biomass Fresh weight [gr.] | | | | | Plant Biomass Dry Weight [gr.] | | |
|---|---|---|---|---|---|---|---|---|---|
| Gene Name | Event # | Ave. | p-value | % incr. | Gene Name | Event # | Ave. | p-value | % incr. |
| LNU124 | 14502.7 | 0.097 | 0.521 | 7.9 | LNU140 | 14111.6 | 0.005 | 0.301 | 20.0 |
| LNU132 | 14102.7 | 0.134 | 0.043 | 48.6 | LNU180 | 24724.3 | 0.009 | 0.010 | 124.5 |
| LNU132 | 14102.9 | 0.109 | 0.119 | 20.7 | LNU180 | 24723.3 | 0.006 | 0.280 | 47.7 |
| LNU132 | 14101.9 | 0.106 | 0.158 | 18.3 | LNU196 | 25534.1 | 0.006 | 0.024 | 63.9 |
| LNU140 | 14112.7 | 0.142 | 0.291 | 58.4 | LNU196 | 25533.3 | 0.005 | 0.509 | 18.7 |
| LNU140 | 14111.6 | 0.117 | 0.190 | 29.7 | LNU196 | 25533.1 | 0.005 | 0.110 | 16.8 |
| LNU140 | 14114.8 | 0.097 | 0.690 | 8.4 | LNU20 | 24933.2 | 0.005 | 0.323 | 34.8 |
| LNU180 | 24724.3 | 0.172 | 0.000 | 91.7 | LNU36 | 25562.3 | 0.006 | 0.034 | 47.7 |
| LNU180 | 24723.3 | 0.148 | 0.172 | 64.5 | LNU36 | 25562.4 | 0.005 | 0.040 | 31.0 |
| LNU180 | 24721.4 | 0.100 | 0.586 | 11.3 | LNU36 | 25561.2 | 0.004 | 0.628 | 3.9 |
| LNU180 | 24724.1 | 0.096 | 0.736 | 7.2 | LNU71 | 25853.4 | 0.007 | 0.004 | 92.9 |
| LNU196 | 25534.1 | 0.141 | 0.012 | 56.4 | LNU71 | 25852.4 | 0.005 | 0.206 | 23.9 |
| LNU196 | 25533.3 | 0.114 | 0.448 | 27.2 | CONT. | — | 0.004 | — | 0.0 |
| LNU196 | 25533.1 | 0.102 | 0.223 | 13.9 | LNU1 | 24681.3 | 0.008 | 0.000 | 108.6 |
| LNU20 | 24933.2 | 0.132 | 0.237 | 46.5 | LNU1 | 24683.2 | 0.004 | 0.244 | 15.5 |
| LNU20 | 24933.1 | 0.094 | 0.794 | 4.7 | LNU110 | 24953.3 | 0.005 | 0.197 | 39.9 |
| LNU36 | 25562.3 | 0.134 | 0.001 | 48.8 | LNU110 | 24952.3 | 0.005 | 0.321 | 35.9 |
| LNU36 | 25562.4 | 0.130 | 0.212 | 44.1 | LNU175 | 24732.2 | 0.009 | 0.151 | 132.3 |
| LNU36 | 25561.2 | 0.095 | 0.689 | 5.1 | LNU175 | 24733.4 | 0.007 | 0.054 | 98.4 |
| LNU71 | 25853.4 | 0.165 | 0.001 | 83.4 | LNU175 | 24732.1 | 0.004 | 0.537 | 13.5 |
| LNU71 | 25852.4 | 0.147 | 0.020 | 63.7 | LNU175 | 24734.4 | 0.004 | 0.573 | 8.0 |
| CONT. | — | 0.125 | — | 0.0 | LNU19 | 25151.1 | 0.008 | 0.031 | 107.2 |
| LNU1 | 24681.3 | 0.180 | 0.092 | 44.5 | LNU19 | 25153.3 | 0.006 | 0.059 | 52.9 |
| LNU110 | 24952.3 | 0.148 | 0.419 | 18.6 | LNU19 | 25153.1 | 0.004 | 0.328 | 10.1 |
| LNU175 | 24732.2 | 0.199 | 0.237 | 59.6 | LNU215 | 24663.4 | 0.013 | 0.209 | 259.4 |
| LNU175 | 24733.4 | 0.177 | 0.071 | 41.9 | LNU215 | 24663.1 | 0.007 | 0.365 | 95.0 |
| LNU19 | 25151.1 | 0.185 | 0.230 | 48.6 | LNU215 | 24663.3 | 0.005 | 0.123 | 30.4 |
| LNU215 | 24663.4 | 0.203 | 0.008 | 63.3 | LNU215 | 24664.2 | 0.004 | 0.411 | 17.5 |
| LNU215 | 24663.3 | 0.134 | 0.681 | 7.9 | LNU27 | 24873.1 | 0.009 | 0.000 | 131.0 |
| LNU27 | 24873.1 | 0.210 | 0.005 | 68.6 | LNU27 | 24873.4 | 0.005 | 0.420 | 29.1 |
| LNU27 | 24873.4 | 0.152 | 0.570 | 21.9 | LNU44 | 24924.2 | 0.021 | 0.318 | 464.5 |
| LNU44 | 24924.3 | 0.207 | 0.068 | 66.3 | LNU44 | 24924.3 | 0.009 | 0.095 | 140.5 |
| LNU44 | 24923.1 | 0.150 | 0.444 | 20.2 | LNU44 | 24923.1 | 0.006 | 0.185 | 69.2 |
| LNU44 | 24924.2 | 0.138 | 0.646 | 10.6 | LNU44 | 24922.3 | 0.005 | 0.387 | 26.4 |
| LNU54 | 24903.5 | 0.191 | 0.146 | 53.5 | LNU54 | 24903.5 | 0.008 | 0.035 | 107.9 |
| LNU54 | 24903.3 | 0.145 | 0.354 | 16.1 | LNU54 | 24903.3 | 0.006 | 0.010 | 58.3 |
| LNU54 | 24901.2 | 0.138 | 0.645 | 11.0 | LNU79 | 24881.1 | 0.008 | 0.016 | 119.4 |
| LNU79 | 24884.4 | 0.212 | 0.005 | 70.5 | LNU79 | 24884.4 | 0.008 | 0.062 | 112.6 |
| LNU79 | 24881.1 | 0.177 | 0.036 | 41.9 | LNU79 | 24884.3 | 0.005 | 0.166 | 47.4 |
| LNU79 | 24884.3 | 0.167 | 0.173 | 33.8 | LNU79 | 24882.2 | 0.004 | 0.169 | 18.2 |
| CONT. | — | 0.132 | — | 0.0 | CONT. | — | 0.006 | — | 0.0 |
| LNU109 | 24891.2 | 0.198 | 0.021 | 49.7 | LNU109 | 24891.2 | 0.010 | 0.003 | 69.3 |
| LNU109 | 24892.6 | 0.180 | 0.074 | 36.2 | LNU109 | 24892.6 | 0.009 | 0.113 | 41.8 |
| LNU109 | 24891.5 | 0.165 | 0.048 | 25.0 | LNU109 | 24891.5 | 0.009 | 0.109 | 39.3 |
| LNU109 | 24892.5 | 0.160 | 0.367 | 20.9 | LNU109 | 24892.5 | 0.008 | 0.290 | 26.2 |
| LNU110 | 24952.1 | 0.241 | 0.008 | 81.9 | LNU110 | 24952.1 | 0.012 | 0.000 | 100.4 |
| LNU110 | 24953.2 | 0.208 | 0.030 | 57.3 | LNU110 | 24954.1 | 0.010 | 0.019 | 66.4 |
| LNU110 | 24954.1 | 0.194 | 0.011 | 46.8 | LNU110 | 24953.2 | 0.010 | 0.013 | 63.1 |
| LNU110 | 24952.3 | 0.183 | 0.046 | 38.1 | LNU110 | 24952.3 | 0.009 | 0.061 | 54.5 |
| LNU110 | 24954.3 | 0.142 | 0.445 | 7.7 | LNU110 | 24954.3 | 0.008 | 0.030 | 25.8 |
| LNU133 | 24741.2 | 0.249 | 0.014 | 88.2 | LNU133 | 24741.2 | 0.014 | 0.019 | 127.0 |
| LNU133 | 24744.3 | 0.232 | 0.011 | 75.6 | LNU133 | 24741.1 | 0.011 | 0.004 | 82.4 |
| LNU133 | 24741.1 | 0.229 | 0.010 | 73.5 | LNU133 | 24744.3 | 0.011 | 0.033 | 76.2 |
| LNU133 | 24742.2 | 0.199 | 0.123 | 50.5 | LNU133 | 24744.2 | 0.010 | 0.015 | 68.0 |
| LNU133 | 24744.2 | 0.186 | 0.055 | 40.8 | LNU133 | 24742.2 | 0.010 | 0.019 | 63.1 |
| LNU19 | 25151.1 | 0.253 | 0.026 | 91.0 | LNU19 | 25151.1 | 0.012 | 0.020 | 104.5 |
| LNU19 | 25153.3 | 0.166 | 0.349 | 25.3 | LNU19 | 25153.3 | 0.009 | 0.158 | 43.4 |
| LNU27 | 24873.4 | 0.293 | 0.029 | 121.4 | LNU19 | 25151.11 | 0.006 | 0.617 | 3.3 |
| LNU27 | 24871.4 | 0.159 | 0.476 | 20.6 | LNU27 | 24873.4 | 0.015 | 0.032 | 150.8 |
| LNU44 | 24922.3 | 0.218 | 0.021 | 64.5 | LNU27 | 24871.4 | 0.007 | 0.420 | 20.1 |
| LNU44 | 24923.1 | 0.153 | 0.200 | 15.6 | LNU27 | 24873.1 | 0.006 | 0.737 | 3.7 |
| LNU44 | 24924.3 | 0.151 | 0.470 | 14.4 | LNU44 | 24922.3 | 0.011 | 0.009 | 84.0 |
| LNU44 | 24923.3 | 0.139 | 0.676 | 5.3 | LNU44 | 24923.1 | 0.008 | 0.058 | 27.9 |
| LNU54 | 24903.5 | 0.286 | 0.027 | 116.3 | LNU44 | 24924.3 | 0.008 | 0.214 | 27.0 |
| LNU54 | 24902.4 | 0.221 | 0.294 | 67.4 | LNU54 | 24903.5 | 0.015 | 0.022 | 142.6 |
| LNU54 | 24901.2 | 0.159 | 0.479 | 19.9 | LNU54 | 24902.4 | 0.011 | 0.184 | 83.6 |
| LNU6 | 24992.3 | 0.240 | 0.066 | 81.6 | LNU54 | 24901.2 | 0.009 | 0.194 | 43.9 |
| LNU6 | 24994.5 | 0.240 | 0.121 | 81.6 | LNU6 | 24992.3 | 0.012 | 0.082 | 91.4 |
| LNU6 | 24994.1 | 0.166 | 0.219 | 25.6 | LNU6 | 24994.5 | 0.012 | 0.172 | 90.2 |
| LNU79 | 24881.1 | 0.255 | 0.038 | 92.8 | LNU6 | 24994.1 | 0.009 | 0.167 | 40.2 |
| LNU79 | 24882.2 | 0.232 | 0.026 | 75.6 | LNU6 | 24994.2 | 0.008 | 0.345 | 24.6 |

TABLE 70-continued

Genes showing improved plant performance at standard nitrogen growth conditions (T2 generation)

| Gene Name | Event # | Plant Biomass Fresh weight [gr.] Ave. | p-value | % incr. | Gene Name | Event # | Plant Biomass Dry Weight [gr.] Ave. | p-value | % incr. |
|---|---|---|---|---|---|---|---|---|---|
| LNU79 | 24884.4 | 0.226 | 0.163 | 70.7 | LNU79 | 24881.1 | 0.012 | 0.007 | 99.6 |
| LNU79 | 24883.2 | 0.198 | 0.041 | 49.9 | LNU79 | 24882.2 | 0.012 | 0.031 | 94.7 |
| LNU79 | 24884.3 | 0.190 | 0.074 | 43.8 | LNU79 | 24883.2 | 0.011 | 0.011 | 88.1 |
| CONT. | — | 0.119 | — | 0.0 | LNU79 | 24884.4 | 0.010 | 0.083 | 62.7 |
| LNU109 | 24892.8 | 0.195 | 0.058 | 63.2 | LNU79 | 24884.3 | 0.010 | 0.028 | 61.1 |
| LNU109 | 24891.5 | 0.188 | 0.135 | 57.1 | CONT. | — | 0.005 | — | 0.0 |
| LNU109 | 24891.2 | 0.139 | 0.570 | 16.6 | LNU109 | 24892.8 | 0.010 | 0.063 | 89.5 |
| LNU154 | 14604.7 | 0.162 | 0.247 | 35.9 | LNU109 | 24891.5 | 0.008 | 0.243 | 50.7 |
| LNU154 | 14604.6 | 0.131 | 0.719 | 9.4 | LNU109 | 24891.2 | 0.007 | 0.486 | 26.5 |
| LNU196 | 25532.2 | 0.223 | 0.133 | 86.8 | LNU143 | 25975.2 | 0.007 | 0.556 | 21.0 |
| LNU196 | 25534.1 | 0.129 | 0.790 | 7.6 | LNU154 | 14604.7 | 0.009 | 0.192 | 56.2 |
| LNU207 | 24642.5 | 0.226 | 0.071 | 89.3 | LNU196 | 25532.2 | 0.011 | 0.119 | 108.7 |
| LNU52 | 25723.2 | 0.168 | 0.216 | 40.9 | LNU196 | 25534.1 | 0.006 | 0.650 | 16.9 |
| LNU52 | 25721.4 | 0.128 | 0.799 | 7.2 | LNU207 | 24642.5 | 0.010 | 0.121 | 82.6 |
| CONT. | — | 0.128 | — | 0.0 | LNU50 | 26025.4 | 0.006 | 0.785 | 11.4 |
| LNU154 | 14601.6 | 0.171 | 0.487 | 33.7 | LNU52 | 25723.2 | 0.008 | 0.335 | 38.8 |
| LNU207 | 24642.5 | 0.220 | 0.093 | 72.5 | LNU52 | 25721.3 | 0.006 | 0.723 | 16.9 |
| LNU207 | 24642.4 | 0.181 | 0.203 | 41.6 | CONT. | — | 0.006 | — | 0.0 |
| LNU211 | 24771.1 | 0.200 | 0.078 | 56.5 | LNU154 | 14601.6 | 0.009 | 0.459 | 48.4 |
| LNU52 | 25721.4 | 0.221 | 0.057 | 73.3 | LNU207 | 24642.5 | 0.011 | 0.016 | 69.6 |
| LNU52 | 25721.1 | 0.172 | 0.133 | 34.9 | LNU207 | 24642.4 | 0.009 | 0.061 | 41.8 |
| LNU52 | 25723.1 | 0.154 | 0.093 | 20.9 | LNU211 | 24771.1 | 0.011 | 0.128 | 64.9 |
| LNU69 | 14571.1 | 0.224 | 0.035 | 75.6 | LNU52 | 25721.4 | 0.011 | 0.050 | 75.5 |
| LNU69 | 14572.8 | 0.141 | 0.441 | 10.5 | LNU52 | 25721.1 | 0.008 | 0.231 | 33.1 |
| CONT. | — | 0.120 | — | 0.0 | LNU52 | 25723.1 | 0.007 | 0.628 | 5.6 |
| LNU150 | 24843.9 | 0.179 | 0.091 | 49.0 | LNU69 | 14571.1 | 0.010 | 0.057 | 49.2 |
| LNU150 | 24841.9 | 0.178 | 0.015 | 47.8 | CONT. | — | 0.005 | — | 0.0 |
| LNU150 | 24843.5 | 0.167 | 0.002 | 38.6 | LNU150 | 24841.9 | 0.009 | 0.021 | 64.5 |
| LNU150 | 24842.9 | 0.143 | 0.103 | 18.6 | LNU150 | 24843.5 | 0.008 | 0.003 | 52.8 |
| LNU179 | 24632.5 | 0.127 | 0.762 | 5.6 | LNU150 | 24843.9 | 0.007 | 0.017 | 38.0 |
| LNU179 | 24631.7 | 0.126 | 0.771 | 4.9 | LNU150 | 24842.9 | 0.007 | 0.112 | 30.5 |
| LNU232 | 26003.7 | 0.130 | 0.584 | 8.4 | LNU232 | 26003.7 | 0.007 | 0.248 | 23.6 |
| LNU232 | 26001.5 | 0.130 | 0.608 | 7.8 | LNU232 | 26001.5 | 0.006 | 0.712 | 4.5 |
| LNU242 | 25474.1 | 0.167 | 0.058 | 38.9 | LNU235 | 26184.4 | 0.006 | 0.747 | 4.5 |
| LNU242 | 25473.1 | 0.142 | 0.301 | 17.8 | LNU242 | 25474.1 | 0.008 | 0.167 | 43.1 |
| LNU76 | 26421.2 | 0.164 | 0.265 | 36.3 | LNU242 | 25473.1 | 0.007 | 0.191 | 27.3 |
| LNU76 | 26421.1 | 0.158 | 0.389 | 31.9 | LNU76 | 26421.1 | 0.008 | 0.060 | 51.5 |
| LNU76 | 26422.2 | 0.133 | 0.607 | 11.0 | LNU76 | 26421.2 | 0.008 | 0.154 | 40.3 |
| LNU95 | 13985.11 | 0.186 | 0.040 | 55.1 | LNU76 | 26422.2 | 0.007 | 0.226 | 26.4 |
| LNU95 | 13985.15 | 0.139 | 0.296 | 15.8 | LNU76 | 26425.1 | 0.006 | 0.700 | 4.5 |
| LNU95 | 13985.16 | 0.136 | 0.281 | 12.9 | LNU95 | 13985.11 | 0.009 | 0.069 | 76.1 |
| LNU95 | 13985.12 | 0.129 | 0.576 | 7.3 | LNU95 | 13985.15 | 0.008 | 0.146 | 39.8 |
| LNU95 | 13985.19 | 0.128 | 0.702 | 6.8 | LNU95 | 13985.19 | 0.006 | 0.641 | 12.9 |
| CONT. | — | 0.129 | — | 0.0 | LNU95 | 13985.16 | 0.006 | 0.466 | 10.1 |
| LNU118 | 14013.8 | 0.227 | 0.027 | 75.7 | CONT. | — | 0.006 | — | 0.0 |
| LNU118 | 14013.6 | 0.219 | 0.057 | 69.9 | LNU118 | 14013.8 | 0.011 | 0.008 | 80.1 |
| LNU118 | 14012.12 | 0.187 | 0.147 | 45.1 | LNU118 | 14013.6 | 0.010 | 0.015 | 67.7 |
| LNU118 | 14012.15 | 0.179 | 0.077 | 38.8 | LNU118 | 14012.12 | 0.010 | 0.060 | 55.3 |
| LNU118 | 14012.14 | 0.134 | 0.788 | 3.7 | LNU118 | 14012.15 | 0.009 | 0.147 | 38.8 |
| LNU150 | 24842.9 | 0.248 | 0.035 | 91.7 | LNU118 | 14012.14 | 0.008 | 0.152 | 20.9 |
| LNU150 | 24841.9 | 0.161 | 0.111 | 24.7 | LNU150 | 24842.9 | 0.012 | 0.066 | 89.8 |
| LNU150 | 24841.6 | 0.150 | 0.150 | 16.3 | LNU150 | 24841.9 | 0.008 | 0.019 | 30.8 |
| LNU150 | 24843.5 | 0.144 | 0.664 | 11.6 | LNU150 | 24843.5 | 0.008 | 0.389 | 20.4 |
| LNU179 | 24632.7 | 0.186 | 0.022 | 44.1 | LNU150 | 24841.6 | 0.007 | 0.632 | 5.9 |
| LNU179 | 24631.7 | 0.173 | 0.184 | 33.8 | LNU179 | 24632.7 | 0.011 | 0.015 | 73.3 |
| LNU179 | 24631.9 | 0.137 | 0.716 | 6.3 | LNU179 | 24631.7 | 0.008 | 0.235 | 27.6 |
| LNU232 | 26001.5 | 0.187 | 0.033 | 44.6 | LNU232 | 26001.5 | 0.009 | 0.014 | 41.2 |
| LNU232 | 26003.3 | 0.147 | 0.238 | 13.5 | LNU232 | 26003.3 | 0.007 | 0.469 | 9.1 |
| LNU232 | 26003.6 | 0.136 | 0.661 | 5.6 | LNU232 | 26003.3 | 0.007 | 0.439 | 7.5 |
| LNU235 | 26184.4 | 0.278 | 0.001 | 115.4 | LNU235 | 26184.4 | 0.014 | 0.006 | 124.7 |
| LNU235 | 26184.2 | 0.243 | 0.004 | 88.4 | LNU235 | 26185.2 | 0.011 | 0.000 | 77.7 |
| LNU235 | 26185.2 | 0.226 | 0.017 | 75.1 | LNU235 | 26184.2 | 0.011 | 0.000 | 72.5 |
| LNU235 | 26182.1 | 0.137 | 0.751 | 6.0 | LNU235 | 26182.1 | 0.007 | 0.064 | 19.6 |
| LNU242 | 25474.1 | 0.158 | 0.238 | 22.6 | LNU242 | 25474.1 | 0.007 | 0.176 | 13.5 |
| LNU288 | 14563.9 | 0.274 | 0.006 | 112.2 | LNU288 | 14563.9 | 0.016 | 0.002 | 152.4 |
| LNU288 | 14562.1 | 0.196 | 0.026 | 51.7 | LNU288 | 14562.1 | 0.010 | 0.001 | 62.9 |
| LNU288 | 14564.9 | 0.172 | 0.261 | 33.5 | LNU288 | 14564.9 | 0.008 | 0.366 | 28.4 |
| LNU288 | 14563.6 | 0.144 | 0.420 | 11.2 | LNU288 | 14562.7 | 0.007 | 0.580 | 20.0 |
| LNU288 | 14562.7 | 0.143 | 0.684 | 10.5 | LNU288 | 14563.6 | 0.007 | 0.207 | 15.9 |
| LNU76 | 26421.2 | 0.175 | 0.261 | 35.2 | LNU76 | 26421.2 | 0.008 | 0.238 | 30.8 |
| LNU76 | 26422.2 | 0.153 | 0.210 | 18.4 | LNU76 | 26422.2 | 0.008 | 0.325 | 22.0 |

TABLE 70-continued

Genes showing improved plant performance at standard nitrogen growth conditions (T2 generation)

| Gene Name | Event # | Plant Biomass Fresh weight [gr.] | | | Gene Name | Event # | Plant Biomass Dry Weight [gr.] | | |
|---|---|---|---|---|---|---|---|---|---|
| | | Ave. | p-value | % incr. | | | Ave. | p-value | % incr. |
| LNU76 | 26423.1 | 0.142 | 0.444 | 9.8 | LNU76 | 26423.1 | 0.006 | 0.747 | 3.9 |
| LNU95 | 13985.16 | 0.265 | 0.008 | 105.4 | LNU95 | 13985.16 | 0.014 | 0.015 | 117.5 |
| LNU95 | 13985.12 | 0.198 | 0.016 | 53.2 | LNU95 | 13985.12 | 0.010 | 0.052 | 67.7 |
| LNU95 | 13985.15 | 0.183 | 0.016 | 41.3 | LNU95 | 13985.15 | 0.010 | 0.024 | 52.5 |
| CONT. | — | 0.144 | — | 0.0 | LNU95 | 13985.19 | 0.007 | 0.340 | 12.7 |
| LNU101 | 27632.1 | 0.177 | 0.162 | 23.0 | CONT. | — | 0.007 | — | 0.0 |
| LNU101 | 27635.1 | 0.159 | 0.359 | 10.4 | LNU101 | 27635.1 | 0.008 | 0.360 | 9.9 |
| LNU128 | 26515.3 | 0.181 | 0.160 | 26.1 | LNU101 | 27632.1 | 0.007 | 0.800 | 4.2 |
| LNU128 | 26515.2 | 0.161 | 0.642 | 12.0 | LNU128 | 26515.3 | 0.010 | 0.119 | 39.9 |
| LNU192 | 28312.2 | 0.164 | 0.707 | 13.7 | LNU128 | 26515.2 | 0.009 | 0.223 | 34.5 |
| LNU192 | 28315.2 | 0.163 | 0.168 | 13.6 | LNU192 | 28315.2 | 0.009 | 0.052 | 26.0 |
| LNU192 | 28313.2 | 0.151 | 0.614 | 5.1 | LNU192 | 28313.2 | 0.008 | 0.224 | 17.8 |
| LNU206 | 27621.1 | 0.160 | 0.460 | 11.0 | LNU206 | 27621.1 | 0.007 | 0.783 | 6.0 |
| LNU211 | 24771.1 | 0.250 | 0.046 | 73.5 | LNU211 | 24771.1 | 0.013 | 0.024 | 85.5 |
| LNU211 | 24773.1 | 0.182 | 0.452 | 26.2 | LNU211 | 24773.1 | 0.009 | 0.342 | 29.5 |
| LNU282 | 27563.3 | 0.180 | 0.036 | 24.8 | LNU282 | 27563.3 | 0.009 | 0.164 | 32.7 |
| LNU69 | 14571.1 | 0.199 | 0.150 | 38.2 | LNU69 | 14571.1 | 0.011 | 0.056 | 57.4 |
| LNU69 | 14573.5 | 0.148 | 0.713 | 2.7 | LNU69 | 14573.5 | 0.009 | 0.003 | 23.5 |
| LNU75 | 27572.1 | 0.185 | 0.012 | 28.7 | LNU69 | 14572.9 | 0.007 | 0.741 | 2.4 |
| LNU75 | 27572.2 | 0.162 | 0.409 | 12.3 | LNU75 | 27572.1 | 0.009 | 0.020 | 29.9 |
| CONT. | — | 0.122 | — | 0.0 | LNU75 | 27572.2 | 0.009 | 0.095 | 28.5 |
| LNU101 | 27632.5 | 0.184 | 0.165 | 50.5 | CONT. | — | 0.005 | — | 0.0 |
| LNU118 | 14013.6 | 0.199 | 0.023 | 62.9 | LNU101 | 27632.5 | 0.009 | 0.151 | 69.4 |
| LNU118 | 14012.15 | 0.167 | 0.037 | 36.3 | LNU118 | 14013.6 | 0.010 | 0.026 | 87.5 |
| LNU118 | 14013.9 | 0.147 | 0.325 | 20.0 | LNU118 | 14012.15 | 0.009 | 0.029 | 68.0 |
| LNU206 | 27621.2 | 0.203 | 0.058 | 66.4 | LNU118 | 14013.9 | 0.007 | 0.194 | 28.5 |
| LNU249 | 26153.1 | 0.221 | 0.052 | 81.0 | LNU118 | 14013.8 | 0.006 | 0.581 | 15.5 |
| LNU249 | 26152.4 | 0.137 | 0.578 | 12.4 | LNU118 | 14012.12 | 0.006 | 0.582 | 7.7 |
| LNU282 | 27563.1 | 0.199 | 0.029 | 63.0 | LNU206 | 27621.2 | 0.008 | 0.034 | 56.8 |
| LNU288 | 14563.9 | 0.247 | 0.017 | 101.9 | LNU206 | 27621.1 | 0.006 | 0.604 | 9.0 |
| LNU288 | 14564.8 | 0.225 | 0.000 | 84.2 | LNU249 | 26153.1 | 0.010 | 0.027 | 86.1 |
| LNU288 | 14562.7 | 0.175 | 0.197 | 43.4 | LNU249 | 26152.4 | 0.006 | 0.799 | 5.3 |
| LNU288 | 14562.9 | 0.167 | 0.185 | 36.6 | LNU282 | 27563.1 | 0.009 | 0.021 | 68.9 |
| LNU288 | 14563.6 | 0.149 | 0.366 | 21.9 | LNU288 | 14563.9 | 0.013 | 0.001 | 135.7 |
| LNU75 | 27571.4 | 0.216 | 0.002 | 76.8 | LNU288 | 14564.8 | 0.011 | 0.001 | 99.1 |
| LNU75 | 27572.3 | 0.199 | 0.029 | 62.9 | LNU288 | 14562.7 | 0.009 | 0.270 | 68.0 |
| LNU75 | 27571.2 | 0.166 | 0.041 | 35.9 | LNU288 | 14562.9 | 0.009 | 0.100 | 62.9 |
| LNU75 | 27572.2 | 0.165 | 0.174 | 35.3 | LNU288 | 14563.6 | 0.006 | 0.439 | 17.9 |
| CONT. | — | 0.130 | — | 0.0 | LNU75 | 27571.4 | 0.010 | 0.007 | 83.8 |
| LNU11 | 28204.1 | 0.145 | 0.596 | 11.2 | LNU75 | 27572.3 | 0.008 | 0.109 | 57.3 |
| LNU11 | 28204.3 | 0.144 | 0.455 | 11.0 | LNU75 | 27572.2 | 0.008 | 0.162 | 48.5 |
| LNU183 | 24863.12 | 0.180 | 0.020 | 38.4 | LNU75 | 27571.2 | 0.008 | 0.037 | 44.8 |
| LNU183 | 24863.1 | 0.149 | 0.202 | 14.3 | CONT. | — | 0.006 | — | 0.0 |
| LNU183 | 24865.1 | 0.135 | 0.742 | 4.1 | LNU11 | 28204.1 | 0.007 | 0.585 | 6.6 |
| LNU268 | 26044.2 | 0.180 | 0.339 | 38.8 | LNU11 | 28204.3 | 0.007 | 0.685 | 5.8 |
| CONT. | — | 0.110 | — | 0.0 | LNU183 | 24863.12 | 0.008 | 0.306 | 25.6 |
| LNU11 | 28205.1 | 0.150 | 0.052 | 35.7 | LNU268 | 26044.2 | 0.008 | 0.393 | 32.8 |
| LNU11 | 28205.2 | 0.150 | 0.041 | 35.6 | CONT. | — | 0.005 | — | 0.0 |
| LNU11 | 28204.1 | 0.127 | 0.270 | 14.9 | LNU11 | 28205.1 | 0.007 | 0.134 | 30.1 |
| LNU11 | 28203.2 | 0.114 | 0.769 | 3.7 | LNU11 | 28205.2 | 0.007 | 0.117 | 24.5 |
| LNU11 | 28204.3 | 0.114 | 0.794 | 3.1 | LNU11 | 28204.3 | 0.006 | 0.214 | 16.2 |
| LNU112 | 28212.3 | 0.132 | 0.202 | 19.4 | LNU11 | 28203.2 | 0.006 | 0.430 | 10.6 |
| LNU112 | 28212.4 | 0.126 | 0.280 | 14.2 | LNU112 | 28212.4 | 0.006 | 0.448 | 10.2 |
| LNU14 | 27821.3 | 0.164 | 0.101 | 49.0 | LNU14 | 27821.3 | 0.008 | 0.119 | 49.1 |
| LNU14 | 27821.4 | 0.116 | 0.729 | 4.8 | LNU183 | 24865.1 | 0.012 | 0.000 | 118.5 |
| LNU183 | 24863.1 | 0.263 | 0.045 | 138.7 | LNU183 | 24863.1 | 0.010 | 0.002 | 88.0 |
| LNU183 | 24865.1 | 0.254 | 0.000 | 130.0 | LNU183 | 24863.12 | 0.010 | 0.028 | 82.4 |
| LNU183 | 24864.6 | 0.208 | 0.017 | 88.8 | LNU183 | 24864.6 | 0.009 | 0.001 | 69.0 |
| LNU183 | 24863.12 | 0.199 | 0.004 | 80.5 | LNU191 | 28323.1 | 0.008 | 0.147 | 40.3 |
| LNU191 | 28324.2 | 0.154 | 0.034 | 39.9 | LNU191 | 28324.2 | 0.008 | 0.058 | 39.4 |
| LNU191 | 28325.4 | 0.152 | 0.015 | 38.2 | LNU191 | 28325.4 | 0.007 | 0.023 | 34.7 |
| LNU191 | 28323.1 | 0.145 | 0.229 | 31.4 | LNU191 | 28325.3 | 0.006 | 0.413 | 18.5 |
| LNU191 | 28325.3 | 0.136 | 0.156 | 23.3 | LNU201 | 28222.2 | 0.010 | 0.022 | 85.6 |
| LNU201 | 28222.2 | 0.216 | 0.005 | 96.0 | LNU201 | 28221.3 | 0.007 | 0.124 | 25.5 |
| LNU201 | 28223.3 | 0.149 | 0.123 | 35.0 | LNU201 | 28223.3 | 0.006 | 0.741 | 6.0 |
| LNU201 | 28221.3 | 0.135 | 0.148 | 22.5 | LNU268 | 26041.4 | 0.008 | 0.016 | 54.2 |
| LNU201 | 28222.3 | 0.118 | 0.612 | 7.3 | LNU268 | 26043.4 | 0.007 | 0.077 | 30.1 |
| LNU268 | 26043.4 | 0.173 | 0.019 | 56.8 | LNU268 | 26045.1 | 0.007 | 0.334 | 21.0 |
| LNU268 | 26041.4 | 0.168 | 0.039 | 52.0 | CONT. | — | 0.004 | — | 0.0 |
| LNU268 | 26045.1 | 0.144 | 0.074 | 30.2 | LNU107 | 14584.9 | 0.007 | 0.003 | 75.5 |
| LNU268 | 26041.6 | 0.126 | 0.498 | 14.6 | LNU107 | 14585.5 | 0.006 | 0.369 | 45.7 |

TABLE 70-continued

Genes showing improved plant performance at standard nitrogen growth conditions (T2 generation)

| Gene Name | Event # | Plant Biomass Fresh weight [gr.] | | | Gene Name | Event # | Plant Biomass Dry Weight [gr.] | | |
|---|---|---|---|---|---|---|---|---|---|
| | | Ave. | p-value | % incr. | | | Ave. | p-value | % incr. |
| LNU268 | 26044.2 | 0.119 | 0.679 | 7.6 | LNU107 | 14583.8 | 0.005 | 0.059 | 44.4 |
| CONT. | — | 0.079 | — | 0.0 | LNU107 | 14583.7 | 0.004 | 0.660 | 6.0 |
| LNU107 | 14584.9 | 0.159 | 0.047 | 100.2 | LNU116 | 14493.6 | 0.006 | 0.045 | 67.5 |
| LNU107 | 14585.5 | 0.143 | 0.183 | 79.7 | LNU116 | 14494.5 | 0.006 | 0.005 | 51.7 |
| LNU107 | 14583.8 | 0.120 | 0.064 | 50.6 | LNU116 | 14492.9 | 0.006 | 0.015 | 49.0 |
| LNU107 | 14583.7 | 0.094 | 0.281 | 18.2 | LNU116 | 14492.5 | 0.004 | 0.421 | 9.9 |
| LNU116 | 14493.6 | 0.201 | 0.106 | 152.6 | LNU12 | 27371.1 | 0.004 | 0.750 | 4.0 |
| LNU116 | 14494.5 | 0.125 | 0.020 | 56.9 | LNU12 | 27372.5 | 0.004 | 0.737 | 4.0 |
| LNU116 | 14492.9 | 0.124 | 0.067 | 55.8 | LNU121 | 25642.2 | 0.009 | 0.002 | 150.3 |
| LNU116 | 14492.5 | 0.110 | 0.012 | 38.2 | LNU121 | 27713.1 | 0.007 | 0.000 | 88.1 |
| LNU121 | 25642.2 | 0.193 | 0.010 | 142.4 | LNU121 | 27713.4 | 0.007 | 0.017 | 85.4 |
| LNU121 | 27713.1 | 0.168 | 0.002 | 111.8 | LNU121 | 27711.1 | 0.007 | 0.037 | 73.5 |
| LNU121 | 27711.1 | 0.153 | 0.000 | 92.5 | LNU126 | 25345.1 | 0.008 | 0.008 | 99.3 |
| LNU121 | 27713.4 | 0.148 | 0.002 | 86.8 | LNU126 | 25343.1 | 0.007 | 0.071 | 80.8 |
| LNU126 | 25345.1 | 0.163 | 0.006 | 104.8 | LNU126 | 25343.3 | 0.007 | 0.000 | 76.2 |
| LNU126 | 25343.3 | 0.154 | 0.020 | 93.9 | LNU126 | 25343.4 | 0.004 | 0.144 | 17.9 |
| LNU126 | 25343.1 | 0.137 | 0.103 | 72.4 | LNU158 | 27433.3 | 0.008 | 0.010 | 118.5 |
| LNU126 | 25343.4 | 0.101 | 0.120 | 27.4 | LNU158 | 27433.2 | 0.007 | 0.005 | 94.0 |
| LNU126 | 25341.1 | 0.093 | 0.472 | 17.1 | LNU158 | 27432.5 | 0.005 | 0.077 | 43.0 |
| LNU158 | 27433.3 | 0.193 | 0.007 | 142.3 | LNU177 | 24762.6 | 0.006 | 0.055 | 69.5 |
| LNU158 | 27433.2 | 0.145 | 0.000 | 82.0 | LNU177 | 24764.9 | 0.005 | 0.115 | 30.5 |
| LNU158 | 27432.5 | 0.129 | 0.011 | 62.9 | LNU177 | 24764.12 | 0.004 | 0.524 | 17.9 |
| LNU158 | 27434.1 | 0.087 | 0.526 | 9.9 | LNU177 | 24765.2 | 0.004 | 0.540 | 11.3 |
| LNU177 | 24762.6 | 0.142 | 0.012 | 79.1 | LNU182 | 25384.1 | 0.008 | 0.015 | 102.6 |
| LNU177 | 24764.9 | 0.127 | 0.003 | 59.2 | LNU182 | 25384.5 | 0.006 | 0.021 | 68.2 |
| LNU177 | 24764.12 | 0.103 | 0.280 | 29.4 | LNU182 | 27521.4 | 0.006 | 0.177 | 57.0 |
| LNU177 | 24765.2 | 0.098 | 0.191 | 23.3 | LNU182 | 25384.2 | 0.006 | 0.015 | 55.0 |
| LNU182 | 25384.2 | 0.177 | 0.063 | 122.7 | LNU2 | 25713.1 | 0.006 | 0.007 | 67.5 |
| LNU182 | 25384.1 | 0.156 | 0.022 | 96.2 | LNU2 | 27842.3 | 0.005 | 0.059 | 37.1 |
| LNU182 | 25384.5 | 0.155 | 0.047 | 95.5 | LNU2 | 27842.1 | 0.005 | 0.517 | 35.8 |
| LNU182 | 27521.4 | 0.136 | 0.225 | 71.0 | LNU225 | 25991.5 | 0.008 | 0.039 | 109.9 |
| LNU2 | 25713.1 | 0.140 | 0.006 | 75.9 | LNU225 | 25991.2 | 0.005 | 0.097 | 22.5 |
| LNU2 | 27842.1 | 0.127 | 0.182 | 60.4 | LNU225 | 25991.1 | 0.004 | 0.627 | 9.9 |
| LNU2 | 27842.3 | 0.103 | 0.058 | 29.2 | LNU225 | 25991.8 | 0.004 | 0.678 | 8.6 |
| LNU225 | 25991.5 | 0.169 | 0.013 | 112.9 | LNU239 | 26284.1 | 0.006 | 0.118 | 47.0 |
| LNU225 | 25991.8 | 0.134 | 0.177 | 68.3 | LNU239 | 26281.1 | 0.004 | 0.382 | 18.5 |
| LNU225 | 25991.3 | 0.115 | 0.264 | 45.3 | LNU57 | 27854.5 | 0.005 | 0.120 | 37.7 |
| LNU225 | 25991.2 | 0.105 | 0.071 | 31.6 | LNU57 | 27855.1 | 0.005 | 0.110 | 30.5 |
| LNU225 | 25991.1 | 0.097 | 0.169 | 22.6 | LNU57 | 27854.3 | 0.004 | 0.214 | 18.5 |
| LNU239 | 26284.1 | 0.111 | 0.154 | 39.4 | LNU83 | 27681.4 | 0.005 | 0.101 | 27.2 |
| LNU239 | 26283.2 | 0.104 | 0.056 | 30.3 | LNU83 | 27684.1 | 0.005 | 0.092 | 23.8 |
| LNU239 | 26281.1 | 0.102 | 0.034 | 28.0 | LNU83 | 27685.1 | 0.004 | 0.575 | 16.6 |
| LNU239 | 26284.2 | 0.086 | 0.431 | 8.2 | CONT. | — | 0.005 | — | 0.0 |
| LNU57 | 27854.5 | 0.151 | 0.015 | 90.2 | LNU107 | 14584.9 | 0.012 | 0.000 | 135.8 |
| LNU57 | 27854.3 | 0.133 | 0.034 | 67.1 | LNU107 | 14585.2 | 0.007 | 0.067 | 49.4 |
| LNU57 | 27855.1 | 0.119 | 0.146 | 49.5 | LNU107 | 14583.8 | 0.005 | 0.598 | 9.0 |
| LNU57 | 27851.2 | 0.091 | 0.383 | 14.4 | LNU107 | 14585.5 | 0.005 | 0.488 | 8.4 |
| LNU57 | 27852.1 | 0.088 | 0.323 | 10.2 | LNU116 | 14493.6 | 0.009 | 0.144 | 89.3 |
| LNU83 | 27685.2 | 0.121 | 0.242 | 52.9 | LNU116 | 14491.5 | 0.009 | 0.003 | 74.9 |
| LNU83 | 27681.4 | 0.116 | 0.066 | 46.5 | LNU116 | 14492.5 | 0.008 | 0.003 | 71.9 |
| LNU83 | 27685.1 | 0.114 | 0.414 | 43.8 | LNU116 | 14494.5 | 0.007 | 0.202 | 40.7 |
| LNU83 | 27684.1 | 0.104 | 0.250 | 30.3 | LNU121 | 27713.4 | 0.015 | 0.000 | 214.6 |
| CONT. | — | 0.132 | — | 0.0 | LNU121 | 27713.1 | 0.010 | 0.049 | 104.1 |
| LNU107 | 14584.9 | 0.254 | 0.000 | 92.8 | LNU121 | 25642.2 | 0.007 | 0.146 | 42.2 |
| LNU107 | 14585.2 | 0.157 | 0.116 | 19.2 | LNU121 | 27713.3 | 0.007 | 0.042 | 39.6 |
| LNU116 | 14491.5 | 0.191 | 0.020 | 45.3 | LNU121 | 27711.1 | 0.006 | 0.484 | 16.6 |
| LNU116 | 14492.5 | 0.178 | 0.032 | 35.2 | LNU126 | 25343.1 | 0.005 | 0.646 | 9.0 |
| LNU116 | 14493.6 | 0.177 | 0.130 | 34.3 | LNU158 | 27433.3 | 0.010 | 0.007 | 109.7 |
| LNU116 | 14494.5 | 0.146 | 0.513 | 10.8 | LNU158 | 27432.5 | 0.009 | 0.002 | 88.2 |
| LNU121 | 27713.4 | 0.302 | 0.000 | 129.5 | LNU158 | 27433.2 | 0.006 | 0.187 | 28.9 |
| LNU121 | 27713.1 | 0.221 | 0.148 | 68.0 | LNU177 | 24764.12 | 0.006 | 0.192 | 26.3 |
| LNU121 | 27713.3 | 0.189 | 0.103 | 43.2 | LNU182 | 25384.6 | 0.006 | 0.063 | 27.4 |
| LNU121 | 25642.2 | 0.181 | 0.269 | 37.7 | LNU182 | 25384.1 | 0.006 | 0.393 | 18.7 |
| LNU121 | 27711.1 | 0.146 | 0.459 | 10.7 | LNU182 | 25384.2 | 0.005 | 0.497 | 9.5 |
| LNU126 | 25343.1 | 0.145 | 0.561 | 9.9 | LNU2 | 27842.3 | 0.009 | 0.049 | 76.0 |
| LNU158 | 27432.5 | 0.223 | 0.000 | 69.6 | LNU2 | 27845.3 | 0.006 | 0.106 | 27.9 |
| LNU158 | 27433.3 | 0.216 | 0.018 | 64.2 | LNU2 | 27842.1 | 0.006 | 0.353 | 21.7 |
| LNU158 | 27433.2 | 0.151 | 0.438 | 14.9 | LNU2 | 25713.1 | 0.005 | 0.786 | 7.9 |
| LNU177 | 24762.6 | 0.154 | 0.335 | 16.9 | LNU225 | 25991.2 | 0.015 | 0.007 | 206.9 |
| LNU177 | 24764.12 | 0.139 | 0.715 | 5.3 | LNU225 | 25991.3 | 0.009 | 0.088 | 90.3 |
| LNU182 | 25384.6 | 0.139 | 0.656 | 5.6 | LNU225 | 25991.8 | 0.006 | 0.224 | 20.7 |

TABLE 70-continued

Genes showing improved plant performance at standard nitrogen growth conditions (T2 generation)

| | | Plant Biomass Fresh weight [gr.] | | | | | Plant Biomass Dry Weight [gr.] | | |
|---|---|---|---|---|---|---|---|---|---|
| Gene Name | Event # | Ave. | p-value | % incr. | Gene Name | Event # | Ave. | p-value | % incr. |
| LNU2 | 27842.3 | 0.220 | 0.023 | 67.2 | LNU239 | 26281.1 | 0.006 | 0.206 | 26.3 |
| LNU2 | 27842.1 | 0.165 | 0.250 | 25.4 | LNU239 | 26283.2 | 0.006 | 0.056 | 25.3 |
| LNU2 | 27845.3 | 0.162 | 0.280 | 23.1 | LNU239 | 26284.2 | 0.006 | 0.450 | 19.7 |
| LNU225 | 25991.2 | 0.297 | 0.008 | 125.7 | LNU57 | 27852.1 | 0.007 | 0.084 | 48.8 |
| LNU225 | 25991.3 | 0.206 | 0.142 | 56.2 | LNU57 | 27851.2 | 0.007 | 0.026 | 47.8 |
| LNU225 | 25991.8 | 0.155 | 0.226 | 17.7 | LNU57 | 27854.5 | 0.007 | 0.117 | 33.5 |
| LNU239 | 26281.1 | 0.156 | 0.176 | 18.1 | LNU83 | 27685.2 | 0.008 | 0.235 | 59.1 |
| LNU239 | 26284.2 | 0.153 | 0.408 | 16.1 | LNU83 | 27685.1 | 0.008 | 0.089 | 56.5 |
| LNU239 | 26283.2 | 0.139 | 0.709 | 5.5 | LNU83 | 27681.4 | 0.006 | 0.184 | 25.8 |
| LNU57 | 27854.5 | 0.179 | 0.112 | 35.6 | CONT. | — | 0.0037 | | |
| LNU57 | 27852.1 | 0.172 | 0.171 | 30.2 | LNU12 | 27371.1 | 0.004 | 0.749 | 3.4 |
| LNU57 | 27851.2 | 0.171 | 0.158 | 29.6 | LNU12 | 27372.5 | 0.004 | 0.749 | 3.4 |
| LNU83 | 27685.2 | 0.208 | 0.139 | 58.1 | CONT. | — | 0.0051 | | |
| LNU83 | 27685.1 | 0.155 | 0.346 | 17.7 | LNU17 | 13991.1 | 0.0068 | 0.04 | 32.2 |
| CONT. | — | 0.116 | — | 0.0 | LNU17 | 13991.14 | 0.0053 | 0.88 | 2.2 |
| LNU17 | 13991.1 | 0.137 | 0.2 | 17.7 | | | | | |

Table 70.
"CONT."—Control;
"Ave."—Average;
"% Incr." = % increment.

TABLE 71

Genes showing improved plant performance at standard nitrogen growth conditions (T2 generation)

| | | Leaf Area [cm2] | | |
|---|---|---|---|---|
| Gene Name | Event # | Average | p-value | % increment |
| CONTROL | — | 0.520 | — | 0.0 |
| LNU100 | 14474.3 | 0.909 | 0.052 | 75.0 |
| LNU100 | 14474.4 | 0.612 | 0.433 | 17.7 |
| LNU100 | 14471.4 | 0.547 | 0.605 | 5.3 |
| LNU104 | 25033.3 | 0.792 | 0.040 | 52.4 |
| LNU213 | 24654.4 | 0.962 | 0.029 | 85.0 |
| LNU213 | 24653.2 | 0.955 | 0.001 | 83.8 |
| LNU213 | 24651.1 | 0.658 | 0.045 | 26.6 |
| LNU218 | 24783.2 | 1.103 | 0.029 | 112.3 |
| LNU218 | 24781.7 | 0.689 | 0.037 | 32.6 |
| LNU218 | 24781.4 | 0.539 | 0.771 | 3.7 |
| LNU4 | 25134.1 | 0.737 | 0.008 | 41.7 |
| LNU4 | 25134.2 | 0.615 | 0.188 | 18.4 |
| LNU48 | 24803.2 | 0.798 | 0.007 | 53.5 |
| LNU48 | 24802.2 | 0.679 | 0.033 | 30.6 |
| LNU48 | 24804.4 | 0.672 | 0.056 | 29.2 |
| LNU8 | 25063.1 | 0.823 | 0.008 | 58.4 |
| LNU8 | 25062.2 | 0.780 | 0.032 | 50.0 |
| LNU8 | 25063.6 | 0.711 | 0.017 | 36.8 |
| LNU8 | 25061.2 | 0.537 | 0.772 | 3.3 |
| LNU94 | 24833.3 | 0.656 | 0.045 | 26.2 |
| LNU94 | 24834.4 | 0.542 | 0.751 | 4.3 |
| LNU94 | 24834.1 | 0.540 | 0.785 | 3.8 |
| CONTROL | — | 0.743 | — | 0.0 |
| LNU1 | 24681.3 | 0.883 | 0.305 | 18.9 |
| LNU1 | 24682.2 | 0.822 | 0.490 | 10.7 |
| LNU1 | 24682.1 | 0.783 | 0.569 | 5.4 |
| LNU1 | 24684.1 | 0.761 | 0.775 | 2.5 |
| LNU133 | 24741.1 | 1.297 | 0.027 | 74.7 |
| LNU133 | 24744.3 | 1.285 | 0.000 | 73.0 |
| LNU175 | 24732.1 | 1.056 | 0.030 | 42.2 |
| LNU175 | 24734.4 | 1.042 | 0.041 | 40.3 |
| LNU175 | 24732.4 | 0.874 | 0.310 | 17.6 |
| LNU178 | 14614.5 | 1.008 | 0.060 | 35.7 |
| LNU178 | 14611.5 | 0.899 | 0.050 | 21.1 |
| LNU178 | 14611.1 | 0.774 | 0.665 | 4.2 |
| LNU215 | 24664.3 | 1.274 | 0.006 | 71.5 |
| LNU215 | 24661.4 | 0.826 | 0.308 | 11.2 |
| LNU24 | 24973.1 | 1.027 | 0.018 | 38.3 |
| LNU24 | 24971.4 | 0.935 | 0.029 | 25.9 |
| LNU24 | 24971.2 | 0.860 | 0.152 | 15.7 |
| LNU6 | 24992.3 | 1.411 | 0.054 | 90.0 |
| LNU6 | 24993.3 | 0.888 | 0.363 | 19.6 |
| LNU82 | 24823.1 | 1.043 | 0.214 | 40.5 |
| LNU9 | 25001.3 | 1.094 | 0.004 | 47.4 |
| LNU9 | 25001.1 | 0.779 | 0.631 | 4.9 |
| CONTROL | — | 0.451 | — | 0.0 |
| LNU120 | 25463.7 | 0.713 | 0.036 | 58.0 |
| LNU120 | 25463.3 | 0.645 | 0.006 | 42.8 |
| LNU120 | 25463.6 | 0.551 | 0.020 | 22.0 |
| LNU124 | 14501.7 | 0.732 | 0.000 | 62.2 |
| LNU124 | 14501.1 | 0.634 | 0.005 | 40.5 |
| LNU124 | 14502.7 | 0.526 | 0.283 | 16.4 |
| LNU132 | 14102.7 | 0.596 | 0.007 | 32.0 |
| LNU132 | 14102.9 | 0.546 | 0.025 | 21.0 |
| LNU132 | 14101.9 | 0.486 | 0.368 | 7.7 |
| LNU140 | 14112.7 | 0.666 | 0.098 | 47.5 |
| LNU140 | 14111.6 | 0.565 | 0.074 | 25.1 |
| LNU180 | 24724.3 | 0.805 | 0.000 | 78.4 |
| LNU180 | 24723.3 | 0.630 | 0.212 | 39.6 |
| LNU180 | 24721.4 | 0.508 | 0.401 | 12.5 |
| LNU196 | 25534.1 | 0.735 | 0.003 | 62.7 |
| LNU196 | 25533.1 | 0.536 | 0.064 | 18.8 |
| LNU196 | 25533.3 | 0.513 | 0.552 | 13.7 |
| LNU20 | 24933.2 | 0.653 | 0.075 | 44.8 |
| LNU36 | 25562.3 | 0.665 | 0.001 | 47.2 |
| LNU36 | 25562.4 | 0.540 | 0.131 | 19.5 |
| LNU71 | 25853.4 | 0.741 | 0.001 | 64.1 |
| LNU71 | 25852.4 | 0.510 | 0.187 | 13.0 |
| CONTROL | — | 0.595 | — | 0.0 |
| LNU1 | 24681.3 | 0.709 | 0.020 | 19.2 |
| LNU110 | 24952.3 | 0.665 | 0.293 | 11.8 |
| LNU110 | 24953.3 | 0.636 | 0.554 | 6.9 |
| LNU175 | 24733.4 | 0.921 | 0.050 | 54.8 |
| LNU175 | 24732.2 | 0.777 | 0.288 | 30.7 |
| LNU19 | 25151.1 | 0.781 | 0.024 | 31.3 |

TABLE 71-continued

Genes showing improved plant performance at standard nitrogen growth conditions (T2 generation)

| Gene Name | Event # | Leaf Area [cm2] Average | p-value | % increment |
|---|---|---|---|---|
| LNU215 | 24663.4 | 0.833 | 0.092 | 40.0 |
| LNU27 | 24873.1 | 0.882 | 0.005 | 48.4 |
| LNU44 | 24924.3 | 0.871 | 0.059 | 46.4 |
| LNU54 | 24903.5 | 0.780 | 0.169 | 31.1 |
| LNU79 | 24884.4 | 0.866 | 0.000 | 45.6 |
| LNU79 | 24881.1 | 0.810 | 0.007 | 36.3 |
| LNU79 | 24884.3 | 0.696 | 0.240 | 17.0 |
| CONTROL | — | 0.674 | — | 0.0 |
| LNU109 | 24891.2 | 1.109 | 0.005 | 64.4 |
| LNU109 | 24892.6 | 0.925 | 0.007 | 37.1 |
| LNU109 | 24892.5 | 0.848 | 0.274 | 25.7 |
| LNU109 | 24891.5 | 0.790 | 0.157 | 17.2 |
| LNU110 | 24952.1 | 1.232 | 0.008 | 82.7 |
| LNU110 | 24954.1 | 1.043 | 0.005 | 54.6 |
| LNU110 | 24953.2 | 0.971 | 0.000 | 44.0 |
| LNU110 | 24952.3 | 0.971 | 0.064 | 44.0 |
| LNU110 | 24954.3 | 0.816 | 0.036 | 21.0 |
| LNU133 | 24741.2 | 1.252 | 0.000 | 85.6 |
| LNU133 | 24741.1 | 1.225 | 0.000 | 81.7 |
| LNU133 | 24744.3 | 1.178 | 0.000 | 74.7 |
| LNU133 | 24742.2 | 0.924 | 0.057 | 37.0 |
| LNU133 | 24744.2 | 0.886 | 0.033 | 31.4 |
| LNU19 | 25151.1 | 1.249 | 0.001 | 85.2 |
| LNU19 | 25153.3 | 0.867 | 0.184 | 28.5 |
| LNU19 | 25151.11 | 0.689 | 0.740 | 2.1 |
| LNU27 | 24873.4 | 1.248 | 0.017 | 85.1 |
| LNU27 | 24871.4 | 0.847 | 0.076 | 25.5 |
| LNU27 | 24873.1 | 0.750 | 0.098 | 11.2 |
| LNU44 | 24922.3 | 1.096 | 0.008 | 62.6 |
| LNU44 | 24924.3 | 0.924 | 0.016 | 37.0 |
| LNU44 | 24923.1 | 0.801 | 0.040 | 18.7 |
| LNU54 | 24903.5 | 1.320 | 0.005 | 95.8 |
| LNU54 | 24902.4 | 1.016 | 0.094 | 50.6 |
| LNU54 | 24901.2 | 0.862 | 0.242 | 27.8 |
| LNU6 | 24994.5 | 1.197 | 0.051 | 77.4 |
| LNU6 | 24992.3 | 1.154 | 0.013 | 71.0 |
| LNU6 | 24994.1 | 0.800 | 0.326 | 18.6 |
| LNU6 | 24994.2 | 0.772 | 0.294 | 14.5 |
| LNU79 | 24882.2 | 1.111 | 0.005 | 64.8 |
| LNU79 | 24881.1 | 1.064 | 0.014 | 57.8 |
| LNU79 | 24884.4 | 1.023 | 0.070 | 51.7 |
| LNU79 | 24883.2 | 0.958 | 0.079 | 42.1 |
| LNU79 | 24884.3 | 0.910 | 0.051 | 34.9 |
| CONTROL | — | 0.559 | — | 0.0 |
| LNU109 | 24892.8 | 1.054 | 0.000 | 88.6 |
| LNU109 | 24891.5 | 0.876 | 0.050 | 56.8 |
| LNU109 | 24891.2 | 0.860 | 0.022 | 53.8 |
| LNU143 | 25975.2 | 0.731 | 0.020 | 30.8 |
| LNU143 | 25972.1 | 0.719 | 0.187 | 28.7 |
| LNU143 | 25975.3 | 0.619 | 0.264 | 10.8 |
| LNU154 | 14604.7 | 0.890 | 0.003 | 59.3 |
| LNU154 | 14601.6 | 0.747 | 0.029 | 33.6 |
| LNU154 | 14604.6 | 0.695 | 0.143 | 24.3 |
| LNU154 | 14602.8 | 0.661 | 0.147 | 18.3 |
| LNU196 | 25532.2 | 1.107 | 0.041 | 98.0 |
| LNU196 | 25534.1 | 0.910 | 0.002 | 62.8 |
| LNU196 | 25531.2 | 0.644 | 0.401 | 15.2 |
| LNU207 | 24642.5 | 1.002 | 0.017 | 79.2 |
| LNU207 | 24642.4 | 0.734 | 0.031 | 31.3 |
| LNU207 | 24644.18 | 0.653 | 0.190 | 16.7 |
| LNU207 | 24644.13 | 0.593 | 0.657 | 6.0 |
| LNU288 | 14564.9 | 0.770 | 0.011 | 37.8 |
| LNU288 | 14562.12 | 0.740 | 0.130 | 32.4 |
| LNU288 | 14562.7 | 0.669 | 0.149 | 19.7 |
| LNU288 | 14562.9 | 0.647 | 0.157 | 15.8 |
| LNU288 | 14562.1 | 0.629 | 0.249 | 12.6 |
| LNU50 | 26024.2 | 0.845 | 0.009 | 51.2 |
| LNU50 | 26025.4 | 0.731 | 0.051 | 30.8 |
| LNU50 | 26023.2 | 0.598 | 0.452 | 7.0 |
| LNU52 | 25723.2 | 0.891 | 0.002 | 59.4 |
| LNU52 | 25721.3 | 0.878 | 0.031 | 57.1 |
| LNU52 | 25721.4 | 0.735 | 0.149 | 31.5 |
| CONTROL | — | 0.682 | — | 0.0 |
| LNU154 | 14601.6 | 0.842 | 0.479 | 23.4 |
| LNU207 | 24642.5 | 1.017 | 0.003 | 49.0 |
| LNU207 | 24642.4 | 0.762 | 0.283 | 11.7 |
| LNU52 | 25721.4 | 0.962 | 0.049 | 41.1 |
| LNU52 | 25721.1 | 0.841 | 0.089 | 23.3 |
| LNU52 | 25723.1 | 0.796 | 0.166 | 16.7 |
| LNU69 | 14571.1 | 0.857 | 0.065 | 25.6 |
| LNU69 | 14572.8 | 0.721 | 0.699 | 5.8 |
| CONTROL | — | 0.671 | — | 0.0 |
| LNU150 | 24843.5 | 0.871 | 0.043 | 29.8 |
| LNU150 | 24842.9 | 0.819 | 0.046 | 22.1 |
| LNU150 | 24841.9 | 0.792 | 0.226 | 17.9 |
| LNU150 | 24843.9 | 0.703 | 0.750 | 4.7 |
| LNU232 | 26003.7 | 0.797 | 0.151 | 18.7 |
| LNU242 | 25474.1 | 0.929 | 0.011 | 38.4 |
| LNU242 | 25473.1 | 0.807 | 0.260 | 20.2 |
| LNU242 | 25471.1 | 0.727 | 0.448 | 8.3 |
| LNU76 | 26421.2 | 0.849 | 0.257 | 26.5 |
| LNU76 | 26422.2 | 0.709 | 0.692 | 5.6 |
| LNU95 | 13985.15 | 0.775 | 0.359 | 15.4 |
| LNU95 | 13985.11 | 0.773 | 0.220 | 15.2 |
| CONTROL | — | 0.673 | — | 0.0 |
| LNU118 | 14013.8 | 0.865 | 0.061 | 28.5 |
| LNU118 | 14013.6 | 0.858 | 0.008 | 27.3 |
| LNU118 | 14012.15 | 0.830 | 0.176 | 23.3 |
| LNU118 | 14012.12 | 0.755 | 0.105 | 12.1 |
| LNU118 | 14012.14 | 0.747 | 0.298 | 11.0 |
| LNU150 | 24842.9 | 1.049 | 0.004 | 55.7 |
| LNU150 | 24841.9 | 0.886 | 0.001 | 31.6 |
| LNU150 | 24841.6 | 0.706 | 0.577 | 4.8 |
| LNU179 | 24632.7 | 0.863 | 0.063 | 28.1 |
| LNU179 | 24631.7 | 0.822 | 0.051 | 22.1 |
| LNU179 | 24631.6 | 0.724 | 0.338 | 7.5 |
| LNU179 | 24632.5 | 0.721 | 0.567 | 7.1 |
| LNU232 | 26001.5 | 0.850 | 0.038 | 26.2 |
| LNU232 | 26003.3 | 0.728 | 0.265 | 8.1 |
| LNU232 | 26003.6 | 0.693 | 0.747 | 2.8 |
| LNU235 | 26184.4 | 1.120 | 0.011 | 66.3 |
| LNU235 | 26184.2 | 0.945 | 0.003 | 40.3 |
| LNU235 | 26185.2 | 0.930 | 0.006 | 38.1 |
| LNU235 | 26182.1 | 0.700 | 0.566 | 3.9 |
| LNU242 | 25474.1 | 0.813 | 0.050 | 20.7 |
| LNU288 | 14563.9 | 1.152 | 0.001 | 71.1 |
| LNU288 | 14562.1 | 0.970 | 0.007 | 44.0 |
| LNU288 | 14564.9 | 0.863 | 0.189 | 28.2 |
| LNU288 | 14563.6 | 0.799 | 0.109 | 18.7 |
| LNU288 | 14562.7 | 0.768 | 0.398 | 14.1 |
| LNU76 | 26421.2 | 0.775 | 0.254 | 15.0 |
| LNU76 | 26422.2 | 0.730 | 0.443 | 8.4 |
| LNU76 | 26425.1 | 0.723 | 0.524 | 7.3 |
| LNU76 | 26423.1 | 0.721 | 0.490 | 7.1 |
| LNU95 | 13985.16 | 1.140 | 0.004 | 69.3 |
| LNU95 | 13985.15 | 1.040 | 0.019 | 54.4 |
| LNU95 | 13985.12 | 0.863 | 0.019 | 28.2 |
| LNU95 | 13985.19 | 0.742 | 0.339 | 10.1 |
| CONTROL | — | 0.587 | — | 0.0 |
| LNU101 | 27635.1 | 0.700 | 0.037 | 19.3 |
| LNU101 | 27632.1 | 0.693 | 0.073 | 18.0 |
| LNU101 | 27632.7 | 0.630 | 0.160 | 7.3 |
| LNU128 | 26515.3 | 0.812 | 0.011 | 38.3 |
| LNU128 | 26515.2 | 0.700 | 0.303 | 19.3 |
| LNU192 | 28315.2 | 0.682 | 0.177 | 16.2 |
| LNU192 | 28313.2 | 0.609 | 0.756 | 3.8 |
| LNU206 | 27621.1 | 0.621 | 0.678 | 5.8 |
| LNU211 | 24771.1 | 0.785 | 0.066 | 33.7 |
| LNU282 | 27563.3 | 0.811 | 0.008 | 38.2 |
| LNU69 | 14571.1 | 0.824 | 0.009 | 40.3 |
| LNU69 | 14573.5 | 0.681 | 0.042 | 16.0 |
| LNU69 | 14572.9 | 0.629 | 0.134 | 7.2 |
| LNU75 | 27572.1 | 0.820 | 0.003 | 39.6 |
| LNU75 | 27572.2 | 0.691 | 0.164 | 17.7 |
| CONTROL | — | 0.552 | — | 0.0 |
| LNU101 | 27632.5 | 0.745 | 0.060 | 34.9 |

TABLE 71-continued

Genes showing improved plant performance at standard nitrogen growth conditions (T2 generation)

| Gene Name | Event # | Leaf Area [cm2] Average | p-value | % increment |
|---|---|---|---|---|
| LNU118 | 14013.6 | 0.692 | 0.094 | 25.3 |
| LNU118 | 14012.15 | 0.649 | 0.267 | 17.5 |
| LNU118 | 14013.9 | 0.570 | 0.713 | 3.2 |
| LNU206 | 27621.2 | 0.776 | 0.001 | 40.5 |
| LNU206 | 27621.1 | 0.644 | 0.120 | 16.7 |
| LNU249 | 26153.1 | 0.883 | 0.034 | 59.9 |
| LNU282 | 27563.1 | 0.724 | 0.117 | 31.1 |
| LNU282 | 27565.2 | 0.611 | 0.277 | 10.7 |
| LNU288 | 14563.9 | 0.866 | 0.002 | 57.0 |
| LNU288 | 14564.8 | 0.854 | 0.000 | 54.7 |
| LNU288 | 14562.9 | 0.730 | 0.072 | 32.2 |
| LNU288 | 14562.7 | 0.643 | 0.244 | 16.5 |
| LNU288 | 14563.6 | 0.600 | 0.538 | 8.7 |
| LNU75 | 27571.4 | 0.782 | 0.049 | 41.7 |
| LNU75 | 27572.3 | 0.743 | 0.085 | 34.5 |
| LNU75 | 27572.2 | 0.691 | 0.169 | 25.1 |
| LNU75 | 27571.2 | 0.641 | 0.112 | 16.1 |
| CONTROL | — | 0.642 | — | 0.0 |
| LNU11 | 28204.3 | 0.685 | 0.490 | 6.6 |
| LNU11 | 28204.1 | 0.676 | 0.655 | 5.2 |
| LNU14 | 27824.2 | 0.763 | 0.613 | 18.8 |
| LNU183 | 24863.12 | 1.132 | 0.001 | 76.2 |
| LNU183 | 24863.1 | 0.922 | 0.003 | 43.6 |
| LNU183 | 24865.1 | 0.908 | 0.018 | 41.3 |
| LNU183 | 24864.6 | 0.736 | 0.125 | 14.5 |
| LNU201 | 28223.1 | 0.662 | 0.688 | 3.1 |
| LNU268 | 26044.2 | 0.758 | 0.210 | 18.0 |
| LNU268 | 26045.1 | 0.719 | 0.210 | 11.9 |
| CONTROL | — | 0.542 | — | 0.0 |
| LNU11 | 28204.1 | 0.672 | 0.073 | 24.1 |
| LNU11 | 28205.1 | 0.652 | 0.233 | 20.4 |
| LNU11 | 28205.2 | 0.652 | 0.099 | 20.4 |
| LNU11 | 28203.2 | 0.615 | 0.226 | 13.6 |
| LNU11 | 28204.3 | 0.603 | 0.316 | 11.4 |
| LNU112 | 28212.4 | 0.688 | 0.070 | 27.1 |
| LNU112 | 28212.1 | 0.605 | 0.413 | 11.8 |
| LNU14 | 27821.4 | 0.673 | 0.156 | 24.3 |
| LNU14 | 27821.3 | 0.671 | 0.217 | 24.0 |
| LNU14 | 27823.2 | 0.638 | 0.158 | 17.8 |
| LNU183 | 24865.1 | 1.352 | 0.000 | 149.7 |
| LNU183 | 24863.12 | 1.265 | 0.011 | 133.6 |
| LNU183 | 24863.1 | 1.237 | 0.000 | 128.4 |
| LNU183 | 24864.6 | 1.231 | 0.000 | 127.3 |
| LNU183 | 24864.7 | 0.586 | 0.464 | 8.2 |
| LNU191 | 28325.4 | 0.740 | 0.061 | 36.6 |
| LNU191 | 28324.2 | 0.718 | 0.046 | 32.6 |
| LNU191 | 28325.3 | 0.664 | 0.080 | 22.5 |
| LNU191 | 28323.1 | 0.653 | 0.442 | 20.6 |
| LNU201 | 28222.2 | 0.891 | 0.036 | 64.5 |
| LNU201 | 28223.3 | 0.616 | 0.301 | 13.7 |
| LNU201 | 28221.3 | 0.561 | 0.783 | 3.6 |
| LNU268 | 26043.4 | 0.715 | 0.025 | 32.0 |
| LNU268 | 26041.4 | 0.685 | 0.049 | 26.5 |
| LNU268 | 26041.6 | 0.588 | 0.639 | 8.6 |
| LNU268 | 26045.1 | 0.578 | 0.753 | 6.8 |
| CONTROL | — | 0.441 | — | 0.0 |
| LNU107 | 14585.5 | 0.576 | 0.422 | 30.6 |
| LNU107 | 14583.8 | 0.573 | 0.226 | 29.9 |
| LNU107 | 14584.9 | 0.534 | 0.315 | 21.0 |
| LNU116 | 14494.5 | 0.616 | 0.067 | 39.7 |
| LNU116 | 14493.6 | 0.594 | 0.075 | 34.7 |
| LNU116 | 14492.9 | 0.539 | 0.011 | 22.2 |
| LNU116 | 14492.5 | 0.530 | 0.156 | 20.3 |
| LNU121 | 25642.2 | 0.892 | 0.002 | 102.2 |
| LNU121 | 27713.4 | 0.708 | 0.004 | 60.6 |
| LNU121 | 27713.1 | 0.689 | 0.064 | 56.1 |
| LNU121 | 27711.1 | 0.666 | 0.064 | 50.9 |
| LNU126 | 25343.3 | 0.680 | 0.000 | 54.1 |
| LNU126 | 25345.1 | 0.656 | 0.054 | 48.8 |
| LNU126 | 25343.1 | 0.618 | 0.135 | 40.0 |
| LNU158 | 27433.3 | 0.633 | 0.045 | 43.5 |
| LNU158 | 27433.2 | 0.556 | 0.195 | 26.1 |
| LNU158 | 27432.5 | 0.520 | 0.523 | 17.8 |
| LNU177 | 24762.6 | 0.626 | 0.100 | 41.9 |
| LNU177 | 24765.2 | 0.531 | 0.253 | 20.4 |
| LNU177 | 24764.9 | 0.500 | 0.348 | 13.4 |
| LNU182 | 25384.5 | 0.581 | 0.034 | 31.8 |
| LNU182 | 27521.4 | 0.553 | 0.394 | 25.3 |
| LNU182 | 25384.1 | 0.529 | 0.310 | 20.0 |
| LNU182 | 25384.2 | 0.497 | 0.219 | 12.7 |
| LNU2 | 25713.1 | 0.618 | 0.057 | 40.0 |
| LNU2 | 27842.1 | 0.519 | 0.628 | 17.6 |
| LNU2 | 27842.3 | 0.497 | 0.464 | 12.7 |
| LNU225 | 25991.5 | 0.547 | 0.210 | 24.0 |
| LNU225 | 25991.2 | 0.487 | 0.532 | 10.3 |
| LNU239 | 26284.1 | 0.652 | 0.019 | 47.7 |
| LNU239 | 26283.2 | 0.527 | 0.219 | 19.4 |
| LNU239 | 26281.1 | 0.472 | 0.550 | 6.9 |
| LNU57 | 27854.3 | 0.491 | 0.236 | 11.3 |
| LNU83 | 27684.1 | 0.490 | 0.592 | 11.0 |
| LNU83 | 27681.4 | 0.472 | 0.584 | 7.1 |
| CONTROL | — | 0.297 | — | 0.0 |
| LNU107 | 14584.9 | 0.620 | 0.002 | 108.6 |
| LNU107 | 14585.2 | 0.527 | 0.063 | 77.1 |
| LNU107 | 14585.1 | 0.435 | 0.088 | 46.4 |
| LNU107 | 14583.8 | 0.370 | 0.175 | 24.3 |
| LNU107 | 14583.1 | 0.344 | 0.429 | 15.7 |
| LNU116 | 14492.5 | 0.627 | 0.035 | 110.8 |
| LNU116 | 14493.6 | 0.482 | 0.085 | 62.1 |
| LNU116 | 14491.5 | 0.470 | 0.086 | 57.9 |
| LNU116 | 14494.5 | 0.401 | 0.051 | 34.8 |
| LNU116 | 14492.9 | 0.365 | 0.320 | 22.8 |
| LNU121 | 27713.4 | 0.901 | 0.001 | 202.9 |
| LNU121 | 27713.1 | 0.656 | 0.008 | 120.7 |
| LNU121 | 27713.3 | 0.544 | 0.002 | 83.0 |
| LNU121 | 25642.2 | 0.534 | 0.012 | 79.7 |
| LNU121 | 27711.1 | 0.494 | 0.080 | 66.1 |
| LNU126 | 25343.1 | 0.564 | 0.001 | 89.8 |
| LNU126 | 25343.3 | 0.435 | 0.286 | 46.3 |
| LNU126 | 25343.4 | 0.366 | 0.124 | 23.2 |
| LNU126 | 25345.1 | 0.365 | 0.150 | 22.7 |
| LNU158 | 27433.3 | 0.707 | 0.011 | 137.7 |
| LNU158 | 27432.5 | 0.696 | 0.000 | 134.0 |
| LNU158 | 27433.2 | 0.584 | 0.020 | 96.3 |
| LNU158 | 27434.5 | 0.338 | 0.249 | 13.7 |
| LNU158 | 27434.1 | 0.310 | 0.798 | 4.3 |
| LNU177 | 24762.6 | 0.434 | 0.130 | 46.1 |
| LNU177 | 24763.6 | 0.352 | 0.452 | 18.5 |
| LNU177 | 24764.12 | 0.348 | 0.287 | 17.1 |
| LNU182 | 25384.1 | 0.515 | 0.026 | 73.2 |
| LNU182 | 25384.6 | 0.510 | 0.161 | 71.7 |
| LNU182 | 25384.2 | 0.451 | 0.001 | 51.6 |
| LNU182 | 25384.5 | 0.353 | 0.448 | 18.7 |
| LNU182 | 27521.4 | 0.328 | 0.531 | 10.3 |
| LNU2 | 27845.3 | 0.556 | 0.109 | 87.0 |
| LNU2 | 25713.1 | 0.522 | 0.023 | 75.5 |
| LNU2 | 27842.3 | 0.503 | 0.001 | 69.3 |
| LNU2 | 27842.1 | 0.453 | 0.019 | 52.4 |
| LNU2 | 27845.2 | 0.352 | 0.351 | 18.4 |
| LNU225 | 25991.2 | 0.762 | 0.000 | 156.2 |
| LNU225 | 25991.3 | 0.582 | 0.016 | 95.9 |
| LNU225 | 25991.1 | 0.473 | 0.147 | 59.1 |
| LNU225 | 25991.6 | 0.472 | 0.067 | 58.9 |
| LNU225 | 25991.5 | 0.331 | 0.343 | 11.2 |
| LNU239 | 26284.2 | 0.503 | 0.042 | 69.2 |
| LNU239 | 26283.2 | 0.491 | 0.014 | 65.2 |
| LNU239 | 26281.1 | 0.475 | 0.029 | 59.7 |
| LNU239 | 26284.1 | 0.430 | 0.145 | 44.6 |
| LNU239 | 26283.3 | 0.422 | 0.161 | 41.9 |
| LNU57 | 27852.1 | 0.508 | 0.006 | 71.0 |
| LNU57 | 27851.2 | 0.472 | 0.001 | 58.6 |
| LNU57 | 27854.5 | 0.330 | 0.420 | 11.1 |
| LNU83 | 27685.1 | 0.554 | 0.099 | 86.4 |
| LNU83 | 27685.2 | 0.510 | 0.000 | 71.7 |
| LNU83 | 27681.4 | 0.399 | 0.286 | 34.3 |
| LNU83 | 27682.1 | 0.368 | 0.168 | 24.0 |

TABLE 71-continued

Genes showing improved plant performance at standard nitrogen growth conditions (T2 generation)

| Gene Name | Event # | Leaf Area [cm2] Average | p-value | % increment |
|---|---|---|---|---|
| LNU83 | 27684.1 | 0.336 | 0.653 | 12.9 |
| CONTROL | — | 0.467 | | 0.0 |
| LNU129 | 27501.2 | 0.636 | <0.1 | 36.3 |
| LNU129 | 27502.4 | 0.527 | <0.4 | 13.0 |
| LNU129 | 27504.2 | 0.687 | <0.1 | 47.1 |
| LNU129 | 27504.3 | 0.897 | <0.1 | 92.2 |
| LNU147 | 27513.2 | 0.654 | <0.1 | 40.2 |
| LNU147 | 27514.1 | 0.540 | <0.4 | 15.6 |
| LNU147 | 27514.2 | 0.536 | <0.4 | 14.8 |
| LNU153 | 24851.3 | 0.490 | <0.7 | 5.0 |
| LNU189 | 26382.3 | 0.626 | <0.1 | 34.0 |
| LNU189 | 26382.4 | 0.597 | <0.1 | 28.0 |
| LNU189 | 26383.1 | 0.666 | <0.1 | 42.6 |
| LNU189 | 26385.1 | 0.524 | <0.4 | 12.3 |
| LNU189 | 26385.2 | 0.513 | <0.7 | 9.9 |
| LNU219 | 27461.1 | 0.784 | <0.1 | 67.9 |
| LNU219 | 27462.1 | 0.773 | <0.1 | 65.6 |
| LNU219 | 27462.2 | 0.644 | <0.1 | 38.0 |
| LNU219 | 27464.1 | 0.499 | <0.7 | 7.0 |
| LNU256 | 26212.3 | 0.650 | <0.1 | 39.3 |
| LNU256 | 26213.1 | 0.630 | <0.1 | 34.9 |
| LNU256 | 26214.1 | 0.649 | <0.1 | 39.0 |
| LNU257 | 26254.1 | 0.522 | <0.4 | 11.9 |
| LNU257 | 26254.3 | 0.883 | <0.1 | 89.1 |
| LNU257 | 26254.7 | 0.589 | <0.2 | 26.1 |
| LNU257 | 26255.3 | 0.589 | <0.2 | 26.1 |
| LNU261 | 27403.2 | 0.646 | <0.1 | 38.3 |
| LNU261 | 27405.1 | 0.646 | <0.1 | 38.5 |
| LNU33 | 25552.2 | 0.679 | <0.1 | 45.4 |
| LNU33 | 25553.2 | 0.592 | <0.2 | 26.9 |
| LNU33 | 25555.1 | 0.503 | <0.7 | 7.9 |
| LNU35 | 27421.2 | 0.574 | <0.2 | 22.9 |
| LNU35 | 27422.1 | 0.903 | <0.1 | 93.4 |
| LNU35 | 27423.3 | 0.615 | <0.1 | 31.8 |
| LNU35 | 27424.3 | 0.584 | <0.2 | 25.1 |
| LNU35 | 27424.4 | 0.607 | <0.1 | 30.1 |
| LNU50 | 26022.1 | 0.725 | <0.1 | 55.3 |
| LNU50 | 26023.2 | 0.604 | <0.1 | 29.4 |
| LNU50 | 26023.3 | 0.557 | <0.2 | 19.2 |
| LNU50 | 26024.1 | 0.730 | <0.1 | 56.3 |
| LNU50 | 26025.3 | 0.859 | <0.1 | 84.0 |
| LNU70 | 25313.1 | 0.735 | <0.1 | 57.5 |
| LNU70 | 25313.2 | 0.657 | <0.1 | 40.8 |

Table 71.

TABLE 72

Genes showing improved plant performance at standard nitrogen growth conditions (T1 generation)

| Gene Name | Plant Biomass Fresh Weight [gr.] Ave. | p-value | % incr. | Gene Name | Plant Biomass Dry Weight [gr.] Ave. | p-value | % incr. |
|---|---|---|---|---|---|---|---|
| CONT. | 0.160 | — | 0.0 | CONT. | 0.008 | — | 0.0 |
| LNU121 | 0.176 | 0.305 | 9.8 | LNU121 | 0.009 | 0.243 | 19.5 |
| LNU150 | 0.160 | 0.987 | 0.2 | LNU154 | 0.008 | 0.489 | 11.3 |
| LNU154 | 0.166 | 0.808 | 4.0 | CONT. | 0.005 | — | 0.0 |
| CONT. | 0.118 | — | 0.0 | LNU275 | 0.010 | 0.005 | 85.2 |
| LNU275 | 0.189 | 0.022 | 60.3 | LNU57 | 0.006 | 0.574 | 10.3 |
| LNU57 | 0.124 | 0.697 | 5.1 | LNU64 | 0.006 | 0.254 | 14.1 |
| LNU64 | 0.127 | 0.509 | 7.6 | LNU83 | 0.006 | 0.295 | 18.9 |
| LNU83 | 0.132 | 0.385 | 12.1 | CONT. | 0.005 | — | 0.0 |
| CONT. | 0.110 | — | 0.0 | LNU59 | 0.005 | 0.560 | 12.0 |
| LNU176 | 0.115 | 0.670 | 4.5 | LNU60 | 0.006 | 0.553 | 12.5 |
| LNU247 | 0.112 | 0.884 | 1.6 | | | | |
| LNU284 | 0.112 | 0.941 | 1.5 | | | | |

TABLE 72-continued

Genes showing improved plant performance at standard nitrogen growth conditions (T1 generation)

| Gene Name | Plant Biomass Fresh Weight [gr.] Ave. | p-value | % incr. | Gene Name | Plant Biomass Dry Weight [gr.] Ave. | p-value | % incr. |
|---|---|---|---|---|---|---|---|
| CONT. | 0.128 | — | 0.0 | | | | |
| LNU59 | 0.134 | 0.717 | 5.0 | | | | |
| LNU60 | 0.135 | 0.703 | 5.5 | | | | |

Table 72.

"CONT."—Control;

"Ave."—Average;

"% Incr." = % increment.

TABLE 73

Genes showing improved plant performance at standard nitrogen growth conditions (T1 generation)

| Gene Name | Time Point | Leaf Area [cm2] Average | p-value | % increment |
|---|---|---|---|---|
| CONTROL | Leaf_Area_TP2 | 0.328 | — | 0.0 |
| LNU154 | Leaf_Area_TP2 | 0.334 | 0.886 | 1.6 |
| CONTROL | Leaf_Area_TP3 | 0.629 | — | 0.0 |
| LNU121 | Leaf_Area_TP3 | 0.649 | 0.667 | 3.1 |
| CONTROL | Leaf_Area_TP2 | 0.289 | — | 0.0 |
| LNU127 | Leaf_Area_TP2 | 0.295 | 0.783 | 2.3 |
| LNU275 | Leaf_Area_TP2 | 0.492 | 0.000 | 70.5 |
| LNU32 | Leaf_Area_TP2 | 0.309 | 0.519 | 7.1 |
| LNU57 | Leaf_Area_TP2 | 0.313 | 0.309 | 8.4 |
| LNU58 | Leaf_Area_TP2 | 0.305 | 0.421 | 5.8 |
| LNU83 | Leaf_Area_TP2 | 0.381 | 0.032 | 32.1 |
| CONTROL | Leaf_Area_TP3 | 0.626 | — | 0.0 |
| LNU275 | Leaf_Area_TP3 | 0.981 | 0.004 | 56.7 |
| LNU57 | Leaf_Area_TP3 | 0.691 | 0.354 | 10.3 |
| LNU64 | Leaf_Area_TP3 | 0.630 | 0.935 | 0.7 |
| LNU83 | Leaf_Area_TP3 | 0.781 | 0.069 | 24.7 |
| CONTROL | Leaf_Area_TP2 | 0.298 | — | 0.0 |
| LNU59 | Leaf_Area_TP2 | 0.302 | 0.885 | 1.4 |
| CONTROL | Leaf_Area_TP3 | 0.606 | — | 0.0 |
| LNU59 | Leaf_Area_TP3 | 0.631 | 0.619 | 4.1 |

Table 73.

The genes listed in Tables 74 and 75 improved plant NUE when grown at standard nitrogen concentration levels. These genes produced larger root biomass (root length and root coverage) when grown under standard nitrogen growth conditions, compared to control plants. Plants producing larger root biomass have better possibilities to absorb larger amount of nitrogen from soil. The genes were cloned under the regulation of a constitutive promoter (At6669) or root preferred promoter (RootP). The evaluation of each gene was performed by testing the performance of different number of events. Some of the genes were evaluated in more than one tissue culture assay resulting in positive results as well. Event with p-value <0.1 was considered statistically significant

TABLE 74

Genes showing improved root performance at standard nitrogen growth conditions (T2 generation)

| | | Roots Length [cm] | | | | | Roots Coverage [cm2] | | |
|---|---|---|---|---|---|---|---|---|---|
| Gene Name | Event # | Ave. | p-value | % incr. | Gene Name | Event # | Ave. | p-value | % incr. |
| CONT. | — | 4.849 | — | 0.0 | CONT. | — | 3.976 | — | 0.0 |
| LNU100 | 14474.3 | 6.391 | 0.001 | 31.8 | LNU100 | 14474.3 | 5.804 | 0.076 | 46.0 |
| LNU100 | 14471.4 | 6.031 | 0.073 | 24.4 | LNU100 | 14474.4 | 5.605 | 0.215 | 41.0 |
| LNU100 | 14474.4 | 5.910 | 0.082 | 21.9 | LNU100 | 14471.4 | 5.036 | 0.150 | 26.7 |
| LNU100 | 14473.1 | 5.412 | 0.078 | 11.6 | LNU104 | 25033.3 | 5.092 | 0.128 | 28.1 |
| LNU100 | 14473.3 | 5.137 | 0.473 | 5.9 | LNU213 | 24654.4 | 6.150 | 0.072 | 54.7 |
| LNU104 | 25033.3 | 6.109 | 0.003 | 26.0 | LNU213 | 24653.2 | 5.740 | 0.034 | 44.4 |
| LNU104 | 25032.1 | 5.255 | 0.247 | 8.4 | LNU213 | 24651.1 | 4.940 | 0.159 | 24.3 |
| LNU104 | 25033.1 | 5.022 | 0.613 | 3.6 | LNU218 | 24783.2 | 7.745 | 0.049 | 94.8 |
| LNU104 | 25032.2 | 4.979 | 0.747 | 2.7 | LNU218 | 24781.2 | 4.894 | 0.179 | 23.1 |
| LNU213 | 24653.2 | 6.170 | 0.004 | 27.2 | LNU218 | 24781.7 | 4.617 | 0.254 | 16.1 |
| LNU213 | 24654.4 | 6.029 | 0.014 | 24.3 | LNU218 | 24781.4 | 4.145 | 0.714 | 4.3 |
| LNU213 | 24651.1 | 5.610 | 0.111 | 15.7 | LNU4 | 25134.1 | 4.657 | 0.201 | 17.1 |
| LNU213 | 24653.1 | 5.144 | 0.485 | 6.1 | LNU48 | 24802.2 | 4.922 | 0.256 | 23.8 |
| LNU218 | 24783.2 | 7.188 | 0.000 | 48.2 | LNU48 | 24804.4 | 4.630 | 0.443 | 16.5 |
| LNU218 | 24781.1 | 5.595 | 0.039 | 15.4 | LNU48 | 24803.2 | 4.430 | 0.384 | 11.4 |
| LNU218 | 24781.7 | 5.435 | 0.155 | 12.1 | LNU8 | 25063.1 | 7.354 | 0.004 | 85.0 |
| LNU218 | 24781.4 | 5.290 | 0.210 | 9.1 | LNU8 | 25062.2 | 5.008 | 0.068 | 26.0 |
| LNU218 | 24781.2 | 5.196 | 0.253 | 7.2 | LNU8 | 25063.6 | 4.121 | 0.730 | 3.7 |
| LNU4 | 25131.1 | 6.021 | 0.008 | 24.2 | LNU94 | 24833.1 | 4.236 | 0.661 | 6.5 |
| LNU4 | 25134.1 | 5.680 | 0.098 | 17.1 | LNU94 | 24834.4 | 4.130 | 0.709 | 3.9 |
| LNU4 | 25134.2 | 5.462 | 0.041 | 12.6 | CONT. | — | 5.584 | — | 0.0 |
| LNU4 | 25133.3 | 5.018 | 0.587 | 3.5 | LNU1 | 24682.2 | 7.395 | 0.107 | 32.4 |
| LNU48 | 24804.4 | 5.956 | 0.010 | 22.8 | LNU1 | 24682.1 | 6.727 | 0.071 | 20.5 |
| LNU48 | 24802.2 | 5.586 | 0.106 | 15.2 | LNU1 | 24684.1 | 6.661 | 0.177 | 19.3 |
| LNU48 | 24803.2 | 5.049 | 0.544 | 4.1 | LNU1 | 24681.1 | 6.270 | 0.284 | 12.3 |
| LNU8 | 25063.1 | 6.763 | 0.000 | 39.5 | LNU133 | 24744.3 | 9.891 | 0.000 | 77.1 |
| LNU8 | 25062.2 | 6.296 | 0.001 | 29.8 | LNU133 | 24741.1 | 9.192 | 0.066 | 64.6 |
| LNU8 | 25063.6 | 5.123 | 0.416 | 5.7 | LNU133 | 24741.2 | 6.714 | 0.087 | 20.2 |
| LNU8 | 25062.1 | 5.016 | 0.610 | 3.5 | LNU175 | 24732.1 | 9.540 | 0.038 | 70.8 |
| LNU94 | 24834.4 | 5.557 | 0.058 | 14.6 | LNU175 | 24732.4 | 9.071 | 0.011 | 62.5 |
| LNU94 | 24833.3 | 5.351 | 0.233 | 10.4 | LNU175 | 24734.4 | 8.342 | 0.004 | 49.4 |
| CONT. | — | 6.645 | — | 0.0 | LNU175 | 24731.2 | 5.955 | 0.657 | 6.6 |
| LNU1 | 24682.2 | 6.883 | 0.409 | 3.6 | LNU178 | 14614.5 | 8.913 | 0.010 | 59.6 |
| LNU1 | 24684.1 | 6.833 | 0.350 | 2.8 | LNU178 | 14611.5 | 7.578 | 0.133 | 35.7 |
| LNU133 | 24744.3 | 6.958 | 0.328 | 4.7 | LNU178 | 14612.1 | 6.454 | 0.303 | 15.6 |
| LNU175 | 24732.1 | 7.028 | 0.152 | 5.8 | LNU178 | 14611.4 | 5.776 | 0.777 | 3.4 |
| LNU175 | 24732.4 | 6.739 | 0.677 | 1.4 | LNU215 | 24664.3 | 9.619 | 0.027 | 72.3 |
| LNU178 | 14614.5 | 7.100 | 0.133 | 6.8 | LNU215 | 24661.4 | 7.432 | 0.016 | 33.1 |
| LNU215 | 24664.2 | 6.776 | 0.643 | 2.0 | LNU215 | 24663.4 | 6.228 | 0.402 | 11.5 |
| LNU215 | 24664.3 | 6.739 | 0.765 | 1.4 | LNU215 | 24664.2 | 5.760 | 0.756 | 3.2 |
| CONT. | — | 5.816 | — | 0.0 | LNU24 | 24971.4 | 8.367 | 0.080 | 49.8 |
| LNU120 | 25463.7 | 7.237 | 0.001 | 24.4 | LNU24 | 24973.1 | 7.707 | 0.151 | 38.0 |
| LNU120 | 25463.6 | 6.531 | 0.009 | 12.3 | LNU6 | 24992.3 | 9.043 | 0.105 | 61.9 |
| LNU120 | 25463.3 | 6.304 | 0.096 | 8.4 | LNU6 | 24993.3 | 7.325 | 0.282 | 31.2 |
| LNU124 | 14502.1 | 6.609 | 0.003 | 13.6 | LNU82 | 24823.1 | 7.225 | 0.154 | 29.4 |
| LNU124 | 14502.7 | 6.545 | 0.113 | 12.5 | LNU82 | 24824.3 | 5.882 | 0.638 | 5.4 |
| LNU124 | 14501.1 | 6.332 | 0.094 | 8.9 | LNU9 | 25001.3 | 8.110 | 0.025 | 45.2 |
| LNU124 | 14501.7 | 5.964 | 0.685 | 2.5 | LNU9 | 25001.1 | 7.174 | 0.035 | 28.5 |
| LNU132 | 14102.9 | 6.457 | 0.057 | 11.0 | LNU9 | 25001.2 | 6.256 | 0.317 | 12.0 |
| LNU132 | 14102.7 | 6.113 | 0.611 | 5.1 | CONT. | — | 4.531 | — | 0.0 |
| LNU140 | 14114.8 | 6.579 | 0.061 | 13.1 | LNU120 | 25463.7 | 7.868 | 0.038 | 73.6 |
| LNU140 | 14111.6 | 6.576 | 0.004 | 13.1 | LNU120 | 25463.6 | 5.970 | 0.030 | 31.8 |
| LNU140 | 14112.7 | 5.926 | 0.577 | 1.9 | LNU120 | 25463.3 | 5.164 | 0.181 | 14.0 |
| LNU180 | 24723.3 | 6.266 | 0.142 | 7.7 | LNU124 | 14502.7 | 5.914 | 0.076 | 30.5 |
| LNU180 | 24724.3 | 6.232 | 0.321 | 7.1 | LNU124 | 14501.7 | 5.595 | 0.192 | 23.5 |
| LNU180 | 24724.1 | 6.204 | 0.096 | 6.7 | LNU124 | 14502.1 | 5.257 | 0.081 | 16.0 |
| LNU196 | 25534.1 | 5.957 | 0.581 | 2.4 | LNU122 | 14501.1 | 5.079 | 0.170 | 12.1 |
| LNU196 | 25533.3 | 5.955 | 0.740 | 2.4 | LNU132 | 14102.7 | 5.508 | 0.146 | 21.6 |
| LNU20 | 24933.2 | 6.550 | 0.079 | 12.6 | LNU132 | 14102.9 | 5.228 | 0.247 | 15.4 |
| LNU20 | 24933.4 | 6.103 | 0.334 | 4.9 | LNU140 | 14111.6 | 5.840 | 0.083 | 28.9 |
| LNU36 | 25562.3 | 7.052 | 0.001 | 21.2 | LNU140 | 14112.7 | 5.539 | 0.146 | 22.2 |
| LNU36 | 25562.4 | 6.098 | 0.448 | 4.9 | LNU140 | 14114.8 | 5.460 | 0.025 | 20.5 |
| LNU71 | 25852.5 | 5.985 | 0.623 | 2.9 | LNU180 | 24724.3 | 6.600 | 0.013 | 45.7 |
| CONT. | — | 5.715 | — | 0.0 | LNU180 | 241233 | 5.650 | 0.177 | 24.7 |
| LNU1 | 24684.1 | 5.994 | 0.624 | 4.9 | LNU180 | 24721.4 | 4.990 | 0.306 | 10.1 |
| LNU1 | 24682.1 | 5.985 | 0.700 | 4.7 | LNU180 | 24724.1 | 4.848 | 0.394 | 7.0 |
| LNU110 | 24953.2 | 6.472 | 0.204 | 13.2 | LNU196 | 25534.1 | 5.798 | 0.172 | 28.0 |
| LNU110 | 24954.3 | 6.240 | 0.371 | 9.2 | LNU196 | 25533.3 | 4.974 | 0.596 | 9.8 |
| LNU110 | 24953.3 | 5.887 | 0.761 | 3.0 | LNU196 | 25533.1 | 4.907 | 0.537 | 8.3 |
| LNU175 | 24733.4 | 7.017 | 0.056 | 22.8 | LNU20 | 24933.2 | 6.361 | 0.076 | 40.4 |
| LNU175 | 24732.1 | 6.599 | 0.155 | 15.5 | LNU20 | 24932.4 | 5.171 | 0.277 | 14.1 |

TABLE 74-continued

Genes showing improved root performance at standard nitrogen growth conditions (T2 generation)

| | | Roots Length [cm] | | | | | Roots Coverage [cm2] | | |
|---|---|---|---|---|---|---|---|---|---|
| Gene Name | Event # | Ave. | p-value | % incr. | Gene Name | Event # | Ave. | p-value | % incr. |
| LNU175 | 24734.4 | 6.338 | 0.297 | 10.9 | LNU20 | 24933.4 | 4.880 | 0.392 | 7.7 |
| LNU19 | 25151.11 | 5.917 | 0.721 | 3.5 | LNU36 | 25562.3 | 7.451 | 0.014 | 64.4 |
| LNU215 | 24664.2 | 6.822 | 0.089 | 19.4 | LNU36 | 25562.4 | 5.452 | 0.174 | 20.3 |
| LNU215 | 24663.3 | 6.562 | 0.164 | 14.8 | LNU71 | 25853.4 | 6.607 | 0.024 | 45.8 |
| LNU215 | 24663.4 | 6.429 | 0.239 | 12.5 | CONT. | — | 5.186 | — | 0.0 |
| LNU215 | 24661.4 | 6.327 | 0.285 | 10.7 | LNU1 | 24681.3 | 6.080 | 0.219 | 17.2 |
| LNU27 | 24873.1 | 6.861 | 0.096 | 20.0 | LNU110 | 24952.3 | 5.702 | 0.579 | 10.0 |
| LNU27 | 24871.4 | 6.399 | 0.243 | 12.0 | LNU175 | 24733.4 | 9.339 | 0.011 | 80.1 |
| LNU27 | 24873.4 | 5.879 | 0.794 | 2.9 | LNU175 | 24732.2 | 6.572 | 0.148 | 26.7 |
| LNU44 | 24923.3 | 6.618 | 0.168 | 15.8 | LNU175 | 24734.4 | 5.788 | 0.436 | 11.6 |
| LNU44 | 24924.2 | 6.437 | 0.234 | 12.6 | LNU175 | 24732.1 | 5.692 | 0.490 | 9.8 |
| LNU44 | 24922.3 | 6.341 | 0.322 | 11.0 | LNU19 | 25151.1 | 5.793 | 0.383 | 11.7 |
| LNU44 | 24923.1 | 5.999 | 0.607 | 5.0 | LNU215 | 24663.4 | 7.608 | 0.035 | 46.7 |
| LNU54 | 24901.2 | 7.145 | 0.047 | 25.0 | LNU215 | 24664.2 | 6.954 | 0.131 | 34.1 |
| LNU54 | 24902.4 | 7.103 | 0.062 | 24.3 | LNU215 | 24663.3 | 5.781 | 0.411 | 11.5 |
| LNU54 | 24902.7 | 6.053 | 0.543 | 5.9 | LNU215 | 24663.1 | 5.562 | 0.795 | 7.3 |
| LNU54 | 24903.3 | 5.999 | 0.668 | 5.0 | LNU27 | 24873.1 | 8.055 | 0.022 | 55.3 |
| LNU54 | 24903.5 | 5.976 | 0.679 | 4.6 | LNU27 | 24873.4 | 5.906 | 0.364 | 13.9 |
| LNU79 | 24881.1 | 7.091 | 0.049 | 24.1 | LNU27 | 24871.4 | 5.882 | 0.322 | 13.4 |
| LNU79 | 24882.2 | 6.898 | 0.082 | 20.7 | LNU44 | 24924.2 | 6.515 | 0.098 | 25.6 |
| LNU79 | 24883.2 | 6.280 | 0.322 | 9.9 | LNU44 | 24924.3 | 6.346 | 0.246 | 22.4 |
| LNU79 | 24884.4 | 6.016 | 0.595 | 5.3 | LNU44 | 24923.3 | 6.219 | 0.267 | 19.9 |
| CONT. | — | 6.033 | — | 0.0 | LNU44 | 24922.3 | 5.394 | 0.779 | 4.0 |
| LNU109 | 24892.6 | 6.662 | 0.003 | 10.4 | LNU54 | 24902.4 | 7.593 | 0.092 | 46.4 |
| LNU109 | 24892.8 | 6.584 | 0.089 | 9.1 | LNU54 | 24901.2 | 7.095 | 0.160 | 36.8 |
| LNU109 | 24892.5 | 6.471 | 0.091 | 7.3 | LNU54 | 24903.5 | 6.720 | 0.141 | 29.6 |
| LNU109 | 24891.5 | 6.398 | 0.149 | 6.0 | LNU54 | 24903.3 | 6.233 | 0.284 | 20.2 |
| LNU109 | 24891.2 | 6.168 | 0.624 | 2.2 | LNU79 | 24881.1 | 9.394 | 0.001 | 81.1 |
| LNU110 | 24952.1 | 7.116 | 0.032 | 17.9 | LNU79 | 24884.4 | 6.787 | 0.061 | 30.9 |
| LNU110 | 24952.3 | 6.584 | 0.252 | 9.1 | LNU79 | 24884.3 | 5.863 | 0.407 | 13.1 |
| LNU110 | 24954.1 | 6.477 | 0.388 | 7.4 | LNU79 | 24882.2 | 5.824 | 0.552 | 12.3 |
| LNU110 | 24953.2 | 6.476 | 0.414 | 7.3 | CONT. | — | 5.925 | — | 0.0 |
| LNU110 | 24954.3 | 6.318 | 0.252 | 4.7 | LNU109 | 24892.6 | 9.651 | 0.001 | 62.9 |
| LNU133 | 24744.3 | 7.193 | 0.003 | 19.2 | LNU109 | 24892.5 | 8.357 | 0.129 | 41.1 |
| LNU133 | 24741.2 | 6.655 | 0.043 | 10.3 | LNU109 | 24891.2 | 7.582 | 0.064 | 28.0 |
| LNU133 | 24741.1 | 6.592 | 0.059 | 9.3 | LNU109 | 24891.5 | 7.440 | 0.090 | 25.6 |
| LNU133 | 24742.2 | 6.248 | 0.133 | 3.6 | LNU109 | 24892.8 | 6.366 | 0.511 | 7.5 |
| LNU19 | 25151.1 | 6.386 | 0.125 | 5.9 | LNU110 | 24952.1 | 10.431 | 0.010 | 76.1 |
| LNU27 | 24873.1 | 7.085 | 0.070 | 17.4 | LNU110 | 24954.1 | 9.168 | 0.016 | 54.7 |
| LNU27 | 24871.4 | 7.029 | 0.003 | 16.5 | LNU110 | 24953.2 | 8.763 | 0.119 | 47.9 |
| LNU27 | 24873.4 | 6.424 | 0.115 | 6.5 | LNU110 | 24954.3 | 8.415 | 0.020 | 42.0 |
| LNU27 | 24872.3 | 6.125 | 0.692 | 1.5 | LNU110 | 24952.3 | 8.298 | 0.094 | 40.1 |
| LNU44 | 24922.3 | 6.695 | 0.003 | 11.0 | LNU133 | 24744.3 | 9.969 | 0.000 | 68.3 |
| LNU44 | 24923.3 | 6.472 | 0.305 | 7.3 | LNU133 | 24741.2 | 9.419 | 0.006 | 59.0 |
| LNU44 | 24924.3 | 6.113 | 0.701 | 1.3 | LNU133 | 24741.1 | 9.029 | 0.014 | 52.4 |
| LNU54 | 24901.2 | 6.844 | 0.049 | 13.4 | LNU133 | 24742.2 | 8.023 | 0.041 | 35.4 |
| LNU54 | 24903.5 | 6.790 | 0.005 | 12.5 | LNU133 | 24744.2 | 7.532 | 0.080 | 27.1 |
| LNU54 | 24902.4 | 6.782 | 0.066 | 12.4 | LNU19 | 25151.1 | 9.075 | 0.003 | 53.2 |
| LNU54 | 24903.3 | 6.624 | 0.045 | 9.8 | LNU19 | 25153.3 | 7.527 | 0.201 | 27.0 |
| LNU54 | 24902.7 | 6.298 | 0.398 | 4.4 | LNU19 | 25151.11 | 7.438 | 0.043 | 25.6 |
| LNU6 | 24994.2 | 6.782 | 0.062 | 12.4 | LNU27 | 24873.4 | 8.650 | 0.067 | 46.0 |
| LNU6 | 24992.3 | 6.759 | 0.044 | 12.0 | LNU27 | 24871.4 | 8.011 | 0.092 | 35.2 |
| LNU6 | 24994.5 | 6.673 | 0.102 | 10.6 | LNU27 | 24873.1 | 7.767 | 0.045 | 31.1 |
| LNU6 | 24993.3 | 6.261 | 0.154 | 3.8 | LNU44 | 24922.3 | 10.244 | 0.000 | 72.9 |
| LNU79 | 24884.4 | 6.952 | 0.014 | 15.2 | LNU44 | 24923.3 | 8.210 | 0.130 | 38.6 |
| LNU79 | 24881.1 | 6.550 | 0.233 | 8.6 | LNU44 | 24924.3 | 6.559 | 0.435 | 10.7 |
| LNU79 | 24882.2 | 6.508 | 0.140 | 7.9 | LNU44 | 24923.1 | 6.379 | 0.492 | 7.7 |
| LNU79 | 24883.2 | 6.422 | 0.119 | 6.4 | LNU54 | 24903.5 | 9.523 | 0.016 | 60.7 |
| CONT. | — | 6.265 | — | 0.0 | LNU54 | 24902.4 | 7.707 | 0.237 | 30.1 |
| LNU109 | 24892.8 | 6.456 | 0.444 | 3.1 | LNU54 | 24901.2 | 7.417 | 0.368 | 25.2 |
| LNU143 | 25975.3 | 6.422 | 0.445 | 2.5 | LNU54 | 24903.3 | 6.587 | 0.292 | 11.2 |
| LNU154 | 14601.6 | 6.582 | 0.290 | 5.1 | LNU6 | 24992.3 | 9.573 | 0.029 | 61.6 |
| LNU196 | 25534.1 | 6.487 | 0.491 | 3.5 | LNU6 | 24994.5 | 9.480 | 0.098 | 60.0 |
| LNU207 | 24642.5 | 6.853 | 0.030 | 9.4 | LNU6 | 24994.2 | 8.627 | 0.028 | 45.6 |
| LNU207 | 24641.1 | 6.636 | 0.131 | 5.9 | LNU6 | 24994.1 | 6.376 | 0.617 | 7.6 |
| LNU50 | 26023.2 | 6.670 | 0.171 | 6.5 | LNU79 | 24884.4 | 9.253 | 0.084 | 56.2 |
| LNU50 | 26024.2 | 6.465 | 0.315 | 3.2 | LNU79 | 24881.1 | 8.970 | 0.067 | 51.4 |
| LNU52 | 25723.2 | 6.373 | 0.746 | 1.7 | LNU79 | 24883.2 | 8.450 | 0.010 | 42.6 |
| CONT. | — | 5.225 | — | 0.0 | LNU79 | 24884.3 | 8.381 | 0.068 | 41.5 |
| LNU143 | 25971.2 | 6.542 | 0.010 | 25.2 | LNU79 | 24882.2 | 8.338 | 0.007 | 40.7 |
| LNU143 | 25975.3 | 6.302 | 0.007 | 20.6 | CONT. | — | 5.283 | — | 0.0 |
| LNU143 | 25975.2 | 5.975 | 0.034 | 14.4 | LNU109 | 24892.8 | 7.899 | 0.001 | 49.5 |

TABLE 74-continued

Genes showing improved root performance at standard nitrogen growth conditions (T2 generation)

| | | Roots Length [cm] | | | | | Roots Coverage [cm2] | | |
|---|---|---|---|---|---|---|---|---|---|
| Gene Name | Event # | Ave. | p-value | % incr. | Gene Name | Event # | Ave. | p-value | % incr. |
| LNU143 | 25971.5 | 5.900 | 0.059 | 12.9 | LNU109 | 24891.5 | 7.630 | 0.001 | 44.4 |
| LNU143 | 25972.1 | 5.684 | 0.234 | 8.8 | LNU143 | 25975.2 | 6.615 | 0.035 | 25.2 |
| LNU154 | 14601.6 | 6.510 | 0.005 | 24.6 | LNU143 | 25972.1 | 5.812 | 0.490 | 10.0 |
| LNU207 | 24641.1 | 6.531 | 0.170 | 25.0 | LNU143 | 25975.3 | 5.802 | 0.294 | 9.8 |
| LNU207 | 24642.5 | 6.154 | 0.029 | 17.8 | LNU154 | 14604.7 | 7.402 | 0.014 | 40.1 |
| LNU207 | 24642.4 | 5.651 | 0.193 | 8.2 | LNU154 | 14601.6 | 6.345 | 0.203 | 20.1 |
| LNU211 | 24771.1 | 6.217 | 0.015 | 19.0 | LNU196 | 25532.2 | 7.364 | 0.294 | 39.4 |
| LNU211 | 24771.3 | 5.368 | 0.648 | 2.7 | LNU196 | 25534.1 | 6.774 | 0.009 | 28.2 |
| LNU52 | 25723.1 | 6.492 | 0.004 | 24.3 | LNU207 | 24642.5 | 7.232 | 0.151 | 36.9 |
| LNU52 | 25721.2 | 5.400 | 0.761 | 3.4 | LNU207 | 24642.4 | 6.473 | 0.126 | 22.5 |
| LNU52 | 25721.1 | 5.342 | 0.673 | 2.3 | LNU207 | 24644.18 | 6.146 | 0.444 | 16.3 |
| LNU69 | 14571.1 | 6.159 | 0.119 | 17.9 | LNU207 | 24644.13 | 5.800 | 0.264 | 9.8 |
| LNU69 | 14573.3 | 5.824 | 0.070 | 11.5 | LNU207 | 24641.1 | 5.667 | 0.688 | 7.3 |
| LNU69 | 14572.8 | 5.559 | 0.427 | 6.4 | LNU288 | 14562.9 | 6.574 | 0.223 | 24.4 |
| CONT. | — | 4.818 | — | 0.0 | LNU288 | 14564.9 | 6.230 | 0.216 | 17.9 |
| LNU150 | 24842.9 | 6.440 | 0.000 | 33.7 | LNU288 | 14562.7 | 5.939 | 0.495 | 12.4 |
| LNU150 | 24843.5 | 6.075 | 0.018 | 26.1 | LNU288 | 14562.12 | 5.738 | 0.647 | 8.6 |
| LNU150 | 24841.9 | 5.578 | 0.117 | 15.8 | LNU50 | 26025.4 | 7.278 | 0.006 | 37.8 |
| LNU150 | 24842.5 | 5.570 | 0.008 | 15.6 | LNU50 | 26024.2 | 7.156 | 0.012 | 35.5 |
| LNU179 | 24631.9 | 6.537 | 0.001 | 35.7 | LNU50 | 26023.5 | 6.065 | 0.332 | 14.8 |
| LNU179 | 24632.5 | 6.033 | 0.024 | 25.2 | LNU50 | 26023.2 | 5.464 | 0.644 | 3.4 |
| LNU179 | 24631.6 | 5.461 | 0.031 | 13.4 | LNU52 | 25723.2 | 7.247 | 0.018 | 37.2 |
| LNU179 | 24632.7 | 5.320 | 0.170 | 10.4 | LNU52 | 25721.4 | 6.053 | 0.380 | 14.6 |
| LNU179 | 24631.7 | 5.063 | 0.520 | 5.1 | LNU52 | 25721.3 | 6.011 | 0.283 | 13.8 |
| LNU232 | 26003.3 | 6.508 | 0.000 | 35.1 | CONT. | — | 6.028 | — | 0.0 |
| LNU232 | 26003.7 | 5.627 | 0.034 | 16.8 | LNU143 | 25975.3 | 6.851 | 0.315 | 13.6 |
| LNU232 | 26001.5 | 5.375 | 0.159 | 11.6 | LNU143 | 25975.2 | 6.827 | 0.345 | 13.3 |
| LNU232 | 26001.2 | 5.282 | 0.078 | 9.6 | LNU154 | 14601.6 | 8.039 | 0.364 | 33.4 |
| LNU232 | 26003.6 | 5.071 | 0.682 | 5.3 | LNU207 | 24641.1 | 7.283 | 0.464 | 20.8 |
| LNU235 | 26184.4 | 6.139 | 0.000 | 27.4 | LNU207 | 24642.5 | 7.096 | 0.217 | 17.7 |
| LNU235 | 26185.3 | 5.962 | 0.005 | 23.7 | LNU207 | 24642.4 | 6.809 | 0.368 | 13.0 |
| LNU235 | 26182.1 | 5.822 | 0.006 | 20.9 | LNU211 | 24771.1 | 7.170 | 0.287 | 18.9 |
| LNU235 | 26184.2 | 5.461 | 0.120 | 13.3 | LNU52 | 25723.1 | 7.431 | 0.307 | 23.3 |
| LNU242 | 25474.1 | 6.568 | 0.008 | 36.3 | LNU69 | 14571.1 | 7.692 | 0.211 | 27.6 |
| LNU242 | 25473.1 | 6.326 | 0.000 | 31.3 | LNU69 | 14573.3 | 6.458 | 0.686 | 7.1 |
| LNU242 | 25473.3 | 6.163 | 0.003 | 27.9 | LNU69 | 14572.8 | 6.374 | 0.697 | 5.7 |
| LNU242 | 25471.1 | 6.004 | 0.000 | 24.6 | CONT. | — | 4.102 | — | 0.0 |
| LNU242 | 25472.1 | 5.035 | 0.595 | 4.5 | LNU150 | 24843.5 | 7.038 | 0.000 | 71.6 |
| LNU76 | 26421.2 | 6.376 | 0.020 | 32.3 | LNU150 | 24842.9 | 7.011 | 0.010 | 70.9 |
| LNU76 | 26421.1 | 5.555 | 0.007 | 15.3 | LNU150 | 24841.9 | 6.414 | 0.003 | 56.4 |
| LNU76 | 26422.2 | 5.466 | 0.117 | 13.4 | LNU150 | 24843.9 | 5.198 | 0.098 | 26.7 |
| LNU76 | 26425.1 | 5.383 | 0.280 | 11.7 | LNU179 | 24631.9 | 5.977 | 0.047 | 45.7 |
| LNU76 | 26423.1 | 5.317 | 0.252 | 10.4 | LNU179 | 24632.5 | 5.099 | 0.209 | 24.3 |
| LNU95 | 13985.11 | 6.468 | 0.007 | 34.3 | LNU232 | 26003.7 | 6.928 | 0.092 | 68.9 |
| LNU95 | 13985.16 | 5.968 | 0.001 | 23.9 | LNU232 | 26003.3 | 6.034 | 0.029 | 47.1 |
| LNU95 | 13985.19 | 5.886 | 0.023 | 22.2 | LNU232 | 26003.6 | 4.465 | 0.691 | 8.8 |
| LNU95 | 13985.15 | 5.821 | 0.033 | 20.8 | LNU232 | 26001.5 | 4.325 | 0.792 | 5.4 |
| LNU95 | 13985.12 | 5.454 | 0.255 | 13.2 | LNU235 | 26185.3 | 5.570 | 0.023 | 35.8 |
| CONT. | — | 5.596 | — | 0.0 | LNU235 | 26184.4 | 5.454 | 0.110 | 33.0 |
| LNU150 | 24842.9 | 6.495 | 0.077 | 16.1 | LNU235 | 26182.1 | 4.710 | 0.157 | 14.8 |
| LNU150 | 24843.5 | 5.728 | 0.782 | 2.4 | LNU235 | 26184.2 | 4.681 | 0.569 | 14.1 |
| LNU179 | 24631.7 | 6.000 | 0.346 | 7.2 | LNU242 | 25474.1 | 7.610 | 0.042 | 85.5 |
| LNU179 | 24631.6 | 5.967 | 0.337 | 6.6 | LNU242 | 25473.1 | 5.905 | 0.000 | 44.0 |
| LNU179 | 24632.5 | 5.884 | 0.329 | 5.1 | LNU242 | 25471.1 | 5.858 | 0.000 | 42.8 |
| LNU232 | 26001.5 | 6.960 | 0.001 | 24.4 | LNU242 | 25473.3 | 4.707 | 0.315 | 14.8 |
| LNU232 | 26003.3 | 6.334 | 0.055 | 13.2 | LNU242 | 25472.1 | 4.342 | 0.761 | 5.8 |
| LNU235 | 26184.4 | 6.801 | 0.001 | 21.5 | LNU76 | 26421.2 | 7.302 | 0.025 | 78.0 |
| LNU235 | 26185.2 | 6.719 | 0.002 | 20.1 | LNU76 | 26421.1 | 5.648 | 0.015 | 37.7 |
| LNU235 | 26184.2 | 6.703 | 0.030 | 19.8 | LNU76 | 26423.1 | 4.653 | 0.574 | 13.4 |
| LNU235 | 26182.1 | 6.005 | 0.414 | 7.3 | LNU76 | 26422.2 | 4.641 | 0.416 | 13.1 |
| LNU242 | 25474.1 | 6.141 | 0.238 | 9.7 | LNU76 | 26425.1 | 4.577 | 0.624 | 11.6 |
| LNU288 | 14563.9 | 6.445 | 0.009 | 15.2 | LNU95 | 13985.11 | 7.498 | 0.065 | 82.8 |
| LNU288 | 14562.1 | 6.389 | 0.118 | 14.2 | LNU95 | 13985.15 | 6.783 | 0.001 | 65.4 |
| LNU288 | 14563.6 | 6.158 | 0.246 | 10.1 | LNU95 | 13985.16 | 5.850 | 0.119 | 42.6 |
| LNU288 | 14562.7 | 5.913 | 0.492 | 5.7 | LNU95 | 13985.19 | 5.634 | 0.228 | 37.3 |
| LNU288 | 14564.9 | 5.793 | 0.539 | 3.5 | LNU95 | 13985.12 | 4.641 | 0.605 | 13.1 |
| LNU76 | 26421.2 | 5.827 | 0.492 | 4.1 | CONT. | — | 5.171 | — | 0.0 |
| LNU95 | 13985.11 | 6.313 | 0.049 | 12.8 | LNU118 | 14013.6 | 6.735 | 0.106 | 30.3 |
| LNU95 | 13985.12 | 6.257 | 0.025 | 11.8 | LNU118 | 14012.15 | 6.697 | 0.326 | 29.5 |
| LNU95 | 13985.16 | 6.116 | 0.328 | 9.3 | LNU150 | 24842.9 | 7.643 | 0.119 | 47.8 |
| LNU95 | 13985.15 | 6.092 | 0.238 | 8.9 | LNU150 | 24841.9 | 6.335 | 0.177 | 22.5 |
| LNU95 | 13985.19 | 5.758 | 0.625 | 2.9 | LNU150 | 24843.5 | 6.217 | 0.117 | 20.2 |

TABLE 74-continued

Genes showing improved root performance at standard nitrogen growth conditions (T2 generation)

| Gene Name | Event # | Roots Length [cm] Ave. | p-value | % incr. | Gene Name | Event # | Roots Coverage [cm2] Ave. | p-value | % incr. |
|---|---|---|---|---|---|---|---|---|---|
| CONT. | — | 5.840 | — | 0.0 | LNU150 | 24841.6 | 5.370 | 0.709 | 3.8 |
| LNU101 | 27632.5 | 6.847 | 0.035 | 17.2 | LNU179 | 24632.7 | 6.009 | 0.211 | 16.2 |
| LNU101 | 27635.1 | 6.709 | 0.082 | 14.9 | LNU179 | 24631.7 | 5.926 | 0.488 | 14.6 |
| LNU101 | 27632.7 | 6.522 | 0.040 | 11.7 | LNU232 | 26001.5 | 8.215 | 0.001 | 58.9 |
| LNU101 | 27632.1 | 6.490 | 0.176 | 11.1 | LNU232 | 26003.3 | 7.174 | 0.037 | 38.7 |
| LNU101 | 27632.6 | 6.066 | 0.662 | 3.9 | LNU235 | 26184.4 | 10.268 | 0.005 | 98.6 |
| LNU128 | 26511.4 | 6.453 | 0.186 | 10.5 | LNU235 | 26185.2 | 7.934 | 0.016 | 53.4 |
| LNU128 | 26515.3 | 6.427 | 0.238 | 10.1 | LNU235 | 26184.2 | 7.761 | 0.020 | 50.1 |
| LNU128 | 26515.2 | 6.181 | 0.362 | 5.8 | LNU235 | 26182.1 | 5.904 | 0.305 | 14.2 |
| LNU128 | 26511.5 | 6.170 | 0.399 | 5.7 | LNU242 | 25474.1 | 7.459 | 0.024 | 44.2 |
| LNU192 | 28313.3 | 6.947 | 0.003 | 19.0 | LNU288 | 14563.9 | 8.852 | 0.004 | 71.2 |
| LNU192 | 28315.2 | 6.906 | 0.021 | 18.3 | LNU288 | 14562.1 | 7.472 | 0.019 | 44.5 |
| LNU192 | 28313.2 | 6.630 | 0.147 | 13.5 | LNU288 | 14563.6 | 6.435 | 0.217 | 24.4 |
| LNU206 | 27621.2 | 6.699 | 0.296 | 14.7 | LNU288 | 14564.9 | 5.887 | 0.167 | 13.9 |
| LNU206 | 27622.1 | 5.925 | 0.681 | 1.5 | LNU288 | 14562.7 | 5.436 | 0.775 | 5.1 |
| LNU282 | 27563.3 | 6.365 | 0.161 | 9.0 | LNU76 | 26421.2 | 5.861 | 0.250 | 13.3 |
| LNU69 | 14573.5 | 6.062 | 0.437 | 3.8 | LNU76 | 26425.1 | 5.685 | 0.341 | 9.9 |
| LNU69 | 14571.1 | 5.886 | 0.769 | 0.8 | LNU76 | 26422.2 | 5.561 | 0.685 | 7.5 |
| LNU75 | 27572.1 | 6.841 | 0.023 | 17.2 | LNU76 | 26423.1 | 5.357 | 0.778 | 3.6 |
| LNU75 | 27572.2 | 6.360 | 0.207 | 8.9 | LNU95 | 13985.15 | 7.642 | 0.003 | 47.8 |
| LNU75 | 27571.4 | 6.307 | 0.312 | 8.0 | LNU95 | 13985.16 | 7.507 | 0.080 | 45.2 |
| CONT. | — | 5.421 | — | 0.0 | LNU95 | 13985.12 | 6.609 | 0.092 | 27.8 |
| LNU101 | 27635.1 | 6.330 | 0.001 | 16.8 | CONT. | — | 5.155 | — | 0.0 |
| LNU101 | 27632.5 | 6.284 | 0.042 | 15.9 | LNU101 | 27632.1 | 6.954 | 0.000 | 34.9 |
| LNU118 | 14013.9 | 5.551 | 0.582 | 2.4 | LNU101 | 27635.1 | 6.553 | 0.015 | 27.1 |
| LNU128 | 26515.3 | 6.567 | 0.004 | 21.2 | LNU101 | 27632.5 | 6.041 | 0.341 | 17.2 |
| LNU206 | 27621.2 | 7.079 | 0.000 | 30.6 | LNU101 | 27632.6 | 5.659 | 0.660 | 9.8 |
| LNU206 | 27622.4 | 6.005 | 0.027 | 10.8 | LNU128 | 26515.3 | 8.036 | 0.036 | 55.9 |
| LNU206 | 27622.1 | 5.675 | 0.201 | 4.7 | LNU128 | 26515.2 | 6.980 | 0.059 | 35.4 |
| LNU249 | 26152.4 | 6.731 | 0.047 | 24.2 | LNU128 | 26511.4 | 6.416 | 0.275 | 24.5 |
| LNU249 | 26152.2 | 6.097 | 0.021 | 12.5 | LNU192 | 28315.2 | 7.992 | 0.006 | 55.0 |
| LNU249 | 26151.1 | 5.809 | 0.442 | 7.2 | LNU192 | 28313.2 | 7.389 | 0.056 | 43.3 |
| LNU249 | 26153.1 | 5.805 | 0.330 | 7.1 | LNU192 | 28313.3 | 6.309 | 0.015 | 22.4 |
| LNU282 | 27565.2 | 6.755 | 0.000 | 24.6 | LNU206 | 27621.2 | 7.023 | 0.099 | 36.2 |
| LNU282 | 27562.1 | 6.371 | 0.181 | 17.5 | LNU206 | 27621.1 | 6.013 | 0.362 | 16.6 |
| LNU282 | 27563.3 | 6.358 | 0.001 | 17.3 | LNU211 | 24771.1 | 6.969 | 0.137 | 35.2 |
| LNU282 | 27563.1 | 5.930 | 0.327 | 9.4 | LNU282 | 27563.3 | 6.654 | 0.242 | 29.1 |
| LNU282 | 27565.1 | 5.878 | 0.248 | 8.4 | LNU69 | 14571.1 | 6.648 | 0.029 | 29.0 |
| LNU288 | 14563.6 | 6.686 | 0.019 | 23.3 | LNU69 | 14573.5 | 6.575 | 0.082 | 27.5 |
| LNU288 | 14564.8 | 5.991 | 0.025 | 10.5 | LNU75 | 27572.2 | 7.816 | 0.048 | 51.6 |
| LNU288 | 14562.9 | 5.894 | 0.051 | 8.7 | LNU75 | 27572.3 | 6.896 | 0.047 | 33.8 |
| LNU288 | 14563.9 | 5.770 | 0.351 | 6.4 | LNU75 | 27572.1 | 6.642 | 0.116 | 28.8 |
| LNU288 | 14562.7 | 5.498 | 0.730 | 1.4 | LNU75 | 27571.4 | 5.830 | 0.472 | 13.1 |
| LNU75 | 27571.4 | 6.877 | 0.013 | 26.9 | CONT. | — | 5.119 | — | 0.0 |
| LNU75 | 27571.2 | 6.627 | 0.007 | 22.3 | LNU101 | 27632.5 | 7.394 | 0.082 | 44.4 |
| LNU75 | 27572.2 | 6.434 | 0.000 | 18.7 | LNU101 | 27635.1 | 5.507 | 0.659 | 7.6 |
| LNU75 | 27572.1 | 6.343 | 0.001 | 17.0 | LNU118 | 14012.15 | 6.364 | 0.142 | 24.3 |
| LNU75 | 27572.3 | 6.135 | 0.197 | 13.2 | LNU118 | 14013.6 | 6.134 | 0.192 | 19.8 |
| CONT. | — | 5.851 | — | 0.0 | LNU118 | 14013.9 | 5.512 | 0.470 | 7.7 |
| LNU11 | 28203.2 | 6.770 | 0.084 | 15.7 | LNU206 | 27621.2 | 7.528 | 0.002 | 47.1 |
| LNU11 | 28202.5 | 6.655 | 0.030 | 13.7 | LNU249 | 26153.1 | 6.400 | 0.084 | 25.0 |
| LNU11 | 28205.2 | 6.256 | 0.263 | 6.9 | LNU249 | 26152.4 | 5.917 | 0.429 | 15.6 |
| LNU11 | 28204.1 | 5.953 | 0.773 | 1.7 | LNU282 | 27563.1 | 6.191 | 0.310 | 20.9 |
| LNU112 | 28212.1 | 7.103 | 0.025 | 21.4 | LNU282 | 27565.2 | 5.531 | 0.547 | 8.0 |
| LNU112 | 28212.4 | 6.658 | 0.025 | 13.8 | LNU288 | 14564.8 | 7.100 | 0.026 | 38.7 |
| LNU14 | 27823.2 | 6.785 | 0.007 | 16.0 | LNU288 | 14563.6 | 6.894 | 0.136 | 34.7 |
| LNU14 | 27821.1 | 6.697 | 0.015 | 14.5 | LNU288 | 14562.9 | 6.758 | 0.062 | 32.0 |
| LNU14 | 27821.3 | 6.536 | 0.084 | 11.7 | LNU288 | 14563.9 | 6.601 | 0.128 | 28.9 |
| LNU183 | 24864.6 | 6.449 | 0.296 | 10.2 | LNU288 | 14562.7 | 5.378 | 0.745 | 5.1 |
| LNU201 | 28223.1 | 6.657 | 0.018 | 13.8 | LNU75 | 27572.2 | 7.467 | 0.086 | 45.9 |
| LNU201 | 28222.3 | 6.486 | 0.069 | 10.9 | LNU75 | 27571.4 | 7.273 | 0.099 | 42.1 |
| LNU201 | 28223.3 | 6.296 | 0.220 | 7.6 | LNU75 | 27571.2 | 6.832 | 0.023 | 33.5 |
| LNU201 | 28222.2 | 6.038 | 0.526 | 3.2 | LNU75 | 27572.3 | 6.252 | 0.407 | 22.1 |
| LNU268 | 26044.2 | 6.891 | 0.055 | 17.8 | CONT. | — | 6.888 | — | 0.0 |
| LNU268 | 26041.6 | 6.017 | 0.556 | 2.8 | LNU14 | 27821.3 | 7.893 | 0.445 | 14.6 |
| CONT. | — | 6.335 | — | 0.0 | LNU14 | 27823.2 | 7.231 | 0.669 | 5.0 |
| LNU11 | 28205.2 | 7.266 | 0.038 | 14.7 | LNU183 | 24863.12 | 7.193 | 0.724 | 4.4 |
| LNU11 | 28203.2 | 6.971 | 0.204 | 10.0 | LNU268 | 26044.2 | 8.591 | 0.288 | 24.7 |
| LNU11 | 28204.3 | 6.549 | 0.598 | 3.4 | CONT. | — | 6.290 | — | 0.0 |
| LNU112 | 28212.4 | 6.616 | 0.460 | 4.4 | LNU11 | 28205.2 | 9.031 | 0.002 | 43.6 |
| LNU112 | 28212.1 | 6.561 | 0.530 | 3.6 | LNU11 | 28203.2 | 8.193 | 0.057 | 30.3 |
| LNU14 | 27821.3 | 7.170 | 0.048 | 13.2 | LNU11 | 28205.1 | 7.731 | 0.091 | 22.9 |

TABLE 74-continued

Genes showing improved root performance at standard nitrogen growth conditions (T2 generation)

| | | Roots Length [cm] | | | | | Roots Coverage [cm2] | | |
|---|---|---|---|---|---|---|---|---|---|
| Gene Name | Event # | Ave. | p-value | % incr. | Gene Name | Event # | Ave. | p-value | % incr. |
| LNU183 | 24863.1 | 6.996 | 0.242 | 10.4 | LNU11 | 28204.3 | 7.658 | 0.100 | 21.8 |
| LNU183 | 24864.6 | 6.598 | 0.474 | 4.2 | LNU11 | 28202.5 | 7.517 | 0.152 | 19.5 |
| LNU191 | 28323.1 | 6.529 | 0.614 | 3.1 | LNU11 | 28204.1 | 6.773 | 0.246 | 7.7 |
| LNU201 | 28222.2 | 6.989 | 0.131 | 10.3 | LNU112 | 28212.4 | 7.304 | 0.058 | 16.1 |
| LNU268 | 26043.4 | 6.545 | 0.603 | 3.3 | LNU112 | 28212.1 | 6.984 | 0.195 | 11.0 |
| CONT. | — | 5.852 | — | 0.0 | LNU14 | 27821.3 | 8.988 | 0.064 | 42.9 |
| LNU107 | 14585.5 | 6.287 | 0.288 | 7.4 | LNU14 | 27823.2 | 7.003 | 0.606 | 11.3 |
| LNU116 | 14492.5 | 6.136 | 0.610 | 4.8 | LNU183 | 24865.1 | 11.077 | 0.001 | 76.1 |
| LNU121 | 27711.1 | 6.388 | 0.223 | 9.2 | LNU183 | 24863.1 | 10.729 | 0.057 | 70.6 |
| LNU121 | 27713.4 | 6.358 | 0.207 | 8.7 | LNU183 | 24863.12 | 8.917 | 0.023 | 41.8 |
| LNU126 | 25343.3 | 6.722 | 0.055 | 14.9 | LNU183 | 24864.6 | 8.916 | 0.003 | 41.8 |
| LNU126 | 25345.1 | 6.584 | 0.135 | 12.5 | LNU191 | 28323.1 | 8.175 | 0.253 | 30.0 |
| LNU126 | 25343.1 | 6.437 | 0.194 | 10.0 | LNU191 | 28325.4 | 6.688 | 0.356 | 6.3 |
| LNU126 | 25343.4 | 6.144 | 0.489 | 5.0 | LNU201 | 28222.2 | 10.400 | 0.029 | 65.4 |
| LNU158 | 27433.3 | 7.014 | 0.109 | 19.9 | LNU201 | 28223.1 | 6.822 | 0.376 | 8.5 |
| LNU158 | 27433.2 | 6.299 | 0.374 | 7.6 | LNU268 | 26043.4 | 8.266 | 0.057 | 31.4 |
| LNU158 | 27432.5 | 6.176 | 0.436 | 5.5 | LNU268 | 26041.6 | 7.535 | 0.443 | 19.8 |
| LNU158 | 27434.5 | 6.080 | 0.686 | 3.9 | LNU268 | 26041.4 | 7.476 | 0.159 | 18.9 |
| LNU177 | 24765.2 | 7.112 | 0.025 | 21.5 | LNU268 | 26044.2 | 6.808 | 0.370 | 8.2 |
| LNU177 | 24762.6 | 6.607 | 0.070 | 12.9 | CONT. | — | 5.249 | — | 0.0 |
| LNU177 | 24764.9 | 6.268 | 0.392 | 7.1 | LNU107 | 14585.5 | 6.577 | 0.434 | 25.3 |
| LNU177 | 24763.6 | 6.176 | 0.396 | 5.5 | LNU107 | 14583.8 | 6.445 | 0.293 | 22.8 |
| LNU182 | 27521.4 | 6.800 | 0.042 | 16.2 | LNU107 | 14584.9 | 5.987 | 0.175 | 14.1 |
| LNU182 | 25384.5 | 6.767 | 0.101 | 15.6 | LNU116 | 14492.5 | 5.750 | 0.366 | 9.5 |
| LNU182 | 25384.1 | 6.019 | 0.762 | 2.8 | LNU116 | 14494.5 | 5.574 | 0.589 | 6.2 |
| LNU2 | 27842.3 | 6.959 | 0.029 | 18.9 | LNU116 | 14492.9 | 5.515 | 0.583 | 5.1 |
| LNU2 | 25713.1 | 6.193 | 0.445 | 5.8 | LNU121 | 27713.4 | 8.247 | 0.002 | 57.1 |
| LNU225 | 25991.5 | 7.007 | 0.038 | 19.7 | LNU121 | 25642.2 | 7.499 | 0.133 | 42.9 |
| LNU225 | 25991.2 | 6.717 | 0.114 | 14.8 | LNU121 | 27711.1 | 7.285 | 0.022 | 38.8 |
| LNU225 | 25991.3 | 6.613 | 0.172 | 13.0 | LNU121 | 27713.1 | 5.912 | 0.261 | 12.6 |
| LNU225 | 25991.1 | 6.286 | 0.464 | 7.4 | LNU126 | 25345.1 | 7.763 | 0.024 | 47.9 |
| LNU239 | 26284.1 | 6.856 | 0.025 | 17.2 | LNU126 | 25343.3 | 6.965 | 0.016 | 32.7 |
| LNU239 | 26284.2 | 6.651 | 0.068 | 13.7 | LNU126 | 25343.1 | 6.521 | 0.210 | 24.2 |
| LNU239 | 26281.1 | 6.264 | 0.439 | 7.0 | LNU126 | 25343.4 | 5.499 | 0.674 | 4.8 |
| LNU239 | 26283.3 | 6.028 | 0.712 | 3.0 | LNU158 | 27433.3 | 8.968 | 0.137 | 70.8 |
| LNU57 | 27852.1 | 6.999 | 0.020 | 19.6 | LNU158 | 27433.2 | 8.046 | 0.004 | 53.3 |
| LNU57 | 27854.3 | 6.744 | 0.059 | 15.2 | LNU158 | 27432.5 | 6.290 | 0.360 | 19.8 |
| LNU83 | 27684.1 | 6.527 | 0.133 | 11.5 | LNU177 | 24762.6 | 8.887 | 0.085 | 69.3 |
| LNU83 | 27681.4 | 6.381 | 0.260 | 9.0 | LNU177 | 24765.2 | 7.192 | 0.269 | 37.0 |
| LNU83 | 27682.1 | 6.213 | 0.357 | 6.2 | LNU177 | 24764.9 | 5.932 | 0.179 | 13.0 |
| LNU83 | 27685.1 | 5.973 | 0.771 | 2.1 | LNU182 | 25384.5 | 7.997 | 0.058 | 52.3 |
| CONT. | — | 5.715 | — | 0.0 | LNU182 | 27521.4 | 7.490 | 0.053 | 42.7 |
| LNU107 | 14584.9 | 6.891 | 0.021 | 20.6 | LNU182 | 25384.1 | 6.840 | 0.039 | 30.3 |
| LNU107 | 14583.8 | 6.667 | 0.061 | 16.7 | LNU2 | 27842.3 | 7.641 | 0.069 | 45.6 |
| LNU107 | 14585.5 | 6.158 | 0.237 | 7.8 | LNU2 | 25713.1 | 7.344 | 0.011 | 39.9 |
| LNU116 | 14491.5 | 6.504 | 0.094 | 13.8 | LNU2 | 27842.1 | 6.809 | 0.436 | 29.7 |
| LNU116 | 14494.5 | 5.784 | 0.774 | 1.2 | LNU225 | 25991.5 | 9.233 | 0.029 | 75.9 |
| LNU121 | 27713.1 | 7.058 | 0.001 | 23.5 | LNU225 | 25991.2 | 7.038 | 0.116 | 34.1 |
| LNU121 | 27711.1 | 6.792 | 0.005 | 18.9 | LNU225 | 25991.1 | 6.470 | 0.244 | 23.3 |
| LNU121 | 27713.4 | 6.571 | 0.098 | 15.0 | LNU225 | 25991.3 | 6.141 | 0.551 | 17.0 |
| LNU126 | 25343.1 | 7.209 | 0.000 | 26.2 | LNU239 | 26284.1 | 6.751 | 0.113 | 28.6 |
| LNU126 | 25343.4 | 6.524 | 0.086 | 14.2 | LNU239 | 26283.2 | 5.920 | 0.548 | 12.8 |
| LNU126 | 25345.1 | 6.324 | 0.216 | 10.7 | LNU239 | 26281.1 | 5.794 | 0.397 | 10.4 |
| LNU126 | 25343.3 | 6.246 | 0.108 | 9.3 | LNU57 | 27852.1 | 7.854 | 0.013 | 49.6 |
| LNU158 | 27433.3 | 7.495 | 0.000 | 31.2 | LNU57 | 27854.3 | 6.344 | 0.102 | 20.9 |
| LNU158 | 27432.5 | 7.179 | 0.000 | 25.6 | LNU57 | 27854.5 | 5.880 | 0.366 | 12.0 |
| LNU158 | 27433.2 | 7.006 | 0.002 | 22.6 | LNU83 | 27681.4 | 7.249 | 0.097 | 38.1 |
| LNU158 | 27434.1 | 6.795 | 0.000 | 18.9 | LNU83 | 27684.1 | 5.767 | 0.589 | 9.9 |
| LNU158 | 27434.5 | 6.698 | 0.055 | 17.2 | LNU83 | 27685.1 | 5.561 | 0.651 | 5.9 |
| LNU177 | 24764.12 | 7.403 | 0.006 | 29.6 | CONT. | — | 4.915 | — | 0.0 |
| LNU177 | 24763.6 | 7.161 | 0.001 | 25.3 | LNU107 | 14584.9 | 10.490 | 0.008 | 113.4 |
| LNU177 | 24765.2 | 7.070 | 0.000 | 23.7 | LNU107 | 14583.8 | 7.949 | 0.019 | 61.7 |
| LNU177 | 24764.9 | 5.894 | 0.552 | 3.1 | LNU107 | 14585.2 | 6.870 | 0.009 | 39.8 |
| LNU182 | 25384.2 | 6.882 | 0.008 | 20.4 | LNU107 | 14583.1 | 5.412 | 0.458 | 10.1 |
| LNU182 | 25384.6 | 6.781 | 0.012 | 18.7 | LNU107 | 14585.5 | 5.284 | 0.413 | 7.5 |
| LNU182 | 27521.4 | 6.773 | 0.017 | 18.5 | LNU116 | 14493.6 | 7.433 | 0.046 | 51.2 |
| LNU182 | 25384.1 | 6.597 | 0.012 | 15.5 | LNU116 | 14494.5 | 7.121 | 0.098 | 44.9 |
| LNU182 | 25384.5 | 6.430 | 0.002 | 12.5 | LNU116 | 14491.5 | 7.065 | 0.145 | 43.8 |
| LNU2 | 27842.1 | 7.238 | 0.000 | 26.7 | LNU116 | 14492.5 | 6.075 | 0.007 | 23.6 |
| LNU2 | 25713.1 | 6.894 | 0.001 | 20.6 | LNU116 | 14492.9 | 5.198 | 0.791 | 5.8 |
| LNU2 | 27842.3 | 6.701 | 0.035 | 17.3 | LNU121 | 27713.4 | 10.520 | 0.009 | 114.1 |
| LNU225 | 25991.3 | 7.743 | 0.000 | 35.5 | LNU121 | 27713.1 | 9.336 | 0.011 | 90.0 |

TABLE 74-continued

Genes showing improved root performance at standard nitrogen growth conditions (T2 generation)

| | Roots Length [cm] | | | | Roots Coverage [cm2] | | | |
|---|---|---|---|---|---|---|---|---|
| Gene Name | Event # | Ave. | p-value | % incr. | Gene Name | Event # | Ave. | p-value | % incr. |
| LNU225 | 25991.5 | 7.166 | 0.001 | 25.4 | LNU121 | 27711.1 | 7.107 | 0.029 | 44.6 |
| LNU225 | 25991.2 | 6.660 | 0.008 | 16.6 | LNU121 | 25642.2 | 5.748 | 0.472 | 17.0 |
| LNU225 | 25991.8 | 6.386 | 0.139 | 11.7 | LNU126 | 25343.1 | 7.086 | 0.055 | 44.2 |
| LNU225 | 25991.1 | 6.180 | 0.020 | 8.1 | LNU126 | 25343.3 | 5.673 | 0.262 | 15.4 |
| LNU239 | 26284.1 | 6.838 | 0.005 | 19.7 | LNU126 | 25343.4 | 5.597 | 0.015 | 13.9 |
| LNU239 | 26281.1 | 6.800 | 0.002 | 19.0 | LNU126 | 25345.1 | 5.517 | 0.332 | 12.3 |
| LNU239 | 26283.3 | 6.798 | 0.002 | 19.0 | LNU158 | 27433.3 | 10.395 | 0.000 | 111.5 |
| LNU239 | 26284.2 | 6.544 | 0.042 | 14.5 | LNU158 | 27432.5 | 10.059 | 0.009 | 104.7 |
| LNU239 | 26283.2 | 6.142 | 0.233 | 7.5 | LNU158 | 27433.2 | 7.322 | 0.044 | 49.0 |
| LNU57 | 27852.1 | 7.280 | 0.003 | 27.4 | LNU158 | 27434.5 | 7.124 | 0.031 | 44.9 |
| LNU57 | 27854.5 | 7.061 | 0.000 | 23.6 | LNU158 | 27434.1 | 6.038 | 0.135 | 22.9 |
| LNU57 | 27851.2 | 7.054 | 0.000 | 23.4 | LNU177 | 24764.12 | 7.964 | 0.000 | 62.1 |
| LNU57 | 27854.3 | 6.356 | 0.004 | 11.2 | LNU177 | 24763.6 | 6.811 | 0.057 | 38.6 |
| LNU83 | 27685.1 | 7.354 | 0.000 | 28.7 | LNU177 | 24765.2 | 5.371 | 0.457 | 9.3 |
| LNU83 | 27682.1 | 7.128 | 0.034 | 24.7 | LNU182 | 25384.6 | 8.604 | 0.031 | 75.1 |
| LNU83 | 27685.2 | 7.081 | 0.000 | 23.9 | LNU182 | 25384.1 | 7.588 | 0.003 | 54.4 |
| LNU83 | 27681.4 | 6.754 | 0.002 | 18.2 | LNU182 | 25384.2 | 7.046 | 0.020 | 43.4 |
| LNU83 | 27684.1 | 6.555 | 0.118 | 14.7 | LNU182 | 27521.4 | 6.026 | 0.156 | 22.6 |
| | | | | | LNU182 | 25384.5 | 5.953 | 0.156 | 21.1 |
| | | | | | LNU2 | 27842.1 | 8.180 | 0.000 | 66.4 |
| | | | | | LNU2 | 27842.3 | 7.899 | 0.005 | 60.7 |
| | | | | | LNU2 | 25713.1 | 7.574 | 0.090 | 54.1 |
| | | | | | LNU2 | 27845.2 | 5.617 | 0.386 | 14.3 |
| | | | | | LNU225 | 25991.2 | 11.048 | 0.002 | 124.8 |
| | | | | | LNU225 | 25991.3 | 10.621 | 0.024 | 116.1 |
| | | | | | LNU225 | 25991.8 | 7.226 | 0.094 | 47.0 |
| | | | | | LNU225 | 25991.5 | 6.962 | 0.001 | 41.7 |
| | | | | | LNU225 | 25991.1 | 6.869 | 0.003 | 39.8 |
| | | | | | LNU239 | 26283.3 | 7.477 | 0.057 | 52.1 |
| | | | | | LNU239 | 26281.1 | 7.013 | 0.013 | 42.7 |
| | | | | | LNU239 | 26284.2 | 5.944 | 0.170 | 21.0 |
| | | | | | LNU239 | 26284.1 | 5.651 | 0.207 | 15.0 |
| | | | | | LNU239 | 26283.2 | 5.605 | 0.113 | 14.0 |
| | | | | | LNU57 | 27854.5 | 9.187 | 0.002 | 86.9 |
| | | | | | LNU57 | 27851.2 | 9.142 | 0.003 | 86.0 |
| | | | | | LNU57 | 27852.1 | 8.944 | 0.006 | 82.0 |
| | | | | | LNU57 | 27854.3 | 5.731 | 0.095 | 16.6 |
| | | | | | LNU83 | 27685.1 | 8.992 | 0.003 | 83.0 |
| | | | | | LNU83 | 27685.2 | 8.420 | 0.046 | 71.3 |
| | | | | | LNU83 | 27682.1 | 7.321 | 0.092 | 49.0 |
| | | | | | LNU83 | 27681.4 | 6.918 | 0.004 | 40.8 |
| | | | | | LNU83 | 27684.1 | 5.685 | 0.383 | 15.7 |
| | | | | | CONT. | — | 7.469 | — | |
| | | | | | LNU17 | 13991.1 | 8.395 | 0.2 | 12.3 |
| | | | | | CONT. | — | 5.518 | | 0.0 |
| | | | | | LNU129 | 27501.2 | 7.071 | <0.1 | 28.2 |
| | | | | | LNU129 | 27502.4 | 6.038 | <0.8 | 9.4 |
| | | | | | LNU129 | 27503.4 | 5.784 | <0.8 | 4.8 |
| | | | | | LNU129 | 27504.3 | 9.078 | <0.05 | 64.5 |
| | | | | | LNU147 | 27513.2 | 7.281 | <0.1 | 32.0 |
| | | | | | LNU147 | 27514.2 | 6.115 | <0.8 | 10.8 |
| | | | | | LNU153 | 24851.3 | 7.253 | <0.1 | 31.4 |
| | | | | | LNU189 | 26382.4 | 6.849 | <0.2 | 24.1 |
| | | | | | LNU189 | 26383.1 | 6.937 | <0.2 | 25.7 |
| | | | | | LNU189 | 26385.1 | 6.744 | <0.2 | 22.2 |
| | | | | | LNU219 | 27462.1 | 8.526 | <0.1 | 54.5 |
| | | | | | LNU219 | 27464.2 | 7.111 | <0.1 | 28.9 |
| | | | | | LNU256 | 26212.3 | 5.987 | <0.8 | 8.5 |
| | | | | | LNU256 | 26214.1 | 8.193 | <0.05 | 48.5 |
| | | | | | LNU256 | 26214.2 | 6.910 | <0.2 | 25.2 |
| | | | | | LNU257 | 26254.1 | 6.804 | <0.2 | 23.3 |
| | | | | | LNU257 | 26254.3 | 9.461 | <0.05 | 71.5 |
| | | | | | LNU257 | 26255.3 | 6.481 | <0.5 | 17.5 |
| | | | | | LNU261 | 27403.2 | 5.664 | <0.9 | 2.7 |
| | | | | | LNU33 | 25552.2 | 7.217 | <0.1 | 30.8 |
| | | | | | LNU33 | 25555.1 | 5.970 | <0.8 | 8.2 |
| | | | | | LNU35 | 27422.1 | 7.462 | <0.1 | 35.2 |
| | | | | | LNU35 | 27424.3 | 6.419 | | 16.3 |
| | | | | | LNU35 | 27424.4 | 7.739 | <0.05 | 40.2 |
| | | | | | LNU50 | 26022.1 | 7.402 | <0.05 | 34.1 |
| | | | | | LNU50 | 26024.1 | 7.051 | <0.1 | 27.8 |
| | | | | | LNU50 | 26025.3 | 8.616 | <0.05 | 56.1 |

TABLE 74-continued

Genes showing improved root performance at standard nitrogen growth conditions
(T2 generation)

| Gene Name | Event # | Ave. | p-value | % incr. | Gene Name | Event # | Ave. | p-value | % incr. |
|---|---|---|---|---|---|---|---|---|---|
| | | | | | LNU70 | 25311.3 | 5.862 | <0.8 | 6.2 |
| | | | | | LNU70 | 25311.4 | 6.021 | <0.8 | 9.1 |
| | | | | | LNU70 | 25313.1 | 6.324 | <0.7 | 14.6 |

Table 74.
"CONT."—Control;
"Ave"—Average;
"% Incr." = % increment.

TABLE 75

Genes showing improved root performance at standard nitrogen growth conditions
(T1 generation)

| Gene Name | Time Point | Ave. | p-value | % incr. | Gene Name | Time Point | Ave. | p-value | % incr. |
|---|---|---|---|---|---|---|---|---|---|
| CONT. | Roots Length TP2 | 1.840 | — | 0.0 | CONT. | Roots Coverage TP2 | 0.925 | — | 0.0 |
| LNU107 | Roots Length TP2 | 1.922 | 0.619 | 4.4 | LNU118 | Roots Coverage TP2 | 0.951 | 0.651 | 2.9 |
| LNU181 | Roots Length TP2 | 1.856 | 0.869 | 0.9 | LNU121 | Roots Coverage TP2 | 1.581 | 0.007 | 70.9 |
| LNU121 | Roots Length TP2 | 2.431 | 0.015 | 32.1 | LNU150 | Roots Coverage TP2 | 0.939 | 0.839 | 1.6 |
| LNU154 | Roots Length TP2 | 2.237 | 0.176 | 21.5 | LNU154 | Roots Coverage TP2 | 1.227 | 0.250 | 32.7 |
| LNU210 | Roots Length TP2 | 2.124 | 0.122 | 15.4 | LNU210 | Roots Coverage TP2 | 1.180 | 0.032 | 27.7 |
| LNU68 | Roots Length TP2 | 1.915 | 0.646 | 4.1 | LNU68 | Roots Coverage TP2 | 0.931 | 0.961 | 0.6 |
| CONT. | Roots_Length_TP3 | 3.468 | — | 0.0 | CONT. | Roots Coverage TP3 | 2.488 | — | 0.0 |
| LNU121 | Roots_Length_TP3 | 4.286 | 0.007 | 23.6 | LNU121 | Roots Coverage TP3 | 4.048 | 0.000 | 62.7 |
| LNU154 | Roots_Length_TP3 | 3.653 | 0.613 | 5.4 | LNU154 | Roots Coverage TP3 | 2.785 | 0.583 | 12.0 |
| LNU210 | Roots_Length_TP3 | 3.707 | 0.366 | 6.9 | LNU210 | Roots Coverage TP3 | 2.770 | 0.188 | 11.3 |
| CONT. | Roots Length TP2 | 1.572 | — | 0.0 | CONT. | Roots Coverage TP2 | 1.015 | — | 0.0 |
| LNU127 | Roots Length TP2 | 1.797 | 0.327 | 14.3 | LNU265 | Roots Coverage TP2 | 1.029 | 0.935 | 1.3 |
| LNU188 | Roots Length TP2 | 1.769 | 0.191 | 12.5 | LNU275 | Roots Coverage TP2 | 2.413 | 0.003 | 137.6 |
| LNU2 | Roots Length TP2 | 1.673 | 0.574 | 6.4 | LNU57 | Roots Coverage TP2 | 1.571 | 0.008 | 54.7 |
| LNU239 | Roots Length TP2 | 1.895 | 0.214 | 20.5 | LNU58 | Roots Coverage TP2 | 1.301 | 0.143 | 28.1 |

TABLE 75-continued

Genes showing improved root performance at standard nitrogen growth conditions
(T1 generation)

| Gene Name | Time Point | Roots Length [cm] Ave. | p-value | % incr. | Gene Name | Time Point | Roots Coverage [cm2] Ave. | p-value | % incr. |
|---|---|---|---|---|---|---|---|---|---|
| LNU258 | Roots Length TP2 | 1.648 | 0.689 | 4.8 | LNU83 | Roots Coverage TP2 | 1.659 | 0.013 | 63.3 |
| LNU265 | Roots Length TP2 | 1.947 | 0.030 | 23.8 | CONT. | Roots Coverage TP3 | 2.621 | — | 0.0 |
| LNU275 | Roots Length TP2 | 2.607 | 0.002 | 65.8 | LNU275 | Roots Coverage TP3 | 7.009 | 0.005 | 167.5 |
| LNU32 | Roots Length TP2 | 1.886 | 0.107 | 20.0 | LNU57 | Roots Coverage TP3 | 4.363 | 0.004 | 66.5 |
| LNU57 | Roots Length TP2 | 2.332 | 0.000 | 48.3 | LNU58 | Roots Coverage TP3 | 3.190 | 0.066 | 21.7 |
| LNU58 | Roots Length TP2 | 2.138 | 0.001 | 36.0 | LNU83 | Roots Coverage TP3 | 4.487 | 0.007 | 71.2 |
| LNU64 | Roots Length TP2 | 1.642 | 0.633 | 4.4 | CONT. | Roots Coverage TP2 | 0.613 | — | 0.0 |
| LNU83 | Roots Length TP2 | 2.568 | 0.001 | 63.3 | LNU176 | Roots Coverage TP2 | 0.663 | 0.738 | 8.2 |
| CONT. | Roots_Length_TP3 | 3.387 | — | 0.0 | LNU214 | Roots Coverage TP2 | 0.845 | 0.016 | 38.0 |
| LNU239 | Roots_Length_TP3 | 3.480 | 0.842 | 2.7 | LNU223 | Roots Coverage TP2 | 0.741 | 0.189 | 20.9 |
| LNU265 | Roots_Length_TP3 | 3.489 | 0.675 | 3.0 | LNU233 | Roots Coverage TP2 | 0.764 | 0.159 | 24.7 |
| LNU275 | Roots_Length_TP3 | 4.574 | 0.017 | 35.0 | LNU245 | Roots Coverage TP2 | 0.794 | 0.027 | 29.6 |
| LNU57 | Roots_Length_TP3 | 4.598 | 0.002 | 35.7 | LNU247 | Roots Coverage TP2 | 0.673 | 0.653 | 9.9 |
| LNU58 | Roots_Length_TP3 | 3.745 | 0.059 | 10.5 | LNU251 | Roots Coverage TP2 | 0.645 | 0.748 | 5.2 |
| LNU83 | Roots_Length_TP3 | 4.733 | 0.003 | 39.7 | LNU284 | Roots Coverage TP2 | 0.710 | 0.330 | 15.8 |
| CONT. | Roots Length TP2 | 1.563 | — | 0.0 | LNU289 | Roots Coverage TP2 | 0.880 | 0.014 | 43.6 |
| LNU176 | Roots Length TP2 | 1.695 | 0.430 | 8.4 | LNU70 | Roots Coverage TP2 | 0.902 | 0.041 | 47.1 |
| LNU214 | Roots Length TP2 | 2.127 | 0.006 | 36.1 | LNU85 | Roots Coverage TP2 | 0.852 | 0.012 | 39.0 |
| LNU223 | Roots Length TP2 | 1.907 | 0.005 | 22.0 | LNU86 | Roots Coverage TP2 | 0.665 | 0.618 | 8.5 |
| LNU233 | Roots Length TP2 | 1.932 | 0.003 | 23.6 | CONT. | Roots Coverage TP3 | 1.504 | — | 0.0 |
| LNU245 | Roots Length TP2 | 2.021 | 0.001 | 29.3 | LNU176 | Roots Coverage TP3 | 2.038 | 0.118 | 35.5 |
| LNU247 | Roots Length TP2 | 1.690 | 0.621 | 8.1 | LNU214 | Roots Coverage TP3 | 1.816 | 0.190 | 20.7 |
| LNU251 | Roots Length TP2 | 1.944 | 0.251 | 24.4 | LNU223 | Roots Coverage TP3 | 1.925 | 0.066 | 27.9 |

TABLE 75-continued

Genes showing improved root performance at standard nitrogen growth conditions (T1 generation)

| Gene Name | Time Point | Roots Length [cm] Ave. | p-value | % incr. | Gene Name | Time Point | Roots Coverage [cm2] Ave. | p-value | % incr. |
|---|---|---|---|---|---|---|---|---|---|
| LNU284 | Roots Length TP2 | 1.925 | 0.198 | 23.2 | LNU233 | Roots Coverage TP3 | 1.884 | 0.253 | 25.2 |
| LNU289 | Roots Length TP2 | 2.082 | 0.003 | 33.2 | LNU245 | Roots Coverage TP3 | 1.644 | 0.332 | 9.3 |
| LNU70 | Roots Length TP2 | 1.921 | 0.157 | 22.9 | LNU247 | Roots Coverage TP3 | 1.527 | 0.933 | 1.5 |
| LNU85 | Roots Length TP2 | 2.118 | 0.007 | 35.5 | LNU284 | Roots Coverage TP3 | 1.802 | 0.345 | 19.8 |
| LNU86 | Roots Length TP2 | 1.690 | 0.435 | 8.1 | LNU289 | Roots Coverage TP3 | 1.991 | 0.011 | 32.4 |
| CONT. | Roots_Length_TP3 | 2.862 | — | 0.0 | LNU70 | Roots Coverage TP3 | 2.020 | 0.140 | 34.2 |
| LNU176 | Roots_Length_TP3 | 3.292 | 0.150 | 15.0 | LNU85 | Roots Coverage TP3 | 2.097 | 0.066 | 39.4 |
| LNU214 | Roots_Length_TP3 | 3.448 | 0.062 | 20.5 | LNU86 | Roots Coverage TP3 | 1.521 | 0.955 | 1.1 |
| LNU223 | Roots_Length_TP3 | 3.310 | 0.050 | 15.6 | CONT. | Roots Coverage TP2 | 1.338 | — | 0.0 |
| LNU233 | Roots_Length_TP3 | 3.361 | 0.073 | 17.5 | LNU105 | Roots Coverage TP2 | 1.395 | 0.693 | 4.3 |
| LNU245 | Roots_Length_TP3 | 3.407 | 0.043 | 19.0 | LNU115 | Roots Coverage TP2 | 1.405 | 0.617 | 5.0 |
| LNU247 | Roots_Length_TP3 | 2.993 | 0.659 | 4.6 | LNU134 | Roots Coverage TP2 | 1.689 | 0.236 | 26.2 |
| LNU251 | Roots_Length_TP3 | 2.986 | 0.779 | 4.3 | LNU190 | Roots Coverage TP2 | 1.556 | 0.392 | 16.3 |
| LNU284 | Roots_Length_TP3 | 3.321 | 0.267 | 16.0 | LNU198 | Roots Coverage TP2 | 1.410 | 0.715 | 5.4 |
| LNU289 | Roots_Length_TP3 | 3.375 | 0.016 | 17.9 | LNU200 | Roots Coverage TP2 | 1.753 | 0.054 | 31.0 |
| LNU70 | Roots_Length_TP3 | 3.398 | 0.192 | 18.7 | CONT. | Roots Coverage TP3 | 3.172 | — | 0.0 |
| LNU85 | Roots_Length_TP3 | 3.726 | 0.032 | 30.2 | LNU105 | Roots Coverage TP3 | 3.383 | 0.707 | 6.7 |
| CONT. | Roots Length TP2 | 2.410 | — | 0.0 | LNU115 | Roots Coverage TP3 | 3.577 | 0.321 | 12.8 |
| LNU105 | Roots Length TP2 | 2.686 | 0.077 | 11.5 | LNU134 | Roots Coverage TP3 | 3.704 | 0.399 | 16.8 |
| LNU115 | Roots Length TP2 | 2.523 | 0.420 | 4.7 | LNU190 | Roots Coverage TP3 | 3.202 | 0.958 | 1.0 |
| LNU123 | Roots Length TP2 | 2.532 | 0.386 | 5.1 | LNU198 | Roots Coverage TP3 | 3.239 | 0.885 | 2.1 |
| LNU134 | Roots Length TP2 | 2.759 | 0.093 | 14.4 | LNU200 | Roots Coverage TP3 | 3.387 | 0.625 | 6.8 |

TABLE 75-continued

Genes showing improved root performance at standard nitrogen growth conditions (T1 generation)

| Gene Name | Time Point | Roots Length [cm] Ave. | p-value | % incr. | Gene Name | Time Point | Roots Coverage [cm2] Ave. | p-value | % incr. |
|---|---|---|---|---|---|---|---|---|---|
| LNU190 | Roots Length TP2 | 2.613 | 0.533 | 8.4 | CONT. | Roots Coverage TP2 | 1.312 | — | 0.0 |
| LNU198 | Roots Length TP2 | 2.559 | 0.606 | 6.2 | LNU51 | Roots Coverage TP2 | 1.395 | 0.554 | 6.4 |
| LNU200 | Roots Length TP2 | 2.803 | 0.129 | 16.3 | LNU59 | Roots Coverage TP2 | 1.312 | 0.999 | 0.0 |
| CONT. | Roots_Length_TP3 | 3.919 | — | 0.0 | CONT. | Roots Coverage TP3 | 3.140 | — | 0.0 |
| LNU105 | Roots_Length_TP3 | 4.351 | 0.235 | 11.0 | LNU51 | Roots Coverage TP3 | 3.256 | 0.671 | 3.7 |
| LNU115 | Roots_Length_TP3 | 4.242 | 0.218 | 8.3 | LNU59 | Roots Coverage TP3 | 3.253 | 0.612 | 3.6 |
| LNU134 | Roots_Length_TP3 | 4.380 | 0.178 | 11.8 | | | | | |
| LNU190 | Roots_Length_TP3 | 3.931 | 0.978 | 0.3 | | | | | |
| LNU198 | Roots_Length_TP3 | 4.030 | 0.799 | 2.9 | | | | | |
| LNU200 | Roots_Length_TP3 | 4.038 | 0.734 | 3.0 | | | | | |
| CONT. | Roots Length TP2 | 2.210 | — | 0.0 | | | | | |
| LNU225 | Roots Length TP2 | 2.248 | 0.809 | 1.7 | | | | | |
| LNU243 | Roots Length TP2 | 2.283 | 0.627 | 3.3 | | | | | |
| LNU244 | Roots Length TP2 | 2.266 | 0.846 | 2.6 | | | | | |
| LNU51 | Roots Length TP2 | 2.712 | 0.022 | 22.7 | | | | | |
| LNU59 | Roots Length TP2 | 2.522 | 0.315 | 14.1 | | | | | |
| LNU60 | Roots Length TP2 | 2.420 | 0.377 | 9.5 | | | | | |
| CONT. | Roots_Length_TP3 | 4.117 | — | 0.0 | | | | | |
| LNU225 | Roots_Length_TP3 | 4.183 | 0.834 | 1.6 | | | | | |
| LNU244 | Roots_Length_TP3 | 4.133 | 0.973 | 0.4 | | | | | |
| LNU51 | Roots_Length_TP3 | 4.561 | 0.105 | 10.8 | | | | | |
| LNU59 | Roots_Length_TP3 | 4.405 | 0.210 | 7.0 | | | | | |
| LNU60 | Roots_Length_TP3 | 4.125 | 0.984 | 0.2 | | | | | |

Table 75.
"CONT."—Control;
"Ave."—Average;
"% Incr." = % increment.

The genes listed in Tables 76 and 77 improved plant growth rate (leaf area, root length and root coverage growth rate) when grown at standard nitrogen concentration levels. These produced plants that grew faster than control plants when grown under standard nitrogen growth conditions. Faster growth was observed when growth rate of leaf area and root length and coverage was measured. The genes were cloned under the regulation of a constitutive promoter (At6669) or root preferred promoter (RootP). Evaluation of each gene was performed by testing the performance of different number of events. Some of the genes were evaluated in more than one tissue culture assay resulting in positive results as well. Event with p-value <0.1 was considered statistically significant

TABLE 76

Genes showing improved growth rate at standard nitrogen growth conditions (T2 generation)

| | | RGR Of Leaf Area | | | | | RGR Of Roots Coverage | | | | | RGR Of Roots Length | | |
|---|---|---|---|---|---|---|---|---|---|---|---|---|---|---|
| Gene Name | Event # | Ave. | p-value | % incr. | Gene Name | Event # | Ave. | p-value | % incr. | Gene Name | Event # | Ave. | p-value | % incr. |
| CONT. | — | 0.05 | — | 0 | CONT. | — | 0.47 | — | 0 | CONT. | — | 0.42 | — | 0 |
| LNU100 | 14474.3 | 0.09 | 0.02 | 72 | LNU100 | 14474.3 | 0.67 | 0.03 | 42 | LNU100 | 14471.4 | 0.49 | 0.34 | 16 |
| LNU100 | 14474.4 | 0.06 | 0.20 | 29 | LNU100 | 14474.4 | 0.66 | 0.08 | 42 | LNU100 | 14474.4 | 0.48 | 0.29 | 13 |
| LNU100 | 14471.4 | 0.05 | 0.50 | 10 | LNU100 | 14471.4 | 0.60 | 0.09 | 29 | LNU100 | 14474.3 | 0.47 | 0.19 | 11 |
| LNU104 | 25033.3 | 0.07 | 0.03 | 51 | LNU104 | 25033.3 | 0.60 | 0.09 | 28 | LNU100 | 14473.1 | 0.46 | 0.26 | 10 |
| LNU213 | 24654.4 | 0.09 | 0.01 | 81 | LNU213 | 24654.4 | 0.73 | 0.01 | 56 | LNU100 | 14473.3 | 0.44 | 0.72 | 4 |
| LNU213 | 24653.2 | 0.09 | 0.00 | 79 | LNU213 | 24653.2 | 0.66 | 0.01 | 41 | LNU104 | 25033.3 | 0.49 | 0.07 | 17 |
| LNU213 | 24651.1 | 0.06 | 0.04 | 31 | LNU213 | 24651.1 | 0.58 | 0.11 | 24 | LNU213 | 24654.4 | 0.49 | 0.14 | 17 |
| LNU218 | 24783.2 | 0.11 | 0.00 | 121 | LNU218 | 24783.2 | 0.93 | 0.00 | 98 | LNU213 | 24653.2 | 0.48 | 0.14 | 15 |
| LNU218 | 24781.7 | 0.06 | 0.07 | 31 | LNU218 | 24781.2 | 0.57 | 0.16 | 22 | LNU213 | 24651.1 | 0.45 | 0.61 | 6 |
| LNU4 | 25134.1 | 0.07 | 0.01 | 41 | LNU218 | 24781.7 | 0.55 | 0.20 | 18 | LNU218 | 24783.2 | 0.65 | 0.00 | 54 |
| LNU4 | 25134.2 | 0.05 | 0.51 | 10 | LNU4 | 25134.1 | 0.55 | 0.18 | 19 | LNU218 | 24781.2 | 0.45 | 0.35 | 8 |
| LNU48 | 24803.2 | 0.08 | 0.01 | 53 | LNU48 | 24802.2 | 0.58 | 0.15 | 25 | LNU218 | 24781.7 | 0.45 | 0.46 | 8 |
| LNU48 | 24802.2 | 0.06 | 0.07 | 28 | LNU48 | 24804.4 | 0.54 | 0.43 | 15 | LNU4 | 25134.1 | 0.48 | 0.28 | 14 |
| LNU48 | 24804.4 | 0.06 | 0.21 | 21 | LNU48 | 24803.2 | 0.53 | 0.38 | 12 | LNU4 | 25131.1 | 0.44 | 0.67 | 4 |
| LNU8 | 25063.1 | 0.08 | 0.01 | 57 | LNU8 | 25063.1 | 0.87 | 0.00 | 87 | LNU48 | 24802.2 | 0.44 | 0.65 | 5 |
| LNU8 | 25062.2 | 0.07 | 0.04 | 45 | LNU8 | 25062.2 | 0.58 | 0.08 | 24 | LNU48 | 24804.4 | 0.44 | 0.64 | 5 |
| LNU8 | 25063.6 | 0.06 | 0.08 | 29 | LNU94 | 24833.1 | 0.49 | 0.73 | 5 | LNU8 | 25063.1 | 0.57 | 0.00 | 36 |
| LNU94 | 24833.3 | 0.06 | 0.17 | 20 | CONT. | — | 0.64 | — | 0 | LNU8 | 25062.2 | 0.49 | 0.10 | 17 |
| LNU94 | 24834.1 | 0.05 | 0.78 | 5 | LNU1 | 24682.2 | 0.87 | 0.04 | 36 | LNU94 | 24834.1 | 0.43 | 0.80 | 3 |
| CONT. | — | 0.08 | — | 0 | LNU1 | 24684.1 | 0.77 | 0.13 | 20 | CONT. | — | 0.56 | — | 0 |
| LNU1 | 24681.3 | 0.09 | 0.30 | 19 | LNU1 | 24682.1 | 0.77 | 0.08 | 20 | LNU1 | 24682.2 | 0.59 | 0.70 | 4 |
| LNU1 | 24682.2 | 0.09 | 0.37 | 15 | LNU1 | 24681.1 | 0.71 | 0.36 | 11 | LNU178 | 14614.5 | 0.59 | 0.51 | 5 |
| LNU133 | 24744.3 | 0.13 | 0.00 | 70 | LNU133 | 24744.3 | 1.13 | 0.00 | 77 | LNU215 | 24661.4 | 0.58 | 0.79 | 3 |
| LNU133 | 24741.1 | 0.13 | 0.01 | 69 | LNU133 | 24741.1 | 1.06 | 0.02 | 65 | CONT. | — | 0.53 | — | 0 |
| LNU175 | 24732.1 | 0.11 | 0.03 | 42 | LNU133 | 24741.2 | 0.74 | 0.16 | 16 | LNU120 | 25463.7 | 0.71 | 0.00 | 34 |
| LNU175 | 24734.4 | 0.11 | 0.03 | 42 | LNU175 | 24732.1 | 1.10 | 0.00 | 71 | LNU120 | 25463.6 | 0.58 | 0.18 | 11 |
| LNU175 | 24732.4 | 0.09 | 0.47 | 12 | LNU175 | 24732.4 | 1.05 | 0.00 | 64 | LNU120 | 25463.3 | 0.58 | 0.23 | 10 |
| LNU175 | 24731.2 | 0.08 | 0.66 | 7 | LNU175 | 24734.4 | 0.98 | 0.00 | 53 | LNU120 | 25464.1 | 0.55 | 0.68 | 4 |
| LNU178 | 14614.5 | 0.10 | 0.09 | 29 | LNU175 | 24731.2 | 0.70 | 0.52 | 10 | LNU124 | 14502.7 | 0.59 | 0.17 | 12 |
| LNU178 | 14611.5 | 0.09 | 0.10 | 19 | LNU178 | 14614.5 | 1.05 | 0.00 | 63 | LNU124 | 14501.1 | 0.57 | 0.33 | 8 |
| LNU178 | 14611.1 | 0.08 | 0.77 | 3 | LNU178 | 14611.5 | 0.89 | 0.05 | 40 | LNU124 | 14502.1 | 0.55 | 0.53 | 5 |
| LNU215 | 24664.3 | 0.13 | 0.00 | 69 | LNU178 | 14612.1 | 0.74 | 0.31 | 15 | LNU124 | 14501.7 | 0.55 | 0.62 | 4 |
| LNU215 | 24661.4 | 0.09 | 0.32 | 12 | LNU178 | 14611.4 | 0.67 | 0.73 | 4 | LNU132 | 14102.9 | 0.58 | 0.19 | 11 |
| LNU24 | 24973.1 | 0.10 | 0.03 | 36 | LNU215 | 24664.3 | 1.12 | 0.00 | 74 | LNU132 | 14102.7 | 0.54 | 0.78 | 3 |
| LNU24 | 24971.4 | 0.09 | 0.08 | 21 | LNU215 | 24661.4 | 0.88 | 0.00 | 38 | LNU140 | 14111.6 | 0.57 | 0.22 | 9 |
| LNU24 | 24971.2 | 0.08 | 0.39 | 10 | LNU215 | 24663.4 | 0.70 | 0.47 | 10 | LNU140 | 14114.8 | 0.57 | 0.36 | 8 |
| LNU6 | 24992.3 | 0.14 | 0.02 | 85 | LNU215 | 24664.2 | 0.67 | 0.73 | 4 | LNU140 | 14112.7 | 0.55 | 0.62 | 4 |
| LNU6 | 24993.3 | 0.09 | 0.46 | 15 | LNU24 | 24971.4 | 0.98 | 0.02 | 53 | LNU180 | 24723.3 | 0.60 | 0.10 | 14 |
| LNU82 | 24823.1 | 0.11 | 0.21 | 37 | LNU24 | 24973.1 | 0.90 | 0.07 | 40 | LNU180 | 24724.3 | 0.59 | 0.22 | 11 |
| LNU9 | 25001.3 | 0.11 | 0.00 | 45 | LNU6 | 24992.3 | 1.04 | 0.03 | 63 | LNU196 | 25533.3 | 0.55 | 0.65 | 4 |
| CONT. | — | 0.04 | — | 0 | LNU6 | 24993.3 | 0.78 | 0.38 | 22 | LNU20 | 24933.2 | 0.59 | 0.20 | 11 |
| LNU120 | 25463.7 | 0.08 | 0.00 | 74 | LNU82 | 24823.1 | 0.84 | 0.10 | 32 | LNU20 | 24933.4 | 0.55 | 0.52 | 5 |
| LNU120 | 25463.3 | 0.06 | 0.00 | 39 | LNU82 | 24824.3 | 0.68 | 0.59 | 7 | LNU36 | 25562.3 | 0.62 | 0.04 | 17 |
| LNU120 | 25463.6 | 0.06 | 0.01 | 34 | LNU9 | 25001.3 | 0.96 | 0.00 | 49 | LNU71 | 25853.4 | 0.54 | 0.78 | 2 |
| LNU124 | 14501.7 | 0.07 | 0.00 | 69 | LNU9 | 25001.1 | 0.83 | 0.03 | 29 | CONT. | — | 0.51 | — | 0 |
| LNU124 | 14501.1 | 0.06 | 0.01 | 35 | LNU9 | 25001.2 | 0.71 | 0.37 | 11 | LNU1 | 24682.1 | 0.56 | 0.52 | 10 |
| LNU124 | 14502.7 | 0.05 | 0.10 | 25 | CONT. | — | 0.54 | — | 0 | LNU1 | 24683.2 | 0.56 | 0.54 | 10 |
| LNU124 | 14502.1 | 0.05 | 0.58 | 6 | LNU120 | 25463.7 | 0.96 | 0.00 | 77 | LNU1 | 24681.1 | 0.55 | 0.64 | 7 |
| LNU132 | 14102.7 | 0.06 | 0.00 | 40 | LNU120 | 25463.6 | 0.72 | 0.02 | 33 | LNU1 | 24681.3 | 0.54 | 0.70 | 6 |
| LNU132 | 14102.9 | 0.06 | 0.02 | 29 | LNU120 | 25463.3 | 0.62 | 0.22 | 14 | LNU110 | 24953.2 | 0.63 | 0.12 | 24 |
| LNU132 | 14101.9 | 0.05 | 0.62 | 6 | LNU124 | 14502.7 | 0.72 | 0.02 | 32 | LNU110 | 24954.3 | 0.58 | 0.34 | 13 |
| LNU140 | 14112.7 | 0.07 | 0.01 | 51 | LNU124 | 14501.7 | 0.68 | 0.09 | 25 | LNU175 | 24733.4 | 0.61 | 0.19 | 19 |
| LNU140 | 14111.6 | 0.06 | 0.05 | 27 | LNU124 | 14502.1 | 0.62 | 0.20 | 15 | LNU175 | 24732.1 | 0.60 | 0.20 | 18 |
| LNU140 | 14114.8 | 0.05 | 0.38 | 10 | LNU124 | 14501.1 | 0.60 | 0.40 | 11 | LNU175 | 24734.4 | 0.58 | 0.36 | 13 |
| LNU180 | 24724.3 | 0.08 | 0.00 | 87 | LNU132 | 14102.7 | 0.66 | 0.11 | 22 | LNU175 | 24733.1 | 0.58 | 0.40 | 13 |
| LNU180 | 24723.3 | 0.06 | 0.05 | 45 | LNU132 | 14102.9 | 0.63 | 0.21 | 16 | LNU175 | 24732.2 | 0.54 | 0.65 | 6 |
| LNU180 | 24721.4 | 0.05 | 0.18 | 20 | LNU140 | 14111.6 | 0.70 | 0.04 | 29 | LNU19 | 25151.11 | 0.54 | 0.71 | 5 |
| LNU196 | 25534.1 | 0.07 | 0.00 | 66 | LNU140 | 14112.7 | 0.67 | 0.10 | 23 | LNU215 | 24664.2 | 0.65 | 0.07 | 27 |
| LNU196 | 25533.1 | 0.05 | 0.06 | 24 | LNU140 | 14114.8 | 0.65 | 0.09 | 21 | LNU215 | 24663.4 | 0.59 | 0.31 | 15 |
| LNU196 | 25533.3 | 0.05 | 0.22 | 23 | LNU180 | 24724.3 | 0.80 | 0.00 | 47 | LNU215 | 24663.3 | 0.59 | 0.29 | 15 |
| LNU20 | 24933.2 | 0.07 | 0.01 | 52 | LNU180 | 24723.3 | 0.69 | 0.06 | 27 | LNU215 | 24661.4 | 0.57 | 0.39 | 12 |
| LNU20 | 24932.4 | 0.05 | 0.73 | 4 | LNU180 | 24721.4 | 0.59 | 0.42 | 10 | LNU27 | 24873.1 | 0.60 | 0.23 | 18 |
| LNU36 | 25562.3 | 0.07 | 0.00 | 50 | LNU180 | 24724.1 | 0.58 | 0.58 | 6 | LNU27 | 24871.4 | 0.57 | 0.40 | 12 |
| LNU36 | 25562.4 | 0.05 | 0.10 | 23 | LNU196 | 25534.1 | 0.70 | 0.06 | 29 | LNU27 | 24873.4 | 0.57 | 0.48 | 11 |
| LNU36 | 25561.2 | 0.05 | 0.48 | 9 | LNU196 | 25533.3 | 0.60 | 0.46 | 11 | LNU44 | 24922.3 | 0.62 | 0.16 | 21 |
| LNU71 | 25853.4 | 0.08 | 0.00 | 72 | LNU196 | 25533.1 | 0.59 | 0.51 | 9 | LNU44 | 24924.2 | 0.61 | 0.25 | 18 |
| LNU71 | 25852.4 | 0.05 | 0.07 | 23 | LNU20 | 24933.2 | 0.77 | 0.01 | 42 | LNU44 | 24923.3 | 0.58 | 0.34 | 14 |
| CONT. | — | 0.06 | — | 0 | LNU20 | 24932.4 | 0.62 | 0.25 | 15 | LNU44 | 24923.1 | 0.57 | 0.43 | 11 |
| LNU1 | 24681.3 | 0.07 | 0.01 | 24 | LNU20 | 24933.4 | 0.57 | 0.66 | 5 | LNU54 | 24901.2 | 0.69 | 0.03 | 34 |
| LNU110 | 24952.3 | 0.06 | 0.42 | 8 | LNU36 | 25562.3 | 0.90 | 0.00 | 66 | LNU54 | 24902.4 | 0.67 | 0.06 | 31 |
| LNU110 | 24953.3 | 0.06 | 0.76 | 4 | LNU36 | 25562.4 | 0.65 | 0.15 | 20 | LNU54 | 24902.7 | 0.59 | 0.27 | 15 |

TABLE 76-continued

Genes showing improved growth rate at standard nitrogen growth conditions (T2 generation)

| | | RGR Of Leaf Area | | | | | RGR Of Roots Coverage | | | | | RGR Of Roots Length | | |
|---|---|---|---|---|---|---|---|---|---|---|---|---|---|---|
| Gene Name | Event # | Ave. | p-value | % incr. | Gene Name | Event # | Ave. | p-value | % incr. | Gene Name | Event # | Ave. | p-value | % incr. |
| LNU175 | 24733.4 | 0.09 | 0.00 | 53 | LNU71 | 25853.4 | 0.80 | 0.00 | 48 | LNU54 | 24903.3 | 0.57 | 0.50 | 11 |
| LNU175 | 24732.2 | 0.08 | 0.15 | 37 | CONT. | — | 0.60 | — | 0 | LNU54 | 24903.5 | 0.54 | 0.74 | 5 |
| LNU19 | 25151.1 | 0.08 | 0.01 | 31 | LNU1 | 24681.3 | 0.74 | 0.12 | 23 | LNU79 | 24881.1 | 0.66 | 0.05 | 29 |
| LNU215 | 24663.4 | 0.09 | 0.01 | 48 | LNU1 | 24683.2 | 0.63 | 0.80 | 5 | LNU79 | 24882.2 | 0.62 | 0.14 | 22 |
| LNU27 | 24873.1 | 0.09 | 0.00 | 53 | LNU110 | 24952.3 | 0.67 | 0.49 | 11 | LNU79 | 24884.4 | 0.54 | 0.67 | 6 |
| LNU44 | 24924.3 | 0.09 | 0.01 | 44 | LNU110 | 24953.3 | 0.62 | 0.80 | 4 | CONT. | — | 0.51 | — | 0 |
| LNU54 | 24903.5 | 0.08 | 0.07 | 32 | LNU175 | 24733.4 | 1.10 | 0.00 | 83 | LNU109 | 24892.6 | 0.58 | 0.03 | 14 |
| LNU54 | 24902.4 | 0.07 | 0.43 | 9 | LNU175 | 24732.2 | 0.80 | 0.07 | 32 | LNU109 | 24892.5 | 0.56 | 0.14 | 10 |
| LNU79 | 24884.4 | 0.09 | 0.00 | 51 | LNU175 | 24734.4 | 0.69 | 0.34 | 14 | LNU109 | 24891.2 | 0.54 | 0.37 | 6 |
| LNU79 | 24881.1 | 0.08 | 0.00 | 41 | LNU175 | 24732.1 | 0.68 | 0.40 | 13 | LNU109 | 24892.8 | 0.53 | 0.59 | 4 |
| LNU79 | 24884.3 | 0.07 | 0.09 | 22 | LNU19 | 25151.1 | 0.69 | 0.29 | 15 | LNU109 | 24891.5 | 0.52 | 0.68 | 2 |
| CONT. | — | 0.07 | — | 0 | LNU19 | 25153.3 | 0.63 | 0.73 | 5 | LNU110 | 24952.3 | 0.59 | 0.10 | 15 |
| LNU109 | 24891.2 | 0.11 | 0.00 | 71 | LNU215 | 24663.4 | 0.92 | 0.01 | 53 | LNU110 | 24952.1 | 0.58 | 0.18 | 13 |
| LNU109 | 24892.6 | 0.10 | 0.00 | 50 | LNU215 | 24664.2 | 0.83 | 0.05 | 39 | LNU110 | 24953.2 | 0.56 | 0.49 | 9 |
| LNU109 | 24892.5 | 0.09 | 0.12 | 33 | LNU215 | 24663.3 | 0.68 | 0.39 | 13 | LNU110 | 24954.1 | 0.56 | 0.37 | 9 |
| LNU109 | 24891.5 | 0.08 | 0.08 | 23 | LNU215 | 24663.1 | 0.65 | 0.71 | 9 | LNU110 | 24954.3 | 0.53 | 0.57 | 4 |
| LNU110 | 24952.1 | 0.13 | 0.00 | 88 | LNU27 | 24873.1 | 0.96 | 0.00 | 60 | LNU133 | 24744.3 | 0.61 | 0.04 | 19 |
| LNU110 | 24954.1 | 0.11 | 0.00 | 67 | LNU27 | 24873.4 | 0.72 | 0.27 | 19 | LNU133 | 24741.2 | 0.56 | 0.16 | 10 |
| LNU110 | 24952.3 | 0.10 | 0.01 | 52 | LNU27 | 24871.4 | 0.70 | 0.27 | 17 | LNU133 | 24741.1 | 0.56 | 0.20 | 10 |
| LNU110 | 24953.2 | 0.10 | 0.00 | 51 | LNU44 | 24924.2 | 0.78 | 0.05 | 30 | LNU133 | 24742.2 | 0.54 | 0.34 | 5 |
| LNU110 | 24954.3 | 0.09 | 0.01 | 36 | LNU44 | 24924.3 | 0.76 | 0.14 | 26 | LNU19 | 25151.11 | 0.54 | 0.38 | 6 |
| LNU133 | 24741.2 | 0.13 | 0.00 | 93 | LNU44 | 24923.3 | 0.74 | 0.21 | 22 | LNU19 | 25151.1 | 0.53 | 0.62 | 3 |
| LNU133 | 24741.1 | 0.13 | 0.00 | 89 | LNU44 | 24922.3 | 0.65 | 0.61 | 8 | LNU27 | 24873.1 | 0.62 | 0.05 | 21 |
| LNU133 | 24744.3 | 0.12 | 0.00 | 81 | LNU44 | 24923.1 | 0.63 | 0.78 | 4 | LNU27 | 24871.4 | 0.61 | 0.00 | 19 |
| LNU133 | 24742.2 | 0.10 | 0.00 | 54 | LNU54 | 24902.4 | 0.91 | 0.02 | 52 | LNU27 | 24873.4 | 0.54 | 0.39 | 5 |
| LNU133 | 24744.2 | 0.10 | 0.00 | 47 | LNU54 | 24901.2 | 0.85 | 0.06 | 41 | LNU44 | 24924.3 | 0.54 | 0.29 | 6 |
| LNU19 | 25151.1 | 0.13 | 0.00 | 89 | LNU54 | 24903.5 | 0.80 | 0.06 | 34 | LNU44 | 24923.3 | 0.54 | 0.64 | 5 |
| LNU19 | 25153.3 | 0.09 | 0.06 | 39 | LNU54 | 24903.3 | 0.76 | 0.15 | 26 | LNU44 | 24922.3 | 0.53 | 0.56 | 4 |
| LNU19 | 25151.11 | 0.08 | 0.20 | 14 | LNU79 | 24881.1 | 1.13 | 0.00 | 88 | LNU54 | 24901.2 | 0.60 | 0.01 | 18 |
| LNU27 | 24873.4 | 0.13 | 0.00 | 94 | LNU79 | 24884.3 | 0.82 | 0.03 | 36 | LNU54 | 24902.4 | 0.56 | 0.26 | 9 |
| LNU27 | 24871.4 | 0.09 | 0.02 | 35 | LNU79 | 24884.3 | 0.70 | 0.28 | 17 | LNU54 | 24903.5 | 0.56 | 0.16 | 8 |
| LNU27 | 24873.1 | 0.08 | 0.12 | 16 | LNU79 | 24882.2 | 0.69 | 0.45 | 14 | LNU54 | 24903.3 | 0.53 | 0.67 | 3 |
| LNU44 | 24922.3 | 0.11 | 0.00 | 69 | CONT. | — | 0.70 | — | 0 | LNU6 | 24992.3 | 0.60 | 0.08 | 17 |
| LNU44 | 24924.3 | 0.09 | 0.01 | 38 | LNU109 | 24892.6 | 1.14 | 0.00 | 64 | LNU6 | 24994.2 | 0.60 | 0.02 | 17 |
| LNU44 | 24923.1 | 0.08 | 0.03 | 24 | LNU109 | 24892.5 | 0.98 | 0.05 | 41 | LNU6 | 24994.5 | 0.58 | 0.11 | 12 |
| LNU44 | 24924.2 | 0.07 | 0.75 | 4 | LNU109 | 24891.2 | 0.88 | 0.06 | 26 | LNU79 | 24882.2 | 0.57 | 0.18 | 10 |
| LNU54 | 24903.5 | 0.13 | 0.00 | 100 | LNU109 | 24891.5 | 0.86 | 0.09 | 23 | LNU79 | 24881.1 | 0.56 | 0.27 | 9 |
| LNU54 | 24902.4 | 0.10 | 0.02 | 54 | LNU109 | 24892.8 | 0.72 | 0.78 | 3 | LNU79 | 24883.2 | 0.56 | 0.18 | 8 |
| LNU54 | 24901.2 | 0.09 | 0.04 | 36 | LNU110 | 24952.1 | 1.18 | 0.00 | 69 | LNU79 | 24884.4 | 0.55 | 0.31 | 7 |
| LNU6 | 24994.5 | 0.12 | 0.00 | 85 | LNU110 | 24954.1 | 1.06 | 0.00 | 51 | CONT. | — | 0.47 | — | 0 |
| LNU6 | 24992.3 | 0.12 | 0.00 | 84 | LNU110 | 24953.2 | 1.04 | 0.03 | 49 | LNU109 | 24892.8 | 0.59 | 0.00 | 25 |
| LNU6 | 24994.2 | 0.09 | 0.06 | 30 | LNU110 | 24952.3 | 0.99 | 0.02 | 42 | LNU109 | 24892.6 | 0.51 | 0.44 | 8 |
| LNU6 | 24994.1 | 0.09 | 0.13 | 28 | LNU110 | 24954.3 | 0.98 | 0.01 | 40 | LNU109 | 24891.5 | 0.51 | 0.35 | 8 |
| LNU79 | 24882.2 | 0.12 | 0.00 | 76 | LNU133 | 24744.3 | 1.15 | 0.00 | 65 | LNU143 | 25972.1 | 0.56 | 0.11 | 18 |
| LNU79 | 24881.1 | 0.11 | 0.00 | 68 | LNU133 | 24741.2 | 1.09 | 0.00 | 56 | LNU143 | 25975.3 | 0.53 | 0.04 | 12 |
| LNU79 | 24884.4 | 0.10 | 0.01 | 55 | LNU133 | 24741.1 | 1.05 | 0.00 | 53 | LNU143 | 25971.5 | 0.52 | 0.18 | 11 |
| LNU79 | 24883.2 | 0.10 | 0.01 | 52 | LNU133 | 24742.2 | 0.92 | 0.04 | 33 | LNU143 | 25975.2 | 0.50 | 0.60 | 5 |
| LNU79 | 24884.3 | 0.10 | 0.01 | 49 | LNU133 | 24744.2 | 0.87 | 0.08 | 25 | LNU154 | 14601.6 | 0.55 | 0.04 | 17 |
| CONT. | — | 0.05 | — | 0 | LNU19 | 25151.1 | 1.04 | 0.00 | 50 | LNU154 | 14604.6 | 0.50 | 0.48 | 6 |
| LNU109 | 24892.8 | 0.11 | 0.00 | 100 | LNU19 | 25151.11 | 0.88 | 0.04 | 27 | LNU154 | 14604.5 | 0.49 | 0.68 | 3 |
| LNU109 | 24891.5 | 0.09 | 0.02 | 61 | LNU19 | 25153.3 | 0.88 | 0.13 | 27 | LNU196 | 25532.2 | 0.53 | 0.19 | 13 |
| LNU109 | 24891.2 | 0.08 | 0.04 | 47 | LNU27 | 24873.4 | 1.01 | 0.02 | 45 | LNU196 | 25534.1 | 0.52 | 0.29 | 10 |
| LNU109 | 24892.6 | 0.06 | 0.63 | 10 | LNU27 | 24873.1 | 0.92 | 0.03 | 32 | LNU207 | 24641.1 | 0.55 | 0.04 | 17 |
| LNU143 | 25975.2 | 0.07 | 0.01 | 35 | LNU27 | 24871.4 | 0.92 | 0.05 | 32 | LNU207 | 24644.18 | 0.52 | 0.30 | 11 |
| LNU143 | 25972.1 | 0.07 | 0.14 | 33 | LNU44 | 24922.3 | 1.19 | 0.00 | 71 | LNU207 | 24642.5 | 0.52 | 0.30 | 10 |
| LNU143 | 25975.3 | 0.06 | 0.22 | 14 | LNU44 | 24923.3 | 0.97 | 0.05 | 39 | LNU207 | 24642.4 | 0.51 | 0.40 | 9 |
| LNU154 | 14604.7 | 0.09 | 0.00 | 55 | LNU44 | 24924.3 | 0.76 | 0.50 | 9 | LNU207 | 24644.13 | 0.51 | 0.27 | 8 |
| LNU154 | 14601.6 | 0.07 | 0.14 | 27 | LNU44 | 24923.1 | 0.74 | 0.63 | 6 | LNU288 | 14562.7 | 0.55 | 0.04 | 17 |
| LNU154 | 14604.6 | 0.07 | 0.15 | 27 | LNU54 | 24903.5 | 1.09 | 0.00 | 56 | LNU288 | 14562.9 | 0.51 | 0.43 | 9 |
| LNU154 | 14602.8 | 0.07 | 0.18 | 19 | LNU54 | 24902.4 | 0.88 | 0.20 | 26 | LNU288 | 14564.9 | 0.50 | 0.48 | 5 |
| LNU196 | 25532.2 | 0.11 | 0.01 | 98 | LNU54 | 24901.2 | 0.84 | 0.25 | 21 | LNU288 | 14562.1 | 0.49 | 0.71 | 3 |
| LNU196 | 25534.1 | 0.09 | 0.00 | 59 | LNU54 | 24903.3 | 0.76 | 0.41 | 10 | LNU50 | 26025.4 | 0.53 | 0.09 | 13 |
| LNU196 | 25531.2 | 0.06 | 0.40 | 16 | LNU6 | 24992.3 | 1.13 | 0.00 | 62 | LNU50 | 26024.2 | 0.53 | 0.08 | 12 |
| LNU207 | 24642.5 | 0.10 | 0.00 | 82 | LNU6 | 24994.5 | 1.11 | 0.02 | 59 | LNU50 | 26023.2 | 0.52 | 0.18 | 11 |
| LNU207 | 24642.4 | 0.07 | 0.05 | 32 | LNU6 | 24994.2 | 1.03 | 0.01 | 47 | LNU52 | 25723.2 | 0.50 | 0.56 | 6 |
| LNU207 | 24644.18 | 0.07 | 0.15 | 22 | LNU6 | 24994.1 | 0.77 | 0.54 | 10 | LNU52 | 25721.3 | 0.50 | 0.63 | 6 |
| LNU207 | 24644.13 | 0.06 | 0.39 | 14 | LNU79 | 24884.4 | 1.05 | 0.02 | 51 | CONT. | — | 0.44 | — | 0 |
| LNU207 | 24641.1 | 0.06 | 0.42 | 10 | LNU79 | 24881.1 | 1.02 | 0.00 | 46 | LNU143 | 25971.2 | 0.56 | 0.03 | 28 |
| LNU288 | 14564.9 | 0.08 | 0.01 | 46 | LNU79 | 24883.2 | 0.98 | 0.01 | 41 | LNU143 | 25975.3 | 0.54 | 0.05 | 23 |
| LNU288 | 14562.12 | 0.07 | 0.11 | 31 | LNU79 | 24884.3 | 0.98 | 0.03 | 40 | LNU143 | 25975.2 | 0.52 | 0.07 | 19 |
| LNU288 | 14562.7 | 0.07 | 0.18 | 21 | LNU79 | 24882.2 | 0.96 | 0.01 | 38 | LNU143 | 25971.5 | 0.51 | 0.22 | 16 |
| LNU288 | 14562.1 | 0.07 | 0.14 | 20 | CONT. | — | 0.59 | — | 0 | LNU143 | 25972.1 | 0.47 | 0.52 | 8 |

TABLE 76-continued

Genes showing improved growth rate at standard nitrogen growth conditions (T2 generation)

| | | RGR Of Leaf Area | | | | | RGR Of Roots Coverage | | | | | RGR Of Roots Length | | |
|---|---|---|---|---|---|---|---|---|---|---|---|---|---|---|
| Gene Name | Event # | Ave. | p-value | % incr. | Gene Name | Event # | Ave. | p-value | % incr. | Gene Name | Event # | Ave. | p-value | % incr. |
| LNU288 | 14562.9 | 0.07 | 0.15 | 20 | LNU109 | 24892.8 | 0.94 | 0.00 | 59 | LNU154 | 14601.6 | 0.59 | 0.00 | 36 |
| LNU50 | 26024.2 | 0.08 | 0.01 | 50 | LNU109 | 24891.5 | 0.87 | 0.00 | 47 | LNU207 | 24641.1 | 0.58 | 0.06 | 33 |
| LNU50 | 26025.4 | 0.07 | 0.04 | 34 | LNU143 | 25975.2 | 0.75 | 0.05 | 27 | LNU207 | 24642.5 | 0.53 | 0.08 | 22 |
| LNU50 | 26023.5 | 0.06 | 0.80 | 4 | LNU143 | 25972.1 | 0.67 | 0.43 | 13 | LNU207 | 24642.4 | 0.49 | 0.26 | 13 |
| LNU52 | 25721.3 | 0.09 | 0.01 | 59 | LNU143 | 25975.3 | 0.66 | 0.39 | 12 | LNU207 | 24644.15 | 0.49 | 0.42 | 12 |
| LNU52 | 25723.2 | 0.08 | 0.00 | 54 | LNU154 | 14604.7 | 0.77 | 0.03 | 30 | LNU211 | 24771.1 | 0.58 | 0.01 | 33 |
| LNU52 | 25721.4 | 0.07 | 0.18 | 29 | LNU154 | 14601.6 | 0.73 | 0.15 | 23 | LNU211 | 24774.4 | 0.47 | 0.49 | 8 |
| CONT. | — | 0.07 | — | 0 | LNU196 | 25532.2 | 0.86 | 0.15 | 45 | LNU211 | 24771.3 | 0.47 | 0.48 | 8 |
| LNU154 | 14601.6 | 0.08 | 0.38 | 25 | LNU196 | 25534.1 | 0.78 | 0.01 | 33 | LNU211 | 24773.7 | 0.46 | 0.77 | 4 |
| LNU207 | 24642.5 | 0.10 | 0.00 | 47 | LNU207 | 24642.5 | 0.77 | 0.16 | 31 | LNU52 | 25723.1 | 0.57 | 0.01 | 30 |
| LNU207 | 24642.4 | 0.08 | 0.27 | 17 | LNU207 | 24642.4 | 0.75 | 0.12 | 27 | LNU52 | 25721.1 | 0.47 | 0.44 | 8 |
| LNU52 | 25721.4 | 0.09 | 0.02 | 40 | LNU207 | 24644.18 | 0.72 | 0.29 | 22 | LNU69 | 14571.1 | 0.57 | 0.04 | 30 |
| LNU52 | 25721.1 | 0.08 | 0.11 | 24 | LNU207 | 24644.13 | 0.67 | 0.27 | 14 | LNU69 | 14573.3 | 0.51 | 0.12 | 17 |
| LNU52 | 25723.1 | 0.08 | 0.31 | 15 | LNU207 | 24641.1 | 0.65 | 0.59 | 10 | LNU69 | 14572.8 | 0.51 | 0.23 | 16 |
| LNU69 | 14571.1 | 0.08 | 0.11 | 25 | LNU288 | 14562.9 | 0.78 | 0.13 | 31 | CONT. | — | 0.39 | — | 0 |
| LNU69 | 14572.8 | 0.07 | 0.68 | 7 | LNU288 | 14564.9 | 0.70 | 0.26 | 18 | LNU150 | 24842.9 | 0.59 | 0.01 | 51 |
| CONT. | — | 0.06 | — | 0 | LNU288 | 14562.7 | 0.69 | 0.37 | 17 | LNU150 | 24841.9 | 0.47 | 0.25 | 21 |
| LNU150 | 24843.5 | 0.09 | 0.15 | 32 | LNU288 | 14562.12 | 0.63 | 0.69 | 7 | LNU150 | 24843.9 | 0.46 | 0.33 | 19 |
| LNU150 | 24841.9 | 0.09 | 0.15 | 32 | LNU50 | 26025.4 | 0.84 | 0.00 | 43 | LNU150 | 24842.5 | 0.46 | 0.32 | 18 |
| LNU150 | 24842.9 | 0.08 | 0.22 | 26 | LNU50 | 26024.2 | 0.83 | 0.02 | 41 | LNU150 | 24843.5 | 0.45 | 0.40 | 16 |
| LNU150 | 24843.9 | 0.07 | 0.49 | 15 | LNU50 | 26023.5 | 0.70 | 0.26 | 18 | LNU179 | 24631.9 | 0.57 | 0.02 | 45 |
| LNU232 | 26003.7 | 0.08 | 0.20 | 28 | LNU50 | 26023.2 | 0.62 | 0.69 | 5 | LNU179 | 24632.7 | 0.48 | 0.20 | 24 |
| LNU235 | 26184.4 | 0.07 | 0.73 | 7 | LNU52 | 25723.2 | 0.82 | 0.01 | 39 | LNU179 | 24631.6 | 0.47 | 0.24 | 21 |
| LNU242 | 25474.1 | 0.09 | 0.04 | 45 | LNU52 | 25721.4 | 0.70 | 0.29 | 19 | LNU179 | 24631.7 | 0.45 | 0.37 | 17 |
| LNU242 | 25473.1 | 0.08 | 0.27 | 25 | LNU52 | 25721.3 | 0.70 | 0.22 | 18 | LNU179 | 24632.5 | 0.43 | 0.60 | 10 |
| LNU242 | 25471.1 | 0.07 | 0.56 | 12 | CONT. | — | 0.70 | — | 0 | LNU232 | 26003.3 | 0.53 | 0.06 | 36 |
| LNU76 | 26421.2 | 0.09 | 0.13 | 36 | LNU143 | 25975.3 | 0.81 | 0.31 | 16 | LNU232 | 26003.7 | 0.50 | 0.11 | 29 |
| LNU76 | 26422.2 | 0.07 | 0.69 | 9 | LNU143 | 25975.2 | 0.81 | 0.31 | 16 | LNU232 | 26001.5 | 0.46 | 0.35 | 17 |
| LNU76 | 26421.1 | 0.07 | 0.76 | 7 | LNU154 | 14601.6 | 0.96 | 0.18 | 37 | LNU232 | 26001.2 | 0.45 | 0.39 | 16 |
| LNU95 | 13985.15 | 0.08 | 0.21 | 28 | LNU207 | 24641.1 | 0.86 | 0.30 | 23 | LNU232 | 26003.6 | 0.44 | 0.47 | 14 |
| LNU95 | 13985.11 | 0.08 | 0.33 | 21 | LNU207 | 24642.5 | 0.83 | 0.22 | 19 | LNU235 | 26184.4 | 0.50 | 0.13 | 28 |
| CONT. | — | 0.07 | — | 0 | LNU207 | 24642.4 | 0.81 | 0.33 | 16 | LNU235 | 26185.3 | 0.49 | 0.17 | 25 |
| LNU118 | 14013.8 | 0.09 | 0.03 | 36 | LNU211 | 24771.1 | 0.84 | 0.24 | 21 | LNU235 | 26184.2 | 0.48 | 0.22 | 23 |
| LNU118 | 14013.6 | 0.09 | 0.07 | 29 | LNU52 | 25723.1 | 0.86 | 0.23 | 24 | LNU235 | 26182.1 | 0.47 | 0.27 | 20 |
| LNU118 | 14012.15 | 0.08 | 0.25 | 19 | LNU52 | 25721.1 | 0.73 | 0.76 | 5 | LNU235 | 26185.2 | 0.43 | 0.55 | 11 |
| LNU118 | 14012.12 | 0.08 | 0.29 | 16 | LNU69 | 14571.1 | 0.90 | 0.13 | 30 | LNU242 | 25473.3 | 0.56 | 0.02 | 43 |
| LNU118 | 14012.14 | 0.07 | 0.60 | 9 | LNU69 | 14573.3 | 0.76 | 0.62 | 9 | LNU242 | 25474.1 | 0.54 | 0.05 | 39 |
| LNU150 | 24842.9 | 0.10 | 0.00 | 54 | LNU69 | 14572.8 | 0.75 | 0.63 | 8 | LNU242 | 25471.1 | 0.51 | 0.08 | 32 |
| LNU150 | 24841.9 | 0.08 | 0.07 | 28 | CONT. | — | 0.47 | — | 0 | LNU242 | 25473.1 | 0.51 | 0.09 | 31 |
| LNU150 | 24841.6 | 0.07 | 0.69 | 6 | LNU150 | 24842.9 | 0.83 | 0.00 | 76 | LNU242 | 25472.1 | 0.41 | 0.73 | 6 |
| LNU179 | 24632.7 | 0.08 | 0.09 | 28 | LNU150 | 24843.5 | 0.79 | 0.00 | 68 | LNU76 | 26421.2 | 0.55 | 0.04 | 42 |
| LNU179 | 24631.7 | 0.08 | 0.20 | 20 | LNU150 | 24841.9 | 0.74 | 0.00 | 58 | LNU76 | 26421.1 | 0.49 | 0.14 | 27 |
| LNU179 | 24632.5 | 0.07 | 0.68 | 7 | LNU150 | 24843.9 | 0.62 | 0.06 | 33 | LNU76 | 26422.2 | 0.43 | 0.57 | 11 |
| LNU232 | 26001.5 | 0.09 | 0.06 | 30 | LNU179 | 24631.9 | 0.71 | 0.00 | 51 | LNU76 | 26423.1 | 0.43 | 0.58 | 10 |
| LNU232 | 26003.3 | 0.07 | 0.51 | 10 | LNU179 | 24632.5 | 0.56 | 0.24 | 21 | LNU76 | 26425.1 | 0.42 | 0.66 | 8 |
| LNU232 | 26003.6 | 0.07 | 0.65 | 7 | LNU232 | 26003.7 | 0.82 | 0.00 | 75 | LNU95 | 13985.11 | 0.53 | 0.07 | 35 |
| LNU235 | 26184.4 | 0.12 | 0.00 | 76 | LNU232 | 26003.3 | 0.68 | 0.01 | 45 | LNU95 | 13985.15 | 0.50 | 0.12 | 29 |
| LNU235 | 26185.2 | 0.09 | 0.01 | 40 | LNU232 | 26003.6 | 0.51 | 0.64 | 9 | LNU95 | 13985.19 | 0.48 | 0.19 | 25 |
| LNU235 | 26184.2 | 0.09 | 0.02 | 37 | LNU235 | 26185.3 | 0.63 | 0.05 | 34 | LNU95 | 13985.16 | 0.48 | 0.22 | 23 |
| LNU235 | 26182.1 | 0.07 | 0.67 | 6 | LNU235 | 26184.4 | 0.62 | 0.07 | 32 | LNU95 | 13985.12 | 0.46 | 0.34 | 18 |
| LNU242 | 25474.1 | 0.08 | 0.12 | 24 | LNU235 | 26182.1 | 0.54 | 0.35 | 15 | CONT. | — | 0.44 | — | 0 |
| LNU288 | 14563.9 | 0.12 | 0.00 | 76 | LNU235 | 26184.2 | 0.54 | 0.42 | 15 | LNU118 | 14013.6 | 0.48 | 0.65 | 9 |
| LNU288 | 14562.1 | 0.09 | 0.07 | 31 | LNU242 | 25474.1 | 0.87 | 0.00 | 86 | LNU118 | 14012.12 | 0.47 | 0.77 | 6 |
| LNU288 | 14563.6 | 0.08 | 0.14 | 23 | LNU242 | 25471.1 | 0.69 | 0.01 | 47 | LNU150 | 24842.9 | 0.54 | 0.27 | 22 |
| LNU288 | 14564.9 | 0.08 | 0.20 | 23 | LNU242 | 25473.1 | 0.68 | 0.01 | 46 | LNU150 | 24843.5 | 0.47 | 0.74 | 6 |
| LNU288 | 14562.7 | 0.08 | 0.40 | 14 | LNU242 | 25473.3 | 0.56 | 0.26 | 19 | LNU179 | 24632.5 | 0.50 | 0.47 | 13 |
| LNU76 | 26421.2 | 0.08 | 0.18 | 21 | LNU242 | 25472.1 | 0.51 | 0.65 | 8 | LNU179 | 24631.7 | 0.48 | 0.64 | 9 |
| LNU76 | 26423.1 | 0.07 | 0.48 | 11 | LNU76 | 26421.2 | 0.84 | 0.00 | 80 | LNU232 | 26001.5 | 0.52 | 0.40 | 16 |
| LNU76 | 26422.2 | 0.07 | 0.60 | 8 | LNU76 | 26421.1 | 0.67 | 0.01 | 43 | LNU232 | 26003.3 | 0.52 | 0.39 | 16 |
| LNU76 | 26425.1 | 0.07 | 0.63 | 8 | LNU76 | 26422.2 | 0.54 | 0.37 | 15 | LNU235 | 26185.2 | 0.52 | 0.38 | 16 |
| LNU95 | 13985.16 | 0.11 | 0.00 | 66 | LNU76 | 26425.1 | 0.53 | 0.48 | 13 | LNU235 | 26184.4 | 0.49 | 0.57 | 11 |
| LNU95 | 13985.15 | 0.10 | 0.01 | 44 | LNU76 | 26423.1 | 0.51 | 0.65 | 8 | LNU235 | 26184.2 | 0.48 | 0.64 | 9 |
| LNU95 | 13985.12 | 0.08 | 0.10 | 26 | LNU95 | 13985.11 | 0.86 | 0.00 | 83 | LNU235 | 26182.1 | 0.48 | 0.65 | 9 |
| CONT. | — | 0.06 | — | 0 | LNU95 | 13985.15 | 0.81 | 0.00 | 73 | LNU242 | 25474.1 | 0.53 | 0.33 | 18 |
| LNU101 | 27635.1 | 0.07 | 0.03 | 24 | LNU95 | 13985.19 | 0.67 | 0.03 | 43 | LNU288 | 14563.9 | 0.54 | 0.27 | 21 |
| LNU101 | 27632.1 | 0.07 | 0.18 | 14 | LNU95 | 13985.16 | 0.66 | 0.03 | 42 | LNU288 | 14563.6 | 0.51 | 0.43 | 15 |
| LNU128 | 26515.3 | 0.08 | 0.00 | 35 | LNU95 | 13985.12 | 0.40 | 0.40 | 16 | LNU288 | 14562.1 | 0.49 | 0.63 | 9 |
| LNU128 | 26515.2 | 0.07 | 0.15 | 18 | CONT. | — | 0.58 | — | 0 | LNU288 | 14562.7 | 0.48 | 0.70 | 7 |
| LNU192 | 28315.2 | 0.07 | 0.06 | 22 | LNU118 | 14013.6 | 0.77 | 0.08 | 33 | LNU76 | 26421.2 | 0.49 | 0.60 | 10 |
| LNU192 | 28313.2 | 0.07 | 0.36 | 11 | LNU118 | 14012.15 | 0.76 | 0.14 | 31 | LNU76 | 26425.1 | 0.48 | 0.68 | 8 |
| LNU211 | 24771.1 | 0.08 | 0.00 | 37 | LNU118 | 14013.8 | 0.61 | 0.78 | 5 | LNU95 | 13985.11 | 0.55 | 0.21 | 23 |
| LNU282 | 27563.3 | 0.08 | 0.00 | 34 | LNU150 | 24842.9 | 0.84 | 0.03 | 45 | LNU95 | 13985.12 | 0.50 | 0.49 | 13 |

TABLE 76-continued

Genes showing improved growth rate at standard nitrogen growth conditions (T2 generation)

| | | RGR Of Leaf Area | | | | | RGR Of Roots Coverage | | | | | RGR Of Roots Length | | |
|---|---|---|---|---|---|---|---|---|---|---|---|---|---|---|
| Gene Name | Event # | Ave. | p-value | % incr. | Gene Name | Event # | Ave. | p-value | % incr. | Gene Name | Event # | Ave. | p-value | % incr. |
| LNU69 | 14571.1 | 0.08 | 0.00 | 39 | LNU150 | 24843.5 | 0.71 | 0.20 | 23 | LNU95 | 13985.16 | 0.49 | 0.58 | 10 |
| LNU69 | 14573.5 | 0.07 | 0.22 | 13 | LNU150 | 24841.9 | 0.68 | 0.34 | 18 | LNU95 | 13985.15 | 0.48 | 0.71 | 7 |
| LNU69 | 14572.9 | 0.06 | 0.60 | 5 | LNU179 | 24632.7 | 0.65 | 0.49 | 13 | CONT. | — | 0.52 | — | 0 |
| LNU75 | 27572.1 | 0.08 | 0.00 | 36 | LNU179 | 24631.7 | 0.64 | 0.60 | 10 | LNU101 | 27632.5 | 0.64 | 0.01 | 24 |
| LNU75 | 27572.2 | 0.07 | 0.18 | 15 | LNU179 | 24632.5 | 0.61 | 0.76 | 6 | LNU101 | 27635.1 | 0.57 | 0.31 | 9 |
| LNU75 | 27572.3 | 0.06 | 0.58 | 6 | LNU232 | 26001.5 | 0.93 | 0.00 | 60 | LNU101 | 27632.1 | 0.55 | 0.50 | 6 |
| CONT. | — | 0.05 | — | 0 | LNU232 | 26003.3 | 0.83 | 0.02 | 42 | LNU101 | 27632.6 | 0.55 | 0.54 | 6 |
| LNU101 | 27632.5 | 0.08 | 0.03 | 38 | LNU235 | 26184.4 | 1.17 | 0.00 | 101 | LNU128 | 26511.4 | 0.59 | 0.15 | 14 |
| LNU118 | 14012.15 | 0.07 | 0.16 | 23 | LNU235 | 26185.2 | 0.88 | 0.01 | 52 | LNU128 | 26511.5 | 0.54 | 0.70 | 4 |
| LNU118 | 14013.6 | 0.07 | 0.14 | 23 | LNU235 | 26184.2 | 0.85 | 0.01 | 47 | LNU192 | 28313.3 | 0.63 | 0.01 | 22 |
| LNU118 | 14013.9 | 0.06 | 0.54 | 8 | LNU235 | 26182.1 | 0.68 | 0.32 | 18 | LNU192 | 28315.2 | 0.63 | 0.04 | 21 |
| LNU206 | 27621.2 | 0.07 | 0.01 | 38 | LNU242 | 25474.1 | 0.88 | 0.01 | 51 | LNU192 | 28313.2 | 0.56 | 0.49 | 7 |
| LNU206 | 27621.1 | 0.06 | 0.38 | 13 | LNU288 | 14563.9 | 0.99 | 0.00 | 71 | LNU206 | 27621.2 | 0.59 | 0.24 | 13 |
| LNU249 | 26153.1 | 0.09 | 0.00 | 57 | LNU288 | 14562.1 | 0.80 | 0.04 | 38 | LNU282 | 27563.3 | 0.54 | 0.69 | 4 |
| LNU282 | 27563.1 | 0.07 | 0.05 | 33 | LNU288 | 14563.6 | 0.73 | 0.17 | 26 | CONT. | — | 0.50 | — | 0 |
| LNU282 | 27565.2 | 0.06 | 0.79 | 4 | LNU288 | 14562.7 | 0.61 | 0.78 | 5 | LNU101 | 27635.1 | 0.58 | 0.02 | 17 |
| LNU288 | 14564.8 | 0.09 | 0.00 | 67 | LNU76 | 26421.2 | 0.66 | 0.43 | 14 | LNU101 | 27632.5 | 0.56 | 0.13 | 12 |
| LNU288 | 14563.9 | 0.08 | 0.00 | 56 | LNU76 | 26423.1 | 0.63 | 0.60 | 9 | LNU118 | 14012.15 | 0.56 | 0.13 | 11 |
| LNU288 | 14562.9 | 0.07 | 0.04 | 35 | LNU76 | 26425.1 | 0.63 | 0.62 | 9 | LNU118 | 14013.6 | 0.51 | 0.73 | 3 |
| LNU288 | 14562.7 | 0.07 | 0.13 | 24 | LNU76 | 26422.2 | 0.63 | 0.66 | 8 | LNU128 | 26515.3 | 0.60 | 0.01 | 19 |
| LNU288 | 14563.6 | 0.06 | 0.33 | 15 | LNU95 | 13985.15 | 0.87 | 0.01 | 44 | LNU192 | 28315.2 | 0.54 | 0.30 | 9 |
| LNU75 | 27571.4 | 0.08 | 0.03 | 42 | LNU95 | 13985.16 | 0.86 | 0.01 | 48 | LNU206 | 27621.2 | 0.58 | 0.03 | 17 |
| LNU75 | 27572.3 | 0.07 | 0.07 | 33 | LNU95 | 13985.12 | 0.73 | 0.16 | 26 | LNU206 | 27622.4 | 0.53 | 0.37 | 6 |
| LNU75 | 27572.2 | 0.07 | 0.08 | 30 | CONT. | — | 0.61 | — | 0 | LNU249 | 26152.2 | 0.58 | 0.03 | 16 |
| LNU75 | 27571.2 | 0.06 | 0.23 | 17 | LNU101 | 27632.1 | 0.83 | 0.00 | 36 | LNU249 | 26152.4 | 0.55 | 0.26 | 11 |
| CONT. | — | 0.06 | — | 0 | LNU101 | 27635.1 | 0.77 | 0.02 | 25 | LNU249 | 26151.1 | 0.52 | 0.68 | 4 |
| LNU11 | 28204.3 | 0.07 | 0.63 | 6 | LNU101 | 27632.5 | 0.73 | 0.13 | 19 | LNU249 | 26153.1 | 0.52 | 0.70 | 4 |
| LNU11 | 28204.1 | 0.07 | 0.73 | 4 | LNU101 | 27632.6 | 0.67 | 0.47 | 9 | LNU282 | 27563.3 | 0.56 | 0.09 | 12 |
| LNU112 | 28212.4 | 0.07 | 0.64 | 6 | LNU128 | 26515.3 | 0.95 | 0.00 | 55 | LNU282 | 27563.1 | 0.55 | 0.26 | 11 |
| LNU14 | 27824.2 | 0.08 | 0.22 | 32 | LNU128 | 26515.2 | 0.82 | 0.00 | 35 | LNU282 | 27562.1 | 0.55 | 0.42 | 10 |
| LNU183 | 24863.12 | 0.12 | 0.00 | 81 | LNU128 | 26511.4 | 0.76 | 0.06 | 24 | LNU282 | 27565.2 | 0.53 | 0.41 | 6 |
| LNU183 | 24863.1 | 0.10 | 0.00 | 50 | LNU128 | 26511.5 | 0.63 | 0.77 | 3 | LNU282 | 27565.1 | 0.51 | 0.79 | 2 |
| LNU183 | 24865.1 | 0.09 | 0.00 | 46 | LNU192 | 28315.2 | 0.95 | 0.00 | 56 | LNU288 | 14563.6 | 0.62 | 0.01 | 24 |
| LNU183 | 24864.6 | 0.07 | 0.25 | 14 | LNU192 | 28315.3 | 0.88 | 0.00 | 44 | LNU288 | 14564.8 | 0.60 | 0.01 | 19 |
| LNU191 | 28323.1 | 0.07 | 0.70 | 6 | LNU192 | 28313.3 | 0.74 | 0.04 | 21 | LNU288 | 14562.9 | 0.56 | 0.12 | 12 |
| LNU201 | 28223.1 | 0.07 | 0.71 | 4 | LNU206 | 27621.2 | 0.83 | 0.00 | 36 | LNU288 | 14562.7 | 0.51 | 0.67 | 3 |
| LNU268 | 26044.2 | 0.08 | 0.20 | 18 | LNU206 | 27621.1 | 0.72 | 0.14 | 17 | LNU75 | 27572.2 | 0.61 | 0.00 | 23 |
| LNU268 | 26045.1 | 0.07 | 0.32 | 12 | LNU211 | 24771.1 | 0.81 | 0.01 | 32 | LNU75 | 27571.4 | 0.60 | 0.03 | 20 |
| CONT. | — | 0.05 | — | 0 | LNU282 | 27563.3 | 0.79 | 0.02 | 30 | LNU75 | 27572.1 | 0.57 | 0.05 | 15 |
| LNU11 | 28204.1 | 0.07 | 0.08 | 32 | LNU69 | 14571.1 | 0.79 | 0.01 | 29 | LNU75 | 27571.2 | 0.54 | 0.30 | 8 |
| LNU11 | 28205.2 | 0.07 | 0.09 | 29 | LNU69 | 14573.5 | 0.78 | 0.02 | 28 | CONT. | — | 0.50 | — | 0 |
| LNU11 | 28205.1 | 0.07 | 0.13 | 29 | LNU75 | 27572.2 | 0.94 | 0.00 | 53 | LNU11 | 28203.2 | 0.55 | 0.43 | 11 |
| LNU11 | 28203.2 | 0.06 | 0.12 | 25 | LNU75 | 27572.3 | 0.81 | 0.00 | 33 | LNU11 | 28202.5 | 0.55 | 0.45 | 10 |
| LNU11 | 28204.3 | 0.06 | 0.25 | 18 | LNU75 | 27572.1 | 0.78 | 0.02 | 27 | LNU112 | 28212.1 | 0.62 | 0.09 | 24 |
| LNU11 | 28202.5 | 0.05 | 0.78 | 5 | LNU75 | 27571.4 | 0.70 | 0.25 | 14 | LNU112 | 28212.4 | 0.52 | 0.72 | 5 |
| LNU112 | 28212.4 | 0.07 | 0.03 | 40 | CONT. | — | 0.61 | — | 0 | LNU14 | 27823.2 | 0.56 | 0.37 | 13 |
| LNU112 | 28212.1 | 0.06 | 0.22 | 22 | LNU101 | 27632.5 | 0.86 | 0.03 | 42 | LNU14 | 27821.1 | 0.55 | 0.49 | 10 |
| LNU112 | 28211.2 | 0.06 | 0.52 | 11 | LNU101 | 27635.1 | 0.65 | 0.69 | 7 | LNU183 | 24864.6 | 0.56 | 0.38 | 13 |
| LNU14 | 27821.3 | 0.07 | 0.07 | 38 | LNU118 | 14012.15 | 0.77 | 0.11 | 26 | LNU201 | 28223.1 | 0.57 | 0.27 | 15 |
| LNU14 | 27821.4 | 0.07 | 0.17 | 29 | LNU118 | 14013.6 | 0.74 | 0.19 | 21 | LNU201 | 28222.3 | 0.55 | 0.40 | 11 |
| LNU14 | 27823.2 | 0.07 | 0.13 | 27 | LNU118 | 14013.9 | 0.65 | 0.60 | 8 | LNU201 | 28223.3 | 0.52 | 0.76 | 4 |
| LNU183 | 24865.1 | 0.14 | 0.00 | 176 | LNU206 | 27621.2 | 0.88 | 0.01 | 45 | LNU268 | 26044.2 | 0.58 | 0.25 | 16 |
| LNU183 | 24863.12 | 0.13 | 0.00 | 158 | LNU249 | 26153.1 | 0.76 | 0.10 | 26 | LNU268 | 26041.6 | 0.54 | 0.52 | 8 |
| LNU183 | 24863.1 | 0.13 | 0.00 | 156 | LNU249 | 26152.4 | 0.70 | 0.38 | 15 | LNU268 | 26041.4 | 0.53 | 0.68 | 6 |
| LNU183 | 24864.6 | 0.13 | 0.00 | 147 | LNU282 | 27563.1 | 0.74 | 0.21 | 22 | LNU268 | 26045.1 | 0.52 | 0.78 | 4 |
| LNU183 | 24864.7 | 0.06 | 0.21 | 22 | LNU282 | 27565.2 | 0.64 | 0.74 | 5 | CONT. | — | 0.60 | — | 0 |
| LNU191 | 28325.4 | 0.08 | 0.02 | 49 | LNU288 | 14564.8 | 0.86 | 0.01 | 42 | LNU11 | 28205.2 | 0.67 | 0.31 | 12 |
| LNU191 | 28324.2 | 0.07 | 0.04 | 42 | LNU288 | 14563.6 | 0.83 | 0.05 | 37 | LNU11 | 28204.3 | 0.65 | 0.43 | 9 |
| LNU191 | 28323.1 | 0.07 | 0.16 | 37 | LNU288 | 14562.9 | 0.81 | 0.04 | 34 | LNU11 | 28204.1 | 0.63 | 0.57 | 6 |
| LNU191 | 28325.3 | 0.07 | 0.06 | 34 | LNU288 | 14563.9 | 0.75 | 0.16 | 24 | LNU11 | 28203.2 | 0.63 | 0.60 | 6 |
| LNU191 | 28321.3 | 0.06 | 0.57 | 10 | LNU75 | 27572.2 | 0.90 | 0.01 | 49 | LNU112 | 28212.4 | 0.62 | 0.70 | 4 |
| LNU201 | 28222.2 | 0.09 | 0.00 | 82 | LNU75 | 27571.4 | 0.86 | 0.03 | 41 | LNU14 | 27821.3 | 0.64 | 0.45 | 8 |
| LNU201 | 28223.3 | 0.06 | 0.20 | 23 | LNU75 | 27571.2 | 0.80 | 0.04 | 31 | LNU183 | 24863.1 | 0.72 | 0.08 | 21 |
| LNU201 | 28221.3 | 0.06 | 0.42 | 14 | LNU75 | 27572.3 | 0.74 | 0.29 | 21 | LNU183 | 24864.6 | 0.63 | 0.63 | 5 |
| LNU201 | 28223.1 | 0.06 | 0.48 | 13 | CONT. | — | 0.81 | — | 0 | LNU201 | 28222.2 | 0.63 | 0.59 | 6 |
| LNU201 | 28222.3 | 0.05 | 0.72 | 6 | LNU14 | 27821.3 | 0.92 | 0.41 | 14 | LNU268 | 26043.4 | 0.63 | 0.55 | 7 |
| LNU268 | 26043.4 | 0.08 | 0.01 | 47 | LNU183 | 24863.12 | 0.84 | 0.78 | 4 | CONT. | — | 0.53 | — | 0 |
| LNU268 | 26041.4 | 0.07 | 0.03 | 39 | LNU268 | 26044.2 | 1.01 | 0.17 | 25 | LNU116 | 14492.5 | 0.58 | 0.46 | 10 |
| LNU268 | 26041.6 | 0.06 | 0.31 | 22 | CONT. | — | 0.75 | — | 0 | LNU121 | 27713.4 | 0.55 | 0.76 | 4 |
| LNU268 | 26045.1 | 0.06 | 0.48 | 14 | LNU11 | 28205.2 | 1.10 | 0.00 | 46 | LNU126 | 25343.3 | 0.57 | 0.59 | 7 |
| LNU268 | 26044.2 | 0.06 | 0.68 | 7 | LNU11 | 28203.2 | 0.99 | 0.04 | 32 | LNU158 | 27433.3 | 0.60 | 0.38 | 13 |
| CONT. | — | 0.04 | — | 0 | LNU11 | 28205.1 | 0.94 | 0.09 | 25 | LNU177 | 24765.2 | 0.60 | 0.38 | 14 |

TABLE 76-continued

Genes showing improved growth rate at standard nitrogen growth conditions (T2 generation)

| | | RGR Of Leaf Area | | | | | RGR Of Roots Coverage | | | | | RGR Of Roots Length | | |
|---|---|---|---|---|---|---|---|---|---|---|---|---|---|---|
| Gene Name | Event # | Ave. | p-value | % incr. | Gene Name | Event # | Ave. | p-value | % incr. | Gene Name | Event # | Ave. | p-value | % incr. |
| LNU107 | 14585.5 | 0.06 | 0.17 | 32 | LNU11 | 28204.3 | 0.93 | 0.10 | 24 | LNU177 | 24762.6 | 0.56 | 0.67 | 5 |
| LNU107 | 14584.9 | 0.05 | 0.31 | 18 | LNU11 | 28202.5 | 0.91 | 0.15 | 21 | LNU177 | 24764.9 | 0.56 | 0.69 | 5 |
| LNU107 | 14583.8 | 0.05 | 0.44 | 14 | LNU11 | 28204.1 | 0.82 | 0.48 | 9 | LNU182 | 25384.5 | 0.58 | 0.48 | 10 |
| LNU116 | 14493.6 | 0.06 | 0.02 | 38 | LNU112 | 28212.4 | 0.89 | 0.22 | 18 | LNU2 | 27842.3 | 0.60 | 0.35 | 13 |
| LNU116 | 14494.5 | 0.06 | 0.07 | 30 | LNU112 | 28212.1 | 0.85 | 0.35 | 12 | LNU225 | 25991.2 | 0.59 | 0.41 | 12 |
| LNU116 | 14492.9 | 0.05 | 0.02 | 28 | LNU14 | 27821.3 | 1.08 | 0.01 | 44 | LNU225 | 25991.5 | 0.59 | 0.47 | 11 |
| LNU116 | 14492.5 | 0.05 | 0.13 | 21 | LNU14 | 27823.2 | 0.85 | 0.46 | 14 | LNU239 | 26284.1 | 0.60 | 0.32 | 14 |
| LNU121 | 25642.2 | 0.08 | 0.00 | 99 | LNU183 | 24865.1 | 1.33 | 0.00 | 11 | LNU239 | 26284.2 | 0.57 | 0.57 | 1 |
| LNU121 | 27713.4 | 0.07 | 0.00 | 60 | LNU183 | 24863.1 | 1.32 | 0.00 | 75 | LNU57 | 27852.1 | 0.59 | 0.39 | 12 |
| LNU121 | 27711.1 | 0.06 | 0.04 | 40 | LNU183 | 24864.6 | 1.09 | 0.01 | 45 | LNU83 | 27684.1 | 0.56 | 0.64 | 7 |
| LNU121 | 27713.1 | 0.06 | 0.07 | 36 | LNU183 | 24863.12 | 1.09 | 0.01 | 45 | LNU83 | 27682.1 | 0.55 | 0.76 | 4 |
| LNU126 | 25345.1 | 0.07 | 0.00 | 57 | LNU191 | 28323.1 | 0.97 | 0.15 | 29 | CONT. | — | 0.51 | — | 0 |
| LNU126 | 25343.3 | 0.07 | 0.00 | 57 | LNU191 | 28325.4 | 0.81 | 0.54 | 8 | LNU107 | 14584.9 | 0.66 | 0.14 | 29 |
| LNU126 | 25343.1 | 0.06 | 0.05 | 40 | LNU201 | 28222.2 | 1.26 | 0.00 | 67 | LNU107 | 14583.8 | 0.64 | 0.14 | 26 |
| LNU158 | 27433.3 | 0.06 | 0.05 | 33 | LNU201 | 28223.1 | 0.82 | 0.50 | 10 | LNU107 | 14585.2 | 0.61 | 0.22 | 20 |
| LNU158 | 27433.2 | 0.05 | 0.28 | 19 | LNU268 | 26043.4 | 1.00 | 0.03 | 33 | LNU107 | 14585.5 | 0.58 | 0.40 | 13 |
| LNU158 | 27432.5 | 0.05 | 0.64 | 10 | LNU268 | 26041.4 | 0.91 | 0.14 | 21 | LNU116 | 14491.5 | 0.61 | 0.28 | 19 |
| LNU177 | 24765.2 | 0.05 | 0.08 | 28 | LNU268 | 26041.6 | 0.90 | 0.31 | 20 | LNU116 | 14492.9 | 0.55 | 0.61 | 8 |
| LNU177 | 24762.6 | 0.05 | 0.15 | 26 | LNU268 | 26044.2 | 0.80 | 0.61 | 6 | LNU121 | 27713.1 | 0.68 | 0.05 | 33 |
| LNU177 | 24764.9 | 0.05 | 0.54 | 8 | CONT. | — | 0.61 | — | 0 | LNU121 | 27713.4 | 0.63 | 0.20 | 22 |
| LNU182 | 25384.5 | 0.06 | 0.03 | 30 | LNU107 | 14585.5 | 0.74 | 0.27 | 21 | LNU121 | 27711.1 | 0.62 | 0.18 | 21 |
| LNU182 | 27521.4 | 0.05 | 0.22 | 27 | LNU107 | 14583.8 | 0.74 | 0.20 | 20 | LNU126 | 25343.1 | 0.63 | 0.17 | 22 |
| LNU182 | 25384.1 | 0.05 | 0.53 | 11 | LNU107 | 14584.9 | 0.69 | 0.32 | 13 | LNU126 | 25343.4 | 0.62 | 0.18 | 21 |
| LNU2 | 25713.1 | 0.05 | 0.06 | 29 | LNU116 | 14492.5 | 0.67 | 0.43 | 10 | LNU126 | 25343.3 | 0.53 | 0.80 | 4 |
| LNU2 | 27842.1 | 0.05 | 0.59 | 15 | LNU116 | 14492.9 | 0.65 | 0.59 | 7 | LNU158 | 27433.3 | 0.69 | 0.06 | 35 |
| LNU2 | 27842.3 | 0.05 | 0.55 | 9 | LNU116 | 14494.5 | 0.65 | 0.61 | 7 | LNU158 | 27433.2 | 0.66 | 0.09 | 29 |
| LNU225 | 25991.5 | 0.05 | 0.46 | 14 | LNU121 | 27713.4 | 0.96 | 0.00 | 57 | LNU158 | 27432.5 | 0.65 | 0.11 | 27 |
| LNU225 | 25991.2 | 0.05 | 0.55 | 9 | LNU121 | 25642.2 | 0.87 | 0.02 | 43 | LNU158 | 27434.1 | 0.61 | 0.17 | 19 |
| LNU239 | 26284.1 | 0.06 | 0.01 | 40 | LNU121 | 27711.1 | 0.85 | 0.01 | 39 | LNU158 | 27434.5 | 0.56 | 0.56 | 10 |
| LNU239 | 26283.2 | 0.05 | 0.41 | 12 | LNU121 | 27713.1 | 0.69 | 0.34 | 12 | LNU177 | 24763.6 | 0.68 | 0.07 | 33 |
| LNU239 | 26281.1 | 0.05 | 0.63 | 6 | LNU126 | 25345.1 | 0.89 | 0.00 | 46 | LNU177 | 24764.12 | 0.66 | 0.07 | 29 |
| LNU57 | 27852.1 | 0.05 | 0.23 | 15 | LNU126 | 25343.3 | 0.80 | 0.02 | 31 | LNU177 | 24765.2 | 0.64 | 0.12 | 25 |
| LNU57 | 27854.3 | 0.05 | 0.35 | 12 | LNU126 | 25343.1 | 0.75 | 0.14 | 23 | LNU177 | 24764.9 | 0.58 | 0.38 | 14 |
| CONT. | — | 0.03 | — | 0 | LNU158 | 27433.3 | 1.04 | 0.01 | 71 | LNU182 | 25384.2 | 0.67 | 0.08 | 31 |
| LNU107 | 14584.9 | 0.06 | 0.00 | 151 | LNU158 | 27433.2 | 0.94 | 0.00 | 54 | LNU182 | 25384.1 | 0.60 | 0.24 | 18 |
| LNU107 | 14585.2 | 0.05 | 0.02 | 105 | LNU158 | 27432.5 | 0.71 | 0.37 | 16 | LNU182 | 25384.5 | 0.59 | 0.30 | 16 |
| LNU107 | 14585.5 | 0.04 | 0.09 | 64 | LNU177 | 24762.6 | 1.04 | 0.00 | 71 | LNU182 | 25384.6 | 0.59 | 0.37 | 16 |
| LNU107 | 14583.8 | 0.04 | 0.31 | 41 | LNU177 | 24765.2 | 0.83 | 0.11 | 35 | LNU182 | 27521.4 | 0.55 | 0.63 | 8 |
| LNU107 | 14583.1 | 0.03 | 0.35 | 34 | LNU177 | 24764.9 | 0.69 | 0.28 | 13 | LNU2 | 27842.1 | 0.65 | 0.14 | 26 |
| LNU116 | 14492.5 | 0.06 | 0.01 | 126 | LNU182 | 25384.5 | 0.91 | 0.01 | 49 | LNU2 | 27842.3 | 0.62 | 0.20 | 21 |
| LNU116 | 14493.6 | 0.05 | 0.05 | 81 | LNU182 | 27521.4 | 0.84 | 0.02 | 38 | LNU2 | 25713.1 | 0.58 | 0.36 | 13 |
| LNU116 | 14491.5 | 0.05 | 0.10 | 77 | LNU182 | 25384.1 | 0.80 | 0.03 | 31 | LNU225 | 25991.3 | 0.65 | 0.12 | 28 |
| LNU116 | 14494.5 | 0.03 | 0.59 | 26 | LNU2 | 27842.3 | 0.90 | 0.01 | 47 | LNU225 | 25991.2 | 0.62 | 0.21 | 22 |
| LNU116 | 14492.9 | 0.03 | 0.72 | 15 | LNU2 | 25713.1 | 0.85 | 0.01 | 39 | LNU225 | 25991.5 | 0.62 | 0.22 | 21 |
| LNU121 | 27713.4 | 0.09 | 0.00 | 258 | LNU2 | 27842.1 | 0.77 | 0.31 | 26 | LNU225 | 25991.8 | 0.59 | 0.34 | 16 |
| LNU121 | 27713.1 | 0.06 | 0.01 | 145 | LNU225 | 25991.5 | 1.09 | 0.00 | 78 | LNU239 | 26283.3 | 0.59 | 0.33 | 16 |
| LNU121 | 27713.3 | 0.05 | 0.01 | 113 | LNU225 | 25991.2 | 0.81 | 0.05 | 32 | LNU239 | 26284.1 | 0.58 | 0.37 | 14 |
| LNU121 | 25642.2 | 0.05 | 0.01 | 99 | LNU225 | 25991.1 | 0.75 | 0.15 | 22 | LNU239 | 26281.1 | 0.58 | 0.42 | 14 |
| LNU121 | 27711.1 | 0.05 | 0.10 | 79 | LNU225 | 25991.3 | 0.68 | 0.55 | 12 | LNU239 | 26284.2 | 0.54 | 0.70 | 6 |
| LNU126 | 25343.1 | 0.05 | 0.01 | 111 | LNU239 | 26284.1 | 0.78 | 0.06 | 28 | LNU57 | 27854.5 | 0.66 | 0.11 | 29 |
| LNU126 | 25343.3 | 0.04 | 0.14 | 66 | LNU239 | 26283.2 | 0.68 | 0.48 | 12 | LNU57 | 27852.1 | 0.64 | 0.12 | 26 |
| LNU126 | 25343.4 | 0.03 | 0.53 | 20 | LNU239 | 26281.1 | 0.67 | 0.48 | 9 | LNU57 | 27851.2 | 0.63 | 0.16 | 23 |
| LNU126 | 25345.1 | 0.03 | 0.53 | 19 | LNU57 | 27852.1 | 0.92 | 0.00 | 50 | LNU57 | 27854.3 | 0.59 | 0.29 | 16 |
| LNU158 | 27432.5 | 0.07 | 0.00 | 170 | LNU57 | 27854.3 | 0.71 | 0.25 | 16 | LNU83 | 27685.1 | 0.71 | 0.05 | 39 |
| LNU158 | 27433.3 | 0.07 | 0.00 | 159 | LNU57 | 27854.5 | 0.68 | 0.39 | 12 | LNU83 | 27682.1 | 0.66 | 0.11 | 30 |
| LNU158 | 27433.2 | 0.05 | 0.02 | 105 | LNU83 | 27681.4 | 0.85 | 0.02 | 38 | LNU83 | 27685.2 | 0.66 | 0.08 | 29 |
| LNU158 | 27434.1 | 0.03 | 0.56 | 21 | LNU83 | 27684.1 | 0.66 | 0.60 | 8 | LNU83 | 27681.4 | 0.59 | 0.34 | 15 |
| LNU158 | 27434.5 | 0.03 | 0.67 | 16 | LNU83 | 27685.1 | 0.64 | 0.78 | 4 | LNU83 | 27684.1 | 0.58 | 0.39 | 14 |
| LNU177 | 24762.6 | 0.04 | 0.09 | 60 | CONT. | — | 0.58 | — | 0 | | | | | |
| LNU177 | 24764.12 | 0.03 | 0.41 | 30 | LNU107 | 14584.9 | 1.26 | 0.00 | 118 | | | | | |
| LNU177 | 24763.6 | 0.03 | 0.51 | 26 | LNU107 | 14583.8 | 0.96 | 0.00 | 66 | | | | | |
| LNU182 | 25384.1 | 0.05 | 0.02 | 103 | LNU107 | 14585.2 | 0.84 | 0.00 | 45 | | | | | |
| LNU182 | 25384.6 | 0.05 | 0.04 | 101 | LNU107 | 14583.1 | 0.60 | 0.40 | 11 | | | | | |
| LNU182 | 25384.2 | 0.04 | 0.08 | 72 | LNU107 | 14585.5 | 0.63 | 0.56 | 8 | | | | | |
| LNU182 | 25384.5 | 0.03 | 0.43 | 31 | LNU116 | 14493.6 | 0.91 | 0.00 | 56 | | | | | |
| LNU182 | 27521.4 | 0.03 | 0.76 | 11 | LNU116 | 14494.5 | 0.86 | 0.02 | 48 | | | | | |
| LNU2 | 27845.3 | 0.05 | 0.02 | 105 | LNU116 | 14491.5 | 0.85 | 0.03 | 48 | | | | | |
| LNU2 | 25713.1 | 0.05 | 0.04 | 95 | LNU116 | 14492.5 | 0.73 | 0.06 | 26 | | | | | |
| LNU2 | 27842.3 | 0.05 | 0.09 | 85 | LNU116 | 14492.9 | 0.63 | 0.64 | 9 | | | | | |
| LNU2 | 27842.1 | 0.04 | 0.09 | 72 | LNU121 | 27713.4 | 1.28 | 0.00 | 120 | | | | | |
| LNU2 | 27845.2 | 0.03 | 0.46 | 30 | LNU121 | 27713.1 | 1.13 | 0.00 | 95 | | | | | |
| LNU225 | 25991.2 | 0.08 | 0.00 | 207 | LNU121 | 27711.1 | 0.85 | 0.01 | 47 | | | | | |

TABLE 76-continued

Genes showing improved growth rate at standard nitrogen growth conditions (T2 generation)

| | RGR Of Leaf Area | | | | | RGR Of Roots Coverage | | | | | RGR Of Roots Length | | | |
|---|---|---|---|---|---|---|---|---|---|---|---|---|---|---|
| Gene Name | Event # | Ave. | p-value | % incr. | Gene Name | Event # | Ave. | p-value | % incr. | Gene Name | Event # | Ave. | p-value | % incr. |
| LNU225 | 25991.3 | 0.05 | 0.03 | 110 | LNU121 | 25642.2 | 0.70 | 0.23 | 20 | | | | | |
| LNU225 | 25991.1 | 0.05 | 0.05 | 80 | LNU126 | 25343.1 | 0.85 | 0.02 | 46 | | | | | |
| LNU225 | 25991.8 | 0.04 | 0.12 | 68 | LNU126 | 25343.4 | 0.68 | 0.24 | 17 | | | | | |
| LNU225 | 25991.5 | 0.03 | 0.58 | 19 | LNU126 | 25343.3 | 0.66 | 0.35 | 14 | | | | | |
| LNU239 | 26284.2 | 0.05 | 0.02 | 102 | LNU126 | 25345.1 | 0.63 | 0.56 | 9 | | | | | |
| LNU239 | 26281.1 | 0.04 | 0.11 | 71 | LNU158 | 27433.3 | 1.25 | 0.00 | 117 | | | | | |
| LNU239 | 26283.2 | 0.04 | 0.11 | 67 | LNU158 | 27432.5 | 1.22 | 0.00 | 110 | | | | | |
| LNU239 | 26283.3 | 0.04 | 0.27 | 53 | LNU158 | 27433.2 | 0.88 | 0.00 | 52 | | | | | |
| LNU239 | 26284.1 | 0.04 | 0.27 | 44 | LNU158 | 27434.5 | 0.84 | 0.01 | 46 | | | | | |
| LNU57 | 27852.1 | 0.05 | 0.07 | 81 | LNU158 | 27434.1 | 0.71 | 0.15 | 23 | | | | | |
| LNU57 | 27851.2 | 0.04 | 0.08 | 62 | LNU177 | 24764.12 | 0.96 | 0.00 | 65 | | | | | |
| LNU57 | 27854.5 | 0.03 | 0.43 | 27 | LNU177 | 24763.6 | 0.82 | 0.01 | 42 | | | | | |
| LNU83 | 27685.1 | 0.05 | 0.04 | 110 | LNU177 | 24765.2 | 0.63 | 0.58 | 9 | | | | | |
| LNU83 | 27685.2 | 0.05 | 0.03 | 91 | LNU182 | 25384.6 | 1.03 | 0.00 | 78 | | | | | |
| LNU83 | 27681.4 | 0.04 | 0.17 | 53 | LNU182 | 25384.1 | 0.91 | 0.00 | 58 | | | | | |
| LNU83 | 27682.1 | 0.03 | 0.41 | 34 | LNU182 | 25384.2 | 0.84 | 0.01 | 46 | | | | | |
| LNU83 | 27684.1 | 0.03 | 0.69 | 16 | LNU182 | 27521.4 | 0.71 | 0.16 | 23 | | | | | |
| | | | | | LNU182 | 25384.5 | 0.70 | 0.18 | 21 | | | | | |
| | | | | | LNU2 | 27842.1 | 0.98 | 0.00 | 69 | | | | | |
| | | | | | LNU2 | 27842.3 | 0.95 | 0.00 | 64 | | | | | |
| | | | | | LNU2 | 25713.1 | 0.89 | 0.02 | 54 | | | | | |
| | | | | | LNU2 | 27845.2 | 0.68 | 0.27 | 18 | | | | | |
| | | | | | LNU225 | 25991.2 | 1.35 | 0.00 | 133 | | | | | |
| | | | | | LNU225 | 25991.3 | 1.27 | 0.00 | 119 | | | | | |
| | | | | | LNU225 | 25991.8 | 0.87 | 0.01 | 50 | | | | | |
| | | | | | LNU225 | 25991.1 | 0.82 | 0.00 | 42 | | | | | |
| | | | | | LNU225 | 25991.5 | 0.82 | 0.01 | 41 | | | | | |
| | | | | | LNU239 | 26283.3 | 0.88 | 0.01 | 51 | | | | | |
| | | | | | LNU239 | 26281.1 | 0.82 | 0.02 | 42 | | | | | |
| | | | | | LNU239 | 26284.2 | 0.70 | 0.15 | 20 | | | | | |
| | | | | | LNU239 | 26284.1 | 0.66 | 0.33 | 14 | | | | | |
| | | | | | LNU239 | 26283.2 | 0.65 | 0.36 | 12 | | | | | |
| | | | | | LNU57 | 27854.5 | 1.11 | 0.00 | 92 | | | | | |
| | | | | | LNU57 | 27851.2 | 1.11 | 0.00 | 91 | | | | | |
| | | | | | LNU57 | 27852.1 | 1.08 | 0.00 | 86 | | | | | |
| | | | | | LNU57 | 27854.3 | 0.69 | 0.16 | 19 | | | | | |
| | | | | | LNU83 | 27685.1 | 1.10 | 0.00 | 89 | | | | | |
| | | | | | LNU83 | 27685.2 | 1.02 | 0.00 | 76 | | | | | |
| | | | | | LNU83 | 27682.1 | 0.88 | 0.01 | 51 | | | | | |
| | | | | | LNU83 | 27681.4 | 0.83 | 0.00 | 43 | | | | | |
| | | | | | LNU83 | 27684.1 | 0.68 | 0.35 | 17 | | | | | |

Table 76.
"CONT."—Control;
"Ave."—Average;
"% Incr." = % increment.

TABLE 77

Genes showing improved growth rate at standard nitrogen growth conditions (T1 generation)

| | RGR Of Leaf Area | | | | RGR Of Roots Coverage | | | | RGR Of Roots Length | | |
|---|---|---|---|---|---|---|---|---|---|---|---|
| Gene Name | Ave. | p-value | % incr. | Gene Name | Ave. | p-value | % incr. | Gene Name | Ave. | p-value | % incr. |
| CONT. | 0.064 | — | 0.0 | CONT. | 0.308 | — | 0.0 | CONT. | 0.401 | — | 0 |
| LNU121 | 0.070 | 0.313 | 8.9 | LNU121 | 0.498 | 0.000 | 61.7 | LNU121 | 0.480 | 0.002 | 19.8 |
| CONT. | 0.065 | — | 0.0 | LNU154 | 0.341 | 0.475 | 10.6 | LNU154 | 0.402 | 0.971 | 0.36 |
| LNU275 | 0.103 | 0.000 | 59.6 | LNU210 | 0.339 | 0.326 | 10.2 | LNU210 | 0.417 | 0.531 | 4 |
| LNU57 | 0.073 | 0.309 | 13.4 | CONT. | 0.322 | — | 0.0 | CONT. | 0.386 | — | 0 |
| LNU64 | 0.068 | 0.723 | 4.5 | LNU275 | 0.862 | 0.000 | 167.2 | LNU275 | 0.509 | 0.002 | 32 |
| LNU83 | 0.084 | 0.033 | 29.3 | LNU57 | 0.535 | 0.000 | 66.0 | LNU57 | 0.515 | 0.000 | 34 |
| CONT. | 0.063 | — | 0.0 | LNU58 | 0.387 | 0.154 | 20.1 | LNU58 | 0.407 | 0.473 | 5.7 |
| LNU59 | 0.065 | 0.738 | 3.5 | LNU83 | 0.549 | 0.000 | 70.2 | LNU64 | 0.388 | 0.954 | 0.5 |
| CONT. | 0.229 | — | 0.0 | CONT. | 0.186 | — | 0.0 | LNU83 | 0.528 | 0.000 | 37 |

TABLE 77-continued

Genes showing improved growth rate at standard nitrogen growth conditions (T1 generation)

| Gene Name | RGR Of Leaf Area Ave. | p-value | % incr. | Gene Name | RGR Of Roots Coverage Ave. | p-value | % incr. | Gene Name | RGR Of Roots Length Ave. | p-value | % incr. |
|---|---|---|---|---|---|---|---|---|---|---|---|
| LNU222_H6 | 0.258 | 0.65 | 13 | LNU176 | 0.250 | 0.043 | 34.6 | CONT. | 0.326 | — | 0 |
| | | | | LNU214 | 0.219 | 0.210 | 18.2 | LNU176 | 0.371 | 0.101 | 14 |
| | | | | LNU223 | 0.234 | 0.060 | 26.2 | LNU214 | 0.368 | 0.120 | 13 |
| | | | | LNU233 | 0.230 | 0.129 | 23.9 | LNU223 | 0.364 | 0.097 | 12 |
| | | | | LNU245 | 0.200 | 0.513 | 7.7 | LNU233 | 0.372 | 0.061 | 14 |
| | | | | LNU247 | 0.187 | 0.961 | 0.7 | LNU245 | 0.375 | 0.045 | 16 |
| | | | | LNU284 | 0.222 | 0.220 | 19.5 | LNU247 | 0.335 | 0.745 | 3 |
| | | | | LNU289 | 0.241 | 0.020 | 30.1 | LNU284 | 0.377 | 0.105 | 16 |
| | | | | LNU70 | 0.247 | 0.038 | 32.9 | LNU289 | 0.366 | 0.086 | 13 |
| | | | | LNU85 | 0.256 | 0.013 | 38.2 | LNU70 | 0.377 | 0.112 | 16 |
| | | | | CONT. | 0.380 | — | 0.0 | LNU85 | 0.416 | 0.002 | 28 |
| | | | | LNU105 | 0.400 | 0.710 | 5.2 | CONT. | 0.413 | — | 0 |
| | | | | LNU115 | 0.432 | 0.278 | 13.6 | LNU105 | 0.446 | 0.325 | 8.1 |
| | | | | LNU134 | 0.434 | 0.339 | 14.2 | LNU115 | 0.455 | 0.168 | 10 |
| | | | | LNU198 | 0.385 | 0.925 | 1.2 | LNU134 | 0.446 | 0.328 | 8 |
| | | | | LNU200 | 0.391 | 0.820 | 3.0 | LNU198 | 0.415 | 0.966 | 0.4 |
| | | | | CONT. | 0.838 | — | 0.0 | CONT. | 0.468 | — | 0 |
| | | | | LNU51 | 0.395 | 0.870 | 1.8 | LNU225 | 0.478 | 0.756 | 2.3 |
| | | | | LNU59 | 0.402 | 0.703 | 3.7 | LNU51 | 0.488 | 0.541 | 4.5 |
| | | | | CONT. | 0.429 | | | LNU59 | 0.502 | 0.320 | 7.3 |
| | | | | LNU258 | 0.522 | 0.25 | 21.7 | | | | |

Table 77.
"CONT."—Control;
"Ave."—Average;
"% Incr." = % increment.

Example 15

Evaluation of Transgenic *Arabidopsis* NUE, Yield and Plant Growth Rate Under Low or Normal Nitrogen Fertilization in Greenhouse Assay Assay 1: Nitrogen Use efficiency: Seed yield plant biomass and plant growth rate at limited and optimal nitrogen concentration under greenhouse conditions—This assay follows seed yield production, the biomass formation and the rosette area growth of plants grown in the greenhouse at limiting and non-limiting nitrogen growth conditions. Transgenic *Arabidopsis* seeds were sown in agar media supplemented with ½ MS medium and a selection agent (Kanamycin). The T2 transgenic seedlings were then transplanted to 1.7 trays filled with peat and perlite in a 1:1 ratio. The trays were irrigated with a solution containing nitrogen limiting conditions, which were achieved by irrigating the plants with a solution containing 1.5 mM inorganic nitrogen in the form of $KNO_3$, supplemented with 1 mM $KH_2PO_4$, 1 mM $MgSO_4$, 3.6 mM KCl, 2 mM $CaCl_2$ and microelements, while normal nitrogen levels were achieved by applying a solution of 6 mM inorganic nitrogen also in the form of $KNO_3$ with 1 mM $KH_2PO_4$, 1 mM $MgSO_4$, 2 mM $CaCl_2$ and microelements. All plants were grown in the greenhouse until mature seeds. Seeds were harvested, extracted and weight. The remaining plant biomass (the above ground tissue) was also harvested, and weighted immediately or following drying in oven at 50° C. for 24 hours.

Each construct was validated at its $T_2$ generation. Transgenic plants transformed with a construct conformed by an empty vector carrying the 35S promoter and the selectable marker was used as control.

The plants were analyzed for their overall size, growth rate, flowering, seed yield, 1,000-seed weight, dry matter and harvest index (HI—seed yield/dry matter).

Transgenic plants performance was compared to control plants grown in parallel under the same conditions. Mock-transgenic plants expressing the uidA reporter gene (GUS-Intron) or with no gene at all, under the same promoter were used as control.

The experiment was planned in nested randomized plot distribution. For each gene of the invention three to five independent transformation events were analyzed from each construct.

Digital imaging—A laboratory image acquisition system, which consists of a digital reflex camera (Canon EOS 300D) attached with a 55 mm focal length lens (Canon EF-S series), mounted on a reproduction device (Kaiser RS), which includes 4 light units (4×150 Watts light bulb) is used for capturing images of plant samples.

The image capturing process is repeated every 2 days starting from day 1 after transplanting till day 15. Same camera, placed in a custom made iron mount, is used for capturing images of larger plants sawn in white tubs in an environmental controlled greenhouse. The tubs are square shape include 1.7 liter trays. During the capture process, the tubs are placed beneath the iron mount, while avoiding direct sun light and casting of shadows.

An image analysis system is used, which consists of a personal desktop computer (Intel P4 3.0 GHz processor) and a public domain program—ImageJ 1.39 [Java based image processing program which was developed at the U.S. National Institutes of Health and freely available on the internet at Hypertext Transfer Protocol://rsbweb (dot) nih (dot) gov/]. Images are captured in resolution of 10 Mega Pixels (3888×2592 pixels) and stored in a low compression JPEG (Joint Photographic Experts Group standard) format. Next, analyzed data is saved to text files and processed using the JMP statistical analysis software (SAS institute).

Leaf analysis—Using the digital analysis leaves data is calculated, including leaf number, rosette area, rosette diameter, leaf blade area.

Vegetative growth rate: the relative growth rate (RGR) of leaf number [formula X (described above)], rosette area (formula XV), plot coverage (formula XVI) and harvest index (formula IV) is calculated with the indicated formulas.

Relative growth rate of rosette area=Regression coefficient of rosette area along time course.    Formula XV:

Relative growth rate of plot coverage=Regression coefficient of plot coverage along time course.    Formula XVI Seeds average weight—At the end of the experiment all seeds are collected. The seeds are scattered on a glass tray and a picture was taken. Using the digital analysis, the number of seeds in each sample is calculated.

Dry weight and seed yield—On about day 80 from sowing, the plants are harvested and left to dry at 30° C. in a drying chamber. The biomass and seed weight of each plot are measured and divided by the number of plants in each plot. Dry weight=total weight of the vegetative portion above ground (excluding roots) after drying at 30° C. in a drying chamber; Seed yield per plant=total seed weight per plant (gr). 1000 seed weight (the weight of 1000 seeds) (gr.).

The harvest index (HI) was calculated using Formula IV as described above.

Oil percentage in seeds—At the end of the experiment all seeds from each plot are collected. Seeds from 3 plots are mixed grounded and then mounted onto the extraction chamber. 210 ml of n-Hexane (Cat No. 080951 Biolab Ltd.) are used as the solvent. The extraction is performed for 30 hours at medium heat 50° C. Once the extraction has ended the n-Hexane was evaporated using the evaporator at 35° C. and vacuum conditions. The process is repeated twice. The information gained from the Soxhlet extractor (Soxhlet, F. Die gewichtsanalytische Bestimmung des Milchfettes, Polytechnisches J. (Dingler's) 1879, 232, 461) is used to create a calibration curve for the Low Resonance NMR. The content of oil of all seed samples is determined using the Low Resonance NMR (MARAN Ultra—Oxford Instrument) and its MultiQuant software package Silique length analysis—On day 50 from sowing, 30 siliques from different plants in each plot are sampled in block A. The chosen siliques are green-yellow in color and are collected from the bottom parts of a grown plant's stem. A digital photograph is taken to determine silique's length.

Statistical analyses—To identify genes conferring significantly improved tolerance to abiotic stresses, the results obtained from the transgenic plants are compared to those obtained from control plants. To identify outperforming genes and constructs, results from the independent transformation events tested are analyzed separately. Data is analyzed using Student's t-test and results are considered significant if the p value was less than 0.1. The JMP statistics software package is used (Version 5.2.1, SAS Institute Inc., Cary, N.C., USA).

Example 16

Evaluation of Transgenic *Arabidopsis* NUE, Yield and Plant Growth Rate Under Low or Normal Nitrogen Fertilization in Greenhouse Assay Assay 2: Nitrogen Use efficiency measured until bolting stage: plant biomass and plant growth rate at limited and optimal nitrogen concentration under greenhouse conditions—This assay follows the plant biomass formation and the rosette area growth of plants grown in the greenhouse at limiting and non-limiting nitrogen growth conditions. Transgenic *Arabidopsis* seeds were sown in agar media supplemented with ½ MS medium and a selection agent (Kanamycin). The T2 transgenic seedlings were then transplanted to 1.7 trays filled with peat and perlite in a 1:1 ratio. The trays were irrigated with a solution containing nitrogen limiting conditions, which were achieved by irrigating the plants with a solution containing 1.5 mM inorganic nitrogen in the form of $KNO_3$, supplemented with 1 mM $KH_2PO_4$, 1 mM $MgSO_4$, 3.6 mM KCl, 2 mM $CaCl_2$ and microelements, while normal nitrogen levels were achieved by applying a solution of 6 mM inorganic nitrogen also in the form of $KNO_3$ with 1 mM $KH_2PO_4$, 1 mM $MgSO_4$, 2 mM $CaCl_2$ and microelements. All plants were grown in the greenhouse until mature seeds. Plant biomass (the above ground tissue) was weight in directly after harvesting the rosette (plant fresh weight [FW]). Following plants were dried in an oven at 50° C. for 48 hours and weighted (plant dry weight [DW]).

Each construct was validated at its $T_2$ generation. Transgenic plants transformed with a construct conformed by an empty vector carrying the 35S promoter and the selectable marker was used as control.

The plants were analyzed for their overall size, growth rate, fresh weight and dry matter. Transgenic plants performance was compared to control plants grown in parallel under the same conditions. Mock-transgenic plants expressing the uidA reporter gene (GUS-Intron) or with no gene at all, under the same promoter were used as control.

The experiment was planned in nested randomized plot distribution. For each gene of the invention three to five independent transformation events were analyzed from each construct.

Digital imaging—A laboratory image acquisition system, which consists of a digital reflex camera (Canon EOS 300D) attached with a 55 mm focal length lens (Canon EF-S series), mounted on a reproduction device (Kaiser RS), which includes 4 light units (4×150 Watts light bulb) was used for capturing images of plant samples.

The image capturing process was repeated every 2 days starting from day 1 after transplanting till day 15. Same camera, placed in a custom made iron mount, was used for capturing images of larger plants sawn in white tubs in an environmental controlled greenhouse. The tubs were square shape include 1.7 liter trays. During the capture process, the tubes were placed beneath the iron mount, while avoiding direct sun light and casting of shadows.

An image analysis system was used, which consists of a personal desktop computer (Intel P4 3.0 GHz processor) and a public domain program—ImageJ 1.39 [Java based image processing program which was developed at the U.S. National Institutes of Health and freely available on the internet at Hypertext Transfer Protocol://rsbweb (dot) nih (dot) gov/]. Images were captured in resolution of 10 Mega Pixels (3888×2592 pixels) and stored in a low compression JPEG (Joint Photographic Experts Group standard) format. Next, analyzed data was saved to text files and processed using the JMP statistical analysis software (SAS institute).

Leaf analysis—Using the digital analysis leaves data was calculated, including leaf number, rosette area, rosette diameter, leaf blade area.

Vegetative growth rate: the relative growth rate (RGR) of leaf number (Formula X, described above), rosette area (Formula XV described above) and plot coverage (Formula XVI, described above) are calculated using the indicated formulas.

Plant Fresh and Dry weight—On about day 80 from sowing, the plants were harvested and directly weight for the determination of the plant fresh weight (FW) and left to dry at 50° C. in a drying chamber for about 48 hours before weighting to determine plant dry weight (DW).

Statistical analyses—To identify genes conferring significantly improved tolerance to abiotic stresses, the results obtained from the transgenic plants were compared to those obtained from control plants. To identify outperforming genes and constructs, results from the independent transformation events tested were analyzed separately. Data was analyzed using Student's t-test and results are considered significant if the p value was less than 0.1. The JMP statistics software package was used (Version 5.2.1, SAS Institute Inc., Cary, N.C., USA).

Experimental Results:

The genes listed in Tables 78 and 79 improved plant NUE when grown at limiting nitrogen concentration levels. These genes produced larger plants with a larger photosynthetic area, biomass (fresh weight, dry weight, rosette diameter, rosette area and plot coverage) when grown under limiting nitrogen conditions. The genes were cloned under the regulation of a constitutive (At6669) and root preferred promoter (RootP). The evaluation of each gene was performed by testing the performance of different number of events. Event with p-value <0.1 was considered statistically significant

TABLE 78

Genes showing improved plant biomass production at limiting nitrogen growth conditions

| | | Dry Weight [g] | | | | | Fresh Weight [g] | | |
|---|---|---|---|---|---|---|---|---|---|
| Gene Name | Event # | Ave. | P-Value | % incr. | Gene Name | Event # | Ave. | P-Value | % incr. |
| CONT. | — | 0.139 | — | 0.0 | CONT. | — | 0.890 | — | 0.0 |
| LNU100 | 14471.4 | 0.157 | 0.252 | 12.8 | LNU104 | 25032.2 | 0.956 | 0.646 | 7.4 |
| LNU104 | 25032.2 | 0.160 | 0.429 | 15.0 | LNU106 | 14481.1 | 0.981 | 0.117 | 10.2 |
| LNU104 | 25033.3 | 0.156 | 0.439 | 11.9 | LNU106 | 14483.5 | 0.981 | 0.664 | 10.2 |
| LNU106 | 14483.5 | 0.163 | 0.499 | 16.8 | LNU114 | 25042.1 | 1.000 | 0.461 | 12.3 |
| LNU106 | 14483.2 | 0.162 | 0.637 | 16.4 | LNU155 | 14525.1 | 0.975 | 0.648 | 9.5 |
| LNU106 | 14481.1 | 0.160 | 0.084 | 15.0 | LNU213 | 24654.4 | 0.975 | 0.028 | 9.5 |
| LNU106 | 14484.3 | 0.146 | 0.658 | 4.7 | LNU218 | 24781.4 | 0.919 | 0.410 | 3.2 |
| LNU114 | 25042.1 | 0.166 | 0.483 | 19.0 | LNU23 | 25163.6 | 0.919 | 0.710 | 3.2 |
| LNU155 | 14525.1 | 0.169 | 0.360 | 21.3 | LNU23 | 25163.2 | 0.913 | 0.610 | 2.5 |
| LNU213 | 24654.4 | 0.168 | 0.222 | 20.8 | LNU28 | 25171.2 | 1.000 | 0.008 | 12.3 |
| LNU218 | 24781.4 | 0.156 | 0.134 | 12.3 | LNU4 | 25134.1 | 0.956 | 0.430 | 7.4 |
| LNU23 | 25163.6 | 0.159 | 0.032 | 14.1 | LNU40 | 24792.1 | 0.994 | 0.670 | 11.6 |
| LNU23 | 25163.2 | 0.156 | 0.333 | 12.3 | LNU40 | 24794.4 | 0.946 | 0.664 | 6.3 |
| LNU23 | 25163.5 | 0.148 | 0.677 | 6.0 | LNU46 | 14462.5 | 0.988 | 0.329 | 10.9 |
| LNU28 | 25171.2 | 0.169 | 0.004 | 21.3 | LNU46 | 14462.1 | 0.975 | 0.190 | 9.5 |
| LNU28 | 25171.1 | 0.146 | 0.395 | 4.7 | LNU48 | 24804.4 | 0.963 | 0.502 | 8.1 |
| LNU4 | 25134.1 | 0.164 | 0.007 | 18.1 | LNU63 | 24814.2 | 1.056 | 0.077 | 18.6 |
| LNU4 | 25131.1 | 0.159 | 0.146 | 14.1 | LNU63 | 24811.2 | 1.050 | 0.606 | 17.9 |
| LNU4 | 25133.3 | 0.146 | 0.374 | 5.1 | LNU7 | 25082.7 | 0.956 | 0.116 | 7.4 |
| LNU40 | 24794.4 | 0.164 | 0.399 | 17.8 | LNU8 | 25062.2 | 1.019 | 0.009 | 14.4 |
| LNU40 | 24792.1 | 0.155 | 0.607 | 11.4 | LNU94 | 24833.1 | 0.969 | 0.502 | 8.8 |
| LNU40 | 24794.3 | 0.151 | 0.254 | 8.7 | LNU94 | 24834.4 | 0.946 | 0.742 | 6.2 |
| LNU40 | 24792.2 | 0.148 | 0.782 | 6.7 | LNU96 | 25073.3 | 0.956 | 0.335 | 7.4 |
| LNU46 | 14462.5 | 0.172 | 0.487 | 23.5 | CONT. | — | 0.761 | — | 0.0 |
| LNU46 | 14464.4 | 0.148 | 0.461 | 6.5 | LNU113 | 25631.3 | 0.900 | 0.458 | 18.3 |
| LNU46 | 14462.1 | 0.146 | 0.699 | 5.1 | LNU113 | 25631.7 | 0.894 | 0.196 | 17.5 |
| LNU48 | 24804.4 | 0.159 | 0.209 | 14.6 | LNU113 | 25631.9 | 0.875 | 0.032 | 15.0 |
| LNU48 | 24801.4 | 0.146 | 0.584 | 4.7 | LNU113 | 25631.4 | 0.863 | 0.232 | 13.4 |
| LNU63 | 24811.2 | 0.184 | 0.571 | 32.5 | LNU113 | 25631.1 | 0.813 | 0.149 | 6.8 |
| LNU63 | 24814.2 | 0.168 | 0.222 | 20.8 | LNU120 | 25463.3 | 1.119 | 0.016 | 47.1 |
| LNU7 | 25082.7 | 0.142 | 0.765 | 2.0 | LNU120 | 25465.3 | 0.856 | 0.204 | 12.6 |
| LNU8 | 25062.2 | 0.170 | 0.276 | 22.2 | LNU124 | 14501.1 | 0.813 | 0.475 | 6.8 |
| LNU8 | 25061.2 | 0.159 | 0.721 | 14.6 | LNU124 | 14502.1 | 0.794 | 0.388 | 4.4 |
| LNU8 | 25063.1 | 0.149 | 0.503 | 7.4 | LNU124 | 14504.5 | 0.788 | 0.439 | 3.5 |
| LNU94 | 24833.1 | 0.161 | 0.205 | 15.9 | LNU132 | 14102.6 | 1.013 | 0.141 | 33.1 |
| LNU94 | 24834.4 | 0.161 | 0.651 | 15.9 | LNU132 | 14102.7 | 0.906 | 0.345 | 19.2 |
| LNU94 | 24833.3 | 0.147 | 0.413 | 5.7 | LNU140 | 14112.6 | 0.931 | 0.000 | 22.4 |
| LNU96 | 25073.3 | 0.163 | 0.341 | 17.3 | LNU140 | 14111.6 | 0.844 | 0.139 | 10.9 |
| LNU96 | 25071.2 | 0.149 | 0.707 | 7.4 | LNU148 | 25685.6 | 0.906 | 0.174 | 19.2 |
| LNU96 | 25073.4 | 0.147 | 0.602 | 5.6 | LNU148 | 25685.2 | 0.881 | 0.057 | 15.9 |
| CONT. | — | 0.122 | — | 0.0 | LNU148 | 25685.1 | 0.831 | 0.046 | 9.3 |
| LNU113 | 25631.7 | 0.146 | 0.446 | 20.1 | LNU148 | 25685.9 | 0.813 | 0.475 | 6.8 |
| LNU113 | 25631.3 | 0.133 | 0.620 | 9.4 | LNU287 | 24674.6 | 1.006 | 0.270 | 32.3 |
| LNU113 | 25631.1 | 0.131 | 0.398 | 7.3 | LNU287 | 24674.3 | 0.775 | 0.732 | 1.9 |
| LNU120 | 25463.3 | 0.173 | 0.184 | 41.7 | LNU37 | 14064.7 | 0.775 | 0.653 | 1.9 |
| LNU120 | 25463.7 | 0.125 | 0.732 | 2.6 | LNU5 | 14042.7 | 0.869 | 0.168 | 14.2 |
| LNU132 | 14102.7 | 0.143 | 0.245 | 17.6 | LNU5 | 14043.7 | 0.788 | 0.529 | 3.5 |
| LNU132 | 14102.6 | 0.140 | 0.451 | 15.0 | LNU72 | 24962.3 | 0.800 | 0.264 | 5.2 |
| LNU140 | 14112.6 | 0.149 | 0.329 | 22.7 | LNU74 | 25443.3 | 0.956 | 0.259 | 25.7 |
| LNU148 | 25685.6 | 0.144 | 0.002 | 18.6 | LNU82 | 24823.1 | 0.850 | 0.014 | 11.8 |
| LNU148 | 25685.2 | 0.138 | 0.321 | 13.0 | LNU84 | 25621.8 | 0.831 | 0.790 | 9.3 |
| LNU148 | 25685.9 | 0.129 | 0.199 | 6.3 | LNU84 | 25621.2 | 0.794 | 0.498 | 4.4 |
| LNU148 | 25685.1 | 0.127 | 0.651 | 4.2 | LNU87 | 24712.1 | 0.869 | 0.657 | 14.2 |

TABLE 78-continued

Genes showing improved plant biomass production at limiting nitrogen growth conditions

| | | Dry Weight [g] | | | | | Fresh Weight [g] | | |
|---|---|---|---|---|---|---|---|---|---|
| Gene Name | Event # | Ave. | P-Value | % incr. | Gene Name | Event # | Ave. | P-Value | % incr. |
| LNU287 | 24674.6 | 0.156 | 0.008 | 28.4 | LNU87 | 24711.3 | 0.825 | 0.542 | 8.5 |
| LNU74 | 25443.3 | 0.151 | 0.071 | 24.2 | LNU87 | 24713.2 | 0.794 | 0.318 | 4.4 |
| LNU74 | 25443.5 | 0.138 | 0.626 | 13.0 | LNU87 | 24714.3 | 0.794 | 0.756 | 4.4 |
| LNU74 | 25444.1 | 0.135 | 0.209 | 10.9 | LNU98 | 25761.6 | 0.900 | 0.422 | 18.3 |
| LNU74 | 25443.2 | 0.126 | 0.521 | 3.2 | LNU98 | 25762.2 | 0.794 | 0.756 | 4.4 |
| LNU82 | 24823.1 | 0.152 | 0.303 | 24.8 | CONT. | — | 0.974 | — | 0.0 |
| LNU84 | 25621.8 | 0.146 | 0.652 | 19.6 | LNU84 | 25621.2 | 1.031 | 0.280 | 5.9 |
| LNU84 | 25621.2 | 0.128 | 0.540 | 4.7 | CONT. | — | 0.851 | — | 0.0 |
| LNU87 | 24712.1 | 0.148 | 0.595 | 21.2 | LNU117 | 25933.3 | 1.113 | 0.657 | 30.8 |
| LNU87 | 24714.3 | 0.143 | 0.613 | 17.1 | LNU117 | 25931.2 | 1.050 | 0.004 | 23.4 |
| LNU87 | 24712.4 | 0.126 | 0.762 | 3.7 | LNU117 | 25932.4 | 0.975 | 0.272 | 14.6 |
| LNU87 | 24713.2 | 0.124 | 0.757 | 2.2 | LNU122 | 25333.2 | 1.481 | 0.233 | 74.1 |
| LNU98 | 25761.6 | 0.132 | 0.543 | 8.3 | LNU122 | 25332.2 | 1.181 | 0.387 | 38.9 |
| LNU98 | 25762.2 | 0.131 | 0.639 | 7.8 | LNU122 | 25333.1 | 1.031 | 0.101 | 21.2 |
| LNU98 | 25763.2 | 0.125 | 0.722 | 2.7 | LNU125 | 25944.3 | 1.256 | 0.343 | 47.7 |
| CONT. | — | 0.129 | — | 0.0 | LNU125 | 25941.4 | 1.244 | 0.381 | 46.2 |
| LNU82 | 24823.1 | 0.144 | 0.134 | 11.9 | LNU125 | 25941.2 | 1.081 | 0.443 | 27.1 |
| LNU84 | 25621.2 | 0.149 | 0.002 | 15.3 | LNU138 | 14074.5 | 1.488 | 0.001 | 74.9 |
| LNU98 | 25763.2 | 0.133 | 0.619 | 3.2 | LNU138 | 14071.5 | 1.425 | 0.157 | 67.5 |
| CONT. | — | 0.124 | — | 0.0 | LNU138 | 14074.6 | 1.413 | 0.048 | 66.1 |
| LNU117 | 25933.3 | 0.160 | 0.692 | 29.2 | LNU138 | 14072.8 | 1.244 | 0.394 | 46.2 |
| LNU117 | 25931.2 | 0.135 | 0.237 | 9.0 | LNU138 | 14072.5 | 1.138 | 0.422 | 33.7 |
| LNU122 | 25333.2 | 0.228 | 0.287 | 84.3 | LNU180 | 24724.1 | 1.200 | 0.533 | 41.1 |
| LNU122 | 25332.2 | 0.180 | 0.412 | 45.4 | LNU180 | 24721.4 | 1.119 | 0.135 | 31.5 |
| LNU122 | 25333.1 | 0.144 | 0.003 | 16.1 | LNU180 | 24721.2 | 1.100 | 0.043 | 29.3 |
| LNU125 | 25944.3 | 0.179 | 0.470 | 44.9 | LNU180 | 24722.2 | 0.944 | 0.039 | 11.0 |
| LNU125 | 25941.4 | 0.179 | 0.500 | 44.4 | LNU180 | 24723.1 | 0.881 | 0.361 | 3.6 |
| LNU125 | 25941.2 | 0.157 | 0.624 | 26.7 | LNU220 | 25405.1 | 1.038 | 0.453 | 22.0 |
| LNU138 | 14074.5 | 0.224 | 0.031 | 81.2 | LNU220 | 25405.3 | 0.969 | 0.699 | 13.9 |
| LNU138 | 14071.5 | 0.216 | 0.199 | 74.7 | LNU220 | 25405.5 | 0.931 | 0.368 | 9.5 |
| LNU138 | 14074.6 | 0.205 | 0.091 | 65.6 | LNU230 | 25413.1 | 1.338 | 0.437 | 57.2 |
| LNU138 | 14072.8 | 0.169 | 0.584 | 36.3 | LNU230 | 25412.2 | 1.212 | 0.205 | 42.4 |
| LNU138 | 14072.5 | 0.147 | 0.695 | 18.6 | LNU230 | 25413.2 | 1.019 | 0.475 | 19.8 |
| LNU180 | 24724.1 | 0.180 | 0.575 | 45.4 | LNU230 | 25412.1 | 0.913 | 0.311 | 7.3 |
| LNU180 | 24721.4 | 0.159 | 0.346 | 28.2 | LNU234 | 25014.5 | 1.544 | 0.386 | 81.5 |
| LNU180 | 24721.2 | 0.151 | 0.119 | 22.2 | LNU234 | 25014.4 | 1.056 | 0.657 | 24.2 |
| LNU220 | 25405.3 | 0.148 | 0.660 | 19.1 | LNU234 | 25014.8 | 1.013 | 0.706 | 19.0 |
| LNU220 | 25405.1 | 0.143 | 0.642 | 15.6 | LNU25 | 14083.7 | 1.100 | 0.429 | 29.3 |
| LNU230 | 25413.1 | 0.193 | 0.512 | 55.5 | LNU25 | 14084.6 | 1.038 | 0.606 | 22.0 |
| LNU230 | 25412.2 | 0.183 | 0.218 | 47.5 | LNU25 | 14082.8 | 0.981 | 0.466 | 15.4 |
| LNU230 | 25413.2 | 0.149 | 0.654 | 20.1 | LNU254 | 25782.5 | 1.463 | 0.185 | 71.9 |
| LNU230 | 25412.1 | 0.134 | 0.269 | 8.0 | LNU254 | 25781.3 | 1.256 | 0.328 | 47.7 |
| LNU234 | 25014.5 | 0.221 | 0.492 | 78.2 | LNU254 | 25782.4 | 1.094 | 0.559 | 28.6 |
| LNU234 | 25014.4 | 0.152 | 0.664 | 22.7 | LNU254 | 25781.5 | 0.969 | 0.024 | 13.9 |
| LNU234 | 25014.8 | 0.151 | 0.725 | 21.7 | LNU263 | 25794.6 | 1.138 | 0.366 | 33.7 |
| LNU25 | 14084.6 | 0.154 | 0.634 | 24.2 | LNU263 | 25794.3 | 1.106 | 0.003 | 30.1 |
| LNU25 | 14083.7 | 0.148 | 0.668 | 19.1 | LNU263 | 25791.3 | 1.069 | 0.339 | 25.6 |
| LNU254 | 25782.5 | 0.226 | 0.199 | 82.2 | LNU263 | 25794.8 | 0.956 | 0.030 | 12.4 |
| LNU254 | 25782.4 | 0.171 | 0.547 | 37.8 | LNU263 | 25792.2 | 0.869 | 0.680 | 2.1 |
| LNU254 | 25781.3 | 0.166 | 0.527 | 34.3 | LNU267 | 25804.3 | 1.269 | 0.334 | 49.2 |
| LNU254 | 25781.5 | 0.129 | 0.138 | 4.5 | LNU267 | 25803.1 | 1.106 | 0.003 | 30.1 |
| LNU263 | 25794.6 | 0.163 | 0.456 | 31.3 | LNU271 | 25912.1 | 1.150 | 0.626 | 35.2 |
| LNU263 | 25794.8 | 0.138 | 0.011 | 11.6 | LNU271 | 25913.3 | 1.119 | 0.529 | 31.5 |
| LNU263 | 25794.3 | 0.138 | 0.018 | 11.1 | LNU278 | 25812.3 | 0.913 | 0.311 | 7.3 |
| LNU263 | 25791.3 | 0.129 | 0.765 | 4.5 | LNU278 | 25814.1 | 0.900 | 0.140 | 5.8 |
| LNU267 | 25804.3 | 0.197 | 0.323 | 59.0 | LNU278 | 25814.3 | 0.900 | 0.252 | 5.8 |
| LNU267 | 25803.1 | 0.156 | 0.034 | 26.2 | LNU278 | 25813.2 | 0.888 | 0.660 | 4.3 |
| LNU267 | 25804.4 | 0.134 | 0.759 | 8.0 | LNU36 | 25561.2 | 1.250 | 0.571 | 47.0 |
| LNU271 | 25913.3 | 0.168 | 0.604 | 35.8 | LNU36 | 25562.3 | 1.050 | 0.519 | 23.4 |
| LNU271 | 25912.1 | 0.167 | 0.666 | 34.9 | LNU36 | 25562.2 | 0.938 | 0.665 | 10.2 |
| LNU278 | 25814.3 | 0.129 | 0.708 | 4.0 | LNU36 | 25562.9 | 0.925 | 0.548 | 8.7 |
| LNU278 | 25812.3 | 0.126 | 0.674 | 1.5 | LNU43 | 14422.8 | 1.156 | 0.394 | 35.9 |
| LNU36 | 25561.2 | 0.193 | 0.589 | 55.5 | LNU43 | 14421.1 | 1.150 | 0.219 | 35.2 |
| LNU36 | 25562.3 | 0.149 | 0.429 | 20.1 | LNU43 | 14423.6 | 0.938 | 0.207 | 10.2 |
| LNU36 | 25562.4 | 0.138 | 0.749 | 11.6 | LNU45 | 25052.11 | 1.050 | 0.538 | 23.4 |
| LNU43 | 14421.1 | 0.159 | 0.254 | 28.2 | LNU45 | 25052.9 | 0.931 | 0.786 | 9.5 |
| LNU43 | 14422.8 | 0.159 | 0.580 | 28.2 | LNU45 | 25052.12 | 0.906 | 0.797 | 6.5 |
| LNU67 | 25824.5 | 0.156 | 0.585 | 26.2 | LNU67 | 25824.5 | 1.194 | 0.287 | 40.3 |
| LNU67 | 25824.3 | 0.154 | 0.513 | 24.7 | LNU67 | 25824.3 | 1.050 | 0.600 | 23.4 |
| CONT. | — | 0.179 | — | 0.0 | LNU67 | 25821.5 | 0.900 | 0.252 | 5.8 |
| LNU100 | 14474.2 | 0.222 | 0.512 | 24.2 | CONT. | — | 1.058 | — | 0.0 |
| LNU104 | 25033.3 | 0.213 | 0.558 | 19.3 | LNU100 | 14474.2 | 1.325 | 0.357 | 25.2 |
| LNU106 | 14483.2 | 0.232 | 0.720 | 29.8 | LNU100 | 14473.3 | 1.269 | 0.718 | 19.9 |

TABLE 78-continued

Genes showing improved plant biomass production at limiting nitrogen growth conditions

| | | Dry Weight [g] | | | | | Fresh Weight [g] | | |
|---|---|---|---|---|---|---|---|---|---|
| Gene Name | Event # | Ave. | P-Value | % incr. | Gene Name | Event # | Ave. | P-Value | % incr. |
| LNU114 | 25041.2 | 0.215 | 0.661 | 20.4 | LNU100 | 14472.1 | 1.144 | 0.663 | 8.1 |
| LNU117 | 25932.4 | 0.363 | 0.306 | 103.3 | LNU104 | 25033.3 | 1.288 | 0.462 | 21.7 |
| LNU180 | 24723.1 | 0.341 | 0.543 | 90.7 | LNU106 | 14483.2 | 1.369 | 0.687 | 29.4 |
| LNU218 | 24781.2 | 0.278 | 0.651 | 55.7 | LNU114 | 25041.2 | 1.206 | 0.671 | 14.0 |
| LNU218 | 24781.1 | 0.227 | 0.359 | 27.0 | LNU117 | 25932.4 | 1.931 | 0.268 | 82.5 |
| LNU254 | 25781.3 | 0.333 | 0.021 | 86.1 | LNU180 | 24723.1 | 1.844 | 0.530 | 74.3 |
| LNU254 | 25782.5 | 0.217 | 0.285 | 21.4 | LNU218 | 24781.2 | 1.450 | 0.684 | 37.1 |
| LNU4 | 25133.3 | 0.256 | 0.106 | 43.4 | LNU218 | 24781.1 | 1.406 | 0.410 | 32.9 |
| LNU4 | 25134.2 | 0.193 | 0.707 | 8.1 | LNU254 | 25781.3 | 1.750 | 0.038 | 65.4 |
| LNU40 | 24794.3 | 0.259 | 0.557 | 45.2 | LNU254 | 25782.5 | 1.181 | 0.425 | 11.7 |
| LNU40 | 24793.1 | 0.254 | 0.522 | 42.4 | LNU4 | 25133.3 | 1.400 | 0.093 | 32.3 |
| LNU63 | 24814.7 | 0.333 | 0.446 | 86.1 | LNU4 | 25134.3 | 1.206 | 0.509 | 14.0 |
| LNU63 | 24814.2 | 0.283 | 0.221 | 58.5 | LNU4 | 25134.2 | 1.163 | 0.479 | 9.9 |
| LNU63 | 24812.3 | 0.256 | 0.305 | 43.4 | LNU40 | 24794.3 | 1.544 | 0.515 | 45.9 |
| LNU7 | 25082.2 | 0.197 | 0.697 | 10.2 | LNU40 | 24793.1 | 1.431 | 0.486 | 35.3 |
| LNU7 | 25083.3 | 0.189 | 0.753 | 5.7 | LNU40 | 24792.1 | 1.231 | 0.695 | 16.4 |
| LNU8 | 25063.6 | 0.193 | 0.669 | 7.8 | LNU48 | 24803.2 | 1.144 | 0.774 | 8.1 |
| CONT. | — | 0.106 | — | 0.0 | LNU48 | 24802.2 | 1.139 | 0.581 | 7.7 |
| LNU122 | 25332.2 | 0.119 | 0.161 | 11.8 | LNU63 | 24814.7 | 1.813 | 0.453 | 71.3 |
| LNU122 | 25333.2 | 0.113 | 0.223 | 5.9 | LNU63 | 24814.2 | 1.613 | 0.140 | 52.4 |
| LNU125 | 25941.4 | 0.126 | 0.010 | 18.2 | LNU63 | 24812.3 | 1.494 | 0.216 | 41.2 |
| LNU125 | 25943.2 | 0.121 | 0.009 | 13.5 | LNU7 | 25082.2 | 1.206 | 0.354 | 14.0 |
| LNU138 | 14072.5 | 0.114 | 0.426 | 7.6 | LNU7 | 25083.3 | 1.169 | 0.454 | 10.5 |
| LNU178 | 14612.1 | 0.127 | 0.001 | 19.4 | LNU7 | 25083.1 | 1.144 | 0.696 | 8.1 |
| LNU178 | 14614.5 | 0.124 | 0.302 | 16.5 | LNU8 | 25063.6 | 1.231 | 0.319 | 16.4 |
| LNU220 | 25405.1 | 0.116 | 0.533 | 8.8 | CONT. | — | 0.690 | — | 0.0 |
| LNU220 | 25405.5 | 0.114 | 0.260 | 7.6 | LNU122 | 25332.2 | 0.775 | 0.505 | 12.4 |
| LNU220 | 25405.6 | 0.108 | 0.798 | 1.2 | LNU125 | 25941.4 | 0.775 | 0.586 | 12.4 |
| LNU234 | 25014.6 | 0.128 | 0.076 | 20.6 | LNU178 | 14612.1 | 0.838 | 0.235 | 21.4 |
| LNU236 | 25425.4 | 0.134 | 0.302 | 25.9 | LNU178 | 14614.5 | 0.781 | 0.147 | 13.3 |
| LNU236 | 25424.2 | 0.118 | 0.690 | 10.6 | LNU220 | 25405.1 | 0.806 | 0.468 | 16.9 |
| LNU236 | 25423.3 | 0.116 | 0.436 | 8.8 | LNU220 | 25405.5 | 0.756 | 0.004 | 9.6 |
| LNU25 | 14082.8 | 0.119 | 0.185 | 12.4 | LNU234 | 25014.6 | 0.763 | 0.443 | 10.5 |
| LNU271 | 25911.4 | 0.124 | 0.033 | 16.5 | LNU236 | 25425.4 | 0.838 | 0.373 | 21.4 |
| LNU271 | 25913.3 | 0.109 | 0.633 | 2.9 | LNU236 | 25424.2 | 0.781 | 0.546 | 13.3 |
| LNU278 | 25814.1 | 0.111 | 0.707 | 4.7 | LNU236 | 25423.3 | 0.731 | 0.508 | 6.0 |
| LNU43 | 14423.6 | 0.118 | 0.062 | 11.2 | LNU25 | 14082.8 | 0.900 | 0.066 | 30.5 |
| LNU43 | 14423.7 | 0.111 | 0.511 | 4.1 | LNU271 | 25911.4 | 0.738 | 0.065 | 6.9 |
| LNU45 | 25052.12 | 0.123 | 0.467 | 15.3 | LNU271 | 25913.2 | 0.725 | 0.360 | 5.1 |
| LNU45 | 25053.4 | 0.121 | 0.004 | 14.1 | LNU278 | 25814.1 | 0.738 | 0.507 | 6.9 |
| LNU45 | 25052.11 | 0.118 | 0.341 | 10.6 | LNU278 | 25814.3 | 0.719 | 0.334 | 4.2 |
| LNU67 | 25821.5 | 0.150 | 0.379 | 41.2 | LNU43 | 14423.6 | 0.775 | 0.007 | 12.4 |
| LNU67 | 25823.5 | 0.126 | 0.010 | 18.2 | LNU43 | 14422.9 | 0.731 | 0.197 | 6.0 |
| LNU67 | 25824.3 | 0.118 | 0.045 | 10.6 | LNU43 | 14423.7 | 0.700 | 0.767 | 1.5 |
| LNU9 | 25001.2 | 0.122 | 0.205 | 14.7 | LNU45 | 25052.12 | 0.813 | 0.431 | 17.8 |
| LNU9 | 25003.1 | 0.118 | 0.341 | 10.6 | LNU45 | 25053.4 | 0.813 | 0.139 | 17.8 |
| LNU9 | 25001.3 | 0.110 | 0.710 | 3.5 | LNU67 | 25821.5 | 0.994 | 0.378 | 44.1 |
| CONT. | — | 0.110 | — | 0.0 | LNU67 | 25821.4 | 0.831 | 0.000 | 20.5 |
| LNU157 | 24982.8 | 0.130 | 0.146 | 18.6 | LNU67 | 25823.5 | 0.775 | 0.099 | 12.4 |
| LNU157 | 24982.4 | 0.123 | 0.285 | 11.8 | LNU67 | 25824.3 | 0.763 | 0.014 | 10.5 |
| LNU157 | 24983.3 | 0.120 | 0.318 | 9.5 | LNU67 | 25824.5 | 0.738 | 0.507 | 6.9 |
| LNU168 | 24754.2 | 0.116 | 0.617 | 5.5 | LNU9 | 25003.1 | 0.819 | 0.238 | 18.7 |
| LNU173 | 25451.5 | 0.164 | 0.027 | 49.4 | LNU9 | 25001.7 | 0.725 | 0.510 | 5.1 |
| LNU173 | 25451.11 | 0.155 | 0.001 | 41.4 | LNU9 | 25001.2 | 0.706 | 0.562 | 2.4 |
| LNU173 | 25451.1 | 0.140 | 0.140 | 27.8 | CONT. | — | 0.728 | — | 0.0 |
| LNU173 | 25451.2 | 0.139 | 0.337 | 27.2 | LNU157 | 24982.8 | 0.856 | 0.199 | 17.7 |
| LNU173 | 25451.12 | 0.131 | 0.235 | 19.2 | LNU157 | 24982.4 | 0.794 | 0.422 | 9.1 |
| LNU178 | 14612.1 | 0.126 | 0.575 | 14.6 | LNU168 | 24754.2 | 0.856 | 0.199 | 17.7 |
| LNU178 | 14611.5 | 0.122 | 0.233 | 11.2 | LNU173 | 25451.5 | 1.069 | 0.001 | 46.9 |
| LNU178 | 14611.4 | 0.121 | 0.239 | 10.6 | LNU173 | 25451.11 | 1.019 | 0.002 | 40.0 |
| LNU178 | 14611.1 | 0.120 | 0.419 | 9.5 | LNU173 | 25451.2 | 0.950 | 0.073 | 30.5 |
| LNU184 | 25393.3 | 0.163 | 0.236 | 48.3 | LNU173 | 25451.1 | 0.938 | 0.047 | 28.8 |
| LNU184 | 25393.1 | 0.148 | 0.007 | 34.6 | LNU173 | 25451.12 | 0.888 | 0.399 | 21.9 |
| LNU184 | 25393.2 | 0.147 | 0.109 | 34.0 | LNU178 | 14611.4 | 0.913 | 0.019 | 25.4 |
| LNU184 | 25395.1 | 0.132 | 0.075 | 20.3 | LNU178 | 14612.1 | 0.869 | 0.525 | 19.4 |
| LNU184 | 25394.3 | 0.121 | 0.239 | 10.6 | LNU178 | 14611.5 | 0.850 | 0.092 | 16.8 |
| LNU20 | 24933.4 | 0.154 | 0.034 | 40.9 | LNU178 | 14611.1 | 0.800 | 0.286 | 9.9 |
| LNU20 | 24932.4 | 0.143 | 0.431 | 30.0 | LNU184 | 25393.1 | 0.994 | 0.013 | 36.5 |
| LNU20 | 24934.1 | 0.142 | 0.019 | 29.5 | LNU184 | 25393.3 | 0.994 | 0.100 | 36.5 |
| LNU20 | 24933.1 | 0.120 | 0.617 | 9.5 | LNU184 | 25393.2 | 0.975 | 0.027 | 34.0 |
| LNU230 | 25413.2 | 0.162 | 0.022 | 47.7 | LNU184 | 25395.1 | 0.888 | 0.103 | 21.9 |
| LNU230 | 25413.1 | 0.144 | 0.005 | 31.7 | LNU184 | 25394.3 | 0.856 | 0.077 | 17.7 |
| LNU230 | 25415.1 | 0.144 | 0.007 | 31.2 | LNU20 | 24933.4 | 1.088 | 0.002 | 49.4 |

TABLE 78-continued

Genes showing improved plant biomass production at limiting nitrogen growth conditions

| | | Dry Weight [g] | | | | | Fresh Weight [g] | | |
|---|---|---|---|---|---|---|---|---|---|
| Gene Name | Event # | Ave. | P-Value | % incr. | Gene Name | Event # | Ave. | P-Value | % incr. |
| LNU230 | 25412.2 | 0.126 | 0.148 | 15.2 | LNU20 | 24934.1 | 0.950 | 0.010 | 30.5 |
| LNU230 | 25412.1 | 0.119 | 0.510 | 8.4 | LNU20 | 24932.4 | 0.851 | 0.585 | 16.9 |
| LNU236 | 25425.4 | 0.153 | 0.002 | 39.2 | LNU20 | 24933.1 | 0.825 | 0.280 | 13.4 |
| LNU236 | 25424.2 | 0.124 | 0.160 | 12.9 | LNU230 | 25413.2 | 1.131 | 0.000 | 55.4 |
| LNU236 | 25422.4 | 0.119 | 0.502 | 8.9 | LNU230 | 25413.1 | 0.969 | 0.043 | 33.1 |
| LNU236 | 25423.3 | 0.119 | 0.343 | 8.4 | LNU230 | 25415.1 | 0.925 | 0.014 | 27.1 |
| LNU236 | 25425.3 | 0.116 | 0.546 | 5.5 | LNU230 | 25412.2 | 0.913 | 0.024 | 25.4 |
| LNU24 | 24971.3 | 0.158 | 0.001 | 44.3 | LNU230 | 25412.1 | 0.800 | 0.315 | 9.9 |
| LNU24 | 24971.2 | 0.143 | 0.029 | 30.6 | LNU236 | 25425.4 | 1.031 | 0.001 | 41.7 |
| LNU24 | 24971.4 | 0.136 | 0.141 | 24.3 | LNU236 | 25422.4 | 0.863 | 0.271 | 18.5 |
| LNU24 | 24974.2 | 0.123 | 0.205 | 11.8 | LNU236 | 25424.2 | 0.850 | 0.092 | 16.8 |
| LNU24 | 24972.1 | 0.116 | 0.533 | 5.5 | LNU236 | 25423.3 | 0.831 | 0.141 | 14.2 |
| LNU263 | 25794.8 | 0.156 | 0.050 | 42.0 | LNU236 | 25425.3 | 0.800 | 0.315 | 9.9 |
| LNU263 | 25794.6 | 0.146 | 0.047 | 33.5 | LNU24 | 24971.3 | 0.994 | 0.003 | 36.5 |
| LNU263 | 25794.3 | 0.141 | 0.162 | 28.9 | LNU24 | 24971.2 | 0.963 | 0.104 | 32.3 |
| LNU263 | 25791.3 | 0.138 | 0.021 | 26.0 | LNU24 | 24971.4 | 0.869 | 0.282 | 19.4 |
| LNU263 | 25792.2 | 0.129 | 0.524 | 18.1 | LNU24 | 24974.2 | 0.863 | 0.067 | 18.5 |
| LNU276 | 25433.2 | 0.144 | 0.006 | 31.2 | LNU24 | 24972.1 | 0.831 | 0.141 | 14.2 |
| LNU276 | 25433.1 | 0.133 | 0.362 | 20.9 | LNU263 | 25794.8 | 0.988 | 0.004 | 35.7 |
| LNU276 | 25433.3 | 0.131 | 0.045 | 19.8 | LNU263 | 25794.6 | 0.938 | 0.011 | 28.8 |
| LNU276 | 25433.5 | 0.124 | 0.685 | 12.9 | LNU263 | 25794.3 | 0.913 | 0.164 | 25.4 |
| LNU276 | 25431.1 | 0.117 | 0.611 | 6.7 | LNU263 | 25792.2 | 0.900 | 0.186 | 23.7 |
| LNU279 | 25481.5 | 0.165 | 0.000 | 50.6 | LNU263 | 25791.3 | 0.888 | 0.043 | 21.9 |
| LNU279 | 25481.3 | 0.163 | 0.000 | 48.3 | LNU276 | 25433.2 | 0.944 | 0.100 | 29.7 |
| LNU279 | 25481.4 | 0.146 | 0.022 | 32.9 | LNU276 | 25433.1 | 0.881 | 0.139 | 21.1 |
| LNU279 | 25481.2 | 0.144 | 0.237 | 31.7 | LNU276 | 25433.3 | 0.838 | 0.230 | 15.1 |
| LNU279 | 25484.3 | 0.132 | 0.137 | 20.3 | LNU276 | 25433.5 | 0.831 | 0.601 | 14.2 |
| LNU36 | 25561.2 | 0.188 | 0.000 | 71.1 | LNU276 | 25431.1 | 0.819 | 0.231 | 12.5 |
| LNU36 | 25562.3 | 0.183 | 0.214 | 66.5 | LNU279 | 25481.5 | 1.063 | 0.001 | 46.0 |
| LNU36 | 25562.7 | 0.131 | 0.057 | 19.2 | LNU279 | 25481.2 | 0.981 | 0.228 | 34.8 |
| LNU36 | 25562.9 | 0.123 | 0.367 | 11.8 | LNU279 | 25484.3 | 0.981 | 0.016 | 34.8 |
| LNU53 | 25674.1 | 0.136 | 0.022 | 23.8 | LNU279 | 25481.4 | 0.975 | 0.056 | 34.0 |
| LNU53 | 25674.3 | 0.119 | 0.502 | 8.9 | LNU279 | 25481.3 | 0.931 | 0.333 | 28.0 |
| LNU53 | 25674.6 | 0.118 | 0.383 | 7.8 | LNU36 | 25562.3 | 1.325 | 0.249 | 82.1 |
| LNU53 | 25674.2 | 0.114 | 0.659 | 3.8 | LNU36 | 25561.2 | 1.175 | 0.000 | 61.5 |
| LNU56 | 24693.1 | 0.164 | 0.042 | 49.4 | LNU36 | 25562.9 | 0.938 | 0.013 | 28.8 |
| LNU56 | 24691.2 | 0.151 | 0.006 | 37.5 | LNU36 | 25562.7 | 0.913 | 0.019 | 25.4 |
| LNU56 | 24693.2 | 0.137 | 0.187 | 24.9 | LNU53 | 25674.1 | 0.906 | 0.058 | 24.5 |
| LNU56 | 24694.2 | 0.133 | 0.032 | 21.5 | LNU53 | 25674.6 | 0.831 | 0.178 | 14.2 |
| LNU56 | 24694.1 | 0.133 | 0.186 | 20.9 | LNU53 | 25674.3 | 0.819 | 0.545 | 12.5 |
| LNU73 | 25755.1 | 0.142 | 0.008 | 29.5 | LNU53 | 25674.2 | 0.781 | 0.423 | 7.3 |
| LNU73 | 25751.9 | 0.138 | 0.129 | 25.5 | LNU56 | 24693.1 | 1.125 | 0.000 | 54.6 |
| LNU73 | 25751.1 | 0.133 | 0.063 | 21.5 | LNU56 | 24693.2 | 0.988 | 0.023 | 35.7 |
| LNU73 | 25751.8 | 0.118 | 0.628 | 7.2 | LNU56 | 24691.2 | 0.938 | 0.010 | 28.8 |
| LNU73 | 25754.2 | 0.116 | 0.488 | 6.1 | LNU56 | 24694.1 | 0.938 | 0.047 | 28.8 |
| LNU9 | 25001.7 | 0.163 | 0.236 | 48.3 | LNU56 | 24694.2 | 0.925 | 0.014 | 27.1 |
| LNU9 | 25001.1 | 0.137 | 0.020 | 24.9 | LNU73 | 25751.9 | 0.963 | 0.007 | 32.3 |
| LNU9 | 25001.3 | 0.119 | 0.314 | 8.9 | LNU73 | 25755.1 | 0.894 | 0.225 | 22.8 |
| LNU9 | 25001.2 | 0.116 | 0.655 | 6.1 | LNU73 | 25751.1 | 0.881 | 0.041 | 21.1 |
| CONT. | — | 0.112 | — | 0.0 | LNU73 | 25751.8 | 0.806 | 0.557 | 10.8 |
| LNU131 | 14005.5 | 0.150 | 0.000 | 34.2 | LNU73 | 25754.2 | 0.763 | 0.650 | 4.8 |
| LNU131 | 14002.15 | 0.138 | 0.186 | 23.0 | LNU9 | 25001.7 | 1.031 | 0.213 | 41.7 |
| LNU131 | 14005.2 | 0.133 | 0.015 | 18.5 | LNU9 | 25001.1 | 0.981 | 0.004 | 34.8 |
| LNU131 | 14002.12 | 0.119 | 0.302 | 6.8 | LNU9 | 25001.3 | 0.863 | 0.079 | 18.5 |
| LNU135 | 26204.2 | 0.156 | 0.103 | 39.2 | LNU9 | 25001.2 | 0.794 | 0.343 | 9.1 |
| LNU135 | 26203.4 | 0.137 | 0.363 | 22.4 | CONT. | — | 0.865 | — | 0.0 |
| LNU135 | 26203.6 | 0.128 | 0.021 | 14.6 | LNU131 | 14002.15 | 0.981 | 0.019 | 13.4 |
| LNU135 | 26203.1 | 0.125 | 0.074 | 11.8 | LNU131 | 14005.5 | 0.931 | 0.259 | 7.6 |
| LNU135 | 26204.4 | 0.118 | 0.315 | 5.1 | LNU131 | 14005.2 | 0.925 | 0.193 | 6.9 |
| LNU161 | 14552.7 | 0.124 | 0.673 | 10.7 | LNU135 | 26204.2 | 1.063 | 0.003 | 22.8 |
| LNU161 | 14553.4 | 0.123 | 0.207 | 9.6 | LNU135 | 26203.4 | 0.956 | 0.542 | 10.5 |
| LNU161 | 14553.6 | 0.122 | 0.343 | 9.0 | LNU135 | 26203.6 | 0.950 | 0.202 | 9.8 |
| LNU161 | 14552.9 | 0.121 | 0.457 | 7.9 | LNU135 | 26203.1 | 0.906 | 0.471 | 4.7 |
| LNU173 | 25451.5 | 0.119 | 0.455 | 6.2 | LNU161 | 14552.9 | 0.956 | 0.220 | 10.5 |
| LNU173 | 25451.11 | 0.115 | 0.753 | 2.9 | LNU161 | 14552.7 | 0.925 | 0.690 | 6.9 |
| LNU181 | 25771.6 | 0.116 | 0.522 | 3.4 | LNU161 | 14553.4 | 0.881 | 0.722 | 1.9 |
| LNU181 | 25771.2 | 0.115 | 0.516 | 2.9 | LNU184 | 25395.1 | 1.031 | 0.181 | 19.2 |
| LNU184 | 25395.1 | 0.153 | 0.000 | 36.4 | LNU184 | 25393.5 | 0.975 | 0.054 | 12.7 |
| LNU184 | 25394.3 | 0.134 | 0.104 | 20.2 | LNU184 | 25394.1 | 0.931 | 0.561 | 7.6 |
| LNU184 | 25394.1 | 0.131 | 0.039 | 16.9 | LNU184 | 25394.3 | 0.913 | 0.594 | 5.5 |
| LNU184 | 25393.3 | 0.127 | 0.007 | 13.5 | LNU224 | 25874.4 | 1.063 | 0.166 | 22.8 |
| LNU224 | 25874.4 | 0.141 | 0.250 | 26.4 | LNU224 | 25872.2 | 1.013 | 0.051 | 17.0 |
| LNU224 | 25871.3 | 0.136 | 0.001 | 21.9 | LNU224 | 25871.3 | 0.956 | 0.220 | 10.5 |

TABLE 78-continued

Genes showing improved plant biomass production at limiting nitrogen growth conditions

| Gene Name | Event # | Dry Weight [g] Ave. | P-Value | % incr. | Gene Name | Event # | Fresh Weight [g] Ave. | P-Value | % incr. |
|---|---|---|---|---|---|---|---|---|---|
| LNU224 | 25872.2 | 0.136 | 0.068 | 21.9 | LNU224 | 25872.3 | 0.904 | 0.500 | 4.5 |
| LNU224 | 25872.3 | 0.133 | 0.063 | 19.0 | LNU246 | 25744.2 | 1.044 | 0.312 | 20.6 |
| LNU224 | 25874.1 | 0.132 | 0.076 | 18.0 | LNU246 | 25743.1 | 0.963 | 0.049 | 11.2 |
| LNU246 | 25744.2 | 0.140 | 0.232 | 25.2 | LNU246 | 25743.2 | 0.963 | 0.082 | 11.2 |
| LNU246 | 25743.1 | 0.135 | 0.211 | 20.8 | LNU250 | 25592.1 | 1.000 | 0.135 | 15.6 |
| LNU246 | 25743.2 | 0.131 | 0.143 | 16.9 | LNU250 | 25592.2 | 0.963 | 0.049 | 11.2 |
| LNU250 | 25592.2 | 0.149 | 0.195 | 33.1 | LNU276 | 25433.5 | 1.163 | 0.004 | 34.4 |
| LNU250 | 25592.1 | 0.132 | 0.008 | 18.0 | LNU276 | 25433.6 | 0.931 | 0.704 | 7.6 |
| LNU260 | 26404.8 | 0.126 | 0.021 | 12.9 | LNU276 | 25433.3 | 0.919 | 0.353 | 6.2 |
| LNU260 | 26404.7 | 0.125 | 0.585 | 11.8 | LNU276 | 25433.1 | 0.894 | 0.670 | 3.3 |
| LNU260 | 26403.1 | 0.121 | 0.239 | 7.9 | LNU279 | 25481.2 | 1.106 | 0.146 | 27.9 |
| LNU260 | 26403.2 | 0.115 | 0.566 | 2.9 | LNU279 | 25481.3 | 1.100 | 0.038 | 27.1 |
| LNU276 | 25433.5 | 0.146 | 0.113 | 30.3 | LNU279 | 25481.4 | 1.094 | 0.023 | 26.4 |
| LNU276 | 25433.6 | 0.133 | 0.212 | 19.1 | LNU279 | 25484.3 | 1.088 | 0.000 | 25.7 |
| LNU276 | 25433.1 | 0.122 | 0.407 | 9.0 | LNU279 | 25481.5 | 1.025 | 0.095 | 18.5 |
| LNU276 | 25433.3 | 0.119 | 0.164 | 6.8 | LNU3 | 26124.1 | 1.106 | 0.146 | 27.9 |
| LNU276 | 25431.1 | 0.113 | 0.800 | 1.2 | LNU3 | 26122.2 | 1.100 | 0.082 | 27.1 |
| LNU279 | 25481.3 | 0.151 | 0.320 | 35.3 | LNU3 | 26123.6 | 0.994 | 0.011 | 14.9 |
| LNU279 | 25484.3 | 0.149 | 0.000 | 33.6 | LNU3 | 26123.5 | 0.894 | 0.791 | 3.3 |
| LNU279 | 25481.4 | 0.148 | 0.120 | 31.9 | LNU33 | 25553.2 | 1.010 | 0.103 | 16.7 |
| LNU279 | 25481.2 | 0.134 | 0.104 | 20.2 | LNU33 | 25552.2 | 0.906 | 0.404 | 4.7 |
| LNU279 | 25481.5 | 0.129 | 0.268 | 15.7 | CONT. | — | 0.723 | — | 0.0 |
| LNU3 | 26122.2 | 0.147 | 0.000 | 31.4 | LNU119 | 26142.8. | 0.988 | 0.051 | 36.7 |
| LNU3 | 26124.1 | 0.141 | 0.344 | 25.8 | LNU119 | 26144.2. | 0.913 | 0.000 | 26.3 |
| LNU3 | 26123.6 | 0.126 | 0.230 | 12.4 | LNU119 | 26142.5. | 0.869 | 0.035 | 20.2 |
| LNU3 | 26124.3 | 0.121 | 0.067 | 8.5 | LNU119 | 26141.1. | 0.819 | 0.563 | 13.3 |
| LNU3 | 26123.5 | 0.121 | 0.459 | 8.5 | LNU130 | 24912.7. | 1.119 | 0.093 | 54.8 |
| LNU33 | 25553.2 | 0.140 | 0.293 | 25.6 | LNU130 | 24911.7. | 1.113 | 0.000 | 54.0 |
| LNU33 | 25552.2 | 0.138 | 0.161 | 23.6 | LNU130 | 24913.5. | 0.931 | 0.052 | 28.9 |
| LNU33 | 25551.1 | 0.123 | 0.571 | 10.1 | LNU130 | 24913.6. | 0.913 | 0.000 | 26.3 |
| CONT. | — | 0.072 | — | 0.0 | LNU130 | 24914.5. | 0.863 | 0.380 | 19.4 |
| LNU119 | 26142.8. | 0.094 | 0.155 | 30.0 | LNU136 | 14511.10. | 1.213 | 0.000 | 67.8 |
| LNU119 | 26144.2. | 0.088 | 0.179 | 21.3 | LNU136 | 14514.8. | 1.163 | 0.000 | 60.9 |
| LNU119 | 26141.1. | 0.081 | 0.474 | 12.7 | LNU136 | 14515.5. | 1.144 | 0.086 | 58.3 |
| LNU130 | 24911.7. | 0.118 | 0.000 | 63.8 | LNU136 | 14513.6. | 1.007 | 0.171 | 39.4 |
| LNU130 | 24912.7. | 0.114 | 0.189 | 58.6 | LNU136 | 14515.1. | 1.006 | 0.000 | 39.3 |
| LNU130 | 24913.6. | 0.098 | 0.003 | 36.0 | LNU142 | 27541.1. | 1.194 | 0.001 | 65.2 |
| LNU130 | 24914.5. | 0.094 | 0.405 | 30.8 | LNU142 | 27545.1. | 0.969 | 0.000 | 34.1 |
| LNU130 | 24913.5. | 0.091 | 0.129 | 26.5 | LNU142 | 27546.1. | 0.919 | 0.015 | 27.2 |
| LNU136 | 14511.10. | 0.131 | 0.018 | 82.0 | LNU142 | 27546.2. | 0.894 | 0.338 | 23.7 |
| LNU136 | 14515.5. | 0.124 | 0.014 | 72.4 | LNU142 | 27541.2. | 0.816 | 0.322 | 13.0 |
| LNU136 | 14514.8. | 0.114 | 0.000 | 58.6 | LNU149 | 26175.3. | 1.309 | 0.001 | 81.2 |
| LNU136 | 14515.1. | 0.102 | 0.000 | 41.2 | LNU149 | 26175.1. | 1.094 | 0.016 | 51.4 |
| LNU136 | 14513.6. | 0.099 | 0.068 | 37.2 | LNU149 | 26175.7. | 0.855 | 0.575 | 18.4 |
| LNU142 | 27541.1. | 0.126 | 0.003 | 74.2 | LNU149 | 26174.4. | 0.838 | 0.699 | 15.9 |
| LNU142 | 27546.2. | 0.101 | 0.007 | 40.4 | LNU149 | 26174.6. | 0.813 | 0.655 | 12.5 |
| LNU142 | 27546.1. | 0.095 | 0.188 | 31.7 | LNU15 | 14123.11. | 1.121 | 0.146 | 55.1 |
| LNU142 | 27545.1. | 0.094 | 0.056 | 30.0 | LNU15 | 14123.13. | 0.994 | 0.410 | 37.5 |
| LNU142 | 27541.2. | 0.080 | 0.450 | 10.3 | LNU15 | 14122.8. | 0.988 | 0.387 | 36.7 |
| LNU149 | 26175.3. | 0.135 | 0.098 | 86.9 | LNU15 | 14122.9. | 0.969 | 0.352 | 34.1 |
| LNU149 | 26175.1. | 0.116 | 0.002 | 61.2 | LNU15 | 14124.12. | 0.844 | 0.521 | 16.8 |
| LNU149 | 26174.4. | 0.094 | 0.352 | 30.8 | LNU185 | 26475.1. | 1.131 | 0.381 | 56.6 |
| LNU149 | 26175.7. | 0.093 | 0.203 | 28.6 | LNU185 | 26474.1. | 0.956 | 0.368 | 32.4 |
| LNU149 | 26174.6. | 0.081 | 0.651 | 12.7 | LNU185 | 26473.1. | 0.950 | 0.413 | 31.5 |
| LNU15 | 14123.11. | 0.118 | 0.012 | 63.2 | LNU185 | 26474.2. | 0.919 | 0.448 | 27.2 |
| LNU15 | 14122.8. | 0.103 | 0.403 | 43.0 | LNU212 | 25834.4. | 1.294 | 0.095 | 79.1 |
| LNU15 | 14122.9. | 0.103 | 0.401 | 42.1 | LNU212 | 25834.5. | 1.250 | 0.131 | 73.0 |
| LNU15 | 14124.12. | 0.092 | 0.246 | 27.4 | LNU212 | 25834.1. | 1.081 | 0.208 | 49.7 |
| LNU15 | 14123.13. | 0.091 | 0.183 | 26.5 | LNU212 | 25833.2. | 1.056 | 0.173 | 46.2 |
| LNU185 | 26475.1. | 0.120 | 0.272 | 66.4 | LNU212 | 25832.1. | 1.019 | 0.026 | 41.0 |
| LNU185 | 26474.2. | 0.108 | 0.374 | 49.9 | LNU216 | 25985.4. | 1.313 | 0.000 | 81.7 |
| LNU185 | 26474.1. | 0.094 | 0.429 | 30.8 | LNU216 | 25982.1. | 1.150 | 0.046 | 59.2 |
| LNU185 | 26473.1. | 0.093 | 0.297 | 28.2 | LNU216 | 25984.6. | 0.938 | 0.027 | 29.8 |
| LNU212 | 25834.5. | 0.134 | 0.024 | 86.3 | LNU216 | 25982.2. | 0.863 | 0.001 | 19.4 |
| LNU212 | 25834.4. | 0.126 | 0.092 | 74.2 | LNU216 | 25984.1. | 0.844 | 0.602 | 16.8 |
| LNU212 | 25833.2. | 0.121 | 0.082 | 67.2 | LNU228 | 26222.4. | 1.275 | 0.000 | 76.5 |
| LNU212 | 25834.1. | 0.116 | 0.118 | 60.3 | LNU228 | 26222.1. | 1.181 | 0.100 | 63.5 |
| LNU212 | 25832.1. | 0.103 | 0.006 | 42.1 | LNU228 | 26224.7. | 1.019 | 0.004 | 41.0 |
| LNU216 | 25985.4. | 0.119 | 0.097 | 64.6 | LNU228 | 26225.2. | 0.856 | 0.615 | 18.5 |
| LNU216 | 25982.1. | 0.109 | 0.103 | 50.8 | LNU228 | 26224.6. | 0.775 | 0.471 | 7.3 |
| LNU216 | 25984.6. | 0.084 | 0.015 | 16.1 | LNU229 | 26112.3. | 1.131 | 0.013 | 56.6 |
| LNU216 | 25984.1. | 0.083 | 0.586 | 14.4 | LNU229 | 26111.5. | 0.838 | 0.607 | 15.9 |
| LNU216 | 25982.2. | 0.076 | 0.437 | 4.9 | LNU241 | 26232.4. | 0.800 | 0.751 | 10.7 |

TABLE 78-continued

Genes showing improved plant biomass production at limiting nitrogen growth conditions

| | | Dry Weight [g] | | | | | Fresh Weight [g] | | |
|---|---|---|---|---|---|---|---|---|---|
| Gene Name | Event # | Ave. | P-Value | % incr. | Gene Name | Event # | Ave. | P-Value | % incr. |
| LNU228 | 26222.4. | 0.133 | 0.000 | 83.7 | LNU274 | 26261.3. | 0.794 | 0.305 | 9.9 |
| LNU228 | 26222.1. | 0.115 | 0.215 | 59.4 | LNU280 | 26164.4. | 0.843 | 0.137 | 16.7 |
| LNU228 | 26224.7. | 0.100 | 0.215 | 38.6 | LNU280 | 26162.1. | 0.800 | 0.765 | 10.7 |
| LNU228 | 26225.2. | 0.091 | 0.511 | 26.5 | LNU55 | 26013.9. | 0.756 | 0.491 | 4.7 |
| LNU228 | 26224.6. | 0.086 | 0.448 | 18.7 | LNU55 | 26015.1. | 0.750 | 0.396 | 3.8 |
| LNU229 | 26112.3. | 0.113 | 0.117 | 56.0 | LNU81 | 26034.2. | 0.806 | 0.530 | 11.6 |
| LNU229 | 26111.5. | 0.086 | 0.658 | 19.6 | CONT. | — | 0.625 | — | 0.0 |
| LNU241 | 26232.4. | 0.078 | 0.767 | 8.3 | LNU119 | 26141.1. | 0.769 | 0.001 | 23.0 |
| LNU274 | 26261.3. | 0.084 | 0.101 | 16.1 | LNU119 | 26142.8. | 0.719 | 0.318 | 15.0 |
| LNU274 | 26263.2. | 0.074 | 0.613 | 3.0 | LNU119 | 26142.5. | 0.688 | 0.554 | 10.0 |
| LNU280 | 26162.1. | 0.085 | 0.545 | 17.9 | LNU119 | 26144.1. | 0.681 | 0.053 | 9.0 |
| LNU280 | 26164.4. | 0.083 | 0.027 | 14.5 | LNU119 | 26144.2. | 0.650 | 0.708 | 4.0 |
| LNU81 | 26034.2. | 0.083 | 0.301 | 14.4 | LNU130 | 24913.5. | 0.856 | 0.067 | 37.0 |
| LNU81 | 26034.3. | 0.075 | 0.477 | 4.0 | LNU130 | 24911.7. | 0.794 | 0.446 | 27.0 |
| CONT. | — | 0.084 | — | 0.0 | LNU130 | 24912.7. | 0.719 | 0.388 | 15.0 |
| LNU119 | 26142.8. | 0.097 | 0.259 | 15.4 | LNU130 | 24913.6. | 0.681 | 0.053 | 9.0 |
| LNU119 | 26142.5. | 0.093 | 0.583 | 10.2 | LNU136 | 14514.8. | 0.713 | 0.011 | 14.0 |
| LNU119 | 26141.1. | 0.092 | 0.136 | 9.4 | LNU136 | 14515.1. | 0.694 | 0.492 | 11.0 |
| LNU130 | 24913.5. | 0.104 | 0.006 | 23.6 | LNU136 | 14515.5. | 0.669 | 0.204 | 7.0 |
| LNU130 | 24911.7. | 0.094 | 0.675 | 11.7 | LNU142 | 27546.1. | 0.681 | 0.742 | 9.0 |
| LNU130 | 24913.6. | 0.094 | 0.448 | 11.7 | LNU142 | 27545.1. | 0.656 | 0.678 | 5.0 |
| LNU130 | 24912.7. | 0.092 | 0.680 | 9.4 | LNU142 | 27546.2. | 0.644 | 0.798 | 3.0 |
| LNU149 | 26174.6. | 0.102 | 0.307 | 21.4 | LNU149 | 26174.6. | 0.869 | 0.147 | 39.0 |
| LNU149 | 26175.3. | 0.096 | 0.416 | 14.6 | LNU149 | 26175.3. | 0.844 | 0.025 | 35.0 |
| LNU149 | 26174.7. | 0.089 | 0.592 | 5.7 | LNU149 | 26174.7. | 0.781 | 0.005 | 25.0 |
| LNU15 | 14122.9. | 0.093 | 0.441 | 10.2 | LNU149 | 26174.8. | 0.669 | 0.638 | 7.0 |
| LNU15 | 14123.13. | 0.087 | 0.788 | 3.5 | LNU149 | 26175.1. | 0.656 | 0.729 | 5.0 |
| LNU185 | 26475.1. | 0.093 | 0.213 | 10.2 | LNU15 | 14122.9. | 0.825 | 0.160 | 32.0 |
| LNU212 | 25834.1. | 0.128 | 0.278 | 51.9 | LNU15 | 14122.8. | 0.750 | 0.605 | 20.0 |
| LNU212 | 25834.5. | 0.119 | 0.326 | 42.2 | LNU15 | 14123.11. | 0.694 | 0.026 | 11.0 |
| LNU212 | 25833.2. | 0.106 | 0.326 | 25.8 | LNU15 | 14123.13. | 0.650 | 0.511 | 4.0 |
| LNU212 | 25833.1. | 0.101 | 0.381 | 20.6 | LNU185 | 26475.1. | 0.756 | 0.223 | 21.0 |
| LNU212 | 25834.4. | 0.096 | 0.410 | 13.9 | LNU185 | 26474.1. | 0.706 | 0.364 | 13.0 |
| LNU216 | 25985.4. | 0.131 | 0.110 | 56.3 | LNU185 | 26474.2. | 0.669 | 0.204 | 7.0 |
| LNU216 | 25984.1. | 0.123 | 0.002 | 45.9 | LNU212 | 25834.1. | 1.150 | 0.214 | 84.0 |
| LNU216 | 25984.6. | 0.109 | 0.336 | 30.3 | LNU212 | 25834.5. | 0.975 | 0.310 | 56.0 |
| LNU216 | 25982.1. | 0.102 | 0.218 | 21.3 | LNU212 | 25833.2. | 0.894 | 0.282 | 43.0 |
| LNU216 | 25982.2. | 0.097 | 0.037 | 15.4 | LNU212 | 25834.4. | 0.888 | 0.000 | 42.0 |
| LNU228 | 26222.4. | 0.138 | 0.102 | 64.5 | LNU212 | 25833.1. | 0.844 | 0.206 | 35.0 |
| LNU228 | 26225.2. | 0.138 | 0.000 | 63.8 | LNU216 | 25985.4. | 1.325 | 0.006 | 112.0 |
| LNU228 | 26222.1. | 0.136 | 0.067 | 61.5 | LNU216 | 25984.1. | 1.056 | 0.180 | 69.0 |
| LNU228 | 26224.7. | 0.133 | 0.000 | 57.9 | LNU216 | 25984.6. | 0.963 | 0.320 | 54.0 |
| LNU228 | 26224.6. | 0.132 | 0.097 | 57.1 | LNU216 | 25982.2. | 0.794 | 0.106 | 27.0 |
| LNU229 | 26112.4. | 0.139 | 0.032 | 65.3 | LNU216 | 25982.1. | 0.781 | 0.239 | 25.0 |
| LNU229 | 26111.7. | 0.136 | 0.017 | 62.3 | LNU228 | 26224.7. | 1.302 | 0.001 | 108.3 |
| LNU229 | 26112.3. | 0.123 | 0.058 | 45.9 | LNU228 | 26222.4. | 1.300 | 0.145 | 108.0 |
| LNU229 | 26111.5. | 0.121 | 0.007 | 43.7 | LNU228 | 26224.6. | 1.231 | 0.127 | 97.0 |
| LNU241 | 26234.1. | 0.119 | 0.069 | 41.4 | LNU228 | 26222.1. | 1.219 | 0.000 | 95.0 |
| LNU241 | 26233.2. | 0.104 | 0.114 | 23.6 | LNU228 | 26225.2. | 1.038 | 0.092 | 66.0 |
| LNU241 | 26232.4. | 0.103 | 0.007 | 22.8 | LNU229 | 26111.7. | 1.219 | 0.016 | 95.0 |
| LNU241 | 26232.1. | 0.099 | 0.080 | 18.4 | LNU229 | 26111.5. | 1.169 | 0.000 | 87.0 |
| LNU241 | 26233.3. | 0.094 | 0.322 | 11.7 | LNU229 | 26112.4. | 1.169 | 0.038 | 87.0 |
| LNU253 | 26241.1. | 0.129 | 0.000 | 54.1 | LNU229 | 26112.3. | 1.150 | 0.001 | 84.0 |
| LNU253 | 26245.1. | 0.125 | 0.000 | 48.9 | LNU229 | 26114.1. | 0.763 | 0.392 | 22.0 |
| LNU253 | 26242.1. | 0.124 | 0.110 | 47.4 | LNU241 | 26234.1. | 1.150 | 0.029 | 84.0 |
| LNU253 | 26243.3. | 0.105 | 0.004 | 25.1 | LNU241 | 26232.4. | 0.863 | 0.131 | 38.0 |
| LNU253 | 26244.2. | 0.103 | 0.329 | 22.8 | LNU241 | 26233.3. | 0.831 | 0.000 | 33.0 |
| LNU274 | 26261.3. | 0.126 | 0.575 | 50.4 | LNU241 | 26232.1. | 0.794 | 0.042 | 27.0 |
| LNU274 | 26262.2. | 0.126 | 0.050 | 50.4 | LNU241 | 26233.2. | 0.794 | 0.000 | 27.0 |
| LNU274 | 26264.2. | 0.121 | 0.000 | 43.7 | LNU253 | 26245.1. | 1.150 | 0.010 | 84.0 |
| LNU274 | 26263.2. | 0.116 | 0.033 | 37.7 | LNU253 | 26242.1. | 1.081 | 0.093 | 73.0 |
| LNU274 | 26265.1. | 0.111 | 0.063 | 32.5 | LNU253 | 26241.1. | 1.056 | 0.026 | 69.0 |
| LNU277 | 25844.3. | 0.116 | 0.412 | 37.7 | LNU253 | 26243.3. | 1.013 | 0.000 | 62.0 |
| LNU277 | 25842.3. | 0.115 | 0.001 | 37.0 | LNU253 | 26244.2. | 0.944 | 0.138 | 51.0 |
| LNU277 | 25844.4. | 0.105 | 0.102 | 25.1 | LNU274 | 26263.2. | 1.156 | 0.161 | 85.0 |
| LNU277 | 25841.3. | 0.097 | 0.497 | 15.4 | LNU274 | 26262.2. | 1.125 | 0.130 | 80.0 |
| LNU277 | 25845.1. | 0.091 | 0.696 | 8.3 | LNU274 | 26261.3. | 1.025 | 0.537 | 64.0 |
| LNU280 | 26164.3. | 0.131 | 0.132 | 56.3 | LNU274 | 26264.2. | 0.994 | 0.000 | 59.0 |
| LNU280 | 26162.1. | 0.126 | 0.227 | 49.6 | LNU274 | 26265.1. | 0.994 | 0.230 | 59.0 |
| LNU280 | 26162.7. | 0.111 | 0.493 | 32.1 | LNU277 | 25842.3. | 0.925 | 0.004 | 48.0 |
| LNU280 | 26164.4. | 0.098 | 0.223 | 17.0 | LNU277 | 25844.3. | 0.919 | 0.388 | 47.0 |
| LNU280 | 26164.2. | 0.098 | 0.332 | 16.1 | LNU277 | 25841.3. | 0.825 | 0.110 | 32.0 |
| LNU55 | 26013.9. | 0.099 | 0.467 | 17.6 | LNU277 | 25844.4. | 0.819 | 0.234 | 31.0 |

TABLE 78-continued

Genes showing improved plant biomass production at limiting nitrogen growth conditions

| Gene Name | Event # | Dry Weight [g] Ave. | P-Value | % incr. | Gene Name | Event # | Fresh Weight [g] Ave. | P-Value | % incr. |
|---|---|---|---|---|---|---|---|---|---|
| LNU81 | 26034.3. | 0.098 | 0.141 | 16.1 | LNU277 | 25845.1. | 0.750 | 0.556 | 20.0 |
| | | | | | LNU280 | 26164.3. | 1.119 | 0.189 | 79.0 |
| | | | | | LNU280 | 26162.1. | 1.038 | 0.316 | 66.0 |
| | | | | | LNU280 | 26162.7. | 0.953 | 0.360 | 52.4 |
| | | | | | LNU280 | 26164.4. | 0.928 | 0.346 | 48.4 |
| | | | | | LNU280 | 26164.2. | 0.800 | 0.356 | 28.0 |
| | | | | | LNU55 | 26013.9. | 0.806 | 0.363 | 29.0 |
| | | | | | LNU55 | 26013.3. | 0.731 | 0.565 | 17.0 |
| | | | | | LNU81 | 26034.3. | 0.756 | 0.010 | 21.0 |
| | | | | | LNU81 | 26034.2. | 0.681 | 0.053 | 9.0 |

Table 78.
"CONT."—Control;
"Ave."—Average;
"% Incr." = % increment.

TABLE 79

Genes showing improved plant biomass production at limiting nitrogen growth conditions

| Gene Name | Event # | Rosette Diameter [cm] Ave. | P-Value | % incr. | Gene Name | Event # | Rosette Area [cm2] Ave. | P-Value | % incr. | Gene Name | Event # | Plot Coverage [%] Ave. | P-Value | % incr. |
|---|---|---|---|---|---|---|---|---|---|---|---|---|---|---|
| CONT. | — | 3.606 | — | 0 | CONT. | — | 4.630 | — | 0 | CONT. | — | 36.6 | — | 0 |
| LNU100 | 14472.2 | 4.256 | 0.154 | 18 | LNU100 | 14472.2 | 6.287 | 0.060 | 36 | LNU100 | 14472.2 | 50.3 | 0.050 | 37 |
| LNU100 | 14471.4 | 4.115 | 0.102 | 14 | LNU100 | 14471.4 | 5.556 | 0.016 | 20 | LNU100 | 14471.4 | 44.5 | 0.012 | 21 |
| LNU100 | 14474.3 | 3.819 | 0.148 | 6 | LNU100 | 14473.3 | 4.782 | 0.448 | 3 | LNU100 | 14473.3 | 38.3 | 0.339 | 5 |
| LNU100 | 14473.3 | 3.744 | 0.244 | 4 | LNU100 | 14474.3 | 4.748 | 0.505 | 3 | LNU100 | 14474.3 | 38.0 | 0.375 | 4 |
| LNU104 | 25033.3 | 4.546 | 0.000 | 26 | LNU104 | 25033.3 | 6.633 | 0.000 | 43 | LNU104 | 25033.3 | 53.1 | 0.000 | 45 |
| LNU104 | 25032.2 | 4.232 | 0.000 | 17 | LNU104 | 25032.2 | 6.169 | 0.166 | 33 | LNU104 | 25032.2 | 49.4 | 0.154 | 35 |
| LNU104 | 25032.1 | 4.113 | 0.187 | 14 | LNU104 | 25032.1 | 5.559 | 0.115 | 20 | LNU104 | 25032.1 | 44.5 | 0.097 | 22 |
| LNU104 | 25033.1 | 3.852 | 0.005 | 7 | LNU104 | 25033.1 | 5.070 | 0.158 | 10 | LNU104 | 25033.1 | 40.6 | 0.126 | 11 |
| LNU106 | 14481.1 | 4.267 | 0.237 | 18 | LNU106 | 14481.1 | 6.059 | 0.128 | 31 | LNU106 | 14481.1 | 48.5 | 0.115 | 32 |
| LNU106 | 14483.5 | 4.070 | 0.260 | 13 | LNU106 | 14483.5 | 5.508 | 0.264 | 19 | LNU106 | 14483.5 | 44.1 | 0.243 | 20 |
| LNU106 | 14484.3 | 3.952 | 0.004 | 10 | LNU106 | 14483.2 | 5.269 | 0.017 | 14 | LNU106 | 14483.2 | 42.2 | 0.013 | 15 |
| LNU106 | 14483.2 | 3.927 | 0.059 | 9 | LNU106 | 14484.3 | 5.251 | 0.041 | 13 | LNU106 | 14484.3 | 42.0 | 0.031 | 15 |
| LNU114 | 25042.1 | 3.824 | 0.009 | 6 | LNU114 | 25041.2 | 5.048 | 0.584 | 9 | LNU114 | 25041.2 | 40.4 | 0.544 | 10 |
| LNU114 | 25041.2 | 3.809 | 0.559 | 6 | LNU114 | 25042.1 | 5.030 | 0.127 | 9 | LNU114 | 25042.1 | 37.8 | 0.797 | 3 |
| LNU114 | 25041.1 | 3.764 | 0.650 | 4 | LNU155 | 14525.1 | 5.470 | 0.145 | 18 | LNU155 | 14525.1 | 43.8 | 0.125 | 20 |
| LNU155 | 14525.1 | 3.907 | 0.281 | 8 | LNU155 | 14523.5 | 5.131 | 0.517 | 11 | LNU155 | 14523.5 | 41.1 | 0.480 | 12 |
| LNU155 | 14523.5 | 3.768 | 0.668 | 4 | LNU213 | 24654.4 | 5.291 | 0.068 | 14 | LNU213 | 24654.4 | 42.3 | 0.053 | 16 |
| LNU213 | 24652.4 | 3.789 | 0.690 | 5 | LNU218 | 24781.7 | 5.948 | 0.000 | 28 | LNU218 | 24781.7 | 47.6 | 0.000 | 30 |
| LNU213 | 24654.4 | 3.787 | 0.032 | 5 | LNU218 | 24781.4 | 5.916 | 0.220 | 28 | LNU218 | 24781.4 | 47.3 | 0.206 | 29 |
| LNU213 | 24653.2 | 3.731 | 0.735 | 3 | LNU218 | 24784.2 | 5.573 | 0.127 | 20 | LNU218 | 24784.2 | 44.6 | 0.109 | 22 |
| LNU218 | 24781.7 | 4.252 | 0.031 | 18 | LNU23 | 25163.5 | 5.631 | 0.533 | 22 | LNU218 | 24781.2 | 37.5 | 0.666 | 3 |
| LNU218 | 24781.4 | 4.196 | 0.104 | 16 | LNU23 | 25163.6 | 5.104 | 0.623 | 10 | LNU23 | 25163.5 | 45.1 | 0.515 | 23 |
| LNU218 | 24784.2 | 3.967 | 0.003 | 10 | LNU28 | 25171.2 | 5.541 | 0.000 | 20 | LNU23 | 25163.6 | 40.8 | 0.589 | 12 |
| LNU218 | 24781.2 | 3.729 | 0.137 | 3 | LNU28 | 25171.1 | 5.522 | 0.000 | 19 | LNU28 | 25171.2 | 44.3 | 0.000 | 21 |
| LNU23 | 25163.5 | 4.157 | 0.442 | 15 | LNU4 | 25133.3 | 5.633 | 0.001 | 22 | LNU28 | 25171.1 | 44.2 | 0.001 | 21 |
| LNU23 | 25163.6 | 3.923 | 0.471 | 9 | LNU4 | 25134.1 | 4.919 | 0.614 | 6 | LNU4 | 25133.3 | 45.1 | 0.001 | 23 |
| LNU23 | 25162.1 | 3.663 | 0.407 | 2 | LNU40 | 24794.3 | 5.925 | 0.016 | 28 | LNU4 | 25134.1 | 39.4 | 0.557 | 8 |
| LNU28 | 25171.1 | 4.244 | 0.001 | 18 | LNU40 | 24794.4 | 5.510 | 0.201 | 19 | LNU40 | 24794.3 | 47.4 | 0.012 | 30 |
| LNU28 | 25171.2 | 4.046 | 0.000 | 12 | LNU46 | 14462.5 | 7.136 | 0.169 | 54 | LNU40 | 24794.4 | 41.5 | 0.529 | 13 |
| LNU28 | 25174.5 | 3.751 | 0.795 | 4 | LNU46 | 14464.4 | 6.666 | 0.333 | 44 | LNU46 | 14462.5 | 57.1 | 0.163 | 56 |
| LNU4 | 25133.3 | 4.119 | 0.000 | 14 | LNU46 | 14463.1 | 5.094 | 0.053 | 10 | LNU46 | 14464.4 | 53.3 | 0.325 | 46 |
| LNU4 | 25134.1 | 3.793 | 0.427 | 5 | LNU46 | 14464.1 | 5.091 | 0.285 | 10 | LNU46 | 14463.1 | 40.8 | 0.042 | 11 |
| LNU4 | 25131.1 | 3.711 | 0.305 | 3 | LNU46 | 14462.1 | 4.978 | 0.516 | 8 | LNU46 | 14464.1 | 40.7 | 0.244 | 11 |
| LNU40 | 24794.3 | 4.091 | 0.000 | 13 | LNU48 | 24801.4 | 6.013 | 0.000 | 30 | LNU46 | 14462.1 | 39.8 | 0.463 | 9 |
| LNU40 | 24794.4 | 4.033 | 0.018 | 12 | LNU48 | 24802.1 | 5.221 | 0.008 | 13 | LNU48 | 24801.4 | 48.1 | 0.000 | 31 |
| LNU46 | 14462.5 | 4.468 | 0.163 | 24 | LNU48 | 24804.4 | 4.891 | 0.171 | 6 | LNU48 | 24802.1 | 41.8 | 0.007 | 14 |
| LNU46 | 14464.4 | 4.460 | 0.263 | 24 | LNU63 | 24814.2 | 5.537 | 0.003 | 20 | LNU48 | 24804.4 | 39.1 | 0.131 | 7 |
| LNU46 | 14464.1 | 3.912 | 0.179 | 8 | LNU63 | 24814.3 | 5.022 | 0.132 | 8 | LNU63 | 24814.2 | 44.3 | 0.002 | 21 |
| LNU46 | 14463.1 | 3.806 | 0.215 | 6 | LNU63 | 24811.2 | 4.848 | 0.409 | 5 | LNU63 | 24814.3 | 40.2 | 0.102 | 10 |
| LNU46 | 14462.1 | 3.803 | 0.317 | 5 | LNU7 | 25081.1 | 5.350 | 0.006 | 16 | LNU63 | 24811.2 | 38.8 | 0.326 | 6 |
| LNU48 | 24801.4 | 4.262 | 0.000 | 18 | LNU7 | 25082.2 | 5.052 | 0.320 | 9 | LNU7 | 25081.1 | 42.8 | 0.005 | 17 |
| LNU48 | 24802.1 | 3.989 | 0.000 | 11 | LNU8 | 25062.1 | 5.062 | 0.031 | 9 | LNU7 | 25082.2 | 40.4 | 0.275 | 10 |
| LNU48 | 24804.4 | 3.707 | 0.232 | 3 | LNU8 | 25063.6 | 5.017 | 0.229 | 8 | LNU8 | 25062.1 | 40.5 | 0.027 | 11 |
| LNU63 | 24814.2 | 4.060 | 0.000 | 13 | LNU8 | 25062.2 | 4.960 | 0.219 | 7 | LNU8 | 25063.6 | 40.1 | 0.185 | 10 |

TABLE 79-continued

Genes showing improved plant biomass production at limiting nitrogen growth conditions

| Gene Name | Event # | Rosette Diameter [cm] Ave. | P-Value | % incr. | Gene Name | Event # | Rosette Area [cm2] Ave. | P-Value | % incr. | Gene Name | Event # | Plot Coverage [%] Ave. | P-Value | % incr. |
|---|---|---|---|---|---|---|---|---|---|---|---|---|---|---|
| LNU63 | 24814.3 | 3.864 | 0.004 | 7 | LNU8 | 25061.2 | 4.837 | 0.300 | 4 | LNU8 | 25062.2 | 39.7 | 0.172 | 8 |
| LNU63 | 24811.2 | 3.717 | 0.286 | 3 | LNU94 | 24833.3 | 5.355 | 0.037 | 16 | LNU8 | 25061.2 | 38.7 | 0.226 | 6 |
| LNU7 | 25081.1 | 3.996 | 0.002 | 11 | LNU96 | 25071.2 | 5.810 | 0.305 | 25 | LNU94 | 24833.3 | 40.1 | 0.178 | 10 |
| LNU7 | 25082.2 | 3.864 | 0.348 | 7 | LNU96 | 25073.4 | 4.985 | 0.729 | 8 | LNU96 | 25071.2 | 46.5 | 0.290 | 27 |
| LNU8 | 25063.6 | 3.835 | 0.028 | 6 | LNU96 | 25071.3 | 4.854 | 0.524 | 5 | LNU96 | 25073.4 | 39.9 | 0.693 | 9 |
| LNU8 | 25061.2 | 3.731 | 0.387 | 3 | CONT. | — | 5.751 | — | 0 | CONT. | — | 46.0 | — | 0 |
| LNU8 | 25062.2 | 3.731 | 0.092 | 3 | LNU113 | 25631.7 | 6.330 | 0.502 | 10 | LNU113 | 25631.7 | 50.6 | 0.502 | 10 |
| LNU8 | 25062.1 | 3.659 | 0.573 | 1 | LNU113 | 25631.3 | 6.104 | 0.634 | 6 | LNU113 | 25631.3 | 48.8 | 0.634 | 6 |
| LNU94 | 24833.3 | 3.913 | 0.030 | 9 | LNU113 | 25631.1 | 5.964 | 0.236 | 4 | LNU113 | 25631.1 | 47.7 | 0.236 | 4 |
| LNU96 | 25071.2 | 4.171 | 0.281 | 16 | LNU120 | 25463.6 | 5.862 | 0.757 | 2 | LNU120 | 25463.6 | 46.9 | 0.757 | 2 |
| LNU96 | 25073.4 | 3.883 | 0.603 | 8 | LNU140 | 14115.1 | 6.053 | 0.639 | 5 | LNU140 | 14115.1 | 48.4 | 0.639 | 5 |
| LNU96 | 25071.3 | 3.827 | 0.491 | 6 | LNU148 | 25685.6 | 7.625 | 0.100 | 33 | LNU148 | 25685.6 | 61.0 | 0.100 | 33 |
| CONT. | — | 3.931 | — | 0 | LNU148 | 25685.1 | 6.612 | 0.066 | 15 | LNU148 | 25685.1 | 52.9 | 0.066 | 15 |
| LNU113 | 25631.3 | 4.273 | 0.384 | 9 | LNU148 | 25685.9 | 6.006 | 0.756 | 4 | LNU148 | 25685.9 | 48.1 | 0.756 | 4 |
| LNU113 | 25631.7 | 4.196 | 0.311 | 7 | LNU287 | 24674.6 | 5.818 | 0.717 | 1 | LNU287 | 24674.6 | 46.5 | 0.717 | 1 |
| LNU113 | 25631.1 | 4.081 | 0.064 | 4 | LNU5 | 14043.7 | 6.452 | 0.317 | 12 | LNU5 | 14043.7 | 51.6 | 0.317 | 12 |
| LNU120 | 25463.3 | 4.027 | 0.218 | 2 | LNU68 | 14035.5 | 5.933 | 0.381 | 3 | LNU68 | 14035.5 | 47.5 | 0.381 | 3 |
| LNU124 | 14501.1 | 4.008 | 0.346 | 2 | LNU74 | 25444.1 | 6.292 | 0.127 | 9 | LNU74 | 25444.1 | 50.3 | 0.127 | 9 |
| LNU132 | 14102.6 | 4.040 | 0.554 | 3 | LNU74 | 25443.2 | 5.820 | 0.674 | 1 | LNU74 | 25443.2 | 46.6 | 0.674 | 1 |
| LNU140 | 14115.1 | 4.026 | 0.704 | 2 | LNU98 | 25763.2 | 5.892 | 0.745 | 2 | LNU98 | 25763.2 | 47.1 | 0.745 | 2 |
| LNU148 | 25685.6 | 4.481 | 0.166 | 14 | CONT. | — | 5.257 | — | 0 | CONT. | — | 41.6 | — | 0 |
| LNU148 | 25685.1 | 4.295 | 0.056 | 9 | LNU113 | 25631.9 | 5.826 | 0.342 | 11 | LNU113 | 25631.9 | 46.6 | 0.302 | 12 |
| LNU287 | 24674.6 | 4.081 | 0.322 | 4 | LNU148 | 25685.1 | 5.876 | 0.263 | 12 | LNU148 | 25685.1 | 47.0 | 0.228 | 13 |
| LNU5 | 14043.7 | 4.199 | 0.258 | 7 | LNU72 | 24963.7 | 5.957 | 0.447 | 13 | LNU72 | 24963.7 | 47.7 | 0.417 | 15 |
| LNU68 | 14035.5 | 4.069 | 0.056 | 4 | LNU72 | 24962.3 | 5.592 | 0.691 | 6 | LNU72 | 24962.3 | 44.7 | 0.643 | 8 |
| LNU74 | 25444.1 | 4.110 | 0.149 | 5 | LNU98 | 25763.2 | 5.771 | 0.476 | 10 | LNU98 | 25763.2 | 46.2 | 0.434 | 11 |
| LNU74 | 25443.2 | 3.977 | 0.479 | 1 | CONT. | — | 4.937 | — | 0 | CONT. | — | 38.1 | — | 0 |
| LNU98 | 25763.2 | 4.019 | 0.561 | 2 | LNU117 | 25931.4 | 8.201 | 0.038 | 66 | LNU117 | 25931.4 | 65.6 | 0.031 | 72 |
| CONT. | — | 3.861 | — | 0 | LNU117 | 25931.2 | 7.079 | 0.047 | 43 | LNU117 | 25931.2 | 56.6 | 0.055 | 49 |
| LNU113 | 25631.7 | 4.102 | 0.390 | 6 | LNU117 | 25933.3 | 6.946 | 0.038 | 41 | LNU117 | 25933.3 | 55.6 | 0.058 | 46 |
| LNU113 | 25631.3 | 3.943 | 0.755 | 2 | LNU117 | 25931.1 | 6.455 | 0.297 | 31 | LNU117 | 25931.1 | 51.6 | 0.257 | 35 |
| LNU148 | 25685.1 | 4.083 | 0.380 | 6 | LNU117 | 25932.4 | 6.152 | 0.430 | 25 | LNU117 | 25932.4 | 49.2 | 0.381 | 29 |
| LNU72 | 24963.7 | 4.114 | 0.536 | 7 | LNU122 | 25333.2 | 7.762 | 0.015 | 57 | LNU122 | 25333.2 | 62.1 | 0.029 | 63 |
| LNU98 | 25763.2 | 4.030 | 0.446 | 4 | LNU122 | 25332.1 | 7.548 | 0.257 | 53 | LNU122 | 25332.1 | 60.4 | 0.226 | 58 |
| CONT. | — | 3.681 | — | 0 | LNU122 | 25332.2 | 6.704 | 0.053 | 36 | LNU122 | 25332.2 | 53.6 | 0.083 | 41 |
| LNU117 | 25931.4 | 4.672 | 0.079 | 27 | LNU122 | 25332.5 | 6.165 | 0.112 | 25 | LNU122 | 25332.5 | 49.3 | 0.145 | 29 |
| LNU117 | 25933.3 | 4.364 | 0.041 | 19 | LNU122 | 25333.1 | 6.130 | 0.142 | 24 | LNU122 | 25333.1 | 49.0 | 0.160 | 29 |
| LNU117 | 25931.2 | 4.320 | 0.047 | 17 | LNU125 | 25941.4 | 8.098 | 0.097 | 64 | LNU125 | 25941.4 | 64.8 | 0.074 | 70 |
| LNU117 | 25932.4 | 4.197 | 0.333 | 14 | LNU125 | 25943.3 | 7.176 | 0.030 | 45 | LNU125 | 25943.3 | 57.4 | 0.053 | 51 |
| LNU117 | 25931.1 | 4.189 | 0.192 | 14 | LNU125 | 25943.2 | 6.828 | 0.370 | 38 | LNU125 | 25943.2 | 54.6 | 0.334 | 43 |
| LNU122 | 25332.1 | 4.536 | 0.164 | 23 | LNU125 | 25941.2 | 6.448 | 0.309 | 31 | LNU125 | 25941.2 | 51.6 | 0.268 | 35 |
| LNU122 | 25333.2 | 4.522 | 0.024 | 23 | LNU125 | 25944.3 | 6.167 | 0.380 | 25 | LNU125 | 25944.3 | 49.3 | 0.333 | 29 |
| LNU122 | 25332.2 | 4.252 | 0.076 | 16 | LNU138 | 14074.5 | 7.777 | 0.014 | 58 | LNU138 | 14074.5 | 62.2 | 0.029 | 63 |
| LNU122 | 25333.1 | 4.135 | 0.102 | 12 | LNU138 | 14074.6 | 7.468 | 0.181 | 51 | LNU138 | 14074.6 | 59.7 | 0.149 | 57 |
| LNU122 | 25332.5 | 4.098 | 0.228 | 11 | LNU138 | 14071.5 | 6.727 | 0.051 | 36 | LNU138 | 14071.5 | 53.8 | 0.074 | 41 |
| LNU125 | 25941.4 | 4.714 | 0.088 | 28 | LNU138 | 14072.5 | 5.184 | 0.664 | 5 | LNU138 | 14072.5 | 41.5 | 0.580 | 9 |
| LNU125 | 25943.3 | 4.442 | 0.039 | 21 | LNU180 | 24721.2 | 9.058 | 0.043 | 83 | LNU138 | 14072.5 | 40.1 | 0.740 | 5 |
| LNU125 | 25943.2 | 4.326 | 0.317 | 18 | LNU180 | 24723.1 | 8.587 | 0.010 | 74 | LNU180 | 24721.2 | 72.5 | 0.030 | 90 |
| LNU125 | 25941.2 | 4.212 | 0.315 | 14 | LNU180 | 24721.4 | 8.409 | 0.017 | 70 | LNU180 | 24723.1 | 68.7 | 0.014 | 80 |
| LNU125 | 25944.3 | 4.191 | 0.197 | 14 | LNU180 | 24722.2 | 7.901 | 0.179 | 60 | LNU180 | 24721.4 | 67.3 | 0.018 | 76 |
| LNU138 | 14074.5 | 4.654 | 0.016 | 26 | LNU180 | 24724.1 | 7.457 | 0.117 | 51 | LNU180 | 24722.2 | 63.2 | 0.150 | 66 |
| LNU138 | 14074.6 | 4.553 | 0.132 | 24 | LNU220 | 25405.2 | 7.726 | 0.048 | 56 | LNU180 | 24724.1 | 59.7 | 0.093 | 56 |
| LNU138 | 14071.5 | 4.284 | 0.060 | 16 | LNU220 | 25405.5 | 7.662 | 0.086 | 55 | LNU220 | 25405.2 | 61.8 | 0.041 | 62 |
| LNU138 | 14072.5 | 3.780 | 0.639 | 3 | LNU220 | 25405.1 | 7.524 | 0.216 | 52 | LNU220 | 25405.5 | 61.3 | 0.068 | 61 |
| LNU138 | 14072.5 | 3.760 | 0.685 | 2 | LNU220 | 25405.6 | 6.268 | 0.091 | 27 | LNU220 | 25405.1 | 60.2 | 0.184 | 58 |
| LNU180 | 24721.2 | 5.125 | 0.010 | 39 | LNU220 | 25405.3 | 5.915 | 0.406 | 20 | LNU220 | 25405.6 | 50.1 | 0.130 | 32 |
| LNU180 | 24723.1 | 4.878 | 0.018 | 33 | LNU230 | 25413.1 | 8.332 | 0.014 | 69 | LNU220 | 25405.3 | 47.3 | 0.356 | 24 |
| LNU180 | 24721.4 | 4.870 | 0.010 | 32 | LNU230 | 25412.1 | 7.791 | 0.079 | 58 | LNU230 | 25413.1 | 66.7 | 0.018 | 75 |
| LNU180 | 24722.2 | 4.783 | 0.121 | 30 | LNU230 | 25415.1 | 7.230 | 0.167 | 46 | LNU230 | 25412.1 | 62.3 | 0.061 | 63 |
| LNU180 | 24724.1 | 4.538 | 0.062 | 23 | LNU230 | 25412.2 | 6.904 | 0.045 | 40 | LNU230 | 25415.1 | 57.8 | 0.137 | 52 |
| LNU220 | 25405.5 | 4.611 | 0.090 | 25 | LNU230 | 25413.2 | 6.826 | 0.274 | 38 | LNU230 | 25413.2 | 54.6 | 0.236 | 43 |
| LNU220 | 25405.1 | 4.497 | 0.217 | 22 | LNU234 | 25014.8 | 7.333 | 0.034 | 49 | LNU230 | 25412.2 | 51.7 | 0.100 | 36 |
| LNU220 | 25405.2 | 4.485 | 0.035 | 22 | LNU234 | 25014.1 | 6.560 | 0.125 | 33 | LNU234 | 25014.8 | 58.7 | 0.053 | 54 |
| LNU220 | 25405.6 | 4.220 | 0.089 | 15 | LNU234 | 25014.6 | 6.438 | 0.079 | 30 | LNU234 | 25014.1 | 52.5 | 0.119 | 38 |
| LNU220 | 25405.3 | 4.043 | 0.244 | 10 | LNU234 | 25014.4 | 6.183 | 0.121 | 25 | LNU234 | 25014.6 | 51.5 | 0.113 | 35 |
| LNU230 | 25413.1 | 4.814 | 0.021 | 31 | LNU234 | 25014.5 | 5.958 | 0.451 | 21 | LNU234 | 25014.4 | 49.5 | 0.146 | 30 |
| LNU230 | 25412.1 | 4.738 | 0.044 | 29 | LNU234 | 25014.5 | 7.851 | 0.067 | 59 | LNU234 | 25014.5 | 47.7 | 0.398 | 25 |
| LNU230 | 25415.1 | 4.453 | 0.193 | 21 | LNU25 | 14083.7 | 7.683 | 0.025 | 56 | LNU25 | 14082.8 | 62.8 | 0.052 | 65 |
| LNU230 | 25412.2 | 4.390 | 0.049 | 19 | LNU25 | 14082.9 | 7.494 | 0.021 | 52 | LNU25 | 14083.7 | 61.5 | 0.041 | 61 |
| LNU230 | 25413.2 | 4.226 | 0.340 | 15 | LNU25 | 14084.6 | 7.440 | 0.229 | 51 | LNU25 | 14082.9 | 59.9 | 0.040 | 57 |
| LNU234 | 25014.8 | 4.643 | 0.017 | 26 | LNU25 | 14083.1 | 7.369 | 0.024 | 49 | LNU25 | 14084.6 | 59.5 | 0.196 | 56 |
| LNU234 | 25014.1 | 4.390 | 0.202 | 19 | LNU254 | 25782.4 | 8.004 | 0.020 | 62 | LNU25 | 14083.1 | 58.9 | 0.044 | 55 |

TABLE 79-continued

Genes showing improved plant biomass production at limiting nitrogen growth conditions

| Gene Name | Event # | Rosette Diameter [cm] | | | Gene Name | Event # | Rosette Area [cm2] | | | Gene Name | Event # | Plot Coverage [%] | | |
|---|---|---|---|---|---|---|---|---|---|---|---|---|---|---|
| | | Ave. | P-Value | % incr. | | | Ave. | P-Value | % incr. | | | Ave. | P-Value | % incr. |
| LNU234 | 25014.6 | 4.206 | 0.086 | 14 | LNU254 | 25781.3 | 7.690 | 0.025 | 56 | LNU254 | 25782.4 | 64.0 | 0.034 | 68 |
| LNU234 | 25014.5 | 4.196 | 0.250 | 14 | LNU254 | 25781.5 | 7.136 | 0.064 | 45 | LNU254 | 25781.3 | 61.5 | 0.031 | 61 |
| LNU234 | 25014.4 | 4.160 | 0.121 | 13 | LNU254 | 25782.5 | 6.589 | 0.062 | 33 | LNU254 | 25781.5 | 57.1 | 0.062 | 50 |
| LNU25 | 14082.8 | 4.776 | 0.101 | 30 | LNU254 | 25783.1 | 6.556 | 0.250 | 33 | LNU254 | 25782.5 | 52.7 | 0.086 | 38 |
| LNU25 | 14082.9 | 4.731 | 0.018 | 29 | LNU263 | 25794.8 | 7.806 | 0.182 | 58 | LNU254 | 25783.1 | 52.5 | 0.214 | 38 |
| LNU25 | 14083.1 | 4.630 | 0.018 | 26 | LNU263 | 25794.3 | 7.786 | 0.015 | 58 | LNU263 | 25794.8 | 62.4 | 0.152 | 64 |
| LNU25 | 14083.7 | 4.596 | 0.033 | 25 | LNU263 | 25791.3 | 7.761 | 0.041 | 57 | LNU263 | 25794.3 | 62.3 | 0.027 | 63 |
| LNU25 | 14084.6 | 4.556 | 0.263 | 24 | LNU263 | 25794.6 | 7.305 | 0.024 | 48 | LNU263 | 25791.3 | 62.1 | 0.037 | 63 |
| LNU254 | 25782.4 | 4.741 | 0.020 | 29 | LNU263 | 25792.2 | 7.079 | 0.031 | 43 | LNU263 | 25794.6 | 58.4 | 0.045 | 53 |
| LNU254 | 25781.3 | 4.696 | 0.046 | 28 | LNU267 | 25804.4 | 7.228 | 0.038 | 46 | LNU263 | 25792.2 | 56.6 | 0.051 | 49 |
| LNU254 | 25781.5 | 4.485 | 0.027 | 22 | LNU267 | 25804.3 | 7.196 | 0.098 | 46 | LNU267 | 25804.4 | 57.8 | 0.058 | 52 |
| LNU254 | 25782.5 | 4.354 | 0.060 | 18 | LNU267 | 25801.1 | 6.656 | 0.227 | 35 | LNU267 | 25804.3 | 57.6 | 0.082 | 51 |
| LNU254 | 25783.1 | 4.174 | 0.325 | 13 | LNU267 | 25803.1 | 6.585 | 0.059 | 33 | LNU267 | 25801.1 | 53.2 | 0.193 | 40 |
| LNU263 | 25794.8 | 4.696 | 0.165 | 28 | LNU267 | 25802.1 | 6.188 | 0.147 | 25 | LNU267 | 25803.1 | 52.7 | 0.092 | 38 |
| LNU263 | 25794.3 | 4.651 | 0.022 | 26 | LNU271 | 25911.4 | 8.631 | 0.011 | 75 | LNU267 | 25802.1 | 49.5 | 0.156 | 30 |
| LNU263 | 25791.3 | 4.640 | 0.023 | 26 | LNU271 | 25912.1 | 7.598 | 0.052 | 54 | LNU271 | 25911.4 | 69.1 | 0.021 | 81 |
| LNU263 | 25794.6 | 4.565 | 0.022 | 24 | LNU271 | 25913.3 | 6.587 | 0.069 | 33 | LNU271 | 25912.1 | 57.3 | 0.192 | 50 |
| LNU263 | 25792.2 | 4.422 | 0.034 | 20 | LNU271 | 25912.2 | 6.006 | 0.141 | 22 | LNU271 | 25913.3 | 52.7 | 0.089 | 38 |
| LNU267 | 25804.3 | 4.532 | 0.064 | 23 | LNU271 | 25913.2 | 5.306 | 0.743 | 7 | LNU271 | 25912.2 | 48.1 | 0.181 | 26 |
| LNU267 | 25804.4 | 4.525 | 0.032 | 23 | LNU278 | 25814.3 | 8.097 | 0.011 | 64 | LNU271 | 25913.2 | 42.4 | 0.653 | 11 |
| LNU267 | 25803.1 | 4.381 | 0.052 | 19 | LNU278 | 25812.3 | 8.034 | 0.021 | 63 | LNU278 | 25814.3 | 64.8 | 0.022 | 70 |
| LNU267 | 25801.1 | 4.216 | 0.143 | 15 | LNU278 | 25812.2 | 6.641 | 0.088 | 35 | LNU278 | 25812.3 | 64.3 | 0.034 | 69 |
| LNU267 | 25802.1 | 4.181 | 0.156 | 14 | LNU278 | 25814.1 | 6.351 | 0.218 | 29 | LNU278 | 25812.2 | 53.1 | 0.094 | 39 |
| LNU271 | 25911.4 | 5.046 | 0.006 | 37 | LNU278 | 25813.2 | 5.577 | 0.364 | 13 | LNU278 | 25814.1 | 50.8 | 0.191 | 33 |
| LNU271 | 25912.1 | 4.508 | 0.033 | 22 | LNU36 | 25562.9 | 7.926 | 0.019 | 61 | LNU278 | 25813.2 | 44.6 | 0.349 | 17 |
| LNU271 | 25913.3 | 4.382 | 0.064 | 19 | LNU36 | 25562.3 | 6.823 | 0.049 | 38 | LNU36 | 25562.9 | 63.4 | 0.033 | 66 |
| LNU271 | 25912.2 | 4.152 | 0.102 | 13 | LNU36 | 25562.4 | 6.281 | 0.088 | 27 | LNU36 | 25562.3 | 54.6 | 0.076 | 43 |
| LNU271 | 25913.2 | 3.894 | 0.579 | 6 | LNU36 | 25562.7 | 5.943 | 0.154 | 20 | LNU36 | 25562.4 | 50.3 | 0.125 | 32 |
| LNU278 | 25812.3 | 4.752 | 0.020 | 29 | LNU36 | 25561.2 | 5.749 | 0.222 | 16 | LNU36 | 25562.7 | 47.5 | 0.194 | 25 |
| LNU278 | 25814.3 | 4.655 | 0.028 | 26 | LNU43 | 14422.8 | 7.369 | 0.026 | 49 | LNU36 | 25561.2 | 46.0 | 0.256 | 21 |
| LNU278 | 25812.2 | 4.267 | 0.059 | 16 | LNU43 | 14422.9 | 6.842 | 0.040 | 39 | LNU43 | 14422.8 | 59.0 | 0.046 | 55 |
| LNU278 | 25814.1 | 4.121 | 0.113 | 12 | LNU43 | 14421.1 | 6.814 | 0.042 | 38 | LNU43 | 14422.9 | 54.7 | 0.065 | 44 |
| LNU278 | 25813.2 | 3.927 | 0.294 | 7 | LNU43 | 14423.6 | 6.361 | 0.080 | 29 | LNU43 | 14421.1 | 54.5 | 0.068 | 43 |
| LNU36 | 25562.9 | 4.633 | 0.027 | 26 | LNU43 | 14423.7 | 6.061 | 0.312 | 23 | LNU43 | 14423.6 | 50.9 | 0.113 | 33 |
| LNU36 | 25562.3 | 4.246 | 0.070 | 15 | LNU45 | 25052.12 | 7.449 | 0.059 | 51 | LNU43 | 14423.7 | 48.5 | 0.275 | 27 |
| LNU36 | 25561.2 | 4.090 | 0.137 | 11 | LNU45 | 25052.8 | 7.250 | 0.025 | 47 | LNU45 | 25052.12 | 59.6 | 0.052 | 56 |
| LNU36 | 25562.7 | 4.023 | 0.177 | 9 | LNU45 | 25052.9 | 6.722 | 0.055 | 36 | LNU45 | 25052.8 | 58.0 | 0.045 | 52 |
| LNU36 | 25562.4 | 4.008 | 0.221 | 9 | LNU45 | 25053.4 | 6.464 | 0.464 | 31 | LNU45 | 25052.9 | 53.8 | 0.075 | 41 |
| LNU43 | 14422.8 | 4.553 | 0.028 | 24 | LNU45 | 25052.11 | 5.637 | 0.269 | 14 | LNU45 | 25053.4 | 51.7 | 0.424 | 36 |
| LNU43 | 14421.1 | 4.514 | 0.032 | 23 | LNU67 | 25821.5 | 6.477 | 0.348 | 31 | LNU45 | 25052.11 | 45.1 | 0.297 | 18 |
| LNU43 | 14422.9 | 4.354 | 0.042 | 18 | LNU67 | 25824.5 | 6.258 | 0.293 | 27 | LNU67 | 25821.5 | 51.8 | 0.306 | 36 |
| LNU43 | 14423.6 | 4.283 | 0.088 | 16 | LNU67 | 25823.5 | 6.011 | 0.155 | 22 | LNU67 | 25824.5 | 50.1 | 0.255 | 31 |
| LNU43 | 14423.7 | 4.074 | 0.318 | 11 | LNU67 | 25821.4 | 5.761 | 0.238 | 17 | LNU67 | 25823.5 | 48.1 | 0.181 | 26 |
| LNU45 | 25052.12 | 4.543 | 0.106 | 23 | LNU67 | 25824.3 | 5.603 | 0.597 | 13 | LNU67 | 25821.4 | 46.1 | 0.257 | 21 |
| LNU45 | 25052.8 | 4.344 | 0.057 | 18 | CONT. | — | 3.923 | — | 0 | LNU67 | 25824.3 | 44.8 | 0.528 | 18 |
| LNU45 | 25052.9 | 4.226 | 0.108 | 15 | LNU100 | 14474.2 | 5.788 | 0.078 | 48 | CONT. | — | 31.4 | — | 0 |
| LNU45 | 25053.4 | 4.169 | 0.483 | 13 | LNU100 | 14472.1 | 5.604 | 0.332 | 43 | LNU100 | 14474.2 | 46.3 | 0.078 | 48 |
| LNU45 | 25052.11 | 3.898 | 0.323 | 6 | LNU100 | 14473.3 | 5.227 | 0.373 | 33 | LNU100 | 14472.1 | 44.8 | 0.332 | 43 |
| LNU67 | 25821.5 | 4.189 | 0.385 | 14 | LNU100 | 14473.1 | 5.199 | 0.202 | 33 | LNU100 | 14473.3 | 41.8 | 0.373 | 33 |
| LNU67 | 25824.5 | 4.160 | 0.342 | 13 | LNU100 | 14471.4 | 4.583 | 0.510 | 17 | LNU100 | 14473.1 | 41.6 | 0.202 | 33 |
| LNU67 | 25823.5 | 4.049 | 0.152 | 10 | LNU104 | 25032.2 | 4.811 | 0.483 | 23 | LNU100 | 14471.4 | 36.7 | 0.510 | 17 |
| LNU67 | 25824.3 | 4.010 | 0.423 | 9 | LNU104 | 25033.1 | 4.727 | 0.319 | 21 | LNU104 | 25032.2 | 38.5 | 0.483 | 23 |
| LNU67 | 25821.4 | 3.971 | 0.295 | 8 | LNU104 | 25032.1 | 4.607 | 0.401 | 17 | LNU104 | 25033.1 | 37.8 | 0.319 | 21 |
| CONT. | — | 3.345 | — | 0 | LNU104 | 25033.3 | 4.515 | 0.021 | 15 | LNU104 | 25032.1 | 36.9 | 0.401 | 17 |
| LNU100 | 14474.2 | 4.215 | 0.024 | 26 | LNU106 | 14483.2 | 5.906 | 0.009 | 51 | LNU104 | 25033.3 | 36.1 | 0.021 | 15 |
| LNU100 | 14472.1 | 4.080 | 0.377 | 22 | LNU106 | 14481.1 | 5.002 | 0.460 | 28 | LNU106 | 14483.2 | 47.3 | 0.009 | 51 |
| LNU100 | 14473.3 | 3.988 | 0.272 | 19 | LNU106 | 14483.5 | 4.726 | 0.003 | 20 | LNU106 | 14481.1 | 40.0 | 0.460 | 28 |
| LNU100 | 14473.1 | 3.860 | 0.145 | 15 | LNU106 | 14484.3 | 4.471 | 0.599 | 14 | LNU106 | 14483.5 | 37.8 | 0.003 | 20 |
| LNU100 | 14471.4 | 3.657 | 0.440 | 9 | LNU114 | 25044.11 | 5.196 | 0.404 | 32 | LNU106 | 14484.3 | 35.8 | 0.599 | 14 |
| LNU104 | 25033.1 | 3.784 | 0.440 | 13 | LNU114 | 25041.2 | 5.087 | 0.105 | 30 | LNU114 | 25044.11 | 41.6 | 0.404 | 32 |
| LNU104 | 25033.3 | 3.769 | 0.127 | 13 | LNU114 | 25042.1 | 4.666 | 0.316 | 19 | LNU114 | 25041.2 | 40.7 | 0.105 | 30 |
| LNU104 | 25032.1 | 3.733 | 0.185 | 12 | LNU114 | 25041.1 | 4.424 | 0.790 | 13 | LNU114 | 25042.1 | 37.3 | 0.316 | 19 |
| LNU104 | 25032.2 | 3.695 | 0.465 | 11 | LNU114 | 25044.4 | 4.267 | 0.800 | 9 | LNU114 | 25041.1 | 35.4 | 0.790 | 13 |
| LNU106 | 14483.2 | 4.299 | 0.001 | 29 | LNU114 | 25932.4 | 5.264 | 0.026 | 34 | LNU114 | 25044.4 | 34.1 | 0.800 | 9 |
| LNU106 | 14481.1 | 3.952 | 0.369 | 18 | LNU117 | 25931.4 | 5.003 | 0.007 | 28 | LNU117 | 25932.4 | 42.1 | 0.026 | 34 |
| LNU106 | 14483.5 | 3.741 | 0.029 | 12 | LNU117 | 25931.1 | 4.406 | 0.731 | 12 | LNU117 | 25931.4 | 40.0 | 0.007 | 28 |
| LNU106 | 14484.3 | 3.573 | 0.544 | 7 | LNU117 | 25931.2 | 4.256 | 0.596 | 9 | LNU117 | 25931.1 | 35.2 | 0.731 | 12 |
| LNU114 | 25044.11 | 3.992 | 0.266 | 19 | LNU155 | 14523.5 | 5.064 | 0.371 | 29 | LNU117 | 25931.2 | 34.1 | 0.596 | 9 |
| LNU114 | 25041.2 | 3.908 | 0.005 | 17 | LNU155 | 14524.8 | 4.210 | 0.411 | 7 | LNU155 | 14523.5 | 40.5 | 0.371 | 29 |
| LNU114 | 25042.1 | 3.783 | 0.193 | 13 | LNU180 | 24723.1 | 4.999 | 0.001 | 27 | LNU155 | 14524.8 | 33.7 | 0.411 | 7 |
| LNU114 | 25041.1 | 3.667 | 0.691 | 10 | LNU180 | 24722.2 | 4.503 | 0.696 | 15 | LNU180 | 24723.1 | 40.0 | 0.001 | 27 |
| LNU117 | 25932.4 | 4.072 | 0.091 | 22 | LNU218 | 24781.4 | 5.394 | 0.065 | 38 | LNU180 | 24722.2 | 36.0 | 0.696 | 15 |

TABLE 79-continued

Genes showing improved plant biomass production at limiting nitrogen growth conditions

| | | Rosette Diameter [cm] | | | | | Rosette Area [cm2] | | | | | Plot Coverage [%] | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU117 | 25931.4 | 3.797 | 0.001 | 14 | LNU218 | 24781.1 | 4.950 | 0.283 | 26 | LNU218 | 24781.4 | 43.2 | 0.065 | 38 |
| LNU117 | 25931.1 | 3.637 | 0.607 | 9 | LNU218 | 24781.6 | 4.116 | 0.510 | 5 | LNU218 | 24781.1 | 39.6 | 0.283 | 26 |
| LNU117 | 25931.2 | 3.493 | 0.531 | 4 | LNU218 | 24781.2 | 4.052 | 0.541 | 3 | LNU218 | 24781.6 | 32.9 | 0.510 | 5 |
| LNU155 | 14523.5 | 3.825 | 0.342 | 14 | LNU254 | 25782.5 | 4.883 | 0.061 | 24 | LNU218 | 24781.2 | 32.4 | 0.541 | 3 |
| LNU155 | 14524.8 | 3.615 | 0.063 | 8 | LNU4 | 25134.3 | 5.451 | 0.299 | 39 | LNU254 | 25782.5 | 39.1 | 0.061 | 24 |
| LNU180 | 24723.1 | 3.874 | 0.067 | 16 | LNU4 | 25134.2 | 4.702 | 0.210 | 20 | LNU4 | 25134.3 | 43.6 | 0.299 | 39 |
| LNU180 | 24722.2 | 3.708 | 0.619 | 11 | LNU4 | 25131.1 | 4.628 | 0.422 | 18 | LNU4 | 25134.2 | 37.6 | 0.210 | 20 |
| LNU218 | 24781.4 | 4.130 | 0.080 | 23 | LNU4 | 25133.3 | 4.261 | 0.501 | 9 | LNU4 | 25131.1 | 37.0 | 0.422 | 18 |
| LNU218 | 24781.1 | 4.061 | 0.057 | 21 | LNU40 | 24794.3 | 4.596 | 0.661 | 17 | LNU4 | 25133.3 | 34.1 | 0.501 | 9 |
| LNU218 | 24781.2 | 3.582 | 0.031 | 7 | LNU40 | 24792.1 | 4.508 | 0.017 | 15 | LNU40 | 24794.3 | 36.8 | 0.661 | 17 |
| LNU218 | 24781.6 | 3.522 | 0.244 | 5 | LNU40 | 24794.4 | 4.144 | 0.345 | 6 | LNU40 | 24792.1 | 36.1 | 0.017 | 15 |
| LNU254 | 25782.5 | 3.825 | 0.120 | 14 | LNU46 | 14462.5 | 5.330 | 0.315 | 36 | LNU40 | 24794.4 | 33.2 | 0.345 | 6 |
| LNU254 | 25782.4 | 3.387 | 0.697 | 1 | LNU46 | 14464.4 | 4.290 | 0.256 | 9 | LNU46 | 14462.5 | 42.6 | 0.315 | 36 |
| LNU4 | 25134.3 | 4.057 | 0.310 | 21 | LNU46 | 14462.1 | 4.285 | 0.114 | 9 | LNU46 | 14464.4 | 34.3 | 0.256 | 9 |
| LNU4 | 25134.2 | 3.667 | 0.282 | 10 | LNU48 | 24801.4 | 4.780 | 0.139 | 22 | LNU46 | 14462.1 | 34.3 | 0.114 | 9 |
| LNU4 | 25131.1 | 3.643 | 0.535 | 9 | LNU48 | 24803.2 | 4.595 | 0.596 | 17 | LNU48 | 24801.4 | 38.2 | 0.139 | 22 |
| LNU4 | 25133.3 | 3.533 | 0.527 | 6 | LNU63 | 24812.3 | 5.325 | 0.111 | 36 | LNU48 | 24803.2 | 36.8 | 0.596 | 17 |
| LNU40 | 24794.3 | 3.803 | 0.557 | 14 | LNU63 | 24814.7 | 4.440 | 0.426 | 13 | LNU63 | 24812.3 | 42.6 | 0.111 | 36 |
| LNU40 | 24792.1 | 3.682 | 0.005 | 10 | LNU7 | 25082.2 | 4.973 | 0.460 | 27 | LNU63 | 24814.7 | 35.5 | 0.426 | 13 |
| LNU40 | 24794.4 | 3.484 | 0.177 | 4 | LNU7 | 25083.1 | 4.472 | 0.220 | 14 | LNU7 | 25082.2 | 39.8 | 0.460 | 27 |
| LNU46 | 14462.5 | 3.977 | 0.353 | 19 | LNU7 | 25083.3 | 4.378 | 0.198 | 12 | LNU7 | 25083.1 | 35.8 | 0.220 | 14 |
| LNU46 | 14462.1 | 3.575 | 0.041 | 7 | LNU8 | 25063.6 | 5.383 | 0.119 | 37 | LNU7 | 25083.3 | 35.0 | 0.198 | 12 |
| LNU46 | 14464.4 | 3.512 | 0.213 | 5 | LNU8 | 25061.2 | 4.703 | 0.003 | 20 | LNU8 | 25063.6 | 43.1 | 0.119 | 37 |
| LNU48 | 24803.2 | 3.731 | 0.520 | 12 | LNU94 | 24833.3 | 4.639 | 0.511 | 18 | LNU8 | 25061.2 | 37.6 | 0.003 | 20 |
| LNU48 | 24801.4 | 3.724 | 0.156 | 11 | CONT. | — | 5.138 | — | 0 | LNU94 | 24833.3 | 37.1 | 0.511 | 18 |
| LNU48 | 24802.2 | 3.457 | 0.760 | 3 | LNU122 | 25332.1 | 6.084 | 0.057 | 18 | CONT. | — | 41.1 | — | 0 |
| LNU63 | 24812.3 | 4.044 | 0.067 | 21 | LNU122 | 25332.2 | 6.037 | 0.049 | 18 | LNU122 | 25332.1 | 48.7 | 0.057 | 18 |
| LNU63 | 24814.7 | 3.580 | 0.458 | 7 | LNU122 | 25332.5 | 5.627 | 0.601 | 10 | LNU122 | 25332.2 | 48.3 | 0.049 | 18 |
| LNU63 | 24814.2 | 3.498 | 0.361 | 5 | LNU125 | 25943.2 | 5.541 | 0.155 | 8 | LNU122 | 25332.5 | 45.0 | 0.601 | 10 |
| LNU7 | 25082.2 | 3.789 | 0.443 | 13 | LNU125 | 25941.4 | 5.481 | 0.153 | 7 | LNU125 | 25943.2 | 44.3 | 0.155 | 8 |
| LNU7 | 25083.1 | 3.697 | 0.020 | 11 | LNU138 | 14074.5 | 5.527 | 0.128 | 8 | LNU125 | 25941.4 | 43.8 | 0.153 | 7 |
| LNU7 | 25083.3 | 3.566 | 0.325 | 7 | LNU138 | 14071.5 | 5.204 | 0.795 | 1 | LNU138 | 14074.5 | 44.2 | 0.128 | 8 |
| LNU8 | 25063.6 | 4.011 | 0.034 | 20 | LNU157 | 24982.1 | 5.356 | 0.680 | 4 | LNU138 | 14071.5 | 41.6 | 0.795 | 1 |
| LNU8 | 25061.2 | 3.745 | 0.002 | 12 | LNU178 | 14614.5 | 5.971 | 0.096 | 16 | LNU157 | 24982.1 | 42.8 | 0.680 | 4 |
| LNU94 | 24833.3 | 3.572 | 0.610 | 7 | LNU178 | 14611.5 | 5.656 | 0.022 | 10 | LNU178 | 14614.5 | 47.8 | 0.096 | 16 |
| CONT. | — | 3.921 | — | 0 | LNU178 | 14612.1 | 5.477 | 0.551 | 7 | LNU178 | 14611.5 | 45.3 | 0.022 | 10 |
| LNU10 | 25123.5 | 4.081 | 0.621 | 4 | LNU178 | 14611.4 | 5.445 | 0.126 | 6 | LNU178 | 14612.1 | 43.8 | 0.551 | 7 |
| LNU122 | 25332.1 | 4.326 | 0.175 | 10 | LNU220 | 25405.6 | 5.656 | 0.282 | 10 | LNU178 | 14611.4 | 43.6 | 0.126 | 6 |
| LNU122 | 25332.2 | 4.305 | 0.000 | 10 | LNU220 | 25405.1 | 5.643 | 0.024 | 10 | LNU220 | 25405.6 | 45.2 | 0.282 | 10 |
| LNU122 | 25332.5 | 4.214 | 0.324 | 7 | LNU220 | 25405.5 | 5.597 | 0.084 | 9 | LNU220 | 25405.1 | 45.1 | 0.024 | 10 |
| LNU122 | 25333.2 | 3.972 | 0.796 | 1 | LNU220 | 25405.2 | 5.420 | 0.567 | 5 | LNU220 | 25405.5 | 44.8 | 0.084 | 9 |
| LNU125 | 25941.4 | 4.108 | 0.072 | 5 | LNU234 | 25014.6 | 5.343 | 0.764 | 4 | LNU220 | 25405.2 | 43.4 | 0.567 | 5 |
| LNU125 | 25943.2 | 4.065 | 0.372 | 4 | LNU236 | 25424.2 | 6.609 | 0.163 | 29 | LNU234 | 25014.6 | 42.7 | 0.764 | 4 |
| LNU138 | 14074.5 | 4.227 | 0.004 | 8 | LNU236 | 25422.4 | 5.751 | 0.104 | 12 | LNU236 | 25424.2 | 52.9 | 0.163 | 29 |
| LNU138 | 14071.5 | 4.055 | 0.110 | 3 | LNU236 | 25425.4 | 5.715 | 0.461 | 11 | LNU236 | 25422.4 | 46.0 | 0.104 | 12 |
| LNU138 | 14074.6 | 3.995 | 0.626 | 2 | LNU236 | 25423.3 | 5.617 | 0.562 | 9 | LNU236 | 25425.4 | 45.7 | 0.461 | 11 |
| LNU157 | 24982.1 | 4.149 | 0.283 | 6 | LNU24 | 24974.2 | 5.406 | 0.476 | 5 | LNU236 | 25423.3 | 44.9 | 0.562 | 9 |
| LNU178 | 14614.5 | 4.306 | 0.077 | 10 | LNU25 | 14082.8 | 6.389 | 0.000 | 24 | LNU24 | 24974.2 | 43.2 | 0.476 | 5 |
| LNU178 | 14611.5 | 4.250 | 0.119 | 8 | LNU25 | 14082.9 | 5.548 | 0.099 | 8 | LNU25 | 14082.8 | 51.1 | 0.000 | 24 |
| LNU178 | 14611.4 | 4.135 | 0.015 | 8 | LNU25 | 14084.6 | 5.424 | 0.348 | 6 | LNU25 | 14082.9 | 44.4 | 0.099 | 8 |
| LNU178 | 14612.1 | 4.004 | 0.628 | 2 | LNU271 | 25911.4 | 5.716 | 0.647 | 11 | LNU25 | 14084.6 | 43.4 | 0.348 | 6 |
| LNU220 | 25405.6 | 4.098 | 0.215 | 5 | LNU278 | 25814.1 | 5.701 | 0.013 | 11 | LNU271 | 25911.4 | 45.7 | 0.647 | 11 |
| LNU220 | 25405.5 | 4.062 | 0.115 | 4 | LNU278 | 25814.3 | 5.444 | 0.283 | 6 | LNU278 | 25814.1 | 45.6 | 0.013 | 11 |
| LNU220 | 25405.1 | 4.012 | 0.543 | 2 | LNU278 | 25812.2 | 5.272 | 0.492 | 3 | LNU278 | 25814.3 | 43.5 | 0.283 | 6 |
| LNU220 | 25405.2 | 3.998 | 0.620 | 2 | LNU43 | 14423.7 | 5.559 | 0.132 | 8 | LNU278 | 25812.2 | 42.2 | 0.492 | 3 |
| LNU234 | 25014.6 | 4.021 | 0.585 | 3 | LNU45 | 25052.12 | 7.025 | 0.000 | 37 | LNU43 | 14423.7 | 44.5 | 0.132 | 8 |
| LNU234 | 25014.5 | 3.951 | 0.735 | 1 | LNU45 | 25053.4 | 6.516 | 0.308 | 27 | LNU45 | 25052.12 | 56.2 | 0.000 | 37 |
| LNU236 | 25424.2 | 4.580 | 0.101 | 17 | LNU45 | 25052.11 | 5.797 | 0.179 | 13 | LNU45 | 25053.4 | 52.1 | 0.308 | 27 |
| LNU236 | 25423.3 | 4.191 | 0.440 | 7 | LNU45 | 25052.9 | 5.597 | 0.032 | 9 | LNU45 | 25052.11 | 46.4 | 0.179 | 13 |
| LNU236 | 25425.4 | 4.116 | 0.531 | 5 | LNU67 | 25824.3 | 6.189 | 0.000 | 20 | LNU45 | 25052.9 | 44.8 | 0.032 | 9 |
| LNU236 | 25422.4 | 4.101 | 0.033 | 5 | LNU67 | 25824.5 | 5.719 | 0.011 | 11 | LNU67 | 25824.3 | 49.5 | 0.000 | 20 |
| LNU24 | 24974.2 | 4.058 | 0.091 | 3 | LNU67 | 25821.4 | 5.563 | 0.307 | 8 | LNU67 | 25824.5 | 45.7 | 0.011 | 11 |
| LNU24 | 24972.1 | 4.010 | 0.494 | 2 | LNU9 | 25001.1 | 5.942 | 0.008 | 16 | LNU67 | 25821.4 | 44.5 | 0.307 | 8 |
| LNU25 | 14082.8 | 4.402 | 0.000 | 12 | LNU9 | 25001.7 | 5.900 | 0.329 | 15 | LNU9 | 25001.1 | 47.5 | 0.008 | 16 |
| LNU25 | 14082.9 | 4.236 | 0.001 | 8 | LNU9 | 25003.1 | 5.374 | 0.723 | 5 | LNU9 | 25001.7 | 47.2 | 0.329 | 15 |
| LNU25 | 14084.6 | 4.023 | 0.394 | 3 | CONT. | — | 5.507 | — | 0 | LNU9 | 25003.1 | 43.0 | 0.723 | 5 |
| LNU25 | 14083.7 | 3.969 | 0.736 | 1 | LNU10 | 25123.6 | 6.580 | 0.085 | 19 | CONT. | — | 44.1 | — | 0 |
| LNU267 | 25804.4 | 3.994 | 0.576 | 2 | LNU10 | 25123.5 | 5.880 | 0.455 | 7 | LNU10 | 25123.6 | 52.6 | 0.085 | 19 |
| LNU271 | 25911.4 | 4.261 | 0.337 | 9 | LNU157 | 24982.8 | 7.166 | 0.005 | 30 | LNU10 | 25123.5 | 47.0 | 0.455 | 7 |
| LNU271 | 25912.1 | 4.121 | 0.475 | 5 | LNU157 | 24982.4 | 6.039 | 0.298 | 10 | LNU157 | 24982.8 | 57.3 | 0.005 | 30 |
| LNU278 | 25813.2 | 4.096 | 0.393 | 4 | LNU157 | 24983.3 | 5.728 | 0.725 | 4 | LNU157 | 24982.4 | 48.3 | 0.298 | 10 |
| LNU278 | 25814.3 | 4.086 | 0.051 | 4 | LNU173 | 25451.1 | 6.406 | 0.534 | 16 | LNU157 | 24983.3 | 45.8 | 0.725 | 4 |

TABLE 79-continued

Genes showing improved plant biomass production at limiting nitrogen growth conditions

| Gene Name | Event # | Ave. | P-Value | % incr. | Gene Name | Event # | Ave. | P-Value | % incr. | Gene Name | Event # | Ave. | P-Value | % incr. |
|---|---|---|---|---|---|---|---|---|---|---|---|---|---|---|
| | | Rosette Diameter [cm] | | | | | Rosette Area [cm2] | | | | | Plot Coverage [%] | | |
| LNU278 | 25814.1 | 4.075 | 0.297 | 4 | LNU178 | 14611.4 | 7.845 | 0.315 | 42 | LNU173 | 25451.1 | 51.2 | 0.534 | 16 |
| LNU278 | 25812.2 | 3.990 | 0.365 | 2 | LNU178 | 14611.5 | 7.119 | 0.096 | 29 | LNU178 | 14611.4 | 62.8 | 0.315 | 42 |
| LNU43 | 14423.7 | 4.174 | 0.132 | 6 | LNU178 | 14611.1 | 7.075 | 0.374 | 28 | LNU178 | 14611.5 | 57.0 | 0.096 | 29 |
| LNU43 | 14422.9 | 4.066 | 0.685 | 4 | LNU184 | 25393.2 | 6.860 | 0.015 | 25 | LNU178 | 14611.1 | 56.6 | 0.374 | 28 |
| LNU45 | 25052.12 | 4.606 | 0.005 | 17 | LNU184 | 25393.3 | 6.648 | 0.354 | 21 | LNU184 | 25393.2 | 54.9 | 0.015 | 25 |
| LNU45 | 25053.4 | 4.431 | 0.260 | 13 | LNU184 | 25393.1 | 6.580 | 0.617 | 19 | LNU184 | 25393.3 | 53.2 | 0.354 | 21 |
| LNU45 | 25052.11 | 4.149 | 0.297 | 6 | LNU184 | 25395.1 | 6.315 | 0.563 | 15 | LNU184 | 25393.1 | 52.6 | 0.617 | 19 |
| LNU45 | 25052.9 | 4.127 | 0.022 | 5 | LNU230 | 25413.1 | 7.185 | 0.026 | 30 | LNU184 | 25395.1 | 50.5 | 0.563 | 15 |
| LNU67 | 25824.3 | 4.354 | 0.064 | 11 | LNU230 | 25413.2 | 7.178 | 0.136 | 30 | LNU230 | 25413.1 | 57.5 | 0.026 | 30 |
| LNU67 | 25824.5 | 4.312 | 0.001 | 10 | LNU230 | 25412.1 | 6.604 | 0.043 | 20 | LNU230 | 25413.2 | 57.4 | 0.136 | 30 |
| LNU67 | 25821.4 | 4.183 | 0.273 | 7 | LNU230 | 25412.2 | 6.600 | 0.298 | 20 | LNU230 | 25412.1 | 52.8 | 0.043 | 20 |
| LNU9 | 25001.7 | 4.232 | 0.226 | 8 | LNU230 | 25415.1 | 6.466 | 0.149 | 17 | LNU230 | 25412.2 | 52.8 | 0.298 | 20 |
| LNU9 | 25001.1 | 4.204 | 0.007 | 7 | LNU236 | 25425.4 | 8.219 | 0.000 | 49 | LNU230 | 25415.1 | 51.7 | 0.149 | 17 |
| LNU9 | 25003.1 | 4.068 | 0.556 | 4 | LNU236 | 25423.3 | 6.874 | 0.278 | 25 | LNU236 | 25425.4 | 65.8 | 0.000 | 49 |
| LNU9 | 25001.2 | 4.025 | 0.660 | 3 | LNU236 | 25422.4 | 6.448 | 0.170 | 17 | LNU236 | 25423.3 | 55.0 | 0.278 | 25 |
| CONT. | — | 3.944 | — | 0 | LNU236 | 25424.2 | 6.380 | 0.075 | 16 | LNU236 | 25422.4 | 51.6 | 0.170 | 17 |
| LNU10 | 25123.6 | 4.138 | 0.332 | 5 | LNU24 | 24974.2 | 7.569 | 0.002 | 37 | LNU236 | 25424.2 | 51.0 | 0.075 | 16 |
| LNU157 | 24982.8 | 4.444 | 0.034 | 13 | LNU24 | 24971.3 | 6.403 | 0.230 | 16 | LNU24 | 24974.2 | 60.6 | 0.002 | 37 |
| LNU157 | 24982.4 | 4.193 | 0.371 | 6 | LNU24 | 24971.2 | 5.754 | 0.601 | 4 | LNU24 | 24971.3 | 51.2 | 0.230 | 16 |
| LNU173 | 25451.1 | 4.512 | 0.313 | 14 | LNU24 | 24972.1 | 5.719 | 0.665 | 4 | LNU24 | 24971.2 | 46.0 | 0.601 | 4 |
| LNU173 | 25451.11 | 4.050 | 0.602 | 3 | LNU263 | 25791.3 | 7.019 | 0.194 | 27 | LNU24 | 24972.1 | 45.8 | 0.665 | 4 |
| LNU178 | 14611.4 | 4.797 | 0.243 | 22 | LNU263 | 25794.3 | 6.800 | 0.159 | 23 | LNU263 | 25791.3 | 56.2 | 0.194 | 27 |
| LNU178 | 14611.5 | 4.523 | 0.095 | 15 | LNU263 | 25794.8 | 6.413 | 0.261 | 16 | LNU263 | 25794.3 | 54.4 | 0.159 | 23 |
| LNU178 | 14611.1 | 4.401 | 0.349 | 12 | LNU263 | 25792.2 | 6.090 | 0.249 | 11 | LNU263 | 25794.8 | 51.3 | 0.261 | 16 |
| LNU184 | 25393.2 | 4.407 | 0.052 | 12 | LNU276 | 25433.1 | 6.838 | 0.133 | 24 | LNU263 | 25792.2 | 48.7 | 0.249 | 11 |
| LNU184 | 25393.3 | 4.363 | 0.445 | 11 | LNU276 | 25431.1 | 6.701 | 0.131 | 22 | LNU276 | 25433.1 | 54.7 | 0.133 | 24 |
| LNU184 | 25395.1 | 4.336 | 0.494 | 10 | LNU276 | 25433.3 | 6.144 | 0.175 | 12 | LNU276 | 25431.1 | 53.6 | 0.131 | 22 |
| LNU184 | 25393.1 | 4.294 | 0.623 | 9 | LNU279 | 25484.3 | 7.208 | 0.010 | 31 | LNU276 | 25433.3 | 49.1 | 0.175 | 12 |
| LNU20 | 24933.4 | 4.011 | 0.756 | 2 | LNU279 | 25481.5 | 7.101 | 0.255 | 29 | LNU279 | 25484.3 | 57.7 | 0.010 | 31 |
| LNU230 | 25413.2 | 4.579 | 0.204 | 16 | LNU279 | 25481.5 | 6.775 | 0.173 | 23 | LNU279 | 25481.5 | 56.8 | 0.255 | 29 |
| LNU230 | 25413.1 | 4.544 | 0.071 | 15 | LNU279 | 25481.4 | 6.607 | 0.242 | 20 | LNU279 | 25481.5 | 54.2 | 0.173 | 23 |
| LNU230 | 25412.1 | 4.308 | 0.113 | 9 | LNU279 | 25481.2 | 6.433 | 0.660 | 17 | LNU279 | 25481.4 | 52.9 | 0.242 | 20 |
| LNU230 | 25412.2 | 4.279 | 0.300 | 8 | LNU36 | 25562.3 | 7.147 | 0.344 | 30 | LNU279 | 25481.2 | 51.5 | 0.660 | 17 |
| LNU230 | 25415.1 | 4.195 | 0.242 | 6 | LNU36 | 25562.7 | 7.019 | 0.528 | 27 | LNU36 | 25562.3 | 57.2 | 0.344 | 30 |
| LNU236 | 25425.4 | 4.953 | 0.001 | 26 | LNU36 | 25561.2 | 6.466 | 0.436 | 17 | LNU36 | 25562.7 | 56.2 | 0.528 | 27 |
| LNU236 | 25423.3 | 4.397 | 0.278 | 11 | LNU56 | 24694.1 | 6.943 | 0.530 | 26 | LNU36 | 25561.2 | 51.7 | 0.436 | 17 |
| LNU236 | 25422.4 | 4.229 | 0.174 | 7 | LNU56 | 24693.1 | 6.813 | 0.402 | 24 | LNU56 | 24694.1 | 55.5 | 0.530 | 26 |
| LNU236 | 25424.2 | 4.222 | 0.203 | 7 | LNU56 | 24691.2 | 6.571 | 0.207 | 19 | LNU56 | 24693.1 | 54.5 | 0.402 | 24 |
| LNU24 | 24974.2 | 4.724 | 0.003 | 20 | LNU56 | 24694.2 | 6.087 | 0.583 | 11 | LNU56 | 24691.2 | 52.6 | 0.207 | 19 |
| LNU24 | 24971.3 | 4.446 | 0.030 | 13 | LNU73 | 25755.1 | 8.249 | 0.000 | 50 | LNU56 | 24694.2 | 48.7 | 0.583 | 11 |
| LNU24 | 24971.4 | 4.323 | 0.630 | 10 | LNU73 | 25751.1 | 7.035 | 0.007 | 28 | LNU73 | 25755.1 | 66.0 | 0.000 | 50 |
| LNU24 | 24971.2 | 4.177 | 0.306 | 6 | LNU73 | 25751.9 | 7.002 | 0.057 | 27 | LNU73 | 25751.1 | 56.3 | 0.007 | 28 |
| LNU24 | 24972.1 | 4.036 | 0.670 | 2 | LNU73 | 25751.8 | 6.744 | 0.478 | 22 | LNU73 | 25751.9 | 56.0 | 0.057 | 27 |
| LNU263 | 25791.3 | 4.414 | 0.206 | 12 | LNU73 | 25754.2 | 6.571 | 0.510 | 19 | LNU73 | 25751.8 | 53.9 | 0.478 | 22 |
| LNU263 | 25794.3 | 4.382 | 0.058 | 11 | LNU9 | 25001.1 | 7.060 | 0.030 | 28 | LNU73 | 25754.2 | 52.6 | 0.510 | 19 |
| LNU263 | 25794.8 | 4.364 | 0.160 | 11 | LNU9 | 25001.7 | 7.045 | 0.272 | 28 | LNU9 | 25001.1 | 56.5 | 0.030 | 28 |
| LNU263 | 25794.6 | 4.133 | 0.664 | 5 | LNU9 | 25001.2 | 6.492 | 0.050 | 18 | LNU9 | 25001.7 | 56.4 | 0.272 | 28 |
| LNU263 | 25792.2 | 4.105 | 0.417 | 4 | CONT. | — | 4.310 | — | 0 | LNU9 | 25001.2 | 51.9 | 0.050 | 18 |
| LNU276 | 25433.1 | 4.519 | 0.043 | 15 | LNU131 | 14005.5 | 8.645 | 0.001 | 101 | CONT. | — | 34.1 | — | 0 |
| LNU276 | 25431.1 | 4.420 | 0.058 | 12 | LNU131 | 14005.2 | 6.311 | 0.274 | 46 | LNU131 | 14005.5 | 69.2 | 0.001 | 103 |
| LNU276 | 25433.3 | 4.065 | 0.546 | 3 | LNU131 | 14002.15 | 5.784 | 0.140 | 34 | LNU131 | 14005.2 | 50.5 | 0.269 | 48 |
| LNU276 | 25433.2 | 4.058 | 0.721 | 3 | LNU135 | 26204.2 | 8.965 | 0.258 | 108 | LNU131 | 14002.15 | 46.3 | 0.137 | 36 |
| LNU279 | 25481.3 | 4.560 | 0.121 | 16 | LNU135 | 26203.6 | 6.304 | 0.010 | 46 | LNU135 | 26204.2 | 71.7 | 0.257 | 110 |
| LNU279 | 25484.3 | 4.429 | 0.045 | 12 | LNU135 | 26203.4 | 6.171 | 0.448 | 43 | LNU135 | 26203.6 | 50.4 | 0.010 | 48 |
| LNU279 | 25481.4 | 4.402 | 0.080 | 12 | LNU135 | 26203.1 | 5.922 | 0.000 | 37 | LNU135 | 26203.4 | 49.4 | 0.441 | 45 |
| LNU279 | 25481.5 | 4.265 | 0.415 | 8 | LNU135 | 26203.3 | 5.009 | 0.698 | 16 | LNU135 | 26203.1 | 47.4 | 0.000 | 39 |
| LNU279 | 25481.2 | 4.214 | 0.715 | 7 | LNU161 | 14553.5 | 6.325 | 0.483 | 47 | LNU135 | 26203.3 | 40.1 | 0.682 | 17 |
| LNU36 | 25562.3 | 4.718 | 0.145 | 20 | LNU161 | 14553.6 | 5.177 | 0.010 | 20 | LNU161 | 14553.5 | 50.6 | 0.476 | 48 |
| LNU36 | 25562.7 | 4.472 | 0.522 | 13 | LNU173 | 25451.2 | 4.840 | 0.090 | 12 | LNU161 | 14553.6 | 41.4 | 0.006 | 21 |
| LNU36 | 25561.2 | 4.392 | 0.185 | 11 | LNU173 | 25451.5 | 4.762 | 0.536 | 10 | LNU173 | 25451.2 | 38.7 | 0.062 | 13 |
| LNU36 | 25562.9 | 4.067 | 0.606 | 3 | LNU181 | 25771.2 | 6.501 | 0.126 | 51 | LNU173 | 25451.5 | 38.1 | 0.503 | 12 |
| LNU53 | 25674.1 | 4.109 | 0.434 | 4 | LNU181 | 25771.11 | 5.656 | 0.001 | 31 | LNU173 | 25451.11 | 35.2 | 0.767 | 3 |
| LNU56 | 24694.1 | 4.545 | 0.384 | 15 | LNU181 | 25771.6 | 5.580 | 0.028 | 29 | LNU181 | 25771.2 | 52.0 | 0.125 | 52 |
| LNU56 | 24693.1 | 4.456 | 0.334 | 13 | LNU181 | 25774.1 | 5.207 | 0.009 | 21 | LNU181 | 25771.11 | 45.3 | 0.001 | 33 |
| LNU56 | 24691.2 | 4.309 | 0.335 | 9 | LNU181 | 25771.8 | 4.592 | 0.664 | 7 | LNU181 | 25771.6 | 44.6 | 0.026 | 31 |
| LNU56 | 24694.2 | 4.131 | 0.682 | 5 | LNU181 | 25771.5 | 4.521 | 0.499 | 5 | LNU181 | 25774.1 | 41.7 | 0.005 | 22 |
| LNU73 | 25755.1 | 4.907 | 0.002 | 24 | LNU184 | 25395.1 | 7.171 | 0.277 | 66 | LNU181 | 25771.8 | 36.7 | 0.620 | 8 |
| LNU73 | 25751.1 | 4.566 | 0.021 | 16 | LNU184 | 25394.3 | 7.043 | 0.350 | 63 | LNU181 | 25771.5 | 36.2 | 0.405 | 6 |
| LNU73 | 25751.9 | 4.543 | 0.012 | 15 | LNU184 | 25394.1 | 6.482 | 0.289 | 50 | LNU184 | 25395.1 | 57.4 | 0.274 | 68 |
| LNU73 | 25751.8 | 4.499 | 0.356 | 14 | LNU184 | 25393.3 | 6.186 | 0.067 | 44 | LNU184 | 25394.3 | 56.3 | 0.346 | 65 |

TABLE 79-continued

Genes showing improved plant biomass production at limiting nitrogen growth conditions

| Gene Name | Event # | Rosette Diameter [cm] Ave. | P-Value | % incr. | Gene Name | Event # | Rosette Area [cm2] Ave. | P-Value | % incr. | Gene Name | Event # | Plot Coverage [%] Ave. | P-Value | % incr. |
|---|---|---|---|---|---|---|---|---|---|---|---|---|---|---|
| LNU73 | 25754.2 | 4.393 | 0.435 | 11 | LNU184 | 25393.2 | 5.114 | 0.046 | 19 | LNU184 | 25394.1 | 51.9 | 0.285 | 52 |
| LNU9 | 25001.1 | 4.617 | 0.008 | 17 | LNU184 | 25393.1 | 5.009 | 0.591 | 16 | LNU184 | 25393.3 | 49.5 | 0.067 | 45 |
| LNU9 | 25001.7 | 4.463 | 0.087 | 13 | LNU224 | 25871.3 | 7.087 | 0.000 | 64 | LNU184 | 25393.2 | 40.9 | 0.036 | 20 |
| LNU9 | 25001.2 | 4.305 | 0.092 | 9 | LNU224 | 25874.1 | 6.965 | 0.008 | 62 | LNU184 | 25393.1 | 40.1 | 0.572 | 17 |
| LNU9 | 25001.3 | 4.015 | 0.712 | 2 | LNU224 | 25872.2 | 6.385 | 0.001 | 48 | LNU224 | 25871.3 | 56.7 | 0.000 | 66 |
| CONT. | — | 3.452 | — | 0 | LNU224 | 25872.3 | 5.780 | 0.001 | 34 | LNU224 | 25874.1 | 55.7 | 0.009 | 63 |
| LNU131 | 14005.5 | 4.854 | 0.000 | 41 | LNU224 | 25874.4 | 5.469 | 0.321 | 27 | LNU224 | 25872.2 | 51.1 | 0.001 | 50 |
| LNU131 | 14005.2 | 4.227 | 0.316 | 22 | LNU246 | 25743.2 | 7.125 | 0.404 | 65 | LNU224 | 25874.4 | 43.7 | 0.311 | 28 |
| LNU131 | 14002.15 | 4.036 | 0.002 | 17 | LNU246 | 25743.1 | 6.759 | 0.276 | 57 | LNU224 | 25872.3 | 43.4 | 0.207 | 27 |
| LNU135 | 26204.2 | 5.120 | 0.162 | 48 | LNU246 | 25744.2 | 6.626 | 0.387 | 54 | LNU246 | 25743.2 | 57.0 | 0.399 | 67 |
| LNU135 | 26203.6 | 4.181 | 0.042 | 21 | LNU246 | 25744.4 | 6.098 | 0.515 | 41 | LNU246 | 25743.1 | 54.1 | 0.273 | 58 |
| LNU135 | 26203.4 | 4.131 | 0.450 | 20 | LNU246 | 25744.3 | 5.273 | 0.176 | 22 | LNU246 | 25744.2 | 53.0 | 0.382 | 55 |
| LNU135 | 26203.1 | 4.001 | 0.021 | 16 | LNU250 | 25592.2 | 6.367 | 0.000 | 48 | LNU246 | 25744.4 | 48.8 | 0.507 | 43 |
| LNU135 | 26203.3 | 3.773 | 0.675 | 9 | LNU250 | 25592.1 | 5.181 | 0.475 | 20 | LNU246 | 25744.3 | 42.2 | 0.166 | 24 |
| LNU161 | 14553.5 | 4.024 | 0.540 | 17 | LNU250 | 25591.1 | 5.156 | 0.269 | 20 | LNU250 | 25592.2 | 50.9 | 0.000 | 49 |
| LNU161 | 14553.6 | 3.716 | 0.062 | 8 | LNU260 | 26404.8 | 5.607 | 0.297 | 30 | LNU250 | 25592.1 | 41.4 | 0.459 | 21 |
| LNU173 | 25451.5 | 3.669 | 0.516 | 6 | LNU260 | 26404.7 | 5.580 | 0.506 | 29 | LNU250 | 25591.1 | 41.2 | 0.254 | 21 |
| LNU173 | 25451.2 | 3.600 | 0.279 | 4 | LNU260 | 26404.1 | 5.285 | 0.546 | 23 | LNU260 | 26404.8 | 44.9 | 0.289 | 31 |
| LNU173 | 25451.11 | 3.547 | 0.642 | 3 | LNU260 | 26403.1 | 4.649 | 0.651 | 8 | LNU260 | 26404.7 | 44.6 | 0.496 | 31 |
| LNU181 | 25771.2 | 4.262 | 0.041 | 23 | LNU260 | 26403.2 | 4.396 | 0.800 | 2 | LNU260 | 26404.1 | 42.3 | 0.532 | 24 |
| LNU181 | 25771.6 | 3.935 | 0.165 | 14 | LNU276 | 25433.6 | 5.708 | 0.197 | 32 | LNU260 | 26403.1 | 37.2 | 0.613 | 9 |
| LNU181 | 25771.11 | 3.894 | 0.004 | 13 | LNU276 | 25433.5 | 5.179 | 0.140 | 20 | LNU260 | 26403.2 | 35.2 | 0.699 | 3 |
| LNU181 | 25774.1 | 3.818 | 0.017 | 11 | LNU276 | 25431.1 | 5.161 | 0.011 | 20 | LNU276 | 25433.6 | 45.7 | 0.191 | 34 |
| LNU181 | 25771.8 | 3.674 | 0.280 | 6 | LNU276 | 25433.1 | 4.426 | 0.713 | 3 | LNU276 | 25433.5 | 41.4 | 0.128 | 21 |
| LNU184 | 25395.1 | 4.492 | 0.290 | 30 | LNU279 | 25484.3 | 6.354 | 0.341 | 47 | LNU276 | 25431.1 | 41.3 | 0.006 | 21 |
| LNU184 | 25394.3 | 4.482 | 0.323 | 30 | LNU279 | 25481.3 | 5.756 | 0.587 | 34 | LNU276 | 25433.1 | 35.4 | 0.607 | 4 |
| LNU184 | 25394.1 | 4.177 | 0.252 | 21 | LNU279 | 25481.5 | 5.435 | 0.007 | 26 | LNU279 | 25484.3 | 50.8 | 0.335 | 49 |
| LNU184 | 25393.3 | 4.133 | 0.020 | 20 | LNU279 | 25481.4 | 5.033 | 0.497 | 17 | LNU279 | 25481.3 | 46.0 | 0.578 | 35 |
| LNU184 | 25393.2 | 3.813 | 0.014 | 10 | LNU3 | 26122.2 | 5.909 | 0.425 | 37 | LNU279 | 25481.5 | 43.5 | 0.005 | 27 |
| LNU184 | 25393.1 | 3.705 | 0.662 | 7 | LNU33 | 25553.3 | 6.560 | 0.006 | 52 | LNU279 | 25481.4 | 40.3 | 0.477 | 18 |
| LNU224 | 25871.3 | 4.493 | 0.000 | 30 | LNU33 | 25553.2 | 5.801 | 0.285 | 35 | LNU3 | 26122.2 | 47.3 | 0.417 | 38 |
| LNU224 | 25874.1 | 4.356 | 0.000 | 26 | LNU33 | 25552.2 | 5.752 | 0.591 | 33 | LNU33 | 25553.3 | 52.5 | 0.007 | 54 |
| LNU224 | 25872.2 | 4.309 | 0.000 | 25 | LNU33 | 25553.1 | 4.961 | 0.698 | 15 | LNU33 | 25552.2 | 46.0 | 0.582 | 35 |
| LNU224 | 25872.3 | 3.908 | 0.128 | 13 | LNU53 | 25674.6 | 5.147 | 0.323 | 19 | LNU33 | 25553.2 | 43.1 | 0.124 | 26 |
| LNU224 | 25874.4 | 3.833 | 0.404 | 11 | LNU56 | 24694.2 | 4.436 | 0.766 | 3 | LNU33 | 25553.1 | 39.7 | 0.681 | 16 |
| LNU246 | 25743.2 | 4.424 | 0.405 | 28 | LNU73 | 25751.8 | 4.966 | 0.726 | 15 | LNU53 | 25674.6 | 41.2 | 0.307 | 21 |
| LNU246 | 25743.1 | 4.343 | 0.295 | 26 | CONT. | — | 7.009 | — | 0 | LNU56 | 24694.2 | 35.5 | 0.687 | 4 |
| LNU246 | 25744.2 | 4.321 | 0.372 | 25 | LNU119 | 26144.2. | 7.422 | 0.040 | 6 | LNU56 | 24693.1 | 35.2 | 0.768 | 3 |
| LNU246 | 25744.4 | 4.129 | 0.544 | 20 | LNU130 | 24913.6. | 8.010 | 0.031 | 14 | LNU73 | 25751.8 | 39.7 | 0.710 | 16 |
| LNU246 | 25744.3 | 3.791 | 0.027 | 10 | LNU130 | 24912.7. | 8.000 | 0.563 | 14 | CONT. | — | 56.1 | — | 0 |
| LNU250 | 25592.2 | 4.190 | 0.000 | 21 | LNU130 | 24914.5. | 7.702 | 0.630 | 10 | LNU119 | 26144.2. | 59.4 | 0.040 | 6 |
| LNU250 | 25591.1 | 3.850 | 0.300 | 12 | LNU130 | 24911.7. | 7.358 | 0.707 | 5 | LNU130 | 24913.6. | 64.1 | 0.031 | 14 |
| LNU250 | 25592.1 | 3.821 | 0.500 | 11 | LNU136 | 14511.10. | 8.765 | 0.000 | 25 | LNU130 | 24912.7. | 64.0 | 0.563 | 14 |
| LNU260 | 26404.7 | 3.957 | 0.497 | 15 | LNU136 | 14515.5. | 8.318 | 0.421 | 19 | LNU130 | 24914.5. | 61.6 | 0.630 | 10 |
| LNU260 | 26404.8 | 3.890 | 0.165 | 13 | LNU142 | 27541.1. | 8.194 | 0.001 | 17 | LNU130 | 24911.7. | 58.9 | 0.707 | 5 |
| LNU260 | 26404.1 | 3.770 | 0.526 | 9 | LNU142 | 27546.1. | 7.204 | 0.712 | 3 | LNU136 | 14511.10. | 70.1 | 0.000 | 25 |
| LNU260 | 26403.1 | 3.649 | 0.489 | 6 | LNU149 | 26175.3. | 7.709 | 0.362 | 10 | LNU136 | 14515.5. | 66.5 | 0.421 | 19 |
| LNU276 | 25433.6 | 3.990 | 0.171 | 16 | LNU15 | 14123.11. | 7.968 | 0.426 | 14 | LNU142 | 27541.1. | 65.6 | 0.001 | 17 |
| LNU276 | 25431.1 | 3.781 | 0.144 | 10 | LNU15 | 14123.13. | 7.941 | 0.000 | 13 | LNU142 | 27546.1. | 57.6 | 0.712 | 3 |
| LNU276 | 25433.5 | 3.747 | 0.110 | 9 | LNU185 | 26474.2. | 8.650 | 0.453 | 23 | LNU149 | 26175.3. | 57.6 | 0.306 | 3 |
| LNU279 | 25484.3 | 4.239 | 0.327 | 23 | LNU185 | 26475.1. | 8.305 | 0.283 | 19 | LNU15 | 14123.13. | 63.5 | 0.000 | 13 |
| LNU279 | 25481.3 | 4.086 | 0.519 | 18 | LNU185 | 26474.1. | 7.750 | 0.681 | 11 | LNU15 | 14123.11. | 60.1 | 0.749 | 7 |
| LNU279 | 25481.5 | 3.904 | 0.006 | 13 | LNU212 | 25833.2. | 9.276 | 0.130 | 32 | LNU185 | 26474.2. | 69.2 | 0.453 | 23 |
| LNU279 | 25481.4 | 3.752 | 0.483 | 8 | LNU212 | 25834.4. | 8.993 | 0.223 | 28 | LNU185 | 26475.1. | 66.4 | 0.283 | 19 |
| LNU279 | 25481.2 | 3.509 | 0.721 | 2 | LNU212 | 25834.5. | 8.125 | 0.046 | 16 | LNU185 | 26474.1. | 62.0 | 0.681 | 11 |
| LNU3 | 26122.2 | 4.147 | 0.367 | 20 | LNU212 | 25832.1. | 7.353 | 0.652 | 5 | LNU212 | 25833.2. | 74.2 | 0.130 | 32 |
| LNU33 | 25553.3 | 4.335 | 0.017 | 26 | LNU216 | 25985.4. | 9.065 | 0.247 | 29 | LNU212 | 25834.4. | 71.9 | 0.223 | 28 |
| LNU33 | 25552.2 | 4.067 | 0.541 | 18 | LNU216 | 25982.1. | 8.548 | 0.051 | 22 | LNU212 | 25834.5. | 65.0 | 0.046 | 16 |
| LNU33 | 25553.2 | 3.973 | 0.017 | 15 | LNU216 | 25984.1. | 8.543 | 0.361 | 22 | LNU212 | 25832.1. | 58.8 | 0.652 | 5 |
| LNU33 | 25553.1 | 3.716 | 0.678 | 8 | LNU216 | 25984.6. | 7.518 | 0.254 | 7 | LNU216 | 25985.4. | 72.5 | 0.247 | 29 |
| LNU53 | 25674.6 | 3.826 | 0.360 | 11 | LNU228 | 26224.7. | 8.690 | 0.000 | 24 | LNU216 | 25982.1. | 68.4 | 0.051 | 22 |
| LNU53 | 25674.3 | 3.496 | 0.751 | 1 | LNU228 | 26222.4. | 7.798 | 0.004 | 11 | LNU216 | 25984.1. | 68.3 | 0.361 | 22 |
| LNU56 | 24694.2 | 3.551 | 0.538 | 3 | LNU229 | 26112.3. | 8.196 | 0.000 | 17 | LNU216 | 25984.6. | 60.1 | 0.254 | 7 |
| LNU56 | 24693.1 | 3.515 | 0.785 | 2 | LNU253 | 26241.1. | 8.044 | 0.163 | 15 | LNU228 | 26224.7. | 69.5 | 0.000 | 24 |
| LNU73 | 25751.8 | 3.799 | 0.677 | 10 | LNU274 | 26261.3. | 7.172 | 0.369 | 2 | LNU228 | 26222.4. | 62.4 | 0.004 | 11 |
| CONT. | — | 4.516 | — | 0 | LNU280 | 26162.1. | 8.341 | 0.473 | 19 | LNU229 | 26112.3. | 65.6 | 0.000 | 17 |
| LNU119 | 26144.2. | 4.661 | 0.249 | 3 | LNU55 | 26015.1. | 7.969 | 0.422 | 14 | LNU253 | 26241.1. | 64.4 | 0.163 | 15 |
| LNU130 | 24912.7. | 5.046 | 0.322 | 12 | LNU81 | 26031.9. | 7.582 | 0.756 | 8 | LNU274 | 26261.3. | 57.4 | 0.369 | 2 |
| LNU130 | 24914.5. | 4.894 | 0.471 | 8 | LNU81 | 26034.2. | 7.572 | 0.684 | 8 | LNU280 | 26162.1. | 66.7 | 0.473 | 19 |
| LNU130 | 24911.7. | 4.783 | 0.342 | 6 | CONT. | — | 6.912 | — | 0 | LNU55 | 26015.1. | 63.8 | 0.422 | 14 |

TABLE 79-continued

Genes showing improved plant biomass production at limiting nitrogen growth conditions

| | | Rosette Diameter [cm] | | | | | Rosette Area [cm2] | | | | | Plot Coverage [%] | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU130 | 24913.6. | 4.731 | 0.324 | 5 | LNU119 | 26141.1. | 8.792 | 0.468 | 27 | LNU81 | 26031.9. | 60.7 | 0.756 | 8 |
| LNU136 | 14511.10. | 5.012 | 0.068 | 11 | LNU119 | 26142.5. | 7.376 | 0.586 | 7 | LNU81 | 26034.2. | 60.6 | 0.684 | 8 |
| LNU136 | 14515.5. | 4.893 | 0.486 | 8 | LNU130 | 24913.5. | 7.963 | 0.260 | 15 | CONT. | — | 55.3 | — | 0 |
| LNU142 | 27541.1. | 5.007 | 0.001 | 11 | LNU130 | 24914.5. | 7.654 | 0.394 | 11 | LNU119 | 26141.1. | 70.3 | 0.468 | 27 |
| LNU142 | 27546.1. | 4.599 | 0.429 | 2 | LNU130 | 24913.6. | 7.350 | 0.664 | 6 | LNU119 | 26142.5. | 59.0 | 0.586 | 7 |
| LNU149 | 26175.3. | 4.779 | 0.002 | 6 | LNU136 | 14515.1. | 7.530 | 0.508 | 9 | LNU130 | 24913.5. | 63.7 | 0.260 | 15 |
| LNU15 | 14123.13. | 4.878 | 0.001 | 8 | LNU136 | 14511.10. | 7.444 | 0.692 | 8 | LNU130 | 24914.5. | 61.2 | 0.394 | 11 |
| LNU15 | 14123.11. | 4.818 | 0.550 | 7 | LNU136 | 14514.8. | 7.389 | 0.728 | 7 | LNU130 | 24913.6. | 58.8 | 0.664 | 6 |
| LNU185 | 26474.2. | 5.052 | 0.503 | 12 | LNU142 | 27546.2. | 7.551 | 0.642 | 9 | LNU136 | 14515.1. | 60.2 | 0.508 | 9 |
| LNU185 | 26475.1. | 4.953 | 0.147 | 10 | LNU142 | 27546.1. | 7.487 | 0.504 | 8 | LNU136 | 14511.10. | 59.6 | 0.692 | 8 |
| LNU185 | 26474.1. | 4.889 | 0.530 | 8 | LNU142 | 27545.1. | 7.329 | 0.792 | 6 | LNU136 | 14514.8. | 59.1 | 0.728 | 7 |
| LNU212 | 25834.4. | 5.219 | 0.236 | 16 | LNU149 | 26174.7. | 7.171 | 0.788 | 4 | LNU142 | 27546.2. | 60.4 | 0.642 | 9 |
| LNU212 | 25833.2. | 5.176 | 0.153 | 15 | LNU15 | 14124.12. | 8.132 | 0.349 | 18 | LNU142 | 27546.1. | 59.9 | 0.504 | 8 |
| LNU212 | 25834.5. | 5.085 | 0.167 | 13 | LNU15 | 14122.8. | 8.027 | 0.486 | 16 | LNU142 | 27545.1. | 58.6 | 0.792 | 6 |
| LNU212 | 25834.1. | 4.707 | 0.624 | 4 | LNU15 | 14123.13. | 7.620 | 0.415 | 10 | LNU149 | 26174.7. | 57.4 | 0.788 | 4 |
| LNU212 | 25832.1. | 4.689 | 0.346 | 4 | LNU185 | 26474.1. | 8.921 | 0.055 | 29 | LNU15 | 14124.12. | 65.1 | 0.349 | 18 |
| LNU216 | 25982.1. | 5.253 | 0.053 | 16 | LNU212 | 25834.4. | 8.727 | 0.084 | 26 | LNU15 | 14122.8. | 64.2 | 0.486 | 16 |
| LNU216 | 25985.4. | 5.187 | 0.306 | 15 | LNU212 | 25834.5. | 8.061 | 0.217 | 17 | LNU15 | 14123.13. | 61.0 | 0.415 | 10 |
| LNU216 | 25984.1. | 5.160 | 0.310 | 14 | LNU212 | 25833.2. | 7.256 | 0.683 | 5 | LNU185 | 26474.1. | 71.4 | 0.055 | 29 |
| LNU216 | 25984.6. | 4.889 | 0.000 | 8 | LNU216 | 25985.4. | 9.450 | 0.146 | 37 | LNU212 | 25834.4. | 69.8 | 0.084 | 26 |
| LNU228 | 26224.7. | 5.104 | 0.000 | 13 | LNU216 | 25982.1. | 7.955 | 0.280 | 15 | LNU212 | 25834.5. | 64.5 | 0.217 | 17 |
| LNU228 | 26222.4. | 4.805 | 0.198 | 6 | LNU216 | 25984.6. | 7.667 | 0.701 | 11 | LNU212 | 25833.2. | 58.1 | 0.683 | 5 |
| LNU229 | 26112.3. | 4.981 | 0.000 | 10 | LNU216 | 25982.2. | 7.312 | 0.641 | 6 | LNU216 | 25985.4. | 75.6 | 0.146 | 37 |
| LNU253 | 26241.1. | 4.900 | 0.000 | 9 | LNU228 | 26225.2. | 9.276 | 0.044 | 34 | LNU216 | 25982.1. | 63.6 | 0.280 | 15 |
| LNU253 | 26245.1. | 4.580 | 0.372 | 1 | LNU228 | 26224.7. | 8.572 | 0.399 | 24 | LNU216 | 25984.6. | 61.3 | 0.701 | 11 |
| LNU274 | 26264.2. | 4.699 | 0.606 | 4 | LNU228 | 26222.4. | 8.339 | 0.137 | 21 | LNU216 | 25982.2. | 58.5 | 0.641 | 6 |
| LNU280 | 26162.1. | 5.073 | 0.376 | 12 | LNU228 | 26222.1. | 8.289 | 0.164 | 20 | LNU228 | 26225.2. | 74.2 | 0.044 | 34 |
| LNU55 | 26015.1. | 4.909 | 0.385 | 9 | LNU228 | 26224.6. | 8.203 | 0.319 | 19 | LNU228 | 26222.4. | 66.7 | 0.137 | 21 |
| LNU81 | 26034.2. | 4.657 | 0.745 | 3 | LNU229 | 26112.4. | 8.649 | 0.257 | 25 | LNU228 | 26222.1. | 66.3 | 0.164 | 20 |
| LNU81 | 26034.3. | 4.588 | 0.501 | 2 | LNU229 | 26111.7. | 8.573 | 0.438 | 24 | LNU228 | 26224.6. | 65.6 | 0.319 | 19 |
| CONT. | — | 4.514 | — | 0 | LNU229 | 26111.5. | 8.441 | 0.277 | 22 | LNU228 | 26224.7. | 58.7 | 0.616 | 6 |
| LNU119 | 26141.1. | 5.132 | 0.455 | 14 | LNU229 | 26112.3. | 8.225 | 0.344 | 19 | LNU229 | 26112.4. | 69.2 | 0.257 | 25 |
| LNU119 | 26142.5. | 4.717 | 0.517 | 4 | LNU241 | 26232.4. | 8.028 | 0.230 | 16 | LNU229 | 26111.7. | 68.6 | 0.438 | 24 |
| LNU130 | 24913.5. | 4.742 | 0.500 | 5 | LNU241 | 26233.3. | 7.906 | 0.658 | 14 | LNU229 | 26111.5. | 67.5 | 0.277 | 22 |
| LNU130 | 24913.6. | 4.712 | 0.574 | 4 | LNU241 | 26234.1. | 7.487 | 0.502 | 8 | LNU229 | 26112.3. | 65.8 | 0.344 | 19 |
| LNU130 | 24914.5. | 4.685 | 0.604 | 4 | LNU253 | 26242.1. | 7.550 | 0.652 | 9 | LNU241 | 26232.4. | 64.2 | 0.230 | 16 |
| LNU136 | 14511.10. | 4.806 | 0.556 | 6 | LNU253 | 26241.1. | 7.211 | 0.734 | 4 | LNU241 | 26233.3. | 63.2 | 0.658 | 14 |
| LNU136 | 14514.8. | 4.785 | 0.592 | 6 | LNU274 | 26265.1. | 7.782 | 0.634 | 13 | LNU241 | 26234.1. | 59.9 | 0.502 | 8 |
| LNU136 | 14515.1. | 4.727 | 0.548 | 5 | LNU274 | 26262.2. | 7.698 | 0.582 | 11 | LNU253 | 26242.1. | 60.4 | 0.652 | 9 |
| LNU142 | 27546.2. | 4.748 | 0.558 | 5 | LNU280 | 26162.1. | 8.526 | 0.144 | 23 | LNU253 | 26241.1. | 57.7 | 0.734 | 4 |
| LNU142 | 27546.1. | 4.712 | 0.515 | 4 | LNU280 | 26164.4. | 7.630 | 0.408 | 10 | LNU274 | 26265.1. | 62.3 | 0.634 | 13 |
| LNU142 | 27545.1. | 4.687 | 0.683 | 4 | LNU55 | 26013.4. | 7.698 | 0.433 | 11 | LNU274 | 26262.2. | 61.6 | 0.582 | 11 |
| LNU15 | 14122.8. | 4.959 | 0.461 | 10 | LNU55 | 26015.1. | 7.646 | 0.435 | 11 | LNU280 | 26162.1. | 68.2 | 0.144 | 23 |
| LNU15 | 14123.13. | 4.837 | 0.301 | 7 | LNU55 | 26013.3. | 7.634 | 0.782 | 10 | LNU55 | 26013.4. | 61.6 | 0.433 | 11 |
| LNU15 | 14124.12. | 4.773 | 0.572 | 6 | LNU81 | 26031.10. | 8.300 | 0.656 | 20 | LNU55 | 26015.1. | 61.2 | 0.435 | 11 |
| LNU185 | 26474.1. | 5.288 | 0.053 | 17 | LNU81 | 26031.2. | 7.932 | 0.410 | 15 | LNU55 | 26013.3. | 61.1 | 0.782 | 10 |
| LNU185 | 26473.1. | 4.624 | 0.722 | 2 | CONTROL | — | 5.130 | — | 0.0 | LNU81 | 26031.10. | 66.4 | 0.656 | 20 |
| LNU212 | 25834.4. | 5.158 | 0.069 | 14 | LNU61 | 26134.4 | 6.167 | 0.034 | 20.22 | LNU81 | 26031.2. | 63.5 | 0.410 | 15 |
| LNU212 | 25834.5. | 4.908 | 0.226 | 9 | LNU61 | 26135.3 | 5.575 | 0.338 | 8.68 | CONT. | — | 40.689 | — | 0.0 |
| LNU212 | 25834.1. | 4.682 | 0.593 | 4 | CONT. | — | 5.130 | — | 0.0 | LNU61 | 26134.4 | 49.340 | 0.02 | 21.26 |
| LNU216 | 25985.4. | 5.308 | 0.120 | 18 | LNU115 | 27584.2 | 5.790 | <0.4 | 12.9 | LNU61 | 26135.3 | 44.604 | 0.33 | 9.62 |
| LNU216 | 25982.1. | 4.804 | 0.348 | 6 | LNU115 | 27586.2 | 6.387 | <0.1 | 24.5 | CONT. | — | 40.689 | — | 0.0 |
| LNU216 | 25982.2. | 4.712 | 0.619 | 4 | LNU115 | 27586.3 | 5.314 | <0.7 | 3.6 | LNU115 | 27584.2 | 46.316 | <0.3 | 13.8 |
| LNU216 | 25984.6. | 4.658 | 0.782 | 3 | LNU123 | 27721.1 | 5.768 | <0.4 | 12.4 | LNU115 | 27586.2 | 51.093 | <0.1 | 25.6 |
| LNU216 | 25984.1. | 4.639 | 0.747 | 3 | LNU123 | 27721.2 | 6.131 | <0.4 | 19.5 | LNU115 | 27586.3 | 42.513 | <0.9 | 4.5 |
| LNU228 | 26225.2. | 5.360 | 0.060 | 19 | LNU123 | 27722.1 | 6.229 | <0.1 | 21.4 | LNU123 | 27721.1 | 46.143 | <0.3 | 13.4 |
| LNU228 | 26224.4. | 5.173 | 0.325 | 15 | LNU123 | 27722.4 | 6.830 | <0.1 | 33.1 | LNU123 | 27721.2 | 49.044 | <0.1 | 20.5 |
| LNU228 | 26222.1. | 5.005 | 0.185 | 11 | LNU123 | 27724.1 | 5.298 | <0.8 | 3.3 | LNU123 | 27722.1 | 49.835 | <0.1 | 22.5 |
| LNU228 | 26224.6. | 4.928 | 0.350 | 9 | LNU123 | 27724.2 | 5.585 | <0.6 | 8.9 | LNU123 | 27722.4 | 54.642 | <0.1 | 34.3 |
| LNU228 | 26222.4. | 4.759 | 0.423 | 5 | LNU127 | 27601.2 | 6.811 | <0.1 | 32.8 | LNU123 | 27724.1 | 42.383 | <0.9 | 4.2 |
| LNU229 | 26111.7. | 5.050 | 0.417 | 12 | LNU127 | 27601.3 | 6.212 | <0.1 | 21.1 | LNU123 | 27724.2 | 44.676 | <0.5 | 9.8 |
| LNU229 | 26112.3. | 5.016 | 0.412 | 11 | LNU127 | 27601.4 | 7.362 | <0.1 | 43.5 | LNU127 | 27601.2 | 54.489 | <0.1 | 33.9 |
| LNU229 | 26112.4. | 4.983 | 0.320 | 10 | LNU127 | 27603.1 | 6.636 | <0.1 | 29.3 | LNU127 | 27601.3 | 49.696 | <0.1 | 22.1 |
| LNU229 | 26111.5. | 4.884 | 0.337 | 8 | LNU127 | 27603.5 | 6.058 | <0.4 | 18.1 | LNU127 | 27601.4 | 58.894 | <0.1 | 44.7 |
| LNU241 | 26233.3. | 5.068 | 0.575 | 12 | LNU134 | 29191.3 | 6.109 | <0.4 | 19.1 | LNU127 | 27603.1 | 53.084 | <0.1 | 30.5 |
| LNU241 | 26232.4. | 5.012 | 0.163 | 11 | LNU134 | 29191.6 | 5.673 | <0.6 | 10.6 | LNU127 | 27603.5 | 48.464 | <0.3 | 19.1 |
| LNU241 | 26234.1. | 4.673 | 0.598 | 4 | LNU134 | 29192.1 | 7.116 | <0.1 | 38.7 | LNU134 | 29191.3 | 48.868 | <0.1 | 20.1 |
| LNU253 | 26242.1. | 4.850 | 0.331 | 7 | LNU134 | 29193.2 | 5.921 | <0.4 | 15.4 | LNU134 | 29191.6 | 45.388 | <0.5 | 11.5 |

TABLE 79-continued

Genes showing improved plant biomass production at limiting nitrogen growth conditions

| Gene Name | Event # | Ave. | P-Value | % incr. | Gene Name | Event # | Ave. | P-Value | % incr. | Gene Name | Event # | Ave. | P-Value | % incr. |
|---|---|---|---|---|---|---|---|---|---|---|---|---|---|---|
| | | Rosette Diameter [cm] | | | | | Rosette Area [cm2] | | | | | Plot Coverage [%] | | |
| LNU253 | 26241.1. | 4.677 | 0.604 | 4 | LNU190 | 27555.2 | 5.704 | <0.6 | 11.2 | LNU134 | 29192.1 | 56.931 | <0.1 | 39.9 |
| LNU274 | 26262.2. | 4.923 | 0.343 | 9 | LNU198 | 27731.2 | 5.550 | <0.6 | 8.2 | LNU134 | 29193.2 | 47.367 | <0.3 | 16.4 |
| LNU274 | 26265.1. | 4.804 | 0.680 | 6 | LNU198 | 27734.4 | 5.441 | <0.8 | 6.1 | LNU190 | 27555.2 | 45.636 | <0.5 | 12.2 |
| LNU280 | 26162.1. | 5.140 | 0.227 | 14 | LNU198 | 27735.4 | 5.535 | <0.6 | 7.9 | LNU198 | 27731.2 | 44.399 | <0.5 | 9.1 |
| LNU280 | 26164.4 | 4.779 | 0.510 | 6 | LNU200 | 27991.2 | 5.736 | <0.6 | 11.8 | LNU198 | 27734.4 | 43.531 | <0.7 | 7.0 |
| LNU55 | 26013.3. | 4.868 | 0.663 | 8 | LNU200 | 27992.2 | 5.827 | <0.4 | 13.6 | LNU198 | 27735.4 | 44.277 | <0.5 | 8.8 |
| LNU55 | 26013.4. | 4.795 | 0.535 | 6 | LNU200 | 27992.3 | 6.394 | <0.1 | 24.6 | LNU200 | 27991.2 | 45.887 | <0.5 | 12.8 |
| LNU55 | 26015.1. | 4.687 | 0.636 | 4 | LNU200 | 27993.4 | 6.850 | <0.1 | 33.5 | LNU200 | 27992.2 | 46.620 | <0.3 | 14.6 |
| LNU81 | 26031.10. | 4.970 | 0.569 | 10 | LNU200 | 27994.3 | 6.408 | <0.1 | 24.9 | LNU200 | 27992.3 | 51.155 | <0.1 | 25.7 |
| LNU81 | 26031.2. | 4.792 | 0.582 | 6 | LNU217 | 28231.3 | 6.348 | <0.1 | 23.7 | LNU200 | 27993.4 | 54.797 | <0.1 | 34.7 |
| CONT. | — | 4.055 | — | 0.0 | LNU217 | 28234.1 | 6.165 | <0.1 | 20.2 | LNU200 | 27994.3 | 51.262 | <0.1 | 26.0 |
| LNU115 | 27584.2 | 4.302 | <0.6 | 6.1 | LNU244 | 28013.6 | 6.179 | <0.1 | 20.4 | LNU217 | 28231.3 | 50.780 | <0.1 | 24.8 |
| LNU115 | 27586.2 | 4.561 | <0.1 | 12.5 | LNU244 | 28013.8 | 6.185 | <0.1 | 20.6 | LNU217 | 28234.1 | 45.735 | <0.5 | 12.4 |
| LNU123 | 27721.1 | 4.234 | <0.6 | 4.4 | LNU244 | 28014.3 | 5.743 | <0.6 | 11.9 | LNU244 | 28013.6 | 49.429 | <0.1 | 21.5 |
| LNU123 | 27721.2 | 4.546 | <0.1 | 12.1 | LNU244 | 28014.4 | 6.687 | <0.1 | 30.4 | LNU244 | 28013.8 | 49.477 | <0.1 | 21.6 |
| LNU123 | 27722.1 | 4.427 | 0.25 | 9.2 | LNU244 | 28015.1 | 6.208 | <0.1 | 21.0 | LNU244 | 28014.3 | 45.945 | <0.5 | 12.9 |
| LNU123 | 27722.4 | 4.726 | <0.1 | 16.6 | LNU262 | 27591.3 | 5.986 | <0.4 | 16.7 | LNU244 | 28014.4 | 53.499 | <0.1 | 31.5 |
| LNU123 | 27724.1 | 4.230 | <0.6 | 4.3 | LNU262 | 27591.7 | 6.332 | <0.1 | 23.4 | LNU244 | 28015.1 | 49.667 | <0.1 | 22.1 |
| LNU127 | 27601.2 | 4.661 | <0.1 | 15.0 | LNU262 | 27593.6 | 6.748 | <0.1 | 31.5 | LNU262 | 27591.3 | 47.887 | <0.3 | 17.7 |
| LNU127 | 27601.3 | 4.404 | <0.25 | 8.6 | LNU262 | 27595.4 | 6.770 | <0.1 | 32.0 | LNU262 | 27591.7 | 50.657 | <0.1 | 24.5 |
| LNU127 | 27601.4 | 4.689 | <0.1 | 15.7 | LNU266 | 27932.1 | 6.839 | <0.1 | 33.3 | LNU262 | 27593.6 | 53.987 | <0.1 | 32.7 |
| LNU127 | 27603.1 | 4.461 | <0.25 | 10.0 | LNU266 | 27935.3 | 5.920 | <0.4 | 15.4 | LNU262 | 27595.2 | 41.885 | <0.9 | 2.9 |
| LNU127 | 27603.5 | 4.477 | <0.25 | 10.4 | LNU266 | 27935.4 | 6.236 | <0.1 | 21.6 | LNU262 | 27595.4 | 54.162 | <0.1 | 33.1 |
| LNU134 | 29191.3 | 4.275 | <0.6 | 5.4 | LNU29 | 27651.3 | 5.393 | <0.8 | 5.1 | LNU266 | 27932.1 | 54.714 | <0.1 | 34.5 |
| LNU134 | 29192.1 | 4.774 | <0.1 | 17.7 | LNU29 | 27653.1 | 6.158 | <0.1 | 20.0 | LNU266 | 27935.3 | 47.363 | <0.3 | 16.4 |
| LNU190 | 27555.2 | 4.209 | <0.7 | 3.8 | LNU32 | 29251.1 | 5.634 | <0.6 | 9.8 | LNU266 | 27935.4 | 49.891 | <0.1 | 22.6 |
| LNU198 | 27734.4 | 4.216 | <0.7 | 4.0 | LNU32 | 29252.6 | 5.641 | <0.6 | 10.0 | LNU29 | 27651.3 | 43.145 | <0.7 | 6.0 |
| LNU200 | 27991.2 | 4.293 | <0.6 | 5.9 | LNU51 | 27611.1 | 5.810 | <0.4 | 13.3 | LNU29 | 27653.1 | 49.264 | <0.1 | 21.1 |
| LNU200 | 27992.2 | 4.337 | <0.6 | 7.0 | LNU51 | 27613.3 | 5.593 | <0.6 | 9.0 | LNU29 | 27654.1 | 41.748 | <0.9 | 2.6 |
| LNU200 | 27992.3 | 4.609 | <0.1 | 13.7 | LNU51 | 27614.2 | 5.505 | <0.8 | 7.3 | LNU32 | 29251.1 | 45.070 | <0.5 | 10.8 |
| LNU200 | 27993.4 | 4.754 | <0.1 | 17.3 | LNU58 | 27673.2 | 6.263 | <0.1 | 22.1 | LNU32 | 29252.6 | 45.129 | <0.5 | 10.9 |
| LNU200 | 27994.3 | 4.487 | <0.25 | 10.7 | LNU58 | 27673.3 | 5.560 | <0.6 | 8.4 | LNU51 | 27611.1 | 46.483 | <0.3 | 14.2 |
| LNU217 | 28231.3 | 4.431 | <0.25 | 9.3 | LNU58 | 27673.4 | 5.416 | <0.8 | 5.6 | LNU51 | 27613.3 | 44.746 | <0.5 | 10.0 |
| LNU217 | 28234.1 | 4.432 | <0.25 | 9.3 | LNU58 | 27673.6 | 5.456 | <0.8 | 6.3 | LNU51 | 27614.2 | 44.042 | <0.5 | 8.2 |
| LNU244 | 28013.6 | 4.470 | <0.25 | 10.2 | LNU58 | 27673.8 | 5.481 | <0.8 | 6.8 | LNU58 | 27673.2 | 50.103 | <0.1 | 23.1 |
| LNU244 | 28013.8 | 4.365 | <0.6 | 7.6 | CONT. | 8252.24 | 1.222 | — | 0.0 | LNU58 | 27673.3 | 44.483 | <0.5 | 9.3 |
| LNU244 | 28014.3 | 4.337 | <0.6 | 7.0 | LNU89 | 25325.1 | 1.521 | 0.03 | 24.5 | LNU58 | 27673.4 | 43.332 | <0.7 | 6.5 |
| LNU244 | 28014.4 | 4.543 | <0.1 | 12.0 | LNU89 | 27193.2 | 1.438 | 0.11 | 17.7 | LNU58 | 27673.8 | 43.851 | <0.7 | 7.8 |
| LNU244 | 28015.1 | 4.451 | <0.25 | 9.8 | | | | | | CONT. | — | 8.301 | — | 0.0 |
| LNU262 | 27591.3 | 4.358 | <0.6 | 7.5 | | | | | | LNU89 | 25325.1 | 12.168 | 0.0005 | 46.6 |
| LNU262 | 27591.7 | 4.642 | <0.1 | 14.5 | | | | | | LNU89 | 27193.2 | 10.064 | 0.047 | 21.2 |
| LNU262 | 27593.6 | 4.659 | <0.1 | 14.9 | | | | | | | | | | |
| LNU262 | 27595.4 | 4.664 | <0.1 | 15.0 | | | | | | | | | | |
| LNU266 | 27932.1 | 4.708 | <0.1 | 16.1 | | | | | | | | | | |
| LNU266 | 27935.3 | 4.412 | <0.25 | 8.8 | | | | | | | | | | |
| LNU266 | 27935.4 | 4.558 | <0.1 | 12.4 | | | | | | | | | | |
| LNU29 | 27653.1 | 4.643 | <0.1 | 14.5 | | | | | | | | | | |
| LNU32 | 29251.1 | 4.206 | <0.7 | 3.7 | | | | | | | | | | |
| LNU51 | 27614.2 | 4.177 | <0.7 | 3.0 | | | | | | | | | | |
| LNU58 | 27673.2 | 4.410 | <0.25 | 8.8 | | | | | | | | | | |
| LNU58 | 27673.3 | 4.331 | <0.6 | 6.8 | | | | | | | | | | |
| CONT. | 8252.24 | 1.922 | — | 0.0 | | | | | | | | | | |
| LNU89 | 25325.1 | 2.153 | 0.07 | 12.0 | | | | | | | | | | |
| LNU89 | 27193.2 | 2.107 | 0.14 | 9.6 | | | | | | | | | | |

Table 79.
"CONT."—Control;
"Ave."—Average;
"% Incr." = % increment.

The genes listed in Table 80 improved plant NUE when grown at limiting nitrogen concentration levels. These genes produced photosynthetic areas as seen by their larger leaf number, leaf blade area and petiole area. The genes were cloned under the regulation of a constitutive (At6669) and root preferred promoter (RootP). The evaluation of each gene was performed by testing the performance of different number of events. Event with p-value <0.1 was considered statistically significant.

TABLE 80

Genes showing improved plant photosynthetic capacity at limiting nitrogen growth conditions

| | | Leaf Number | | | | | Leaf Blade Area [cm2] | | | | | Leaf Petiole Length [cm] | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| CONT. | — | 10.679 | — | 0 | CONT. | — | 0.634 | — | 0 | CONT. | — | 0.725 | — | 0 |
| LNU100 | 14472.2 | 11.125 | 0.089 | 4 | LNU100 | 14472.2 | 0.811 | 0.001 | 28 | LNU100 | 14472.2 | 0.902 | 0.008 | 24 |
| LNU100 | 14471.4 | 10.813 | 0.513 | 1 | LNU100 | 14471.4 | 0.765 | 0.110 | 21 | LNU100 | 14471.4 | 0.822 | 0.000 | 13 |
| LNU104 | 25033.1 | 11.313 | 0.237 | 6 | LNU100 | 14474.3 | 0.703 | 0.314 | 11 | LNU100 | 14474.3 | 0.785 | 0.198 | 8 |
| LNU104 | 25033.3 | 11.313 | 0.083 | 6 | LNU100 | 14473.3 | 0.674 | 0.112 | 6 | LNU100 | 14473.3 | 0.744 | 0.413 | 3 |
| LNU104 | 25032.1 | 10.938 | 0.390 | 2 | LNU104 | 25033.3 | 0.862 | 0.000 | 36 | LNU104 | 25033.3 | 0.943 | 0.002 | 30 |
| LNU106 | 14481.1 | 11.188 | 0.027 | 5 | LNU104 | 25032.2 | 0.854 | 0.000 | 35 | LNU104 | 25032.2 | 0.842 | 0.008 | 16 |
| LNU106 | 14483.5 | 11.063 | 0.412 | 4 | LNU104 | 25032.1 | 0.775 | 0.133 | 22 | LNU104 | 25032.1 | 0.823 | 0.294 | 13 |
| LNU114 | 25042.1 | 11.021 | 0.501 | 3 | LNU104 | 25033.1 | 0.694 | 0.027 | 9 | LNU104 | 25033.1 | 0.819 | 0.036 | 13 |
| LNU155 | 14525.1 | 11.250 | 0.190 | 5 | LNU104 | 25034.1 | 0.653 | 0.743 | 3 | LNU104 | 25034.1 | 0.764 | 0.636 | 5 |
| LNU155 | 14523.1 | 11.063 | 0.079 | 4 | LNU106 | 14481.1 | 0.829 | 0.076 | 31 | LNU106 | 14481.1 | 0.878 | 0.028 | 21 |
| LNU218 | 24784.2 | 11.500 | 0.009 | 8 | LNU106 | 14483.5 | 0.768 | 0.284 | 21 | LNU106 | 14483.2 | 0.869 | 0.001 | 20 |
| LNU218 | 24781.4 | 11.000 | 0.636 | 3 | LNU106 | 14484.3 | 0.739 | 0.000 | 17 | LNU106 | 14483.5 | 0.862 | 0.206 | 19 |
| LNU218 | 24781.7 | 10.938 | 0.390 | 2 | LNU106 | 14483.2 | 0.725 | 0.001 | 14 | LNU106 | 14484.3 | 0.757 | 0.195 | 4 |
| LNU218 | 24781.1 | 10.750 | 0.762 | 1 | LNU114 | 25042.1 | 0.705 | 0.024 | 11 | LNU114 | 25041.1 | 0.806 | 0.377 | 11 |
| LNU23 | 25163.2 | 11.063 | 0.079 | 4 | LNU114 | 25041.2 | 0.702 | 0.432 | 11 | LNU114 | 25042.1 | 0.786 | 0.417 | 8 |
| LNU23 | 25162.1 | 10.839 | 0.767 | 1 | LNU114 | 25041.1 | 0.659 | 0.664 | 4 | LNU114 | 25041.2 | 0.779 | 0.504 | 7 |
| LNU23 | 25163.6 | 10.813 | 0.513 | 1 | LNU155 | 14525.1 | 0.718 | 0.110 | 13 | LNU155 | 14525.1 | 0.799 | 0.295 | 10 |
| LNU28 | 25171.4 | 11.042 | 0.727 | 3 | LNU155 | 14523.5 | 0.711 | 0.251 | 12 | LNU155 | 14523.5 | 0.757 | 0.671 | 4 |
| LNU28 | 25171.1 | 11.000 | 0.543 | 3 | LNU213 | 24654.4 | 0.716 | 0.002 | 13 | LNU213 | 24653.2 | 0.821 | 0.312 | 13 |
| LNU28 | 25171.2 | 10.813 | 0.643 | 1 | LNU218 | 24781.7 | 0.811 | 0.001 | 28 | LNU213 | 24654.4 | 0.782 | 0.419 | 8 |
| LNU4 | 25133.3 | 11.161 | 0.432 | 5 | LNU218 | 24781.4 | 0.788 | 0.140 | 24 | LNU218 | 24781.4 | 0.905 | 0.003 | 25 |
| LNU40 | 24794.3 | 11.438 | 0.186 | 7 | LNU218 | 24784.2 | 0.710 | 0.247 | 12 | LNU218 | 24781.7 | 0.892 | 0.002 | 23 |
| LNU40 | 24794.4 | 11.229 | 0.371 | 5 | LNU218 | 24781.1 | 0.658 | 0.336 | 4 | LNU218 | 24784.2 | 0.809 | 0.312 | 12 |
| LNU40 | 24792.2 | 11.000 | 0.119 | 3 | LNU23 | 25163.2 | 0.767 | 0.469 | 21 | LNU218 | 24781.1 | 0.794 | 0.396 | 10 |
| LNU46 | 14462.5 | 11.938 | 0.000 | 12 | LNU23 | 25163.6 | 0.687 | 0.670 | 8 | LNU23 | 25163.5 | 0.800 | 0.652 | 10 |
| LNU46 | 14464.4 | 11.313 | 0.083 | 6 | LNU23 | 25163.2 | 0.660 | 0.733 | 4 | LNU23 | 25162.1 | 0.792 | 0.188 | 9 |
| LNU46 | 14462.1 | 11.000 | 0.197 | 3 | LNU28 | 25171.1 | 0.782 | 0.046 | 23 | LNU23 | 25163.6 | 0.773 | 0.607 | 7 |
| LNU46 | 14463.1 | 10.875 | 0.320 | 2 | LNU28 | 25171.2 | 0.772 | 0.000 | 22 | LNU23 | 25163.2 | 0.747 | 0.751 | 3 |
| LNU48 | 24801.4 | 11.750 | 0.161 | 10 | LNU28 | 25174.5 | 0.684 | 0.751 | 8 | LNU28 | 25171.1 | 0.860 | 0.000 | 19 |
| LNU48 | 24802.1 | 11.188 | 0.309 | 5 | LNU4 | 25133.3 | 0.755 | 0.000 | 19 | LNU28 | 25171.4 | 0.827 | 0.407 | 14 |
| LNU48 | 24804.4 | 10.875 | 0.320 | 2 | LNU4 | 25134.1 | 0.693 | 0.527 | 9 | LNU28 | 25171.2 | 0.822 | 0.000 | 13 |
| LNU63 | 24814.2 | 10.813 | 0.752 | 1 | LNU4 | 25131.1 | 0.653 | 0.785 | 3 | LNU28 | 25174.5 | 0.764 | 0.710 | 5 |
| LNU8 | 25062.1 | 11.063 | 0.229 | 4 | LNU40 | 24794.3 | 0.782 | 0.000 | 23 | LNU4 | 25133.3 | 0.861 | 0.033 | 19 |
| LNU8 | 25061.2 | 10.875 | 0.586 | 2 | LNU40 | 24794.4 | 0.745 | 0.154 | 18 | LNU4 | 25131.1 | 0.761 | 0.268 | 5 |
| LNU8 | 25063.6 | 10.813 | 0.643 | 1 | LNU46 | 14464.4 | 0.883 | 0.291 | 39 | LNU4 | 25134.1 | 0.759 | 0.361 | 5 |
| LNU94 | 24833.3 | 11.250 | 0.190 | 5 | LNU46 | 14462.5 | 0.861 | 0.185 | 36 | LNU40 | 24794.3 | 0.850 | 0.166 | 17 |
| LNU96 | 25071.2 | 10.813 | 0.643 | 1 | LNU46 | 14463.1 | 0.700 | 0.088 | 10 | LNU40 | 24794.4 | 0.835 | 0.000 | 15 |
| CONT. | — | 10.798 | — | 0 | LNU46 | 14464.1 | 0.695 | 0.200 | 10 | LNU40 | 24792.1 | 0.754 | 0.372 | 4 |
| LNU113 | 25631.1 | 11.563 | 0.204 | 7 | LNU46 | 14462.1 | 0.666 | 0.666 | 5 | LNU40 | 24792.2 | 0.746 | 0.307 | 3 |
| LNU120 | 25464.1 | 11.375 | 0.628 | 5 | LNU48 | 24801.4 | 0.790 | 0.000 | 25 | LNU46 | 14462.5 | 0.963 | 0.219 | 33 |
| LNU120 | 25463.6 | 11.188 | 0.219 | 4 | LNU48 | 24802.1 | 0.691 | 0.018 | 9 | LNU46 | 14464.4 | 0.905 | 0.299 | 25 |
| LNU120 | 25463.3 | 10.938 | 0.375 | 1 | LNU48 | 24804.4 | 0.667 | 0.178 | 5 | LNU46 | 14463.1 | 0.796 | 0.003 | 10 |
| LNU120 | 25463.7 | 10.929 | 0.419 | 1 | LNU63 | 24814.2 | 0.756 | 0.000 | 19 | LNU46 | 14464.1 | 0.766 | 0.049 | 6 |
| LNU124 | 14502.1 | 11.188 | 0.025 | 4 | LNU63 | 24814.3 | 0.696 | 0.020 | 10 | LNU46 | 14462.1 | 0.762 | 0.584 | 5 |
| LNU124 | 14502.7 | 11.000 | 0.756 | 2 | LNU63 | 24811.2 | 0.693 | 0.025 | 9 | LNU48 | 24802.1 | 0.878 | 0.000 | 21 |
| LNU124 | 14501.1 | 10.875 | 0.699 | 1 | LNU7 | 25081.1 | 0.722 | 0.002 | 14 | LNU48 | 24801.4 | 0.853 | 0.000 | 18 |
| LNU132 | 14102.6 | 11.125 | 0.148 | 3 | LNU7 | 25082.2 | 0.694 | 0.150 | 9 | LNU48 | 24803.2 | 0.733 | 0.701 | 1 |
| LNU132 | 14102.7 | 11.000 | 0.564 | 2 | LNU8 | 25063.6 | 0.693 | 0.345 | 9 | LNU63 | 24814.2 | 0.810 | 0.002 | 12 |
| LNU140 | 14115.1 | 11.250 | 0.527 | 4 | LNU8 | 25062.1 | 0.679 | 0.076 | 7 | LNU63 | 24814.3 | 0.797 | 0.003 | 10 |
| LNU148 | 25685.6 | 11.875 | 0.000 | 10 | LNU8 | 25062.2 | 0.649 | 0.460 | 2 | LNU63 | 24811.2 | 0.745 | 0.671 | 3 |
| LNU148 | 25685.1 | 11.563 | 0.067 | 7 | LNU8 | 25061.2 | 0.643 | 0.650 | 2 | LNU7 | 25081.1 | 0.849 | 0.000 | 17 |
| LNU148 | 25685.9 | 11.375 | 0.032 | 5 | LNU94 | 24833.3 | 0.714 | 0.054 | 13 | LNU7 | 25082.2 | 0.812 | 0.082 | 12 |
| LNU287 | 24674.6 | 11.000 | 0.686 | 2 | LNU96 | 25071.2 | 0.801 | 0.130 | 26 | LNU7 | 25083.3 | 0.770 | 0.598 | 6 |
| LNU37 | 14061.7 | 11.063 | 0.547 | 2 | LNU96 | 25073.4 | 0.701 | 0.694 | 11 | LNU8 | 25063.6 | 0.792 | 0.013 | 9 |
| LNU5 | 14043.7 | 11.063 | 0.721 | 2 | LNU96 | 25071.3 | 0.681 | 0.268 | 8 | LNU8 | 25061.2 | 0.765 | 0.536 | 5 |
| LNU5 | 14043.9 | 10.938 | 0.736 | 1 | CONT. | — | 0.788 | — | 0 | LNU8 | 25062.1 | 0.754 | 0.485 | 4 |
| LNU72 | 24962.3 | 10.938 | 0.375 | 1 | LNU113 | 25631.7 | 0.894 | 0.290 | 13 | LNU94 | 24833.3 | 0.795 | 0.003 | 10 |
| LNU74 | 25444.1 | 11.188 | 0.531 | 4 | LNU113 | 25631.3 | 0.853 | 0.488 | 8 | LNU96 | 25071.2 | 0.893 | 0.225 | 23 |
| LNU74 | 25443.2 | 11.125 | 0.537 | 3 | LNU140 | 14115.1 | 0.806 | 0.789 | 2 | LNU96 | 25074.1 | 0.786 | 0.362 | 8 |
| LNU87 | 24712.4 | 11.313 | 0.006 | 5 | LNU148 | 25685.6 | 0.979 | 0.181 | 24 | LNU96 | 25073.3 | 0.784 | 0.469 | 8 |
| LNU87 | 24714.3 | 11.188 | 0.613 | 4 | LNU148 | 25685.1 | 0.868 | 0.009 | 10 | LNU96 | 25073.4 | 0.781 | 0.578 | 8 |
| LNU98 | 25763.2 | 10.938 | 0.736 | 1 | LNU5 | 14043.7 | 0.859 | 0.400 | 9 | LNU96 | 25071.3 | 0.779 | 0.407 | 7 |
| CONT. | — | 10.726 | — | 0 | LNU68 | 14035.5 | 0.816 | 0.192 | 4 | CONT. | — | 0.754 | — | 0 |
| LNU113 | 25631.9 | 11.063 | 0.461 | 3 | LNU74 | 25444.1 | 0.878 | 0.151 | 11 | LNU113 | 25631.7 | 0.807 | 0.570 | 7 |
| LNU113 | 25631.3 | 10.938 | 0.772 | 2 | LNU74 | 25443.2 | 0.803 | 0.536 | 2 | LNU113 | 25631.3 | 0.793 | 0.424 | 5 |
| LNU120 | 25463.6 | 11.438 | 0.416 | 7 | LNU98 | 25763.2 | 0.823 | 0.203 | 5 | LNU113 | 25631.1 | 0.768 | 0.530 | 2 |
| LNU124 | 14504.5 | 11.063 | 0.750 | 3 | CONT. | — | 0.712 | — | 0 | LNU120 | 25463.3 | 0.763 | 0.796 | 1 |
| LNU148 | 25685.1 | 11.375 | 0.021 | 6 | LNU113 | 25631.9 | 0.783 | 0.320 | 10 | LNU124 | 14501.1 | 0.782 | 0.372 | 4 |
| LNU148 | 25685.2 | 10.938 | 0.218 | 2 | LNU120 | 25463.3 | 0.734 | 0.786 | 3 | LNU132 | 14102.6 | 0.794 | 0.132 | 5 |
| LNU72 | 24962.3 | 11.188 | 0.164 | 4 | LNU148 | 25685.1 | 0.771 | 0.122 | 8 | LNU140 | 14115.1 | 0.770 | 0.380 | 2 |
| LNU72 | 24963.7 | 11.000 | 0.737 | 3 | LNU72 | 24963.7 | 0.789 | 0.543 | 11 | LNU148 | 25685.6 | 0.845 | 0.270 | 12 |

TABLE 80-continued

Genes showing improved plant photosynthetic capacity at limiting nitrogen growth conditions

| Gene Name | Event # | Leaf Number Ave. | P-Value | % incr. | Gene Name | Event # | Leaf Blade Area [cm2] Ave. | P-Value | % incr. | Gene Name | Event # | Leaf Petiole Length [cm] Ave. | P-Value | % incr. |
|---|---|---|---|---|---|---|---|---|---|---|---|---|---|---|
| LNU74 | 25443.5 | 11.000 | 0.219 | 3 | LNU72 | 24962.3 | 0.740 | 0.793 | 4 | LNU148 | 25685.1 | 0.835 | 0.191 | 11 |
| CONT. | — | 10.625 | — | 0 | LNU98 | 25763.2 | 0.802 | 0.253 | 13 | LNU287 | 24674.6 | 0.784 | 0.613 | 4 |
| LNU117 | 25933.3 | 11.688 | 0.143 | 10 | CONT. | — | 0.692 | — | 0 | LNU5 | 14043.7 | 0.783 | 0.413 | 4 |
| LNU117 | 25931.4 | 11.125 | 0.398 | 5 | LNU117 | 25931.4 | 1.085 | 0.072 | 57 | LNU74 | 25443.3 | 0.794 | 0.491 | 5 |
| LNU117 | 25932.4 | 11.063 | 0.436 | 4 | LNU117 | 25931.2 | 0.951 | 0.036 | 37 | LNU74 | 25444.1 | 0.767 | 0.671 | 2 |
| LNU117 | 25931.2 | 10.875 | 0.632 | 2 | LNU117 | 25933.3 | 0.927 | 0.043 | 34 | LNU74 | 25443.2 | 0.759 | 0.757 | 1 |
| LNU122 | 25333.2 | 12.188 | 0.068 | 15 | LNU117 | 25931.1 | 0.897 | 0.110 | 30 | LNU87 | 24713.2 | 0.780 | 0.758 | 3 |
| LNU122 | 25332.5 | 11.375 | 0.225 | 7 | LNU117 | 25932.4 | 0.841 | 0.457 | 22 | LNU98 | 25763.2 | 0.775 | 0.386 | 3 |
| LNU122 | 25333.1 | 11.375 | 0.225 | 7 | LNU122 | 25332.1 | 0.985 | 0.158 | 42 | CONT. | — | 0.753 | — | 0 |
| LNU122 | 25332.1 | 11.250 | 0.307 | 6 | LNU122 | 25333.3 | 0.959 | 0.030 | 39 | LNU113 | 25631.9 | 0.794 | 0.664 | 5 |
| LNU122 | 25332.2 | 11.000 | 0.483 | 4 | LNU122 | 25332.2 | 0.842 | 0.096 | 22 | LNU148 | 25685.1 | 0.781 | 0.655 | 4 |
| LNU125 | 25941.4 | 12.063 | 0.114 | 14 | LNU122 | 25332.5 | 0.837 | 0.092 | 21 | LNU72 | 24962.3 | 0.793 | 0.677 | 5 |
| LNU125 | 25941.1 | 11.625 | 0.150 | 9 | LNU122 | 25333.1 | 0.796 | 0.383 | 15 | LNU98 | 25763.2 | 0.794 | 0.125 | 5 |
| LNU125 | 25943.3 | 11.313 | 0.256 | 6 | LNU125 | 25941.4 | 1.017 | 0.107 | 47 | CONT. | — | 0.663 | — | 0 |
| LNU125 | 25943.2 | 10.875 | 0.738 | 2 | LNU125 | 25943.3 | 0.935 | 0.027 | 35 | LNU117 | 25931.4 | 0.906 | 0.055 | 37 |
| LNU125 | 25944.3 | 10.813 | 0.724 | 2 | LNU125 | 25943.2 | 0.918 | 0.310 | 33 | LNU117 | 25933.3 | 0.845 | 0.077 | 27 |
| LNU138 | 14074.6 | 11.438 | 0.200 | 8 | LNU125 | 25941.4 | 0.814 | 0.516 | 18 | LNU117 | 25932.4 | 0.812 | 0.161 | 23 |
| LNU138 | 14074.5 | 11.375 | 0.230 | 7 | LNU125 | 25944.3 | 0.811 | 0.427 | 17 | LNU117 | 25931.2 | 0.809 | 0.121 | 22 |
| LNU138 | 14071.5 | 10.875 | 0.695 | 2 | LNU138 | 14074.5 | 1.033 | 0.015 | 49 | LNU117 | 25931.1 | 0.745 | 0.545 | 12 |
| LNU180 | 24721.4 | 12.000 | 0.075 | 13 | LNU38 | 14074.6 | 0.962 | 0.273 | 39 | LNU122 | 25333.2 | 0.878 | 0.054 | 32 |
| LNU180 | 24722.2 | 11.750 | 0.124 | 11 | LNU38 | 14071.5 | 0.904 | 0.041 | 31 | LNU122 | 25332.1 | 0.821 | 0.124 | 24 |
| LNU180 | 24724.1 | 11.750 | 0.124 | 11 | LNU38 | 14072.5 | 0.714 | 0.781 | 3 | LNU122 | 25333.1 | 0.792 | 0.169 | 19 |
| LNU180 | 24721.2 | 11.563 | 0.180 | 9 | LNU80 | 24721.2 | 1.181 | 0.022 | 71 | LNU122 | 25332.5 | 0.772 | 0.278 | 17 |
| LNU180 | 24723.1 | 11.375 | 0.230 | 7 | LNU80 | 24723.1 | 1.124 | 0.008 | 62 | LNU122 | 25332.2 | 0.751 | 0.385 | 13 |
| LNU220 | 25405.5 | 11.313 | 0.258 | 6 | LNU80 | 24721.1 | 1.097 | 0.116 | 59 | LNU125 | 25941.4 | 0.885 | 0.230 | 33 |
| LNU220 | 25405.1 | 11.250 | 0.361 | 6 | LNU80 | 24722.2 | 1.065 | 0.090 | 54 | LNU125 | 25941.1 | 0.817 | 0.141 | 23 |
| LNU220 | 25405.2 | 11.125 | 0.398 | 5 | LNU80 | 24724.1 | 0.963 | 0.058 | 39 | LNU125 | 25943.2 | 0.799 | 0.269 | 21 |
| LNU220 | 25405.6 | 11.000 | 0.513 | 4 | LNU220 | 25405.2 | 1.026 | 0.043 | 48 | LNU125 | 25943.3 | 0.795 | 0.181 | 20 |
| LNU220 | 25405.3 | 10.813 | 0.724 | 2 | LNU220 | 25405.5 | 1.019 | 0.106 | 47 | LNU125 | 25944.3 | 0.768 | 0.253 | 16 |
| LNU230 | 25415.1 | 11.750 | 0.150 | 11 | LNU220 | 25405.1 | 1.011 | 0.233 | 46 | LNU138 | 14074.5 | 0.867 | 0.075 | 31 |
| LNU230 | 25413.2 | 11.500 | 0.537 | 8 | LNU220 | 25405.6 | 0.889 | 0.048 | 29 | LNU138 | 14074.6 | 0.851 | 0.104 | 28 |
| LNU230 | 25413.1 | 11.313 | 0.495 | 6 | LNU220 | 25405.3 | 0.802 | 0.515 | 16 | LNU138 | 14071.5 | 0.791 | 0.165 | 19 |
| LNU230 | 25412.2 | 11.277 | 0.274 | 6 | LNU230 | 25413.1 | 1.105 | 0.109 | 60 | LNU138 | 14072.8 | 0.737 | 0.338 | 11 |
| LNU230 | 25412.1 | 11.188 | 0.328 | 5 | LNU230 | 25412.1 | 1.014 | 0.101 | 46 | LNU180 | 24721.2 | 0.952 | 0.026 | 44 |
| LNU234 | 25014.6 | 11.313 | 0.258 | 6 | LNU230 | 25415.1 | 0.966 | 0.211 | 40 | LNU180 | 24722.2 | 0.918 | 0.037 | 38 |
| LNU234 | 25014.5 | 11.063 | 0.598 | 4 | LNU230 | 25413.2 | 0.911 | 0.239 | 32 | LNU180 | 24723.1 | 0.914 | 0.051 | 38 |
| LNU234 | 25014.1 | 10.938 | 0.552 | 3 | LNU230 | 25412.2 | 0.891 | 0.048 | 29 | LNU180 | 24721.4 | 0.889 | 0.055 | 34 |
| LNU234 | 25014.4 | 10.938 | 0.566 | 3 | LNU234 | 25014.8 | 1.020 | 0.016 | 47 | LNU180 | 24724.1 | 0.858 | 0.107 | 29 |
| LNU25 | 14082.9 | 11.688 | 0.134 | 10 | LNU234 | 25014.1 | 0.930 | 0.131 | 34 | LNU220 | 25405.1 | 0.822 | 0.179 | 24 |
| LNU25 | 14083.1 | 11.625 | 0.321 | 9 | LNU234 | 25014.6 | 0.843 | 0.090 | 22 | LNU220 | 25405.5 | 0.808 | 0.171 | 22 |
| LNU25 | 14084.6 | 11.500 | 0.230 | 8 | LNU234 | 25014.4 | 0.834 | 0.101 | 20 | LNU220 | 25405.2 | 0.767 | 0.217 | 16 |
| LNU25 | 14082.8 | 11.000 | 0.488 | 4 | LNU234 | 25014.5 | 0.818 | 0.435 | 18 | LNU220 | 25405.6 | 0.746 | 0.441 | 11 |
| LNU254 | 25781.3 | 11.625 | 0.143 | 9 | LNU25 | 14083.7 | 1.052 | 0.010 | 52 | LNU220 | 25405.3 | 0.739 | 0.385 | 11 |
| LNU254 | 25781.5 | 11.625 | 0.145 | 9 | LNU25 | 14082.8 | 1.052 | 0.103 | 52 | LNU230 | 25412.1 | 0.896 | 0.045 | 35 |
| LNU254 | 25782.5 | 11.500 | 0.299 | 8 | LNU25 | 14082.9 | 0.982 | 0.022 | 42 | LNU230 | 25413.1 | 0.856 | 0.073 | 29 |
| LNU254 | 25783.1 | 11.313 | 0.258 | 6 | LNU25 | 14084.6 | 0.981 | 0.399 | 42 | LNU230 | 25412.2 | 0.807 | 0.133 | 22 |
| LNU254 | 25782.4 | 11.125 | 0.337 | 5 | LNU25 | 14083.1 | 0.973 | 0.028 | 41 | LNU230 | 25415.1 | 0.775 | 0.349 | 17 |
| LNU263 | 25794.6 | 11.813 | 0.101 | 11 | LNU254 | 25782.4 | 1.061 | 0.014 | 53 | LNU230 | 25413.2 | 0.772 | 0.438 | 16 |
| LNU263 | 25794.8 | 11.500 | 0.185 | 8 | LNU254 | 25781.3 | 0.995 | 0.022 | 44 | LNU234 | 25014.8 | 0.872 | 0.123 | 31 |
| LNU263 | 25792.2 | 11.188 | 0.373 | 5 | LNU254 | 25781.5 | 0.956 | 0.029 | 38 | LNU234 | 25014.1 | 0.856 | 0.319 | 29 |
| LNU263 | 25791.3 | 11.125 | 0.452 | 5 | LNU254 | 25783.1 | 0.868 | 0.371 | 25 | LNU234 | 25014.6 | 0.815 | 0.113 | 23 |
| LNU263 | 25794.3 | 11.063 | 0.476 | 4 | LNU254 | 25782.5 | 0.828 | 0.199 | 20 | LNU234 | 25014.5 | 0.780 | 0.359 | 18 |
| LNU267 | 25804.3 | 11.250 | 0.307 | 6 | LNU263 | 25791.3 | 1.060 | 0.056 | 53 | LNU234 | 25014.4 | 0.762 | 0.283 | 15 |
| LNU267 | 25803.1 | 11.188 | 0.373 | 5 | LNU263 | 25794.8 | 1.042 | 0.269 | 51 | LNU25 | 14082.8 | 0.932 | 0.040 | 41 |
| LNU267 | 25804.4 | 11.125 | 0.452 | 5 | LNU263 | 25794.4 | 1.015 | 0.013 | 49 | LNU25 | 14082.9 | 0.920 | 0.035 | 39 |
| LNU267 | 25802.1 | 10.813 | 0.751 | 2 | LNU263 | 25794.3 | 1.003 | 0.032 | 45 | LNU25 | 14083.7 | 0.901 | 0.173 | 36 |
| LNU271 | 25912.2 | 11.563 | 0.164 | 9 | LNU263 | 25792.2 | 0.934 | 0.058 | 35 | LNU25 | 14084.6 | 0.896 | 0.145 | 35 |
| LNU271 | 25911.4 | 11.500 | 0.178 | 8 | LNU267 | 25804.4 | 0.986 | 0.021 | 43 | LNU25 | 14083.1 | 0.890 | 0.047 | 34 |
| LNU271 | 25913.2 | 11.250 | 0.361 | 6 | LNU267 | 25804.3 | 0.959 | 0.265 | 39 | LNU254 | 25782.4 | 0.870 | 0.067 | 31 |
| LNU271 | 25912.1 | 11.161 | 0.539 | 5 | LNU267 | 25801.1 | 0.938 | 0.107 | 36 | LNU254 | 25781.3 | 0.859 | 0.079 | 30 |
| LNU271 | 25913.3 | 10.813 | 0.751 | 2 | LNU267 | 25803.1 | 0.904 | 0.040 | 31 | LNU254 | 25783.1 | 0.832 | 0.227 | 26 |
| LNU278 | 25814.3 | 11.438 | 0.200 | 8 | LNU267 | 25802.1 | 0.877 | 0.188 | 27 | LNU254 | 25782.5 | 0.825 | 0.101 | 24 |
| LNU278 | 25812.3 | 11.375 | 0.237 | 7 | LNU271 | 25911.4 | 1.163 | 0.010 | 68 | LNU254 | 25781.5 | 0.819 | 0.118 | 23 |
| LNU278 | 25813.2 | 11.250 | 0.289 | 6 | LNU271 | 25912.1 | 1.012 | 0.014 | 46 | LNU263 | 25791.3 | 0.911 | 0.043 | 37 |
| LNU278 | 25812.2 | 11.063 | 0.436 | 4 | LNU271 | 25913.3 | 0.909 | 0.053 | 31 | LNU263 | 25794.6 | 0.892 | 0.892 | 34 |
| LNU36 | 25562.3 | 11.188 | 0.328 | 5 | LNU271 | 25912.2 | 0.796 | 0.173 | 15 | LNU263 | 25794.8 | 0.866 | 0.866 | 31 |
| LNU36 | 25562.7 | 11.188 | 0.658 | 5 | LNU278 | 25812.3 | 1.100 | 0.012 | 59 | LNU263 | 25794.3 | 0.859 | 0.859 | 30 |
| LNU36 | 25561.2 | 11.063 | 0.436 | 4 | LNU278 | 25814.3 | 1.093 | 0.010 | 58 | LNU263 | 25792.2 | 0.815 | 0.121 | 23 |
| LNU43 | 14423.6 | 11.688 | 0.125 | 10 | LNU278 | 25814.1 | 0.901 | 0.155 | 30 | LNU267 | 25803.1 | 0.812 | 0.128 | 22 |
| LNU43 | 14422.9 | 11.313 | 0.256 | 6 | LNU278 | 25812.2 | 0.882 | 0.072 | 28 | LNU267 | 25804.4 | 0.809 | 0.266 | 22 |
| LNU43 | 14421.1 | 11.188 | 0.334 | 5 | LNU278 | 25813.2 | 0.777 | 0.319 | 12 | LNU267 | 25804.3 | 0.808 | 0.250 | 22 |
| LNU43 | 14422.8 | 11.000 | 0.621 | 4 | LNU36 | 25562.9 | 1.095 | 0.021 | 58 | LNU267 | 25801.1 | 0.760 | 0.238 | 15 |

TABLE 80-continued

Genes showing improved plant photosynthetic capacity at limiting nitrogen growth conditions

| | | Leaf Number | | | | | Leaf Blade Area [cm2] | | | | | Leaf Petiole Length [cm] | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU45 | 25052.12 | 11.688 | 0.143 | 10 | LNU36 | 25562.3 | 0.896 | 0.048 | 30 | LNU267 | 25802.1 | 0.747 | 0.299 | 13 |
| LNU45 | 25052.9 | 11.500 | 0.178 | 8 | LNU36 | 25562.4 | 0.884 | 0.048 | 28 | LNU271 | 25911.4 | 0.953 | 0.035 | 44 |
| LNU45 | 25053.4 | 11.375 | 0.237 | 7 | LNU36 | 25562.7 | 0.874 | 0.101 | 26 | LNU271 | 25912.1 | 0.861 | 0.094 | 30 |
| LNU45 | 25052.11 | 11.188 | 0.328 | 5 | LNU36 | 25561.2 | 0.752 | 0.400 | 9 | LNU271 | 25913.3 | 0.794 | 0.162 | 20 |
| LNU45 | 25052.8 | 10.813 | 0.712 | 2 | LNU43 | 14422.8 | 1.015 | 0.022 | 47 | LNU271 | 25912.2 | 0.775 | 0.197 | 17 |
| LNU67 | 25821.5 | 11.250 | 0.361 | 6 | LNU43 | 14422.9 | 0.941 | 0.033 | 36 | LNU271 | 25913.2 | 0.744 | 0.382 | 12 |
| LNU67 | 25824.5 | 10.875 | 0.656 | 2 | LNU43 | 14421.1 | 0.912 | 0.044 | 32 | LNU278 | 25812.3 | 0.892 | 0.057 | 35 |
| LNU67 | 25821.4 | 10.813 | 0.784 | 2 | LNU43 | 14423.7 | 0.859 | 0.267 | 24 | LNU278 | 25814.3 | 0.816 | 0.122 | 23 |
| CONT. | — | 10.125 | — | 0 | LNU43 | 14423.6 | 0.833 | 0.125 | 20 | LNU278 | 25812.2 | 0.783 | 0.172 | 18 |
| LNU100 | 14474.2 | 11.063 | 0.319 | 9 | LNU45 | 25052.8 | 0.979 | 0.026 | 41 | LNU278 | 25814.1 | 0.776 | 0.192 | 17 |
| LNU100 | 14472.1 | 10.813 | 0.065 | 7 | LNU45 | 25052.12 | 0.957 | 0.172 | 38 | LNU278 | 25813.2 | 0.744 | 0.312 | 12 |
| LNU100 | 14473.3 | 10.625 | 0.381 | 5 | LNU45 | 25052.9 | 0.920 | 0.062 | 33 | LNU36 | 25562.9 | 0.862 | 0.069 | 30 |
| LNU100 | 14473.1 | 10.500 | 0.487 | 4 | LNU45 | 25053.4 | 0.871 | 0.507 | 26 | LNU36 | 25561.2 | 0.796 | 0.147 | 20 |
| LNU104 | 25033.1 | 10.750 | 0.033 | 6 | LNU45 | 25052.11 | 0.755 | 0.339 | 9 | LNU36 | 25562.7 | 0.735 | 0.346 | 11 |
| LNU104 | 25032.1 | 10.688 | 0.490 | 6 | LNU67 | 25823.5 | 0.875 | 0.062 | 26 | LNU36 | 25562.3 | 0.719 | 0.445 | 8 |
| LNU104 | 25032.2 | 10.688 | 0.655 | 6 | LNU67 | 25824.5 | 0.871 | 0.368 | 26 | LNU36 | 25562.4 | 0.686 | 0.744 | 3 |
| LNU104 | 25033.3 | 10.625 | 0.037 | 5 | LNU67 | 25821.5 | 0.864 | 0.355 | 26 | LNU43 | 14421.1 | 0.890 | 0.047 | 34 |
| LNU106 | 14483.2 | 11.000 | 0.300 | 9 | LNU67 | 25821.4 | 0.830 | 0.175 | 20 | LNU43 | 14422.8 | 0.853 | 0.075 | 29 |
| LNU106 | 14483.5 | 10.813 | 0.009 | 7 | LNU67 | 25824.3 | 0.752 | 0.732 | 9 | LNU43 | 14422.9 | 0.845 | 0.091 | 27 |
| LNU106 | 14482.3 | 10.375 | 0.502 | 2 | CONT. | — | 0.585 | — | 0 | LNU43 | 14423.6 | 0.786 | 0.172 | 19 |
| LNU106 | 14481.1 | 10.313 | 0.797 | 2 | LNU100 | 14474.2 | 0.838 | 0.093 | 43 | LNU43 | 14423.7 | 0.746 | 0.296 | 13 |
| LNU106 | 14484.3 | 10.250 | 0.619 | 1 | LNU100 | 14472.1 | 0.812 | 0.381 | 39 | LNU45 | 25052.12 | 0.902 | 0.052 | 36 |
| LNU114 | 25041.2 | 10.700 | 0.247 | 6 | LNU100 | 14473.3 | 0.753 | 0.372 | 29 | LNU45 | 25052.8 | 0.818 | 0.119 | 23 |
| LNU114 | 25044.4 | 10.625 | 0.624 | 5 | LNU100 | 14473.1 | 0.750 | 0.198 | 28 | LNU45 | 25053.4 | 0.813 | 0.204 | 23 |
| LNU114 | 25042.1 | 10.250 | 0.728 | 1 | LNU100 | 14471.4 | 0.698 | 0.385 | 19 | LNU45 | 25052.9 | 0.796 | 0.153 | 20 |
| LNU117 | 25931.4 | 10.500 | 0.160 | 4 | LNU104 | 25032.2 | 0.686 | 0.492 | 17 | LNU45 | 25052.11 | 0.749 | 0.283 | 13 |
| LNU117 | 25931.2 | 10.438 | 0.767 | 3 | LNU104 | 25033.3 | 0.668 | 0.006 | 14 | LNU67 | 25821.5 | 0.774 | 0.285 | 17 |
| LNU117 | 25932.4 | 10.438 | 0.603 | 3 | LNU104 | 25032.1 | 0.655 | 0.457 | 12 | LNU67 | 25823.5 | 0.772 | 0.210 | 17 |
| LNU155 | 14523.5 | 10.563 | 0.188 | 4 | LNU104 | 25033.1 | 0.648 | 0.408 | 11 | LNU67 | 25824.5 | 0.767 | 0.395 | 16 |
| LNU180 | 24723.1 | 10.250 | 0.728 | 1 | LNU106 | 14483.2 | 0.845 | 0.000 | 44 | LNU67 | 25824.3 | 0.740 | 0.351 | 12 |
| LNU182 | 24781.4 | 10.563 | 0.488 | 4 | LNU106 | 14481.1 | 0.753 | 0.355 | 29 | LNU67 | 25821.4 | 0.698 | 0.610 | 5 |
| LNU254 | 25782.4 | 10.563 | 0.188 | 4 | LNU106 | 14483.5 | 0.711 | 0.001 | 21 | CONT. | — | 0.683 | — | 0 |
| LNU4 | 25134.3 | 10.938 | 0.003 | 8 | LNU106 | 14484.3 | 0.664 | 0.541 | 13 | LNU100 | 14473.3 | 0.874 | 0.197 | 28 |
| LNU4 | 25134.2 | 10.875 | 0.244 | 2 | LNU114 | 25044.11 | 0.787 | 0.364 | 34 | LNU100 | 14474.2 | 0.827 | 0.155 | 21 |
| LNU40 | 24794.4 | 10.375 | 0.256 | 2 | LNU114 | 25042.1 | 0.718 | 0.140 | 23 | LNU100 | 14472.1 | 0.806 | 0.320 | 18 |
| LNU40 | 24792.1 | 10.313 | 0.665 | 2 | LNU114 | 25041.2 | 0.716 | 0.100 | 22 | LNU100 | 14473.1 | 0.756 | 0.005 | 11 |
| LNU46 | 14462.5 | 10.750 | 0.033 | 6 | LNU114 | 25041.1 | 0.658 | 0.757 | 12 | LNU104 | 25033.1 | 0.862 | 0.461 | 26 |
| LNU46 | 14464.4 | 10.625 | 0.073 | 5 | LNU117 | 25932.4 | 0.791 | 0.009 | 35 | LNU104 | 25033.3 | 0.826 | 0.197 | 21 |
| LNU46 | 14462.1 | 10.313 | 0.797 | 2 | LNU117 | 25931.4 | 0.725 | 0.025 | 24 | LNU104 | 25032.2 | 0.766 | 0.309 | 12 |
| LNU48 | 24801.4 | 10.813 | 0.328 | 7 | LNU117 | 25931.1 | 0.693 | 0.592 | 18 | LNU104 | 25032.1 | 0.758 | 0.594 | 11 |
| LNU48 | 24803.2 | 10.313 | 0.797 | 2 | LNU117 | 25931.2 | 0.633 | 0.340 | 8 | LNU106 | 14483.2 | 0.865 | 0.175 | 27 |
| LNU63 | 24812.3 | 10.500 | 0.487 | 4 | LNU117 | 25933.3 | 0.631 | 0.731 | 5 | LNU106 | 14481.1 | 0.849 | 0.409 | 24 |
| LNU7 | 25082.2 | 10.625 | 0.037 | 5 | LNU155 | 14523.5 | 0.741 | 0.313 | 27 | LNU106 | 14483.5 | 0.751 | 0.017 | 10 |
| LNU8 | 25061.2 | 10.813 | 0.009 | 7 | LNU155 | 14524.8 | 0.630 | 0.220 | 8 | LNU106 | 14484.3 | 0.710 | 0.741 | 4 |
| LNU8 | 25063.6 | 10.688 | 0.490 | 6 | LNU180 | 24723.1 | 0.755 | 0.062 | 29 | LNU114 | 25044.11 | 0.864 | 0.115 | 27 |
| LNU94 | 24833.3 | 10.375 | 0.627 | 2 | LNU180 | 24722.2 | 0.641 | 0.737 | 10 | LNU114 | 25041.2 | 0.788 | 0.001 | 15 |
| CONT. | — | 9.886 | — | 0 | LNU218 | 24781.4 | 0.780 | 0.088 | 33 | LNU114 | 25044.4 | 0.743 | 0.698 | 9 |
| LNU122 | 25332.2 | 10.250 | 0.130 | 4 | LNU218 | 24781.1 | 0.712 | 0.255 | 22 | LNU114 | 25041.1 | 0.731 | 0.649 | 7 |
| LNU122 | 25332.5 | 9.938 | 0.775 | 1 | LNU218 | 24781.6 | 0.631 | 0.212 | 8 | LNU114 | 25042.1 | 0.727 | 0.336 | 6 |
| LNU125 | 25944.1 | 10.188 | 0.113 | 3 | LNU218 | 24781.2 | 0.615 | 0.328 | 5 | LNU117 | 25932.4 | 0.849 | 0.304 | 24 |
| LNU220 | 25405.1 | 10.000 | 0.740 | 1 | LNU254 | 25782.4 | 0.723 | 0.169 | 24 | LNU117 | 25931.4 | 0.788 | 0.149 | 15 |
| LNU236 | 25422.4 | 10.375 | 0.244 | 5 | LNU4 | 25134.3 | 0.798 | 0.251 | 36 | LNU117 | 25931.2 | 0.732 | 0.038 | 7 |
| LNU236 | 25425.4 | 9.938 | 0.775 | 1 | LNU4 | 25131.1 | 0.699 | 0.398 | 19 | LNU117 | 25931.1 | 0.711 | 0.466 | 4 |
| LNU45 | 25052.11 | 10.188 | 0.113 | 3 | LNU4 | 25134.2 | 0.673 | 0.270 | 15 | LNU155 | 14523.5 | 0.785 | 0.420 | 15 |
| LNU45 | 25052.12 | 10.125 | 0.508 | 2 | LNU4 | 25133.3 | 0.647 | 0.479 | 11 | LNU180 | 24723.1 | 0.812 | 0.294 | 19 |
| LNU45 | 25053.4 | 10.000 | 0.740 | 1 | LNU40 | 24794.3 | 0.687 | 0.571 | 17 | LNU180 | 24722.2 | 0.725 | 0.790 | 6 |
| CONT. | — | 10.528 | — | 0 | LNU40 | 24792.1 | 0.683 | 0.015 | 17 | LNU218 | 24781.1 | 0.844 | 0.000 | 24 |
| LNU10 | 25123.5 | 11.438 | 0.233 | 9 | LNU40 | 24794.4 | 0.631 | 0.149 | 8 | LNU218 | 24781.4 | 0.834 | 0.270 | 22 |
| LNU10 | 25123.6 | 11.063 | 0.063 | 5 | LNU46 | 14462.1 | 0.746 | 0.301 | 21 | LNU218 | 24781.2 | 0.746 | 0.039 | 9 |
| LNU157 | 24982.8 | 11.250 | 0.018 | 7 | LNU46 | 14462.5 | 0.653 | 0.087 | 12 | LNU254 | 25782.4 | 0.738 | 0.022 | 8 |
| LNU173 | 25451.1 | 11.375 | 0.504 | 8 | LNU46 | 14464.4 | 0.615 | 0.486 | 5 | LNU4 | 25134.3 | 0.841 | 0.486 | 23 |
| LNU173 | 25451.5 | 10.688 | 0.624 | 2 | LNU48 | 24801.4 | 0.694 | 0.254 | 19 | LNU4 | 25134.2 | 0.743 | 0.463 | 9 |
| LNU178 | 14611.5 | 11.500 | 0.004 | 9 | LNU48 | 24803.2 | 0.666 | 0.605 | 14 | LNU4 | 25133.3 | 0.705 | 0.354 | 3 |
| LNU178 | 14611.4 | 11.313 | 0.445 | 7 | LNU63 | 24812.3 | 0.777 | 0.125 | 33 | LNU40 | 24792.1 | 0.852 | 0.011 | 25 |
| LNU178 | 14611.1 | 11.250 | 0.557 | 7 | LNU63 | 24814.7 | 0.649 | 0.437 | 11 | LNU40 | 24794.3 | 0.786 | 0.579 | 15 |
| LNU184 | 25393.2 | 11.125 | 0.505 | 6 | LNU63 | 24814.2 | 0.603 | 0.689 | 3 | LNU40 | 24793.1 | 0.696 | 0.779 | 2 |
| LNU184 | 25393.3 | 10.688 | 0.719 | 2 | LNU7 | 25082.2 | 0.672 | 0.441 | 15 | LNU40 | 24794.4 | 0.694 | 0.703 | 2 |
| LNU230 | 25413.1 | 11.625 | 0.002 | 10 | LNU7 | 25083.1 | 0.678 | 0.034 | 16 | LNU46 | 14462.5 | 0.860 | 0.259 | 26 |
| LNU230 | 25413.2 | 11.625 | 0.226 | 10 | LNU7 | 25083.3 | 0.642 | 0.070 | 10 | LNU46 | 14464.4 | 0.714 | 0.544 | 5 |
| LNU230 | 25415.1 | 11.125 | 0.004 | 6 | LNU8 | 25063.6 | 0.779 | 0.138 | 33 | LNU48 | 24803.2 | 0.804 | 0.393 | 18 |
| LNU230 | 25412.1 | 11.063 | 0.063 | 5 | LNU8 | 25061.2 | 0.682 | 0.002 | 16 | LNU48 | 24804.4 | 0.770 | 0.443 | 13 |
| LNU230 | 25412.2 | 10.813 | 0.787 | 3 | LNU94 | 24833.3 | 0.696 | 0.405 | 19 | LNU48 | 24801.4 | 0.735 | 0.573 | 8 |

TABLE 80-continued

Genes showing improved plant photosynthetic capacity at limiting nitrogen growth conditions

| | Leaf Number | | | | Leaf Blade Area [cm2] | | | | | Leaf Petiole Length [cm] | | | |
|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU236 | 25422.4 | 11.188 | 0.081 | 6 | CONT. | — | 0.766 | — | 0 | LNU63 | 24812.3 | 0.848 | 0.008 | 24 |
| LNU236 | 25425.4 | 11.063 | 0.063 | 5 | LNU10 | 25123.5 | 0.818 | 0.561 | 7 | LNU63 | 24814.2 | 0.758 | 0.189 | 11 |
| LNU236 | 25423.3 | 10.938 | 0.237 | 4 | LNU122 | 25332.1 | 0.907 | 0.025 | 18 | LNU63 | 24814.7 | 0.745 | 0.616 | 9 |
| LNU236 | 25424.2 | 10.813 | 0.288 | 3 | LNU122 | 25332.2 | 0.884 | 0.168 | 15 | LNU7 | 25082.2 | 0.754 | 0.399 | 10 |
| LNU24 | 24974.2 | 11.000 | 0.122 | 4 | LNU122 | 25332.5 | 0.835 | 0.623 | 9 | LNU7 | 25083.3 | 0.736 | 0.035 | 8 |
| LNU24 | 24971.2 | 10.813 | 0.394 | 3 | LNU125 | 25943.2 | 0.822 | 0.518 | 7 | LNU7 | 25083.1 | 0.736 | 0.328 | 8 |
| LNU24 | 24972.1 | 10.688 | 0.785 | 2 | LNU125 | 25941.4 | 0.814 | 0.156 | 6 | LNU8 | 25063.6 | 0.778 | 0.001 | 14 |
| LNU263 | 25792.2 | 11.188 | 0.338 | 6 | LNU138 | 14074.5 | 0.860 | 0.075 | 12 | LNU8 | 25061.2 | 0.704 | 0.537 | 3 |
| LNU263 | 25794.3 | 11.063 | 0.139 | 5 | LNU138 | 14071.5 | 0.807 | 0.136 | 5 | LNU94 | 24833.3 | 0.705 | 0.723 | 3 |
| LNU263 | 25791.3 | 10.750 | 0.669 | 2 | LNU138 | 14074.6 | 0.782 | 0.570 | 2 | CONT. | — | 0.808 | — | 0 |
| LNU276 | 25431.1 | 11.438 | 0.006 | 9 | LNU157 | 24982.1 | 0.831 | 0.413 | 8 | LNU122 | 25332.1 | 0.856 | 0.240 | 6 |
| LNU276 | 25433.3 | 10.750 | 0.388 | 2 | LNU178 | 14614.5 | 0.896 | 0.071 | 17 | LNU122 | 25332.2 | 0.844 | 0.239 | 5 |
| LNU276 | 25433.1 | 10.688 | 0.624 | 2 | LNU178 | 14612.1 | 0.826 | 0.469 | 8 | LNU122 | 25332.5 | 0.830 | 0.586 | 3 |
| LNU279 | 25481.4 | 10.813 | 0.288 | 3 | LNU178 | 14611.5 | 0.824 | 0.042 | 8 | LNU138 | 14071.5 | 0.851 | 0.003 | 5 |
| LNU279 | 25484.3 | 10.750 | 0.565 | 2 | LNU178 | 14611.4 | 0.824 | 0.040 | 8 | LNU138 | 14074.6 | 0.821 | 0.726 | 2 |
| LNU36 | 25562.7 | 11.250 | 0.119 | 7 | LNU220 | 25405.6 | 0.875 | 0.048 | 14 | LNU178 | 14614.5 | 0.864 | 0.384 | 7 |
| LNU36 | 25562.3 | 10.777 | 0.613 | 2 | LNU220 | 25405.5 | 0.874 | 0.028 | 14 | LNU178 | 14611.5 | 0.848 | 0.005 | 5 |
| LNU36 | 25561.2 | 10.750 | 0.565 | 2 | LNU220 | 25405.1 | 0.835 | 0.086 | 9 | LNU234 | 25014.6 | 0.828 | 0.146 | 3 |
| LNU56 | 24693.1 | 10.875 | 0.725 | 3 | LNU220 | 25405.2 | 0.823 | 0.324 | 7 | LNU236 | 25424.2 | 0.936 | 0.000 | 16 |
| LNU56 | 24694.2 | 10.688 | 0.785 | 2 | LNU234 | 25014.4 | 0.848 | 0.669 | 11 | LNU236 | 25425.4 | 0.865 | 0.308 | 7 |
| LNU73 | 25755.1 | 11.375 | 0.083 | 8 | LNU234 | 25014.5 | 0.806 | 0.678 | 5 | LNU236 | 25423.3 | 0.857 | 0.623 | 6 |
| LNU73 | 25751.1 | 11.125 | 0.505 | 6 | LNU236 | 25424.2 | 0.980 | 0.000 | 28 | LNU236 | 25422.4 | 0.827 | 0.683 | 2 |
| LNU73 | 25751.8 | 10.938 | 0.392 | 4 | LNU236 | 25425.4 | 0.868 | 0.476 | 13 | LNU25 | 14082.8 | 0.897 | 0.036 | 11 |
| LNU73 | 25751.9 | 10.688 | 0.624 | 2 | LNU236 | 25423.3 | 0.868 | 0.428 | 13 | LNU25 | 14082.9 | 0.848 | 0.438 | 5 |
| LNU9 | 25001.2 | 11.063 | 0.414 | 5 | LNU236 | 25422.4 | 0.843 | 0.244 | 10 | LNU267 | 25804.4 | 0.823 | 0.592 | 2 |
| LNU9 | 25001.7 | 10.875 | 0.613 | 3 | LNU24 | 24974.2 | 0.821 | 0.216 | 7 | LNU271 | 25911.4 | 0.830 | 0.124 | 3 |
| LNU9 | 25001.1 | 10.813 | 0.288 | 3 | LNU24 | 24972.1 | 0.800 | 0.590 | 4 | LNU271 | 25912.1 | 0.824 | 0.783 | 2 |
| CONT. | — | 8.400 | — | 0 | LNU25 | 14082.8 | 0.954 | 0.000 | 25 | LNU278 | 25812.2 | 0.815 | 0.595 | 1 |
| LNU131 | 14005.5 | 9.750 | 0.071 | 16 | LNU25 | 14082.9 | 0.847 | 0.009 | 11 | LNU43 | 14422.9 | 0.842 | 0.585 | 4 |
| LNU131 | 14002.15 | 9.438 | 0.000 | 12 | LNU25 | 14084.6 | 0.840 | 0.043 | 10 | LNU43 | 14423.7 | 0.814 | 0.754 | 1 |
| LNU131 | 14005.2 | 9.188 | 0.208 | 9 | LNU25 | 14083.7 | 0.797 | 0.375 | 4 | LNU45 | 25052.12 | 0.935 | 0.030 | 16 |
| LNU135 | 26204.2 | 9.750 | 0.211 | 16 | LNU267 | 25804.4 | 0.796 | 0.733 | 4 | LNU45 | 25052.11 | 0.905 | 0.000 | 12 |
| LNU135 | 26203.1 | 9.313 | 0.000 | 11 | LNU271 | 25911.4 | 0.855 | 0.666 | 12 | LNU45 | 25053.4 | 0.856 | 0.604 | 6 |
| LNU135 | 26203.6 | 9.125 | 0.000 | 9 | LNU271 | 25912.1 | 0.840 | 0.774 | 10 | LNU45 | 25052.9 | 0.833 | 0.049 | 3 |
| LNU135 | 26203.3 | 8.750 | 0.609 | 4 | LNU278 | 25814.1 | 0.877 | 0.012 | 14 | LNU67 | 25824.3 | 0.853 | 0.105 | 6 |
| LNU161 | 14553.5 | 9.500 | 0.094 | 13 | LNU278 | 25814.3 | 0.843 | 0.027 | 10 | LNU67 | 25824.5 | 0.842 | 0.011 | 4 |
| LNU161 | 14553.6 | 8.750 | 0.369 | 4 | LNU278 | 25812.2 | 0.816 | 0.071 | 7 | LNU67 | 25821.4 | 0.822 | 0.706 | 2 |
| LNU173 | 25451.1 | 8.813 | 0.513 | 5 | LNU278 | 25812.1 | 0.789 | 0.649 | 4 | LNU9 | 25001.1 | 0.870 | 0.249 | 8 |
| LNU173 | 25451.2 | 8.563 | 0.237 | 2 | LNU43 | 14423.7 | 0.873 | 0.014 | 14 | LNU9 | 25001.7 | 0.831 | 0.059 | 3 |
| LNU173 | 25451.5 | 8.438 | 0.776 | 0 | LNU43 | 14422.9 | 0.815 | 0.697 | 6 | CONT. | — | 0.804 | — | 0 |
| LNU181 | 25771.2 | 9.250 | 0.327 | 10 | LNU45 | 25052.12 | 1.036 | 0.000 | 35 | LNU10 | 25123.6 | 0.832 | 0.506 | 4 |
| LNU181 | 25774.1 | 9.188 | 0.077 | 9 | LNU45 | 25053.4 | 0.932 | 0.327 | 22 | LNU157 | 24982.8 | 0.901 | 0.119 | 12 |
| LNU181 | 25771.6 | 9.063 | 0.000 | 8 | LNU45 | 25052.9 | 0.856 | 0.031 | 12 | LNU157 | 24982.4 | 0.885 | 0.385 | 10 |
| LNU181 | 25771.11 | 8.750 | 0.515 | 4 | LNU45 | 25052.11 | 0.831 | 0.448 | 9 | LNU157 | 24983.3 | 0.852 | 0.542 | 6 |
| LNU184 | 25394.3 | 9.688 | 0.000 | 15 | LNU67 | 25824.3 | 0.949 | 0.000 | 24 | LNU173 | 25451.1 | 0.884 | 0.386 | 10 |
| LNU184 | 25393.3 | 9.313 | 0.268 | 11 | LNU67 | 25824.5 | 0.889 | 0.001 | 16 | LNU173 | 25451.1 | 0.817 | 0.776 | 2 |
| LNU184 | 25395.1 | 9.250 | 0.507 | 10 | LNU67 | 25821.4 | 0.845 | 0.196 | 10 | LNU178 | 14611.4 | 0.962 | 0.394 | 20 |
| LNU184 | 25394.1 | 9.125 | 0.375 | 9 | LNU9 | 25001.7 | 0.910 | 0.345 | 19 | LNU178 | 14611.1 | 0.906 | 0.339 | 13 |
| LNU184 | 25393.1 | 8.813 | 0.395 | 5 | LNU9 | 25001.1 | 0.896 | 0.149 | 17 | LNU178 | 14611.5 | 0.843 | 0.669 | 5 |
| LNU224 | 25874.1 | 9.875 | 0.133 | 18 | LNU9 | 25003.1 | 0.830 | 0.544 | 8 | LNU184 | 25393.3 | 0.906 | 0.385 | 13 |
| LNU224 | 25872.3 | 9.375 | 0.009 | 12 | LNU9 | 25001.3 | 0.792 | 0.359 | 3 | LNU184 | 25393.2 | 0.864 | 0.196 | 7 |
| LNU224 | 25871.3 | 9.188 | 0.208 | 9 | LNU9 | 25001.2 | 0.782 | 0.798 | 2 | LNU184 | 25395.1 | 0.820 | 0.703 | 2 |
| LNU224 | 25874.4 | 9.063 | 0.251 | 8 | CONT. | — | 0.791 | — | 0 | LNU230 | 25413.2 | 0.942 | 0.260 | 17 |
| LNU224 | 25872.2 | 8.875 | 0.270 | 6 | LNU10 | 25123.6 | 0.909 | 0.068 | 15 | LNU230 | 25413.1 | 0.914 | 0.384 | 14 |
| LNU246 | 25743.2 | 9.688 | 0.251 | 15 | LNU157 | 24982.8 | 0.994 | 0.003 | 26 | LNU230 | 25415.1 | 0.850 | 0.299 | 6 |
| LNU246 | 25744.2 | 9.250 | 0.327 | 10 | LNU157 | 24982.4 | 0.887 | 0.133 | 12 | LNU230 | 25412.2 | 0.849 | 0.332 | 6 |
| LNU246 | 25744.4 | 9.250 | 0.327 | 10 | LNU157 | 24983.3 | 0.865 | 0.270 | 9 | LNU230 | 25412.1 | 0.843 | 0.419 | 5 |
| LNU246 | 25744.3 | 9.188 | 0.208 | 9 | LNU168 | 24751.2 | 0.836 | 0.791 | 6 | LNU236 | 25425.4 | 0.949 | 0.007 | 18 |
| LNU246 | 25743.1 | 8.938 | 0.002 | 6 | LNU173 | 25451.1 | 0.853 | 0.607 | 8 | LNU236 | 25423.3 | 0.850 | 0.558 | 6 |
| LNU250 | 25592.2 | 9.188 | 0.077 | 9 | LNU178 | 14611.4 | 1.015 | 0.297 | 28 | LNU24 | 24974.2 | 0.928 | 0.016 | 15 |
| LNU250 | 25591.1 | 8.750 | 0.008 | 4 | LNU178 | 14611.1 | 0.964 | 0.288 | 22 | LNU24 | 24971.3 | 0.893 | 0.066 | 11 |
| LNU250 | 25592.1 | 8.750 | 0.609 | 4 | LNU178 | 14611.5 | 0.954 | 0.156 | 21 | LNU24 | 24971.4 | 0.878 | 0.718 | 9 |
| LNU250 | 25591.3 | 8.563 | 0.774 | 2 | LNU184 | 25393.2 | 0.975 | 0.005 | 23 | LNU24 | 24971.2 | 0.818 | 0.758 | 2 |
| LNU250 | 25594.1 | 8.563 | 0.695 | 2 | LNU184 | 25393.3 | 0.939 | 0.361 | 19 | LNU263 | 25791.3 | 0.913 | 0.118 | 14 |
| LNU260 | 26404.8 | 9.125 | 0.163 | 9 | LNU184 | 25393.1 | 0.914 | 0.620 | 16 | LNU263 | 25794.8 | 0.882 | 0.199 | 10 |
| LNU260 | 26404.1 | 9.000 | 0.510 | 7 | LNU184 | 25395.1 | 0.887 | 0.517 | 12 | LNU263 | 25794.6 | 0.858 | 0.757 | 7 |
| LNU260 | 26404.7 | 8.938 | 0.426 | 6 | LNU184 | 25394.3 | 0.819 | 0.705 | 4 | LNU263 | 25794.3 | 0.854 | 0.301 | 6 |
| LNU260 | 26403.1 | 8.750 | 0.124 | 4 | LNU230 | 25413.1 | 0.972 | 0.024 | 23 | LNU276 | 25431.1 | 0.878 | 0.174 | 9 |
| LNU276 | 25433.6 | 10.000 | 0.056 | 19 | LNU230 | 25413.2 | 0.953 | 0.221 | 20 | LNU276 | 25433.1 | 0.837 | 0.547 | 4 |
| LNU276 | 25433.1 | 8.938 | 0.002 | 6 | LNU230 | 25412.1 | 0.922 | 0.035 | 17 | LNU279 | 25481.3 | 0.906 | 0.317 | 13 |
| LNU276 | 25431.1 | 8.813 | 0.595 | 5 | LNU230 | 25412.2 | 0.916 | 0.204 | 16 | LNU279 | 25481.4 | 0.889 | 0.207 | 10 |
| LNU276 | 25433.5 | 8.438 | 0.776 | 0 | LNU230 | 25415.1 | 0.891 | 0.225 | 13 | LNU279 | 25484.3 | 0.852 | 0.277 | 6 |

TABLE 80-continued

Genes showing improved plant photosynthetic capacity at limiting nitrogen growth conditions

| | Leaf Number | | | | | Leaf Blade Area [cm2] | | | | | Leaf Petiole Length [cm] | | |
|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU279 | 25484.3 | 9.500 | 0.258 | 13 | LNU236 | 25425.4 | 1.093 | 0.001 | 38 | LNU279 | 25481.2 | 0.829 | 0.799 | 3 |
| LNU279 | 25481.5 | 9.000 | 0.338 | 7 | LNU236 | 25423.3 | 0.973 | 0.352 | 23 | LNU36 | 25562.3 | 0.988 | 0.131 | 23 |
| LNU279 | 25481.4 | 8.875 | 0.062 | 6 | LNU236 | 25422.4 | 0.885 | 0.262 | 12 | LNU36 | 25561.2 | 0.930 | 0.306 | 16 |
| LNU279 | 25481.3 | 8.688 | 0.628 | 3 | LNU236 | 25424.2 | 0.885 | 0.093 | 12 | LNU36 | 25562.7 | 0.856 | 0.749 | 6 |
| LNU3 | 26124.3 | 8.875 | 0.062 | 6 | LNU24 | 24974.2 | 1.048 | 0.032 | 32 | LNU53 | 25674.1 | 0.826 | 0.614 | 3 |
| LNU3 | 26122.2 | 8.750 | 0.515 | 4 | LNU24 | 24971.3 | 0.905 | 0.200 | 14 | LNU56 | 24694.1 | 0.940 | 0.502 | 17 |
| LNU33 | 25553.2 | 9.107 | 0.447 | 8 | LNU263 | 25791.3 | 1.005 | 0.067 | 27 | LNU56 | 24693.1 | 0.910 | 0.267 | 13 |
| LNU33 | 25553.3 | 9.63 | 0.000 | 8 | LNU263 | 25794.3 | 0.951 | 0.177 | 20 | LNU56 | 24691.2 | 0.862 | 0.484 | 7 |
| LNU33 | 25552.2 | 9.000 | 0.000 | 7 | LNU263 | 25794.8 | 0.897 | 0.286 | 13 | LNU56 | 24694.2 | 0.861 | 0.547 | 7 |
| LNU53 | 25674.6 | 8.563 | 0.695 | 2 | LNU263 | 25792.2 | 0.843 | 0.326 | 7 | LNU73 | 25755.1 | 1.002 | 0.062 | 25 |
| LNU56 | 24694.2 | 8.813 | 0.210 | 5 | LNU276 | 25433.1 | 0.972 | 0.193 | 23 | LNU73 | 25751.9 | 0.974 | 0.003 | 21 |
| LNU56 | 24693.1 | 8.750 | 0.515 | 4 | LNU276 | 25431.1 | 0.920 | 0.211 | 16 | LNU73 | 25751.8 | 0.962 | 0.259 | 20 |
| LNU73 | 25751.9 | 8.500 | 0.592 | 1 | LNU276 | 25433.3 | 0.891 | 0.078 | 13 | LNU73 | 25751.1 | 0.878 | 0.177 | 9 |
| CONT. | — | 10.300 | — | 0 | LNU276 | 25433.2 | 0.839 | 0.705 | 6 | LNU73 | 25754.2 | 0.878 | 0.393 | 9 |
| LNU130 | 24913.6. | 10.625 | 0.391 | 3 | LNU279 | 25481.3 | 0.999 | 0.223 | 26 | LNU9 | 25001.1 | 0.934 | 0.049 | 16 |
| LNU136 | 14511.10. | 11.375 | 0.002 | 10 | LNU279 | 25484.3 | 0.995 | 0.011 | 26 | LNU9 | 25001.7 | 0.899 | 0.313 | 12 |
| LNU136 | 14513.6. | 10.563 | 0.174 | 3 | LNU279 | 25481.5 | 0.973 | 0.141 | 25 | LNU9 | 25003.1 | 0.886 | 0.650 | 10 |
| LNU136 | 14515.5. | 10.500 | 0.759 | 2 | LNU279 | 25481.2 | 0.953 | 0.575 | 20 | LNU9 | 25001.3 | 0.858 | 0.278 | 7 |
| LNU136 | 14515.1. | 10.375 | 0.666 | 1 | LNU279 | 25481.4 | 0.920 | 0.251 | 16 | LNU9 | 25001.2 | 0.833 | 0.627 | 4 |
| LNU142 | 27546.1. | 10.875 | 0.193 | 6 | LNU36 | 25562.3 | 1.007 | 0.297 | 27 | CONT. | — | 0.562 | — | 0 |
| LNU142 | 27541.1. | 10.500 | 0.264 | 2 | LNU36 | 25562.7 | 0.933 | 0.623 | 18 | LNU131 | 14005.5 | 0.869 | 0.001 | 55 |
| LNU15 | 14123.13. | 11.063 | 0.304 | 7 | LNU36 | 25561.2 | 0.907 | 0.401 | 15 | LNU131 | 14005.2 | 0.772 | 0.276 | 37 |
| LNU15 | 14123.11. | 10.917 | 0.474 | 6 | LNU36 | 25562.4 | 0.829 | 0.518 | 5 | LNU131 | 14002.15 | 0.714 | 0.004 | 27 |
| LNU185 | 26474.2. | 10.875 | 0.521 | 6 | LNU53 | 25674.1 | 0.818 | 0.774 | 3 | LNU131 | 14001.16 | 0.603 | 0.721 | 7 |
| LNU185 | 26475.1. | 10.750 | 0.424 | 4 | LNU56 | 24694.1 | 0.987 | 0.484 | 25 | LNU135 | 26204.2 | 0.930 | 0.182 | 66 |
| LNU212 | 25833.2. | 11.438 | 0.109 | 11 | LNU56 | 24693.1 | 0.979 | 0.356 | 24 | LNU135 | 26203.6 | 0.708 | 0.177 | 26 |
| LNU212 | 25834.4. | 11.250 | 0.358 | 9 | LNU56 | 24691.2 | 0.926 | 0.180 | 17 | LNU135 | 26203.3 | 0.686 | 0.434 | 22 |
| LNU212 | 25834.5. | 10.813 | 0.134 | 5 | LNU56 | 24694.2 | 0.850 | 0.624 | 7 | LNU135 | 26203.4 | 0.676 | 0.509 | 20 |
| LNU212 | 25832.1. | 10.500 | 0.573 | 2 | LNU73 | 25755.1 | 1.109 | 0.000 | 40 | LNU135 | 26203.1 | 0.647 | 0.276 | 15 |
| LNU216 | 25984.1. | 11.125 | 0.326 | 8 | LNU73 | 25751.9 | 0.997 | 0.079 | 26 | LNU161 | 14553.5 | 0.787 | 0.366 | 40 |
| LNU216 | 25985.4. | 10.688 | 0.056 | 4 | LNU73 | 25751.1 | 0.985 | 0.011 | 25 | LNU161 | 14552.7 | 0.603 | 0.548 | 7 |
| LNU216 | 25984.6. | 10.563 | 0.550 | 3 | LNU73 | 25754.2 | 0.974 | 0.426 | 23 | LNU173 | 25451.11 | 0.635 | 0.423 | 13 |
| LNU228 | 26224.7. | 11.000 | 0.456 | 7 | LNU73 | 25751.8 | 0.965 | 0.469 | 22 | LNU173 | 25451.5 | 0.585 | 0.523 | 4 |
| LNU228 | 26222.4. | 10.688 | 0.614 | 4 | LNU9 | 25001.1 | 1.001 | 0.015 | 28 | LNU181 | 25771.2 | 0.721 | 0.112 | 28 |
| LNU228 | 26225.2. | 10.625 | 0.632 | 3 | LNU9 | 25001.7 | 0.979 | 0.222 | 24 | LNU181 | 25774.1 | 0.651 | 0.165 | 16 |
| LNU229 | 26111.7. | 10.813 | 0.017 | 5 | LNU9 | 25001.2 | 0.890 | 0.107 | 12 | LNU181 | 25771.5 | 0.638 | 0.124 | 14 |
| LNU229 | 26112.3. | 10.750 | 0.270 | 4 | LNU9 | 25001.3 | 0.821 | 0.598 | 4 | LNU181 | 25771.6 | 0.637 | 0.042 | 13 |
| LNU229 | 26112.6. | 10.375 | 0.733 | 1 | CONT. | — | 0.609 | — | 0 | LNU181 | 25771.11 | 0.597 | 0.228 | 6 |
| LNU241 | 26234.1. | 10.938 | 0.520 | 6 | LNU131 | 14005.5 | 1.234 | 0.000 | 79 | LNU181 | 25771.8 | 0.577 | 0.596 | 3 |
| LNU253 | 26241.1. | 10.938 | 0.005 | 6 | LNU131 | 14005.2 | 0.916 | 0.334 | 33 | LNU184 | 25394.3 | 0.813 | 0.180 | 45 |
| LNU274 | 26261.3. | 10.625 | 0.391 | 3 | LNU131 | 14002.15 | 0.843 | 0.195 | 22 | LNU184 | 25393.3 | 0.799 | 0.071 | 42 |
| LNU274 | 26625.1. | 10.563 | 0.768 | 3 | LNU135 | 26204.2 | 1.253 | 0.247 | 82 | LNU184 | 25394.1 | 0.755 | 0.192 | 34 |
| LNU280 | 26162.1. | 10.580 | 0.507 | 3 | LNU135 | 26203.6 | 0.954 | 0.040 | 38 | LNU184 | 25395.1 | 0.719 | 0.636 | 28 |
| LNU280 | 26164.4. | 10.479 | 0.461 | 2 | LNU135 | 26203.4 | 0.904 | 0.479 | 31 | LNU184 | 25393.1 | 0.640 | 0.376 | 14 |
| LNU55 | 26015.1. | 10.563 | 0.174 | 3 | LNU135 | 26203.1 | 0.874 | 0.039 | 27 | LNU184 | 25393.2 | 0.634 | 0.177 | 13 |
| LNU81 | 26034.2. | 10.750 | 0.270 | 4 | LNU135 | 26203.3 | 0.790 | 0.705 | 15 | LNU224 | 25871.3 | 0.797 | 0.041 | 42 |
| LNU81 | 26031.2. | 10.688 | 0.056 | 4 | LNU161 | 14553.5 | 0.916 | 0.565 | 33 | LNU224 | 25872.2 | 0.751 | 0.000 | 34 |
| LNU81 | 26031.9. | 10.563 | 0.656 | 3 | LNU161 | 14553.6 | 0.776 | 0.049 | 12 | LNU224 | 25874.1 | 0.726 | 0.011 | 29 |
| CONT. | — | 10.021 | — | 0 | LNU173 | 25451.5 | 0.736 | 0.714 | 7 | LNU224 | 25872.3 | 0.690 | 0.203 | 23 |
| LNU119 | 26144.1. | 10.500 | 0.098 | 5 | LNU173 | 25451.2 | 0.718 | 0.488 | 4 | LNU224 | 25874.4 | 0.662 | 0.314 | 18 |
| LNU119 | 26142.5. | 10.313 | 0.280 | 3 | LNU181 | 25771.2 | 0.966 | 0.125 | 40 | LNU246 | 25743.2 | 0.819 | 0.360 | 46 |
| LNU130 | 24914.5. | 10.688 | 0.037 | 7 | LNU181 | 25771.11 | 0.876 | 0.000 | 27 | LNU246 | 25744.4 | 0.760 | 0.459 | 35 |
| LNU130 | 24913.6. | 10.500 | 0.124 | 5 | LNU181 | 25771.6 | 0.862 | 0.004 | 25 | LNU246 | 25744.2 | 0.744 | 0.439 | 32 |
| LNU130 | 24913.5. | 10.313 | 0.280 | 3 | LNU181 | 25774.1 | 0.763 | 0.105 | 11 | LNU246 | 25743.1 | 0.712 | 0.087 | 27 |
| LNU136 | 14511.10. | 10.688 | 0.430 | 5 | LNU181 | 25771.8 | 0.751 | 0.478 | 9 | LNU246 | 25744.3 | 0.653 | 0.399 | 16 |
| LNU136 | 14514.8. | 10.500 | 0.124 | 5 | LNU181 | 25771.5 | 0.731 | 0.334 | 6 | LNU250 | 25592.2 | 0.752 | 0.213 | 34 |
| LNU136 | 14515.1. | 10.438 | 0.506 | 4 | LNU184 | 25395.1 | 1.054 | 0.264 | 53 | LNU250 | 25591.1 | 0.673 | 0.248 | 20 |
| LNU136 | 14515.5. | 10.438 | 0.506 | 4 | LNU184 | 25394.3 | 1.053 | 0.371 | 53 | LNU250 | 25592.1 | 0.640 | 0.589 | 14 |
| LNU142 | 27546.2. | 10.250 | 0.779 | 2 | LNU184 | 25394.1 | 0.951 | 0.294 | 38 | LNU250 | 25591.3 | 0.582 | 0.622 | 4 |
| LNU142 | 27546.1. | 10.188 | 0.607 | 2 | LNU184 | 25393.3 | 0.929 | 0.024 | 35 | LNU260 | 26404.8 | 0.683 | 0.025 | 22 |
| LNU149 | 26174.7. | 10.250 | 0.424 | 2 | LNU184 | 25393.2 | 0.782 | 0.035 | 13 | LNU260 | 26404.1 | 0.679 | 0.418 | 21 |
| LNU15 | 14123.13. | 10.875 | 0.015 | 9 | LNU184 | 25393.1 | 0.753 | 0.732 | 9 | LNU260 | 26403.1 | 0.656 | 0.142 | 17 |
| LNU15 | 14124.12. | 10.688 | 0.037 | 7 | LNU224 | 25871.3 | 1.095 | 0.000 | 59 | LNU260 | 26403.2 | 0.622 | 0.084 | 11 |
| LNU15 | 14122.9. | 10.313 | 0.628 | 3 | LNU224 | 25874.1 | 1.000 | 0.000 | 45 | LNU260 | 26404.7 | 0.619 | 0.672 | 10 |
| LNU185 | 26474.1. | 10.500 | 0.124 | 5 | LNU224 | 25872.2 | 0.981 | 0.000 | 42 | LNU276 | 25433.6 | 0.741 | 0.251 | 32 |
| LNU185 | 26475.1. | 10.125 | 0.677 | 1 | LNU224 | 25872.3 | 0.841 | 0.025 | 22 | LNU276 | 25431.1 | 0.651 | 0.008 | 16 |
| LNU212 | 25834.4. | 11.063 | 0.198 | 10 | LNU224 | 25874.4 | 0.807 | 0.382 | 17 | LNU276 | 25433.1 | 0.598 | 0.619 | 6 |
| LNU212 | 25834.1. | 10.750 | 0.027 | 7 | LNU246 | 25743.2 | 1.000 | 0.316 | 45 | LNU279 | 25481.5 | 0.724 | 0.000 | 29 |
| LNU212 | 25834.5. | 10.375 | 0.512 | 4 | LNU246 | 25743.1 | 0.986 | 0.464 | 43 | LNU279 | 25481.3 | 0.695 | 0.581 | 24 |
| LNU212 | 25833.1. | 10.188 | 0.607 | 2 | LNU246 | 25744.2 | 0.977 | 0.436 | 42 | LNU279 | 25484.3 | 0.694 | 0.583 | 24 |
| LNU216 | 25982.2. | 11.188 | 0.081 | 12 | LNU246 | 25744.4 | 0.900 | 0.570 | 30 | LNU279 | 25481.2 | 0.592 | 0.694 | 5 |
| LNU216 | 25985.4. | 11.000 | 0.009 | 10 | LNU246 | 25744.3 | 0.766 | 0.516 | 11 | LNU3 | 26122.2 | 0.726 | 0.545 | 29 |

TABLE 80-continued

Genes showing improved plant photosynthetic capacity at limiting nitrogen growth conditions

| Leaf Number | | | | | Leaf Blade Area [cm2] | | | | | Leaf Petiole Length [cm] | | | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU216 | 25982.1. | 10.938 | 0.234 | 9 | LNU250 | 25592.2 | 0.925 | 0.000 | 34 | LNU3 | 26124.3 | 0.684 | 0.377 | 22 |
| LNU216 | 25984.6. | 10.313 | 0.746 | 3 | LNU250 | 25591.1 | 0.792 | 0.492 | 15 | LNU3 | 26123.5 | 0.643 | 0.491 | 15 |
| LNU228 | 26225.2. | 10.938 | 0.033 | 9 | LNU250 | 25592.1 | 0.772 | 0.626 | 12 | LNU3 | 26124.1 | 0.627 | 0.549 | 12 |
| LNU228 | 26224.7. | 10.771 | 0.553 | 7 | LNU260 | 26404.7 | 0.835 | 0.567 | 21 | LNU33 | 25553.3 | 0.772 | 0.058 | 37 |
| LNU228 | 26222.4. | 10.750 | 0.027 | 7 | LNU260 | 26404.1 | 0.830 | 0.519 | 20 | LNU33 | 25552.2 | 0.729 | 0.384 | 30 |
| LNU228 | 26224.6. | 10.375 | 0.672 | 4 | LNU260 | 26404.8 | 0.822 | 0.210 | 19 | LNU33 | 25553.2 | 0.703 | 0.091 | 25 |
| LNU228 | 26222.1. | 10.313 | 0.280 | 3 | LNU276 | 25433.6 | 0.852 | 0.275 | 23 | LNU33 | 25553.1 | 0.699 | 0.464 | 24 |
| LNU229 | 26112.3. | 10.938 | 0.394 | 9 | LNU276 | 25433.5 | 0.811 | 0.162 | 17 | LNU53 | 25674.6 | 0.675 | 0.202 | 20 |
| LNU229 | 26111.5. | 10.688 | 0.336 | 7 | LNU276 | 25431.1 | 0.795 | 0.020 | 15 | LNU53 | 25674.3 | 0.621 | 0.284 | 11 |
| LNU229 | 26112.4. | 10.625 | 0.175 | 6 | LNU279 | 25481.3 | 0.943 | 0.510 | 37 | LNU56 | 24694.2 | 0.667 | 0.187 | 19 |
| LNU229 | 26111.7. | 10.375 | 0.377 | 4 | LNU279 | 25484.3 | 0.927 | 0.303 | 34 | LNU56 | 24693.1 | 0.623 | 0.497 | 11 |
| LNU241 | 26233.3. | 10.313 | 0.697 | 3 | LNU279 | 25481.5 | 0.884 | 0.004 | 28 | LNU73 | 25751.8 | 0.621 | 0.689 | 11 |
| LNU241 | 26232.4. | 10.125 | 0.781 | 1 | LNU279 | 25481.4 | 0.754 | 0.618 | 9 | CONT. | — | 0.920 | — | 0 |
| LNU253 | 26242.1. | 10.375 | 0.672 | 4 | LNU3 | 26122.2 | 0.888 | 0.481 | 29 | LNU130 | 24912.7. | 0.993 | 0.491 | 8 |
| LNU274 | 26265.1. | 10.625 | 0.065 | 6 | LNU33 | 25553.3 | 0.988 | 0.000 | 43 | LNU130 | 24911.7. | 0.932 | 0.736 | 1 |
| LNU274 | 26261.3. | 10.375 | 0.607 | 4 | LNU33 | 25552.2 | 0.881 | 0.639 | 28 | LNU130 | 24913.6. | 0.928 | 0.690 | 1 |
| LNU274 | 26264.2. | 10.250 | 0.659 | 2 | LNU33 | 25553.2 | 0.860 | 0.276 | 25 | LNU136 | 14511.10. | 1.024 | 0.000 | 11 |
| LNU280 | 26164.4. | 10.652 | 0.132 | 6 | LNU33 | 25553.1 | 0.793 | 0.638 | 15 | LNU136 | 14514.8. | 0.976 | 0.214 | 6 |
| LNU280 | 26162.1. | 10.438 | 0.506 | 4 | LNU53 | 25674.6 | 0.831 | 0.271 | 20 | LNU142 | 27546.1. | 0.931 | 0.592 | 1 |
| LNU55 | 26013.4. | 10.563 | 0.072 | 5 | LNU56 | 24694.2 | 0.718 | 0.699 | 4 | LNU149 | 26175.3. | 0.950 | 0.244 | 3 |
| LNU55 | 26013.3. | 10.438 | 0.734 | 4 | LNU73 | 25751.8 | 0.793 | 0.713 | 15 | LNU15 | 14123.13. | 0.985 | 0.389 | 7 |
| LNU55 | 26013.9. | 10.313 | 0.383 | 3 | CONT. | — | 0.998 | — | 0 | LNU15 | 14123.11. | 0.973 | 0.646 | 6 |
| LNU81 | 26031.2. | 10.813 | 0.019 | 8 | LNU119 | 26144.2. | 1.111 | 0.000 | 11 | LNU15 | 14122.8. | 0.927 | 0.724 | 1 |
| LNU81 | 26031.10. | 10.500 | 0.637 | 5 | LNU130 | 24912.7. | 1.170 | 0.471 | 17 | LNU185 | 26475.1. | 1.017 | 0.001 | 11 |
| | | | | | LNU130 | 24913.6. | 1.124 | 0.000 | 13 | LNU185 | 26474.1. | 1.017 | 0.224 | 11 |
| | | | | | LNU130 | 24914.5. | 1.091 | 0.507 | 9 | LNU185 | 26474.2. | 1.012 | 0.558 | 10 |
| | | | | | LNU130 | 24911.7. | 1.065 | 0.479 | 7 | LNU212 | 25834.4. | 1.093 | 0.186 | 19 |
| | | | | | LNU136 | 14511.10. | 1.152 | 0.000 | 15 | LNU212 | 25834.5. | 1.044 | 0.000 | 14 |
| | | | | | LNU136 | 14515.5. | 1.131 | 0.504 | 13 | LNU212 | 25833.2. | 1.029 | 0.044 | 12 |
| | | | | | LNU142 | 27541.1. | 1.162 | 0.162 | 16 | LNU212 | 25834.1. | 1.003 | 0.439 | 9 |
| | | | | | LNU149 | 26175.3. | 1.088 | 0.262 | 9 | LNU212 | 25832.1. | 0.977 | 0.024 | 6 |
| | | | | | LNU15 | 14123.11. | 1.074 | 0.619 | 8 | LNU216 | 25982.1. | 1.110 | 0.000 | 21 |
| | | | | | LNU15 | 14123.13. | 1.060 | 0.270 | 6 | LNU216 | 25984.1. | 1.095 | 0.394 | 19 |
| | | | | | LNU185 | 26474.2. | 1.181 | 0.474 | 18 | LNU216 | 25984.6. | 1.011 | 0.199 | 10 |
| | | | | | LNU185 | 26475.1. | 1.164 | 0.276 | 17 | LNU216 | 25985.4. | 1.008 | 0.361 | 10 |
| | | | | | LNU185 | 26474.1. | 1.075 | 0.648 | 8 | LNU216 | 25982.2. | 0.946 | 0.569 | 3 |
| | | | | | LNU212 | 25833.2. | 1.253 | 0.141 | 26 | LNU228 | 26222.4. | 0.994 | 0.311 | 8 |
| | | | | | LNU212 | 25834.4. | 1.144 | 0.191 | 15 | LNU228 | 26224.7. | 0.980 | 0.433 | 7 |
| | | | | | LNU212 | 25834.5. | 1.137 | 0.293 | 14 | LNU228 | 26224.6. | 0.974 | 0.335 | 6 |
| | | | | | LNU212 | 25832.1. | 1.024 | 0.771 | 3 | LNU229 | 26112.3. | 1.010 | 0.108 | 10 |
| | | | | | LNU216 | 25985.4. | 1.190 | 0.281 | 19 | LNU229 | 26111.7. | 0.932 | 0.754 | 1 |
| | | | | | LNU216 | 25982.1. | 1.189 | 0.144 | 19 | LNU253 | 26241.1. | 0.970 | 0.691 | 5 |
| | | | | | LNU216 | 25984.1. | 1.159 | 0.328 | 16 | LNU274 | 26262.2. | 0.933 | 0.628 | 1 |
| | | | | | LNU216 | 25984.6. | 1.047 | 0.057 | 5 | LNU280 | 26162.1. | 1.053 | 0.427 | 15 |
| | | | | | LNU228 | 26224.7. | 1.169 | 0.003 | 17 | LNU81 | 26031.9. | 0.939 | 0.770 | 2 |
| | | | | | LNU228 | 26222.4. | 1.089 | 0.204 | 9 | LNU81 | 26034.2. | 0.931 | 0.798 | 1 |
| | | | | | LNU229 | 26112.3. | 1.154 | 0.000 | 16 | CONT. | — | 0.912 | — | 0 |
| | | | | | LNU253 | 26241.1. | 1.110 | 0.200 | 11 | LNU119 | 26142.5. | 0.983 | 0.375 | 8 |
| | | | | | LNU253 | 26245.1. | 1.050 | 0.357 | 5 | LNU119 | 26141.1. | 0.981 | 0.501 | 8 |
| | | | | | LNU274 | 26261.3. | 1.028 | 0.543 | 3 | LNU136 | 14514.8. | 0.989 | 0.455 | 8 |
| | | | | | LNU277 | 25844.4. | 1.059 | 0.506 | 6 | LNU136 | 14511.10. | 0.982 | 0.508 | 8 |
| | | | | | LNU280 | 26162.1. | 1.139 | 0.546 | 14 | LNU142 | 27546.2. | 0.967 | 0.635 | 6 |
| | | | | | LNU55 | 26015.1. | 1.133 | 0.325 | 14 | LNU142 | 27545.1. | 0.962 | 0.742 | 6 |
| | | | | | LNU81 | 26031.9. | 1.080 | 0.744 | 8 | LNU149 | 26174.7. | 0.936 | 0.711 | 3 |
| | | | | | LNU8 | 26034.2. | 1.063 | 0.673 | 6 | LNU15 | 14122.8. | 1.050 | 0.456 | 15 |
| | | | | | CONT. | — | 0.973 | — | 0 | LNU15 | 14123.13. | 0.994 | 0.220 | 9 |
| | | | | | LNU119 | 26141.1. | 1.245 | 0.391 | 28 | LNU15 | 14122.9. | 0.966 | 0.725 | 6 |
| | | | | | LNU119 | 26142.8. | 1.071 | 0.613 | 10 | LNU15 | 14124.12. | 0.932 | 0.764 | 2 |
| | | | | | LNU119 | 26142.5. | 1.063 | 0.417 | 9 | LNU185 | 26474.1. | 1.126 | 0.129 | 23 |
| | | | | | LNU130 | 24913.5. | 1.121 | 0.205 | 15 | LNU185 | 26473.1. | 0.976 | 0.332 | 7 |
| | | | | | LNU130 | 24914.5. | 1.060 | 0.457 | 9 | LNU212 | 25834.4. | 1.075 | 0.053 | 18 |
| | | | | | LNU130 | 24912.7. | 1.044 | 0.766 | 7 | LNU212 | 25834.1. | 0.952 | 0.524 | 4 |
| | | | | | LNU130 | 24913.6. | 1.041 | 0.655 | 7 | LNU212 | 25833.2. | 0.940 | 0.733 | 3 |
| | | | | | LNU136 | 14515.1. | 1.065 | 0.451 | 9 | LNU216 | 25985.4. | 1.081 | 0.242 | 19 |
| | | | | | LNU136 | 14514.8. | 1.048 | 0.675 | 8 | LNU216 | 25982.2. | 1.023 | 0.157 | 12 |
| | | | | | LNU136 | 14511.10. | 1.040 | 0.682 | 7 | LNU216 | 25982.1. | 1.010 | 0.295 | 11 |
| | | | | | LNU142 | 27546.1. | 1.048 | 0.483 | 8 | LNU216 | 25984.6. | 0.974 | 0.511 | 7 |
| | | | | | LNU142 | 27546.2. | 1.048 | 0.622 | 8 | LNU228 | 26225.2. | 1.054 | 0.065 | 16 |
| | | | | | LNU149 | 26174.7. | 1.017 | 0.729 | 5 | LNU228 | 26222.4. | 1.004 | 0.233 | 10 |
| | | | | | LNU15 | 14124.12. | 1.132 | 0.340 | 16 | LNU228 | 26222.1. | 0.978 | 0.304 | 7 |
| | | | | | LNU15 | 14122.8. | 1.119 | 0.482 | 15 | LNU228 | 26224.6. | 0.951 | 0.727 | 4 |
| | | | | | LNU15 | 14123.11. | 1.082 | 0.717 | 11 | LNU229 | 26111.5. | 1.050 | 0.063 | 15 |

TABLE 80-continued

Genes showing improved plant photosynthetic capacity at limiting nitrogen growth conditions

| Gene Name | Event # | Ave. | P-Value | % incr. | Gene Name | Event # | Ave. | P-Value | % incr. | Gene Name | Event # | Ave. | P-Value | % incr. |
|---|---|---|---|---|---|---|---|---|---|---|---|---|---|---|
| | | | Leaf Number | | | | | Leaf Blade Area [cm2] | | | | | Leaf Petiole Length [cm] | |
| | | | | | LNU15 | 14123.13. | 1.052 | 0.469 | 8 | LNU229 | 26112.3. | 1.039 | 0.668 | 14 |
| | | | | | LNU185 | 26474.1. | 1.258 | 0.042 | 29 | LNU229 | 26111.7. | 1.035 | 0.371 | 13 |
| | | | | | LNU185 | 26473.1. | 1.004 | 0.773 | 3 | LNU229 | 26112.4. | 0.971 | 0.420 | 6 |
| | | | | | LNU212 | 25834.4. | 1.176 | 0.138 | 21 | LNU253 | 26242.1. | 0.986 | 0.260 | 8 |
| | | | | | LNU212 | 25834.5. | 1.099 | 0.265 | 13 | LNU253 | 26241.1. | 0.953 | 0.786 | 4 |
| | | | | | LNU212 | 25833.2. | 1.063 | 0.408 | 9 | LNU274 | 26262.2. | 0.967 | 0.439 | 6 |
| | | | | | LNU216 | 25985.4. | 1.248 | 0.201 | 28 | LNU280 | 26162.1. | 1.023 | 0.127 | 12 |
| | | | | | LNU216 | 25984.6. | 1.077 | 0.653 | 11 | LNU55 | 26013.4. | 0.969 | 0.639 | 6 |
| | | | | | LNU216 | 25982.1. | 1.068 | 0.386 | 10 | LNU55 | 26013.9. | 0.936 | 0.738 | 3 |
| | | | | | LNU216 | 25984.4. | 1.025 | 0.757 | 5 | LNU81 | 26031.2. | 1.025 | 0.455 | 12 |
| | | | | | LNU228 | 26225.2. | 1.254 | 0.054 | 29 | LNU81 | 26031.10. | 0.974 | 0.759 | 7 |
| | | | | | LNU228 | 26222.1. | 1.154 | 0.136 | 19 | | | | | |
| | | | | | LNU228 | 26224.7. | 1.153 | 0.423 | 19 | | | | | |
| | | | | | LNU228 | 26222.4. | 1.135 | 0.165 | 17 | | | | | |
| | | | | | LNU228 | 26224.6. | 1.123 | 0.227 | 15 | | | | | |
| | | | | | LNU229 | 26112.4. | 1.185 | 0.331 | 22 | | | | | |
| | | | | | LNU229 | 26111.7. | 1.176 | 0.394 | 21 | | | | | |
| | | | | | LNU229 | 26111.5. | 1.160 | 0.295 | 19 | | | | | |
| | | | | | LNU229 | 26112.3. | 1.129 | 0.305 | 16 | | | | | |
| | | | | | LNU241 | 26233.3. | 1.137 | 0.596 | 17 | | | | | |
| | | | | | LNU241 | 26234.1. | 1.068 | 0.385 | 10 | | | | | |
| | | | | | LNU241 | 26232.4. | 1.065 | 0.399 | 9 | | | | | |
| | | | | | LNU253 | 26242.1. | 1.053 | 0.632 | 8 | | | | | |
| | | | | | LNU253 | 26241.1. | 1.045 | 0.505 | 7 | | | | | |
| | | | | | LNU274 | 26265.1. | 1.098 | 0.634 | 13 | | | | | |
| | | | | | LNU274 | 26262.1. | 1.056 | 0.558 | 8 | | | | | |
| | | | | | LNU280 | 26162.1. | 1.190 | 0.211 | 22 | | | | | |
| | | | | | LNU55 | 26015.1. | 1.104 | 0.272 | 13 | | | | | |
| | | | | | LNU55 | 26013.4. | 1.084 | 0.388 | 11 | | | | | |
| | | | | | LNU81 | 26031.10. | 1.169 | 0.541 | 20 | | | | | |
| | | | | | LNU81 | 26031.2. | 1.089 | 0.427 | 12 | | | | | |

"CONT."—Control; "Ave."—Average; "% Incr." = % increment.

The genes listed in Table 81 improved plant NUE when grown at standard nitrogen concentration levels. These genes produced faster developing plants when grown under limiting nitrogen growth conditions, compared to control plants as measured by growth rate of rosette area, rosette diameter and plot coverage. The genes were cloned under the regulation of a constitutive (At6669) and root preferred promoter (RootP). The evaluation of each gene was performed by testing the performance of different number of events. Event with p-value <0.1 was considered statistically significant.

TABLE 81

Genes showing improved rosette growth performance at limiting nitrogen growth conditions

| Gene Name | Event # | Ave. | P-Value | % incr. | Gene Name | Event # | Ave. | P-Value | % incr. | Gene Name | Event # | Ave. | P-Value | % incr. |
|---|---|---|---|---|---|---|---|---|---|---|---|---|---|---|
| | | | RGR Of Rosette Area | | | | | RGR Of Rosette Diameter | | | | | RGR Of Plot Coverage | |
| CONT. | — | 0.488 | — | 0 | CONT. | — | 0.279 | — | 0 | CONT. | — | 3.86 | — | 0 |
| LNU100 | 14472.2 | 0.673 | 0.007 | 38 | LNU100 | 14472.2 | 0.341 | 0.009 | 22 | LNU100 | 14472.2 | 5.39 | 0.008 | 39 |
| LNU100 | 14471.4 | 0.573 | 0.204 | 17 | LNU100 | 14471.4 | 0.314 | 0.127 | 13 | LNU100 | 14471.4 | 4.59 | 0.190 | 19 |
| LNU104 | 25033.3 | 0.708 | 0.002 | 45 | LNU100 | 14474.3 | 0.294 | 0.500 | 5 | LNU100 | 14474.3 | 4.01 | 0.785 | 4 |
| LNU104 | 25032.2 | 0.654 | 0.019 | 34 | LNU100 | 14473.3 | 0.293 | 0.539 | 5 | LNU104 | 25033.3 | 5.66 | 0.002 | 47 |
| LNU104 | 25032.1 | 0.590 | 0.122 | 21 | LNU104 | 25033.3 | 0.359 | 0.001 | 29 | LNU104 | 25032.2 | 5.24 | 0.018 | 36 |
| LNU104 | 25033.1 | 0.539 | 0.432 | 10 | LNU104 | 25032.1 | 0.321 | 0.078 | 15 | LNU104 | 25032.1 | 4.72 | 0.115 | 22 |
| LNU106 | 14481.1 | 0.646 | 0.025 | 32 | LNU104 | 25032.2 | 0.315 | 0.115 | 13 | LNU104 | 25033.1 | 4.31 | 0.400 | 12 |
| LNU106 | 14483.5 | 0.591 | 0.140 | 21 | LNU104 | 25033.1 | 0.299 | 0.369 | 7 | LNU106 | 14481.1 | 5.17 | 0.024 | 34 |
| LNU106 | 14483.2 | 0.555 | 0.315 | 14 | LNU106 | 14481.1 | 0.341 | 0.015 | 22 | LNU106 | 14483.5 | 4.73 | 0.132 | 22 |
| LNU106 | 14484.3 | 0.543 | 0.412 | 11 | LNU106 | 14483.5 | 0.331 | 0.042 | 19 | LNU106 | 14483.2 | 4.44 | 0.292 | 15 |
| LNU114 | 25041.2 | 0.534 | 0.497 | 9 | LNU106 | 14483.2 | 0.305 | 0.245 | 9 | LNU106 | 14484.3 | 4.34 | 0.381 | 13 |
| LNU114 | 25042.1 | 0.528 | 0.545 | 8 | LNU106 | 14484.3 | 0.296 | 0.446 | 6 | LNU114 | 25041.2 | 4.27 | 0.461 | 11 |
| LNU155 | 14525.1 | 0.573 | 0.193 | 17 | LNU114 | 25041.2 | 0.299 | 0.401 | 7 | LNU155 | 14525.1 | 4.58 | 0.181 | 19 |
| LNU155 | 14523.5 | 0.542 | 0.422 | 11 | LNU114 | 25041.1 | 0.295 | 0.506 | 6 | LNU155 | 14523.5 | 4.34 | 0.391 | 12 |
| LNU213 | 24654.4 | 0.558 | 0.285 | 14 | LNU114 | 25042.1 | 0.289 | 0.660 | 4 | LNU213 | 24654.4 | 4.46 | 0.265 | 16 |
| LNU218 | 24781.7 | 0.637 | 0.029 | 31 | LNU213 | 24653.2 | 0.307 | 0.264 | 10 | LNU218 | 24781.7 | 5.10 | 0.029 | 32 |
| LNU218 | 24781.4 | 0.628 | 0.046 | 29 | LNU213 | 24652.4 | 0.295 | 0.527 | 6 | LNU218 | 24781.4 | 5.02 | 0.045 | 30 |
| LNU218 | 24784.2 | 0.586 | 0.152 | 20 | LNU218 | 24781.7 | 0.353 | 0.002 | 27 | LNU218 | 24784.2 | 4.68 | 0.143 | 21 |
| LNU23 | 25163.5 | 0.601 | 0.157 | 23 | LNU218 | 24781.4 | 0.328 | 0.045 | 18 | LNU23 | 25163.5 | 4.81 | 0.147 | 25 |

TABLE 81-continued

Genes showing improved rosette growth performance at limiting nitrogen growth conditions

| | | RGR Of Rosette Area | | | | | RGR Of Rosette Diameter | | | | | RGR Of Plot Coverage | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU23 | 25163.6 | 0.537 | 0.492 | 10 | LNU218 | 24784.2 | 0.314 | 0.139 | 13 | LNU23 | 25163.6 | 4.29 | 0.457 | 11 |
| LNU28 | 25171.2 | 0.588 | 0.137 | 20 | LNU218 | 24781.2 | 0.286 | 0.762 | 2 | LNU28 | 25171.2 | 4.70 | 0.129 | 22 |
| LNU28 | 25171.1 | 0.583 | 0.157 | 19 | LNU23 | 25163.5 | 0.341 | 0.050 | 22 | LNU28 | 25171.1 | 4.66 | 0.148 | 21 |
| LNU28 | 25174.5 | 0.520 | 0.677 | 7 | LNU23 | 25163.6 | 0.309 | 0.239 | 11 | LNU28 | 25174.5 | 4.16 | 0.633 | 8 |
| LNU4 | 25133.3 | 0.591 | 0.127 | 21 | LNU28 | 25171.1 | 0.349 | 0.003 | 25 | LNU4 | 25133.3 | 4.73 | 0.120 | 22 |
| LNU4 | 25134.1 | 0.515 | 0.691 | 5 | LNU28 | 25171.2 | 0.327 | 0.034 | 17 | LNU4 | 25134.1 | 4.12 | 0.641 | 7 |
| LNU40 | 24794.3 | 0.619 | 0.053 | 27 | LNU28 | 25174.5 | 0.305 | 0.374 | 9 | LNU40 | 24794.3 | 4.95 | 0.051 | 28 |
| LNU40 | 24794.4 | 0.585 | 0.153 | 20 | LNU28 | 25171.4 | 0.289 | 0.676 | 4 | LNU40 | 24794.4 | 4.41 | 0.346 | 14 |
| LNU46 | 14462.5 | 0.751 | 0.001 | 54 | LNU4 | 25133.3 | 0.317 | 0.088 | 14 | LNU46 | 14462.5 | 6.01 | 0.001 | 56 |
| LNU46 | 14464.4 | 0.712 | 0.008 | 46 | LNU4 | 25134.1 | 0.291 | 0.636 | 4 | LNU46 | 14464.4 | 5.69 | 0.008 | 47 |
| LNU46 | 14464.1 | 0.540 | 0.430 | 11 | LNU4 | 25131.1 | 0.288 | 0.705 | 3 | LNU46 | 14464.1 | 4.32 | 0.398 | 12 |
| LNU46 | 14462.1 | 0.532 | 0.511 | 9 | LNU40 | 24794.4 | 0.326 | 0.045 | 17 | LNU46 | 14462.1 | 4.26 | 0.473 | 10 |
| LNU46 | 14463.1 | 0.532 | 0.506 | 9 | LNU40 | 24794.3 | 0.304 | 0.256 | 9 | LNU46 | 14463.1 | 4.25 | 0.468 | 10 |
| LNU48 | 24801.4 | 0.634 | 0.032 | 30 | LNU46 | 14464.4 | 0.356 | 0.010 | 28 | LNU48 | 24801.4 | 5.07 | 0.032 | 31 |
| LNU48 | 24802.1 | 0.557 | 0.289 | 14 | LNU46 | 14462.5 | 0.338 | 0.020 | 21 | LNU48 | 24802.1 | 4.46 | 0.268 | 15 |
| LNU48 | 24804.4 | 0.512 | 0.714 | 5 | LNU46 | 14464.1 | 0.304 | 0.264 | 9 | LNU48 | 24804.4 | 4.09 | 0.661 | 6 |
| LNU63 | 24814.2 | 0.572 | 0.210 | 17 | LNU46 | 14462.1 | 0.298 | 0.416 | 7 | LNU63 | 24814.2 | 4.58 | 0.196 | 19 |
| LNU63 | 24814.3 | 0.529 | 0.538 | 8 | LNU46 | 14463.1 | 0.290 | 0.614 | 4 | LNU63 | 24814.3 | 4.23 | 0.498 | 10 |
| LNU63 | 24811.2 | 0.511 | 0.723 | 5 | LNU48 | 24801.4 | 0.335 | 0.015 | 20 | LNU63 | 24811.2 | 4.09 | 0.670 | 6 |
| LNU7 | 25081.1 | 0.570 | 0.217 | 17 | LNU48 | 24802.1 | 0.312 | 0.132 | 12 | LNU7 | 25081.1 | 4.56 | 0.203 | 18 |
| LNU7 | 25082.2 | 0.540 | 0.431 | 11 | LNU63 | 24814.3 | 0.307 | 0.219 | 10 | LNU7 | 25082.2 | 4.32 | 0.399 | 12 |
| LNU8 | 25063.6 | 0.531 | 0.508 | 9 | LNU63 | 24814.2 | 0.300 | 0.368 | 7 | LNU8 | 25063.6 | 4.25 | 0.469 | 10 |
| LNU8 | 25062.1 | 0.530 | 0.516 | 9 | LNU63 | 24811.2 | 0.289 | 0.636 | 4 | LNU8 | 25062.1 | 4.24 | 0.478 | 10 |
| LNU8 | 25061.2 | 0.512 | 0.712 | 5 | LNU7 | 25081.1 | 0.315 | 0.109 | 13 | LNU8 | 25061.2 | 4.10 | 0.660 | 6 |
| LNU8 | 25062.2 | 0.511 | 0.734 | 5 | LNU7 | 25082.2 | 0.312 | 0.187 | 12 | LNU8 | 25062.2 | 4.09 | 0.681 | 6 |
| LNU94 | 24833.3 | 0.560 | 0.273 | 15 | LNU8 | 25061.2 | 0.294 | 0.504 | 5 | LNU94 | 24833.3 | 4.19 | 0.543 | 9 |
| LNU96 | 25071.2 | 0.621 | 0.062 | 27 | LNU8 | 25063.6 | 0.287 | 0.699 | 3 | LNU96 | 25071.2 | 4.96 | 0.060 | 29 |
| LNU96 | 25073.4 | 0.524 | 0.612 | 7 | LNU94 | 24833.3 | 0.298 | 0.382 | 7 | LNU96 | 25073.4 | 4.19 | 0.569 | 9 |
| LNU96 | 25071.3 | 0.510 | 0.738 | 4 | LNU96 | 25071.2 | 0.321 | 0.091 | 15 | CONT. | — | 5.49 | — | 0 |
| CONT. | — | 0.686 | — | 0 | LNU96 | 25073.4 | 0.301 | 0.419 | 8 | LNU113 | 25631.7 | 6.03 | 0.397 | 10 |
| LNU113 | 25631.7 | 0.754 | 0.397 | 10 | LNU96 | 25071.3 | 0.294 | 0.527 | 5 | LNU113 | 25631.3 | 5.87 | 0.555 | 7 |
| LNU113 | 25631.3 | 0.733 | 0.555 | 7 | LNU96 | 25074.1 | 0.292 | 0.559 | 5 | LNU113 | 25631.1 | 5.75 | 0.676 | 5 |
| LNU113 | 25631.1 | 0.718 | 0.676 | 5 | CONT. | — | 0.328 | — | 0 | LNU140 | 14115.1 | 5.68 | 0.766 | 3 |
| LNU140 | 14115.1 | 0.710 | 0.766 | 3 | LNU113 | 25631.3 | 0.376 | 0.086 | 15 | LNU148 | 25685.6 | 7.18 | 0.010 | 31 |
| LNU148 | 25685.6 | 0.898 | 0.010 | 31 | LNU113 | 25631.7 | 0.355 | 0.277 | 8 | LNU148 | 25685.1 | 6.24 | 0.232 | 14 |
| LNU148 | 25685.1 | 0.779 | 0.232 | 14 | LNU113 | 25631.1 | 0.347 | 0.436 | 6 | LNU148 | 25685.9 | 5.67 | 0.772 | 3 |
| LNU148 | 25685.9 | 0.709 | 0.772 | 3 | LNU120 | 25463.3 | 0.335 | 0.779 | 2 | LNU5 | 14043.7 | 6.18 | 0.270 | 13 |
| LNU5 | 14043.7 | 0.773 | 0.270 | 13 | LNU132 | 14102.6 | 0.348 | 0.435 | 6 | LNU74 | 25444.1 | 6.11 | 0.317 | 11 |
| LNU74 | 25444.1 | 0.763 | 0.317 | 11 | LNU148 | 25685.6 | 0.366 | 0.136 | 12 | LNU98 | 25763.2 | 5.77 | 0.655 | 5 |
| LNU98 | 25763.2 | 0.721 | 0.655 | 5 | LNU148 | 25685.1 | 0.357 | 0.244 | 9 | CONT. | — | 5.16 | — | 0 |
| CONT. | — | 0.653 | — | 0 | LNU148 | 25685.9 | 0.338 | 0.668 | 3 | LNU113 | 25631.9 | 5.82 | 0.422 | 13 |
| LNU113 | 25631.9 | 0.727 | 0.470 | 11 | LNU287 | 24674.6 | 0.336 | 0.749 | 3 | LNU148 | 25685.1 | 5.80 | 0.439 | 12 |
| LNU148 | 25685.1 | 0.725 | 0.488 | 11 | LNU5 | 14043.7 | 0.358 | 0.226 | 9 | LNU72 | 24963.7 | 5.72 | 0.507 | 11 |
| LNU72 | 24963.7 | 0.715 | 0.559 | 9 | LNU68 | 14035.5 | 0.335 | 0.761 | 2 | LNU72 | 24962.3 | 5.56 | 0.633 | 8 |
| LNU72 | 24962.3 | 0.695 | 0.690 | 6 | LNU74 | 25444.1 | 0.348 | 0.418 | 6 | LNU98 | 25763.2 | 5.81 | 0.437 | 12 |
| LNU98 | 25763.2 | 0.726 | 0.486 | 11 | LNU74 | 25441.2 | 0.343 | 0.592 | 5 | CONT. | — | 4.13 | — | 0 |
| CONT. | — | 0.534 | — | 0 | LNU74 | 25443.3 | 0.340 | 0.633 | 4 | LNU117 | 25931.4 | 7.72 | 0.000 | 87 |
| LNU117 | 25931.4 | 0.965 | 0.000 | 81 | LNU74 | 25443.2 | 0.336 | 0.746 | 2 | LNU117 | 25931.2 | 6.79 | 0.005 | 64 |
| LNU117 | 25931.2 | 0.849 | 0.002 | 59 | LNU87 | 24714.3 | 0.335 | 0.771 | 2 | LNU117 | 25933.3 | 6.49 | 0.006 | 57 |
| LNU117 | 25933.3 | 0.811 | 0.001 | 52 | CONT. | — | 0.333 | — | 0 | LNU117 | 25931.1 | 6.13 | 0.040 | 49 |
| LNU117 | 25931.1 | 0.767 | 0.027 | 44 | LNU113 | 25631.9 | 0.355 | 0.607 | 7 | LNU117 | 25932.4 | 5.82 | 0.116 | 41 |
| LNU117 | 25932.4 | 0.728 | 0.107 | 36 | LNU148 | 25685.1 | 0.351 | 0.669 | 6 | LNU122 | 25333.2 | 7.24 | 0.002 | 75 |
| LNU122 | 25333.2 | 0.905 | 0.000 | 69 | LNU74 | 25443.5 | 0.344 | 0.792 | 3 | LNU122 | 25332.1 | 6.68 | 0.017 | 62 |
| LNU122 | 25332.1 | 0.835 | 0.011 | 56 | LNU98 | 25763.2 | 0.353 | 0.647 | 6 | LNU122 | 25332.2 | 6.18 | 0.015 | 50 |
| LNU122 | 25332.2 | 0.773 | 0.005 | 45 | CONT. | — | 0.241 | — | 0 | LNU122 | 25333.1 | 5.72 | 0.064 | 38 |
| LNU122 | 25333.1 | 0.715 | 0.041 | 34 | LNU117 | 25931.4 | 0.364 | 0.004 | 51 | LNU122 | 25332.5 | 5.66 | 0.056 | 37 |
| LNU122 | 25332.5 | 0.708 | 0.029 | 32 | LNU117 | 25931.2 | 0.357 | 0.003 | 48 | LNU125 | 25941.4 | 7.61 | 0.001 | 84 |
| LNU125 | 25941.4 | 0.951 | 0.000 | 78 | LNU117 | 25931.1 | 0.335 | 0.026 | 39 | LNU125 | 25943.3 | 6.79 | 0.003 | 64 |
| LNU125 | 25943.3 | 0.849 | 0.001 | 59 | LNU117 | 25933.3 | 0.332 | 0.026 | 38 | LNU125 | 25943.2 | 6.47 | 0.043 | 57 |
| LNU125 | 25943.2 | 0.809 | 0.036 | 51 | LNU117 | 25932.4 | 0.331 | 0.098 | 37 | LNU125 | 25941.2 | 6.03 | 0.055 | 46 |
| LNU125 | 25941.2 | 0.754 | 0.041 | 41 | LNU122 | 25333.2 | 0.339 | 0.011 | 41 | LNU125 | 25944.3 | 5.66 | 0.113 | 37 |
| LNU125 | 25944.3 | 0.707 | 0.096 | 32 | LNU122 | 25332.1 | 0.316 | 0.078 | 31 | LNU138 | 14074.5 | 7.47 | 0.001 | 81 |
| LNU138 | 14074.5 | 0.933 | 0.000 | 75 | LNU122 | 25332.2 | 0.316 | 0.047 | 31 | LNU138 | 14074.6 | 7.05 | 0.010 | 71 |
| LNU138 | 14074.6 | 0.882 | 0.006 | 65 | LNU122 | 25333.1 | 0.313 | 0.055 | 30 | LNU138 | 14071.5 | 6.56 | 0.009 | 59 |
| LNU138 | 14071.5 | 0.820 | 0.003 | 54 | LNU122 | 25332.5 | 0.299 | 0.138 | 24 | LNU138 | 14072.8 | 4.88 | 0.351 | 18 |
| LNU138 | 14072.8 | 0.610 | 0.348 | 14 | LNU125 | 25941.4 | 0.359 | 0.006 | 49 | LNU138 | 14072.5 | 4.76 | 0.424 | 15 |
| LNU138 | 14072.5 | 0.595 | 0.436 | 11 | LNU125 | 25943.2 | 0.340 | 0.057 | 41 | LNU180 | 24721.2 | 8.62 | 0.000 | 109 |
| LNU180 | 24721.2 | 1.077 | 0.000 | 102 | LNU125 | 25943.3 | 0.339 | 0.013 | 41 | LNU180 | 24723.1 | 8.22 | 0.000 | 99 |
| LNU180 | 24723.1 | 1.028 | 0.000 | 92 | LNU125 | 25944.3 | 0.322 | 0.043 | 34 | LNU180 | 24721.4 | 8.02 | 0.000 | 94 |
| LNU180 | 24721.4 | 1.002 | 0.000 | 88 | LNU125 | 25941.2 | 0.321 | 0.079 | 33 | LNU180 | 24722.2 | 7.40 | 0.005 | 79 |

TABLE 81-continued

Genes showing improved rosette growth performance at limiting nitrogen growth conditions

| | | RGR Of Rosette Area | | | | | RGR Of Rosette Diameter | | | | | RGR Of Plot Coverage | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU180 | 24722.2 | 0.925 | 0.003 | 73 | LNU138 | 14074.5 | 0.375 | 0.001 | 55 | LNU180 | 24724.1 | 7.06 | 0.008 | 71 |
| LNU180 | 24724.1 | 0.883 | 0.004 | 65 | LNU138 | 14074.6 | 0.360 | 0.011 | 49 | LNU220 | 25405.2 | 7.25 | 0.002 | 76 |
| LNU220 | 25405.2 | 0.906 | 0.001 | 70 | LNU138 | 14071.5 | 0.355 | 0.003 | 47 | LNU220 | 25405.5 | 7.21 | 0.003 | 75 |
| LNU220 | 25405.5 | 0.901 | 0.001 | 69 | LNU138 | 14072.5 | 0.312 | 0.045 | 30 | LNU220 | 25405.1 | 7.03 | 0.006 | 70 |
| LNU220 | 25405.1 | 0.879 | 0.003 | 64 | LNU138 | 14072.8 | 0.299 | 0.100 | 24 | LNU220 | 25405.6 | 5.97 | 0.036 | 45 |
| LNU220 | 25405.6 | 0.746 | 0.020 | 40 | LNU180 | 24721.2 | 0.404 | 0.000 | 67 | LNU220 | 25405.3 | 5.49 | 0.133 | 33 |
| LNU220 | 25405.3 | 0.686 | 0.111 | 28 | LNU180 | 24721.4 | 0.397 | 0.001 | 65 | LNU230 | 25413.1 | 7.87 | 0.001 | 90 |
| LNU230 | 25413.1 | 0.983 | 0.000 | 84 | LNU180 | 24723.1 | 0.393 | 0.000 | 63 | LNU230 | 25412.1 | 7.21 | 0.003 | 75 |
| LNU230 | 25412.1 | 0.902 | 0.001 | 69 | LNU180 | 24722.2 | 0.372 | 0.007 | 54 | LNU230 | 25415.1 | 6.63 | 0.013 | 60 |
| LNU230 | 25415.1 | 0.828 | 0.007 | 55 | LNU180 | 24724.1 | 0.355 | 0.026 | 47 | LNU230 | 25413.2 | 6.35 | 0.031 | 54 |
| LNU230 | 25412.2 | 0.807 | 0.005 | 51 | LNU220 | 25405.5 | 0.369 | 0.003 | 53 | LNU230 | 25412.2 | 6.05 | 0.032 | 46 |
| LNU230 | 25413.2 | 0.793 | 0.021 | 48 | LNU220 | 25405.2 | 0.353 | 0.009 | 47 | LNU234 | 25014.8 | 6.95 | 0.002 | 68 |
| LNU234 | 25014.8 | 0.868 | 0.001 | 63 | LNU220 | 25405.6 | 0.340 | 0.010 | 41 | LNU234 | 25014.1 | 6.22 | 0.021 | 51 |
| LNU234 | 25014.1 | 0.778 | 0.010 | 46 | LNU220 | 25405.1 | 0.332 | 0.043 | 38 | LNU234 | 25014.6 | 6.08 | 0.019 | 47 |
| LNU234 | 25014.6 | 0.759 | 0.007 | 42 | LNU220 | 25405.3 | 0.320 | 0.039 | 33 | LNU234 | 25014.4 | 5.76 | 0.047 | 40 |
| LNU234 | 25014.4 | 0.720 | 0.024 | 35 | LNU230 | 25413.1 | 0.382 | 0.003 | 59 | LNU234 | 25014.5 | 5.67 | 0.121 | 37 |
| LNU234 | 25014.5 | 0.709 | 0.107 | 33 | LNU230 | 25412.1 | 0.363 | 0.004 | 51 | LNU25 | 14082.8 | 7.38 | 0.002 | 79 |
| LNU25 | 14082.8 | 0.923 | 0.001 | 73 | LNU230 | 25412.2 | 0.331 | 0.024 | 37 | LNU25 | 14083.7 | 7.21 | 0.001 | 75 |
| LNU25 | 14083.7 | 0.901 | 0.000 | 69 | LNU230 | 25415.1 | 0.323 | 0.091 | 34 | LNU25 | 14082.9 | 7.12 | 0.001 | 72 |
| LNU25 | 14082.9 | 0.890 | 0.000 | 67 | LNU230 | 25413.2 | 0.317 | 0.083 | 32 | LNU25 | 14084.6 | 7.08 | 0.008 | 71 |
| LNU25 | 14084.6 | 0.885 | 0.005 | 66 | LNU234 | 25014.8 | 0.370 | 0.004 | 54 | LNU25 | 14083.1 | 6.98 | 0.012 | 69 |
| LNU25 | 14083.1 | 0.873 | 0.000 | 63 | LNU234 | 25014.1 | 0.339 | 0.026 | 41 | LNU254 | 25782.4 | 7.44 | 0.001 | 80 |
| LNU254 | 25782.4 | 0.931 | 0.000 | 74 | LNU234 | 25014.5 | 0.336 | 0.038 | 39 | LNU254 | 25781.3 | 7.41 | 0.001 | 79 |
| LNU254 | 25781.3 | 0.927 | 0.000 | 73 | LNU234 | 25014.6 | 0.325 | 0.019 | 35 | LNU254 | 25781.5 | 6.76 | 0.005 | 64 |
| LNU254 | 25781.5 | 0.845 | 0.002 | 58 | LNU234 | 25014.4 | 0.323 | 0.035 | 34 | LNU254 | 25783.1 | 6.35 | 0.026 | 54 |
| LNU254 | 25783.1 | 0.793 | 0.017 | 48 | LNU25 | 14082.9 | 0.381 | 0.001 | 58 | LNU254 | 25782.5 | 6.16 | 0.018 | 49 |
| LNU254 | 25782.5 | 0.769 | 0.007 | 44 | LNU25 | 14082.8 | 0.367 | 0.013 | 52 | LNU263 | 25794.3 | 7.49 | 0.001 | 81 |
| LNU263 | 25794.3 | 0.937 | 0.000 | 75 | LNU25 | 14083.1 | 0.361 | 0.002 | 50 | LNU263 | 25794.8 | 7.41 | 0.004 | 79 |
| LNU263 | 25794.8 | 0.926 | 0.003 | 73 | LNU25 | 14084.6 | 0.356 | 0.038 | 47 | LNU263 | 25791.3 | 7.30 | 0.001 | 77 |
| LNU263 | 25791.3 | 0.912 | 0.000 | 71 | LNU25 | 14083.7 | 0.343 | 0.014 | 42 | LNU263 | 25794.6 | 7.09 | 0.002 | 72 |
| LNU263 | 25794.6 | 0.886 | 0.001 | 66 | LNU254 | 25781.3 | 0.376 | 0.002 | 56 | LNU263 | 25792.2 | 6.66 | 0.006 | 61 |
| LNU263 | 25792.2 | 0.833 | 0.002 | 56 | LNU254 | 25782.4 | 0.363 | 0.007 | 50 | LNU267 | 25804.3 | 6.91 | 0.006 | 67 |
| LNU267 | 25804.3 | 0.864 | 0.003 | 62 | LNU254 | 25781.5 | 0.356 | 0.003 | 48 | LNU267 | 25804.4 | 6.88 | 0.002 | 67 |
| LNU267 | 25804.4 | 0.860 | 0.000 | 61 | LNU254 | 25782.5 | 0.345 | 0.007 | 43 | LNU267 | 25801.1 | 6.29 | 0.022 | 52 |
| LNU267 | 25801.1 | 0.786 | 0.012 | 47 | LNU254 | 25783.1 | 0.335 | 0.028 | 39 | LNU267 | 25803.1 | 6.23 | 0.013 | 51 |
| LNU267 | 25803.1 | 0.778 | 0.004 | 46 | LNU263 | 25794.3 | 0.383 | 0.000 | 59 | LNU267 | 25802.1 | 5.92 | 0.039 | 43 |
| LNU267 | 25802.1 | 0.740 | 0.022 | 39 | LNU263 | 25794.6 | 0.374 | 0.002 | 55 | LNU271 | 25911.4 | 8.12 | 0.000 | 97 |
| LNU271 | 25911.4 | 1.015 | 0.000 | 90 | LNU263 | 25794.8 | 0.370 | 0.007 | 53 | LNU271 | 25912.1 | 6.51 | 0.019 | 58 |
| LNU271 | 25912.1 | 0.862 | 0.001 | 61 | LNU263 | 25791.3 | 0.354 | 0.005 | 47 | LNU271 | 25913.3 | 6.28 | 0.014 | 52 |
| LNU271 | 25913.3 | 0.785 | 0.005 | 47 | LNU263 | 25792.2 | 0.350 | 0.010 | 45 | LNU271 | 25912.2 | 5.66 | 0.057 | 37 |
| LNU271 | 25912.2 | 0.707 | 0.030 | 32 | LNU267 | 25804.3 | 0.367 | 0.006 | 52 | LNU271 | 25913.2 | 4.79 | 0.488 | 16 |
| LNU271 | 25913.2 | 0.599 | 0.531 | 12 | LNU267 | 25803.1 | 0.357 | 0.003 | 48 | LNU278 | 25812.3 | 7.83 | 0.000 | 89 |
| LNU278 | 25812.3 | 0.978 | 0.000 | 83 | LNU267 | 25802.1 | 0.346 | 0.008 | 43 | LNU278 | 25814.3 | 7.58 | 0.000 | 84 |
| LNU278 | 25814.3 | 0.948 | 0.000 | 77 | LNU267 | 25804.4 | 0.335 | 0.010 | 39 | LNU278 | 25812.2 | 6.21 | 0.018 | 50 |
| LNU278 | 25812.2 | 0.776 | 0.008 | 45 | LNU267 | 25801.1 | 0.319 | 0.053 | 32 | LNU278 | 25814.1 | 5.82 | 0.051 | 41 |
| LNU278 | 25814.1 | 0.727 | 0.030 | 36 | LNU271 | 25911.4 | 0.399 | 0.000 | 65 | LNU278 | 25813.2 | 5.19 | 0.173 | 26 |
| LNU278 | 25813.2 | 0.648 | 0.132 | 21 | LNU271 | 25913.3 | 0.359 | 0.004 | 49 | LNU36 | 25562.9 | 7.33 | 0.000 | 78 |
| LNU36 | 25562.9 | 0.917 | 0.000 | 72 | LNU271 | 25912.2 | 0.332 | 0.013 | 38 | LNU36 | 25562.3 | 6.37 | 0.011 | 54 |
| LNU36 | 25562.3 | 0.797 | 0.004 | 49 | LNU271 | 25912.1 | 0.317 | 0.056 | 31 | LNU36 | 25562.4 | 5.88 | 0.031 | 42 |
| LNU36 | 25562.4 | 0.735 | 0.013 | 38 | LNU271 | 25913.2 | 0.265 | 0.611 | 10 | LNU36 | 25562.7 | 5.45 | 0.090 | 32 |
| LNU36 | 25562.7 | 0.681 | 0.053 | 27 | LNU278 | 25812.3 | 0.398 | 0.000 | 65 | LNU36 | 25561.2 | 5.42 | 0.105 | 31 |
| LNU36 | 25561.2 | 0.678 | 0.069 | 27 | LNU278 | 25814.3 | 0.352 | 0.006 | 46 | LNU43 | 14422.8 | 6.93 | 0.002 | 68 |
| LNU43 | 14422.8 | 0.867 | 0.000 | 62 | LNU278 | 25812.2 | 0.330 | 0.019 | 37 | LNU43 | 14422.9 | 6.46 | 0.007 | 56 |
| LNU43 | 14422.9 | 0.808 | 0.002 | 51 | LNU278 | 25814.1 | 0.290 | 0.263 | 20 | LNU43 | 14421.1 | 6.45 | 0.008 | 56 |
| LNU43 | 14421.1 | 0.806 | 0.002 | 51 | LNU278 | 25813.2 | 0.282 | 0.286 | 17 | LNU43 | 14423.6 | 5.85 | 0.033 | 42 |
| LNU43 | 14423.6 | 0.731 | 0.014 | 37 | LNU36 | 25562.9 | 0.342 | 0.013 | 42 | LNU43 | 14423.7 | 5.70 | 0.082 | 38 |
| LNU43 | 14423.7 | 0.712 | 0.060 | 33 | LNU36 | 25561.2 | 0.326 | 0.021 | 35 | LNU45 | 25052.12 | 7.16 | 0.003 | 73 |
| LNU45 | 25052.12 | 0.896 | 0.001 | 68 | LNU36 | 25562.3 | 0.324 | 0.025 | 34 | LNU45 | 25052.8 | 6.58 | 0.004 | 59 |
| LNU45 | 25052.8 | 0.823 | 0.001 | 54 | LNU36 | 25562.4 | 0.300 | 0.110 | 24 | LNU45 | 25052.9 | 6.10 | 0.017 | 48 |
| LNU45 | 25052.9 | 0.762 | 0.006 | 43 | LNU36 | 25562.7 | 0.288 | 0.196 | 19 | LNU45 | 25053.4 | 5.57 | 0.185 | 35 |
| LNU45 | 25053.4 | 0.697 | 0.182 | 30 | LNU43 | 14422.8 | 0.347 | 0.006 | 44 | LNU45 | 25052.11 | 5.20 | 0.176 | 26 |
| LNU45 | 25052.11 | 0.650 | 0.138 | 22 | LNU43 | 14422.9 | 0.336 | 0.013 | 39 | LNU67 | 25821.5 | 5.92 | 0.062 | 43 |
| LNU67 | 25821.5 | 0.740 | 0.046 | 39 | LNU43 | 14421.1 | 0.335 | 0.014 | 39 | LNU67 | 25824.5 | 5.91 | 0.067 | 43 |
| LNU67 | 25824.5 | 0.739 | 0.051 | 38 | LNU43 | 14423.6 | 0.325 | 0.027 | 35 | LNU67 | 25823.5 | 5.42 | 0.149 | 31 |
| LNU67 | 25823.5 | 0.678 | 0.127 | 27 | LNU43 | 14423.7 | 0.306 | 0.158 | 27 | LNU67 | 25824.3 | 5.29 | 0.208 | 28 |
| LNU67 | 25824.3 | 0.661 | 0.194 | 24 | LNU45 | 25052.12 | 0.365 | 0.006 | 51 | LNU67 | 25821.4 | 4.98 | 0.267 | 21 |
| LNU67 | 25821.4 | 0.623 | 0.236 | 17 | LNU45 | 25052.8 | 0.303 | 0.099 | 26 | CONT. | — | 3.80 | — | 0 |
| CONT. | — | 0.475 | — | 0 | LNU45 | 25052.11 | 0.302 | 0.097 | 25 | LNU100 | 14474.2 | 5.66 | 0.002 | 49 |
| LNU100 | 14474.2 | 0.708 | 0.002 | 49 | LNU45 | 25052.9 | 0.295 | 0.152 | 22 | LNU100 | 14472.1 | 5.36 | 0.011 | 41 |
| LNU100 | 14472.1 | 0.670 | 0.011 | 41 | LNU45 | 25053.4 | 0.266 | 0.626 | 10 | LNU100 | 14473.1 | 5.14 | 0.018 | 35 |

TABLE 81-continued

Genes showing improved rosette growth performance at limiting nitrogen growth conditions

| Gene Name | Event # | RGR Of Rosette Area Ave. | P-Value | % incr. | Gene Name | Event # | RGR Of Rosette Diameter Ave. | P-Value | % incr. | Gene Name | Event # | RGR Of Plot Coverage Ave. | P-Value | % incr. |
|---|---|---|---|---|---|---|---|---|---|---|---|---|---|---|
| LNU100 | 14473.1 | 0.642 | 0.018 | 35 | LNU67 | 25824.5 | 0.320 | 0.090 | 33 | LNU100 | 14473.3 | 5.11 | 0.031 | 34 |
| LNU100 | 14473.3 | 0.638 | 0.031 | 34 | LNU67 | 25824.3 | 0.316 | 0.058 | 31 | LNU100 | 14471.4 | 4.46 | 0.241 | 17 |
| LNU100 | 14471.4 | 0.557 | 0.241 | 17 | LNU67 | 25821.5 | 0.307 | 0.124 | 27 | LNU104 | 25033.1 | 4.65 | 0.121 | 23 |
| LNU104 | 25033.1 | 0.582 | 0.121 | 23 | LNU67 | 25823.5 | 0.284 | 0.341 | 18 | LNU104 | 25032.2 | 4.64 | 0.146 | 22 |
| LNU104 | 25032.2 | 0.580 | 0.146 | 22 | LNU67 | 25821.4 | 0.252 | 0.790 | 4 | LNU104 | 25032.1 | 4.40 | 0.263 | 16 |
| LNU104 | 25032.1 | 0.550 | 0.263 | 16 | CONT. | — | 0.289 | — | 0 | LNU104 | 25033.3 | 4.39 | 0.253 | 16 |
| LNU104 | 25033.3 | 0.549 | 0.253 | 16 | LNU100 | 14474.2 | 0.374 | 0.011 | 29 | LNU104 | 25033.8 | 4.02 | 0.705 | 6 |
| LNU104 | 25033.8 | 0.502 | 0.705 | 6 | LNU100 | 14473.3 | 0.359 | 0.039 | 24 | LNU106 | 14483.2 | 5.70 | 0.001 | 50 |
| LNU106 | 14483.2 | 0.713 | 0.001 | 50 | LNU100 | 14472.1 | 0.356 | 0.060 | 23 | LNU106 | 14481.1 | 4.90 | 0.066 | 29 |
| LNU106 | 14481.1 | 0.612 | 0.066 | 29 | LNU100 | 14473.1 | 0.351 | 0.053 | 22 | LNU106 | 14483.5 | 4.59 | 0.134 | 21 |
| LNU106 | 14483.5 | 0.573 | 0.134 | 21 | LNU100 | 14471.4 | 0.335 | 0.163 | 16 | LNU106 | 14484.3 | 4.41 | 0.281 | 16 |
| LNU106 | 14484.3 | 0.551 | 0.281 | 16 | LNU104 | 25033.3 | 0.334 | 0.157 | 15 | LNU114 | 25044.11 | 5.15 | 0.023 | 36 |
| LNU114 | 25044.11 | 0.643 | 0.023 | 36 | LNU104 | 25033.1 | 0.330 | 0.247 | 14 | LNU114 | 25041.2 | 4.91 | 0.044 | 29 |
| LNU114 | 25041.2 | 0.614 | 0.044 | 29 | LNU104 | 25032.1 | 0.324 | 0.262 | 12 | LNU114 | 25042.1 | 4.54 | 0.175 | 19 |
| LNU114 | 25042.1 | 0.567 | 0.175 | 19 | LNU104 | 25033.8 | 0.315 | 0.468 | 9 | LNU114 | 25041.1 | 4.37 | 0.379 | 15 |
| LNU114 | 25041.1 | 0.546 | 0.379 | 15 | LNU104 | 25032.2 | 0.312 | 0.475 | 8 | LNU114 | 25044.4 | 4.13 | 0.578 | 9 |
| LNU114 | 25044.4 | 0.516 | 0.578 | 9 | LNU106 | 14483.2 | 0.397 | 0.001 | 38 | LNU117 | 25932.4 | 5.18 | 0.013 | 36 |
| LNU117 | 25932.4 | 0.647 | 0.013 | 36 | LNU106 | 14481.1 | 0.345 | 0.110 | 19 | LNU117 | 25931.4 | 4.89 | 0.043 | 29 |
| LNU117 | 25931.4 | 0.612 | 0.043 | 29 | LNU106 | 14483.5 | 0.326 | 0.241 | 13 | LNU117 | 25931.1 | 4.26 | 0.438 | 12 |
| LNU117 | 25931.1 | 0.532 | 0.438 | 12 | LNU106 | 14484.3 | 0.317 | 0.401 | 10 | LNU117 | 25931.2 | 4.20 | 0.448 | 11 |
| LNU117 | 25931.2 | 0.525 | 0.448 | 11 | LNU114 | 25044.11 | 0.348 | 0.075 | 20 | LNU155 | 14523.5 | 4.92 | 0.050 | 30 |
| LNU155 | 14523.5 | 0.616 | 0.050 | 30 | LNU114 | 25041.2 | 0.347 | 0.066 | 20 | LNU155 | 14524.8 | 4.12 | 0.540 | 9 |
| LNU155 | 14524.8 | 0.515 | 0.540 | 9 | LNU114 | 25041.1 | 0.338 | 0.204 | 17 | LNU180 | 24723.1 | 4.93 | 0.037 | 30 |
| LNU180 | 24723.1 | 0.617 | 0.037 | 30 | LNU114 | 25042.1 | 0.335 | 0.153 | 16 | LNU180 | 24722.2 | 4.47 | 0.282 | 18 |
| LNU180 | 24722.2 | 0.559 | 0.282 | 18 | LNU117 | 25932.4 | 0.374 | 0.011 | 30 | LNU218 | 24781.4 | 5.34 | 0.007 | 41 |
| LNU218 | 24781.4 | 0.668 | 0.007 | 41 | LNU117 | 25931.4 | 0.326 | 0.236 | 13 | LNU218 | 24781.1 | 4.83 | 0.066 | 27 |
| LNU218 | 24781.1 | 0.604 | 0.066 | 27 | LNU117 | 25931.2 | 0.316 | 0.405 | 9 | LNU218 | 24781.6 | 4.00 | 0.696 | 5 |
| LNU218 | 24781.6 | 0.501 | 0.696 | 5 | LNU117 | 25931.1 | 0.314 | 0.458 | 9 | LNU218 | 24781.2 | 3.96 | 0.758 | 4 |
| LNU218 | 24781.2 | 0.495 | 0.758 | 4 | LNU155 | 14523.5 | 0.329 | 0.228 | 14 | LNU254 | 25782.5 | 4.78 | 0.073 | 26 |
| LNU254 | 25782.5 | 0.598 | 0.073 | 26 | LNU155 | 14524.8 | 0.320 | 0.324 | 11 | LNU4 | 25134.3 | 5.40 | 0.009 | 42 |
| LNU4 | 25134.3 | 0.675 | 0.009 | 42 | LNU180 | 24722.2 | 0.354 | 0.102 | 23 | LNU4 | 25134.2 | 4.65 | 0.115 | 23 |
| LNU4 | 25134.2 | 0.581 | 0.115 | 23 | LNU180 | 24723.1 | 0.349 | 0.060 | 21 | LNU4 | 25131.1 | 4.56 | 0.170 | 20 |
| LNU4 | 25131.1 | 0.570 | 0.170 | 20 | LNU180 | 24721.2 | 0.304 | 0.629 | 5 | LNU4 | 25133.3 | 4.15 | 0.504 | 9 |
| LNU4 | 25133.3 | 0.519 | 0.504 | 9 | LNU218 | 24781.4 | 0.386 | 0.004 | 34 | LNU40 | 24794.3 | 4.55 | 0.220 | 20 |
| LNU40 | 24794.3 | 0.569 | 0.220 | 20 | LNU218 | 24781.1 | 0.365 | 0.020 | 27 | LNU40 | 24792.1 | 4.42 | 0.230 | 17 |
| LNU40 | 24792.1 | 0.553 | 0.230 | 17 | LNU218 | 24781.2 | 0.329 | 0.201 | 14 | LNU40 | 24794.4 | 4.00 | 0.696 | 5 |
| LNU40 | 24794.4 | 0.500 | 0.696 | 5 | LNU218 | 24781.6 | 0.314 | 0.430 | 9 | LNU46 | 14462.5 | 5.13 | 0.024 | 35 |
| LNU46 | 14462.5 | 0.642 | 0.024 | 35 | LNU254 | 25782.5 | 0.353 | 0.046 | 22 | LNU46 | 14462.1 | 4.18 | 0.458 | 10 |
| LNU46 | 14462.1 | 0.523 | 0.458 | 10 | LNU4 | 25134.3 | 0.368 | 0.029 | 28 | LNU46 | 14464.4 | 4.16 | 0.488 | 10 |
| LNU46 | 14464.4 | 0.520 | 0.488 | 10 | LNU4 | 25134.2 | 0.324 | 0.272 | 12 | LNU48 | 24801.4 | 4.69 | 0.098 | 24 |
| LNU48 | 24801.4 | 0.586 | 0.098 | 24 | LNU4 | 25131.1 | 0.324 | 0.294 | 12 | LNU48 | 24803.2 | 4.49 | 0.231 | 18 |
| LNU48 | 24803.2 | 0.562 | 0.231 | 18 | LNU4 | 25133.3 | 0.314 | 0.437 | 9 | LNU63 | 24812.3 | 5.17 | 0.015 | 36 |
| LNU48 | 24802.2 | 0.503 | 0.687 | 6 | LNU40 | 24794.3 | 0.336 | 0.199 | 16 | LNU63 | 24814.7 | 4.35 | 0.320 | 14 |
| LNU63 | 24812.3 | 0.646 | 0.015 | 36 | LNU40 | 24792.1 | 0.311 | 0.470 | 8 | LNU7 | 25082.2 | 4.87 | 0.070 | 28 |
| LNU63 | 24814.7 | 0.543 | 0.320 | 14 | LNU40 | 24794.4 | 0.310 | 0.496 | 7 | LNU7 | 25083.1 | 4.37 | 0.289 | 15 |
| LNU7 | 25082.2 | 0.609 | 0.070 | 28 | LNU46 | 14462.5 | 0.335 | 0.190 | 16 | LNU7 | 25083.3 | 4.21 | 0.443 | 11 |
| LNU7 | 25083.1 | 0.546 | 0.289 | 15 | LNU46 | 14462.1 | 0.323 | 0.265 | 12 | LNU8 | 25063.6 | 5.22 | 0.013 | 37 |
| LNU7 | 25083.3 | 0.526 | 0.443 | 11 | LNU46 | 14464.4 | 0.312 | 0.454 | 8 | LNU8 | 25061.2 | 4.50 | 0.179 | 19 |
| LNU8 | 25063.6 | 0.652 | 0.013 | 37 | LNU48 | 24803.2 | 0.337 | 0.175 | 17 | LNU94 | 24833.3 | 4.45 | 0.240 | 17 |
| LNU8 | 25061.2 | 0.563 | 0.179 | 19 | LNU48 | 24801.4 | 0.334 | 0.166 | 16 | CONT. | — | 5.26 | — | 0 |
| LNU94 | 24833.3 | 0.556 | 0.240 | 17 | LNU48 | 24802.2 | 0.310 | 0.515 | 7 | LNU122 | 25332.1 | 6.26 | 0.154 | 19 |
| CONT. | — | 0.658 | — | 0 | LNU48 | 24804.4 | 0.300 | 0.715 | 4 | LNU122 | 25332.2 | 6.17 | 0.190 | 17 |
| LNU122 | 25332.1 | 0.782 | 0.154 | 19 | LNU63 | 24812.3 | 0.356 | 0.041 | 23 | LNU122 | 25332.5 | 5.78 | 0.455 | 10 |
| LNU122 | 25332.2 | 0.771 | 0.190 | 17 | LNU63 | 24814.7 | 0.327 | 0.239 | 13 | LNU125 | 25943.2 | 5.69 | 0.530 | 8 |
| LNU122 | 25332.5 | 0.723 | 0.455 | 10 | LNU63 | 24814.2 | 0.310 | 0.494 | 7 | LNU125 | 25941.4 | 5.58 | 0.643 | 6 |
| LNU125 | 25943.2 | 0.711 | 0.530 | 8 | LNU7 | 25082.2 | 0.341 | 0.128 | 18 | LNU125 | 25944.1 | 5.44 | 0.797 | 3 |
| LNU125 | 25941.4 | 0.697 | 0.643 | 6 | LNU7 | 25083.1 | 0.339 | 0.114 | 17 | LNU138 | 14074.5 | 5.71 | 0.514 | 8 |
| LNU125 | 25944.1 | 0.681 | 0.797 | 3 | LNU8 | 25063.6 | 0.354 | 0.046 | 23 | LNU157 | 24982.1 | 5.62 | 0.607 | 7 |
| LNU138 | 14074.5 | 0.714 | 0.514 | 8 | LNU8 | 25061.2 | 0.324 | 0.254 | 12 | LNU178 | 14614.5 | 6.17 | 0.189 | 17 |
| LNU157 | 24982.1 | 0.703 | 0.607 | 7 | CONT. | — | 0.352 | — | 0 | LNU178 | 14611.5 | 5.80 | 0.430 | 10 |
| LNU178 | 14614.5 | 0.771 | 0.189 | 17 | LNU10 | 25123.5 | 0.379 | 0.378 | 8 | LNU178 | 14612.1 | 5.63 | 0.595 | 7 |
| LNU178 | 14611.5 | 0.725 | 0.430 | 10 | LNU122 | 25332.2 | 0.399 | 0.125 | 13 | LNU178 | 14611.4 | 5.56 | 0.664 | 6 |
| LNU178 | 14612.1 | 0.704 | 0.595 | 7 | LNU122 | 25332.1 | 0.394 | 0.177 | 12 | LNU220 | 25405.6 | 5.86 | 0.398 | 11 |
| LNU178 | 14611.4 | 0.695 | 0.664 | 6 | LNU122 | 25332.5 | 0.388 | 0.241 | 10 | LNU220 | 25405.5 | 5.83 | 0.409 | 11 |
| LNU220 | 25405.6 | 0.732 | 0.398 | 11 | LNU125 | 25944.1 | 0.370 | 0.592 | 5 | LNU220 | 25405.1 | 5.79 | 0.438 | 10 |
| LNU220 | 25405.5 | 0.729 | 0.409 | 11 | LNU125 | 25943.2 | 0.367 | 0.611 | 4 | LNU220 | 25405.2 | 5.59 | 0.633 | 6 |
| LNU220 | 25405.1 | 0.723 | 0.438 | 10 | LNU125 | 25941.2 | 0.367 | 0.639 | 4 | LNU234 | 25014.4 | 5.62 | 0.621 | 7 |
| LNU220 | 25405.2 | 0.699 | 0.633 | 6 | LNU138 | 14074.5 | 0.393 | 0.180 | 12 | LNU234 | 25014.6 | 5.50 | 0.728 | 5 |
| LNU234 | 25014.4 | 0.703 | 0.621 | 7 | LNU138 | 14071.5 | 0.376 | 0.424 | 7 | LNU236 | 25424.2 | 6.84 | 0.028 | 30 |
| LNU234 | 25014.6 | 0.688 | 0.728 | 5 | LNU138 | 14074.6 | 0.371 | 0.526 | 5 | LNU236 | 25422.4 | 5.91 | 0.336 | 12 |
| LNU236 | 25424.2 | 0.855 | 0.028 | 30 | LNU157 | 24982.1 | 0.399 | 0.137 | 13 | LNU236 | 25425.4 | 5.82 | 0.420 | 11 |
| LNU236 | 25422.4 | 0.739 | 0.336 | 12 | LNU157 | 24983.3 | 0.365 | 0.675 | 4 | LNU236 | 25423.3 | 5.76 | 0.479 | 9 |

TABLE 81-continued

Genes showing improved rosette growth performance at limiting nitrogen growth conditions

| Gene Name | Event # | RGR Of Rosette Area Ave. | P-Value | % incr. | Gene Name | Event # | RGR Of Rosette Diameter Ave. | P-Value | % incr. | Gene Name | Event # | RGR Of Plot Coverage Ave. | P-Value | % incr. |
|---|---|---|---|---|---|---|---|---|---|---|---|---|---|---|
| LNU236 | 25425.4 | 0.728 | 0.420 | 11 | LNU178 | 14611.5 | 0.382 | 0.336 | 8 | LNU24 | 24974.2 | 5.55 | 0.672 | 5 |
| LNU236 | 25423.3 | 0.720 | 0.479 | 9 | LNU178 | 14614.5 | 0.381 | 0.325 | 8 | LNU24 | 24972.1 | 5.45 | 0.786 | 4 |
| LNU24 | 24974.2 | 0.694 | 0.672 | 5 | LNU178 | 14611.1 | 0.370 | 0.552 | 5 | LNU25 | 14082.8 | 6.62 | 0.055 | 26 |
| LNU24 | 24972.1 | 0.681 | 0.786 | 4 | LNU178 | 14611.4 | 0.366 | 0.648 | 4 | LNU25 | 14082.9 | 5.75 | 0.484 | 9 |
| LNU25 | 14082.8 | 0.827 | 0.055 | 26 | LNU178 | 14612.1 | 0.363 | 0.717 | 3 | LNU25 | 14084.6 | 5.55 | 0.670 | 6 |
| LNU25 | 14082.9 | 0.719 | 0.484 | 9 | LNU220 | 25405.2 | 0.382 | 0.336 | 8 | LNU271 | 25911.4 | 5.93 | 0.358 | 13 |
| LNU25 | 14084.6 | 0.694 | 0.670 | 6 | LNU220 | 25405.5 | 0.376 | 0.427 | 7 | LNU278 | 25814.1 | 5.78 | 0.448 | 10 |
| LNU271 | 25911.4 | 0.741 | 0.358 | 13 | LNU220 | 25405.6 | 0.367 | 0.635 | 4 | LNU278 | 25814.3 | 5.50 | 0.720 | 5 |
| LNU278 | 25814.1 | 0.722 | 0.448 | 10 | LNU234 | 25014.6 | 0.368 | 0.595 | 5 | LNU278 | 25812.2 | 5.47 | 0.754 | 4 |
| LNU278 | 25814.3 | 0.688 | 0.720 | 5 | LNU236 | 25424.2 | 0.423 | 0.025 | 20 | LNU43 | 14423.7 | 5.68 | 0.545 | 8 |
| LNU278 | 25812.2 | 0.684 | 0.754 | 4 | LNU236 | 25423.3 | 0.379 | 0.418 | 8 | LNU43 | 14422.9 | 5.46 | 0.777 | 4 |
| LNU43 | 14423.7 | 0.709 | 0.545 | 8 | LNU236 | 25422.4 | 0.366 | 0.629 | 4 | LNU45 | 25052.12 | 7.19 | 0.008 | 36 |
| LNU43 | 14422.9 | 0.683 | 0.777 | 4 | LNU24 | 24972.1 | 0.372 | 0.522 | 6 | LNU45 | 25053.4 | 6.71 | 0.048 | 27 |
| LNU45 | 25052.12 | 0.898 | 0.008 | 36 | LNU24 | 24971.2 | 0.365 | 0.689 | 4 | LNU45 | 25052.11 | 5.94 | 0.317 | 13 |
| LNU45 | 25053.4 | 0.839 | 0.048 | 27 | LNU24 | 24974.2 | 0.364 | 0.696 | 3 | LNU45 | 25052.9 | 5.75 | 0.471 | 9 |
| LNU45 | 25052.11 | 0.742 | 0.317 | 13 | LNU25 | 14082.8 | 0.395 | 0.154 | 12 | LNU67 | 25824.3 | 6.41 | 0.104 | 22 |
| LNU45 | 25052.9 | 0.719 | 0.471 | 9 | LNU25 | 14082.9 | 0.393 | 0.184 | 12 | LNU67 | 25824.5 | 5.89 | 0.354 | 12 |
| LNU67 | 25824.3 | 0.801 | 0.104 | 22 | LNU271 | 25911.4 | 0.388 | 0.243 | 10 | LNU67 | 25821.4 | 5.70 | 0.521 | 8 |
| LNU67 | 25824.5 | 0.736 | 0.354 | 12 | LNU271 | 25912.1 | 0.362 | 0.743 | 3 | LNU9 | 25001.1 | 6.13 | 0.201 | 16 |
| LNU67 | 25821.4 | 0.713 | 0.521 | 8 | LNU278 | 25813.2 | 0.382 | 0.340 | 8 | LNU9 | 25001.7 | 6.03 | 0.271 | 15 |
| LNU9 | 25001.1 | 0.767 | 0.201 | 16 | LNU43 | 14422.9 | 0.379 | 0.417 | 8 | LNU9 | 25003.1 | 5.56 | 0.670 | 6 |
| LNU9 | 25001.7 | 0.754 | 0.271 | 15 | LNU43 | 14423.7 | 0.377 | 0.421 | 7 | CONT. | — | 5.11 | — | 0 |
| LNU9 | 25003.1 | 0.695 | 0.670 | 6 | LNU43 | 14423.6 | 0.365 | 0.680 | 4 | LNU10 | 25123.6 | 6.24 | 0.253 | 22 |
| CONT. | — | 0.638 | — | 0 | LNU45 | 25052.12 | 0.407 | 0.076 | 16 | LNU157 | 24982.8 | 6.83 | 0.093 | 34 |
| LNU10 | 25123.6 | 0.779 | 0.253 | 22 | LNU45 | 25053.4 | 0.397 | 0.161 | 13 | LNU157 | 24982.4 | 5.78 | 0.506 | 13 |
| LNU157 | 24982.8 | 0.853 | 0.093 | 34 | LNU45 | 25052.9 | 0.368 | 0.599 | 4 | LNU157 | 24983.3 | 5.44 | 0.736 | 7 |
| LNU157 | 24982.4 | 0.723 | 0.506 | 13 | LNU67 | 25824.3 | 0.395 | 0.165 | 12 | LNU168 | 24751.2 | 5.47 | 0.732 | 7 |
| LNU157 | 24983.3 | 0.680 | 0.736 | 7 | LNU67 | 25824.5 | 0.393 | 0.173 | 12 | LNU173 | 25451.1 | 6.15 | 0.322 | 20 |
| LNU168 | 24751.2 | 0.683 | 0.732 | 7 | LNU67 | 25821.4 | 0.368 | 0.597 | 5 | LNU178 | 14611.4 | 7.38 | 0.047 | 45 |
| LNU173 | 25451.1 | 0.768 | 0.322 | 20 | LNU67 | 25821.5 | 0.364 | 0.712 | 3 | LNU178 | 14611.5 | 6.73 | 0.122 | 32 |
| LNU178 | 14611.4 | 0.923 | 0.047 | 45 | LNU9 | 25001.7 | 0.379 | 0.381 | 8 | LNU178 | 14611.1 | 6.59 | 0.187 | 29 |
| LNU178 | 14611.5 | 0.842 | 0.122 | 32 | LNU9 | 25001.2 | 0.378 | 0.396 | 7 | LNU184 | 25393.2 | 6.42 | 0.202 | 26 |
| LNU178 | 14611.1 | 0.823 | 0.187 | 29 | LNU9 | 25003.1 | 0.370 | 0.566 | 5 | LNU184 | 25393.3 | 6.25 | 0.281 | 22 |
| LNU184 | 25393.2 | 0.803 | 0.202 | 26 | LNU9 | 25001.1 | 0.368 | 0.580 | 5 | LNU184 | 25393.1 | 6.04 | 0.411 | 18 |
| LNU184 | 25393.3 | 0.782 | 0.281 | 22 | CONT. | — | 0.307 | — | 0 | LNU184 | 25395.1 | 5.98 | 0.419 | 17 |
| LNU184 | 25393.1 | 0.755 | 0.411 | 18 | LNU157 | 24982.8 | 0.372 | 0.169 | 21 | LNU230 | 25413.1 | 6.82 | 0.101 | 34 |
| LNU184 | 25395.1 | 0.747 | 0.419 | 17 | LNU157 | 24982.4 | 0.354 | 0.335 | 16 | LNU230 | 25413.2 | 6.73 | 0.124 | 32 |
| LNU230 | 25413.1 | 0.852 | 0.101 | 34 | LNU157 | 24983.3 | 0.319 | 0.797 | 4 | LNU230 | 25412.1 | 6.22 | 0.275 | 22 |
| LNU230 | 25413.2 | 0.841 | 0.124 | 32 | LNU168 | 24751.2 | 0.346 | 0.435 | 13 | LNU230 | 25412.2 | 6.09 | 0.339 | 19 |
| LNU230 | 25412.1 | 0.778 | 0.275 | 22 | LNU173 | 25451.1 | 0.399 | 0.076 | 30 | LNU230 | 25415.1 | 6.04 | 0.370 | 18 |
| LNU230 | 25412.2 | 0.761 | 0.339 | 19 | LNU173 | 25451.11 | 0.337 | 0.519 | 10 | LNU236 | 25425.4 | 7.78 | 0.014 | 52 |
| LNU230 | 25415.1 | 0.755 | 0.370 | 18 | LNU173 | 25451.2 | 0.335 | 0.563 | 9 | LNU236 | 25423.3 | 6.50 | 0.189 | 27 |
| LNU236 | 25425.4 | 0.973 | 0.014 | 52 | LNU178 | 14611.4 | 0.400 | 0.074 | 30 | LNU236 | 25422.4 | 5.94 | 0.416 | 16 |
| LNU236 | 25423.3 | 0.813 | 0.189 | 27 | LNU178 | 14611.5 | 0.379 | 0.143 | 24 | LNU236 | 25424.2 | 5.93 | 0.419 | 16 |
| LNU236 | 25422.4 | 0.743 | 0.416 | 16 | LNU178 | 14611.1 | 0.353 | 0.368 | 15 | LNU24 | 24974.2 | 7.22 | 0.048 | 41 |
| LNU236 | 25424.2 | 0.741 | 0.419 | 16 | LNU184 | 25393.3 | 0.368 | 0.232 | 20 | LNU24 | 24971.3 | 6.02 | 0.366 | 18 |
| LNU24 | 24974.2 | 0.903 | 0.048 | 41 | LNU184 | 25393.2 | 0.358 | 0.291 | 17 | LNU263 | 25791.3 | 6.66 | 0.142 | 30 |
| LNU24 | 24971.3 | 0.753 | 0.366 | 18 | LNU184 | 25395.1 | 0.354 | 0.364 | 15 | LNU263 | 25794.3 | 6.36 | 0.229 | 25 |
| LNU263 | 25791.3 | 0.832 | 0.142 | 30 | LNU184 | 25393.1 | 0.344 | 0.492 | 12 | LNU263 | 25794.8 | 6.23 | 0.272 | 22 |
| LNU263 | 25794.3 | 0.795 | 0.229 | 25 | LNU184 | 25394.3 | 0.325 | 0.701 | 6 | LNU263 | 25792.2 | 5.56 | 0.649 | 9 |
| LNU263 | 25794.8 | 0.779 | 0.272 | 22 | LNU20 | 24933.4 | 0.348 | 0.400 | 13 | LNU276 | 25433.1 | 6.40 | 0.218 | 25 |
| LNU263 | 25792.2 | 0.695 | 0.649 | 9 | LNU230 | 25413.2 | 0.382 | 0.133 | 25 | LNU276 | 25431.1 | 6.37 | 0.226 | 25 |
| LNU276 | 25433.1 | 0.800 | 0.218 | 25 | LNU230 | 25413.1 | 0.373 | 0.175 | 22 | LNU276 | 25433.3 | 6.01 | 0.361 | 18 |
| LNU276 | 25431.1 | 0.796 | 0.226 | 25 | LNU230 | 25412.1 | 0.352 | 0.348 | 15 | LNU279 | 25484.3 | 6.77 | 0.111 | 33 |
| LNU276 | 25433.3 | 0.752 | 0.361 | 18 | LNU230 | 25415.1 | 0.340 | 0.486 | 11 | LNU279 | 25481.3 | 6.62 | 0.165 | 30 |
| LNU279 | 25484.3 | 0.846 | 0.111 | 33 | LNU230 | 25412.2 | 0.327 | 0.684 | 7 | LNU279 | 25481.5 | 6.32 | 0.245 | 24 |
| LNU279 | 25481.3 | 0.827 | 0.165 | 30 | LNU236 | 25425.4 | 0.426 | 0.018 | 39 | LNU279 | 25481.2 | 6.07 | 0.400 | 19 |
| LNU279 | 25481.5 | 0.790 | 0.245 | 24 | LNU236 | 25423.3 | 0.352 | 0.365 | 15 | LNU279 | 25481.4 | 6.07 | 0.356 | 19 |
| LNU279 | 25481.2 | 0.759 | 0.400 | 19 | LNU236 | 25424.2 | 0.352 | 0.351 | 15 | LNU36 | 25562.3 | 6.64 | 0.161 | 30 |
| LNU279 | 25481.4 | 0.759 | 0.356 | 19 | LNU236 | 25422.4 | 0.325 | 0.705 | 6 | LNU36 | 25562.7 | 6.54 | 0.219 | 28 |
| LNU36 | 25562.3 | 0.830 | 0.161 | 30 | LNU24 | 24974.2 | 0.401 | 0.057 | 31 | LNU36 | 25561.2 | 6.18 | 0.307 | 21 |
| LNU36 | 25562.7 | 0.817 | 0.219 | 28 | LNU24 | 24971.3 | 0.361 | 0.263 | 18 | LNU56 | 24694.1 | 6.66 | 0.177 | 31 |
| LNU36 | 25561.2 | 0.772 | 0.307 | 21 | LNU24 | 24971.4 | 0.348 | 0.467 | 14 | LNU56 | 24693.1 | 6.41 | 0.228 | 25 |
| LNU56 | 24694.1 | 0.833 | 0.177 | 31 | LNU24 | 24971.2 | 0.323 | 0.729 | 5 | LNU56 | 24691.2 | 6.26 | 0.267 | 23 |
| LNU56 | 24693.1 | 0.801 | 0.228 | 25 | LNU263 | 25791.3 | 0.362 | 0.271 | 18 | LNU56 | 24694.2 | 5.66 | 0.598 | 11 |
| LNU56 | 24691.2 | 0.783 | 0.267 | 23 | LNU263 | 25794.8 | 0.361 | 0.260 | 18 | LNU73 | 25755.1 | 7.76 | 0.015 | 52 |
| LNU56 | 24694.2 | 0.707 | 0.598 | 11 | LNU263 | 25794.3 | 0.354 | 0.328 | 15 | LNU73 | 25751.1 | 6.71 | 0.120 | 31 |
| LNU73 | 25755.1 | 0.970 | 0.015 | 52 | LNU263 | 25794.6 | 0.341 | 0.506 | 11 | LNU73 | 25751.9 | 6.57 | 0.163 | 29 |
| LNU73 | 25751.1 | 0.839 | 0.120 | 31 | LNU276 | 25433.1 | 0.382 | 0.135 | 25 | LNU73 | 25751.8 | 6.32 | 0.271 | 24 |
| LNU73 | 25751.9 | 0.822 | 0.163 | 29 | LNU276 | 25431.1 | 0.374 | 0.174 | 22 | LNU73 | 25754.2 | 6.25 | 0.291 | 22 |

TABLE 81-continued

Genes showing improved rosette growth performance at limiting nitrogen growth conditions

| | | RGR Of Rosette Area | | | | | RGR Of Rosette Diameter | | | | | RGR Of Plot Coverage | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU73 | 25751.8 | 0.790 | 0.271 | 24 | LNU276 | 25433.3 | 0.346 | 0.409 | 13 | LNU9 | 25001.7 | 6.80 | 0.115 | 33 |
| LNU73 | 25754.2 | 0.782 | 0.291 | 22 | LNU276 | 25433.2 | 0.338 | 0.534 | 10 | LNU9 | 25001.1 | 6.51 | 0.177 | 27 |
| LNU9 | 25001.7 | 0.851 | 0.115 | 33 | LNU279 | 25481.3 | 0.372 | 0.202 | 21 | LNU9 | 25001.2 | 6.05 | 0.356 | 18 |
| LNU9 | 25001.1 | 0.813 | 0.177 | 27 | LNU279 | 25484.3 | 0.367 | 0.215 | 20 | CONT. | — | 3.57 | — | 0 |
| LNU9 | 25001.2 | 0.756 | 0.356 | 18 | LNU279 | 25481.4 | 0.355 | 0.331 | 16 | LNU131 | 14005.5 | 7.37 | 0.000 | 106 |
| CONT. | — | 0.451 | — | 0 | LNU279 | 25481.2 | 0.346 | 0.475 | 13 | LNU131 | 14005.2 | 5.32 | 0.050 | 49 |
| LNU131 | 14005.5 | 0.921 | 0.000 | 104 | LNU279 | 25481.5 | 0.341 | 0.485 | 11 | LNU131 | 14002.15 | 4.88 | 0.135 | 36 |
| LNU131 | 14005.2 | 0.665 | 0.059 | 47 | LNU36 | 25562.3 | 0.393 | 0.090 | 28 | LNU135 | 26204.2 | 7.67 | 0.000 | 115 |
| LNU131 | 14002.15 | 0.609 | 0.154 | 35 | LNU36 | 25561.2 | 0.371 | 0.195 | 21 | LNU135 | 26203.6 | 5.27 | 0.052 | 48 |
| LNU135 | 26204.2 | 0.959 | 0.000 | 113 | LNU36 | 25562.7 | 0.361 | 0.323 | 18 | LNU135 | 26203.4 | 5.22 | 0.074 | 46 |
| LNU135 | 26203.6 | 0.659 | 0.061 | 46 | LNU36 | 25562.4 | 0.331 | 0.618 | 8 | LNU135 | 26203.1 | 4.95 | 0.109 | 39 |
| LNU135 | 26203.4 | 0.653 | 0.085 | 45 | LNU36 | 25562.9 | 0.321 | 0.763 | 5 | LNU135 | 26203.3 | 4.18 | 0.494 | 17 |
| LNU135 | 26203.1 | 0.619 | 0.126 | 37 | LNU53 | 25674.1 | 0.328 | 0.660 | 7 | LNU161 | 14553.5 | 5.35 | 0.060 | 50 |
| LNU135 | 26203.3 | 0.522 | 0.528 | 16 | LNU53 | 25674.3 | 0.324 | 0.716 | 6 | LNU161 | 14553.6 | 4.33 | 0.372 | 21 |
| LNU161 | 14553.5 | 0.669 | 0.069 | 48 | LNU53 | 25674.6 | 0.322 | 0.759 | 5 | LNU173 | 25451.2 | 4.03 | 0.583 | 13 |
| LNU161 | 14553.6 | 0.541 | 0.404 | 20 | LNU56 | 24694.1 | 0.381 | 0.171 | 24 | LNU173 | 25451.5 | 3.89 | 0.709 | 9 |
| LNU173 | 25451.2 | 0.504 | 0.620 | 12 | LNU56 | 24694.1 | 0.372 | 0.204 | 21 | LNU181 | 25771.2 | 5.43 | 0.036 | 52 |
| LNU173 | 25451.5 | 0.486 | 0.746 | 8 | LNU56 | 24691.2 | 0.368 | 0.220 | 20 | LNU181 | 25771.11 | 4.74 | 0.176 | 33 |
| LNU181 | 25771.2 | 0.679 | 0.044 | 51 | LNU56 | 24694.2 | 0.343 | 0.477 | 12 | LNU181 | 25771.6 | 4.74 | 0.171 | 33 |
| LNU181 | 25771.11 | 0.593 | 0.198 | 31 | LNU73 | 25755.1 | 0.405 | 0.051 | 32 | LNU181 | 25774.1 | 4.36 | 0.350 | 22 |
| LNU181 | 25771.6 | 0.593 | 0.194 | 31 | LNU73 | 25751.1 | 0.387 | 0.103 | 26 | LNU181 | 25771.8 | 3.81 | 0.783 | 7 |
| LNU181 | 25774.1 | 0.545 | 0.382 | 21 | LNU73 | 25751.8 | 0.379 | 0.165 | 24 | LNU184 | 25395.1 | 6.17 | 0.006 | 73 |
| LNU184 | 25395.1 | 0.771 | 0.007 | 71 | LNU73 | 25754.2 | 0.378 | 0.171 | 23 | LNU184 | 25394.3 | 6.00 | 0.010 | 68 |
| LNU184 | 25394.3 | 0.750 | 0.012 | 66 | LNU73 | 25751.9 | 0.377 | 0.145 | 23 | LNU184 | 25394.1 | 5.43 | 0.040 | 52 |
| LNU184 | 25394.1 | 0.678 | 0.047 | 50 | LNU9 | 25001.7 | 0.374 | 0.163 | 22 | LNU184 | 25393.3 | 5.24 | 0.057 | 47 |
| LNU184 | 25393.3 | 0.655 | 0.068 | 45 | LNU9 | 25001.2 | 0.370 | 0.207 | 21 | LNU184 | 25393.2 | 4.23 | 0.436 | 18 |
| LNU184 | 25393.2 | 0.529 | 0.470 | 17 | LNU9 | 25001.2 | 0.350 | 0.362 | 14 | LNU184 | 25393.1 | 4.19 | 0.472 | 17 |
| LNU184 | 25393.1 | 0.524 | 0.506 | 16 | LNU9 | 25001.3 | 0.326 | 0.687 | 6 | LNU224 | 25871.3 | 5.98 | 0.008 | 67 |
| LNU224 | 25871.3 | 0.747 | 0.010 | 66 | LNU9 | 25003.1 | 0.325 | 0.718 | 6 | LNU224 | 25874.1 | 5.87 | 0.010 | 64 |
| LNU224 | 25874.1 | 0.734 | 0.013 | 63 | CONT. | — | 0.287 | — | 0 | LNU224 | 25872.2 | 5.35 | 0.047 | 50 |
| LNU224 | 25872.2 | 0.669 | 0.056 | 48 | LNU131 | 14005.5 | 0.396 | 0.020 | 38 | LNU224 | 25874.4 | 4.53 | 0.266 | 27 |
| LNU224 | 25872.3 | 0.601 | 0.174 | 33 | LNU131 | 14005.2 | 0.353 | 0.165 | 23 | LNU224 | 25872.3 | 4.51 | 0.278 | 26 |
| LNU224 | 25874.4 | 0.567 | 0.294 | 26 | LNU131 | 14002.15 | 0.328 | 0.376 | 14 | LNU246 | 25743.2 | 5.97 | 0.014 | 67 |
| LNU246 | 25743.2 | 0.747 | 0.017 | 66 | LNU135 | 26204.2 | 0.437 | 0.003 | 52 | LNU246 | 25743.1 | 5.65 | 0.024 | 58 |
| LNU246 | 25743.1 | 0.707 | 0.029 | 57 | LNU135 | 26203.4 | 0.343 | 0.244 | 20 | LNU246 | 25744.2 | 5.49 | 0.039 | 54 |
| LNU246 | 25744.2 | 0.687 | 0.046 | 52 | LNU135 | 26203.6 | 0.336 | 0.290 | 17 | LNU246 | 25744.4 | 5.08 | 0.111 | 42 |
| LNU246 | 25744.4 | 0.635 | 0.126 | 41 | LNU135 | 26203.1 | 0.315 | 0.540 | 10 | LNU246 | 25744.3 | 4.48 | 0.282 | 26 |
| LNU246 | 25744.3 | 0.561 | 0.311 | 24 | LNU135 | 26203.3 | 0.310 | 0.641 | 8 | LNU250 | 25592.2 | 5.37 | 0.043 | 50 |
| LNU250 | 25592.2 | 0.672 | 0.051 | 49 | LNU161 | 14553.5 | 0.320 | 0.500 | 11 | LNU250 | 25592.1 | 4.28 | 0.412 | 20 |
| LNU250 | 25592.1 | 0.535 | 0.445 | 19 | LNU181 | 25771.2 | 0.339 | 0.265 | 18 | LNU250 | 25591.1 | 4.28 | 0.410 | 20 |
| LNU250 | 25591.1 | 0.535 | 0.444 | 18 | LNU181 | 25771.6 | 0.327 | 0.380 | 14 | LNU260 | 26404.8 | 4.71 | 0.191 | 32 |
| LNU260 | 26404.8 | 0.589 | 0.213 | 31 | LNU181 | 25771.11 | 0.318 | 0.505 | 11 | LNU260 | 26404.7 | 4.63 | 0.238 | 30 |
| LNU260 | 26404.7 | 0.579 | 0.263 | 28 | LNU181 | 25774.1 | 0.309 | 0.638 | 7 | LNU260 | 26404.1 | 4.46 | 0.311 | 25 |
| LNU260 | 26404.1 | 0.558 | 0.340 | 24 | LNU181 | 25771.8 | 0.299 | 0.795 | 4 | LNU260 | 26403.1 | 3.81 | 0.777 | 7 |
| LNU276 | 25433.6 | 0.602 | 0.175 | 33 | LNU184 | 25395.1 | 0.377 | 0.063 | 31 | LNU276 | 25433.6 | 4.82 | 0.154 | 35 |
| LNU276 | 25431.1 | 0.542 | 0.404 | 20 | LNU184 | 25394.3 | 0.362 | 0.119 | 26 | LNU276 | 25431.1 | 4.33 | 0.371 | 21 |
| LNU276 | 25433.5 | 0.532 | 0.459 | 18 | LNU184 | 25394.1 | 0.333 | 0.318 | 16 | LNU276 | 25433.5 | 4.26 | 0.426 | 19 |
| LNU279 | 25484.3 | 0.667 | 0.061 | 48 | LNU184 | 25393.3 | 0.330 | 0.355 | 15 | LNU279 | 25484.3 | 5.34 | 0.052 | 49 |
| LNU279 | 25481.3 | 0.604 | 0.202 | 34 | LNU184 | 25393.1 | 0.304 | 0.714 | 6 | LNU279 | 25481.3 | 4.83 | 0.182 | 35 |
| LNU279 | 25481.5 | 0.568 | 0.292 | 26 | LNU184 | 25393.2 | 0.303 | 0.726 | 6 | LNU279 | 25481.5 | 4.54 | 0.265 | 27 |
| LNU279 | 25481.4 | 0.525 | 0.497 | 16 | LNU224 | 25871.3 | 0.367 | 0.086 | 28 | LNU279 | 25481.4 | 4.20 | 0.463 | 18 |
| LNU3 | 26122.2 | 0.614 | 0.157 | 36 | LNU224 | 25872.2 | 0.364 | 0.104 | 27 | LNU3 | 26122.2 | 4.91 | 0.139 | 37 |
| LNU33 | 25553.3 | 0.686 | 0.040 | 52 | LNU224 | 25874.1 | 0.355 | 0.138 | 24 | LNU33 | 25553.3 | 5.48 | 0.034 | 54 |
| LNU33 | 25552.3 | 0.615 | 0.142 | 36 | LNU224 | 25872.3 | 0.315 | 0.548 | 10 | LNU33 | 25552.2 | 4.78 | 0.197 | 34 |
| LNU33 | 25552.2 | 0.598 | 0.218 | 32 | LNU246 | 25743.2 | 0.369 | 0.100 | 29 | LNU33 | 25552.2 | 4.57 | 0.246 | 28 |
| LNU33 | 25553.1 | 0.522 | 0.527 | 16 | LNU246 | 25743.1 | 0.354 | 0.164 | 23 | LNU33 | 25553.1 | 4.18 | 0.493 | 17 |
| LNU53 | 25674.6 | 0.546 | 0.383 | 21 | LNU246 | 25744.2 | 0.347 | 0.216 | 21 | LNU53 | 25674.6 | 4.37 | 0.352 | 22 |
| LNU73 | 25751.8 | 0.521 | 0.539 | 16 | LNU246 | 25744.4 | 0.344 | 0.256 | 20 | LNU73 | 25751.8 | 4.17 | 0.506 | 17 |
| CONT. | — | 0.809 | — | 0 | LNU246 | 25744.3 | 0.313 | 0.570 | 9 | CONT. | — | 6.47 | — | 0 |
| LNU119 | 26144.2. | 0.861 | 0.646 | 6 | LNU250 | 25592.2 | 0.359 | 0.121 | 25 | LNU119 | 26144.2. | 6.89 | 0.646 | 6 |
| LNU130 | 24912.7. | 0.932 | 0.319 | 15 | LNU250 | 25592.1 | 0.308 | 0.649 | 7 | LNU130 | 24912.7. | 7.45 | 0.319 | 15 |
| LNU130 | 24913.6. | 0.926 | 0.303 | 14 | LNU250 | 25591.1 | 0.301 | 0.772 | 5 | LNU130 | 24913.6. | 7.41 | 0.303 | 14 |
| LNU130 | 24914.5. | 0.893 | 0.475 | 10 | LNU260 | 26404.7 | 0.321 | 0.485 | 12 | LNU130 | 24914.5. | 7.14 | 0.475 | 10 |
| LNU130 | 24911.7. | 0.860 | 0.661 | 6 | LNU260 | 26404.8 | 0.316 | 0.529 | 10 | LNU130 | 24911.7. | 6.88 | 0.661 | 6 |
| LNU136 | 14511.10. | 1.025 | 0.060 | 27 | LNU276 | 25433.6 | 0.332 | 0.330 | 16 | LNU136 | 14511.10. | 8.20 | 0.060 | 27 |
| LNU136 | 14515.5. | 0.969 | 0.180 | 20 | LNU276 | 25431.1 | 0.302 | 0.738 | 5 | LNU136 | 14515.5. | 7.75 | 0.180 | 20 |
| LNU142 | 27541.1. | 0.946 | 0.231 | 17 | LNU279 | 25481.3 | 0.346 | 0.238 | 21 | LNU142 | 27541.1. | 7.57 | 0.231 | 17 |
| LNU149 | 26175.3. | 0.901 | 0.415 | 11 | LNU279 | 25484.3 | 0.345 | 0.234 | 20 | LNU149 | 26175.3. | 6.73 | 0.773 | 4 |
| LNU15 | 14123.13. | 0.904 | 0.411 | 12 | LNU279 | 25481.5 | 0.323 | 0.444 | 12 | LNU15 | 14123.13. | 7.23 | 0.411 | 12 |
| LNU15 | 14123.11. | 0.901 | 0.455 | 11 | LNU279 | 25481.4 | 0.310 | 0.615 | 8 | LNU15 | 14123.11. | 6.81 | 0.737 | 5 |
| LNU185 | 26474.2. | 1.021 | 0.089 | 26 | LNU3 | 26122.2 | 0.336 | 0.309 | 17 | LNU185 | 26474.2. | 8.17 | 0.089 | 26 |
| LNU185 | 26475.1. | 0.982 | 0.132 | 21 | LNU33 | 25553.3 | 0.364 | 0.103 | 27 | LNU185 | 26475.1. | 7.86 | 0.132 | 21 |

TABLE 81-continued

Genes showing improved rosette growth performance at limiting nitrogen growth conditions

| Gene Name | Event # | RGR Of Rosette Area Ave. | P-Value | % incr. | Gene Name | Event # | RGR Of Rosette Diameter Ave. | P-Value | % incr. | Gene Name | Event # | RGR Of Plot Coverage Ave. | P-Value | % incr. |
|---|---|---|---|---|---|---|---|---|---|---|---|---|---|---|
| LNU185 | 26474.1. | 0.893 | 0.487 | 10 | LNU33 | 25552.2 | 0.339 | 0.288 | 18 | LNU185 | 26474.1. | 7.14 | 0.487 | 10 |
| LNU212 | 25833.2. | 1.095 | 0.020 | 35 | LNU33 | 25553.2 | 0.329 | 0.365 | 14 | LNU212 | 25833.2. | 8.76 | 0.020 | 35 |
| LNU212 | 25834.4. | 1.035 | 0.067 | 28 | LNU33 | 25553.1 | 0.320 | 0.487 | 11 | LNU212 | 25834.4. | 8.28 | 0.067 | 28 |
| LNU212 | 25834.5. | 0.941 | 0.254 | 16 | LNU53 | 25674.6 | 0.311 | 0.601 | 8 | LNU212 | 25834.5. | 7.53 | 0.254 | 16 |
| LNU212 | 25832.1. | 0.863 | 0.630 | 7 | LNU56 | 24694.2 | 0.303 | 0.733 | 5 | LNU212 | 25832.1. | 6.91 | 0.630 | 7 |
| LNU216 | 25985.4. | 1.045 | 0.062 | 29 | LNU73 | 25751.8 | 0.329 | 0.404 | 14 | LNU216 | 25985.4. | 8.36 | 0.062 | 29 |
| LNU216 | 25984.1. | 1.010 | 0.104 | 25 | CONT. | — | 0.359 | — | 0 | LNU216 | 25984.1. | 8.08 | 0.104 | 25 |
| LNU216 | 25982.1. | 1.005 | 0.090 | 24 | LNU119 | 26144.2. | 0.399 | 0.196 | 11 | LNU216 | 25982.1. | 8.04 | 0.090 | 24 |
| LNU216 | 25984.6. | 0.878 | 0.537 | 9 | LNU130 | 24912.7. | 0.417 | 0.098 | 16 | LNU216 | 25984.6. | 7.02 | 0.537 | 9 |
| LNU228 | 26224.7. | 0.989 | 0.123 | 22 | LNU130 | 24911.7. | 0.407 | 0.136 | 13 | LNU228 | 26224.7. | 7.91 | 0.123 | 22 |
| LNU228 | 26222.4. | 0.907 | 0.385 | 12 | LNU130 | 24914.5. | 0.398 | 0.243 | 11 | LNU228 | 26222.4. | 7.26 | 0.385 | 12 |
| LNU229 | 26112.3. | 0.956 | 0.208 | 18 | LNU130 | 24913.6. | 0.378 | 0.541 | 5 | LNU229 | 26112.3. | 7.65 | 0.208 | 18 |
| LNU253 | 26241.1. | 0.935 | 0.281 | 16 | LNU136 | 14510.10. | 0.415 | 0.062 | 15 | LNU253 | 26241.1. | 7.48 | 0.281 | 16 |
| LNU280 | 26162.1. | 0.941 | 0.274 | 16 | LNU136 | 14515.5. | 0.388 | 0.397 | 8 | LNU280 | 26162.1. | 7.53 | 0.274 | 16 |
| LNU55 | 26015.1. | 0.911 | 0.389 | 13 | LNU136 | 14514.8. | 0.378 | 0.553 | 5 | LNU55 | 26015.1. | 7.28 | 0.389 | 13 |
| LNU81 | 26034.2. | 0.891 | 0.476 | 10 | LNU136 | 14515.1. | 0.369 | 0.761 | 3 | LNU81 | 26034.2. | 7.13 | 0.476 | 10 |
| LNU81 | 26031.9. | 0.891 | 0.493 | 10 | LNU142 | 27541.1. | 0.391 | 0.310 | 9 | LNU81 | 26031.9. | 7.13 | 0.493 | 10 |
| CONT. | — | 0.822 | — | 0 | LNU149 | 26175.3. | 0.393 | 0.257 | 9 | CONT. | — | 6.58 | — | 0 |
| LNU119 | 26141.1. | 1.016 | 0.363 | 24 | LNU149 | 26175.1. | 0.373 | 0.647 | 4 | LNU119 | 26141.1. | 8.13 | 0.363 | 24 |
| LNU119 | 26142.5. | 0.876 | 0.777 | 7 | LNU15 | 14123.13. | 0.399 | 0.197 | 11 | LNU119 | 26142.5. | 7.01 | 0.777 | 7 |
| LNU130 | 24913.5. | 0.946 | 0.514 | 15 | LNU15 | 14123.11. | 0.387 | 0.443 | 8 | LNU130 | 24913.5. | 7.57 | 0.514 | 15 |
| LNU130 | 24914.5. | 0.903 | 0.668 | 10 | LNU15 | 14122.9. | 0.374 | 0.645 | 5 | LNU130 | 24914.5. | 7.22 | 0.668 | 10 |
| LNU136 | 14515.1. | 0.892 | 0.711 | 8 | LNU185 | 26474.2. | 0.414 | 0.133 | 15 | LNU136 | 14515.1. | 7.13 | 0.711 | 8 |
| LNU142 | 27546.2. | 0.902 | 0.680 | 10 | LNU185 | 26475.1. | 0.399 | 0.193 | 11 | LNU142 | 27546.2. | 7.22 | 0.680 | 10 |
| LNU142 | 27545.1. | 0.876 | 0.780 | 7 | LNU185 | 26474.1. | 0.399 | 0.242 | 11 | LNU142 | 27545.1. | 7.01 | 0.780 | 7 |
| LNU15 | 14124.12. | 0.984 | 0.405 | 20 | LNU212 | 25833.2. | 0.436 | 0.019 | 21 | LNU15 | 14124.12. | 7.87 | 0.405 | 20 |
| LNU15 | 14122.8. | 0.942 | 0.541 | 15 | LNU212 | 25834.4. | 0.435 | 0.026 | 21 | LNU15 | 14122.8. | 7.54 | 0.541 | 15 |
| LNU15 | 14123.13. | 0.904 | 0.666 | 10 | LNU212 | 25834.5. | 0.431 | 0.028 | 20 | LNU15 | 14123.13. | 7.23 | 0.666 | 10 |
| LNU185 | 26474.1. | 1.074 | 0.194 | 31 | LNU212 | 25834.4. | 0.404 | 0.167 | 13 | LNU185 | 26474.1. | 8.59 | 0.194 | 31 |
| LNU212 | 25834.4. | 1.045 | 0.255 | 27 | LNU212 | 25832.1. | 0.391 | 0.298 | 9 | LNU212 | 25834.4. | 8.36 | 0.255 | 27 |
| LNU212 | 25834.5. | 0.924 | 0.596 | 12 | LNU216 | 25984.1. | 0.448 | 0.011 | 25 | LNU212 | 25834.5. | 7.39 | 0.596 | 12 |
| LNU216 | 25985.4. | 1.096 | 0.186 | 33 | LNU216 | 25982.1. | 0.445 | 0.005 | 24 | LNU216 | 25985.4. | 8.77 | 0.186 | 33 |
| LNU216 | 25982.1. | 0.951 | 0.499 | 16 | LNU216 | 25985.4. | 0.425 | 0.060 | 18 | LNU216 | 25982.1. | 7.61 | 0.499 | 16 |
| LNU216 | 25984.6. | 0.925 | 0.610 | 12 | LNU216 | 25984.6. | 0.400 | 0.175 | 11 | LNU216 | 25984.6. | 7.40 | 0.610 | 12 |
| LNU228 | 26225.2. | 1.099 | 0.161 | 34 | LNU228 | 26222.4. | 0.401 | 0.170 | 12 | LNU228 | 26225.2. | 8.79 | 0.161 | 34 |
| LNU228 | 26224.7. | 1.018 | 0.337 | 24 | LNU228 | 26224.7. | 0.385 | 0.414 | 7 | LNU228 | 26224.6. | 7.80 | 0.434 | 19 |
| LNU228 | 26224.6. | 0.974 | 0.434 | 19 | LNU228 | 26224.6. | 0.383 | 0.450 | 7 | LNU228 | 26222.4. | 7.58 | 0.509 | 15 |
| LNU228 | 26222.4. | 0.948 | 0.509 | 15 | LNU228 | 26222.1. | 0.379 | 0.588 | 5 | LNU228 | 26222.1. | 7.54 | 0.528 | 15 |
| LNU228 | 26222.1. | 0.943 | 0.528 | 15 | LNU229 | 26112.3. | 0.419 | 0.057 | 17 | LNU229 | 26111.7. | 8.25 | 0.318 | 25 |
| LNU229 | 26111.7. | 1.031 | 0.318 | 25 | LNU229 | 26112.6. | 0.371 | 0.710 | 3 | LNU229 | 26111.5. | 8.05 | 0.348 | 22 |
| LNU229 | 26111.5. | 1.006 | 0.348 | 22 | LNU253 | 26241.1. | 0.402 | 0.172 | 12 | LNU229 | 26112.4. | 7.87 | 0.406 | 20 |
| LNU229 | 26112.4. | 0.984 | 0.406 | 20 | LNU253 | 26245.1. | 0.385 | 0.402 | 7 | LNU229 | 26112.3. | 7.83 | 0.423 | 19 |
| LNU229 | 26112.3. | 0.978 | 0.423 | 19 | LNU274 | 26264.2. | 0.383 | 0.481 | 7 | LNU241 | 26232.4. | 7.72 | 0.458 | 17 |
| LNU241 | 26232.4. | 0.965 | 0.458 | 17 | LNU274 | 26263.2. | 0.372 | 0.661 | 4 | LNU241 | 26233.3. | 7.50 | 0.574 | 14 |
| LNU241 | 26233.3. | 0.938 | 0.574 | 14 | LNU280 | 26162.1. | 0.404 | 0.172 | 13 | LNU241 | 26234.1. | 7.10 | 0.729 | 8 |
| LNU241 | 26234.1. | 0.888 | 0.729 | 8 | LNU280 | 26164.4. | 0.367 | 0.797 | 2 | LNU253 | 26242.1. | 7.19 | 0.695 | 9 |
| LNU253 | 26242.1. | 0.899 | 0.695 | 9 | LNU55 | 26015.1. | 0.382 | 0.493 | 6 | LNU274 | 26265.1. | 7.39 | 0.618 | 12 |
| LNU274 | 26265.1. | 0.923 | 0.618 | 12 | LNU81 | 26031.9. | 0.378 | 0.557 | 5 | LNU274 | 26262.2. | 7.31 | 0.646 | 11 |
| LNU274 | 26262.2. | 0.913 | 0.646 | 11 | LNU81 | 26034.3. | 0.373 | 0.646 | 4 | LNU280 | 26162.1. | 7.93 | 0.386 | 21 |
| LNU280 | 26162.1. | 0.992 | 0.386 | 21 | CONT. | — | 0.401 | — | 0 | LNU55 | 26013.3. | 7.44 | 0.609 | 13 |
| LNU280 | 26164.4. | 0.904 | 0.662 | 10 | LNU119 | 26141.1. | 0.431 | 0.688 | 8 | LNU55 | 26015.1. | 7.37 | 0.602 | 12 |
| LNU55 | 26013.3. | 0.930 | 0.609 | 13 | LNU130 | 24912.7. | 0.420 | 0.792 | 5 | LNU55 | 26013.4. | 7.34 | 0.613 | 12 |
| LNU55 | 26015.1. | 0.922 | 0.602 | 12 | LNU15 | 14122.8. | 0.431 | 0.661 | 8 | LNU81 | 26031.10. | 7.95 | 0.440 | 21 |
| LNU55 | 26013.4. | 0.917 | 0.613 | 12 | LNU15 | 14124.12. | 0.425 | 0.727 | 6 | LNU81 | 26031.2. | 7.50 | 0.541 | 14 |
| LNU81 | 26031.10. | 0.994 | 0.440 | 21 | LNU185 | 26474.1. | 0.469 | 0.311 | 17 | | | | | |
| LNU81 | 26031.2. | 0.937 | 0.541 | 14 | LNU212 | 25834.4. | 0.443 | 0.521 | 11 | | | | | |
| | | | | | LNU216 | 25985.4. | 0.437 | 0.596 | 9 | | | | | |
| | | | | | LNU216 | 25982.1. | 0.424 | 0.725 | 6 | | | | | |
| | | | | | LNU228 | 26224.7. | 0.460 | 0.397 | 15 | | | | | |
| | | | | | LNU228 | 26225.2. | 0.456 | 0.410 | 14 | | | | | |
| | | | | | LNU228 | 26224.6. | 0.428 | 0.686 | 7 | | | | | |
| | | | | | LNU229 | 26112.3. | 0.463 | 0.366 | 16 | | | | | |
| | | | | | LNU229 | 26111.7. | 0.455 | 0.448 | 13 | | | | | |
| | | | | | LNU229 | 26111.5. | 0.418 | 0.794 | 4 | | | | | |
| | | | | | LNU241 | 26232.4. | 0.460 | 0.380 | 15 | | | | | |
| | | | | | LNU241 | 26233.3. | 0.445 | 0.562 | 11 | | | | | |
| | | | | | LNU253 | 26241.1. | 0.424 | 0.720 | 6 | | | | | |
| | | | | | LNU274 | 26262.2. | 0.431 | 0.660 | 8 | | | | | |
| | | | | | LNU274 | 26263.2. | 0.421 | 0.764 | 5 | | | | | |
| | | | | | LNU280 | 26162.1. | 0.438 | 0.582 | 9 | | | | | |
| | | | | | LNU280 | 26164.4. | 0.424 | 0.725 | 6 | | | | | |
| | | | | | LNU55 | 26013.3. | 0.448 | 0.529 | 12 | | | | | |

TABLE 81-continued

Genes showing improved rosette growth performance at limiting nitrogen growth conditions

| Gene Name | Event # | RGR Of Rosette Area Ave. | P-Value | % incr. | Gene Name | Event # | RGR Of Rosette Diameter Ave. | P-Value | % incr. | Gene Name | Event # | RGR Of Plot Coverage Ave. | P-Value | % incr. |
|---|---|---|---|---|---|---|---|---|---|---|---|---|---|---|
| | | | | | LNU81 | 26031.10. | 0.432 | 0.675 | 8 | | | | | |
| | | | | | LNU81 | 26034.3. | 0.426 | 0.732 | 6 | | | | | |

Table 81.
"CONT."—Control;
"Ave."—Average;
"% Incr." = % increment.

The genes listed in Tables 82 and 83 improved plant NUE when grown at standard nitrogen concentration levels. These genes produced larger plants with a larger photosynthetic area and increased biomass (fresh weight, dry weight, rosette diameter, rosette area and plot coverage) when grown under standard nitrogen conditions. The genes were cloned under the regulation of a constitutive (At6669) and root preferred promoter (RootP). The evaluation of each gene was performed by testing the performance of different number of events. Event with p-value <0.1 was considered statistically significant.

TABLE 82

Genes showing improved plant biomass production at standard nitrogen growth conditions

| Gene Name | Event # | Dry Weight [g] Ave. | P-Value | % incr. | Gene Name | Event # | Fresh Weight [g] Ave. | P-Value | % incr. |
|---|---|---|---|---|---|---|---|---|---|
| CONT. | — | 0.241 | — | 0 | CONT. | — | 2.503 | — | 0 |
| LNU100 | 14473.3 | 0.264 | 0.319 | 9 | LNU104 | 25033.1 | 2.750 | 0.418 | 10 |
| LNU104 | 25033.1 | 0.279 | 0.272 | 16 | LNU104 | 25032.2 | 2.563 | 0.745 | 2 |
| LNU104 | 25032.2 | 0.273 | 0.000 | 13 | LNU106 | 14484.3 | 3.125 | 0.148 | 25 |
| LNU104 | 25033.3 | 0.259 | 0.039 | 7 | LNU114 | 25044.4 | 2.800 | 0.512 | 12 |
| LNU104 | 25034.1 | 0.253 | 0.337 | 5 | LNU114 | 25044.3 | 2.788 | 0.003 | 11 |
| LNU106 | 14484.3 | 0.314 | 0.221 | 30 | LNU114 | 25041.1 | 2.681 | 0.625 | 7 |
| LNU106 | 14482.3 | 0.279 | 0.125 | 16 | LNU155 | 14524.8 | 3.067 | 0.330 | 23 |
| LNU106 | 14483.5 | 0.251 | 0.655 | 4 | LNU155 | 14525.6 | 2.706 | 0.290 | 8 |
| LNU114 | 25041.1 | 0.260 | 0.304 | 8 | LNU218 | 24781.2 | 2.750 | 0.168 | 10 |
| LNU114 | 25044.3 | 0.253 | 0.075 | 5 | LNU218 | 24781.1 | 2.738 | 0.261 | 9 |
| LNU114 | 25044.4 | 0.253 | 0.698 | 5 | LNU218 | 24781.4 | 2.563 | 0.437 | 2 |
| LNU114 | 25042.1 | 0.246 | 0.762 | 2 | LNU28 | 25174.5 | 2.625 | 0.650 | 5 |
| LNU155 | 14524.8 | 0.288 | 0.471 | 19 | LNU4 | 25134.1 | 2.800 | 0.582 | 12 |
| LNU155 | 14525.6 | 0.258 | 0.146 | 7 | LNU40 | 24794.4 | 2.756 | 0.006 | 10 |
| LNU213 | 24653.2 | 0.277 | 0.088 | 15 | LNU48 | 24801.4 | 2.656 | 0.741 | 6 |
| LNU218 | 24781.7 | 0.319 | 0.224 | 32 | LNU63 | 24811.2 | 2.704 | 0.336 | 8 |
| LNU218 | 24781.2 | 0.271 | 0.380 | 12 | LNU7 | 25083.3 | 3.006 | 0.323 | 20 |
| LNU218 | 24781.1 | 0.256 | 0.113 | 6 | LNU8 | 25062.2 | 2.656 | 0.200 | 6 |
| LNU218 | 24781.4 | 0.252 | 0.389 | 4 | LNU8 | 25063.1 | 2.631 | 0.691 | 5 |
| LNU23 | 25163.5 | 0.283 | 0.597 | 17 | LNU8 | 25061.2 | 2.594 | 0.722 | 4 |
| LNU23 | 25163.4 | 0.263 | 0.493 | 9 | LNU94 | 24833.3 | 2.675 | 0.541 | 7 |
| LNU28 | 25171.2 | 0.275 | 0.429 | 14 | CONT. | — | 2.638 | — | 0 |
| LNU28 | 25174.3 | 0.267 | 0.526 | 11 | LNU132 | 14102.6 | 2.794 | 0.720 | 6 |
| LNU28 | 25174.5 | 0.251 | 0.251 | 4 | LNU65 | 24703.1 | 3.006 | 0.684 | 14 |
| LNU28 | 25171.4 | 0.249 | 0.762 | 3 | CONT. | — | 2.303 | — | 0 |
| LNU4 | 25134.1 | 0.281 | 0.255 | 17 | LNU113 | 25631.1 | 2.631 | 0.213 | 14 |
| LNU4 | 25134.2 | 0.253 | 0.690 | 5 | LNU113 | 25631.3 | 2.500 | 0.261 | 9 |
| LNU4 | 25133.3 | 0.248 | 0.681 | 3 | LNU120 | 25463.7 | 2.500 | 0.059 | 9 |
| LNU40 | 24794.3 | 0.260 | 0.212 | 8 | LNU120 | 25464.1 | 2.344 | 0.420 | 2 |
| LNU40 | 24794.4 | 0.259 | 0.435 | 7 | LNU148 | 25685.2 | 2.719 | 0.315 | 18 |
| LNU46 | 14462.1 | 0.273 | 0.121 | 13 | LNU148 | 25683.2 | 2.544 | 0.533 | 10 |
| LNU48 | 24802.2 | 0.281 | 0.000 | 16 | LNU148 | 25685.1 | 2.519 | 0.537 | 9 |
| LNU48 | 24801.4 | 0.268 | 0.360 | 11 | LNU287 | 24674.3 | 2.419 | 0.730 | 5 |
| LNU48 | 24802.1 | 0.258 | 0.018 | 7 | LNU287 | 24674.2 | 2.331 | 0.726 | 1 |
| LNU63 | 24811.2 | 0.285 | 0.475 | 18 | LNU37 | 14064.7 | 2.719 | 0.186 | 18 |
| LNU63 | 24814.2 | 0.262 | 0.293 | 9 | LNU37 | 14064.1 | 2.575 | 0.275 | 12 |
| LNU7 | 25083.3 | 0.357 | 0.496 | 48 | LNU37 | 14064.6 | 2.375 | 0.637 | 3 |
| LNU7 | 25083.3 | 0.248 | 0.326 | 3 | LNU5 | 14043.7 | 2.750 | 0.000 | 19 |
| LNU8 | 25062.2 | 0.268 | 0.001 | 11 | LNU65 | 24702.3 | 2.644 | 0.025 | 15 |
| LNU8 | 25063.1 | 0.259 | 0.403 | 7 | LNU65 | 24703.3 | 2.400 | 0.393 | 4 |
| LNU8 | 25061.2 | 0.249 | 0.759 | 3 | LNU65 | 24703.6 | 2.381 | 0.593 | 3 |
| LNU94 | 24833.3 | 0.273 | 0.455 | 13 | LNU68 | 14034.13 | 2.569 | 0.000 | 12 |
| LNU94 | 24834.4 | 0.247 | 0.369 | 2 | LNU68 | 14033.1 | 2.413 | 0.457 | 5 |

TABLE 82-continued

Genes showing improved plant biomass production at standard nitrogen growth conditions

| Gene Name | Event # | Dry Weight [g] Ave. | P-Value | % incr. | Gene Name | Event # | Fresh Weight [g] Ave. | P-Value | % incr. |
|---|---|---|---|---|---|---|---|---|---|
| LNU94 | 24831.4 | 0.244 | 0.781 | 1 | LNU68 | 14034.1 | 2.394 | 0.544 | 4 |
| LNU96 | 25073.4 | 0.279 | 0.590 | 16 | LNU71 | 25853.1 | 2.613 | 0.152 | 13 |
| CONT. | — | 0.302 | — | 0 | LNU71 | 25851.4 | 2.594 | 0.213 | 13 |
| LNU132 | 14102.6 | 0.431 | 0.245 | 43 | LNU71 | 25853.3 | 2.475 | 0.565 | 7 |
| LNU140 | 14114.8 | 0.331 | 0.380 | 10 | LNU71 | 25852.4 | 2.469 | 0.376 | 7 |
| LNU148 | 25685.1 | 0.339 | 0.184 | 12 | LNU71 | 25852.5 | 2.456 | 0.362 | 7 |
| LNU287 | 24674.6 | 0.346 | 0.699 | 15 | LNU72 | 24962.3 | 2.575 | 0.213 | 12 |
| LNU5 | 14043.9 | 0.334 | 0.186 | 11 | LNU72 | 24963.7 | 2.450 | 0.527 | 6 |
| LNU65 | 24703.7 | 0.418 | 0.117 | 38 | LNU72 | 24962.2 | 2.406 | 0.650 | 4 |
| LNU65 | 24702.3 | 0.351 | 0.681 | 16 | LNU72 | 24963.8 | 2.344 | 0.711 | 2 |
| LNU71 | 25851.4 | 0.419 | 0.686 | 39 | LNU74 | 25444.1 | 2.575 | 0.000 | 12 |
| LNU98 | 25761.6 | 0.369 | 0.365 | 22 | LNU74 | 25443.3 | 2.569 | 0.202 | 12 |
| CONT. | — | 0.243 | — | 0 | LNU74 | 25443.2 | 2.525 | 0.363 | 10 |
| LNU113 | 25631.1 | 0.269 | 0.122 | 11 | LNU82 | 24823.1 | 2.538 | 0.000 | 10 |
| LNU113 | 25631.3 | 0.261 | 0.116 | 7 | LNU84 | 25621.2 | 2.413 | 0.499 | 5 |
| LNU148 | 25685.2 | 0.283 | 0.365 | 16 | LNU84 | 25621.6 | 2.356 | 0.674 | 2 |
| LNU148 | 25683.2 | 0.261 | 0.583 | 7 | LNU84 | 25623.1 | 2.350 | 0.724 | 2 |
| LNU148 | 25685.1 | 0.261 | 0.416 | 7 | CONT. | — | 1.523 | — | 0 |
| LNU287 | 24674.3 | 0.252 | 0.757 | 4 | LNU117 | 25931.2 | 1.844 | 0.247 | 21 |
| LNU37 | 14064.1 | 0.275 | 0.009 | 13 | LNU117 | 25931.1 | 1.806 | 0.190 | 19 |
| LNU37 | 14064.7 | 0.271 | 0.296 | 11 | LNU117 | 25931.4 | 1.750 | 0.384 | 15 |
| LNU5 | 14043.7 | 0.269 | 0.003 | 11 | LNU117 | 25932.4 | 1.731 | 0.227 | 14 |
| LNU65 | 24702.3 | 0.266 | 0.007 | 9 | LNU122 | 25332.1 | 1.725 | 0.581 | 13 |
| LNU65 | 24703.6 | 0.250 | 0.621 | 3 | LNU122 | 25332.5 | 1.706 | 0.380 | 12 |
| LNU65 | 24703.3 | 0.249 | 0.443 | 2 | LNU122 | 25333.1 | 1.700 | 0.012 | 11 |
| LNU68 | 14034.13 | 0.276 | 0.000 | 14 | LNU122 | 25332.2 | 1.694 | 0.015 | 11 |
| LNU68 | 14033.1 | 0.258 | 0.350 | 6 | LNU122 | 25333.2 | 1.681 | 0.600 | 10 |
| LNU71 | 25853.1 | 0.278 | 0.131 | 14 | LNU125 | 25944.3 | 1.588 | 0.593 | 4 |
| LNU71 | 25851.4 | 0.271 | 0.002 | 12 | LNU125 | 25943.3 | 1.569 | 0.430 | 3 |
| LNU71 | 25852.5 | 0.264 | 0.501 | 9 | LNU138 | 14074.5 | 1.738 | 0.103 | 14 |
| LNU71 | 25853.4 | 0.259 | 0.473 | 7 | LNU138 | 14074.6 | 1.644 | 0.551 | 8 |
| LNU71 | 25852.4 | 0.249 | 0.521 | 2 | LNU138 | 14072.8 | 1.619 | 0.366 | 6 |
| LNU72 | 24962.3 | 0.252 | 0.757 | 4 | LNU180 | 24722.2 | 1.625 | 0.095 | 7 |
| LNU72 | 24963.7 | 0.251 | 0.739 | 3 | LNU230 | 25413.1 | 1.775 | 0.510 | 17 |
| LNU72 | 24963.8 | 0.250 | 0.621 | 3 | LNU230 | 25412.2 | 1.638 | 0.267 | 8 |
| LNU72 | 24962.2 | 0.249 | 0.666 | 3 | LNU254 | 25781.3 | 1.638 | 0.054 | 8 |
| LNU74 | 25444.1 | 0.259 | 0.174 | 7 | LNU254 | 25783.1 | 1.594 | 0.173 | 5 |
| LNU74 | 25443.2 | 0.256 | 0.627 | 5 | LNU263 | 25791.3 | 1.544 | 0.673 | 1 |
| LNU74 | 25443.3 | 0.252 | 0.624 | 4 | LNU271 | 25912.1 | 1.588 | 0.534 | 4 |
| LNU82 | 24823.1 | 0.272 | 0.080 | 12 | LNU278 | 25814.3 | 1.581 | 0.244 | 4 |
| LNU82 | 24823.3 | 0.248 | 0.746 | 2 | LNU43 | 14422.8 | 1.625 | 0.230 | 7 |
| LNU84 | 25621.2 | 0.261 | 0.351 | 7 | LNU43 | 14423.6 | 1.594 | 0.327 | 5 |
| LNU84 | 25623.1 | 0.249 | 0.666 | 3 | LNU43 | 14423.7 | 1.569 | 0.370 | 3 |
| LNU87 | 24713.2 | 0.247 | 0.743 | 2 | LNU45 | 25053.4 | 1.613 | 0.105 | 6 |
| CONT. | — | 0.162 | — | 0 | LNU67 | 25824.5 | 1.688 | 0.319 | 11 |
| LNU117 | 25931.4 | 0.200 | 0.003 | 24 | CONT. | — | 2.439 | — | 0 |
| LNU117 | 25931.2 | 0.193 | 0.055 | 20 | LNU100 | 14472.1 | 2.956 | 0.299 | 21 |
| LNU117 | 25931.1 | 0.192 | 0.094 | 19 | LNU100 | 14473.1 | 2.763 | 0.147 | 13 |
| LNU117 | 25932.4 | 0.181 | 0.091 | 12 | LNU100 | 14473.3 | 2.613 | 0.002 | 7 |
| LNU117 | 25933.3 | 0.175 | 0.554 | 8 | LNU104 | 25032.2 | 2.944 | 0.331 | 21 |
| LNU122 | 25332.2 | 0.190 | 0.009 | 18 | LNU104 | 25033.1 | 2.581 | 0.465 | 6 |
| LNU122 | 25332.1 | 0.189 | 0.434 | 17 | LNU104 | 25033.3 | 2.544 | 0.030 | 4 |
| LNU122 | 25332.5 | 0.186 | 0.008 | 15 | LNU104 | 25033.8 | 2.544 | 0.567 | 4 |
| LNU122 | 25333.1 | 0.184 | 0.013 | 14 | LNU104 | 25032.1 | 2.519 | 0.358 | 3 |
| LNU122 | 25333.2 | 0.181 | 0.367 | 12 | LNU106 | 14483.2 | 3.163 | 0.391 | 30 |
| LNU125 | 25944.3 | 0.183 | 0.192 | 13 | LNU106 | 14484.5 | 2.856 | 0.330 | 17 |
| LNU125 | 25943.3 | 0.175 | 0.148 | 8 | LNU114 | 25044.11 | 2.731 | 0.403 | 12 |
| LNU125 | 25941.4 | 0.169 | 0.592 | 5 | LNU114 | 25041.2 | 2.713 | 0.374 | 11 |
| LNU138 | 14074.5 | 0.196 | 0.013 | 22 | LNU114 | 25041.1 | 2.688 | 0.036 | 10 |
| LNU138 | 14074.6 | 0.186 | 0.348 | 15 | LNU114 | 25042.1 | 2.688 | 0.499 | 10 |
| LNU180 | 24723.1 | 0.173 | 0.655 | 7 | LNU114 | 25044.4 | 2.519 | 0.700 | 3 |
| LNU180 | 24722.2 | 0.171 | 0.132 | 6 | LNU117 | 25931.4 | 2.669 | 0.000 | 9 |
| LNU180 | 24721.2 | 0.164 | 0.691 | 1 | LNU117 | 25932.4 | 2.631 | 0.249 | 8 |
| LNU220 | 25405.1 | 0.163 | 0.798 | 1 | LNU117 | 25931.1 | 2.538 | 0.536 | 4 |
| LNU230 | 25413.1 | 0.196 | 0.390 | 22 | LNU117 | 25931.2 | 2.525 | 0.541 | 4 |
| LNU230 | 25412.2 | 0.176 | 0.287 | 9 | LNU155 | 14523.5 | 2.644 | 0.232 | 8 |
| LNU230 | 25413.2 | 0.164 | 0.795 | 2 | LNU155 | 14525.1 | 2.550 | 0.344 | 5 |
| LNU25 | 14083.1 | 0.176 | 0.287 | 9 | LNU180 | 24722.4 | 2.700 | 0.153 | 11 |
| LNU254 | 25781.3 | 0.179 | 0.048 | 11 | LNU180 | 24724.1 | 2.582 | 0.687 | 6 |
| LNU254 | 25783.1 | 0.170 | 0.585 | 5 | LNU180 | 24723.1 | 2.531 | 0.214 | 4 |
| LNU263 | 25791.3 | 0.178 | 0.331 | 10 | LNU218 | 24781.4 | 2.731 | 0.244 | 12 |
| LNU263 | 25794.8 | 0.178 | 0.038 | 10 | LNU218 | 24781.1 | 2.631 | 0.249 | 8 |

TABLE 82-continued

Genes showing improved plant biomass production at standard nitrogen growth conditions

| | | Dry Weight [g] | | | | | Fresh Weight [g] | | |
|---|---|---|---|---|---|---|---|---|---|
| Gene Name | Event # | Ave. | P-Value | % incr. | Gene Name | Event # | Ave. | P-Value | % incr. |
| LNU263 | 25794.6 | 0.173 | 0.405 | 7 | LNU218 | 24781.6 | 2.606 | 0.004 | 7 |
| LNU267 | 25804.3 | 0.166 | 0.772 | 3 | LNU254 | 25782.4 | 3.331 | 0.467 | 37 |
| LNU271 | 25912.1 | 0.178 | 0.061 | 10 | LNU254 | 25782.5 | 2.950 | 0.570 | 21 |
| LNU271 | 25913.3 | 0.166 | 0.469 | 3 | LNU254 | 25781.5 | 2.630 | 0.090 | 8 |
| LNU278 | 25814.3 | 0.173 | 0.086 | 7 | LNU254 | 25783.1 | 2.600 | 0.368 | 7 |
| LNU278 | 25813.2 | 0.166 | 0.606 | 3 | LNU4 | 25134.2 | 2.688 | 0.009 | 10 |
| LNU36 | 25562.3 | 0.171 | 0.448 | 6 | LNU4 | 25134.3 | 2.650 | 0.000 | 9 |
| LNU36 | 25561.2 | 0.167 | 0.414 | 3 | LNU4 | 25133.3 | 2.519 | 0.110 | 3 |
| LNU43 | 14423.6 | 0.180 | 0.176 | 11 | LNU40 | 24792.2 | 2.881 | 0.134 | 18 |
| LNU43 | 14422.8 | 0.178 | 0.031 | 10 | LNU40 | 24794.3 | 2.763 | 0.281 | 13 |
| LNU43 | 14423.7 | 0.173 | 0.534 | 7 | LNU40 | 24793.1 | 2.744 | 0.513 | 12 |
| LNU43 | 14421.1 | 0.169 | 0.552 | 5 | LNU40 | 24792.1 | 2.681 | 0.058 | 10 |
| LNU45 | 25053.4 | 0.172 | 0.147 | 6 | LNU46 | 14462.5 | 2.588 | 0.247 | 6 |
| LNU45 | 25052.9 | 0.169 | 0.734 | 4 | LNU46 | 14463.2 | 2.563 | 0.086 | 5 |
| LNU67 | 25821.5 | 0.182 | 0.016 | 13 | LNU46 | 14462.1 | 2.525 | 0.064 | 4 |
| LNU67 | 25824.5 | 0.181 | 0.019 | 12 | LNU46 | 14464.4 | 2.500 | 0.245 | 3 |
| CONT. | — | 0.256 | — | 0 | LNU48 | 24801.4 | 3.004 | 0.165 | 23 |
| LNU100 | 14472.1 | 0.345 | 0.295 | 35 | LNU48 | 24803.2 | 2.931 | 0.241 | 20 |
| LNU100 | 14473.1 | 0.279 | 0.113 | 9 | LNU48 | 24804.4 | 2.625 | 0.001 | 8 |
| LNU100 | 14473.3 | 0.272 | 0.724 | 6 | LNU48 | 24802.2 | 2.575 | 0.669 | 6 |
| LNU104 | 25032.2 | 0.361 | 0.403 | 41 | LNU48 | 24802.1 | 2.538 | 0.235 | 4 |
| LNU106 | 14483.2 | 0.414 | 0.483 | 62 | LNU63 | 24814.7 | 2.806 | 0.166 | 15 |
| LNU106 | 14484.3 | 0.363 | 0.263 | 42 | LNU63 | 24812.2 | 2.663 | 0.267 | 9 |
| LNU114 | 25044.11 | 0.358 | 0.468 | 40 | LNU63 | 24812.3 | 2.575 | 0.332 | 6 |
| LNU114 | 25042.1 | 0.316 | 0.479 | 24 | LNU63 | 24814.2 | 2.531 | 0.051 | 4 |
| LNU114 | 25041.2 | 0.280 | 0.462 | 9 | LNU7 | 25083.3 | 2.725 | 0.360 | 12 |
| LNU114 | 25041.1 | 0.266 | 0.507 | 4 | LNU7 | 25081.1 | 2.713 | 0.006 | 11 |
| LNU117 | 25931.2 | 0.292 | 0.022 | 14 | LNU7 | 25083.1 | 2.700 | 0.409 | 11 |
| LNU117 | 25931.4 | 0.279 | 0.113 | 9 | LNU8 | 25062.1 | 2.633 | 0.253 | 8 |
| LNU117 | 25931.1 | 0.268 | 0.394 | 5 | LNU8 | 25061.2 | 2.550 | 0.112 | 5 |
| LNU117 | 25932.4 | 0.264 | 0.686 | 3 | LNU94 | 24831.4 | 2.704 | 0.083 | 11 |
| LNU155 | 14523.5 | 0.264 | 0.686 | 3 | LNU94 | 24833.3 | 2.613 | 0.002 | 7 |
| LNU180 | 24722.4 | 0.315 | 0.247 | 23 | LNU94 | 24834.1 | 2.538 | 0.738 | 4 |
| LNU180 | 24724.1 | 0.283 | 0.759 | 11 | LNU96 | 25071.2 | 2.725 | 0.315 | 12 |
| LNU180 | 24723.1 | 0.282 | 0.353 | 10 | LNU96 | 25073.4 | 2.681 | 0.351 | 10 |
| LNU218 | 24781.4 | 0.308 | 0.558 | 20 | LNU96 | 25071.3 | 2.525 | 0.690 | 4 |
| LNU218 | 24781.1 | 0.271 | 0.342 | 6 | LNU96 | 25074.1 | 2.506 | 0.497 | 3 |
| LNU254 | 25782.4 | 0.448 | 0.464 | 75 | CONT. | — | 2.048 | — | 0 |
| LNU254 | 25782.5 | 0.377 | 0.491 | 47 | LNU10 | 25123.6 | 2.244 | 0.002 | 10 |
| LNU254 | 25781.5 | 0.282 | 0.573 | 10 | LNU10 | 25123.5 | 2.200 | 0.009 | 7 |
| LNU254 | 25781.3 | 0.262 | 0.655 | 2 | LNU122 | 25332.1 | 2.438 | 0.000 | 19 |
| LNU4 | 25133.3 | 0.279 | 0.100 | 9 | LNU122 | 25332.5 | 2.275 | 0.041 | 11 |
| LNU4 | 25134.1 | 0.270 | 0.319 | 6 | LNU122 | 25332.2 | 2.106 | 0.486 | 3 |
| LNU4 | 25134.2 | 0.267 | 0.429 | 4 | LNU125 | 25941.4 | 2.325 | 0.207 | 14 |
| LNU40 | 24793.1 | 0.323 | 0.561 | 26 | LNU125 | 25944.1 | 2.213 | 0.012 | 8 |
| LNU40 | 24792.2 | 0.314 | 0.299 | 23 | LNU125 | 25941.2 | 2.175 | 0.597 | 6 |
| LNU40 | 24794.3 | 0.311 | 0.535 | 22 | LNU125 | 25943.2 | 2.106 | 0.409 | 3 |
| LNU40 | 24792.1 | 0.268 | 0.372 | 5 | LNU125 | 25944.3 | 2.088 | 0.421 | 2 |
| LNU40 | 24794.4 | 0.268 | 0.372 | 5 | LNU178 | 14611.5 | 2.138 | 0.353 | 4 |
| LNU46 | 14462.1 | 0.289 | 0.424 | 13 | LNU178 | 14611.1 | 2.081 | 0.679 | 2 |
| LNU46 | 14462.5 | 0.279 | 0.693 | 9 | LNU234 | 25014.1 | 2.288 | 0.000 | 12 |
| LNU48 | 24803.2 | 0.318 | 0.465 | 24 | LNU234 | 25014.6 | 2.188 | 0.319 | 7 |
| LNU48 | 24801.4 | 0.301 | 0.009 | 18 | LNU234 | 25014.5 | 2.125 | 0.248 | 4 |
| LNU48 | 24804.4 | 0.288 | 0.069 | 13 | LNU236 | 25424.2 | 2.200 | 0.049 | 7 |
| LNU48 | 24802.2 | 0.269 | 0.362 | 5 | LNU236 | 25423.3 | 2.131 | 0.101 | 4 |
| LNU48 | 24802.1 | 0.261 | 0.730 | 2 | LNU24 | 24974.2 | 2.319 | 0.159 | 13 |
| LNU63 | 24814.7 | 0.288 | 0.183 | 12 | LNU24 | 24972.1 | 2.175 | 0.293 | 6 |
| LNU7 | 25083.3 | 0.316 | 0.394 | 23 | LNU25 | 14082.8 | 2.275 | 0.132 | 11 |
| LNU7 | 25082.7 | 0.281 | 0.763 | 10 | LNU271 | 25912.1 | 2.188 | 0.026 | 7 |
| LNU7 | 25081.1 | 0.269 | 0.406 | 5 | LNU271 | 25913.3 | 2.181 | 0.245 | 7 |
| LNU8 | 25061.2 | 0.264 | 0.584 | 3 | LNU271 | 25911.4 | 2.144 | 0.363 | 5 |
| LNU94 | 24833.3 | 0.271 | 0.626 | 6 | LNU278 | 25814.3 | 2.369 | 0.058 | 16 |
| LNU94 | 24831.4 | 0.265 | 0.497 | 4 | LNU278 | 25814.1 | 2.250 | 0.470 | 10 |
| LNU96 | 25073.4 | 0.307 | 0.516 | 20 | LNU278 | 25812.2 | 2.188 | 0.262 | 7 |
| LNU96 | 25073.3 | 0.303 | 0.664 | 18 | LNU278 | 25813.2 | 2.138 | 0.630 | 4 |
| LNU96 | 25071.2 | 0.301 | 0.535 | 17 | LNU43 | 14423.7 | 2.450 | 0.132 | 20 |
| LNU96 | 25074.1 | 0.267 | 0.440 | 4 | LNU43 | 14423.6 | 2.275 | 0.084 | 11 |
| CONT. | — | 0.243 | — | 0 | LNU43 | 14421.1 | 2.106 | 0.646 | 3 |
| LNU10 | 25123.6 | 0.283 | 0.160 | 17 | LNU43 | 14422.8 | 2.100 | 0.750 | 3 |
| LNU10 | 25123.5 | 0.265 | 0.218 | 9 | LNU45 | 25053.4 | 2.356 | 0.000 | 15 |
| LNU10 | 25123.1 | 0.246 | 0.773 | 1 | LNU45 | 25052.12 | 2.244 | 0.010 | 10 |
| LNU122 | 25332.1 | 0.277 | 0.167 | 14 | LNU45 | 25052.11 | 2.106 | 0.409 | 3 |

TABLE 82-continued

Genes showing improved plant biomass production at standard nitrogen growth conditions

| Gene Name | Event # | Dry Weight [g] Ave. | P-Value | % incr. | Gene Name | Event # | Fresh Weight [g] Ave. | P-Value | % incr. |
|---|---|---|---|---|---|---|---|---|---|
| LNU122 | 25332.5 | 0.266 | 0.002 | 9 | LNU67 | 25823.5 | 2.331 | 0.000 | 14 |
| LNU125 | 25941.4 | 0.285 | 0.000 | 17 | LNU67 | 25824.5 | 2.313 | 0.000 | 13 |
| LNU125 | 25944.1 | 0.275 | 0.000 | 13 | LNU67 | 25821.5 | 2.288 | 0.009 | 12 |
| LNU125 | 25943.2 | 0.264 | 0.003 | 9 | LNU67 | 25824.3 | 2.194 | 0.587 | 7 |
| LNU125 | 25941.2 | 0.261 | 0.562 | 7 | LNU67 | 25821.4 | 2.169 | 0.025 | 6 |
| LNU157 | 24982.8 | 0.259 | 0.114 | 7 | LNU9 | 25003.1 | 2.219 | 0.171 | 8 |
| LNU178 | 14611.5 | 0.265 | 0.295 | 9 | LNU9 | 25001.7 | 2.156 | 0.243 | 5 |
| LNU234 | 25014.4 | 0.267 | 0.253 | 10 | LNU9 | 25001.3 | 2.138 | 0.189 | 4 |
| LNU234 | 25014.5 | 0.262 | 0.005 | 8 | LNU9 | 25001.2 | 2.113 | 0.668 | 3 |
| LNU234 | 25014.1 | 0.258 | 0.552 | 6 | CONT. | — | 2.362 | — | 0 |
| LNU234 | 25014.8 | 0.257 | 0.466 | 6 | LNU10 | 25121.8 | 2.531 | 0.266 | 7 |
| LNU234 | 25014.6 | 0.246 | 0.774 | 1 | LNU10 | 25121.6 | 2.494 | 0.083 | 6 |
| LNU236 | 25424.2 | 0.266 | 0.006 | 9 | LNU10 | 25123.6 | 2.469 | 0.186 | 5 |
| LNU236 | 25425.3 | 0.258 | 0.016 | 6 | LNU157 | 24982.1 | 2.525 | 0.348 | 7 |
| LNU236 | 25422.4 | 0.253 | 0.256 | 4 | LNU157 | 24983.3 | 2.506 | 0.325 | 6 |
| LNU24 | 24972.1 | 0.280 | 0.454 | 15 | LNU157 | 24982.7 | 2.431 | 0.736 | 3 |
| LNU24 | 24974.2 | 0.273 | 0.015 | 12 | LNU168 | 24754.2 | 2.650 | 0.001 | 12 |
| LNU24 | 24971.2 | 0.256 | 0.425 | 6 | LNU168 | 24753.8 | 2.563 | 0.018 | 9 |
| LNU25 | 14082.8 | 0.265 | 0.002 | 9 | LNU168 | 24753.5 | 2.456 | 0.695 | 4 |
| LNU267 | 25804.4 | 0.253 | 0.338 | 4 | LNU168 | 24753.2 | 2.450 | 0.234 | 4 |
| LNU271 | 25911.4 | 0.264 | 0.353 | 9 | LNU173 | 25451.1 | 3.063 | 0.024 | 30 |
| LNU271 | 25912.1 | 0.256 | 0.045 | 6 | LNU173 | 25451.12 | 2.839 | 0.335 | 20 |
| LNU271 | 25913.3 | 0.249 | 0.780 | 2 | LNU173 | 25451.2 | 2.825 | 0.126 | 20 |
| LNU278 | 25814.3 | 0.277 | 0.404 | 14 | LNU173 | 25451.5 | 2.688 | 0.001 | 14 |
| LNU278 | 25814.1 | 0.268 | 0.028 | 10 | LNU173 | 25451.11 | 2.481 | 0.144 | 5 |
| LNU278 | 25812.3 | 0.264 | 0.089 | 9 | LNU178 | 14611.4 | 2.788 | 0.021 | 18 |
| LNU278 | 25813.2 | 0.261 | 0.522 | 7 | LNU178 | 14612.1 | 2.638 | 0.142 | 12 |
| LNU43 | 14423.7 | 0.292 | 0.267 | 20 | LNU178 | 14611.5 | 2.463 | 0.280 | 4 |
| LNU43 | 14422.8 | 0.276 | 0.000 | 14 | LNU178 | 14614.5 | 2.463 | 0.173 | 4 |
| LNU43 | 14423.6 | 0.269 | 0.001 | 11 | LNU178 | 14611.1 | 2.456 | 0.212 | 4 |
| LNU45 | 25052.12 | 0.271 | 0.104 | 11 | LNU184 | 25393.1 | 2.725 | 0.371 | 15 |
| LNU45 | 25053.4 | 0.271 | 0.143 | 11 | LNU184 | 25394.3 | 2.675 | 0.001 | 13 |
| LNU67 | 25823.5 | 0.284 | 0.018 | 17 | LNU184 | 25393.3 | 2.638 | 0.016 | 12 |
| LNU67 | 25824.3 | 0.277 | 0.222 | 14 | LNU184 | 25395.1 | 2.569 | 0.443 | 9 |
| LNU67 | 25824.5 | 0.270 | 0.371 | 11 | LNU20 | 24933.4 | 2.775 | 0.009 | 18 |
| LNU67 | 25821.5 | 0.265 | 0.387 | 9 | LNU20 | 24933.1 | 2.550 | 0.019 | 8 |
| LNU67 | 25821.4 | 0.252 | 0.137 | 4 | LNU20 | 24933.2 | 2.538 | 0.228 | 7 |
| LNU9 | 25003.1 | 0.274 | 0.013 | 13 | LNU20 | 24932.4 | 2.525 | 0.037 | 7 |
| LNU9 | 25001.2 | 0.259 | 0.011 | 7 | LNU20 | 24934.1 | 2.506 | 0.697 | 6 |
| LNU9 | 25001.3 | 0.254 | 0.592 | 5 | LNU230 | 25413.2 | 2.769 | 0.084 | 17 |
| CONT. | — | 0.240 | — | 0 | LNU230 | 25415.1 | 2.744 | 0.227 | 16 |
| LNU10 | 25123.6 | 0.256 | 0.224 | 7 | LNU230 | 25412.2 | 2.656 | 0.001 | 12 |
| LNU10 | 25121.8 | 0.253 | 0.717 | 5 | LNU230 | 25412.1 | 2.625 | 0.003 | 11 |
| LNU10 | 25121.6 | 0.248 | 0.530 | 3 | LNU230 | 25413.1 | 2.563 | 0.014 | 9 |
| LNU157 | 24982.4 | 0.265 | 0.764 | 10 | LNU236 | 25425.4 | 2.725 | 0.000 | 15 |
| LNU157 | 24982.1 | 0.262 | 0.085 | 9 | LNU236 | 25422.4 | 2.650 | 0.409 | 12 |
| LNU157 | 24982.8 | 0.261 | 0.293 | 9 | LNU236 | 25424.2 | 2.638 | 0.142 | 12 |
| LNU168 | 24754.2 | 0.259 | 0.131 | 8 | LNU236 | 25425.3 | 2.625 | 0.322 | 11 |
| LNU168 | 24751.2 | 0.253 | 0.333 | 5 | LNU236 | 25423.3 | 2.519 | 0.188 | 7 |
| LNU168 | 24753.2 | 0.250 | 0.647 | 4 | LNU24 | 24974.2 | 2.775 | 0.000 | 18 |
| LNU173 | 25451.1 | 0.295 | 0.044 | 23 | LNU24 | 24971.2 | 2.581 | 0.447 | 9 |
| LNU173 | 25451.2 | 0.274 | 0.032 | 14 | LNU24 | 24971.4 | 2.550 | 0.066 | 8 |
| LNU173 | 25451.12 | 0.259 | 0.643 | 8 | LNU24 | 24971.3 | 2.506 | 0.588 | 6 |
| LNU173 | 25451.5 | 0.251 | 0.396 | 4 | LNU263 | 25791.3 | 2.738 | 0.376 | 16 |
| LNU173 | 25451.11 | 0.250 | 0.411 | 4 | LNU263 | 25794.8 | 2.675 | 0.466 | 13 |
| LNU178 | 14611.4 | 0.275 | 0.011 | 14 | LNU263 | 25792.2 | 2.606 | 0.636 | 10 |
| LNU178 | 14612.1 | 0.256 | 0.279 | 6 | LNU263 | 25794.6 | 2.556 | 0.531 | 8 |
| LNU178 | 14611.5 | 0.253 | 0.427 | 5 | LNU263 | 25794.3 | 2.456 | 0.200 | 4 |
| LNU178 | 14614.5 | 0.251 | 0.584 | 5 | LNU276 | 25431.1 | 2.513 | 0.418 | 4 |
| LNU184 | 25393.1 | 0.276 | 0.409 | 15 | LNU276 | 25433.1 | 2.413 | 0.714 | 2 |
| LNU184 | 25395.1 | 0.275 | 0.074 | 14 | LNU279 | 25481.4 | 2.644 | 0.009 | 12 |
| LNU184 | 25393.2 | 0.259 | 0.724 | 8 | LNU279 | 25481.3 | 2.563 | 0.014 | 9 |
| LNU184 | 25393.3 | 0.258 | 0.155 | 7 | LNU279 | 25484.3 | 2.425 | 0.386 | 3 |
| LNU184 | 25394.3 | 0.249 | 0.468 | 4 | LNU279 | 25481.5 | 2.406 | 0.534 | 2 |
| LNU20 | 24933.2 | 0.278 | 0.604 | 16 | LNU279 | 25481.2 | 2.381 | 0.783 | 1 |
| LNU20 | 24933.4 | 0.275 | 0.053 | 14 | LNU36 | 25562.9 | 2.706 | 0.051 | 15 |
| LNU20 | 24934.1 | 0.261 | 0.418 | 9 | LNU36 | 25561.2 | 2.675 | 0.544 | 13 |
| LNU20 | 24933.1 | 0.257 | 0.184 | 7 | LNU36 | 25562.4 | 2.656 | 0.109 | 12 |
| LNU230 | 25415.1 | 0.277 | 0.258 | 15 | LNU36 | 25562.3 | 2.513 | 0.514 | 6 |
| LNU230 | 25413.2 | 0.264 | 0.084 | 10 | LNU36 | 25562.7 | 2.456 | 0.335 | 4 |
| LNU230 | 25413.1 | 0.258 | 0.159 | 7 | LNU53 | 25674.1 | 2.669 | 0.203 | 13 |
| LNU230 | 25412.1 | 0.253 | 0.282 | 5 | LNU53 | 25674.6 | 2.563 | 0.137 | 9 |

TABLE 82-continued

Genes showing improved plant biomass production at standard nitrogen growth conditions

| Gene Name | Event # | Dry Weight [g] Ave. | P-Value | % incr. | Gene Name | Event # | Fresh Weight [g] Ave. | P-Value | % incr. |
|---|---|---|---|---|---|---|---|---|---|
| LNU230 | 25412.2 | 0.248 | 0.538 | 3 | LNU53 | 25674.5 | 2.506 | 0.217 | 6 |
| LNU236 | 25422.4 | 0.281 | 0.397 | 17 | LNU53 | 25674.2 | 2.488 | 0.576 | 5 |
| LNU236 | 25425.4 | 0.273 | 0.047 | 13 | LNU56 | 24694.1 | 2.694 | 0.120 | 14 |
| LNU236 | 25424.2 | 0.261 | 0.362 | 9 | LNU56 | 24693.2 | 2.656 | 0.020 | 12 |
| LNU236 | 25425.3 | 0.257 | 0.172 | 7 | LNU56 | 24694.2 | 2.625 | 0.192 | 11 |
| LNU24 | 24971.2 | 0.269 | 0.225 | 12 | LNU56 | 24693.1 | 2.531 | 0.355 | 7 |
| LNU24 | 24974.2 | 0.260 | 0.139 | 8 | LNU73 | 25751.8 | 2.463 | 0.231 | 4 |
| LNU24 | 24971.4 | 0.259 | 0.148 | 8 | LNU73 | 25751.1 | 2.450 | 0.446 | 4 |
| LNU24 | 24971.3 | 0.251 | 0.381 | 4 | LNU9 | 25001.3 | 2.725 | 0.000 | 15 |
| LNU263 | 25794.8 | 0.306 | 0.504 | 27 | LNU9 | 25001.7 | 2.719 | 0.136 | 15 |
| LNU263 | 25791.3 | 0.271 | 0.586 | 13 | LNU9 | 25001.2 | 2.600 | 0.431 | 10 |
| LNU263 | 25792.2 | 0.270 | 0.759 | 12 | LNU9 | 25003.1 | 2.475 | 0.585 | 5 |
| LNU263 | 25794.6 | 0.267 | 0.369 | 11 | CONT. | — | 2.036 | — | 0 |
| LNU263 | 25794.3 | 0.254 | 0.535 | 6 | LNU173 | 25451.5 | 2.394 | 0.002 | 18 |
| LNU276 | 25431.1 | 0.290 | 0.201 | 21 | LNU173 | 25451.2 | 2.369 | 0.294 | 16 |
| LNU276 | 25433.2 | 0.248 | 0.544 | 3 | LNU173 | 25451.1 | 2.189 | 0.154 | 8 |
| LNU276 | 25433.1 | 0.246 | 0.665 | 2 | LNU181 | 25771.2 | 2.338 | 0.095 | 15 |
| LNU279 | 25481.4 | 0.268 | 0.417 | 11 | LNU181 | 25771.5 | 2.275 | 0.509 | 12 |
| LNU279 | 25481.3 | 0.265 | 0.201 | 10 | LNU181 | 25771.6 | 2.219 | 0.332 | 9 |
| LNU279 | 25481.5 | 0.250 | 0.431 | 4 | LNU181 | 25771.8 | 2.150 | 0.206 | 6 |
| LNU279 | 25481.2 | 0.246 | 0.759 | 3 | LNU184 | 25394.1 | 2.338 | 0.521 | 15 |
| LNU36 | 25562.4 | 0.269 | 0.404 | 12 | LNU184 | 25393.2 | 2.238 | 0.279 | 10 |
| LNU36 | 25561.2 | 0.269 | 0.305 | 12 | LNU184 | 25393.3 | 2.220 | 0.530 | 9 |
| LNU36 | 25562.9 | 0.252 | 0.406 | 5 | LNU184 | 25394.3 | 2.106 | 0.663 | 3 |
| LNU36 | 25562.3 | 0.249 | 0.479 | 4 | LNU224 | 25872.3 | 2.344 | 0.144 | 15 |
| LNU53 | 25674.1 | 0.260 | 0.355 | 8 | LNU224 | 25874.1 | 2.269 | 0.018 | 11 |
| LNU53 | 25674.2 | 0.246 | 0.679 | 2 | LNU224 | 25874.4 | 2.250 | 0.016 | 11 |
| LNU53 | 25674.6 | 0.245 | 0.697 | 2 | LNU224 | 25872.2 | 2.188 | 0.166 | 7 |
| LNU56 | 24694.1 | 0.261 | 0.109 | 9 | LNU246 | 25744.2 | 2.331 | 0.080 | 15 |
| LNU56 | 24694.2 | 0.254 | 0.445 | 6 | LNU246 | 25743.1 | 2.287 | 0.001 | 12 |
| LNU56 | 24693.1 | 0.246 | 0.711 | 2 | LNU246 | 25743.2 | 2.188 | 0.027 | 7 |
| LNU73 | 25751.1 | 0.259 | 0.621 | 8 | LNU246 | 25744.3 | 2.106 | 0.663 | 3 |
| LNU9 | 25001.7 | 0.264 | 0.193 | 10 | LNU250 | 25592.1 | 2.319 | 0.535 | 14 |
| LNU9 | 25001.2 | 0.264 | 0.063 | 10 | LNU250 | 25592.2 | 2.319 | 0.023 | 14 |
| LNU9 | 25003.1 | 0.256 | 0.343 | 7 | LNU250 | 25591.1 | 2.113 | 0.244 | 4 |
| LNU9 | 25001.3 | 0.252 | 0.359 | 5 | LNU260 | 26403.1 | 2.194 | 0.513 | 8 |
| CONT. | — | 0.178 | — | 0 | LNU260 | 26404.7 | 2.163 | 0.079 | 6 |
| LNU131 | 14005.5 | 0.208 | 0.034 | 17 | LNU260 | 26404.1 | 2.144 | 0.325 | 5 |
| LNU131 | 14005.2 | 0.204 | 0.069 | 14 | LNU260 | 26403.2 | 2.081 | 0.774 | 2 |
| LNU135 | 26204.2 | 0.206 | 0.109 | 16 | LNU276 | 25433.3 | 2.356 | 0.000 | 16 |
| LNU135 | 26203.6 | 0.204 | 0.230 | 14 | CONT. | — | 1.044 | — | 0 |
| LNU135 | 26203.4 | 0.196 | 0.793 | 10 | LNU136 | 14515.1 | 1.313 | 0.374 | 26 |
| LNU135 | 26203.1 | 0.188 | 0.712 | 5 | LNU136 | 14515.5 | 1.263 | 0.005 | 21 |
| LNU173 | 25451.2 | 0.239 | 0.030 | 34 | LNU136 | 14511.10 | 1.150 | 0.466 | 10 |
| LNU173 | 25451.5 | 0.226 | 0.009 | 27 | LNU142 | 27541.1 | 1.344 | 0.125 | 29 |
| LNU173 | 25451.11 | 0.205 | 0.421 | 15 | LNU142 | 27541.2 | 1.219 | 0.389 | 17 |
| LNU173 | 25451.1 | 0.193 | 0.703 | 8 | LNU149 | 26175.1 | 1.225 | 0.480 | 17 |
| LNU181 | 25771.6 | 0.224 | 0.281 | 25 | LNU149 | 26175.3 | 1.131 | 0.404 | 8 |
| LNU181 | 25771.2 | 0.217 | 0.010 | 22 | LNU149 | 26175.7 | 1.131 | 0.337 | 8 |
| LNU181 | 25771.8 | 0.209 | 0.086 | 17 | LNU15 | 14123.13 | 1.244 | 0.123 | 19 |
| LNU181 | 25771.5 | 0.204 | 0.423 | 14 | LNU15 | 14122.8 | 1.163 | 0.061 | 11 |
| LNU181 | 25771.11 | 0.200 | 0.105 | 12 | LNU15 | 14122.9 | 1.156 | 0.304 | 11 |
| LNU184 | 25394.1 | 0.236 | 0.114 | 32 | LNU15 | 14123.11 | 1.156 | 0.112 | 11 |
| LNU184 | 25393.2 | 0.229 | 0.001 | 28 | LNU185 | 26474.2 | 1.206 | 0.066 | 16 |
| LNU184 | 25395.1 | 0.215 | 0.088 | 20 | LNU185 | 26475.1 | 1.144 | 0.102 | 10 |
| LNU184 | 25393.3 | 0.207 | 0.186 | 16 | LNU185 | 26474.1 | 1.131 | 0.714 | 8 |
| LNU184 | 25394.3 | 0.203 | 0.287 | 14 | LNU212 | 25834.1 | 1.356 | 0.269 | 30 |
| LNU184 | 25393.1 | 0.196 | 0.175 | 10 | LNU212 | 25832.1 | 1.233 | 0.246 | 18 |
| LNU224 | 25874.1 | 0.223 | 0.003 | 25 | LNU212 | 25834.4 | 1.195 | 0.255 | 14 |
| LNU224 | 25872.3 | 0.214 | 0.418 | 20 | LNU212 | 25833.2 | 1.150 | 0.605 | 10 |
| LNU224 | 25874.4 | 0.214 | 0.011 | 20 | LNU212 | 25834.5 | 1.138 | 0.552 | 9 |
| LNU224 | 25871.3 | 0.206 | 0.219 | 15 | LNU216 | 25985.4 | 1.369 | 0.232 | 31 |
| LNU224 | 25872.2 | 0.194 | 0.465 | 9 | LNU216 | 25982.1 | 1.363 | 0.223 | 31 |
| LNU246 | 25744.3 | 0.237 | 0.000 | 33 | LNU228 | 26222.1 | 1.269 | 0.306 | 22 |
| LNU246 | 25744.2 | 0.231 | 0.030 | 30 | LNU228 | 26222.4 | 1.169 | 0.049 | 12 |
| LNU246 | 25743.1 | 0.223 | 0.003 | 25 | LNU228 | 26224.6 | 1.119 | 0.466 | 7 |
| LNU246 | 25743.2 | 0.218 | 0.028 | 22 | LNU229 | 26112.3 | 1.094 | 0.659 | 5 |
| LNU246 | 25744.4 | 0.212 | 0.097 | 19 | LNU277 | 25842.3 | 1.150 | 0.545 | 10 |
| LNU250 | 25591.1 | 0.221 | 0.016 | 24 | LNU280 | 26162.1 | 1.394 | 0.038 | 34 |
| LNU250 | 25592.2 | 0.216 | 0.013 | 21 | LNU280 | 26162.7 | 1.166 | 0.378 | 12 |
| LNU250 | 25592.1 | 0.213 | 0.159 | 19 | LNU280 | 26164.4 | 1.144 | 0.211 | 10 |
| LNU250 | 25591.3 | 0.186 | 0.684 | 4 | LNU55 | 26015.1 | 1.356 | 0.006 | 30 |

TABLE 82-continued

Genes showing improved plant biomass production at standard nitrogen growth conditions

| Gene Name | Event # | Dry Weight [g] Ave. | P-Value | % incr. | Gene Name | Event # | Fresh Weight [g] Ave. | P-Value | % incr. |
|---|---|---|---|---|---|---|---|---|---|
| LNU260 | 26404.1 | 0.215 | 0.032 | 20 | LNU55 | 26015.3 | 1.219 | 0.011 | 17 |
| LNU260 | 26404.7 | 0.211 | 0.027 | 18 | LNU81 | 26034.3 | 1.194 | 0.140 | 14 |
| LNU260 | 26403.1 | 0.204 | 0.119 | 15 | LNU81 | 26031.2 | 1.125 | 0.172 | 8 |
| LNU260 | 26403.2 | 0.195 | 0.312 | 9 | CONT. | — | 1.494 | — | 0 |
| LNU260 | 26404.8 | 0.185 | 0.681 | 4 | LNU119 | 26141.1 | 1.806 | 0.082 | 21 |
| LNU276 | 25433.3 | 0.218 | 0.006 | 22 | LNU119 | 26142.8 | 1.744 | 0.472 | 17 |
| LNU276 | 25433.6 | 0.213 | 0.066 | 19 | LNU119 | 26144.1 | 1.613 | 0.619 | 8 |
| LNU276 | 25433.5 | 0.188 | 0.475 | 5 | LNU119 | 26144.2 | 1.606 | 0.157 | 8 |
| LNU276 | 25431.1 | 0.185 | 0.614 | 4 | LNU119 | 26142.5 | 1.575 | 0.705 | 5 |
| LNU279 | 25484.3 | 0.216 | 0.017 | 21 | LNU130 | 24913.5 | 1.856 | 0.340 | 24 |
| LNU279 | 25481.5 | 0.215 | 0.046 | 20 | LNU130 | 24911.7 | 1.813 | 0.030 | 21 |
| LNU279 | 25481.3 | 0.199 | 0.223 | 11 | LNU130 | 24913.6 | 1.700 | 0.219 | 14 |
| LNU279 | 25481.4 | 0.184 | 0.646 | 3 | LNU130 | 24912.7 | 1.675 | 0.371 | 12 |
| LNU3 | 26124.3 | 0.218 | 0.073 | 22 | LNU136 | 14514.8 | 1.906 | 0.106 | 28 |
| LNU3 | 26122.2 | 0.205 | 0.050 | 15 | LNU136 | 14511.10 | 1.731 | 0.165 | 16 |
| LNU3 | 26123.5 | 0.203 | 0.162 | 14 | LNU136 | 14515.1 | 1.725 | 0.192 | 15 |
| LNU3 | 26124.1 | 0.193 | 0.528 | 8 | LNU142 | 27546.2 | 2.000 | 0.300 | 34 |
| LNU33 | 25552.2 | 0.223 | 0.023 | 25 | LNU142 | 27541.2 | 1.919 | 0.001 | 28 |
| LNU33 | 25551.1 | 0.186 | 0.589 | 4 | LNU142 | 27545.1 | 1.844 | 0.100 | 23 |
| CONT. | — | 0.079 | — | 0 | LNU142 | 27546.1 | 1.769 | 0.266 | 18 |
| LNU119 | 26142.5 | 0.085 | 0.725 | 8 | LNU142 | 27541.1 | 1.625 | 0.157 | 9 |
| LNU130 | 24914.5 | 0.085 | 0.186 | 8 | LNU149 | 26174.7 | 1.756 | 0.306 | 18 |
| LNU130 | 24913.6 | 0.084 | 0.792 | 7 | LNU149 | 26174.6 | 1.659 | 0.375 | 11 |
| LNU130 | 24912.7 | 0.083 | 0.422 | 5 | LNU149 | 26175.3 | 1.638 | 0.321 | 10 |
| LNU136 | 14515.5 | 0.108 | 0.000 | 38 | LNU149 | 26174.8 | 1.538 | 0.272 | 3 |
| LNU136 | 14515.1 | 0.108 | 0.377 | 37 | LNU15 | 14122.8 | 1.894 | 0.001 | 27 |
| LNU136 | 14511.10 | 0.092 | 0.107 | 17 | LNU15 | 14123.11 | 1.713 | 0.281 | 15 |
| LNU142 | 27541.1 | 0.111 | 0.000 | 41 | LNU15 | 14124.12 | 1.625 | 0.510 | 9 |
| LNU142 | 27541.2 | 0.093 | 0.086 | 18 | LNU185 | 26474.1 | 1.806 | 0.283 | 21 |
| LNU142 | 27545.1 | 0.088 | 0.528 | 12 | LNU185 | 26473.1 | 1.750 | 0.206 | 17 |
| LNU142 | 27546.2 | 0.085 | 0.411 | 8 | LNU185 | 26475.1 | 1.694 | 0.102 | 13 |
| LNU149 | 26175.1 | 0.104 | 0.357 | 33 | LNU185 | 26474.2 | 1.644 | 0.376 | 10 |
| LNU149 | 26175.3 | 0.095 | 0.463 | 21 | LNU212 | 25834.4 | 2.106 | 0.000 | 41 |
| LNU149 | 26175.7 | 0.084 | 0.421 | 7 | LNU212 | 25834.5 | 2.094 | 0.000 | 40 |
| LNU15 | 14123.11 | 0.104 | 0.000 | 33 | LNU212 | 25834.1 | 2.019 | 0.079 | 35 |
| LNU15 | 14123.13 | 0.102 | 0.304 | 30 | LNU212 | 25833.2 | 1.944 | 0.118 | 30 |
| LNU15 | 14122.9 | 0.100 | 0.016 | 27 | LNU212 | 25833.1 | 1.600 | 0.705 | 7 |
| LNU15 | 14122.8 | 0.099 | 0.033 | 26 | LNU216 | 25984.1 | 2.238 | 0.043 | 50 |
| LNU185 | 26474.2 | 0.099 | 0.001 | 26 | LNU216 | 25982.2 | 2.169 | 0.073 | 45 |
| LNU185 | 26473.1 | 0.088 | 0.651 | 12 | LNU216 | 25985.4 | 2.113 | 0.239 | 41 |
| LNU185 | 26474.1 | 0.088 | 0.084 | 11 | LNU216 | 25984.6 | 2.094 | 0.000 | 40 |
| LNU212 | 25832.1 | 0.115 | 0.117 | 46 | LNU216 | 25982.1 | 1.850 | 0.000 | 24 |
| LNU212 | 25834.4 | 0.107 | 0.172 | 36 | LNU228 | 26222.1 | 2.688 | 0.000 | 80 |
| LNU212 | 25834.1 | 0.101 | 0.043 | 29 | LNU228 | 26224.7 | 2.381 | 0.040 | 59 |
| LNU212 | 25833.2 | 0.094 | 0.565 | 19 | LNU228 | 26222.4 | 2.301 | 0.066 | 54 |
| LNU212 | 25834.5 | 0.094 | 0.425 | 19 | LNU228 | 26225.2 | 2.256 | 0.000 | 51 |
| LNU216 | 25982.1 | 0.114 | 0.219 | 45 | LNU228 | 26224.6 | 2.081 | 0.244 | 39 |
| LNU216 | 25985.4 | 0.108 | 0.055 | 37 | LNU229 | 26111.5 | 2.194 | 0.002 | 47 |
| LNU228 | 26222.1 | 0.103 | 0.001 | 30 | LNU229 | 26112.4 | 2.175 | 0.000 | 46 |
| LNU228 | 26222.4 | 0.098 | 0.002 | 24 | LNU229 | 26111.7 | 2.163 | 0.000 | 45 |
| LNU228 | 26224.6 | 0.094 | 0.238 | 19 | LNU229 | 26112.3 | 2.038 | 0.243 | 36 |
| LNU228 | 26224.7 | 0.083 | 0.422 | 5 | LNU229 | 26114.1 | 1.931 | 0.185 | 29 |
| LNU229 | 26112.3 | 0.096 | 0.466 | 22 | LNU241 | 26232.4 | 2.163 | 0.000 | 45 |
| LNU253 | 26241.1 | 0.083 | 0.514 | 6 | LNU241 | 26234.1 | 2.163 | 0.018 | 45 |
| LNU277 | 25842.3 | 0.099 | 0.370 | 26 | LNU241 | 26232.1 | 1.881 | 0.209 | 26 |
| LNU277 | 25844.4 | 0.089 | 0.166 | 14 | LNU241 | 26233.2 | 1.881 | 0.383 | 26 |
| LNU277 | 25844.3 | 0.082 | 0.765 | 4 | LNU241 | 26233.3 | 1.744 | 0.415 | 17 |
| LNU280 | 26162.1 | 0.114 | 0.002 | 45 | LNU253 | 26242.1 | 2.175 | 0.000 | 46 |
| LNU280 | 26162.7 | 0.096 | 0.081 | 23 | LNU253 | 26241.1 | 2.100 | 0.000 | 41 |
| LNU280 | 26164.4 | 0.092 | 0.053 | 17 | LNU253 | 26243.3 | 2.069 | 0.169 | 38 |
| LNU280 | 26164.2 | 0.083 | 0.374 | 6 | LNU253 | 26245.1 | 1.794 | 0.707 | 20 |
| LNU55 | 26015.1 | 0.097 | 0.100 | 23 | LNU253 | 26244.2 | 1.781 | 0.165 | 19 |
| LNU55 | 26015.3 | 0.094 | 0.006 | 20 | LNU264 | 26264.2 | 2.331 | 0.030 | 56 |
| LNU81 | 26031.2 | 0.099 | 0.077 | 26 | LNU274 | 26265.1 | 2.238 | 0.147 | 50 |
| LNU81 | 26034.3 | 0.092 | 0.311 | 17 | LNU274 | 26262.2 | 2.225 | 0.087 | 49 |
| LNU81 | 26031.10 | 0.088 | 0.570 | 11 | LNU274 | 26263.2 | 2.225 | 0.113 | 49 |
| CONT. | — | 0.150 | — | 0 | LNU274 | 26261.3 | 2.113 | 0.008 | 41 |
| LNU119 | 26142.8 | 0.160 | 0.721 | 7 | LNU277 | 25844.3 | 2.094 | 0.000 | 40 |
| LNU119 | 26141.1 | 0.157 | 0.673 | 5 | LNU277 | 25842.3 | 2.013 | 0.028 | 35 |
| LNU130 | 24913.5 | 0.168 | 0.234 | 12 | LNU277 | 25844.4 | 1.988 | 0.136 | 33 |
| LNU130 | 24913.6 | 0.159 | 0.303 | 6 | LNU277 | 25841.3 | 1.881 | 0.230 | 26 |
| LNU130 | 24911.7 | 0.156 | 0.412 | 4 | LNU277 | 25845.1 | 1.625 | 0.589 | 9 |

TABLE 82-continued

Genes showing improved plant biomass production at standard nitrogen growth conditions

| Gene Name | Event # | Dry Weight [g] Ave. | P-Value | % incr. | Gene Name | Event # | Fresh Weight [g] Ave. | P-Value | % incr. |
|---|---|---|---|---|---|---|---|---|---|
| LNU136 | 14514.8 | 0.193 | 0.421 | 28 | LNU280 | 26162.1 | 2.469 | 0.006 | 65 |
| LNU136 | 14511.10 | 0.164 | 0.110 | 10 | LNU280 | 26164.4 | 2.263 | 0.001 | 51 |
| LNU136 | 14515.1 | 0.163 | 0.361 | 8 | LNU280 | 26162.7 | 2.094 | 0.368 | 40 |
| LNU142 | 27546.2 | 0.176 | 0.494 | 17 | LNU280 | 26164.3 | 1.888 | 0.255 | 26 |
| LNU142 | 27541.2 | 0.171 | 0.037 | 14 | LNU280 | 26164.2 | 1.700 | 0.487 | 14 |
| LNU142 | 27545.1 | 0.171 | 0.032 | 14 | LNU55 | 26013.9 | 2.219 | 0.067 | 49 |
| LNU142 | 27546.1 | 0.153 | 0.768 | 2 | LNU55 | 26013.3 | 2.181 | 0.000 | 46 |
| LNU15 | 14123.11 | 0.171 | 0.491 | 14 | LNU55 | 26015.1 | 1.881 | 0.001 | 26 |
| LNU15 | 14122.8 | 0.166 | 0.087 | 11 | LNU81 | 26034.2 | 1.956 | 0.572 | 31 |
| LNU15 | 14124.12 | 0.160 | 0.721 | 7 | LNU81 | 26031.10 | 1.781 | 0.671 | 19 |
| LNU185 | 26473.1 | 0.174 | 0.019 | 16 | LNU81 | 26034.3 | 1.581 | 0.514 | 6 |
| LNU185 | 26474.1 | 0.170 | 0.236 | 13 | | | | | |
| LNU185 | 26475.1 | 0.157 | 0.757 | 5 | | | | | |
| LNU212 | 25834.5 | 0.186 | 0.004 | 24 | | | | | |
| LNU212 | 25833.2 | 0.178 | 0.250 | 18 | | | | | |
| LNU212 | 25834.1 | 0.175 | 0.016 | 17 | | | | | |
| LNU212 | 25834.4 | 0.175 | 0.015 | 17 | | | | | |
| LNU216 | 25982.1 | 0.194 | 0.348 | 30 | | | | | |
| LNU216 | 25982.2 | 0.192 | 0.002 | 28 | | | | | |
| LNU216 | 25985.4 | 0.179 | 0.237 | 19 | | | | | |
| LNU216 | 25984.1 | 0.178 | 0.146 | 18 | | | | | |
| LNU216 | 25984.6 | 0.171 | 0.204 | 14 | | | | | |
| LNU228 | 26222.1 | 0.251 | 0.000 | 67 | | | | | |
| LNU228 | 26222.4 | 0.206 | 0.108 | 37 | | | | | |
| LNU228 | 26224.7 | 0.199 | 0.024 | 33 | | | | | |
| LNU228 | 26225.2 | 0.196 | 0.081 | 31 | | | | | |
| LNU228 | 26224.6 | 0.171 | 0.365 | 14 | | | | | |
| LNU229 | 26111.7 | 0.190 | 0.006 | 27 | | | | | |
| LNU229 | 26111.5 | 0.184 | 0.056 | 23 | | | | | |
| LNU229 | 26112.4 | 0.184 | 0.007 | 23 | | | | | |
| LNU229 | 26114.1 | 0.167 | 0.397 | 11 | | | | | |
| LNU229 | 26112.3 | 0.163 | 0.123 | 9 | | | | | |
| LNU241 | 26232.4 | 0.190 | 0.002 | 27 | | | | | |
| LNU241 | 26234.1 | 0.183 | 0.008 | 22 | | | | | |
| LNU241 | 26232.1 | 0.171 | 0.129 | 14 | | | | | |
| LNU241 | 26233.2 | 0.169 | 0.467 | 13 | | | | | |
| LNU241 | 26233.3 | 0.153 | 0.719 | 2 | | | | | |
| LNU253 | 26242.1 | 0.188 | 0.003 | 25 | | | | | |
| LNU253 | 26241.1 | 0.185 | 0.005 | 23 | | | | | |
| LNU253 | 26243.3 | 0.171 | 0.057 | 14 | | | | | |
| LNU253 | 26244.2 | 0.156 | 0.523 | 4 | | | | | |
| LNU274 | 26264.2 | 0.211 | 0.000 | 40 | | | | | |
| LNU274 | 26263.2 | 0.193 | 0.025 | 28 | | | | | |
| LNU274 | 26262.2 | 0.190 | 0.269 | 27 | | | | | |
| LNU274 | 26261.3 | 0.188 | 0.003 | 25 | | | | | |
| LNU274 | 26265.1 | 0.179 | 0.465 | 20 | | | | | |
| LNU277 | 25844.3 | 0.198 | 0.003 | 32 | | | | | |
| LNU277 | 25841.3 | 0.181 | 0.434 | 20 | | | | | |
| LNU277 | 25844.4 | 0.171 | 0.204 | 14 | | | | | |
| LNU277 | 25842.3 | 0.160 | 0.348 | 7 | | | | | |
| LNU280 | 26162.1 | 0.216 | 0.134 | 44 | | | | | |
| LNU280 | 26164.4 | 0.191 | 0.002 | 28 | | | | | |
| LNU280 | 26162.7 | 0.169 | 0.673 | 13 | | | | | |
| LNU280 | 26164.3 | 0.169 | 0.491 | 13 | | | | | |
| LNU55 | 26013.3 | 0.194 | 0.042 | 29 | | | | | |
| LNU55 | 26013.9 | 0.190 | 0.227 | 27 | | | | | |
| LNU55 | 26015.1 | 0.168 | 0.057 | 12 | | | | | |
| LNU81 | 26034.2 | 0.174 | 0.732 | 16 | | | | | |

Table 82.
"CONT."—Control;
"Ave."—Average;
"% Incr." = % increment.

TABLE 83

Genes showing improved plant biomass production at standard nitrogen growth conditions

| | Rosette Diameter [cm] | | | | | Rosette Area [cm2] | | | | | Plot Coverage [%] | | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| CONT. | — | 3.65 | — | 0 | CONT. | — | 4.53 | — | 0 | CONT. | — | 35.85 | — | 0 |
| LNU100 | 14471.4 | 4.39 | 0.208 | 20 | LNU100 | 14471.4 | 6.19 | 0.343 | 37 | LNU100 | 14471.4 | 49.56 | 0.334 | 38 |
| LNU100 | 14474.3 | 4.22 | 0.051 | 16 | LNU100 | 14474.3 | 5.82 | 0.061 | 28 | LNU100 | 14474.3 | 46.53 | 0.052 | 30 |
| LNU100 | 14472.2 | 4.16 | 0.159 | 14 | LNU100 | 14473.3 | 5.78 | 0.148 | 27 | LNU100 | 14473.3 | 46.21 | 0.136 | 29 |
| LNU100 | 14473.3 | 4.07 | 0.105 | 12 | LNU100 | 14472.2 | 5.61 | 0.199 | 24 | LNU100 | 14472.2 | 44.86 | 0.184 | 25 |
| LNU104 | 25032.2 | 4.52 | 0.083 | 24 | LNU104 | 25032.2 | 7.12 | 0.090 | 57 | LNU104 | 25032.2 | 56.93 | 0.085 | 59 |
| LNU104 | 25033.1 | 4.46 | 0.131 | 22 | LNU104 | 25033.1 | 6.47 | 0.063 | 43 | LNU104 | 25033.1 | 51.77 | 0.056 | 44 |
| LNU104 | 25032.1 | 4.32 | 0.074 | 18 | LNU104 | 25032.1 | 6.29 | 0.129 | 39 | LNU104 | 25032.1 | 50.31 | 0.121 | 40 |
| LNU104 | 25033.3 | 4.26 | 0.023 | 17 | LNU104 | 25033.3 | 6.07 | 0.000 | 34 | LNU104 | 25033.3 | 48.53 | 0.000 | 35 |
| LNU104 | 25034.1 | 3.84 | 0.276 | 5 | LNU104 | 25034.1 | 5.06 | 0.235 | 12 | LNU104 | 25034.1 | 40.49 | 0.204 | 13 |
| LNU106 | 14482.3 | 4.27 | 0.401 | 17 | LNU106 | 14482.3 | 5.94 | 0.358 | 31 | LNU106 | 14482.3 | 47.55 | 0.347 | 33 |
| LNU106 | 14483.5 | 4.19 | 0.000 | 15 | LNU106 | 14483.5 | 5.72 | 0.063 | 26 | LNU106 | 14483.5 | 45.73 | 0.054 | 28 |
| LNU106 | 14483.2 | 4.11 | 0.218 | 13 | LNU106 | 14483.2 | 5.69 | 0.340 | 26 | LNU106 | 14483.2 | 45.51 | 0.326 | 27 |
| LNU106 | 14481.1 | 3.77 | 0.065 | 3 | LNU114 | 25041.1 | 6.77 | 0.000 | 49 | LNU114 | 25041.1 | 54.13 | 0.000 | 51 |
| LNU114 | 25041.1 | 4.54 | 0.000 | 24 | LNU114 | 25042.1 | 5.62 | 0.144 | 24 | LNU114 | 25042.1 | 44.92 | 0.130 | 25 |
| LNU114 | 25042.1 | 4.13 | 0.084 | 13 | LNU114 | 25041.2 | 5.18 | 0.018 | 14 | LNU114 | 25041.2 | 41.40 | 0.013 | 15 |
| LNU114 | 25041.2 | 3.96 | 0.112 | 9 | LNU155 | 14525.6 | 5.63 | 0.118 | 24 | LNU155 | 14525.6 | 45.03 | 0.105 | 26 |
| LNU155 | 14525.6 | 4.16 | 0.115 | 14 | LNU155 | 14525.1 | 5.43 | 0.517 | 20 | LNU155 | 14525.1 | 43.44 | 0.499 | 21 |
| LNU155 | 14525.1 | 3.97 | 0.517 | 9 | LNU213 | 24653.2 | 6.87 | 0.000 | 51 | LNU213 | 24653.2 | 54.92 | 0.000 | 53 |
| LNU213 | 24653.2 | 4.55 | 0.000 | 25 | LNU213 | 24652.4 | 6.04 | 0.458 | 33 | LNU213 | 24652.4 | 48.29 | 0.448 | 35 |
| LNU213 | 24652.4 | 4.25 | 0.477 | 16 | LNU213 | 24653.1 | 5.21 | 0.001 | 15 | LNU213 | 24653.1 | 41.64 | 0.001 | 16 |
| LNU213 | 24653.1 | 3.88 | 0.004 | 6 | LNU218 | 24781.1 | 6.41 | 0.167 | 41 | LNU218 | 24781.1 | 51.27 | 0.159 | 43 |
| LNU213 | 24654.4 | 3.79 | 0.713 | 4 | LNU218 | 24781.7 | 6.10 | 0.215 | 35 | LNU218 | 24781.7 | 48.78 | 0.206 | 36 |
| LNU218 | 24781.1 | 4.43 | 0.199 | 21 | LNU218 | 24781.2 | 5.24 | 0.306 | 16 | LNU218 | 24781.2 | 41.96 | 0.282 | 17 |
| LNU218 | 24781.7 | 4.30 | 0.190 | 18 | LNU23 | 25163.5 | 6.90 | 0.010 | 52 | LNU23 | 25163.5 | 55.20 | 0.008 | 54 |
| LNU218 | 24781.2 | 3.98 | 0.000 | 9 | LNU23 | 25163.6 | 5.17 | 0.442 | 14 | LNU23 | 25163.6 | 41.39 | 0.416 | 15 |
| LNU23 | 25163.5 | 4.47 | 0.000 | 23 | LNU28 | 25171.2 | 6.00 | 0.122 | 32 | LNU28 | 25171.2 | 47.99 | 0.112 | 34 |
| LNU23 | 25163.6 | 3.87 | 0.342 | 6 | LNU28 | 25174.3 | 5.31 | 0.173 | 17 | LNU28 | 25174.3 | 42.47 | 0.154 | 18 |
| LNU23 | 25163.4 | 3.72 | 0.764 | 2 | LNU28 | 25171.1 | 5.15 | 0.003 | 14 | LNU28 | 25171.1 | 38.56 | 0.403 | 8 |
| LNU28 | 25171.2 | 4.17 | 0.193 | 14 | LNU28 | 25171.4 | 4.82 | 0.522 | 6 | LNU28 | 25171.4 | 38.54 | 0.464 | 8 |
| LNU28 | 25171.1 | 4.04 | 0.215 | 11 | LNU28 | 25174.5 | 4.72 | 0.769 | 4 | LNU28 | 25174.5 | 37.74 | 0.713 | 5 |
| LNU28 | 25174.3 | 3.93 | 0.086 | 8 | LNU4 | 25134.1 | 6.45 | 0.020 | 42 | LNU4 | 25134.1 | 51.60 | 0.015 | 44 |
| LNU28 | 25171.4 | 3.82 | 0.422 | 5 | LNU4 | 25133.3 | 5.78 | 0.001 | 28 | LNU4 | 25133.3 | 46.23 | 0.001 | 29 |
| LNU28 | 25174.5 | 3.74 | 0.715 | 3 | LNU4 | 25134.3 | 5.42 | 0.390 | 20 | LNU4 | 25134.3 | 43.35 | 0.372 | 21 |
| LNU4 | 25134.1 | 4.33 | 0.052 | 19 | LNU4 | 25134.2 | 5.00 | 0.352 | 10 | LNU4 | 25134.2 | 40.03 | 0.315 | 12 |
| LNU4 | 25133.3 | 4.26 | 0.004 | 17 | LNU4 | 25131.1 | 4.82 | 0.730 | 6 | LNU4 | 25131.1 | 38.56 | 0.689 | 8 |
| LNU4 | 25134.3 | 3.95 | 0.423 | 8 | LNU40 | 24794.3 | 6.09 | 0.075 | 34 | LNU40 | 24794.3 | 48.69 | 0.066 | 36 |
| LNU4 | 25134.2 | 3.82 | 0.388 | 5 | LNU40 | 24794.4 | 5.79 | 0.278 | 28 | LNU40 | 24794.4 | 46.29 | 0.265 | 29 |
| LNU4 | 25131.1 | 3.78 | 0.702 | 4 | LNU40 | 24792.1 | 4.96 | 0.024 | 9 | LNU40 | 24792.1 | 39.69 | 0.019 | 11 |
| LNU40 | 24794.3 | 4.22 | 0.021 | 16 | LNU40 | 24792.2 | 4.93 | 0.568 | 9 | LNU40 | 24792.2 | 39.44 | 0.528 | 10 |
| LNU40 | 24794.4 | 4.12 | 0.136 | 13 | LNU46 | 14464.4 | 6.71 | 0.233 | 48 | LNU46 | 14464.4 | 53.69 | 0.227 | 50 |
| LNU40 | 24792.1 | 3.78 | 0.048 | 4 | LNU46 | 14463.1 | 6.56 | 0.339 | 45 | LNU46 | 14463.1 | 52.50 | 0.331 | 46 |
| LNU46 | 14463.1 | 4.49 | 0.310 | 23 | LNU46 | 14462.5 | 6.24 | 0.000 | 38 | LNU46 | 14462.5 | 49.91 | 0.000 | 39 |
| LNU46 | 14464.4 | 4.38 | 0.219 | 20 | LNU46 | 14462.1 | 5.39 | 0.339 | 19 | LNU46 | 14462.1 | 40.68 | 0.601 | 13 |
| LNU46 | 14462.5 | 4.34 | 0.000 | 19 | LNU48 | 24801.4 | 7.25 | 0.000 | 60 | LNU48 | 24801.4 | 58.02 | 0.000 | 62 |
| LNU46 | 14462.1 | 3.98 | 0.418 | 9 | LNU48 | 24802.2 | 6.41 | 0.050 | 41 | LNU48 | 24802.2 | 51.27 | 0.044 | 43 |
| LNU48 | 24801.4 | 4.61 | 0.000 | 26 | LNU48 | 24802.1 | 6.01 | 0.051 | 33 | LNU48 | 24802.1 | 48.11 | 0.044 | 34 |
| LNU48 | 24802.1 | 4.41 | 0.039 | 21 | LNU63 | 24814.2 | 6.06 | 0.418 | 34 | LNU63 | 24814.2 | 48.51 | 0.408 | 35 |
| LNU48 | 24802.2 | 4.33 | 0.026 | 19 | LNU63 | 24812.2 | 5.31 | 0.254 | 17 | LNU63 | 24812.2 | 42.49 | 0.233 | 19 |
| LNU63 | 24814.2 | 4.25 | 0.454 | 17 | LNU63 | 24814.3 | 5.22 | 0.391 | 15 | LNU63 | 24814.3 | 41.77 | 0.367 | 17 |
| LNU63 | 24814.3 | 3.97 | 0.477 | 9 | LNU63 | 24811.2 | 4.78 | 0.772 | 6 | LNU7 | 25081.1 | 45.92 | 0.015 | 28 |
| LNU63 | 24812.2 | 3.93 | 0.357 | 8 | LNU7 | 25081.1 | 5.74 | 0.019 | 27 | LNU7 | 25083.1 | 44.18 | 0.044 | 23 |
| LNU7 | 25083.1 | 4.12 | 0.000 | 13 | LNU7 | 25083.1 | 5.52 | 0.053 | 22 | LNU7 | 25083.3 | 40.05 | 0.530 | 12 |
| LNU7 | 25081.1 | 4.09 | 0.000 | 12 | LNU7 | 25083.3 | 5.01 | 0.563 | 10 | LNU7 | 25082.2 | 37.72 | 0.193 | 5 |
| LNU7 | 25083.3 | 3.74 | 0.704 | 3 | LNU7 | 25082.2 | 4.71 | 0.267 | 4 | LNU8 | 25063.6 | 46.26 | 0.036 | 29 |
| LNU7 | 25082.2 | 3.73 | 0.217 | 2 | LNU8 | 25063.6 | 5.78 | 0.043 | 28 | LNU8 | 25062.2 | 42.10 | 0.315 | 17 |
| LNU8 | 25063.6 | 4.19 | 0.064 | 15 | LNU8 | 25062.2 | 5.26 | 0.338 | 16 | LNU8 | 25061.2 | 38.84 | 0.393 | 8 |
| LNU8 | 25062.2 | 3.85 | 0.582 | 6 | LNU8 | 25061.2 | 4.86 | 0.447 | 7 | LNU8 | 25063.1 | 38.51 | 0.289 | 7 |
| LNU8 | 25061.2 | 3.84 | 0.299 | 5 | LNU8 | 25063.1 | 4.81 | 0.351 | 6 | LNU94 | 24833.3 | 47.02 | 0.289 | 31 |
| LNU8 | 25063.1 | 3.77 | 0.071 | 3 | LNU94 | 24833.3 | 5.88 | 0.301 | 30 | LNU94 | 24831.4 | 45.54 | 0.000 | 27 |
| LNU94 | 24833.3 | 4.12 | 0.202 | 13 | LNU94 | 24831.4 | 5.69 | 0.000 | 26 | LNU94 | 24834.4 | 42.80 | 0.036 | 19 |
| LNU94 | 24831.4 | 4.00 | 0.001 | 10 | LNU94 | 24834.4 | 5.35 | 0.046 | 18 | LNU94 | 24831.3 | 39.16 | 0.691 | 9 |
| LNU94 | 24834.4 | 3.99 | 0.101 | 9 | LNU94 | 24833.1 | 4.89 | 0.724 | 8 | LNU96 | 25073.3 | 42.52 | 0.451 | 19 |
| LNU94 | 24833.1 | 3.77 | 0.724 | 3 | LNU96 | 25073.3 | 5.31 | 0.472 | 17 | LNU96 | 25071.3 | 41.84 | 0.050 | 17 |
| LNU96 | 25073.3 | 4.05 | 0.372 | 11 | LNU96 | 25071.3 | 5.23 | 0.063 | 15 | CONT. | — | 56.10 | — | 0 |
| LNU96 | 25071.3 | 3.92 | 0.111 | 7 | CONT. | — | 7.01 | — | 0 | LNU148 | 25685.6 | 59.24 | 0.687 | 6 |
| LNU96 | 25073.4 | 3.76 | 0.755 | 3 | LNU148 | 25685.6 | 7.41 | 0.687 | 6 | LNU5 | 14042.7 | 61.42 | 0.016 | 9 |
| CONT. | — | 4.37 | — | 0 | LNU5 | 14042.7 | 7.68 | 0.016 | 9 | LNU72 | 24962.3 | 60.29 | 0.584 | 7 |
| LNU5 | 14042.7 | 4.56 | 0.028 | 4 | LNU72 | 24962.3 | 7.54 | 0.584 | 7 | LNU98 | 25763.2 | 58.27 | 0.297 | 4 |
| LNU72 | 24962.3 | 4.58 | 0.611 | 5 | LNU98 | 25763.2 | 7.28 | 0.297 | 4 | CONT. | — | 49.17 | — | 0 |
| LNU98 | 25763.2 | 4.53 | 0.195 | 4 | CONT. | — | 6.21 | — | 0 | LNU113 | 25631.1 | 57.73 | 0.070 | 17 |

TABLE 83-continued

Genes showing improved plant biomass production at standard nitrogen growth conditions

| Gene Name | Event # | Rosette Diameter [cm] Ave. | P-Value | % incr. | Gene Name | Event # | Rosette Area [cm2] Ave. | P-Value | % incr. | Gene Name | Event # | Plot Coverage [%] Ave. | P-Value | % incr. |
|---|---|---|---|---|---|---|---|---|---|---|---|---|---|---|
| CONT. | — | 4.09 | — | 0 | LNU113 | 25631.1 | 7.22 | 0.082 | 16 | LNU113 | 25631.3 | 56.54 | 0.380 | 15 |
| LNU113 | 25631.1 | 4.59 | 0.128 | 12 | LNU113 | 25631.3 | 7.07 | 0.406 | 14 | LNU124 | 14504.5 | 56.31 | 0.308 | 15 |
| LNU113 | 25631.3 | 4.47 | 0.296 | 9 | LNU124 | 14504.5 | 7.04 | 0.335 | 13 | LNU148 | 25685.1 | 56.54 | 0.036 | 15 |
| LNU124 | 14504.5 | 4.52 | 0.176 | 11 | LNU148 | 25685.1 | 7.07 | 0.044 | 14 | LNU148 | 25685.2 | 54.69 | 0.758 | 11 |
| LNU132 | 14102.9 | 4.33 | 0.705 | 6 | LNU148 | 25685.2 | 6.84 | 0.778 | 10 | LNU37 | 14064.7 | 63.16 | 0.018 | 28 |
| LNU148 | 25685.1 | 4.40 | 0.068 | 7 | LNU37 | 14064.7 | 7.89 | 0.021 | 27 | LNU37 | 14064.6 | 54.98 | 0.659 | 12 |
| LNU287 | 24674.3 | 4.30 | 0.654 | 5 | LNU37 | 14064.6 | 6.87 | 0.684 | 11 | LNU5 | 14043.9 | 63.55 | 0.068 | 29 |
| LNU37 | 14064.7 | 4.77 | 0.034 | 16 | LNU5 | 14043.9 | 7.94 | 0.075 | 28 | LNU5 | 14043.7 | 51.12 | 0.681 | 4 |
| LNU37 | 14064.6 | 4.55 | 0.461 | 11 | LNU5 | 14043.7 | 6.39 | 0.757 | 3 | LNU65 | 24702.3 | 52.18 | 0.687 | 6 |
| LNU5 | 14043.9 | 4.52 | 0.129 | 11 | LNU65 | 24702.3 | 6.52 | 0.734 | 5 | LNU68 | 14034.13 | 64.85 | 0.369 | 32 |
| LNU65 | 24703.6 | 4.32 | 0.434 | 6 | LNU68 | 14034.13 | 8.11 | 0.379 | 31 | LNU71 | 25852.5 | 62.11 | 0.105 | 26 |
| LNU65 | 24702.3 | 4.28 | 0.759 | 5 | LNU71 | 25852.5 | 7.76 | 0.114 | 25 | LNU71 | 25853.1 | 61.33 | 0.002 | 25 |
| LNU68 | 14034.13 | 4.73 | 0.410 | 16 | LNU71 | 25853.1 | 7.67 | 0.003 | 23 | LNU71 | 25851.4 | 55.90 | 0.258 | 14 |
| LNU71 | 25853.1 | 4.76 | 0.000 | 16 | LNU71 | 25851.4 | 6.99 | 0.287 | 13 | LNU72 | 24963.7 | 55.78 | 0.372 | 13 |
| LNU71 | 25852.5 | 4.67 | 0.198 | 14 | LNU72 | 24963.7 | 6.97 | 0.402 | 12 | LNU72 | 24963.8 | 50.14 | 0.789 | 2 |
| LNU71 | 25851.4 | 4.57 | 0.245 | 12 | LNU74 | 25443.3 | 7.10 | 0.538 | 14 | LNU74 | 25443.3 | 56.78 | 0.515 | 15 |
| LNU72 | 24963.7 | 4.47 | 0.518 | 9 | LNU82 | 24823.1 | 6.66 | 0.450 | 7 | LNU82 | 24823.1 | 53.30 | 0.399 | 8 |
| LNU72 | 24963.8 | 4.16 | 0.749 | 2 | LNU84 | 25621.2 | 6.58 | 0.562 | 6 | LNU84 | 25621.2 | 52.68 | 0.506 | 7 |
| LNU74 | 25443.3 | 4.58 | 0.398 | 12 | LNU84 | 25621.4 | 6.55 | 0.392 | 5 | LNU84 | 25621.4 | 52.36 | 0.324 | 6 |
| LNU74 | 25444.1 | 4.20 | 0.485 | 3 | CONT. | — | 7.69 | — | 0 | CONT. | — | 60.12 | — | 0 |
| LNU82 | 24823.1 | 4.32 | 0.164 | 6 | LNU117 | 25931.4 | 10.65 | 0.009 | 38 | LNU117 | 25931.4 | 85.18 | 0.007 | 42 |
| LNU84 | 25621.2 | 4.39 | 0.279 | 7 | LNU117 | 25933.3 | 10.29 | 0.003 | 34 | LNU117 | 25933.3 | 82.33 | 0.005 | 37 |
| LNU84 | 25621.4 | 4.25 | 0.299 | 4 | LNU117 | 25931.1 | 8.36 | 0.259 | 9 | LNU117 | 25931.1 | 66.92 | 0.211 | 11 |
| LNU87 | 24742.1 | 4.29 | 0.647 | 5 | LNU117 | 25932.4 | 8.00 | 0.520 | 4 | LNU117 | 25932.4 | 63.99 | 0.400 | 6 |
| CONT. | — | 4.56 | — | 0 | LNU117 | 25931.2 | 7.88 | 0.794 | 2 | LNU117 | 25931.2 | 63.01 | 0.633 | 5 |
| LNU117 | 25931.4 | 5.36 | 0.121 | 18 | LNU122 | 25333.2 | 10.01 | 0.004 | 30 | LNU122 | 25333.2 | 80.11 | 0.007 | 33 |
| LNU117 | 25933.3 | 5.32 | 0.013 | 17 | LNU122 | 25333.1 | 9.61 | 0.013 | 25 | LNU122 | 25333.1 | 76.90 | 0.015 | 28 |
| LNU117 | 25931.1 | 4.81 | 0.421 | 5 | LNU122 | 25332.2 | 9.57 | 0.061 | 24 | LNU122 | 25332.2 | 76.60 | 0.047 | 27 |
| LNU117 | 25932.4 | 4.74 | 0.194 | 4 | LNU122 | 25332.5 | 9.29 | 0.340 | 21 | LNU122 | 25332.5 | 74.32 | 0.298 | 24 |
| LNU117 | 25931.2 | 4.72 | 0.564 | 3 | LNU122 | 25332.1 | 9.00 | 0.309 | 17 | LNU122 | 25332.1 | 72.00 | 0.260 | 20 |
| LNU122 | 25333.2 | 5.09 | 0.046 | 12 | LNU125 | 25941.4 | 9.65 | 0.009 | 25 | LNU125 | 25941.4 | 77.19 | 0.012 | 28 |
| LNU122 | 25332.2 | 5.06 | 0.023 | 11 | LNU125 | 25944.3 | 8.58 | 0.410 | 12 | LNU125 | 25944.3 | 68.65 | 0.342 | 14 |
| LNU122 | 25332.1 | 5.01 | 0.165 | 10 | LNU125 | 25941.2 | 8.07 | 0.588 | 5 | LNU125 | 25941.2 | 64.54 | 0.464 | 7 |
| LNU122 | 25333.1 | 4.99 | 0.040 | 9 | LNU138 | 14074.6 | 9.67 | 0.108 | 26 | LNU138 | 14074.6 | 77.36 | 0.083 | 29 |
| LNU122 | 25332.5 | 4.93 | 0.447 | 8 | LNU138 | 14074.5 | 9.38 | 0.024 | 22 | LNU138 | 14074.5 | 75.02 | 0.025 | 25 |
| LNU125 | 25941.4 | 5.22 | 0.062 | 14 | LNU180 | 24722.2 | 8.14 | 0.371 | 6 | LNU180 | 24722.2 | 65.08 | 0.298 | 8 |
| LNU125 | 25944.3 | 4.83 | 0.100 | 6 | LNU180 | 24724.1 | 8.16 | 0.413 | 6 | LNU180 | 24724.1 | 62.46 | 0.776 | 4 |
| LNU138 | 14074.5 | 5.17 | 0.005 | 13 | LNU220 | 25405.1 | 8.07 | 0.724 | 5 | LNU220 | 25405.1 | 65.27 | 0.324 | 9 |
| LNU138 | 14074.6 | 5.12 | 0.008 | 12 | LNU230 | 25413.1 | 9.23 | 0.467 | 20 | LNU220 | 25405.6 | 64.54 | 0.617 | 7 |
| LNU180 | 24724.1 | 4.69 | 0.503 | 3 | LNU230 | 25412.2 | 9.22 | 0.477 | 20 | LNU220 | 25405.3 | 63.52 | 0.713 | 6 |
| LNU180 | 24722.2 | 4.68 | 0.399 | 3 | LNU230 | 25413.2 | 8.92 | 0.659 | 16 | LNU220 | 25405.2 | 62.55 | 0.703 | 4 |
| LNU180 | 24723.1 | 4.64 | 0.532 | 2 | LNU25 | 14083.7 | 8.47 | 0.614 | 10 | LNU230 | 25413.1 | 73.84 | 0.427 | 23 |
| LNU220 | 25405.6 | 4.82 | 0.397 | 6 | LNU25 | 14083.1 | 8.41 | 0.174 | 9 | LNU230 | 25412.2 | 73.79 | 0.437 | 23 |
| LNU230 | 25413.1 | 5.04 | 0.391 | 11 | LNU25 | 14082.8 | 8.39 | 0.185 | 9 | LNU230 | 25413.2 | 71.33 | 0.619 | 19 |
| LNU230 | 25412.2 | 4.99 | 0.456 | 9 | LNU25 | 14082.9 | 8.01 | 0.505 | 4 | LNU25 | 14083.7 | 67.72 | 0.546 | 13 |
| LNU230 | 25413.2 | 4.89 | 0.710 | 7 | LNU254 | 25782.4 | 8.05 | 0.580 | 5 | LNU25 | 14083.1 | 67.24 | 0.158 | 12 |
| LNU230 | 25412.1 | 4.66 | 0.755 | 2 | LNU254 | 25781.3 | 7.96 | 0.605 | 3 | LNU25 | 14082.8 | 67.09 | 0.166 | 12 |
| LNU25 | 14082.8 | 4.86 | 0.066 | 7 | LNU263 | 25791.3 | 9.99 | 0.294 | 30 | LNU25 | 14082.9 | 64.08 | 0.390 | 7 |
| LNU25 | 14082.9 | 4.79 | 0.207 | 5 | LNU263 | 25794.8 | 9.48 | 0.103 | 23 | LNU254 | 25782.4 | 64.44 | 0.454 | 7 |
| LNU25 | 14083.1 | 4.77 | 0.146 | 5 | LNU267 | 25804.3 | 8.13 | 0.675 | 6 | LNU254 | 25781.3 | 63.70 | 0.462 | 6 |
| LNU25 | 14083.7 | 4.70 | 0.756 | 3 | LNU271 | 25912.1 | 8.11 | 0.778 | 5 | LNU263 | 25791.3 | 79.91 | 0.265 | 33 |
| LNU254 | 25781.3 | 4.71 | 0.283 | 3 | LNU278 | 25814.3 | 8.80 | 0.498 | 14 | LNU263 | 25794.8 | 75.84 | 0.080 | 26 |
| LNU254 | 25782.5 | 4.70 | 0.435 | 3 | LNU278 | 25814.1 | 8.01 | 0.539 | 4 | LNU263 | 25794.6 | 61.72 | 0.759 | 3 |
| LNU254 | 25782.4 | 4.68 | 0.777 | 3 | LNU278 | 25812.3 | 7.95 | 0.661 | 3 | LNU267 | 25804.3 | 65.00 | 0.570 | 8 |
| LNU263 | 25791.3 | 5.30 | 0.257 | 16 | LNU36 | 25562.3 | 8.31 | 0.386 | 8 | LNU271 | 25913.3 | 63.74 | 0.687 | 6 |
| LNU263 | 25794.8 | 5.21 | 0.133 | 14 | LNU43 | 14422.8 | 8.81 | 0.099 | 14 | LNU278 | 25814.3 | 70.43 | 0.444 | 17 |
| LNU263 | 25794.6 | 4.65 | 0.738 | 2 | LNU43 | 14423.6 | 8.66 | 0.549 | 13 | LNU278 | 25814.1 | 64.05 | 0.414 | 7 |
| LNU267 | 25804.3 | 4.66 | 0.579 | 2 | LNU43 | 14421.1 | 8.62 | 0.403 | 12 | LNU278 | 25812.3 | 63.60 | 0.510 | 6 |
| LNU271 | 25913.3 | 4.84 | 0.510 | 6 | LNU45 | 25053.4 | 9.41 | 0.017 | 22 | LNU36 | 25562.3 | 66.51 | 0.306 | 11 |
| LNU271 | 25912.1 | 4.73 | 0.729 | 4 | LNU67 | 25824.5 | 10.02 | 0.103 | 30 | LNU43 | 14422.8 | 70.46 | 0.087 | 17 |
| LNU278 | 25814.3 | 4.79 | 0.556 | 5 | LNU67 | 25821.5 | 9.56 | 0.213 | 24 | LNU43 | 14423.6 | 69.31 | 0.490 | 15 |
| LNU278 | 25814.1 | 4.71 | 0.273 | 3 | LNU67 | 25823.5 | 7.91 | 0.742 | 3 | LNU43 | 14421.1 | 68.95 | 0.337 | 15 |
| LNU278 | 25812.3 | 4.65 | 0.552 | 2 | CONT. | — | 5.51 | — | 0 | LNU43 | 14422.9 | 61.94 | 0.683 | 3 |
| LNU36 | 25562.3 | 4.84 | 0.280 | 6 | LNU100 | 14472.1 | 7.25 | 0.214 | 32 | LNU45 | 25053.4 | 75.26 | 0.020 | 25 |
| LNU43 | 14421.1 | 5.03 | 0.265 | 10 | LNU100 | 14473.1 | 6.68 | 0.126 | 21 | LNU67 | 25824.5 | 80.13 | 0.080 | 33 |
| LNU43 | 14423.6 | 4.98 | 0.534 | 9 | LNU100 | 14473.3 | 6.65 | 0.202 | 21 | LNU67 | 25821.5 | 76.49 | 0.178 | 27 |
| LNU43 | 14422.8 | 4.91 | 0.059 | 8 | LNU104 | 25032.3 | 8.31 | 0.061 | 51 | LNU67 | 25823.5 | 63.25 | 0.582 | 5 |
| LNU43 | 14422.9 | 4.69 | 0.341 | 3 | LNU104 | 25033.3 | 7.18 | 0.094 | 30 | LNU67 | 25821.4 | 61.30 | 0.796 | 2 |
| LNU45 | 25053.4 | 5.08 | 0.048 | 12 | LNU104 | 25032.1 | 6.09 | 0.137 | 10 | CONT. | — | 43.28 | — | 0 |
| LNU67 | 25824.5 | 5.33 | 0.013 | 17 | LNU106 | 14483.2 | 6.84 | 0.395 | 24 | LNU100 | 14472.1 | 58.02 | 0.197 | 34 |
| LNU67 | 25821.5 | 5.01 | 0.414 | 10 | LNU106 | 14483.5 | 6.54 | 0.277 | 19 | LNU100 | 14473.1 | 53.48 | 0.103 | 24 |

TABLE 83-continued

Genes showing improved plant biomass production at standard nitrogen growth conditions

| | Rosette Diameter [cm] | | | | | Rosette Area [cm2] | | | | | Plot Coverage [%] | | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU67 | 25823.5 | 4.69 | 0.594 | 3 | LNU106 | 14481.1 | 6.47 | 0.545 | 17 | LNU100 | 14473.3 | 53.22 | 0.176 | 23 |
| LNU67 | 25821.4 | 4.66 | 0.659 | 2 | LNU106 | 14484.3 | 5.67 | 0.734 | 3 | LNU104 | 25032.2 | 66.45 | 0.052 | 54 |
| CONT. | — | 4.04 | — | 0 | LNU114 | 25041.2 | 7.36 | 0.173 | 34 | LNU104 | 25033.3 | 57.45 | 0.078 | 33 |
| LNU100 | 14472.1 | 4.66 | 0.122 | 15 | LNU114 | 25044.4 | 6.15 | 0.537 | 12 | LNU104 | 25032.1 | 48.73 | 0.095 | 13 |
| LNU100 | 14473.1 | 4.55 | 0.001 | 12 | LNU114 | 25041.1 | 5.89 | 0.758 | 7 | LNU104 | 25033.8 | 44.10 | 0.672 | 2 |
| LNU100 | 14473.3 | 4.45 | 0.361 | 10 | LNU117 | 25931.4 | 6.66 | 0.186 | 21 | LNU106 | 14483.2 | 54.74 | 0.371 | 26 |
| LNU104 | 25032.2 | 4.96 | 0.095 | 23 | LNU117 | 25931.1 | 5.91 | 0.423 | 7 | LNU106 | 14483.5 | 52.35 | 0.247 | 21 |
| LNU104 | 25033.3 | 4.73 | 0.150 | 17 | LNU155 | 14523.5 | 5.99 | 0.663 | 9 | LNU106 | 14481.1 | 51.74 | 0.511 | 20 |
| LNU104 | 25032.1 | 4.25 | 0.102 | 5 | LNU218 | 24781.4 | 6.59 | 0.002 | 20 | LNU114 | 25041.2 | 58.92 | 0.158 | 36 |
| LNU106 | 14483.2 | 4.55 | 0.371 | 13 | LNU218 | 24781.6 | 6.06 | 0.519 | 10 | LNU114 | 25044.4 | 49.23 | 0.487 | 14 |
| LNU106 | 14481.1 | 4.50 | 0.556 | 11 | LNU218 | 24781.1 | 5.78 | 0.271 | 5 | LNU114 | 25041.1 | 47.15 | 0.701 | 9 |
| LNU106 | 14483.5 | 4.40 | 0.277 | 9 | LNU254 | 25782.4 | 6.21 | 0.006 | 13 | LNU114 | 25042.1 | 45.58 | 0.794 | 5 |
| LNU106 | 14484.3 | 4.18 | 0.404 | 3 | LNU4 | 25133.3 | 6.38 | 0.118 | 16 | LNU117 | 25931.4 | 53.31 | 0.161 | 23 |
| LNU114 | 25041.2 | 4.64 | 0.072 | 15 | LNU4 | 25134.3 | 6.31 | 0.001 | 14 | LNU117 | 25931.1 | 47.29 | 0.337 | 9 |
| LNU114 | 25044.4 | 4.22 | 0.627 | 4 | LNU4 | 25134.2 | 6.01 | 0.517 | 9 | LNU155 | 14523.5 | 47.93 | 0.605 | 11 |
| LNU114 | 25041.1 | 4.20 | 0.685 | 4 | LNU40 | 24792.1 | 7.46 | 0.301 | 35 | LNU218 | 24781.4 | 52.74 | 0.001 | 22 |
| LNU117 | 25931.4 | 4.55 | 0.106 | 12 | LNU40 | 24794.4 | 6.15 | 0.536 | 12 | LNU218 | 24781.6 | 48.47 | 0.459 | 12 |
| LNU117 | 25931.1 | 4.15 | 0.711 | 3 | LNU40 | 24794.3 | 5.94 | 0.458 | 8 | LNU218 | 24781.1 | 46.21 | 0.160 | 7 |
| LNU155 | 14523.5 | 4.30 | 0.554 | 6 | LNU40 | 24792.2 | 5.64 | 0.769 | 2 | LNU254 | 25782.4 | 49.64 | 0.004 | 15 |
| LNU218 | 24781.4 | 4.53 | 0.000 | 12 | LNU46 | 14462.5 | 7.95 | 0.292 | 44 | LNU4 | 25133.3 | 51.05 | 0.090 | 18 |
| LNU218 | 24781.6 | 4.39 | 0.371 | 9 | LNU46 | 14462.1 | 7.10 | 0.000 | 29 | LNU4 | 25134.3 | 50.45 | 0.001 | 17 |
| LNU218 | 24781.1 | 4.24 | 0.138 | 5 | LNU48 | 24801.4 | 7.08 | 0.007 | 28 | LNU4 | 25134.2 | 48.07 | 0.452 | 11 |
| LNU254 | 25782.4 | 4.26 | 0.046 | 5 | LNU48 | 24802.1 | 6.43 | 0.546 | 17 | LNU40 | 24792.1 | 59.71 | 0.285 | 38 |
| LNU4 | 25133.3 | 4.50 | 0.233 | 11 | LNU48 | 24803.2 | 5.82 | 0.623 | 6 | LNU40 | 24794.4 | 49.18 | 0.486 | 14 |
| LNU4 | 25134.2 | 4.26 | 0.337 | 5 | LNU63 | 24814.2 | 6.82 | 0.060 | 24 | LNU40 | 24794.3 | 47.49 | 0.377 | 10 |
| LNU4 | 25134.3 | 4.25 | 0.069 | 5 | LNU63 | 24814.6 | 6.19 | 0.055 | 12 | LNU40 | 24792.2 | 45.13 | 0.611 | 4 |
| LNU40 | 24792.1 | 4.82 | 0.229 | 19 | LNU63 | 24812.3 | 5.68 | 0.410 | 3 | LNU46 | 14462.5 | 63.58 | 0.280 | 47 |
| LNU40 | 24794.4 | 4.40 | 0.436 | 9 | LNU7 | 25081.1 | 6.87 | 0.077 | 25 | LNU46 | 14462.1 | 56.79 | 0.000 | 31 |
| LNU40 | 24794.3 | 4.20 | 0.287 | 4 | LNU7 | 25083.1 | 5.88 | 0.710 | 7 | LNU48 | 24801.4 | 53.00 | 0.046 | 22 |
| LNU40 | 24792.2 | 4.16 | 0.413 | 3 | LNU7 | 25083.3 | 5.67 | 0.536 | 3 | LNU48 | 24802.1 | 51.43 | 0.511 | 19 |
| LNU46 | 14462.5 | 4.78 | 0.258 | 18 | LNU8 | 25063.1 | 6.90 | 0.262 | 25 | LNU48 | 24803.2 | 46.55 | 0.528 | 8 |
| LNU46 | 14462.1 | 4.60 | 0.009 | 14 | LNU8 | 25062.1 | 6.81 | 0.405 | 24 | LNU63 | 24814.2 | 54.54 | 0.044 | 26 |
| LNU48 | 24801.4 | 4.57 | 0.000 | 13 | LNU8 | 25062.2 | 6.00 | 0.024 | 9 | LNU63 | 24814.6 | 49.55 | 0.035 | 14 |
| LNU48 | 24802.1 | 4.44 | 0.480 | 10 | LNU8 | 25061.2 | 5.96 | 0.360 | 8 | LNU63 | 24812.3 | 45.47 | 0.234 | 5 |
| LNU48 | 24803.2 | 4.12 | 0.714 | 2 | LNU94 | 24833.1 | 6.98 | 0.006 | 27 | LNU63 | 24814.7 | 44.44 | 0.562 | 3 |
| LNU63 | 24814.2 | 4.54 | 0.028 | 12 | LNU94 | 24831.4 | 6.89 | 0.092 | 25 | LNU7 | 25081.1 | 54.97 | 0.061 | 27 |
| LNU63 | 24814.6 | 4.48 | 0.004 | 11 | LNU94 | 24833.3 | 6.88 | 0.101 | 25 | LNU7 | 25083.1 | 47.07 | 0.643 | 9 |
| LNU63 | 24814.7 | 4.13 | 0.375 | 2 | LNU94 | 24834.4 | 6.54 | 0.594 | 19 | LNU7 | 25083.3 | 45.32 | 0.338 | 5 |
| LNU7 | 25081.1 | 4.63 | 0.039 | 14 | LNU96 | 25071.2 | 6.37 | 0.261 | 16 | LNU8 | 25063.1 | 55.17 | 0.240 | 27 |
| LNU7 | 25083.1 | 4.32 | 0.569 | 7 | LNU96 | 25073.4 | 6.26 | 0.027 | 14 | LNU8 | 25062.1 | 51.57 | 0.580 | 19 |
| LNU8 | 25063.1 | 4.59 | 0.202 | 13 | LNU96 | 25071.3 | 6.25 | 0.601 | 13 | LNU8 | 25062.2 | 47.97 | 0.015 | 11 |
| LNU8 | 25062.1 | 4.43 | 0.453 | 10 | CONT. | — | 5.52 | — | 0 | LNU8 | 25061.2 | 47.65 | 0.283 | 10 |
| LNU8 | 25062.2 | 4.28 | 0.023 | 6 | LNU10 | 25123.5 | 6.36 | 0.501 | 15 | LNU94 | 24833.1 | 55.84 | 0.003 | 29 |
| LNU8 | 25061.2 | 4.23 | 0.060 | 5 | LNU122 | 25332.5 | 7.43 | 0.076 | 35 | LNU94 | 24833.3 | 55.01 | 0.082 | 27 |
| LNU94 | 24831.4 | 4.57 | 0.059 | 13 | LNU122 | 25332.2 | 6.54 | 0.271 | 6 | LNU94 | 24834.4 | 52.33 | 0.564 | 21 |
| LNU94 | 24833.1 | 4.54 | 0.234 | 12 | LNU122 | 25332.1 | 5.85 | 0.107 | 6 | LNU94 | 24831.4 | 51.83 | 0.377 | 20 |
| LNU94 | 24833.3 | 4.47 | 0.001 | 10 | LNU125 | 25941.4 | 6.33 | 0.058 | 15 | LNU96 | 25071.2 | 50.95 | 0.223 | 18 |
| LNU94 | 24834.4 | 4.28 | 0.678 | 6 | LNU125 | 25943.2 | 6.05 | 0.017 | 10 | LNU96 | 25073.4 | 50.07 | 0.016 | 16 |
| LNU96 | 25071.2 | 4.32 | 0.311 | 7 | LNU178 | 14611.5 | 6.41 | 0.271 | 16 | LNU96 | 25071.3 | 50.01 | 0.560 | 16 |
| LNU96 | 25073.4 | 4.27 | 0.121 | 6 | LNU178 | 14611.1 | 5.90 | 0.494 | 7 | CONT. | — | 44.13 | — | 0 |
| LNU96 | 25071.3 | 4.23 | 0.729 | 5 | LNU178 | 14612.1 | 5.77 | 0.771 | 5 | LNU10 | 25123.5 | 50.86 | 0.501 | 15 |
| CONT. | — | 4.07 | — | 0 | LNU234 | 25014.4 | 6.04 | 0.267 | 9 | LNU122 | 25332.5 | 59.44 | 0.076 | 35 |
| LNU10 | 25123.5 | 4.50 | 0.413 | 11 | LNU236 | 25423.3 | 6.00 | 0.132 | 9 | LNU122 | 25332.2 | 52.35 | 0.271 | 19 |
| LNU122 | 25332.5 | 4.69 | 0.003 | 15 | LNU236 | 25425.3 | 5.96 | 0.660 | 8 | LNU122 | 25332.1 | 46.78 | 0.107 | 6 |
| LNU122 | 25332.2 | 4.35 | 0.245 | 7 | LNU236 | 25424.2 | 5.95 | 0.471 | 8 | LNU125 | 25941.4 | 50.64 | 0.058 | 15 |
| LNU122 | 25332.1 | 4.27 | 0.198 | 5 | LNU236 | 25425.4 | 5.73 | 0.639 | 4 | LNU125 | 25943.2 | 48.42 | 0.017 | 10 |
| LNU125 | 25941.4 | 4.41 | 0.004 | 8 | LNU236 | 25422.4 | 5.73 | 0.273 | 4 | LNU178 | 14611.5 | 51.30 | 0.271 | 16 |
| LNU125 | 25943.2 | 4.20 | 0.109 | 3 | LNU25 | 14083.7 | 5.87 | 0.090 | 13 | LNU178 | 14611.1 | 47.22 | 0.494 | 7 |
| LNU178 | 14611.5 | 4.38 | 0.025 | 8 | LNU25 | 14082.8 | 6.00 | 0.068 | 9 | LNU178 | 14612.1 | 46.17 | 0.771 | 5 |
| LNU178 | 14611.1 | 4.23 | 0.524 | 4 | LNU271 | 25911.4 | 6.14 | 0.007 | 11 | LNU234 | 25014.4 | 48.31 | 0.267 | 9 |
| LNU234 | 25014.4 | 4.35 | 0.065 | 7 | LNU278 | 25814.1 | 6.84 | 0.000 | 24 | LNU236 | 25423.3 | 48.03 | 0.132 | 9 |
| LNU236 | 25425.4 | 4.29 | 0.469 | 5 | LNU278 | 25814.3 | 6.80 | 0.049 | 23 | LNU236 | 25425.3 | 47.68 | 0.660 | 8 |
| LNU236 | 25425.3 | 4.27 | 0.665 | 5 | LNU278 | 25813.2 | 5.87 | 0.769 | 6 | LNU236 | 25424.2 | 47.58 | 0.471 | 8 |
| LNU236 | 25423.3 | 4.18 | 0.177 | 3 | LNU278 | 25812.3 | 5.80 | 0.562 | 5 | LNU236 | 25425.4 | 45.87 | 0.639 | 4 |
| LNU25 | 14083.7 | 4.37 | 0.179 | 7 | LNU278 | 25812.2 | 5.74 | 0.748 | 4 | LNU236 | 25422.4 | 45.86 | 0.273 | 4 |
| LNU25 | 14082.8 | 4.28 | 0.102 | 5 | LNU43 | 14423.7 | 5.87 | 0.454 | 6 | LNU25 | 14083.7 | 49.87 | 0.090 | 13 |
| LNU267 | 25803.1 | 4.17 | 0.224 | 2 | LNU43 | 14423.6 | 5.85 | 0.597 | 6 | LNU25 | 14082.8 | 48.04 | 0.068 | 9 |
| LNU271 | 25911.4 | 4.32 | 0.005 | 6 | LNU45 | 25052.12 | 7.09 | 0.347 | 29 | LNU271 | 25911.4 | 49.15 | 0.007 | 11 |
| LNU271 | 25913.3 | 4.17 | 0.665 | 2 | LNU45 | 25053.4 | 7.03 | 0.158 | 28 | LNU278 | 25814.1 | 54.73 | 0.000 | 24 |
| LNU278 | 25814.1 | 4.53 | 0.014 | 11 | LNU45 | 25052.11 | 6.11 | 0.526 | 11 | LNU278 | 25814.3 | 54.39 | 0.049 | 23 |
| LNU278 | 25814.3 | 4.51 | 0.018 | 11 | LNU45 | 25052.9 | 5.81 | 0.542 | 5 | LNU278 | 25813.2 | 46.93 | 0.769 | 6 |

TABLE 83-continued

Genes showing improved plant biomass production at standard nitrogen growth conditions

| Gene Name | Event # | Rosette Diameter [cm] Ave. | P-Value | % incr. | Gene Name | Event # | Rosette Area [cm2] Ave. | P-Value | % incr. | Gene Name | Event # | Plot Coverage [%] Ave. | P-Value | % incr. |
|---|---|---|---|---|---|---|---|---|---|---|---|---|---|---|
| LNU278 | 25812.2 | 4.29 | 0.549 | 5 | LNU67 | 25823.5 | 7.64 | 0.000 | 39 | LNU278 | 25812.3 | 46.39 | 0.562 | 5 |
| LNU278 | 25813.2 | 4.23 | 0.708 | 4 | LNU67 | 25824.5 | 5.73 | 0.563 | 4 | LNU278 | 25812.2 | 45.95 | 0.748 | 4 |
| LNU278 | 25812.3 | 4.21 | 0.465 | 3 | LNU67 | 25821.5 | 5.65 | 0.575 | 2 | LNU43 | 14423.7 | 46.93 | 0.454 | 6 |
| LNU43 | 14423.7 | 4.28 | 0.436 | 5 | LNU9 | 25001.7 | 6.07 | 0.382 | 10 | LNU43 | 14423.6 | 46.77 | 0.597 | 6 |
| LNU43 | 14423.6 | 4.22 | 0.486 | 4 | LNU9 | 25001.1 | 5.69 | 0.730 | 3 | LNU45 | 25052.12 | 56.76 | 0.347 | 29 |
| LNU45 | 25052.12 | 4.65 | 0.342 | 14 | LNU9 | 25003.1 | 5.68 | 0.610 | 3 | LNU45 | 25053.4 | 56.27 | 0.158 | 28 |
| LNU45 | 25053.4 | 4.56 | 0.208 | 12 | CONT. | — | 7.52 | — | 0 | LNU45 | 25052.11 | 48.88 | 0.526 | 11 |
| LNU45 | 25052.11 | 4.24 | 0.619 | 4 | LNU10 | 25123.6 | 9.66 | 0.315 | 29 | LNU45 | 25052.9 | 46.47 | 0.542 | 5 |
| LNU45 | 25052.9 | 4.21 | 0.378 | 3 | LNU10 | 25123.5 | 8.34 | 0.102 | 11 | LNU67 | 25823.5 | 61.12 | 0.000 | 39 |
| LNU67 | 25823.5 | 4.72 | 0.004 | 16 | LNU157 | 24982.8 | 7.91 | 0.274 | 5 | LNU67 | 25824.5 | 45.84 | 0.563 | 4 |
| LNU67 | 25824.3 | 4.23 | 0.447 | 4 | LNU168 | 24753.5 | 8.14 | 0.367 | 8 | LNU67 | 25821.5 | 45.21 | 0.575 | 2 |
| LNU9 | 25001.7 | 4.29 | 0.201 | 6 | LNU173 | 25451.1 | 8.31 | 0.009 | 15 | LNU9 | 25001.7 | 48.58 | 0.382 | 10 |
| LNU9 | 25003.1 | 4.19 | 0.138 | 3 | LNU173 | 25451.2 | 7.86 | 0.634 | 5 | LNU9 | 25001.1 | 45.53 | 0.730 | 3 |
| LNU9 | 25001.1 | 4.15 | 0.729 | 2 | LNU178 | 14611.5 | 9.41 | 0.002 | 25 | LNU9 | 25003.1 | 45.46 | 0.610 | 3 |
| CONT. | — | 4.68 | — | 0 | LNU178 | 14611.4 | 9.14 | 0.223 | 22 | CONT. | — | 60.15 | — | 0 |
| LNU10 | 25123.6 | 5.27 | 0.289 | 13 | LNU178 | 14611.1 | 9.08 | 0.135 | 21 | LNU10 | 25123.6 | 77.30 | 0.315 | 29 |
| LNU10 | 25123.5 | 4.98 | 0.007 | 7 | LNU184 | 25393.1 | 9.32 | 0.512 | 24 | LNU10 | 25123.5 | 66.75 | 0.102 | 11 |
| LNU157 | 24982.8 | 4.91 | 0.084 | 5 | LNU184 | 25393.2 | 9.21 | 0.123 | 22 | LNU157 | 24982.8 | 63.29 | 0.274 | 5 |
| LNU168 | 24753.5 | 4.93 | 0.301 | 6 | LNU184 | 25394.3 | 9.18 | 0.443 | 22 | LNU168 | 24753.5 | 65.11 | 0.367 | 8 |
| LNU173 | 25451.1 | 5.21 | 0.016 | 11 | LNU184 | 25395.1 | 8.66 | 0.155 | 15 | LNU173 | 25451.1 | 66.45 | 0.009 | 10 |
| LNU173 | 25451.2 | 4.77 | 0.648 | 2 | LNU230 | 25415.1 | 10.23 | 0.024 | 36 | LNU173 | 25451.2 | 62.87 | 0.634 | 5 |
| LNU178 | 14611.5 | 5.23 | 0.136 | 12 | LNU230 | 25413.2 | 9.09 | 0.162 | 21 | LNU178 | 14611.5 | 75.30 | 0.002 | 25 |
| LNU178 | 14611.4 | 5.15 | 0.052 | 10 | LNU230 | 25412.1 | 8.84 | 0.000 | 18 | LNU178 | 14611.4 | 73.11 | 0.223 | 22 |
| LNU178 | 14611.1 | 5.05 | 0.206 | 8 | LNU230 | 25413.1 | 8.51 | 0.025 | 13 | LNU178 | 14611.1 | 72.61 | 0.135 | 21 |
| LNU184 | 25394.3 | 5.28 | 0.400 | 13 | LNU230 | 25412.2 | 8.44 | 0.068 | 12 | LNU184 | 25393.1 | 74.53 | 0.512 | 24 |
| LNU184 | 25393.1 | 5.26 | 0.428 | 12 | LNU236 | 25425.4 | 9.76 | 0.202 | 30 | LNU184 | 25393.2 | 73.66 | 0.123 | 22 |
| LNU184 | 25393.2 | 5.14 | 0.273 | 10 | LNU236 | 25424.2 | 9.53 | 0.078 | 27 | LNU184 | 25394.3 | 73.42 | 0.443 | 22 |
| LNU184 | 25395.1 | 5.09 | 0.015 | 9 | LNU236 | 25423.3 | 8.78 | 0.364 | 17 | LNU184 | 25395.1 | 69.24 | 0.155 | 15 |
| LNU230 | 25415.1 | 5.42 | 0.002 | 16 | LNU236 | 25422.4 | 8.71 | 0.006 | 16 | LNU230 | 25415.1 | 81.83 | 0.024 | 36 |
| LNU230 | 25413.2 | 5.11 | 0.006 | 9 | LNU24 | 24974.2 | 8.96 | 0.272 | 19 | LNU230 | 25413.2 | 72.72 | 0.162 | 21 |
| LNU230 | 25412.1 | 5.07 | 0.001 | 8 | LNU24 | 24971.2 | 8.70 | 0.001 | 16 | LNU230 | 25412.1 | 70.74 | 0.000 | 18 |
| LNU230 | 25413.1 | 4.97 | 0.028 | 6 | LNU24 | 24971.3 | 8.53 | 0.547 | 13 | LNU230 | 25413.1 | 68.11 | 0.025 | 13 |
| LNU230 | 25412.2 | 4.97 | 0.186 | 6 | LNU24 | 24972.1 | 8.05 | 0.085 | 7 | LNU230 | 25412.2 | 67.54 | 0.068 | 12 |
| LNU236 | 25425.4 | 5.38 | 0.204 | 15 | LNU24 | 24971.4 | 7.76 | 0.788 | 3 | LNU236 | 25425.4 | 78.05 | 0.202 | 30 |
| LNU236 | 25424.2 | 5.33 | 0.121 | 14 | LNU263 | 25794.8 | 9.47 | 0.222 | 26 | LNU236 | 25424.2 | 76.22 | 0.078 | 27 |
| LNU236 | 25423.3 | 5.08 | 0.329 | 9 | LNU276 | 25433.3 | 9.55 | 0.001 | 27 | LNU236 | 25423.3 | 70.24 | 0.364 | 17 |
| LNU236 | 25422.4 | 4.95 | 0.044 | 6 | LNU276 | 25431.1 | 7.87 | 0.282 | 5 | LNU236 | 25422.4 | 69.67 | 0.006 | 16 |
| LNU24 | 24971.2 | 5.23 | 0.032 | 12 | LNU279 | 25481.3 | 9.22 | 0.414 | 23 | LNU24 | 24974.2 | 71.68 | 0.272 | 19 |
| LNU24 | 24974.2 | 5.09 | 0.352 | 9 | LNU279 | 25481.4 | 8.87 | 0.167 | 18 | LNU24 | 24971.2 | 69.57 | 0.001 | 16 |
| LNU24 | 24971.3 | 5.03 | 0.556 | 8 | LNU279 | 25481.5 | 8.81 | 0.413 | 17 | LNU24 | 24971.3 | 68.22 | 0.547 | 13 |
| LNU24 | 24972.1 | 4.81 | 0.229 | 3 | LNU36 | 25562.3 | 7.66 | 0.786 | 2 | LNU24 | 24972.1 | 64.42 | 0.085 | 7 |
| LNU24 | 24971.4 | 4.80 | 0.482 | 3 | LNU36 | 25562.7 | 7.66 | 0.594 | 2 | LNU24 | 24971.4 | 62.06 | 0.788 | 3 |
| LNU263 | 25794.8 | 5.31 | 0.121 | 14 | LNU53 | 25674.1 | 9.58 | 0.175 | 27 | LNU263 | 25794.8 | 75.78 | 0.222 | 26 |
| LNU276 | 25433.3 | 5.25 | 0.002 | 12 | LNU53 | 25674.2 | 7.84 | 0.722 | 4 | LNU276 | 25433.3 | 76.41 | 0.001 | 27 |
| LNU276 | 25431.1 | 4.81 | 0.282 | 3 | LNU53 | 25674.6 | 7.72 | 0.545 | 3 | LNU276 | 25431.1 | 62.93 | 0.282 | 5 |
| LNU279 | 25481.4 | 5.08 | 0.321 | 9 | LNU56 | 24693.1 | 8.44 | 0.356 | 12 | LNU279 | 25481.3 | 73.77 | 0.414 | 23 |
| LNU279 | 25481.3 | 5.02 | 0.552 | 7 | LNU56 | 24694.1 | 8.33 | 0.056 | 11 | LNU279 | 25481.4 | 70.96 | 0.167 | 18 |
| LNU279 | 25481.5 | 5.01 | 0.447 | 7 | LNU56 | 24693.2 | 7.76 | 0.556 | 3 | LNU279 | 25481.5 | 70.48 | 0.413 | 17 |
| LNU36 | 25562.3 | 4.96 | 0.429 | 6 | LNU73 | 25755.1 | 9.11 | 0.194 | 21 | LNU36 | 25562.3 | 61.29 | 0.786 | 2 |
| LNU53 | 25674.1 | 5.35 | 0.188 | 14 | LNU73 | 25751.1 | 8.87 | 0.641 | 18 | LNU36 | 25562.7 | 61.26 | 0.594 | 2 |
| LNU53 | 25674.2 | 4.85 | 0.112 | 4 | LNU73 | 25754.2 | 8.51 | 0.642 | 13 | LNU53 | 25674.1 | 76.62 | 0.175 | 27 |
| LNU53 | 25674.6 | 4.85 | 0.235 | 4 | LNU73 | 25751.8 | 8.46 | 0.566 | 12 | LNU53 | 25674.2 | 62.69 | 0.722 | 4 |
| LNU56 | 24693.1 | 5.02 | 0.358 | 7 | LNU73 | 25751.9 | 8.14 | 0.255 | 8 | LNU53 | 25674.6 | 61.73 | 0.545 | 3 |
| LNU56 | 24694.1 | 4.95 | 0.147 | 6 | LNU9 | 25001.1 | 9.43 | 0.119 | 25 | LNU56 | 24693.1 | 67.51 | 0.356 | 12 |
| LNU73 | 25751.1 | 5.16 | 0.600 | 10 | LNU9 | 25001.7 | 9.08 | 0.159 | 21 | LNU56 | 24694.1 | 66.68 | 0.056 | 11 |
| LNU73 | 25755.1 | 5.13 | 0.188 | 10 | LNU9 | 25001.2 | 8.80 | 0.315 | 17 | LNU56 | 24693.2 | 62.11 | 0.556 | 3 |
| LNU73 | 25754.2 | 5.05 | 0.562 | 8 | LNU9 | 25001.3 | 8.59 | 0.527 | 14 | LNU73 | 25755.1 | 72.87 | 0.194 | 21 |
| LNU73 | 25751.8 | 5.02 | 0.539 | 7 | CONT. | — | 5.46 | — | 0 | LNU73 | 25751.1 | 70.95 | 0.641 | 18 |
| LNU73 | 25751.9 | 4.87 | 0.323 | 4 | LNU131 | 14005.2 | 8.63 | 0.000 | 58 | LNU73 | 25754.2 | 68.05 | 0.642 | 13 |
| LNU9 | 25001.1 | 5.27 | 0.006 | 13 | LNU131 | 14005.5 | 7.70 | 0.000 | 41 | LNU73 | 25751.8 | 67.65 | 0.566 | 12 |
| LNU9 | 25001.7 | 5.23 | 0.108 | 12 | LNU131 | 14002.15 | 5.68 | 0.675 | 4 | LNU73 | 25751.9 | 65.14 | 0.255 | 8 |
| LNU9 | 25001.2 | 5.00 | 0.381 | 7 | LNU135 | 26203.1 | 6.47 | 0.756 | 15 | LNU9 | 25001.1 | 75.41 | 0.119 | 25 |
| LNU9 | 25001.3 | 4.93 | 0.552 | 5 | LNU135 | 26204.2 | 6.39 | 0.071 | 17 | LNU9 | 25001.7 | 72.60 | 0.159 | 21 |
| CONT. | — | 3.89 | — | 0 | LNU135 | 26203.4 | 6.30 | 0.740 | 15 | LNU9 | 25001.2 | 70.42 | 0.315 | 17 |
| LNU131 | 14005.2 | 4.95 | 0.001 | 27 | LNU135 | 26203.6 | 5.91 | 0.651 | 8 | LNU9 | 25001.3 | 68.74 | 0.527 | 14 |
| LNU131 | 14005.5 | 4.66 | 0.000 | 20 | LNU135 | 26203.2 | 5.59 | 0.723 | 2 | CONT. | — | 43.36 | — | 0 |
| LNU135 | 26203.4 | 4.17 | 0.763 | 7 | LNU161 | 14552.9 | 5.58 | 0.793 | 2 | LNU131 | 14005.2 | 69.03 | 0.000 | 59 |
| LNU135 | 26204.2 | 4.15 | 0.173 | 7 | LNU173 | 25451.2 | 7.12 | 0.405 | 30 | LNU131 | 14005.5 | 61.62 | 0.000 | 42 |
| LNU135 | 26203.6 | 4.04 | 0.754 | 4 | LNU173 | 25451.5 | 5.78 | 0.563 | 6 | LNU131 | 14002.15 | 45.46 | 0.614 | 5 |
| LNU173 | 25451.2 | 4.44 | 0.465 | 14 | LNU181 | 25771.8 | 7.22 | 0.385 | 32 | LNU135 | 26203.1 | 51.73 | 0.746 | 19 |
| LNU181 | 25771.8 | 4.49 | 0.391 | 15 | LNU181 | 25771.6 | 6.86 | 0.005 | 25 | LNU135 | 26204.2 | 51.12 | 0.062 | 18 |

TABLE 83-continued

Genes showing improved plant biomass production at standard nitrogen growth conditions

| | Rosette Diameter [cm] | | | | | Rosette Area [cm2] | | | | | Plot Coverage [%] | | |
|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU181 | 25771.6 | 4.32 | 0.006 | 11 | LNU181 | 25774.1 | 6.52 | 0.018 | 19 | LNU135 | 26203.4 | 50.44 | 0.727 | 16 |
| LNU181 | 25771.5 | 4.21 | 0.573 | 8 | LNU181 | 25771.5 | 6.38 | 0.548 | 17 | LNU135 | 26203.6 | 47.26 | 0.621 | 9 |
| LNU181 | 25774.1 | 4.10 | 0.130 | 5 | LNU184 | 25393.2 | 7.56 | 0.000 | 38 | LNU135 | 26203.3 | 44.70 | 0.629 | 3 |
| LNU184 | 25393.2 | 4.54 | 0.000 | 17 | LNU184 | 25394.1 | 7.46 | 0.238 | 36 | LNU161 | 14552.9 | 44.61 | 0.713 | 3 |
| LNU184 | 25394.1 | 4.52 | 0.195 | 16 | LNU184 | 25393.1 | 6.68 | 0.061 | 22 | LNU173 | 25451.2 | 56.96 | 0.397 | 31 |
| LNU184 | 25393.3 | 4.34 | 0.530 | 11 | LNU184 | 25393.3 | 6.64 | 0.595 | 21 | LNU173 | 25451.5 | 46.25 | 0.512 | 7 |
| LNU184 | 25393.1 | 4.32 | 0.096 | 11 | LNU184 | 25394.3 | 6.51 | 0.645 | 19 | LNU181 | 25771.8 | 57.77 | 0.377 | 33 |
| LNU184 | 25394.3 | 4.27 | 0.603 | 10 | LNU184 | 25395.1 | 6.01 | 0.471 | 10 | LNU181 | 25771.6 | 54.86 | 0.004 | 27 |
| LNU184 | 25395.1 | 3.96 | 0.799 | 2 | LNU224 | 25872.3 | 9.03 | 0.019 | 65 | LNU181 | 25774.1 | 52.14 | 0.014 | 20 |
| LNU224 | 25872.3 | 5.01 | 0.045 | 29 | LNU224 | 25874.4 | 8.06 | 0.136 | 47 | LNU181 | 25771.5 | 51.03 | 0.532 | 18 |
| LNU224 | 25874.1 | 4.62 | 0.275 | 19 | LNU224 | 25874.1 | 7.70 | 0.317 | 41 | LNU184 | 25393.2 | 60.48 | 0.000 | 39 |
| LNU224 | 25874.4 | 4.61 | 0.105 | 18 | LNU224 | 25872.2 | 7.18 | 0.359 | 31 | LNU184 | 25394.1 | 59.65 | 0.232 | 38 |
| LNU224 | 25872.2 | 4.45 | 0.255 | 14 | LNU224 | 25871.3 | 5.78 | 0.451 | 6 | LNU184 | 25393.1 | 53.47 | 0.055 | 23 |
| LNU246 | 25744.3 | 4.64 | 0.491 | 19 | LNU246 | 25744.3 | 7.98 | 0.492 | 46 | LNU184 | 25394.3 | 52.09 | 0.633 | 20 |
| LNU246 | 25744.2 | 4.64 | 0.043 | 19 | LNU246 | 25744.2 | 7.83 | 0.167 | 43 | LNU184 | 25393.3 | 50.56 | 0.719 | 17 |
| LNU246 | 25744.4 | 4.60 | 0.531 | 18 | LNU246 | 25744.4 | 7.70 | 0.539 | 41 | LNU184 | 25395.1 | 48.06 | 0.440 | 11 |
| LNU246 | 25743.1 | 4.44 | 0.177 | 14 | LNU246 | 25743.1 | 6.94 | 0.175 | 27 | LNU224 | 25872.3 | 72.21 | 0.019 | 67 |
| LNU246 | 25743.2 | 4.24 | 0.017 | 9 | LNU246 | 25743.2 | 6.60 | 0.006 | 21 | LNU224 | 25874.4 | 64.48 | 0.133 | 49 |
| LNU250 | 25591.1 | 4.80 | 0.006 | 23 | LNU250 | 25591.1 | 8.34 | 0.140 | 53 | LNU224 | 25874.1 | 61.56 | 0.311 | 42 |
| LNU250 | 25592.2 | 4.41 | 0.001 | 13 | LNU250 | 25592.2 | 6.69 | 0.003 | 22 | LNU224 | 25872.2 | 57.46 | 0.351 | 33 |
| LNU260 | 26404.1 | 4.10 | 0.473 | 5 | LNU260 | 26404.1 | 6.08 | 0.526 | 11 | LNU224 | 25871.3 | 46.25 | 0.391 | 7 |
| LNU276 | 25433.6 | 4.57 | 0.306 | 17 | LNU260 | 26403.1 | 5.88 | 0.523 | 8 | LNU246 | 25744.3 | 63.80 | 0.486 | 47 |
| LNU276 | 25433.5 | 4.20 | 0.487 | 8 | LNU276 | 25433.6 | 7.47 | 0.273 | 37 | LNU246 | 25744.2 | 62.63 | 0.163 | 44 |
| LNU279 | 25481.3 | 4.68 | 0.457 | 20 | LNU276 | 25433.5 | 6.51 | 0.490 | 19 | LNU246 | 25744.4 | 61.63 | 0.533 | 42 |
| LNU279 | 25484.3 | 4.60 | 0.331 | 18 | LNU276 | 25433.3 | 5.80 | 0.607 | 6 | LNU246 | 25743.2 | 52.80 | 0.005 | 22 |
| LNU279 | 25481.2 | 3.96 | 0.708 | 2 | LNU279 | 25484.3 | 7.86 | 0.232 | 44 | LNU246 | 25743.1 | 51.76 | 0.010 | 19 |
| LNU3 | 26124.3 | 4.05 | 0.307 | 4 | LNU279 | 25481.3 | 7.80 | 0.383 | 43 | LNU250 | 25591.1 | 66.75 | 0.137 | 54 |
| LNU33 | 25553.3 | 4.15 | 0.416 | 7 | LNU279 | 25481.2 | 6.22 | 0.206 | 14 | LNU250 | 25592.2 | 53.50 | 0.002 | 23 |
| LNU53 | 25674.5 | 4.05 | 0.348 | 4 | LNU279 | 25481.5 | 6.02 | 0.769 | 10 | LNU260 | 26404.1 | 48.66 | 0.501 | 12 |
| LNU56 | 24694.2 | 4.01 | 0.359 | 3 | LNU3 | 26122.2 | 5.76 | 0.546 | 5 | LNU260 | 26403.1 | 47.04 | 0.484 | 8 |
| CONT. | — | 4.57 | — | 0 | LNU3 | 26124.3 | 5.71 | 0.636 | 4 | LNU276 | 25433.6 | 59.76 | 0.267 | 38 |
| LNU130 | 24912.7 | 5.24 | 0.000 | 15 | LNU33 | 25553.3 | 6.36 | 0.406 | 16 | LNU276 | 25433.5 | 52.07 | 0.476 | 20 |
| LNU130 | 24913.5 | 4.81 | 0.452 | 5 | LNU33 | 25552.2 | 5.73 | 0.453 | 5 | LNU276 | 25433.3 | 46.39 | 0.563 | 7 |
| LNU130 | 24911.7 | 4.79 | 0.709 | 5 | LNU53 | 25674.5 | 6.02 | 0.129 | 10 | LNU279 | 25484.3 | 62.91 | 0.228 | 45 |
| LNU136 | 14515.1 | 5.09 | 0.087 | 12 | LNU56 | 24694.2 | 5.79 | 0.346 | 6 | LNU279 | 25481.3 | 62.39 | 0.377 | 44 |
| LNU142 | 27541.1 | 4.78 | 0.662 | 5 | CONT. | — | 7.19 | — | 0 | LNU279 | 25481.2 | 49.74 | 0.186 | 15 |
| LNU15 | 14123.13 | 4.85 | 0.095 | 6 | LNU119 | 26142.8 | 7.51 | 0.405 | 4 | LNU279 | 25481.5 | 48.15 | 0.752 | 11 |
| LNU15 | 14123.11 | 4.83 | 0.046 | 6 | LNU130 | 24912.7 | 8.81 | 0.058 | 23 | LNU3 | 26122.2 | 46.10 | 0.489 | 6 |
| LNU185 | 26475.1 | 4.91 | 0.486 | 8 | LNU130 | 24913.5 | 7.84 | 0.354 | 9 | LNU3 | 26124.3 | 45.68 | 0.578 | 5 |
| LNU185 | 26474.2 | 4.77 | 0.091 | 4 | LNU130 | 24911.7 | 7.63 | 0.793 | 6 | LNU33 | 25553.3 | 50.90 | 0.388 | 17 |
| LNU212 | 25834.5 | 4.87 | 0.163 | 7 | LNU130 | 24913.6 | 7.54 | 0.613 | 5 | LNU33 | 25552.2 | 45.87 | 0.382 | 6 |
| LNU212 | 25834.1 | 4.85 | 0.527 | 6 | LNU136 | 14515.1 | 8.58 | 0.046 | 19 | LNU53 | 25674.5 | 48.16 | 0.103 | 11 |
| LNU216 | 25985.4 | 4.95 | 0.714 | 8 | LNU142 | 27541.1 | 8.08 | 0.487 | 12 | LNU56 | 24694.2 | 46.36 | 0.287 | 7 |
| LNU216 | 25982.1 | 4.72 | 0.350 | 3 | LNU142 | 27545.1 | 7.62 | 0.787 | 6 | CONT. | — | 57.54 | — | 0 |
| LNU216 | 25982.2 | 4.65 | 0.766 | 2 | LNU142 | 27546.1 | 7.55 | 0.280 | 5 | LNU119 | 26142.8 | 60.06 | 0.405 | 4 |
| LNU228 | 26222.4 | 4.93 | 0.168 | 8 | LNU15 | 14123.13 | 8.21 | 0.064 | 14 | LNU130 | 24912.7 | 70.52 | 0.058 | 23 |
| LNU228 | 26224.7 | 4.76 | 0.623 | 4 | LNU15 | 14123.11 | 7.71 | 0.257 | 7 | LNU130 | 24913.5 | 62.68 | 0.354 | 9 |
| LNU241 | 26232.4 | 4.79 | 0.104 | 5 | LNU185 | 26475.1 | 8.28 | 0.371 | 15 | LNU130 | 24911.7 | 61.01 | 0.793 | 6 |
| LNU241 | 26233.2 | 4.77 | 0.290 | 4 | LNU185 | 26474.2 | 7.75 | 0.352 | 8 | LNU130 | 24913.6 | 60.30 | 0.613 | 5 |
| LNU277 | 25845.1 | 4.73 | 0.691 | 4 | LNU212 | 25834.5 | 8.45 | 0.003 | 18 | LNU136 | 14515.1 | 68.61 | 0.046 | 19 |
| LNU280 | 26162.1 | 5.13 | 0.547 | 12 | LNU212 | 25834.1 | 7.98 | 0.668 | 11 | LNU142 | 27541.1 | 64.66 | 0.487 | 12 |
| LNU280 | 26162.7 | 4.79 | 0.255 | 5 | LNU216 | 25985.4 | 8.64 | 0.625 | 20 | LNU142 | 27545.1 | 60.95 | 0.787 | 6 |
| LNU55 | 26015.1 | 4.82 | 0.304 | 5 | LNU216 | 25982.1 | 7.69 | 0.532 | 7 | LNU142 | 27546.1 | 60.40 | 0.280 | 5 |
| LNU81 | 26034.3 | 5.23 | 0.040 | 14 | LNU216 | 25982.2 | 7.54 | 0.539 | 5 | LNU15 | 14123.13 | 65.70 | 0.064 | 14 |
| CONT. | — | 4.91 | — | 0 | LNU228 | 26222.4 | 8.01 | 0.037 | 11 | LNU15 | 14123.11 | 61.64 | 0.257 | 7 |
| LNU119 | 26141.1 | 5.35 | 0.525 | 9 | LNU228 | 26224.7 | 7.58 | 0.588 | 5 | LNU185 | 26475.1 | 66.26 | 0.371 | 15 |
| LNU119 | 26142.8 | 5.22 | 0.246 | 6 | LNU241 | 26233.2 | 7.94 | 0.271 | 10 | LNU185 | 26474.2 | 61.98 | 0.352 | 8 |
| LNU130 | 24914.5 | 5.30 | 0.068 | 8 | LNU274 | 26265.1 | 7.38 | 0.559 | 2 | LNU212 | 25834.5 | 67.62 | 0.003 | 18 |
| LNU136 | 14515.1 | 5.19 | 0.363 | 6 | LNU277 | 25845.1 | 8.19 | 0.506 | 14 | LNU212 | 25834.1 | 63.81 | 0.668 | 11 |
| LNU142 | 27541.2 | 5.19 | 0.243 | 6 | LNU280 | 26162.1 | 9.03 | 0.532 | 26 | LNU216 | 25985.4 | 69.11 | 0.625 | 20 |
| LNU142 | 27541. | 5.18 | 0.641 | 6 | LNU280 | 26162.7 | 7.81 | 0.372 | 9 | LNU216 | 25982.1 | 61.50 | 0.532 | 7 |
| LNU142 | 27545.1 | 5.11 | 0.039 | 4 | LNU55 | 26015.1 | 7.57 | 0.495 | 5 | LNU216 | 25982.2 | 60.31 | 0.539 | 5 |
| LNU15 | 14123.11 | 5.64 | 0.450 | 15 | LNU55 | 26015.3 | 7.33 | 0.676 | 2 | LNU228 | 26222.4 | 64.07 | 0.037 | 11 |
| LNU15 | 14122.8 | 5.43 | 0.709 | 11 | LNU81 | 26034.3 | 9.24 | 0.001 | 28 | LNU228 | 26224.7 | 60.67 | 0.588 | 5 |
| LNU15 | 14123.13 | 5.36 | 0.081 | 9 | CONT. | — | 8.21 | — | 0 | LNU241 | 26233.2 | 63.55 | 0.271 | 10 |
| LNU212 | 25834.5 | 5.27 | 0.020 | 7 | LNU119 | 26142.8 | 9.21 | 0.257 | 12 | LNU274 | 26265.1 | 59.07 | 0.559 | 3 |
| LNU212 | 25834.1 | 5.09 | 0.469 | 4 | LNU119 | 26141.1 | 8.81 | 0.725 | 7 | LNU277 | 25845.1 | 65.53 | 0.506 | 14 |
| LNU212 | 25834.4 | 5.04 | 0.481 | 3 | LNU130 | 24914.5 | 9.08 | 0.160 | 11 | LNU280 | 26162.1 | 72.23 | 0.532 | 26 |
| LNU216 | 25984.6 | 5.11 | 0.290 | 4 | LNU130 | 24913.5 | 8.41 | 0.792 | 2 | LNU55 | 26015.1 | 60.59 | 0.495 | 5 |
| LNU216 | 25984.1 | 5.11 | 0.459 | 4 | LNU136 | 14515.1 | 8.81 | 0.488 | 7 | LNU55 | 26015.3 | 58.66 | 0.676 | 2 |
| LNU228 | 26224.7 | 5.49 | 0.069 | 12 | LNU142 | 27541.1 | 8.99 | 0.680 | 10 | LNU81 | 26034.3 | 73.89 | 0.001 | 28 |

TABLE 83-continued

Genes showing improved plant biomass production at standard nitrogen growth conditions

| Gene Name | Event # | Rosette Diameter [cm] Ave. | P-Value | % incr. | Gene Name | Event # | Rosette Area [cm2] Ave. | P-Value | % incr. | Gene Name | Event # | Plot Coverage [%] Ave. | P-Value | % incr. |
|---|---|---|---|---|---|---|---|---|---|---|---|---|---|---|
| LNU228 | 26222.1 | 5.32 | 0.001 | 8 | LNU142 | 27541.2 | 8.81 | 0.265 | 7 | CONT. | — | 65.65 | — | 0 |
| LNU229 | 26111.5 | 5.30 | 0.002 | 8 | LNU142 | 27545.1 | 8.76 | 0.036 | 7 | LNU119 | 26142.8 | 73.65 | 0.257 | 12 |
| LNU241 | 26232.4 | 5.31 | 0.438 | 8 | LNU149 | 26174.7 | 8.81 | 0.799 | 7 | LNU130 | 24914.5 | 72.61 | 0.160 | 11 |
| LNU274 | 26262.2 | 5.10 | 0.464 | 4 | LNU15 | 14123.11 | 10.26 | 0.454 | 25 | LNU130 | 24913.5 | 67.25 | 0.792 | 2 |
| LNU277 | 25842.3 | 5.28 | 0.524 | 7 | LNU15 | 14122.8 | 10.12 | 0.624 | 23 | LNU136 | 14515.1 | 70.47 | 0.488 | 7 |
| LNU280 | 26164.4 | 5.21 | 0.005 | 6 | LNU15 | 14123.13 | 9.22 | 0.424 | 12 | LNU142 | 27541.1 | 71.91 | 0.680 | 10 |
| LNU280 | 26164.3 | 5.11 | 0.061 | 4 | LNU212 | 25834.5 | 9.20 | 0.260 | 12 | LNU142 | 27541.2 | 70.52 | 0.265 | 7 |
| LNU280 | 26162.1 | 5.10 | 0.346 | 4 | LNU212 | 25834.4 | 8.59 | 0.703 | 5 | LNU142 | 27545.1 | 70.07 | 0.036 | 7 |
| LNU81 | 26031.10 | 5.59 | 0.339 | 14 | LNU216 | 25984.1 | 9.00 | 0.597 | 10 | LNU149 | 26174.7 | 70.46 | 0.799 | 7 |
| LNU81 | 26034.3 | 5.12 | 0.770 | 4 | LNU216 | 25982.2 | 8.73 | 0.147 | 6 | LNU15 | 14123.11 | 82.11 | 0.454 | 25 |
| LNU81 | 26034.2 | 5.12 | 0.022 | 4 | LNU216 | 25984.6 | 8.55 | 0.486 | 4 | LNU15 | 14122.8 | 80.97 | 0.624 | 23 |
| CONT. | | 4.203 | — | 0.0 | LNU228 | 26222.1 | 9.79 | 0.004 | 19 | LNU15 | 14123.13 | 73.80 | 0.424 | 12 |
| LNU61 | 26134.4 | 4.780 | 0.02 | 13.7 | LNU228 | 26224.7 | 9.60 | 0.018 | 17 | LNU212 | 25834.5 | 73.62 | 0.260 | 12 |
| CONT. | — | 4.203 | — | 0.0 | LNU229 | 26111.5 | 8.83 | 0.421 | 8 | LNU212 | 25834.4 | 68.74 | 0.703 | 5 |
| LNU134 | 29191.3 | 4.344 | <0.8 | 3.3 | LNU241 | 26232.4 | 9.50 | 0.384 | 16 | LNU216 | 25984.1 | 71.97 | 0.597 | 10 |
| LNU134 | 29191.6 | 4.524 | <0.3 | 7.6 | LNU274 | 26262.2 | 8.45 | 0.409 | 3 | LNU216 | 25982.2 | 69.80 | 0.147 | 6 |
| LNU134 | 29194.1 | 4.365 | <0.7 | 3.8 | LNU277 | 25842.3 | 9.21 | 0.560 | 12 | LNU216 | 25984.6 | 68.39 | 0.486 | 4 |
| LNU198 | 27735.4 | 4.406 | <0.7 | 4.8 | LNU280 | 26164.4 | 9.50 | 0.000 | 16 | LNU228 | 26222.1 | 78.34 | 0.004 | 19 |
| LNU200 | 27992.2 | 4.704 | <0.1 | 11.9 | LNU280 | 26162.1 | 8.65 | 0.122 | 5 | LNU228 | 26224.7 | 76.83 | 0.018 | 17 |
| LNU200 | 27992.3 | 4.608 | <0.3 | 9.6 | LNU81 | 26031.10 | 10.53 | 0.247 | 28 | LNU229 | 26111.5 | 70.61 | 0.421 | 8 |
| LNU200 | 27993.4 | 4.735 | <0.1 | 12.6 | LNU81 | 26034.3 | 8.79 | 0.743 | 7 | LNU241 | 26232.4 | 76.03 | 0.384 | 16 |
| LNU200 | 27994.3 | 4.378 | <0.8 | 4.1 | LNU81 | 26031.9 | 8.48 | 0.768 | 3 | LNU274 | 26262.2 | 67.61 | 0.409 | 3 |
| LNU244 | 28013.6 | 4.584 | <0.3 | 9.1 | CONT. | | 5.508 | — | 0.0 | LNU277 | 25842.3 | 73.68 | 0.560 | 12 |
| LNU244 | 28013.8 | 4.635 | <0.3 | 10.3 | LNU61 | 26134.4 | 6.634 | 0.045 | 20.5 | LNU280 | 26164.4 | 76.02 | 0.000 | 16 |
| LNU244 | 28014.4 | 4.673 | <0.1 | 11.2 | LNU61 | 26135.3 | 5.827 | 0.55 | 5.8 | LNU280 | 26162.1 | 69.21 | 0.122 | 5 |
| LNU244 | 28015.1 | 4.628 | <0.3 | 10.1 | CONT. | — | 5.508 | — | 0.0 | LNU81 | 26031.10 | 84.26 | 0.247 | 28 |
| LNU262 | 27591.3 | 4.517 | <0.3 | 7.5 | LNU123 | 27722.4 | 5.740 | <0.8 | 4.2 | LNU81 | 26034.3 | 70.32 | 0.743 | 7 |
| LNU262 | 27591.7 | 4.740 | <0.1 | 12.8 | LNU134 | 29191.3 | 5.789 | <0.8 | 5.1 | LNU81 | 26031.9 | 67.84 | 0.768 | 3 |
| LNU262 | 27593.1 | 4.860 | <0.1 | 15.6 | LNU134 | 29191.6 | 6.647 | <0.1 | 20.7 | CONT. | — | 44.061 | — | 0.0 |
| LNU262 | 27593.6 | 4.849 | <0.1 | 15.4 | LNU134 | 29194.1 | 6.208 | <0.4 | 12.7 | LNU61 | 26134.4 | 53.071 | 0.045 | 20.5 |
| LNU262 | 27595.2 | 4.884 | <0.1 | 16.2 | LNU198 | 27735.4 | 6.147 | <0.4 | 11.6 | LNU61 | 26135.3 | 46.614 | 0.55 | 5.8 |
| LNU266 | 27931.5 | 4.544 | <0.3 | 8.1 | LNU200 | 27992.2 | 6.852 | <0.1 | 24.4 | CONT. | — | 44.061 | — | 0.0 |
| LNU266 | 27932.1 | 4.312 | <0.8 | 2.6 | LNU200 | 27992.3 | 6.540 | <0.1 | 18.7 | LNU123 | 27722.4 | 45.924 | <0.7 | 4.2 |
| LNU266 | 27935.3 | 4.632 | <0.3 | 10.2 | LNU200 | 27993.4 | 6.516 | <0.1 | 18.3 | LNU134 | 29191.6 | 53.174 | <0.1 | 20.7 |
| LNU266 | 27935.4 | 4.449 | <0.7 | 5.8 | LNU200 | 27994.3 | 6.021 | <0.4 | 9.3 | LNU134 | 29194.1 | 49.666 | <0.3 | 12.7 |
| LNU29 | 27652.2 | 4.297 | <0.8 | 2.2 | LNU244 | 28013.6 | 6.619 | <0.1 | 20.2 | LNU198 | 27735.4 | 49.176 | <0.7 | 11.6 |
| LNU29 | 27653.1 | 4.758 | <0.1 | 13.2 | LNU244 | 28013.8 | 6.593 | <0.1 | 19.7 | LNU200 | 27992.2 | 54.815 | <0.1 | 24.4 |
| LNU29 | 27654.1 | 4.748 | <0.1 | 13.0 | LNU244 | 28014.4 | 6.854 | <0.1 | 24.4 | LNU200 | 27992.3 | 52.322 | <0.1 | 18.7 |
| LNU29 | 27655.1 | 4.751 | <0.1 | 13.0 | LNU244 | 28015.1 | 6.623 | <0.1 | 20.3 | LNU200 | 27993.4 | 52.124 | <0.1 | 18.3 |
| LNU32 | 29252.6 | 4.427 | <0.3 | 5.3 | LNU262 | 27591.3 | 6.548 | <0.1 | 18.9 | LNU200 | 27994.3 | 48.167 | <0.7 | 9.3 |
| LNU51 | 27612.2 | 4.681 | <0.1 | 11.4 | LNU262 | 27591.7 | 6.654 | <0.1 | 20.8 | LNU244 | 28013.6 | 52.951 | <0.1 | 20.2 |
| LNU51 | 27614.4 | 4.482 | <0.3 | 6.6 | LNU262 | 27593.1 | 7.392 | <0.1 | 34.2 | LNU244 | 28013.8 | 52.747 | <0.1 | 19.7 |
| LNU51 | 27616.1 | 4.677 | <0.3 | 11.3 | LNU262 | 27593.6 | 7.160 | <0.1 | 30.0 | LNU244 | 28014.4 | 54.828 | <0.1 | 24.4 |
| LNU58 | 27673.4 | 4.505 | <0.3 | 7.2 | LNU262 | 27595.2 | 7.217 | <0.1 | 31.0 | LNU244 | 28015.1 | 52.986 | <0.1 | 20.3 |
| CONT. | 8252.24 | 2.097 | | 0.0 | LNU266 | 27931.5 | 6.158 | <0.4 | 11.8 | LNU262 | 27591.3 | 52.382 | <0.1 | 18.9 |
| LNU89 | 25325.2 | 2.217 | 0.7 | 5.7 | LNU266 | 27932.1 | 5.966 | <0.4 | 8.3 | LNU262 | 27591.7 | 53.232 | <0.1 | 20.8 |
| | | | | | LNU266 | 27935.3 | 6.563 | <0.1 | 19.2 | LNU262 | 27593.1 | 59.137 | <0.1 | 34.2 |
| | | | | | LNU266 | 27935.4 | 6.305 | <0.4 | 14.5 | LNU262 | 27593.6 | 57.278 | <0.1 | 30.0 |
| | | | | | LNU29 | 27653.1 | 7.013 | <0.1 | 27.3 | LNU262 | 27595.2 | 57.740 | <0.1 | 31.0 |
| | | | | | LNU29 | 27654.1 | 6.500 | <0.1 | 18.0 | LNU266 | 27931.5 | 49.265 | <0.7 | 11.8 |
| | | | | | LNU29 | 27655.1 | 6.526 | <0.1 | 18.5 | LNU266 | 27932.1 | 47.729 | <0.7 | 8.3 |
| | | | | | LNU32 | 29251.1 | 5.912 | <0.8 | 7.3 | LNU266 | 27935.3 | 52.505 | <0.1 | 19.2 |
| | | | | | LNU32 | 29252.6 | 6.123 | <0.4 | 11.2 | LNU266 | 27935.4 | 50.439 | <0.3 | 14.5 |
| | | | | | LNU51 | 27612.2 | 6.630 | <0.1 | 20.4 | LNU29 | 27653.1 | 56.105 | <0.1 | 27.3 |
| | | | | | LNU51 | 27614.4 | 6.359 | <0.4 | 15.5 | LNU29 | 27654.1 | 51.998 | <0.1 | 18.0 |
| | | | | | LNU51 | 27616.1 | 6.922 | <0.1 | 25.7 | LNU29 | 27655.1 | 52.211 | <0.1 | 18.5 |
| | | | | | LNU58 | 27673.2 | 5.906 | <0.8 | 7.2 | LNU32 | 29251.1 | 47.296 | <0.7 | 7.3 |
| | | | | | LNU58 | 27673.4 | 6.527 | <0.1 | 18.5 | LNU32 | 29252.6 | 48.987 | <0.7 | 11.2 |
| | | | | | | | | | | LNU51 | 27612.2 | 53.044 | <0.1 | 20.4 |
| | | | | | | | | | | LNU51 | 27614.4 | 50.868 | <0.1 | 15.5 |
| | | | | | | | | | | LNU51 | 27616.1 | 55.376 | <0.1 | 25.7 |
| | | | | | | | | | | LNU58 | 27673.2 | 47.248 | <0.3 | 7.2 |
| | | | | | | | | | | LNU58 | 27673.4 | 52.219 | <0.15 | 18.5 |
| | | | | | | | | | | CONT. | 8252.24 | 10.791 | | 0.0 |
| | | | | | | | | | | LNU89 | 25325.1 | 11.960 | 0.3 | 10.8 |
| | | | | | | | | | | LNU89 | 25325.2 | 11.480 | 0.54 | 6.4 |

Table 83.
"CONT."—Control;
"Ave."—Average;
"% Incr." = % increment.

The genes listed in Table 84 improved plant NUE when grown at standard nitrogen concentration levels. These genes produced larger photosynthetic areas as it can be observed by their larger leaf blade area and leaf petiole length. The genes were cloned under the regulation of a constitutive (At6669) and root preferred promoter (RootP). The evaluation of each gene was performed by testing the performance of different number of events. Event with p-value <0.1 was considered statistically significant

TABLE 84

Genes showing improved photosynthetic capacity at standard nitrogen growth conditions

| | Leaf Number | | | | | Leaf Blade Area [cm2] | | | | | Leaf Petiole Length [cm] | | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| CONT. | — | 10.49 | — | 0 | CONT. | — | 0.64 | — | 0 | CONT. | — | 0.76 | — | 0 |
| LNU100 | 14471.4 | 11.25 | 0.262 | 7 | LNU100 | 14471.4 | 0.81 | 0.306 | 28 | LNU100 | 14471.4 | 0.88 | 0.214 | 16 |
| LNU100 | 14473.3 | 11.13 | 0.024 | 6 | LNU100 | 14474.3 | 0.77 | 0.003 | 21 | LNU100 | 14473.3 | 0.87 | 0.001 | 14 |
| LNU100 | 14474.3 | 11.13 | 0.024 | 6 | LNU100 | 14473.3 | 0.77 | 0.117 | 20 | LNU100 | 14472.2 | 0.85 | 0.002 | 11 |
| LNU100 | 14472.2 | 10.75 | 0.472 | 2 | LNU100 | 14472.2 | 0.75 | 0.256 | 17 | LNU100 | 14474.3 | 0.84 | 0.102 | 10 |
| LNU100 | 14474.4 | 10.69 | 0.639 | 2 | LNU104 | 25032.2 | 0.91 | 0.059 | 43 | LNU104 | 25033.1 | 0.96 | 0.055 | 26 |
| LNU104 | 25032.2 | 12.13 | 0.001 | 16 | LNU104 | 25033.1 | 0.89 | 0.159 | 39 | LNU104 | 25032.2 | 0.95 | 0.179 | 25 |
| LNU104 | 25034.1 | 11.00 | 0.048 | 5 | LNU104 | 25032.1 | 0.88 | 0.076 | 38 | LNU104 | 25033.3 | 0.90 | 0.002 | 18 |
| LNU104 | 25032.1 | 10.94 | 0.631 | 4 | LNU104 | 25033.3 | 0.84 | 0.007 | 31 | LNU104 | 25032.1 | 0.89 | 0.157 | 17 |
| LNU104 | 25033.3 | 10.94 | 0.015 | 4 | LNU104 | 25034.1 | 0.70 | 0.146 | 10 | LNU104 | 25034.1 | 0.80 | 0.437 | 4 |
| LNU104 | 25033.1 | 10.69 | 0.639 | 2 | LNU106 | 14482.3 | 0.79 | 0.371 | 24 | LNU106 | 14482.3 | 0.90 | 0.441 | 19 |
| LNU106 | 14483.5 | 11.06 | 0.115 | 5 | LNU106 | 14483.5 | 0.78 | 0.140 | 22 | LNU106 | 14483.5 | 0.90 | 0.000 | 17 |
| LNU106 | 14482.3 | 10.88 | 0.329 | 4 | LNU106 | 14483.2 | 0.76 | 0.264 | 20 | LNU106 | 14483.2 | 0.83 | 0.043 | 8 |
| LNU106 | 14483.2 | 10.75 | 0.610 | 2 | LNU106 | 14481.1 | 0.66 | 0.416 | 3 | LNU114 | 25041.1 | 0.99 | 0.000 | 29 |
| LNU114 | 25041.1 | 11.94 | 0.000 | 14 | LNU114 | 25041.1 | 0.86 | 0.000 | 35 | LNU114 | 25042.1 | 0.85 | 0.000 | 12 |
| LNU114 | 25041.2 | 11.00 | 0.048 | 5 | LNU114 | 25042.1 | 0.77 | 0.122 | 21 | LNU114 | 25041.2 | 0.84 | 0.250 | 10 |
| LNU114 | 25042.1 | 10.69 | 0.222 | 2 | LNU114 | 25041.2 | 0.70 | 0.018 | 9 | LNU155 | 14525.1 | 0.85 | 0.540 | 12 |
| LNU213 | 24653.2 | 11.50 | 0.090 | 10 | LNU155 | 14525.6 | 0.78 | 0.126 | 23 | LNU155 | 14525.6 | 0.85 | 0.231 | 11 |
| LNU213 | 24653.1 | 10.75 | 0.472 | 2 | LNU155 | 14525.1 | 0.71 | 0.598 | 12 | LNU213 | 24653.2 | 1.00 | 0.000 | 32 |
| LNU218 | 24781.2 | 11.00 | 0.486 | 5 | LNU213 | 24652.2 | 0.88 | 0.000 | 39 | LNU213 | 24652.4 | 0.88 | 0.468 | 15 |
| LNU218 | 24781.1 | 10.81 | 0.591 | 3 | LNU213 | 24652.4 | 0.83 | 0.472 | 31 | LNU213 | 24653.1 | 0.83 | 0.200 | 8 |
| LNU218 | 24781.7 | 10.75 | 0.230 | 2 | LNU213 | 24653.1 | 0.74 | 0.000 | 16 | LNU218 | 24781.7 | 0.91 | 0.091 | 20 |
| LNU23 | 25163.5 | 11.06 | 0.401 | 5 | LNU213 | 24654.4 | 0.68 | 0.754 | 7 | LNU218 | 24781.1 | 0.89 | 0.004 | 16 |
| LNU28 | 25171.1 | 10.88 | 0.688 | 4 | LNU218 | 24781.1 | 0.82 | 0.211 | 29 | LNU218 | 24781.2 | 0.85 | 0.001 | 11 |
| LNU28 | 25171.2 | 10.88 | 0.102 | 4 | LNU218 | 24781.7 | 0.80 | 0.254 | 25 | LNU23 | 25163.5 | 0.91 | 0.234 | 19 |
| LNU4 | 25134.1 | 11.25 | 0.262 | 7 | LNU218 | 24781.2 | 0.70 | 0.232 | 11 | LNU23 | 25163.6 | 0.83 | 0.193 | 9 |
| LNU4 | 25134.3 | 11.06 | 0.282 | 5 | LNU23 | 25163.5 | 0.90 | 0.028 | 41 | LNU28 | 25171.2 | 0.89 | 0.143 | 16 |
| LNU4 | 25133.3 | 10.94 | 0.015 | 4 | LNU23 | 25163.6 | 0.70 | 0.546 | 9 | LNU28 | 25171.1 | 0.80 | 0.064 | 5 |
| LNU4 | 25134.2 | 10.69 | 0.639 | 2 | LNU28 | 25171.2 | 0.81 | 0.201 | 28 | LNU28 | 25171.4 | 0.79 | 0.610 | 4 |
| LNU40 | 24794.4 | 10.88 | 0.102 | 4 | LNU28 | 25174.3 | 0.78 | 0.071 | 23 | LNU28 | 25174.3 | 0.78 | 0.381 | 2 |
| LNU46 | 14464.4 | 11.69 | 0.196 | 11 | LNU28 | 25171.1 | 0.72 | 0.240 | 13 | LNU4 | 25134.1 | 0.89 | 0.116 | 16 |
| LNU46 | 14463.1 | 11.31 | 0.371 | 8 | LNU28 | 25174.5 | 0.68 | 0.508 | 7 | LNU4 | 25133.3 | 0.86 | 0.225 | 12 |
| LNU46 | 14462.5 | 11.19 | 0.079 | 7 | LNU28 | 25171.4 | 0.65 | 0.790 | 3 | LNU4 | 25134.3 | 0.83 | 0.476 | 9 |
| LNU48 | 24802.2 | 12.00 | 0.182 | 14 | LNU4 | 25134.1 | 0.86 | 0.062 | 35 | LNU4 | 25134.2 | 0.80 | 0.164 | 4 |
| LNU48 | 24801.4 | 11.25 | 0.000 | 7 | LNU4 | 25133.3 | 0.77 | 0.000 | 22 | LNU40 | 24794.3 | 0.88 | 0.322 | 15 |
| LNU48 | 24802.1 | 11.13 | 0.001 | 6 | LNU4 | 25134.3 | 0.76 | 0.419 | 20 | LNU40 | 24794.4 | 0.86 | 0.221 | 13 |
| LNU63 | 24812.2 | 11.06 | 0.282 | 5 | LNU4 | 25131.1 | 0.69 | 0.563 | 9 | LNU40 | 24792.1 | 0.81 | 0.029 | 6 |
| LNU63 | 24814.2 | 10.94 | 0.483 | 4 | LNU4 | 25134.2 | 0.69 | 0.404 | 8 | LNU46 | 14463.1 | 0.92 | 0.307 | 21 |
| LNU7 | 25083.1 | 11.13 | 0.024 | 6 | LNU40 | 24794.3 | 0.83 | 0.013 | 30 | LNU46 | 14464.4 | 0.92 | 0.125 | 21 |
| LNU7 | 25082.2 | 11.00 | 0.384 | 5 | LNU40 | 24794.4 | 0.78 | 0.248 | 22 | LNU46 | 14462.5 | 0.89 | 0.001 | 17 |
| LNU7 | 25081.1 | 10.81 | 0.060 | 3 | LNU40 | 24792.1 | 0.70 | 0.011 | 10 | LNU46 | 14462.1 | 0.80 | 0.321 | 4 |
| LNU7 | 25082.7 | 10.69 | 0.473 | 2 | LNU40 | 24792.2 | 0.67 | 0.582 | 6 | LNU48 | 24801.4 | 0.95 | 0.000 | 25 |
| LNU8 | 25062.2 | 10.88 | 0.647 | 4 | LNU46 | 14463.1 | 0.83 | 0.288 | 30 | LNU48 | 24802.2 | 0.92 | 0.214 | 21 |
| LNU8 | 25063.1 | 10.75 | 0.748 | 2 | LNU46 | 14464.4 | 0.83 | 0.258 | 30 | LNU48 | 24802.1 | 0.90 | 0.216 | 17 |
| LNU8 | 25063.6 | 10.69 | 0.639 | 2 | LNU46 | 14462.5 | 0.82 | 0.000 | 29 | LNU63 | 24814.2 | 0.87 | 0.489 | 14 |
| LNU94 | 24833.3 | 11.13 | 0.001 | 6 | LNU46 | 14462.1 | 0.75 | 0.214 | 17 | LNU63 | 24812.2 | 0.83 | 0.441 | 9 |
| LNU94 | 24831.4 | 11.00 | 0.048 | 5 | LNU48 | 24801.4 | 0.93 | 0.004 | 46 | LNU63 | 24811.2 | 0.80 | 0.686 | 5 |
| LNU94 | 24834.4 | 10.69 | 0.473 | 2 | LNU48 | 24802.1 | 0.81 | 0.017 | 28 | LNU7 | 25081.1 | 0.90 | 0.013 | 17 |
| LNU96 | 25071.3 | 11.06 | 0.004 | 5 | LNU48 | 24802.2 | 0.81 | 0.000 | 27 | LNU7 | 25083.3 | 0.84 | 0.415 | 10 |
| LNU96 | 25073.3 | 11.03 | 0.530 | 5 | LNU63 | 24814.2 | 0.81 | 0.376 | 28 | LNU7 | 25083.1 | 0.82 | 0.009 | 8 |
| LNU96 | 25073.4 | 10.69 | 0.222 | 2 | LNU63 | 24812.2 | 0.72 | 0.265 | 13 | LNU8 | 25063.6 | 0.85 | 0.045 | 12 |
| CONT. | — | 11.17 | — | 0 | LNU63 | 24814.3 | 0.71 | 0.507 | 12 | LNU8 | 25062.2 | 0.80 | 0.132 | 5 |
| LNU124 | 14501.1 | 11.56 | 0.231 | 4 | LNU63 | 24811.2 | 0.68 | 0.730 | 7 | LNU94 | 24831.4 | 0.86 | 0.027 | 12 |
| LNU132 | 14103.9 | 11.38 | 0.297 | 2 | LNU7 | 25081.1 | 0.78 | 0.003 | 22 | LNU94 | 24834.4 | 0.84 | 0.002 | 9 |
| LNU140 | 14112.7 | 11.38 | 0.552 | 2 | LNU7 | 25083.1 | 0.76 | 0.003 | 20 | LNU94 | 24833.3 | 0.79 | 0.598 | 4 |
| LNU37 | 14064.7 | 11.56 | 0.010 | 4 | LNU7 | 25083.3 | 0.69 | 0.445 | 9 | LNU96 | 25071.3 | 0.81 | 0.395 | 7 |
| LNU72 | 24962.3 | 11.69 | 0.002 | 5 | LNU7 | 25082.2 | 0.65 | 0.268 | 3 | LNU96 | 25073.4 | 0.81 | 0.464 | 7 |
| LNU82 | 24823.1 | 11.75 | 0.221 | 5 | LNU8 | 25063.6 | 0.77 | 0.240 | 21 | LNU96 | 25073.3 | 0.81 | 0.763 | 6 |
| LNU84 | 25621.2 | 11.38 | 0.297 | 2 | LNU8 | 25062.2 | 0.72 | 0.202 | 13 | CONT. | — | 0.84 | — | 0 |
| LNU87 | 24712.4 | 11.44 | 0.761 | 2 | LNU8 | 25063.1 | 0.68 | 0.036 | 7 | LNU5 | 14042.7 | 0.91 | 0.264 | 8 |
| LNU98 | 25762.2 | 11.75 | 0.045 | 5 | LNU8 | 25061.2 | 0.68 | 0.124 | 6 | LNU72 | 24962.3 | 0.91 | 0.559 | 8 |
| CONT. | — | 10.96 | — | 0 | LNU94 | 24833.3 | 0.79 | 0.280 | 25 | LNU87 | 24714.3 | 0.87 | 0.753 | 3 |
| LNU124 | 14504.5 | 11.38 | 0.076 | 4 | LNU94 | 24834.4 | 0.75 | 0.015 | 19 | LNU98 | 25763.2 | 0.86 | 0.757 | 2 |
| LNU148 | 25685.6 | 11.81 | 0.567 | 8 | LNU94 | 24831.4 | 0.74 | 0.005 | 17 | CONT. | — | 0.76 | — | 0 |

TABLE 84-continued

Genes showing improved photosynthetic capacity at standard nitrogen growth conditions

| | | Leaf Number | | | | | Leaf Blade Area [cm2] | | | | | Leaf Petiole Length [cm] | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU148 | 25685.2 | 11.63 | 0.140 | 6 | LNU94 | 24833.1 | 0.71 | 0.624 | 11 | LNU113 | 25631.1 | 0.92 | 0.325 | 20 |
| LNU148 | 25683.2 | 11.19 | 0.459 | 2 | LNU96 | 25073.3 | 0.75 | 0.357 | 17 | LNU113 | 25631.3 | 0.85 | 0.570 | 11 |
| LNU37 | 14064.7 | 11.25 | 0.198 | 3 | LNU96 | 25071.3 | 0.71 | 0.238 | 12 | LNU124 | 14504.5 | 0.84 | 0.388 | 11 |
| LNU5 | 14043.9 | 11.19 | 0.603 | 2 | LNU96 | 25073.4 | 0.67 | 0.521 | 6 | LNU132 | 14102.9 | 0.86 | 0.489 | 12 |
| LNU68 | 14034.13 | 11.56 | 0.092 | 6 | CONT. | — | 0.92 | — | 0 | LNU140 | 14115.1 | 0.78 | 0.771 | 2 |
| LNU68 | 14033.9 | 11.31 | 0.562 | 3 | LNU148 | 25685.6 | 0.97 | 0.438 | 6 | LNU148 | 25685.1 | 0.83 | 0.065 | 8 |
| LNU68 | 14034.1 | 11.31 | 0.641 | 3 | LNU5 | 14042.7 | 1.01 | 0.003 | 9 | LNU148 | 25683.2 | 0.79 | 0.454 | 3 |
| LNU71 | 25852.5 | 11.75 | 0.475 | 7 | LNU72 | 24962.3 | 0.99 | 0.393 | 8 | LNU287 | 24674.3 | 0.81 | 0.628 | 7 |
| LNU71 | 25851.4 | 11.25 | 0.269 | 3 | LNU98 | 25763.2 | 0.98 | 0.024 | 7 | LNU37 | 14064.7 | 0.97 | 0.300 | 27 |
| LNU74 | 25441.2 | 11.56 | 0.018 | 6 | CONT. | — | 0.82 | — | 0 | LNU37 | 14064.6 | 0.93 | 0.434 | 21 |
| LNU74 | 25444.1 | 11.38 | 0.127 | 4 | LNU113 | 25631.3 | 1.00 | 0.210 | 23 | LNU5 | 14043.9 | 0.81 | 0.406 | 6 |
| LNU74 | 25443.2 | 11.25 | 0.443 | 3 | LNU113 | 25631.1 | 0.98 | 0.043 | 19 | LNU5 | 14043.7 | 0.78 | 0.587 | 2 |
| LNU87 | 24712.1 | 11.25 | 0.665 | 3 | LNU124 | 14504.5 | 0.91 | 0.218 | 11 | LNU65 | 24703.6 | 0.89 | 0.001 | 17 |
| CONT. | — | 11.68 | — | 0 | LNU132 | 14102.9 | 0.89 | 0.737 | 9 | LNU65 | 24702.3 | 0.82 | 0.643 | 8 |
| LNU117 | 25931.4 | 12.13 | 0.429 | 4 | LNU148 | 25685.1 | 0.97 | 0.016 | 18 | LNU68 | 14034.13 | 0.90 | 0.525 | 18 |
| LNU117 | 25933.3 | 12.13 | 0.281 | 4 | LNU148 | 25685.2 | 0.91 | 0.781 | 11 | LNU68 | 14034.1 | 0.83 | 0.225 | 8 |
| LNU122 | 25332.2 | 12.63 | 0.009 | 8 | LNU287 | 24674.3 | 0.87 | 0.766 | 7 | LNU71 | 25852.5 | 0.93 | 0.211 | 21 |
| LNU122 | 25332.5 | 12.63 | 0.078 | 8 | LNU37 | 14064.7 | 1.02 | 0.001 | 25 | LNU71 | 25853.1 | 0.89 | 0.012 | 16 |
| LNU122 | 25333.1 | 12.19 | 0.066 | 4 | LNU37 | 14064.6 | 0.94 | 0.579 | 14 | LNU71 | 25851.4 | 0.88 | 0.005 | 15 |
| LNU122 | 25333.2 | 12.19 | 0.313 | 4 | LNU5 | 14043.9 | 1.04 | 0.159 | 27 | LNU72 | 24963.7 | 0.90 | 0.324 | 18 |
| LNU122 | 25332.1 | 12.13 | 0.123 | 4 | LNU5 | 14043.7 | 0.85 | 0.539 | 4 | LNU72 | 24962.3 | 0.80 | 0.774 | 5 |
| LNU125 | 25944.3 | 12.25 | 0.633 | 5 | LNU65 | 24702.3 | 0.91 | 0.471 | 11 | LNU74 | 25443.3 | 0.92 | 0.166 | 20 |
| LNU25 | 14082.8 | 12.19 | 0.646 | 4 | LNU65 | 24703.6 | 0.88 | 0.539 | 7 | LNU82 | 24823.1 | 0.81 | 0.171 | 6 |
| LNU267 | 25804.3 | 12.25 | 0.525 | 5 | LNU68 | 14034.13 | 1.07 | 0.318 | 25 | LNU84 | 25621.2 | 0.78 | 0.779 | 3 |
| LNU45 | 25053.4 | 12.13 | 0.281 | 4 | LNU71 | 25853.1 | 1.03 | 0.001 | 26 | LNU84 | 25621.4 | 0.78 | 0.734 | 2 |
| LNU67 | 25821.5 | 12.31 | 0.238 | 5 | LNU71 | 25852.5 | 0.99 | 0.014 | 22 | LNU87 | 24712.1 | 0.84 | 0.600 | 10 |
| CONT. | — | 10.39 | — | 0 | LNU71 | 25851.4 | 0.95 | 0.352 | 16 | LNU98 | 25763.2 | 0.81 | 0.213 | 6 |
| LNU100 | 14472.1 | 11.19 | 0.381 | 8 | LNU72 | 24963.7 | 0.95 | 0.423 | 16 | CONT. | — | 0.84 | — | 0 |
| LNU100 | 14473.1 | 11.19 | 0.065 | 8 | LNU74 | 25443.3 | 0.95 | 0.507 | 15 | LNU117 | 25933.3 | 1.05 | 0.197 | 25 |
| LNU100 | 14473.3 | 11.13 | 0.000 | 7 | LNU82 | 24823.1 | 0.89 | 0.342 | 9 | LNU117 | 25931.4 | 1.00 | 0.145 | 20 |
| LNU104 | 25032.1 | 11.81 | 0.165 | 14 | LNU84 | 25621.2 | 0.93 | 0.311 | 13 | LNU117 | 25931.1 | 0.92 | 0.407 | 10 |
| LNU104 | 25032.2 | 11.69 | 0.000 | 13 | LNU84 | 25621.4 | 0.91 | 0.089 | 11 | LNU117 | 25931.2 | 0.87 | 0.716 | 3 |
| LNU104 | 25033.3 | 11.56 | 0.030 | 11 | CONT. | — | 1.01 | — | 0 | LNU117 | 25932.4 | 0.86 | 0.577 | 3 |
| LNU104 | 25033.8 | 10.94 | 0.416 | 5 | LNU117 | 25931.4 | 1.38 | 0.070 | 37 | LNU122 | 25332.5 | 0.95 | 0.368 | 13 |
| LNU104 | 25033.1 | 10.88 | 0.576 | 5 | LNU117 | 25933.3 | 1.26 | 0.013 | 25 | LNU122 | 25332.1 | 0.95 | 0.014 | 13 |
| LNU106 | 14483.5 | 11.00 | 0.028 | 6 | LNU117 | 25932.4 | 1.10 | 0.235 | 8 | LNU122 | 25333.1 | 0.92 | 0.412 | 9 |
| LNU106 | 14483.2 | 10.94 | 0.416 | 5 | LNU117 | 25931.1 | 1.09 | 0.286 | 8 | LNU122 | 25332.2 | 0.89 | 0.313 | 6 |
| LNU106 | 14484.3 | 10.78 | 0.451 | 4 | LNU117 | 25931.2 | 1.04 | 0.773 | 2 | LNU122 | 25333.2 | 0.88 | 0.182 | 5 |
| LNU114 | 25041.2 | 11.31 | 0.049 | 9 | LNU122 | 25333.2 | 1.24 | 0.029 | 23 | LNU125 | 25941.4 | 0.98 | 0.080 | 17 |
| LNU114 | 25041.1 | 11.13 | 0.149 | 7 | LNU122 | 25332.2 | 1.20 | 0.063 | 19 | LNU125 | 25944.3 | 0.97 | 0.096 | 15 |
| LNU114 | 25042.1 | 10.69 | 0.063 | 3 | LNU122 | 25333.1 | 1.20 | 0.045 | 19 | LNU125 | 25941.2 | 0.88 | 0.608 | 5 |
| LNU117 | 25931.4 | 10.94 | 0.297 | 5 | LNU122 | 25332.5 | 1.15 | 0.331 | 14 | LNU138 | 14074.6 | 0.98 | 0.005 | 17 |
| LNU155 | 14525.1 | 11.06 | 0.001 | 6 | LNU122 | 25332.1 | 1.14 | 0.392 | 13 | LNU138 | 14074.5 | 0.97 | 0.064 | 15 |
| LNU218 | 24781.2 | 10.94 | 0.568 | 5 | LNU125 | 25941.4 | 1.28 | 0.010 | 26 | LNU180 | 24723.1 | 0.89 | 0.138 | 7 |
| LNU218 | 24781.6 | 10.94 | 0.128 | 5 | LNU125 | 25941.2 | 1.06 | 0.598 | 6 | LNU180 | 24724.1 | 0.89 | 0.519 | 6 |
| LNU218 | 24781.1 | 10.88 | 0.255 | 5 | LNU138 | 14074.5 | 1.24 | 0.018 | 23 | LNU180 | 24722.2 | 0.87 | 0.400 | 4 |
| LNU254 | 25782.4 | 11.56 | 0.000 | 11 | LNU138 | 14074.6 | 1.23 | 0.080 | 22 | LNU180 | 24721.2 | 0.87 | 0.704 | 3 |
| LNU4 | 25134.1 | 11.63 | 0.000 | 12 | LNU180 | 24722.2 | 1.07 | 0.420 | 6 | LNU220 | 25405.6 | 0.93 | 0.053 | 11 |
| LNU4 | 25133.3 | 11.06 | 0.239 | 6 | LNU220 | 25405.1 | 1.11 | 0.197 | 10 | LNU230 | 25413.2 | 0.96 | 0.537 | 14 |
| LNU4 | 25131.1 | 11.00 | 0.427 | 6 | LNU220 | 25405.3 | 1.08 | 0.473 | 7 | LNU230 | 25412.2 | 0.91 | 0.548 | 8 |
| LNU4 | 25134.3 | 10.88 | 0.255 | 5 | LNU220 | 25405.6 | 1.07 | 0.722 | 6 | LNU230 | 25413.1 | 0.90 | 0.566 | 8 |
| LNU40 | 24792.1 | 11.56 | 0.030 | 11 | LNU230 | 25413.1 | 1.26 | 0.345 | 25 | LNU230 | 25412.1 | 0.87 | 0.343 | 4 |
| LNU40 | 24794.3 | 10.88 | 0.255 | 5 | LNU230 | 25412.2 | 1.20 | 0.501 | 19 | LNU25 | 14082.8 | 0.97 | 0.007 | 16 |
| LNU40 | 24794.4 | 10.81 | 0.381 | 4 | LNU230 | 25413.2 | 1.16 | 0.643 | 15 | LNU25 | 14082.9 | 0.93 | 0.069 | 11 |
| LNU46 | 14462.5 | 11.50 | 0.082 | 11 | LNU25 | 14083.7 | 1.14 | 0.520 | 12 | LNU25 | 14083.1 | 0.93 | 0.025 | 11 |
| LNU46 | 14462.1 | 11.06 | 0.089 | 6 | LNU25 | 14082.9 | 1.10 | 0.226 | 9 | LNU254 | 25782.4 | 0.92 | 0.529 | 9 |
| LNU48 | 24802.2 | 11.50 | 0.004 | 11 | LNU25 | 14083.1 | 1.10 | 0.227 | 9 | LNU254 | 25781.3 | 0.88 | 0.169 | 5 |
| LNU48 | 24804.4 | 10.81 | 0.194 | 4 | LNU25 | 14082.8 | 1.07 | 0.473 | 6 | LNU254 | 25782.5 | 0.87 | 0.508 | 4 |
| LNU48 | 24802.1 | 10.75 | 0.502 | 3 | LNU254 | 25781.3 | 1.09 | 0.263 | 8 | LNU263 | 25791.3 | 1.03 | 0.308 | 23 |
| LNU48 | 24801.4 | 10.70 | 0.320 | 3 | LNU254 | 25782.5 | 1.07 | 0.363 | 6 | LNU263 | 25794.8 | 1.01 | 0.074 | 20 |
| LNU63 | 24814.2 | 11.13 | 0.149 | 7 | LNU254 | 25782.4 | 1.06 | 0.671 | 5 | LNU267 | 25804.3 | 0.89 | 0.244 | 7 |
| LNU63 | 24814.7 | 10.94 | 0.297 | 5 | LNU263 | 25791.3 | 1.25 | 0.376 | 23 | LNU271 | 25913.3 | 0.93 | 0.373 | 11 |
| LNU7 | 25081.1 | 11.56 | 0.271 | 11 | LNU263 | 25794.8 | 1.22 | 0.078 | 21 | LNU278 | 25812.3 | 0.94 | 0.232 | 12 |
| LNU8 | 25063.1 | 11.38 | 0.098 | 10 | LNU267 | 25804.3 | 1.03 | 0.799 | 2 | LNU278 | 25814.1 | 0.88 | 0.251 | 4 |
| LNU8 | 25062.1 | 11.23 | 0.337 | 8 | LNU271 | 25913.3 | 1.10 | 0.642 | 9 | LNU36 | 25562.3 | 0.90 | 0.540 | 7 |
| LNU8 | 25061.2 | 11.06 | 0.001 | 6 | LNU271 | 25912.1 | 1.05 | 0.719 | 4 | LNU36 | 25562.9 | 0.87 | 0.797 | 4 |
| LNU8 | 25062.2 | 10.81 | 0.586 | 4 | LNU278 | 25814.3 | 1.16 | 0.190 | 15 | LNU36 | 25562.7 | 0.87 | 0.704 | 3 |
| LNU94 | 24833.3 | 11.50 | 0.252 | 11 | LNU278 | 25812.3 | 1.07 | 0.388 | 6 | LNU43 | 14421.1 | 0.99 | 0.255 | 18 |
| LNU94 | 24834.4 | 11.13 | 0.149 | 7 | LNU36 | 25562.3 | 1.15 | 0.107 | 14 | LNU43 | 14422.8 | 0.96 | 0.014 | 15 |
| LNU94 | 24831.4 | 10.88 | 0.401 | 5 | LNU43 | 14423.6 | 1.21 | 0.313 | 20 | LNU43 | 14423.6 | 0.93 | 0.587 | 11 |
| LNU94 | 24833.1 | 10.81 | 0.381 | 4 | LNU43 | 14422.8 | 1.13 | 0.122 | 12 | LNU43 | 14423.7 | 0.88 | 0.607 | 5 |

TABLE 84-continued

Genes showing improved photosynthetic capacity at standard nitrogen growth conditions

| | | Leaf Number | | | | | Leaf Blade Area [cm2] | | | | | Leaf Petiole Length [cm] | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU96 | 25071.2 | 11.44 | 0.141 | 10 | LNU43 | 14421.1 | 1.11 | 0.465 | 10 | LNU45 | 25053.4 | 0.93 | 0.154 | 11 |
| LNU96 | 25071.3 | 11.19 | 0.299 | 8 | LNU43 | 14422.9 | 1.08 | 0.337 | 7 | LNU45 | 25052.9 | 0.86 | 0.458 | 3 |
| LNU96 | 25073.4 | 11.13 | 0.149 | 7 | LNU45 | 25053.4 | 1.22 | 0.027 | 21 | LNU67 | 25824.5 | 1.02 | 0.168 | 21 |
| CONT. | — | 10.00 | — | 0 | LNU67 | 25824.5 | 1.29 | 0.024 | 28 | LNU67 | 25821.5 | 0.97 | 0.324 | 16 |
| LNU122 | 25332.5 | 10.88 | 0.388 | 9 | LNU67 | 25821.5 | 1.27 | 0.200 | 26 | LNU67 | 25823.5 | 0.91 | 0.481 | 9 |
| LNU122 | 25332.2 | 10.63 | 0.323 | 6 | LNU67 | 25823.5 | 1.06 | 0.563 | 5 | LNU67 | 25821.4 | 0.90 | 0.545 | 7 |
| LNU125 | 25944.1 | 10.69 | 0.089 | 7 | CONT. | — | 0.78 | — | 0 | CONTROL | — | 0.82 | — | 0 |
| LNU125 | 25941.4 | 10.56 | 0.292 | 6 | LNU100 | 14472.1 | 0.96 | 0.137 | 23 | LNU100 | 14473.1 | 0.98 | 0.000 | 18 |
| LNU125 | 25943.2 | 10.31 | 0.297 | 3 | LNU100 | 14473.3 | 0.92 | 0.300 | 19 | LNU100 | 14472.1 | 0.94 | 0.041 | 15 |
| LNU178 | 14611.5 | 10.31 | 0.603 | 3 | LNU100 | 14473.1 | 0.92 | 0.061 | 18 | LNU100 | 14473.3 | 0.86 | 0.298 | 5 |
| LNU236 | 25425.3 | 10.50 | 0.003 | 5 | LNU104 | 25032.2 | 1.05 | 0.002 | 35 | LNU104 | 25032.2 | 1.02 | 0.179 | 24 |
| LNU236 | 25422.4 | 10.31 | 0.053 | 3 | LNU104 | 25033.3 | 0.97 | 0.085 | 24 | LNU104 | 25033.3 | 1.00 | 0.144 | 21 |
| LNU236 | 25424.2 | 10.25 | 0.488 | 3 | LNU104 | 25032.1 | 0.84 | 0.203 | 8 | LNU104 | 25032.1 | 0.87 | 0.339 | 6 |
| LNU25 | 14082.8 | 10.44 | 0.493 | 4 | LNU106 | 14483.2 | 0.94 | 0.396 | 21 | LNU106 | 14481.1 | 0.92 | 0.716 | 11 |
| LNU271 | 25912.1 | 10.19 | 0.492 | 2 | LNU106 | 14483.5 | 0.90 | 0.119 | 16 | LNU106 | 14483.5 | 0.90 | 0.549 | 9 |
| LNU278 | 25814.3 | 10.38 | 0.394 | 5 | LNU106 | 14481.1 | 0.90 | 0.504 | 15 | LNU106 | 14483.2 | 0.85 | 0.510 | 3 |
| LNU278 | 25814.1 | 10.25 | 0.238 | 3 | LNU106 | 14484.3 | 0.83 | 0.332 | 6 | LNU106 | 14484.3 | 0.85 | 0.708 | 3 |
| LNU45 | 25053.4 | 10.50 | 0.394 | 5 | LNU114 | 25041.2 | 1.01 | 0.294 | 29 | LNU114 | 25041.1 | 0.95 | 0.413 | 15 |
| LNU45 | 25052.11 | 10.38 | 0.108 | 4 | LNU114 | 25044.4 | 0.86 | 0.562 | 10 | LNU114 | 25041.2 | 0.89 | 0.303 | 8 |
| LNU45 | 25052.12 | 10.25 | 0.795 | 3 | LNU114 | 25041.1 | 0.82 | 0.781 | 5 | LNU117 | 25931.4 | 0.97 | 0.303 | 17 |
| LNU67 | 25823.5 | 10.63 | 0.028 | 6 | LNU114 | 25042.1 | 0.81 | 0.797 | 4 | LNU117 | 25932.4 | 0.92 | 0.034 | 11 |
| CONT. | — | 11.19 | — | 0 | LNU117 | 25931.4 | 0.96 | 0.082 | 23 | LNU117 | 25931.2 | 0.85 | 0.452 | 3 |
| LNU168 | 24753.5 | 11.75 | 0.638 | 5 | LNU117 | 25931.1 | 0.86 | 0.211 | 11 | LNU218 | 24781.6 | 0.94 | 0.521 | 15 |
| LNU173 | 25451.1 | 11.69 | 0.034 | 4 | LNU155 | 14523.5 | 0.83 | 0.659 | 7 | LNU218 | 24781.4 | 0.92 | 0.006 | 12 |
| LNU173 | 25451.2 | 11.50 | 0.417 | 3 | LNU218 | 24781.4 | 0.95 | 0.000 | 22 | LNU218 | 24781.1 | 0.85 | 0.709 | 4 |
| LNU178 | 14611.1 | 12.00 | 0.002 | 7 | LNU218 | 24781.6 | 0.85 | 0.545 | 9 | LNU254 | 25782.4 | 0.87 | 0.129 | 6 |
| LNU178 | 14611.5 | 11.94 | 0.185 | 7 | LNU218 | 24781.1 | 0.81 | 0.390 | 5 | LNU4 | 25133.3 | 0.94 | 0.351 | 15 |
| LNU184 | 25393.1 | 11.56 | 0.425 | 3 | LNU254 | 25782.4 | 0.86 | 0.005 | 11 | LNU4 | 25134.3 | 0.85 | 0.490 | 4 |
| LNU230 | 25412.2 | 11.75 | 0.194 | 5 | LNU4 | 25133.3 | 0.88 | 0.002 | 13 | LNU40 | 24792.1 | 1.00 | 0.002 | 22 |
| LNU230 | 25413.1 | 11.63 | 0.282 | 4 | LNU4 | 25134.3 | 0.84 | 0.020 | 8 | LNU40 | 24794.4 | 0.93 | 0.513 | 13 |
| LNU236 | 25425.4 | 11.63 | 0.666 | 4 | LNU4 | 25134.2 | 0.82 | 0.704 | 5 | LNU40 | 24794.3 | 0.84 | 0.528 | 2 |
| LNU236 | 25423.3 | 11.44 | 0.263 | 2 | LNU40 | 24792.1 | 1.04 | 0.308 | 34 | LNU46 | 14462.1 | 0.92 | 0.101 | 12 |
| LNU236 | 25424.2 | 11.44 | 0.263 | 2 | LNU40 | 24794.4 | 0.86 | 0.426 | 11 | LNU46 | 14462.5 | 0.92 | 0.485 | 12 |
| LNU24 | 24971.2 | 11.81 | 0.239 | 6 | LNU40 | 24792.2 | 0.82 | 0.640 | 5 | LNU46 | 14463.2 | 0.89 | 0.140 | 8 |
| LNU263 | 25794.8 | 11.44 | 0.578 | 2 | LNU40 | 24794.3 | 0.81 | 0.695 | 4 | LNU48 | 24801.4 | 0.96 | 0.263 | 17 |
| LNU276 | 25431.1 | 12.13 | 0.282 | 8 | LNU46 | 14462.5 | 1.05 | 0.329 | 35 | LNU48 | 24802.1 | 0.90 | 0.388 | 10 |
| LNU276 | 25433.3 | 12.00 | 0.002 | 7 | LNU46 | 14462.1 | 0.97 | 0.001 | 24 | LNU48 | 24804.4 | 0.86 | 0.455 | 4 |
| LNU279 | 25481.3 | 11.44 | 0.420 | 2 | LNU48 | 24801.4 | 0.95 | 0.000 | 22 | LNU48 | 24802.2 | 0.85 | 0.800 | 3 |
| LNU53 | 25674.6 | 11.63 | 0.103 | 4 | LNU48 | 24802.1 | 0.92 | 0.437 | 18 | LNU63 | 24814.6 | 0.93 | 0.402 | 13 |
| LNU73 | 25751.9 | 11.63 | 0.103 | 4 | LNU48 | 24803.2 | 0.81 | 0.631 | 3 | LNU63 | 24814.7 | 0.86 | 0.545 | 4 |
| LNU9 | 25001.2 | 11.50 | 0.417 | 3 | LNU63 | 24814.2 | 0.93 | 0.009 | 20 | LNU63 | 24814.2 | 0.86 | 0.533 | 4 |
| LNU9 | 25001.7 | 11.50 | 0.417 | 3 | LNU63 | 24814.6 | 0.88 | 0.064 | 13 | LNU7 | 25081.1 | 0.92 | 0.467 | 12 |
| LNU9 | 25001.3 | 11.44 | 0.578 | 2 | LNU63 | 24812.2 | 0.80 | 0.703 | 3 | LNU8 | 25063.1 | 0.91 | 0.182 | 11 |
| CONT. | — | 8.52 | — | 0 | LNU63 | 24812.3 | 0.80 | 0.542 | 2 | LNU8 | 25062.1 | 0.89 | 0.508 | 9 |
| LNU131 | 14005.2 | 9.63 | 0.000 | 13 | LNU7 | 25081.1 | 0.91 | 0.017 | 17 | LNU8 | 25062.2 | 0.87 | 0.493 | 6 |
| LNU131 | 14002.15 | 9.25 | 0.371 | 9 | LNU7 | 25083.1 | 0.82 | 0.766 | 5 | LNU8 | 25061.2 | 0.85 | 0.329 | 4 |
| LNU131 | 14005.5 | 9.25 | 0.000 | 9 | LNU7 | 25083.3 | 0.81 | 0.337 | 4 | LNU94 | 24831.4 | 0.94 | 0.025 | 15 |
| LNU135 | 26204.4 | 9.25 | 0.444 | 9 | LNU8 | 25063.1 | 0.96 | 0.184 | 23 | LNU94 | 24833.1 | 0.90 | 0.463 | 9 |
| LNU135 | 26204.2 | 9.13 | 0.033 | 7 | LNU8 | 25062.1 | 0.89 | 0.480 | 14 | LNU94 | 24833.3 | 0.86 | 0.278 | 5 |
| LNU135 | 26203.1 | 9.06 | 0.505 | 6 | LNU8 | 25061.2 | 0.84 | 0.400 | 8 | LNU96 | 25071.3 | 0.87 | 0.751 | 6 |
| LNU135 | 26203.3 | 9.06 | 0.140 | 6 | LNU8 | 25062.2 | 0.82 | 0.204 | 6 | LNU96 | 25071.2 | 0.87 | 0.169 | 6 |
| LNU135 | 26203.4 | 9.06 | 0.622 | 6 | LNU94 | 24833.1 | 0.95 | 0.000 | 22 | CONT. | — | 0.83 | — | 0 |
| LNU173 | 25451.2 | 9.56 | 0.417 | 12 | LNU94 | 24833.3 | 0.94 | 0.127 | 21 | LNU10 | 25123.5 | 0.90 | 0.591 | 8 |
| LNU173 | 25451.5 | 9.13 | 0.202 | 7 | LNU94 | 24831.4 | 0.94 | 0.036 | 21 | LNU122 | 25332.5 | 0.93 | 0.021 | 11 |
| LNU181 | 25774.1 | 9.44 | 0.000 | 11 | LNU94 | 24834.4 | 0.90 | 0.624 | 15 | LNU122 | 25332.2 | 0.88 | 0.460 | 6 |
| LNU181 | 25771.6 | 9.31 | 0.076 | 9 | LNU96 | 25071.2 | 0.86 | 0.223 | 10 | LNU122 | 25332.1 | 0.85 | 0.615 | 3 |
| LNU181 | 25771.8 | 8.88 | 0.118 | 4 | LNU96 | 25073.4 | 0.86 | 0.195 | 10 | LNU125 | 25941.4 | 0.92 | 0.309 | 11 |
| LNU181 | 25771.5 | 8.81 | 0.508 | 3 | LNU96 | 25071.3 | 0.82 | 0.753 | 6 | LNU178 | 14611.1 | 0.86 | 0.609 | 3 |
| LNU181 | 25771.2 | 8.69 | 0.762 | 2 | CONT. | — | 0.80 | — | 0 | LNU234 | 25014.4 | 0.93 | 0.115 | 12 |
| LNU184 | 25393.2 | 9.56 | 0.000 | 12 | LNU10 | 25123.5 | 0.95 | 0.358 | 19 | LNU236 | 25425.3 | 0.92 | 0.298 | 11 |
| LNU184 | 25394.1 | 9.13 | 0.202 | 7 | LNU122 | 25332.5 | 1.04 | 0.000 | 30 | LNU236 | 25425.4 | 0.89 | 0.516 | 8 |
| LNU184 | 25393.1 | 9.06 | 0.140 | 6 | LNU122 | 25332.2 | 0.93 | 0.177 | 17 | LNU236 | 25423.3 | 0.86 | 0.230 | 3 |
| LNU184 | 25394.2 | 9.06 | 0.420 | 6 | LNU122 | 25332.1 | 0.88 | 0.010 | 10 | LNU25 | 14082.8 | 0.93 | 0.045 | 12 |
| LNU184 | 25393.3 | 9.04 | 0.334 | 6 | LNU125 | 25941.4 | 0.91 | 0.015 | 14 | LNU25 | 14083.7 | 0.91 | 0.407 | 9 |
| LNU184 | 25395.1 | 9.00 | 0.407 | 6 | LNU125 | 25943.2 | 0.87 | 0.021 | 10 | LNU267 | 25803.1 | 0.87 | 0.095 | 5 |
| LNU224 | 25872.3 | 9.75 | 0.080 | 14 | LNU178 | 14611.5 | 0.94 | 0.197 | 18 | LNU271 | 25913.3 | 0.91 | 0.307 | 10 |
| LNU224 | 25874.1 | 9.69 | 0.131 | 14 | LNU178 | 14611.1 | 0.89 | 0.325 | 12 | LNU271 | 25911.4 | 0.85 | 0.380 | 3 |
| LNU224 | 25874.4 | 9.56 | 0.150 | 12 | LNU178 | 14612.1 | 0.85 | 0.692 | 6 | LNU278 | 25814.1 | 0.93 | 0.001 | 12 |
| LNU224 | 25872.2 | 9.00 | 0.678 | 6 | LNU220 | 25405.1 | 0.82 | 0.402 | 3 | LNU278 | 25814.3 | 0.88 | 0.054 | 6 |
| LNU224 | 25871.3 | 8.88 | 0.118 | 4 | LNU234 | 25014.5 | 0.91 | 0.519 | 14 | LNU278 | 25812.2 | 0.86 | 0.687 | 4 |
| LNU246 | 25744.2 | 9.69 | 0.131 | 14 | LNU234 | 25014.4 | 0.89 | 0.324 | 12 | LNU43 | 14423.7 | 0.86 | 0.635 | 3 |

TABLE 84-continued

Genes showing improved photosynthetic capacity at standard nitrogen growth conditions

| | | Leaf Number | | | | | Leaf Blade Area [cm2] | | | | | Leaf Petiole Length [cm] | | |
|---|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU246 | 25744.3 | 9.69 | 0.039 | 14 | LNU234 | 25014.6 | 0.88 | 0.716 | 11 | LNU45 | 25052.12 | 0.95 | 0.351 | 15 |
| LNU246 | 25744.4 | 9.13 | 0.505 | 7 | LNU236 | 25423.3 | 0.87 | 0.160 | 10 | LNU45 | 25053.4 | 0.92 | 0.098 | 10 |
| LNU246 | 25743.2 | 8.81 | 0.508 | 3 | LNU236 | 25424.2 | 0.85 | 0.481 | 7 | LNU45 | 25052.11 | 0.86 | 0.741 | 3 |
| LNU246 | 25743.1 | 8.77 | 0.634 | 3 | LNU236 | 25425.3 | 0.84 | 0.790 | 5 | LNU67 | 25823.5 | 0.96 | 0.000 | 15 |
| LNU250 | 25591.1 | 9.44 | 0.174 | 11 | LNU236 | 25425.4 | 0.83 | 0.385 | 5 | LNU9 | 25001.1 | 0.88 | 0.507 | 7 |
| LNU250 | 25592.2 | 8.94 | 0.388 | 5 | LNU25 | 14083.7 | 0.93 | 0.119 | 17 | LNU9 | 25001.7 | 0.85 | 0.430 | 2 |
| LNU250 | 25591.3 | 8.88 | 0.118 | 4 | LNU25 | 14082.8 | 0.85 | 0.075 | 7 | CONT. | — | 0.91 | — | 0 |
| LNU260 | 26404.1 | 9.44 | 0.059 | 11 | LNU267 | 25803.1 | 0.83 | 0.236 | 4 | LNU10 | 25123.6 | 0.99 | 0.534 | 9 |
| LNU260 | 26403.1 | 8.88 | 0.007 | 4 | LNU271 | 25911.4 | 0.92 | 0.001 | 16 | LNU157 | 24982.7 | 0.96 | 0.550 | 5 |
| LNU260 | 26404.7 | 8.81 | 0.317 | 3 | LNU271 | 25913.3 | 0.82 | 0.358 | 3 | LNU168 | 24753.5 | 0.98 | 0.046 | 8 |
| LNU276 | 25433.6 | 9.56 | 0.304 | 12 | LNU271 | 25912.1 | 0.81 | 0.607 | 2 | LNU173 | 25451.1 | 1.04 | 0.071 | 14 |
| LNU276 | 25433.3 | 9.19 | 0.247 | 8 | LNU278 | 25814.3 | 0.98 | 0.000 | 23 | LNU178 | 14611.4 | 1.02 | 0.358 | 12 |
| LNU276 | 25433.5 | 9.00 | 0.407 | 6 | LNU278 | 25814.1 | 0.97 | 0.000 | 22 | LNU178 | 14611.5 | 1.00 | 0.524 | 9 |
| LNU276 | 25431.1 | 8.75 | 0.511 | 3 | LNU278 | 25812.3 | 0.89 | 0.147 | 12 | LNU178 | 14611.1 | 0.98 | 0.049 | 7 |
| LNU279 | 25484.3 | 9.38 | 0.131 | 10 | LNU278 | 25813.2 | 0.88 | 0.659 | 10 | LNU184 | 25395.1 | 1.04 | 0.002 | 14 |
| LNU279 | 25481.3 | 9.19 | 0.000 | 8 | LNU278 | 25812.2 | 0.85 | 0.696 | 6 | LNU184 | 25393.1 | 1.03 | 0.381 | 13 |
| LNU279 | 25481.2 | 8.88 | 0.118 | 4 | LNU43 | 14423.6 | 0.89 | 0.316 | 12 | LNU184 | 25394.3 | 1.03 | 0.335 | 13 |
| LNU279 | 25481.4 | 8.69 | 0.680 | 2 | LNU43 | 14423.7 | 0.85 | 0.376 | 7 | LNU184 | 25393.2 | 1.01 | 0.354 | 11 |
| LNU3 | 26124.3 | 9.06 | 0.002 | 6 | LNU45 | 25052.12 | 1.00 | 0.263 | 26 | LNU230 | 25413.2 | 1.06 | 0.291 | 17 |
| LNU3 | 26122.2 | 8.75 | 0.643 | 3 | LNU45 | 25053.4 | 0.97 | 0.179 | 21 | LNU230 | 25415.1 | 1.05 | 0.005 | 16 |
| LNU33 | 25552.2 | 9.25 | 0.020 | 9 | LNU45 | 25052.9 | 0.88 | 0.137 | 10 | LNU230 | 25412.2 | 1.02 | 0.344 | 12 |
| LNU33 | 25553.3 | 9.19 | 0.355 | 8 | LNU45 | 25052.11 | 0.86 | 0.590 | 8 | LNU230 | 25413.1 | 1.00 | 0.012 | 10 |
| LNU53 | 25674.5 | 8.69 | 0.214 | 2 | LNU67 | 25823.5 | 1.10 | 0.003 | 38 | LNU230 | 25412.1 | 0.93 | 0.714 | 2 |
| LNU53 | 25674.6 | 8.69 | 0.762 | 2 | LNU67 | 25824.3 | 0.83 | 0.751 | 5 | LNU236 | 25424.2 | 1.06 | 0.447 | 16 |
| CONT. | — | 10.18 | — | 0 | LNU67 | 25824.5 | 0.82 | 0.693 | 3 | LNU236 | 25425.4 | 1.03 | 0.545 | 13 |
| LNU119 | 26142.8 | 10.44 | 0.112 | 3 | LNU67 | 25821.5 | 0.82 | 0.558 | 3 | LNU236 | 25423.3 | 1.01 | 0.324 | 11 |
| LNU130 | 24913.6 | 10.75 | 0.206 | 6 | LNU9 | 25001.7 | 0.89 | 0.264 | 12 | LNU24 | 24971.2 | 1.08 | 0.157 | 19 |
| LNU130 | 24912.7 | 10.56 | 0.222 | 4 | LNU9 | 25003.1 | 0.85 | 0.350 | 6 | LNU24 | 24974.2 | 0.99 | 0.440 | 9 |
| LNU130 | 24911.7 | 10.38 | 0.567 | 2 | LNU9 | 25001.3 | 0.82 | 0.418 | 3 | LNU24 | 24971.3 | 0.97 | 0.303 | 6 |
| LNU136 | 14515.1 | 11.06 | 0.051 | 9 | CONT. | — | 1.00 | — | 0 | LNU24 | 24971.4 | 0.93 | 0.796 | 2 |
| LNU142 | 27541.1 | 10.63 | 0.009 | 4 | LNU10 | 25123.6 | 1.30 | 0.206 | 30 | LNU263 | 25794.8 | 1.04 | 0.342 | 14 |
| LNU142 | 27545.1 | 10.50 | 0.632 | 3 | LNU10 | 25123.5 | 1.16 | 0.000 | 16 | LNU276 | 25433.3 | 1.00 | 0.036 | 9 |
| LNU142 | 27546.2 | 10.44 | 0.363 | 3 | LNU157 | 24982.8 | 1.11 | 0.005 | 11 | LNU276 | 25431.1 | 0.93 | 0.716 | 2 |
| LNU149 | 26175.1 | 10.88 | 0.458 | 7 | LNU157 | 24982.4 | 1.09 | 0.165 | 9 | LNU279 | 25481.3 | 0.98 | 0.043 | 8 |
| LNU149 | 26175.7 | 10.69 | 0.143 | 5 | LNU168 | 24753.5 | 1.05 | 0.467 | 5 | LNU279 | 25481.4 | 0.96 | 0.480 | 6 |
| LNU15 | 14123.11 | 10.44 | 0.363 | 3 | LNU173 | 25451.1 | 1.08 | 0.026 | 8 | LNU36 | 25562.3 | 1.00 | 0.294 | 10 |
| LNU185 | 26474.2 | 11.00 | 0.242 | 8 | LNU173 | 25451.2 | 1.05 | 0.537 | 5 | LNU53 | 25674.1 | 1.08 | 0.187 | 18 |
| LNU185 | 26475.1 | 10.38 | 0.567 | 2 | LNU178 | 14611.5 | 1.20 | 0.032 | 20 | LNU53 | 25674.2 | 1.06 | 0.073 | 16 |
| LNU212 | 25834.1 | 10.75 | 0.002 | 6 | LNU178 | 14611.4 | 1.19 | 0.217 | 19 | LNU53 | 25674.6 | 0.96 | 0.197 | 5 |
| LNU212 | 25834.5 | 10.69 | 0.007 | 5 | LNU178 | 14611.1 | 1.18 | 0.069 | 18 | LNU56 | 24694.1 | 1.01 | 0.043 | 11 |
| LNU212 | 25834.4 | 10.37 | 0.772 | 2 | LNU184 | 25393.2 | 1.28 | 0.000 | 28 | LNU56 | 24694.2 | 0.98 | 0.420 | 8 |
| LNU212 | 25832.1 | 10.35 | 0.224 | 2 | LNU184 | 25393.1 | 1.25 | 0.468 | 25 | LNU56 | 24693.1 | 0.98 | 0.048 | 7 |
| LNU216 | 25982.2 | 10.69 | 0.439 | 5 | LNU184 | 25394.3 | 1.21 | 0.440 | 21 | LNU56 | 24693.2 | 0.96 | 0.202 | 6 |
| LNU216 | 25984.6 | 10.69 | 0.143 | 5 | LNU184 | 25395.1 | 1.19 | 0.089 | 19 | LNU73 | 25751.1 | 1.06 | 0.531 | 16 |
| LNU216 | 25985.4 | 10.50 | 0.539 | 3 | LNU184 | 25393.3 | 1.02 | 0.563 | 2 | LNU73 | 25755.1 | 1.04 | 0.223 | 14 |
| LNU216 | 25982.1 | 10.44 | 0.363 | 3 | LNU230 | 25415.1 | 1.34 | 0.109 | 34 | LNU73 | 25754.2 | 1.00 | 0.624 | 9 |
| LNU228 | 26224.7 | 10.81 | 0.002 | 6 | LNU230 | 25412.1 | 1.18 | 0.043 | 18 | LNU73 | 25751.9 | 0.99 | 0.205 | 8 |
| LNU228 | 26222.4 | 10.56 | 0.222 | 4 | LNU230 | 25413.2 | 1.17 | 0.119 | 17 | LNU73 | 25751.8 | 0.97 | 0.778 | 6 |
| LNU228 | 26224.6 | 10.44 | 0.549 | 3 | LNU230 | 25413.1 | 1.15 | 0.021 | 15 | LNU9 | 25001.7 | 1.07 | 0.049 | 17 |
| LNU274 | 26265.1 | 10.44 | 0.112 | 3 | LNU230 | 25412.2 | 1.13 | 0.020 | 13 | LNU9 | 25001.2 | 1.03 | 0.562 | 13 |
| LNU274 | 26262.2 | 10.38 | 0.689 | 2 | LNU236 | 25425.4 | 1.25 | 0.002 | 25 | LNU9 | 25001.1 | 1.00 | 0.008 | 10 |
| LNU277 | 25845.1 | 10.56 | 0.413 | 4 | LNU236 | 25424.2 | 1.22 | 0.064 | 23 | LNU9 | 25001.3 | 0.97 | 0.625 | 6 |
| LNU280 | 26164.2 | 10.88 | 0.001 | 7 | LNU236 | 25422.4 | 1.17 | 0.000 | 17 | LNU9 | 25003.1 | 0.96 | 0.591 | 5 |
| LNU280 | 26164.4 | 10.69 | 0.591 | 5 | LNU236 | 25423.3 | 1.17 | 0.372 | 17 | CONT. | — | 0.60 | — | 0 |
| LNU280 | 26162.1 | 10.56 | 0.413 | 4 | LNU24 | 24974.2 | 1.19 | 0.247 | 20 | LNU131 | 14005.2 | 0.87 | 0.000 | 45 |
| LNU55 | 26015.3 | 10.56 | 0.028 | 4 | LNU24 | 24971.3 | 1.16 | 0.500 | 16 | LNU131 | 14005.5 | 0.78 | 0.003 | 29 |
| LNU81 | 26034.2 | 10.50 | 0.632 | 3 | LNU24 | 24971.2 | 1.10 | 0.172 | 10 | LNU135 | 26203.1 | 0.78 | 0.594 | 29 |
| LNU81 | 26034.3 | 10.50 | 0.632 | 3 | LNU24 | 24972.1 | 1.07 | 0.056 | 7 | LNU135 | 26204.2 | 0.70 | 0.288 | 16 |
| CONT. | — | 10.58 | — | 0 | LNU24 | 24971.4 | 1.03 | 0.781 | 3 | LNU135 | 26203.4 | 0.68 | 0.746 | 13 |
| LNU119 | 26142.8 | 10.81 | 0.330 | 2 | LNU263 | 25794.8 | 1.28 | 0.169 | 28 | LNU135 | 26203.3 | 0.62 | 0.559 | 3 |
| LNU130 | 24913.5 | 11.44 | 0.040 | 8 | LNU263 | 25791.3 | 1.11 | 0.713 | 11 | LNU161 | 14552.9 | 0.70 | 0.356 | 16 |
| LNU136 | 14511.10 | 11.19 | 0.032 | 6 | LNU276 | 25433.3 | 1.28 | 0.035 | 29 | LNU173 | 25451.2 | 0.72 | 0.605 | 19 |
| LNU136 | 14515.1 | 10.88 | 0.444 | 3 | LNU276 | 25431.1 | 1.03 | 0.504 | 3 | LNU181 | 25774.1 | 0.76 | 0.002 | 26 |
| LNU142 | 27545.1 | 11.38 | 0.106 | 7 | LNU279 | 25481.3 | 1.24 | 0.341 | 24 | LNU181 | 25771.8 | 0.76 | 0.085 | 26 |
| LNU142 | 27541.1 | 11.19 | 0.100 | 6 | LNU279 | 25481.5 | 1.20 | 0.322 | 20 | LNU181 | 25771.6 | 0.69 | 0.368 | 14 |
| LNU212 | 25834.5 | 11.44 | 0.262 | 8 | LNU279 | 25481.4 | 1.18 | 0.055 | 18 | LNU181 | 25771.5 | 0.66 | 0.207 | 9 |
| LNU212 | 25833.2 | 11.19 | 0.249 | 6 | LNU279 | 25484.3 | 1.05 | 0.606 | 5 | LNU184 | 25393.1 | 0.79 | 0.182 | 31 |
| LNU216 | 25984.6 | 11.06 | 0.165 | 5 | LNU36 | 25562.3 | 1.06 | 0.391 | 6 | LNU184 | 25393.3 | 0.79 | 0.416 | 30 |
| LNU216 | 25982.2 | 10.88 | 0.444 | 3 | LNU36 | 25562.7 | 1.05 | 0.251 | 5 | LNU184 | 25394.1 | 0.74 | 0.234 | 23 |
| LNU216 | 25984.1 | 10.81 | 0.459 | 2 | LNU53 | 25674.1 | 1.30 | 0.163 | 30 | LNU184 | 25394.3 | 0.74 | 0.498 | 23 |
| LNU228 | 26222.1 | 11.00 | 0.302 | 4 | LNU53 | 25674.2 | 1.07 | 0.456 | 7 | LNU184 | 25393.2 | 0.71 | 0.003 | 18 |

TABLE 84-continued

Genes showing improved photosynthetic capacity at standard nitrogen growth conditions

| | Leaf Number | | | | Leaf Blade Area [cm2] | | | | | Leaf Petiole Length [cm] | | | |
|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| LNU228 | 26224.7 | 10.94 | 0.276 | 3 | LNU53 | 25674.6 | 1.07 | 0.042 | 7 | LNU184 | 25395.1 | 0.65 | 0.404 | 8 |
| LNU274 | 26264.2 | 11.06 | 0.165 | 5 | LNU56 | 24693.1 | 1.14 | 0.252 | 14 | LNU224 | 25872.3 | 0.93 | 0.003 | 54 |
| LNU277 | 25842.3 | 10.88 | 0.275 | 3 | LNU56 | 24694.1 | 1.13 | 0.018 | 13 | LNU224 | 25874.4 | 0.82 | 0.142 | 36 |
| LNU280 | 26164.4 | 11.00 | 0.099 | 4 | LNU56 | 24693.2 | 1.08 | 0.395 | 8 | LNU224 | 25874.1 | 0.77 | 0.387 | 28 |
| LNU55 | 26013.9 | 10.81 | 0.756 | 2 | LNU73 | 25755.1 | 1.22 | 0.115 | 22 | LNU224 | 25872.2 | 0.77 | 0.403 | 27 |
| LNU81 | 26034.2 | 11.00 | 0.552 | 4 | LNU73 | 25751.1 | 1.19 | 0.593 | 19 | LNU224 | 25871.3 | 0.63 | 0.558 | 4 |
| LNU81 | 26031.10 | 10.88 | 0.665 | 3 | LNU73 | 25754.2 | 1.16 | 0.492 | 16 | LNU246 | 25744.2 | 0.79 | 0.201 | 32 |
| LNU81 | 26034.3 | 10.88 | 0.578 | 3 | LNU73 | 25751.8 | 1.14 | 0.457 | 14 | LNU246 | 25744.3 | 0.78 | 0.375 | 29 |
| | | | | | LNU73 | 25751.9 | 1.09 | 0.180 | 9 | LNU246 | 25744.4 | 0.77 | 0.608 | 27 |
| | | | | | LNU9 | 25001.1 | 1.30 | 0.010 | 30 | LNU250 | 25591.1 | 0.90 | 0.167 | 49 |
| | | | | | LNU9 | 25001.7 | 1.19 | 0.260 | 19 | LNU250 | 25592.2 | 0.81 | 0.002 | 34 |
| | | | | | LNU9 | 25001.3 | 1.16 | 0.365 | 16 | LNU260 | 26404.1 | 0.66 | 0.499 | 10 |
| | | | | | LNU9 | 25001.2 | 1.14 | 0.394 | 14 | LNU260 | 26403.1 | 0.64 | 0.234 | 6 |
| | | | | | CONT. | — | 0.86 | — | 0 | LNU276 | 25433.6 | 0.83 | 0.201 | 37 |
| | | | | | LNU131 | 14005.2 | 1.26 | 0.000 | 46 | LNU276 | 25433.5 | 0.74 | 0.245 | 22 |
| | | | | | LNU131 | 14005.5 | 1.13 | 0.000 | 31 | LNU279 | 25481.3 | 0.86 | 0.338 | 43 |
| | | | | | LNU135 | 26203.4 | 0.96 | 0.768 | 11 | LNU279 | 25484.3 | 0.71 | 0.486 | 17 |
| | | | | | LNU135 | 26204.2 | 0.93 | 0.333 | 8 | LNU279 | 25481.5 | 0.69 | 0.577 | 14 |
| | | | | | LNU173 | 25451.2 | 0.99 | 0.530 | 15 | LNU3 | 26123.5 | 0.71 | 0.515 | 18 |
| | | | | | LNU181 | 25771.8 | 1.10 | 0.417 | 27 | LNU3 | 26124.1 | 0.70 | 0.779 | 15 |
| | | | | | LNU181 | 25771.5 | 1.00 | 0.513 | 16 | LNU3 | 26124.3 | 0.67 | 0.035 | 12 |
| | | | | | LNU181 | 25771.6 | 1.00 | 0.014 | 16 | LNU3 | 26123.6 | 0.66 | 0.533 | 9 |
| | | | | | LNU181 | 25774.1 | 0.94 | 0.123 | 9 | LNU3 | 26122.2 | 0.65 | 0.194 | 8 |
| | | | | | LNU184 | 25393.2 | 1.11 | 0.000 | 29 | LNU33 | 25552.2 | 0.67 | 0.463 | 11 |
| | | | | | LNU184 | 25394.1 | 1.07 | 0.293 | 24 | LNU33 | 25553.3 | 0.66 | 0.224 | 10 |
| | | | | | LNU184 | 25393.1 | 0.99 | 0.197 | 15 | LNU53 | 25674.5 | 0.72 | 0.129 | 19 |
| | | | | | LNU184 | 25393.3 | 0.99 | 0.655 | 15 | LNU53 | 25674.1 | 0.68 | 0.641 | 13 |
| | | | | | LNU184 | 25394.3 | 0.95 | 0.736 | 11 | LNU53 | 25674.6 | 0.63 | 0.661 | 4 |
| | | | | | LNU224 | 25872.3 | 1.26 | 0.036 | 46 | LNU56 | 24694.2 | 0.70 | 0.010 | 16 |
| | | | | | LNU224 | 25874.4 | 1.11 | 0.110 | 29 | CONT. | — | 0.88 | — | 0 |
| | | | | | LNU224 | 25874.1 | 1.11 | 0.416 | 29 | LNU130 | 24912.7 | 1.07 | 0.223 | 21 |
| | | | | | LNU224 | 25872.2 | 1.08 | 0.309 | 25 | LNU130 | 24911.7 | 1.00 | 0.492 | 13 |
| | | | | | LNU246 | 25744.4 | 1.13 | 0.553 | 31 | LNU130 | 24913.6 | 0.95 | 0.430 | 8 |
| | | | | | LNU246 | 25744.3 | 1.13 | 0.587 | 31 | LNU130 | 24914.5 | 0.90 | 0.785 | 3 |
| | | | | | LNU246 | 25744.2 | 1.10 | 0.259 | 28 | LNU136 | 14515.1 | 1.01 | 0.272 | 14 |
| | | | | | LNU246 | 25743.1 | 1.06 | 0.214 | 23 | LNU142 | 27541.1 | 0.96 | 0.031 | 9 |
| | | | | | LNU246 | 25743.9 | 0.95 | 0.095 | 11 | LNU149 | 26175.1 | 0.92 | 0.662 | 5 |
| | | | | | LNU250 | 25591.1 | 1.23 | 0.129 | 43 | LNU15 | 14123.11 | 1.01 | 0.138 | 15 |
| | | | | | LNU250 | 25592.2 | 1.01 | 0.010 | 17 | LNU15 | 14122.9 | 0.95 | 0.466 | 8 |
| | | | | | LNU260 | 26404.1 | 0.91 | 0.655 | 5 | LNU15 | 14122.8 | 0.94 | 0.149 | 7 |
| | | | | | LNU276 | 25433.6 | 1.12 | 0.280 | 30 | LNU15 | 14123.13 | 0.93 | 0.183 | 6 |
| | | | | | LNU276 | 25433.5 | 0.96 | 0.621 | 12 | LNU185 | 26475.1 | 1.03 | 0.395 | 18 |
| | | | | | LNU279 | 25481.3 | 1.19 | 0.435 | 38 | LNU185 | 26472.1 | 0.99 | 0.436 | 13 |
| | | | | | LNU279 | 25484.3 | 1.16 | 0.212 | 34 | LNU185 | 26474.2 | 0.98 | 0.028 | 11 |
| | | | | | LNU279 | 25481.5 | 0.97 | 0.605 | 12 | LNU212 | 25834.5 | 0.98 | 0.025 | 12 |
| | | | | | LNU279 | 25481.2 | 0.96 | 0.279 | 12 | LNU212 | 25834.1 | 0.96 | 0.391 | 10 |
| | | | | | LNU33 | 25553.3 | 0.96 | 0.576 | 11 | LNU216 | 25982.1 | 1.01 | 0.001 | 15 |
| | | | | | LNU53 | 25674.5 | 0.92 | 0.285 | 7 | LNU216 | 25985.4 | 0.97 | 0.557 | 10 |
| | | | | | LNU56 | 24694.2 | 0.93 | 0.292 | 8 | LNU216 | 25984.1 | 0.91 | 0.292 | 4 |
| | | | | | CONT. | — | 1.03 | — | 0 | LNU216 | 25984.6 | 0.90 | 0.693 | 2 |
| | | | | | LNU119 | 26142.8 | 1.07 | 0.559 | 4 | LNU228 | 26222.4 | 1.10 | 0.057 | 25 |
| | | | | | LNU130 | 24912.7 | 1.26 | 0.102 | 23 | LNU228 | 26222.1 | 0.95 | 0.291 | 8 |
| | | | | | LNU130 | 24913.5 | 1.14 | 0.374 | 11 | LNU228 | 26224.6 | 0.93 | 0.423 | 6 |
| | | | | | LNU130 | 24911.7 | 1.11 | 0.732 | 7 | LNU229 | 26112.3 | 0.96 | 0.264 | 9 |
| | | | | | LNU130 | 24913.6 | 1.07 | 0.672 | 4 | LNU229 | 26111.7 | 0.95 | 0.079 | 8 |
| | | | | | LNU136 | 14515.1 | 1.18 | 0.067 | 15 | LNU241 | 26232.4 | 0.99 | 0.432 | 12 |
| | | | | | LNU142 | 27541.1 | 1.13 | 0.533 | 10 | LNU241 | 26233.2 | 0.92 | 0.441 | 5 |
| | | | | | LNU142 | 27545.1 | 1.10 | 0.737 | 6 | LNU253 | 26243.3 | 0.90 | 0.536 | 2 |
| | | | | | LNU15 | 14123.13 | 1.15 | 0.362 | 11 | LNU274 | 26262.2 | 0.95 | 0.487 | 8 |
| | | | | | LNU15 | 14123.11 | 1.11 | 0.073 | 8 | LNU280 | 26162.1 | 1.04 | 0.456 | 18 |
| | | | | | LNU185 | 26475.1 | 1.18 | 0.387 | 15 | LNU280 | 26162.7 | 0.96 | 0.248 | 9 |
| | | | | | LNU185 | 26474.2 | 1.07 | 0.388 | 4 | LNU280 | 26164.4 | 0.95 | 0.713 | 7 |
| | | | | | LNU212 | 25834.5 | 1.20 | 0.002 | 16 | LNU55 | 26015.1 | 1.05 | 0.364 | 19 |
| | | | | | LNU212 | 25834.1 | 1.11 | 0.719 | 8 | LNU55 | 26015.3 | 0.92 | 0.303 | 5 |
| | | | | | LNU216 | 25985.4 | 1.17 | 0.706 | 13 | LNU81 | 26034.3 | 1.01 | 0.003 | 14 |
| | | | | | LNU216 | 25982.1 | 1.10 | 0.527 | 6 | CONT. | — | 0.94 | — | 0 |
| | | | | | LNU228 | 26224.7 | 1.09 | 0.568 | 6 | LNU119 | 26142.8 | 1.05 | 0.360 | 12 |
| | | | | | LNU228 | 26222.4 | 1.09 | 0.344 | 6 | LNU119 | 26144.2 | 1.03 | 0.028 | 9 |
| | | | | | LNU241 | 26233.2 | 1.11 | 0.160 | 8 | LNU119 | 26141.1 | 1.03 | 0.219 | 9 |
| | | | | | LNU241 | 26232. | 1.06 | 0.592 | 3 | LNU130 | 24913.5 | 1.06 | 0.379 | 12 |
| | | | | | LNU274 | 26262.2 | 1.08 | 0.753 | 5 | LNU130 | 24914.5 | 1.03 | 0.141 | 10 |

TABLE 84-continued

Genes showing improved photosynthetic capacity at standard nitrogen growth conditions

| Leaf Number | | | | | Leaf Blade Area [cm2] | | | | | Leaf Petiole Length [cm] | | | |
|---|---|---|---|---|---|---|---|---|---|---|---|---|---|
| Gene Name | Event # | Ave. | P-Value | % incr. | Gene Name | Event # | Ave. | P-Value | % incr. | Gene Name | Event # | Ave. | P-Value | % incr. |
| | | | | | LNU274 | 26265.1 | 1.06 | 0.397 | 3 | LNU136 | 14515.1 | 1.06 | 0.310 | 13 |
| | | | | | LNU277 | 25845.1 | 1.18 | 0.363 | 15 | LNU142 | 27541.2 | 1.06 | 0.366 | 13 |
| | | | | | LNU280 | 26162.1 | 1.23 | 0.563 | 20 | LNU142 | 27541.1 | 1.03 | 0.521 | 10 |
| | | | | | LNU280 | 26162.7 | 1.15 | 0.086 | 12 | LNU142 | 27545.1 | 1.03 | 0.100 | 9 |
| | | | | | LNU55 | 26015.1 | 1.12 | 0.158 | 9 | LNU149 | 26174.7 | 1.05 | 0.622 | 12 |
| | | | | | LNU55 | 26015.3 | 1.05 | 0.540 | 2 | LNU15 | 14122.8 | 1.20 | 0.478 | 28 |
| | | | | | LNU81 | 26034.3 | 1.26 | 0.001 | 22 | LNU15 | 14123.11 | 1.12 | 0.500 | 19 |
| | | | | | CONT. | — | 1.10 | — | 0 | LNU15 | 14123.13 | 1.05 | 0.263 | 12 |
| | | | | | LNU119 | 26142.8 | 1.27 | 0.139 | 16 | LNU15 | 14122.9 | 0.99 | 0.563 | 5 |
| | | | | | LNU119 | 26141.1 | 1.27 | 0.565 | 15 | LNU185 | 26472.1 | 1.04 | 0.507 | 11 |
| | | | | | LNU130 | 24914.5 | 1.32 | 0.004 | 20 | LNU185 | 26474.2 | 0.98 | 0.645 | 4 |
| | | | | | LNU136 | 14515.1 | 1.21 | 0.274 | 10 | LNU185 | 26474.1 | 0.96 | 0.547 | 2 |
| | | | | | LNU142 | 27541.1 | 1.21 | 0.638 | 10 | LNU212 | 25834.5 | 1.05 | 0.388 | 11 |
| | | | | | LNU142 | 27541.2 | 1.17 | 0.098 | 6 | LNU212 | 25834.1 | 1.04 | 0.612 | 11 |
| | | | | | LNU15 | 14123.11 | 1.42 | 0.327 | 29 | LNU212 | 25833.2 | 1.04 | 0.551 | 11 |
| | | | | | LNU15 | 14122.8 | 1.36 | 0.570 | 24 | LNU212 | 25834.4 | 1.00 | 0.545 | 6 |
| | | | | | LNU15 | 14123.13 | 1.25 | 0.308 | 13 | LNU216 | 25984.6 | 1.09 | 0.113 | 16 |
| | | | | | LNU185 | 26474.1 | 1.20 | 0.433 | 9 | LNU216 | 25984.1 | 1.05 | 0.100 | 12 |
| | | | | | LNU212 | 25834.5 | 1.24 | 0.411 | 13 | LNU216 | 25982.2 | 0.99 | 0.087 | 6 |
| | | | | | LNU212 | 25834.4 | 1.18 | 0.605 | 7 | LNU216 | 25982.1 | 0.98 | 0.148 | 5 |
| | | | | | LNU212 | 25834.1 | 1.17 | 0.479 | 6 | LNU228 | 26224.7 | 1.17 | 0.050 | 25 |
| | | | | | LNU212 | 25833.2 | 1.15 | 0.765 | 4 | LNU228 | 26224.6 | 1.04 | 0.620 | 11 |
| | | | | | LNU216 | 25984.1 | 1.19 | 0.587 | 8 | LNU228 | 26222.1 | 1.04 | 0.028 | 11 |
| | | | | | LNU216 | 25982.2 | 1.16 | 0.031 | 6 | LNU228 | 26225.2 | 0.99 | 0.120 | 5 |
| | | | | | LNU216 | 25984.6 | 1.14 | 0.675 | 4 | LNU229 | 26111.5 | 1.00 | 0.301 | 6 |
| | | | | | LNU228 | 26224.7 | 1.33 | 0.012 | 21 | LNU241 | 26232.4 | 1.06 | 0.094 | 13 |
| | | | | | LNU228 | 26222.1 | 1.30 | 0.015 | 18 | LNU253 | 26243.3 | 1.03 | 0.292 | 9 |
| | | | | | LNU228 | 26225.2 | 1.14 | 0.627 | 3 | LNU274 | 26262.2 | 1.00 | 0.069 | 6 |
| | | | | | LNU229 | 26111.5 | 1.27 | 0.000 | 15 | LNU277 | 25842.3 | 1.09 | 0.283 | 16 |
| | | | | | LNU229 | 26112.4 | 1.13 | 0.720 | 3 | LNU277 | 25844.3 | 0.98 | 0.547 | 5 |
| | | | | | LNU241 | 26232.4 | 1.30 | 0.340 | 18 | LNU280 | 26164.3 | 1.08 | 0.014 | 15 |
| | | | | | LNU253 | 26242.1 | 1.17 | 0.621 | 6 | LNU280 | 26162.7 | 1.06 | 0.452 | 13 |
| | | | | | LNU274 | 26262.2 | 1.15 | 0.489 | 5 | LNU280 | 26164.4 | 1.04 | 0.114 | 11 |
| | | | | | LNU277 | 25842.3 | 1.24 | 0.486 | 13 | LNU280 | 26162.1 | 1.04 | 0.496 | 11 |
| | | | | | LNU280 | 26164.4 | 1.25 | 0.101 | 13 | LNU55 | 26013.4 | 0.96 | 0.409 | 3 |
| | | | | | LNU280 | 26162.1 | 1.18 | 0.024 | 7 | LNU81 | 26031.10 | 1.14 | 0.307 | 21 |
| | | | | | LNU81 | 26031.10 | 1.38 | 0.204 | 25 | LNU81 | 26034.3 | 1.11 | 0.438 | 18 |
| | | | | | LNU81 | 26031.9 | 1.17 | 0.607 | 6 | LNU81 | 26034.2 | 1.05 | 0.021 | 12 |
| | | | | | | | | | | LNU81 | 26031.9 | 0.97 | 0.711 | 3 |

Table 84.
"CONT."—Control;
"Ave."—Average;
"% Incr." = % increment.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09096865B2). An electronic copy of the "Sequence Listing" will also be available from the USPTO upon request and payment of the fee set forth in 37 CFR 1.19(b)(3).

What is claimed is:

1. A method of increasing nitrogen use efficiency, yield, biomass, growth rate, vigor, and/or tolerance to nitrogen deficiency of a plant, comprising expressing within the plant an exogenous polynucleotide comprising the nucleic acid sequence set forth in SEQ ID NO:420, thereby increasing the nitrogen use efficiency, yield, biomass, growth rate, vigor, and/or tolerance to nitrogen deficiency of the plant.

2. A method of increasing nitrogen use efficiency, yield, biomass, growth rate, vigor, and/or tolerance to nitrogen deficiency of a plant, comprising expressing within the plant an exogenous polynucleotide comprising a nucleic acid sequence encoding the polypeptide set forth in SEQ ID NO: 634, thereby increasing the nitrogen use efficiency, yield, biomass, growth rate, vigor, and/or tolerance to nitrogen deficiency of the plant.

3. The method of claim 1, wherein the yield comprises seed yield or oil yield.

4. The method of claim 1, further comprising growing the plant expressing said exogenous polynucleotide under nitrogen-limiting conditions.

5. The method of claim 2, wherein said nucleic acid sequence is set forth by SEQ ID NO: 167.

6. The method of claim 1, further comprising selecting a plant expressing said exogenous polynucleotide for an increased biomass as compared to a non-transformed plant grown under the same growth conditions.

7. The method of claim 1, further comprising selecting a plant expressing said exogenous polynucleotide for an increased yield as compared to a non-transformed plant grown under the same growth conditions.

8. The method of claim 1, further comprising selecting a plant expressing said exogenous polynucleotide for an increased nitrogen use efficiency as compared to a non-transformed plant grown under the same growth conditions.

9. The method of claim 1, further comprising selecting a plant expressing said exogenous polynucleotide for an increased growth rate as compared to a non-transformed plant grown under the same growth conditions.

10. The method of claim 1, further comprising selecting a plant expressing said exogenous polynucleotide for an increased tolerance to nitrogen deficiency as compared to a non-transformed plant grown under the same growth conditions.

11. The method of claim 2, further comprising selecting a plant expressing said exogenous polynucleotide for an increased biomass as compared to a non-transformed plant grown under the same growth conditions.

12. The method of claim 2, further comprising selecting a plant expressing said exogenous polynucleotide for an increased yield as compared to a non-transformed plant grown under the same growth conditions.

13. The method of claim 2, further comprising selecting a plant expressing said exogenous polynucleotide for an increased nitrogen use efficiency as compared to a non-transformed plant grown under the same growth conditions.

14. The method of claim 2, further comprising selecting a plant expressing said exogenous polynucleotide for an increased growth rate as compared to a non-transformed plant grown under the same growth conditions.

15. The method of claim 2, further comprising selecting a plant expressing said exogenous polynucleotide for an increased tolerance to nitrogen deficiency as compared to a non-transformed plant grown under the same growth conditions.

* * * * *